United States Patent
Vakalopoulos et al.

(10) Patent No.: US 10,662,185 B2
(45) Date of Patent: *May 26, 2020

(54) AMINO-SUBSTITUTED IMIDAZO[1,2-A] PYRIDINECARBOXAMIDES AND THEIR USE

(71) Applicant: BAYER PHARMA AKTIENGESELLSCHAFT, Berlin (DE)

(72) Inventors: Alexandros Vakalopoulos, Hilden (DE); Markus Follman, Köln (DE); Ingo Hartung, Berlin (DE); Philipp Buchgraber, Wuppertal (DE); Rolf Jautelat, Haan (DE); Jorma Haßfeld, Düsseldorf (DE); Niels Lindner, Wuppertal (DE); Alexey Gromov, Erkrath (DE); Frank Wunder, Wuppertal (DE); Johannes-Peter Stasch, Solingen (DE); Gorden Redlich, Bochum (DE); Volkhart Min-Jian Li, Velbert (DE); Eva Maria Becker-Pelster, Wuppertal (DE); Andreas Knorr, Erkrath (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/025,087

(22) Filed: Jul. 2, 2018

(65) Prior Publication Data

US 2018/0319794 A1 Nov. 8, 2018
US 2019/0248783 A9 Aug. 15, 2019

Related U.S. Application Data

(60) Continuation of application No. 15/447,205, filed on Mar. 2, 2017, now Pat. No. 10,052,312, which is a (Continued)

(30) Foreign Application Priority Data

Nov. 5, 2012 (EP) .................................... 12191201
Jul. 26, 2013 (EP) .................................... 13178248

(51) Int. Cl.
*C07D 471/04* (2006.01)
*A61K 31/437* (2006.01)
(Continued)

(52) U.S. Cl.
CPC .......... *C07D 471/04* (2013.01); *A61K 31/437* (2013.01); *A61K 31/439* (2013.01); *A61K 31/4375* (2013.01); *A61K 31/444* (2013.01); *A61K 31/4545* (2013.01); *A61K 31/4709* (2013.01); *A61K 31/4725* (2013.01); *A61K 31/496* (2013.01); *A61K 31/4985* (2013.01); *A61K 31/5377* (2013.01); *A61K 31/541* (2013.01); *A61K 31/55* (2013.01); *A61K 45/06* (2013.01); *C07D 471/08* (2013.01); *C07D 519/00* (2013.01)

(58) Field of Classification Search
CPC .................................................. C07D 471/04
See application file for complete search history.

(56) References Cited

U.S. PATENT DOCUMENTS 5,459,132 A 10/1995 Bru-Magniez et al.
5,593,993 A 1/1997 Morin et al.
(Continued)

FOREIGN PATENT DOCUMENTS

CA 2836202 A1 12/2012
EP 0266890 A1 5/1988
(Continued)

OTHER PUBLICATIONS

Jones, E. S. et al. "Cardioprotective effects in aged spontaneously hypertensive rats due to chronic stimulation/activation of sGC without hypotension," BMC Pharmacol. 2009; 9:P29. [abstract].
Masuyama, H. et al. "Soluble guanylate cyclase stimulation on cardiovascular remodeling in angiotensin II-induced hypertensive rats," Hypertension, 2006; 48:972-978.
Masuyama, H. et al. "Pressure-independent effects of pharmacological stimulation of soluble guanylate cyclase on fibrosis in pressure-overloaded rat heart," Hypertens Res. 2009; 32:597-603
Methner, C. et al. "Riociguat Reduces Infarct Size and Post-Infarct Heart Failure in Mouse Hearts: Insights from MRI/PET Imaging," PLOS One, Dec. 2013; 8(12):e83910, 1-8.
(Continued)

*Primary Examiner* — Brian E McDowell
(74) *Attorney, Agent, or Firm* — Quarles & Brady LLP

(57) ABSTRACT

The present application relates to novel substituted imidazo[1,2-a]pyridine-3-carboxamides of the general formula (I)

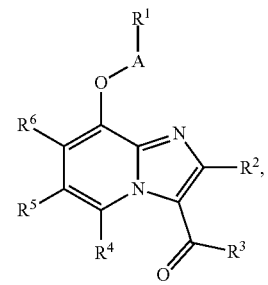

to processes for their preparation, to their use alone or in combinations for the treatment and/or prophylaxis of diseases and to their use for preparing medicaments for the treatment and/or prophylaxis of diseases, in particular for the treatment and/or prophylaxis of cardiovascular disorders.

9 Claims, No Drawings

Related U.S. Application Data division of application No. 14/070,180, filed on Nov. 1, 2013, now Pat. No. 9,624,214.

(51) Int. Cl.

| | |
|---|---|
| *A61K 31/439* | (2006.01) |
| *A61K 31/4985* | (2006.01) |
| *A61K 45/06* | (2006.01) |
| *C07D 471/08* | (2006.01) |
| *A61K 31/496* | (2006.01) |
| *A61K 31/5377* | (2006.01) |
| *A61K 31/541* | (2006.01) |
| *C07D 519/00* | (2006.01) |
| *A61K 31/444* | (2006.01) |
| *A61K 31/4545* | (2006.01) |
| *A61K 31/4709* | (2006.01) |
| *A61K 31/55* | (2006.01) |
| *A61K 31/4375* | (2006.01) |
| *A61K 31/4725* | (2006.01) |

(56) References Cited

U.S. PATENT DOCUMENTS

| | | |
|---|---|---|
| 5,691,336 A | 11/1997 | Dorn et al. |
| 5,698,704 A | 12/1997 | Jackson |
| 5,935,984 A | 8/1999 | Goldmann et al. |
| 6,180,656 B1 | 1/2001 | Furster et al. |
| 6,403,588 B1 | 6/2002 | Hayakawa |
| 7,935,722 B2 | 5/2011 | Fales et al. |
| 8,163,773 B2 | 4/2012 | Breitenstein et al. |
| 8,198,449 B2 | 6/2012 | Pracitto et al. |
| 8,212,041 B2 | 7/2012 | Albrecht et al. |
| 8,536,338 B2 | 9/2013 | Pracitto et al. |
| 8,778,964 B2 | 7/2014 | Vakalopoulos et al. |
| 8,796,305 B2 | 8/2014 | Vakalopoulos et al. |
| 8,865,734 B2 | 10/2014 | No et al. |
| 8,946,215 B2 | 2/2015 | Vakalopoulos et al. |
| 8,969,045 B2 | 3/2015 | Burkhardt et al. |
| 9,126,998 B2 | 9/2015 | Vakalopoulos et al. |
| 9,278,968 B2 | 3/2016 | Kurosaki et al. |
| 9,447,090 B2 | 9/2016 | Koga et al. |
| 9,624,214 B2 | 4/2017 | Vakalopoulos et al. |
| 2004/0180896 A1 | 9/2004 | Munson |
| 2008/0051409 A1 | 2/2008 | Gmeiner et al. |
| 2008/0103183 A1 | 5/2008 | Ackermann et al. |
| 2008/0194629 A1 | 8/2008 | Baeschlin et al. |
| 2009/0124612 A1 | 5/2009 | Albecht et al. |
| 2010/0092966 A1 | 4/2010 | Burkhardt et al. |
| 2013/0203751 A1 | 7/2013 | Hubsch et al. |
| 2014/0128372 A1 | 5/2014 | Vakalopoulos |
| 2015/0274719 A1 | 10/2015 | Vakalopoulos |
| 2016/0122341 A1 | 5/2016 | Vakalopoulos |
| 2016/0176880 A1 | 6/2016 | Vakalopoulos |
| 2016/0185775 A1 | 6/2016 | Vakalopoulos |
| 2016/0347770 A1 | 12/2016 | Vakalopoulos |
| 2016/0362408 A1 | 12/2016 | Vakalopoulos |
| 2017/0050961 A1 | 2/2017 | Vakalopoulos et al. |
| 2017/0050962 A1 | 2/2017 | Vakalopoulos et al. |
| 2017/0057954 A1 | 3/2017 | Vakalopoulos et al. |

FOREIGN PATENT DOCUMENTS

| | | |
|---|---|---|
| EP | 1277754 A1 | 2/2003 |
| JP | H01258674 | 10/1989 |
| WO | 8903833 A1 | 5/1989 |
| WO | 9634866 A1 | 11/1996 |
| WO | 2008082490 A2 | 7/2008 |
| WO | 2008134553 A1 | 11/2008 |
| WO | 2010030538 A2 | 3/2010 |
| WO | 2011113606 A1 | 9/2011 |
| WO | 2011141409 A1 | 11/2011 |
| WO | 2011149921 A1 | 12/2011 |
| WO | 2011161099 A1 | 12/2011 |
| WO | 2012143796 A2 | 10/2012 |
| WO | 2012165399 A1 | 12/2012 |
| WO | 2015082411 | 6/2015 |
| WO | 2015124544 | 8/2015 |
| WO | 2015140199 | 9/2015 |
| WO | 2015140254 | 9/2015 |

OTHER PUBLICATIONS

Pieske, B. "Vericiguat in patients with worsening chronic heart failure and preserved ejection fraction: results of the SOluble guanylate Cyclase stimulatoR in heArT failurE patientS with Preserved EF (Socrates-Preserved) study," European Heart Journal, 2017; 38:1119-1127.

Sharkovska, Y. et al. "Nitric oxide-independent stimulation of soluble guanylate cyclase reduces organ damage in experimental low-renin and high-renin models," Journal of Hypertension 2010; 28:1666-1675.

Stasch, J. et al. "Soluble Guanylate Cyclase as an Emerging TherapeuticTarget in Cardiopulmonary Disease," Circulation, 2011; 123:2263-2273.

Stasch, J. et al. "Renal effects of soluble guanylate cyclase stimulators and activators: A review of the preclinical evidence," Current Opinion in Pharmacology 2015; 21:95-104.

Wang, Y. et al. "Enhancing cGMP in experimental progressive renal fibrosis: soluble guanylate cyclase stimulation vs. phosphodiesterase inhibition," Am J Physiol Renal Physiol, 2006; 290:F167-F176.

Wang, Y. et al. "Stimulation of soluble guanylate cyclase slows progression in anti-thy1-induced chronic glomerulosclerosis, " Kidney Int 2005; 68:47-61.

International Search Report dated Dec. 13, 2013, by the European Patent Office as the International Searching Authority in International Application No. PCT/EP2013/072891. (8 pages).

Written Opinion of the International Search Authority dated May 5, 2015 in International Application No. PCT/EP2013/072891. (12 pages).

Ihien-nien et al., "Cyclic Guanosine Monophosphate Signalling Pathway In Pulmonary Arterial Hypertension," Vascular Pharmacology, 2013, 58:211-218.

Chien-nien et al., "Cyclic Guanosine Monophosphate Signalling Pathway In Pulmonary Arterial Hypertension," Vascular Pharmacology, 2013, 58:211-218.

Dembinski et al., "Recent Advances in the Mitsunobu Reaction: Modified Reagents and the Questfor Chromatography-Free Separation, " Eur. J. Org. Chem., 2004, 13:2763-2772.

Deng et al., "Studies on Phosphoroheterocycle Chemistry II A Simple and New Route to 1, 3, 2-Diazaphospholidine-4-thione 2-sulfide Derivatives," Synthesis, 2001, 16:2445-2449.

Gensini et al., "3-Azabicyclo[3.1.0]hex-1-ylamines by Ti-Mediated Intramolecular ReductiveCyclopropanation of a-(N-Allylamino)-Substituted N,N-Dialkylcarbizamidesand Carbonitries," Eur. J. Org. Chem., 2002, 15: 2499-2507.

Glass et al., "Stimulation of Human Platelet Guanylate Cyclase by Fatty Acides," J. Biol. Chem., Feb. 1977, 252(4):1279-1285.

Greene et al., Greene's Protective Groups in Organic Synthesis, 4th ed., chapter 1, "The Role of Protective Groups in Organic Synthesis," 2007, Published by John Wiley & Sons, New York.

Hjorringgaard et al., "An Automatic Solid-Phase Synthesis of Peptaibols," J. Org. Chem. 2009, 74:1329-1332.

Hoenicka et al. "Purified Soluble Guanylyl Cyclase Expressed in A Baculovirus/Sf9 System: Stimulation Ny YC-1, Nitric Oxide, and Carbon Monoxide," J. Mol. Med., 1999, 77:14-23.

Hughes et al., "The Mitsunobu Reaction," Organic Reactions, vol. 42, 1992, Chapter 2, Published by John Wiley & Sons, Inc., pp. 335-395 and 636-656.

Kozo et al., International Review of Experimental Pathology, vol. 7, 1969, chapter 2, "Spontaneous Hypertension in Rats," Published by Academic Press, Inc., New York, 227-270.

Lasker et al., "Targeting soluble guanylate cyclase for the treatment of pulmonary hypertension," Expert Rev Respir Med., Apr. 2011, 5(2):153-161.

(56) References Cited

OTHER PUBLICATIONS

Maarten van den Buuse, "Circadian Rhythms of Blood Pressure, Heart Rate, and Locomotor Activity in Spontaneously Hypertensive Rats as Measured with Radio-Telemetry," Physiology & Behavior, 1994, 55:(4) 783-787.
Altuna-Urquijo et al., "A Convenient Synthesis of Pyridine and 2,2'-Bipyridine Derivatives," Tetrahedron, (2009), vol. 65, Issue 5, pp. 975-984.
Bai et al., "Lewis Acid Catalyzed Intramolecular [4+2] and [3+2] Cross-Cycloaddition of Alkynylcyclopropane Ketones with Carbonyl Compounds and Imines," Angewandte Chem. Int. Ed. 2012, 51, pp. 4112-4116.
Bergmann E.D. et al., "Organic Fluorine Compounds. Part XXVII. Fluorinated alpha-Aminoisobutyric Acids," Journal of the Chemical Society 1963, 3462-3463.
Bitler et al., "The Preparation and Properties of Crystalline Firefly Luciferin," Archives of Biochemistry and Biophysics, (1957), vol. 72, No. 2, pp. 358-368.
Chen et al., "Radical Formation in the Oxidation of 2,2'-Azo-2-methyl-6-heptene by Thianthrene Cation Radical," Journal of Organic Chemistry, 1996, 61, pp. 4716-4719.
Hamill et al., "Improved Patch-Clamp Techniques for High-Resolution Current Recording from Cells and Cell-Free Membrane Patches", Pfluegers Arch, 1981, vol. 391, 85-100.
Hassan et al., "Aryl-Aryl Bond Formation One Century after the Discovery of the Ullmann Reaction," Chem. Rev., 2002, vol. 102, 1359-1469.
Himmel et al., "Suitability of commonly used excipients for electrophysiological in-vitro safety pharmacology assessment of effects on hERG potassium current and on rabbit Purkinje fiber action potential", J Pharmacol Toxicol Methods, 2007, vol. 56, 145-158.
Hiroi et al., "A Novel Method for Direct Construction of Indole Skeletons by Intramolecular Carbopalladation of Allenes Followed by Nucleophilic Substitution," Synlett, 2001, No. 2, 263-265.
Johnson A. W., "Chapter 1 Carbon Compounds: Bonding and Structure," Invitation to Organic Chemistry, 1999 Jones and Bartlett Publishers Sudbury, MA, p. 24.
Ko et al., "YC-1, a novel activator of platelet guanylate cyclase," Blood, 1994, 84(12): 4226-4233.
McConathy J. et al., "Radiolabeled Amino Acids for Tumor Imaging with PET: Radiosynthesis and Biological Evaluation of 2-Amino-3-[18F]fluoro-2-methylpropanoic Acid and 3-[18F]Fluoro-2-methyl-2-(methylamino)propanoic Acid", Journal of Medicinal Chemistry 2002, 45, 2240-2249.
Mikami et al., "Applications of the Tandem [2,3]-Wittig-Oxy-Cope Rearrangement to Syntheses of exo-Brevicomin and Oxocrinol. The Scope and Limitation of the Sigmatropic Sequences as a Synthetic Method for δ, ε-Unsaturated Ketones", Chemistry Letters, The Chemical Society of Japan 1982, 1349-1352.
Mülsch et al., "Effect of YC-1, An NO-independent, Superoxide-senstive Stimulator of Soluble Guanylyl Cyclase, On Smooth Muscle Responsiveness to Nitrovasodilators," British Journal Pharmacology 1997, 120:681-689.
Ogrel et al., "Synthesis of 15N-Labelled D-Isovaline and á-Aminoisobutyric Acid," Eur. J. Org. Chem., 2000, 5:857-859.
Ostermann et al., "A Novel Class of Oral Direct Renin Inhibitors: Highly Potent 3,5-Disubstituted Piperidines Bearing a Tricyclic P3-P1 Pharmacophore," Journal of Medicinal Chemistry, (2013), vol. 56, No. 6, pp. 2196-2206.
Patani et al., "Bioisosterism: A Rational Approach in Drug Design," Chem. Rev. 1996, 96, 3147-3176.
Pettibone et al., "A Structurally Novel Stimulator of Guanylate Cyclase With Long-Lasting Hypotensive Activity In The Dog," European Journal of Pharmacology, 1985, 116:307-312.
Rubottom et al., "Preparation of Methyl Ketones by the Sequential Treatment of Carboxylic Acids with Methyllithium and Chlorotrimethylsilane," Journal of Organic Chemistry, 1983, 48, 1550-1552.
Scheel et al., "Introduction of a Modular Automated Voltage-Clamp Platform and Its Correlation with Manual Human Ether-a'-go-go Related Gene Voltage-Clamp Data", Assay Drug Dev Technol, Dec. 2011, vol. 9, 600-607.
Soler et al., "Betulinic Acid Derivatives: A New Class of Specific Inhibitors of Human Immunodeficiency Virus Type 1 Entry," Journal Med. Chem., 1996, 39:1069-1083.
Stasch et al., "Cardiovascular actions of a novel NO-independent guanylyl cyclase stimulator, BAY 41-8543: in vivo studies," Br. J. Pharmacol 2002, 135(2):344-355.
Witte et al., "Experimental heart failure in rats: effects on cardiovascular circadian rhythms and on myocardial β-adrenergic signaling," Cardiovascular Research, 2000, 47:350-358.
Weidmann et al., "2-[(2-Pyridylmethyl)Sulfinyl]-1H-Thieno[3-4-d]Imidazoles. A Novel Class of Gastric H+/K+-ATPase Inhibitors", J. Med. Chem. 1992, vol. 35, pp. 438-450.
Wermuth, "Molecular Variations Based on Isosteric Replacements," Chapter 13 in The Practice of Medicinal Chemistry Academic: 1996.
Wube et al., "Design, synthesis and antimycobacterial activities of 1-methyl-2-alkenyl-4(1H)-quinolones", Bioorganic & Medicinal Chemistry, 2011, vol. 19, pp. 567-579.
Wunder et al., "A cell-based cGMP assay useful for ultra-high-throughput screening and identification of modulators of the nitric oxide/cGMP pathway," Analytical Biochemistry, 2005, 339:104-112.
Yu et al., "Vasorelaxant Effect of Isoliquiritigenin, A Novel Soluble Guanylate Cyclase Activator, In Rat Aorta," British Journal of Pharmacology, 1995, 114:1587-1594.
Zhou et al., "Properties of HERG Channels Stably Expressed in HEK 293 Cells Studied at Physiological Temperature", Biophys Journal, Jan. 1998, pp. 230-241, vol. 74.
Boerrigter, G, et al. "Cardiorenal and humoral properties of a novel direct soluble guanylate cyclase stimulator BAY 41-2272 in experimental congestive heart failure," Circulation, 2003; 107:686-689.
Breitenstein S. et al., "Novel sGC Stimulators and sGC Activators for the Treatment of Heart Failure" in J. Bauersachs et al. (eds.), Heart Failure, Handbook of Experimental Pharmacology, 243, Springer International Publishing AG (2016), 225-247.
Costell, M. et al. "Comparison of soluble guanylate cyclase stimulators and activators in models of cardiovascular disease associated with oxidative stress," Frontiers in Pharmacology, Jul. 2012; 3:128, 1-14.
Follmann, M. et al. "Discovery of the Soluble Guanylate Cyclase Stimulator Vericiguat (BAY 1021189) for the Treatment of Chronic Heart Failure," J. Med. Chem., Jun. 22, 2017; 60:5146-5161.
Geschka, S. et al. "Soluble Guanylate Cyclase Stimulation Prevents Fibrotic Tissue Remodeling and Improves Survival in Salt-Sensitive Dahl Rats," PLoS ONE Jul. 2011; 6:e21853, 1-10.
Gheorghiade M., et al. "Effect of Vericiguat, a Soluble Guanylate Cyclase Stimulator, on Natriuretic Peptide Levels in Patients With Worsening Chronic Heart Failure and Reduced Ejection Fraction The Socrates-Reduced Randomized Trial," JAMA 2015; 314(21):2251-2262.

AMINO-SUBSTITUTED IMIDAZO[1,2-A] PYRIDINECARBOXAMIDES AND THEIR USE

CROSS-REFERENCE TO RELATED APPLICATIONS

This application is a continuation of U.S. application Ser. No. 15/447,205, filed Mar. 2, 2017, now U.S. Pat. No. 10,052,312, which is a divisional of U.S. application Ser. No. 14/070,180, filed Nov. 1, 2013, now U.S. Pat. No. 9,624,214, which claims priority to European Patent Application No. EP13178248.4, filed Jul. 26, 2013, and European Patent Application No. EP12191201.8, filed Nov. 5, 2012.

The present application relates to novel substituted imidazo[1,2-a]pyridine-3-carboxamides, to processes for their preparation, to their use alone or in combinations for the treatment and/or prophylaxis of diseases and to their use for preparing medicaments for the treatment and/or prophylaxis of diseases, in particular for the treatment and/or prophylaxis of cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory site. The latter is of central importance for the mechanism of activation. NO is able to bind to the iron atom of haem and thus markedly increase the activity of the enzyme. Haem-free preparations cannot, by contrast, be stimulated by NO. Carbon monoxide (CO) is also able to attach to the central iron atom of haem, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, myocardial infarction, thromboses, stroke and sexual dysfunction.

A possible way of treating such disorders which is independent of NO and aims at influencing the cGMP signaling pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of haem. Besides the side effects, the development of tolerance is one of the crucial disadvantages of this mode of treatment.

Over the last years, a number of substances which stimulate soluble guanylate cyclase directly. i.e. without prior release of NO, have been described, for example 3-(5'-hydroxymethyl-2'-furyl)-1-benzylindazole [YC-1; Wu et al., Blood 84 (1994), 4226; Mülsch et al., Brit. J. Pharmacol. 120 (1997), 681], fatty acids [Goldberg et al., J. Biol. Chem. 252 (1977), 1279], diphenyliodonium hexafluorophosphate [Pettibone et al., Eur. J. Pharmacol. 116 (1985), 307], isoliquiritigenin [Yu et al., Brit. J Pharmacol. 114 (1995), 1587], and also various substituted pyrazole derivatives (WO 98/16223).

EP 0 266 890-A1, WO 89/03833-A1, JP 01258674-A [cf. Chem. Abstr. 112:178986], WO 96/34866-A1, EP 1 277 754-A1, WO 2006/015737-A1, WO 2008/008539-A2, WO 2008/082490-A2, WO 2008/134553-A1, WO 2010/030538-A2, WO 2011/113606-A1 and WO 2012/165399 A1 inter alia, describe various imidazo[1,2-a]pyridine derivatives which can be used for treating disorders.

It was an object of the present invention to provide novel substances which act as stimulators of soluble guanylate cyclase and, as such, are suitable for the treatment and/or prophylaxis of diseases.

The present invention provides compounds of the general formula (I)

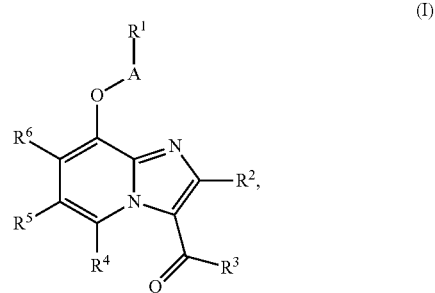

in which
A represents $CH_2$, $CD_2$ or $CH(CH_3)$,
$R^1$ represents $(C_4$-$C_6)$-alkyl, $(C_3$-$C_7)$-cycloalkyl or phenyl,
where $(C_4$-$C_6)$-alkyl may be substituted up to six times by fluorine,
where $(C_3$-$C_7)$-cycloalkyl may be substituted by 1 to 4 substituents independently of one another selected from the group consisting of fluorine, trifluoromethyl and $(C_1$-$C_4)$-alkyl,
and
where phenyl may be substituted by 1 to 4 substituents independently of one another selected from the group consisting of halogen, cyano, monofluoromethyl, difluoromethyl, trifluoromethyl, $(C_1$-$C_4)$-alkyl, $(C_1$-$C_4)$-alkoxy, difluoromethoxy and trifluoromethoxy,
$R^2$ represents hydrogen, $(C_1$-$C_4)$-alkyl, cyclopropyl, monofluoromethyl, difluoromethyl or trifluoromethyl,
$R^3$ represents a group of the formula

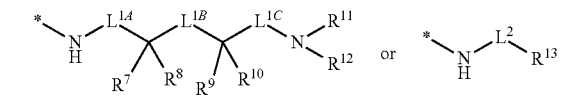

where
* represents the point of attachment to the carbonyl group,
$L^{1A}$ represents a bond or $(C_1$-$C_4)$-alkanediyl, where (C$_1$-C$_4$)-alkanediyl may be substituted by 1 to 3 substituents independently of one another selected from the group consisting of fluorine, trifluoromethyl, (C$_1$-C$_4$)-alkyl, (C$_3$-C$_7$)-cycloalkyl, hydroxy and (C$_1$-C$_4$)-alkoxy, L$^{1B}$ represents a bond or (C$_1$-C$_4$)-alkanediyl, L$^{1C}$ represents a bond or (C$_1$-C$_4$)-alkanediyl, where (C$_1$-C$_4$)-alkanediyl may be substituted by 1 to 3 substituents independently of one another selected from the group consisting of fluorine, trifluoromethyl, (C$_1$-C$_4$)-alkyl, (C$_3$-C$_7$)-cycloalkyl, hydroxy and (C$_1$-C$_4$)-alkoxy, R$^7$ represents hydrogen, (C$_1$-C$_6$)-alkyl, (C$_2$-C$_6$)-alkenyl, (C$_2$-C$_6$)-alkynyl, (C$_3$-C$_7$)-cycloalkyl, 5- or 6-membered heteroaryl or phenyl, where (C$_1$-C$_6$)-alkyl may be substituted by 1 to 3 substituents independently of one another selected from the group consisting of fluorine, difluoromethyl, trifluoromethyl, difluoromethoxy, trifluoromethoxy, hydroxy, (C$_1$-C$_4$)-alkoxy, (C$_1$-C$_4$)-alkoxycarbonyl, (C$_1$-C$_4$)-alkylsulphonyl, phenyl, phenoxy and benzyloxy, where phenyl, phenoxy and benzyloxy for their part may be substituted by 1 to 3 halogen substituents, where (C$_3$-C$_7$)-cycloalkyl may be substituted by 1 or 2 substituents independently of one another selected from the group consisting of fluorine, trifluoromethyl, (C$_1$-C$_4$)-alkyl and (C$_1$-C$_4$)-alkoxy, and where phenyl and 5- or 6-membered heteroaryl may be substituted by 1 to 3 substituents independently of one another selected from the group consisting of halogen, cyano, trifluoromethyl, (C$_1$-C$_4$)-alkyl, (C$_1$-C$_4$)-alkylsulphonyl and (C$_1$-C$_4$)-alkoxy, R$^8$ represents hydrogen or (C$_1$-C$_4$)-alkyl, or R$^7$ and R$^8$ together with the carbon atom to which they are attached form a 3- to 7-membered carbocycle or a 4- to 7-membered heterocycle, where the 3- to 7-membered carbocycle and the 4- to 7-membered heterocycle for their part may be substituted by 1 or 2 substituents independently of one another selected from the group consisting of fluorine and (C$_1$-C$_4$)-alkyl, R$^9$ represents hydrogen, (C$_1$-C$_6$)-alkyl, (C$_2$-C$_6$)-alkenyl, (C$_2$-C$_6$)-alkynyl, (C$_3$-C$_7$)-cycloalkyl, 5- or 6-membered heteroaryl or phenyl, where (C$_1$-C$_6$)-alkyl may be substituted by 1 to 3 substituents independently of one another selected from the group consisting of fluorine, trifluoromethyl, difluoromethoxy, trifluoromethoxy, hydroxy, (C$_1$-C$_4$)-alkoxy, (C$_1$-C$_4$)-alkoxycarbonyl, (C$_1$-C$_4$)-alkylsulphonyl, phenyl, phenoxy and benzyloxy, where phenyl, phenoxy and benzyloxy for their part may be substituted by 1 to 3 halogen substituents, where (C$_3$-C$_7$)-cycloalkyl may be substituted by 1 or 2 substituents independently of one another selected from the group consisting of fluorine, trifluoromethyl, (C$_1$-C$_4$)-alkyl and (C$_1$-C$_4$)-alkoxy, and where phenyl and 5- or 6-membered heteroaryl may be substituted by 1 to 3 substituents independently of one another selected from the group consisting of halogen, cyano, trifluoromethyl, (C$_1$-C$_4$)-alkyl, (C$_1$-C$_4$)-alkoxy and (C$_1$-C$_4$)-alkylsulphonyl, R$^{10}$ represents hydrogen or (C$_1$-C$_4$)-alkyl, or R$^9$ and R$^{10}$ together with the carbon atom to which they are attached form a 3- to 7-membered carbocycle or a 4- to 7-membered heterocycle, where the 3- to 7-membered carbocycle and the 4- to 7-membered heterocycle for their part may be substituted by 1 or 2 substituents independently of one another selected from the group consisting of fluorine and (C$_1$-C$_4$)-alkyl, with the proviso that the radicals R$^7$ and R$^9$ do not both simultaneously represent phenyl, or R$^7$ and R$^9$ together with the carbon atoms to which they are attached and with the group L$^{1B}$ form a 5- to 7-membered carbocycle or a 4- to 7-membered heterocycle, with the proviso that not more than one of the radical pairs R$^7$ and R$^8$, R$^9$ and R$^{10}$ and R$^7$ and R$^9$, respectively, simultaneously forms a carbo- or heterocycle, R$^{11}$ represents hydrogen or (C$_1$-C$_4$)-alkyl, where (C$_1$-C$_4$)-alkyl may be substituted by 1 to 3 substituents independently of one another selected from the group consisting of fluorine, trifluoromethyl, hydroxy and (C$_1$-C$_4$)-alkoxy, R$^{12}$ represents hydrogen, (C$_1$-C$_6$)-alkyl, (C$_3$-C$_7$)-cycloalkyl, phenyl or benzyl, where (C$_1$-C$_6$)-alkyl may be substituted by 1 to 3 substituents independently of one another selected from the group consisting of fluorine, trifluoromethyl, hydroxy, (C$_1$-C$_4$)-alkoxy and phenoxy, and where phenyl and benzyl may be substituted by 1 to 3 substituents independently of one another selected from the group consisting of halogen and trifluoromethyl, or R$^{11}$ and R$^{12}$ together with the nitrogen atom to which they are attached form a 4- to 7-membered azaheterocycle, where the 4- to 7-membered azaheterocycle may be substituted by 1 or 2 substituents independently of one another selected from the group consisting of fluorine, trifluoromethyl, (C$_1$-C$_4$)-alkyl, (C$_3$-C$_7$)-cycloalkyl, hydroxy, (C$_1$-C$_4$)-alkoxy and 4- to 7-membered heterocyclyl, and L$^2$ represents a bond or (C$_1$-C$_4$)-alkanediyl, R$^{13}$ represents 5- to 9-membered azaheterocyclyl which is attached via a ring carbon atom, where 5- to 9-membered azaheterocyclyl may be substituted by 1 to 5 substituents independently of one another selected from the group consisting of fluorine, trifluoromethyl, (C$_1$-C$_4$)-alkyl, (C$_3$-C$_7$)-cycloalkyl and benzyl, and where 5- to 9-membered azaheterocyclyl may be fused to a phenyl ring which for its part may be substituted by 1 or 2 substituents selected from the group consisting of halogen, (C$_1$-C$_4$)-alkyl and trifluoromethyl, R$^4$ represents hydrogen, R$^5$ represents hydrogen, halogen, cyano, difluoromethyl, trifluoromethyl, (C$_1$-C$_4$)-alkyl, (C$_3$-C$_7$)-cycloalkyl, (C$_2$-C$_4$)-alkynyl, difluoromethoxy, trifluoromethoxy, (C$_1$-C$_4$)-alkoxy, amino, 4- to 7-membered heterocyclyl or 5- or 6-membered heteroaryl, R$^6$ represents hydrogen, cyano or halogen, and their N-oxides, salts, solvates, salts of the N-oxides and solvates of the N-oxides and salts.

The present invention provides compounds of the general formula (I)

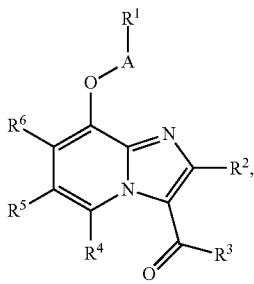

in which
A represents $CH_2$, $CD_2$ or $CH(CH_3)$,
$R^1$ represents $(C_4-C_6)$-alkyl, $(C_3-C_7)$-cycloalkyl or phenyl,
  where $(C_4-C_6)$-alkyl may be substituted up to six times by fluorine,
  where $(C_3-C_7)$-cycloalkyl may be substituted by 1 to 4 substituents independently of one another selected from the group consisting of fluorine, trifluoromethyl and $(C_1-C_4)$-alkyl,
  and
  where phenyl may be substituted by 1 to 4 substituents independently of one another selected from the group consisting of halogen, cyano, monofluoromethyl, difluoromethyl, trifluoromethyl, $(C_1-C_4)$-alkyl, $(C_1-C_4)$-alkoxy, difluoromethoxy and trifluoromethoxy,
$R^2$ represents hydrogen, $(C_1-C_4)$-alkyl, cyclopropyl, monofluoromethyl, difluoromethyl or trifluoromethyl,
$R^3$ represents a group of the formula

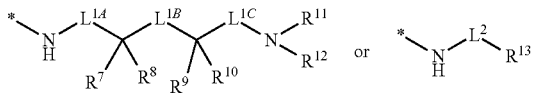

where
* represents the point of attachment to the carbonyl group,
$L^{1A}$ represents a bond or $(C_1-C_4)$-alkanediyl,
  where $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy,
$L^{1B}$ represents a bond or $(C_1-C_4)$-alkanediyl,
$L^{1C}$ represents a bond or $(C_1-C_4)$-alkanediyl,
  where $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy,
$R^7$ represents hydrogen, $(C_1-C_6)$-alkyl, $(C_2-C_6)$-alkenyl, $(C_2-C_6)$-alkynyl, $(C_3-C_7)$-cycloalkyl, cyano, 5- to 10-membered heteroaryl, naphthyl or phenyl,
  where $(C_1-C_6)$-alkyl may be substituted by 1 to 3 substituents independently of one another selected from the group consisting of fluorine, difluoromethyl, trifluoromethyl, difluoromethoxy, trifluoromethoxy, hydroxy, $(C_1-C_4)$-alkoxy, $(C_1-C_4)$-alkoxycarbonyl, $(C_1-C_4)$-alkylsulphonyl, phenyl, phenoxy and benzyloxy,
    where phenyl, phenoxy and benzyloxy for their part may be substituted by 1 to 3 halogen or $(C_1-C_4)$-alkoxy substituents,
  where $(C_3-C_7)$-cycloalkyl may be substituted by 1 or 2 substituents independently of one another selected from the group consisting of fluorine, trifluoromethyl, $(C_1-C_4)$-alkyl and $(C_1-C_4)$-alkoxy,
  and
  where phenyl and 5- to 10-membered heteroaryl may be substituted by 1 to 3 substituents independently of one another selected from the group consisting of halogen, cyano, nitro, difluoromethyl, trifluoromethyl, difluoromethoxy, trifluoromethoxy, —NH(CO)$CH_3$, $(C_1-C_4)$-alkyl, $(C_1-C_4)$-cycloalkyl, $(C_1-C_4)$-alkenyl, $(C_1-C_4)$-alkylsulphonyl, $(C_1-C_4)$-alkoxycarbonyl and $(C_1-C_4)$-alkoxy,
    where $(C_1-C_4)$-alkoxy may be substituted by hydroxy,
    and
    in which 2 adjacent carbon atoms of the phenyl may be substituted by a difluoromethylenedioxy bridge,
$R^8$ represents hydrogen or $(C_1-C_4)$-alkyl,
or
$R^7$ and $R^8$ together with the carbon atom to which they are attached form a 3- to 7-membered carbocycle or a 4- to 7-membered heterocycle,
  where the 3- to 7-membered carbocycle and the 4- to 7-membered heterocycle for their part may be substituted by 1 or 2 substituents independently of one another selected from the group consisting of fluorine and $(C_1-C_4)$-alkyl,
$R^9$ represents hydrogen, $(C_1-C_6)$-alkyl, $(C_2-C_6)$-alkenyl, $(C_2-C_6)$-alkynyl, $(C_3-C_7)$-cycloalkyl, 5- to 10-membered heteroaryl or phenyl,
  where $(C_1-C_6)$-alkyl may be substituted by 1 to 3 substituents independently of one another selected from the group consisting of fluorine, trifluoromethyl, difluoromethoxy, trifluoromethoxy, hydroxy, $(C_1-C_4)$-alkoxy, $(C_1-C_4)$-alkoxycarbonyl, $(C_1-C_4)$-alkylsulphonyl, 5- or 6-membered heteroaryl, phenyl, phenoxy and benzyloxy,
    where phenyl, phenoxy and benzyloxy for their part may be substituted by 1 to 3 halogen or $(C_1-C_4)$-alkoxy substituents,
    where 5- or 6-membered heteroaryl may be benzofused or substituted by a 5- or 6-membered heteroaryl,
      where 5- or 6-membered heteroaryl may be substituted by $(C_1-C_4)$-alkyl or trifluoromethyl,
  where $(C_3-C_7)$-cycloalkyl may be substituted by 1 or 2 substituents independently of one another selected from the group consisting of fluorine, trifluoromethyl, $(C_1-C_4)$-alkyl and $(C_1-C_4)$-alkoxy,
  and
  where phenyl and 5- to 10-membered heteroaryl may be substituted by 1 to 3 substituents independently of one another selected from the group consisting of halogen, cyano, difluoromethyl, trifluoromethyl, difluoromethoxy, trifluoromethoxy, $(C_1-C_4)$-alkyl, $(C_1-C_4)$-cycloalkyl, $(C_1-C_4)$-alkoxy, $(C_1-C_4)$-alkoxycarbonyl and $(C_1-C_4)$-alkylsulphonyl,
    where $(C_1-C_4)$-alkoxy may be substituted by hydroxy,
    and
    where the phenyl may be substituted on two adjacent carbon atoms by a difluoromethylenedioxy bridge, $R^{10}$ represents hydrogen or $(C_1-C_4)$-alkyl,
or
$R^9$ and $R^{10}$ together with the carbon atom to which they are attached form a 3- to 7-membered carbocycle or a 4- to 7-membered heterocycle,
  where the 3- to 7-membered carbocycle and the 4- to 7-membered heterocycle for their part may be substituted by 1 or 2 substituents independently of one another selected from the group consisting of fluorine, benzyl and $(C_1-C_4)$-alkyl,
with the proviso that the radicals $R^7$ and $R^9$ do not both simultaneously represent phenyl,
or
$R^7$ and $R^9$ together with the carbon atoms to which they are attached and the group $L^{1B}$ form a 3- to 7-membered carbocycle or a 4- to 7-membered heterocycle,
  where the 3- to 7-membered carbocycle may be substituted by 1 or 2 substituents independently of one another selected from the group consisting of $(C_1-C_4)$-alkyl, fluorine, hydroxy and $(C_1-C_4)$-alkoxy,
with the proviso that not more than one of the radical pairs $R^7$ and $R^8$, $R^9$ and $R^{10}$ and $R^7$ and $R^9$, respectively, simultaneously forms a carbo- or heterocycle,
$R^{11}$ represents hydrogen or $(C_1-C_4)$-alkyl,
  where $(C_1-C_4)$-alkyl may be substituted by 1 to 3 substituents independently of one another selected from the group consisting of fluorine, trifluoromethyl, hydroxy and $(C_1-C_4)$-alkoxy,
$R^{12}$ represents hydrogen, $(C_1-C_6)$-alkyl, $(C_3-C_7)$-cycloalkyl, phenyl or benzyl,
  where $(C_1-C_6)$-alkyl may be substituted by 1 to 3 substituents independently of one another selected from the group consisting of fluorine, trifluoromethyl, hydroxy, $(C_1-C_4)$-alkoxy and phenoxy, and
  where phenyl and benzyl may be substituted by 1 to 3 substituents independently of one another selected from the group consisting of halogen and trifluoromethyl,
or
$R^{11}$ and $R^{12}$ together with the nitrogen atom to which they are attached form a 4- to 7-membered azaheterocycle,
  where the 4- to 7-membered azaheterocycle may be substituted by 1 or 2 substituents independently of one another selected from the group consisting of fluorine, trifluoromethyl, $(C_1-C_4)$-alkyl, $(C_3-C_7)$-cycloalkyl, hydroxy, $(C_1-C_4)$-alkoxy and 4- to 7-membered heterocyclyl,
and
$L^2$ represents a bond or $(C_1-C_4)$-alkanediyl,
$R^{13}$ represents 5- to 9-membered azaheterocyclyl which is attached via a ring carbon atom,
  where 5- to 9-membered azaheterocyclyl may be substituted by 1 to 5 substituents independently of one another selected from the group consisting of fluorine, trifluoromethyl, $(C_1-C_4)$-alkyl, $(C_3-C_7)$-cycloalkyl and benzyl,
  and
  where 5- to 9-membered azaheterocyclyl may be fused to a phenyl ring which for its part may be substituted by 1 or 2 substituents selected from the group consisting of halogen, $(C_1-C_4)$-alkyl, $(C_1-C_4)$-alkoxy and trifluoromethyl,
or
represents adamantyl,
$R^4$ represents hydrogen,
$R^5$ represents hydrogen, halogen, cyano, monofluoromethyl, difluoromethyl, trifluoromethyl, $(C_1-C_4)$-alkyl, $(C_3-C_7)$-cycloalkyl, $(C_2-C_4)$-alkynyl, difluoromethoxy, trifluoromethoxy, $(C_1-C_4)$-alkoxy, amino, 4- to 7-membered heterocyclyl or 5- or 6-membered heteroaryl,
$R^6$ represents hydrogen, cyano or halogen,
and its N-oxides, salts, solvates, salts of the N-oxides and solvates of the N-oxides and salts.

Compounds according to the invention are the compounds of the formula (I) and their salts, solvates and solvates of the salts, the compounds included in the formula (I) of the formulae mentioned in the following and their salts, solvates and solvates of the salts, and the compounds included in the formula (I) and mentioned in the following as embodiment examples and their salts, solvates and solvates of the salts, where the compounds included in the formula (I) and mentioned in the following are not already salts, solvates and solvates of the salts.

Preferred salts in the context of the present invention are physiologically acceptable salts of the compounds according to the invention. Salts which are not themselves suitable for pharmaceutical uses but can be used, for example, for isolation or purification of the compounds according to the invention are also included.

Physiologically acceptable salts of the compounds according to the invention include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid, and benzoic acid.

Physiologically acceptable salts of the compounds according to the invention also include salts of conventional bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanol-amine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are designated as those forms of the compounds according to the invention which form a complex in the solid or liquid state by coordination with solvent molecules. Hydrates are a specific form of solvates, in which the coordination takes place with water. Hydrates are preferred solvates in the context of the present invention.

The compounds according to the invention can exist in different stereoisomeric forms depending on their structure, i.e. in the form of configuration isomers or optionally also as conformation isomers (enantiomers and/or diastereomers, including those in the case of atropisomers). The present invention therefore includes the enantiomers and diastereomers and their particular mixtures. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention can occur in tautomeric forms, the present invention includes all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^{2}$H (deuterium), $^{3}$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^{3}$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by processes known to those skilled in the art, for example by the methods described below and the methods described in the working examples, by using corresponding isotopic modifications of the particular reagents and/or starting compounds therein.

The present invention moreover also includes prodrugs of the compounds according to the invention. The term "prodrugs" here designates compounds which themselves can be biologically active or inactive, but are converted (for example metabolically or hydrolytically) into compounds according to the invention during their dwell time in the body.

In the context of the present invention, the substituents have the following meaning, unless specified otherwise:

Alkyl in the context of the invention represents a straight-chain or branched alkyl radical having the number of carbon atoms stated in each case. The following may be mentioned by way of example and by way of preference: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl, 2-ethylbutyl.

Cycloalkyl or carbocycle in the context of the invention represents a monocyclic saturated alkyl radical having the number of ring carbon atoms stated in each case. The following may be mentioned by way of example and by way of preference: cyclopropyl, cyclobutyl, cyclopentyl, cyclohexyl and cycloheptyl.

Alkenyl in the context of the invention represents a straight-chain or branched alkenyl radical having 2 to 6 carbon atoms and one or two double bonds. Preference is given to a straight-chain or branched alkenyl radical having 2 to 4 carbon atoms and one double bond. The following may be mentioned by way of example and by way of preference: vinyl, allyl, isopropenyl and n-but-2-en-1-yl.

Alkynyl in the context of the invention represents a straight-chain or branched alkynyl radical having 2 to 6 carbon atoms and one triple bond. The following may be mentioned by way of example and by way of preference: ethynyl, n-prop-1-yn-1-yl, n-prop-2-yn-1-yl, n-but-2-yn-1-yl and n-but-3-yn-1-yl.

Alkanediyl in the context of the invention represents a straight-chain or branched divalent alkyl radical having 1 to 4 carbon atoms. The following may be mentioned by way of example and by way of preference: methylene, 1,2-ethylene, ethane-1,1-diyl, 1,3-propylene, propane-1,1-diyl, propane-1,2-diyl, propane-2,2-diyl, 1,4-butylene, butane-1,2-diyl, butane-1,3-diyl and butane-2,3-diyl.

Alkoxy in the context of the invention represents a straight-chain or branched alkoxy radical having 1 to 4 carbon atoms. The following may be mentioned by way of example and by way of preference: methoxy, ethoxy, n-propoxy, isopropoxy, 1-methylpropoxy, n-butoxy, isobutoxy and tert-butoxy.

Alkoxycarbonyl in the context of the invention represents a straight-chain or branched alkoxy radical having 1 to 4 carbon atoms and a carbonyl group attached at the oxygen atom. The following may be mentioned by way of example and by way of preference: methoxycarbonyl, ethoxycarbonyl, n-propoxycarbonyl, isopropoxycarbonyl and tert-butoxycarbonyl.

Alkylsulphonyl in the context of the invention represents a straight-chain or branched alkyl radical which has 1 to 4 carbon atoms and is attached via a sulphonyl group. The following may be mentioned by way of example and by way of preference: methylsulphonyl, ethylsulphonyl, n-propylsulphonyl, isopropylsulphonyl, n-butylsulphonyl and tert-butylsulphonyl.

A 4- to 7-membered heterocycle in the context of the invention represents a monocyclic saturated heterocycle which has a total of 4 to 7 ring atoms, which contains one or two ring heteroatoms from the group consisting of N, O, S, SO and SO$_2$ and which is attached via a ring carbon atom or, if appropriate, a ring nitrogen atom. The following may be mentioned by way of example: azetidinyl, oxetanyl, pyrrolidinyl, pyrazolidinyl, tetrahydrofuranyl, thiolanyl, piperidinyl, piperazinyl, tetrahydropyranyl, tetrahydrothiopyranyl, morpholinyl, thiomorpholinyl, hexahydroazepinyl and hexahydro-1,4-diazepinyl. Preference is given to azetidinyl, oxetanyl, pyrrolidinyl, tetrahydrofuranyl, piperidinyl, piperazinyl, tetrahydropyranyl and morpholinyl.

A 4- to 7-membered azaheterocycle in the context of the invention represents a monocyclic saturated heterocycle which has a total of 4 to 7 ring atoms, which contains one nitrogen atom and which may additionally contain a further ring heteroatom from the group consisting of N, O, S, SO and SO$_2$ and is attached via a ring nitrogen atom. The following may be mentioned by way of example: azetidinyl, pyrrolidinyl, pyrazolidinyl, piperidinyl, piperazinyl, morpholinyl, thiomorpholinyl, 1,1-dioxothiomorpholinyl, hexahydroazepinyl and hexahydro-1,4-diazepinyl.

5- to 9-membered azaheterocyclyl in the context of the invention represents a monocyclic or bicyclic saturated or partially unsaturated heterocycle which has a total of 5 to 9 ring atoms, which contains a nitrogen atom and which may additionally contain one or two further ring heteroatoms from the group consisting of N, O, S, SO and SO$_2$ and is attached via a ring carbon atom. The following may be mentioned by way of example: pyrrolidinyl, pyrazolidinyl, piperidinyl, piperazinyl, morpholinyl, thiomorpholinyl, 1,1-dioxothiomorpholinyl, hexahydroazepinyl, hexahydro-1,4-diazepinyl, 1,2,3,4-tetrahydroisoquinolinyl, 1,2,3,4-tetrahydroquinolinyl, indolinyl, 8-azabicyclo[3.2.1]octanyl, 9-azabicyclo[3.3.1]nonanyl, 3-azabicyclo[4.1.0]heptanyl and quinuclidinyl.

Heteroaryl in the context of the invention represents a mono- or optionally bicyclic aromatic heterocycle (heteroaromatic) having a total of 5 to 10 ring atoms which contains up to three identical or different ring heteroatoms from the group consisting of N, O and/or S and is attached via a ring carbon atom or optionally via a ring nitrogen atom. The following may be mentioned by way of example: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl, triazinyl, benzofuranyl, benzothienyl, benzimidazolyl, benzoxazolyl, benzothiazolyl, benzotriazolyl, indolyl, indazolyl, quinolinyl, isoquinolinyl, naphthyridinyl, quinazolinyl, quinoxalinyl, phthalazinyl, pyrazolo[3,4-b]pyridinyl. Heteroaryl in the context of the invention preferably represents a monocyclic aromatic heterocycle (heteroaromatic) which has a total of 5 or 6 ring atoms, which contains up to three identical or different ring heteroatoms from the group consisting of N, O and S and is attached via a ring carbon atom or, if appropriate, a ring nitrogen atom. The following may be mentioned by way of example and by way of preference: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl and triazinyl.

Halogen in the context of the invention includes fluorine, chlorine, bromine and iodine. Preference is given to chlorine or fluorine.

In the formula of the group which may represent $R^3$ or $R^1$, the end point of the line marked by a * or # label does not represent a carbon atom or a $CH_2$ group but forms part of the bond to the atom which is designated in each case and to which $R^3$ and $R^1$, respectively, are attached.

If radicals in the compounds according to the invention are substituted, the radicals may, unless specified otherwise, be mono- or polysubstituted. In the context of the present invention, all radicals which occur more than once are defined independently of one another. Substitution by one, two or three identical or different substituents is preferred.

In the context of the present invention, the term "treatment" or "treat" includes the inhibition, delay, arrest, amelioration, attenuation, limitation, reduction, suppression, reversal or cure of a disease, a condition, a disorder, an injury and a health impairment, of the development, course or the progression of such states and/or the symptoms of such states. Here, the term "therapy" is understood to be synonymous with the term "treatment".

In the context of the present invention, the terms "prevention", "prophylaxis" or "precaution" are used synonymously and refer to the avoidance or reduction of the risk to get, to contract, to suffer from or to have a disease, a condition, a disorder, an injury or a health impairment, a development or a progression of such states and/or the symptoms of such states.

The treatment or the prevention of a disease, a condition, a disorder, an injury or a health impairment may take place partially or completely.

In the context of the present invention, preference is given to compounds of the formula (I) in which A represents $CH_2$, $CD_2$ or $CH(CH_3)$, $R^1$ represents $(C_4-C_6)$-alkyl, $(C_4-C_6)$-cycloalkyl or phenyl,
where $(C_4-C_6)$-alkyl may be substituted up to six times by fluorine,
where $(C_4-C_6)$-cycloalkyl may be substituted by 1 or 2 substituents independently of one another selected from the group consisting of fluorine, trifluoromethyl and methyl, and
where phenyl may be substituted by 1 to 4 substituents independently of one another selected from the group consisting of fluorine, chlorine, cyano, methoxy, difluoromethyl, trifluoromethyl and methyl, $R^2$ represents hydrogen, trifluoromethyl, $(C_1-C_4)$-alkyl or cyclopropyl, $R^3$ represents a group of the formula

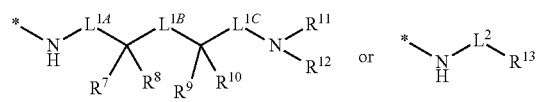

where
* represents the point of attachment to the carbonyl group,
$L^{1A}$ represents a bond,
$L^{1B}$ represents a bond, methylene or 1,2-ethanediyl,
$L^{1C}$ represents a bond or methylene,
where methylene may be substituted by 1 or 2 substituents independently of one another selected from the group consisting of trifluoromethyl, $(C_1-C_4)$-alkyl, cyclopropyl and cyclobutyl, $R^7$ represents hydrogen, trifluoromethyl, $(C_1-C_6)$-alkyl, $(C_3-C_6)$-cycloalkyl, 5- or 6-membered heteroaryl or phenyl,
where $(C_1-C_6)$-alkyl may be substituted by 1 or 2 substituents independently of one another selected from the group consisting of fluorine, trifluoromethyl, difluoromethoxy, trifluoromethoxy, hydroxy, $(C_1-C_4)$-alkoxy, phenyl, phenoxy and benzyloxy,
where phenyl, phenoxy and benzyloxy for their part may be substituted by 1 or 2 substituents selected from the group consisting of fluorine and chlorine,
where $(C_3-C_6)$-cycloalkyl may be substituted by 1 or 2 substituents independently of one another selected from the group consisting of fluorine, trifluoromethyl, methyl and ethyl,
and
where phenyl and 5- or 6-membered heteroaryl may be substituted by 1 or 2 substituents independently of one another selected from the group consisting of fluorine, chlorine, cyano, methyl and trifluoromethyl, $R^8$ represents hydrogen, methyl or ethyl,
or
$R^7$ and $R^8$ together with the carbon atom to which they are attached form a 3- to 6-membered carbocycle or an oxetanyl, tetrahydrofuranyl, tetrahydropyranyl, azetidinyl, pyrrolidinyl or piperidinyl ring,
where the 3- to 6-membered carbocycle and the oxetanyl, tetrahydrofuranyl, tetrahydropyranyl, azetidinyl, pyrrolidinyl or piperidinyl ring may be substituted by 1 or 2 substituents independently of one another selected from the group consisting of fluorine and methyl, $R^9$ represents hydrogen, 1,1,2,2-tetrafluoroethyl, trifluoromethyl, $(C_1-C_6)$-alkyl, $(C_3-C_6)$-cycloalkyl, 5- or 6-membered heteroaryl or phenyl,
where $(C_1-C_6)$-alkyl may be substituted by 1 or 2 substituents independently of one another selected from the group consisting of fluorine, trifluoromethyl, difluoromethoxy, trifluoromethoxy, hydroxy, $(C_1-C_4)$-alkoxy, phenyl, phenoxy and benzyloxy, where phenyl, phenoxy and benzyloxy for their part may be substituted by 1 or 2 substituents selected from the group consisting of fluorine and chlorine,
where $(C_3-C_6)$-cycloalkyl may be substituted by 1 or 2 substituents independently of one another selected from the group consisting of fluorine, trifluoromethyl, methyl and ethyl,
and
where phenyl and 5- or 6-membered heteroaryl may be substituted by 1 or 2 substituents independently of one another selected from the group consisting of fluorine, chlorine, cyano, methyl and trifluoromethyl,
$R^{10}$ represents hydrogen, methyl or ethyl,
or
$R^9$ and $R^{10}$ together with the carbon atom to which they are attached form a 3- to 6-membered carbocycle or an oxetanyl, tetrahydrofuranyl, tetrahydropyranyl, azetidinyl, pyrrolidinyl or piperidinyl ring,
where the 3- to 6-membered carbocycle and the oxetanyl, tetrahydrofuranyl, tetrahydropyranyl, azetidinyl, pyrrolidinyl or piperidinyl ring may be substituted by 1 or 2 substituents independently of one another selected from the group consisting of fluorine and methyl,
with the proviso that the radicals $R^7$ and $R^9$ do not both simultaneously represent phenyl,
or
$R^7$ and $R^9$ together with the carbon atoms to which they are attached and with the group $L^{1B}$ form a cyclopentyl, cyclohexyl, azetidinyl, oxetanyl, pyrrolidinyl, tetrahydrofuranyl, piperidinyl or tetrahydropyranyl ring,
with the proviso that not more than one of the radical pairs $R^7$ and $R^8$, $R^9$ and $R^{10}$ and $R^7$ and $R^9$, respectively, simultaneously forms one of the carbo- or heterocycles mentioned above,
$R^{11}$ represents hydrogen or $(C_1-C_3)$-alkyl,
where $(C_1-C_3)$-alkyl may be substituted by 1 or 2 substituents independently of one another selected from the group consisting of fluorine, trifluoromethyl, hydroxy, methoxy and ethoxy,
$R^{12}$ represents hydrogen, $(C_1-C_4)$-alkyl, cyclopropyl, cyclobutyl, phenyl or benzyl, where $(C_1-C_4)$-alkyl may be substituted by 1 or 2 substituents independently of one another selected from the group consisting of fluorine, trifluoromethyl, hydroxy, $(C_1-C_4)$-alkoxy and phenoxy,
and
where phenyl and benzyl may be substituted by 1 to 3 substituents independently of one another selected from the group consisting of fluorine, chlorine and trifluoromethyl,
or
$R^{11}$ and $R^{12}$ together with the nitrogen atom to which they are attached form an azetidinyl, pyrrolidinyl, piperidinyl, morpholinyl, piperazinyl, thiomorpholinyl or 1,1-dioxothiomorpholinyl ring,
where the azetidinyl, pyrrolidinyl, piperidinyl, morpholinyl, piperazinyl, thiomorpholinyl and 1,1-dioxothiomorpholinyl ring may be substituted by 1 or 2 substituents independently of one another selected from the group consisting of fluorine, trifluoromethyl, methyl, ethyl, cyclopropyl, cyclobutyl, azetidinyl, pyrrolidinyl and piperidinyl,
and
$L^2$ represents a bond, methylene or 1,1-ethanediyl,
$R^{13}$ represents pyrrolidinyl, piperidinyl, 1,2,3,4-tetrahydroisoquinolinyl, 1,2,3,4-tetrahydroquinolinyl, indolinyl, 8-azabicyclo[3.2.1]octanyl, 9-azabicyclo[3.3.1]nonanyl, 3-azabicyclo-[4.1.0]heptanyl and quinuclidinyl attached via a ring carbon atom,
where pyrrolidinyl, piperidinyl, 1,2,3,4-tetrahydroisoquinolinyl, 1,2,3,4-tetrahydroquinolinyl, indolinyl, 8-azabicyclo[3.2.1]octanyl, 9-azabicyclo[3.3.1]nonanyl, 3-azabicyclo[4.1.0]heptanyl and quinuclidinyl may be substituted by 1 to 5 substituents independently of one another selected from the group consisting of fluorine, trifluoromethyl, methyl, ethyl, cyclopropyl, cyclobutyl and benzyl,
$R^4$ represents hydrogen,
$R^5$ represents hydrogen, fluorine, chlorine, bromine, cyano, methyl, ethyl or cyclopropyl,
$R^6$ represents hydrogen or fluorine,
and to N-oxides, salts, solvates, salts of the N-oxides and solvates of the N-oxides and salts thereof.

In the context of the present invention, preference is given to compounds of the formula (I) in which
A represents $CH_2$,
$R^1$ represents $(C_4-C_6)$-alkyl, $(C_4-C_6)$-cycloalkyl or phenyl,
where $(C_4-C_6)$-alkyl may be substituted up to six times by fluorine, where $(C_4-C_6)$-cycloalkyl may be substituted by 1 or 2 substituents independently of one another selected from the group consisting of fluorine, trifluoromethyl and methyl,
and
where phenyl may be substituted by 1 to 4 substituents independently of one another selected from the group consisting of fluorine, chlorine, difluoromethyl, trifluoromethyl and methyl,
$R^2$ represents $(C_1-C_3)$-alkyl, trifluoromethyl or cyclopropyl,
$R^3$ represents a group of the formula

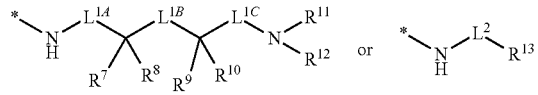

where
* represents the point of attachment to the carbonyl group,
$L^{1A}$ represents a bond,
$L^{1B}$ represents a bond or methylene,
$L^{1C}$ represents a bond or methylene,
where methylene may be substituted by 1 or 2 substituents independently of one another selected from the group consisting of trifluoromethyl, $(C_1-C_4)$-alkyl, cyclopropyl and cyclobutyl,
$R^7$ represents hydrogen, trifluoromethyl, $(C_1-C_6)$-alkyl, $(C_3-C_6)$-cycloalkyl or phenyl,
where $(C_1-C_6)$-alkyl may be substituted by 1 or 2 substituents independently of one another selected from the group consisting of fluorine, trifluoromethyl, hydroxy, $(C_1-C_4)$-alkoxy, phenyl, phenoxy and benzyloxy,
where phenyl, phenoxy and benzyloxy for their part may be substituted by 1 or 2 substituents selected from the group consisting of fluorine and chlorine,
where $(C_3-C_6)$-cycloalkyl may be substituted by 1 or 2 substituents independently of one another selected from the group consisting of fluorine, trifluoromethyl, methyl and ethyl, and
where phenyl may be substituted by 1 or 2 substituents independently of one another selected from the group consisting of fluorine, chlorine, cyano and trifluoromethyl, $R^8$ represents hydrogen, methyl or ethyl, or $R^7$ and $R^8$ together with the carbon atom to which they are attached form a 3- to 6-membered carbocycle or an oxetanyl, tetrahydrofuranyl, tetrahydropyranyl, azetidinyl, pyrrolidinyl or piperidinyl ring,
where the 3- to 6-membered carbocycle and the oxetanyl, tetrahydrofuranyl, tetrahydropyranyl, azetidinyl, pyrrolidinyl or piperidinyl ring may be substituted by 1 or 2 substituents independently of one another selected from the group consisting of fluorine and methyl, $R^9$ represents hydrogen, trifluoromethyl, $(C_1-C_6)$-alkyl, $(C_3-C_6)$-cycloalkyl or phenyl,
where $(C_1-C_6)$-alkyl may be substituted by 1 or 2 substituents independently of one another selected from the group consisting of fluorine, trifluoromethyl, hydroxy, $(C_1-C_4)$-alkoxy, phenyl, phenoxy and benzyloxy,
where phenyl, phenoxy and benzyloxy for their part may be substituted by 1 or 2 substituents selected from the group consisting of fluorine and chlorine,
where $(C_3-C_6)$-cycloalkyl may be substituted by 1 or 2 substituents independently of one another selected from the group consisting of fluorine, trifluoromethyl, methyl and ethyl,
and
where phenyl may be substituted by 1 or 2 substituents independently of one another selected from the group consisting of fluorine, chlorine, cyano and trifluoromethyl, $R^{10}$ represents hydrogen, methyl or ethyl, or $R^9$ and $R^{10}$ together with the carbon atom to which they are attached form a 3- to 6-membered carbocycle or an oxetanyl, tetrahydrofuranyl, tetrahydropyranyl, azetidinyl, pyrrolidinyl or piperidinyl ring,
where the 3- to 6-membered carbocycle and the oxetanyl, tetrahydrofuranyl, tetrahydropyranyl, azetidinyl, pyrrolidinyl or piperidinyl ring may be substituted by 1 or 2 substituents independently of one another selected from the group consisting of fluorine and methyl, with the proviso that the radicals $R^7$ and $R^9$ do not both simultaneously represent phenyl, or $R^7$ and $R^9$ together with the carbon atoms to which they are attached and with the group $L^{1B}$ form a cyclopentyl, cyclohexyl, azetidinyl, oxetanyl, pyrrolidinyl, tetrahydrofuranyl, piperidinyl or tetrahydropyranyl ring, with the proviso that not more than one of the radical pairs $R^7$ and $R^8$, $R^9$ and $R^{10}$ and $R^7$ and $R^9$, respectively, simultaneously forms one of the carbo- or heterocycles mentioned above, $R^{11}$ represents hydrogen or $(C_1-C_3)$-alkyl,
where $(C_1-C_3)$-alkyl may be substituted by 1 or 2 substituents independently of one another selected from the group consisting of fluorine and trifluoromethyl, $R^{12}$ represents hydrogen, $(C_1-C_4)$-alkyl, cyclopropyl or cyclobutyl, where $(C_1-C_4)$-alkyl may be substituted by 1 or 2 substituents independently of one another selected from the group consisting of fluorine and trifluoromethyl, or $R^{11}$ and $R^{12}$ together with the nitrogen atom to which they are attached form an azetidinyl, pyrrolidinyl, piperidinyl or morpholinyl ring,
where the azetidinyl, pyrrolidinyl, piperidinyl and morpholinyl ring may be substituted by 1 or 2 substituents independently of one another selected from the group consisting of fluorine, trifluoromethyl, methyl, ethyl, cyclopropyl and cyclobutyl, and $L^2$ represents a bond or methylene, $R^{13}$ represents pyrrolidinyl, piperidinyl, 1,2,3,4-tetrahydroisoquinolinyl, 1,2,3,4-tetrahydroquinolinyl, indolinyl, 8-azabicyclo[3.2.1]octanyl, 9-azabicyclo[3.3.1]nonanyl, 3-aza-bicyclo[4.1.0]heptanyl and quinuclidinyl attached via a ring carbon atom, or where pyrrolidinyl, piperidinyl, 1,2,3,4-tetrahydroisoquinolinyl, 1,2,3,4-tetrahydroquinolinyl, 8-azabicyclo[3.2.1]octanyl, 9-azabicyclo[3.3.1]nonanyl, 3-azabicyclo[4.1.0]heptanyl and quinuclidinyl may be substituted by 1 to 5 substituents independently of one another selected from the group consisting of fluorine, trifluoromethyl, methyl, ethyl, cyclopropyl, cyclobutyl and benzyl, $R^4$ represents hydrogen, $R^5$ represents hydrogen, fluorine, chlorine, methyl, ethyl or cyclopropyl, $R^6$ represents hydrogen, and to N-oxides, salts, solvates, salts of the N-oxides and solvates of the N-oxides and salts thereof.

In the context of the present invention, particular preference is given to compounds of the formula (I) in which A represents $CH_2$, $R^1$ represents a phenyl group of the formula

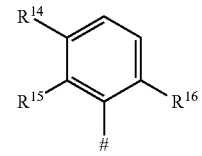

where # represents the point of attachment to A, and $R^{14}$, $R^{15}$ and $R^{16}$ independently of one another represent hydrogen, fluorine or chlorine, with the proviso that at least two of the radicals $R^{14}$, $R^{15}$, $R^{16}$ are different from hydrogen, $R^2$ represents methyl, $R^3$ represents a group of the formula

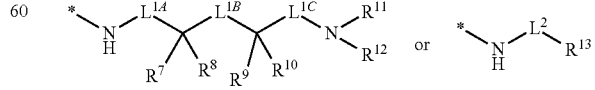

where

* represents the point of attachment to the carbonyl group, $L^{1A}$ represents a bond, $L^{1B}$ represents a bond,
$L^{1C}$ represents a bond,
$R^7$ represents hydrogen, trifluoromethyl, $(C_1-C_6)$-alkyl, $(C_3-C_6)$-cycloalkyl or phenyl,
  where $(C_1-C_6)$-alkyl may be substituted by 1 or 2 substituents independently of one another selected from the group consisting of fluorine, trifluoromethyl, hydroxy, $(C_1-C_4)$-alkoxy and phenyl,
  and
  where phenyl may be substituted by 1 or 2 substituents independently of one another selected from the group consisting of fluorine and chlorine,
$R^8$ represents hydrogen, methyl or ethyl,
$R^9$ represents hydrogen, trifluoromethyl, $(C_1-C_6)$-alkyl, cyclopropyl or phenyl,
  where $(C_1-C_6)$-alkyl may be substituted by 1 or 2 substituents independently of one another selected from the group consisting of fluorine, trifluoromethyl, hydroxy, $(C_1-C_4)$-alkoxy and phenyl,
  and
  where phenyl may be substituted by 1 or 2 substituents independently of one another selected from the group consisting of fluorine and chlorine,
$R^{10}$ represents hydrogen, methyl or ethyl,
or
$R^9$ and $R^{10}$ together with the carbon atom to which they are attached form a 3- to 6-membered carbocycle or an oxetanyl ring,
with the proviso that the radicals $R^7$ and $R^9$ do not both simultaneously represent phenyl,
or
$R^7$ and $R^9$ together with the carbon atoms to which they are attached and the group $L^{1B}$ form a cyclopentyl or cyclohexyl ring,
with the proviso that not more than one of the radical pairs $R^9$ and $R^{10}$ and $R^7$ and $R^9$, respectively, simultaneously forms one of the carbo- or heterocycles mentioned above,
$R^{11}$ represents hydrogen,
$R^{12}$ represents hydrogen,
and
$L^2$ represents a bond,
$R^{13}$ represents piperidin-2-yl, piperidin-3-yl, piperidin-4-yl or 1,2,3,4-tetrahydroquinolin-4-yl,
  where piperidin-2-yl, piperidin-3-yl and piperidin-4-yl may be substituted by 1 to 5 substituents independently of one another selected from trifluoromethyl and methyl,
  and
  where 1,2,3,4-tetrahydroquinolin-4-yl may be substituted by fluorine or trifluoromethyl,
$R^4$ represents hydrogen,
$R^5$ represents hydrogen, fluorine, chlorine or methyl,
$R^6$ represents hydrogen,
and to N-oxides, salts, solvates, salts of the N-oxides and solvates of the N-oxides and salts thereof.

In the context of the present invention, preference is given to compounds of the formula (I) in which
  A represents $CH_2$, $CD_2$ or $CH(CH_3)$,
  $R^1$ represents phenyl,
    where phenyl may be substituted by 1 to 3 substituents independently of one another selected from the group consisting of halogen, cyano, monofluoromethyl, difluoromethyl, trifluoromethyl, $(C_1-C_4)$-alkyl,
    and
    where phenyl is substituted by 1 to 2 substituents selected from the group consisting of $(C_3-C_6)$-cycloalkyl, $(C_1-C_4)$-alkoxy, difluoromethoxy and trifluoromethoxy,
  $R^2$ represents hydrogen, $(C_1-C_4)$-alkyl, cyclopropyl, monofluoromethyl, difluoromethyl or trifluoromethyl,
  $R^3$ represents a group of the formula where
* represents the point of attachment to the carbonyl group,
$L^{1A}$ represents a bond or $(C_1-C_4)$-alkanediyl,
  where $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy,
$L^{1B}$ represents a bond or $(C_1-C_4)$-alkanediyl,
$L^{1C}$ represents a bond or $(C_1-C_4)$-alkanediyl,
  where $(C_1-C_4)$-alkanediyl may be substituted by 1 to 3 substituents independently of one another selected from the group consisting of fluorine, trifluoromethyl $(C_1-C_4)$-alkyl, $(C_3-C_7)$-cycloalkyl, hydroxy and $(C_1-C_4)$-alkoxy,
$R^7$ represents hydrogen, $(C_1-C_6)$-alkyl, $(C_2-C_6)$-alkenyl, $(C_2-C_6)$-alkynyl, $(C_3-C_7)$-cycloalkyl, cyano, 5- or 10-membered heteroaryl, naphthyl or phenyl,
  where $(C_1-C_6)$-alkyl may be substituted by 1 to 3 substituents independently of one another selected from the group consisting of fluorine, trifluoromethyl, difluoromethoxy, trifluoromethoxy, hydroxy, $(C_1-C_4)$-alkoxy, $(C_1-C_4)$-sulphanyl, $(C_1-C_4)$-alkoxycarbonyl, $(C_1-C_4)$-alkylsulphonyl, phenyl, phenoxy and benzyloxy,
    where phenyl, phenoxy and benzyloxy for their part may be substituted by 1 to 3 halogen or $(C_1-C_4)$-alkoxy substituents,
  where $(C_3-C_7)$-cycloalkyl may be substituted by 1 or 2 substituents independently of one another selected from the group consisting of fluorine, trifluoromethyl, $(C_1-C_4)$-alkyl and $(C_1-C_4)$-alkoxy,
  and
  where phenyl and 5- to 10-membered heteroaryl may be substituted by 1 to 3 substituents independently of one another selected from the group consisting of halogen, cyano, nitro, difluoromethyl, trifluoromethyl, difluoromethoxy, trifluoromethoxy, —NH(CO)CH$_3$, $(C_1-C_4)$-alkyl, $(C_1-C_4)$-cycloalkyl, $(C_1-C_4)$-alkenyl, $(C_1-C_4)$-alkylsulphonyl, $(C_1-C_4)$-alkoxycarbonyl and $(C_1-C_4)$-alkoxy,
    where $(C_1-C_4)$-alkoxy may be substituted by hydroxy,
    and
    where the phenyl may be substituted on 2 adjacent carbon atoms by a difluoromethylenedioxy bridge,
$R^8$ represents hydrogen or $(C_1-C_4)$-alkyl,
or
$R^7$ and $R^8$ together with the carbon atom to which they are attached form a 3- to 7-membered carbocycle or a 4- to 7-membered heterocycle, where the 3- to 7-membered carbocycle and the 4- to 7-membered heterocycle for their part may be substituted by 1 or 2 substituents independently of one another selected from the group consisting of fluorine and $(C_1$-$C_4)$-alkyl, $R^9$ represents hydrogen, $(C_1$-$C_6)$-alkyl, $(C_2$-$C_6)$-alkenyl, $(C_2$-$C_6)$-alkynyl, $(C_3$-$C_7)$-cycloalkyl, 5- to 10-membered heteroaryl or phenyl,
  where $(C_1$-$C_6)$-alkyl may be substituted by 1 to 3 substituents independently of one another selected from the group consisting of fluorine, trifluoromethoxy, difluoromethoxy, trifluoromethoxy, hydroxy, $(C_1$-$C_4)$-alkoxy, $(C_1$-$C_4)$-alkoxycarbonyl, $(C_1$-$C_4)$-alkylsulphonyl, 5- or 6-membered heteroaryl, phenyl, phenoxy and benzyloxy,
    where phenyl, phenoxy and benzyloxy for their part may be substituted by 1 to 3 halogen or $(C_1$-$C_4)$-alkoxy substituents,
    where 5- or 6-membered heteroaryl may be benzofused or substituted by a 5- or 6-membered heteroaryl,
      where 5- or 6-membered heteroaryl may be substituted by $(C_1$-$C_4)$-alkyl or trifluoromethyl,
  where $(C_3$-$C_7)$-cycloalkyl may be substituted by 1 or 2 substituents independently of one another selected from the group consisting of fluorine, trifluoromethyl, $(C_1$-$C_4)$-alkyl and $(C_1$-$C_4)$-alkoxy,
  and
  where phenyl and 5- or 6-membered heteroaryl may be substituted by 1 to 3 substituents independently of one another selected from the group consisting of halogen, cyano, difluoromethyl, trifluoromethyl, difluoromethoxy, trifluoromethoxy, $(C_1$-$C_4)$-alkyl, $(C_1$-$C_4)$-cycloalkyl, $(C_1$-$C_4)$-alkoxy, $(C_1$-$C_4)$-alkoxycarbonyl and $(C_1$-$C_4)$-alkylsulphonyl,
    where $(C_1$-$C_4)$-alkoxy may be substituted by hydroxy,
    and
    where the phenyl may be substituted on 2 adjacent carbon atoms by a difluoromethylenedioxy bridge, $R^{10}$ represents hydrogen or $(C_1$-$C_4)$-alkyl, or $R^9$ and $R^{10}$ together with the carbon atom to which they are attached form a 3- to 7-membered carbocycle or a 4- to 7-membered heterocycle,
  where the 3- to 7-membered carbocycle and the 4- to 7-membered heterocycle for their part may be substituted by 1 or 2 substituents independently of on another selected from the group consisting of fluorine, benzyl and $(C_1$-$C_4)$-alkyl, with the proviso that the radicals $R^7$ and $R^9$ do not both simultaneously represent phenyl, or $R^7$ and $R^9$ together with the carbon atoms which they are attached and the group $L^{1B}$ form a 3- to 7-membered carbocycle or a 4- to 7-membered heterocycle,
  where the 3- to 7-membered carbocycle may be substituted by 1 or 2 substituents independently of one another selected from the group consisting of $(C_1$-$C_4)$-alkyl, fluorine, hydroxy and $(C_1$-$C_4)$-alkoxy, with the proviso that not more than one of the radical pairs $R^7$ and $R^8$, $R^9$ and $R^{10}$ and $R^7$ and $R^9$, respectively, simultaneously forms a carbo- or heterocycle, $R^{11}$ represents hydrogen or $(C_1$-$C_4)$-alkyl,
  where $(C_1$-$C_4)$-alkyl may be substituted by 1 to 3 substituents independently of one another selected from the group consisting of fluorine, trifluoromethyl, hydroxy and $(C_1$-$C_4)$-alkoxy, $R^{12}$ represents hydrogen, $(C_1$-$C_6)$-alkyl, $(C_3$-$C_7)$-cycloalkyl, phenyl or benzyl,
  where $(C_1$-$C_6)$-alkyl may be substituted by 1 to 3 substituents independently of one another selected from the group consisting of fluorine, trifluoromethyl, hydroxy, $(C_1$-$C_4)$-alkoxy and phenoxy,
  and
  where phenyl and benzyl may be substituted by 1 to 3 substituents independently of one another selected from the group consisting of halogen and trifluoromethyl, or $R^{11}$ and $R^{12}$ together with the nitrogen atom to which they are attached form a 4- to 7-membered azaheterocycle,
  where the 4- to 7-membered azaheterocycle may be substituted by 1 or 2 substituents independently of one another selected from the group consisting of fluorine, trifluoromethyl, $(C_1$-$C_4)$-alkyl, $(C_3$-$C_7)$-cycloalkyl, hydroxy, $(C_1$-$C_4)$-alkoxy and 4- to 7-membered heterocyclyl,
  and $L^2$ represents a bond or $(C_1$-$C_4)$-alkanediyl, $R^{13}$ represents 5- to 9-membered azaheterocyclyl which is attached via a ring carbon atom,
  where 5- to 9-membered azaheterocyclyl may be substituted by 1 to 5 substituents independently of one another selected from the group consisting of fluorine, trifluoromethyl, $(C_1$-$C_4)$-alkyl, $(C_3$-$C_7)$-cycloalkyl and benzyl,
  and
  where 5- to 9-membered azaheterocyclyl may be fused to a phenyl ring which for its part may be substituted by 1 or 2 substituents selected from the group consisting of halogen, $(C_1$-$C_4)$-alkyl, $(C_1$-$C_4)$-alkoxy and trifluoromethyl, or represents adamantyl, $R^4$ represents hydrogen, $R^5$ represents hydrogen, halogen, cyano, monofluoromethyl, difluoromethyl, trifluoromethyl, $(C_1$-$C_4)$-alkyl, $(C_3$-$C_7)$-cycloalkyl, $(C_2$-$C_4)$-alkynyl, difluoromethoxy, trifluoromethoxy, $(C_1$-$C_4)$-alkoxy, amino, 4- to 7-membered heterocyclyl or 5- or 6-membered heteroaryl, $R^6$ represents hydrogen, cyano or halogen, and their N-oxides, salts, solvates, salts of the N-oxides and solvates of the N-oxides and salts.

Preference in the context of the present invention is given to compounds of the formula (I) in which A represents $CH_2$ or $CH(CH_3)$, $R^1$ represents phenyl,
  where phenyl may be substituted by 1 to 2 substituents independently of one another selected from the group consisting of fluorine, chlorine, cyano, monofluoromethyl, difluoromethyl, trifluoromethyl, $(C_1$-$C_4)$-alkyl,
  and
  where phenyl is substituted by a substituent selected from the group consisting of $(C_3$-$C_6)$-cycloalkyl, $(C_1$-$C_2)$-alkoxy and trifluoromethoxy, $R^2$ represents hydrogen, trifluoromethyl, $(C_1$-$C_3)$-alkyl or cyclopropyl, $R^3$ represents a group of the formula

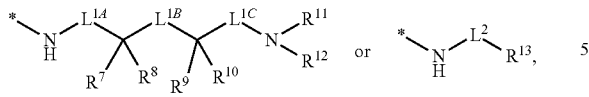

where
* represents the point of attachment to the carbonyl group,
$L^{1A}$ represents a bond,
$L^{1B}$ represents a bond, methylene or 1,2-ethanediyl,
$L^{1C}$ represents a bond or methylene,
 where methylene may be substituted by 1 or 2 substituents independently of one another selected from the group consisting of fluorine, trifluoromethyl, $(C_1-C_4)$-alkyl, cyclopropyl and cyclobutyl,
$R^7$ represents hydrogen, trifluoromethyl, $(C_1-C_6)$-alkyl, $(C_3-C_6)$-cycloalkyl, 5- or 6-membered heteroaryl or phenyl,
 where $(C_1-C_6)$-alkyl may be substituted by 1 or 2 substituents independently of one another selected from the group consisting of fluorine, trifluoromethyl, difluoromethoxy, trifluoromethoxy, hydroxy, $(C_1-C_4)$-alkoxy, phenyl, phenoxy and benzyloxy,
  where phenyl, phenoxy and benzyloxy for their part may be substituted by 1 or 2 substituents selected from the group consisting of fluorine and chlorine,
 where $(C_3-C_6)$-cycloalkyl may be substituted by 1 or 2 substituents independently of one another selected from the group consisting of fluorine, trifluoromethyl, methyl and ethyl,
 and
 where phenyl and 5- or 6-membered heteroaryl may be substituted by 1 or 2 substituents independently of one another selected from the group consisting of fluorine, chlorine, cyano, nitro, trifluoromethyl, difluoromethoxy, trifluoromethoxy, —NH(CO)CH$_3$, methyl, ethenyl, $(C_1-C_4)$-alkoxy and trifluoromethyl,
  where $(C_1-C_4)$-alkoxy may be substituted by hydroxy,
$R^8$ represents hydrogen, methyl or ethyl,
or
$R^7$ and $R^8$ together with the carbon atom to which they are attached form a 3- to 6-membered carbocycle or an oxetanyl, tetrahydrofuranyl, tetrahydropyranyl, azetidinyl, pyrrolidinyl or piperidinyl ring,
 where the 3- to 6-membered carbocycle and the oxetanyl, tetrahydrofuranyl, tetrahydropyranyl, azetidinyl, pyrrolidinyl and piperidinyl ring may be substituted by 1 or 2 substituents independently of one another selected from the group consisting of fluorine and methyl,
$R^9$ represents hydrogen, cyano, 1,1,2,2-tetrafluoroethyl, trifluoromethyl, $(C_1-C_6)$-alkyl, $(C_3-C_6)$-cycloalkyl, 5- or 6-membered heteroaryl or phenyl,
 where $(C_1-C_6)$-alkyl may be substituted by 1 or 2 substituents independently of one another selected from the group consisting of cyano, fluorine, trifluoromethyl, difluoromethoxy, trifluoromethoxy, hydroxy, $(C_1-C_4)$-alkoxy, 5-membered heteroaryl, phenyl, phenoxy and benzyloxy,
  where phenyl, phenoxy and benzyloxy for their part may be substituted by 1 or 2 substituents selected from the group consisting of fluorine and chlorine,
  where 5-membered heteroaryl may be benzo-fused or substituted by a 5-membered heteroaryl,
  where 5- or 6-membered heteroaryl may be substituted by $(C_1-C_4)$-alkyl or trifluoromethyl,
 where $(C_3-C_6)$-cycloalkyl may be substituted by 1 or 2 substituents independently of one another selected from the group consisting of fluorine, trifluoromethyl, methyl and ethyl,
 and
 where phenyl and 5- or 6-membered heteroaryl may be substituted by 1 or 2 substituents independently of one another selected from the group consisting of fluorine, chlorine, cyano, methyl, trifluoromethoxy, difluoromethoxy, $(C_1-C_4)$-alkoxy and trifluoromethyl,
  where $(C_1-C_4)$-alkoxy is substituted by hydroxy,
$R^{10}$ represents hydrogen, methyl or ethyl,
or
$R^9$ and $R^{10}$ together with the carbon atom to which they are attached form a 3- to 6-membered carbocycle or an oxetanyl, tetrahydrofuranyl, tetrahydropyranyl, azetidinyl, pyrrolidinyl or piperidinyl ring,
 where the 3- to 6-membered carbocycle and the oxetanyl, tetrahydrofuranyl, tetrahydropyranyl, azetidinyl, pyrrolidinyl and piperidinyl ring may be substituted by 1 or 2 substituents independently of one another selected from the group consisting of fluorine, benzyl and methyl,
with the proviso that the radicals $R^7$ and $R^9$ do not both simultaneously represent phenyl,
or
$R^7$ and $R^9$ together with the carbon atoms to which they are attached and the group $L^{1B}$ form a cyclopentyl, cyclohexyl, azetidinyl, oxetanyl, pyrrolidinyl, tetrahydrofuranyl, piperidinyl or tetrahydropyranyl ring,
with the proviso that not more than one of the radical pairs $R^7$ and $R^8$, $R^9$ and $R^{10}$ and $R^7$ and $R^9$, respectively, simultaneously forms one of the abovementioned carbo- or heterocycles,
$R^{11}$ represents hydrogen or $(C_1-C_3)$-alkyl,
 where $(C_1-C_3)$-alkyl may be substituted by 1 or 2 substituents independently of one another selected from the group consisting of fluorine, trifluoromethyl, hydroxy, methoxy and ethoxy,
$R^{12}$ represents hydrogen, $(C_1-C_4)$-alkyl, cyclopropyl, cyclobutyl, phenyl or benzyl,
 where $(C_1-C_4)$-alkyl may be substituted by 1 or 2 substituents independently of one another selected from the group consisting of fluorine, trifluoromethyl, hydroxy, $(C_1-C_4)$-alkoxy and phenoxy,
 and
 where phenyl and benzyl may be substituted by 1 to 3 substituents independently of one another selected from the group consisting of fluorine, chlorine and trifluoromethyl,
or
$R^{11}$ and $R^{12}$ together with the nitrogen atom to which they are attached form an azetidinyl, pyrrolidinyl, piperidinyl, morpholinyl, piperazinyl, thiomorpholinyl or 1,1-dioxothiomorpholinyl ring,
 where the azetidinyl, pyrrolidinyl, piperidinyl, morpholinyl, piperazinyl, thiomorpholinyl and 1,1-dioxothiomorpholinyl ring may be substituted by 1 or 2 substituents independently of one another selected from the group consisting of fluorine, trifluoromethyl, methyl, ethyl, cyclopropyl, cyclobutyl, azetidinyl, pyrrolidinyl and piperidinyl, and
L² represents a bond, methylene or 1,1-ethanediyl,
R¹³ represents pyrrolidinyl, piperidinyl, 1,2,3,4-tetrahydroisoquinolinyl, 1,2,3,4-tetrahydroquinolinyl, indolinyl, 8-azabicyclo[3.2.1]octanyl, 9-azabicyclo[3.3.1] nonanyl, 3-azabicyclo[4.1.0]heptanyl and quinuclidinyl, attached via a ring carbon atom,
where pyrrolidinyl, piperidinyl, 1,2,3,4-tetrahydroisoquinolinyl, 1,2,3,4-tetrahydroquinolinyl, indolinyl, 8-azabicyclo[3.2.1]octanyl, 9-aza-bicyclo[3.3.1] nonanyl, 3-azabicyclo[4.1.0]heptanyl and quinuclidinyl may be substituted by 1 to 5 substituents independently from one another selected from the group consisting of fluorine, trifluoromethyl, methyl, ethyl, cyclopropyl, cyclobutyl and benzyl,
R⁴ represents hydrogen,
R⁵ represents hydrogen, fluorine, chlorine, bromine, cyano, methyl, ethyl, monofluoromethyl, ethynyl or cyclopropyl,
R⁶ represents hydrogen or fluorine,
and their N-oxides, salts, solvates, salts of the N-oxides and solvates of the N-oxides and salts.

Preference in the context of the present invention is given to compounds of the formula (I) in which
A represents CH₂,
R¹ represents phenyl,
where phenyl is substituted by 1 to 2 fluorine,
and
where phenyl is substituted by a substituent selected from the group consisting of cyclopropyl and methoxy,
R² represents trifluoromethyl, methyl, ethyl or cyclopropyl,
R³ represents a group of the formula

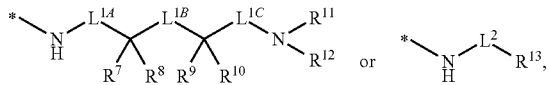

where
* represents the point of attachment to the carbonyl group,
L¹ᴬ represents a bond,
L¹ᴮ represents a bond or methylene,
L¹ᶜ represents a bond or methylene,
where methylene may be substituted by 1 or 2 substituents independently of one another selected from the group consisting of trifluoromethyl, (C₁-C₄)-alkyl, cyclopropyl and cyclobutyl,
R⁷ represents hydrogen, trifluoromethyl, (C₁-C₆)-alkyl, (C₃-C₆)-cycloalkyl or phenyl,
where (C₁-C₆)-alkyl may be substituted by 1 or 2 substituents independently of one another selected from the group consisting of fluorine, trifluoromethyl, hydroxy, (C₁-C₄)-alkoxy, phenyl, phenoxy and benzyloxy,
where phenyl, phenoxy and benzyloxy for their part may be substituted by 1 or 2 substituents selected from the group consisting of fluorine and chlorine,
where (C₃-C₆)-cycloalkyl may be substituted by 1 or 2 substituents independently of one another selected from the group consisting of fluorine, trifluoromethyl, methyl and ethyl,
and
where phenyl may be substituted by 1 or 2 substituents independently of one another selected from the group consisting of fluorine, chlorine, cyano, nitro, difluoromethoxy, trifluoromethoxy, —NH(CO)CH₃, ethenyl, ethoxy and trifluoromethyl,
where ethoxy may be substituted by hydroxy,
R⁸ represents hydrogen, methyl or ethyl,
or
R⁷ and R⁸ together with the carbon atom to which they are attached form a 3- to 6-membered carbocycle or an oxetanyl, tetrahydrofuranyl, tetrahydropyranyl, azetidinyl, pyrrolidinyl or piperidinyl ring,
where the 3- to 6-membered carbocycle and the oxetanyl, tetrahydrofuranyl, tetrahydropyranyl, azetidinyl, pyrrolidinyl and piperidinyl ring may be substituted by 1 or 2 substituents independently of one another selected from the group consisting of fluorine and methyl,
R⁹ represents hydrogen, cyano, trifluoromethyl, (C₁-C₆)-alkyl, (C₃-C₆)-cycloalkyl or phenyl,
where (C₁-C₆)-alkyl may be substituted by 1 or 2 substituents independently of one another selected from the group consisting of cyano, fluorine, trifluoromethyl, hydroxy, (C₁-C₄)-alkoxy, phenyl, phenoxy and benzyloxy,
where phenyl, phenoxy and benzyloxy for their part may be substituted by 1 or 2 substituents selected from the group consisting of fluorine and chlorine,
where (C₃-C₆)-cycloalkyl may be substituted by 1 or 2 substituents independently of one another selected from the group consisting of fluorine, trifluoromethyl, methyl and ethyl,
and
where phenyl may be substituted by 1 or 2 substituents independently of one another selected from the group consisting of fluorine, chlorine, cyano, trifluoromethoxy, difluoromethoxy, ethoxy and trifluoromethyl,
where ethoxy may be substituted by hydroxy,
R¹⁰ represents hydrogen, methyl or ethyl,
or
R⁹ and R¹⁰ together with the carbon atom to which they are attached form a 3- to 6-membered carbocycle or an oxetanyl, tetrahydrofuranyl, tetrahydropyranyl, azetidinyl, pyrrolidinyl or piperidinyl ring,
where the 3- to 6-membered carbocycle and the oxetanyl, tetrahydrofuranyl, tetrahydropyranyl, azetidinyl, pyrrolidinyl and piperidinyl ring may be substituted by 1 or 2 substituents independently of one another selected from the group consisting of fluorine, benzyl and methyl,
with the proviso that the radicals R⁷ and R⁹ do not both simultaneously represent phenyl,
or
R⁷ and R⁹ together with the carbon atoms to which they are attached and the group
L¹ᴮ form a cyclopentyl, cyclohexyl, azetidinyl, oxetanyl, pyrrolidinyl, tetrahydrofuranyl, piperidinyl or tetrahydropyranyl ring,
with the proviso that not more than one of the radical pairs R⁷ and R⁸, R⁹ and R¹⁰ and R⁷ and R⁹, respectively, simultaneously forms one of the abovementioned carbo- or heterocycles,
R¹¹ represents hydrogen or (C₁-C₃)-alkyl,
where (C₁-C₃)-alkyl may be substituted by 1 or 2 substituents independently of one another selected from the group consisting of fluorine and trifluoromethyl,
R¹² represents hydrogen, (C₁-C₄)-alkyl, cyclopropyl or cyclobutyl, where $(C_1-C_4)$-alkyl may be substituted by 1 or 2 substituents independently of one another selected from the group consisting of fluorine and trifluoromethyl,
or
$R^{11}$ and $R^{12}$ together with the nitrogen atom to which they are attached form an azetidinyl, pyrrolidinyl, piperidinyl or morpholinyl ring,
where the azetidinyl, pyrrolidinyl, piperidinyl and morpholinyl ring may be substituted by 1 or 2 substituents independently of one another selected from the group consisting of fluorine, trifluoromethyl, methyl, ethyl, cyclopropyl and cyclobutyl,
and
$L^2$ represents a bond or methylene,
$R^{13}$ represents pyrrolidinyl, piperidinyl, 1,2,3,4-tetrahydroisoquinolinyl, 1,2,3,4-tetrahydroquinolinyl, indolinyl, 8-azabicyclo[3.2.1]octanyl, 9-azabicyclo[3.3.1]nonanyl, 3-aza-bicyclo[4.1.0]heptanyl or quinuclidinyl, attached via a ring carbon atom,
in which pyrrolidinyl, piperidinyl, 1,2,3,4-tetrahydroisoquinolinyl, 1,2,3,4-tetrahydroquinolinyl, 8-azabicyclo[3.2.1]octanyl, 9-azabicyclo[3.3.1]nonanyl, 3-aza-bicyclo[4.1.0]heptanyl and quinuclidinyl may be substituted by 1 to 5 substituents independently of one another selected from the group consisting of fluorine, trifluoromethyl, methyl, ethyl, cyclopropyl, cyclobutyl and benzyl,
$R^4$ represents hydrogen,
$R^5$ represents hydrogen, fluorine, chlorine, methyl, ethyl, monofluoromethyl, ethynyl or cyclopropyl,
$R^6$ represents hydrogen,
and their N-oxides, salts, solvates, salts of the N-oxides and solvates of the N-oxides and salts.

Preference in the context of the present invention is given to compounds of the formula (I) in which
A represents $CH_2$,
$R^1$ represents phenyl,
where phenyl is substituted by 1 to 2 fluorine,
and
where phenyl is substituted by a substituent selected from the group consisting of cyclopropyl and methoxy,
$R^2$ represents methyl,
$R^3$ represents a group of the formula

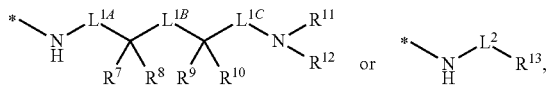

where
* represents the point of attachment to the carbonyl group,
$L^{1A}$ represents a bond,
$L^{1B}$ represents a bond,
$L^{1C}$ represents a bond,
$R^7$ represents hydrogen, trifluoromethyl, $(C_1-C_6)$-alkyl, $(C_3-C_6)$-cycloalkyl or phenyl,
where $(C_1-C_6)$-alkyl may be substituted by 1 or 2 substituents independently of one another selected from the group consisting of fluorine, trifluoromethyl, hydroxy, $(C_1-C_4)$-alkoxy and phenyl,
and
where phenyl may be substituted by 1 or 2 substituents independently of one another selected from the group consisting of fluorine, difluoromethoxy, trifluoromethoxy, ethenyl, ethoxy and chlorine,
where ethoxy may be substituted by hydroxy, $R^8$ represents hydrogen, methyl or ethyl,
$R^9$ represents hydrogen, cyano, trifluoromethyl, $(C_1-C_6)$-alkyl, cyclopropyl or phenyl,
where $(C_1-C_6)$-alkyl may be substituted by 1 or 2 substituents independently of one another selected from the group consisting of cyano, fluorine, trifluoromethyl, hydroxy, $(C_1-C_4)$-alkoxy and phenyl,
and
where phenyl may be substituted by 1 or 2 substituents independently of one another selected from the group consisting of fluorine, trifluoromethoxy, difluoromethoxy, ethoxy and chlorine,
where ethoxy may be substituted by hydroxy,
$R^{10}$ represents hydrogen, methyl or ethyl,
or
$R^9$ and $R^{10}$ together with the carbon atom to which they are attached form a 3- to 6-membered carbocycle or an oxetanyl ring,
with the proviso that the radicals $R^7$ and $R^9$ do not both simultaneously represent phenyl,
or
$R^7$ and $R^9$ together with the carbon atoms to which they are attached and the group $L^{1B}$ form a cyclopentyl or cyclohexyl ring,
with the proviso that not more than one of the radical pairs $R^9$ and $R^{10}$ and $R^7$ and $R^9$, respectively, simultaneously forms one of the abovementioned carbo- or heterocycles,
$R^{11}$ represents hydrogen,
$R^{12}$ represents hydrogen,
and
$L^2$ represents a bond,
$R^{13}$ represents piperidin-2-yl, piperidin-3-yl, piperidin-4-yl or 1,2,3,4-tetrahydroquinolin-4-yl,
where piperidin-2-yl, piperidin-3-yl and piperidin-4-yl may be substituted by 1 to 5 substituents independently of one another selected from the group consisting of trifluoromethyl and methyl,
and
where 1,2,3,4-tetrahydroquinolin-4-yl may be substituted by fluorine or trifluoromethyl,
$R^4$ represents hydrogen,
$R^5$ represents hydrogen, fluorine, chlorine, monofluoromethyl, ethynyl or methyl,
$R^6$ represents hydrogen,
and their N-oxides, salts, solvates, salts of the N-oxides and solvates of the N-oxides and salts.

Preference in the context of the present invention is given to compounds of the formula (I) in which
A represents $CH_2$, $CD_2$ or $CH(CH_3)$,
$R^1$ represents $(C_4-C_6)$-alkyl, $(C_3-C_7)$-cycloalkyl or phenyl,
where $(C_4-C_6)$-alkyl may be substituted up to six times by fluorine,
where $(C_3-C_7)$-cycloalkyl may be substituted by 1 to 4 substituents independently of one another selected from the group consisting of fluorine, trifluoromethyl and $(C_1-C_4)$-alkyl,
and
where phenyl may be substituted by 1 to 4 substituents independently of one another selected from the group consisting of halogen, cyano, monofluoromethyl, difluoromethyl, trifluoromethyl, $(C_1-C_4)$-alkyl, $(C_1-C_4)$-alkoxy, $(C_3-C_6)$-cycloalkyl, difluoromethoxy and trifluoromethoxy,
$R^2$ represents hydrogen, $(C_1-C_4)$-alkyl, cyclopropyl, monofluoromethyl, difluoromethyl or trifluoromethyl, $R^3$ represents a group of the formula

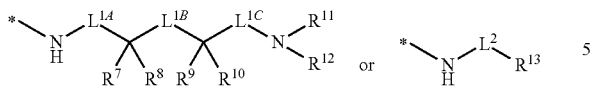

where
* represents the point of attachment to the carbonyl group,
$L^{1A}$ represents a bond or $(C_1-C_4)$-alkanediyl,
where $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy,
$L^{1B}$ represents a bond or $(C_1-C_4)$-alkanediyl,
$L^{1C}$ represents a bond or $(C_1-C_4)$-alkanediyl,
where $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy,
$R^7$ represents hydrogen, $(C_1-C_6)$-alkyl, $(C_2-C_6)$-alkenyl, $(C_2-C_6)$-alkynyl, $(C_3-C_7)$-cycloalkyl, cyano, 5- to 10-membered heteroaryl, naphthyl or phenyl,
where $(C_1-C_6)$-alkyl may be substituted by 1 to 3 substituents independently of one another selected from the group consisting of fluorine, trifluoromethyl, difluoromethoxy, trifluoromethoxy, hydroxy, $(C_1-C_4)$-alkoxy, $(C_1-C_4)$-alkoxycarbonyl, $(C_1-C_4)$-alkylsulphonyl, phenyl, phenoxy and benzyloxy,
where phenyl, phenoxy and benzyloxy for their part may be substituted by 1 to 3 halogen or $(C_1-C_4)$-alkoxy substituents,
where $(C_3-C_7)$-cycloalkyl may be substituted by 1 or 2 substituents independently of one another selected from the group consisting of fluorine, trifluoromethyl, $(C_1-C_4)$-alkyl and $(C_1-C_4)$-alkoxy,
and
where phenyl and 5- to 10-membered heteroaryl may be substituted by 1 to 3 substituents independently of one another selected from the group consisting of halogen, cyano, nitro, difluoromethyl, trifluoromethyl, difluoromethoxy, trifluoromethoxy, —NH(CO)CH$_3$, $(C_1-C_4)$-alkyl, $(C_1-C_4)$-cycloalkyl, $(C_1-C_4)$-alkenyl, $(C_1-C_4)$-alkylsulphonyl, $(C_1-C_4)$-alkoxycarbonyl and $(C_1-C_4)$-alkoxy,
where $(C_1-C_4)$-alkoxy may be substituted by hydroxy,
and
in which 2 adjacent carbon atoms of the phenyl may be substituted by a difluoromethylenedioxy bridge,
$R^8$ represents hydrogen or $(C_1-C_4)$-alkyl,
or
$R^7$ and $R^8$ together with the carbon atom to which they are attached form a 3- to 7-membered carbocycle or a 4- to 7-membered heterocycle,
where the 3- to 7-membered carbocycle and the 4- to 7-membered heterocycle for their part may be substituted by 1 or 2 substituents independently of one another selected from the group consisting of fluorine and $(C_1-C_4)$-alkyl,
$R^9$ represents hydrogen, cyano, $(C_1-C_6)$-alkyl, $(C_2-C_6)$-alkenyl, $(C_2-C_6)$-alkynyl, $(C_3-C_7)$-cycloalkyl, 5- to 10-membered heteroaryl or phenyl,
where $(C_1-C_6)$-alkyl may be substituted by 1 to 3 substituents independently of one another selected from the group consisting of fluorine, difluoromethyl, trifluoromethyl, difluoromethoxy, trifluoromethoxy, hydroxy, cyano, $(C_1-C_4)$-alkoxy, $(C_1-C_4)$-alkoxycarbonyl, $(C_1-C_4)$-alkylsulphonyl, 5- or 6-membered heteroaryl, phenyl, phenoxy and benzyloxy,
where phenyl, phenoxy and benzyloxy for their part may be substituted by 1 to 3 halogen or $(C_1-C_4)$-alkoxy substituents,
where 5- or 6-membered heteroaryl may be benzofused or substituted by a 5- or 6-membered heteroaryl,
where 5- or 6-membered heteroaryl may be substituted by $(C_1-C_4)$-alkyl or trifluoromethyl,
where $(C_3-C_7)$-cycloalkyl may be substituted by 1 or 2 substituents independently of one another selected from the group consisting of fluorine, trifluoromethyl, $(C_1-C_4)$-alkyl and $(C_1-C_4)$-alkoxy,
and
where phenyl and 5- to 10-membered heteroaryl may be substituted by 1 to 3 substituents independently of one another selected from the group consisting of halogen, cyano, difluoromethyl, trifluoromethyl, difluoromethoxy, trifluoromethoxy, $(C_1-C_4)$-alkyl, $(C_1-C_4)$-cycloalkyl, $(C_1-C_4)$-alkoxy, $(C_1-C_4)$-alkoxycarbonyl and $(C_1-C_4)$-alkylsulphonyl,
where $(C_1-C_4)$-alkoxy may be substituted by hydroxy, and
where the phenyl may be substituted on two adjacent carbon atoms by a difluoromethylenedioxy bridge,
$R^{10}$ represents hydrogen or $(C_1-C_4)$-alkyl,
or
$R^9$ and $R^{10}$ together with the carbon atom to which they are attached form a 3- to 7-membered carbocycle or a 4- to 7-membered heterocycle,
where the 3- to 7-membered carbocycle and the 4- to 7-membered heterocycle for their part may be substituted by 1 or 2 substituents independently of one another selected from the group consisting of fluorine, benzyl and $(C_1-C_4)$-alkyl,
with the proviso that the radicals $R^7$ and $R^9$ do not both simultaneously represent phenyl,
or
$R^7$ and $R^9$ together with the carbon atoms to which they are attached and the group $L^{1B}$ form a 3- to 7-membered carbocycle or a 4- to 7-membered heterocycle,
where the 3- to 7-membered carbocycle may be substituted by 1 or 2 substituents independently of one another selected from the group consisting of $(C_1-C_4)$-alkyl, fluorine, hydroxy and $(C_1-C_4)$-alkoxy,
with the proviso that not more than one of the radical pairs $R^7$ and $R^8$, $R^9$ and $R^{10}$ and $R^7$ and $R^9$, respectively, simultaneously forms a carbo- or heterocycle,
$R^{11}$ represents hydrogen or $(C_1-C_4)$-alkyl,
where $(C_1-C_4)$-alkyl may be substituted by 1 to 3 substituents independently of one another selected from the group consisting of fluorine, trifluoromethyl, hydroxy and $(C_1-C_4)$-alkoxy,
$R^{12}$ represents hydrogen, $(C_1-C_6)$-alkyl, $(C_3-C_7)$-cycloalkyl, phenyl or benzyl,
where $(C_1-C_6)$-alkyl may be substituted by 1 to 3 substituents independently of one another selected from the group consisting of fluorine, trifluoromethyl, hydroxy, $(C_1-C_4)$-alkoxy and phenoxy, and
where phenyl and benzyl may be substituted by 1 to 3 substituents independently of one another selected from the group consisting of halogen and trifluoromethyl, or $R^{11}$ and $R^{12}$ together with the nitrogen atom to which they are attached form a 4- to 7-membered azaheterocycle,
where the 4- to 7-membered azaheterocycle may be substituted by 1 or 2 substituents independently of one another selected from the group consisting of fluorine, trifluoromethyl, $(C_1-C_4)$-alkyl, $(C_3-C_7)$-cycloalkyl, hydroxy, $(C_1-C_4)$-alkoxy and 4- to 7-membered heterocyclyl, and $L^2$ represents a bond or $(C_1-C_4)$-alkanediyl, $R^{13}$ represents 5- to 9-membered azaheterocyclyl which is attached via a ring carbon atom,
where 5- to 9-membered azaheterocyclyl may be substituted by 1 to 5 substituents independently of one another selected from the group consisting of fluorine, trifluoromethyl, $(C_1-C_4)$-alkyl, $(C_3-C_7)$-cycloalkyl and benzyl,
and
where 5- to 9-membered azaheterocyclyl may be fused to a phenyl ring which for its part may be substituted by 1 or 2 substituents selected from the group consisting of halogen, $(C_1-C_4)$-alkyl, $(C_1-C_4)$-alkoxy and trifluoromethyl, or represents adamantyl, $R^4$ represents hydrogen, $R^5$ represents monofluoromethyl, difluoromethyl, trifluoromethyl, $(C_2-C_4)$-alkenyl, $(C_2-C_4)$-alkynyl, $(C_3-C_6)$-cycloalkyl, difluoromethoxy, trifluoromethoxy, $(C_1-C_4)$-alkoxy, amino, 4- to 7-membered heterocyclyl or 5- or 6-membered heteroaryl, $R^6$ represents hydrogen, cyano or halogen, and their N-oxides, salts, solvates, salts of the N-oxides and solvates of the N-oxides and salts.

Preference in the context of the present invention is given to compounds of the formula (I) in which A represents $CH_2$, $CD_2$ or $CH(CH_3)$, $R^1$ represents $(C_4-C_6)$-alkyl, $(C_4-C_6)$-cycloalkyl or phenyl,
where $(C_4-C_6)$-alkyl may be substituted up to six times by fluorine,
where $(C_4-C_6)$-cycloalkyl may be substituted by 1 or 2 substituents independently of one another selected from the group consisting of fluorine, trifluoromethyl and methyl,
and
where phenyl may be substituted by 1 to 4 substituents independently of one another selected from the group consisting of fluorine, chlorine, cyano, methoxy, ethoxy, difluoromethyl, trifluoromethyl, $(C_3-C_6)$-cycloalkyl and methyl, $R^2$ represents hydrogen, trifluoromethyl, $(C_1-C_3)$-alkyl or cyclopropyl, $R^3$ represents a group of the formula

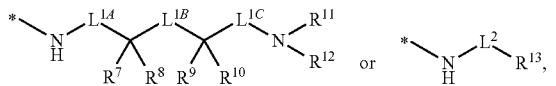

where

\* represents the point of attachment to the carbonyl group, $L^{1A}$ represents a bond, $L^{1B}$ represents a bond, methylene or 1,2-ethanediyl, $L^{1C}$ represents a bond or methylene,
where methylene may be substituted by 1 or 2 substituents independently of one another selected from the group consisting of fluorine, trifluoromethyl, $(C_1-C_4)$-alkyl, cyclopropyl and cyclobutyl, $R^7$ represents hydrogen, trifluoromethyl, $(C_1-C_6)$-alkyl, $(C_3-C_6)$-cycloalkyl, 5- or 6-membered heteroaryl or phenyl,
where $(C_1-C_6)$-alkyl may be substituted by 1 or 2 substituents independently of one another selected from the group consisting of fluorine, trifluoromethyl, difluoromethoxy, trifluoromethoxy, hydroxy, $(C_1-C_4)$-alkoxy, phenyl, phenoxy and benzyloxy,
where phenyl, phenoxy and benzyloxy for their part may be substituted by 1 or 2 substituents selected from the group consisting of fluorine and chlorine,
where $(C_3-C_6)$-cycloalkyl may be substituted by 1 or 2 substituents independently of one another selected from the group consisting of fluorine, trifluoromethyl, methyl and ethyl,
and
where phenyl and 5- or 6-membered heteroaryl may be substituted by 1 or 2 substituents independently of one another selected from the group consisting of fluorine, chlorine, cyano, nitro, methyl, ethenyl, difluoromethoxy, trifluoromethoxy, —NH(CO)CH$_3$, $(C_1-C_4)$-alkoxy and trifluoromethyl,
where $(C_1-C_4)$-alkoxy may be substituted by hydroxy, $R^8$ represents hydrogen, methyl or ethyl, or $R^7$ and $R^8$ together with the carbon atom to which they are attached form a 3- to 6-membered carbocycle or an oxetanyl, tetrahydrofuranyl, tetrahydropyranyl, azetidinyl, pyrrolidinyl or piperidinyl ring,
where the 3- to 6-membered carbocycle and the oxetanyl, tetrahydrofuranyl, tetrahydropyranyl, azetidinyl, pyrrolidinyl and piperidinyl ring may be substituted by 1 or 2 substituents independently of one another selected from the group consisting of fluorine and methyl, $R^9$ represents hydrogen, cyano, 1,1,2,2-tetrafluoroethyl, trifluoromethyl, $(C_1-C_6)$-alkyl, $(C_3-C_6)$-cycloalkyl, 5- or 6-membered heteroaryl or phenyl,
where $(C_1-C_6)$-alkyl may be substituted by 1 or 2 substituents independently of one another selected from the group consisting of cyano, fluorine, trifluoromethyl, difluoromethoxy, trifluoromethoxy, hydroxy, $(C_1-C_4)$-alkoxy, 5-membered heteroaryl, phenyl, phenoxy and benzyloxy,
where phenyl, phenoxy and benzyloxy for their part may be substituted by 1 or 2 substituents selected from the group consisting of fluorine and chlorine,
where 5-membered heteroaryl may be benzo-fused or substituted by a 5-membered heteroaryl,
where $(C_3-C_6)$-cycloalkyl may be substituted by 1 or 2 substituents independently of one another selected from the group consisting of fluorine, trifluoromethyl, methyl and ethyl,
and
where phenyl and 5- or 6-membered heteroaryl may be substituted by 1 or 2 substituents independently of one another selected from the group consisting of fluorine, chlorine, cyano, methyl, difluoromethoxy, trifluoromethoxy, $(C_1$-$C_4)$-alkoxy and trifluoromethyl,
    where $(C_1$-$C_4)$-alkoxy may be substituted by hydroxy,
$R^{10}$ represents hydrogen, methyl or ethyl,
or
$R^9$ and $R^{10}$ together with the carbon atom to which they are attached form a 3- to 6-membered carbocycle or an oxetanyl, tetrahydrofuranyl, tetrahydropyranyl, azetidinyl, pyrrolidinyl or piperidinyl ring,
    where the 3- to 6-membered carbocycle and the oxetanyl, tetrahydrofuranyl, tetrahydropyranyl, azetidinyl, pyrrolidinyl and piperidinyl ring may be substituted by 1 or 2 substituents independently of one another selected from the group consisting of fluorine, benzyl and methyl,
with the proviso that the radicals $R^7$ and $R^9$ do not both simultaneously represent phenyl,
or
$R^7$ and $R^9$ together with the carbon atoms to which they are attached and the group
$L^{1B}$ form a cyclopentyl, cyclohexyl, azetidinyl, oxetanyl, pyrrolidinyl, tetrahydrofuranyl, piperidinyl or tetrahydropyranyl ring,
with the proviso that not more than one of the radical pairs $R^7$ and $R^8$, $R^9$ and $R^{10}$ and $R^7$ and $R^9$, respectively, simultaneously forms one of the abovementioned carbo- or heterocycles,
$R^{11}$ represents hydrogen or $(C_1$-$C_3)$-alkyl,
where $(C_1$-$C_3)$-alkyl may be substituted by 1 or 2 substituents independently of one another selected from the group consisting of fluorine, trifluoromethyl, hydroxy, methoxy and ethoxy,
$R^{12}$ represents hydrogen, $(C_1$-$C_4)$-alkyl, cyclopropyl, cyclobutyl, phenyl or benzyl,
    where $(C_1$-$C_4)$-alkyl may be substituted by 1 or 2 substituents independently of one another selected from the group consisting of fluorine, trifluoromethyl, hydroxy, $(C_1$-$C_4)$-alkoxy and phenoxy,
    and
    where phenyl and benzyl may be substituted by 1 to 3 substituents independently of one another selected from the group consisting of fluorine, chlorine and trifluoromethyl,
or
$R^{11}$ and $R^{12}$ together with the nitrogen atom to which they are attached form an azetidinyl, pyrrolidinyl, piperidinyl, morpholinyl, piperazinyl, thiomorpholinyl or 1,1-dioxothiomorpholinyl ring,
    where the azetidinyl, pyrrolidinyl, piperidinyl, morpholinyl, piperazinyl, thiomorpholinyl and 1,1-dioxothiomorpholinyl ring may be substituted by 1 or 2 substituents independently of one another selected from the group consisting of fluorine, trifluoromethyl, methyl, ethyl, cyclopropyl, cyclobutyl, azetidinyl, pyrrolidinyl and piperidinyl,
and
$L^2$ represents a bond, methylene or 1,1-ethanediyl,
$R^{13}$ represents pyrrolidinyl, piperidinyl, 1,2,3,4-tetrahydroisoquinolinyl, 1,2,3,4-tetrahydroquinolinyl, indolinyl, 8-azabicyclo[3.2.1]octanyl, 9-azabicyclo[3.3.1]nonanyl, 3-azabicyclo[4.1.0]heptanyl and quinuclidinyl, attached via a ring carbon atom,
    where pyrrolidinyl, piperidinyl, 1,2,3,4-tetrahydroisoquinolinyl, 1,2,3,4-tetrahydroquinolinyl, indolinyl, 8-azabicyclo[3.2.1]octanyl, 9-aza-bicyclo[3.3.1]nonanyl, 3-azabicyclo[4.1.0]heptanyl and quinuclidinyl may be substituted by 1 to 5 substituents independently of one another selected from the group consisting of fluorine, trifluoromethyl, methyl, ethyl, cyclopropyl, cyclobutyl and benzyl,
$R^4$ represents hydrogen,
$R^5$ represents monofluoromethyl, difluoromethyl, trifluoromethyl, $(C_2$-$C_4)$-alkenyl, $(C_2$-$C_4)$-alkynyl, $(C_3$-$C_6)$-cycloalkyl, difluoromethoxy, trifluoromethoxy, $(C_1$-$C_4)$-alkoxy, 5- to 6-membered heterocyclyl or 5- or 6-membered heteroaryl,
$R^6$ represents hydrogen or fluorine,
and their N-oxides, salts, solvates, salts of the N-oxides and solvates of the N-oxides and salts.

Preference in the context of the present invention is given to compounds of the formula (I) in which
A represents $CH_2$,
$R^1$ represents $(C_4$-$C_6)$-alkyl, $(C_4$-$C_6)$-cycloalkyl or phenyl,
    where $(C_4$-$C_6)$-alkyl may be substituted up to six times by fluorine,
    where $(C_4$-$C_6)$-cycloalkyl may be substituted by 1 or 2 substituents independently of one another selected from the group consisting of fluorine, trifluoromethyl and methyl,
    and
    where phenyl may be substituted by 1 to 3 substituents independently of one another selected from the group consisting of fluorine, chlorine, cyclopropyl, methoxy and methyl,
$R^2$ represents trifluoromethyl, methyl, ethyl or cyclopropyl,
$R^3$ represents a group of the formula

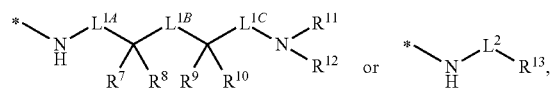

where
\* represents the point of attachment to the carbonyl group,
$L^{1A}$ represents a bond,
$L^{1B}$ represents a bond or methylene,
$L^{1C}$ represents a bond or methylene,
    where methylene may be substituted by 1 or 2 substituents independently of one another selected from the group consisting of trifluoromethyl, $(C_1$-$C_4)$-alkyl, cyclopropyl and cyclobutyl,
$R^7$ represents hydrogen, trifluoromethyl, $(C_1$-$C_6)$-alkyl, $(C_3$-$C_6)$-cycloalkyl or phenyl,
    where $(C_1$-$C_6)$-alkyl may be substituted by 1 or 2 substituents independently of one another selected from the group consisting of fluorine, trifluoromethyl, hydroxy, $(C_1$-$C_4)$-alkoxy, phenyl, phenoxy and benzyloxy,
        where phenyl, phenoxy and benzyloxy for their part may be substituted by 1 or 2 substituents selected from the group consisting of fluorine and chlorine,
    where $(C_3$-$C_6)$-cycloalkyl may be substituted by 1 or 2 substituents independently of one another selected from the group consisting of fluorine, trifluoromethyl, methyl and ethyl,
    and
    where phenyl may be substituted by 1 or 2 substituents independently of one another selected from the group consisting of fluorine, chlorine, cyano, nitro, ethenyl, difluoromethoxy, trifluoromethoxy, —NH(CO)CH$_3$, ethoxy and trifluoromethyl,
where ethoxy may be substituted by hydroxy,
$R^8$ represents hydrogen, methyl or ethyl,
or
$R^7$ and $R^8$ together with the carbon atom to which they are attached form a 3- to 6-membered carbocycle or an oxetanyl, tetrahydrofuranyl, tetrahydropyranyl, azetidinyl, pyrrolidinyl or piperidinyl ring,
where the 3- to 6-membered carbocycle and the oxetanyl, tetrahydrofuranyl, tetrahydropyranyl, azetidinyl, pyrrolidinyl and piperidinyl ring may be substituted by 1 or 2 substituents independently of one another selected from the group consisting of fluorine and methyl,
$R^9$ represents hydrogen, cyano, trifluoromethyl, ($C_1$-$C_6$)-alkyl, ($C_3$-$C_6$)-cycloalkyl or phenyl,
where ($C_1$-$C_6$)-alkyl may be substituted by 1 or 2 substituents independently of one another selected from the group consisting of cyano, fluorine, trifluoromethyl, hydroxy, ($C_1$-$C_4$)-alkoxy, phenyl, phenoxy and benzyloxy,
where phenyl, phenoxy and benzyloxy for their part may be substituted by 1 or 2 substituents selected from the group consisting of fluorine and chlorine,
where ($C_3$-$C_6$)-cycloalkyl may be substituted by 1 or 2 substituents independently of one another selected from the group consisting of fluorine, trifluoromethyl, methyl and ethyl,
and
where phenyl may be substituted by 1 or 2 substituents independently of one another selected from the group consisting of fluorine, chlorine, cyano, difluoromethoxy, trifluoromethoxy, ethoxy and trifluoromethyl,
where ethoxy may be substituted by hydroxy,
$R^{10}$ represents hydrogen, methyl or ethyl,
or
$R^9$ and $R^{10}$ together with the carbon atom to which they are attached form a 3- to 6-membered carbocycle or an oxetanyl, tetrahydrofuranyl, tetrahydropyranyl, azetidinyl, pyrrolidinyl or piperidinyl ring,
where the 3- to 6-membered carbocycle and the oxetanyl, tetrahydrofuranyl, tetrahydropyranyl, azetidinyl, pyrrolidinyl and piperidinyl ring may be substituted by 1 or 2 substituents independently of one another selected from the group consisting of fluorine, benzyl and methyl,
with the proviso that the radicals $R^7$ and $R^9$ do not both simultaneously represent phenyl,
or
$R^7$ and $R^9$ together with the carbon atoms to which they are attached and the group $L^{1B}$ form a cyclopentyl, cyclohexyl, azetidinyl, oxetanyl, pyrrolidinyl, tetrahydrofuranyl, piperidinyl or tetrahydropyranyl ring,
with the proviso that not more than one of the radical pairs $R^7$ and $R^8$, $R^9$ and $R^{10}$ and $R^7$ and $R^9$, respectively, simultaneously forms one of the carbo- or heterocycles mentioned above,
$R^{11}$ represents hydrogen or ($C_1$-$C_3$)-alkyl,
where ($C_1$-$C_3$)-alkyl may be substituted by 1 or 2 substituents independently of one another selected from the group consisting of fluorine and trifluoromethyl, $R^{12}$ represents hydrogen, ($C_1$-$C_4$)-alkyl, cyclopropyl or cyclobutyl,
where ($C_1$-$C_4$)-alkyl may be substituted by 1 or 2 substituents independently of one another selected from the group consisting of fluorine and trifluoromethyl,
or
$R^{11}$ and $R^{12}$ together with the nitrogen atom to which they are attached form an azetidinyl, pyrrolidinyl, piperidinyl or morpholinyl ring,
where the azetidinyl, pyrrolidinyl, piperidinyl and morpholinyl ring may be substituted by 1 or 2 substituents independently of one another selected from the group consisting of fluorine, trifluoromethyl, methyl, ethyl, cyclopropyl and cyclobutyl,
and
$L^2$ represents a bond or methylene,
$R^{13}$ represents pyrrolidinyl, piperidinyl, 1,2,3,4-tetrahydroisoquinolinyl, 1,2,3,4-tetrahydroquinolinyl, indolinyl, 8-azabicyclo[3.2.1]octanyl, 9-azabicyclo[3.3.1]nonanyl, 3-aza-bicyclo[4.1.0]heptanyl or quinuclidinyl, attached via a ring carbon atom,
where pyrrolidinyl, piperidinyl, 1,2,3,4-tetrahydroisoquinolinyl, 1,2,3,4-tetrahydroquinolinyl, 8-azabicyclo[3.2.1]octanyl, 9-azabicyclo[3.3.1]nonanyl, 3-azabicyclo[4.1.0]heptanyl and quinuclidinyl may be substituted by 1 to 5 substituents independently of one another selected from the group consisting of fluorine, trifluoromethyl, methyl, ethyl, cyclopropyl, cyclobutyl and benzyl,
$R^4$ represents hydrogen,
$R^5$ represents monofluoromethyl, difluoromethyl, trifluoromethyl, cyclopropyl, ethynyl, methoxy, morpholino,
$R^6$ represents hydrogen,
and their N-oxides, salts, solvates, salts of the N-oxides and solvates of the N-oxides and salts.
Preference in the context of the present invention is given to compounds of the formula (I) in which
A represents CH$_2$,
$R^1$ represents a phenyl group of the formula

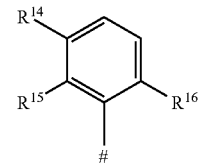

where
# represents the point of attachment to A,
and
$R^{14}$, $R^{15}$ and $R^{16}$ independently of one another represent hydrogen, fluorine, methoxy, cyclopropyl or chlorine,
with the proviso that at least two of the radicals $R^{14}$, $R^{15}$, $R^{16}$ are different from hydrogen,
$R^2$ represents methyl,
$R^3$ represents a group of the formula

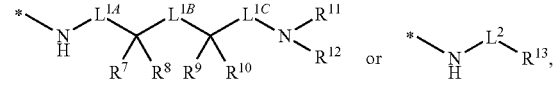

where
* represents the point of attachment to the carbonyl group,
$L^{1A}$ represents a bond,
$L^{1B}$ represents a bond,
$L^{1C}$ represents a bond,
$R^7$ represents hydrogen, trifluoromethyl, $(C_1-C_6)$-alkyl, $(C_3-C_6)$-cycloalkyl or phenyl,
where $(C_1-C_6)$-alkyl may be substituted by 1 or 2 substituents independently of one another selected from the group consisting of fluorine, trifluoromethyl, hydroxy, $(C_1-C_4)$-alkoxy and phenyl,
and
where phenyl may be substituted by 1 or 2 substituents independently of one another selected from the group consisting of fluorine, ethenyl, difluoromethoxy, trifluoromethoxy, ethoxy and chlorine,
where ethoxy may be substituted by hydroxy,
$R^8$ represents hydrogen, methyl or ethyl,
$R^9$ represents hydrogen, cyano, trifluoromethyl, $(C_1-C_6)$-alkyl, cyclopropyl or phenyl,
where $(C_1-C_6)$-alkyl may be substituted by 1 or 2 substituents independently of one another selected from the group consisting of cyano, fluorine, trifluoromethyl, hydroxy, $(C_1-C_4)$-alkoxy and phenyl,
and
where phenyl may be substituted by 1 or 2 substituents independently of one another selected from the group consisting of fluorine, difluoromethoxy, trifluoromethoxy, ethoxy and chlorine,
where ethoxy may be substituted by hydroxy,
$R^{10}$ represents hydrogen, methyl or ethyl,
or
$R^9$ and $R^{10}$ together with the carbon atom to which they are attached form a 3- to 6-membered carbocycle or an oxetanyl ring,
with the proviso that the radicals $R^7$ and $R^9$ do not both simultaneously represent phenyl,
or
$R^7$ and $R^9$ together with the carbon atoms to which they are attached and the group $L^{1B}$ form a cyclopentyl or cyclohexyl ring,
with the proviso that not more than one of the radical pairs $R^9$ and $R^{10}$ and $R^7$ and $R^9$, respectively, simultaneously forms one of the carbo- or heterocycles mentioned above,
$R^{11}$ represents hydrogen,
$R^{12}$ represents hydrogen,
and
$L^2$ represents a bond,
$R^{13}$ represents piperidin-2-yl, piperidin-3-yl, piperidin-4-yl or 1,2,3,4-tetrahydroquinolin-4-yl,
where piperidin-2-yl, piperidin-3-yl and piperidin-4-yl may be substituted by 1 to 5 substituents independently of one another selected from the group consisting of trifluoromethyl and methyl,
and
where 1,2,3,4-tetrahydroquinolin-4-yl may be substituted by fluorine or trifluoromethyl,
$R^4$ represents hydrogen,
$R^5$ represents monofluoromethyl, difluoromethyl, trifluoromethyl, cyclopropyl, ethynyl, methoxy, morpholino,
$R^6$ represents hydrogen,
and their N-oxides, salts, solvates, salts of the N-oxides and solvates of the N-oxides and salts.

Preference in the context of the present invention is given to compounds of the formula (I) in which
A represents $CH_2$, $CD_2$ or $CH(CH_3)$,
$R^1$ represents $(C_4-C_6)$-alkyl, $(C_3-C_7)$-cycloalkyl or phenyl,
where $(C_4-C_6)$-alkyl may be substituted up to six times by fluorine,
where $(C_3-C_7)$-cycloalkyl may be substituted by 1 to 4 substituents independently of one another selected from the group consisting of fluorine, trifluoromethyl and $(C_1-C_4)$-alkyl,
and
where phenyl may be substituted by 1 to 4 substituents independently of one another selected from the group consisting of halogen, cyano, monofluoromethyl, difluoromethyl, trifluoromethyl, $(C_1-C_4)$-alkyl, $(C_1-C_4)$-alkoxy, $(C_3-C_6)$-cycloalkyl, difluoromethoxy and trifluoromethoxy,
$R^2$ represents hydrogen, $(C_1-C_4)$-alkyl, cyclopropyl, monofluoromethyl, difluoromethyl or trifluoromethyl,
$R^3$ represents a group of the formula

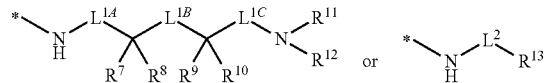

where
represents the point of attachment to the carbonyl group,
$L^{1A}$ represents a bond or $(C_1-C_4)$-alkanediyl,
where $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy,
$L^{1B}$ represents a bond or $(C_1-C_4)$-alkanediyl,
$L^{1C}$ represents a bond or $(C_1-C_4)$-alkanediyl,
where $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy,
$R^7$ represents $(C_1-C_6)$-alkyl, $(C_2-C_6)$-alkynyl, cyano or phenyl,
where $(C_1-C_6)$-alkyl is substituted by 1 to 3 substituents independently of one another selected from the group consisting of fluorine, trifluoromethyl, difluoromethoxy, trifluoromethoxy and phenoxy,
where phenoxy may be substituted by 1 to 3 halogen substituents,
where phenyl is substituted by 1 to 2 substituents independently of one another selected from the group consisting of cyano, nitro, difluoromethoxy, trifluoromethoxy, $(C_1-C_4)$-alkoxy, —NH(CO)CH$_3$ and $(C_1-C_4)$-alkenyl,
where $(C_1-C_4)$-alkoxy is substituted by hydroxy,
$R^8$ represents hydrogen or $(C_1-C_4)$-alkyl,
$R^9$ $R^9$ represents hydrogen, cyano, $(C_1-C_6)$-alkyl, $(C_2-C_6)$-alkenyl, $(C_2-C_6)$-alkynyl, $(C_3-C_7)$-cycloalkyl, 5- to 10-membered heteroaryl or phenyl,
where $(C_1-C_6)$-alkyl may be substituted by 1 to 3 substituents independently of one another selected from the group consisting of fluorine, difluoromethyl, trifluoromethyl, difluoromethoxy, trifluoromethoxy, hydroxy, cyano, $(C_1-C_4)$-alkoxy, $(C_1$-

$C_4$)-alkoxycarbonyl, ($C_1$-$C_4$)-alkylsulphonyl, 5- or 6-membered heteroaryl, phenyl, phenoxy and benzyloxy,
  where phenyl, phenoxy and benzyloxy for their part may be substituted by 1 to 3 halogen or ($C_1$-$C_4$)-alkoxy substituents,
  where 5- or 6-membered heteroaryl may be benzofused or substituted by a 5- or 6-membered heteroaryl,
    where 5- or 6-membered heteroaryl may be substituted by ($C_1$-$C_4$)-alkyl or trifluoromethyl,
  where ($C_3$-$C_7$)-cycloalkyl may be substituted by 1 or 2 substituents independently of one another selected from the group consisting of fluorine, trifluoromethyl, ($C_1$-$C_4$)-alkyl and ($C_1$-$C_4$)-alkoxy,
  and
  where phenyl and 5- to 10-membered heteroaryl may be substituted by 1 to 3 substituents independently of one another selected from the group consisting of halogen, cyano, difluoromethyl, trifluoromethyl, difluoromethoxy, trifluoromethoxy, ($C_1$-$C_4$)-alkyl, ($C_1$-$C_4$)-cycloalkyl, ($C_1$-$C_4$)-alkoxy, ($C_1$-$C_4$)-alkoxycarbonyl and ($C_1$-$C_4$)-alkylsulphonyl,
    where ($C_1$-$C_4$)-alkoxy may be substituted by hydroxy,
    and
    where the phenyl may be substituted on two adjacent carbon atoms by a difluoromethylenedioxy bridge,
$R^{10}$ represents hydrogen or ($C_1$-$C_4$)-alkyl,
or
$R^9$ and $R^{10}$ together with the carbon atom to which they are attached form a 3- to 7-membered carbocycle or a 4- to 7-membered heterocycle,
  where the 3- to 7-membered carbocycle and the 4- to 7-membered heterocycle for their part may be substituted by 1 or 2 substituents independently of one another selected from the group consisting of fluorine, benzyl and ($C_1$-$C_4$)-alkyl,
with the proviso that the radicals $R^7$ and $R^9$ do not both simultaneously represent phenyl,
$R^{11}$ represents hydrogen or ($C_1$-$C_4$)-alkyl,
  where ($C_1$-$C_4$)-alkyl may be substituted by 1 to 3 substituents independently of one another selected from the group consisting of fluorine, trifluoromethyl, hydroxy and ($C_1$-$C_4$)-alkoxy,
$R^{12}$ represents hydrogen, ($C_1$-$C_6$)-alkyl, ($C_3$-$C_7$)-cycloalkyl, phenyl or benzyl,
  where ($C_1$-$C_6$)-alkyl may be substituted by 1 to 3 substituents independently of one another selected from the group consisting of fluorine, trifluoromethyl, hydroxy, ($C_1$-$C_4$)-alkoxy and phenoxy,
  and
  where phenyl and benzyl may be substituted by 1 to 3 substituents independently of one another selected from the group consisting of halogen and trifluoromethyl,
or
$R^{11}$ and $R^{12}$ together with the nitrogen atom to which they are attached form a 4- to 7-membered azaheterocycle,
  where the 4- to 7-membered azaheterocycle may be substituted by 1 or 2 substituents independently of one another selected from the group consisting of fluorine, trifluoromethyl, ($C_1$-$C_4$)-alkyl, ($C_3$-$C_7$)-cycloalkyl, hydroxy, ($C_1$-$C_4$)-alkoxy and 4- to 7-membered heterocyclyl,
and
$L^2$ represents a bond or ($C_1$-$C_4$)-alkanediyl,
$R^{13}$ represents 5- to 9-membered azaheterocyclyl which is attached via a ring carbon atom,
  where 5- to 9-membered azaheterocyclyl may be substituted by 1 to 5 substituents independently of one another selected from the group consisting of fluorine, trifluoromethyl, ($C_1$-$C_4$)-alkyl, ($C_3$-$C_7$)-cycloalkyl and benzyl,
  and
  where 5- to 9-membered azaheterocyclyl may be fused to a phenyl ring which for its part may be substituted by 1 or 2 substituents selected from the group consisting of halogen, ($C_1$-$C_4$)-alkyl, ($C_1$-$C_4$)-alkoxy and trifluoromethyl,
or
represents adamantyl,
$R^4$ represents hydrogen,
$R^5$ represents hydrogen, halogen, cyano, monofluoromethyl, difluoromethyl, trifluoromethyl, ($C_1$-$C_4$)-alkyl, ($C_2$-$C_4$)-alkenyl, ($C_2$-$C_4$)-alkynyl, ($C_3$-$C_6$)-cycloalkyl, difluoromethoxy, trifluoromethoxy, ($C_1$-$C_4$)-alkoxy, amino, 4- to 7-membered heterocyclyl or 5- or 6-membered heteroaryl,
$R^6$ represents hydrogen, cyano or halogen,
and their N-oxides, salts, solvates, salts of the N-oxides and solvates of the N-oxides and salts.

Preference in the context of the present invention is given to compounds of the formula (I) in which
A represents $CH_2$, $CD_2$ or $CH(CH_3)$,
$R^1$ represents ($C_4$-$C_6$)-alkyl, ($C_4$-$C_6$)-cycloalkyl or phenyl,
  where ($C_4$-$C_6$)-alkyl may be substituted up to six times by fluorine,
  where ($C_4$-$C_6$)-cycloalkyl may be substituted by 1 or 2 substituents independently of one another selected from the group consisting of fluorine, trifluoromethyl and methyl,
  and
  where phenyl may be substituted by 1 to 4 substituents independently of one another selected from the group consisting of fluorine, chlorine, cyano, methoxy, ethoxy, difluoromethyl, trifluoromethyl, ($C_3$-$C_6$)-cycloalkyl and methyl,
$R^2$ represents hydrogen, trifluoromethyl, ($C_1$-$C_3$)-alkyl and cyclopropyl,
$R^3$ represents a group of the formula

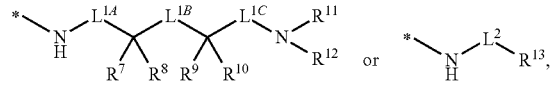

where
* represents the point of attachment to the carbonyl group,
$L^{1A}$ represents a bond,
$L^{1B}$ represents a bond, methylene or 1,2-ethanediyl,
$L^{1C}$ represents a bond or methylene,
  where methylene may be substituted by 1 or 2 substituents independently of one another selected from the group consisting of fluorine, trifluoromethyl, ($C_1$-$C_4$)-alkyl, cyclopropyl and cyclobutyl, R⁷ represents (C₁-C₆)-alkyl, (C₂-C₆)-alkynyl, cyano or phenyl,
  where (C₁-C₆)-alkyl is substituted by 1 to 3 substituents independently of one another selected from the group consisting of fluorine, trifluoromethyl, difluoromethoxy, trifluoromethoxy and phenoxy,
    where phenoxy may be substituted by 1 to 3 fluorine,
  where phenyl is substituted by 1 to 2 substituents independently of one another selected from the group consisting of cyano, nitro, difluoromethoxy, trifluoromethoxy, (C₁-C₄)-alkoxy, —NH(CO)CH₃ and (C₁-C₄)-alkenyl,
    where (C₁-C₄)-alkoxy is substituted by hydroxy,
R⁸ represents hydrogen or (C₁-C₄)-alkyl,
R⁹ represents hydrogen, cyano, 1,1,2,2-tetrafluoroethyl, trifluoromethyl, (C₁-C₆)-alkyl, (C₃-C₆)-cycloalkyl, 5- or 6-membered heteroaryl or phenyl,
  where (C₁-C₆)-alkyl may be substituted by 1 or 2 substituents independently of one another selected from the group consisting of cyano, fluorine, trifluoromethyl, difluoromethoxy, trifluoromethoxy, hydroxy, (C₁-C₄)-alkoxy, 5-membered heteroaryl, phenyl, phenoxy and benzyloxy,
    where phenyl, phenoxy and benzyloxy for their part may be substituted by 1 or 2 substituents selected from the group consisting of fluorine and chlorine,
    where 5-membered heteroaryl may be benzofused or substituted by a 5-membered heteroaryl,
  where (C₃-C₆)-cycloalkyl may be substituted by 1 or 2 substituents independently of one another selected from the group consisting of fluorine, trifluoromethyl, methyl and ethyl,
  and
  where phenyl and 5- or 6-membered heteroaryl may be substituted by 1 or 2 substituents independently of one another selected from the group consisting of fluorine, chlorine, cyano, methyl, difluoromethoxy, trifluoromethoxy, (C₁-C₄)-alkoxy and trifluoromethyl,
    where (C₁-C₄)-alkoxy may be substituted by hydroxy,
R¹⁰ represents hydrogen, methyl or ethyl,
or
R⁹ and R¹⁰ together with the carbon atom to which they are attached form a 3- to 6-membered carbocycle or an oxetanyl, tetrahydrofuranyl, tetrahydropyranyl, azetidinyl, pyrrolidinyl or piperidinyl ring,
  where the 3- to 6-membered carbocycle and the oxetanyl, tetrahydrofuranyl, tetrahydropyranyl, azetidinyl, pyrrolidinyl and piperidinyl ring may be substituted by 1 or 2 substituents independently of one another selected from the group consisting of fluorine, benzyl and methyl,
with the proviso that the radicals R⁷ and R⁹ do not both simultaneously represent phenyl,
or
R¹¹ represents hydrogen or (C₁-C₃)-alkyl,
  where (C₁-C₃)-alkyl may be substituted by 1 or 2 substituents independently of one another selected from the group consisting of fluorine, trifluoromethyl, hydroxy, methoxy and ethoxy,
R¹² represents hydrogen, (C₁-C₄)-alkyl, cyclopropyl, cyclobutyl, phenyl or benzyl,
  where (C₁-C₄)-alkyl may be substituted by 1 or 2 substituents independently of one another selected from the group consisting of fluorine, trifluoromethyl, hydroxy, (C₁-C₄)-alkoxy and phenoxy,
  and
  where phenyl and benzyl may be substituted by 1 to 3 substituents independently of one another selected from the group consisting of fluorine, chlorine and trifluoromethyl,
or
R¹¹ and R¹² together with the nitrogen atom to which they are attached form an azetidinyl, pyrrolidinyl, piperidinyl, morpholinyl, piperazinyl, thiomorpholinyl or 1,1-dioxothiomorpholinyl ring,
  where the azetidinyl, pyrrolidinyl, piperidinyl, morpholinyl, piperazinyl, thiomorpholinyl and 1,1-dioxothiomorpholinyl ring may be substituted by 1 or 2 substituents independently of one another selected from the group consisting of fluorine, trifluoromethyl, methyl, ethyl, cyclopropyl, cyclobutyl, azetidinyl, pyrrolidinyl and piperidinyl,
  and
L² represents a bond, methylene or 1,1-ethanediyl,
R¹³ represents pyrrolidinyl, piperidinyl, 1,2,3,4-tetrahydroisoquinolinyl, 1,2,3,4-tetrahydroquinolinyl, indolinyl, 8-azabicyclo[3.2.1]octanyl, 9-azabicyclo[3.3.1]nonanyl, 3-azabicyclo[4.1.0]heptanyl and quinuclidinyl, attached via a ring carbon atom,
  where pyrrolidinyl, piperidinyl, 1,2,3,4-tetrahydroisoquinolinyl, 1,2,3,4-tetrahydroquinolinyl, indolinyl, 8-azabicyclo[3.2.1]octanyl, 9-aza-bicyclo[3.3.1]nonanyl, 3-azabicyclo[4.1.0]heptanyl and quinuclidinyl may be substituted by 1 to 5 substituents independently of one another selected from the group consisting of fluorine, trifluoromethyl, methyl, ethyl, cyclopropyl, cyclobutyl and benzyl,
R⁴ represents hydrogen,
R⁵ represents hydrogen, fluorine, chlorine, bromine, cyano, methyl, ethyl, monofluoromethyl, methoxy, ethynyl or cyclopropyl,
R⁶ represents hydrogen or fluorine,
and their N-oxides, salts, solvates, salts of the N-oxides and solvates of the N-oxides and salts.

Preference in the context of the present invention is given to compounds of the formula (I) in which
A represents CH₂,
R¹ represents (C₄-C₆)-alkyl, (C₄-C₆)-cycloalkyl or phenyl,
  where (C₄-C₆)-alkyl may be substituted up to six times by fluorine,
  where (C₄-C₆)-cycloalkyl may be substituted by 1 or 2 substituents independently of one another selected from the group consisting of fluorine, trifluoromethyl and methyl,
  and
  where phenyl may be substituted by 1 to 3 substituents independently of one another selected from the group consisting of fluorine, chlorine, cyclopropyl, methoxy and methyl,
R² represents trifluoromethyl, methyl, ethyl or cyclopropyl,
R³ represents a group of the formula

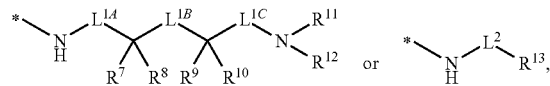

where
* represents the point of attachment to the carbonyl group,
$L^{1A}$ represents a bond,
$L^{1B}$ represents a bond or methylene,
$L^{1C}$ represents a bond or methylene,
  where methylene may be substituted by 1 or 2 substituents independently of one another selected from the group consisting of trifluoromethyl, $(C_1-C_4)$-alkyl, cyclopropyl and cyclobutyl,
$R^7$ represents $(C_1-C_4)$-alkyl, cyano or phenyl,
  where $(C_1-C_4)$-alkyl is substituted by 1 to 3 substituents independently of one another selected from the group consisting of fluorine, trifluoromethyl and phenoxy,
    where phenoxy may be substituted by 1 to 3 fluorine substituents,
  where phenyl is substituted by 1 to 2 substituents independently of one another selected from the group consisting of cyano, difluoromethoxy, trifluoromethoxy, ethoxy, —NH(CO)CH$_3$ and ethenyl,
    where ethoxy is substituted by hydroxy,
$R^8$ represents hydrogen,
$R^9$ represents hydrogen, cyano, trifluoromethyl, $(C_1-C_6)$-alkyl, $(C_3-C_6)$-cycloalkyl or phenyl,
  where $(C_1-C_6)$-alkyl may be substituted by 1 or 2 substituents independently from one another selected from the group consisting of cyano, fluorine, trifluoromethyl, hydroxy, $(C_1-C_4)$-alkoxy, phenyl, phenoxy and benzyloxy,
    where phenyl, phenoxy and benzyloxy for their part may be substituted by 1 or 2 substituents selected from the group consisting of fluorine and chlorine,
  where $(C_3-C_6)$-cycloalkyl may be substituted by 1 or 2 substituents independently of one another selected from the group consisting of fluorine, trifluoromethyl, methyl and ethyl,
  and
  where phenyl may be substituted by 1 or 2 substituents independently of one another selected from the group consisting of fluorine, chlorine, difluoromethoxy, trifluoromethoxy, ethoxy, cyano and trifluoromethyl,
    where ethoxy may be substituted by hydroxy,
$R^{10}$ represents hydrogen, methyl or ethyl,
or
$R^9$ and $R^{10}$ together with the carbon atom to which they are attached form a 3- to 6-membered carbocycle or an oxetanyl, tetrahydrofuranyl, tetrahydropyranyl, azetidinyl, pyrrolidinyl or piperidinyl ring,
  where the 3- to 6-membered carbocycle and the oxetanyl, tetrahydrofuranyl, tetrahydropyranyl, azetidinyl, pyrrolidinyl and piperidinyl ring may be substituted by 1 or 2 substituents independently of one another selected from the group consisting of fluorine, benzyl and methyl,
with the proviso that the radicals $R^7$ and $R^9$ do not both simultaneously represent phenyl,
or
$R^{11}$ represents hydrogen or $(C_1-C_3)$-alkyl,
  where $(C_1-C_3)$-alkyl may be substituted by 1 or 2 substituents independently of one another selected from the group consisting of fluorine and trifluoromethyl,
$R^{12}$ represents hydrogen, $(C_1-C_4)$-alkyl, cyclopropyl or cyclobutyl,
  where $(C_1-C_4)$-alkyl may be substituted by 1 or 2 substituents independently of one another selected from the group consisting of fluorine and trifluoromethyl,
or
$R^{11}$ and $R^{12}$ together with the nitrogen atom to which they are attached form an azetidinyl, pyrrolidinyl, piperidinyl or morpholinyl ring,
  where the azetidinyl, pyrrolidinyl, piperidinyl and morpholinyl ring may be substituted by 1 or 2 substituents independently of one another selected from the group consisting of fluorine, trifluoromethyl, methyl, ethyl, cyclopropyl and cyclobutyl,
and
$L^2$ represents a bond or methylene,
$R^{13}$ represents pyrrolidinyl, piperidinyl, 1,2,3,4-tetrahydroisoquinolinyl, 1,2,3,4-tetrahydroquinolinyl, indolinyl, 8-azabicyclo[3.2.1]octanyl, 9-azabicyclo[3.3.1]nonanyl, 3-azabicyclo[4.1.0]heptanyl or quinuclidinyl, attached via a ring carbon atom,
  where pyrrolidinyl, piperidinyl, 1,2,3,4-tetrahydroisoquinolinyl, 1,2,3,4-tetrahydroquinolinyl, 8-azabicyclo[3.2.1]octanyl, 9-azabicyclo[3.3.1]nonanyl, 3-azabicyclo[4.1.0]heptanyl and quinuclidinyl may be substituted by 1 to 5 substituents independently of one another selected from the group consisting of fluorine, trifluoromethyl, methyl, ethyl, cyclopropyl, cyclobutyl and benzyl,
$R^4$ represents hydrogen,
$R^5$ represents hydrogen, fluorine, chlorine, methyl, ethyl, monofluoromethyl, methoxy, ethynyl or cyclopropyl,
$R^6$ represents hydrogen,
and their N-oxides, salts, solvates, salts of the N-oxides and solvates of the N-oxides and salts.

Preference in the context of the present invention is given to compounds of the formula (I) in which
A represents CH$_2$,
$R^1$ represents a phenyl group of the formula

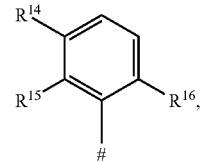

where
# represents the point of attachment to A,
and
$R^{14}$, $R^{15}$ and $R^{16}$ independently of one another represent hydrogen, fluorine, methoxy, cyclopropyl or chlorine,
with the proviso that at least two of the radicals $R^4$, $R^5$, $R^{16}$ are different from hydrogen,
$R^2$ represents methyl,
$R^3$ represents a group of the formula

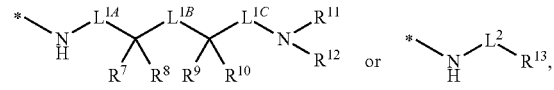

where
* represents the point of attachment to the carbonyl group,
$L^{1A}$ represents a bond,
$L^{1B}$ represents a bond,
$L^{1C}$ represents a bond,
$R^7$ represents $(C_1$-$C_4)$-alkyl, cyano or phenyl,
where $(C_1$-$C_4)$-alkyl is substituted up to five times by fluorine,
and
where phenyl is substituted by cyano, difluoromethoxy, trifluoromethoxy, ethoxy, —NH(CO)CH$_3$ or ethenyl,
where ethoxy is substituted by hydroxy,
$R^8$ represents hydrogen,
$R^9$ represents hydrogen, cyano, trifluoromethyl, $(C_1$-$C_6)$-alkyl, cyclopropyl or phenyl,
where $(C_1$-$C_6)$-alkyl may be substituted by 1 or 2 substituents independently of one another selected from the group consisting of cyano, fluorine, trifluoromethyl, hydroxy, $(C_1$-$C_4)$-alkoxy and phenyl,
and
where phenyl may be substituted by 1 or 2 substituents independently of one another selected from the group consisting of fluorine, difluoromethoxy, trifluoromethoxy, ethoxy, and chlorine,
where ethoxy may be substituted by hydroxy,
$R^{10}$ represents hydrogen, methyl or ethyl,
or
$R^9$ and $R^{10}$ together with the carbon atom to which they are attached form a 3- to 6-membered carbocycle or an oxetanyl ring,
with the proviso that the radicals $R^7$ and $R^9$ do not both simultaneously represent phenyl,
$R^{11}$ represents hydrogen,
$R^{12}$ represents hydrogen,
and
$L^2$ represents a bond,
$R^{13}$ represents piperidin-2-yl, piperidin-3-yl, piperidin-4-yl or 1,2,3,4-tetrahydroquinolin-4-yl,
where piperidin-2-yl, piperidin-3-yl and piperidin-4-yl may be substituted by 1 to 5 substituents independently of one another selected from the group consisting of trifluoromethyl and methyl,
and
where 1,2,3,4-tetrahydroquinolin-4-yl may be substituted by fluorine or trifluoromethyl,
$R^4$ represents hydrogen,
$R^5$ represents hydrogen, fluorine, chlorine, monofluoromethyl, ethynyl or methyl,
$R^6$ represents hydrogen,
and their N-oxides, salts, solvates, salts of the N-oxides and solvates of the N-oxides and salts.

Preference in the context of the present invention is given to compounds of the formula (I) in which
A represents CH$_2$, CD$_2$ or CH(CH$_3$),
$R^1$ represents $(C_4$-$C_6)$-alkyl, $(C_3$-$C_7)$-cycloalkyl or phenyl,
where $(C_4$-$C_6)$-alkyl may be substituted up to six times by fluorine,
where $(C_3$-$C_7)$-cycloalkyl may be substituted by 1 to 4 substituents independently of one another selected from the group consisting of fluorine, trifluoromethyl and $(C_1$-$C_4)$-alkyl,
and
where phenyl may be substituted by 1 to 4 substituents independently of one another selected from the group consisting of halogen, cyano, monofluoromethyl, difluoromethyl, trifluoromethyl, $(C_1$-$C_4)$-alkyl, $(C_1$-$C_4)$-alkoxy, $(C_3$-$C_6)$-cycloalkyl, difluoromethoxy and trifluoromethoxy,
$R^2$ represents hydrogen, $(C_1$-$C_4)$-alkyl, cyclopropyl, monofluoromethyl, difluoromethyl or trifluoromethyl,
$R^3$ represents a group of the formula

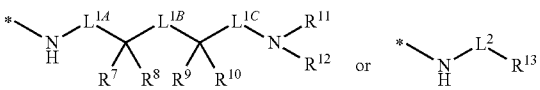

where
* represents the point of attachment to the carbonyl group,
$L^{1A}$ represents a bond or $(C_1$-$C_4)$-alkanediyl,
where $(C_1$-$C_4)$-alkanediyl may be substituted by 1 to 3 substituents independently of one another selected from the group consisting of fluorine, trifluoromethyl, $(C_1$-$C_4)$-alkyl, $(C_3$-$C_7)$-cycloalkyl, hydroxy and $(C_1$-$C_4)$-alkoxy,
$L^{1B}$ represents a bond or $(C_1$-$C_4)$-alkanediyl,
$L^{1C}$ represents a bond or $(C_1$-$C_4)$-alkanediyl,
where $(C_1$-$C_4)$-alkanediyl may be substituted by 1 to 3 substituents independently of one another selected from the group consisting of fluorine, trifluoromethyl, $(C_1$-$C_4)$-alkyl, $(C_3$-$C_7)$-cycloalkyl, hydroxy and $(C_1$-$C_4)$-alkoxy,
$R^7$ represents hydrogen, $(C_1$-$C_6)$-alkyl, $(C_2$-$C_6)$-alkenyl, $(C_2$-$C_6)$-alkynyl, $(C_3$-$C_7)$-cycloalkyl, cyano, 5- to 10-membered heteroaryl, naphthyl or phenyl,
where $(C_1$-$C_6)$-alkyl may be substituted by 1 to 3 substituents independently of one another selected from the group consisting of fluorine, trifluoromethyl, difluoromethoxy, trifluoromethoxy, hydroxy, $(C_1$-$C_4)$-alkoxy, $(C_1$-$C_4)$-alkoxycarbonyl, $(C_1$-$C_4)$-alkylsulphonyl, phenyl, phenoxy and benzyloxy,
where phenyl, phenoxy and benzyloxy for their part may be substituted by 1 to 3 halogen or $(C_1$-$C_4)$-alkoxy substituents,
where $(C_3$-$C_7)$-cycloalkyl may be substituted by 1 or 2 substituents independently of one another selected from the group consisting of fluorine, trifluoromethyl, $(C_1$-$C_4)$-alkyl and $(C_1$-$C_4)$-alkoxy,
and
where phenyl and 5- to 10-membered heteroaryl may be substituted by 1 to 3 substituents independently of one another selected from the group consisting of halogen, cyano, nitro, difluoromethyl, trifluoromethyl, difluoromethoxy, trifluoromethoxy, —NH(CO)CH$_3$, $(C_1$-$C_4)$-alkyl, $(C_1$-$C_4)$-cycloalkyl, $(C_1$-$C_4)$-alkenyl, $(C_1$-$C_4)$-alkylsulphonyl, $(C_1$-$C_4)$-alkoxycarbonyl and $(C_1$-$C_4)$-alkoxy,
where $(C_1$-$C_4)$-alkoxy may be substituted by hydroxy,
and
in which 2 adjacent carbon atoms of the phenyl may be substituted by a difluoromethylenedioxy bridge, $R^8$ represents hydrogen or $(C_1\text{-}C_4)$-alkyl, or $R^7$ and $R^8$ together with the carbon atom to which they are attached form a 3- to 7-membered carbocycle or a 4- to 7-membered heterocycle, where the 3- to 7-membered carbocycle and the 4- to 7-membered heterocycle for their part may be substituted by 1 or 2 substituents independently of one another selected from the group consisting of fluorine and $(C_1\text{-}C_4)$-alkyl, $R^9$ represents $(C_1\text{-}C_6)$-alkyl, cyano or phenyl, where $(C_1\text{-}C_6)$-alkyl is substituted by 1 to 3 substituents independently of one another selected from the group consisting of fluorine, difluoromethyl, trifluoromethyl, difluoromethoxy, trifluoromethoxy, 5- or 6-membered heteroaryl, phenoxy and benzyloxy, where phenoxy is substituted by 1 to 3 halogen substituents, where benzyloxy may be substituted by 1 to 3 halogen substituents, where 5- or 6-membered heteroaryl is substituted by a 5- or 6-membered heteroaryl, where 5- or 6-membered heteroaryl for its part may be substituted by $(C_1\text{-}C_4)$-alkyl, where phenyl is substituted by 1 to 2 substituents independently of one another selected from the group consisting of cyano, difluoromethoxy, trifluoromethoxy and $(C_1\text{-}C_4)$-alkoxy, where $(C_1\text{-}C_4)$-alkoxy is substituted by hydroxy, $R^{10}$ represents hydrogen or $(C_1\text{-}C_4)$-alkyl, $R^{11}$ represents hydrogen or $(C_1\text{-}C_4)$-alkyl, where $(C_1\text{-}C_4)$-alkyl may be substituted by 1 to 3 substituents independently of one another selected from the group consisting of fluorine, trifluoromethyl, hydroxy and $(C_1\text{-}C_4)$-alkoxy, $R^{12}$ represents hydrogen, $(C_1\text{-}C_6)$-alkyl, $(C_3\text{-}C_7)$-cycloalkyl, phenyl or benzyl, where $(C_1\text{-}C_6)$-alkyl may be substituted by 1 to 3 substituents independently of one another selected from the group consisting of fluorine, trifluoromethyl, hydroxy, $(C_1\text{-}C_4)$-alkoxy and phenoxy, and where phenyl and benzyl may be substituted by 1 to 3 substituents independently of one another selected from the group consisting of halogen and trifluoromethyl, or $R^{11}$ and $R^{12}$ together with the nitrogen atom to which they are attached form a 4- to 7-membered azaheterocycle, where the 4- to 7-membered azaheterocycle may be substituted by 1 or 2 substituents independently of one another selected from the group consisting of fluorine, trifluoromethyl, $(C_1\text{-}C_4)$-alkyl, $(C_3\text{-}C_7)$-cycloalkyl, hydroxy, $(C_1\text{-}C_4)$-alkoxy and 4- to 7-membered heterocyclyl, and $L^2$ represents a bond or $(C_1\text{-}C_4)$-alkanediyl, $R^{13}$ represents 5- to 9-membered azaheterocyclyl which is attached via a ring carbon atom, where 5- to 9-membered azaheterocyclyl may be substituted by 1 to 5 substituents independently of one another selected from the group consisting of fluorine, trifluoromethyl, $(C_1\text{-}C_4)$-alkyl, $(C_3\text{-}C_7)$-cycloalkyl and benzyl, and where 5- to 9-membered azaheterocyclyl may be fused to a phenyl ring which for its part may be substituted by 1 or 2 substituents selected from the group consisting of halogen, $(C_1\text{-}C_4)$-alkyl, $(C_1\text{-}C_4)$-alkoxy and trifluoromethyl, or represents adamantyl, $R^4$ represents hydrogen, $R^5$ represents hydrogen, halogen, cyano, monofluoromethyl, difluoromethyl, trifluoromethyl, $(C_1\text{-}C_4)$-alkyl, $(C_2\text{-}C_4)$-alkenyl, $(C_2\text{-}C_4)$-alkynyl, $(C_3\text{-}C_6)$-cycloalkyl, difluoromethoxy, trifluoromethoxy, $(C_1\text{-}C_4)$-alkoxy, amino, 4- to 7-membered heterocyclyl or 5- or 6-membered heteroaryl, $R^6$ represents hydrogen, cyano or halogen, and their N-oxides, salts, solvates, salts of the N-oxides and solvates of the N-oxides and salts.

Preference in the context of the present invention is given to compounds of the formula (I) in which A represents $CH_2$, $CD_2$ or $CH(CH_3)$, $R^1$ represents $(C_4\text{-}C_6)$-alkyl, $(C_4\text{-}C_6)$-cycloalkyl or phenyl, where $(C_4\text{-}C_6)$-alkyl may be substituted up to six times by fluorine, where $(C_4\text{-}C_6)$-cycloalkyl may be substituted by 1 or 2 substituents independently of one another selected from the group consisting of fluorine, trifluoromethyl and methyl, and where phenyl may be substituted by 1 to 4 substituents independently of one another selected from the group consisting of fluorine, chlorine, cyano, methoxy, ethoxy, difluoromethyl, trifluoromethyl, $(C_3\text{-}C_6)$-cycloalkyl and methyl, $R^2$ represents hydrogen, trifluoromethyl, $(C_1\text{-}C_3)$-alkyl or cyclopropyl, $R^3$ represents a group of the formula

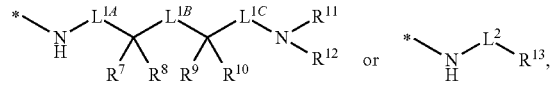

where

* represents the point of attachment to the carbonyl group, $L^{1A}$ represents a bond, $L^{1B}$ represents a bond, methylene or 1-2-ethanediyl, $L^{1C}$ represents a bond or methylene, where methylene may be substituted by 1 or 2 substituents independently of one another selected from the group consisting of fluorine, trifluoromethyl, $(C_1\text{-}C_4)$-alkyl, cyclopropyl and cyclobutyl, $R^7$ represents hydrogen, trifluoromethyl, $(C_1\text{-}C_6)$-alkyl, $(C_3\text{-}C_6)$-cycloalkyl, 5- or 6-membered heteroaryl or phenyl, where $(C_1\text{-}C_6)$-alkyl may be substituted by 1 or 2 substituents independently of one another selected from the group consisting of fluorine, trifluoromethyl, difluoromethoxy, trifluoromethoxy, hydroxy, $(C_1\text{-}C_4)$-alkoxy, phenyl, phenoxy and benzyloxy, where phenyl, phenoxy and benzyloxy for their part may be substituted by 1 or 2 substituents selected from the group consisting of fluorine and chlorine, where $(C_3\text{-}C_6)$-cycloalkyl may be substituted by 1 or 2 substituents independently of one another selected from the group consisting of fluorine, trifluoromethyl, methyl and ethyl,
and
where phenyl and 5- or 6-membered heteroaryl may be substituted by 1 or 2 substituents independently of one another selected from the group consisting of fluorine, chlorine, cyano, methyl, ethenyl, nitro, difluoromethoxy, trifluoromethoxy, —NH(CO)CH$_3$, (C$_1$-C$_4$)-alkoxy and trifluoromethyl,
where (C$_1$-C$_4$)-alkoxy may be substituted by hydroxy, $R^8$ represents hydrogen, methyl or ethyl,
or
$R^7$ and $R^8$ together with the carbon atom to which they are attached form a 3- to 6-membered carbocycle or an oxetanyl, tetrahydrofuranyl, tetrahydropyranyl, azetidinyl, pyrrolidinyl or piperidinyl ring,
where the 3- to 6-membered carbocycle and the oxetanyl, tetrahydrofuranyl, tetrahydropyranyl, azetidinyl, pyrrolidinyl and piperidinyl ring may be substituted by 1 or 2 substituents independently from one another selected from the group consisting of fluorine and methyl, $R^9$ represents (C$_1$-C$_4$)-alkyl, cyano or phenyl,
where (C$_1$-C$_4$)-alkyl is substituted by 1 to 3 substituents independently of one another selected from the group consisting of fluorine, difluoromethyl, trifluoromethyl, difluoromethoxy, trifluoromethoxy, 5-membered heteroaryl and benzyloxy,
where benzyloxy may be substituted by 1 to 3 halogen substituents,
where 5-membered heteroaryl is substituted by a 5-membered heteroaryl,
where 5-membered heteroaryl for its part may be substituted by (C$_1$-C$_4$)-alkyl,
where phenyl is substituted by 1 to 2 substituents independently of one another selected from the group consisting of cyano, difluoromethoxy, trifluoromethoxy and (C$_1$-C$_4$)-alkoxy,
where (C$_1$-C$_4$)-alkoxy is substituted by hydroxy, $R^{10}$ represents hydrogen or methyl,
$R^{11}$ represents hydrogen or (C$_1$-C$_3$)-alkyl,
where (C$_1$-C$_3$)-alkyl may be substituted by 1 or 2 substituents independently of one another selected from the group consisting of fluorine, trifluoromethyl, hydroxy, methoxy and ethoxy, $R^{12}$ represents hydrogen, (C$_1$-C$_4$)-alkyl, cyclopropyl, cyclobutyl, phenyl or benzyl,
where (C$_1$-C$_4$)-alkyl may be substituted by 1 or 2 substituents independently of one another selected from the group consisting of fluorine, trifluoromethyl, hydroxy, (C$_1$-C$_4$)-alkoxy and phenoxy,
and
where phenyl and benzyl may be substituted by 1 to 3 substituents independently of one another selected from the group consisting of fluorine, chlorine and trifluoromethyl,
or
$R^{11}$ and $R^{12}$ together with the nitrogen atom to which they are attached form an azetidinyl, pyrrolidinyl, piperidinyl, morpholinyl, piperazinyl, thiomorpholinyl or 1,1-dioxothiomorpholinyl ring,
where the azetidinyl, pyrrolidinyl, piperidinyl, morpholinyl, piperazinyl, thiomorpholinyl and 1,1-dioxothiomorpholinyl ring may be substituted by 1 or 2 substituents independently of one another selected from the group consisting of fluorine, trifluoromethyl, methyl, ethyl, cyclopropyl, cyclobutyl, azetidinyl, pyrrolidinyl and piperidinyl,
and $L^2$ represents a bond, methylene or 1,1-ethanediyl,
$R^{13}$ represents pyrrolidinyl, piperidinyl, 1,2,3,4-tetrahydroisoquinolinyl, 1,2,3,4-tetrahydroquinolinyl, indolinyl, 8-azabicyclo[3.2.1]octanyl, 9-azabicyclo[3.3.1]nonanyl, 3-azabicyclo[4.1.0]heptanyl and quinuclidinyl, attached via a ring carbon atom,
where pyrrolidinyl, piperidinyl, 1,2,3,4-tetrahydroisoquinolinyl, 1,2,3,4-tetrahydroquinolinyl, indolinyl, 8-azabicyclo[3.2.1]octanyl, 9-aza-bicyclo[3.3.1]nonanyl, 3-azabicyclo[4.1.0]heptanyl and quinuclidinyl may be substituted by 1 to 5 substituents independently of one another selected from the group consisting of fluorine, trifluoromethyl, methyl, ethyl, cyclopropyl, cyclobutyl and benzyl, $R^4$ represents hydrogen,
$R^5$ represents hydrogen, fluorine, chlorine, bromine, cyano, methyl, ethyl, monofluoromethyl, methoxy, ethynyl or cyclopropyl,
$R^6$ represents hydrogen or fluorine,
and their N-oxides, salts, solvates, salts of the N-oxides and solvates of the N-oxides and salts.

Preference in the context of the present invention is given to compounds of the formula (I) in which
A represents CH$_2$,
$R^1$ represents (C$_4$-C$_6$)-alkyl, (C$_4$-C$_6$)-cycloalkyl or phenyl,
where (C$_4$-C$_6$)-alkyl may be substituted up to six times by fluorine,
where (C$_4$-C$_6$)-cycloalkyl may be substituted by 1 or 2 substituents independently of one another selected from the group consisting of fluorine, trifluoromethyl and methyl,
and
where phenyl may be substituted by 1 to 3 substituents independently of one another selected from the group consisting of fluorine, chlorine, cyclopropyl, methoxy and methyl, $R^2$ represents trifluoromethyl, methyl, ethyl or cyclopropyl,
$R^3$ represents a group of the formula

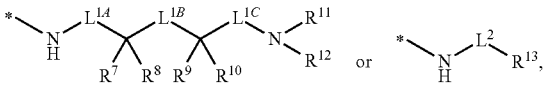

where
* represents the point of attachment to the carbonyl group,
$L^{1A}$ represents a bond,
$L^{1B}$ represents a bond or methylene,
$L^{1C}$ represents a bond or methylene,
where methylene may be substituted by 1 or 2 substituents independently of one another selected from the group consisting of trifluoromethyl, (C$_1$-C$_4$)-alkyl, cyclopropyl and cyclobutyl, $R^7$ represents hydrogen, trifluoromethyl, (C$_1$-C$_6$)-alkyl, (C$_3$-C$_6$)-cycloalkyl or phenyl,
where (C$_1$-C$_6$)-alkyl may be substituted by 1 or 2 substituents independently of one another selected from the group consisting of fluorine, trifluoromethyl, hydroxy, $(C_1-C_4)$-alkoxy, phenyl, phenoxy and benzyloxy,
  where phenyl, phenoxy and benzyloxy for their part may be substituted by 1 or 2 substituents selected from the group consisting of fluorine and chlorine,
where $(C_3-C_6)$-cycloalkyl may be substituted by 1 or 2 substituents independently of one another selected from the group consisting of fluorine, trifluoromethyl, methyl and ethyl,
and
where phenyl may be substituted by 1 or 2 substituents independently of one another selected from the group consisting of fluorine, chlorine, cyano, nitro, difluoromethoxy, trifluoromethoxy, —NH(CO)CH$_3$, ethenyl, ethoxy and trifluoromethyl,
  where ethoxy may be substituted by hydroxy,
$R^8$ represents hydrogen, methyl or ethyl,
or
$R^7$ and $R^8$ together with the carbon atom to which they are attached form a 3- to 6-membered carbocycle or an oxetanyl, tetrahydrofuranyl, tetrahydropyranyl, azetidinyl, pyrrolidinyl or piperidinyl ring,
  where the 3- to 6-membered carbocycle and the oxetanyl, tetrahydrofuranyl, tetrahydropyranyl, azetidinyl, pyrrolidinyl and piperidinyl ring may be substituted by 1 or 2 substituents independently of one another selected from the group consisting of fluorine and methyl,
$R^9$ represents ethyl, propyl, cyano or phenyl,
  where ethyl and propyl are substituted by 1 to 3 substituents independently of one another selected from the group consisting of fluorine, trifluoromethyl and benzyloxy,
    where benzyloxy may be substituted by 1 to 3 halogen substituents,
  where phenyl is substituted by cyano, difluoromethoxy, trifluoromethoxy or ethoxy,
    where ethoxy is substituted by hydroxy,
$R^{10}$ represents hydrogen or methyl,
$R^{11}$ represents hydrogen or $(C_1-C_3)$-alkyl,
  where $(C_1-C_3)$-alkyl may be substituted by 1 or 2 substituents independently of one another selected from the group consisting of fluorine and trifluoromethyl,
$R^{12}$ represents hydrogen, $(C_1-C_4)$-alkyl, cyclopropyl or cyclobutyl,
  where $(C_1-C_4)$-alkyl may be substituted by 1 or 2 substituents independently of one another selected from the group consisting of fluorine and trifluoromethyl,
or
$R^{11}$ and $R^{12}$ together with the nitrogen atom to which they are attached form an azetidinyl, pyrrolidinyl, piperidinyl or morpholinyl ring,
  where the azetidinyl, pyrrolidinyl, piperidinyl and morpholinyl ring may be substituted by 1 or 2 substituents independently of one another selected from the group consisting of fluorine, trifluoromethyl, methyl, ethyl, cyclopropyl and cyclobutyl,
and
$L^2$ represents a bond or methylene,
$R^{13}$ represents pyrrolidinyl, piperidinyl, 1,2,3,4-tetrahydroisoquinolinyl, 1,2,3,4-tetrahydroquinolinyl, indolinyl, 8-azabicyclo[3.2.1]octanyl, 9-azabicyclo[3.3.1]nonanyl, 3-azabicyclo[4.1.0]heptanyl and quinuclidinyl, attached via a ring carbon atom,
  where pyrrolidinyl, piperidinyl, 1,2,3,4-tetrahydroisoquinolinyl, 1,2,3,4-tetrahydroquinolinyl, 8-azabicyclo[3.2.1]octanyl, 9-azabicyclo-[3.3.1]nonanyl, 3-azabicyclo[4.1.0]heptanyl and quinuclidinyl may be substituted by 1 to 5 substituents independently of one another selected from the group consisting of fluorine, trifluoromethyl, methyl, ethyl, cyclopropyl, cyclobutyl and benzyl,
$R^4$ represents hydrogen,
$R^5$ represents hydrogen, fluorine, chlorine, methyl, ethyl, monofluoromethyl, methoxy, ethynyl or cyclopropyl,
$R^6$ represents hydrogen,
and their N-oxides, salts, solvates, salts of the N-oxides and solvates of the N-oxides and salts.

Preference in the context of the present invention is given to compounds of the formula (I) in which
A represents CH$_2$,
$R^1$ represents a phenyl group of the formula

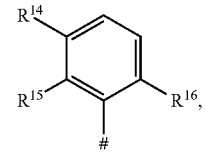

where
# represents the point of attachment to A,
and
$R^{14}$, $R^{15}$ and $R^{16}$ independently of one another represent hydrogen, fluorine, methoxy, cyclopropyl or chlorine, with the proviso that at least two of the radicals $R^{14}$, $R^{15}$, $R^{16}$ are different from hydrogen,
$R^2$ represents methyl,
$R^3$ represents a group of the formula

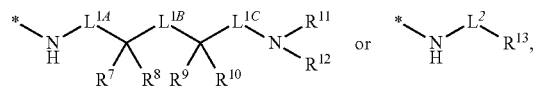

where
* represents the point of attachment to the carbonyl group,
$L^{1A}$ represents a bond,
$L^{1B}$ represents a bond, $L^{1C}$ represents a bond,
$R^7$ represents hydrogen, trifluoromethyl, $(C_1-C_6)$-alkyl, $(C_3-C_6)$-cycloalkyl or phenyl,
  where $(C_1-C_6)$-alkyl may be substituted by 1 or 2 substituents independently of one another selected from the group consisting of fluorine, trifluoromethyl, hydroxy, $(C_1-C_4)$-alkoxy and phenyl,
  and
  where phenyl may be substituted by 1 or 2 substituents independently of one another selected from the group consisting of fluorine, difluoromethoxy, trifluoromethoxy, ethenyl, ethoxy and chlorine,
    where ethoxy may be substituted by hydroxy,
$R^8$ represents hydrogen, methyl or ethyl,
$R^9$ represents ethyl, cyano or phenyl,
  where ethyl is substituted up to five times by fluorine, where phenyl is substituted by cyano, difluoromethoxy, trifluoromethoxy or ethoxy,
where ethoxy is substituted by hydroxy,
$R^{10}$ represents hydrogen or methyl,
$R^{11}$ represents hydrogen,
$R^{12}$ represents hydrogen,
and
$L^2$ represents a bond,
$R^{13}$ represents piperidin-2-yl, piperidin-3-yl, piperidin-4-yl or 1,2,3,4-tetrahydroquinolin-4-yl,
where piperidin-2-yl, piperidin-3-yl and piperidin-4-yl may be substituted by 1 to 5 substituents independently of one another selected from the group consisting of trifluoromethyl and methyl, and
where 1,2,3,4-tetrahydroquinolin-4-yl may be substituted by fluorine or trifluoromethyl,
$R^4$ represents hydrogen,
$R^5$ represents hydrogen, fluorine, chlorine, monofluoromethyl, methoxy, ethynyl or methyl,
$R^6$ represents hydrogen,
and their N-oxides, salts, solvates, salts of the N-oxides and solvates of the N-oxides and salts.

Preference in the context of the present invention is given to compounds of the formula (I) in which
A represents $CH_2$, $CD_2$ or $CH(CH_3)$,
$R^1$ represents $(C_4-C_6)$-alkyl, $(C_3-C_7)$-cycloalkyl or phenyl,
where $(C_4-C_6)$-alkyl may be substituted up to six times by fluorine,
where $(C_3-C_7)$-cycloalkyl may be substituted by 1 to 4 substituents independently of one another selected from the group consisting of fluorine, trifluoromethyl and $(C_1-C_4)$-alkyl,
and
where phenyl may be substituted by 1 to 4 substituents independently of one another selected from the group consisting of halogen, cyano, monofluoromethyl, difluoromethyl, trifluoromethyl, $(C_1-C_4)$-alkyl, $(C_1-C_4)$-alkoxy, $(C_3-C_6)$-cycloalkyl, difluoromethoxy and trifluoromethoxy,
$R^2$ represents hydrogen, $(C_1-C_4)$-alkyl, cyclopropyl, monofluoromethyl, difluoromethyl or trifluoromethyl,
$R^3$ represents a group of the formula

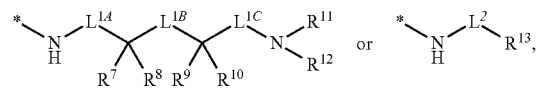

where
* represents the point of attachment to the carbonyl group,
$L^{1A}$ represents a bond or $(C_1-C_4)$-alkanediyl,
where $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy,
$L^{1B}$ represents a bond or $(C_1-C_4)$-alkanediyl,
$L^{1C}$ represents a bond or $(C_1-C_4)$-alkanediyl,
where $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy, $R^7$ represents hydrogen, $(C_1-C_6)$-alkyl, $(C_2-C_6)$-alkenyl, $(C_2-C_6)$-alkynyl, $(C_3-C_7)$-cycloalkyl, cyano, 5- to 10-membered heteroaryl, naphthyl or phenyl,
where $(C_1-C_6)$-alkyl may be substituted by 1 to 3 substituents independently of one another selected from the group consisting of fluorine, trifluoromethyl, difluoromethoxy, trifluoromethoxy, hydroxy, $(C_1-C_4)$-alkoxy, $(C_1-C_4)$-alkoxycarbonyl, $(C_1-C_4)$-alkylsulphonyl, phenyl, phenoxy and benzyloxy,
where phenyl, phenoxy and benzyloxy for their part may be substituted by 1 to 3 halogen or $(C_1-C_4)$-alkoxy substituents,
where $(C_3-C_7)$-cycloalkyl may be substituted by 1 or 2 substituents independently of one another selected from the group consisting of fluorine, trifluoromethyl, $(C_1-C_4)$-alkyl and $(C_1-C_4)$-alkoxy,
and
where phenyl and 5- to 10-membered heteroaryl may be substituted by 1 to 3 substituents independently of one another selected from the group consisting of halogen, cyano, nitro, difluoromethyl, trifluoromethyl, difluoromethoxy, trifluoromethoxy, —NH(CO)$CH_3$, $(C_1-C_4)$-alkyl, $(C_1-C_4)$-cycloalkyl, $(C_1-C_4)$-alkenyl, $(C_1-C_4)$-alkylsulphonyl, $(C_1-C_4)$-alkoxycarbonyl and $(C_1-C_4)$-alkoxy,
where $(C_1-C_4)$-alkoxy may be substituted by hydroxy,
and
where phenyl may be substituted on 2 adjacent carbon atoms by a difluoromethylenedioxy bridge,
$R^8$ represents hydrogen or $(C_1-C_4)$-alkyl,
or
$R^7$ and $R^8$ together with the carbon atom to which they are attached form a 3- to 7-membered carbocycle or a 4- to 7-membered heterocycle,
where the 3- to 7-membered carbocycle and the 4- to 7-membered heterocycle for their part may be substituted by 1 or 2 substituents independently of one another selected from the group consisting of fluorine and $(C_1-C_4)$-alkyl,
$R^9$ represents hydrogen, cyano, $(C_1-C_6)$-alkyl, $(C_2-C_6)$-alkenyl, $(C_2-C_6)$-alkynyl, $(C_3-C_7)$-cycloalkyl, 5- to 10-membered heteroaryl or phenyl,
where $(C_1-C_6)$-alkyl may be substituted by 1 to 3 substituents independently of one another selected from the group consisting of fluorine, difluoromethyl, trifluoromethyl, difluoromethoxy, trifluoromethoxy, hydroxy, cyano, $(C_1-C_4)$-alkoxy, $(C_1-C_4)$-alkoxycarbonyl, $(C_1-C_4)$-alkylsulphonyl, 5- or 6-membered heteroaryl, phenyl, phenoxy and benzyloxy,
where phenyl, phenoxy and benzyloxy for their part may be substituted by 1 to 3 halogen or $(C_1-C_4)$-alkoxy substituents,
where 5- or 6-membered heteroaryl may be benzofused or substituted by a 5- or 6-membered heteroaryl,
where 5- or 6-membered heteroaryl may be substituted by $(C_1-C_4)$-alkyl or trifluoromethyl,
where $(C_3-C_7)$-cycloalkyl may be substituted by 1 or 2 substituents independently of one another selected from the group consisting of fluorine, trifluoromethyl, $(C_1-C_4)$-alkyl and $(C_1-C_4)$-alkoxy, and
where phenyl and 5- to 10-membered heteroaryl may be substituted by 1 to 3 substituents independently of one another selected from the group consisting of halogen, cyano, difluoromethyl, trifluoromethyl, difluoromethoxy, trifluoromethoxy, $(C_1-C_4)$-alkyl, $(C_1-C_4)$-cycloalkyl, $(C_1-C_4)$-alkoxy, $(C_1-C_4)$-alkoxycarbonyl and $(C_1-C_4)$-alkylsulphonyl,
where $(C_1-C_4)$-alkoxy may be substituted by hydroxy,
and
where phenyl may be substituted on 2 adjacent carbon atoms by a difluoromethylenedioxy bridge,
$R^{10}$ represents hydrogen or $(C_1-C_4)$-alkyl,
or
$R^9$ and $R^{10}$ together with the carbon atom to which they are attached form a 3- to 7-membered carbocycle or a 4- to 7-membered heterocycle,
where the 3- to 7-membered carbocycle and the 4- to 7-membered heterocycle for their part may be substituted by 1 or 2 substituents independently of one another selected from the group consisting of fluorine, benzyl and $(C_1-C_4)$-alkyl,
with the proviso that the radicals $R^7$ and $R^9$ do not both simultaneously represent phenyl,
or
$R^7$ and $R^9$ together with the carbon atoms to which they are attached and the group $L^{1B}$ form a 3- to 7-membered carbocycle or a 4- to 7-membered heterocycle,
where the 3- to 7-membered carbocycle may be substituted by 1 or 2 substituents independently of one another selected from the group consisting of $(C_1-C_4)$-alkyl, fluorine, hydroxy and $(C_1-C_4)$-alkoxy,
with the proviso that not more than one of the radical pairs $R^7$ and $R^8$, $R^9$ and $R^{10}$ and $R^7$ and $R^9$, respectively, simultaneously forms a carbo- or heterocycle,
$R^{11}$ represents $(C_1-C_4)$-alkyl,
where $(C_1-C_4)$-alkyl is substituted by 1 to 3 substituents independently of one another selected from the group consisting of fluorine, trifluoromethyl, hydroxy and $(C_1-C_4)$-alkoxy,
$R^{12}$ represents hydrogen, $(C_1-C_6)$-alkyl, $(C_3-C_7)$-cycloalkyl, phenyl or benzyl,
where $(C_1-C_6)$-alkyl may be substituted by 1 to 3 substituents independently of one another selected from the group consisting of fluorine, trifluoromethyl, hydroxy, $(C_1-C_4)$-alkoxy and phenoxy,
and
where phenyl and benzyl may be substituted by 1 to 3 substituents independently of one another consisting of halogen and trifluoromethyl,
or
$R^{11}$ and $R^{12}$ together with the nitrogen atom to which they are attached form a 4- to 7-membered azaheterocycle,
where the 4- to 7-membered azaheterocycle is substituted by 1 or 2 substituents independently of one another selected from the group consisting of $(C_3-C_7)$-cycloalkyl and 4- to 7-membered heterocyclyl,
and
$L^2$ represents a bond or $(C_1-C_4)$-alkanediyl,
$R^{13}$ represents 5- to 9-membered azaheterocyclyl which is attached via a ring carbon atom,
where 5- to 9-membered azaheterocyclyl may be substituted by 1 to 5 substituents independently of one another selected from the group consisting of fluorine, trifluoromethyl, $(C_1-C_4)$-alkyl, $(C_3-C_7)$-cycloalkyl and benzyl,
and
where 5- to 9-membered azaheterocyclyl may be fused to a phenyl ring which for its part may be substituted by 1 or 2 substituents selected from the group consisting of halogen, $(C_1-C_4)$-alkyl, $(C_1-C_4)$-alkoxy and trifluoromethyl,
or
represents adamantyl,
$R^4$ represents hydrogen,
$R^5$ represents hydrogen, halogen, cyano, monofluoromethyl, difluoromethyl, trifluoromethyl, $(C_1-C_4)$-alkyl, $(C_2-C_4)$-alkenyl, $(C_2-C_4)$-alkynyl, $(C_3-C_6)$-cycloalkyl, difluoromethoxy, trifluoromethoxy, $(C_1-C_4)$-alkoxy, amino, 4- to 7-membered heterocyclyl or 5- or 6-membered heteroaryl,
$R^6$ represents hydrogen, cyano or halogen,
and their N-oxides, salts, solvates, salts of the N-oxides and solvates of the N-oxides and salts.

Preference in the context of the present invention is given to compounds of the formula (I) in which
A represents $CH_2$, $CD_2$ or $CH(CH_3)$,
$R^1$ represents $(C_4-C_6)$-alkyl, $(C_4-C_6)$-cycloalkyl or phenyl,
where $(C_4-C_6)$-alkyl may be substituted up to six times by fluorine,
where $(C_4-C_6)$-cycloalkyl may be substituted by 1 or 2 substituents independently of one another selected from the group consisting of fluorine, trifluoromethyl and methyl,
and
where phenyl may be substituted by 1 to 4 substituents independently of one another selected from the group consisting of fluorine, chlorine, cyano, methoxy, ethoxy, difluoromethyl, trifluoromethyl, $(C_3-C_6)$-cycloalkyl and methyl,
$R^2$ represents hydrogen, trifluoromethyl, $(C_1-C_3)$-alkyl and cyclopropyl,
$R^3$ represents a group of the formula

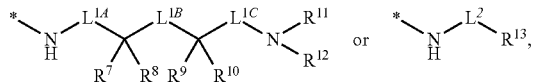

where
* represents the point of attachment to the carbonyl group,
$L^{1A}$ represents a bond,
$L^{1B}$ represents a bond, methylene or 1,2-ethanediyl,
$L^{1C}$ represents a bond or methylene,
where methylene may be substituted by 1 or 2 substituents independently of one another selected from the group consisting of fluorine, trifluoromethyl, $(C_1-C_4)$-alkyl, cyclopropyl and cyclobutyl,
$R^7$ represents hydrogen, trifluoromethyl, $(C_1-C_6)$-alkyl, $(C_3-C_6)$-cycloalkyl, 5- or 6-membered heteroaryl or phenyl,
where $(C_1-C_6)$-alkyl may be substituted by 1 or 2 substituents independently of one another selected from the group consisting of fluorine, trifluoromethyl, difluoromethoxy, trifluoromethoxy, hydroxy, $(C_1-C_4)$-alkoxy, phenyl, phenoxy and benzyloxy, where phenyl, phenoxy and benzyloxy for their part may be substituted by 1 or 2 substituents selected from the group consisting of fluorine and chlorine, where $(C_3-C_6)$-cycloalkyl may be substituted by 1 or 2 substituents independently of one another selected from the group consisting of fluorine, trifluoromethyl, methyl and ethyl, and where phenyl and 5- or 6-membered heteroaryl may be substituted by 1 or 2 substituents independently of one another selected from the group consisting of fluorine, chlorine, cyano, nitro, methyl, ethenyl, difluoromethoxy, trifluoromethoxy, —NH(CO)CH$_3$, $(C_1-C_4)$-alkoxy and trifluoromethyl, where $(C_1-C_4)$-alkoxy may be substituted by hydroxy, $R^8$ represents hydrogen, methyl or ethyl, or $R^7$ and $R^8$ together with the carbon atom to which they are attached form a 3- to 6-membered carbocycle or an oxetanyl, tetrahydrofuranyl, tetrahydropyranyl, azetidinyl, pyrrolidinyl or piperidinyl ring, where the 3- to 6-membered carbocycle and the oxetanyl, tetrahydrofuranyl, tetrahydropyranyl, azetidinyl, pyrrolidinyl and piperidinyl ring may be substituted by 1 or 2 substituents independently of one another selected from the group consisting of fluorine and methyl, $R^9$ represents hydrogen, cyano, 1,1,2,2-tetrafluoroethyl, trifluoromethyl, $(C_1-C_6)$-alkyl, $(C_3-C_6)$-cycloalkyl, 5- or 6-membered heteroaryl or phenyl, where $(C_1-C_6)$-alkyl may be substituted by 1 or 2 substituents independently of one another selected from the group consisting of cyano, fluorine, trifluoromethyl, difluoromethoxy, trifluoromethoxy, hydroxy, $(C_1-C_4)$-alkoxy, 5-membered heteroaryl, phenyl, phenoxy and benzyloxy, where phenyl, phenoxy and benzyloxy for their part may be substituted by 1 or 2 substituents selected from the group consisting of fluorine and chlorine, where 5-membered heteroaryl may be benzofused or substituted by a 5-membered heteroaryl, where $(C_3-C_6)$-cycloalkyl may be substituted by 1 or 2 substituents independently of one another selected from the group consisting of fluorine, trifluoromethyl, methyl and ethyl, and where phenyl and 5- or 6-membered heteroaryl may be substituted by 1 or 2 substituents independently of one another selected from the group consisting of fluorine, chlorine, cyano, methyl, difluoromethoxy, trifluoromethoxy, $(C_1-C_4)$-alkoxy and trifluoromethyl, where $(C_1-C_4)$-alkoxy may be substituted by hydroxy, $R^{10}$ represents hydrogen, methyl or ethyl, or $R^9$ and $R^{10}$ together with the carbon atom to which they are attached form a 3- to 6-membered carbocycle or an oxetanyl, tetrahydrofuranyl, tetrahydropyranyl, azetidinyl, pyrrolidinyl or piperidinyl ring, where the 3- to 6-membered carbocycle and the oxetanyl, tetrahydrofuranyl, tetrahydropyranyl, azetidinyl, pyrrolidinyl and piperidinyl ring may be substituted by 1 or 2 substituents independently of one another selected from the group consisting of fluorine, benzyl and methyl, with the proviso that the radicals $R^7$ and $R^9$ do not both simultaneously represent methyl, or $R^7$ and $R^9$ together with the carbon atoms to which they are attached and the group $L^{1B}$ form a cyclopentyl, cyclohexyl, azetidinyl, oxetanyl, pyrrolidinyl, tetrahydrofuranyl, piperidinyl or tetrahydropyranyl ring, with the proviso that not more than one of the radical pairs $R^7$ and $R^8$, $R^9$ and $R^{10}$ and $R^7$ and $R^9$, respectively, simultaneously represents one of the carbo- or heterocycles mentioned above, $L^2$ represents a bond, methylene or 1,1-ethanediyl, $R^{11}$ represents methyl and ethyl, where methyl and ethyl are substituted by 1 to 3 substituents independently of one another selected from the group consisting of fluorine, trifluoromethyl, hydroxy and methoxy, $R^{12}$ represents hydrogen, $(C_1-C_4)$-alkyl, $(C_3-C_6)$-cycloalkyl, phenyl or benzyl, where $(C_1-C_4)$-alkyl may be substituted by 1 to 3 substituents independently of one another selected from the group consisting of fluorine, trifluoromethyl, hydroxy, $(C_1-C_4)$-alkoxy and phenoxy, and where phenyl and benzyl may be substituted by 1 to 3 substituents independently of one another selected from the group consisting of halogen and trifluoromethyl, or $R^{11}$ and $R^{12}$ together with the nitrogen atom to which they are attached form a 4- to 6-membered azaheterocycle, where the 4- to 6-membered azaheterocycle may be substituted by 1 or 2 substituents independently of one another selected from the group consisting of $(C_3-C_6)$-cycloalkyl and 4- to 6-membered heterocyclyl, $R^{13}$ represents pyrrolidinyl, piperidinyl, 1,2,3,4-tetrahydroisoquinolinyl, 1,2,3,4-tetrahydroquinolinyl, indolinyl, 8-azabicyclo[3.2.1]octanyl, 9-azabicyclo[3.3.1]nonanyl, 3-azabicyclo[4.1.0]heptanyl and quinuclidinyl, attached via a ring carbon atom, where pyrrolidinyl, piperidinyl, 1,2,3,4-tetrahydroisoquinolinyl, 1,2,3,4-tetrahydroquinolinyl, indolinyl, 8-azabicyclo[3.2.1]octanyl, 9-azabicyclo[3.3.1]nonanyl, 3-azabicyclo[4.1.0]heptanyl and quinuclidinyl may be substituted by 1 to 5 substituents independently of one another selected from the group consisting of fluorine, trifluoromethyl, methyl, ethyl, cyclopropyl, cyclobutyl and benzyl, $R^4$ represents hydrogen, $R^5$ represents hydrogen, fluorine, chlorine, bromine, cyano, methyl, ethyl, monofluoromethyl, methoxy, ethynyl or cyclopropyl, $R^6$ represents hydrogen or fluorine, and their N-oxides, salts, solvates, salts of the N-oxides and solvates of the N-oxides and salts.

Preference in the context of the present invention is given to compounds of the formula (I) in which A represents CH$_2$, $R^1$ represents $(C_4-C_6)$-alkyl, $(C_4-C_6)$-cycloalkyl or phenyl, where $(C_4-C_6)$-alkyl may be substituted up to six times by fluorine,
where $(C_4-C_6)$-cycloalkyl may be substituted by 1 or 2 substituents independently of one another selected from the group consisting of fluorine, trifluoromethyl and methyl,
and
where phenyl may be substituted by 1 to 3 substituents independently of one another selected from the group consisting of fluorine, chlorine, cyclopropyl, methoxy and methyl,
$R^2$ represents trifluoromethyl, methyl, ethyl and cyclopropyl,
$R^3$ represents a group of the formula

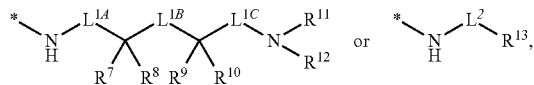

where
* represents the point of attachment to the carbonyl group,
$L^{1A}$ represents a bond,
$L^{1B}$ represents a bond or methylene,
$L^{1C}$ represents a bond or methylene,
where methylene may be substituted by 1 or 2 substituents independently of one another selected from the group consisting of trifluoromethyl, $(C_1-C_4)$-alkyl, cyclopropyl and cyclobutyl,
$R^7$ represents hydrogen, trifluoromethyl, $(C_1-C_6)$-alkyl, $(C_3-C_6)$-cycloalkyl or phenyl,
where $(C_1-C_6)$-alkyl may be substituted by 1 or 2 substituents independently of one another selected from the group consisting of fluorine, trifluoromethyl, hydroxy, $(C_1-C_4)$-alkoxy, phenyl, phenoxy and benzyloxy,
where phenyl, phenoxy and benzyloxy for their part may be substituted by 1 or 2 substituents selected from the group consisting of fluorine and chlorine,
where $(C_3-C_6)$-cycloalkyl may be substituted by 1 or 2 substituents independently of one another selected from the group consisting of fluorine, trifluoromethyl, methyl and ethyl,
and
where phenyl may be substituted by 1 or 2 substituents independently of one another selected from the group consisting of fluorine, chlorine, cyano, nitro, ethenyl, difluoromethoxy, trifluoromethoxy, —NH(CO)CH$_3$, ethoxy and trifluoromethyl,
where ethoxy may be substituted by hydroxy,
$R^8$ represents hydrogen, methyl or ethyl,
or
$R^7$ and $R^8$ together with the carbon atom to which they are attached form a 3- to 6-membered carbocycle or an oxetanyl, tetrahydrofuranyl, tetrahydropyranyl, azetidinyl, pyrrolidinyl or piperidinyl ring,
where the 3- to 6-membered carbocycle and the oxetanyl, tetrahydrofuranyl, tetrahydropyranyl, azetidinyl, pyrrolidinyl and piperidinyl ring may be substituted by 1 or 2 substituents independently of one another selected from the group consisting of fluorine and methyl,
$R^9$ represents hydrogen, cyano, trifluoromethyl, $(C_1-C_6)$-alkyl, $(C_3-C_6)$-cycloalkyl or phenyl,
where $(C_1-C_6)$-alkyl may be substituted by 1 or 2 substituents independently of one another selected from the group consisting of cyano, fluorine, trifluoromethyl, hydroxy, $(C_1-C_4)$-alkoxy, phenyl, phenoxy and benzyloxy,
where phenyl, phenoxy and benzyloxy for their part may be substituted by 1 or 2 substituents selected from the group consisting of fluorine and chlorine,
where $(C_3-C_6)$-cycloalkyl may be substituted by 1 or 2 substituents independently of one another selected from the group consisting of fluorine, trifluoromethyl, methyl and ethyl,
and
where phenyl may be substituted by 1 or 2 substituents independently of one another selected from the group consisting of fluorine, chlorine, cyano, difluoromethoxy, trifluoromethoxy, ethoxy and trifluoromethyl,
where ethoxy may be substituted by hydroxy,
$R^{10}$ represents hydrogen, methyl or ethyl,
or
$R^9$ and $R^{10}$ together with the carbon atom to which they are attached form a 3- to 6-membered carbocycle or an oxetanyl, tetrahydrofuranyl, tetrahydropyranyl, azetidinyl, pyrrolidinyl or piperidinyl ring,
where the 3- to 6-membered carbocycle and the oxetanyl, tetrahydrofuranyl, tetrahydropyranyl, azetidinyl, pyrrolidinyl and piperidinyl ring may be substituted by 1 or 2 substituents independently of one another selected from the group consisting of fluorine, benzyl and methyl,
with the proviso that the radicals $R^7$ and $R^9$ do not both simultaneously represent phenyl,
or
$R^7$ and $R^9$ together with the carbon atoms to which they are attached and the group $L^{1B}$ form a cyclopentyl, cyclohexyl, azetidinyl, oxetanyl, pyrrolidinyl, tetrahydrofuranyl, piperidinyl or tetrahydropyranyl ring,
with the proviso that not more than one of the radical pairs $R^7$ and $R^8$, $R^9$ and $R^{10}$ and $R^7$ and $R^9$, respectively, simultaneously forms one of the carbo- or heterocycles mentioned above,
$R^{11}$ represents methyl or ethyl,
where methyl and ethyl are substituted by 1 to 3 substituents independently of one another selected from the group consisting of fluorine, trifluoromethyl, hydroxy and methoxy,
$R^{12}$ represents hydrogen, $(C_1-C_4)$-alkyl, $(C_3-C_6)$-cycloalkyl, phenyl or benzyl,
where $(C_1-C_4)$-alkyl may be substituted by 1 to 3 substituents independently of one another selected from the group consisting of fluorine, trifluoromethyl, hydroxy, $(C_1-C_4)$-alkoxy and phenoxy,
and
where phenyl and benzyl may be substituted by 1 to 3 substituents independently of one another selected from the group consisting of halogen and trifluoromethyl,
or
$R^{11}$ and $R^{12}$ together with the nitrogen atom to which they are attached form a 4- to 6-membered azaheterocycle,
where the 4- to 6-membered azaheterocycle may be substituted by 1 or 2 substituents independently of one another selected from the group consisting of $(C_3-C_6)$-cycloalkyl and 4- to 6-membered heterocyclyl,
and
$L^2$ represents a bond or methylene,
$R^{13}$ represents pyrrolidinyl, piperidinyl, 1,2,3,4-tetrahydroisoquinolinyl, 1,2,3,4-tetrahydroquinolinyl, indolinyl, 8-azabicyclo[3.2.1]octanyl, 9-aza-bicyclo[3.3.1]nonanyl, 3-azabicyclo[4.1.0]heptanyl and quinuclidinyl, attached via a ring carbon atom,
where pyrrolidinyl, piperidinyl, 1,2,3,4-tetrahydroisoquinolinyl, 1,2,3,4-tetrahydroquinolinyl, 8-azabicyclo[3.2.1]octanyl, 9-aza-bicyclo[3.3.1]nonanyl, 3-azabicyclo[4.1.0]heptanyl and quinuclidinyl may be substituted by 1 to 5 substituents independently of one another selected from the group consisting of fluorine, trifluoromethyl, methyl, ethyl, cyclopropyl, cyclobutyl and benzyl,
$R^4$ represents hydrogen,
$R^5$ represents hydrogen, fluorine, chlorine, methyl, ethyl, monofluoromethyl, methoxy, ethynyl or cyclopropyl,
$R^6$ represents hydrogen,
and their N-oxides, salts, solvates, salts of the N-oxides and solvates of the N-oxides and salts.

Preference in the context of the present invention is given to compounds of the formula (I) in which
A represents $CH_2$,
$R^1$ represents a phenyl group of the formula

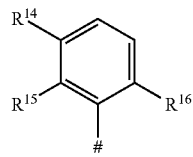

where
# represents the point of attachment to A,
and
$R^{14}$, $R^{15}$ and $R^{16}$ independently of one another represent hydrogen, fluorine, methoxy, cyclopropyl or chlorine,
with the proviso that at two of the radicals $R^{14}$, $R^{15}$, $R^{16}$ are different from hydrogen,
$R^2$ represents methyl,
$R^3$ represents a group of the formula

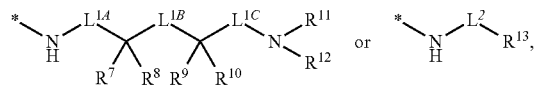

where
* represents the point of attachment to the carbonyl group,
$L^{1A}$ represents a bond,
$L^{1B}$ represents a bond,
$L^{1C}$ represents a bond,
$R^7$ represents hydrogen, trifluoromethyl, $(C_1-C_6)$-alkyl, $(C_3-C_6)$-cycloalkyl or phenyl,
where $(C_1-C_6)$-alkyl may be substituted by 1 or 2 substituents independently of one another selected from the group consisting of fluorine, trifluoromethyl, hydroxy, $(C_1-C_4)$-alkoxy and phenyl,
and
where phenyl may be substituted by 1 or 2 substituents independently of one another selected from the group consisting of fluorine, ethenyl, difluoromethoxy, trifluoromethoxy, ethoxy and chlorine,
where ethoxy may be substituted by hydroxy,
$R^8$ represents hydrogen, methyl or ethyl,
$R^9$ represents hydrogen, cyano, trifluoromethyl, $(C_1-C_6)$-alkyl, cyclopropyl or phenyl,
where $(C_1-C_6)$-alkyl may be substituted by 1 or 2 substituents independently of one another selected from the group consisting of cyano, fluorine, trifluoromethyl, hydroxy, $(C_1-C_4)$-alkoxy and phenyl,
and
where phenyl may be substituted by 1 or 2 substituents independently of one another selected from the group consisting of fluorine, difluoromethoxy, trifluoromethoxy, ethoxy and chlorine,
where ethoxy may be substituted by hydroxy,
$R^{10}$ represents hydrogen, methyl or ethyl,
or
$R^9$ and $R^{10}$ together with the carbon atom to which they are attached form a 3- to 6-membered carbocycle or an oxetanyl ring,
with the proviso that the radicals $R^7$ and $R^9$ do not both simultaneously represent phenyl,
$R^{11}$ represents methyl or ethyl,
where methyl and ethyl are substituted by 1 to 3 substituents independently of one another selected from the group consisting of fluorine, trifluoromethyl, hydroxy and methoxy,
$R^{12}$ represents hydrogen, $(C_1-C_4)$-alkyl, $(C_3-C_6)$-cycloalkyl, phenyl or benzyl,
where $(C_1-C_4)$-alkyl may be substituted by 1 to 3 substituents independently of one another selected from the group consisting of fluorine, trifluoromethyl, hydroxy, $(C_1-C_4)$-alkoxy and phenoxy,
and
where phenyl and benzyl may be substituted by 1 to 3 substituents independently of one another selected from the group consisting of halogen and trifluoromethyl,
or
$R^{11}$ and $R^{12}$ together with the nitrogen atom to which they are attached form a 4- to 6-membered azaheterocycle,
where the 4- to 6-membered azaheterocycle may be substituted by 1 or 2 substituents independently of one another selected from the group consisting of $(C_3-C_6)$-cycloalkyl and 4- to 6-membered heterocyclyl,
and
$L^2$ represents a bond,
$R^{13}$ represents piperidin-2-yl, piperidin-3-yl, piperidin-4-yl or 1,2,3,4-tetrahydroquinolin-4-yl,
where piperidin-2-yl, piperidin-3-yl and piperidin-4-yl may be substituted by 1 to 5 substituents independently of one another selected from the group consisting of trifluoromethyl and methyl,
and
where 1,2,3,4-tetrahydroquinolin-4-yl may be substituted by fluorine or trifluoromethyl,
$R^4$ represents hydrogen,
$R^5$ represents hydrogen, fluorine, chlorine, monofluoromethyl, methoxy, ethynyl or methyl,
$R^6$ represents hydrogen, and their N-oxides, salts, solvates, salts of the N-oxides and solvates of the N-oxides and salts.

Preference in the context of the present invention is given to compounds of the formula (I) in which A represents $CH_2$, $CD_2$ or $CH(CH_3)$, $R^1$ represents $(C_4-C_6)$-alkyl, $(C_3-C_7)$-cycloalkyl or phenyl,
  where $(C_4-C_6)$-alkyl may be substituted up to six times by fluorine,
  where $(C_3-C_7)$-cycloalkyl may be substituted by 1 to 4 substituents independently of one another selected from the group consisting of fluorine, trifluoromethyl and $(C_1-C_4)$-alkyl,
  and
  where phenyl may be substituted by 1 to 4 substituents independently of one another selected from the group consisting of halogen, cyano, monofluoromethyl, difluoromethyl, trifluoromethyl, $(C_1-C_4)$-alkyl, $(C_1-C_4)$-alkoxy, $(C_3-C_6)$-cycloalkyl, difluoromethoxy and trifluoromethoxy, $R^2$ represents hydrogen, $(C_1-C_4)$-alkyl, cyclopropyl, monofluoromethyl, difluoromethyl or trifluoromethyl, $R^3$ represents a group of the formula

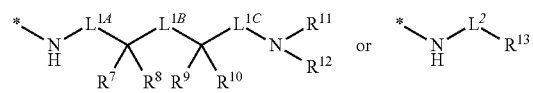

where
* represents the point of attachment to the carbonyl group, $L^{1A}$ represents a bond or $(C_1-C_4)$-alkanediyl,
  where $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy, $L^{1B}$ represents a bond or $(C_1-C_4)$-alkanediyl, $L^{1C}$ represents a bond or $(C_1-C_4)$-alkanediyl,
  where $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy, $R^7$ represents hydrogen, $(C_1-C_6)$-alkyl, $(C_2-C_6)$-alkenyl, $(C_2-C_6)$-alkynyl, $(C_3-C_7)$-cycloalkyl, cyano, 5- to 10-membered heteroaryl, naphthyl or phenyl,
  where $(C_1-C_6)$-alkyl may be substituted by 1 to 3 substituents independently of one another selected from the group consisting of fluorine, trifluoromethyl, difluoromethoxy, trifluoromethoxy, hydroxy, $(C_1-C_4)$-alkoxy, $(C_1-C_4)$-alkoxycarbonyl, $(C_1-C_4)$-alkylsulphonyl, phenyl, phenoxy and benzyloxy,
    where phenyl, phenoxy and benzyloxy for their part may be substituted by 1 to 3 halogen or $(C_1-C_4)$-alkoxy substituents,
  where $(C_3-C_7)$-cycloalkyl may be substituted by 1 or 2 substituents independently of one another selected from the group consisting of fluorine, trifluoromethyl, $(C_1-C_4)$-alkyl and $(C_1-C_4)$-alkoxy,
  and
  where phenyl and 5- to 10-membered heteroaryl may be substituted by 1 to 3 substituents independently of one another selected from the group consisting of halogen, cyano, nitro, difluoromethyl, trifluoromethyl, difluoromethoxy, trifluoromethoxy, $-NH(CO)CH_3$, $(C_1-C_4)$-alkyl, $(C_1-C_4)$-cycloalkyl, $(C_1-C_4)$-alkenyl, $(C_1-C_4)$-alkylsulphonyl, $(C_1-C_4)$-alkoxycarbonyl and $(C_1-C_4)$-alkoxy,
    where $(C_1-C_4)$-alkoxy may be substituted by hydroxy,
    and
    in which 2 adjacent carbon atoms of the phenyl may be substituted by a difluoromethylenedioxy bridge, $R^8$ represents hydrogen or $(C_1-C_4)$-alkyl,
or $R^7$ and $R^8$ together with the carbon atom to which they are attached form a 3- to 7-membered carbocycle or a 4- to 7-membered heterocycle,
  where the 3- to 7-membered carbocycle and the 4- to 7-membered heterocycle for their part may be substituted by 1 or 2 substituents independently of one another selected from the group consisting of fluorine and $(C_1-C_4)$-alkyl, $R^9$ represents hydrogen, cyano, $(C_1-C_6)$-alkyl, $(C_2-C_6)$-alkenyl, $(C_2-C_6)$-alkynyl, $(C_3-C_7)$-cycloalkyl, 5- to 10-membered heteroaryl or phenyl,
  where $(C_1-C_6)$-alkyl may be substituted by 1 to 3 substituents independently of one another selected from the group consisting of fluorine, difluoromethyl, trifluoromethyl, difluoromethoxy, trifluoromethoxy, hydroxy, cyano, $(C_1-C_4)$-alkoxy, $(C_1-C_4)$-alkoxycarbonyl, $(C_1-C_4)$-alkylsulphonyl, 5- or 6-membered heteroaryl, phenyl, phenoxy and benzyloxy,
    where phenyl, phenoxy and benzyloxy for their part may be substituted by 1 to 3 halogen or $(C_1-C_4)$-alkoxy substituents,
    where 5- or 6-membered heteroaryl may be benzofused or substituted by a 5- or 6-membered heteroaryl,
      where 5- or 6-membered heteroaryl may be substituted by $(C_1-C_4)$-alkyl or trifluoromethyl,
  where $(C_3-C_7)$-cycloalkyl may be substituted by 1 or 2 substituents independently of one another selected from the group consisting of fluorine, trifluoromethyl, $(C_1-C_4)$-alkyl and $(C_1-C_4)$-alkoxy,
  and
  where phenyl and 5- to 10-membered heteroaryl may be substituted by 1 to 3 substituents independently of one another selected from the group consisting of halogen, cyano, difluoromethyl, trifluoromethyl, difluoromethoxy, trifluoromethoxy, $(C_1-C_4)$-alkyl, $(C_1-C_4)$-cycloalkyl, $(C_1-C_4)$-alkoxy, $(C_1-C_4)$-alkoxycarbonyl and $(C_1-C_4)$-alkylsulphonyl,
    where $(C_1-C_4)$-alkoxy may be substituted by hydroxy,
    and
    where the phenyl may be substituted on two adjacent carbon atoms by a difluoromethylenedioxy bridge, $R^{10}$ represents hydrogen or $(C_1-C_4)$-alkyl,
or $R^9$ and $R^{10}$ together with the carbon atom to which they are attached form a 3- to 7-membered carbocycle or a 4- to 7-membered heterocycle,
  where the 3- to 7-membered carbocycle and the 4- to 7-membered heterocycle for their part may be substituted by 1 or 2 substituents independently of one another selected from the group consisting of fluorine, benzyl and $(C_1-C_4)$-alkyl,
with the proviso that the radicals $R^7$ and $R^9$ do not both simultaneously represent phenyl,
or
$R^7$ and $R^9$ together with the carbon atoms to which they are attached and the group $L^{1B}$ form a 3- to 7-membered carbocycle or a 4- to 7-membered heterocycle,
where the 3- to 7-membered carbocycle may be substituted by 1 or 2 substituents independently of one another selected from the group consisting of $(C_1-C_4)$-alkyl, fluorine, hydroxy and $(C_1-C_4)$-alkoxy,
with the proviso that not more than one of the radical pairs $R^7$ and $R^8$, $R^9$ and $R^{10}$ and $R^7$ and $R^9$, respectively, simultaneously forms a carbo- or heterocycle,
$R^{11}$ represents hydrogen or $(C_1-C_4)$-alkyl,
where $(C_1-C_4)$-alkyl may be substituted by 1 to 3 substituents independently of one another selected from the group consisting of fluorine, trifluoromethyl, hydroxy and $(C_1-C_4)$-alkoxy,
$R^{12}$ represents hydrogen, $(C_1-C_6)$-alkyl, $(C_3-C_7)$-cycloalkyl, phenyl or benzyl,
where $(C_1-C_6)$-alkyl may be substituted by 1 to 3 substituents independently of one another selected from the group consisting of fluorine, trifluoromethyl, hydroxy, $(C_1-C_4)$-alkoxy and phenoxy,
and
where phenyl and benzyl may be substituted by 1 to 3 substituents independently of one another selected from the group consisting of halogen and trifluoromethyl,
or
$R^{11}$ and $R^{12}$ together with the nitrogen atom to which they are attached form a 4- to 7-membered azaheterocycle,
where the 4- to 7-membered azaheterocycle may be substituted by 1 or 2 substituents independently of one another selected from the group consisting of fluorine, trifluoromethyl, $(C_1-C_4)$-alkyl, $(C_3-C_7)$-cycloalkyl, hydroxy, $(C_1-C_4)$-alkoxy and 4- to 7-membered heterocyclyl,
and
$L^2$ represents a bond or $(C_1-C_4)$-alkanediyl,
$R^{13}$ represents 5- to 9-membered azaheterocyclyl which is attached via a ring carbon atom,
where 5- to 9-membered azaheterocyclyl is substituted by 1 to 5 substituents independently of one another selected from the group consisting of $(C_3-C_7)$-cycloalkyl and benzyl,
$R^4$ represents hydrogen,
$R^5$ represents hydrogen, halogen, cyano, monofluoromethyl, difluoromethyl, trifluoromethyl, $(C_1-C_4)$-alkyl, $(C_2-C_4)$-alkenyl, $(C_2-C_4)$-alkynyl, $(C_3-C_6)$-cycloalkyl, difluoromethoxy, trifluoromethoxy, $(C_1-C_4)$-alkoxy, amino, 4- to 7-membered heterocyclyl or 5- or 6-membered heteroaryl,
$R^6$ represents hydrogen, cyano or halogen,
and their N-oxides, salts, solvates, salts of the N-oxides and solvates of the N-oxides and salts.

Preference in the context of the present invention is given to compounds of the formula (I) in which
A represents $CH_2$, $CD_2$ or $CH(CH_3)$,
$R^1$ represents $(C_4-C_6)$-alkyl, $(C_4-C_6)$-cycloalkyl or phenyl,
where $(C_4-C_6)$-alkyl may be substituted up to six times by fluorine,
where $(C_4-C_6)$-cycloalkyl may be substituted by 1 or 2 substituents independently of one another selected from the group consisting of fluorine, trifluoromethyl and methyl,
and
where phenyl may be substituted by 1 to 4 substituents independently of one another selected from the group consisting of fluorine, chlorine, cyano, methoxy, ethoxy, difluoromethyl, trifluoromethyl, $(C_3-C_6)$-cycloalkyl and methyl,
$R^2$ represents hydrogen, trifluoromethyl, $(C_1-C_3)$-alkyl or cyclopropyl,
$R^3$ represents a group of the formula $$*\underset{H}{N}\diagdown L^{1A}\diagdown\underset{R^7\ R^8}{\diagup}\diagdown L^{1B}\diagdown\underset{R^9\ R^{10}}{\diagup}\diagdown L^{1C}\diagdown N\diagup\underset{R^{12}}{\diagdown}R^{11} \quad \text{or} \quad *\underset{H}{N}\diagdown L^2\diagdown R^{13},$$

where
* represents the point of attachment to the carbonyl group,
$L^{1A}$ represents a bond,
$L^{1B}$ represents a bond, methylene or 1,2-ethanediyl,
$L^{1C}$ represents a bond or methylene,
where methylene may be substituted by 1 or 2 substituents independently of one another selected from the group consisting of fluorine, trifluoromethyl, $(C_1-C_4)$-alkyl, cyclopropyl and cyclobutyl,
$R^7$ represents hydrogen, trifluoromethyl, $(C_1-C_6)$-alkyl, $(C_3-C_6)$-cycloalkyl, 5- or 6-membered heteroaryl or phenyl,
where $(C_1-C_6)$-alkyl may be substituted by 1 or 2 substituents independently of one another selected from the group consisting of fluorine, trifluoromethyl, difluoromethoxy, trifluoromethoxy, hydroxy, $(C_1-C_4)$-alkoxy, phenyl, phenoxy and benzyloxy,
where phenyl, phenoxy and benzyloxy for their part may be substituted by 1 or 2 substituents selected from the group consisting of fluorine and chlorine,
where $(C_3-C_6)$-cycloalkyl may be substituted by 1 or 2 substituents independently of one another selected from the group consisting of fluorine, trifluoromethyl, methyl and ethyl,
and
where phenyl and 5- or 6-membered heteroaryl may be substituted by 1 or 2 substituents independently of one another selected from the group consisting of fluorine, chlorine, cyano, nitro, methyl, ethenyl, difluoromethoxy, trifluoromethoxy, —NH(CO)CH$_3$, $(C_1-C_4)$-alkoxy and trifluoromethyl,
where $(C_1-C_4)$-alkoxy may be substituted by hydroxy,
$R^8$ represents hydrogen, methyl or ethyl,
or
$R^7$ and $R^8$ together with the carbon atom to which they are attached form a 3- to 6-membered carbocycle or an oxetanyl, tetrahydrofuranyl, tetrahydropyranyl, azetidinyl, pyrrolidinyl or piperidinyl ring,
where the 3- to 6-membered carbocycle and the oxetanyl, tetrahydrofuranyl, tetrahydropyranyl, azetidinyl, pyrrolidinyl and piperidinyl ring may be substituted by 1 or 2 substituents independently of one another selected from the group consisting of fluorine and methyl, $R^9$ represents hydrogen, cyano, 1,1,2,2-tetrafluoroethyl, trifluoromethyl, $(C_1-C_6)$-alkyl, $(C_3-C_6)$-cycloalkyl, 5- or 6-membered heteroaryl or phenyl, where $(C_1-C_6)$-alkyl may be substituted by 1 or 2 substituents independently of one another selected from the group consisting of cyano, fluorine, trifluoromethyl, difluoromethoxy, trifluoromethoxy, hydroxy, $(C_1-C_4)$-alkoxy, 5-membered heteroaryl, phenyl, phenoxy and benzyloxy, where phenyl, phenoxy and benzyloxy for their part may be substituted by 1 or 2 substituents selected from the group consisting of fluorine and chlorine, where 5-membered heteroaryl may be benzofused or substituted by a 5-membered heteroaryl, where $(C_3-C_6)$-cycloalkyl may be substituted by 1 or 2 substituents independently of one another selected from the group consisting of fluorine, trifluoromethyl, methyl and ethyl, and where phenyl and 5- or 6-membered heteroaryl may be substituted by 1 or 2 substituents independently of one another selected from the group consisting of fluorine, chlorine, cyano, methyl, difluoromethoxy, trifluoromethoxy, $(C_1-C_4)$-alkoxy and trifluoromethyl, where $(C_1-C_4)$-alkoxy may be substituted by hydroxy, $R^{10}$ represents hydrogen, methyl or ethyl, or $R^9$ and $R^{10}$ together with the carbon atom to which they are attached form a 3- to 6-membered carbocycle or an oxetanyl, tetrahydrofuranyl, tetrahydropyranyl, azetidinyl, pyrrolidinyl or piperidinyl ring, where the 3- to 6-membered carbocycle and the oxetanyl, tetrahydrofuranyl, tetrahydropyranyl, azetidinyl, pyrrolidinyl and piperidinyl ring may be substituted by 1 or 2 substituents independently of one another selected from the group consisting of fluorine, benzyl and methyl, with the proviso that the radicals $R^7$ and $R^9$ do not both simultaneously represent phenyl, or $R^7$ and $R^9$ together with the carbon atoms to which they are attached and the group $L^{1B}$ form a cyclopentyl, cyclohexyl, azetidinyl, oxetanyl, pyrrolidinyl, tetrahydrofuranyl, piperidinyl or tetrahydropyranyl ring, with the proviso that not more than one of the radical pairs $R^7$ and $R^8$, $R^9$ and $R^{10}$ and $R^7$ and $R^9$, respectively, simultaneously forms one of the carbo- or heterocycles mentioned above, $R^{11}$ represents hydrogen or $(C_1-C_3)$-alkyl, where $(C_1-C_3)$-alkyl may be substituted by 1 or 2 substituents independently of one another selected from the group consisting of fluorine, trifluoromethyl, hydroxy, methoxy and ethoxy, $R^{12}$ represents hydrogen, $(C_1-C_4)$-alkyl, cyclopropyl, cyclobutyl, phenyl or benzyl, where $(C_1-C_4)$-alkyl may be substituted by 1 or 2 substituents independently of one another selected from the group consisting of fluorine, trifluoromethyl, hydroxy, $(C_1-C_4)$-alkoxy and phenoxy, and where phenyl and benzyl may be substituted by 1 to 3 substituents independently of one another selected from the group consisting of fluorine, chlorine and trifluoromethyl, or $R^{11}$ and $R^{12}$ together with the nitrogen atom to which they are attached form an azetidinyl, pyrrolidinyl, piperidinyl, morpholinyl, piperazinyl, thiomorpholinyl or 1,1-dioxothiomorpholinyl ring, where the azetidinyl, pyrrolidinyl, piperidinyl, morpholinyl, piperazinyl, thiomorpholinyl and 1,1-dioxothiomorpholinyl ring may be substituted by 1 or 2 substituents independently of one another selected from the group consisting of fluorine, trifluoromethyl, methyl, ethyl, cyclopropyl, cyclobutyl, azetidinyl, pyrrolidinyl and piperidinyl, and $L^2$ represents a bond, methylene or 1,1-ethanediyl, $R^{13}$ represents 5- to 6-membered azaheterocyclyl which is attached via a ring carbon atom, where 5- to 6-membered azaheterocyclyl is substituted by 1 to 3 substituents independently of one another selected from the group consisting of $(C_3-C_7)$-cycloalkyl and benzyl, $R^4$ represents hydrogen, $R^5$ represents hydrogen, fluorine, chlorine, bromine, cyano, methyl, ethyl, monofluoromethyl, methoxy, ethynyl or cyclopropyl, $R^6$ represents hydrogen or fluorine, and their N-oxides, salts, solvates, salts of the N-oxides and solvates of the N-oxides and salts.

Preference in the context of the present invention is given to compounds of the formula (I) in which A represents $CH_2$, $R^1$ represents $(C_4-C_6)$-alkyl, $(C_4-C_6)$-cycloalkyl or phenyl, where $(C_4-C_6)$-alkyl may be substituted up to six times by fluorine, where $(C_4-C_6)$-cycloalkyl may be substituted by 1 or 2 substituents independently of one another selected from the group consisting of fluorine, trifluoromethyl and methyl, and where phenyl may be substituted by 1 to 3 substituents independently of one another selected from the group consisting of fluorine, chlorine, cyclopropyl, methoxy and methyl, $R^2$ represents trifluoromethyl, methyl, ethyl or cyclopropyl, $R^3$ represents a group of the formula

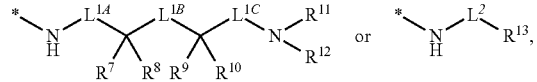

where

* represents the point of attachment to the carbonyl group, $L^{1A}$ represents a bond, $L^{1B}$ represents a bond or methylene, $L^{1C}$ represents a bond or methylene, where methylene may be substituted by 1 or 2 substituents independently of one another selected from the group consisting of trifluoromethyl, ($C_1$-$C_4$)-alkyl, cyclopropyl and cyclobutyl, $R^7$ represents hydrogen, trifluoromethyl, ($C_1$-$C_6$)-alkyl, ($C_3$-$C_6$)-cycloalkyl or phenyl,
where ($C_1$-$C_6$)-alkyl may be substituted by 1 or 2 substituents independently of one another selected from the group consisting of fluorine, trifluoromethyl, hydroxy, ($C_1$-$C_4$)-alkoxy, phenyl, phenoxy and benzyloxy,
where phenyl, phenoxy and benzyloxy for their part may be substituted by 1 or 2 substituents selected from the group consisting of fluorine and chlorine,
where ($C_3$-$C_6$)-cycloalkyl may be substituted by 1 or 2 substituents independently of one another selected from the group consisting of fluorine, trifluoromethyl, methyl and ethyl,
and
where phenyl may be substituted by 1 or 2 substituents independently of one another selected from the group consisting of fluorine, chlorine, cyano, nitro, ethenyl, difluoromethoxy, trifluoromethoxy, —NH(CO)CH$_3$, ethoxy and trifluoromethyl,
where ethoxy may be substituted by hydroxy, $R^8$ represents hydrogen, methyl or ethyl,
or
$R^7$ and $R^8$ together with the carbon atom to which they are attached form a 3- to 6-membered carbocycle or an oxetanyl, tetrahydrofuranyl, tetrahydropyranyl, azetidinyl, pyrrolidinyl or piperidinyl ring,
where the 3- to 6-membered carbocycle and the oxetanyl, tetrahydrofuranyl, tetrahydropyranyl, azetidinyl, pyrrolidinyl and piperidinyl ring may be substituted by 1 or 2 substituents independently of one another selected from the group consisting of fluorine and methyl, $R^9$ represents hydrogen, cyano, trifluoromethyl, ($C_1$-$C_6$)-alkyl, ($C_3$-$C_6$)-cycloalkyl or phenyl,
where ($C_1$-$C_6$)-alkyl may be substituted by 1 or 2 substituents independently of one another selected from the group consisting of cyano, fluorine, trifluoromethyl, hydroxy, ($C_1$-$C_4$)-alkoxy, phenyl, phenoxy and benzyloxy,
where phenyl, phenoxy and benzyloxy for their part may be substituted by 1 or 2 substituents selected from the group consisting of fluorine and chlorine,
where ($C_3$-$C_6$)-cycloalkyl may be substituted by 1 or 2 substituents independently of one another selected from the group consisting of fluorine, trifluoromethyl, methyl and ethyl,
and
where phenyl may be substituted by 1 or 2 substituents independently of one another selected from the group consisting of fluorine, chlorine, cyano, difluoromethoxy, trifluoromethoxy, ethoxy and trifluoromethyl,
where ethoxy may be substituted by hydroxy, $R^{10}$ represents hydrogen, methyl or ethyl,
or
$R^9$ and $R^{10}$ together with the carbon atom to which they are attached form a 3- to 6-membered carbocycle or an oxetanyl, tetrahydrofuranyl, tetrahydropyranyl, azetidinyl, pyrrolidinyl or piperidinyl ring,
where the 3- to 6-membered carbocycle and the oxetanyl, tetrahydrofuranyl, tetrahydropyranyl, azetidinyl, pyrrolidinyl and piperidinyl ring may be substituted by 1 or 2 substituents independently of one another selected from the group consisting of fluorine, benzyl and methyl,
with the proviso that the radicals $R^7$ and $R^9$ do not both simultaneously represent phenyl,
or
$R^7$ and $R^9$ together with the carbon atoms to which they are attached and the group $L^{1B}$ form a cyclopentyl, cyclohexyl, azetidinyl, oxetanyl, pyrrolidinyl, tetrahydrofuranyl, piperidinyl or tetrahydropyranyl ring,
with the proviso that not more than one of the radical pairs $R^7$ and $R^8$, $R^9$ and $R^{10}$ and $R^7$ and $R^9$, respectively, simultaneously forms one of the carbo- or heterocycles mentioned above, $R^{11}$ represents hydrogen or ($C_1$-$C_3$)-alkyl,
where ($C_1$-$C_3$)-alkyl may be substituted by 1 or 2 substituents independently of one another selected from the group consisting of fluorine and trifluoromethyl, $R^{12}$ represents hydrogen, ($C_1$-$C_4$)-alkyl, cyclopropyl or cyclobutyl,
where ($C_1$-$C_4$)-alkyl may be substituted by 1 or 2 substituents independently of one another selected from the group consisting of fluorine and trifluoromethyl,
or
$R^{11}$ and $R^{12}$ together with the nitrogen atom to which they are attached form an azetidinyl, pyrrolidinyl, piperidinyl or morpholinyl ring,
where the azetidinyl, pyrrolidinyl, piperidinyl and morpholinyl ring may be substituted by 1 or 2 substituents independently of one another selected from the group consisting of fluorine, trifluoromethyl, methyl, ethyl, cyclopropyl and cyclobutyl,
and $L^2$ represents a bond or methylene, $R^{13}$ represents 5- to 6-membered azaheterocyclyl which is attached via a ring carbon atom,
where 5- to 6-membered azaheterocyclyl is substituted by 1 to 3 substituents independently of one another selected from the group consisting of ($C_3$-$C_7$)-cycloalkyl and benzyl, $R^4$ represents hydrogen, $R^5$ represents hydrogen, fluorine, chlorine, methyl, ethyl, monofluoromethyl, methoxy, ethynyl or cyclopropyl, $R^6$ represents hydrogen, and their N-oxides, salts, solvates, salts of the N-oxides and solvates of the N-oxides and salts.

Preference in the context of the present invention is given to compounds of the formula (I) in which A represents CH$_2$, $R^1$ represents a phenyl group of the formula

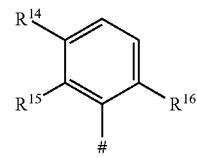

where
# represents the point of attachment to A,
and
$R^{14}$, $R^{15}$ and $R^{16}$ independently of one another represent hydrogen, fluorine, methoxy, cyclopropyl or chlorine, with the proviso that at least two of the radicals $R^{14}$, $R^{15}$, $R^{16}$ are different from hydrogen,
$R^2$ represents methyl,
$R^3$ represents a group of the formula

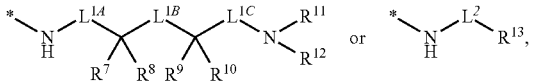 or 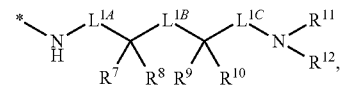

where
* represents the point of attachment to the carbonyl group,
$L^{1A}$ represents a bond,
$L^{1B}$ represents a bond,
$L^{1C}$ represents a bond,
$R^7$ represents hydrogen, trifluoromethyl, $(C_1-C_6)$-alkyl, $(C_3-C_6)$-cycloalkyl or phenyl,
where $(C_1-C_6)$-alkyl may be substituted by 1 or 2 substituents independently of one another selected from the group consisting of fluorine, trifluoromethyl, hydroxy, $(C_1-C_4)$-alkoxy and phenyl,
and
where phenyl may be substituted by 1 or 2 substituents independently of one another selected from the group consisting of fluorine, ethenyl, difluoromethoxy, trifluoromethoxy, ethoxy and chlorine,
where ethoxy may be substituted by hydroxy,
$R^8$ represents hydrogen, methyl or ethyl,
$R^9$ represents hydrogen, cyano, trifluoromethyl, $(C_1-C_6)$-alkyl, cyclopropyl or phenyl,
where $(C_1-C_6)$-alkyl may be substituted by 1 or 2 substituents independently of one another selected from the group consisting of cyano, fluorine, trifluoromethyl, hydroxy, $(C_1-C_4)$-alkoxy and phenyl,
and
where phenyl may be substituted by 1 or 2 substituents independently of one another selected from the group consisting of fluorine, difluoromethoxy, trifluoromethoxy, ethoxy and chlorine,
where ethoxy may be substituted by hydroxy,
$R^{10}$ represents hydrogen, methyl or ethyl,
or
$R^9$ and $R^{10}$ together with the carbon atom to which they are attached form a 3- to 6-membered carbocycle or an oxetanyl ring,
with the proviso that the radicals $R^7$ and $R^9$ do not both simultaneously represent phenyl,
$R^{11}$ represents hydrogen,
$R^{12}$ represents hydrogen,
and
$L^2$ represents a bond,
$R^{13}$ represents 5- to 6-membered azaheterocyclyl which is attached via a ring carbon atom,
where 5- to 6-membered azaheterocyclyl is substituted by 1 to 3 substituents independently of one another selected from the group consisting of $(C_3-C_7)$-cycloalkyl and benzyl,
$R^4$ represents hydrogen,
$R^5$ represents hydrogen, fluorine, chlorine, monofluoromethyl, methoxy, ethynyl or methyl,
$R^6$ represents hydrogen,
and their N-oxides, salts, solvates, salts of the N-oxides and solvates of the N-oxides and salts.

Particular preference in the context of the present invention is given to compounds of the formula (I) in which
A represents $CH_2$,
$R^1$ represents phenyl,
where phenyl is substituted by 2 to 3 fluorine,
$R^2$ represents methyl,
$R^3$ represents a group of the formula

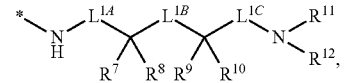

where
* represents the point of attachment to the carbonyl group,
$L^{1A}$ represents a bond,
$L^{1B}$ represents a bond,
$L^{1C}$ represents a bond,
$R^7$ represents hydrogen,
$R^8$ represents hydrogen,
$R^9$ represents hydrogen or $(C_1-C_4)$-alkyl,
$R^{10}$ represents methyl or ethyl, $R^{11}$ represents hydrogen,
$R^{12}$ represents hydrogen,
$R^4$ represents hydrogen,
$R^5$ represents hydrogen or methyl,
$R^6$ represents hydrogen,
and their N-oxides, salts, solvates, salts of the N-oxides and solvates of the N-oxides and salts.

Particular preference in the context of the present invention is given to compounds of the formula (I) in which
A represents $CH_2$,
$R^1$ represents a phenyl group of the formula

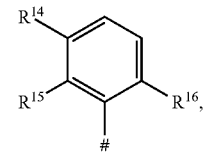

where
\# represents the point of attachment to A,
and
$R^{14}$, $R^{15}$ and $R^{16}$ independently of one another represent hydrogen or fluorine,
with the proviso that at least two of the radicals $R^{14}$, $R^{15}$, $R^{16}$ are different from hydrogen,
$R^2$ represents methyl,
$R^3$ represents a group of the formula

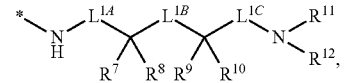

where
* represents the point of attachment to the carbonyl group,
$L^{1A}$ represents a bond,
$L^{1B}$ represents a bond,
$L^{1C}$ represents a bond,
$R^7$ represents hydrogen, $R^8$ represents hydrogen,
$R^9$ represents hydrogen or $(C_1-C_4)$-alkyl,
$R^{10}$ represents methyl or ethyl,
$R^{11}$ represents hydrogen,
$R^{12}$ represents hydrogen,
$R^4$ represents hydrogen,
$R^5$ represents hydrogen or methyl,
$R^6$ represents hydrogen,
and their N-oxides, salts, solvates, salts of the N-oxides and solvates of the N-oxides and salts.

Particular preference in the context of the present invention is given to compounds of the formula (I) in which
A represents $CH_2$,
$R^1$ represents phenyl,
where phenyl is substituted by 2 to 3 fluorine,
$R^2$ represents methyl,
$R^3$ represents a group of the formula

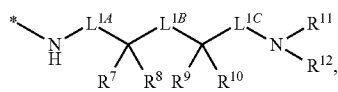

where
* represents the point of attachment to the carbonyl group,
$L^{1A}$ represents a bond,
$L^{1B}$ represents a bond,
$L^{1C}$ represents a bond,
$R^7$ represents hydrogen,
$R^8$ represents hydrogen,
$R^9$ represents $(C_1-C_4)$-alkyl,
where $(C_1-C_4)$-alkyl is substituted up to five times by fluorine,
$R^{10}$ represents methyl or ethyl,
$R^{11}$ represents hydrogen,
$R^{12}$ represents hydrogen,
$R^4$ represents hydrogen,
$R^5$ represents hydrogen or methyl,
$R^6$ represents hydrogen,
and their N-oxides, salts, solvates, salts of the N-oxides and solvates of the N-oxides and salts.

Particular preference in the context of the present invention is given to compounds of the formula (I) in which
A represents $CH_2$,
$R^1$ represents a phenyl group of the formula

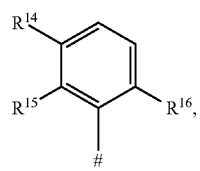

where
# represents the point of attachment to A,
and
$R^{14}$, $R^{15}$ and $R^{16}$ independently of one another represent hydrogen or fluorine,
with the proviso that at least two of the radicals $R^{14}$, $R^{15}$, $R^{16}$ are different from hydrogen, $R^2$ represents methyl,
$R^3$ represents a group of the formula

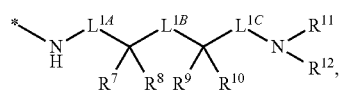

where
* represents the point of attachment to the carbonyl group,
$L^{1A}$ represents a bond,
$L^{1B}$ represents a bond,
$L^{1C}$ represents a bond,
$R^7$ represents hydrogen,
$R^8$ represents hydrogen,
$R^9$ represents $(C_1-C_4)$-alkyl,
where $(C_1-C_4)$-alkyl is substituted up to five times by fluorine,
$R^{10}$ represents methyl or ethyl,
$R^{11}$ represents hydrogen,
$R^{12}$ represents hydrogen,
$R^4$ represents hydrogen,
$R^5$ represents hydrogen or methyl,
$R^6$ represents hydrogen,
and their N-oxides, salts, solvates, salts of the N-oxides and solvates of the N-oxides and salts.

Particular preference is also given to the following compounds

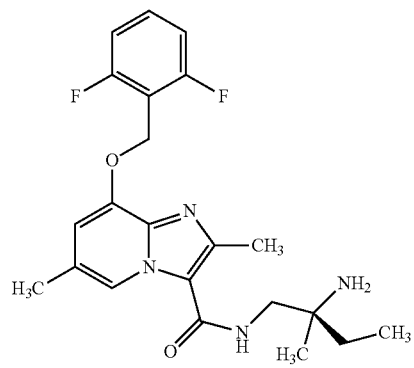

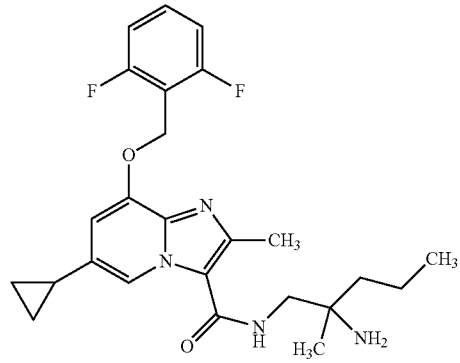

-continued
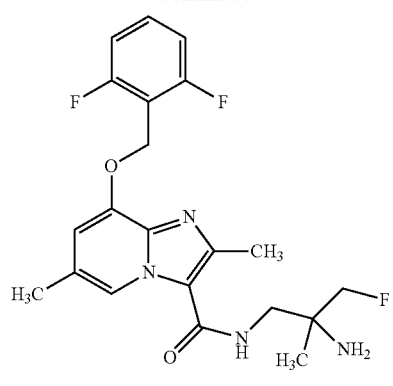
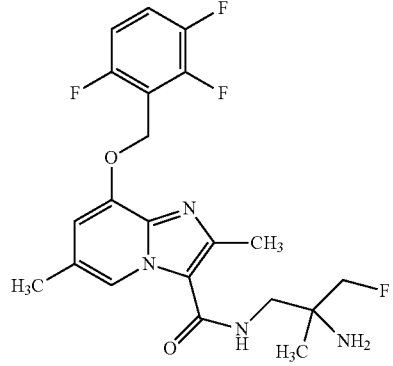
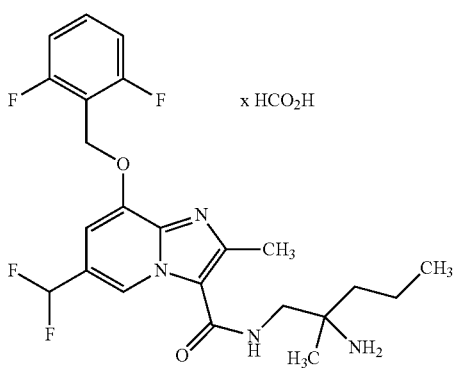
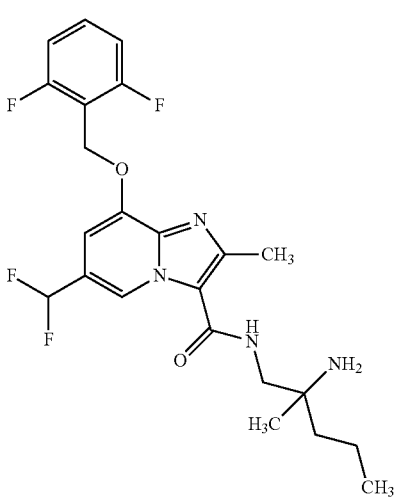
-continued
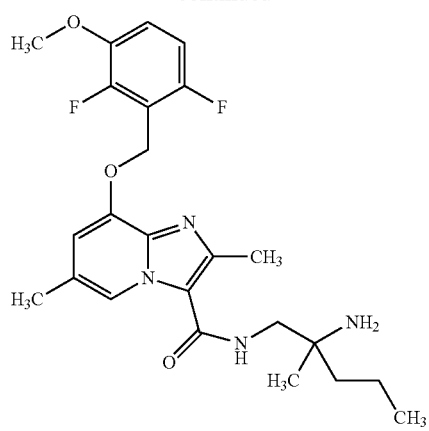
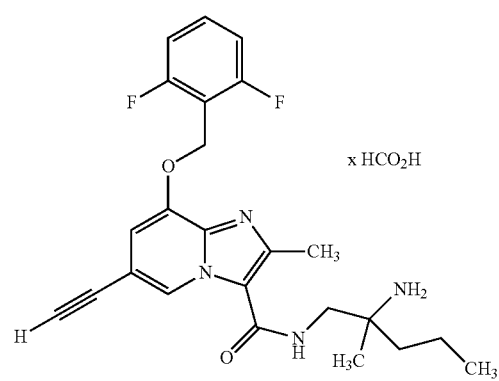
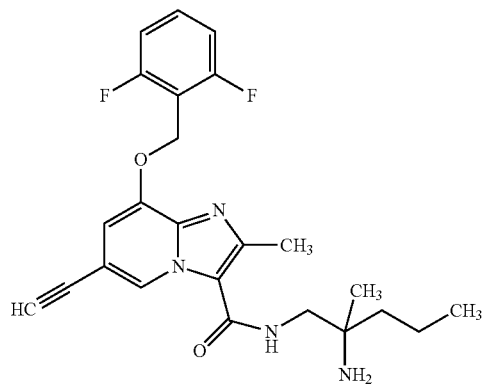
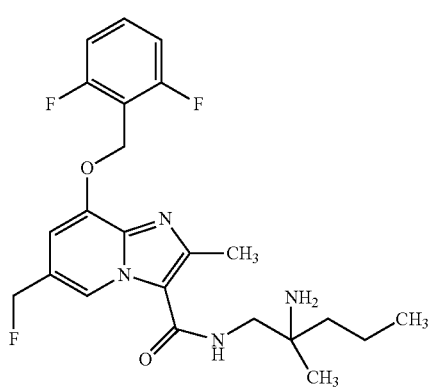

-continued

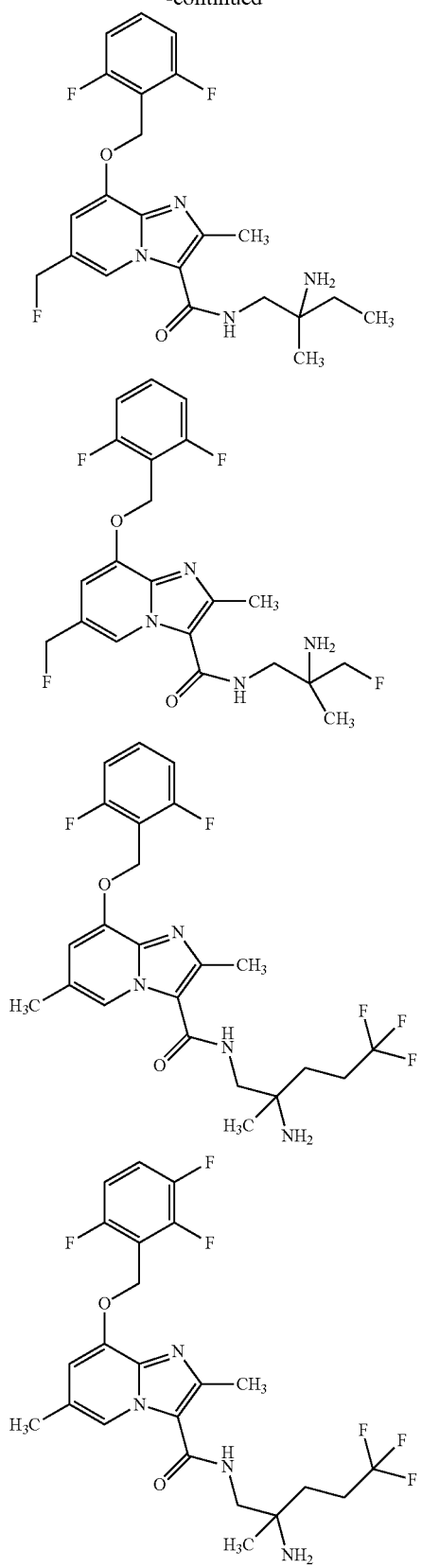

and their N-oxides, salts, solvates, salts of the N-oxides and solvates of the N-oxides and salts.

Particular preference is also given to the following compounds

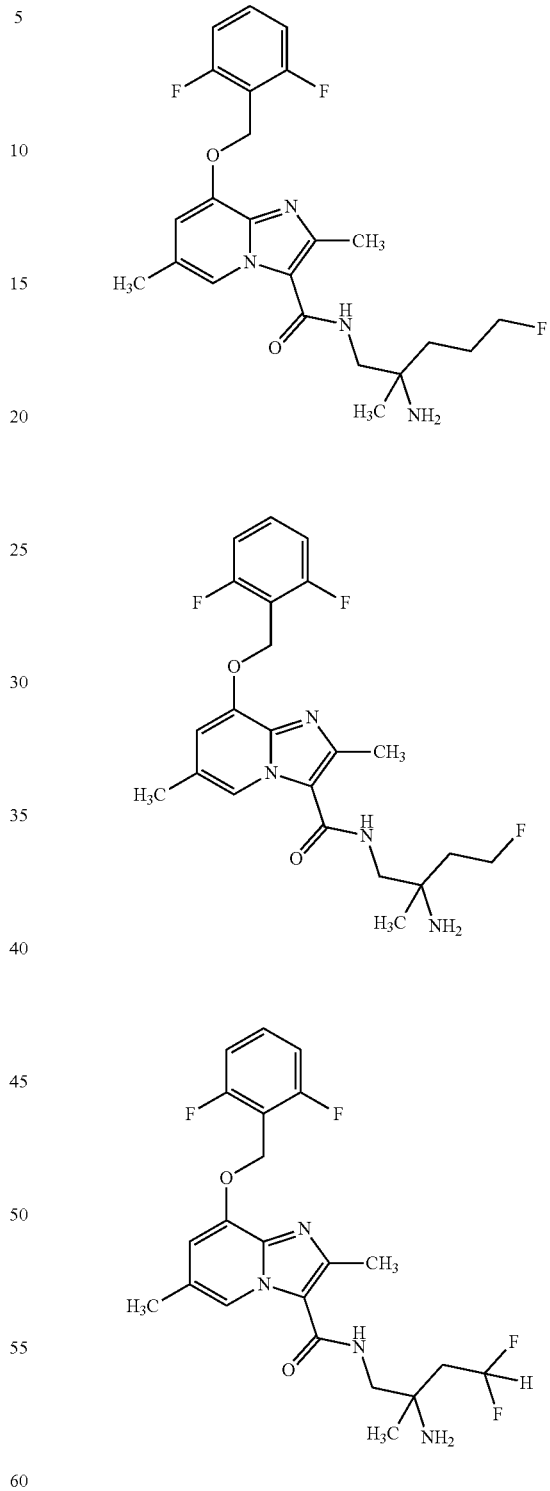

and their N-oxides, salts, solvates, salts of the N-oxides and solvates of the N-oxides and salts.

Those three compounds can be prepared by methods known from the literature and familiar to the person skilled in the art (see Schemes 6-17).

Particular preference is also given to the following compounds

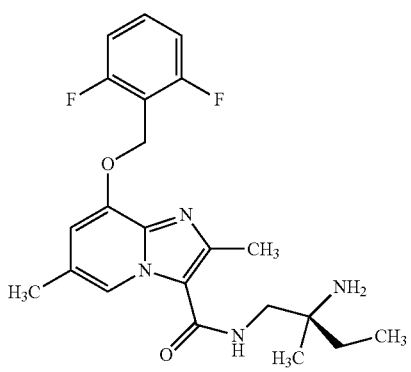

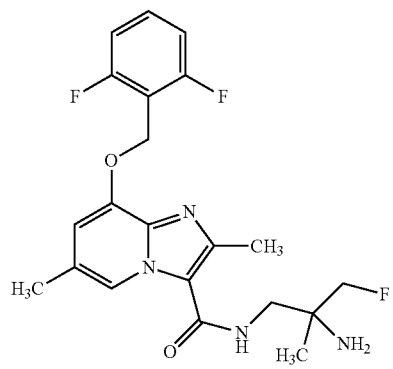

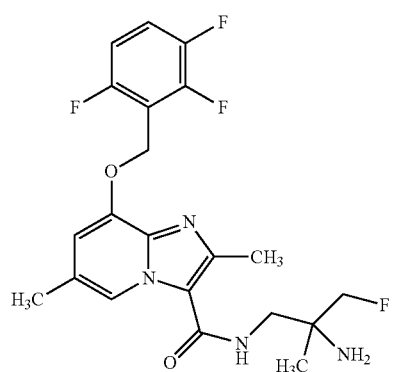

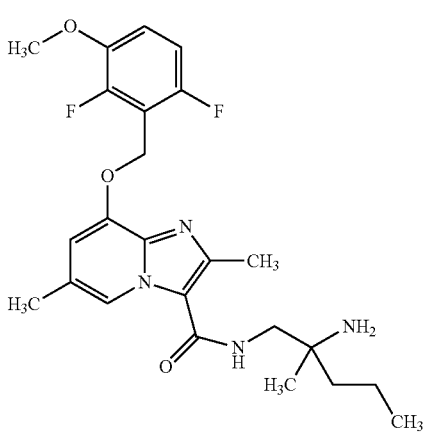

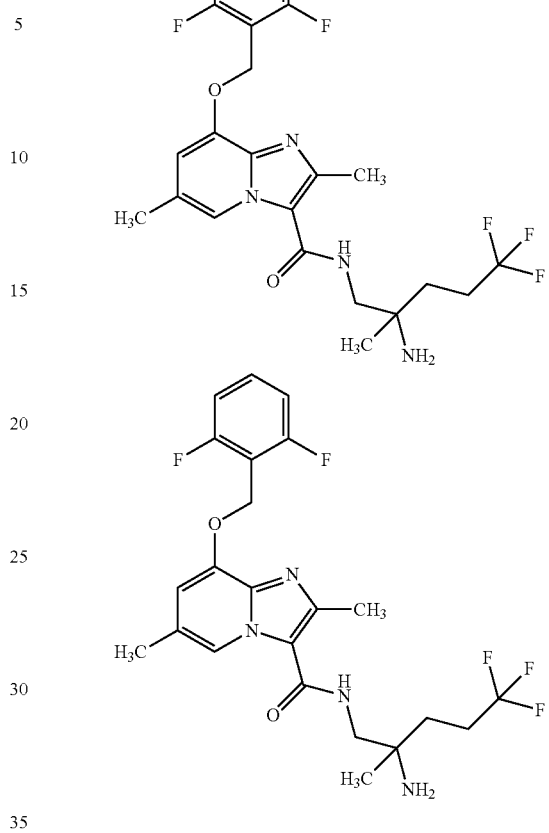

and their N-oxides, salts, solvates, salts of the N-oxides and solvates of the N-oxides and salts.

Preference in the context of the present invention is also given to compounds of the formula (I) in which
R¹ represents a phenyl group of the formula

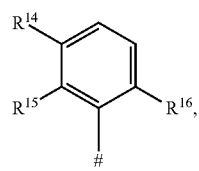

where
# denotes the point of attachment to A,
and
$R^{14}$, $R^{15}$ and $R^{16}$ independently of one another represent hydrogen, fluorine or chlorine,
with the proviso that at least two of the radicals $R^{14}$, $R^{15}$, $R^{16}$ are different from hydrogen,
and their N-oxides, salts, solvates, salts of the N-oxides and solvates of the N-oxides and salts.

Preference in the context of the present invention is also given to compounds of the formula (I) in which
R² represents methyl,
and their N-oxides, salts, solvates, salts of the N-oxides and solvates of the N-oxides and salts.

Preference in the context of the present invention is also given to compounds of the formula (I) in which $R^3$ represents a group of the formula $$*_{\underset{H}{N}}\underset{R^7}{\overset{L^{1A}}{\diagup}}\underset{R^8}{\overset{L^{1B}}{\diagup}}\underset{R^9}{\overset{L^{1C}}{\diagup}}\underset{R^{10}}{\overset{}{\diagup}}N\underset{R^{12}}{\overset{R^{11}}{\diagup}},$$

where
* represents the point of attachment to the carbonyl group,
$L^{1A}$ represents a bond,
$L^{1B}$ represents a bond or methylene,
$L^{1C}$ represents a bond or methylene,
where methylene may be substituted by 1 or 2 substituents independently of one another selected from the group consisting of trifluoromethyl, $(C_1\text{-}C_4)$-alkyl, cyclopropyl and cyclobutyl,
and their N-oxides, salts, solvates, salts of the N-oxides and solvates of the N-oxides and salts.

Preference in the context of the present invention is also given to compounds of the formula (I) in which
$R^3$ represents a group of the formula $$*_{\underset{H}{N}}\underset{R^7}{\overset{L^{1A}}{\diagup}}\underset{R^8}{\overset{L^{1B}}{\diagup}}\underset{R^9}{\overset{L^{1C}}{\diagup}}\underset{R^{10}}{\overset{}{\diagup}}N\underset{R^{12}}{\overset{R^{11}}{\diagup}},$$

where
* represents the point of attachment to the carbonyl group,
$R^8$ represents hydrogen,
and their N-oxides, salts, solvates, salts of the N-oxides and solvates of the N-oxides and salts.

Preference in the context of the present invention is also given to compounds of the formula (I) in which
$R^3$ represents a group of the formula $$*_{\underset{H}{N}}\underset{R^7}{\overset{L^{1A}}{\diagup}}\underset{R^8}{\overset{L^{1B}}{\diagup}}\underset{R^9}{\overset{L^{1C}}{\diagup}}\underset{R^{10}}{\overset{}{\diagup}}N\underset{R^{12}}{\overset{R^{11}}{\diagup}},$$

where
* represents the point of attachment to the carbonyl group,
and
$R^{10}$ represents hydrogen or methyl,
and their N-oxides, salts, solvates, salts of the N-oxides and solvates of the N-oxides and salts.

Preference in the context of the present invention is also given to compounds of the formula (I) in which
$R^5$ represents hydrogen, fluorine, chlorine or methyl,
and their N-oxides, salts, solvates, salts of the N-oxides and solvates of the N-oxides and salts.

Preference in the context of the present invention is also given to compounds of the formula (I) in which
$R^6$ represents hydrogen,
and their N-oxides, salts, solvates, salts of the N-oxides and solvates of the N-oxides and salts.

Preference in the context of the present invention is also given to compounds of the formula (I) in which
$R^1$ represents phenyl,
where phenyl may be substituted by 1 to 3 substituents independently of one another selected from the group consisting of halogen, cyano, monofluoromethyl, difluoromethyl, trifluoromethyl, $(C_1\text{-}C_4)$-alkyl,
and
where phenyl is substituted by 1 to 2 substituents selected from the group consisting of $(C_3\text{-}C_7)$-cycloalkyl, $(C_1\text{-}C_4)$-alkoxy, monofluoromethoxy, difluoromethoxy or trifluoromethoxy,
and their N-oxides, salts, solvates, salts of the N-oxides and solvates of the N-oxides and salts.

Preference in the context of the present invention is also given to compounds of the formula (I) in which
$R^1$ represents phenyl,
where phenyl is substituted by 1 to 2 substituents independently of one another selected from the group consisting of fluorine, chlorine, cyano, monofluoromethyl, difluoromethyl, trifluoromethyl, $(C_1\text{-}C_4)$-alkyl,
and
where phenyl is substituted by a substituent selected from the group consisting of $(C_3\text{-}C_6)$-cycloalkyl, $(C_1\text{-}C_2)$-alkoxy and trifluoromethoxy,
and their N-oxides, salts, solvates, salts of the N-oxides and solvates of the N-oxides and salts.

Preference in the context of the present invention is also given to compounds of the formula (I) in which
$R^1$ represents phenyl,
where phenyl is substituted by 1 to 2 fluorine,
and
where phenyl is substituted by a substituent selected from the group consisting of cyclopropyl and methoxy,
and their N-oxides, salts, solvates, salts of the N-oxides and solvates of the N-oxides and salts.

Preference in the context of the present invention is also given to compounds of the formula (I) in which
$R^5$ represents monofluoromethyl, difluoromethyl, trifluoromethyl, $(C_3\text{-}C_6)$-cycloalkyl, $(C_2\text{-}C_4)$-alkenyl, $(C_2\text{-}C_4)$-alkynyl, difluoromethoxy, trifluoromethoxy, $(C_1\text{-}C_4)$-alkoxy, amino, 4- to 7-membered heterocyclyl or 5- or 6-membered heteroaryl,
and their N-oxides, salts, solvates, salts of the N-oxides and solvates of the N-oxides and salts.

Preference in the context of the present invention is also given to compounds of the formula (I) in which
$R^5$ represents monofluoromethyl, difluoromethyl, trifluoromethyl, $(C_3\text{-}C_6)$-cycloalkyl, $(C_2\text{-}C_4)$-alkynyl, difluoromethoxy, trifluoromethoxy, $(C_1\text{-}C_4)$-alkoxy, 5- to 6-membered heterocyclyl or 5- or 6-membered heteroaryl,
and their N-oxides, salts, solvates, salts of the N-oxides and solvates of the N-oxides and salts.

Preference in the context of the present invention is also given to compounds of the formula (I) in which
$R^5$ represents monofluoromethyl, difluoromethyl, trifluoromethyl, cyclopropyl, $(C_2\text{-}C_4)$-alkynyl, methoxy, morpholino,
and their N-oxides, salts, solvates, salts of the N-oxides and solvates of the N-oxides and salts.

Preference in the context of the present invention is also given to compounds of the formula (I) in which
$R^7$ represents $(C_1\text{-}C_6)$-alkyl, $(C_2\text{-}C_6)$-alkynyl, cyano or phenyl,
where $(C_1\text{-}C_6)$-alkyl is substituted by 1 to 3 substituents independently of one another selected from the group consisting of fluorine, trifluoromethyl, difluoromethoxy, trifluoromethoxy and phenoxy,
where phenoxy may be substituted by 1 to 3 fluorine,
where phenyl is substituted by 1 to 2 substituents independently of one another selected from the group consisting of cyano, nitro, difluoromethoxy, trifluoromethoxy, $(C_1-C_4)$-alkoxy, —NH(CO)CH$_3$ and $(C_1-C_4)$-alkenyl,
where $(C_1-C_4)$-alkoxy is substituted by hydroxy,
$R^8$ represents hydrogen or $(C_1-C_4)$-alkyl,
and their N-oxides, salts, solvates, salts of the N-oxides and solvates of the N-oxides and salts.

Preference in the context of the present invention is also given to compounds of the formula (I) in which
$R^7$ represents $(C_1-C_4)$-alkyl, cyano or phenyl,
where $(C_1-C_4)$-alkyl is substituted up to five times by fluorine,
and
where phenyl is substituted by cyano, difluoromethoxy, trifluoromethoxy, ethoxy, —NH(CO)CH$_3$ or ethenyl,
where ethoxy is substituted by hydroxy,
$R^8$ represents hydrogen,
and their N-oxides, salts, solvates, salts of the N-oxides and solvates of the N-oxides and salts.

Preference in the context of the present invention is also given to compounds of the formula (I) in which
$R^7$ represents $(C_1-C_4)$-alkyl, cyano or phenyl,
where $(C_1-C_4)$-alkyl is substituted up to five times by fluorine,
and
where phenyl is substituted by cyano, difluoromethoxy, trifluoromethoxy, ethoxy, —NH(CO)CH$_3$ or ethenyl,
where ethoxy is substituted by hydroxy,
$R^8$ represents hydrogen,
and their N-oxides, salts, solvates, salts of the N-oxides and solvates of the N-oxides and salts.

Preference in the context of the present invention is also given to compounds of the formula (I) in which
$R^9$ represents $(C_1-C_4)$-alkyl, cyano or phenyl,
where $(C_1-C_4)$-alkyl is substituted by 1 to 3 substituents independently of one another selected from the group consisting of fluorine, difluoromethyl, trifluoromethyl, difluoromethoxy, trifluoromethoxy, 5-membered heteroaryl and benzyloxy,
where benzyloxy may be substituted by 1 to 3 halogen substituents,
where 5-membered heteroaryl is substituted by a 5-membered heteroaryl,
where 5-membered heteroaryl for its part may be substituted by $(C_1-C_4)$-alkyl,
where phenyl is substituted by 1 to 2 substituents independently of one another selected from the group consisting of cyano, difluoromethoxy, trifluoromethoxy and $(C_1-C_4)$-alkoxy,
where $(C_1-C_4)$-alkoxy is substituted by hydroxy,
$R^{10}$ represents hydrogen or methyl,
and their N-oxides, salts, solvates, salts of the N-oxides and solvates of the N-oxides and salts.

Preference in the context of the present invention is also given to compounds of the formula (I) in which
$R^9$ represents ethyl, propyl, cyano or phenyl,
where ethyl and propyl are substituted by 1 to 3 substituents independently of one another selected from the group consisting of fluorine, trifluoromethyl and benzyloxy,
where benzyloxy may be substituted by 1 to 3 halogen substituents,
where phenyl is substituted by cyano, difluoromethoxy, trifluoromethoxy or ethoxy,
where ethoxy is substituted by hydroxy,
$R^{10}$ represents hydrogen or methyl,
and their N-oxides, salts, solvates, salts of the N-oxides and solvates of the N-oxides and salts.

Preference in the context of the present invention is also given to compounds of the formula (I) in which
$R^9$ represents ethyl, cyano or phenyl,
where ethyl is substituted up to five times by fluorine,
where phenyl is substituted by cyano, difluoromethoxy, trifluoromethoxy or ethoxy,
where ethoxy is substituted by hydroxy,
$R^{10}$ represents hydrogen or methyl,
and their N-oxides, salts, solvates, salts of the N-oxides and solvates of the N-oxides and salts.

Preference in the context of the present invention is also given to compounds of the formula (I) in which
$R^{11}$ represents $(C_1-C_4)$-alkyl,
where $(C_1-C_4)$-alkyl is substituted by 1 to 3 substituents independently of one another selected from the group consisting of fluorine, trifluoromethyl, hydroxy and $(C_1-C_4)$-alkoxy,
$R^{12}$ represents hydrogen, $(C_1-C_6)$-alkyl, $(C_3-C_7)$-cycloalkyl, phenyl or benzyl,
where $(C_1-C_6)$-alkyl may be substituted by 1 to 3 substituents independently of one another selected from the group consisting of fluorine, trifluoromethyl, hydroxy, $(C_1-C_4)$-alkoxy and phenoxy,
and
where phenyl and benzyl may be substituted by 1 to 3 substituents independently of one another selected from the group consisting of halogen and trifluoromethyl,
or
$R^{11}$ and $R^{12}$ together with the nitrogen atom to which they are attached form a 4- to 7-membered azaheterocycle,
where the 4- to 7-membered azaheterocycle is substituted by 1 or 2 substituents independently of one another selected from the group consisting of $(C_3-C_7)$-cycloalkyl and 4- to 7-membered heterocyclyl,
and their N-oxides, salts, solvates, salts of the N-oxides and solvates of the N-oxides and salts.

Preference in the context of the present invention is also given to compounds of the formula (I) in which
$R^{11}$ represents methyl or ethyl,
where methyl and ethyl are substituted by 1 to 3 substituents independently of one another selected from the group consisting of fluorine, trifluoromethyl, hydroxy and methoxy,
$R^{12}$ represents hydrogen, $(C_1-C_4)$-alkyl, $(C_3-C_6)$-cycloalkyl, phenyl or benzyl,
where $(C_1-C_4)$-alkyl may be substituted by 1 to 3 substituents independently of one another selected from the group consisting of fluorine, trifluoromethyl, hydroxy, $(C_1-C_4)$-alkoxy and phenoxy,
and
where phenyl and benzyl may be substituted by 1 to 3 substituents independently of one another selected from the group consisting of halogen and trifluoromethyl,
or
$R^{11}$ and $R^{12}$ together with the nitrogen atom to which they are attached form a 4- to 6-membered azaheterocycle,
where the 4- to 6-membered azaheterocycle may be substituted by 1 or 2 substituents independently of one another selected from the group consisting of $(C_3-C_6)$-cycloalkyl and 4- to 6-membered heterocyclyl,
and their N-oxides, salts, solvates, salts of the N-oxides and solvates of the N-oxides and salts.

Preference in the context of the present invention is also given to compounds of the formula (I) in which
R$^{13}$ represents 5- to 9-membered azaheterocyclyl which is attached via a ring carbon atom,
where 5- to 9-membered azaheterocyclyl is substituted by 1 to 5 substituents independently of one another selected from the group consisting of $(C_3-C_7)$-cycloalkyl and benzyl,
and their N-oxides, salts, solvates, salts of the N-oxides and solvates of the N-oxides and salts.

Preference in the context of the present invention is also given to compounds of the formula (I) in which
R$^{13}$ represents 5- to 6-membered azaheterocyclyl which is attached via a ring carbon atom,
where 5- to 6-membered azaheterocyclyl is substituted by 1 to 3 substituents independently of one another selected from the group consisting of $(C_3-C_7)$-cycloalkyl and benzyl,
and their N-oxides, salts, solvates, salts of the N-oxides and solvates of the N-oxides and salts.

The definitions of radicals indicated specifically in the respective combinations or preferred combinations of radicals are replaced as desired irrespective of the particular combinations indicated for the radicals also by definitions of radicals of other combinations.

Combinations of two or more of the preferred ranges mentioned above are particularly preferred.

The invention furthermore provides a process for preparing the compounds of the formula (I) according to the invention, characterized in that
[A] a compound of the formula (II)

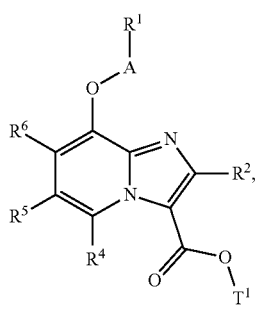

(II)

in which A, R$^1$, R$^2$, R$^4$, R$^5$ and R$^6$ each have the meanings given above and
T$^1$ represents $(C_1-C_4)$-alkyl or benzyl,
is reacted in an inert solvent in the presence of a suitable base or acid to give a carboxylic acid of the formula (III)

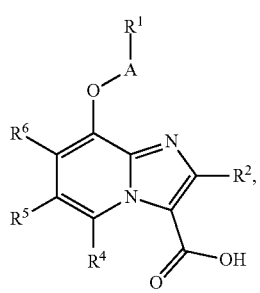

(III)

in which A, R$^1$, R$^2$, R$^4$, R$^5$ and R$^6$ each have the meanings given above,
and this is subsequently reacted in an inert solvent under amide coupling conditions with an amine of the formula (IV-A) or (IV-B)

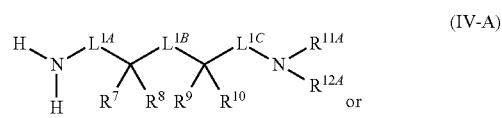

(IV-A)

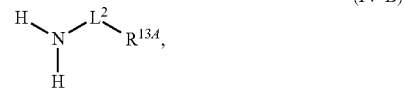

(IV-B)

in which $L^{1A}$, $L^{1B}$, $L^{1C}$, $L^2$, R$^7$, R$^8$, R$^9$, and R$^{10}$ each have the meanings given above
and
R$^{11A}$, R$^{12A}$ and R$^{13A}$ have the meanings given above for R$^{11}$, R$^{12}$ and R$^{13}$, respectively, or represent an amino protective group, for example tert-butoxycarbonyl, benzyloxycarbonyl or benzyl,
or
[B] a compound of the formula (III-B)

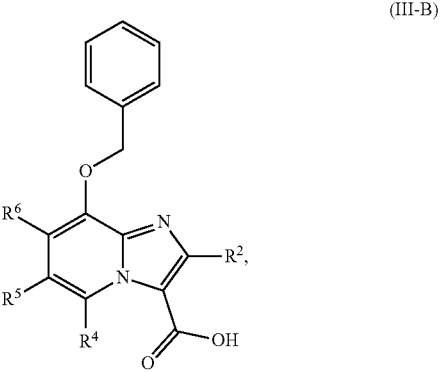

(III-B)

in which R$^2$, R$^4$, R$^5$ and R$^6$ each have the meanings given above,
is reacted in an inert solvent under amide coupling conditions with an amine of the formula (IV) to give a compound of the formula (I-A) and (I-B),

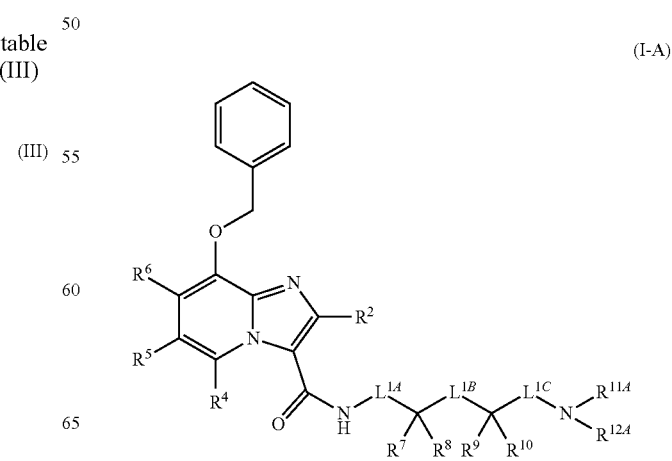

(I-A)

-continued (I-B)

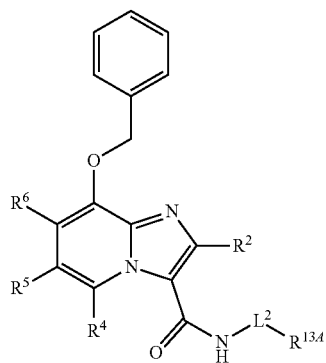

in which $R^2$, $R^4$, $R^5$, $R^6$, $L^{1A}$, $L^{1B}$, $L^{1C}$, $L^2$, $R^7$, $R^8$, $R^9$, $R^{10}$, $R^{11A}$, $R^{12A}$ and $R^{13A}$ each have the meanings given above, from this compound, the benzyl group is subsequently removed using methods known to the person skilled in the art and the resulting compound of the formula (V-A) or (V-B)

(V-A)

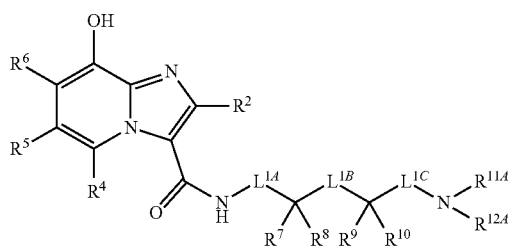

(V-B)

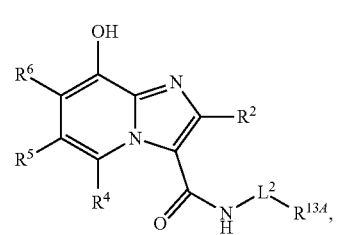

in which $R^2$, $R^4$, $R^5$, $R^6$, $L^{1A}$, $L^{1B}$, $L^{1C}$, $L^2$, $R^7$, $R^8$, $R^9$, $R^{10}$, $R^{11A}$, $R^{12A}$ and $R^{13A}$ each have the meanings given above, is reacted in an inert solvent in the presence of a suitable base with a compound of the formula (VI)

(VI)

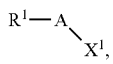

in which A and $R^1$ have the meanings given above and
$X^1$ represents a suitable leaving group, in particular chlorine, bromine, iodine, mesylate, triflate or tosylate,
any protective groups present are subsequently removed, and the resulting compounds of the formula (I) are optionally converted with the appropriate (i) solvents and/or (ii) acids or bases into their solvates, salts and/or solvates of the salts.

The compounds of the formulae (I-A) and (I-B) form a subset of the compounds of the formula (I) according to the invention.

The preparation processes described can be illustrated in an exemplary manner by the synthesis schemes below (Schemes 1 and 2):

Scheme 1:

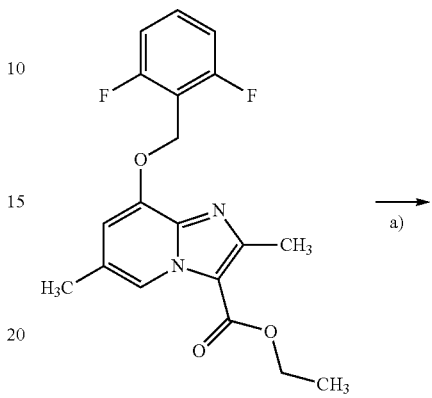

a)

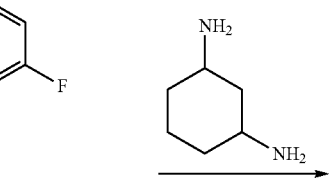

b)

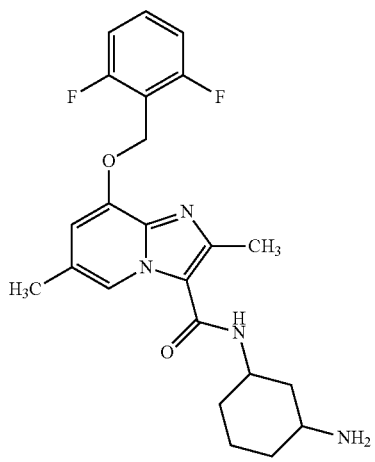

[a]: lithium hydroxide, THF/methanol/H₂O, RT; b): HATU, N,N-diisopropylethylamine, DMF, RT].

Scheme 2:

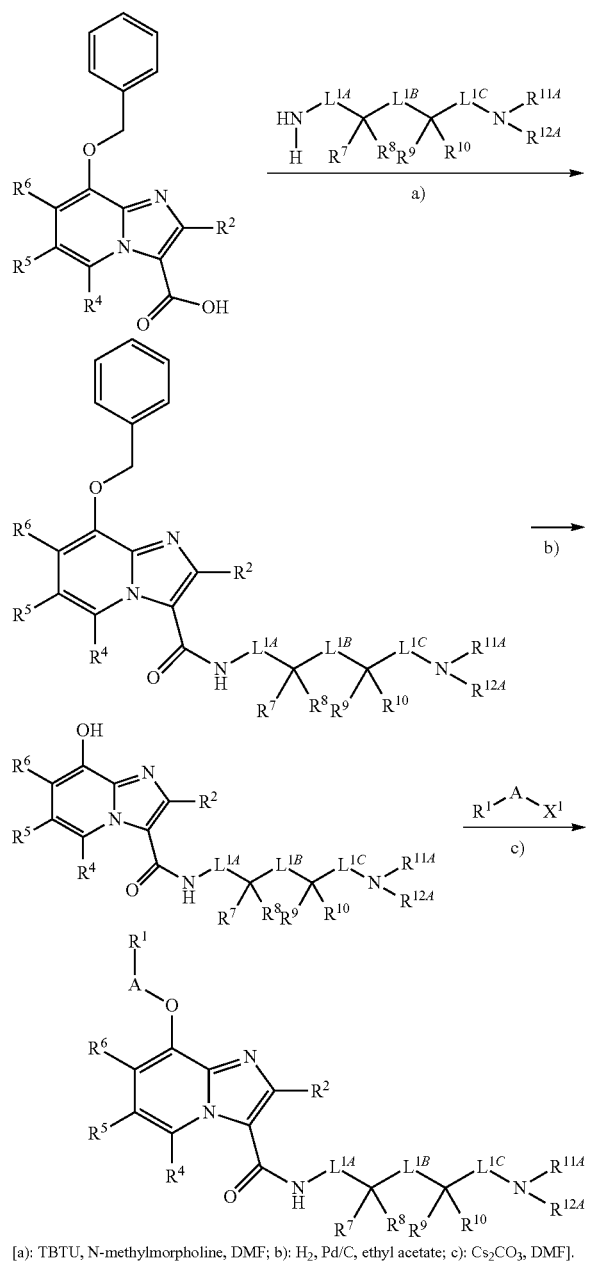

[a]: TBTU, N-methylmorpholine, DMF; b): $H_2$, Pd/C, ethyl acetate; c): $Cs_2CO_3$, DMF].

The compounds of the formulae (IV-A), (IV-B) and (VI) are commercially available, known from the literature or can be prepared analogously to processes known from the literature.

The free bases of (IV-A) can be released from the compounds (IV-A) optionally provided with an amino protective group, for example by using acids such as hydrogen chloride and trifluoroacetic acid in suitable solvents such as diethyl ether, dichloromethane, 1,4-dioxane, water, methanol, ethanol and mixtures thereof.

Inert solvents for the process steps (III)+(IV)→(I) and (III-B)+(IV)→(I-B) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to dichloromethane, tetrahydrofuran, dimethylformamide or mixtures of these solvents.

Suitable condensing agents for the amide formation in process steps (III)+(IV)→(I) and (III-B)+(IV)→(I-B) are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium 3-sulphate or 2-tert-butyl-5-methylisoxazolium perchlorate, acylamino compounds such as 2-ethoxy-1-ethoxycarbonyl-1,2-dihydroquinoline, or isobutyl chloroformate, propanephosphonic anhydride (T3P), 1-chloro-N,N,2-trimethylpropl-ene-1-amine, diethyl cyanophosphonate, bis-(2-oxo-3-oxazolidinyl)phosphoryl chloride, benzotriazol-1-yloxytris(dimethylamino)phosphonium hexafluorophosphate, benzo-triazol-1-yloxytris(pyrrolidino)phosphonium hexafluorophosphate (PyBOP), O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), if appropriate in combination with further auxiliaries such as 1-hydroxy-benzotriazole (HOBt) or N-hydroxysuccinimide (HOSu), and also as bases alkali metal carbonates, for example sodium carbonate or potassium carbonate or sodium bicarbonate or potassium bicarbonate, or organic bases such as trialkylamines, for example triethylamine, N-methylmorpholine, N-methylpiperidine or N,N-diisopropylethylamine. Preference is given to using TBTU in combination with N-methylmorpholine, HATU in combination with N,N-diisopropylethylamine or 1-chloro-N,N,2-trimethylprop-1-ene-1amine.

The condensations (III)+(IV)→(I) and (III-B)+(IV)→(I-B) are generally carried out in a temperature range of from −20° C. to +100° C., preferably at from 0° C. to +60° C. The reaction can be performed at atmospheric, elevated or at reduced pressure (for example from 0.5 to 5 bar). In general, the reaction is carried out at atmospheric pressure.

Alternatively, the carboxylic acids of the formula (III) can also initially be converted into the corresponding carbonyl chloride and this can then be reacted directly or in a separate reaction with an amine of the formula (IV) to give the compounds according to the invention. The formation of carbonyl chlorides from carboxylic acids is carried out by methods known to the person skilled in the art, for example by treatment with thionyl chloride, sulphuryl chloride or oxalyl chloride in the presence of a suitable base, for example in the presence of pyridine, and also optionally with addition of dimethylformamide, optionally in a suitable inert solvent.

The hydrolysis of the ester group $T^1$ of the compounds of the formula (II) is carried out by customary methods by treating the esters in inert solvents with acids or bases, where in the latter case the salts initially formed are converted into the free carboxylic acids by treatment with acid. In the case of the tert-butyl esters the ester cleavage is preferably carried out with acids. In the case of benzyl esters, the ester cleavage is preferably carried out hydrogenolytically using palladium on activated carbon or Raney nickel. Suitable inert solvents for this reaction are water or the organic solvents customary for an ester cleavage. These preferably include alcohols such as methanol, ethanol, n-propanol, isopropanol, n-butanol or tert-butanol, or ethers such as diethyl ether, tetrahydrofuran, 2-methyltetrahydrofuran, dioxane or glycol dimethyl ether, or other solvents such as acetone, dichloromethane, dimethylformamide or dimethyl sulphoxide. It is also possible to use mixtures of the solvents mentioned. In the case of a basic ester hydrolysis, preference is given to using mixtures of water with dioxane, tetrahydrofuran, methanol and/or ethanol.

Suitable bases for the ester hydrolysis are the customary inorganic bases. These preferably include alkali metal or alkaline earth metal hydroxides, for example sodium hydroxide, lithium hydroxide, potassium hydroxide or barium hydroxide, or alkali metal or alkaline earth metal carbonates such as sodium carbonate, potassium carbonate or calcium carbonate. Particular preference is given to sodium hydroxide or lithium hydroxide.

Suitable acids for the ester cleavage are, in general, sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluoromethanesulphonic acid, or mixtures thereof, if appropriate with addition of water. Preference is given to hydrogen chloride or trifluoroacetic acid in the case of the tert-butyl esters and hydrochloric acid in the case of the methyl esters.

The ester cleavage is generally carried out in a temperature range of from 0° C. to +100° C., preferably at from +0° C. to +50° C.

The reactions mentioned can be carried out at atmospheric, elevated or reduced pressure (for example from 0.5 to 5 bar). In general, the reactions are in each case carried out at atmospheric pressure.

Inert solvents for the process step (V)+(VI)→(I) are, for example, halogenated hydrocarbons such as dichloromethane, trichloromethane, carbon tetrachloride, trichloroethylene or chlorobenzene, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, or other solvents such as acetone, methyl ethyl ketone, ethyl acetate, acetonitrile, N,N-dimethylformamide, N,N-dimethylacetamide, dimethyl sulphoxide, N,N'-dimethylpropyleneurea (DMPU), N-methylpyrrolidone (NMP) or pyridine. It is also possible to use mixtures of the solvents mentioned. Preference is given to using dimethylformamide or dimethyl sulphoxide.

Suitable bases for the process step (V)+(VI)→(I) are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, if appropriate with addition of an alkali metal iodide, for example sodium iodide or potassium iodide, alkali alkoxides such as sodium methoxide or potassium methoxide, sodium ethoxide or potassium ethoxide or sodium tert-butoxide or potassium tert-butoxide, alkali metal hydrides such as sodium hydride or potassium hydride, amides such as sodium amide, lithium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 4-(N,N-dimethylamino)pyridine (DMAP), 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using potassium carbonate, caesium carbonate or sodium methoxide.

The reaction is generally carried out in a temperature range of from 0° C. to +120° C., preferably at from +20° C. to +80° C., if appropriate in a microwave. The reaction can be carried out at atmospheric, elevated or reduced pressure (for example from 0.5 to 5 bar).

Preferred for use as amino protective group is tert-butoxycarbonyl (Boc) or benzyloxycarbonyl (Z). As protective group for a hydroxyl or carboxyl function, preference is given to using tert-butyl or benzyl. The removal of these protective groups is carried out by customary methods, preferably by reaction with a strong acid such as hydrogen chloride, hydrogen bromide or trifluoroacetic acid in an inert solvent such as dioxane, diethyl ether, dichloromethane or acetic acid; if appropriate, the removal can also be carried out without any additional inert solvent. In the case of benzyl and benzyloxycarbonyl as protective group, these can also be removed by hydrogenolysis in the presence of a palladium catalyst. If appropriate, the removal of the protective groups mentioned can be performed simultaneously in a one-pot reaction or in separate reaction steps.

Here, the removal of the benzyl group in reaction step (I-B)→(V) is carried out by customary methods known from protective group chemistry, preferably by hydrogenolysis in the presence of a palladium catalyst such as palladium on activated carbon in an inert solvent, for example ethanol or ethyl acetate [see also, for example, T. W. Greene and P. G. M. Wuts, *Protective Groups in Organic Synthesis*, Wiley, New York, 1999].

The compounds of the formula (II) are known from the literature or can be prepared by reacting a compound of the formula (VII)

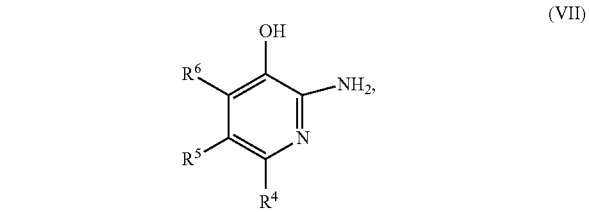

(VII)

in which $R^4$, $R^5$ and $R^6$ have the meanings given above,
in an inert solvent in the presence of a suitable base with a compound of the formula (VI) to give a compound of the formula (VIII)

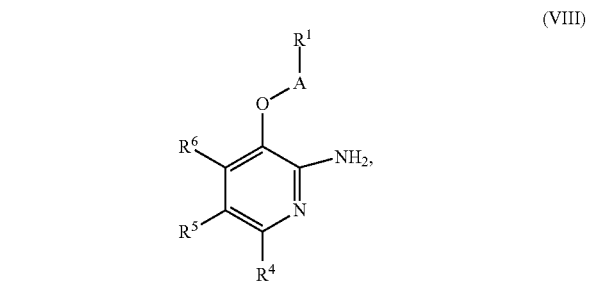

(VIII)

in which $R^1$, $R^4$, $R^5$ and $R^6$ each have the meanings given above,
and this is then reacted in an inert solvent with a compound of the formula (IX)

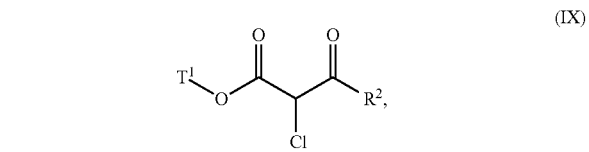

(IX)

in which $R^2$ and $T^1$ each have the meanings given above.

The process described is illustrated in an exemplary manner by the scheme below (Scheme 3):

Scheme 3:

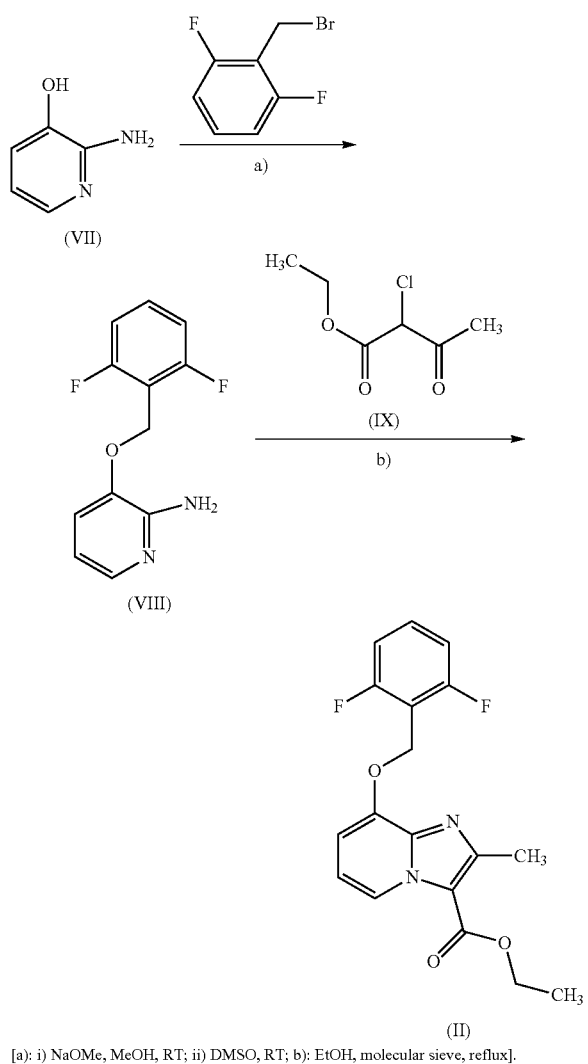

[a): i) NaOMe, MeOH, RT; ii) DMSO, RT; b): EtOH, molecular sieve, reflux].

The synthesis sequence shown can be modified such that the respective reaction steps are carried out in a different order. An example of such a modified synthesis sequence is shown in Scheme 4.

Scheme 4:

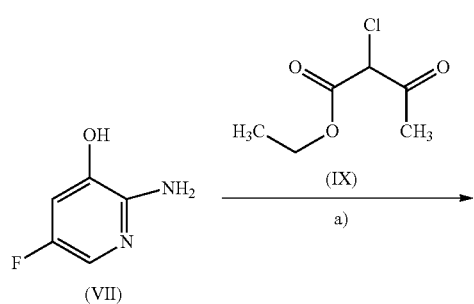

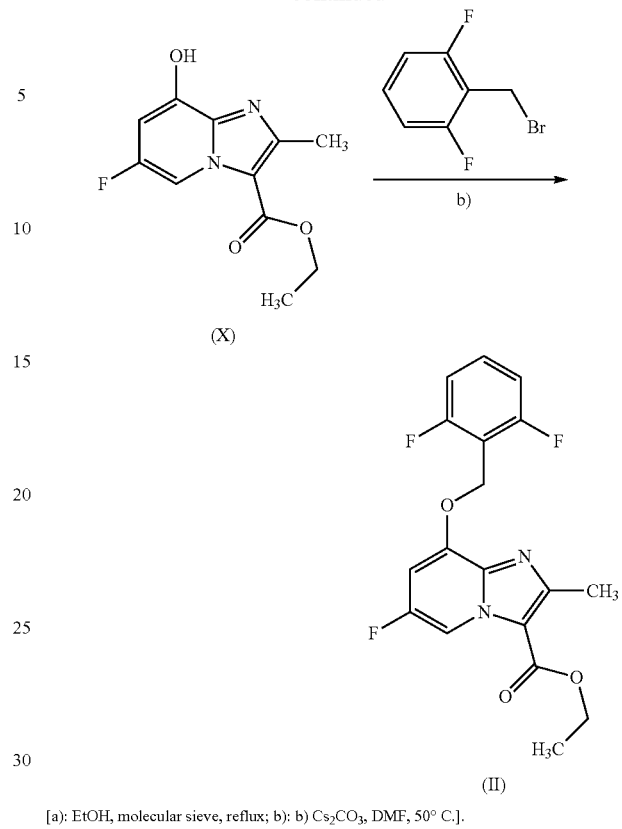

[a): EtOH, molecular sieve, reflux; b) b) $Cs_2CO_3$, DMF, 50° C.].

Inert solvents for the ring closure affording the imidazo[1,2-a]pyridine skeleton (VIII)+(IX)→(II) or (VII)+(IX)→(X) are the customary organic solvents. These preferably include alcohols such as methanol, ethanol, n-propanol, isopropanol, n-butanol, n-pentanol or tert-butanol, or ethers such as diethyl ether, tetrahydrofuran, 2-methyltetrahydrofuran, dioxane or glycol dimethyl ether, or other solvents such as acetone, dichloromethane, 1,2-dichloroethane, acetonitrile, dimethylformamide or dimethyl sulphoxide. It is also possible to use mixtures of the solvents mentioned. Preference is given to using ethanol.

The ring closure is usually carried out in a temperature range from +50° C. to +150° C., preferably at from +50° C. to +100° C., if appropriate in a microwave oven.

The ring closure (VIII)+(IX)→(II) or (VII)+(IX)→(X) is optionally carried out in the presence of dehydrating agents, for example in the presence of molecular sieve (pore size 4 Å) or using a water separator. The reaction (VIII)+(IX)→(II) or (VII)+(IX)→(X) is carried out using an excess of the reagent of the formula (IX), for example using 1 to 20 equivalents of reagent (IX), if appropriate with addition of bases (such as sodium bicarbonate), where the addition of this reagent can be carried out once or in several portions.

Alternatively to the introductions of $R^1$ shown in Schemes 1 to 4 by reaction of the compounds (V), (VII) or (X) with compounds of the formula (VI), it is also possible—as shown in Scheme 5—to react these intermediates with alcohols of the formula (XI) under the conditions of the Mitsunobu reaction.

Scheme 5:

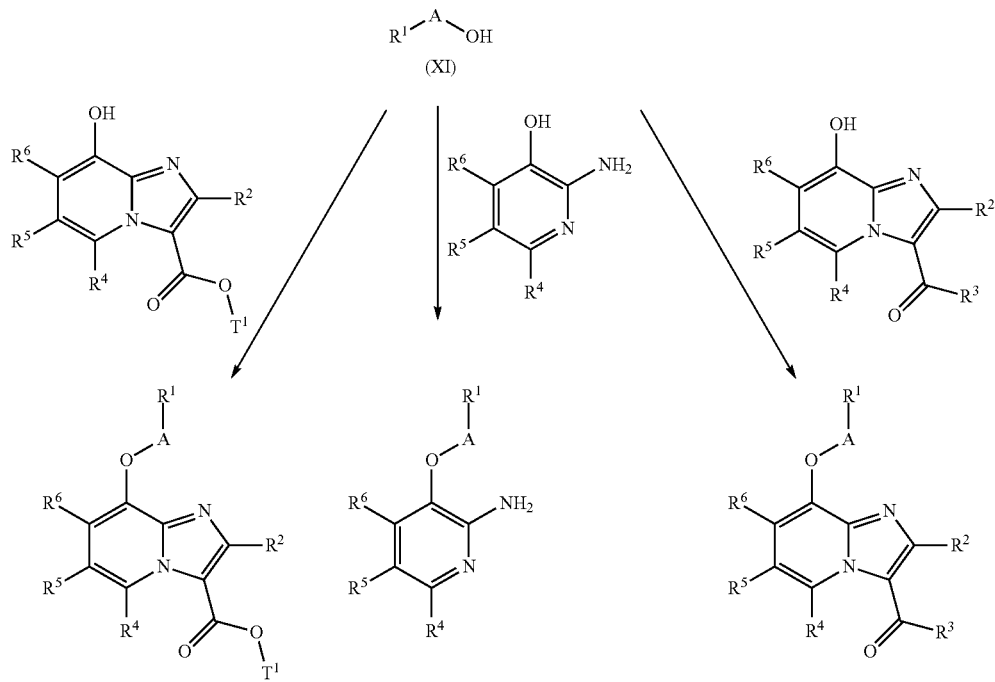

Typical reaction conditions for such Mitsunobu condensations of phenols with alcohols can be found in the relevant literature, for example Hughes, D. L. *Org. React.* 1992, 42, 335; Dembinski, R. *Eur. J. Org. Chem.* 2004, 2763. Typically, the compound is reacted with an activating agent, for example diethyl azodicarboxylate (DEAD) or diisopropyl azodicarboxylate (DIAD), and a phosphine reagent, for example triphenylphosphine or tributylphosphine, in an inert solvent, for example THF, dichloromethane, toluene or DMF, at a temperature between 0° C. and the boiling point of the solvent employed.

Further Working Examples can be prepared by methods known from the literature and familiar to the person skilled in the art, as shown in Schemes 6-17.

Synthesis of the Amines:

Scheme 6:

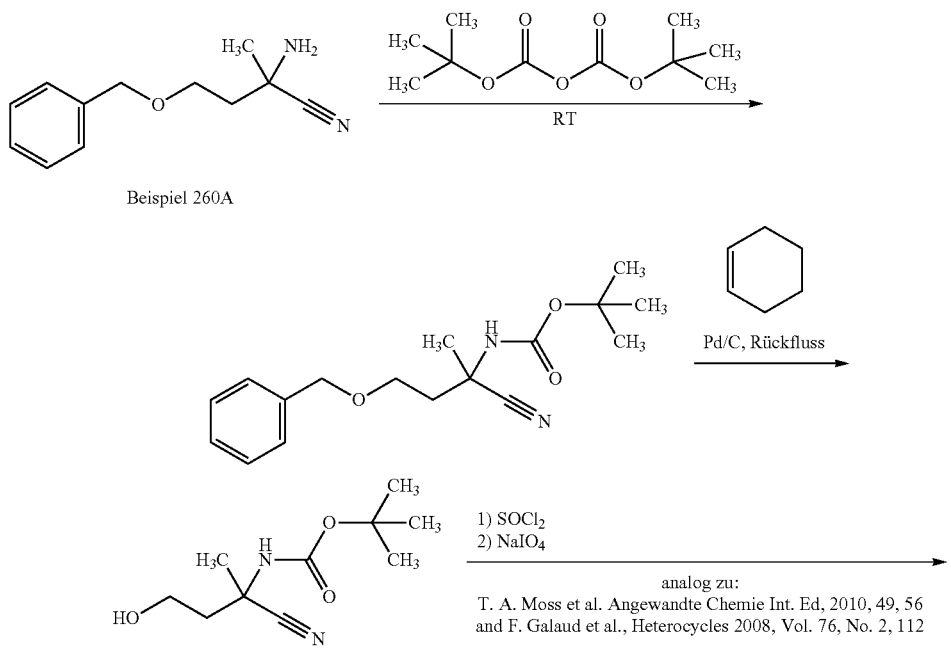

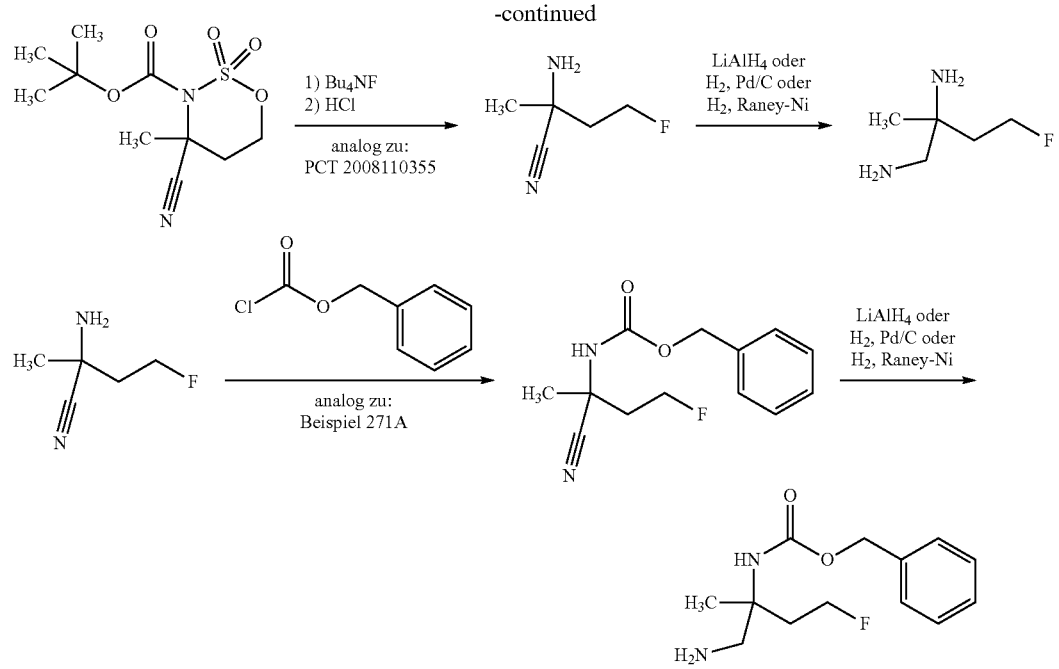
Scheme 7:
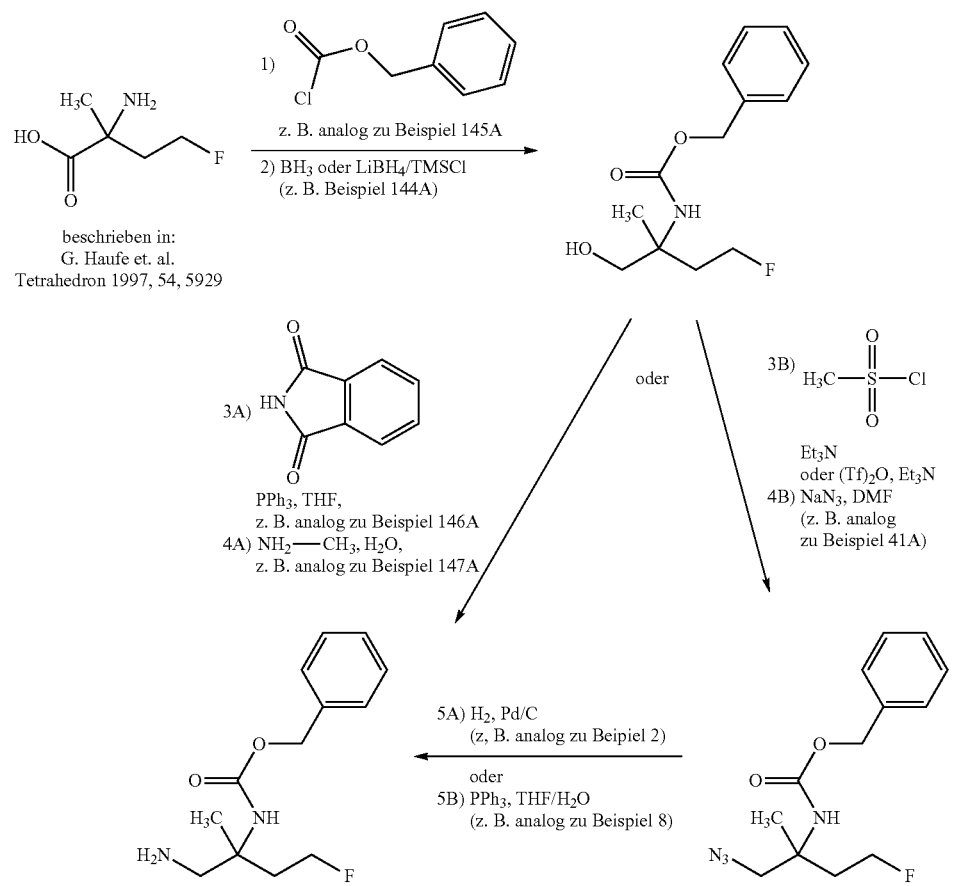

Scheme 8:
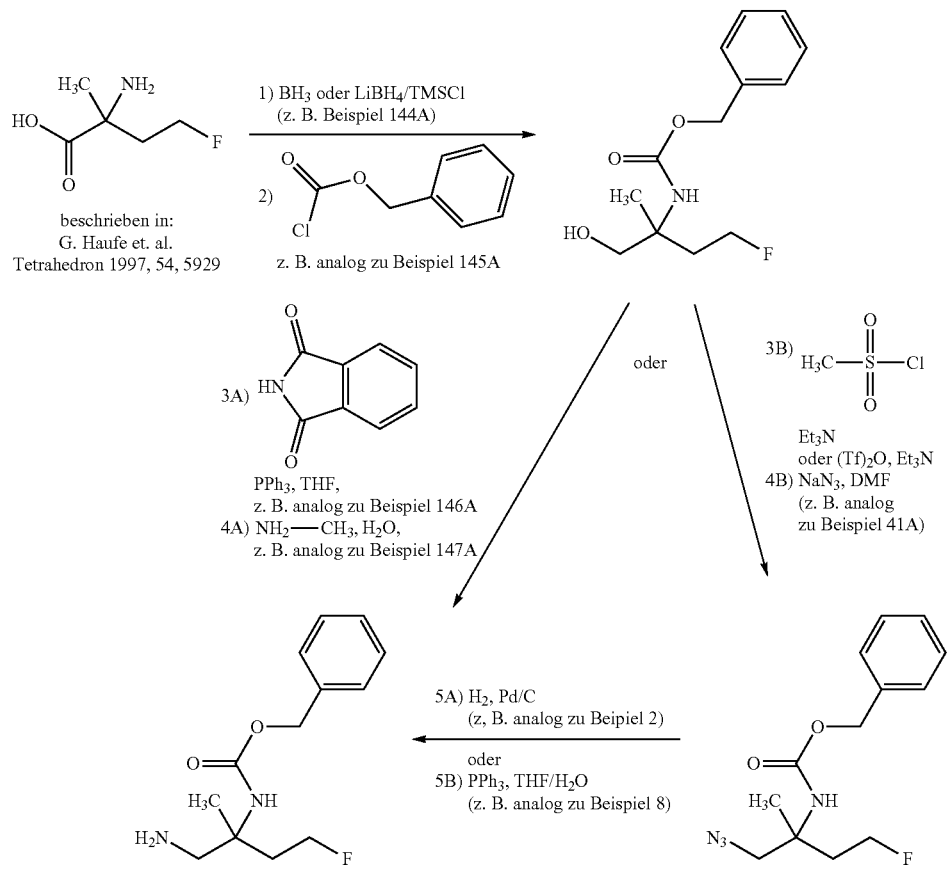
Scheme 9:
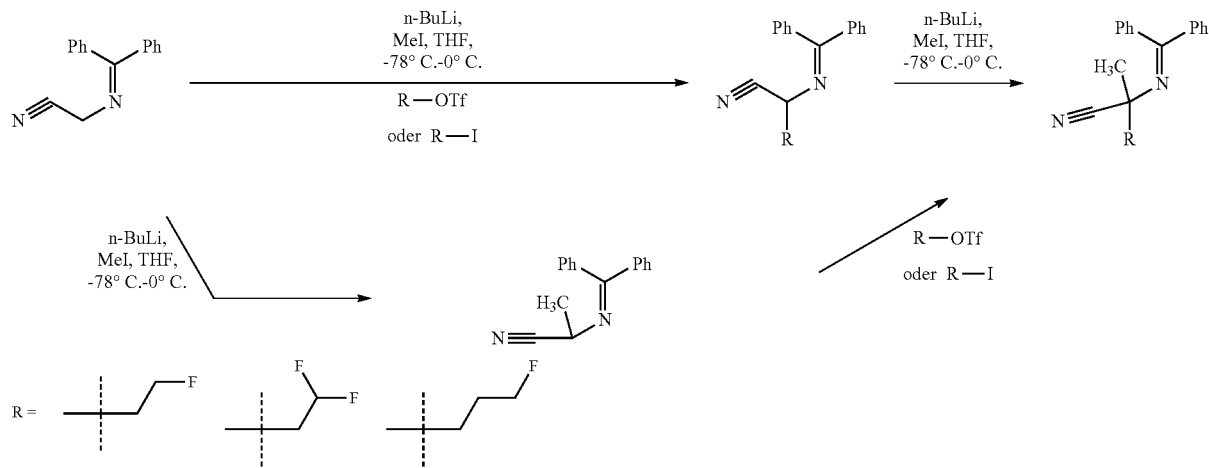

Scheme 10:
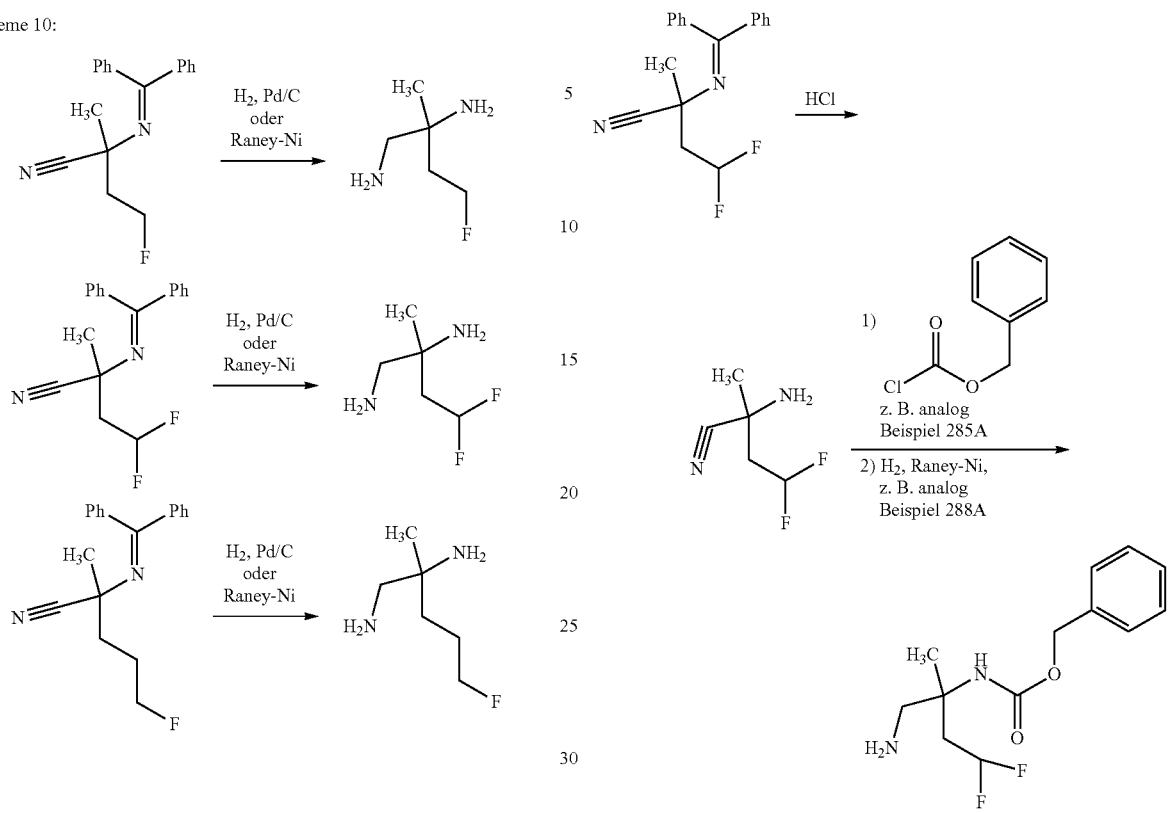
Scheme 11:
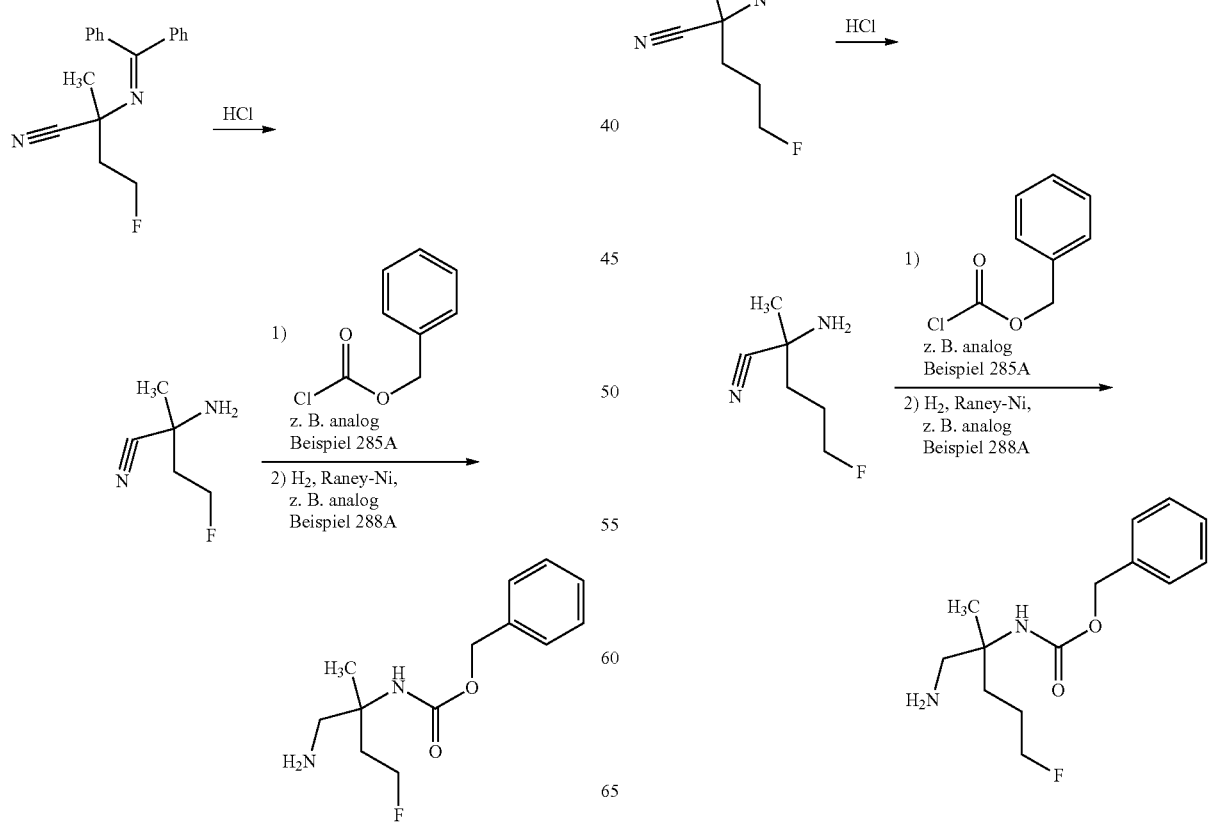

Scheme 12:
analog zu:
A. Perosa et al. J. Chem. Soc. Perkin Trans 2, 1999, 2485 oder
J. O. Opio et al. Synthetic Communications 1991, 21, 1743 oder
O Tsuge et al. Bulletin of the Chemical Society 1987, 60, 3347
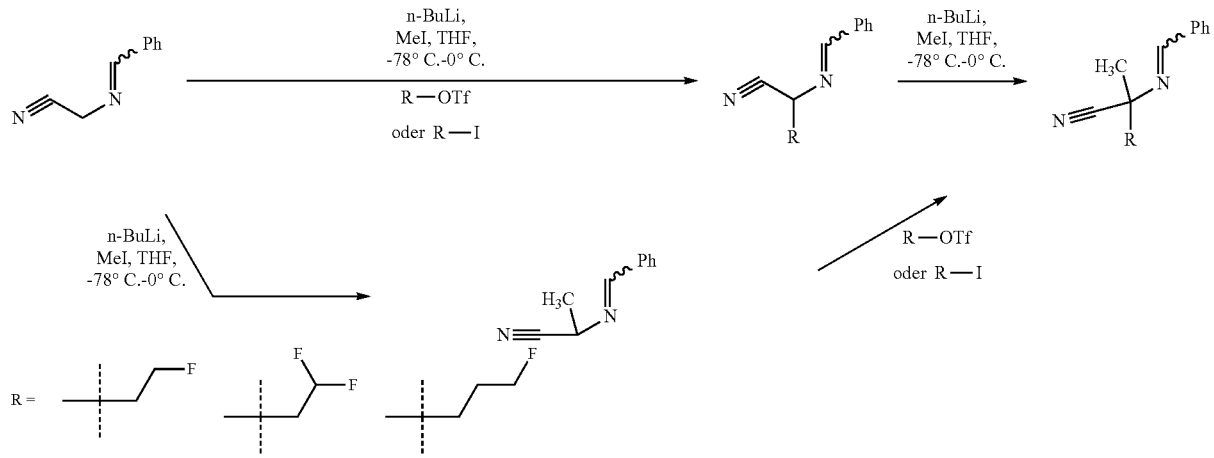
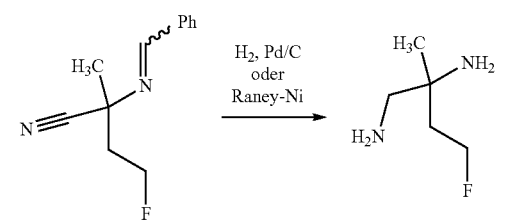
Scheme 13:
Scheme 14:
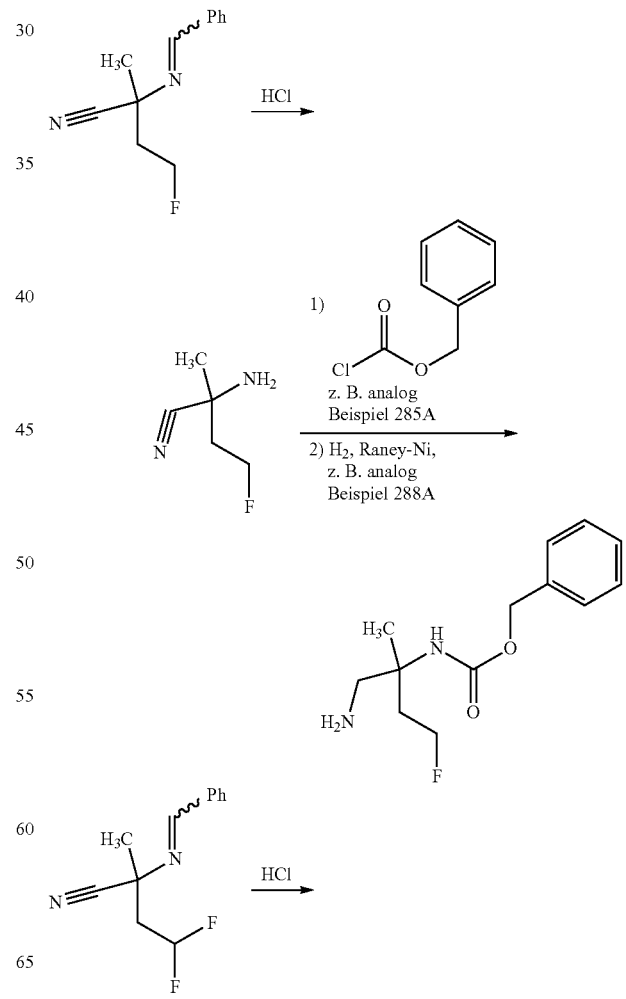

SYNTHESIS OF THE WORKING EXAMPLES
Scheme 15:
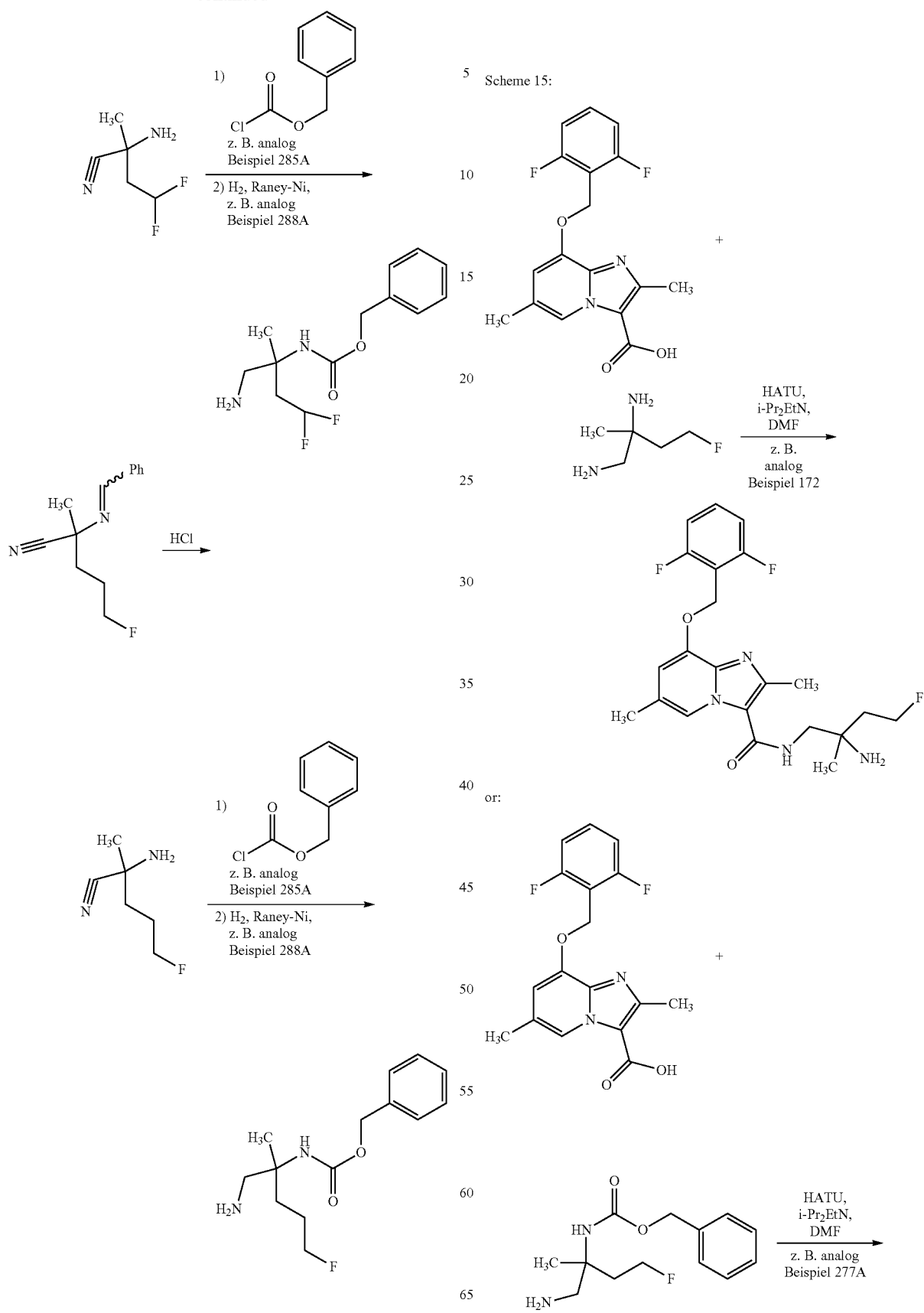

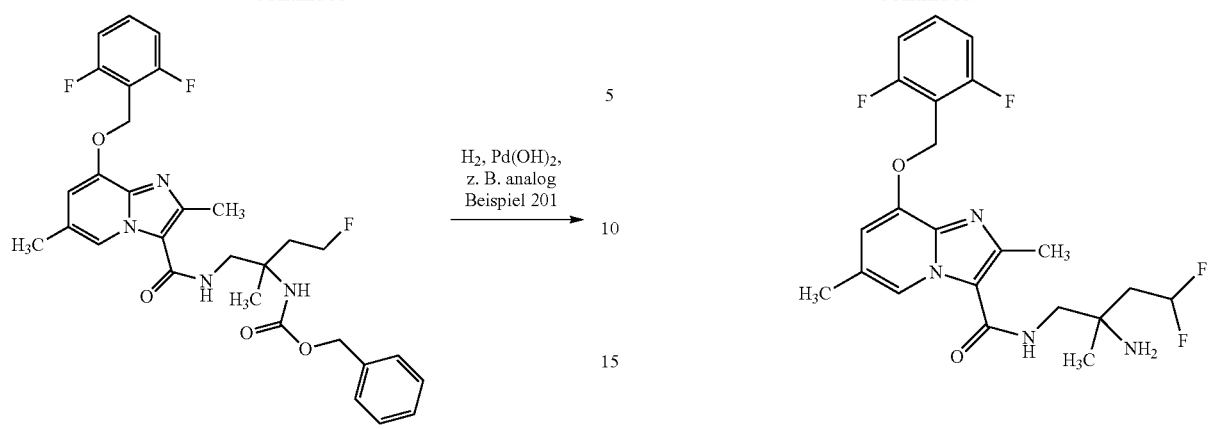
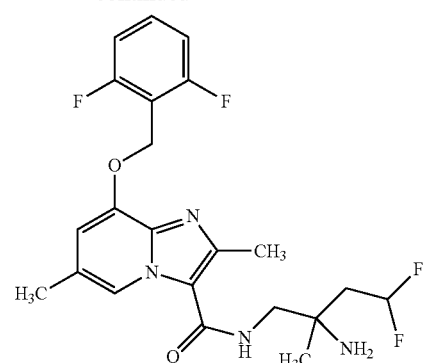
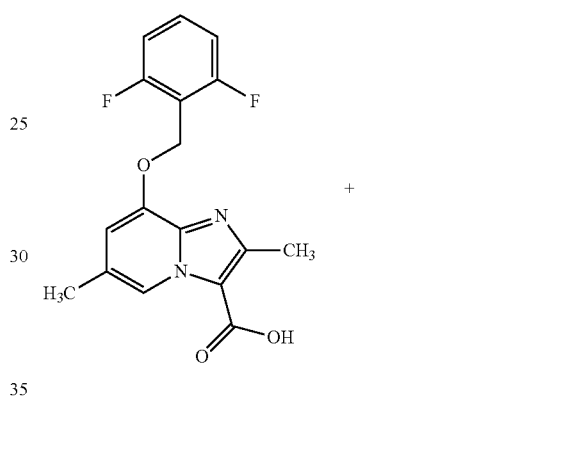
Scheme 16:
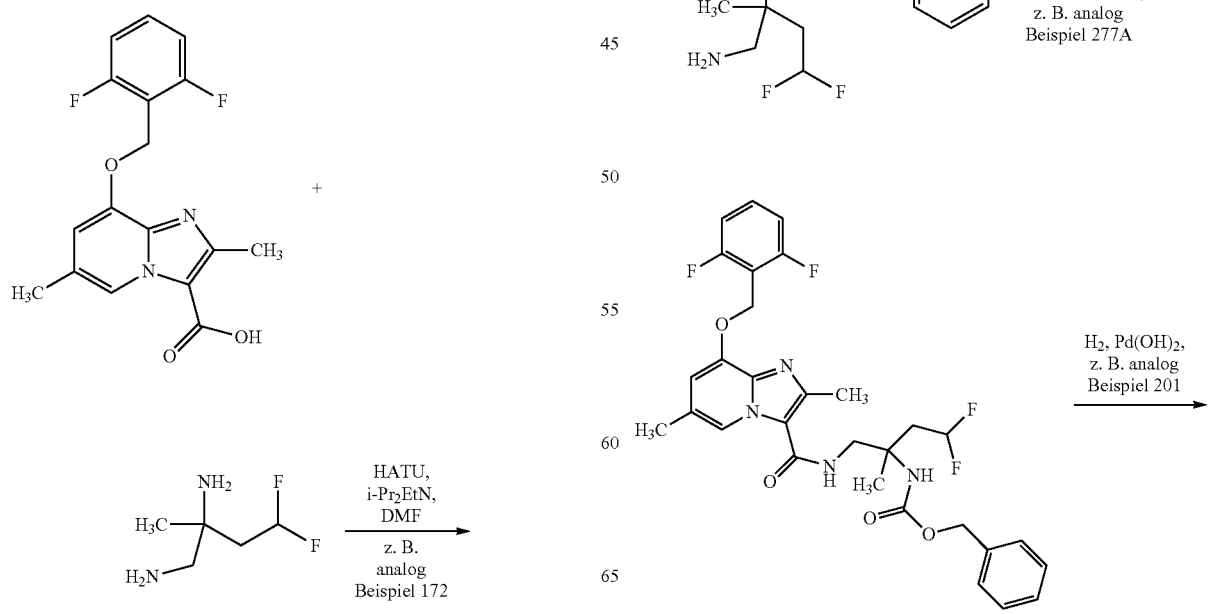

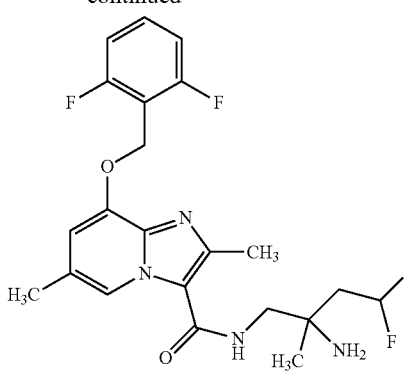

Scheme 17:

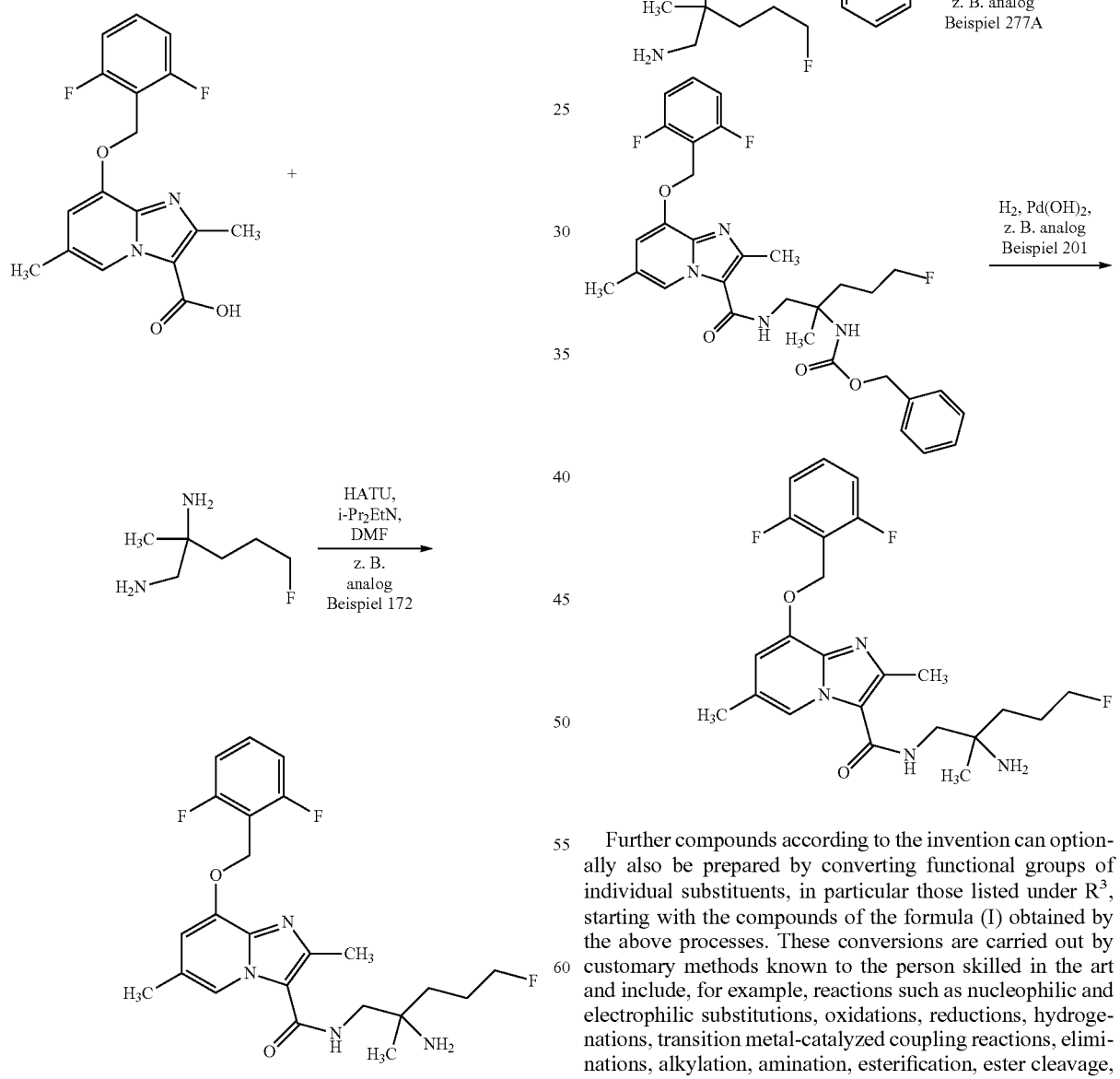

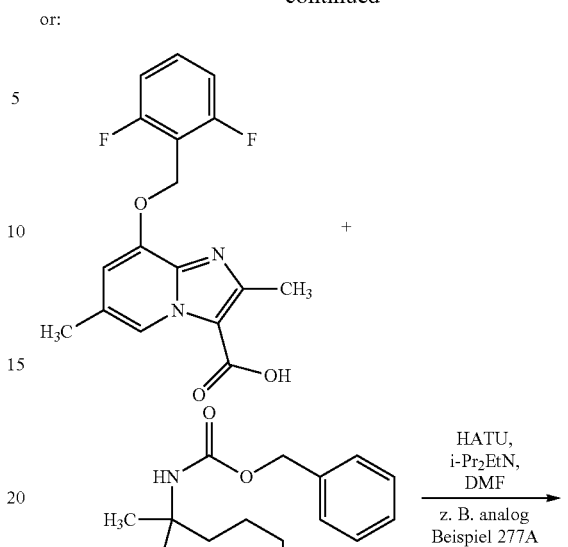

Further compounds according to the invention can optionally also be prepared by converting functional groups of individual substituents, in particular those listed under $R^3$, starting with the compounds of the formula (I) obtained by the above processes. These conversions are carried out by customary methods known to the person skilled in the art and include, for example, reactions such as nucleophilic and electrophilic substitutions, oxidations, reductions, hydrogenations, transition metal-catalyzed coupling reactions, eliminations, alkylation, amination, esterification, ester cleavage, etherification, ether cleavage, formation of carboxamides, and also the introduction and removal of temporary protective groups.

The compounds according to the invention have useful pharmacological properties and can be employed for the prevention and treatment of disorders in humans and animals. The compounds according to the invention open up a further treatment alternative and are therefore an enrichment of pharmacy.

The compounds according to the invention bring about vessel relaxation and inhibition of thrombocyte aggregation and lead to a lowering of blood pressure and to an increase in coronary blood flow. These effects are due to direct stimulation of soluble guanylate cyclase and an increase in intracellular cGMP. Moreover, the compounds according to the invention intensify the action of substances that raise the cGMP level, for example EDRF (endothelium-derived relaxing factor), NO donors, protoporphyrin IX, arachidonic acid or phenylhydrazine derivatives.

The compounds according to the invention are suitable for the treatment and/or prophylaxis of cardiovascular, pulmonary, thromboembolic and fibrotic diseases.

The compounds according to the invention can therefore be used in medicinal products for the treatment and/or prophylaxis of cardiovascular diseases, for example high blood pressure (hypertension), resistant hypertension, acute and chronic heart failure, coronary heart disease, stable and unstable angina pectoris, peripheral and cardiac vascular diseases, arrhythmias, disturbances of atrial and ventricular rhythm and conduction disturbances, for example atrioventricular blocks of degree I-III (AVB I-III), supraventricular tachyarrhythmia, atrial fibrillation, atrial flutter, ventricular fibrillation, ventricular flutter, ventricular tachyarrhythmia, torsade-de-pointes tachycardia, atrial and ventricular extrasystoles, AV-junction extrasystoles, sick-sinus syndrome, syncopes, AV-node reentry tachycardia, Wolff-Parkinson-White syndrome, acute coronary syndrome (ACS), autoimmune heart diseases (pericarditis, endocarditis, valvulitis, aortitis, cardiomyopathies), shock such as cardiogenic shock, septic shock and anaphylactic shock, aneurysms, Boxer cardiomyopathy (premature ventricular contraction (PVC)), for the treatment and/or prophylaxis of thromboembolic diseases and ischaemias such as myocardial ischaemia, myocardial infarction, stroke, cardiac hypertrophy, transient ischaemic attacks, preeclampsia, inflammatory cardiovascular diseases, spasms of the coronary arteries and peripheral arteries, development of oedema, for example pulmonary oedema, cerebral oedema, renal oedema or oedema due to heart failure, peripheral perfusion disturbances, reperfusion injury, arterial and venous thromboses, microalbuminuria, myocardial insufficiency, endothelial dysfunction, for preventing restenoses such as after thrombolysis therapies, percutaneous transluminal angioplasty (PTA), transluminal coronary angioplasty (PTCA), heart transplant and bypass operations, and micro- and macrovascular damage (vasculitis), increased level of fibrinogen and of low-density LDL and increased concentrations of plasminogen activator inhibitor 1 (PAI-1), and for the treatment and/or prophylaxis of erectile dysfunction and female sexual dysfunction.

In the sense of the present invention, the term heart failure comprises both acute and chronic manifestations of heart failure, as well as more specific or related forms of disease such as acute decompensated heart failure, right ventricular failure, left ventricular failure, total heart failure, ischaemic cardiomyopathy, dilatated cardiomyopathy, hypertrophic cardiomyopathy, idiopathic cardiomyopathy, congenital heart defects, heart failure with valvular defects, mitral valve stenosis, mitral valve insufficiency, aortic valve stenosis, aortic valve insufficiency, tricuspid stenosis, tricuspid insufficiency, pulmonary valve stenosis, pulmonary valve insufficiency, combined valvular defects, heart muscle inflammation (Myocarditis), chronic myocarditis, acute myocarditis, viral myocarditis, diabetic heart failure, alcoholic cardiomyopathy, storage cardiomyopathies, diastolic heart failure and also systolic heart failure and acute phases of an existing chronic heart failure (worsening heart failure).

In addition, the compounds according to the invention can also be used for the treatment and/or prophylaxis of arteriosclerosis, disturbances of lipid metabolism, hypolipoproteinaemias, dyslipidaemias, hypertriglyceridaemias, hyperlipidaemias, hypercholesterolaemias, abetalipoproteinaemia, sitosterolaemia, xanthomatosis, Tangier disease, adiposity, obesity, and combined hyperlipidaemias and metabolic syndrome.

Moreover, the compounds according to the invention can be used for the treatment and/or prophylaxis of primary and secondary Raynaud phenomenon, microcirculation disturbances, claudication, peripheral and autonomic neuropathies, diabetic microangiopathies, diabetic retinopathy, diabetic limb ulcers, gangrene, CREST syndrome, erythematous disorders, onychomycosis, rheumatic diseases and for promoting wound healing.

Furthermore, the compounds according to the invention are suitable for treating urological diseases, for example benign prostatic syndrome (BPS), benign prostatic hyperplasia (BPH), benign prostatic enlargement (BPE), bladder outlet obstruction (BOO), lower urinary tract syndromes (LUTS, including feline urological syndrome (FUS)), diseases of the urogenital system including neurogenic overactive bladder (OAB) and (IC), urinary incontinence (UI) for example mixed, urge, stress, or overflow incontinence (MUI, UUI, SUI, OUI), pelvic pains, benign and malignant diseases of the organs of the male and female urogenital system.

Furthermore, the compounds according to the invention are suitable for the treatment and/or prophylaxis of kidney diseases, in particular acute and chronic renal insufficiency, and acute and chronic renal failure. In the sense of the present invention, the term renal insufficiency comprises both acute and chronic manifestations of renal insufficiency, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney transplant rejection, immune complex-induced kidney diseases, nephropathy induced by toxic substances, contrast medium-induced nephropathy, diabetic and non-diabetic nephropathy, pyelonephritis, renal cysts, nephrosclerosis, hypertensive nephrosclerosis and nephrotic syndrome, which can be characterized diagnostically for example by abnormally reduced creatinine and/or water excretion, abnormally increased blood concentrations of urea, nitrogen, potassium and/or creatinine, altered activity of renal enzymes such as e.g. glutamyl synthetase, altered urine osmolarity or urine volume, increased microalbuminuria, macroalbuminuria, lesions of glomeruli and arterioles, tubular dilatation, hyperphosphataemia and/or need for dialysis. The present invention also comprises the use of the compounds according to the invention for the treatment and/or prophylaxis of sequelae of renal insufficiency, for example pulmonary oedema, heart failure, uraemia, anaemia, electrolyte disturbances (e.g. hyperkalaemia, hyponatraemia) and disturbances in bone and carbohydrate metabolism.

Furthermore, the compounds according to the invention are also suitable for the treatment and/or prophylaxis of asthmatic diseases, pulmonary arterial hypertension (PAH) and other forms of pulmonary hypertension (PH), comprising pulmonary hypertension associated with left ventricular disease, HIV, sickle cell anaemia, thromboembolism (CTEPH), sarcoidosis, COPD or pulmonary fibrosis, chronic obstructive pulmonary disease (COPD), acute respiratory distress syndrome (ARDS), acute lung injury (ALI), alpha-1-antitrypsin deficiency (AATD), pulmonary fibrosis, pulmonary emphysema (e.g. smoking-induced pulmonary emphysema) and cystic fibrosis (CF).

The compounds described in the present invention are also active substances for controlling diseases in the central nervous system that are characterized by disturbances of the NO/cGMP system. In particular, they are suitable for improving perception, capacity for concentration, capacity for learning or memory performance after cognitive disturbances, such as occur in particular in situations/diseases/syndromes such as mild cognitive impairment, age-related learning and memory disturbances, age-related memory loss, vascular dementia, head injury, stroke, post-stroke dementia, post-traumatic head injury, general disturbances of concentration, disturbances of concentration in children with learning and memory problems, Alzheimer's disease, Lewy body dementia, dementia with frontal lobe degeneration including Pick's syndrome, Parkinson's disease, progressive nuclear palsy, dementia with corticobasal degeneration, amyotrophic lateral sclerosis (ALS), Huntington's disease, demyelination, multiple sclerosis, thalamic degeneration, Creutzfeldt-Jakob dementia, HIV-dementia, schizophrenia with dementia or Korsakoff psychosis. They are also suitable for the treatment and/or prophylaxis of diseases of the central nervous system such as anxiety, tension and depression, CNS-related sexual dysfunctions and sleep disturbances and for controlling pathological eating disorders and use of luxury foods and addictive drugs.

Furthermore, the compounds according to the invention are also suitable for controlling cerebral perfusion and are effective agents for combating migraines. They are also suitable for the prophylaxis and control of consequences of cerebral infarctions (apoplexia cerebri) such as stroke, cerebral ischaemias and head injury. The compounds according to the invention can also be used for controlling pain states and tinnitus.

In addition, the compounds according to the invention possess anti-inflammatory action and can therefore be used as anti-inflammatory agents for the treatment and/or prophylaxis of sepsis (SIRS), multiple organ failure (MODS, MOF), inflammatory diseases of the kidney, chronic intestinal inflammations (IBD, Crohn's disease, UC), pancreatitis, peritonitis, rheumatoid diseases, inflammatory skin diseases and inflammatory eye diseases.

Moreover, the compounds according to the invention can also be used for the treatment and/or prophylaxis of autoimmune diseases.

Furthermore, the compounds according to the invention are suitable for the treatment and/or prophylaxis of fibrotic diseases of the internal organs, for example of the lung, heart, kidney, bone marrow and in particular of the liver, and dermatological fibroses and fibrotic diseases of the eye.

In the sense of the present invention, the term fibrotic diseases comprises in particular the following terms: hepatic fibrosis, hepatic cirrhosis, pulmonary fibrosis, endomyocardial fibrosis, nephropathy, glomerulonephritis, interstitial renal fibrosis, fibrotic lesions as a consequence of diabetes, bone marrow fibrosis and similar fibrotic diseases, scleroderma, morphea, keloids, hypertrophic scars (including after surgery), naevi, diabetic retinopathy, proliferative vitreoretinopathy and connective tissue diseases (e.g. sarcoidosis).

Furthermore, the compounds according to the invention are suitable for controlling postoperative scarring, e.g. as a result of glaucoma operations.

The compounds according to the invention can also be used cosmetically for ageing and keratinizing skin.

Moreover, the compounds according to the invention are suitable for the treatment and/or prophylaxis of hepatitis, neoplasms, osteoporosis, glaucoma and gastroparesis.

The present invention further relates to the use of the compounds according to the invention for the treatment and/or prophylaxis of diseases, in particular the aforementioned diseases.

The present invention further relates to the use of the compounds according to the invention for the treatment and/or prophylaxis of heart failure, angina pectoris, hypertension, pulmonary hypertension, ischaemias, vascular diseases, renal insufficiency, thromboembolic diseases, fibrotic diseases and arteriosclerosis.

The present invention further relates to the compounds according to the invention for use in a method for the treatment and/or prophylaxis of heart failure, angina pectoris, hypertension, pulmonary hypertension, ischaemias, vascular diseases, renal insufficiency, thromboembolic diseases, fibrotic diseases and arteriosclerosis.

The present invention further relates to the use of the compounds according to the invention for producing a medicinal product for the treatment and/or prophylaxis of diseases, in particular the aforementioned diseases.

The present invention further relates to the use of the compounds according to the invention for producing a medicinal product for the treatment and/or prophylaxis of heart failure, angina pectoris, hypertension, pulmonary hypertension, ischaemias, vascular diseases, renal insufficiency, thromboembolic diseases, fibrotic diseases and arteriosclerosis.

The present invention further relates to a method for the treatment and/or prophylaxis of diseases, in particular the aforementioned diseases, using an effective amount of at least one of the compounds according to the invention.

The present invention further relates to a method for the treatment and/or prophylaxis of heart failure, angina pectoris, hypertension, pulmonary hypertension, ischaemias, vascular diseases, renal insufficiency, thromboembolic diseases, fibrotic diseases and arteriosclerosis, using an effective amount of at least one of the compounds according to the invention.

The compounds according to the invention can be used alone or in combination with other active substances if necessary. The present invention further relates to medicinal products containing at least one of the compounds according to the invention and one or more further active substances, in particular for the treatment and/or prophylaxis of the aforementioned diseases. As suitable combination active substances, we may mention for example and preferably:

organic nitrates and NO-donors, for example sodium nitroprusside, nitroglycerin, isosorbide mononitrate, isosorbide dinitrate, molsidomine or SIN-1, and inhalational NO;

compounds that inhibit the degradation of cyclic guanosine monophosphate (cGMP), for example inhibitors of phosphodiesterases (PDE) 1, 2 and/or 5, in particular PDE-5 inhibitors such as sildenafil, vardenafil and tadalafil;

antithrombotic agents, for example and preferably from the group of platelet aggregation inhibitors, anticoagulants or profibrinolytic substances;

active substances for lowering blood pressure, for example and preferably from the group of calcium antagonists, angiotensin AII antagonists, ACE inhibitors, endothelin antagonists, renin inhibitors, alpha-blockers, beta-blockers, mineralocorticoid receptor antagonists and diuretics; and/or active substances that alter fat metabolism, for example and preferably from the group of thyroid receptor agonists, cholesterol synthesis inhibitors such as for example and preferably HMG-CoA-reductase or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists.

Antithrombotic agents are preferably to be understood as compounds from the group of platelet aggregation inhibitors, anticoagulants or profibrinolytic substances.

In a preferred embodiment of the invention, the compounds according to the invention are administered in combination with a platelet aggregation inhibitor, for example and preferably aspirin, clopidogrel, ticlopidine or dipyridamole.

In a preferred embodiment of the invention, the compounds according to the invention are administered in combination with a thrombin inhibitor, for example and preferably ximelagatran, dabigatran, melagatran, bivalirudin or Clexane.

In a preferred embodiment of the invention, the compounds according to the invention are administered in combination with a GPIIb/IIIa antagonist, for example and preferably tirofiban or abciximab.

In a preferred embodiment of the invention, the compounds according to the invention are administered in combination with a factor Xa inhibitor, for example and preferably rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, for example and preferably coumarin.

The agents for lowering blood pressure are preferably to be understood as compounds from the group of calcium antagonists, angiotensin AII antagonists, ACE inhibitors, endothelin antagonists, renin inhibitors, alpha-blockers, beta-blockers, mineralocorticoid-receptor antagonists and diuretics.

In a preferred embodiment of the invention, the compounds according to the invention are administered in combination with a calcium antagonist, for example and preferably nifedipine, amlodipine, verapamil or diltiazem.

In a preferred embodiment of the invention, the compounds according to the invention are administered in combination with an alpha-1-receptor blocker, for example and preferably prazosin.

In a preferred embodiment of the invention, the compounds according to the invention are administered in combination with a beta-blocker, for example and preferably propranolol, atenolol, timolol, pindolol, alprenolol, oxprenolol, penbutolol, bupranolol, metipranolol, nadolol, mepindolol, carazolol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, for example and preferably losartan, candesartan, valsartan, telmisartan or embursatan.

In a preferred embodiment of the invention, the compounds according to the invention are administered in combination with an ACE inhibitor, for example and preferably enalapril, captopril, lisinopril, ramipril, delapril, fosinopril, quinopril, perindopril or trandopril.

In a preferred embodiment of the invention, the compounds according to the invention are administered in combination with an endothelin antagonist, for example and preferably bosentan, darusentan, ambrisentan or sitaxsentan.

In a preferred embodiment of the invention, the compounds according to the invention are administered in combination with a renin inhibitor, for example and preferably aliskiren, SPP-600 or SPP-800.

In a preferred embodiment of the invention, the compounds according to the invention are administered in combination with a mineralocorticoid-receptor antagonist, for example and preferably spironolactone or eplerenone.

In a preferred embodiment of the invention, the compounds according to the invention are administered in combination with a loop diuretic, for example furosemide, torasemide, bumetanide and piretanide, with potassium-sparing diuretics for example amiloride and triamterene, with aldosterone antagonists, for example spironolactone, potassium canrenoate and eplerenone and thiazide diuretics, for example hydrochlorothiazide, chlorthalidone, xipamide, and indapamide.

Agents altering fat metabolism are preferably to be understood as compounds from the group of CETP inhibitors, thyroid receptor agonists, cholesterol synthesis inhibitors such as HMG-CoA-reductase or squalene synthesis inhibitors, the ACAT inhibitors, MTP inhibitors, PPAR-alpha, PPAR-gamma and/or PPAR-delta agonists, cholesterol-absorption inhibitors, polymeric bile acid adsorbers, bile acid reabsorption inhibitors, lipase inhibitors and the lipoprotein (a) antagonists.

In a preferred embodiment of the invention, the compounds according to the invention are administered in combination with a CETP inhibitor, for example and preferably dalcetrapib, BAY 60-5521, anacetrapib or CETP-vaccine (CETi-1).

In a preferred embodiment of the invention, the compounds according to the invention are administered in combination with a thyroid receptor agonist, for example and preferably D-thyroxin, 3,5,3'-triiodothyronin (T3), CGS 23425 or axitirome (CGS 26214).

In a preferred embodiment of the invention, the compounds according to the invention are administered in combination with an HMG-CoA-reductase inhibitor from the class of statins, for example and preferably lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, for example and preferably BMS-188494 or TAK-475.

In a preferred embodiment of the invention, the compounds according to the invention are administered in combination with an ACAT inhibitor, for example and preferably avasimibe, melinamide, pactimibe, eflucimibe or SMP-797.

In a preferred embodiment of the invention, the compounds according to the invention are administered in combination with an MTP inhibitor, for example and preferably implitapide, BMS-201038, R-103757 or JTT-130.

In a preferred embodiment of the invention, the compounds according to the invention are administered in combination with a PPAR-gamma agonist, for example and preferably pioglitazone or rosiglitazone.

In a preferred embodiment of the invention, the compounds according to the invention are administered in combination with a PPAR-delta agonist, for example and preferably GW 501516 or BAY 68-5042.

In a preferred embodiment of the invention, the compounds according to the invention are administered in combination with a cholesterol-absorption inhibitor, for example and preferably ezetimibe, tiqueside or pamaqueside.

In a preferred embodiment of the invention, the compounds according to the invention are administered in combination with a lipase inhibitor, for example and preferably orlistat.

In a preferred embodiment of the invention, the compounds according to the invention are administered in combination with a polymeric bile acid adsorber, for example and preferably cholestyramine, colestipol, colesolvam, CholestaGel or colestimide.

In a preferred embodiment of the invention, the compounds according to the invention are administered in combination with a bile acid reabsorption inhibitor, for example and preferably ASBT (=IBAT) inhibitors, e.g. AZD-7806, S-8921, AK-105, BARI-1741, SC-435 or SC-635.

In a preferred embodiment of the invention, the compounds according to the invention are administered in combination with a lipoprotein(a) antagonist, for example and preferably gemcabene calcium (CI-1027) or nicotinic acid.

The present invention further relates to medicinal products that contain at least one compound according to the invention, usually together with one or more inert, non-toxic, pharmaceutically suitable excipients, and use thereof for the aforementioned purposes.

The compounds according to the invention can have systemic and/or local action. For this purpose they can be applied in a suitable way, e.g. by oral, parenteral, pulmonary, nasal, sublingual, lingual, buccal, rectal, dermal, transdermal, conjunctival, or otic administration or as implant or stent.

For these routes of application, the compounds according to the invention can be administered in suitable dosage forms.

Dosage forms functioning according to the prior art, for rapid and/or modified release of the compounds according to the invention, which contain the compounds according to the invention in crystalline and/or amorphized and/or dissolved form, e.g. tablets (uncoated or coated tablets, for example with enteric coatings or coatings with delayed dissolution or insoluble coatings, which control the release of the compound according to the invention), tablets or films/wafers that disintegrate rapidly in the oral cavity, films/lyophilizates, capsules (for example hard or soft gelatin capsules), sugar-coated pills, granules, pellets, powders, emulsions, suspensions, aerosols or solutions, are suitable for oral administration.

Parenteral administration can take place avoiding an absorption step (e.g. intravenous, intraarterial, intracardiac, intraspinal or intralumbar) or including absorption (e.g. intramuscular, subcutaneous, intracutaneous, percutaneous or intraperitoneal). Injection and infusion preparations in the form of solutions, suspensions, emulsions, lyophilizates or sterile powders are suitable, among others, as dosage forms for parenteral application.

Inhaled pharmaceutical forms (including powder inhalers, nebulizers), nasal drops, solutions or sprays, tablets, films/wafers or capsules for lingual, sublingual or buccal application, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, dusting powders, implants or stents for example are suitable for other routes of administration.

Oral or parenteral administration is preferred, especially oral administration.

The compounds according to the invention can be transformed to the aforementioned dosage forms. This can take place in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants such as ascorbic acid), colorants (e.g. inorganic pigments, for example iron oxides) and taste and/or odour correctants.

In general, it has proved advantageous, in the case of parenteral administration, to administer amounts of about 0.001 to 1 mg/kg, preferably about 0.01 to 0.5 mg/kg body weight to achieve effective results. For oral application, the dosage is about 0.001 to 2 mg/kg, preferably about 0.001 to 1 mg/kg body weight.

Nevertheless, it may optionally be necessary to deviate from the stated amounts, namely depending on body weight, route of administration, individual response to the active substance, type of preparation and time point or interval when application takes place. Thus, in some cases it may be sufficient to use less than the aforementioned minimum amount, whereas in other cases the stated upper limit must be exceeded. When applying larger amounts, it may be advisable to distribute these in several individual doses throughout the day.

The following practical examples explain the invention. The invention is not limited to the examples.

The percentages in the following tests and examples are percentages by weight, unless stated otherwise; parts are parts by weight. Proportions of solvents, dilution ratios and concentrations for liquid/liquid solutions refer in each case to the volume.

A. EXAMPLES

Abbreviations and Acronyms

| | |
|---|---|
| abs. | absolute (= dried) |
| aq. | aqueous solution |
| br | broad signal (NMR coupling pattern) |
| conc. | concentrated |
| δ | shift in the NMR spectrum (stated in ppm) |

| | |
|---|---|
| d | doublet (NMR coupling pattern) |
| DCI | direct chemical ionization (in MS) |
| DMAP | 4-N,N-dimethylaminopyridine |
| DMF | dimethylformamide |
| DMSO | dimethyl sulphoxide |
| ent | enantiomerically pure |
| eq. | equivalent(s) |
| ESI | electrospray ionization (in MS) |
| Et | ethyl |
| h | hour(s) |
| HATU | (1-[bis(dimethylamino)methylene]-1H-1,2,3-triazolo-[4,5-b]pyridinium 3-oxide hexafluorophosphate) |
| HPLC | high pressure, high performance liquid chromatography |
| HRMS | high resolution mass spectrometry |
| LC/MS | liquid chromatography-coupled mass spectrometry |
| LiHMDS | lithium hexamethyldisilazide |
| m | multiplet |
| Me | methyl |
| min | minute(s) |
| MS | mass spectrometry |
| NMR | nuclear magnetic resonance spectrometry |
| Ph | phenyl |
| q | quartet (NMR coupling pattern) |
| quint. | quintet (NMR coupling pattern) |
| rac | racemic |
| RT | room temperature |
| $R_t$ | retention time (in HPLC) |
| s | singlet (NMR coupling pattern) |
| t | triplet (NMR coupling pattern) |
| TFA | trifluoroacetic acid |
| THF | tetrahydrofuran |
| TBTU | (benzotriazol-1-yloxy)bisdimethylaminomethylium fluoroborate |
| UV | ultraviolet spectrometry |
| v/v | ratio by volume (of a solution) |
| XPHOS | dicyclohexyl-(2',4',6'-triisopropylbiphenyl-2-yl)phosphine |

LC/MS and HPLC Methods:

Method 1 (LC-MS):

Instrument: Micromass Quattro Premier with Waters UPLC Acquity; column: Thermo Hypersil GOLD 1.9μ 50×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A oven: 50° C.; flow rate: 0.33 ml/min; UV detection: 210 nm.

Method 2 (LC-MS):

Instrument: Waters ACQUITY SQD UPLC System; column: Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A oven: 50° C.; flow rate: 0.40 ml/min; UV detection: 210-400 nm.

Method 3 (LC-MS):

MS instrument type: Waters Micromass Quattro Micro; HPLC instrument type: Agilent 1100 Series; column: Thermo Hypersil GOLD 3μ 20 mm×4 mm; mobile phase A: 1 l of water+0.5 ml of 50%-strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 4 (DCI-MS):

Instrument: Thermo Fisher-Scientific DSQ; chemical ionization; reactant gas NH3; source temperature: 200° C.; ionization energy 70 eV.

Method 5 (LC-MS):

MS instrument type: Waters (Micromass) Quattro Micro; HPLC instrument type: Agilent 1100 Series; column: Thermo Hypersil GOLD 3μ 20×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A; oven: 50° C.; flow rate: 2 ml/min; UV detection: 210 nm.

Method 6 (GC-MS):

Instrument: Micromass GCT, GC6890; column: Restek RTX-35, 15 m×200 μm×0.33 μm; constant helium flow rate: 0.88 ml/min; oven: 70° C.; inlet: 250° C.; gradient: 70° C., 30° C./min→310° C. (maintained for 3 min).

Method 7 (LC-MS):

Instrument: Waters ACQUITY SQD UPLC System; column: Waters Acquity UPLC HSS T3 1.8μ 30×2 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A oven: 50° C.; flow rate: 0.60 ml/min; UV detection: 208-400 nm.

Method 8 (LC-MS):

MS instrument: Waters SQD; HPLC instrument: Waters UPLC; column: Zorbax SB-Aq (Agilent), 50 mm×2.1 mm, 1.8 μm; mobile phase A: water+0.025% formic acid, mobile phase B: acetonitrile (ULC)+0.025% formic acid; gradient: 0.0 min 98% A—0.9 min 25% A—1.0 min 5% A—1.4 min 5% A—1.41 min 98% A—1.5 min 98% A; oven: 40° C.; flow rate: 0.600 ml/min; UV detection: DAD; 210 nm.

Method 9 (Preparative HPLC):

Column: Macherey-Nagel VP 50/21 Nucleosil 100-5 C18 Nautilus. Flow rate: 25 ml/min. gradient: A=water+0.1% conc. aqueous ammonia, B=methanol, 0 min=30% B, 2 min=30% B, 6 min=100% B, 7 min=100% B, 7.1 min=30% B, 8 min=30% B, flow rate 25 ml/min, UV detection 220 nm.

Method 10 (FIA/MS, ES):

Instrument: Waters ZQ 2000; electrospray ionization; mobile phase A: 1 l of water+0.25 ml of 99% strength formic acid, mobile phase B: 1 l of acetonitrile+0.25 ml of 99% strength formic acid; 25% A, 75% B; flow rate: 0.25 ml/min Method 11:

MS instrument: Waters (Micromass) Quattro Micro; HPLC instrument: Agilent 1100 Series; column: YMC-Triart C18 3μ 50×3 mm; mobile phase A: 1 l of water+0.01 mol of ammonium carbonate, mobile phase B: 1 l of acetonitrile; gradient: 0.0 min 100% A→2.75 min 5% A→4.5 min 5% A; oven: 40° C.; flow rate: 1.25 ml/min; UV detection: 210 nm Method 12 (preparative LC-MS):

MS instrument: Waters, HPLC instrument: Waters (column Waters X-Bridge C18, 18 mm×50 mm, 5 μm, mobile phase A: water+0.05% triethylamine, mobile phase B: acetonitrile (ULC)+0.05% triethylamine, gradient: 0.0 min 95% A—0.15 min 95% A—8.0 min 5% A—9.0 min 5% A; flow rate: 40 ml/min; UV detection: DAD; 210-400 nm).

or

MS instrument: Waters, HPLC instrument: Waters (column Phenomenex Luna 5μ C18(2) 100 A, AXIA Tech. 50×21.2 mm, mobile phase A: water+0.05% formic acid, mobile phase B: acetonitrile (ULC)+0.05% formic acid, gradient: 0.0 min 95% A—0.15 min 95% A—8.0 min 5% A—9.0 min 5% A; flow rate: 40 ml/min; UV detection: DAD; 210-400 nm).

Method 13

Instrument: Micromass Quattro Premier with Waters UPLC Acquity; column: Thermo Hypersil GOLD 1.9μ 50×1 mm; mobile phase A: 1 l of water+0.5 ml of 50% strength formic acid, mobile phase B: 1 l of acetonitrile+0.5 ml of 50% strength formic acid; gradient: 0.0 min 97% A→0.5 min 97% A→3.2 min 5% A→4.0 min 5% A oven: 50° C.; flow rate: 0.3 ml/min; UV-detection: 210 nm.

Method 14:

Instrument: Thermo Scientific DSQII, Thermo Scientific Trace GC Ultra; column: Restek RTX-35MS, 15 m×200 μm×0.33 μm; constant helium flow rate: 1.20 ml/min; oven: 60° C.; inlet: 220° C.; gradient: 60° C., 30° C./min→300° C. (maintained for 3.33 min).

Method 15:

MS instrument: Waters (Micromass) QM; HPLC instrument: Agilent 1100 Series; column: Agilent ZORBAX Extend-C18 3.0×50 mm 3.5-micron; mobile phase A: 1 l of water+0.01 mol of ammonium carbonate, mobile phase B: 1 l of acetonitrile; gradient: 0.0 min 98% A→0.2 min 98% A→3.0 min 5% A—4.5 min 5% A; oven: 40° C.; flow rate: 1.75 ml/min; UV detection: 210 nm.

Method 16 (LC-MS):

Instrument: Agilent MS Quad 6150; HPLC: Agilent 1290; column: Waters Acquity UPLC HSS T3 1.8μ 50×2.1 mm; mobile phase A: 1 l of water+0.25 ml of 99% strength formic acid, mobile phase B: 1 l of acetonitrile+0.25 ml of 99% strength formic acid; gradient: 0.0 min 90% A→0.3 min 90% A→1.7 min 5% A→3.0 min 5% A oven: 50° C.; flow rate: 1.20 ml/min; UV detection: 205-305 nm.

If compounds according to the invention are purified by preparative HPLC according to the methods described above where the mobile phases contain additives such as trifluoroacetic acid, formic acid or ammonia, the compounds according to the invention may be obtained in salt form, for example as trifluoroacetate, formate or ammonium salt, if the compounds according to the invention contain a functionality which is sufficiently basic or acidic. Such a salt may be converted by various methods known to the person skilled in the art into the corresponding free base or acid, respectively.

Salts may be present in substoichiometric or superstoichiometric amounts, in particular if an amine or a carboxylic acid is present. In addition, in the case of the present imidazopyridines, under acidic conditions there may always be salts present, even in substoichiometric amounts, without this being obvious from the $^1$H NMR, and without particular indication and labelling of these in the respective IUPAC names and structural formulae.

All $^1$H NMR spectra data indicate the chemical shifts δ in ppm.

The multiplicities of proton signals in the $^1$H NMR spectra given in the paragraphs below indicate the signal form observed in each case and do not take into account any higher order signal phenomena.

The methyl group of the chemical system "2-methylimidazo[1,2-a]pyridine" appears in $^1$H NMR spectra as a singlet (often in DMSO-$d_6$ and in the range of 2.40-2.60 ppm) and is either clearly recognizable as such, is superimposed by the solvent signals or is completely under the signals of the solvent. In the $^1$H NMR spectra, this signal can be indicated by way of anticipation.

X-Ray Structure Analysis:

Transmission diffractometer: Bruker diffractometer with Apex-II-CCD detector

Radiation: copper, K alpha

Primary monochromator: focussing X-ray mirror

Measuring range: 4.73-67.08°

Room conditions: 20° C.

GENERAL WORKING PROCEDURES

Representative Working Procedure 1

Reduction of Amino Acids Using Lithium Borohydride and Chlorotrimethylsilane.

1.7-2.5 equivalents of lithium borohydride were initially charged in THF (about 0.1-0.5 M based on the amino acid), 3.4-5.0 equivalents of chlorotrimethylsilane were added (at 0° C. or RT) and the mixture was stirred at RT for five to 30 min. 1 equivalent of the amino acid was then carefully added a little at a time at 0° C. or RT and the reaction mixture was stirred at RT overnight.

Exemplary work-up of the reaction mixture: Methanol was added and the mixture was concentrated. A 20% potassium hydroxide solution was added to the residue and the mixture was extracted three times with dichloromethane. The combined organic phases were dried over sodium sulphate, filtered and concentrated.

Representative Working Procedure 2

Amide Formation Using TBTU as Coupling Agent.

1 equivalent of the carboxylic acid to be coupled (for example Example 3A), 1.1-1.5 equivalents of (benzotriazol-1-yloxy)bisdimethylaminomethylium fluoroborate (TBTU) and 3-6 equivalents of 4-methylmorpholine were initially charged in DMF or dichloromethane (about 0.1-0.2 M based on the carboxylic acid to be coupled). 1.1 to 1.5 equivalents of the amine to be coupled were then added, and the mixture was stirred at RT overnight.

Exemplary work-up of the reaction mixture: Water was added to the reaction solution and the precipitate formed stirred for 0.5-1.0 h, filtered off, washed thoroughly with water and dried under high vacuum overnight. Alternatively, the reaction mixture was concentrated directly, purified further by preparative HPLC and dried under high vacuum overnight.

If appropriate, the reaction mixture was filtered off and the precipitate was washed with diethyl ether and dried under high vacuum.

If appropriate, the reaction mixture was diluted with diethyl ether, the precipitate was filtered off and the filtrate was partitioned between ethyl acetate or dichloromethane and saturated aqueous sodium bicarbonate solution. The organic phase was washed with saturated aqueous sodium chloride solution, dried over sodium sulphate and filtered, and the filtrate was concentrated and dried under high vacuum.

Representative Working Procedure 3

Amide Formation Using HATU as Coupling Agent.

1 equivalent of the carboxylic acid to be coupled (for example Example 3A, 6A, 11A, 16A, 19A, 21A, 25A, 28A or 30A), 1.1 to 2.5 equivalents of O-(7-azabenzotriazol-1-yl)-N,N,N'N'-tetramethyluronium hexafluorophosphate (HATU) and 3 to 4 equivalents of N,N-diisopropylethylamine were initially charged in DMF (about 0.2 M based on the carboxylic acid to be coupled), 1.2 to 2.0 equivalents of the amine to be coupled were added and the mixture was stirred at RT overnight.

Exemplary work-up of the reaction mixture: Water was added to the reaction solution and the precipitate formed stirred for 30 min, filtered off, washed thoroughly with water and dried under high vacuum overnight. Alternatively, either directly after concentration under reduced pressure or after extractive work-up, the reaction mixture was purified further by preparative HPLC.

STARTING MATERIALS AND INTERMEDIATES

Example 1A

3-[(2,6-Difluorobenzyl)oxy]pyridine-2-amine

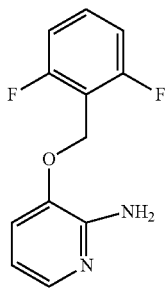 [SMILES: Nc1ncccc1OCc1c(F)cccc1F]

At RT, 51 g of sodium methoxide (953 mmol, 1.05 equivalents) were initially charged in 1000 ml of methanol, 100 g of 2-amino-3-hydroxypyridine (908 mmol, 1 equivalent) were added and the mixture was stirred at RT for another 15 min. The reaction mixture was concentrated under reduced pressure, the residue was taken up in 2500 ml of DMSO and 197 g of 2,6-difluorobenzyl bromide (953 mmol, 1.05 equivalents) were added. After 4 h at RT, the reaction mixture was poured into 20 l of water and stirred for 15 min, and the solid was filtered off. The solid was washed with 1 l of water, 100 ml of isopropanol and 500 ml of petroleum ether and dried under high vacuum. This gave 171 g of the title compound (78% of theory).

$^1$H NMR (400 MHz, DMSO-d$_6$): δ=5.10 (s, 2H); 5.52 (br. s, 2H), 6.52 (dd, 1H); 7.16-7.21 (m, 3H); 7.49-7.56 (m, 2H).

Example 2A

Ethyl 8-[(2,6-difluorobenzyl)oxy]-2-methylimidazo[1,2-a]pyridine-3-carboxylate

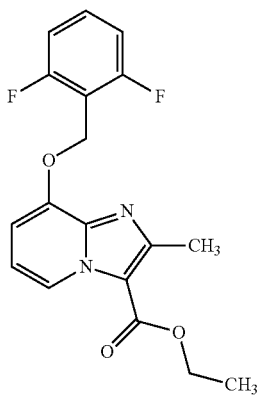 [SMILES: CCOC(=O)c1c(C)nc2c(OCc3c(F)cccc3F)cccn12]

170 g of 3-[(2,6-difluorobenzyl)oxy]pyridine-2-amine (Example 1A; 719 mmol, 1 equivalent) were initially charged in 3800 ml of ethanol, and 151 g of powdered molecular sieve 3 Å and 623 g of ethyl 2-chloroacetoacetate (3.6 mol, 5 equivalents) were added. The reaction mixture was heated at reflux for 24 h and then filtered off through silica gel and concentrated under reduced pressure. The mixture was kept at RT for 48 h, and the solid formed was filtered off. The solid was then stirred three times with a little isopropanol and then filtered off and washed with diethyl ether. This gave 60.8 g (23% of theory) of the title compound. The combined filtrates of the filtration steps were concentrated and the residue was chromatographed on silica gel using cyclohexane/diethyl ether as mobile phase. This gave a further 46.5 g (18% of theory; total yield: 41% of theory) of the title compound.

LC-MS (Method 2): R$_t$=1.01 min

MS (ESpos): m/z=347 (M+H)$^+$ $^1$H NMR (400 MHz, DMSO-d$_6$): δ=1.36 (t, 3H); 2.54 (s, 3H; obscured by DMSO signal); 4.36 (q, 2H); 5.33 (s, 2H); 7.11 (t, 1H); 7.18-7.27 (m, 3H); 7.59 (quint, 1H); 8.88 (d, 1H).

Example 3A

8-[(2,6-Difluorobenzyl)oxy]-2-methylimidazo[1,2-a]pyridine-3-carboxylic acid

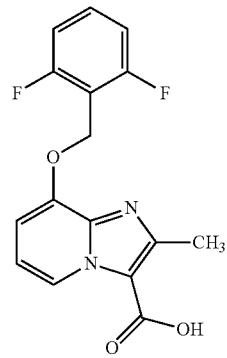

107 g of ethyl 8-[(2,6-difluorobenzyl)oxy]-2-methylimidazo[1,2-a]pyridine-3-carboxylate (Example 2A; 300 mmol, 1 equivalent) were dissolved in 2.8 l of THF/methanol (1:1), 1.5 l of 1 N aqueous lithium hydroxide solution (1.5 mol, 5 equivalents) were added and the mixture was stirred at RT for 16 h. The organic solvents were removed under reduced pressure and the resulting aqueous solution was adjusted in an ice bath to pH 3-4 using 1 N aqueous hydrochloric acid. The resulting solid was filtered off, washed with water and isopropanol and dried under reduced pressure. This gave 92 g (95% of theory) of the title compound.

LC-MS (Method 2): R$_t$=0.62 min

MS (ESpos): m/z=319.1 (M+H)$^+$ $^1$H NMR (400 MHz, DMSO-d$_6$): δ=2.55 (s, 3H; superimposed by DMSO signal); 5.32 (s, 2H); 7.01 (t, 1H); 7.09 (d, 1H); 7.23 (t, 2H); 7.59 (quint, 1H); 9.01 (d, 1H).

Example 4A 3-(Cyclohexylmethoxy)pyridine-2-amine

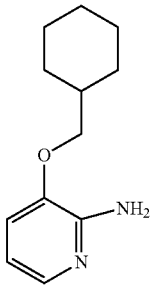 [SMILES: Nc1ncccc1OCC1CCCCC1]

At RT, 96 g of sodium hydroxide 45% strength in water (1081 mmol, 1 equivalent) were initially charged in 1170 ml of methanol, 119 g of 2-amino-3-hydroxypyridine (1080 mmol, 1 equivalent) were added and the mixture was stirred at RT for 10 min. The reaction mixture was concentrated under reduced pressure, the residue was taken up in 2900 ml of DMSO and 101 g of cyclohexylmethyl bromide (1135 mmol, 1.05 equivalents) were added. After 16 h at RT, the reaction mixture was added slowly to 6 l of water and the aqueous solution was extracted twice with in each case 2 l of ethyl acetate. The combined organic phases were washed with in each case 1 l of saturated aqueous sodium bicarbonate solution and water, dried, filtered and concentrated. The residue was triturated with 500 ml of n-pentane, filtered and dried under reduced pressure. This gave 130 g (58% of theory) of the title compound.

LC-MS (Method 3): $R_t$=1.41 min
MS (ESpos): m/z=207.1 (M+H)$^+$

Example 5A

Ethyl 8-(cyclohexylmethoxy)-2-methylimidazo[1,2-a]pyridine-3-carboxylate

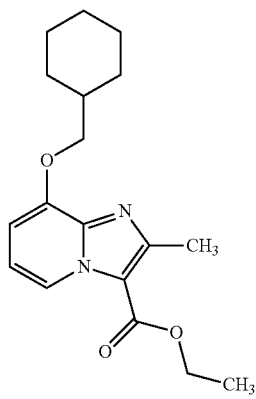 [SMILES: CCOC(=O)c1c(C)nc2c(OCC3CCCCC3)cccn12]

130 g of 3-(cyclohexylmethoxy)pyridine-2-amine (Example 4A; 630 mmol, 1 equivalent) were initially charged in 3950 ml of ethanol, and 436 ml of ethyl 2-chloroacetoacetate (3.2 mol, 5 equivalents) were added. The mixture was heated under reflux for 24 h and then concentrated under reduced pressure. The crude product obtained in this manner was chromatographed on silica gel using cyclohexane/diethyl ether as mobile phase, giving 66.2 g (33% of theory) of the title compound.

LC-MS (Method 2): $R_t$=1.17 min
MS (ESpos): m/z=317.1 (M+H)$^+$
$^1$H NMR (400 MHz, DMSO-$d_6$): δ=1.02-1.31 (m, 5H); 1.36 (t, 3H); 1.64-1.77 (m, 3H); 1.79-1.90 (m, 3H); 2.60 (s, 3H); 3.97 (d, 2H); 4.35 (q, 2H); 6.95 (d, 1H); 7.03 (t, 1H); 8.81 (d, 1H).

Example 6A 8-(Cyclohexylmethoxy)-2-methylimidazo[1,2-a]pyridine-3-carboxylic acid

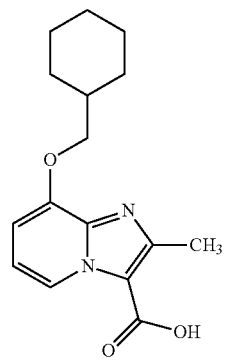 [SMILES: Cc1nc2c(OCC3CCCCC3)cccn2c1C(=O)O]

50 g of ethyl 8-(cyclohexylmethoxy)-2-methylimidazo[1,2-a]pyridine-3-carboxylate (Example 5A; 158 mmol, 1 equivalent) were dissolved in 600 ml of 1,4-dioxane, 790 ml of 2 N aqueous sodium hydroxide solution (1.58 mol, 10 equivalents) were added and the mixture was stirred at RT for 16 h. 316 ml of 6 N hydrochloric acid were added, and the mixture was reduced to about ⅕ of the total volume. The resulting solid was filtered off, washed with water and tert-butyl methyl ether and dried under reduced pressure. This gave 35 g (74% of theory) of the title compound.

LC-MS (Method 2): $R_t$=0.81 min
MS (ESpos): m/z=289.0 (M+H)$^+$
$^1$H NMR (400 MHz, DMSO-$d_6$): δ=1.03-1.44 (m, 5H); 1.64-1.78 (m, 3H); 1.81-1.92 (m, 3H); 2.69 (s, 3H); 4.07 (d, 2H); 7.30-7.36 (m, 2H); 9.01 (d, 1H).

Example 7A

5-Fluoro-2-nitropyridin-3-ol

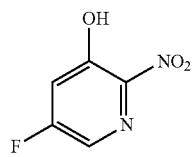

With ice cooling, 5 g of 5-fluoropyridin-3-ol (44 mmol, 1 equivalent) were dissolved in 43 ml of concentrated sulphuric acid, and, at 0° C., 2.8 ml of concentrated nitric acid were added over a period of 5 min. The reaction was warmed to RT, and stirring was continued overnight. The mixture was added to 100 g of ice and stirred for 30 min. The solid obtained was filtered off and dried under reduced pressure. This gave 5.6 g (81% of theory) of the title compound, which were used without further purification for the next reaction.

LC-MS (Method 2): $R_t$=0.45 min
MS (ESneg): m/z=156.9 (M−H)⁻
¹H NMR (400 MHz, DMSO-d₆): δ=7.5 (dd, 1H); 8.08 (d, 1H); 12.2 (br. s, 1H).

Example 8A

2-Amino-5-fluoropyridin-3-ol

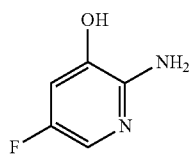

5.6 g of 5-fluoro-2-nitropyridin-3-ol (Example 7A; 36 mmol) were dissolved in 2 l of ethanol, a catalytic amount of palladium on activated carbon (10%) was added and the mixture was hydrogenated under standard hydrogen pressure for 16 h. The mixture was filtered off through silica gel and the filtrate was concentrated (product batch 1). The filter cake was rinsed with methanol until the colour of the filtrate was no longer yellowish. The filtrate was concentrated, giving a second product batch. This gave 4.26 g (85% of theory) of the title compound.

LC-MS (Method 2): $R_t$=0.17 min
MS (ESpos): m/z=128.9 (M+H)⁺
¹H NMR (400 MHz, DMSO-d₆): δ=5.4 (br. s, 2H); 6.8 (dd, 1H); 7.4 (d, 1H).

Example 9A

Ethyl 6-fluoro-8-hydroxy-2-methylimidazo[1,2-a]pyridine-3-carboxylate

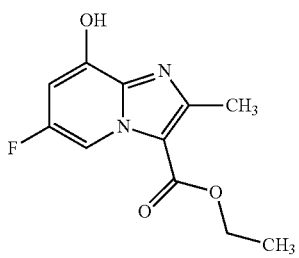 [SMILES: CCOC(=O)c1c(C)nc2c(O)cc(F)cn12]

3.2 g of 2-amino-5-fluoropyridin-3-ol (Example 8A; 25 mmol, 1 equivalent) were initially charged in 155 ml of ethanol, 1.5 g of powdered molecular sieve 3 Å and 20.6 g of ethyl 2-chloroacetoacetate (125 mmol, 5 equivalents) were added and the mixture was boiled at reflux overnight. The reaction solution was concentrated and chromatographed (Biotage Isolera Four; SNAP Cartridge KP-Sil 50 g; cyclohexane/ethyl acetate gradient; then dichloromethane/methanol gradient). The crude product was partly dissolved in a little methanol, and tert-butyl methyl ether was added. The solid was filtered off and washed with tert-butyl methyl ether. This gave 570 mg (10% of theory) of the title compound.

LC-MS (Method 2): $R_t$=0.77 min
MS (ESpos): m/z=239.2 (M+H)⁺
¹H NMR (400 MHz, DMSO-d₆): δ=1.39 (t, 3H); 2.64 (s, 3H); 4.40 (q, 2H); 7.20 (br. d, 1H); 8.9 (dd, 1H); 12.5 (br. s, 1H).

Example 10A

Ethyl 8-[(2,6-difluorobenzyl)oxy]-6-fluoro-2-methylimidazo[1,2-a]pyridine-3-carboxylate

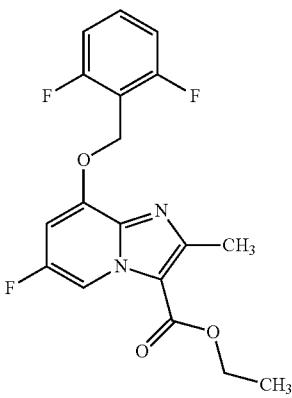 [SMILES: CCOC(=O)c1c(C)nc2c(OCc3c(F)cccc3F)cc(F)cn12]

560 mg of ethyl 6-fluoro-8-hydroxy-2-methylimidazo[1,2-a]pyridine-3-carboxylate (Example 9A; 2.4 mmol, 1.0 equivalent), 1.7 g of caesium carbonate (5.17 mmol, 2.2 equivalents) and 535 mg of 2,6-difluorobenzyl bromide (2.6 mmol, 1.1 equivalents) were initially charged in 34 ml of dry DMF, and the mixture was heated at 50° C. for 15 min. Water was added, the mixture was stirred for 30 min and the solid was filtered off and washed with water. This gave 560 mg of the title compound (65% of theory).

LC-MS (Method 2): $R_t$=1.18 min
MS (ESpos): m/z=365.1 (M+H)⁺
¹H NMR (400 MHz, DMSO-d₆): δ=1.37 (t, 3H); 2.55 (s, 3H; superimposed by DMSO signal); 4.38 (q, 2H); 5.89 (s, 2H); 7.23 (t, 2H); 7.44 (dd, 1H); 7.60 (q, 1H); 8.90 (dd, 1H).

Example 11A

8-[(2,6-Difluorobenzyl)oxy]-6-fluoro-2-methylimidazo[1,2-a]pyridine-3-carboxylic acid

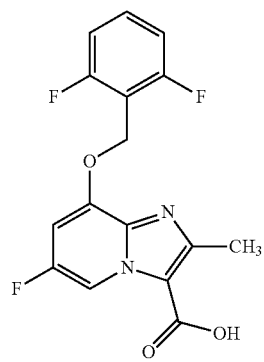 [SMILES: Cc1nc2c(OCc3c(F)cccc3F)cc(F)cn2c1C(=O)O]

550 mg of ethyl 8-[(2,6-difluorobenzyl)oxy]-6-fluoro-2-methylimidazo[1,2-a]pyridine-3-carboxylate (Example 10A; 1.5 mmol, 1 equivalent) were dissolved in 64 ml of THF and 12 ml of methanol, 7.5 ml of 1 N aqueous lithium hydroxide solution were added and the mixture was stirred at RT overnight. 8 ml of 1 N aqueous hydrochloric acid were then added, and the mixture was concentrated under reduced pressure. The solid formed was filtered off and washed with water. This gave 429 mg of the title compound (80% of theory).

LC-MS (Method 1): $R_t$=0.90 min

MS (ESpos): m/z=337.1 (M+H)$^+$ $^1$H NMR (400 MHz, DMSO-d$_6$): δ=2.54 (s, 3H; superimposed by DMSO signal); 5.84 (s, 2H); 7.23 (t, 2H); 7.40 (dd, 1H); 7.51 (q, 1H); 8.92 (dd, 1H); 13.28 (br. s, 1H).

Example 12A

5-Chloro-2-nitropyridin-3-ol

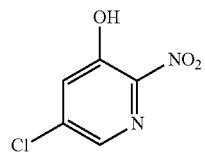 [SMILES: O=[N+]([O-])c1ncc(Cl)cc1O]

With ice cooling, 30 g of 5-chloropyridin-3-ol (232 mmol, 1 equivalent) were dissolved in 228 ml of concentrated sulphuric acid, and, at 0° C., 24 ml of concentrated nitric acid were added slowly. The reaction was warmed to RT, stirred overnight and then stirred into an ice/water mixture and stirred for another 30 min. The solid was filtered off, washed with cold water and air-dried. This gave 33 g (82% of theory) of the title compound, which were used without further purification for the next reaction.

LC-MS (Method 2): $R_t$=0.60 min

MS (ESneg): m/z=172.9/174.9 (M−H)$^-$ $^1$H NMR (400 MHz, DMSO-d$_6$): δ=7.71 (d, 1H); 8.10 (d, 1H); 12.14 (br. 1H).

Example 13A

5-Chloro-3-[(2,6-difluorobenzyl)oxy]-2-nitropyridine

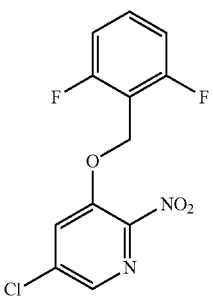 [SMILES: O=[N+]([O-])c1ncc(Cl)cc1OCc1c(F)cccc1F]

33 g of 5-chloro-2-nitropyridin-3-ol (Example 12A; 189 mmol, 1 equivalent) and 61.6 g of caesium carbonate (189 mmol, 1 equivalent) were initially charged in 528 ml of DMF, 40.4 g of 2,6-difluorobenzyl bromide (189 mmol, 1 equivalent) were added and the mixture was stirred at RT overnight. The reaction mixture was stirred into water/1N aqueous hydrochloric acid. The solid was filtered off, washed with water and air-dried. This gave 54.9 g (97% of theory) of the title compound.

$^1$H NMR (400 MHz, DMSO-d$_6$): δ=5.46 (s, 2H); 7.22 (t, 2H); 7.58 (q, 1H); 8.28 (d, 1H); 8.47 (d, 1H).

Example 14A

5-Chloro-3-[(2,6-difluorobenzyl)oxy]pyridine-2-amine

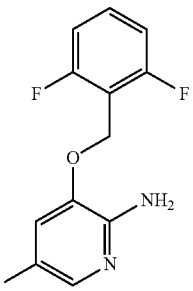

59.7 g of 5-chloro-3-[(2,6-difluorobenzyl)oxy]-2-nitropyridine (Example 13A; 199 mmol, 1 equivalent) were initially charged in 600 ml of ethanol, 34.4 g of iron powder (616 mmol, 3.1 equivalents) were added and the mixture was heated to reflux. 152 ml of concentrated hydrochloric acid were slowly added dropwise and the mixture was boiled at reflux for a further 30 min. The reaction mixture was cooled and stirred into an ice/water mixture. The resulting mixture was adjusted to pH 5 using sodium acetate. The solid was filtered off, washed with water and air-dried and then dried under reduced pressure at 50° C. This gave 52.7 g (98% of theory) of the title compound.

LC-MS (Method 2): $R_t$=0.93 min

MS (ESpos): m/z=271.1/273.1 (M+H)$^+$ $^1$H NMR (400 MHz, DMSO-d$_6$): δ=5.14 (s, 2H); 5.82 (br. s, 2H); 7.20 (t, 2H); 7.35 (d, 1H); 7.55 (q, 1H); 7.56 (d, 1H).

Example 15A

Ethyl 6-chloro-8-[(2,6-difluorobenzyl)oxy]-2-methylimidazo[1,2-a]pyridine-3-carboxylate

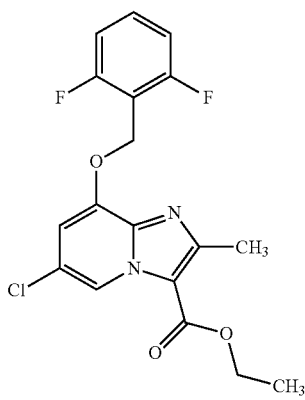 [SMILES: CCOC(=O)c1c(C)nc2c(OCc3c(F)cccc3F)cc(Cl)cn12]

40 g of 5-chloro-3-[(2,6-difluorobenzyl)oxy]pyridine-2-amine (Example 14A; 147.8 mmol; 1 equivalent) were initially charged in 800 ml of ethanol, 30 g of powdered molecular sieve 3 Å and 128 g of ethyl 2-chloroacetoacetate (739 mmol, 5 equivalents) were added and the mixture was heated at reflux overnight. The reaction mixture was concentrated and the residue was taken up in ethyl acetate and filtered. The ethyl acetate phase was washed with water, dried, filtered and concentrated. This gave 44 g (78% of theory) of the title compound.

LC-MS (Method 2): $R_t$=1.27 min

MS (ESpos): m/z=381.2/383.2 (M+H)$^+$ $^1$H NMR (400 MHz, DMSO-d$_6$): δ=1.36 (t, 3H); 2.54 (s, 3H; obscured by DMSO signal); 4.37 (q, 2H); 5.36 (s, 2H); 7.26 (t, 2H); 7.38 (d, 1H); 7.62 (q, 1H); 8.92 (d, 1H).

Example 16A

6-Chloro-8-[(2,6-difluorobenzyl)oxy]-2-methylimidazo[1,2-a]pyridine-3-carboxylic acid

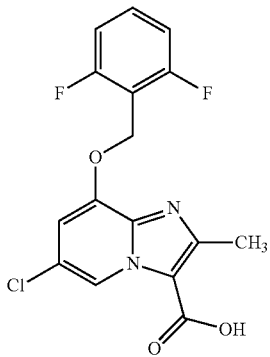

44 g of ethyl 6-chloro-8-[(2,6-difluorobenzyl)oxy]-2-methylimidazo[1,2-a]pyridine-3-carboxylate (Example 15A; 115 mmol, 1 equivalent) were dissolved in 550 ml of THF and 700 ml of methanol, 13.8 g of lithium hydroxide (dissolved in 150 ml of water; 577 mmol, 5 equivalents) were added and the mixture was stirred at RT overnight. 1 N aqueous hydrochloric acid was added and the mixture was concentrated under reduced pressure. The solid obtained was filtered off and washed with water. This gave 34 g of the title compound (84% of theory).

LC-MS (Method 1): $R_t$=1.03 min

MS (ESpos): m/z=353.0/355.0 (M+H)$^+$ $^1$H NMR (400 MHz, DMSO-d$_6$): δ=2.54 (s, 3H; superimposed by DMSO signal); 5.36 (s, 2H); 7.26 (t, 2H); 7.34 (d, 1H); 7.61 (q, 1H); 8.99 (d, 1H); 13.36 (br. s, 1H).

Example 17A

5-Bromo-3-[(2,6-difluorobenzyl)oxy]pyridine-2-amine

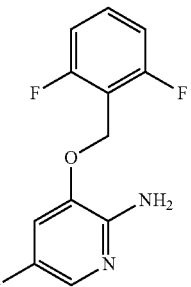

32.6 g of 3-[(2,6-difluorobenzyl)oxy]pyridine-2-amine (Example 1A; 138 mmol, 1 equivalent) were suspended in 552 ml of 10% strength sulphuric acid, and the mixture was cooled to 0° C. 8.5 ml of bromine (165 mmol, 1.2 equivalents) were dissolved in 85 ml of acetic acid and then, over a period of 90 min, added dropwise to the ice-cooled reaction solution. After the dropwise addition had ended, the mixture was stirred at 0° C. for 90 min and then diluted with 600 ml of ethyl acetate, and the aqueous phase was separated off. The aqueous phase was extracted with ethyl acetate. The organic phases were combined, washed with saturated aqueous sodium bicarbonate solution, dried and concentrated. The residue was dissolved in dichloromethane and chromatographed on silica gel (petroleum ether/ethyl acetate gradient as mobile phase). This gave 24 g (55% of theory) of the title compound.

LC-MS (Method 2): $R_t$=0.96 min

MS (ESpos): m/z=315.1/317.1 (M+H)$^+$ $^1$H NMR (400 MHz, DMSO-d$_6$): δ=5.14 (s, 2H); 5.83 (br. s, 2H); 7.20 (t, 2H); 7.42 (d, 1H); 7.54 (q, 1H); 7.62 (d, 1H).

Example 18A

Ethyl 6-bromo-8-[(2,6-difluorobenzyl)oxy]-2-methylimidazo[1,2-a]pyridine-3-carboxylate

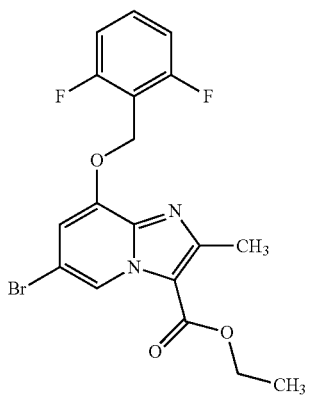

16 g of powdered molecular sieve 3 Å and 52.7 ml of ethyl 2-chloroacetoacetate (380.8 mmol; 5 equivalents) were added to 24 g of 5-bromo-3-[(2,6-difluorobenzyl)oxy]pyridine-2-amine (Example 17A; 76.2 mmol; 1 equivalent) in 400 ml of ethanol, and the mixture was heated at reflux overnight. A further 8 g of molecular sieve were added, and the mixture was heated at reflux for a further 24 h. The reaction mixture was concentrated under reduced pressure and the residue was taken up in dichloromethane and chromatographed on silica gel (dichloromethane/methanol 20:1 as mobile phase). The product-containing fractions were concentrated and the residue was stirred with 100 ml of diethyl ether for 30 min. The product was then filtered off, washed with a little diethyl ether and dried. This gave 15 g (45% of theory) of the title compound.

LC-MS (Method 1): $R_t$=1.43 min

MS (ESpos): m/z=414.9/416.8 (M+H)$^+$ $^1$H NMR (400 MHz, DMSO-d$_6$): δ=1.36 (t, 3H); 2.54 (s, 3H; obscured by DMSO signal); 4.37 (q, 2H); 5.36 (s, 2H); 7.25 (t, 2H); 7.42 (d, 1H); 7.61 (q, 1H); 9.00 (d, 1H).

Example 19A

6-Bromo-8-[(2,6-difluorobenzyl)oxy]-2-methylimidazo[1,2-a]pyridine-3-carboxylic acid

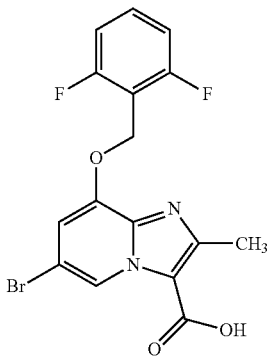 [SMILES: Cc1nc2c(OCc3c(F)cccc3F)cc(Cl)cn2c1C(=O)O]

1.5 g of ethyl 6-bromo-8-[(2,6-difluorobenzyl)oxy]-2-methylimidazo[1,2-a]pyridine-3-carboxylate (Example 18A; 3.5 mmol, 1 equivalent) were dissolved in 72 ml of THF/methanol 5:1, 17.6 ml of 1N aqueous lithium hydroxide solution (17.6 mmol, 5 equivalents) were added and the mixture was warmed to 40° C. and stirred at this temperature for 6 h. Using 6 N aqueous hydrochloric acid, the mixture was then adjusted to pH 4 and concentrated under reduced pressure. Water was added to the solid formed and the solid was triturated, filtered off, washed with water and dried under reduced pressure. This gave 1.24 g of the title compound (88% of theory).

LC-MS (Method 2): $R_t$=0.93 min

MS (ESpos): m/z=397.0/399.1 (M+H)$^+$ $^1$H NMR (400 MHz, DMSO-d$_6$): δ=2.54 (s, 3H; superimposed by DMSO signal); 5.36 (s, 2H); 7.25 (t, 2H); 7.40 (d, 1H); 7.61 (q, 1H); 9.06 (d, 1H); 13.35 (br. s, 1H).

Example 20A

Ethyl 8-[(2,6-difluorobenzyl)oxy]-2,6-dimethylimidazo[1,2-a]pyridine-3-carboxylate

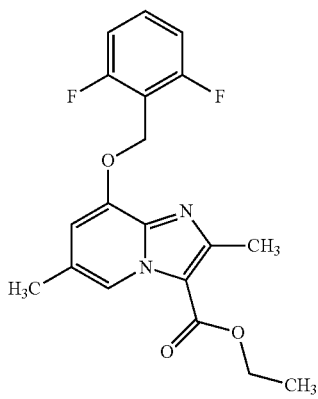 [SMILES: CCOC(=O)c1c(C)nc2c(OCc3c(F)cccc3F)cc(C)cn12]

20.00 g (85.38 mmol) of ethyl 8-hydroxy-2,6-dimethylimidazo[1,2-a]pyridine-3-carboxylate from Example 239A, 19.44 g (93.91 mmol) of 2,6-difluorobenzyl bromide and 61.20 g (187.83 mmol) of caesium carbonate in 1.18 l of DMF were stirred at 60° C. for 5 h. The reaction mixture was then poured into 6.4 l of 10% strength aqueous sodium chloride solution and then extracted twice with ethyl acetate. The combined organic phases were washed with 854 ml of 10% strength aqueous sodium chloride solution, dried, concentrated and dried under high vacuum at RT overnight. This gave 28.2 g (92% of theory; purity about 90%) of the title compound.

LC-MS (Method 2): $R_t$=1.05 min

MS (ESpos): m/z=361.1 (M+H)$^+$ $^1$H NMR (400 MHz, DMSO-d$_6$): δ=1.38 (t, 3H); 2.36 (s, 3H); 4.35 (q, 2H); 5.30 (s, 2H); 7.10 (s, 1H); 7.23 (t, 2H); 7.59 (q, 1H); 8.70 (s, 1H).

Example 21A

8-[(2,6-Difluorobenzyl)oxy]-2,6-dimethylimidazo[1,2-a]pyridine-3-carboxylic acid

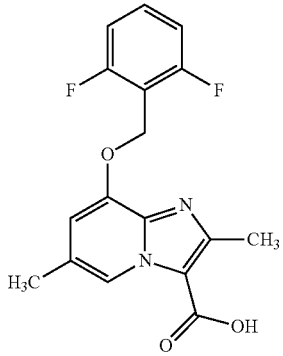

220 mg of ethyl 8-[(2,6-difluorobenzyl)oxy]-2,6-dimethylimidazo[1,2-a]pyridine-3-carboxylate (Example 20A; 0.524 mmol, 1 equivalent) were dissolved in 7 ml of THF/methanol 1:1, 2.6 ml of 1 N aqueous lithium hydroxide solution (2.6 mmol, 5 equivalents) were added and the mixture was stirred at RT for 16 h. The mixture was concentrated under reduced pressure and the residue was acidified with 1N aqueous hydrochloric acid and stirred for 15 min. The solid was filtered off, washed with water and dried under reduced pressure. This gave 120 mg of the title compound (60% of theory).

LC-MS (Method 2): $R_f$=0.68 min

MS (ESpos): m/z=333.1 (M+H)$^+$ $^1$H NMR (400 MHz, DMSO-$d_6$): δ=2.34 (s, 3H); 5.28 (s, 2H); 7.09 (s, 1H); 7.23 (t, 2H); 7.58 (q, 1H); 8.76 (s, 1H); 13.1 (br. s, 1H), [further signal hidden under DMSO signal].

Example 22A

8-[(2,6-Difluorobenzyl)oxy]-2-methylimidazo[1,2-a] pyridine-3-carbonyl chloride hydrochloride

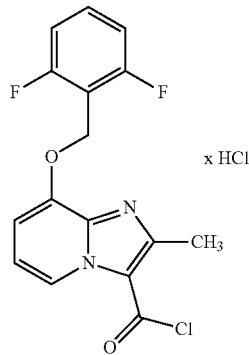 [SMILES: Cc1nc2c(OCc3c(F)cccc3F)cccn2c1C(=O)Cl]

4 drops of DMF were added to 2.0 g of 8-[(2,6-difluorobenzyl)oxy]-2-methylimidazo[1,2-a]-pyridine-3-carboxylic acid (6.28 mmol, 1 equivalent) in 25 ml of dry THF, followed by the dropwise addition of 3.19 g of oxalyl chloride (25.14 mmol, 4 equivalents). The reaction mixture was stirred at RT for 3 h. Another 0.80 g of oxalyl chloride (6.28 mmol, 1 equivalent) were added, and the reaction was stirred at RT for a further 4 h. The reaction mixture was concentrated and co-evaporated with toluene three times, and the residue was dried under high vacuum. This gave 2.43 g of the title compound (103% of theory).

DCI-MS (Method 4): MS (ESpos): m/z=437 (M−HCl+H)$^+$

Example 23A

Ethyl 2-chloro-3-cyclopropyl-3-oxopropanoate

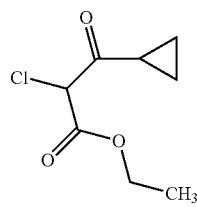

3.1 ml of sulphuryl chloride (38.2 mmol, 1.05 equivalents) were initially charged in 21 ml of dichloromethane, and 5.68 g of ethyl 3-cyclopropyl-3-oxopropanoate (36.4 mmol) were added dropwise on a water bath. The reaction mixture was stirred at RT for 2 h. The mixture was then washed with water, 5% strength aqueous sodium bicarbonate solution and saturated aqueous sodium chloride solution, dried over magnesium sulphate and concentrated. The crude product (6.8 g) was used without further purification for the next reaction.

Example 24A

Ethyl 2-cyclopropyl-8-[(2,6-difluorobenzyl)oxy] imidazo[1,2-a]pyridine-3-carboxylate

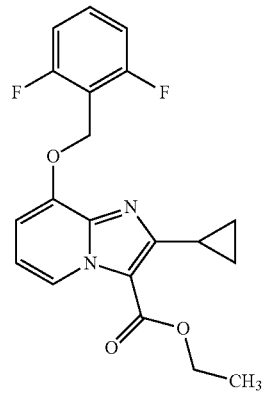 [SMILES: CCOC(=O)c1c(C2CC2)nc2c(OCc3c(F)cccc3F)cccn12]

1.69 g of 3-[(2,6-difluorobenzyl)oxy]pyridine-2-amine (Example 1A; 7.13 mmol, 1 equivalent) were initially charged in 44.4 ml of ethanol, and 425 mg of powdered molecular sieve 3 Å and 6.8 g of ethyl 2-chloro-3-cyclopropyl-3-oxopropanoate (crude product from Example 23A) were added. The reaction mixture was heated at reflux for 48 h and then concentrated under reduced pressure, and the residue was chromatographed (cyclohexane/ethyl acetate as mobile phase). The product-containing fractions were combined and concentrated under reduced pressure. The residue obtained in this manner was taken up in methanol, DMSO and water. The solid obtained was filtered off and dried under high vacuum. This gave 410 mg (15.4% of theory) of the title compound.

LC-MS (Method 2): $R_t$=1.22 min

MS (ESpos): m/z=373.2 (M+H)$^+$ $^1$H NMR (400 MHz, DMSO-$d_6$): δ=0.95-1.05 (m, 4H); 1.39 (t, 3H); 2.36 (s, 3H); 2.70-2.80 (m, 1H); 4.39 (q, 2H); 5.30 (s, 2H); 7.08 (t, 1H); 7.15 (d, 1H); 7.20 (t, 2H); 7.59 (q, 1H); 8.88 (d, 1H).

Example 25A

2-Cyclopropyl-8-[(2,6-difluorobenzyl)oxy]imidazo[1,2-a]pyridine-3-carboxylic acid

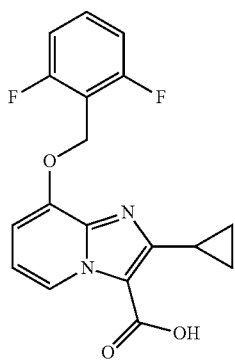 [SMILES: O=C(O)c1c(C2CC2)nc2c(OCc3c(F)cccc3F)cccn12]

410 mg of ethyl 2-cyclopropyl-8-[(2,6-difluorobenzyl)oxy]imidazo[1,2-a]pyridine-3-carboxylate (Example 24A, 1.1 mmol, 1 equivalent) were initially charged in 15 ml of methanol/THF (1:1), and 5.5 ml of a 1 N aqueous lithium hydroxide solution (5.5 mmol, 5 equivalents) were added. The reaction mixture was stirred at RT overnight. Another 5.5 ml of 1 N aqueous lithium hydroxide solution were added, and the mixture was stirred at RT for another night. The mixture was then concentrated under reduced pressure and the residue was taken up in water and acidified with 1 N aqueous hydrochloric acid. The precipitated product was filtered off and dried under high vacuum. This gave 293 mg (77% of theory) of the title compound.

LC-MS (Method 2): $R_t$=0.83 min

MS (ESpos): m/z=345.2 (M+H)$^+$ $^1$H NMR (400 MHz, DMSO-d$_6$): δ=0.95-1.02 (m, 4H); 2.80 (q, 1H); 5.30 (s, 2H); 7.02 (t, 1H); 7.15 (d, 1H); 7.22 (t, 2H); 7.59 (q, 1H); 8.92 (s, 1H); 13.3 (br. s, 1H).

Example 26A

Ethyl 2-chloro-3-oxopropanoate

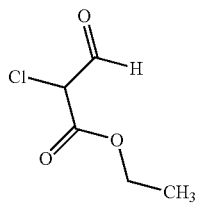

139 ml of a 21% strength solution of sodium ethoxide in ethanol (371 mmol, 0.91 equivalent) were initially charged in 200 ml of diethyl ether, and a solution of 43.7 ml of ethyl chloroacetate (408 mmol, 1 equivalent) and 32.9 ml of ethyl formate (408 mmol, 1 equivalent) in 150 ml of diethyl ether was added dropwise at RT. The reaction mixture was stirred overnight and the solid was filtered off and washed with diethyl ether. The solid was dissolved in water and the aqueous phase was, with ice bath cooling, adjusted to pH4 using concentrated hydrochloric acid. The mixture was extracted repeatedly with diethyl ether and the combined organic phases were washed with saturated aqueous sodium chloride solution, dried with magnesium sulphate, filtered and concentrated. The crude product obtained (8.2 g) was freed from residual solvent under high vacuum and used without further purification for the next reaction.

Example 27A

Ethyl 8-[(2,6-difluorobenzyl)oxy]imidazo[1,2-a]pyridine-3-carboxylate

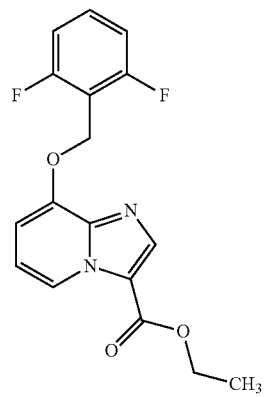 [SMILES: CCOC(=O)c1cnc2c(OCc3c(F)cccc3F)cccn12]

1.93 g of 3-[(2,6-difluorobenzyl)oxy]pyridine-2-amine (Example 1A; 8.2 mmol, 1 equivalent) were initially charged in 50 ml of ethanol, and 8.2 g of ethyl 2-chloro-3-oxopropanoate (75% pure, crude product from Example 26A, 40.8 mmol, 5 equivalents) were added. The reaction mixture was heated at reflux overnight. The mixture was then concentrated under reduced pressure and the crude product obtained was chromatographed on 340 g of silica gel (Biotage Isolera) (mobile phase: cyclohexane:ethyl acetate gradient; $R_f$ value of the product in cyclohexane:ethyl acetate 2:1=0.36). The product fractions were combined and concentrated and the residue obtained was triturated with diisopropyl ether. The solid was filtered off and dried under high vacuum. This gave 2.02 g of the title compound (71% of theory).

LC-MS (Method 2): $R_t$=1.08 min

MS (ESpos): m/z=333.1 (M+H)$^+$ $^1$H NMR (400 MHz, DMSO-d$_6$): δ=1.35 (t, 3H); 4.39 (q, 2H); 5.35 (s, 2H); 7.15-7.28 (m, 4H); 7.58 (q, 1H); 8.18 (s, 1H); 8.90 (d, 1H).

Example 28A

8-[(2,6-Difluorobenzyl)oxy]imidazo[1,2-a]pyridine-3-carboxylic acid

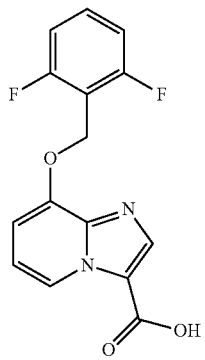 [SMILES: O=C(O)c1cnc2c(OCc3c(F)cccc3F)cccn12]

1 g of ethyl 8-[(2,6-difluorobenzyl)oxy]imidazo[1,2-a]pyridine-3-carboxylate (Example 27A, 3 mmol, 1 equivalent) were initially charged in 60 ml of methanol/THF (5:1), 15 ml of a 1 N aqueous lithium hydroxide solution (15 mmol, 5 equivalents) were added and the mixture was warmed to 40° C. and stirred at this temperature for 4 h. The mixture was then cooled and, with ice cooling, adjusted to pH 4 using 6 N aqueous hydrochloric acid. The organic solvents were removed on a rotary evaporator, water was added to the precipitated product and the product was filtered, washed with water and dried under high vacuum. This gave 797 mg (87% of theory) of the title compound.

LC-MS (Method 2): $R_t$=0.66 min

MS (ESpos): m/z=305.1 (M+H)$^+$

1H NMR (400 MHz, DMSO-d6): δ=5.38 (s, 2H); 7.10-7.28 (m, 4H); 7.59 (q, 1H); 8.12 (s, 1H); 8.92 (s, 1H); 13.1 (br. s, 1H).

Example 29A

Ethyl 8-(benzyloxy)-2-methylimidazo[1,2-a]pyridine-3-carboxylate

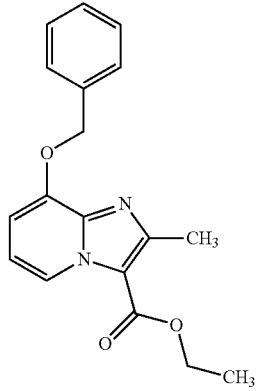 [SMILES: CCOC(=O)c1c(C)nc2c(OCc3ccccc3)cccn12]

25 g of 2-amino-3-benzyloxypyridine (124.8 mmol, 1 equivalent) were dissolved in 781 ml of ethanol, and 102.7 g of ethyl 2-chloroacetoacetate (624.2 mmol, 5 equivalents) and 15 g of 4 Å molecular sieve were added. The mixture was heated at reflux for 2 d (bath temperature 100° C.). The mixture was then concentrated and excess ethyl 2-chloroacetoacetate was distilled off on a rotary evaporator with dry ice-cooling. The residue was purified by silica gel chromatography (mobile phase cyclohexane:ethyl acetate 9:1, 4:1). This gave 20.81 g of the title compound (54% of theory).

LC-MS (Method 1): $R_t$=1.12 min

MS (ESpos): m/z=311 (M+H)$^+$ $^1$H NMR (400 MHz, DMSO-d$_6$): δ=1.35 (t, 3H), 2.59 (s, 3H), 4.34 (q, 2H), 5.32 (s, 2H), 7.01-7.09 (m, 2H), 7.33-7.48 (m, 3H), 7.52 (d, 2H), 8.81-8.86 (m, 1H).

Example 30A 8-(Benzyloxy)-2-methylimidazo[1,2-a]pyridine-3-carboxylic acid

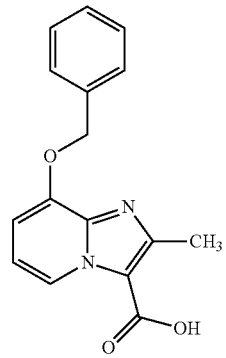 [SMILES: Cc1nc2c(OCc3ccccc3)cccn2c1C(=O)O]

253 ml of 2 N aqueous sodium hydroxide solution were added to a solution of 15.7 g of ethyl 8-(benzyloxy)-2-methylimidazo[1,2-a]pyridine-3-carboxylate (50.59 mmol) in 253 ml of 1,4-dioxane, and the mixture was stirred at RT for 14 h. 101 ml of 6 N aqueous hydrochloric acid were then added. The solid formed was filtered off, washed with water and methyl tert-butyl ether and then dried under reduced pressure at 40° C. overnight. This gave 15.49 g (108% of theory) of 8-(benzyloxy)-2-methylimidazo[1,2-a]pyridine-3-carboxylic acid.

LC-MS (Method 1): $R_t$=0.66 min

MS (ESpos): m/z=283.0 (M+H)$^+$ $^1$H NMR (400 MHz, DMSO-d$_6$): δ=2.67 (s, 3H), 3.2-3.8 (very broad water peak), 5.41 (s, 2H), 7.30 (m, 1H), 7.35-7.48 (m, 4H), 7.57 (d, 2H), 9.02 (d, 1H).

Example 31A rac-2-Amino-4,4,4-trifluorobutan-1-ol

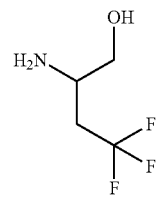

0.32 ml of lithium borohydride (2 M in THF, 0.65 mmol, 2.5 equivalents) were initially charged in 0.5 ml of abs. THF, 0.16 ml of chlorotrimethylsilane (1.28 mmol, 5 equivalents) were added at RT and the mixture was stirred at RT for 5 min. 50 mg of 2-amino-4,4,4-trifluorobutanoic acid hydrochloride (0.26 mmol, 1 equivalent) were then added a little at a time, and the reaction mixture was stirred at RT overnight. 0.5 ml of methanol was added, and the mixture was then concentrated. 0.6 ml of a 20% strength solution of potassium hydroxide was then added, and the mixture was extracted three times with dichloromethane. The combined organic phases were dried over sodium sulphate, filtered and concentrated. This gave 33 mg of the title compound (88% of theory).

DCI-MS (Method 4): MS (ESpos): m/z=144 (M+H)+

$^{1}$H NMR (400 MHz, DMSO-d$_{6}$): δ=2.08-2.20 (m, 1H), 2.22-2.38 (m, 1H), 3.25-3.32 (m, 1H), 3.39-3.44 (m, 1H), 3.59-3.65 (m, 1H).

The examples shown in Table 1A were prepared analogously to Example 31A by reacting lithium borohydride (1.7-2.5 equivalents) and chlorotrimethylsilane (3.4-5 equivalents) with the appropriate commercially available amino acids according to General Working Procedure 1:

TABLE 1A

| Example | IUPAC name/structure (yield) | Analytical data |
|---|---|---|
| 32A | rac-2-amino-6,6,6-trifluorohexan-1-ol<br>(75% of theory) | DCI-MS (Method 4): MS (ESpos): m/z = 172 (M + H)$^{+}$ |
| 33A | rac-2-amino-5,5,5-trifluoro-4-(trifluoromethyl)pentan-1-ol hydrochloride<br>(55% of theory) | DCI-MS (Method 4): MS (ESpos): m/z = 226 (M + H)$^{+}$ |

Example 34A rac-8-[(2,6-Difluorobenzyl)oxy]-2-methyl-N-(4,4,4-trifluoro-1-hydroxybutan-2-yl)imidazo[1,2-a]-pyridine-3-carboxamide

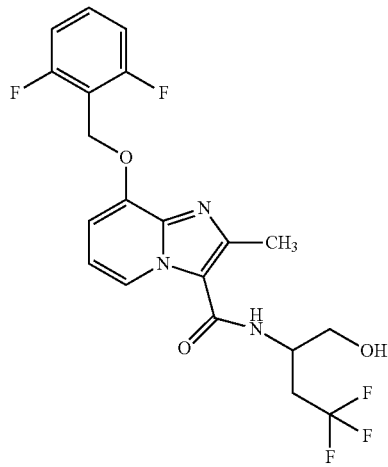 [SMILES: Cc1nc2c(OCc3c(F)cccc3F)cccn2c1C(=O)NC(CO)CC(F)(F)F]

330 mg of 8-[(2,6-difluorobenzyl)oxy]-2-methylimidazo[1,2-a]pyridine-3-carboxylic acid (1.04 mmol), 399 mg of (benzotriazol-1-yloxy)bisdimethylaminomethylium fluoroborate (TBTU, 1.24 mmol) and 524 mg of 4-methylmorpholine (5.18 mmol) were initially charged in 6.6 ml of DMF. After 10 min at RT, 371 mg (1.56 mmol, purity about 60%) of 2-amino-4,4,4-trifluorobutan-1-ol (Example 31A) were added and the mixture was stirred at RT overnight. About 200 ml of water were added, the reaction solution was stirred for another 30 min and the precipitate formed was filtered off, washed with water and dried under high vacuum overnight. This gave 439 mg of the title compound (96% of theory).

LC-MS (Method 5): R$_{t}$=1.62 min

MS (ESpos): m/z=444 (M+H)$^{+}$ $^{1}$H NMR (400 MHz, DMSO-d$_{6}$): δ=2.50 (s, 3H), 2.55-2.72 (m, 2H), 3.38-3.47 (m, 1H), 3.51-3.62 (m, 1H), 4.29-4.40 (m, 1H), 5.12 (t, 1H), 5.30 (s, 2H), 6.92 (t, 1H), 7.02 (d, 1H), 7.23 (t, 2H), 7.59 (quint, 1H), 7.80 (d, 1H), 8.56 (d, 1H).

The examples shown in Table 2A were prepared analogously to Example 34A by reacting 8-[(2,6-difluorobenzyl)oxy]-2-methylimidazo[1,2-a]pyridine-3-carboxylic acid with the appropriate commercially available amines under the reaction conditions described in the General Working Procedure 2:

TABLE 2A

| Example | IUPAC name/structure (yield) | Analytical data |
|---|---|---|
| 35A | rac-8-[(2,6-difluorobenzyl)oxy]-methyl-N-(6,6,6-trifluoro-1-hydroxyhexan-2-yl)imidazo[1,2-a]pyridine-3-carboxamide 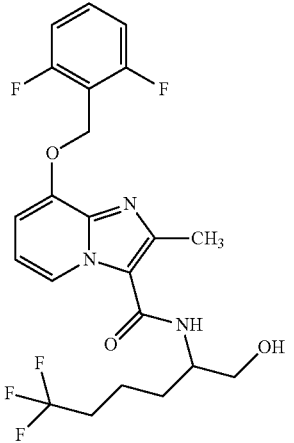 (76% of theory) | LC-MS (Method 2): $R_t$ = 0.88 min<br>MS (ESpos): m/z = 472 (M + H)$^+$<br>$^1$H NMR (400 MHz, DMSO-d$_6$): δ = 1.51-1.79 (m, 4H), 2.19-2.40 (m, 2H), 2.50 (s, 3H), 3.41-3.57 (m, 2H), 3.96-4.08 (m, 1H), 4.82 (t, 1H), 5.30 (s, 2H), 6.91 (t, 1H), 6.99 (d, 1H), 7.22 (t, 2H), 7.56-7.62 (m, 2H), 8.52 (d, 1H). |
| 36A | rac-8-[(2,6-difluorobenzyl)oxy]-2-methyl-N-[5,5,5-trifluoro-1-hydroxy-4-(trifluoromethyl)pentan-2-yl]imidazo[1,2-a]-pyridine-3-carboxamide trifluoroacetate[a)] 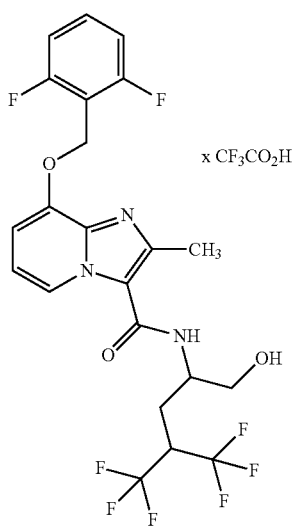 (52% of theory) | LC-MS (Method 2): $R_t$ = 0.90 min<br>MS (ESpos): m/z = 526 (M − TFA + H) |

[a)]Alternative work-up: The crude reaction mixture was purified directly by preparative HPLC (RP18 column, mobile phase: acetonitrile/water gradient with addition of 0.1% TFA).

Example 37A rac-N-(1-Chloro-4,4,4-trifluorobutan-2-yl)-8-[(2,6-difluorobenzyl)oxy]-2-methylimidazo[1,2-a]-pyridine-3-carboxamide hydrochloride

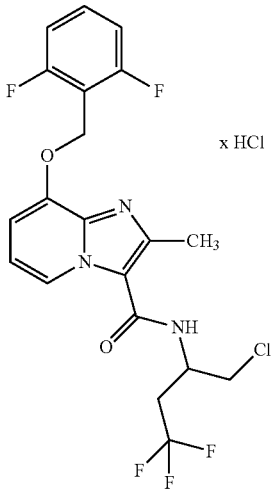 [SMILES: Cc1nc2c(OCc3c(F)cccc3F)cccn2c1C(=O)NC(CCl)CC(F)(F)F]

2.48 g of rac-8-[(2,6-difluorobenzyl)oxy]-2-methyl-N-(4,4,4-trifluoro-1-hydroxybutan-2-yl)-imidazo-[1,2-a]pyridine-3-carboxamide (Example 34A, 5.59 mmol) were initially charged in dichloromethane. At 0° C., 1.22 ml of thionyl chloride (16.77 mmol) were added dropwise, and the mixture was stirred at RT overnight. The reaction solution was concentrated and dried under high vacuum. This gave 2.78 g of the title compound (99.8% of theory).

LC-MS (Method 2): $R_t$=0.94 min

MS (ESpos): m/z=462 (M–HCl+H)$^+$ $^1$H NMR (400 MHz, DMSO-$d_6$): δ=2.60 (s, 3H), 2.70-2.84 (m, 2H), 3.82-3.92 (m, 2H), 4.55-4.67 (m, 1H), 5.43 (s, 2H), 7.23 (t, 2H), 7.31-7.43 (m, 1H), 7.51-7.66 (m, 2H), 8.63 (d, 1H), 8.82 (br s, 1H).

The examples shown in Table 3A were prepared analogously to Example 37A.

TABLE 3A

| Example | IUPAC name/structure (yield) | Analytical data |
|---|---|---|
| 38A | rac-N-(1-chloro-6,6,6-trifluorohexan-2-yl)-8-[(2,6-difluorobenzyl)oxy]-2-methylimidazo[1,2-a]pyridine-3-carboxamide hydrochloride (99% of theory) | LC-MS (Method 2): $R_t$ = 1.05 min<br>MS (ESpos): m/z = 490 (M – HCl + H)$^+$<br>$^1$H NMR (400 MHz, DMSO-$d_6$): δ = 1.52-1.81 (m, 4H), 2.20-2.42 (m, 2H), 2.60 (s, 3H), 3.72-3.87 (m, 2H), 4.21-4.33 (m, 1H), 5.45 (s, 2H), 7.23 (t, 2H), 7.40 (br s, 1H), 7.52-7.68 (m, 2H), 8.54 (br s, 1H), 8.61 (d, 1H). |

TABLE 3A-continued

| Example | IUPAC name/structure (yield) | Analytical data |
|---|---|---|
| 39A | rac-N-[1-chloro-5,5,5-trifluoro-4-(trifluoromethyl)pentan-2-yl]-8-[(2,6-difluorobenzyl)oxy]-2-methylimidazo[1,2-a]-pyridine-3-carboxamide hydrochloride<br>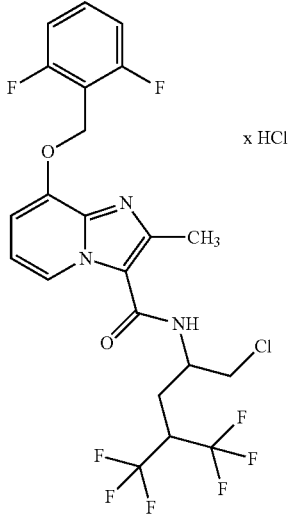<br>(98% of theory) | LC-MS (Method 2): $R_t$ = 1.15 min<br>MS (ESpos): m/z = 544 (M − HCl + H)$^+$ |
| 40A | N-[(2R)-1-chlorohexan-2-yl]-8-[(2,6-difluorobenzyl)oxy]-2-methylimidazo[1,2-a]-pyridine-3-carboxamide hydrochloride<br>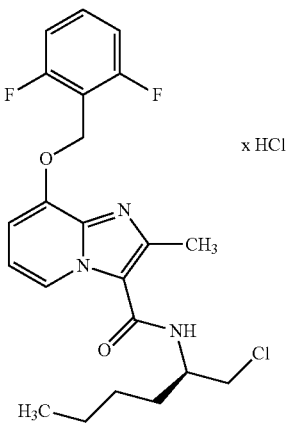<br>(98% of theory) | LC-MS (Method 2): $R_t$ = 1.06 min<br>MS (ESpos): m/z = 436 (M − HCl + H)$^+$ |

Example 41A rac-N-(1-Azido-4,4,4-trifluorobutan-2-yl)-8-[(2,6-difluorobenzyl)oxy]-2-methylimidazo[1,2-a]-pyridine-3-carboxamide

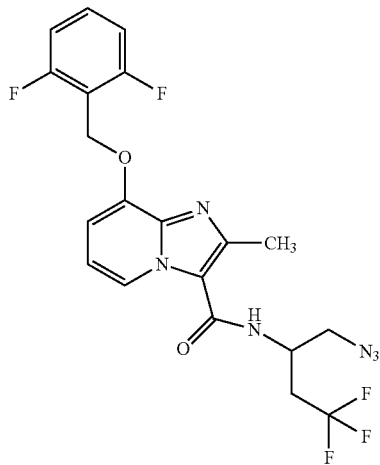 [SMILES: Cc1nc2c(OCc3c(F)cccc3F)cccn2c1C(=O)NC(CN=[N+]=[N-])CC(F)(F)F]

195 mg of rac-N-(1-chloro-4,4,4-trifluorobutan-2-yl)-8-[(2,6-difluorobenzyl)oxy]-2-methylimidazo[1,2-a]pyridine-3-carboxamide hydrochloride (Example 37A, 0.39 mmol) were initially charged in 3.4 ml of DMF, 254 mg of sodium azide (3.91 mmol) were added and the mixture was stirred at 40° C. for 4 h. The mixture was then stirred at 60° C. for 5 h. Water was added, and the reaction mixture was extracted three times with ethyl acetate. The combined organic phases were dried over sodium sulphate and filtered, the filtrate was concentrated and the residue was purified by silica gel chromatography (mobile phase: cyclohexane:ethyl acetate 7:3, isocratic). This gave 50 mg of the title compound (27% of theory).

LC-MS (Method 2): $R_t$=0.97 min
MS (ESpos): m/z=469 (M+H)$^+$
$^1$H NMR (400 MHz, DMSO-$d_6$): δ=2.50 (s, 3H), 2.58-2.78 (m, 2H), 3.52-3.63 (m, 2H), 4.47-4.58 (m, 1H), 5.30 (s, 2H), 6.93 (t, 1H), 7.02 (d, 1H), 7.22 (t, 2H), 7.59 (quint, 1H), 8.09 (d, 1H), 8.55 (d, 1H).

The examples shown in Table 4A were prepared analogously to Example 41A by reacting sodium azide (5-20 equivalents) with the appropriate chlorides. The crude products were purified by silica gel chromatography (mobile phase: cyclohexane:ethyl acetate gradient or isocratic).

TABLE 4A

| Example | IUPAC name/structure (yield) | Analytical data |
|---|---|---|
| 42A | rac-N-(1-azido-6,6,6-trifluorohexan-2-yl)-8-[(2,6-difluorobenzyl)oxy]-2-methylimidazo[1,2-a]pyridine-3-carboxamide$^{a)}$<br><br>(25% of theory) | LC-MS (Method 2): $R_t$ = 1.03 min<br>MS (ESpos): m/z = 497 (M + H)$^+$<br>$^1$H NMR (400 MHz, DMSO-$d_6$): δ = 1.52-1.70 (m, 4H), 2.20-2.41 (m, 2H), 2.50 (s, 3H), 3.52 (d, 2H), 4.18-4.26 (m, 1H), 5.30 (s, 2H), 6.93 (t, 1H), 7.01 (d, 1H), 7.23 (t, 2H), 7.59 (quint, 1H), 7.91 (d, 1H), 8.50 (d, 1H). |

TABLE 4A-continued

| Example | IUPAC name/structure (yield) | Analytical data |
|---|---|---|
| 43A | rac-N-[1-azido-5,5,5-trifluoro-4-(trifluoromethyl)pentan-2-yl]-8-[(2,6-difluorobenzyl)oxy]-2-methylimidazo[1,2-a]-pyridine-3-carboxamide<br>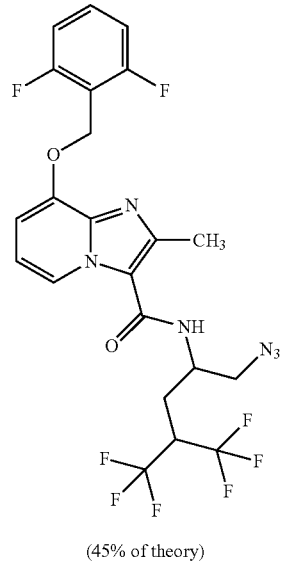<br>(45% of theory) | LC-MS (Method 2): $R_t$ = 1.08 min<br>MS (ESpos): m/z = 551 (M + H)$^+$<br>$^1$H NMR (400 MHz, DMSO-d$_6$):<br>δ = 2.06-2.19 (m, 2H), 2.52 (s, 3H), 3.61 (d, 2H), 3.98-4.13 (m, 1H), 4.26-4.38 (m, 1H), 5.30 (s, 2H), 6.94 (t, 1H), 7.03 (d, 1H), 7.23 (t, 2H), 7.59 (quint, 1H), 7.89 (d, 1H), 8.59 (d, 1H). |
| 44A | ent-N-[(2R)-1-azidohexan-2-yl]-8-[(2,6-difluorobenzy)oxy]-2-methylimidazo[1,2-a]-pyridine-3-carboxamide<br>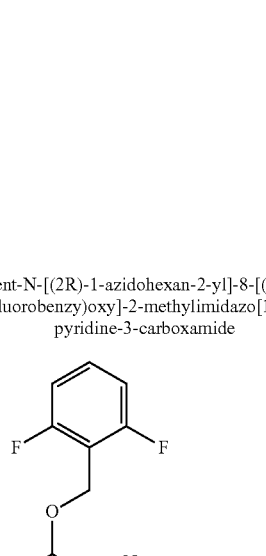<br>(37% of theory) | LC-MS (Method 2): $R_t$ = 1.04 min<br>MS (ESpos): m/z = 443 (M + H)$^+$<br>$^1$H NMR (400 MHz, DMSO-d$_6$):<br>δ = 0.88 (t, 3H), 1.22-1.42 (m, 4H), 1.49-1.61 (m, 2H), 2.50 (s, 3H), 3.48 (d, 2H), 4.10-4.21 (m, 1H), 5.30 (s, 2H), 6.93 (t, 1H), 6.99 (d, 1H), 7.23 (t, 2H), 7.59 (quint, 1H), 7.88 (d, 1H), 8.50 (d, 1H). |

[a]20 equivalents of sodium azide were used.

Example 45A rac-tert-Butyl [2-(4-chlorophenyl)-2-hydroxyethyl]carbamate

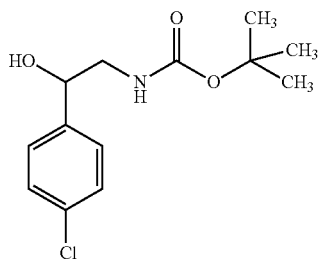 [SMILES: CC(C)(C)OC(=O)NCC(O)c1ccc(Cl)cc1]

First, 2.43 g of triethylamine (24.03 mmol) and then 2.35 g of di-tert-butyl dicarbonate (10.76 mmol) were added to 2.0 g of rac-2-amino-1-(4-chlorophenyl)ethanol hydrochloride (9.61 mmol) in 14 ml of dichloromethane. The reaction mixture was stirred at RT for 2 h. The mixture was diluted with dichloromethane, washed with saturated aqueous sodium bicarbonate solution and with saturated aqueous sodium chloride solution, dried over sodium sulphate, filtered, concentrated under reduced pressure and dried under high vacuum. This gave 2.72 g of the title compound (104% of theory).

LC-MS (Method 2): $R_t$=0.97 min
MS (ESneg): m/z=272 (M+H)$^+$
$^1$H NMR (400 MHz, DMSO-$d_6$): δ=1.33 (s, 9H), 2.97-3.13 (m, 2H), 4.54-4.62 (m, 1H), 5.44 (d, 1H), 6.73 (t, 1H), 7.31 (d, 2H), 7.38 (d, 2H).

The example shown in Table 5A was prepared analogously to Example 45A by reacting di-tert-butyl dicarbonate in dichloromethane with the appropriate commercially available amine.

Example 47A rac-3-(1,3-Dioxo-1,3-dihydro-2H-isoindol-2-yl)-3-(4-fluorophenyl)propanoic acid

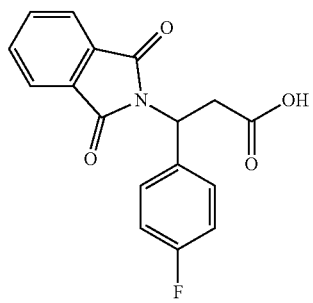 [SMILES: O=C(O)CC(c1ccc(F)cc1)N1C(=O)c2ccccc2C1=O]

2.0 g of rac-3-amino-3-(4-fluorophenyl)propanoic acid (10.92 mmol) and 1.62 g of phthalic anhydride (10.92 mmol) were dissolved in 9 ml of DMF and heated at reflux at 135° C. overnight.

The reaction solution was added to about 200 ml of water. The solid formed was stirred at RT for about 30 min and then filtered off, washed with water and dried under high vacuum. This gave 3.43 g of the title compound (86% of theory, purity about 86%).

LC-MS (Method 1): $R_t$=1.09 min
MS (ESpos): m/z=314 (M+H)$^+$
$^1$H NMR (400 MHz, DMSO-$d_6$): δ=3.24-3.3.34 (m, 1H), 3.44-3.53 (m, 1H), 5.63-5.70 (m, 1H), 7.18 (t, 2H), 7.48 (dd, 1H), 7.82-7.90 (m, 4H), 12.48 (br s, 1H).

TABLE 5A

| Example | IUPAC name/structure (yield) | Analytical data |
|---|---|---|
| 46A | rac-tert-butyl (2-hydroxy-2-phenylethyl)carbamate<br><br>(104% of theory) | LC-MS (Method 4):<br>MS (ESpos): m/z = 272 (M + H)$^+$<br>$^1$H NMR (400 MHz, DMSO-$d_6$):<br>δ = 1.33 (s, 9H), 2.97-3.13 (m, 2H),<br>4.54-4.62 (m, 1H), 5.44 (d, 1H), 6.73<br>(t, 1H), 7.19-7.38 (d, 2H). |

Example 48A rac-3-(3,4-Difluorophenyl)-3-(1,3-dioxo-1,3-dihydro-2H-isoindol-2-yl)propanoic acid

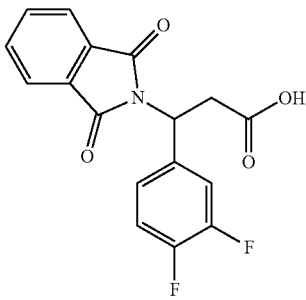 [SMILES: O=C(O)CC(c1ccc(F)c(F)c1)N1C(=O)c2ccccc2C1=O]

Step 1:
Under argon, 697 g of 3,4-difluorobenzaldehyde (4.76 mol, 1 equivalent), 495 g of malonic acid (4.76 mol, 1 equivalent) and 733 g of ammonium acetate (9.52 mol, 2 equivalents) were stirred at reflux in 2788 ml of ethanol for 20 h. The mixture was then cooled to RT and stirred at RT overnight. The precipitated crystals were filtered off with suction, washed with ethanol and diethyl ether and dried under reduced pressure. This gave 590 g (62% of theory) of rac-3-amino-3-(3,4-difluorophenyl)propanoic acid.

rac-3-Amino-3-(3,4-difluorophenyl)propanoic acid:
LC-MS (Method 1): $R_t$=0.27 min
MS (ESpos): m/z=202.0 (M+H)$^+$ Step 2:
0.20 g (0.99 mmol) of rac-3-amino-3-(3,4-difluorophenyl)propanoic acid and 0.15 g (0.99 mmol) of phthalic anhydride were dissolved in 0.8 ml of DMF and heated at reflux at 135° C. overnight. The reaction solution was added to about 9 ml of water. The resulting suspension was extracted twice with ethyl acetate. The combined organic phases were washed with water, dried over sodium sulphate, filtered and concentrated. The crude product was purified by preparative HPLC (RP18 column, mobile phase: acetonitrile/water gradient with addition of 0.1% TFA). This gave 0.2 g of the title compound (61% of theory).

LC-MS (Method 2): $R_t$=0.97 min
MS (ESpos): m/z=332 (M+H)$^+$
$^1$H NMR (400 MHz, DMSO-$d_6$): δ=3.24-3.3.33 (m, 1H), 3.44-3.52 (m, 1H), 5.63-5.70 (m, 1H), 7.23-7.28 (m, 1H), 7.36-7.47 (m, 1H), 7.49-7.57 (m, 1H), 7.82-7.90 (m, 4H), 12.51 (br s, 1H).

Example 49A rac-3-(2,4-Difluorophenyl)-3-(1,3-dioxo-1,3-dihydro-2H-isoindol-2-yl)propanoic acid

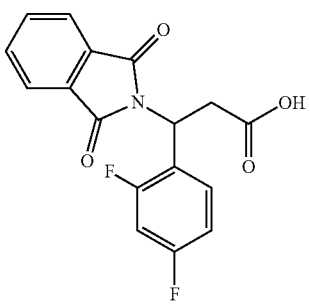 [SMILES: O=C(O)CC(c1ccc(F)cc1F)N1C(=O)c2ccccc2C1=O]

5.0 g of rac-3-amino-3-(2,4-difluorophenyl)propanoic acid (24.85 mmol) and 3.68 g of phthalic anhydride (24.85 mmol) were dissolved in 20 ml of DMF and the mixture was heated at reflux at 135° C. overnight. The reaction solution was added to about 160 ml of water and extracted twice with ethyl acetate. The combined organic phases were washed with water, dried over sodium sulphate, filtered and concentrated. The crude product was purified by silica gel chromatography (mobile phase: dichloromethane/methanol 80:1, isocratic) and then by preparative HPLC (RP18 column, mobile phase: acetonitrile/water gradient with addition of 0.1% TFA). This gave 3.43 g of the title compound (27% of theory).

LC-MS (Method 1): $R_t$=1.11 min
MS (ESpos): m/z=332 (M+H)$^+$
$^1$H NMR (400 MHz, DMSO-$d_6$): δ=3.24-3.3.34 (m, 1H), 3.40-3.49 (m, 1H), 5.89 (t, 1H), 7.09-7.15 (m, 1H), 7.19-7.28 (m, 1H), 7.70 (q, 1H), 7.82-7.89 (m, 4H), 12.55 (br s, 1H).

Example 50A rac-tert-Butyl [2-(4-chlorophenyl)-2-(1,3-dioxo-1,3-dihydro-2H-isoindol-2-yl)ethyl]carbamate

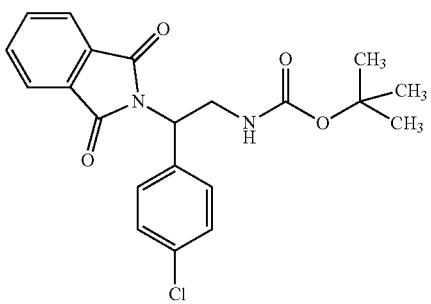

At RT, 2.61 g of rac-tert-butyl [2-(4-chlorophenyl)-2-hydroxyethyl]carbamate (Example 45A, 9.62 mmol), 1.42 g of phthalimide (9.62 mmol) and 3.78 g of triphenylphosphine (14.43 mmol) were initially charged in abs. THF. 4.03 g (14.43 mmol) of diisopropyl azodicarboxylate were then added dropwise, and the mixture was stirred at RT for 30 min. The reaction mixture was concentrated and purified by silica gel chromatography (mobile phase: cyclohexane:ethyl acetate 10:1). This gave 2.92 g of the title compound (55% of theory, purity about 73%).

LC-MS (Method 2): $R_t$=1.22 min
MS (ESpos): m/z=401 (M+H)$^+$
$^1$H NMR (400 MHz, DMSO-$d_6$): δ=1.26 (s, 9H), 3.70-3.79 (m, 1H), 3.82-3.93 (m, 1H), 5.32-5.38 (m, 1H), 7.22 (t, 1H), 7.38-7.44 (m, 4H), 7.80-7.85 (m, 4H).

The example shown in Table 6A was prepared analogously to Example 50A by reacting phthalimide, triphenylphosphine and diisopropyl azodicarboxylate in THF with the appropriate alcohol.

TABLE 6A

| Example | IUPAC name/structure (yield) | Analytical data |
|---|---|---|
| 51A | rac-tert-butyl [2-(1,3-dioxo-1,3-dihydro-2H-isoindol-2-yl)ethyl]carbamate<br><br>(55% of theory, purity about 73%) | LC-MS (Method 2): $R_t$ = 1.22 min<br>MS (ESpos): m/z = 401 (M + H)$^+$<br>$^1$H NMR (400 MHz, DMSO-d$_6$):<br>δ = 1.26 (s, 9H), 3.70-3.79 (m, 1H),<br>3.82-3.93 (m, 1H), 5.32-5.38 (m, 1H),<br>7.22 (t, 1H), 7.38-7.44 (m, 4H), 7.80-7.85 (m, 4H). |

Example 52A rac-tert-Butyl [2-(1,3-dioxo-1,3-dihydro-2H-isoindol-2-yl)-2-(4-fluorophenyl)ethyl]carbamate

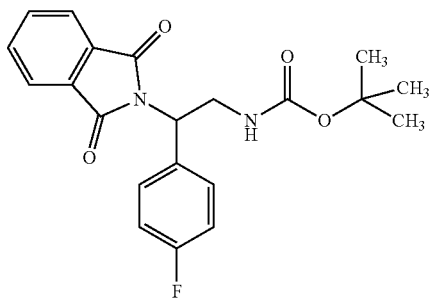 [SMILES: CC(C)(C)OC(=O)NCC(c1ccc(Cl)cc1)N1C(=O)c2ccccc2C1=O]

Under argon, a solution of 3.2 g of rac-3-(1,3-dioxo-1,3-dihydro-2H-isoindol-2-yl)-3-(4-fluorophenyl)propanoic acid (Example 47A, 8.78 mmol) in 32 ml of toluene was initially charged, and 1.33 g of triethylamine (13.18 mmol), 98 mg of 1,4-diazabicyclo[2.2.2]octane (0.88 mmol), 3.14 g of diphenylphosphoryl azide (11.42 mmol) and 6.51 g of tert-butanol (87.84 mmol) were added. The reaction mixture was heated at reflux overnight and then diluted with ethyl acetate and washed with water. The organic phase was dried over sodium sulphate, filtered and concentrated. The crude product was purified by silica gel chromatography (mobile phase: cyclohexane/ethyl acetate 8:1; 6:1). This gave 959 mg of the title compound (28% of theory).

LC-MS (Method 2): $R_t$=1.11 min

MS (ESpos): m/z=385 (M+H)$^+$ $^1$H NMR (400 MHz, DMSO-d$_6$): δ=1.26 (s, 9H), 3.69-3.78 (m, 1H), 3.84-3.95 (m, 1H), 5.32-5.39 (m, 1H), 7.15-7.26 (m, 3H), 7.41-7.48 (m, 2H), 7.80-7.89 (m, 4H).

Example 53A rac-tert-Butyl [2-(3,4-difluorophenyl)-2-(1,3-dioxo-1,3-dihydro-2H-isoindol-2-yl)ethyl]carbamate

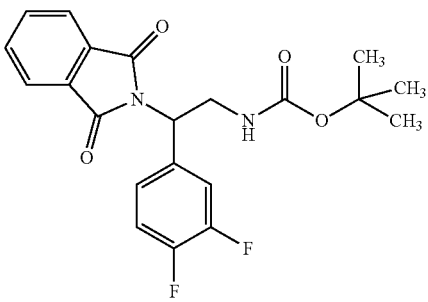 [SMILES: CC(C)(C)OC(=O)NCC(c1ccc(F)c(F)c1)N1C(=O)c2ccccc2C1=O]

Under argon, a solution of 5.0 g of rac-3-(3,4-difluorophenyl)-3-(1,3-dioxo-1,3-dihydro-2H-isoindol-2-yl)propanoic acid (Example 48A, 15.09 mmol) and 3.06 g of triethylamine (30.19 mmol) in 65 ml of toluene was initially charged, 4.36 g of diphenylphosphoryl azide (15.85 mmol) were added and the mixture was stirred at RT for 3.5 h. 65 ml of tert-butanol were then added, and the mixture was stirred under reflux overnight. After cooling, the reaction solution was concentrated and purified by flash chromatography (mobile phase: petroleum ether/ethyl acetate 2:1, isocratic). This gave 3.1 g of the title compound (45% of theory).

LC-MS (Method 2): $R_t$=1.19 min

MS (ESpos): m/z=403 (M+H)$^+$ $^1$H NMR (400 MHz, DMSO-d$_6$): δ=1.26 (s, 9H), 3.73-3.90 (m, 2H), 5.32-5.39 (m, 1H), 7.20-7.27 (m, 2H), 7.36-7.46 (m, 1H), 7.48-7.56 (m, 1H), 7.81-7.91 (m, 4H).

Example 54A rac-tert-Butyl [2-(2,4-difluorophenyl)-2-(1,3-dioxo-1,3-dihydro-2H-isoindol-2-yl)ethyl]carbamate

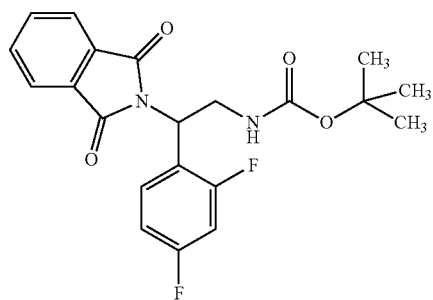 [SMILES: CC(C)(C)OC(=O)NCC(c1ccc(F)cc1F)N1C(=O)c2ccccc2C1=O]

Under argon, 2.17 g of rac-3-(2,4-difluorophenyl)-3-(1,3-dioxo-1,3-dihydro-2H-isoindol-2-yl)-propanoic acid (Example 49A, 6.54 mmol) and 1.32 g of triethylamine (13.07 mmol) were initially charged in 23.8 ml of abs. toluene. 1.89 g of diphenylphosphoryl azide (6.86 mmol) were added at RT, and the mixture was stirred at RT with water cooling for 3.5 h, 23.8 ml of tert-butanol were then added and the mixture was stirred under reflux overnight. After cooling, the reaction solution was concentrated and purified by flash chromatography (mobile phase: cyclohexane/ethyl acetate 2:1). This gave 650 mg of the title compound (24% of theory).

LC-MS (Method 2): $R_t$=1.11 min
MS (ESpos): m/z=403 (M+H)$^+$

Example 55A rac-tert-Butyl [2-amino-2-(3,4-difluorophenyl)ethyl]carbamate

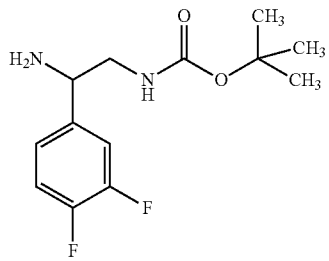 [SMILES: CC(C)(C)OC(=O)NCC(N)c1ccc(F)c(F)c1]

6.13 g of rac-tert-butyl [2-(3,4-difluorophenyl)-2-(1,3-dioxo-1,3-dihydro-2H-isoindol-2-yl)ethyl]-carbamate (Example 53A, purity about 60%, about 9.14 mmol) were initially charged in 13.1 ml of 40% strength aqueous methylamine solution and stirred in a closed vessel at 60° C. overnight. The reaction mixture was concentrated and the residue was purified by silica gel chromatography (mobile phase: dichloromethane:methanol:diethylamine 30:1:0.1; 20:1:0.1). This gave 1.83 g of the title compound (74% of theory).

LC-MS (Method 1): $R_t$=0.65 min
MS (ESpos): m/z=273 (M+H)$^+$
$^1$H NMR (400 MHz, DMSO-d$_6$): δ=1.33 (s, 9H), 1.96 (br s, 2H), 2.92-3.10 (m, 2H), 3.81-3.88 (m, 1H), 6.76-6.82 (m, 1H), 7.11-7.17 (m, 1H), 7.27-7.40 (m, 2H).

The examples shown in Table 7A were prepared analogously to Example 55A by reacting a solution of methylamine with the appropriate phthalimides.

TABLE 7A

| Example | IUPAC name/structure (yield) | Analytical data |
|---|---|---|
| 56A | rac-tert-butyl [2-amino-2-(4-chlorophenyl)ethyl]carbamate trifluoroacetate[1])<br><br>(41% of theory) | LC-MS (Method 2): $R_t$ = 0.68 min<br>MS (ESpos): m/z = 271 (M + H − TFA)$^+$<br>$^1$H NMR (400 MHz, DMSO-d$_6$):<br>δ = 1.31 (s, 9H), 3.28-3.44 (m, 2H),<br>4.31 (br s, 1H), 7.00 (t, 1H), 7.43 (d, 2H), 7.52 (d, 2H), 8.42 (br s, 3H). |
| 57A | rac-tert-butyl (2-amino-2-phenylethyl)carbamate trifluoroacetate[1])<br><br>(45% of theory) | LC-MS (Method 2): $R_t$ = 0.59 min<br>MS (ESpos): m/z = 237 (M + H − TFA)$^+$<br>$^1$H NMR (400 MHz, DMSO-d$_6$):<br>δ = 1.34 (s, 9H), 3.28-3.46 (m, 2H),<br>4.29 (br s, 1H), 7.01 (t, 1H), 7.35-7.48 (m, 5H), 8.43 (br s, 3H). |

TABLE 7A-continued

| Example | IUPAC name/structure (yield) | Analytical data |
|---|---|---|
| 58A | rac-tert-butyl [2-amino-2-(4-fluorophenyl)ethyl]carbamate[2)]<br><br>(85% of theory) | LC-MS (Method 2): $R_t$ = 0.60 min<br>MS (ESpos): m/z = 255 (M + H)$^+$<br>$^1$H NMR (400 MHz, DMSO-$d_6$):<br>δ = 1.33 (s, 9H), 1.89 (br s, 2H), 2.88-2.97 (m, 1H), 3.04-3.11 (m, 1H), 3.84-3.90 (m, 1H), 6.80 (t, 1H), 7.11 (t, 2H), 7.36 (dd, 2H). |
| 59A | rac-tert-butyl [2-amino-2-(2,4-difluorophenyl)ethyl]carbamate<br><br>(about 86% of theory) | LC-MS (Method 2): $R_t$ = 0.65 min<br>MS (ESpos): m/z = 273 (M + H)$^+$<br>$^1$H NMR (400 MHz, DMSO-$d_6$):<br>δ = 1.31 (s, 9H), 1.91 (br s, 2H), 2.97-3.14 (m, 2H), 4.12 (t, 1H), 6.81 (t, 1H), 6.99-7.17 (m, 2H), 7.54 (q, 1H). |

[1)]The crude product obtained was concentrated and re-purified by preparative HPLC (RP18 column, mobile phase: acetonitrile/water gradient with addition of 0.1% TFA).
[2)]Reaction conditions: 20 eq. of methylamine [40% strength solution in water]; 7 h at 60° C.

Example 60A ent-tert-Butyl [2-amino-2-(3,4-difluorophenyl)ethyl] carbamate (Enantiomer A)

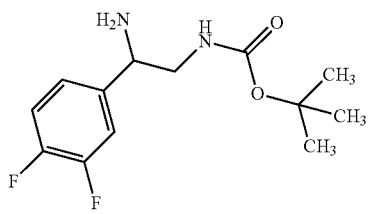 [SMILES: CC(C)(C)OC(=O)NCC(N)c1ccc(F)c(F)c1]

100 mg of rac-tert-butyl [2-amino-2-(3,4-difluorophenyl) ethyl]carbamate (Example 55A) were separated into the enantiomers on a chiral phase [column: Daicel Chiralpak AY-H, 5 µm, 250×20 mm, mobile phase: 80% isohexane, 20% ethanol+0.2% diethylamine, flow rate 15 ml/min; 30° C., detection: 220 nm].

Yield: 43 mg of enantiomer A (99% pure, >99% ee)

$R_t$=4.58 min [Daicel Chiralpak AY-H, 5 m, 250×4.6 mm; mobile phase: 80% isohexane, 20% ethanol+0.2% diethylamine; flow rate 1.0 ml/min; 30° C.; detection: 220 nm].

Example 61A ent-tert-Butyl [2-amino-2-(3,4-difluorophenyl)ethyl] carbamate (Enantiomer B)

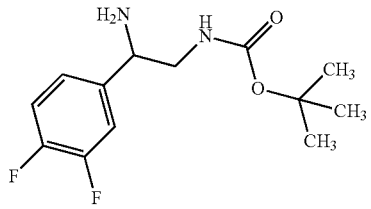 [SMILES: CC(C)(C)OC(=O)NCC(N)c1ccc(F)c(F)c1]

100 mg of rac-tert-butyl [2-amino-2-(3,4-difluorophenyl) ethyl]carbamate (Example 55A) were separated into the enantiomers on a chiral phase [column: Daicel Chiralpak AY-H, 5 µm, 250×20 mm, mobile phase: 80% isohexane, 20% ethanol+0.2% diethylamine, flow rate 15 ml/min; 30° C., detection: 220 nm].

Yield: 44 mg of enantiomer B (99% pure, >99% ee)

$R_t$=5.61 min [Daicel Chiralpak AY-H, 5 m, 250×4.6 mm; mobile phase: 80% isohexane, 20% ethanol+0.2% diethylamine; flow rate 1.0 ml/min; 30° C.; detection: 220 nm].

Example 62A ent-tert-Butyl [2-amino-2-(2,4-difluorophenyl)ethyl] carbamate (Enantiomer A)

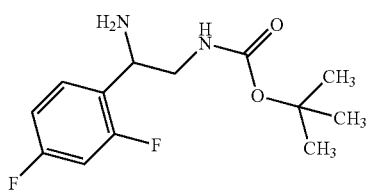 [SMILES: CC(C)(C)OC(=O)NCC(N)c1ccc(F)cc1F]

435 mg of Example 59A were separated into the enantiomers on a chiral phase [column: Daicel Chiralpak AY-H, 5 µm, 250×20 mm, mobile phase: 80% isohexane, 20% ethanol+0.2% diethylamine, flow rate 15 ml/min; 30° C., detection: 220 nm]. To remove residual solvent, the product was dissolved in acetonitrile/water and lyophilized.

Yield: 182 mg (97% pure, >99% ee)

Enantiomer B: $R_t$=5.25 min [Daicel Chiralpak AY-H, 5 µm, 250×4.6 mm; mobile phase: 80% isohexane, 20% ethanol+0.2% diethylamine; flow rate 1.0 ml/min; 30° C.; detection: 220 nm].

Example 63A ent-Benzyl tert-butyl [1-(3,4-difluorophenyl)ethane-1,2-diyl]biscarbamate

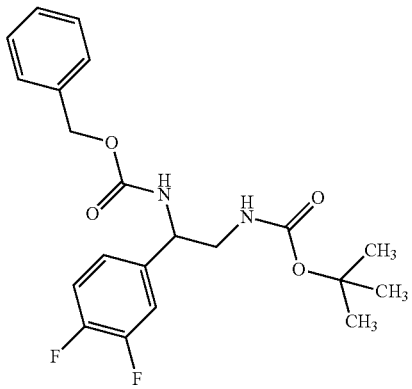 [SMILES: CC(C)(C)OC(=O)NCC(NC(=O)OCc1ccccc1)c1ccc(F)c(F)c1]

300 mg of ent-tert-butyl [2-amino-2-(3,4-difluorophenyl)ethyl]carbamate (enantiomer A) (Example 60A; 1.10 mmol) were initially charged in 5 ml of dry THF, and 1.15 ml of diisopropylethylamine (6.6 mmol, 6 equivalents), 26 mg of N,N-dimethylaminopyridine (0.22 mmol, 0.2 equivalents) and then, dropwise, 0.31 ml of benzyl chloroformate (2.2 mmol, 2 equivalents) were added. The reaction mixture was stirred at RT for 48 h, then concentrated, taken up in ethyl acetate and washed with water. The combined organic phases were washed with saturated aqueous sodium chloride solution, dried over magnesium sulphate, filtered and concentrated. The residue was chromatographed on silica gel (mobile phase: cyclohexane/ethyl acetate 1:1). This gave 336 mg (75% of theory) of the title compound.

LC-MS (Method 2): $R_t$=1.14 min
MS (ESpos): m/z=407.3 (M+H)⁺

$^1$H NMR (400 MHz, DMSO-$d_6$): δ=1.3 (s, 9H); 3.13 (t, 2H); 4.65 (q, 1H); 5.00 (q, 2H); 6.88 (t, 1H); 7.1 (br. s., 1H); 7.21-7.40 (m, 7H); 7.80 (d, 1H).

Example 64A ent-Benzyl [2-amino-1-(3,4-difluorophenyl)ethyl] carbamate

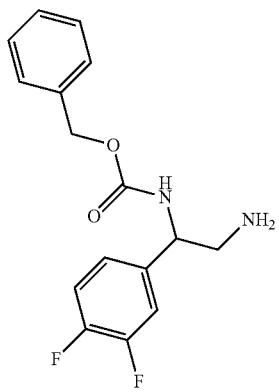 [SMILES: NCC(NC(=O)OCc1ccccc1)c1ccc(F)c(F)c1]

16.5 ml of a 2 N solution of hydrochloric acid in diethyl ether were added to 335 mg of ent-benzyl tert-butyl [1-(3,4-difluorophenyl)ethane-1,2-diyl]biscarbamate (Example 63A; 0.824 mmol), and the mixture was stirred at RT overnight. Another 16.5 ml of a 4 N solution of hydrochloric acid in 1,4-dioxane were added, and the mixture was stirred at RT for a further 3 h. The reaction mixture was concentrated, saturated aqueous sodium bicarbonate solution was added and the mixture was extracted three times with ethyl acetate. The combined organic phases were washed with saturated aqueous sodium chloride solution, dried over magnesium sulphate, filtered and concentrated. This gave 252.4 mg (84% of theory) of the title compound.

LC-MS (Method 2): $R_t$=0.74 min
MS (ESpos): m/z=307.2 (M+H)⁺

$^1$H NMR (400 MHz, DMSO-$d_6$): δ=1.82-1.95 (br. s, 2H); 2.70 (d, 2H); 4.49 (q, 1H); 5.00 (m, 2H); 7.1 (br. s., 1H); 7.21-7.40 (m, 7H); 7.80 (d, 1H).

Example 65A rac-tert-Butyl (3-ethoxy-2-hydroxypropyl)carbamate

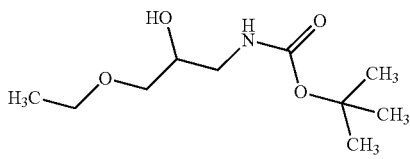

3 g of rac-1-amino-3-ethoxy-2-propanol hydrochloride (19.28 mmol, 1 equivalent) were initially charged in 40 ml of dichloromethane, and 5.7 ml of triethylamine (40.9 mmol, 2.1 equivalents) and then 4.96 ml of di-tert-butyl dicarbonate (21.6 mmol, 1.12 equivalents) were added. The reaction mixture was stirred at RT for 2 h, diluted with dichloromethane and washed with saturated aqueous sodium bicarbonate solution and with saturated aqueous sodium chloride solution. The organic phase was dried with magnesium sulphate, filtered and concentrated. The residue was dried under high vacuum. This gave 3.73 g of crude product (88% of theory) which were reacted further without any work-up.

$^1$H NMR (400 MHz, DMSO-$d_6$): δ=1.10 (t, 3H); 1.39 (s, 9H); 2.85 (dt, 1H); 3.02 (dt, 1H); 3.20-3.30 (m, 2H); 3.40 (q, 2H); 3.55-3.60 (m, 1H); 4.75 (d, 1H); 6.61 (t, 1H).

Example 66A rac-tert-Butyl [2-(1,3-dioxo-1,3-dihydro-2H-isoindol-2-yl)-3-ethoxypropyl]carbamate

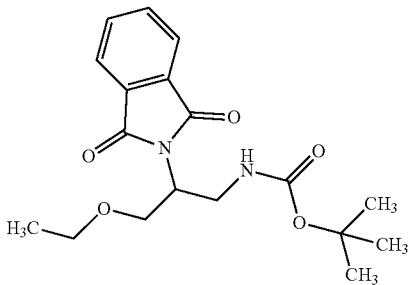 [SMILES: CCOCC(CNC(=O)OC(C)(C)C)N1C(=O)c2ccccc2C1=O]

At RT, 3.73 g of rac-tert-butyl (3-ethoxy-2-hydroxypropyl)carbamate (17 mmol, 1 equivalent), 2.50 g of phthalimide (17 mmol, 1 equivalent) and 6.69 g of triphenylphosphine (25.52 mmol, 1.5 equivalents) were initially charged in 70 ml of dry THF. 5.06 ml of diisopropyl azodicarboxylate (25.5 mmol, 1.5 equivalents) were added dropwise, and the mixture was stirred at RT for 2 h. The reaction mixture was concentrated under reduced pressure. The crude product was diluted with methanol, acetonitrile and water to 90 ml and purified by preparative HPLC (column material: Sunfire C18 5 µm 75×30 mm; flow rate 56 ml/min; mobile phase: 45% Milli-Q-water/50% acetonitrile/5% 1% aqueous formic acid; injection volume: 0.5 ml; detection wavelength: 210 nm). This gave 4.88 g of the title compound (82% of theory).

LC-MS (Method 2): $R_t$=1.04 min
MS (ESpos): m/z=349.3 (M+H)$^+$
$^1$H NMR (400 MHz, DMSO-$d_6$): δ=1.02 (t, 3H); 1.25 (s, 9H); 3.34-3.48 (m, 4H); 3.65 (dd, 1H); 3.81 (dd, 1H); 4.32-4.38 (m, 1H); 7.10 (t, 1H); 7.80-7.90 (m, 4H).

Example 67A rac-tert-Butyl (2-amino-3-ethoxypropyl)carbamate

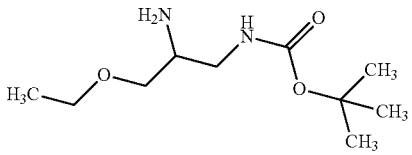

4.88 g of rac-tert-butyl [2-(1,3-dioxo-1,3-dihydro-2H-isoindol-2-yl)-3-ethoxypropyl]carbamate (14.0 mmol, 1 equivalent) were initially charged in 12 ml of 40% strength aqueous methylamine solution and reated in a microwave at 100° C. for 1.5 h. The reaction mixture was concentrated, the residue was taken up in 10 ml of toluene and concentrated again. This step was repeated several times. The residue was then chromatographed on silica gel (mobile phase: dichloromethane/methanol 10:1). This gave 470 mg (15% of theory) of the title compound.

$^1$H NMR (400 MHz, DMSO-$d_6$): δ=1.10 (t, 3H); 1.38 (s, 9H); 3.03-3.20 (m, 3H); 3.34-3.48 (m, 4H); 6.95 (t, 1H).

Example 68A rac-tert-Butyl (2-hydroxy-3-phenoxypropyl)carbamate

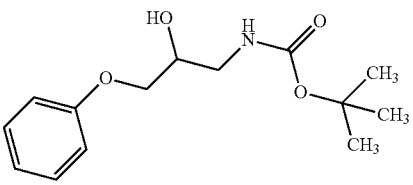 [SMILES: CC(C)(C)OC(=O)NCC(O)COc1ccccc1]

1.13 g of rac-1-amino-3-phenoxypropan-2-ol hydrochloride (5.5 mmol, 1 equivalent) were initially charged in 11.5 ml of dichloromethane, and 1.64 ml of triethylamine (11.7 mmol, 2.1 equivalents) and then 1.43 ml of di-tert-butyl dicarbonate (6.21 mmol, 1.12 equivalents) were added. The reaction mixture was stirred at RT for 2 h, diluted with dichloromethane and washed with saturated aqueous sodium bicarbonate solution and with saturated aqueous sodium chloride solution. The organic phase was dried with magnesium sulphate, filtered and concentrated. The residue was dried under high vacuum. This gave 1.5 g of crude product (quantitative yield) which was reacted further without further purification.

LC-MS (Method 2): $R_t$=0.88 min
MS (ESpos): m/z=268.2 (M+H)$^+$

Example 69A rac-tert-Butyl [2-(1,3-dioxo-1,3-dihydro-2H-isoindol-2-yl)-3-phenoxypropyl]carbamate

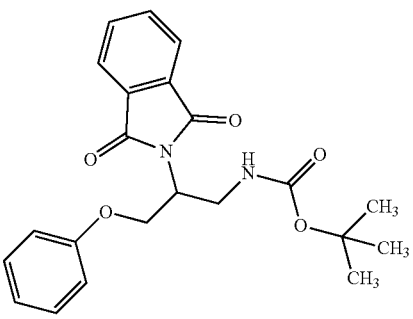 [SMILES: CC(C)(C)OC(=O)NCC(COc1ccccc1)N1C(=O)c2ccccc2C1=O]

At RT, 1.5 g of rac-tert-butyl (2-hydroxy-3-phenoxypropyl)carbamate (5.6 mmol, 1 equivalent), 0.99 g of phthalimide (6.73 mmol, 1.2 equivalents) and 2.21 g of triphenylphosphine (8.4 mmol, 1.5 equivalents) were initially charged in 23 ml of dry tetrahydrofuran. 1.70 ml of diisopropyl azodicarboxylate (8.4 mmol, 1.5 equivalents) were added dropwise, and the mixture was stirred at RT for 2 h. LC/MS showed complete conversion of the reaction. The reaction mixture was concentrated and purified by chromatography on silica gel (Biotage Isolera; cyclohexane/ethyl acetate gradient as mobile phase). This gave 1.08 g of the title compound (48% of theory).

LC-MS (Method 2): $R_t$=1.13 min
MS (ESpos): m/z=397.3 (M+H)$^+$

Example 70A rac-tert-Butyl (2-amino-3-phenoxypropyl)carbamate

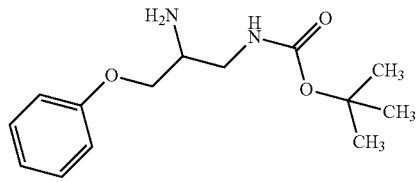 [SMILES: CC(C)(C)OC(=O)NCC(N)COc1ccccc1]

1.08 g of rac-tert-butyl [2-(1,3-dioxo-1,3-dihydro-2H-isoindol-2-yl)-3-phenoxypropyl]carbamate (2.72 mmol, 1 equivalent) were initially charged in 5 ml of 40% strength aqueous methylamine solution and reacted in a microwave at 100° C. for 2 h. The reaction mixture was concentrated and the residue was then chromatographed on silica gel (Biotage Isolera; mobile phase: dichloromethane/methanol gradient). This gave 200 mg (27% of theory) of the title compound.

LC-MS (Method 2): $R_t$=0.57 min
MS (ESpos): m/z=267.1 (M+H)$^+$

Example 71A rac-tert-Butyl [3-(4-fluorophenoxy)-2-hydroxypropyl]carbamate

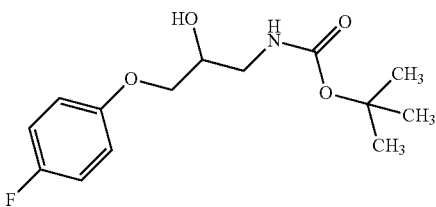 [SMILES: CC(C)(C)OC(=O)NCC(O)COc1ccc(F)cc1]

0.93 g of rac-1-amino-3-(4-fluorophenoxy)propan-2-ol (5.07 mmol, 1 equivalent) were initially charged in 10.5 ml of dichloromethane, and first 1.5 ml of triethylamine (10.7 mmol, 2.1 equivalents) and then 1.31 ml of di-tert-butyl dicarbonate (5.68 mmol, 1.12 equivalents) were added. The reaction mixture was stirred at RT for 2 h. The mixture was then diluted with dichloromethane and washed with saturated aqueous sodium bicarbonate solution and with saturated aqueous sodium chloride solution. The organic phase was dried over magnesium sulphate, filtered and concentrated. The residue was used without further purification for the next reaction.

LC-MS (Method 2): $R_t$=0.89 min
MS (ESpos): m/z=286.2 (M+H)$^+$

Example 72A rac-tert-Butyl [2-(1,3-dioxo-1,3-dihydro-2H-isoindol-2-yl)-3-(4-fluorophenoxy)propyl]carbamate

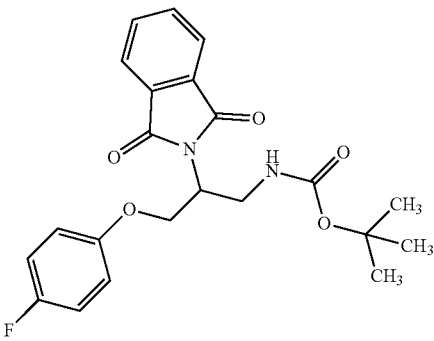 [SMILES: CC(C)(C)OC(=O)NCC(COc1ccc(F)cc1)N1C(=O)c2ccccc2C1=O]

At RT, 1.5 g of rac-tert-butyl [3-(4-fluorophenoxy)-2-hydroxypropyl]carbamate (5.26 mmol, 1 equivalent), 0.93 g of phthalimide (6.31 mmol, 1.2 equivalents) and 2.07 g of triphenylphosphine (7.9 mmol, 1.5 equivalents) were initially charged in 22 ml of dry THF. 1.56 ml of diisopropyl azodicarboxylate (7.9 mmol, 1.5 equivalents) were added dropwise, and the mixture was stirred at RT for 2 h. The reaction mixture was concentrated under reduced pressure and purified by chromatography on silica gel (Biotage Isolera; cyclohexane/ethyl acetate gradient as mobile phase). This gave 1.97 g of the title compound (90% of theory).

LC-MS (Method 2): $R_t$=1.14 min
MS (ESpos): m/z=415.3 (M+H)$^+$

Example 73A rac-tert-Butyl [2-amino-3-(4-fluorophenoxy)propyl]carbamate

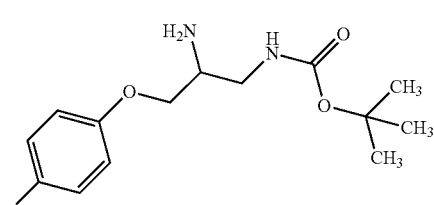

1.97 g of rac-tert-butyl [2-(1,3-dioxo-1,3-dihydro-2H-isoindol-2-yl)-3-(4-fluorophenoxy)propyl]-carbamate (4.75 mmol, 1 equivalent) were initially charged in 5 ml of 40% strength aqueous methylamine solution, and the mixture was reacted in a microwave at 100° C. for 2 h. The reaction mixture was concentrated and the residue was then chromatographed on silica gel (Biotage Isolera; mobile phase: dichloromethane/methanol gradient). This gave 900 mg (67% of theory) of the title compound.

LC-MS (Method 2): $R_t$=0.58 min
MS (ESpos): m/z=285.1 (M+H)$^+$

Example 74A rac-Benzyl (2-hydroxy-3-isopropoxypropyl)carbamate

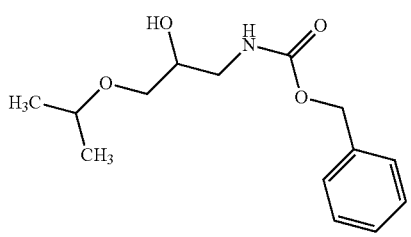 [SMILES: CC(C)OCC(O)CNC(=O)OCc1ccccc1]

1 g of rac-1-amino-3-isopropoxypropan-2-ol (7.5 mmol, 1 equivalent) were initially charged in 25 ml of THF, and 1.16 ml of benzyl chloroformate (8.3 mmol, 1.1 equivalents), 3.9 ml of diisopropylethylamine (22.5 mmol, 3 equivalents) and 183 mg of N,N-dimethylaminopyridine (1.5 mmol, 0.2 equivalents) were added. The reaction mixture was stirred at RT, and after about 30 min 5 ml of DMF were added. After a further 2.5 h at RT, the mixture was concentrated to dryness. The residue was taken up in ethyl acetate and washed with saturated aqueous sodium bicarbonate solution and then with saturated aqueous sodium chloride solution. The organic phase was dried over magnesium sulphate, filtered and concentrated. The residue was used without further purification for the next reaction.

LC-MS (Method 2): $R_f$=0.80 min
MS (ESpos): m/z=268.2 (M+H)$^+$

Example 75A rac-Benzyl [2-(1,3-dioxo-1,3-dihydro-2H-isoindol-2-yl)-3-isopropoxypropyl]carbamate

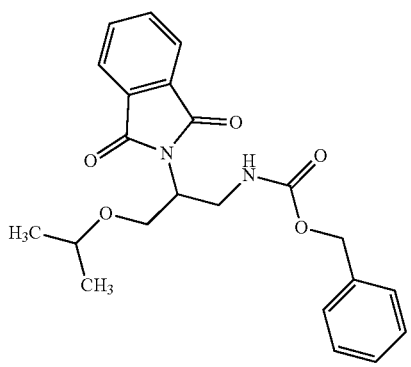 [SMILES: CC(C)OCC(CNC(=O)OCc1ccccc1)N1C(=O)c2ccccc2C1=O]

At RT, 1.28 g of racemic benzyl (2-hydroxy-3-isopropoxypropyl)carbamate (4.79 mmol, 1 equivalent), 0.85 g of phthalimide (5.75 mmol, 1.2 equivalents) and 1.88 g of triphenylphosphine (7.2 mmol, 1.5 equivalent) were initially charged in 20 ml of dry tetrahydrofuran. 1.42 ml of diisopropyl azodicarboxylate (7.2 mmol, 1.5 equivalent) were added dropwise, and the mixture was stirred at RT for 2 h. The reaction mixture was concentrated under reduced pressure and purified by chromatography on silica gel (Biotage Isolera; cyclohexane/ethyl acetate gradient as mobile phase).

This gave 2.3 g (66% pure; 78% of theory) of the title compound (contaminated with diisopropyl hydrazine-1,2-dicarboxylate).

LC-MS (Method 2): $R_f$=1.12 min
MS (ESpos): m/z=397.2 (M+H)$^+$
$^1$H NMR (400 MHz, DMSO-d$_6$): δ=0.91 (d, 3H), 1.00 (d, 3H), 3.42-3.48 (m, 2H), 3.50 (hept, 1H), 3.69 (dd, 1H), 3.79 (t, 1H), 4.31 (q, 1H), 4.91 (s, 2H), 7.20-7.30 (m, 5H), 7.52 (t, 1H), 7.80-7.86 (m, 4H).

Example 76A rac-Benzyl (2-amino-3-isopropoxypropyl)carbamate

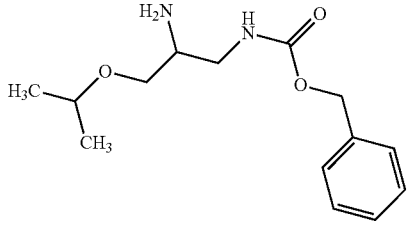 [SMILES: CC(C)OCC(N)CNC(=O)OCc1ccccc1]

2.3 g of rac-benzyl [2-(1,3-dioxo-1,3-dihydro-2H-isoindol-2-yl)-3-isopropoxypropyl]carbamate (5.6 mmol, 1 equivalent) were dissolved in 30 ml of ethanol, 7.3 ml of 40% strength aqueous methylamine solution (84.4 mmol, 15 equivalent) were added and the mixture was stirred at 60° C. overnight. The reaction mixture was concentrated and the residue was then chromatographed on silica gel (Biotage Isolera; mobile phase: dichloromethane/methanol gradient). This gave 730 mg (49% of theory) of the title compound.

LC-MS (Method 2): $R_f$=0.59 min
MS (ESpos): m/z=267.2 (M+H)$^+$
$^1$H NMR (400 MHz, DMSO-d$_6$): δ=1.05 (d, 6H), 1.74 (br. s, 2H), 2.79-2.90 (m, 2H), 3.02-3.12 (m, 1H), 3.18 (dd, 1H), 3.21 (dd, 1H), 3.50 (q, 1H), 5.00 (s, 2H), 7.18 (t, 1H), 7.28-7.39 (m, 5H).

Example 77A rac-tert-Butyl {2-[({8-[(2,6-difluorobenzyl)oxy]-2-methylimidazo[1,2-a]pyridin-3-yl}carbonyl)-amino]-2-(3,4-difluorophenyl)ethyl}carbamate

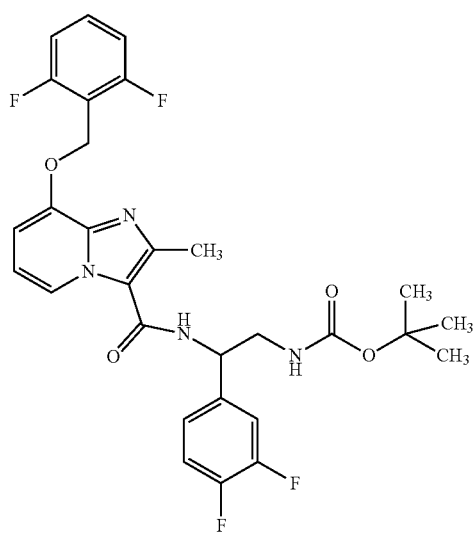 [SMILES: Cc1nc2c(OCc3c(F)cccc3F)cccn2c1C(=O)NC(CNC(=O)OC(C)(C)C)c1ccc(F)c(F)c1]

200 mg of 8-[(2,6-difluorobenzyl)oxy]-2-methylimidazo[1,2-a]pyridine-3-carboxylic acid (0.63 mmol), 242 mg of rac-(benzotriazol-1-yloxy)bisdimethylaminomethylium fluoroborate (TBTU, 0.75 mmol) and 318 mg of 4-methylmorpholine (3.14 mmol) were initially charged in 4.3 ml of DMF. At RT, 242 mg of rac-tert-butyl [2-amino-2-(3,4-difluorophenyl)ethyl]carbamate (Example 55A, 0.75 mmol) were added, and the mixture was stirred at RT overnight. About 16 ml of water were added to the reaction solution, the mixture was stirred for another 30 min and the precipitate formed was filtered off and washed with water. The solid was treated in an ultrasonic bath with about 4 ml of acetonitrile for 10 min, filtered off and dried under high vacuum overnight. This gave 355 mg of the title compound (96% of theory).

LC-MS (Method 2): $R_t$=1.10 min

MS (ESpos): m/z=573 (M+H)⁺

¹H NMR (400 MHz, DMSO-d₆): δ=1.32 (s, 9H), 2.59 (s, 3H), 3.29-3.46 (m, 2H), 5.15 (q, 1H), 5.31 (s, 2H), 6.91 (t, 1H), 7.01 (d, 1H), 7.08 (t, 1H), 7.19-7.27 (m, 3H), 7.36-7.51 (m, 2H), 7.59 (q, 1H), 8.21 (d, 1H), 8.56 (d, 1H).

The examples shown in Table 8A were prepared by reacting 8-[(2,6-difluorobenzyl)oxy]-2-methylimidazo[1,2-a]pyridine-3-carboxylic acid with the amines, prepared as described above or commercially available, (1.1-1.5 equivalents) and 4-methylmorpholine (4-6 equivalents) under the reaction conditions described in the General Working Procedure 3.

TABLE 8A

| Example | IUPAC name/structure (yield) | Analytical data |
|---|---|---|
| 78A | rac-tert-butyl {2-(4-chlorophenyl)-2-[({8-[(2,6-difluorobenzyl)oxy]-2-methylimidazo[1,2-a]-pyridin-3-yl}carbonyl)amino]ethyl}carbamate 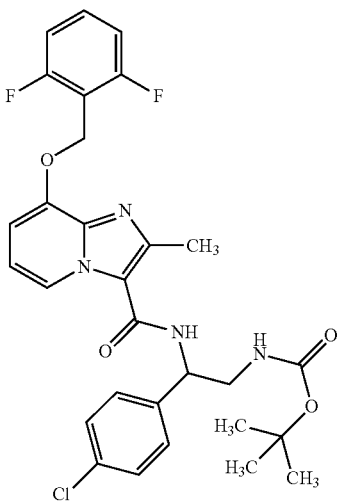 (88% of theory) | LC-MS (Method 2): $R_t$ = 1.13 min<br>MS (ESpos): m/z = 571 (M + H)⁺<br>¹H NMR (400 MHz, DMSO-d₆):<br>δ = 1.32 (s, 9H), 2.58 (s, 3H), 3.29-3.46 (m, 2H), 5.16 (q, 1H), 5.31 (s, 2H), 6.91 (t, 1H), 7.02 (d, 1H), 7.09 (t, 1H), 7.23 (t, 2H), 7.38-7.45 (m, 4H), 7.59 (quint, 1H), 8.21 (d, 1H), 8.56 (d, 1H). |
| 79A | rac-tert-butyl {2-[({8-[(2,6-difluorobenzyl)oxy]-2-methylimidazo[1,2-a]pyridin-3-yl}carbonyl)-amino]-2-(4-fluorophenyl)ethyl}carbamate 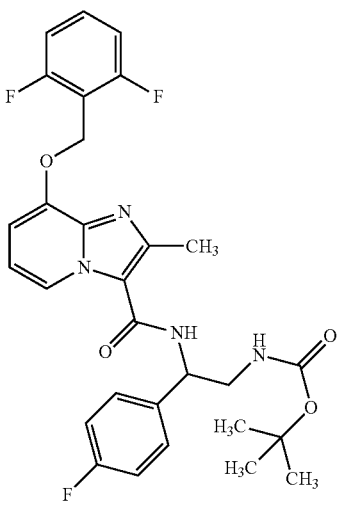 (99% of theory) | LC-MS (Method 2): $R_t$ = 1.03 min<br>MS (ESpos): m/z = 555 (M + H)⁺<br>¹H NMR (400 MHz, DMSO-d₆):<br>δ = 1.32 (s, 9H), 2.58 (s, 3H), 3.29-3.46 (m, 2H), 5.18 (q, 1H), 5.31 (s, 2H), 6.91 (t, 1H), 7.02 (d, 1H), 7.08 (t, 1H), 7.13-7.26 (m, 4H), 7.43 (dd, 2H), 7.59 (quint, 1H), 8.19 (d, 1H), 8.56 (d, 1H). |

TABLE 8A-continued

| Example | IUPAC name/structure (yield) | Analytical data |
|---|---|---|
| 80A | rac-tert-butyl {2-[({8-[(2,6-difluorobenzyl)oxy]-2-methylimidazo[1,2-a]pyridin-3-yl}carbonyl)-amino]-2-phenylethyl}carbamate<br />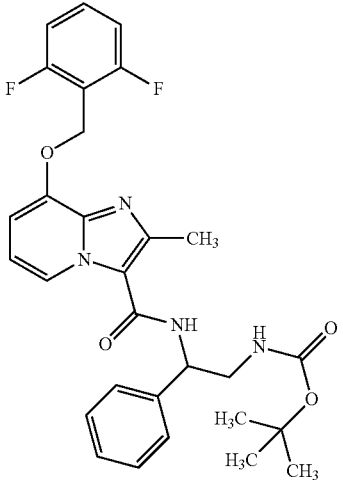<br />(63% of theory) | LC-MS (Method 2): $R_t$ = 1.06 min<br />MS (ESpos): m/z = 537 (M + H)$^+$<br />$^1$H NMR (400 MHz, DMSO-d$_6$):<br />δ = 1.32 (s, 9H), 2.59 (s, 3H), 3.28-3.46 (m, 2H), 5.19 (q, 1H), 5.31 (s, 2H), 6.91 (t, 1H), 7.01 (d, 1H), 7.08 (t, 1H), 7.20-7.28 (m, 3H), 7.38 (t, 2H), 7.40 (d, 2H), 7.59 (quint, 1H), 8.19 (d, 1H), 8.57 (d, 1H). |
| 81A | ent-tert-butyl {2-[({8-[(2,6-difluorobenzyl)oxy]-2-methylimidazo[1,2-a]pyridin-3-yl}carbonyl)-amino]-2-(2,4-difluorophenyl)ethyl}carbamate<br />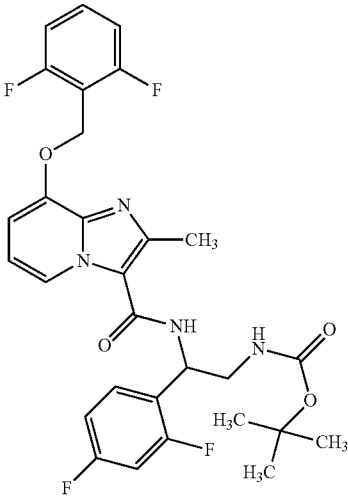<br />(64% of theory) | LC-MS (Method 2): $R_t$ = 1.07 min<br />MS (ESpos): m/z = 573 (M + H)$^+$ |

TABLE 8A-continued

| Example | IUPAC name/structure (yield) | Analytical data |
|---|---|---|
| 82A | rac-tert-butyl [2-({[8-(cyclohexylmethoxy)-2-methylimidazo[1,2-a]pyridin-3-yl]carbonyl}-amino)-2-phenylethyl]cabamate trifluoroacetate 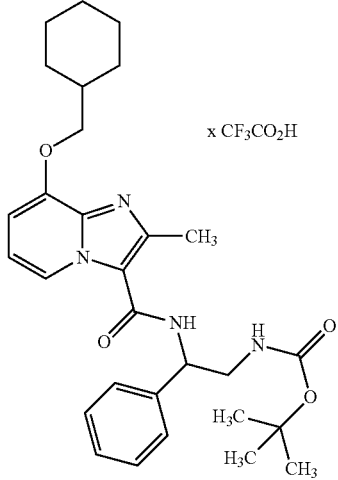 (41% of theory) | LC-MS (Method 2): $R_t$ = 1.09 min<br>MS (ESpos): m/z = 507 (M − TFA + H)$^+$ |
| 83A | rac-tert-butyl [2-(4-chlorophenyl)-2-({[8-(cyclo-hexylmethoxy)-2-methylimidazo[1,2-a]pyridin-3-yl]carbonyl}amino)ethyl]carbamate trifluoroacetate 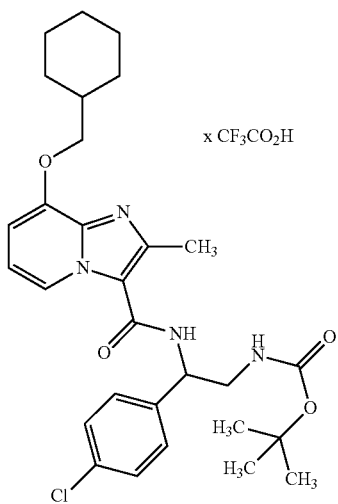 (67% of theory) | LC-MS (Method 2): $R_t$ = 1.17 min<br>MS (ESpos): m/z = 541 (M − TFA + H)$^+$ |

TABLE 8A-continued

| Example | IUPAC name/structure (yield) | Analytical data |
|---|---|---|
| 84A | rac-tert-butyl [2-({[8-(cyclohexylmethoxy)-2-methylimidazo[1,2-a]pyridin-3-yl]carbonyl}-amino)-2-(3,4-difluorophenyl)ethyl]carbamate trifluoroacetate 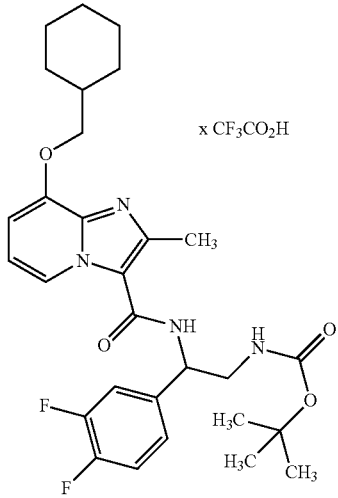 (58% of theory) | LC-MS (Method 2): $R_t$ = 1.17 min<br>MS (ESpos): m/z = 543 (M − TFA + H)$^+$ |
| 85A | ent-tert-butyl [2-({[8-(cyclohexylmethoxy)-2-methylimidazo[1,2-a]pyridin-3-yl]carbonyl}-amino)-2-(2,4-difluorophenyl)ethyl]carbamate trifluoroacetate 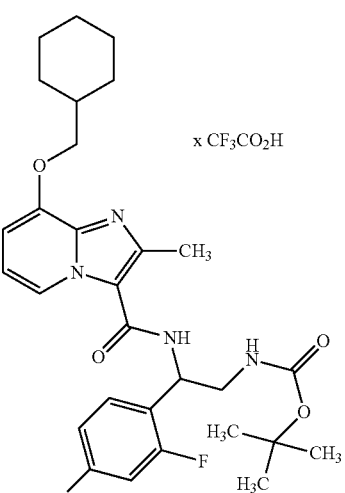 (42% of theory) | LC-MS (Method 2): $R_t$ = 1.17 min<br>MS (ESpos): m/z = 543 (M − TFA + H)$^+$ |

| Example | IUPAC name/structure (yield) | Analytical data |
|---|---|---|
| 86A | rac-tert-butyl {2-[({8-[(2,6-difluorobenzyl)oxy]-2-methylimidazo[1,2-a]pyridin-3-yl}carbonyl)-amino]propyl}carbamate<br>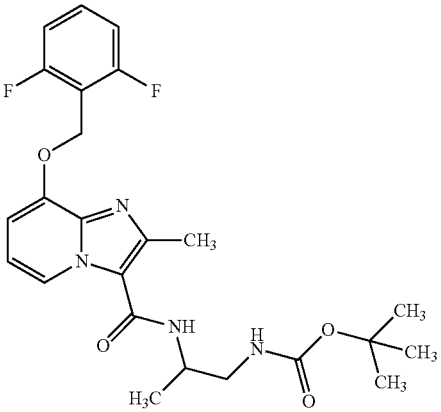<br>(57% of theory) | LC-MS (Method 1): $R_f$ = 1.04 min<br>MS (ESpos): m/z = 475 (M + H)$^+$<br>$^1$H NMR (400 MHz, DMSO-d$_6$):<br>δ = 1.14 (d, 3H), 1.36 (s, 9H), 2.50 (s, 3H), 3.04-3.20 (m, 2H), 4.06-4.16 (m, 1H), 5.30 (s, 2H), 6.89-7.03 (m, 3H), 7.22 (t, 2H), 7.56-7.64 (m, 2H), 8.61 (d, 1H). |
| 87A | rac-tert-butyl {2-[({6-chloro-8-[(2,6-difluoro-benzyl)oxy]-2-methylimidazo[1,2-a]-pyridin-3-yl}carbonyl)amino]propyl}carbamate trifluoroacetate<br>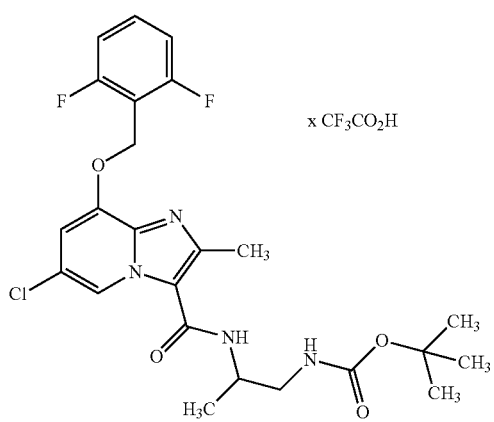<br>(74% of theory, purity about 80%) | LC-MS (Method 2): $R_f$ = 1.11 min<br>MS (ESpos): m/z = 509 (M − TFA + H)$^+$<br>$^1$H NMR (400 MHz, DMSO-d$_6$):<br>δ = 1.15 (d, 3H), 1.37 (s, 9H), 2.50 (s, 3H), 3.05-3.19 (m, 2H), 4.05-4.17 (m, 1H), 5.38 (s, 2H), 6.98 (t, 1H), 7.22 (t, 2H), 7.31 (s, 1H), 7.60 (quintet, 1H), 7.80 (d, 1H), 8.72 (s, 1H). |

TABLE 8A-continued

| Example | IUPAC name/structure (yield) | Analytical data |
|---|---|---|
| 88A | rac-tert-butyl {2-[({8-[(2,6-difluorobenzyl)oxy]-2,6-dimethylimidazo[1,2-a]pyridin-3-yl}carbonyl)amino]propyl}carbamate<br>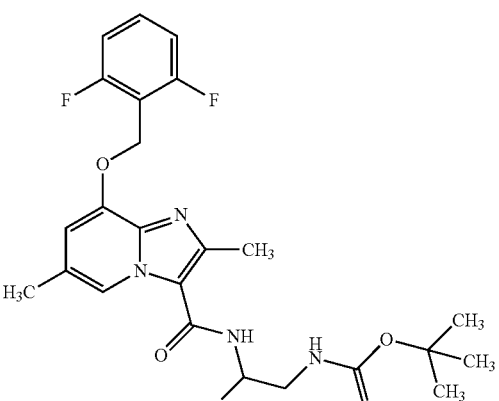<br>(78% of theory, purity about 93%) | LC-MS (Method 2): $R_t$ = 0.95 min<br>MS (ESpos): m/z = 489 (M + H)$^+$<br>$^1$H NMR (400 MHz, DMSO-d$_6$):<br>δ = 1.13 (d, 3H), 1.37 (s, 9H), 2.31 (s, 3H), 2.46 (s, 3H), 3.01-3.19 (m, 2H), 4.05-1.17 (m, 1H), 5.29 (s, 2H), 6.90 (s, 1H), 6.96 (t, 1H), 7.22 (t, 2H), 7.53-7.63 (m, 2H), 8.43 (s, 1H). |
| 89A | rac-tert-butyl {1-[({6-chloro-8-[(2,6-difluorobenzyl)oxy]-2-methylimidazo[1,2-a]pyridin-3-yl}carbonyl)amino]propan-2-yl}carbamate trifluoroacetate[1)]<br>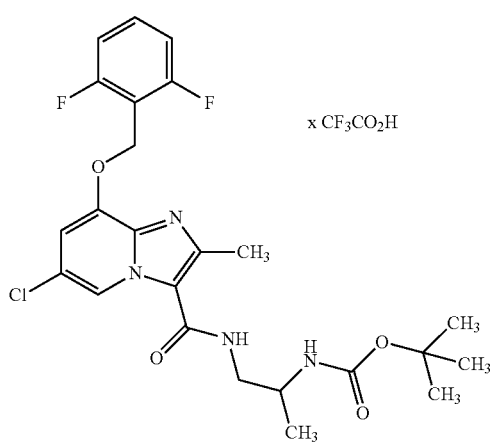<br>(74% of theory) | LC-MS (Method 2): $R_t$ = 1.15 min<br>MS (ESpos): m/z = 509 (M − TFA + H)$^+$<br>$^1$H NMR (400 MHz, DMSO-d$_6$):<br>δ = 1.07 (d, 3H), 1.36 (s, 9H), 2.50 (s, 3H), 3.20-3.37 (m, 2H), 3.69-3.82 (m, 1H), 5.37 (s, 2H), 6.69 (d, 1H), 7.24 (t, 2H), 7.33 (s, 1H), 7.61 (quintet, 1H), 8.02 (br s, 1H), 8.78 (s, 1H). |

TABLE 8A-continued

| Example | IUPAC name/structure (yield) | Analytical data |
|---|---|---|
| 90A | tert-butyl {2-[({6-chloro-8-[(2,6-difluorobenzyl)oxy]-2-methylimidazo[1,2-a]pyridin-3-yl}carbonyl)amino]-2-methylpropyl}carbamate trifluoroacetate[1]<br>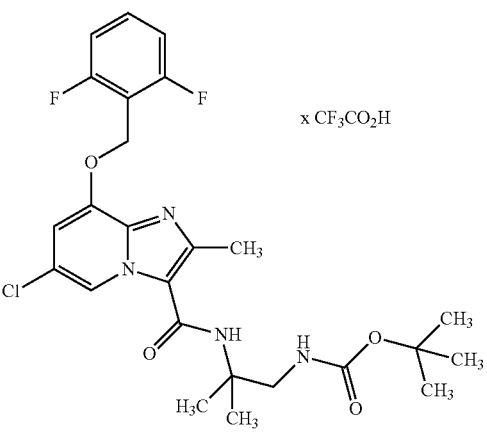<br>(72% of theory) | LC-MS (Method 2): $R_t$ = 1.23 min<br>MS (ESpos): m/z = 523 (M − TFA + H)$^+$<br>$^1$H NMR (400 MHz, DMSO-d$_6$):<br>δ = 1.31 (s, 6H), 1.34 (s, 9H), 2.48 (s, 3H), 3.31 (d, 2H), 5.38 (s, 2H), 7.08 (t, 1H), 7.24 (t, 2H), 7.33 (br s, 1H), 7.58-7.67 (m, 2H), 8.69 (s, 1H). |
| 91A | rac-tert-butyl {1-[({8-[(2,6-difluorobenzyl)oxy]-2,6-dimethylimidazo[1,2-a]pyridin-3-yl}-carbonyl)amino]propan-2-yl}carbamate trifluoracetate[1]<br>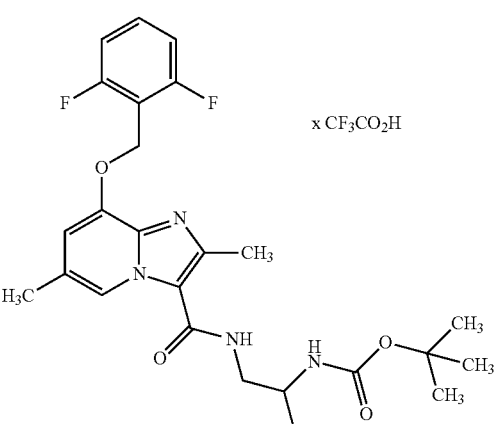<br>(70% of theory) | LC-MS (Method 2): $R_t$ = 0.95 min<br>MS (ESpos): m/z = 489 (M − TFA + H)$^+$<br>$^1$H NMR (400 MHz, DMSO-d$_6$):<br>δ = 1.08 (d, 3H), 1.36 (s, 9H), 2.39 (s, 3H), 2.50 (s, 3H), 3.20-3.38 (m, 2H), 3.69-3.82 (m, 1H), 5.39 (s, 2H), 6.70 (d, 1H), 7.24 (t, 2H), 7.41 (br s, 1H), 7.61 (quintet, 1H), 8.28 (br s, 1H), 8.53 (s, 1H). |

TABLE 8A-continued

| Example | IUPAC name/structure (yield) | Analytical data |
|---|---|---|
| 92A | tert-butyl {2-[({8-[(2,6-difluorobenzyl)oxy]-2,6-dimethylimidazo[1,2-a]pyridin-3-yl}-carbonyl)amino]-2-methylpropyl}carbamate trifluoroacetate[1)] 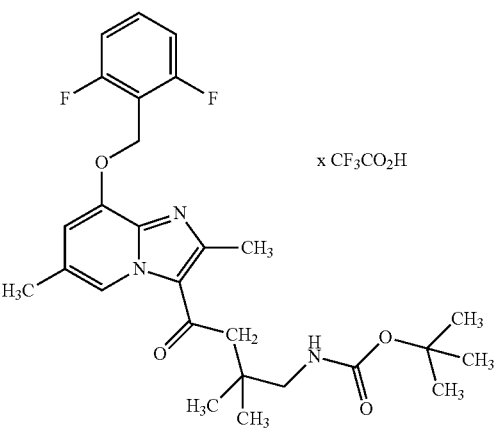 (66% of theory) | LC-MS (Method 2): $R_t$ = 1.00 min<br>MS (ESpos): m/z = 503 (M − TFA + H)$^+$<br>$^1$H NMR (400 MHz, DMSO-d$_6$):<br>δ = 1.32 (s, 6H), 1.34 (s, 9H), 2.42 (s, 3H), 2.50 (s, 3H), 3.32 (d, 2H), 5.41 (s, 2H), 7.09 (t, 1H), 7.24 (t, 2H), 7.50 (br s, 1H), 7.61 (quintet, 1H), 7.88 (br s, 1H), 8.49 (s, 1H). |
| 93A | tert-butyl (1-{2-[({6-chloro-8-[(2,6-difluorobenzyl)oxy]-2-methylimidazo[1,2-a]-pyridin-3-yl}carbonyl)amino]ethyl}cyclo-hexyl)carbamate trifluoroacetate 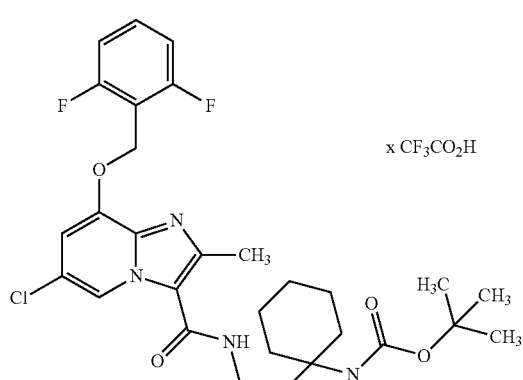 (91% of theory) | LC-MS (Method 2): $R_t$ = 1.36 min<br>MS (ESpos): m/z = 577 (M − TFA + H)$^+$ |

TABLE 8A-continued

| Example | IUPAC name/structure (yield) | Analytical data |
|---|---|---|
| 94A | rac-tert-butyl {1-[({8-[(2,6-difluorobenzyl)oxy]-2-methylimidazo[1,2-a]pyridin-3-yl}-carbonyl)amino]propan-2-yl}carbamate trifluoroacetate<br />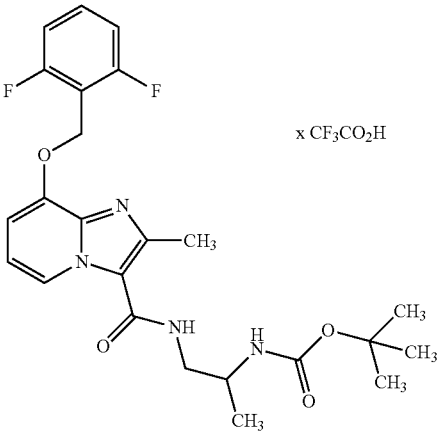<br />(71% of theory) | LC-MS (Method 7): $R_f$ = 0.88 min<br />MS (ESpos): m/z = 475 (M − TFA + H)$^+$ |
| 95A | ent-tert-butyl {(2R)-1-[({6-chloro-8-[(2,6-difluorobenzyl)oxy]-2-methylimidazo[1,2-a]-pyridin-3-yl}carbonyl)amino]butan-2-yl}-carbamate trifluoroacetate<br />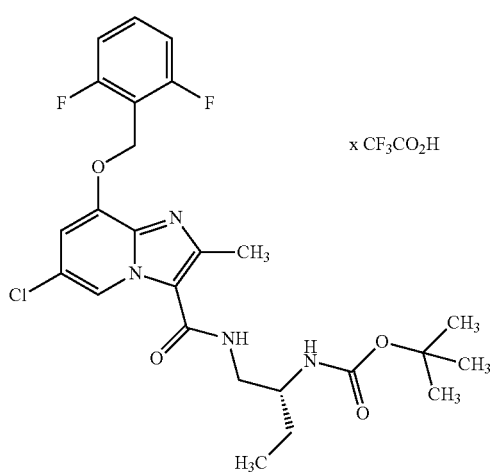<br />(81% of theory) | LC-MS (Method 2): $R_f$ = 1.17 min<br />MS (ESpos): m/z = 523 (M − TFA + H)$^+$ |

TABLE 8A-continued

| Example | IUPAC name/structure (yield) | Analytical data |
|---|---|---|
| 96A | tert-butyl {3-[({6-chloro-8-[(2,6-difluorobenzyl)oxy]-2-methylimidazo[1,2-a]pyridin-3-yl}carbonyl)amino]propyl}carbamate trifluoroacetate<br>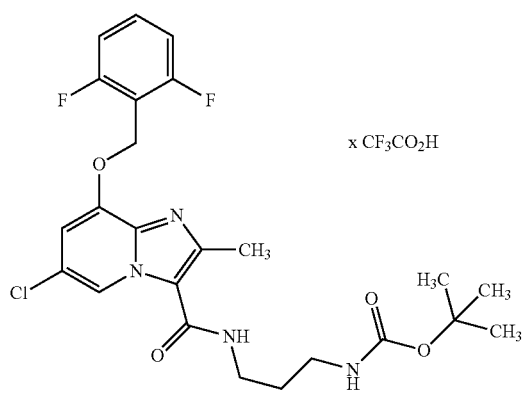<br>(80% of theory) | LC-MS (Method 2): $R_t$ = 1.10 min<br>MS (ESpos): m/z = 509 (M − TFA + H)$^+$ |
| 97A | tert-butyl {2-[({6-chloro-8-[(2,6-difluorobenzyl)oxy]-2-methylimidazo[1,2-a]pyridin-3-yl}carbonyl)amino]ethyl}carbamate trifluoroacetate<br>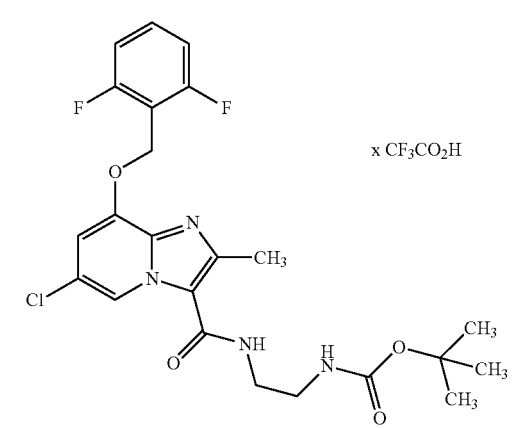<br>(76% of theory) | LC-MS (Method 7): $R_t$ = 1.11 min<br>MS (ESpos): m/z = 495 (M − TFA + H)$^+$ |

TABLE 8A-continued

| Example | IUPAC name/structure (yield) | Analytical data |
|---|---|---|
| 98A | tert-butyl (1-{[({8-[(2,6-difluorobenzyl)oxy]-2-methylimidazo[1,2-a]pyridin-3-yl}carbonyl)-amino]methyl}cyclopropyl)carbamate trifluoroacetate<br />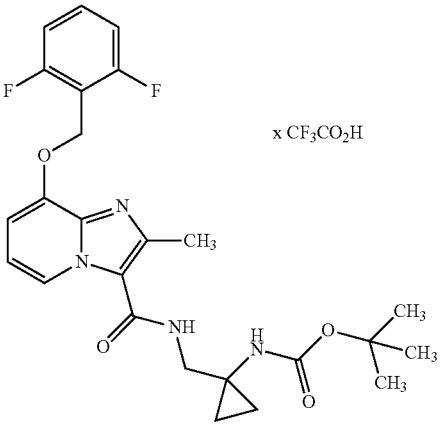<br />(80% of theory) | LC-MS (Method 7): $R_t$ = 0.90 min<br />MS (ESpos): m/z = 487 (M − TFA + H)$^+$ |
| 99A | tert-butyl (1-{[({6-chloro-8-[(2,6-difluorobenzyl)oxy]-2-methylimidazo[1,2-a]-pridin-3-yl}carbonyl)amino]methyl}cyclopropyl)-carbamate trifluoroacetate<br />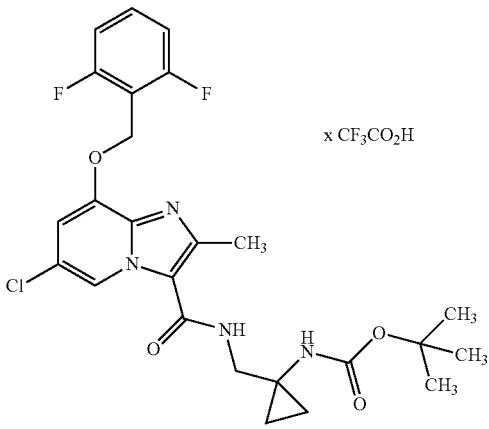<br />(66% of theory) | LC-MS (Method 7): $R_t$ = 1.20 min<br />MS (ESpos): m/z = 521 (M − TFA + H)$^+$ |

TABLE 8A-continued

| Example | IUPAC name/structure (yield) | Analytical data |
|---|---|---|
| 100A | tert-butyl (1-{[({8-[(2,6-difluorobenzyl)oxy]-2,6-dimethylimidazo[1,2-a]pyridin-3-yl}carbonyl)-amino]methyl}cyclopropyl)carbamate trifluoroacetate 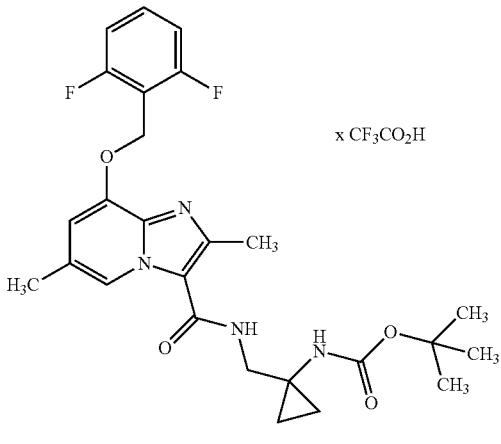 (86% of theory) | LC-MS (Method 7): $R_f$ = 0.93 min<br>MS (ESpos): m/z = 501 (M − TFA + H)$^+$ |
| 101A | tert-butyl (1-{[({8-[(2,6-difluorobenzyl)oxy]-2-methylimidazo[1,2-a]pyridin-3-yl}carbonyl)-amino]methyl}cyclopropyl)carbamate trifluoroacetate 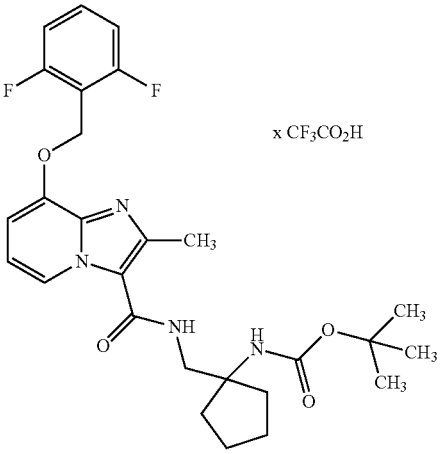 (73% of theory) | LC-MS (Method 7): $R_f$ = 1.04 min<br>MS (ESpos): m/z = 515 (M − TFA + H)$^+$ |

TABLE 8A-continued

| Example | IUPAC name/structure (yield) | Analytical data |
|---|---|---|
| 102A | tert-butyl (1-{[({6-chloro-8-[(2,6-difluorobenzyl)oxy]-2-methylimidazo[1,2-a]-pyridin-3-yl}carbonyl)amino]methyl}cyclopentyl)-cabamate trifluoroacetate<br>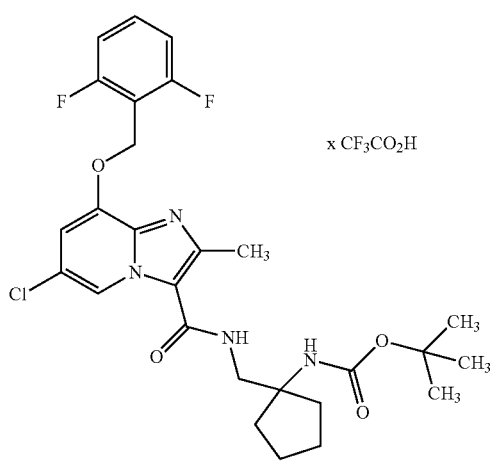<br>(85% of theory) | LC-MS (Method 7): $R_f$ = 1.36 min<br>MS (ESpos): m/z = 549 (M − TFA + H)$^+$ |
| 103A | rac-tert-butyl 3-[({8-[(2,6-difluorobenzyl)oxy]-2-methylimidazo[1,2-a]pyridin-3-yl}carbonyl)-amino]indolin-1-carboxylate<br>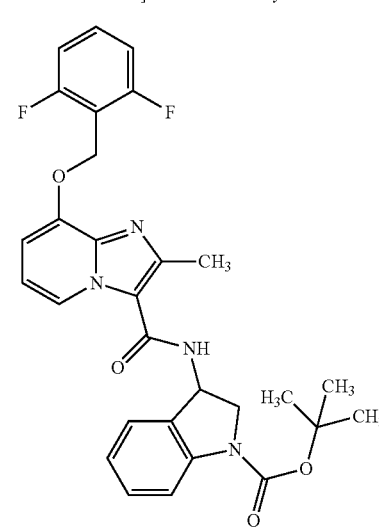<br>(83% of theory) | LC-MS (Method 2): $R_f$ = 1.16 min<br>MS (ESpos): m/z = 535 (M + H)$^+$<br>$^1$H NMR (400 MHz, DMSO-d$_6$):<br>δ = 1.52 (s, 9H), 2.49 (s, 3H), 3.69 (dd, 1H), 4.29 (t, 1H), 5.30 (s, 2H), 5.64-5.73 (m, 1H), 6.94-7.06 (m, 3H), 7.19-7.30 (m, 3H), 7.40 (d, 1H), 7.60 (quintet, 1H), 7.79 (br s, 1H), 8.51 (d, 1H), 8.67 (d, 1H). |

TABLE 8A-continued

| Example | IUPAC name/structure (yield) | Analytical data |
|---|---|---|
| 104A | rac-tert-butyl 3-[({6-chloro-8-[(2,6-difluorobenzyl)oxy]-2-methylimidazo[1,2-a]pyridin-3-yl}carbonyl)amino]indolin-1-carboxylate[2)] 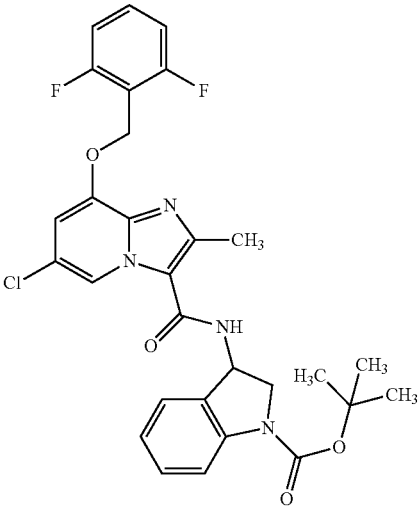 (87% of theory) | LC-MS (Method 2): $R_t$ = 1.39 min<br>MS (ESpos): m/z = 569 (M + H)$^+$ |
| 105A | rac-tert-butyl 4-[({8-[(2,6-difluorobenzyl)oxy]-2-methylimidazo[1,2-a]pyridin-3-yl}carbonyl)amino]-3,4-dihydroquinoline-1(2H)carboxylate[3)] 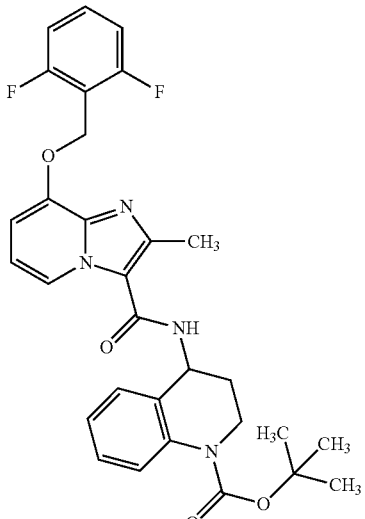 (75% of theory) | LC-MS (Method 2): $R_t$ = 1.14 min<br>MS (ESpos): m/z = 549 (M + H)$^+$<br>$^1$H NMR (400 MHz, DMSO-d$_6$):<br>δ = 1.49 (s, 9H), 1.97-2.08 (m, 1H), 2.12-2.21 (m, 1H), 2.50 (s, 3H), 3.72-3.79 (m, 1H), 3.82-3.90 (m, 1H), 5.27 (q, 1H), 5.31 (s, 2H), 6.94-7.11 (m, 3H), 7.18-7.28 (m, 3H), 7.36 (d, 1H), 7.59 (quintet, 1H), 7.62 (d, 1H), 8.42 (d, 1H), 8.60 (d, 1H). |

[1)]Work-up: The crude reaction mixture was concentrated and purified by preparative HPLC (RP18 column, mobile phase: acetonitrile/water gradient with addition of 0.1% TFA).
[2)]Work-up: The precipitate was purified by silica gel chromatography (mobile phase: dichloromethane:methanol 200:1).
[3)]Work-up: The precipitate was purified by silica gel chromatography (mobile phase: cyclohexane: ethyl acetate 2:1).

Example 106A ent-tert-Butyl {2-[({8-[(2,6-difluorobenzyl)oxy]-6-fluoro-2-methylimidazo[1,2-a]pyridin-3-yl}carbonyl)amino]-2-(3,4-difluorophenyl)ethyl}carbamate

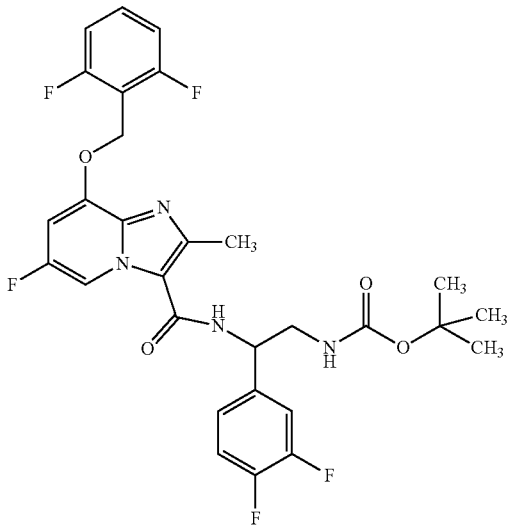 [SMILES: Cc1nc2c(OCc3c(F)cccc3F)cc(F)cn2c1C(=O)NC(CNC(=O)OC(C)(C)C)c1ccc(F)c(F)c1]

90 mg of 8-[(2,6-difluorobenzyl)oxy]-6-fluoro-2-methylimidazo[1,2-a]pyridine-3-carboxylic acid (Example 11A; 0.268 mmol, 1 equivalent), 132 mg of O-(7-azabenzotriazol-1-yl)-N,N,N'N'-tetramethyluronium hexafluorophosphate (0.348 mmol, 1.4 equivalents) and 0.132 ml of N,N-diisopropylethylamine (0.803 mmol, 3 equivalents) were initially charged in 0.85 ml of DMF, 102 mg of ent-tert-butyl [2-amino-2-(3,4-difluorophenyl)ethyl]carbamate (Example 60A) were added at RT and the mixture was stirred at RT overnight. Water was added to the reaction solution, the mixture was stirred for another 30 min and the precipitate formed was filtered off and washed with water, a little acetonitrile and methanol. This gave 148 mg (85% of theory) of the title compound.

LC-MS (Method 2): $R_t$=1.24 min

MS (ESpos): m/z=591.4 (M+H)$^+$ $^1$H NMR (400 MHz, DMSO-d$_6$): δ=1.34 (s, 9H), 2.58 (s, 3H; partially obscured by DMSO signal), 3.35-3.45 (m, 2H; partially superimposed by H$_2$O signal), 5.15 (q, 1H), 5.31 (s, 2H), 7.10 (t, 1H), 7.19-7.27 (m, 4H), 7.36-7.50 (m, 2H), 7.59 (quint, 1H), 8.21 (d, 1H), 8.62 (d, 1H).

The examples shown in Table 9A were prepared by reacting the Examples 3A, 16A, 21A, 25A and 28A, respectively, with the appropriate amines, commercially available or prepared according to the methods described, and N,N-diisopropylethylamine under the reaction conditions described in the representative Working Procedure 3.

TABLE 9A

| Example | IUPAC name/structure (yield) | Analytical data |
|---|---|---|
| 107A | ent-tert-butyl {2-[({8-[(2,6-difluorobenzyl)oxy]-2,6-dimethylimidazo[1,2-a]pyridin-3-yl}carbonyl)amino]-2-(3,4-difluorophenyl)ethyl}carbamate<br><br>(94% of theory) | LC-MS (Method 2): $R_t$ = 1.13 min<br>MS (ESpos): m/z = 587 (M + H)$^+$<br>$^1$H NMR (400 MHz, DMSO-d$_6$):<br>δ = 1.32 (s, 9H), 2.28 (s, 3H); 2.52 (s, 3H), 3.33-3.46 (m, 2H; superimposed by H$_2$O signal), 5.13 (q, 1H), 5.28 (s, 2H), 6.92 (s, 1H), 7.08 (t, 1H), 7.20-7.26 (m, 3H), 7.36-7.51 (m, 2H); 7.60 (quint, 1H), 8.19 (d, 1 H); 8.38 (s, 1H). |

TABLE 9A-continued

| Example | IUPAC name/structure (yield) | Analytical data |
|---|---|---|
| 108A | ent-tert-butyl {2-[({2-cyclopropyl-8-[(2,6-difluorobenzyl) oxy]imidazo[1,2-a]pyridin-3-yl}-carbonyl)amino]-2-(3,4-difluorophenyl)-ethyl}carbamate 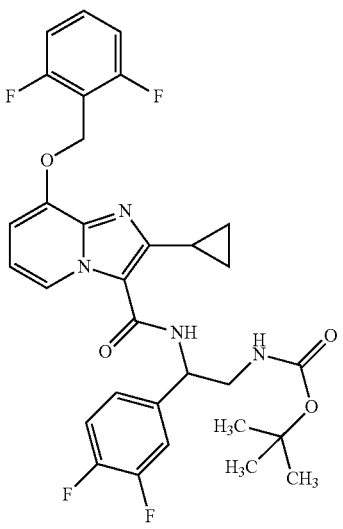 (79% of theory) | LC-MS (Method 2): $R_t$ = 1.23 min<br>MS (ESpos): m/z = 599.4 (M + H)$^+$<br>$^1$H NMR (400 MHz, DMSO-d$_6$):<br>δ = 0.9-1.05 (m, 4 H); 1.35 (s, 9H), 2.40-2.48 (m, 1 H); 3.31-3.48 (m, 2H; superimposed by H$_2$O signal), 5.13 (q, 1H), 5.30 (s, 2H), 6.89 (t, 1H), 7.01 (d, 1H), 7.10 (t, 1H), 7.21 (t, 2H), 7.22 (m, 1 H); 7.35-7.48 (m, 2H), 7.59 (quint, 1H), 8.41 (d, 1 H); 8.51 (d, 1H). |
| 109A | ent-tert-butyl {2-[({8-[(2,6-difluorobenzyl) oxy]imidazo[1,2-a]pyridin-3-yl}carbonyl)amino]-2-(3,4-difluorophenyl)ethyl}carbamate 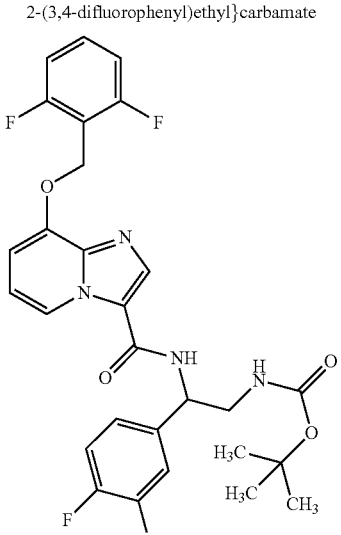 (64% of theory) | LC-MS (Method 2): $R_t$ = 1.13 min<br>MS (ESpos): m/z = 559.4 (M + H)$^+$<br>$^1$H NMR (400 MHz, DMSO-d$_6$):<br>δ = 1.30 (s, 9H), 3.29-3.35 (m, 2H, superimposed by H$_2$O signal), 5.13 (q, 1H), 5.31 (s, 2H), 7.00-7.12 (m, 3 H); 7.21 (m, 1 H); 7.23 (t, 2H), 7.35-7.48 (m, 2H), 7.59 (quint, 1H), 8.30 (s, 1 H); 8.71 (d, 1H), 8.99 (d, 1H). |
| 110A | rac-tert-butyl {2-[({8-[(2,6-difluorobenzyl)oxy]-2-methylimidazo[1,2-a]pyridin-3-yl}carbonyl)amino]-3-ethoxypropyl}carbamate | LC-MS (Method 2): $R_t$ = 0.93 min<br>MS (ESpos): m/z = 519.4 (M + H)$^+$<br>$^1$H NMR (400 MHz, DMSO-d$_6$): |

TABLE 9A-continued

| Example | IUPAC name/structure (yield) | Analytical data |
|---|---|---|
| | 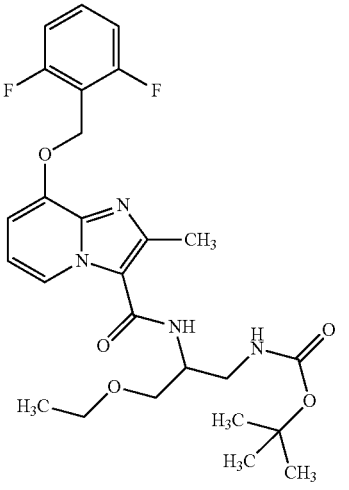<br>(65% of theory) | δ =1.10 (t, 3H); 1.35 (s, 9H), 2.55 (s, 3H; obscured by DMSO signal), 3.23 (t, 2H), 3.45-3.52 (m, 4H); 4.20 (m, 1H); 5.31 (s, 2H), 6.90-7.08 (m, 3 H); 7.20 (t, 2H); 7.52-7.61 (m, 2H); 8.62 (d, 1H). |
| 111A | rac-tert-butyl {2-[({6-chloro-8-[(2,6-difluorobenzyl) oxy]-2-methylimidazo[1,2-a]pyridin-3-yl} carbonyl)amino]-3-ethoxypropyl}carbamate<br>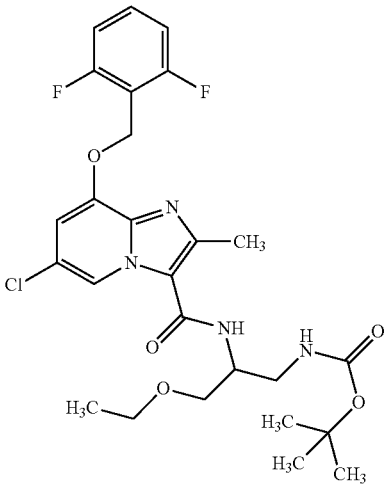<br>(86% of theory) | LC-MS (Method 2): $R_t$ = 1.18 min<br>MS (ESpos): m/z = 553.4 (M + H)$^+$<br>$^1$H NMR (400 MHz, DMSO-$d_6$):<br>δ = 1.10 (t, 3H); 1.37 (s, 9H), 2.55 (s, 3H; superimposed by DMSO signal), 3.18-3.26 (m, 2H), 3.47-3.51 (m, 4H); 4.21 (q, 1H), 5.32 (s, 2H), 6.92 (t, 1H), 7.20 (s, 1H); 7.23 (t, 2H), 7.59 (quint, 1H), 7.61 (d, 1H); 8.70 (s, 1 H). |
| 112A | rac-tert-butyl {2-[({8-[(2,6-difluorobenzyl)oxy]-2-methylimidazo[1,2-a]pyridin-3-yl}carbonyl)amino]-3-(4-fluorophenoxy)propyl}carbamate | LC-MS (Method 2): $R_t$ = 1.09 min<br>MS (ESpos): m/z = 585.2 (M + H)$^+$<br>$^1$H NMR (400 MHz, DMSO-$d_6$): |

TABLE 9A-continued

| Example | IUPAC name/structure (yield) | Analytical data |
|---|---|---|
| | 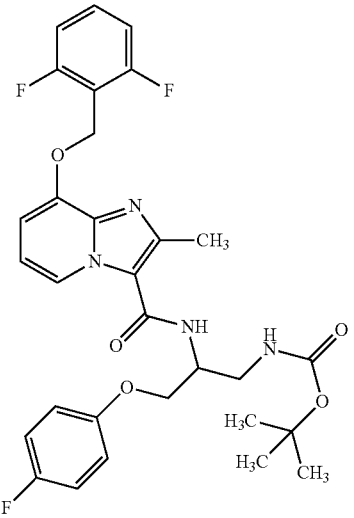<br>(14% of theory) | δ = 1.32 (s, 9H), 2.55 (s, 3H; obscured by DMSO signal), 3.30 (superimposed by water signal; 2H), 4.04 (q, 2H), 4.40 (m, 1H), 5.30 (s, 2H), 6.90-7.05 (m, 4H), 7.09 (t, 1H); 7.11 (t, 2H), 7.21 (t, 2H), 7.60 (q, 1H), 7.75 (d, 1H), 8.60 (d, 1H). |
| 113A | rac-tert-butyl {2-[({8-[(2,6-difluorobenzyl)oxy]-2-methylimidazo[1,2-a]pyridin-3-yl}carbonyl)amino]-3-phenoxy)propyl}carbamate<br>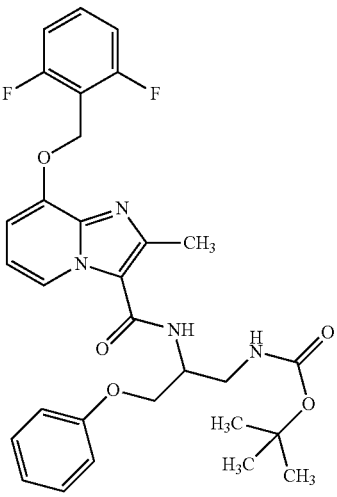<br>(41% of theory) | LC-MS (Method 2): R$_t$ = 1.09 min<br>MS (ESpos): m/z = 557.2 (M + H)$^+$<br>$^1$H NMR (400 MHz, DMSO-d$_6$):<br>δ = 1.34 (s, 9H), 2.55 (s, 3H; obscured by DMSO signal), 3.30 (superimposed by water signal; 2H), 4.08 (m, 2H), 4.42 (m, 1H), 5.30 (s, 2H), 6.90-7.05 (m, 5H), 7.09 (t, 1H); 7.21 (t, 2 H), 7.27 (t, 2H), 7.58 (q, 1H), 7.72 (d, 1H), 8.60 (d, 1H). |
| 114A | ent-tert-butyl (3S)-3-[({8-[(2,6-difluorobenzyl)oxy]-2-methylimidazo[1,2-a]pyridin-3-yl}carbonyl)amino]piperidin-1-carboxylate | LC-MS (Method 2): R$_t$ = 0.95 min<br>MS (ESpos): m/z = 501.4 (M + H)$^+$<br>$^1$H NMR (400 MHz, DMSO-d$_6$): |

TABLE 9A-continued

| Example | IUPAC name/structure (yield) | Analytical data |
|---|---|---|
| | 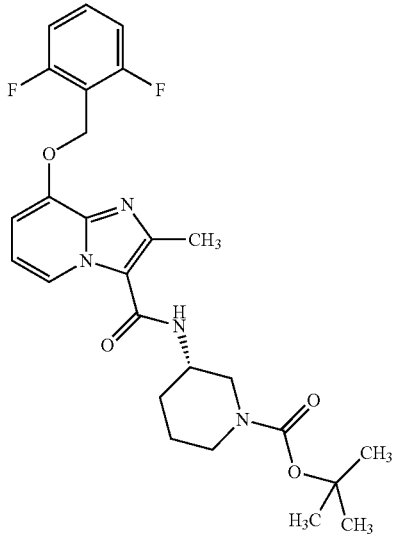(68% of theory) | δ = 1.37 (s, 9H), 1.40-1.48 (m, 1H); 1.60-1.70 (m, 2H); 1.86-1.93 (m, 1 H); 2.55 (s, 3H; superimposed by DMSO signal); 2.85-3.10 (m, 2H); 3.51-3.91 (m, 3H); 5.30 (s, 2H); 6.92 (t, 1H); 7.05 (d, 1H); 7.23 (t, 2H); 7.59 (quint, 1H), 7.71 (br. s, 1H); 8.60 (d, 1H). |
| 115A | ent-benzyl (3S)-3-[({8-[(2,6-difluorobenzyl)oxy]-2-methylimidazo[1,2-a]pyridin-3-yl}-carbonyl)amino]pyrrolidin-1-carboxylate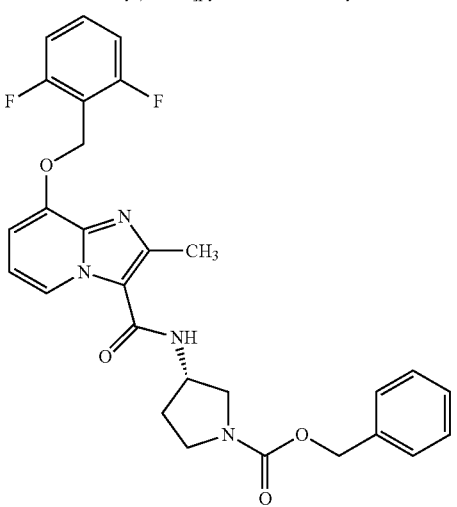(66% of theory) | LC-MS (Method 2): Rt = 0.97 min<br>MS (ESpos): m/z = 521.3 (M + H)+<br>1H NMR (400 MHz, DMSO-$d_6$):<br>δ = 1.90-2.02 (m, 1H); 2.11-2.21 (m, 1H); 2.49 (s, 3H); 3.31-3.69 (m, 4 H); 4.50 (m, 1H); 5.08 (s, 2H); 5.30 (s, 2 H); 6.91 (t, 1H); 7.02 (d, 1 H); 7.23 (t, 2H); 7.25-7.37 (m, 5H); 7.59 (quint, 1H), 8.11 (d, 1H); 8.51 (d, 1H). |
| 116A | rac-benzyl {2-[({8-[(2,6-difluorobenzyl)oxy]-2-methylimidazo[1,2-a]pyridin-3-yl}carbonyl)amino]-3-isopropoxypropyl}carbamate | LC-MS (Method 1): R$_t$ = 1.21 min<br>MS (ESpos): m/z = 567.1 (M + H)+<br>1H NMR (400 MHz, DMSO-$d_6$): |

TABLE 9A-continued

| Example | IUPAC name/structure (yield) | Analytical data |
|---|---|---|
| | 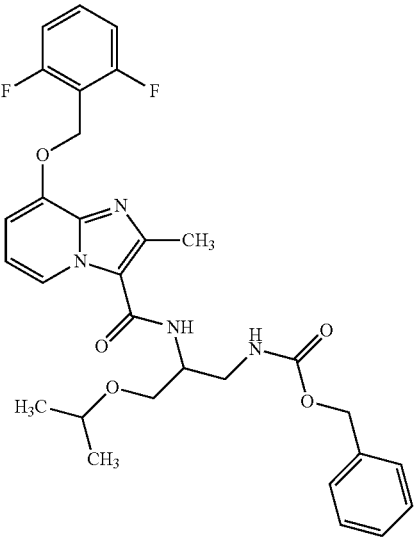<br>(42% of theory) | δ = 1.08 (d, 6H), 2.55 (s, 3H; obscured by DMSO signal), 3.20-3.35 (m, 2H), 3.45 (q, 2H), 3.55 (q, 1 H), 4.20 (m, 1H), 5.00 (s, 2 H), 5.31 (s, 2H), 6.90 (t, 1H), 7.00 (d, 1 H), 7.20-7.30 (m, 7H), 7.38 (t, 1H), 7.50 (d, 1H), 7.60 (q, 1H), 8.60 (d, 1H). |
| 117A | ent-benzyl {2-[({8-[(2,6-difluorobenzyl)oxy]-2-methylimidazo[1,2-a]pyridin-3-yl}carbonyl)amino]-1-(3,4-difluorophenyl)ethyl}carbamate<br>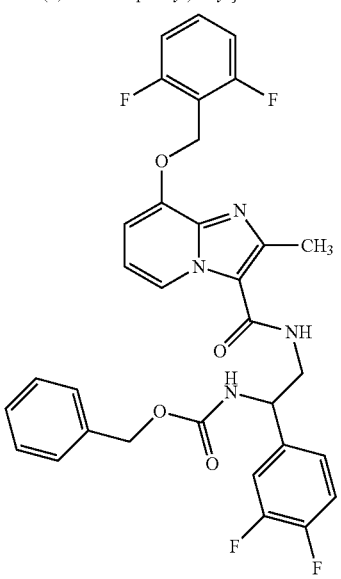<br>(55% of theory)<br>starting with Example 64A | LC-MS (Method 2): Rt = 1.08 min<br>MS (ESpos): m/z = 607.3 (M + H)+<br>1H NMR (400 MHz, DMSO-d$_6$):<br>δ = 2.30 (s, 3H); 3.46-3.63 (m, 2H); 4.88-5.05 (m, 3H); 5.30 (s, 2H); 6.90 (t, 1H); 7.00 (d, 1H); 7.15-7.48 (m, 10H); 7.58 (q, 1H); 7.88 (t, 1H); 7.96 (d, 1H); 8.51 (d, 1H). |

Example 118A ent-tert-Butyl {2-[({8-[(2,6-difluorobenzyl)oxy]-2-methylimidazo[1,2-a]pyridin-3-yl}carbonyl)-amino]-2-(3,4-difluorophenyl)ethyl}carbamate

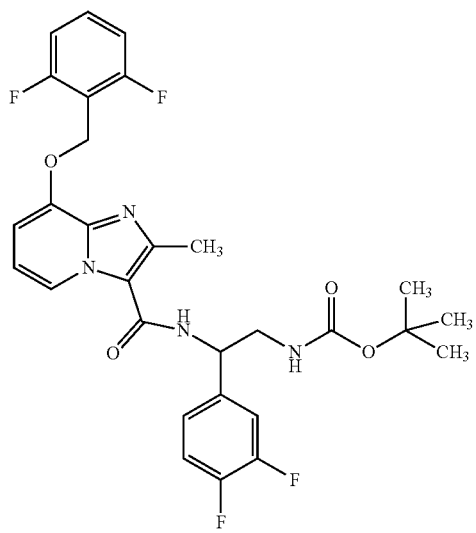 [SMILES: Cc1nc2c(OCc3c(F)cccc3F)cccn2c1C(=O)NC(CNC(=O)OC(C)(C)C)c1ccc(F)c(F)c1]

1.50 g of 8-[(2,6-difluorobenzyl)oxy]-2-methylimidazo[1,2-a]pyridine-3-carboxylic acid (4.71 mmol), 1.67 g of (benzotriazol-1-yloxy)bisdimethylaminomethylium fluoroborate (TBTU, 5.18 mmol) and 2.38 g of 4-methylmorpholine (23.5 mmol) were initially charged in 30 ml of DMF. At RT, 1.48 g of ent-tert-butyl [2-amino-2-(3,4-difluorophenyl)ethyl]carbamate (Example 60A, 5.42 mmol) were added, and the mixture was stirred at RT for 2 h. The reaction mixture was poured into about 250 ml of water and the precipitated solid was stirred at RT for about 30 min. The solid was then filtered off, washed with water and subsequently dried under high vacuum. The crude product was purified by silica gel chromatography (mobile phase: dichloromethane/methanol=100/1). This gave 2.18 g of the title compound (81% of theory).

LC-MS (Method 2): $R_t$=1.12 min
MS (ESpos): m/z=573 (M+H)$^+$
$^1$H NMR (400 MHz, DMSO-d$_6$): δ=1.32 (s, 9H), 2.59 (s, 3H), 3.29-3.46 (m, 2H), 5.15 (q, 1H), 5.31 (s, 2H), 6.91 (t, 1H), 7.01 (d, 1H), 7.08 (t, 1H), 7.19-7.27 (m, 3H), 7.36-7.51 (m, 2H), 7.59 (quint, 1H), 8.21 (d, 1H), 8.56 (d, 1H).

Example 119A ent-tert-Butyl {2-[({6-chloro-8-[(2,6-difluorobenzyl)oxy]-2-methylimidazo[1,2-a]pyridin-3-yl}-carbonyl)amino]propyl}carbamate (Enantiomer A)

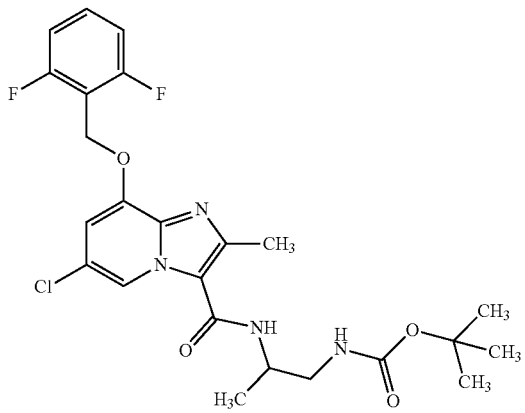 [SMILES: Cc1nc2c(OCc3c(F)cccc3F)cc(Cl)cn2c1C(=O)NC(C)CNC(=O)OC(C)(C)C]

227 mg of Example 87A were separated into the enantiomers on a chiral phase [column: Daicel Chiralpak AD-H, 5 μm, 250×20 mm, mobile phase: 70% isohexane, 30% ethanol, flow rate 20 ml/min; 25° C., detection: 230 nm].

Yield enantiomer A: 74 mg (>99% ee)

Enantiomer A: $R_t$=4.66 min [Daicel Chiralpak AD-H, 5 μm, 250×4.6 mm; mobile phase: 50% isohexane, 50% ethanol; flow rate: 1.0 ml/min; 25° C.; detection: 230 nm].

Example 120A ent-tert-Butyl {2-[({6-chloro-8-[(2,6-difluorobenzyl)oxy]-2-methylimidazo[1,2-a]pyridin-3-yl}-carbonyl)amino]propyl}carbamate (Enantiomer B)

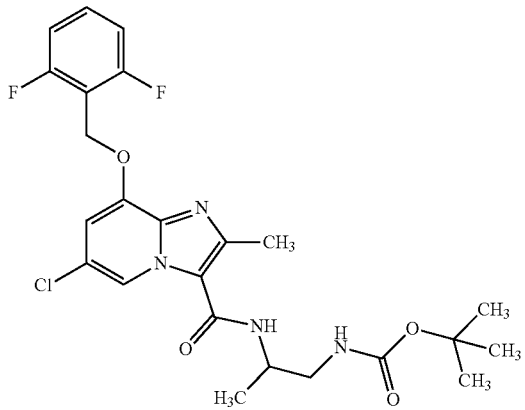

227 mg of Example 87A were separated into the enantiomers on a chiral phase [column: Daicel Chiralpak AD-H, 5 μm, 250×20 mm, mobile phase: 70% isohexane, 30% ethanol, flow rate 20 ml/min; 25° C., detection: 230 nm].

Yield enantiomer B: 58 mg (>99% ee)

Enantiomer B: $R_t$=5.90 min [Daicel Chiralpak AD-H, 5 µm, 250×4.6 mm; mobile phase: 50% isohexane, 50% ethanol; flow rate 1.0 ml/min; 25° C.; detection: 230 nm].

$^1$H NMR (400 MHz, DMSO-$d_6$): δ=1.13 (d, 3H), 1.37 (s, 9H), 2.50 (s, 3H), 3.05-3.19 (m, 2H), 4.05-4.17 (m, 1H), 5.33 (s, 2H), 6.95 (t, 1H), 7.19 (s, 1H), 7.22 (t, 2H), 7.60 (quintet, 1H), 7.68 (d, 1H), 8.71 (s, 1H).

Example 121A ent-tert-Butyl {2-[({8-[(2,6-difluorobenzyl)oxy]-2,6-dimethylimidazo[1,2-a]pyridin-3-yl}-carbonyl)amino]propyl}carbamate (Enantiomer A)

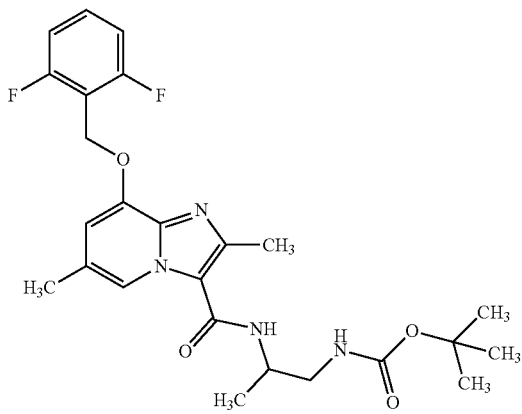 [SMILES: Cc1cc(OCc2c(F)cccc2F)c2nc(C)c(C(=O)NC(C)CNC(=O)OC(C)(C)C)n2c1]

215 mg of Example 88A were separated into the enantiomers on a chiral phase [column: Daicel Chiralpak AD-H, 5 µm, 250×20 mm, mobile phase: 70% isohexane, 30% ethanol+0.2% diethylamine, flow rate: 15 ml/min; 30° C., detection: 220 nm].

Enantiomer A (still contaminated) was dissolved in 0.5 ml of methanol and 2.5 ml of tert-butyl methyl ether and re-purified [column: Daicel Chiralpak IA, 5 µm, 250×20 mm, mobile phase: 70% isohexane, 30% ethanol+0.2% diethylamine, flow rate 25 ml/min; 25° C., detection: 220 nm]

Yield enantiomer A: 48 mg (>99% ee)

Enantiomer A: $R_t$=7.48 min [Daicel Chiralpak AD-H, 5 am, 250×4.6 mm; mobile phase: 70% isohexane, 30% ethanol+0.2% diethylamine; flow rate 1.0 ml/min; 30° C.; detection: 220 nm].

Example 122A ent-tert-Butyl {2-[({8-[(2,6-difluorobenzyl)oxy]-2,6-dimethylimidazo[1,2-a]pyridin-3-yl}-carbonyl)amino]propyl}carbamate (Enantiomer B)

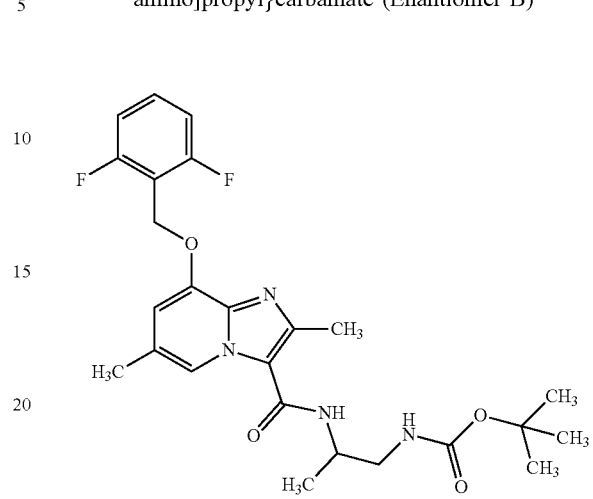

215 mg of Example 88A were separated into the enantiomers on a chiral phase [column: Daicel Chiralpak AD-H, 5 µm, 250×20 mm, mobile phase: 70% isohexane, 30% ethanol+0.2% diethylamine, flow rate: 15 ml/min; 30° C., detection: 220 nm].

Yield enantiomer B: 67 mg (>99% ee)

Enantiomer B: 11.28 min [Daicel Chiralpak AD-H, 5 am, 250×4.6 mm; mobile phase: 70% isohexane, 30% ethanol+0.2% diethylamine; flow rate 1.0 ml/min; 30° C.; detection: 220 nm].

Example 123A ent-tert-Butyl {2-[({8-[(2,6-difluorobenzyl)oxy]-2-methylimidazo[1,2-a]pyridin-3-yl}carbonyl)-amino]-3-ethoxypropyl}carbamate (Enantiomer A)

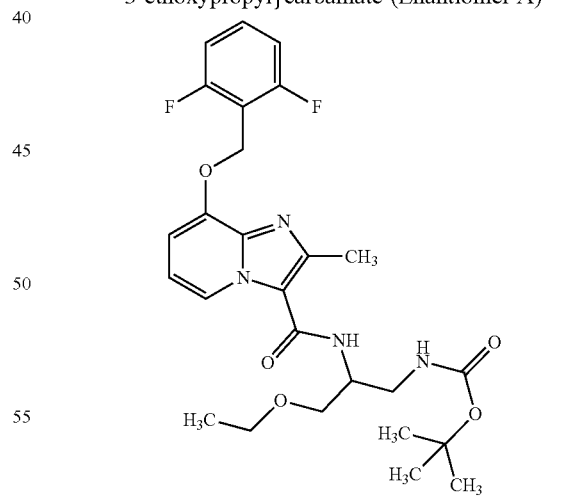

211 mg of Example 110A were separated into the enantiomers on a chiral phase [column: Daicel Chiralpak AD-H, 5 µm, 250×20 mm, mobile phase: 50% isohexane, 50% ethanol, flow rate: 15 ml/min; 30° C., detection: 220 nm].

Yield enantiomer A: 84 mg (99% ee)

Enantiomer A: $R_t$=7.56 min [Daicel Chiralpak AD-H, 5 m, 250×4.6 mm; mobile phase: 50% isohexane, 50% ethanol; flow rate 1.0 ml/min; 30° C.; detection: 220 nm].

Example 124A ent-tert-Butyl {2-[({8-[(2,6-difluorobenzyl)oxy]-2-methylimidazo[1,2-a]pyridin-3-yl}carbonyl)-amino]-3-ethoxypropyl}carbamate (Enantiomer B)

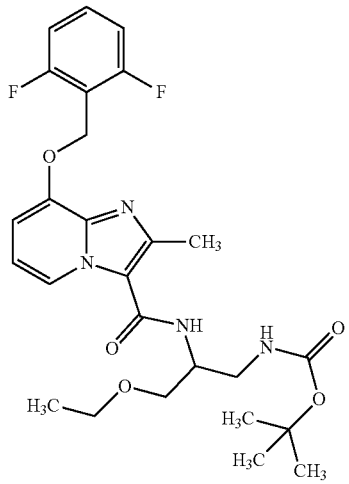 [SMILES: CCOCC(CNC(=O)OC(C)(C)C)NC(=O)c1c(C)nc2c(OCc3c(F)cccc3F)cccn12]

211 mg of Example 110A were separated into the enantiomers on a chiral phase [column: Daicel Chiralpak AD-H, 5 µm, 250×20 mm, mobile phase: 50% isohexane, 50% ethanol, flow rate: 15 ml/min; 30° C., detection: 220 nm].

Yield enantiomer B: 82 mg (99% ee) Enantiomer B: $R_t$=9.71 min [Daicel Chiralpak AD-H, 5 m, 250×4.6 mm; mobile phase: 50% isohexane, 50% ethanol; flow rate 1.0 ml/min; 30° C.; detection: 220 nm].

Example 125A ent-tert-Butyl {2-[({6-chloro-8-[(2,6-difluorobenzyl)oxy]-2-methylimidazo[1,2-a]pyridin-3-yl}-carbonyl)amino]-3-ethoxypropyl}carbamate (Enantiomer A)

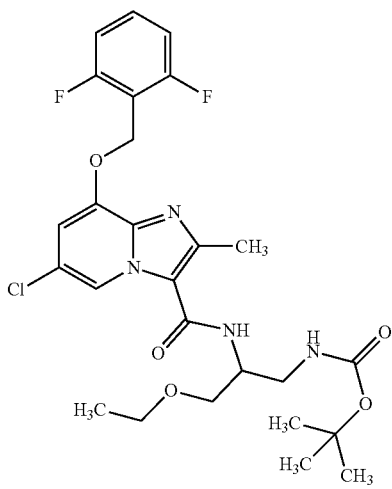 [SMILES: CCOCC(CNC(=O)OC(C)(C)C)NC(=O)c1c(C)nc2c(OCc3c(F)cccc3F)cc(Cl)cn12]

270 mg of Example 111A were separated into the enantiomers on a chiral phase [column: Daicel Chiralpak AD-H, 5 µm, 250×20 mm, mobile phase: 50% isohexane, 50% isopropanol, flow rate: 15 ml/min; 30° C., detection: 220 nm].

Yield enantiomer A: 114 mg (99% ee)

Enantiomer A: $R_t$=4.66 min [Daicel Chiralpak AD-H, 5 m, 250×4.6 mm; mobile phase: 50% isohexane, 50% isopropanol; flow rate 1.0 ml/min; 30° C.; detection: 220 nm].

Example 126A ent-tert-Butyl {2-[({6-chloro-8-[(2,6-difluorobenzyl)oxy]-2-methylimidazo[1,2-a]pyridin-3-yl}-carbonyl)amino]-3-ethoxypropyl}carbamate (Enantiomer B)

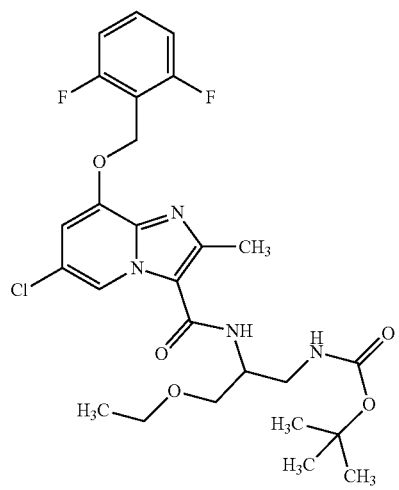 [SMILES: CCOCC(CNC(=O)OC(C)(C)C)NC(=O)c1c(C)nc2c(OCc3c(F)cccc3F)cc(Cl)cn12]

270 mg of Example 111A were separated into the enantiomers on a chiral phase [column: Daicel Chiralpak AD-H, 5 µm, 250×20 mm, mobile phase: 50% isohexane, 50% isopropanol, flow rate: 15 ml/min; 30° C., detection: 220 nm].

Yield enantiomer B: 118 mg (99% ee)

Enantiomer B: $R_t$=6.75 min [Daicel Chiralpak AD-H, 5 m, 250×4.6 mm; mobile phase: 50% isohexane, 50% ethanol; flow rate 1.0 ml/min; 30° C.; detection: 220 nm].

Example 127A tert-Butyl 3-[({8-[(2,6-difluorobenzyl)oxy]-2-methylimidazo[1,2-a]pyridin-3-yl}carbonyl)amino]-9-azabicyclo[3.3.1]nonane-9-carboxylate trifluoroacetate

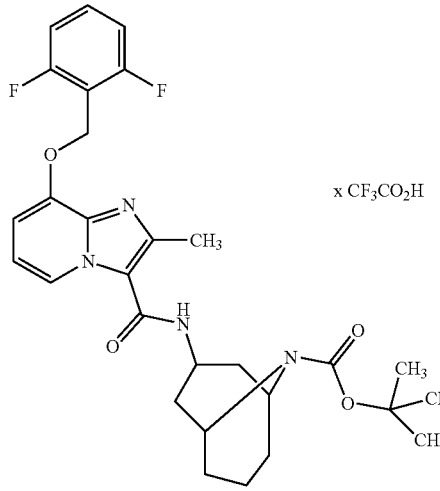

x CF$_3$CO$_2$H 400 mg (1.07 mmol) of (8-[(2,6-difluorobenzyl)oxy]-2-methylimidazo[1,2-a]pyridine-3-carbonyl chloride hydrochloride (Example 22A) were initially charged in 40 ml of dry THF. 309 mg (1.29 mmol) of tert-butyl 3-amino-9-azabicyclo[3.3.1]nonane-9-carboxylate and 554 mg (4.29 mmol) of N,N-diisopropylethylamine were then added, and the mixture was stirred at RT for 1 h. The reaction solution was concentrated and purified by preparative HPLC (RP18 column, mobile phase: acetonitrile/water gradient with addition of 0.1% TFA). This gave 620 mg of the title compound (88% of theory).

LC-MS (Method 2): R$_t$=1.07 min
MS (ESpos): m/z=541 (M−TFA+H)$^+$
$^1$H NMR (400 MHz, DMSO-d$_6$): δ=1.40 (s, 9H), 1.62-1.79 (m, 7H), 1.81-2.06 (m, 3H), 2.50 (s, 3H), 4.22 (d, 2H), 4.78-4.90 (m, 1H), 5.40 (s, 2H), 7.25 (t, 3H), 7.41 (br s, 1H), 7.60 (quint, 1H), 8.09 (br s, 1H), 8.63 (d, 1H).

Example 128A

8-[(2,6-Difluorobenzyl)oxy]-N-[(2R)-1-hydroxyhexan-2-yl]-2-methylimidazo[1,2-a]pyridine-3-carboxamide

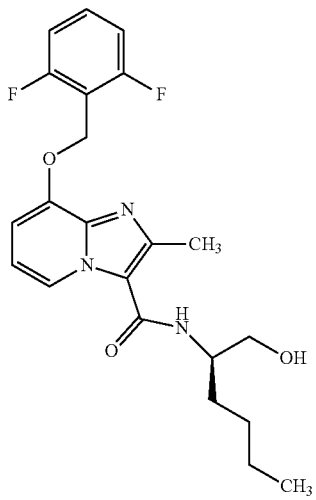 [SMILES: CCCC[C@H](CO)NC(=O)c1c(C)nc2c(OCc3c(F)cccc3F)cccn12]

2 g of 8-[(2,6-difluorobenzyl)oxy]-2-methylimidazo[1,2-a]pyridine-3-carboxylic acid (Example 3A, 6.28 mmol, 1 equivalent), 2.2 g of (benzotriazol-1-yloxy)bisdimethylaminomethylium fluoroborate (TBTU; 6.9 mmol, 1.1 equivalents) and 3.45 ml of 4-methylmorpholine (31.4 mmol, 5 equivalents) were initially charged in 15 ml of dichloromethane and 10 ml of DMF. 810 mg of (R)-(−)-2-amino-1-hexanol (6.9 mmol, 1.1 equivalents) were added at RT, and the mixture was stirred for 3 h. The mixture was then diluted with dichloromethane and adjusted to pH4 with water and 1 N aqueous hydrochloric acid. The organic phase was separated off and the aqueous phase was extracted twice with dichloromethane. The combined organic phases were washed twice with water, dried over sodium sulphate, filtered and concentrated. The crude mixture was purified by preparative HPLC (Method 9). This gave 1066 mg (41% of theory) of the title compound.

LC-MS (Method 2): R$_t$=0.87 min
MS (ESpos): m/z=418.2 (M+H)$^+$
$^1$H NMR (400 MHz, DMSO-d$_6$): δ=0.87 (t, 3H), 1.23-1.70 (m, 6H), 2.54 (s, 3H), 3.39-3.54 (m, 2H), 3.92-4.02 (m, 1H), 4.74 (t, 1H), 5.31 (s, 2H), 6.92 (t, 1H), 6.99 (d, 1H), 7.23 (t, 2H), 7.52 (d, 1H), 7.59 (m, 1H), 8.53 (d, 1H).

Example 129A

8-[(2,6-Difluorobenzyl)oxy]-2-methyl-N-[(2R)-1-oxohexan-2-yl]imidazo[1,2-a]pyridine-3-carboxamide

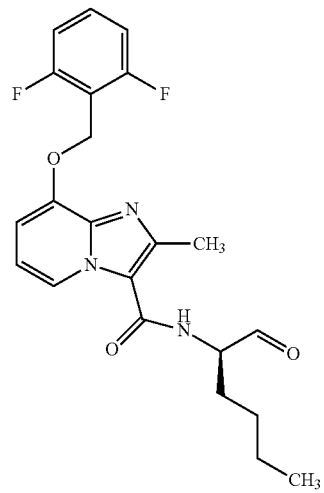 [SMILES: CCCC[C@H](C=O)NC(=O)c1c(C)nc2c(OCc3c(F)cccc3F)cccn12]

1.14 g of Dess-Martin periodinane (2.7 mmol, 1.5 equivalents) were initially charged in 25 ml of dichloromethane, and 0.145 ml of pyridine (1.8 mmol, 1 equivalent) and 750 mg of 8-[(2,6-difluorobenzyl)oxy]-N-[(2R)-1-hydroxyhexan-2-yl]-2-methylimidazo[1,2-a]pyridine-3-carboxamide (Example 3A, 1.8 mmol) were added at −20° C. The reaction mixture was stirred at this temperature for 2 h. 1 N aqueous sodium hydroxide solution was added with ice cooling, and the mixture was extracted three times with ethyl acetate. The combined organic phases were washed with saturated aqueous sodium chloride solution, dried over magnesium sulphate, filtered and concentrated. This gave 899 mg (about 70% pure; 90% of theory) of the target compound which were not purified any further.

LC-MS (Method 2): $R_t$=1.00 min [hydrate: 0.83 min]

MS (ESpos): m/z=416.3 (M+H)$^+$[hydrate: 434.3 (M+H$^+$)]

$^1$H NMR (400 MHz, DMSO-d$_6$): δ=0.87 (t, 3H), 1.20-1.95 (m, 6H), 2.54 (s, 3H), 4.30-4.38 (m, 1H), 5.31 (s, 2H), 6.92 (t, 1H), 7.01 (d, 1H), 7.23 (t, 2H), 7.59 (m, 1H), 8.20 (d, 1H), 8.57 (d, 1H), 9.10 (s, 1H).

Example 130A ent-tert-Butyl [2-({[8-(benzyloxy)-2-methylimidazo[1,2-a]pyridin-3-yl]carbonyl}amino)-2-(3,4-difluorophenyl)ethyl]carbamate

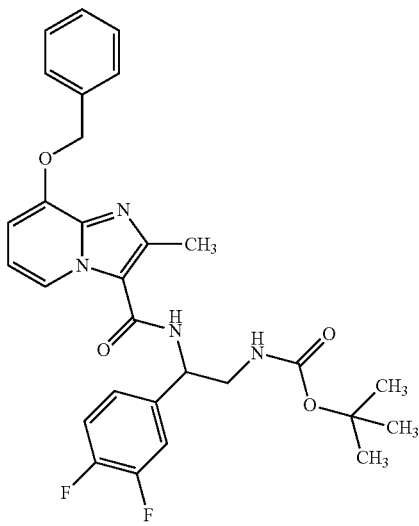 [SMILES: Cc1nc2c(OCc3ccccc3)cccn2c1C(=O)NC(CNC(=O)OC(C)(C)C)c1ccc(F)c(F)c1]

ent-tert-Butyl [2-amino-2-(3,4-difluorophenyl)ethyl]carbamate (Starting material 60A, 19.96 mmol, 1.15 equivalents) was added to 4.90 g of 8-(benzyloxy)-2-methylimidazo[1,2-a]pyridine-3-carboxylic acid (Example 30A, 17.36 mmol, 1 equivalent), 6.13 g of (benzotriazol-1-yloxy)bisdimethylaminomethylium fluoroborate (TBTU, 19 mmol, 1.1 equivalents) and 9.5 ml of N-methylmorpholine (8.78 g, 86.8 mmol, 5 equivalents) in 110 ml of DMF. The reaction mixture was stirred at room temperature for 2 h, then poured into 800 ml of water and extracted with 800 ml and 300 ml of ethyl acetate. The organic phase was washed 300 ml of saturated aqueous sodium chloride solution, dried and concentrated to about 15 ml. The residue was triturated with 90 ml of tert-butyl methyl ether, filtered off, washed with 30 ml of tert-butyl methyl ether and then with n-pentane and dried under reduced pressure. This gave 7.30 g (75% of theory) of the title compound.

LC-MS (Method 7): $R_t$=1.06 min

MS (ESpos): m/z=537.2 (M+H)$^+$ $^1$H NMR (400 MHz, DMSO-d$_6$): δ=ppm 1.33 (s, 9H), 2.61 (s, 3H), 5.11-5.21 (m, 1H), 5.28 (s, 2H), 6.84-6.95 (m, 2H), 7.08 (t, 1H), 7.21-7.28 (m, 1H), 7.43 (m, 7H), 8.20 (d, 2H), 8.52 (d, 2H).

Example 131A ent-tert-Butyl [2-(3,4-difluorophenyl)-2-{[(8-hydroxy-2-methylimidazo[1,2-a]pyridin-3-yl)-carbonyl]amino}ethyl]carbamate

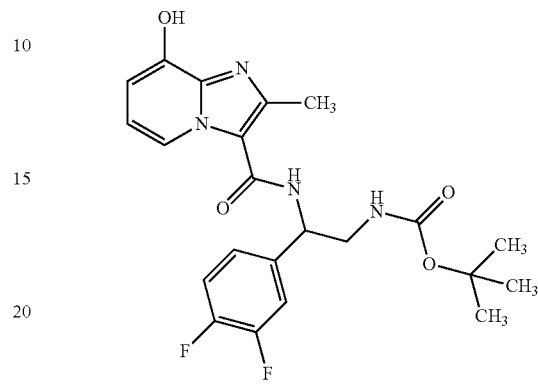

6.90 g of ent-tert-butyl [2-({[8-(benzyloxy)-2-methylimidazo[1,2-a]pyridin-3-yl]carbonyl}amino)-2-(3,4-difluorophenyl)ethyl]carbamate (Example 130A, 12.8 mmol, 1 equivalent) were initially charged in 207 ml of a 1:1:1 mixture of ethanol/THF/dichloromethane, and 0.69 g of 10% palladium on activated carbon were added. The mixture was hydrogenated at RT and standard pressure overnight. 500 ml of dichloromethane were then added, and the reaction mixture was filtered off at 40° C. over silica gel, washed with dichloromethane and dried under reduced pressure. This gave 5.20 g (83% of theory; purity 92%) of the title compound.

LC-MS (Method 2): $R_t$=0.84 min

MS (ESpos): m/z=447.3 (M+H)$^+$ $^1$H NMR (400 MHz, DMSO-d$_6$): δ=1.33 (s, 9H), 2.63 (s, 3H), 5.10-5.22 (m, 1H), 6.65 (d, 1H), 6.80 (t, 1H), 7.08 (t, 1H), 7.20-7.27 (m, 1H), 7.36-7.54 (m, 2H), 8.18 (d, 1H), 8.43 (d, 1H), [further signals hidden under the solvent peaks].

Example 132A rac-Benzyl (2-hydroxy-3-methoxypropyl)carbamate

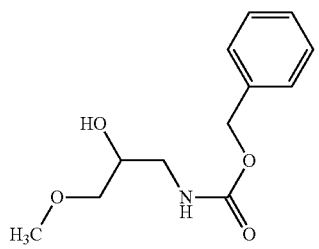 [SMILES: COCC(O)CNC(=O)OCc1ccccc1]

5.0 g (47.6 mmol) of rac-1-amino-3-methoxypropan-2-ol were initially charged in THF (158 ml), and 7.36 ml (52.3 mmol) of benzyl chlorocarbonate, 24.85 ml (142.7 mmol) of N,N-diisopropylethylamine and 1.16 g (9.5 mmol) of 4-dimethylaminopyridine were added. The reaction mixture was stirred at RT for 16 h. 3.7 ml (26.2 mmol) of benzyl chlorocarbonate and then 15 ml of DMF were added, and the reaction solution was stirred at RT overnight. The mixture was concentrated and diluted with ethyl acetate. The mixture was then washed with water, saturated aqueous sodium bicarbonate solution and with saturated aqueous sodium chloride solution. The organic phase was dried over sodium sulphate, filtered off and concentrated. The aqueous phase was concentrated, the residue was taken up in ethyl acetate, the mixture was washed with saturated aqueous sodium bicarbonate solution and with saturated aqueous sodium chloride solution, dried over sodium sulphate, filtered off and concentrated. Both fractions were combined and purified by silica gel chromatography (dichloromethane/methanol gradient: from 100:0 to 10:1). This gave 12.16 g (81% of theory, purity 76%) of the target compound.

LC-MS (Method 7): $R_t$=0.68 min
MS (ESIpos): m/z=240 (M+H)$^+$.
$^1$H NMR (400 MHz, DMSO-$d_6$): δ=2.90-2.98 (m, 1H), 3.03-3.11 (m, 1H), 3.18-3.28 (m, 5H), 3.58-3.66 (m, 1H), 4.85 (d, 1H), 5.01 (s, 2H), 7.17 (t, 1H), 7.28-7.40 (m, 5H).

Example 133A

Benzyl [(2S)-3-hydroxybutan-2-yl]carbamate

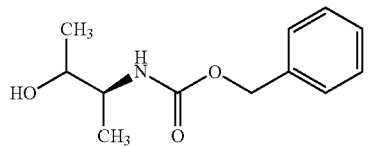

Under argon, 810 mg of benzyl [(2S)-3-oxobutan-2-yl]carbamate (Example 150A, 3.7 mmol, 1 equivalent) were initially charged in 12 ml of dry THF and 12 ml of methanol, and 208 mg of sodium borohydride (5.5 mmol, 1.5 equivalents) were added at 0° C. After 2 h at 0° C., the mixture was concentrated, water and saturated aqueous sodium bicarbonate solution were added to the residue and the mixture was extracted four times with ethyl acetate. The combined organic phases were washed with saturated aqueous sodium chloride solution, dried over magnesium sulphate and concentrated. This gave 777 mg (90% of theory) of the title compound.

Diastereomer mixture in a ratio of 2:1
Main Diastereomer:
LC-MS (Method 2): Rt=0.78 min
MS (ESpos): m/z=224.1 (M+H)$^+$
$^1$H NMR (400 MHz, DMSO-$d_6$): δ=1.01 (m, 6H), 3.43-3.51 (m, 1H), 4.48 (d, 1H), 5.00 (s, 2H), 7.34-7.38 (m, 5H), [further signals hidden under solvent peaks].

Example 134A

Benzyl [(2R)-3-hydroxybutan-2-yl]carbamate

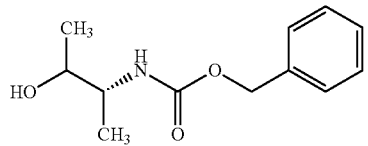

Under argon, 885 mg of benzyl [(2R)-3-oxobutan-2-yl]carbamate (Example 151A, 4 mmol, 1 equivalent) were initially charged in 13 ml of THF and 13 ml of methanol and, analogously to Example 133A, reacted with 227 mg of sodium borohydride (6 mmol, 1.5 equivalents) and worked up. This gave 830 mg (92% of theory) of the title compound.

Diastereomer mixture in a ratio of 2:1
Main Diastereomer:
LC-MS (Method 2): $R_t$=0.78 min
MS (ESpos): m/z=224.1 (M+H)$^+$
$^1$H NMR (400 MHz, DMSO-$d_6$): δ=1.01 (m, 6H), 3.43-3.51 (m, 1H), 4.48 (d, 1H), 5.00 (s, 2H), 7.34-7.38 (m, 5H), [further signals hidden under solvent peaks].

Example 135A rac-Benzyl [3-(3,4-difluorophenoxy)-2-hydroxypropyl]carbamate

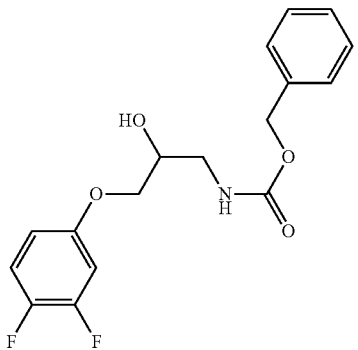 [SMILES: O=C(NCC(O)COc1ccc(F)c(F)c1)OCc1ccccc1]

1 g of rac-1-amino-3-(3,4-difluorophenoxy)propan-2-ol (4.9 mmol, 1 equivalent) was dissolved in 16 ml of THF, and 0.76 ml of benzyl chloroformate (0.9 g, 5.4 mmol, 1.1 equivalents) and then 2.6 ml of N,N-diisopropylethylamine (1.9 g, 14.8 mmol, 3 equivalents) and 0.12 g of 4-dimethylaminopyridine were added. The mixture was stirred at RT for 30 min. 2 ml of DMF were then added, and the mixture was stirred at RT overnight. The mixture was concentrated and the residue was then taken up in ethyl acetate. The organic phase was washed with saturated aqueous sodium bicarbonate solution and saturated aqueous sodium chloride solution, dried over magnesium sulphate, filtered and concentrated. This gave 2.2 g (96% of theory, purity 73%) as a crude product which was reacted without further purification.

LC-MS (Method 2): Rt=1.00 min
MS (ESpos): m/z=338.2 (M+H)$^+$

Example 136A rac-Benzyl [2-(1,3-dioxo-1,3-dihydro-2H-isoindol-2-yl)-3-methoxypropyl]carbamate

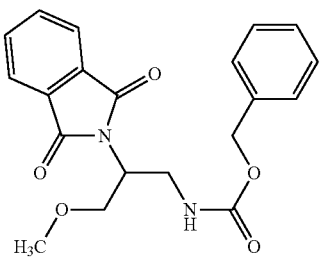 [SMILES: COCC(CNC(=O)OCc1ccccc1)N1C(=O)c2ccccc2C1=O]

12.10 g (38.4 mmol, 76%) rac-benzyl (2-hydroxy-3-methoxypropyl)carbamate (Example 132A), 6.79 g (46.1 mmol) of 1H-isoindole-1,3(2H)-dione and 15.12 g (57.7 mmol) triphenylphosphine were initially charged in THF (158 ml). 11.4 ml (57.7 mmol) of diisopropyl azodicarboxylate were added dropwise, and the mixture was then stirred at RT for 10 min. The mixture was then concentrated and the residue purified by silica gel chromatography (cyclohexane/ethyl acetate gradient: from 3:0 to 2:1). The product fractions were concentrated. This gave 14.84 g (97% of theory, purity 93%) of the target compound.

LC-MS (Method 2): $R_t$=0.95 min.
MS (ESIpos): m/z=369 (M+H)$^+$.
$^1$H NMR (400 MHz, DMSO-d$_6$): δ=3.22 (s, 3H), 3.46 (t, 2H), 3.63 (dd, 1H), 3.80 (t, 1H), 4.37-4.47 (m, 1H), 4.94-4.98 (m, 2H), 7.20-7.35 (m, 5H), 7.56 (t, 1H), 7.81-7.90 (m, 4H).

Example 137A

Benzyl [(2S)-3-(1,3-dioxo-1,3-dihydro-2H-isoindol-2-yl)butan-2-yl]carbamate

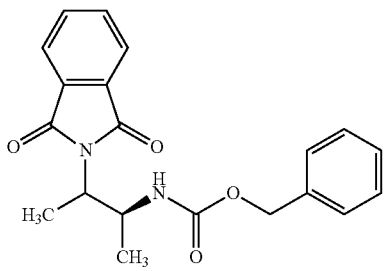 [SMILES: CC([C@H](C)NC(=O)OCc1ccccc1)N1C(=O)c2ccccc2C1=O]

Under argon, 0.72 g of benzyl [(2S)-3-hydroxybutan-2-yl]carbamate (Example 133A, 3.3 mmol, 1 equivalent), 0.57 g of 1H-isoindole-1,3(2H)-dione (3.9 mmol, 1.2 equivalents) and 1.3 g of triphenylphosphine (4.9 mmol, 1.5 equivalents) were dissolved in 15 ml of THF, and 1.1 g of di-tert-butyl (E)-diazene-1,2-dicarboxylate (DIAD, 4.9 mmol, 1.5 equivalents) were added at RT. The mixture was stirred at RT overnight, 2 drops of water and Extrelut® were added and the mixture was concentrated. The residue was purified on a silica gel cartridge (Biotage SNAP Cartridge KP-Sil 25 g) (gradient cyclohexane/ethyl acetate from 5% to 100%). The crude product obtained was left in a mixture of 5 ml of methanol and 1 ml of water overnight. The solid obtained was filtered off, washed with a little methanol/water mixture and dried under reduced pressure. The filtrate was purified by preparative HPLC (Method 9). This gave a total of 692 mg (53% of theory, purity 87%) of the title compound (diastereomer mixture in a ratio of about 4:1).

LC-MS (Method 2): $R_t$=1.02 min
MS (ESpos): m/z=353.2 (M+H)$^+$

Example 138A

Benzyl [(2R)-3-(1,3-dioxo-1,3-dihydro-2H-isoindol-2-yl)butan-2-yl]carbamate

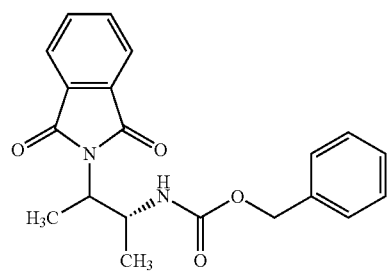 [SMILES: CC([C@@H](C)NC(=O)OCc1ccccc1)N1C(=O)c2ccccc2C1=O]

Under argon, 0.82 g of benzyl [(2R)-3-hydroxybutan-2-yl]carbamate (Example 134A, 3.3 mmol, 1 equivalent) were reacted with 0.57 g of 1H-isoindole-1,3(2H)-dione (phthalimide, 3.9 mmol, 1.1 equivalents) and worked up analogously to Example 137A. This gave 1.25 g (72% of theory; purity 75%) of the title compound (diastereomer ratio about 3:1).

LC-MS (Method 2): $R_t$=1.02 min
MS (ESpos): m/z=353.2 (M+H)$^+$

Example 139A rac-Benzyl [3-(3,4-difluorophenoxy)-2-(1,3-dioxo-1,3-dihydro-2H-isoindol-2-yl)propyl]carbamate

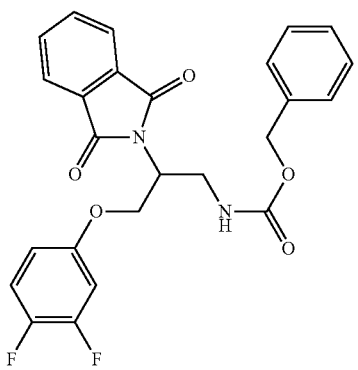 [SMILES: O=C(NCC(COc1ccc(F)c(F)c1)N1C(=O)c2ccccc2C1=O)OCc1ccccc1]

2.2 g of rac-benzyl [3-(3,4-difluorophenoxy)-2-hydroxypropyl]carbamate (Example 135A, 6.5 mmol, 1 equivalent) were reacted with 1.2 g of 1H-isoindole-1,3(2H)-dione (phthalimide, 7.8 mmol, 1.2 equivalents) and worked up analogously to Example 137A. This gave 1.78 g (54% of theory; purity 93%) of the title compound.

LC-MS (Method 2): $R_t$=1.17 min
MS (ESpos): m/z=467.2 (M+H)$^+$

Example 140A rac-Benzyl (2-amino-3-methoxypropyl)carbamate trifluoroacetate

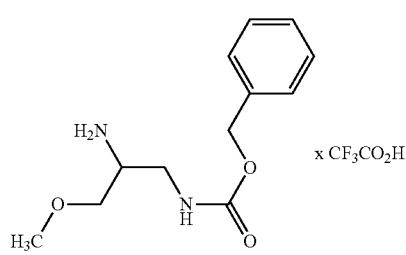 [SMILES: COCC(N)CNC(=O)OCc1ccccc1]

123 ml (1.43 mol) of methylamine (40% in water) were added to 14.13 g (35.7 mmol, 93% pure) of rac-benzyl [2-(1,3-dioxo-1,3-dihydro-2H-isoindol-2-yl)-3-methoxypropyl]carbamate (Example 136A). The reaction mixture was stirred in a closed vessel at 60° C. for 35 min. The mixture was then concentrated and three times taken up in methanol and re-concentrated, and the residue was purified by preparative RP-HPLC (acetonitrile/water gradient with addition of 0.1% TFA). The product fraction, which was still contained, was purified by RP-HPLC (acetonitrile/water gradient with addition of 0.1% TFA). This gave 9.7 g (69.5% of theory, purity 90%) of the target compound.

LC-MS (Method 7): $R_t$=0.46 min.

MS (ESIpos): m/z=239 (M+H)$^+$.

$^1$H NMR (400 MHz, DMSO-d$_6$): δ=3.18-3.58 (m, 8H, superimposed by water signal), 5.05 (s, 2H), 7.29-7.40 (m, 5H), 7.48 (t, 1H), 7.82-8.01 (br. s, 2H).

Example 141A

Benzyl [(2S)-3-aminobutan-2-yl]carbamate

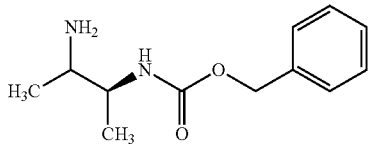

600 mg of benzyl [(2S)-3-(1,3-dioxo-1,3-dihydro-2H-isoindol-2-yl)butan-2-yl]carbamate (Example 137A, 1.7 mmol, 1 equivalent) were suspended in 10 ml of methanol, and 2.9 ml of 40% strength aqueous methylamine solution (2.6 g, 34 mmol, 20 equivalent) were added at RT. The mixture was allowed to stand at RT overnight, and Extrelut® was then added and the mixture was concentrated. The residue was purified on a silica gel cartridge (Biotage Isolera SNAP Cartridge KP-Sil 25 g, mobile phase: dichloromethane/methanol from 95:5 to 0:100). This gave 293 mg (43% of theory) of the title compound.

LC-MS (Method 2): $R_t$=0.49 min

MS (ESpos): m/z=223.2 (M+H)$^+$

Example 142A

Benzyl [(2R)-3-aminobutan-2-yl]carbamate

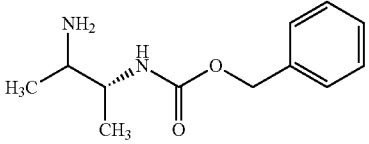 [SMILES: CC(N)[C@@H](C)NC(=O)OCc1ccccc1]

1.2 g of benzyl [(2R)-3-(1,3-dioxo-1,3-dihydro-2H-isoindol-2-yl)butan-2-yl]carbamate (Example 138A, 3.4 mmol, 1 equivalent) were reacted and worked up analogously to Example 141A. The crude product obtained was, after the silica gel chromatography, re-purified by preparative HPLC (Method 9). This gave 147 mg (19% of theory) of the title compound (diastereomer ratio about 3:1).

LC-MS (Method 2): $R_t$=0.48 min

MS (ESpos): m/z=223.1 (M+H)$^+$ $^1$H NMR (400 MHz, DMSO-d$_6$): δ=0.90 (d, 3H), 0.99 (d, 3H), 1.4 (br. s, 2H); 2.63-2.80 (m, 1H), 3.30-3.40 (m, 1H; partially superimposed by water signal); 5.01 (s, 2H), 6.95 (d, 1H), 7.25-7.44 (m, 5H).

Example 143A rac-Benzyl [2-amino-3-(3,4-difluorophenoxy)propyl]carbamate

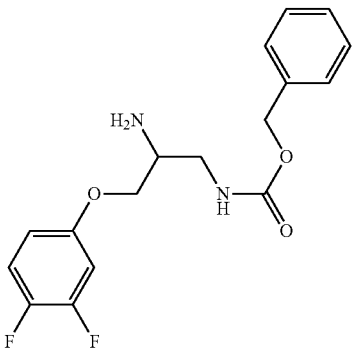 [SMILES: NC(CNC(=O)OCc1ccccc1)COc1ccc(F)c(F)c1]

1.8 g of rac-benzyl [3-(3,4-difluorophenoxy)-2-(1,3-dioxo-1,3-dihydro-2H-isoindol-2-yl)propyl]-carbamate (Example 139A) were dissolved in 25 ml of ethanol, 4.8 ml of 40% strength aqueous methylamine solution (56 mmol, 15 equivalents) were added and the mixture was stirred at 60° C. for 4.5 h. The reaction mixture was concentrated and the residue was then chromatographed on silica gel (Biotage Isolera; mobile phase: dichloromethane/methanol gradient). This gave 600 mg (45% of theory; purity 93%) of the title compound.

LC-MS (Method 2): $R_t$=0.66 min

MS (ESpos): m/z=337.2 (M+H)$^+$

Starting Material 144A rac-2-Amino-4,4,4-trifluorobutan-1-ol

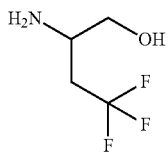

12.9 ml of 2 M lithium borohydride solution in THF (25.8 mmol, 2.5 equivalents) were initially charged in 20 ml of THF, 6.5 ml of chlorotrimethylsilane (51.1 mmol, 5 equivalents) were added and the mixture was stirred at RT for 5 min. 2.0 g of rac-2-amino-4,4,4-trifluorobutanoic acid hydrochloride (10.3 mmol, 1 equivalent) were then added a little at a time, and the mixture was stirred at RT overnight. 20.4 ml of methanol were then added dropwise, and after the addition had ended the mixture was concentrated. 12 ml of a 20% strength aqueous potassium hydroxide solution were added to the residue, and the mixture was extracted three times with dichloromethane. The combined organic solutions were dried over sodium sulphate, filtered and concentrated. This gave 1.58 g (96% of theory; purity 90%) of the title compound.

MS (Method 10): m/z=144.0 (M+H)+
$^1$H NMR (400 MHz, DMSO-$d_6$): δ=1.54 (br. s, 2H), 1.97-2.15 (m, 1H), 2.28-2.45 (m, 1H), 2.84-2.98 (m, 1H), 3.24 (d, 2H), 4.78 (br. s, 1H).

Starting Material 145A rac-Benzyl (4,4,4-trifluoro-1-hydroxybutan-2-yl)carbamate

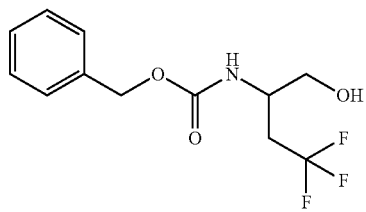 [SMILES: O=C(NC(CO)CC(F)(F)F)OCc1ccccc1]

At RT, 0.38 ml of 50% strength aqueous potassium carbonate solution (1.7 mmol, 0.68 equivalents) and 0.54 ml of benzyl chloroformate (3.8 mmol, 1.5 equivalents) were added to 400 mg of rac-2-amino-4,4,4-trifluorobutan-1-ol (Example 144A, 2.5 mmol, purity about 90%, 1 equivalent) in 36 ml of 1,4-dioxane, and the mixture was stirred at RT for 2 h. Another 0.11 ml of benzyl chloroformate (0.76 mmol, 0.3 equivalents) and 0.08 ml of 50% strength aqueous potassium carbonate solution (0.35 mmol, 0.14 equivalents) were then added, and the mixture was stirred at RT for a further 30 min. After concentration under reduced pressure, the product was purified by preparative HPLC (RP18 column, mobile phase: acetonitrile/water gradient with addition of 0.1% TFA). The crude product obtained was taken up in ethyl acetate and washed twice with saturated aqueous sodium bicarbonate solution. The aqueous phase was extracted with ethyl acetate and the combined organic phases were dried over sodium sulphate, filtered and concentrated. This gave 490 mg (70% of theory) of the title compound.

LC-MS (Method 2): $R_t$=0.81 min
MS (ESpos): m/z=278.1 (M+H)+
$^1$H NMR (400 MHz, DMSO-$d_6$): δ=2.20-2.38 (m, 1H), 3.19-3.27 (m, 1H), 3.28-3.42 (m, 2H), 3.72-3.83 (m, 1H), 4.96-5.08 (m, 3H), 7.26-7.39 (m, 5H).

Starting Material 146A rac-Benzyl [1-(1,3-dioxo-1,3-dihydro-2H-isoindol-2-yl)-4,4,4-trifluorobutan-2-yl]carbamate

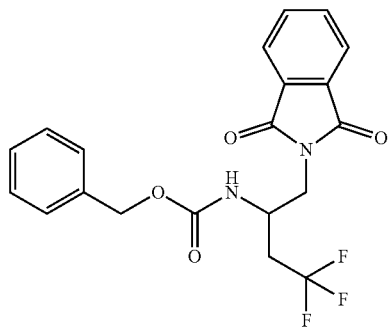 [SMILES: O=C(NC(CN1C(=O)c2ccccc2C1=O)CC(F)(F)F)OCc1ccccc1]

Under argon, 1.58 g of rac-benzyl (4,4,4-trifluoro-1-hydroxybutan-2-yl)carbamate (Example 145A, 5.70 mmol, 1 equivalent), 0.84 g of 1H-isoindole-1,3(2H)-dione (phthalimide, 5.70 mmol, 1 equivalents) and 2.24 g of triphenylphosphine (8.54 mmol, 1.5 equivalents) were dissolved in 28 ml of THF, and 1.84 g of di-tert-butyl (E)-diazene-1,2-dicarboxylate (DIAD, 8.54 mmol, 1.5 equivalents) were added at RT. The mixture was stirred at RT for 30 min and a water/acetonitrile mixture was then added. Purification by preparative HPLC (RP18 column, mobile phase: acetonitrile/water gradient with addition of 0.1% TFA) gave 1.92 g (79% of theory) of the title compound.

LC-MS (Method 2): $R_t$=1.08 min
MS (ESpos): m/z=407.2 (M+H)+

Starting Material 147A rac-Benzyl (1-amino-4,4,4-trifluorobutan-2-yl)carbamate trifluoroacetate

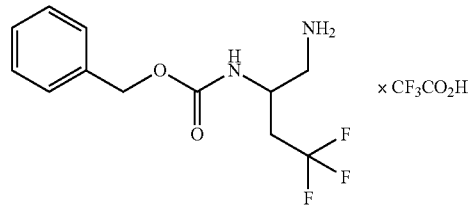 [SMILES: NCC(CC(F)(F)F)NC(=O)OCc1ccccc1]

1.86 g of rac-benzyl [1-(1,3-dioxo-1,3-dihydro-2H-isoindol-2-yl)-4,4,4-trifluorobutan-2-yl]-carbamate (Example 146A, 4.35 mmol, 1 equivalent) were dissolved in 15.0 ml of 40% strength aqueous methylamine solution (174 mmol, 40 equivalents) and stirred in a closed flask at 60° C. for 30 min. The reaction mixture was concentrated and the residue was then purified by preparative HPLC (RP18 column, mobile phase: acetonitrile/water gradient with addition of 0.1% TFA). This gave 1.25 g (74% of theory) of the title compound.

LC-MS (Method 2): $R_t$=0.64 min
MS (ESpos): m/z=277.2 (M+H)$^+$
$^1$H NMR (400 MHz, DMSO-d$_6$): δ=2.57-2.71 (m, 1H), 2.76-2.89 (m, 1H), 2.93-3.04 (m, 1H), 4.00-4.14 (m, 1H), 5.02 (d, 1H), 5.09 (d, 1H), 7.27-7.42 (m, 5H), 7.47-7.53 (m, 1H), 7.88-8.08 (br. s, 3H), [further signal hidden under DMSO peak].

Example 148A ent-Benzyl {(2S)-1-[methoxy(methyl)amino]-1-oxopropan-2-yl}carbamate

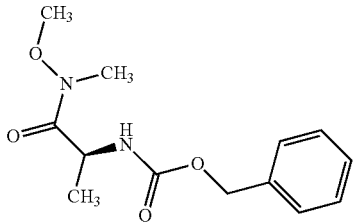 [SMILES: CON(C)C(=O)[C@H](C)NC(=O)OCc1ccccc1]

Under argon, 2 g of N-[(benzyloxy)carbonyl]-L-alanine (9 mmol, 1 equivalent) were dissolved in 30 ml of THF, and after addition of 1.9 g (11 mmol, 1.2 equivalents) of 2-chloro-4,6-dimethoxy-1,3,5-triazine and 3 ml of 4-methylmorpholine (2.7 g, 27 mmol, 3 equivalents) the mixture was stirred at RT for 1 h. 0.96 g (9.8 mmol, 1.1 equivalents) of N,O-dimethylhydroxylamine hydrochloride was added, and the mixture was stirred at RT overnight. The mixture was then concentrated, ethyl acetate was added to the residue, the mixture was washed with 1 N aqueous hydrochloric acid, saturated aqueous sodium bicarbonate solution and saturated aqueous sodium chloride solution, dried over magnesium sulphate and concentrated and the residue was dried under reduced pressure. This gave 2.25 g (61% of theory; purity 65%) of the title compound.

LC-MS (Method 7): $R_t$=0.82 min
MS (ESpos): m/z=267.1 (M+H)$^+$

Example 149A ent-Benzyl {(2R)-1-[methoxy(methyl)amino]-1-oxopropan-2-yl}carbamate

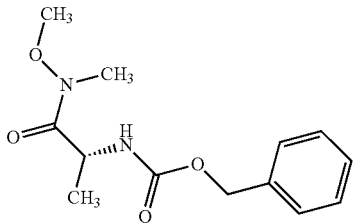 [SMILES: CON(C)C(=O)[C@@H](C)NC(=O)OCc1ccccc1]

Under argon, 2 g of N-[(benzyloxy)carbonyl]-D-alanine (9 mmol, 1 equivalent) were dissolved in 30 ml of THF, and after addition of 1.9 g (11 mmol, 1.2 equivalents) of 2-chloro-4,6-dimethoxy-1,3,5-triazine and 3 ml of 4-methylmorpholine (2.7 g, 27 mmol, 3 equivalents) and 0.96 g (9.8 mmol, 1.1 equivalents) of N,O-dimethylhydroxylamine hydrochloride the mixture was stirred at RT overnight. The mixture was then concentrated, ethyl acetate was added to the residue, the mixture was washed with 1 N aqueous hydrochloric acid, saturated aqueous sodium bicarbonate solution and saturated aqueous sodium chloride solution, dried over magnesium sulphate and concentrated and the residue was dried under reduced pressure. This gave 2.11 g (64% of theory; purity 61%) of the title compound as a colourless oil.

LC-MS (Method 7): $R_t$=0.82 min
MS (ESpos): m/z=267.1 (M+H)$^+$

Example 150A

Benzyl [(2S)-3-oxobutan-2-yl]carbamate

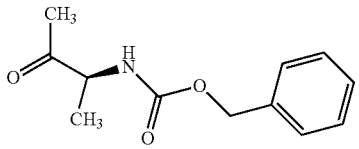 [SMILES: CC(=O)[C@H](C)NC(=O)OCc1ccccc1]

Under argon, 1000 mg of benzyl {(2S)-1-[methoxy(methyl)amino]-1-oxopropan-2-yl}carbamate (Example 148A, 3.8 mmol, 1 equivalent) were dissolved in 19.5 ml of THF and cooled to −78° C. At this temperature, 4 ml of 1.4 M methylmagnesium bromide solution in 1:3 THF/toluene (6 mmol, 1.5 equivalents) were added slowly. The mixture was stirred at −78° C. for 5 min and at RT for 1 h and allowed to stand at RT overnight. 0.27 ml of water was then added with ice cooling, and the mixture was concentrated. The residue was diluted with water and 1 N aqueous hydrochloric acid solution and extracted four times with ethyl acetate. The organic phase was washed with saturated aqueous sodium bicarbonate solution and with saturated aqueous sodium chloride solution, dried over magnesium sulphate, filtered and concentrated. This gave 813 mg (88% of theory; purity 90%) of the title compound.

LC-MS (Method 2): $R_t$=0.77 min
MS (ESpos): m/z=222.1 (M+H)$^+$
$^1$H NMR (400 MHz, DMSO-d$_6$): δ=1.17 (d, 3H), 2.08 (s, 3H), 4.04 (m, 1H), 5.04 (s, 2H), 7.29-7.39 (m, 5H), 7.67 (d, 1H).

Example 151A

Benzyl [(2R)-3-oxobutan-2-yl]carbamate

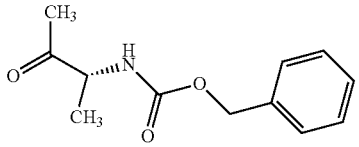 [SMILES: CC(=O)[C@@H](C)NC(=O)OCc1ccccc1]

Under argon, 1000 mg of benzyl {(2R)-1-[methoxy(methyl)amino]-1-oxopropan-2-yl}carbamate (Example 149A, 3.8 mmol, 1 equivalent) were dissolved in 19.5 ml of THF and cooled to −78° C. At this temperature, 4 ml of 1.4 M methylmagnesium bromide solution in 1:3 THF/toluene (6 mmol, 1.5 equivalents) were added slowly. The mixture was then stirred at −78° C. for 5 min and at RT for 1 h and then allowed to stand at RT overnight. 0.27 ml of water was then added with ice cooling, and the mixture was then concentrated. The residue was diluted with water and 1 N aqueous hydrochloric acid solution and extracted four times with ethyl acetate. The organic phase was washed with saturated aqueous sodium bicarbonate solution and with saturated aqueous sodium chloride solution, dried over magnesium sulphate, filtered and concentrated. This gave 888 mg (97% of theory) of the title compound as a colourless oil.

LC-MS (Method 2): $R_t$=0.77 min

MS (ESpos): m/z=222.1 (M+H)$^+$ $^1$H NMR (400 MHz, DMSO-d$_6$): δ=1.17 (d, 3H), 2.08 (s, 3H), 3.99-4.10 (m, 1H), 5.03 (s, 2H), 7.27-7.41 (m, 5H), 7.68 (d, 1H).

Example 152A

3-Bromo-N-(4-fluorophenyl)propanamide

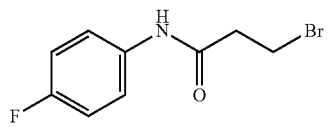 [SMILES: O=C(CCBr)Nc1ccc(F)cc1]

5.75 ml of 4-fluoroaniline (6.65 g, 59.88 mmol, 1 equivalent) were initially charged in 65 ml of THF, 33 ml of 2 M trimethylaluminium solution in hexane (65.87 mmol, 1.1 equivalents) were added at −78° C. and the mixture was stirred for 20 min, slowly warming to RT. At −20° C., this solution was added dropwise to a solution of 6.54 ml (10 g, 59.8 mmol, 1 equivalent) of methyl 3-bromopropanoate in 65 ml of THF and then stirred at RT for 3 h. At 0° C., the reaction solution was acidified carefully with 1 N aqueous hydrochloric acid solution and extracted twice with ethyl acetate. The combined organic phases were dried over sodium sulphate, filtered and concentrated. This gave 12.6 g (67% of theory; purity 78%) of the title compound which was reacted further without purification.

LC-MS (Method 7): $R_t$=0.83 min

MS (ESpos): m/z=248.0 (M+H)$^+$

Example 153A

3-Bromo-N-[4-(trifluoromethyl)phenyl]propanamide

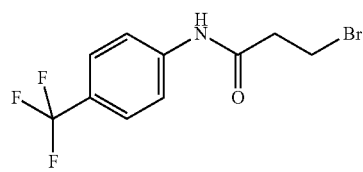 [SMILES: O=C(CCBr)Nc1ccc(C(F)(F)F)cc1]

22.3 ml of 4-(trifluoromethyl)aniline (29 g, 179.6 mmol, 1 equivalent) were reacted with 19.6 ml (30 g, 179.6 mmol, 1 equivalent) of methyl 3-bromopropanoate and worked up analogously to Example 152A. The crude product obtained was then purified on a silica gel column (mobile phase: dichloromethane). This gave 20.3 g (37% of theory) of the title compound.

LC-MS (Method 7): $R_t$=1.03 min

MS (ESpos): m/z=296.0 (M+H)$^+$

Example 154A 1-(4-Fluorophenyl)azetidin-2-one

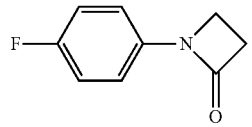 [SMILES: O=C1CCN1c1ccc(F)cc1]

12.60 g of 3-bromo-N-(4-fluorophenyl)propanamide (Example 152A, 39.94 mmol, 1 equivalent) were initially charged in 97.1 ml of dichloromethane, 11.19 g of 1,4,7,10,13,16-hexaoxacyclooctadecane (18-crown-6, 42.33 mmol, 1.06 equivalents) and 2.33 g of potassium hydroxide (41.54 mmol, 1.04 equivalents) were added and the mixture was stirred at RT overnight. 0.35 equivalents of 1,4,7,10,13,16-hexaoxacyclooctadecane and 0.35 equivalents of potassium hydroxide were then added and the mixture was stirred at RT overnight. Saturated aqueous ammonium chloride solution was then added and the mixture was extracted three times with ethyl acetate. The combined organic phases were dried over sodium sulphate and filtered, and the filtrate was concentrated and purified [column: Reprosil C18, 10 μm, Spring Column 470×50 mm; acetonitrile/water gradient; flow rate: 200 ml/min; 22° C.; wavelength: 210 nM]. This gave 3.46 g (38% of theory) of the title compound.

LC-MS (Method 7): $R_t$=0.77 min

MS (ESpos): m/z=166.1 (M+H)$^+$ $^1$H NMR (400 MHz, DMSO-d$_6$): δ=3.08 (t, 2H), 3.62 (t, 2H), 7.18-7.28 (m, 2H), 7.33-7.40 (m, 2H).

Example 155A

1-[4-(Trifluoromethyl)phenyl]azetidin-2-one

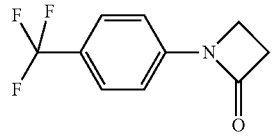

20.30 g of 3-bromo-N-[4-(trifluoromethyl)phenyl]propanamide (Example 153A, 66.16 mmol, 1 equivalent) were initially charged in 161 ml of dichloromethane, 18.54 g of 1,4,7,10,13,16-hexaoxacyclooctadecane (18-crown-6, 70.13 mmol, 1.06 equivalents) and 3.86 g of potassium hydroxide (68.81 mmol, 1.04 equivalents) were added and the mixture was stirred at RT overnight. Saturated aqueous ammonium chloride solution was added and the mixture was extracted three times with ethyl acetate. The combined organic phases were dried over sodium sulphate and filtered and the filtrate was concentrated. This gave 25.0 g (86% of theory; purity about 49%) of the title compound which was reacted further without purification.

LC-MS (Method 7): $R_t$=0.94 min

MS (ESpos): m/z=216.1 (M+H)$^+$ $^1$H NMR (400 MHz, DMSO-d$_6$): δ=3.14 (t, 2H), 3.70 (t, 2H), 7.51 (d, 2H), 7.73 (d, 2H).

Example 156A

6-Fluoro-2,3-dihydroquinolin-4(1H)-one

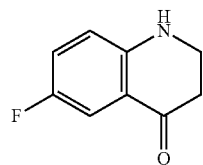 [SMILES: O=C1CCNc2ccc(F)cc21]

500 mg of 1-(4-fluorophenyl)azetidin-2-one (Example 154A, 3.03 mmol, 1 equivalent) were initially charged in 24 ml of dichloromethane, 0.5 ml of trifluoromethanesulphonic acid (909 mg, 6.05 mmol, 2 equivalents) were added at 0° C. and the mixture was stirred at RT for 45 min. Two more times, 0.3 equivalents of trifluoromethanesulphonic acid were added, and after each addition the mixture was stirred for 30 min. With ice cooling, saturated aqueous sodium bicarbonate solution was added carefully, and the reaction mixture was extracted three times with dichloromethane. The combined organic phases were dried over sodium sulphate, filtered and concentrated. This gave 284 mg (57% of theory) of the title compound.

LC-MS (Method 7): $R_t$=0.69 min

MS (ESpos): m/z=166.1 (M+H)$^+$

Example 157A 6-(Trifluoromethyl)-2,3-dihydroquinolin-4(1H)-on

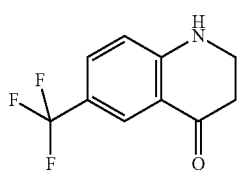 [SMILES: O=C1CCNc2ccc(C(F)(F)F)cc21]

18.77 g of 1-[4-(trifluoromethyl)phenyl]azetidin-2-one (Example 155A, 42.74 mmol, 1 equivalent) were reacted and worked up analogously to Example 156A. The crude product obtained was purified on a silica gel column (mobile phase: cyclohexane/ethyl acetate gradient: from 7:3 to 5:1). This gave 1.75 g (16% of theory; purity 86%) of the title compound.

LC-MS (Method 2): $R_t$=0.89 min

MS (ESpos): m/z=216.1 (M+H)$^+$ $^1$H NMR (400 MHz, DMSO-d$_6$): δ=2.59 (t, 2H), 3.46-3.55 (m, 2H), 6.90 (d, 1H), 7.53 (dd, 2H), 7.80 (s, 1H).

Example 158A tert-Butyl 6-fluoro-4-oxo-3,4-dihydroquinoline-1 (2H)-carboxylate

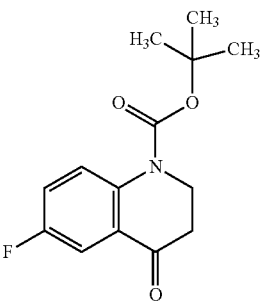 [SMILES: CC(C)(C)OC(=O)N1CCC(=O)c2cc(F)ccc21]

294 mg of 6-fluoro-2,3-dihydroquinolin-4(1H)-one (Example 156A, 1.78 mmol, 1 equivalent) were initially charged in 12.8 ml of THF, 466 mg of di-tert-butyl dicarbonate (2.14 mmol, 1.2 equivalents) and 44 mg of 4-dimethylaminopyridine (0.36 mmol, 0.2 equivalents) were added and the mixture was stirred at RT for 1 h and 15 min. Another 0.2 equivalent of di-tert-butyl dicarbonate was then added, and the mixture was stirred at RT overnight. The reaction solution was diluted with water and extracted three times with ethyl acetate. The combined organic phases were washed with water and with saturated aqueous sodium bicarbonate solution, dried over sodium sulphate, filtered and concentrated. The crude product obtained was purified on a silica gel column (mobile phase: cyclohexane/ethyl acetate 7:3). This gave 394 mg (81% of theory) of the title compound.

LC-MS (Method 5): $R_t$=2.30 min

MS (ESpos): m/z=266.2 (M+H)$^+$ $^1$H NMR (400 MHz, DMSO-d$_6$): δ=1.50 (s, 9H), 2.77 (t, 2H), 4.08 (t, 2H), 7.44-7.54 (m, 2H), 7.79 (dd, 1H).

Example 159A tert-Butyl 4-oxo-6-(trifluoromethyl)-3,4-dihydroquinoline-1 (2H)-carboxylate

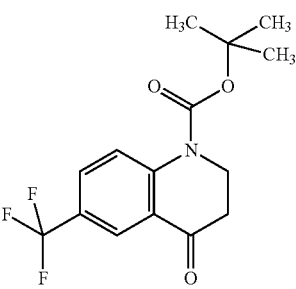 [SMILES: CC(C)(C)OC(=O)N1CCC(=O)c2cc(C(F)(F)F)ccc21]

1.75 g of 6-(trifluoromethyl)-2,3-dihydroquinolin-4(1H)-one (Example 157A, 7.0 mmol, 1 equivalent) were reacted and worked up analogously to Example 158A. The crude product was purified on a silica gel column (mobile phase: cyclohexane/ethyl acetate 4:1). This gave 1.72 g (74% of theory) of the title compound.

LC-MS (Method 7): $R_t$=1.27 min
MS (ESpos): m/z=360.0 (M–H+HCOOH)⁻
¹H NMR (400 MHz, DMSO-d₆): δ=1.52 (s, 9H), 2.83 (t, 2H), 4.15 (t, 2H), 7.89-7.95 (m, 1H), 8.01-8.09 (m, 2H).

Example 160A rac-tert-Butyl 4-amino-6-fluoro-3,4-dihydroquinoline-1(2H)-carboxylate trifluoroacetate

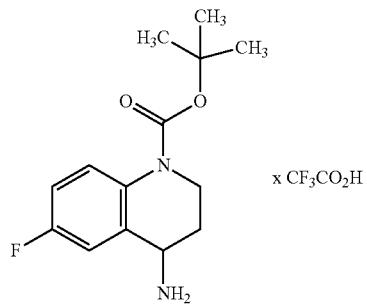 [SMILES: CC(C)(C)OC(=O)N1CCC(N)c2cc(F)ccc21]

295 mg of tert-butyl 6-fluoro-4-oxo-3,4-dihydroquinoline-1(2H)-carboxylate (Example 158A, 1.11 mmol, 1 equivalent) were initially charged in 3.5 ml of ethanol, 1285 mg of ammonium acetate (16.68 mmol, 15 equivalents) and 84 mg of sodium cyanoborohydride (1.33 mmol, 1.2 equivalents) were added and the mixture was reacted in a microwave oven at 130° C. for 2 min. The reaction solution was concentrated and the residue was taken up in ethyl acetate and washed with water.

The organic phase was dried over sodium sulphate, filtered and concentrated. The crude product was purified by preparative HPLC (RP18 column, mobile phase: methanol/water gradient with addition of 0.1% TFA). This gave 185 mg (43% of theory) of the title compound.
LC-MS (Method 7): $R_t$=0.56 min
MS (ESpos): m/z=267.2 (M+H)⁺

Bespiel 161A rac-tert-Butyl 4-amino-6-(trifluoromethyl)-3,4-dihydroquinoline-1(2H)-carboxylate

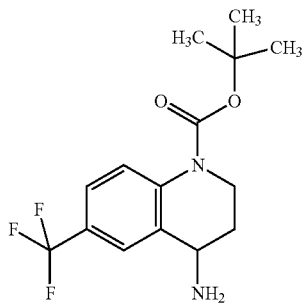

1.3 g of tert-butyl 4-oxo-6-(trifluoromethyl)-3,4-dihydroquinoline-1(2H)-carboxylate (Example 159A, 4 mmol, 1 equivalent) were initially charged in 12.6 ml of ethanol, and 4.6 g of ammonium acetate (59.5 mmol, 15 equivalents) and 0.3 g of sodium cyanoborohydride (4.8 mmol, 1.2 equivalents) were added. The reaction mixture was divided and each portion was irradiated in a microwave oven at 130° C. for 1 min. The mixture was then concentrated and the residue was taken up in ethyl acetate and washed with water. The organic phase was dried over sodium sulphate, filtered and concentrated. The crude product obtained was purified on silica gel (mobile phase: dichloromethane/ethyl acetate: 5/1, then dichloromethane/methanol: 10/1). This gave 0.84 g (78% of theory) of the title compound.
LC-MS (Method 7): $R_t$=0.69 min
MS (ESpos): m/z=317.1 (M+H)⁺

Example 162A (2,6-Difluorophenyl)(²H₂)methanol

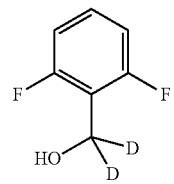 [SMILES: [2H]C([2H])(O)c1c(F)cccc1F]

2.0 g of methyl 2,6-difluorobenzoate (11.6 mmol, 1 equivalent) were initially charged in 40 ml of THF at 0° C., and at this temperature 23.2 ml of 1 M lithium aluminium deuteride solution in THF (23.2 mmol, 2 equivalents) were added slowly. The mixture was stirred for 45 min, and 1.2 ml of water, 1.2 ml of 2 N aqueous sodium hydroxide solution and 2.3 ml of water were then added in succession. The resulting precipitate was filtered off and washed well with THF. The filtrate was concentrated and the residue was reacted further without purification. This gave 1.77 g (104% of theory) of the title compound.
GC-MS (Method 6): $R_t$=2.38 min
MS (EIpos): m/z=146.1 (M)⁺
¹H NMR (400 MHz, DMSO-d₆): δ=5.20 (s, 1H), 7.02-7.12 (m, 2H), 7.24-7.44 (m, 1H).

Example 163A rac-Benzyl 1-amino-3-azabicyclo[4.1.0]heptane-3-carboxylate trifluoroacetate

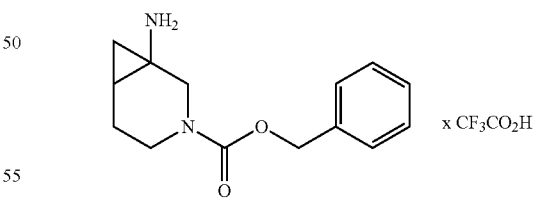

530 mg of rac-3-azabicyclo[4.1.0]heptan-1-amine dihydrochloride (2.86 mmol, 1 equivalent; preparation according to Gensini, M.; Kozhushkov, S. I.; Yufit, D. S.; Howard, J. A. K.; Es-Sayed, M.; De Meijere, A.; *Eur. J. Org. Chem.*, 2002, p. 2499-2507) were dissolved in 11.8 ml of 1,4-dioxane and 14.3 ml of 1 N aqueous sodium hydroxide solution. At 0° C., a solution of 0.3 ml of benzyl chloroformate (366 mg, 2.15 mmol, 0.75 equivalents) in 8.8 ml of 1,4-dioxane was added dropwise over 30 min. The solution was then slowly warmed to RT and stirred at RT for 30 min.

The mixture was freed from 1,4-dioxane under reduced pressure and the aqueous phase was extracted three times with ethyl acetate. The combined organic phases were dried over sodium sulphate, filtered and concentrated. The crude product was purified by preparative HPLC (RP18 column, mobile phase: methanol/water gradient with addition of 0.1% TFA/formic acid). This gave 428 mg (41% of theory) of the title compound.

LC-MS (Method 2): $R_t$=0.55 min
MS (ESpos): m/z=247.2 (M+H)$^+$
$^1$H NMR (400 MHz, DMSO-d$_6$): δ=0.58 (t, 1H), 1.01-1.13 (m, 1H), 1.38-1.47 (m, 1H), 1.49-1.63 (m, 1H), 1.93-2.07 (m, 1H), 2.89-3.10 (m, 1H), 3.91-4.11 (m, 1H), 5.08 (s, 2H), 7.24-7.43 (m, 5H), 8.28 (br. s, 3H), [further signals hidden under solvent peaks].

Example 164A tert-Butyl [2-(3,3-difluoropyrrolidin-1-yl)ethyl]carbamate

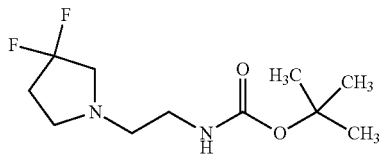 [SMILES: CC(C)(C)OC(=O)NCCN1CCC(F)(F)C1]

900 mg of 3,3-difluoropyrrolidine hydrochloride (6.27 mmol, 1 equivalent) were initially charged in 62 ml of acetonitrile, 1475 mg of tert-butyl (2-bromoethyl)carbamate (6.58 mmol, 1.05 equivalent) and then 3.28 ml of N,N-diisopropylethylamine (2.43 g, 18.81 mmol, 3 equivalents) were added and the mixture was stirred at 80° C. overnight. 0.5 equivalent of 3,3-difluoropyrrolidine hydrochloride (450 mg, 3.14 mmol) was then added, and stirring of the reaction solution was continued at 80° C. overnight. The reaction solution was concentrated and purified on a silica gel column (mobile phase: cyclohexane/ethyl acetate gradient: from 5/1 to pure ethyl acetate). This gave 431 mg (28% of theory) of the title compound.

GC-MS (Method 6): $R_t$=4.81 min
MS (ESpos): m/z=251.0 (M+H)$^+$
$^1$H NMR (400 MHz, DMSO-d$_6$): δ=1.37 (s, 9H), 2.13-2.27 (m, 2H), 2.44 (t, 2H), 2.68 (t, 2H), 2.87 (t, 2H), 2.97-3.05 (m, 2H), 6.76 (t, 1H).

Example 165A tert-Butyl {2-[(2-methoxyethyl)amino]ethyl}carbamate

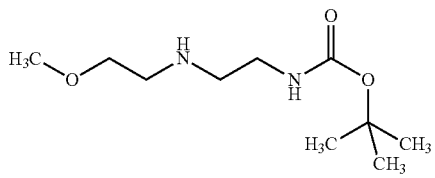

1.57 g of tert-butyl (2-bromoethyl)carbamate (7.0 mmol, 0.7 equivalents) were initially charged in 98.5 ml of acetonitrile, 0.87 ml of 2-methoxyethylamine (750 mg, 10.0 mmol, 1 equivalent) and 3.5 ml of N,N-diisopropylethylamine (2.58 g, 20 mmol, 2 equivalents) were added and the mixture was stirred at 80° C. overnight. The mixture was concentrated and the residue was purified on a silica gel column (mobile phase: dichloromethane/methanol gradient: from 50:1 to 30:1 to 10:1, then dichloromethane/2 N ammonia in methanol: 10:1). This gave 1.69 g (99% of theory; purity about 90%) of the title compound.

MS (Method 10, ESpos): m/z=219.1 (M+H)$^+$

Example 166A tert-Butyl [2-(4,4-difluoropiperidin-1-yl)ethyl]carbamate

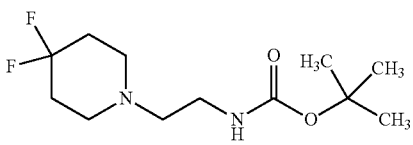 [SMILES: CC(C)(C)OC(=O)NCCN1CCC(F)(F)CC1]

0.90 g of 4,4-difluoropiperidine hydrochloride (5.71 mmol, 1 equivalents) were initially charged in 56 ml of acetonitrile, 1.41 g of tert-butyl (2-bromoethyl)carbamate (6.28 mmol, 1.1 equivalents) and 3 ml of N,N-diisopropylethylamine (2.21 g, 17.13 mmol, 3 equivalents) were added and the mixture was stirred at 80° C. overnight. Twice, 0.4 equivalent of tert-butyl (2-bromoethyl)carbamate was added to the reaction solution, and in each case stirring was continued at 80° C. overnight. The mixture was concentrated and purified on a silica gel column (gradient: from cyclohexane/ethyl acetate: 3:1 to ethyl acetate). This gave 1.28 g (62% of theory; purity 73%) of the title compound.

GC-MS (Method 6): $R_t$=4.87 min
MS (EIpos): m/z=191.1 (M−73)$^+$
MS (Method 10, ESpos): m/z=265.2 (M+H)$^+$ Example 167A 2-(3,3-Difluoropyrrolidin-1-yl)ethanamine dihydrochloride

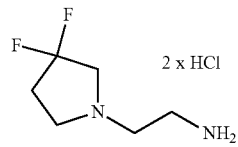

8.6 ml of a 2 N solution of hydrogen chloride in diethyl ether (17.22 mmol, 10 equivalents) were added to 431 mg of tert-butyl [2-(3,3-difluoropyrrolidin-1-yl)ethyl]carbamate (Example 164A, 1.72 mmol, 1 equivalent), and the reaction mixture was stirred at RT overnight. The solvent was then decanted off, the residue was triturated three times with diethyl ether and the residue obtained in this manner was dried under reduced pressure. This gave 410 mg (99% of theory; purity 93%) of the title compound.

MS (Method 10, ESpos): m/z=151.1 (M−2HCl+H)$^+$
$^1$H NMR (400 MHz, DMSO-d$_6$): δ=3.07-3.23 (m, 2H), 3.28-4.13 (m, 8H), 8.34 (br. s, 4H).

Example 168A

N-(2-Methoxyethyl)ethane-1,2-diamine dihydrochloride

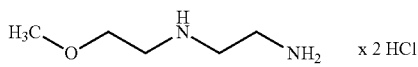

15.5 ml of a 2 N solution of hydrogen chloride in diethyl ether (31 mmol, 10 equivalents) were added to 750 mg of tert-butyl {2-[(2-methoxyethyl)amino]ethyl}carbamate (Example 165A, purity about 90%, 3.1 mmol, 1 equivalent), and the mixture was stirred at RT overnight. The solvent was decanted off, the residue was triturated three times with diethyl ether and the product obtained in this manner was dried under reduced pressure. This gave 482 mg (82% of theory) of the title compound.

MS (Method 10, ESpos): m/z=119 (M−2HCl+H)$^+$ $^1$H NMR (400 MHz, DMSO-d$_6$): δ=3.11-3.24 (m, 6H), 3.30 (s, 3H), 3.61 (t, 2H), 8.19 (br. s, 3H), 9.16 (br. s, 2H).

Example 169A

2-(4,4-Difluoropiperidin-1-yl)ethanamine dihydrochloride

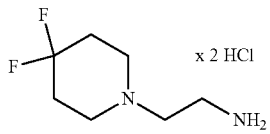

6.9 ml of a 2 N solution of hydrogen chloride in diethyl ether (13.8 mmol, 10 equivalents) were added to 500 mg of tert-butyl [2-(4,4-difluoropiperidin-1-yl)ethyl]carbamate (Example 166A, 1.38 mmol, 1 equivalent), and the mixture was stirred at RT overnight. The solvent was decanted off, the residue was triturated three times with diethyl ether, the diethyl ether was decanted off and the product obtained in this manner was dried under reduced pressure. This gave 448 mg (100% of theory; purity 73%) of the title compound.

MS (Method 10, ESpos): m/z=165.1 (M−2HCl+H)$^+$

Example 170A ent-tert-Butyl [2-(3,4-difluorophenyl)-2-{[(8-{[(2,6-difluorophenyl)($^2$H$_2$)methyl]oxy}-2-methylimidazo[1,2-a]pyridin-3-yl)carbonyl]amino}ethyl]carbamate

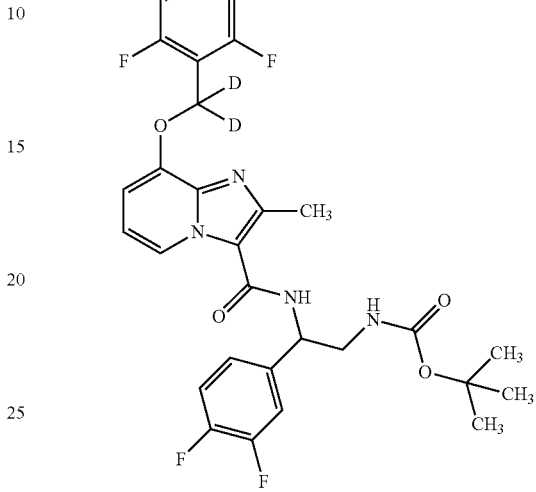

1222 mg of ent-tert-butyl [2-(3,4-difluorophenyl)-2-{[(8-hydroxy-2-methylimidazo[1,2-a]pyridin-3-yl)carbonyl]amino}ethyl]carbamate (Example 131A, 2.7 mmol, 1 equivalent) were suspended in 16.5 ml of toluene, and 600 mg of (2,6-difluorophenyl)($^2$H$_2$)methanol (Example 162A, 4.1 mmol, 1.5 equivalents) and 1148 mg of triphenylphosphine (4.4 mmol, 1.6 equivalents) were added at RT. With ice bath cooling, 12 ml of THF and 0.9 ml of diisopropyl azodicarboxylate (942 mg, 4.4 mmol, 1.6 equivalents) were then added, and the mixture was stirred at RT for 2 days and allowed to stand at RT for 2 days. The solution was extracted three times with ethyl acetate and the combined organic phases were washed with saturated aqueous sodium chloride solution, dried over magnesium sulphate, filtered and concentrated. The crude product obtained was pre-separated on a silica gel column (Biotage Isolera SNAP-Cartrige KP-Sil 100 g; mobile phase: cyclohexane/ethyl acetate: from 12% to 100%) and then re-purified by preparative HPLC (Method 9). This gave 255 mg (16% of theory) of the title compound.

LC-MS (Method 2): R$_t$=1.11 min

MS (ESpos): m/z=575.3 (M+H)$^+$ $^1$H NMR (400 MHz, DMSO-d$_6$): δ=1.32 (s, 9H), 2.58 (s, 3H), 3.37-3.46 (m, 1H), 5.12-5.19 (m, 1H), 6.91 (t, 1H), 7.02 (d, 1H), 7.09 (t, 1H), 7.19-7.27 (m, 3H), 7.36-7.51 (m, 2H), 7.54-7.65 (m, 1H), 8.22 (d, 1H), 8.55 (d, 1H), [further signal hidden under solvent peak].

The examples shown in Table 10A were prepared analogously to Example 34A by reacting 8-[(2,6-difluorobenzyl)oxy]-2-methylimidazo[1,2-a]pyridine-3-carboxylic acid from Example 3A with the appropriate commercially available amines under the reaction conditions described in the General Working Procedure 2.

Exemplary work-up of the reaction mixture: water was added to the reaction solution and the precipitate formed was stirred for another 0.5-1.0 h, filtered off, washed with water and dried under high vacuum overnight. Alternatively, the precipitate or the reaction mixture was purified further directly by preparative HPLC (RP18 column, mobile phase:

acetonitrile/water gradient with addition of 0.1% TFA) and dried under high vacuum overnight. If required, the product fractions were taken up in ethyl acetate or dichloromethane and washed twice with saturated aqueous sodium bicarbonate solution. The aqueous phase was extracted twice with ethyl acetate or dichloromethane. The combined organic phases were dried over sodium sulphate, filtered and concentrated.

TABLE 10A

| Example | IUPAC name/structure (yield) | Analytical data |
|---|---|---|
| 171A | tert-butyl {4-[({8-[(2,6-difluorobenzyl)oxy]-2-methylimidazo[1,2-a]pyridin-3-yl}carbonyl)-amino]-2-methylbutan-2-yl}carbamate trifluoroacetate 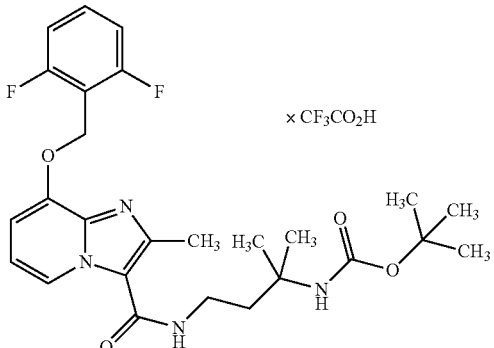 (89% of theory) | LC-MS (Method 1): $R_t$ = 1.16 min<br>MS (ESpos): m/z = 503.1 (M + H)$^+$ |
| 172A | rac-tert-butyl 4-[({8-[(2,6-difluorobenzyl)oxy]-2-methylimidazo[1,2-a]pyridin-3-yl}carbonyl)-amino]-6-fluoro-3,4-dihydroquinoline-1(2H)-carboxylate 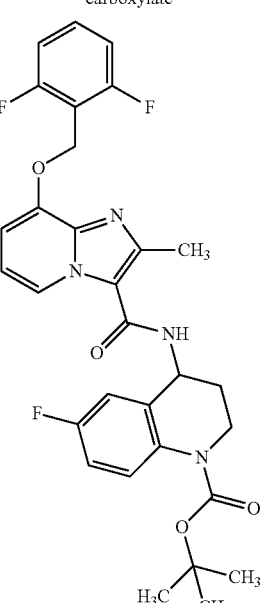 (75% of theory) | LC-MS (Method 7): $R_t$ = 1.16 min<br>MS (ESpos): m/z = 567.2 (M + H)$^+$ |

TABLE 10A-continued

| Example | IUPAC name/structure (yield) | Analytical data |
|---|---|---|
| 173A | rac-tert-butyl 4-[({8-[(2,6-difluorobenzyl)oxy]-2-methylimidazo[1,2-a]pyridin-3-yl}carbonyl)-amino]-3,4-dihydroisoquinoline-2(1H)-carboxylate<br>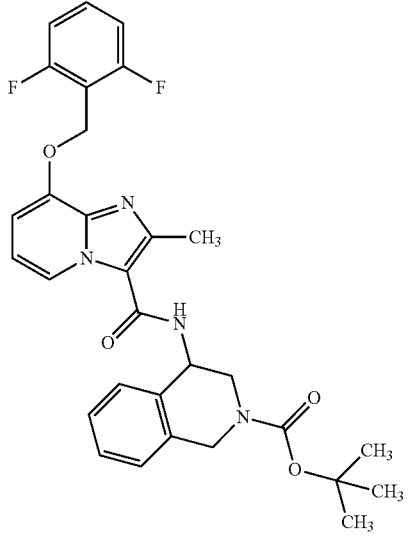<br>(72% of theory) | LC-MS (Method 2): $R_t$ = 1.07 min<br>MS (ESpos): m/z = 549.3 (M + H)$^+$ |
| 174A | rac-tert-butyl 4-[({8-[(2,6-difluorobenzyl)oxy]-2-methylimidazo[1,2-a]pyridin-3-yl}carbonyl)-amino]-6-(trifluoromethyl)-3,4-dihydroquinoline-1(2H)-carboxylate<br>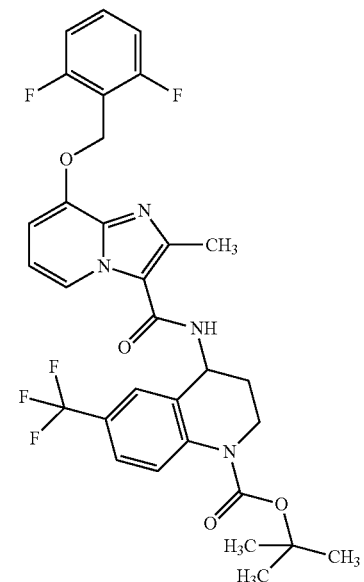<br>(54% of theory) | LC-MS (Method 7): $R_t$ = 1.28 min<br>MS (ESpos): m/z = 617.2 (M + H)$^+$ |

TABLE 10A-continued

| Example | IUPAC name/structure (yield) | Analytical data |
|---|---|---|
| 175A | 8-[(2,6-difluorobenzyl)oxy]-N-(2-hydroxyethyl)-2-methylimidazo[1,2-a]pyridine-3-carboxamide 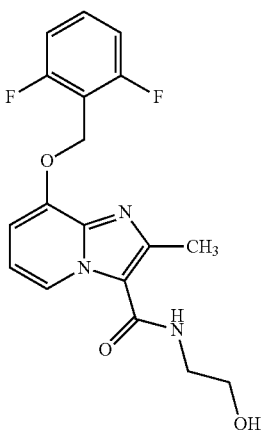 (79% of theory) | LC-MS (Method 7): $R_t$ = 0.57 min<br>MS (ESpos): m/z = 362.1 (M + H)$^+$<br>$^1$H NMR (400 MHz, DMSO-d$_6$):<br>δ = 3.35-3.41 (m, 2H), 3.50-3.59 (m, 2H), 4.77 (t, 1H), 5.30 (s, 2H), 6.93 (t, 1H), 7.01 (d, 1H), 7.24 (t, 2 H), 7.54-7.65 (m, 1H), 7.78 (t, 1H), 8.63 (d, 1H), [further signal hidden under DMSO peak]. |
| 176A | rac-benzyl 1-[({8-[(2,6-difluorobenzyl)oxy]-2-methylimidazo[1,2-a]pyridin-3-yl}carbonyl)-amino]-3-azabicyclo[4.1.0]heptane-3-carboxylate 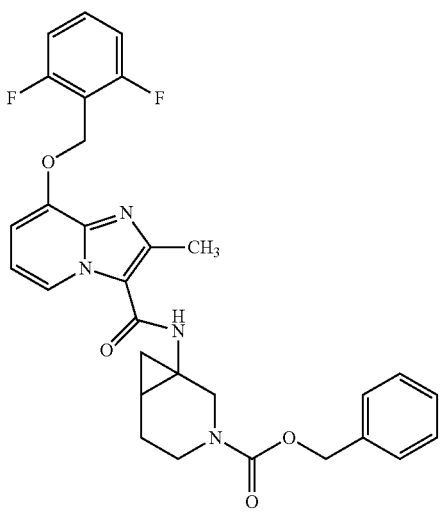 (84% of theory) | LC-MS (Method 2): $R_t$ = 1.00 min<br>MS (ESpos): m/z = 547.3 (M + H)$^+$<br>$^1$H NMR (400 MHz, DMSO-d$_6$):<br>δ = 0.53-0.64 (m, 1H), 0.97 (dd, 1H), 1.29-1.38 (m, 1H), 1.56-1.67 (m, 1H), 2.04-2.16 (m, 1H), 2.45 (s, 3H), 3.05-3.21 (m, 1H), 3.42-3.68 (m, 2H), 4.11 (d, 1H), 5.08 (s, 2H), 5.30 (s, 2H), 6.90-6.97 (m, 1H), 7.02 (d, 1H), 7.23 (t, 2H), 7.27-7.43 (m, 5H), 7.51-7.64 (m, 1H), 8.26 (br. s, 1H), 8.62 (d, 1H). |

TABLE 10A-continued
| Example | IUPAC name/structure (yield) | Analytical data |
|---|---|---|
| 177A | 8-[(2,6-difluorobenzyl)oxy]-N-[(2R)-1-hydroxypropan-2-yl]-2-methylimidazo[1,2-a]-pyridine-3-carboxamide 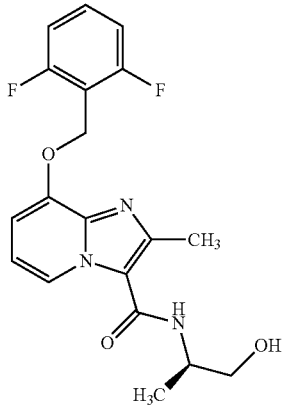 (93% of theory) | LC-MS (Method 1): $R_t$ = 0.74 min<br>MS (ESpos): m/z = 376.1 (M + H)$^+$ |
| 178A | 8-[(2,6-difluorobenzyl)oxy]-N-[(2S)-1-hydroxypropan-2-yl]-2-methylimidazo[1,2-a]-pyridine-3-carboxamide 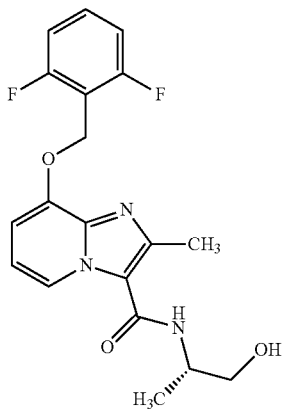 (91% of theory) | LC-MS (Method 1): $R_t$ = 0.74 min<br>MS (ESpos): m/z = 376.1 (M + H)$^+$ |

Example 179A tert-Butyl {4-[({6-chloro-8-[(2,6-difluorobenzyl)oxy]-2-methylimidazo[1,2-a]pyridin-3-yl}-carbonyl)amino]-2-methylbutan-2-yl}carbamate trifluoroacetate

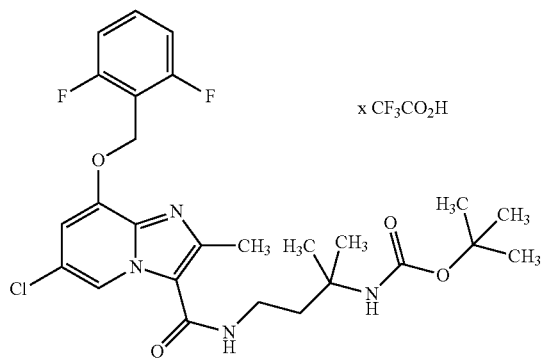 [SMILES: Cc1nc2c(OCc3c(F)cccc3F)cc(Cl)cn2c1C(=O)NCCC(C)(C)NC(=O)OC(C)(C)C]

x CF₃CO₂H 75 mg of 6-chloro-8-[(2,6-difluorobenzyl)oxy]-2-methyl-imidazo[1,2-a]pyridine-3-carboxylic acid (Example 16A, 0.21 mmol, 1 equivalent), 82 mg of (benzotriazol-1-yloxy) bisdimethylaminomethylium fluoroborate (TBTU, 0.26 mmol, 1.2 equivalents) and 108 mg of 4-methylmorpholine (1.06 mmol, 5 equivalents) were initially charged in 1.45 ml of DMF. After 10 min at RT, 56 mg (0.23 mmol, 1.1 equivalents) of tert-butyl-(4-amino-2-methylbutan-2-yl)carbamate hydrochloride were added and the mixture was stirred at RT overnight. Water and trifluoroacetic acid were added and the reaction solution was purified by preparative HPLC (method: RP18 column, mobile phase: acetonitrile/water gradient with addition of 0.1% TFA). This gave 118 mg (84% of theory) of the title compound.

LC-MS (Method 1): $R_t$=1.43 min

MS (ESpos): m/z=537.0 (M−TFA+H)⁺

The examples shown in Table 11A were prepared analogously to Example 179A by reacting 6-chloro-8-[(2,6-difluorobenzyl)oxy]-2-methylimidazo[1,2-a]pyridine-3-carboxylic acid (Example 16A) with the appropriate commercially available or self-prepared amines under the reaction conditions described in the General Working Procedure 2:

TABLE 11A

| Example | IUPAC name/structure (yield) | Analytical data |
|---|---|---|
| 180A | rac-tert-butyl 4-[({6-chloro-8-[(2,6-difluorobenzyl)oxy]-2-methylimidazo[1,2-a]-pyridin-3-yl}carbonyl)amino]-3,4-dihydroisoquinoline-2(1H)-carboxylate<br><br>(70% of theory; purity 90%) | LC-MS (Method 7): $R_t$ = 1.38 min<br>MS (ESpos): m/z = 583.1 (M + H)⁺ |

Example 181A tert-Butyl {2-[({8-[(2,6-difluorobenzyl)oxy]-2,6-dimethylimidazo[1,2-a]pyridin-3-yl}carbonyl)-amino]ethyl}carbamate trifluoroacetate

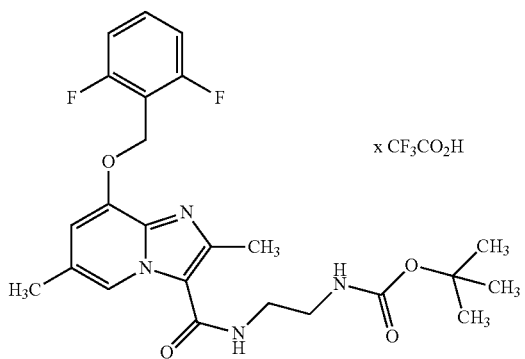 [SMILES: Cc1cc(OCc2c(F)cccc2F)c2nc(C)c(C(=O)NCCNC(=O)OC(C)(C)C)n2c1]

60 mg of 8-[(2,6-difluorobenzyl)oxy]-2,6-dimethylimidazo[1,2-a]pyridine-3-carboxylic acid (Example 21A, 0.18 mmol, 1 equivalent), 70 mg of (benzotriazol-1-yloxy)bisdimethylaminomethylium fluoroborate (TBTU, 0.22 mmol, 1.2 equivalents) and 73 mg of 4-methylmorpholine (0.72 mmol, 4 equivalents) were initially charged in 1.3 ml of DMF. After 10 min at RT, 32 mg of tert-butyl (2-aminoethyl)carbamate (0.2 mmol, 1.1 equivalents) were added and the mixture was stirred at RT overnight. Water and trifluoroacetic acid were added and the reaction solution was purified by preparative HPLC (method: RP18 column, mobile phase: acetonitrile/water gradient with addition of 0.1% TFA). This gave 93 mg (87% of theory) of the title compound.

LC-MS (Method 7): $R_t$=0.88 min
MS (ESpos): m/z=475.2 (M+H)$^+$

The examples shown in Table 12A were prepared analogously to Example 181A by reacting 8-[(2,6-difluorobenzyl)oxy]-2,6-dimethylimidazo[1,2-a]pyridine-3-carboxylic acid (Example 21A) with the appropriate commercially available or self-prepared amines under the reaction conditions described in the General Working Procedure 2:

TABLE 12A

| Example | IUPAC name/structure (yield) | Analytical data |
|---|---|---|
| 182A | tert-butyl {4-[({8-[(2,6-difluorobenzyl)oxy]-2,6-dimethylimidazo[1,2-a]pyridin-3-yl}carbonyl)-amino]-2-methylbutan-2-yl}carbamate trifluoroacetate<br><br>(53% of theory) | LC-MS (Method 2): $R_t$ = 1.01 min<br>MS (ESpos): m/z = 517.3 (M + H)$^+$<br>$^1$H NMR (400 MHz, DMSO-d$_6$):<br>δ = 1.23 (s, 6H), 1.37 (s, 9H), 1.84-1.96 (m, 2H), 2.39 (s, 3H), 3.24-3.33 (m, 2H), 5.39 (s, 2H), 6.51 (br. s, 1H), 7.26 (t, 2H), 7.41 (br. s, 1H), 7.55-7.68 (m, 1H), 8.20 (br. s, 1H), 8.53 (s, 1H), [further signal hidden under solvent peaks]. |

TABLE 12A-continued

| Example | IUPAC name/structure (yield) | Analytical data |
|---|---|---|
| 183A | tert-butyl (2R)-2-{[({8-[(2,6-difluorobenzyl)oxy]-2,6-dimethylimidazo[1,2-a]pyridin-3-yl}-carbonyl)amino]methyl}piperidin-1-carboxylate trifluoroacetate[1)]<br />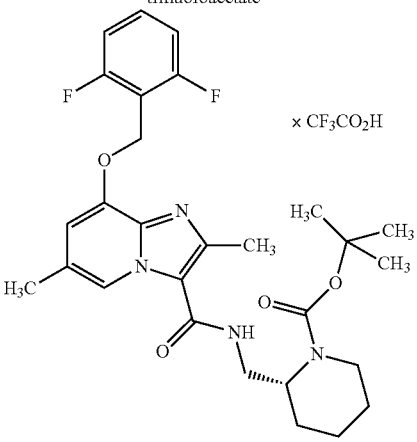<br />(39% of theory) | LC-MS (Method 7): $R_t$ = 1.07 min<br />MS (ESpos): 529.3 m/z = (M + H)$^+$ |

[1)] Coupling agent: HATU

The examples shown in Table 13A were prepared analogously to Example 34A by reacting the appropriate carboxylic acids with the appropriate commercially available amines under the reaction conditions described in the General Working Procedure 2.

Exemplary work-up of the reaction mixture: water was added to the reaction solution and the precipitate formed was stirred for another 0.5-1.0, filtered off, washed with water and dried under high vacuum overnight. Alternatively, the precipitate or the reaction mixture was purified further directly by preparative HPLC (RP18 column, mobile phase: acetonitrile/water gradient with addition of 0.1% TFA) and dried under high vacuum overnight. If required, the product fractions were taken up in ethyl acetate or dichloromethane and washed twice with saturated aqueous sodium bicarbonate solution. The aqueous phase was extracted twice with ethyl acetate or dichloromethane. The combined organic phases were dried over sodium sulphate, filtered and concentrated.

TABLE 13A

| Example | IUPAC name/structure (yield) | Analytical data |
|---|---|---|
| 184A | benzyl {(2R)-3-[({8-[(2,6-difluorobenzyl)oxy]-2-methylimidazo[1,2-a]pyridin-3-yl}carbonyl)-amino]butan-2-yl}carbamate<br />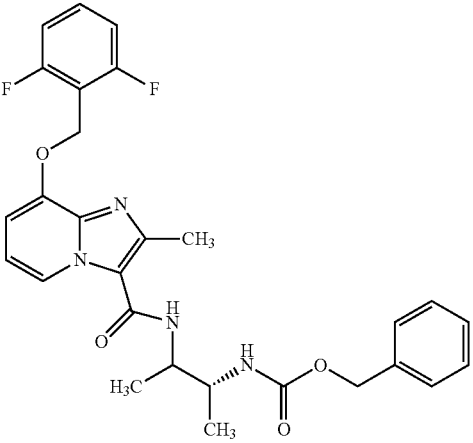<br />(68% of theory; purity 96% diastereomer mixture about 3:1) | LC-MS (Method 7): $R_t$ = 0.94 min<br />MS (ESpos): m/z = 523.2 (M + H)$^+$<br />$^1$H NMR (400 MHz, DMSO-d$_6$):<br />δ = 1.11 (d, 3H), 1.16 (d, 3H), 2.47 (s, 3H), 3.63-3.87 (m, 1H), 4.06-4.15 (m, 1H), 4.94-5.05 (m, 2H), 5.30 (s, 2H), 6.88-6.94 (m, 1H), 7.00 (d, 1H), 7.19-7.38 (m, 8H), 7.54-7.64 (m, 2H), 8.51-8.58 (m, 1H). |

TABLE 13A-continued

| Example | IUPAC name/structure (yield) | Analytical data |
|---|---|---|
| 185A | rac-tert-butyl {3-[({8-[(2,6-difluorobenzyl)oxy]-2-methylimidazo[1,2-a]pyridin-3-yl}carbonyl)-amino]-2-methylpropyl}carbamate<br><br>(61% of theory; purity 96%) | LC-MS (Method 2): $R_t$ = 0.96 min<br>MS (ESpos): m/z = 489.3 (M + H)$^+$<br>$^1$H NMR (400 MHz, DMSO-d$_6$):<br>δ = 0.86 (d, 3H), 1.38 (s, 9H), 1.78-1.91 (m, 1H), 2.82-3.00 (m, 2H), 3.13-3.26 (m, 2H), 5.30 (s, 2H), 6.87-6.96 (m, 2H), 7.01 (d, 1H), 7.24 (t, 2H), 7.54-7.64 (m, 1H), 7.83 (t, 1H), 8.63 (d, 1H), [further signal hidden under the DMSO peak]. |
| 186A | rac-benzyl {2-[({8-[(2,6-difluorobenzyl)oxy]-2-methylimidazo[1,2-a]pyridin-3-yl}-carbonyl)amino]-3-methoxypropyl}carbamate[1)]<br><br>(56% of theory; purity 65%) | LC-MS (Method 7): $R_t$ = 0.90 min<br>MS (ESpos): m/z = 539.2 (M + H)$^+$ |

TABLE 13A-continued

| Example | IUPAC name/structure (yield) | Analytical data |
|---|---|---|
| 187A | rac-benzyl {2-[({8-[(2,6-difluorobenzyl)oxy]-2-methylimidazo[1,2-a]pyridin-3-yl}carbonyl)amino]-3-(3,4-difluorophenoxy)propyl}carbamate[1)]<br>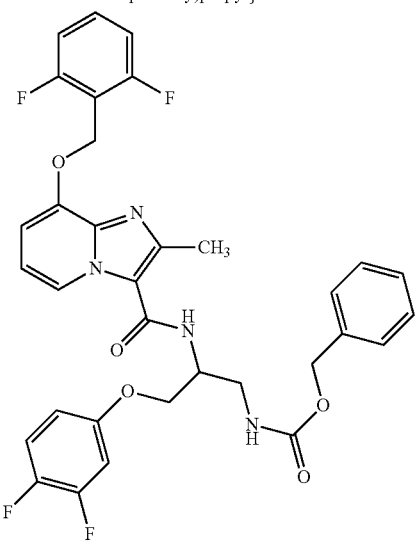<br>(37% of theory; purity 77%) | LC-MS (Method 7): $R_t$ = 1.13 min<br>MS (ESpos): m/z = 637.2 (M + H)$^+$ |
| 188A | tert-butyl {2-[({8-[(2,6-difluorobenzyl)oxy]-2-methylimidazo[1,2-a]pyridin-3-yl}-carbonyl)amino]-2,2-dimethylpropyl}carbamate<br>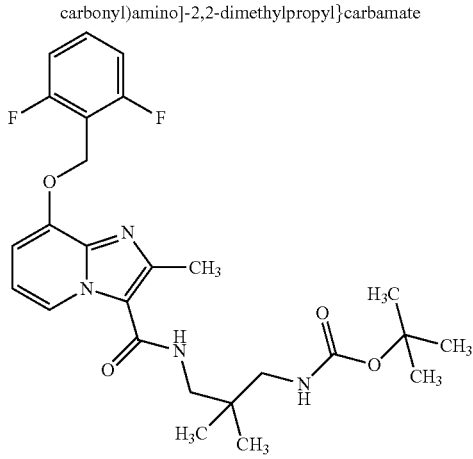<br>(72% of theory; purity 84%) | LC-MS (Method 7): $R_t$ = 1.05 min<br>MS (ESpos): m/z = 503.2 (M + H)$^+$<br>$^1$H NMR (400 MHz, DMSO-d$_6$):<br>δ = 0.84 (s, 6H), 1.39 (s, 9H), 2.58 (s, 3H), 2.80-2.86 (m, 2H), 3.13 (d, 2H),<br>5.31 (s, 2H), 6.89-7.05 (m, 3H),<br>7.17-7.32 (m, 2 H), 7.54-7.64 (m, 1H),<br>7.81 (t, 1H), 8.64 (d, 1H). |

TABLE 13A-continued

| Example | IUPAC name/structure (yield) | Analytical data |
|---|---|---|
| 189A | rac-benzyl {1-[({8-[(2,6-difluorobenzyl)oxy]-2-methylimidazo[1,2-a]pyridin-3-yl}carbonyl)amino]-4,4,4-trifluorobutan-2-yl}carbamate trifluoroacetate<br>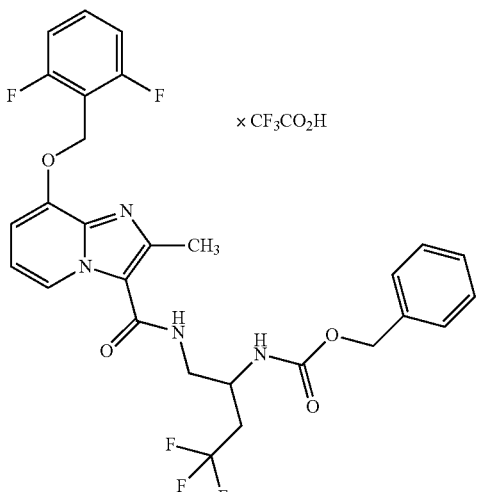<br>(96% of theory) | LC-MS (Method 2): $R_t$ = 0.96 min<br>MS (ESpos): m/z = 577.2 (M + H)$^+$ |
| 190A | rac-benzyl {1-[({8-[(2,6-difluorobenzyl)oxy]-2,6-dimethylimidazo[1,2-a]pyridin-3-yl}carbonyl)amino]-4,4,4-trifluorobutan-2-yl}carbamate trifluoroacetate<br>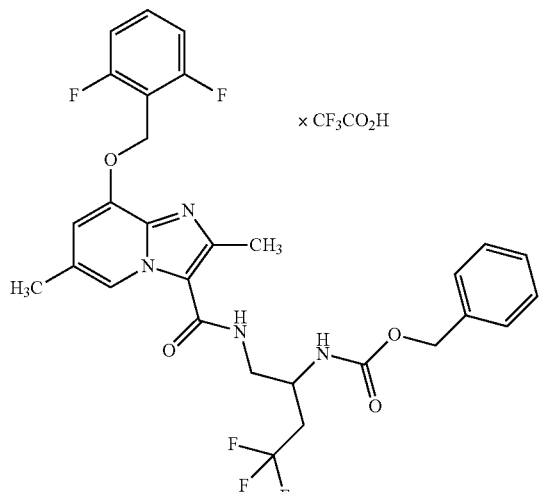<br>(89% of theory; purity 100%) | LC-MS (Method 2): $R_t$ = 0.97 min<br>MS (ESpos): m/z = 591.3 (M + H)$^+$ |

[1])The amine was employed in excess since the exact purity was not known.

Example 191A

Benzyl {(2S)-3-[({6-chloro-8-[(2,6-difluorobenzyl)oxy]-2-methylimidazo[1,2-a]pyridin-3-yl}-carbonyl)amino]butan-2-yl}carbamate

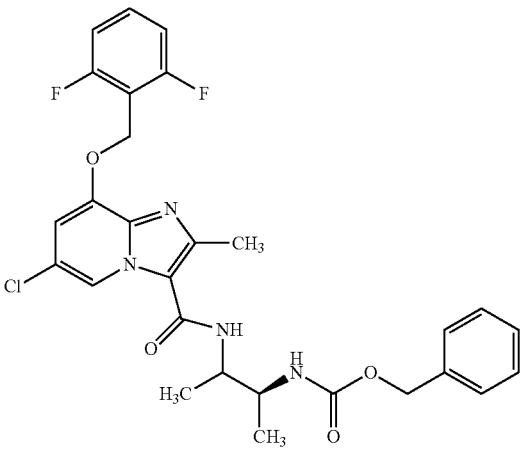 [SMILES: Cc1nc2c(OCc3c(F)cccc3F)cc(Cl)cn2c1C(=O)NC(C)[C@H](C)NC(=O)OCc1ccccc1]

164 mg of 6-chloro-8-[(2,6-difluorobenzyl)oxy]-2-methylimidazo[1,2-a]pyridine-3-carboxylic acid (Example 16A, 0.47 mmol, 1 equivalent) were dissolved in 1.4 ml of DMF, 145 mg of benzyl [(2S)-3-aminobutan-2-yl]carbamate (Example 141A, 0.65 mmol, 1.4 equivalents), 230 mg of O-(7-azabenzotriazol-1-yl)-N,N,N'N'-tetramethyluronium hexafluorophosphate (HATU, 0.6 mmol, 1.3 equivalents) and 180.7 mg of N,N-diisopropylethylamine (0.23 ml, 1.4 mmol, 3 equivalents) were added and the mixture was stirred at RT overnight. A drop of water was then added and the precipitated solid was filtered off and dried under reduced pressure. This gave 160 mg (53% of theory; purity 86%) of the title compound as colourless crystals.

LC-MS (Method 1): $R_t$=2.50 min
MS (ESpos): m/z=557.1 (M+H)$^+$

Example 192A tert-Butyl (2S)-2-{[({8-[(2,6-difluorobenzyl)oxy]-2,6-dimethylimidazo[1,2-a]pyridin-3-yl}-carbonyl)amino]methyl}pyrrolidin-1-carboxylate trifluoroacetate

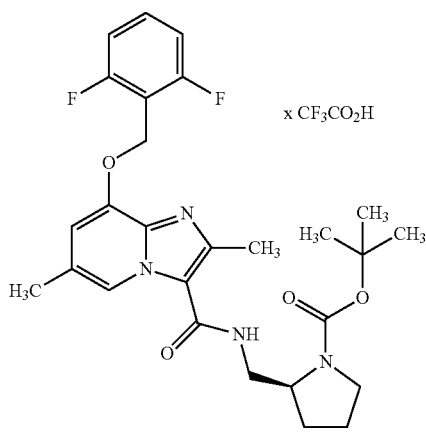 [SMILES: Cc1cc(OCc2c(F)cccc2F)c2nc(C)c(C(=O)NC[C@@H]3CCCN3C(=O)OC(C)(C)C)n2c1]

75 mg of 8-[(2,6-difluorobenzyl)oxy]-2,6-dimethylimidazo[1,2-a]pyridine-3-carboxylic acid (Example 21A, 0.23 mmol, 1 equivalent), 90 mg of O-(7-azabenzotriazol-1-yl)-N,N,N'N'-tetramethyluronium hexafluorophosphate (HATU, 0.24 mmol, 1.05 equivalents) and 88 mg of N,N-diisopropylethylamine (0.12 ml, 0.68 mmol, 3 equivalents) were initially charged in 1.4 ml of DMF and stirred at RT for 20 min. 50 mg (0.25 mmol, 1.1 equivalents) of tert-butyl (2S)-2-(aminomethyl)pyrrolidine-1-carboxylate were then added, and the mixture was stirred at RT overnight. The reaction solution was then diluted with water/TFA and purified by preparative HPLC (method: RP18 column, mobile phase: acetonitrile/water gradient with addition of 0.1% TFA). This gave 143 mg (99% of theory; purity 98%) of the title compound.

LC-MS (Method 2): $R_t$=1.02 min
MS (ESpos): m/z=515.3 (M−TFA+H)$^+$

Example 193A tert-Butyl (2R)-2-{[({8-[(2,6-difluorobenzyl)oxy]-2,6-dimethylimidazo[1,2-a]pyridin-3-yl}-carbonyl)amino]methyl}pyrrolidin-1-carboxylate trifluoroacetate

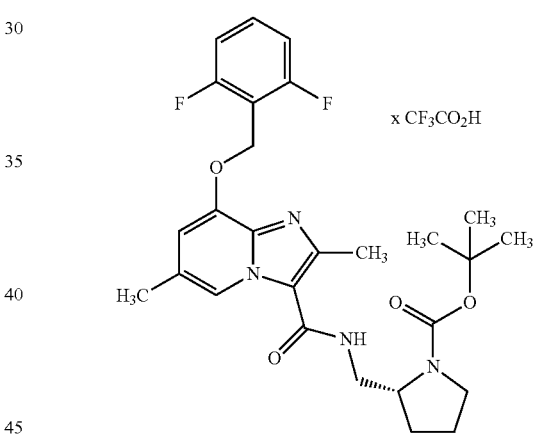

LC-MS (Method 7): $R_t$=1.27 min 75 mg of 8-[(2,6-difluorobenzyl)oxy]-2,6-dimethylimidazo[1,2-a]pyridine-3-carboxylic acid (Example 21A, 0.23 mmol, 1 equivalent), 90 mg of O-(7-azabenzotriazol-1-yl)-N,N,N'N'-tetramethyluronium hexafluorophosphate (HATU, 0.24 mmol, 1.05 equivalents) and 88 mg of N,N-diisopropylethylamine (0.12 ml, 0.68 mmol, 3 equivalents) were initially charged in 1.4 ml of DMF and stirred at RT for 20 min. 50 mg (0.25 mmol, 1.1 equivalents) of tert-butyl (2R)-2-(aminomethyl)pyrrolidine-1-carboxylate were then added, and the mixture was stirred at RT overnight. The reaction solution was diluted with water/TFA and purified by preparative HPLC (method: RP 18 column, mobile phase: acetonitrile/water gradient with addition of 0.1% TFA). This gave 108 mg (76% of theory; purity 100%) of the title compound.

LC-MS (Method 2): $R_t$=1.02 min
MS (ESpos): m/z=515.3 (M−TFA+H)$^+$

Example 194A

8-[(2,6-Difluorobenzyl)oxy]-2-methyl-N-(2-oxoethyl)imidazo[1,2-a]pyridine-3-carboxamide

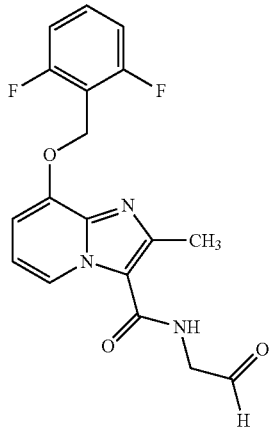 [SMILES: Cc1nc2c(OCc3c(F)cccc3F)cccn2c1C(=O)NCC=O]

Under argon, 1.65 g 1,1,1-triacetoxy-1lambda⁵,2-benziodoxol-3(1H)-one (Dess-Martin periodinane, 3.9 mmol, 1.5 equivalents) were initially charged in 20 ml of dichloromethane. At −25° C., a solution of 1 g of 8-[(2,6-difluorobenzyl)oxy]-N-(2-hydroxyethyl)-2-methylimidazo-[1,2-a]pyridine-3-carboxamide (Example 175A, 2.6 mmol, 1 equivalent) in 32 ml of dichloromethane was slowly added dropwise. The reaction mixture was stirred overnight, warming to RT. The reaction solution was then diluted with about 160 ml of ethyl acetate and washed three times with 1 N aqueous sodium hydroxide solution. The organic phase was washed with saturated aqueous sodium chloride solution until neutral, dried over sodium sulphate, filtered and concentrated. This gave 879 mg (47% of theory; purity about 50%) of the title compound which was reacted further without purification.

LC-MS (Method 2): $R_t$=0.56 min
MS (ESneg): m/z=358 (M−H)⁻

Example 195A

8-[(2,6-Difluorobenzyl)oxy]-2-methyl-N-[(2R)-1-oxopropan-2-yl]imidazo[1,2-a]pyridine-3-carboxamide

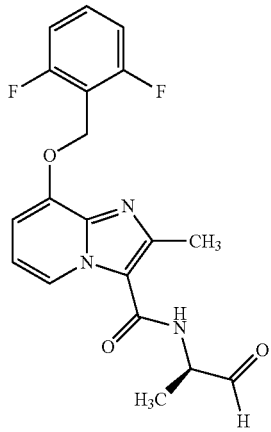 [SMILES: Cc1nc2c(OCc3c(F)cccc3F)cccn2c1C(=O)N[C@H](C)C=O]

Analogously to Example 194A, 500 mg of 8-[(2,6-difluorobenzyl)oxy]-N-[(2R)-1-hydroxypropan-2-yl]-2-methylimidazo[1,2-a]pyridine-3-carboxamide (Example 177A, 1.33 mmol) were oxidized with 847 mg (2.0 mmol) of Dess-Martin periodinane with addition of 0.11 ml of pyridine (105 mg, 1.33 mmol) and worked up. This gave 440 mg (53% of theory; purity 60%) of the title compound which was reacted further without purification.

LC-MS (Method 2): $R_t$=0.64 min
MS (ESneg): m/z=372.1 (M−H)⁺

Example 196A

8-[(2,6-Difluorobenzyl)oxy]-2-methyl-N-[(2S)-1-oxopropan-2-yl]imidazo[1,2-a]pyridine-3-carboxamide

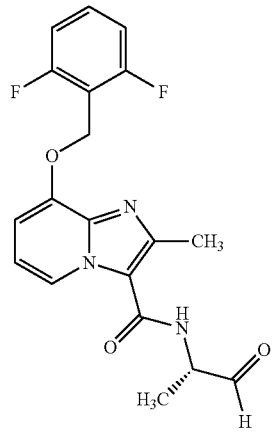 [SMILES: Cc1nc2c(OCc3c(F)cccc3F)cccn2c1C(=O)N[C@@H](C)C=O]

Analogously to Example 194A, 500 mg of 8-[(2,6-difluorobenzyl)oxy]-N-[(2S)-1-hydroxypropan-2-yl]-2-methylimidazo[1,2-a]pyridine-3-carboxamide (Example 178A, 1.33 mmol, 1 equivalent) were oxidized with Dess-Martin periodinane with addition of 0.11 ml of pyridine (105 mg, 1.33 mmol, 1 equivalent) and worked up. This gave 439 mg (53% of theory; purity 60%) of the title compound which was reacted further without purification.

LC-MS (Method 5): $R_t$=1.49 min
MS (ESneg): m/z=372.1 (M−H)⁺

Example 197A ent-tert-Butyl {2-(3,4-difluorophenyl)-2-[({8-[(2-fluorobenzyl)oxy]-2-methylimidazo[1,2-a]-pyridin-3-yl}carbonyl)amino]ethyl}carbamate

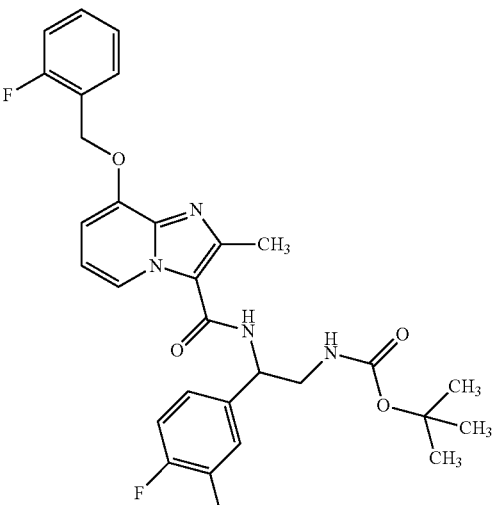

200 mg of ent-tert-butyl [2-(3,4-difluorophenyl)-2-{[(8-hydroxy-2-methylimidazo[1,2-a]pyridin-3-yl)carbonyl]amino}ethyl]carbamate (Example 131A, 0.45 mmol, 1 equivalent), 93 mg of 2-fluorobenzyl bromide (0.49 mmol, 1.1 equivalents) and 321 mg of caesium carbonate (0.99 mmol, 2.2 equivalents) in 10 ml of DMF were stirred at RT overnight. 150 ml of water were then added, and the mixture was stirred at RT for 15 min. The precipitated product was filtered off and dried under reduced pressure. This gave 190 mg (79% of theory; purity 91%) of the title compound.

LC-MS (Method 1): $R_t$=1.06 min
MS (ESpos): m/z=555.3 (M+H)$^+$
$^1$H NMR (400 MHz, DMSO-d$_6$): δ=1.33 (s, 9H), 2.58 (s, 3H), 3.37-3.47 (m, 2H), 5.10-5.22 (m, 1H), 5.32 (s, 2H), 6.89 (t, 1H), 6.97 (d, 1H), 7.08 (t, 1H), 7.20-7.34 (m, 3H), 7.37-7.52 (m, 3H), 7.61 (t, 1H), 8.22 (d, 1H), 8.53 (d, 1H).

The examples shown in Table 14A were prepared analogously to Example 197A by reacting ent-tert-butyl [2-(3,4-difluorophenyl)-2-{[(8-hydroxy-2-methylimidazo[1,2-a]pyridin-3-yl)carbonyl]-amino}ethyl]carbamate (Example 131A) with the appropriate commercially available benzyl bromides:

TABLE 14A

| Example | IUPAC name/structure (yield) | Analytical data |
|---|---|---|
| 198A | ent-tert-butyl {2-[({8-[(2,3-difluorobenzyl)oxy]-2-methylimidazo[1,2-a]pyridin-3-yl}carbonyl)amino]-2-(3,4-difluorophenyl)ethyl}carbamate 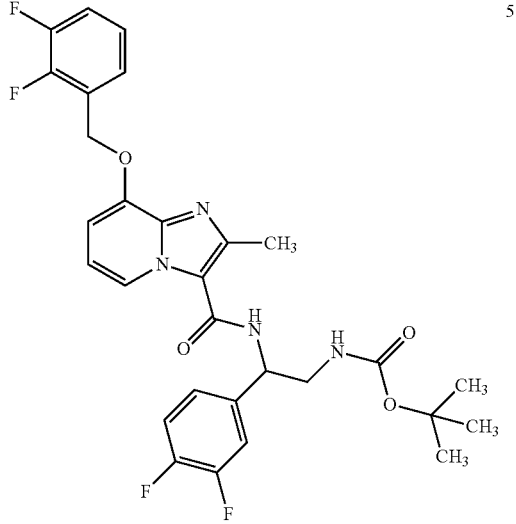 (86% of theory; purity 85%) | LC-MS (Method 1): $R_t$ = 1.33 min<br>MS (ESpos): m/z = 573.1 (M + H)$^+$<br>$^1$H NMR (400 MHz, DMSO-d$_6$):<br>δ = 1.33 (s, 9H), 2.60 (s, 3H), 3.37-3.47 (m, 2H), 5.11-5.20 (m, 1H), 5.39 (s, 2H), 6.90 (t, 1H), 6.98 (d, 1H), 7.09 (t, 1H), 7.21-7.33 (m, 2H), 7.37-7.55 (m, 4H), 8.23 (d, 1 H), 8.54 (d, 1H). |

TABLE 14A-continued

| Example | IUPAC name/structure (yield) | Analytical data |
|---|---|---|
| 199A | ent-tert-butyl {2-(3,4-difluorophenyl)-2-[({2-methyl-8-[(2,3,6-trifluorobenzyl)oxy]imidazo[1,2-a]pyridin-3-yl}carbonyl)amino]ethyl}carbamate<br>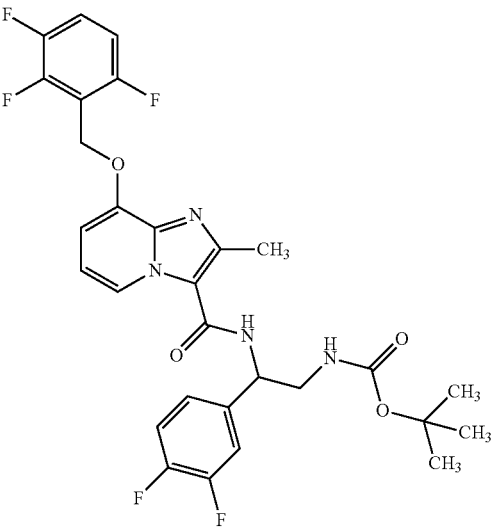<br>(94% of theory; purity 100%) | LC-MS (Method 1): $R_t$ = 1.33 min<br>MS (ESpos): m/z = 591.1 (M + H)$^+$<br>$^1$H NMR (400 MHz, DMSO-$d_6$):<br>δ = 1.32 (s, 9H), 2.58 (s, 3H), 3.37-3.46 (m, 2H), 5.11-5.20 (m, 1H), 5.35 (s, 2H), 6.92 (t, 1H), 7.02 (d, 1H), 7.08 (t, 1H), 7.19-7.33 (m, 2H), 7.35-7.52 (m, 2H), 7.60-7.72 (m, 1 H), 8.22 (d, 1H), 8.56 (d, 1H). |
| 200A | ent-tert-butyl {2-(3,4-difluorophenyl)-2-[({2-methyl-8-[(2,4,6-trifluorobenzyl)oxy]imidazo[1,2-a]pyridin-3-yl}carbonyl)amino]ethyl}carbamate<br>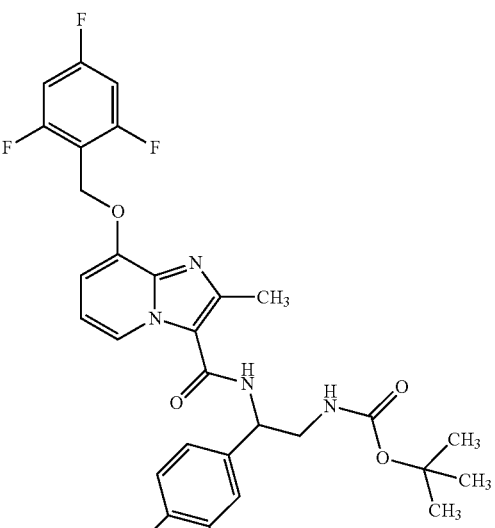<br>(76% of theory; purity 90%) | LC-MS (Method 1): $R_t$ = 1.33 min<br>MS (ESpos): m/z = 591.1 (M + H)$^+$<br>$^1$H NMR (400 MHz, DMSO-$d_6$):<br>δ = 1.32 (s, 9H), 2.58 (s, 3H), 3.37-3.46 (m, 2H), 5.11-5.20 (m, 1H), 5.27 (s, 2H), 6.92 (t, 1H), 7.01 (d, 1H), 7.09 (t, 1H), 7.21-7.27 (m, 1H), 7.30-7.50 (m, 4H), 8.21 (d, 1H), 8.55 (d, 1H). |

TABLE 14A-continued

| Example | IUPAC name/structure (yield) | Analytical data |
|---|---|---|
| 201A | ent-tert-butyl {2-[({8-[(2-chloro-6-fluorobenzyl)oxy]-2-methylimidazo[1,2-a]pyridin-3-yl}carbonyl)amino]-2-(3,4-difluorophenyl)ethyl}carbamate<br><br>(85% of theory; purity 90%) | LC-MS (Method 1): $R_t$ = 1.36 min<br>MS (ESpos): m/z = 589.1 (M + H)$^+$<br>$^1$H NMR (400 MHz, DMSO-d$_6$): δ = 1.33 (s, 9H), 2.58 (s, 3H), 3.36-3.46 (m, 2H), 5.11-5.20 (m, 1H), 5.33 (s, 2H), 6.92 (t, 1H), 7.01-7.12 (m, 2H), 7.21-7.27 (m, 1H), 7.33-7.51 (m, 4H), 7.54-7.62 (m, 1H), 8.21 (d, 1H), 8.54 (d, 1H). |

Example 202A ent-tert-Butyl 4-[({8-[(2,6-difluorobenzyl)oxy]-2-methylimidazo[1,2-a]pyridin-3-yl}carbonyl)-amino]-6-fluoro-3,4-dihydroquinoline-1(2H)-carboxylate (Enantiomer A)

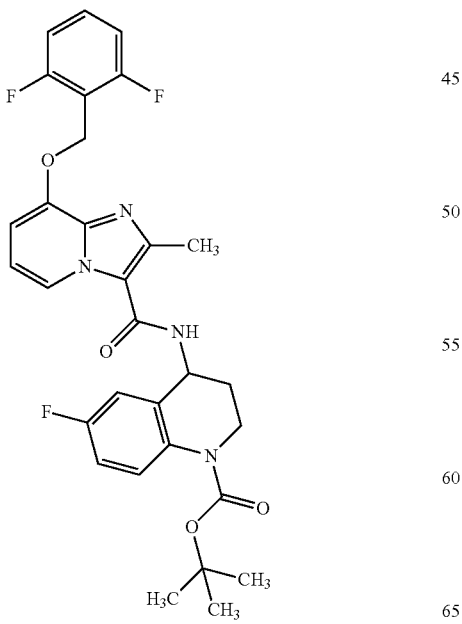

198 mg of Example 172A were separated into the enantiomers on a chiral phase [column: Daicel Chiralpak AD-H, 5 μm, 250×20 mm, mobile phase: 25% isohexane, 75% ethanol, flow rate: 15 ml/min; 40° C., detection: 220 nm].

Yield: Enantiomer A: 76 mg (99% ee)

Enantiomer A: R$_t$=4.20 min [Daicel Chiralpak AD-H, 5 μm, 250×4.6 mm, mobile phase: 25% isohexane, 75% ethanol, flow rate: 1 ml/min; 40° C., detection: 220 nm].

Example 203A ent-tert-Butyl 4-[({8-[(2,6-difluorobenzyl)oxy]-2-methylimidazo[1,2-a]pyridin-3-yl}carbonyl)-amino]-6-fluoro-3,4-dihydroquinoline-1(2H)-carboxylate
(Enantiomer B)

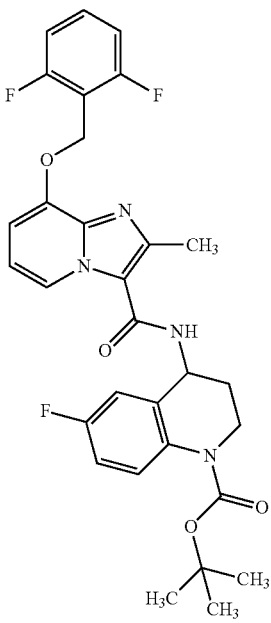 [SMILES: Cc1nc2c(OCc3c(F)cccc3F)cccn2c1C(=O)NC1CCN(C(=O)OC(C)(C)C)c2ccc(F)cc21]

198 mg of Example 172A were separated into the enantiomers on a chiral phase [column: Daicel Chiralpak AD-H, 5 μm, 250×20 mm, mobile phase: 25% isohexane, 75% ethanol, flow rate: 15 ml/min; 40° C., detection: 220 nm].

Yield enantiomer B: 76 mg (99% ee)

Enantiomer B: R$_t$=9.13 min [Daicel Chiralpak AD-H, 5 μm, 250×4.6 mm, mobile phase: 25% isohexane, 75% ethanol, flow rate: 1 ml/min; 40° C., detection: 220 nm].

Example 204A ent-tert-Butyl 4-[({6-chloro-8-[(2,6-difluorobenzyl)oxy]-2-methylimidazo[1,2-a]pyridin-3-yl}-carbonyl)amino]-3,4-dihydroquinoline-1 (2H)carboxylate
(Enantiomer A)

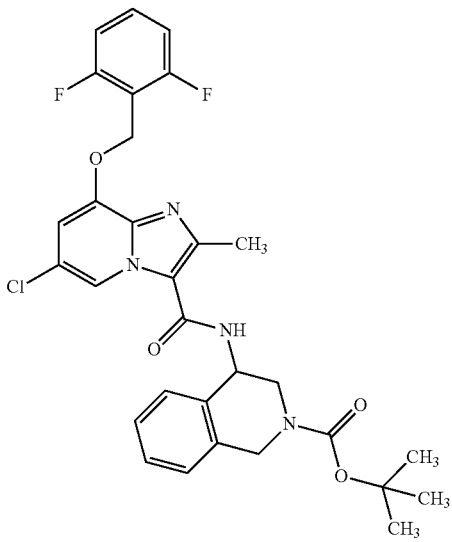 [SMILES: Cc1nc2c(OCc3c(F)cccc3F)cc(Cl)cn2c1C(=O)NC1CN(C(=O)OC(C)(C)C)Cc2ccccc21]

190 mg of Example 180A were separated into the enantiomers on a chiral phase [column: Daicel Chiralpak OZ-H, 5 μm, 250×20 mm, mobile phase: 30% isohexane, 70% ethanol+0.2% diethylamine, flow rate: 15 ml/min; 40° C., detection: 220 nm].

Yield: Enantiomer A: 64 mg (99% ee)

Enantiomer A: R$_t$=4.84 min [Daicel Chiralpak OZ-H, 5 μm, 250×4.6 mm, mobile phase: 30% isohexane, 70% ethanol+0.2% diethylamine, flow rate: 1 ml/min; 40° C., detection: 220 nm].

Example 205A ent-tert-Butyl 4-[({6-chloro-8-[(2,6-difluorobenzyl)oxy]-2-methylimidazo[1,2-a]pyridin-3-yl}-carbonyl)amino]-3,4-dihydroquinoline-1(2H)carboxylate
(Enantiomer B)

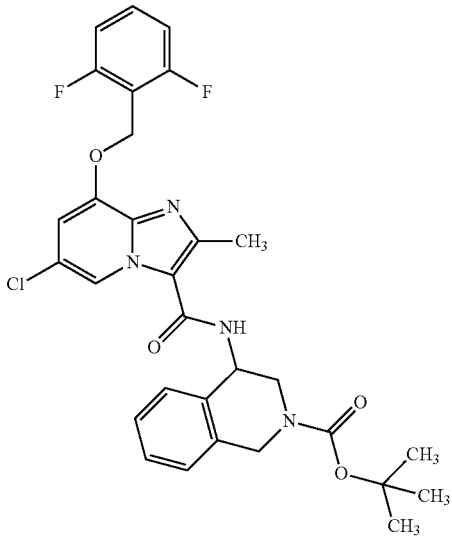 [SMILES: Cc1nc2c(OCc3c(F)cccc3F)cc(Cl)cn2c1C(=O)NC1CN(C(=O)OC(C)(C)C)Cc2ccccc21]

190 mg of Example 180A were separated into the enantiomers on a chiral phase [column: Daicel Chiralpak OZ-H, 5 μm, 250×20 mm, mobile phase: 30% isohexane, 70% ethanol+0.2% diethylamine, flow rate: 15 ml/min; 40° C., detection: 220 nm].

Yield: Enantiomer B: 65 mg (99% ee)

Enantiomer B: $R_t$=5.62 min [Daicel Chiralpak OZ-H, 5 μm, 250×4.6 mm, mobile phase: 30% isohexane, 70% ethanol+0.2% diethylamine, flow rate: 1 ml/min; 40° C., detection: 220 nm].

Example 206A ent-tert-Butyl 4-[({8-[(2,6-difluorobenzyl)oxy]-2-methylimidazo[1,2-a]pyridin-3-yl}carbonyl)-amino]-3,4-dihydroquinoline-1 (2H)-carboxylate
(Enantiomer A)

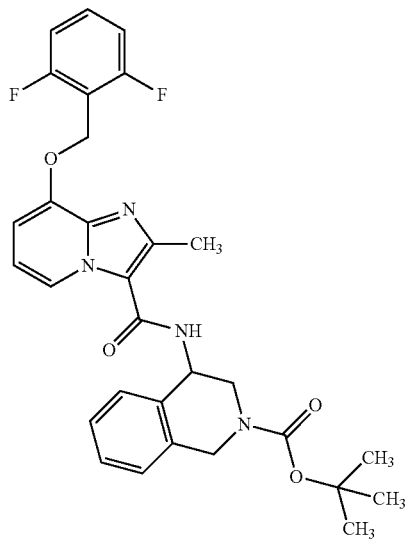 [SMILES: Cc1nc2c(OCc3c(F)cccc3F)cccn2c1C(=O)NC1CN(C(=O)OC(C)(C)C)Cc2ccccc21]

188 mg of Example 173A were separated into the enantiomers on a chiral phase [column: Daicel Chiralpak OZ-H, 5 μm, 250×20 mm, mobile phase: 25% isohexane, 75% ethanol+0.2% diethylamine, flow rate: 15 ml/min; 40° C., detection: 220 nm].

Yield enantiomer A: 80 mg (99% ee)

Enantiomer A: $R_t$=7.44 min [Daicel Chiralpak OZ-H, 5 μm, 250×4.6 mm, mobile phase: 25% isohexane, 75% ethanol+0.2% diethylamine, flow rate: 1.0 ml/min; 40° C., detection: 220 nm].

Example 207A ent-tert-Butyl 4-[({8-[(2,6-difluorobenzyl)oxy]-2-methylimidazo[1,2-a]pyridin-3-yl}carbonyl)-amino]-3,4-dihydroquinoline-1 (2H)-carboxylate
(Enantiomer B)

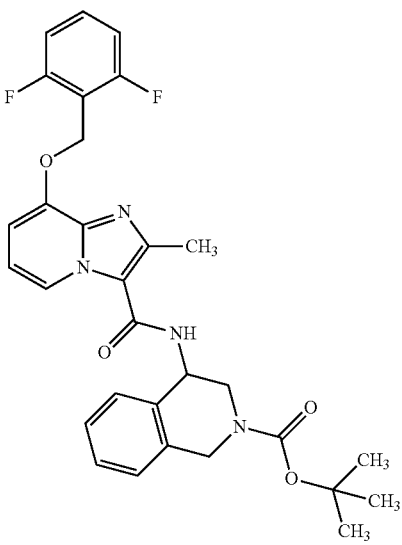 [SMILES: Cc1nc2c(OCc3c(F)cccc3F)cccn2c1C(=O)NC1CN(C(=O)OC(C)(C)C)Cc2ccccc21]

188 mg of Example 173A were separated into the enantiomers on a chiral phase [column: Daicel Chiralpak OZ-H, 5 μm, 250×20 mm, mobile phase: 25% isohexane, 75% ethanol+0.2% diethylamine, flow rate: 15 ml/min; 40° C., detection: 220 nm].

Yield enantiomer B: 81 mg (99% ee)

Enantiomer B: 10.05 min [Daicel Chiralpak OZ-H, 5 μm, 250×4.6 mm, mobile phase: 25% isohexane, 75% ethanol+0.2% diethylamine, flow rate: 1.0 ml/min; 40° C., detection: 220 nm].

Example 208A ent-tert-Butyl 4-[({8-[(2,6-difluorobenzyl)oxy]-2-methylimidazo[1,2-a]pyridin-3-yl}carbonyl)-amino]-6-(trifluoromethyl)-3,4-dihydroquinoline-1(2H)-carboxylate (Enantiomer A)

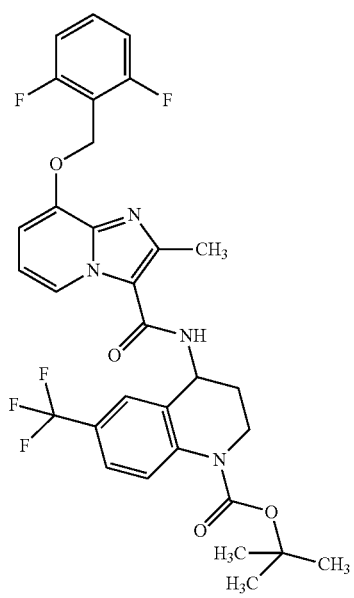 [SMILES: Cc1nc2c(OCc3c(F)cccc3F)cccn2c1C(=O)NC1CCN(C(=O)OC(C)(C)C)c2ccc(C(F)(F)F)cc21]

149 mg of Example 174A were separated into the enantiomers on a chiral phase [column: Daicel Chiralpak AD-H, 5 μm, 250×20 mm, mobile phase: 50% isohexane, 50% isopropanol, flow rate: 20 ml/min; 25° C., detection: 230 nm].

Yield enantiomer A: 56 mg (100% ee)

Enantiomer A: $R_t$=3.90 min [Daicel Chiralpak AD-H, 5 m, 250×4.6 mm; mobile phase: 50% isohexane, 50% isopropanol; flow rate 1.0 ml/min; 25° C.; detection: 220 nm].

Example 209A ent-tert-Butyl 4-[({8-[(2,6-difluorobenzyl)oxy]-2-methylimidazo[1,2-a]pyridin-3-yl}carbonyl)-amino]-6-(trifluoromethyl)-3,4-dihydroquinoline-1(2H)-carboxylate (Enantiomer B)

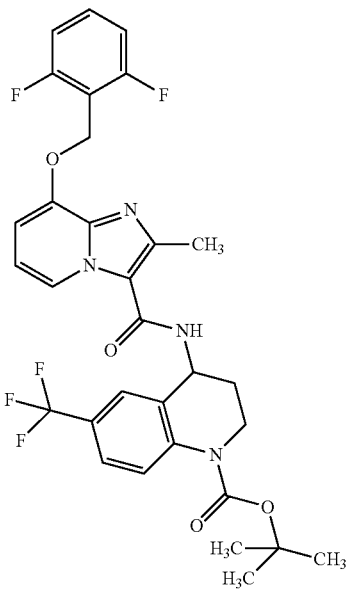 [SMILES: Cc1nc2c(OCc3c(F)cccc3F)cccn2c1C(=O)NC1CCN(C(=O)OC(C)(C)C)c2ccc(C(F)(F)F)cc21]

149 mg of Example 174A were separated into the enantiomers on a chiral phase [column: Daicel Chiralpak AD-H, 5 μm, 250×20 mm, mobile phase: 50% isohexane, 50% isopropanol, flow rate: 20 ml/min; 25° C., detection: 230 nm].

Yield enantiomer B: 55 mg (100% ee)

Enantiomer B: $R_t$=7.60 min [Daicel Chiralpak AD-H, 5 m, 250×4.6 mm; mobile phase: 50% isohexane, 50% isopropanol; flow rate 1.0 ml/min; 25° C.; detection: 220 nm].

Example 210A ent-Benzyl {2-[({8-[(2,6-difluorobenzyl)oxy]-2-methylimidazo[1,2-a]pyridin-3-yl}carbonyl)-amino]-3-methoxypropyl}carbamate (Enantiomer A)

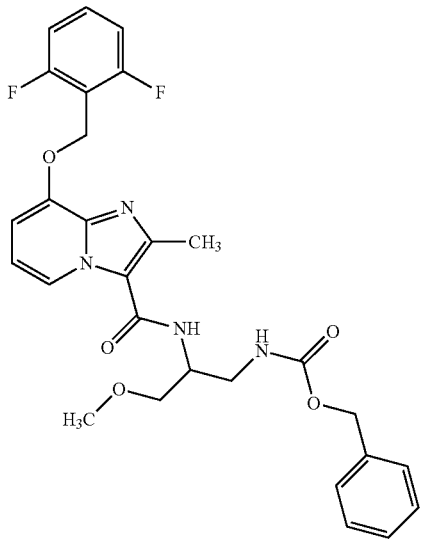 [SMILES: COCC(CNC(=O)OCc1ccccc1)NC(=O)c1c(C)nc2c(OCc3c(F)cccc3F)cccn12]

290 mg of Example 186A were dissolved in 3.5 ml of ethanol and separated into the enantiomers on a chiral phase [column: Daicel Chiralpak OD-H, 5 μm, 250×20 mm, mobile phase: 50% isohexane, 50% ethanol, flow rate: 20 ml/min; 25° C., detection: 220 nm].

Yield enantiomer A: 58 mg (100% ee)

Enantiomer A: $R_f$=5.47 min [Daicel Chiralpak OD-H, 5 m, 250×4.6 mm; mobile phase: 50% isohexane, 50% ethanol; flow rate 1.0 ml/min; 30° C.; detection: 220 nm].

$^1$H NMR (400 MHz, DMSO-$d_6$): δ=2.55 (s, 3H; obscured by DMSO signal), 3.20-3.35 (m, 2H), 3.25 (s, 3H), 3.39-3.49 (m, 2H), 4.20-4.31 (m, 1H), 5.00 (s, 2H), 5.31 (s, 2H), 6.90 (t, 1H), 7.00 (d, 1H), 7.20-7.30 (m, 7H), 7.40 (t, 1H), 7.52 (d, 1H), 7.54-7.64 (m, 1H), 8.60 (d, 1H).

Example 211A ent-Benzyl {2-[({8-[(2,6-difluorobenzyl)oxy]-2-methylimidazo[1,2-a]pyridin-3-yl}carbonyl)-amino]-3-methoxypropyl}carbamate (Enantiomer B)

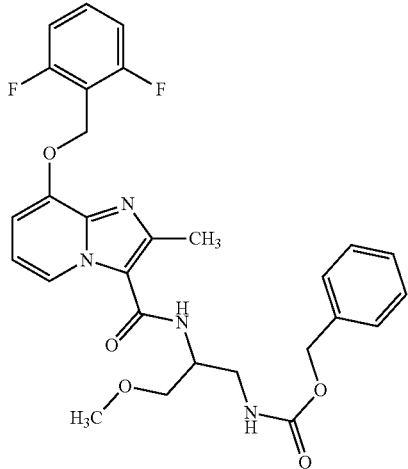 [SMILES: COCC(CNC(=O)OCc1ccccc1)NC(=O)c1c(C)nc2c(OCc3c(F)cccc3F)cccn12]

290 mg of Example 186A were dissolved in 3.5 ml of ethanol and separated into the enantiomers on a chiral phase [column: Daicel Chiralpak OD-H, 5 μm, 250×20 mm, mobile phase: 50% isohexane, 50% ethanol, flow rate: 20 ml/min; 25° C., detection: 220 nm].

Yield enantiomer B: 53 mg (95% ee)

Enantiomer B: $R_f$=6.998 min [Daicel Chiralpak OD-H, 5 m, 250×4.6 mm; mobile phase: 50% isohexane, 50% ethanol; flow rate 1.0 ml/min; 30° C.; detection: 220 nm].

Example 212A ent-Benzyl {2-[({8-[(2,6-difluorobenzyl)oxy]-2-methylimidazo[1,2-a]pyridin-3-yl}carbonyl)-amino]-3-(3,4-difluorophenoxy)propyl}carbamate (Enantiomer B)

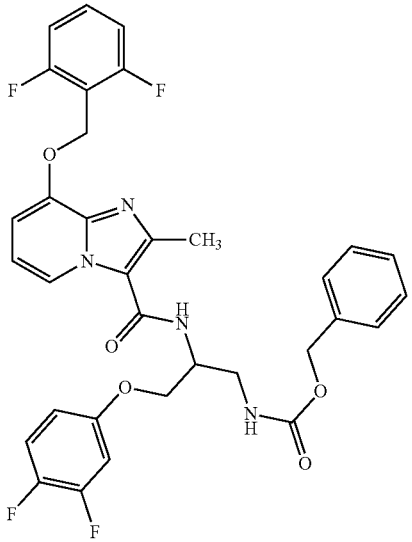 [SMILES: Cc1nc2c(OCc3c(F)cccc3F)cccn2c1C(=O)NC(CNC(=O)OCc1ccccc1)COc1ccc(F)c(F)c1]

350 mg of Example 187A were separated into the enantiomers on a chiral phase [column: Daicel Chiralpak AH-H, 5 μm, 250×20 mm, mobile phase: 25% isohexane, 75% ethanol, flow rate: 15 ml/min; 45° C., detection: 220 nm].

Yield enantiomer B: 110 mg (99% ee)

Enantiomer B: $R_f$=7.66 min [Daicel Chiralcel OD-H, 5 m, 250×4.6 mm; mobile phase: 50% isohexane, 50% ethanol; flow rate 1.0 ml/min; 40° C.; detection: 220 nm].

Example 213A ent-tert-Butyl {3-[({8-[(2,6-difluorobenzyl)oxy]-2-methylimidazo[1,2-a]pyridin-3-yl}carbonyl)-amino]-2-methylpropyl}carbamate (Enantiomer A)

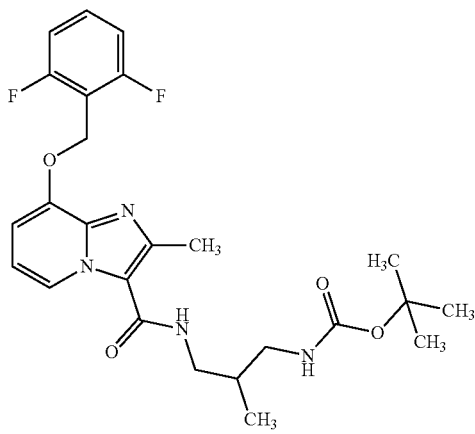 [SMILES: Cc1nc2c(OCc3c(F)cccc3F)cccn2c1C(=O)NCC(C)CNC(=O)OC(C)(C)C]

192 mg of Example 185A were separated into the enantiomers on a chiral phase [column: Daicel Chiralpak AD-H, 5 μm, 250×20 mm, mobile phase: 70% isohexane, 15% ethanol, 15% isopropanol, flow rate: 25 ml/min; 40° C., detection: 210 nm].

Yield enantiomer A: 68 mg (100% ee)

Enantiomer A: $R_t$=8.65 min [Daicel Chiralpak AD-H, 5 μm, 250×4.6 mm, mobile phase: 70% isohexane, 15% ethanol, 15% isopropanol, flow rate: 1.5 ml/min; 30° C., detection: 220 nm].

Example 214A ent-tert-Butyl {3-[({8-[(2,6-difluorobenzyl)oxy]-2-methylimidazo[1,2-a]pyridin-3-yl}carbonyl)-amino]-2-methylpropyl}carbamate (Enantiomer B)

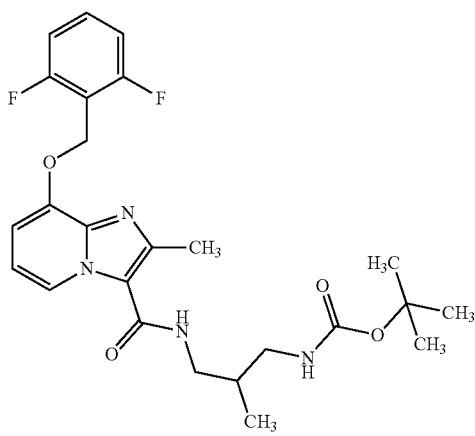 [SMILES: Cc1nc2c(OCc3c(F)cccc3F)cccn2c1C(=O)NCC(C)CNC(=O)OC(C)(C)C]

195 mg of Example 185A were separated into the enantiomers on a chiral phase [column: Daicel Chiralpak AD-H, 5 μm, 250×20 mm, mobile phase: 70% isohexane, 15% ethanol, 15% isopropanol, flow rate: 25 ml/min; 40° C., detection: 210 nm].

Yield enantiomer B: 79 mg (87% ee)

Enantiomer B: 9.24 min [Daicel Chiralpak AD-H, 5 μm, 250×4.6 mm, mobile phase: 70% isohexane, 15% ethanol, 15% isopropanol, flow rate: 1.5 ml/min; 30° C., detection: 220 nm].

Example 215A ent-Benzyl {1-[({8-[(2,6-difluorobenzyl)oxy]-2-methylimidazo[1,2-a]pyridin-3-yl}carbonyl)-amino]-4,4,4-trifluorobutan-2-yl}carbamate (Enantiomer A)

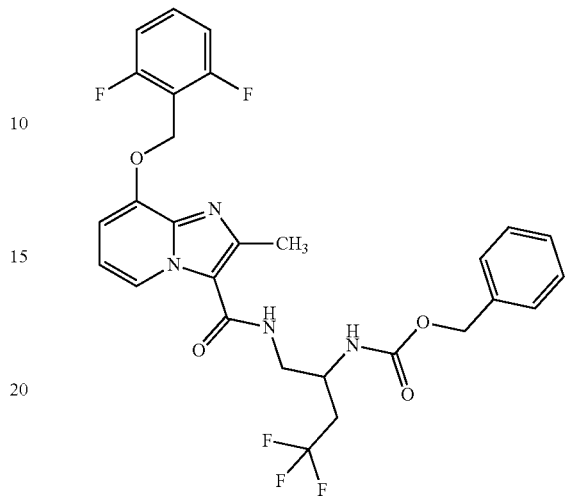

280 mg of Example 189A were separated into the enantiomers on a chiral phase [column: Daicel Chiralpak AZ-H, 5 μm, 250×20 mm, mobile phase: 50% isohexane, 50% ethanol, flow rate: 18 ml/min; 40° C., detection: 210 nm].

Yield enantiomer A: 80 mg (100% ee)

Enantiomer A: $R_t$=8.79 min [Daicel Chiralpak AZ-H, 5 μm, 250×4.6 mm, mobile phase: 50% isohexane, 50% ethanol, flow rate: 1.0 ml/min; 30° C., detection: 220 nm].

Example 216A ent-Benzyl {1-[({8-[(2,6-difluorobenzyl)oxy]-2-methylimidazo[1,2-a]pyridin-3-yl}carbonyl)-amino]-4,4,4-trifluorobutan-2-yl}carbamate (Enantiomer B)

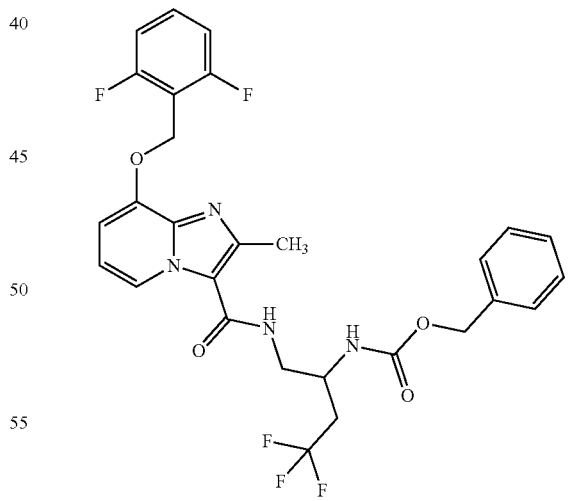

280 mg of Example 189A were separated into the enantiomers on a chiral phase [column: Daicel Chiralpak AZ-H, 5 μm, 250×20 mm, mobile phase: 50% isohexane, 50% ethanol, flow rate: 18 ml/min; 40° C., detection: 210 nm].

Yield enantiomer B: 94 mg (99% ee)

Enantiomer B: $R_t$=11.63 min [Daicel Chiralpak AZ-H, 5 μm, 250×4.6 mm, mobile phase: 50% isohexane, 50% ethanol, flow rate: 1.0 ml/min; 30° C., detection: 220 nm].

Example 217A ent-Benzyl {1-[({8-[(2,6-difluorobenzyl)oxy]-2,6-dimethylimidazo[1,2-a]pyridin-3-yl}carbonyl)-amino]-4,4,4-trifluorobutan-2-yl}carbamate
(Enantiomer A)

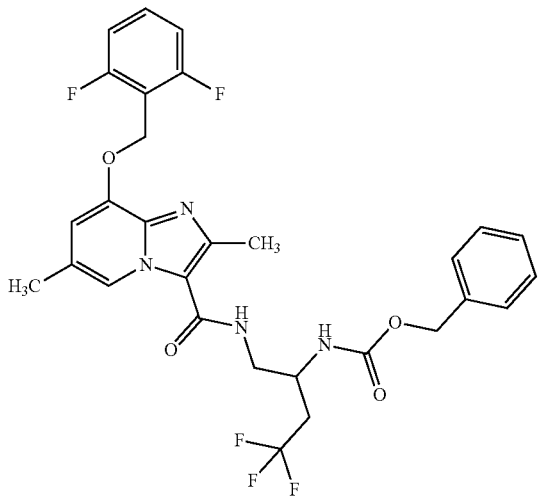 [SMILES: Cc1cc(OCc2c(F)cccc2F)c2nc(C)c(C(=O)NCC(CC(F)(F)F)NC(=O)OCc3ccccc3)n2c1]

260 mg of Example 190A were separated into the enantiomers on a chiral phase [column: Daicel Chiralpak AD-H, 5 µm, 250×20 mm, mobile phase: 50% isohexane, 50% isopropanol, flow rate: 15 ml/min; 40° C., detection: 220 nm].

Yield enantiomer A: 85 mg (>99% ee)

Enantiomer A: $R_t$=4.81 min [Daicel Chiralpak AD-H, 5 µm, 250×4.6 mm, mobile phase: 50% isohexane, 50% isopropanol+0.2% TFA+1% water, flow rate: 1.0 ml/min; 45° C., detection: 220 nm].

Example 218A ent-Benzyl {1-[({8-[(2,6-difluorobenzyl)oxy]-2,6-dimethylimidazo[1,2-a]pyridin-3-yl}carbonyl)-amino]-4,4,4-trifluorobutan-2-yl}carbamate
(Enantiomer B)

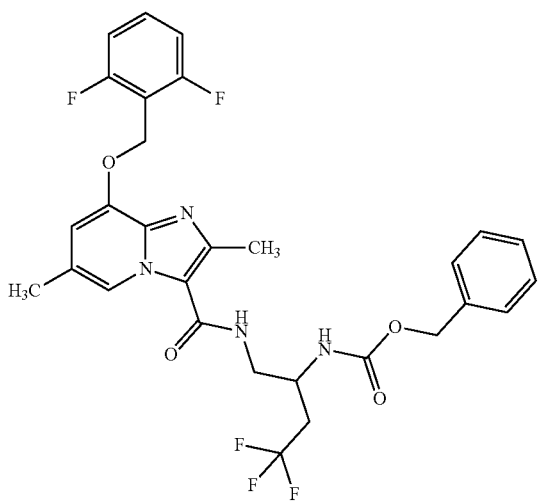 [SMILES: Cc1cc(OCc2c(F)cccc2F)c2nc(C)c(C(=O)NCC(CC(F)(F)F)NC(=O)OCc3ccccc3)n2c1]

260 mg of Example 190A were separated into the enantiomers on a chiral phase [column: Daicel Chiralpak AD-H, 5 µm, 250×20 mm, mobile phase: 50% isohexane, 50% isopropanol, flow rate: 15 ml/min; 40° C., detection: 220 nm].

Yield enantiomer B: 92 mg (99% ee)

Enantiomer B: $R_t$=6.59 min [Daicel Chiralpak AD-H, 5 µm, 250×4.6 mm, mobile phase: 50% isohexane, 50% isopropanol+0.2% TFA+1% water, flow rate: 1.0 ml/min; 45° C., detection: 220 nm].

Example 219A 1-(Azetidin-3-yl)pyrrolidine dihydrochloride

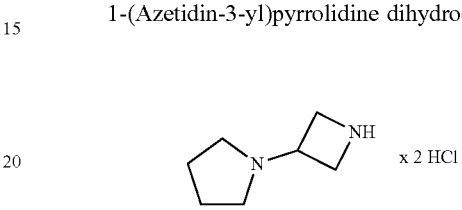

1.00 g (4.42 mmol) of tert-butyl 3-(pyrrolidin-1-yl)azetidin-1-carboxylate was initially charged in 5.3 ml of 1,4-dioxane, 5.3 ml of 4 N hydrochloric acid in 1,4-dioxane were added and the mixture was stirred at RT overnight. The reaction mixture was then concentrated, foamed with dichloromethane and dried under high vacuum. This gave 950 mg (99% of theory; purity 92%) of the title compound.

$^1$H NMR (400 MHz, DMSO-$d_6$): δ=1.82-1.94 (m, 2H), 1.94-2.05 (m, 2H), 2.89-3.00 (m, 2H), 4.07-4.19 (m, 2H), 4.28-4.42 (m, 3H), 9.11 (br. s, 1H), 9.49 (br. s, 1H), 12.33 (br. s, 1H).

Example 220A tert-Butyl {2-[3-(pyrrolidin-1-yl)azetidin-1-yl]ethyl}carbamate

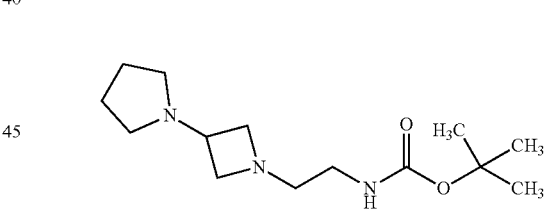

595 mg of 1-(azetidin-3-yl)pyrrolidine dihydrochloride (Example 219A, 2.75 mmol, purity about 92%, 1 equivalent) were reacted in 3 batches. To obtain the free base, the 1-(azetidin-3-yl)pyrrolidine dihydrochloride was passed over a StratoSpheres™ SPE column. To this end, the column was initially moistened with 1 ml of methanol. 1-(Azetidin-3-yl)pyrrolidine dihydrochloride, dissolved in 3 ml of methanol, was then passed over the column and the column was rinsed with 3 ml of methanol. The solution obtained was concentrated (the column retains about 0.9 mmol of salt). The free base was then initially charged in 26.8 ml of acetonitrile, 656 mg of 2-(Boc-amino)ethyl bromide (2.9 mmol, 1.05 equivalents) and 1.45 ml of N,N-diisopropylethylamine (8.25 mmol, 3 equivalents) were added and the mixture was stirred at 80° C. overnight. The reaction mixture was concentrated and purified by silica gel chromatography (mobile phase: cyclohexane/ethyl acetate 5:1; dichloromethane/methanol 10:1; dichloromethane/methanol 4:1 and dichloromethane/1 N ammonia in methanol 4:1). This gave 463 mg (67% of theory) of the title compound.
DCI-MS (Method 4): m/z=270.2 (M+H)⁺

Example 221A

2-[3-(Pyrrolidin-1-yl)azetidin-1-yl]ethanamine dihydrochloride

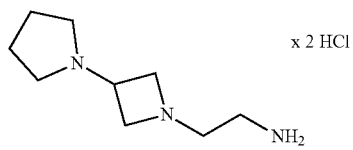 [SMILES: NCCN1CC(N2CCCC2)C1]

x 2 HCl 460 mg of tert-butyl {2-[3-(pyrrolidin-1-yl)azetidin-1-yl]ethyl}carbamate (Example 220A, 1.7 mmol, 1 equivalent) were initially charged in 8.54 ml of 2 N hydrochloric acid in diethyl ether and 1 ml of dioxane, and the mixture was stirred at RT overnight. The precipitated solid was filtered off, washed with diethyl ether and dried under reduced pressure. This gave 390 mg (94% of theory) of the title compound.
DCI-MS (Method 4): m/z=170.2 (M+H)⁺

Example 222A 1-(Aminomethyl)cyclobutanamine

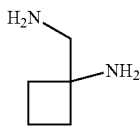

750 mg of 1-aminocyclobutanecarbonitrile (7.8 mmol, 1 equivalent) were initially charged in 16.5 ml of THF, under argon, 23.4 ml of 1 N lithium aluminium hydride solution in THF (23.4 mmol, 3 equivalents) were added dropwise at 0° C. and the mixture was stirred at RT for 3.5 h. Subsequently, 0.8 ml of water, 0.8 ml of 2 N aqueous sodium hydroxide solution and 1.6 ml of water were added to the reaction mixture in succession. The solid formed was filtered off and washed with methanol. The filtrate was concentrated. This gave 1980 mg (76% of theory; assumed purity 30%) of the title compound which was reacted further without purification.
FIA-MS (Method 10, ESpos): m/z=101 (M+H)⁺

Example 223A rac-4,4,4-Trifluorobutane-1,2-diamine dihydrochloride

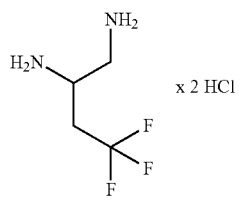

x 2 HCl 130 mg of rac-benzyl (1-amino-4,4,4-trifluorobutan-2-yl)carbamate trifluoroacetate (Example 147 A, 0.33 mmol, 1 equivalent) were initially charged in 8.4 ml of methanol, under argon, 35 mg (0.03 mmol) of 10% palladium on activated carbon were added and the mixture was hydrogenated at RT and atmospheric pressure overnight. The mixture was then filtered through a Millipore® filter, 0.33 ml of 2 N hydrochloric acid in diethyl ether (0.66 mmol, 2 equivalents) was added and the mixture was concentrated. This gave 72 mg (100% of theory) of the title compound.
FIA-MS (Method 10, ESpos): m/z=143.0 (M−2HCl+H)⁺

Example 224A rac-3-Isopropoxypropane-1,2-diamine dihydrochloride

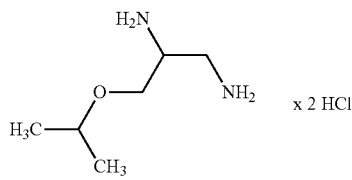

x 2 HCl

Under argon, 218 mg (0.71 mmol, 87% pure) rac-benzyl (2-amino-3-isopropoxypropyl)carbamate from Example 76A were initially charged in ethanol (5.0 ml), and 76 mg (0.07 mmol) of 10% palladium on activated carbon and 2.2 ml (21.36 mmol) of cyclohexene were added. The reaction mixture was stirred under reflux overnight. The mixture was then filtered through a Millipore® filter, the filter cake was washed with ethanol, 0.7 ml (1.42 mmol) of 2 M hydrogen chloride in diethyl ether were added to the filtrate and the mixture was concentrated and dried under high vacuum. This gave 190 mg (99% of theory, purity 76%) of the target compound.
DCI-MS (Method 4): m/z=133 (M−2HCl+H)⁺

Example 225A 3-(Dibenzylamino)oxetane-3-carbonitrile

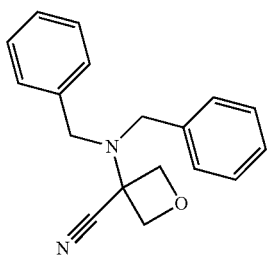 [SMILES: N#CC1(N(Cc2ccccc2)Cc2ccccc2)COC1]

0.63 ml (10.8 mmol) of oxetan-3-one and 3.6 ml (27.1 mmol) of trimethylsilyl cyanide were added to 10.4 ml (54.1 mmol) of dibenzylamine in 72 ml of acetic acid. The reaction mixture was then stirred at RT overnight. The mixture was then concentrated, the residue was dissolved in water/diethyl ether and the aqueous phase was extracted twice with diethyl ether. The combined organic phases were washed twice with saturated aqueous sodium bicarbonate solution, dried over sodium sulphate, filtered and concentrated. The residue was purified by silica gel chromatography (cyclohexane/ethyl acetate from 40:1 to 30:1). This gave 2.39 g (77% of theory, purity 97%) of the target compound.

LC-MS (Method 13): $R_t$=2.53 min.

MS (ESIpos): m/z=279 (M+H)$^+$.

$^1$H NMR (400 MHz, DMSO-$d_6$): δ=3.49 (s, 4H), 4.29 (d, 2H), 4.37 (d, 2H), 7.26-7.39 (m, 10H).

Example 226A 3-(Aminomethyl)oxetane-3-amine dihydrochloride

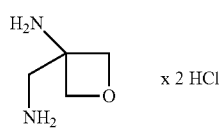

585 mg (2.07 mmol) of 3-(aminomethyl)-N,N-dibenzyloxetane-3-amine [synthesis described in: US2008/103183 A1, 2008; p. 48] were initially charged in ethanol (29.2 ml), and 441 mg (0.41 mmol) of 10% palladium on activated carbon and 6.3 ml (62.2 mmol) of cyclohexene were added. The reaction mixture was stirred under reflux for 8 h. The mixture was then filtered through a Millipore® filter, the filter cake was washed with methanol, 2.6 ml (5.2 mmol) of 2 M hydrogen chloride in diethyl ether were added to the filtrate and the mixture was concentrated and dried under high vacuum. This gave 423 mg (87% of theory, purity 75%) of the target compound.

DCI-MS (Method 4): m/z=103 (M−2HCl+H)$^+$

Example 227A rac-tert-Butyl {1-[({6-chloro-8-[(2,6-difluorobenzyl)oxy]-2-methylimidazo[1,2-a]pyridin-3-yl}-carbonyl)amino]-3-methylbutan-2-yl}carbamate

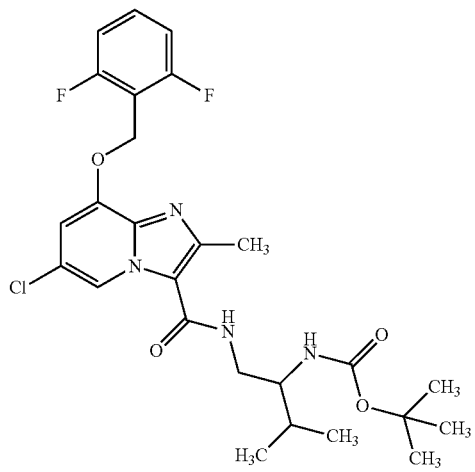 [SMILES: Cc1nc2c(OCc3c(F)cccc3F)cc(Cl)cn2c1C(=O)NCC(NC(=O)OC(C)(C)C)C(C)C]

200 mg (0.57 mmol) of 6-chloro-8-[(2,6-difluorobenzyl)oxy]-2-methylimidazo[1,2-a]pyridine-3-carboxylic acid Example 16A, 191 mg (0.60 mmol) of HATU and 0.19 ml (1.70 mmol) of 4-methylmorpholine in DMF (3.6 ml) were stirred at RT for 20 min. 126 mg (0.62 mmol) of rac-tert-butyl (1-amino-3-methylbutan-2-yl)carbamate were then added and the reaction mixture was stirred at RT overnight. Water/TFA were then added and the mixture was purified by preparative RP-HPLC (acetonitrile/water gradient with addition of 0.1% TFA). The product fractions were concentrated and the residue was taken up in dichloromethane and washed twice with saturated aqueous sodium bicarbonate solution. The aqueous phase was extracted twice with dichloromethane and the combined organic phases were dried over sodium sulphate, filtered off and concentrated. This gave 264 mg (87% of theory, purity 100%) of the target compound.

LC-MS (Method 2): $R_t$=1.23 min.

MS (ESIpos): m/z=537 (M+H)$^+$.

$^1$H NMR (400 MHz, DMSO-$d_6$): δ=0.86 (d, 3H), 0.91 (d, 3H), 1.32 (s, 9H), 1.66-1.78 (m, 1H), 2.47 (s, 3H, signal partially obscured by DMSO peak), 3.20-3.29 (m, 1H), 3.38-3.46 (m, 1H), 3.49-3.60 (m, 1H), 5.34 (s, 2H), 6.62 (d, 1H), 7.19 (d, 1H), 7.22-7.29 (m, 2H), 7.56-7.66 (m, 1H), 7.81 (t, 1H), 8.74 (d, 1H).

Example 228A ent-tert-Butyl {1-[({6-chloro-8-[(2,6-difluorobenzyl)oxy]-2-methylimidazo[1,2-a]pyridin-3-yl}-carbonyl)amino]-3-methylbutan-2-yl}carbamate (Enantiomer A)

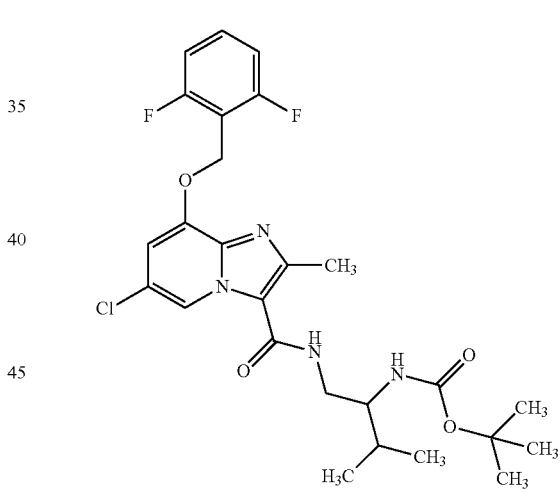

260 mg of Example 227A were separated into the enantiomers by preparative separation on a chiral phase [column: Daicel Chiralpak AD-H, 5 μm, 250×20 mm, mobile phase: 50% isohexane, 50% ethanol, flow rate: 20 ml/min; 40° C., detection: 220 nm].

Enantiomer A:

Yield: 124 mg (99% ee)

$R_t$=3.84 min [Daicel Chiralpak AD-H, 5 m, 250×4.6 mm; mobile phase: 50% isohexane, 50% isopropanol; flow rate 1.0 ml/min; 40° C.; detection: 220 nm].

Example 229A ent-tert-Butyl {1-[({6-chloro-8-[(2,6-difluorobenzyl)oxy]-2-methylimidazo[1,2-a]pyridin-3-yl}-carbonyl)amino]-3-methylbutan-2-yl}carbamate (Enantiomer B)

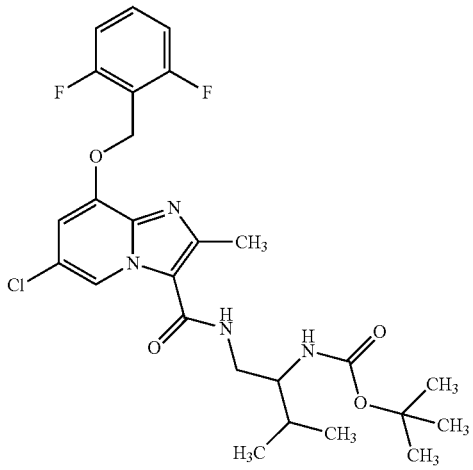 [SMILES: Cc1nc2c(OCc3c(F)cccc3F)cc(Cl)cn2c1C(=O)NCC(NC(=O)OC(C)(C)C)C(C)C]

260 mg of Example 227A were separated into the enantiomers by preparative separation on a chiral phase [column: Daicel Chiralpak AD-H, 5 μm, 250×20 mm, mobile phase: 50% isohexane, 50% ethanol, flow rate: 20 ml/min; 40° C., detection: 220 nm].

Enantiomer B:
Yield: 122 mg (99% ee)
$R_t$=5.97 min [Daicel Chiralpak AD-H, 5 m, 250×4.6 mm; mobile phase: 50% isohexane, 50% isopropanol; flow rate 1.0 ml/min; 40° C.; detection: 220 nm].

Example 230A rac-tert-Butyl {1-[({8-[(2,6-difluorobenzyl)oxy]-2,6-dimethylimidazo[1,2-a]pyridin-3-yl}-carbonyl)amino]-3-methylbutan-2-yl}carbamate

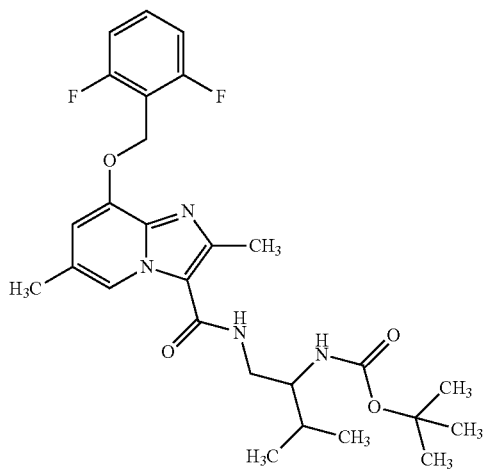 [SMILES: Cc1cc(OCc2c(F)cccc2F)c2nc(C)c(C(=O)NCC(NC(=O)OC(C)(C)C)C(C)C)n2c1]

200 mg (0.60 mmol) of 8-[(2,6-difluorobenzyl)oxy]-2,6-dimethylimidazo[1,2-a]pyridine-3-carboxylic acid from Example 21 A, 203 mg (0.63 mmol) of HATU and 0.20 ml (1.81 mmol) of 4-methylmorpholine were initially charged in DMF (3.8 ml), the mixture was stirred at RT for 20 min, 134 mg (0.66 mmol) of rac-tert-butyl (1-amino-3-methylbutan-2-yl)carbamate were added and the reaction mixture was stirred at RT overnight. Water/TFA were added and the mixture was purified by preparative RP-HPLC (acetonitrile/water gradient with addition of 0.1% TFA). The product fractions were concentrated and the residue was taken up in dichloromethane and washed twice with saturated aqueous sodium bicarbonate solution. The aqueous phase was extracted twice with dichloromethane and the combined organic phases were dried over sodium sulphate, filtered off and concentrated. This gave 262 mg (84% of theory, purity 100%) of the target compound.

LC-MS (Method 2): $R_t$=1.03 min.

MS (ESIpos): m/z=517 (M+H)$^+$.

$^1$H NMR (400 MHz, DMSO-d$_6$): δ=0.86 (d, 3H), 0.90 (d, 3H), 1.33 (s, 9H), 1.68-1.78 (m, 1H), 2.31 (s, 3H), 2.46 (s, 3H), 3.18-3.28 (m, 1H), 3.38-3.46 (m, 1H), 3.50-3.59 (m, 1H), 5.28 (s, 2H), 6.63 (d, 1H), 6.91 (s, 1H), 7.20-7.28 (m, 2H), 7.55-7.64 (m, 1H), 7.67 (t, 1H), 8.47 (s, 1H).

Example 231A ent-tert-Butyl {1-[({8-[(2,6-difluorobenzyl)oxy]-2,6-dimethylimidazo[1,2-a]pyridin-3-yl}-carbonyl)amino]-3-methylbutan-2-yl}carbamate (Enantiomer A)

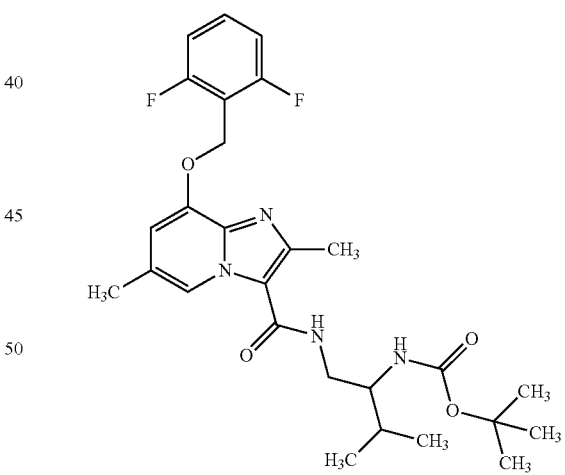

260 mg of Example 230A were separated into the enantiomers by preparative separation on a chiral phase [column: Daicel Chiralpak IA, 5 μm, 250×20 mm, mobile phase: 50% acetonitrile, 50% tert-butyl methyl ether, flow rate: 20 ml/min; 25° C., detection: 220 nm].

Enantiomer A:
Yield: 89 mg (100% ee)
$R_t$=4.04 min [Daicel Chiralpak IA, 5 m, 250×4.6 mm; mobile phase: 50% acetonitrile, 50% tert-butyl-methyl ether; flow rate 1.0 ml/min; 30° C.; detection: 220 nm].

Example 232A ent-tert-Butyl {1-[({8-[(2,6-difluorobenzyl)oxy]-2,6-dimethylimidazo[1,2-a]pyridin-3-yl}-carbonyl)amino]-3-methylbutan-2-yl}carbamate (Enantiomer B)

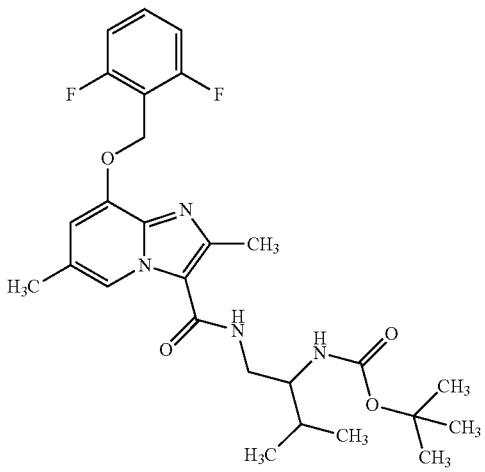 [SMILES: Cc1cc(OCc2c(F)cccc2F)c2nc(C)c(C(=O)NCC(NC(=O)OC(C)(C)C)C(C)C)n2c1]

260 mg of Example 230A were separated into the enantiomers by preparative separation on a chiral phase [column: Daicel Chiralpak IA, 5 μm, 250×20 mm, mobile phase: 50% acetonitrile, 50% tert-butyl methyl ether, flow rate: 20 ml/min; 25° C., detection: 220 nm].

Enantiomer B:

Yield: 93 mg (100% ee)

$R_t$=6.02 min [Daicel Chiralpak IA, 5 m, 250×4.6 mm; mobile phase: 50% acetonitrile, 50% tert-butyl methyl ether; flow rate 1.0 ml/min; 30° C.; detection: 220 nm].

Example 233A rac-tert-Butyl {1-[({8-[(2,6-difluorobenzyl)oxy]-2-methylimidazo[1,2-a]pyridin-3-yl}carbonyl)-amino]-3-methylbutan-2-yl}carbamate

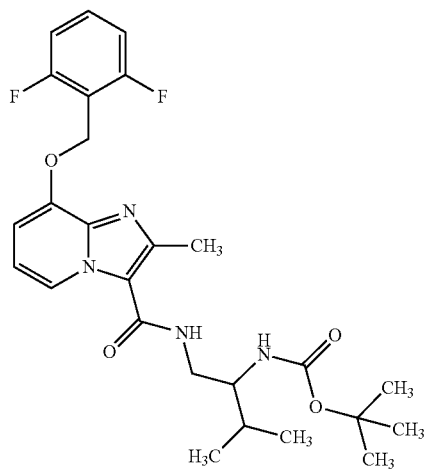 [SMILES: Cc1nc2c(OCc3c(F)cccc3F)cccn2c1C(=O)NCC(NC(=O)OC(C)(C)C)C(C)C]

Preparation and purification of the title compound were carried out analogously to Example 230A. Starting with 200 mg (0.63 mmol) of 8-[(2,6-difluorobenzyl)oxy]-2-methylimidazo[1,2-a]pyridine-3-carboxylic acid from Example 3A and 140 mg (0.69 mmol) of rac-tert-butyl (1-amino-3-methylbutan-2-yl)carbamate, 215 mg (68% of theory, purity 100%) of the target compound were obtained.

LC-MS (Method 2): $R_t$=1.02 min.

MS (ESIpos): m/z=503 (M+H)$^+$.

$^1$H NMR (400 MHz, DMSO-d$_6$): δ=0.86 (d, 3H), 0.90 (d, 3H), 1.33 (s, 9H), 1.68-1.78 (m, 1H), 2.54 (s, 3H, obscured by DMSO signal), 3.19-3.28 (m, 1H), 3.39-3.46 (m, 1H), 3.50-3.59 (m, 1H), 5.30 (s, 2H), 6.64 (d, 1H), 6.93 (t, 1H), 7.01 (d, 1H), 7.20-7.28 (m, 2H), 7.54-7.63 (m, 1H), 7.70 (t, 1H), 8.63 (d, 1H).

Example 234A ent-tert-Butyl {1-[({8-[(2,6-difluorobenzyl)oxy]-2-methylimidazo[1,2-a]pyridin-3-yl}carbonyl)-amino]-3-methylbutan-2-yl}carbamate (Enantiomer A)

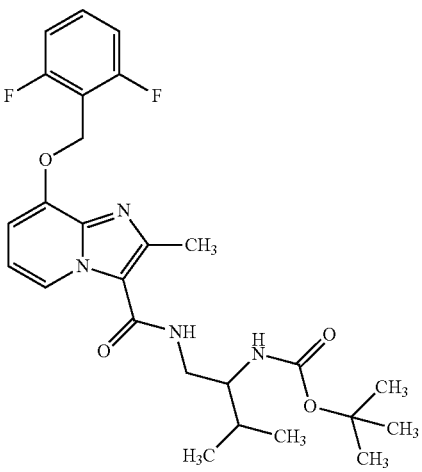 [SMILES: Cc1nc2c(OCc3c(F)cccc3F)cccn2c1C(=O)NCC(NC(=O)OC(C)(C)C)C(C)C]

210 mg of Example 233A were separated into the enantiomers by preparative separation on a chiral phase [column: Daicel Chiralpak IA, 5 μm, 250×20 mm, mobile phase: 20% acetonitrile, 80% tert-butyl methyl ether, flow rate: 20 ml/min; 25° C., detection: 230 nm].

Enantiomer A:

Yield: 89 mg (100% ee)

$R_t$=4.69 min [Daicel Chiralpak IA, 5 m, 250×4.6 mm; mobile phase: 20% acetonitrile, 80% tert-butyl methyl ether; flow rate 1.0 ml/min; 30° C.; detection: 220 nm].

Example 235A ent-tert-Butyl {1-[({8-[(2,6-difluorobenzyl)oxy]-2-methylimidazo[1,2-a]pyridin-3-yl}carbonyl)-amino]-3-methylbutan-2-yl}carbamate (Enantiomer B)

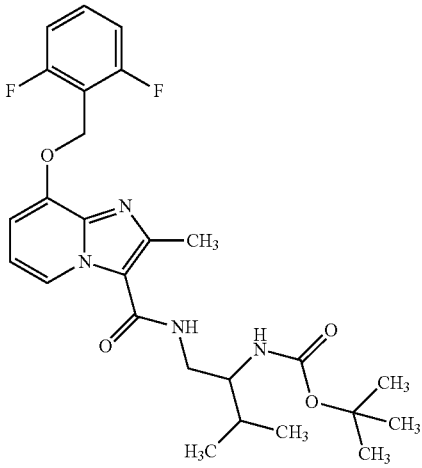 [SMILES: Cc1nc2c(OCc3c(F)cccc3F)cccn2c1C(=O)NCC(NC(=O)OC(C)(C)C)C(C)C]

210 mg of Example 233A were separated into the enantiomers by preparative separation on a chiral phase [column: Daicel Chiralpak IA, 5 µm, 250×20 mm, mobile phase: 20% acetonitrile, 80% tert-butyl methyl ether, flow rate: 20 ml/min; 25° C., detection: 230 nm].

Enantiomer B:
Yield: 73 mg (100% ee)
$R_t$=7.29 min [Daicel Chiralpak IA, 5 m, 250×4.6 mm; mobile phase: 20% acetonitrile, 80% tert-butyl methyl ether; flow rate 1.0 ml/min; 30° C.; detection: 220 nm].

Example 236A 3-(Benzyloxy)-5-bromopyridine-2-amine

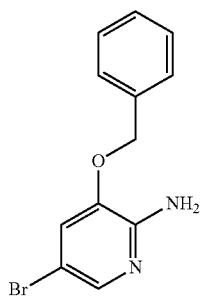 [SMILES: Nc1ncc(Br)cc1OCc1ccccc1]

200 g (1 mol) of 2-amino-3-benzyloxypyridine were initially charged in 4 l of dichloromethane, and a solution of 62 ml (1.2 mol) of bromine in 620 ml of dichloromethane was added at 0° C. over a period of 30 min. After the addition had ended, the reaction solution was stirred at 0° C. for 60 min. About 4 l of saturated aqueous sodium bicarbonate solution were then added to the mixture.

The organic phase was separated off and concentrated. The residue was purified by silica gel column chromatography (petroleum ether:ethyl acetate 6:4) and the product fractions were concentrated. This gave 214 g (77% of theory) of the title compound.

LC-MS (Method 2): $R_t$=0.92 min
MS (ESpos): m/z=279 (M+H)$^+$ $^1$H NMR (400 MHz, DMSO-d$_6$): δ=5.16 (s, 2H), 5.94-6.00 (m, 2H), 7.26-7.29 (m, 1H), 7.31-7.36 (m, 1H), 7.37-7.43 (m, 2H), 7.47-7.52 (m, 2H), 7.57-7.59 (m, 1H).

Example 237A

Ethyl 8-(benzyloxy)-6-bromo-2-methylimidazo[1,2-a]pyridine-3-carboxylate

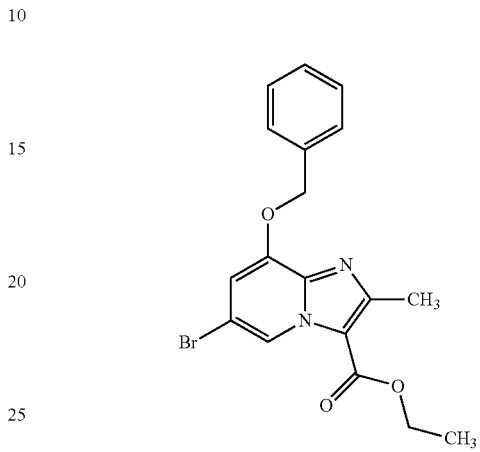

Under argon, 200 g (0.72 mol) of 3-(benzyloxy)-5-bromopyridine-2-amine, 590 g (3.58 mol) of ethyl 2-chloroacetoacetate and 436 g of 3A molecular sieve were suspended in 6 l of ethanol and stirred at reflux for 72 h. The reaction mixture was filtered off through silica gel and concentrated. The residue was purified by silica gel chromatography (petroleum ether:ethyl acetate 9:1, then 6:4) and the product fractions were concentrated. This gave 221 g (79% of theory) of the target compound.

LC-MS (Method 7): $R_t$=1.31 min
MS (ESpos): m/z=389 (M+H)$^+$ $^1$H NMR (400 MHz, DMSO-d$_6$): δ=1.36 (t, 3H), 2.58 (s, 3H), 4.32-4.41 (m, 2H), 5.33 (s, 2H), 7.28-7.32 (m, 1H), 7.36-7.47 (m, 3H), 7.49-7.54 (m, 2H), 8.98 (d, 1H).

Example 238A

Ethyl 8-(benzyloxy)-2,6-dimethylimidazo[1,2-a]pyridine-3-carboxylate

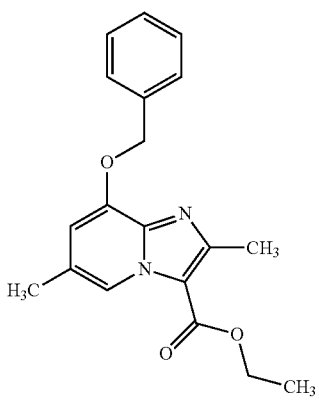 [SMILES: CCOC(=O)c1c(C)nc2c(OCc3ccccc3)cc(C)cn12]

Under argon, 105 g (270 mmol) of ethyl 8-(benzyloxy)-6-bromo-2-methylimidazo[1,2-a]pyridine-3-carboxylate from Example 237A were suspended in 4.2 l of 1,4-dioxane, 135.4 g (539 mmol, purity 50%) of trimethylboroxine, 31.2 g (27 mmol) of tetrakis(triphenylphosphine)palladium(0) and 78.3 g (566 mmol) of potassium carbonate were added in succession and the mixture was stirred under reflux for 8 h. The reaction mixture, cooled to RT, was filtered off from the precipitate over silica gel and the filtrate was concentrated. The residue was dissolved in dichloromethane and purified by silica gel chromatography (dichloromethane:ethyl acetate=9:1). This gave 74 g (84.6% of theory; purity 100%) of the target compound.

LC-MS (Method 7): $R_t$=1.06 min

MS (ESpos): m/z=325 (M+H)$^+$ $^1$H NMR (400 MHz, DMSO-d$_6$): δ=1.35 (t, 3H), 2.34 (br. s, 3H), 2.56 (s, 3H), 4.31-4.38 (m, 2H), 5.28 (br. s, 2H), 6.99-7.01 (m, 1H), 7.35-7.47 (m, 3H), 7.49-7.54 (m, 2H), 8.68-8.70 (m, 1H).

Example 239A

Ethyl 8-hydroxy-2,6-dimethylimidazo[1,2-a]pyridine-3-carboxylate

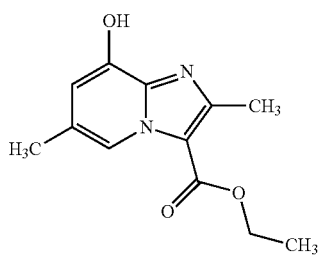 [SMILES: CCOC(=O)c1c(C)nc2c(O)cc(C)cn12]

74 g (228 mmol) of ethyl 8-(benzyloxy)-2,6-dimethylimidazo[1,2-a]pyridine-3-carboxylate from Example 238A were initially charged in 1254 ml of dichloromethane and 251 ml of ethanol, and 20.1 g 10% palladium on activated carbon (moistened with water 50%) were added under argon. The reaction mixture was hydrogenated overnight at RT and atmospheric pressure. The reaction mixture was filtered off through silica gel and concentrated. The crude product was purified by silica gel chromatography (dichloromethane:methanol=95:5). This gave 50.4 g (94% of theory) of the target compound.

DCI-MS: (Method 4) (ESpos): m/z=235.2 (M+H)$^+$ $^1$H NMR (400 MHz, DMSO-d$_6$): δ=1.35 (t, 3H), 2.27 (s, 3H), 2.58 (s, 3H), 4.30-4.38 (m, 2H), 6.65 (d, 1H), 8.59 (s, 1H), 10.57 (br. s, 1H).

Example 240A rac-tert-Butyl 2-{[({8-[(2,6-difluorobenzyl)oxy]-2,6-dimethylimidazo[1,2-a]pyridin-3-yl}-carbonyl)amino]methyl}-3,4-dihydroquinoline-1(2H)-carboxylate

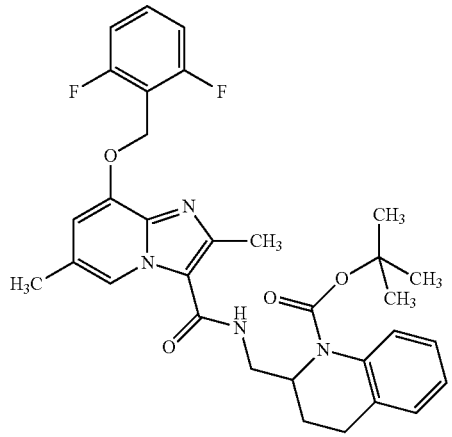 [SMILES: Cc1cc(OCc2c(F)cccc2F)c2nc(C)c(C(=O)NCC3CCc4ccccc4N3C(=O)OC(C)(C)C)n2c1]

120 mg (0.36 mmol) of 8-[(2,6-difluorobenzyl)oxy]-2,6-dimethylimidazo[1,2-a]pyridine-3-carboxylic acid Example 21A, 139 mg (0.43 mmol) of TBTU and 0.20 ml (1.81 mmol) of 4-methylmorpholine in DMF (2.3 ml) were stirred at RT for 10 min, 119 mg (0.40 mmol) of rac-tert-butyl 2-(aminomethyl)-3,4-dihydroquinoline-1(2H)-carboxylate hydrochloride were added and the reaction mixture was stirred at RT overnight. Water was added, and the mixture was stirred at RT for 30 min. The solid formed was filtered off, washed with water and dried under high vacuum. This gave 182 mg (85% of theory, purity 98%) of the target compound.

LC-MS (Method 7): $R_t$=1.13 min.

MS (ESIpos): m/z=577 (M+H)$^+$.

$^1$H NMR (400 MHz, DMSO-d$_6$): δ=1.38 (s, 9H), 1.64-1.75 (m, 1H), 2.10-2.20 (m, 1H), 2.22 (s, 3H), 2.30 (s, 3H), 2.56-2.62 (m, 1H), 2.66-2.76 (m, 1H), 3.09-3.19 (m, 1H), 3.55-3.64 (m, 1H), 4.63-4.72 (m, 1H), 5.27 (s, 2H), 6.90 (s, 1H), 6.99 (t, 1H), 7.05-7.15 (m, 2H), 7.19-7.28 (m, 2H), 7.37 (d, 1H), 7.54-7.64 (m, 1H), 7.80 (t, 1H), 8.40 (s, 1H).

Example 241A

2-Methyl-4-phenyl-2-(trifluoromethyl)-1,3-oxazolidine (diastereomers)

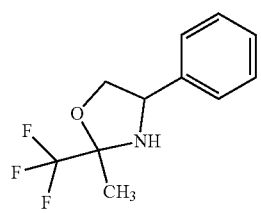 [SMILES: CC1(C(F)(F)F)NC(c2ccccc2)CO1]

45 g (328.0 mmol) of rac-2-amino-2-phenylethanol and 8.24 g (32.8 mmol) of pyridinium p-toluolsulphonate were added to 55.13 g (492.0 mmol) of 1,1,1-trifluoroacetone in toluene (1.35 l).

The reaction mixture was boiled under reflux on a water separator for 16 h. The mixture was cooled to 0° C. and the solid formed was filtered off and dried under high vacuum. This gave 68.6 g (77% of theory, purity 85%) of the target compound.

LC-MS (Method 2): $R_t$=0.99 min
MS (ESIpos): m/z=232 (M+H)$^+$.
$^1$H NMR (400 MHz, DMSO-$d_6$): δ=1.54 (s, 3H), 3.56 (t, 1H), 3.81 (d, 1H), 4.28 (t, 1H), 4.35-4.43 (m, 1H), 7.29-7.47 (m, 5H).

Example 242A 3,3,3-Trifluoro-2-[(2-hydroxy-1-phenylethyl)amino]-2-methylpropionitrile (diastereomers)

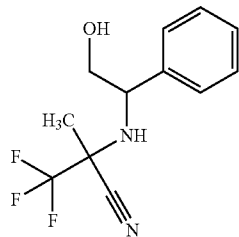 [SMILES: CC(C#N)(NC(CO)c1ccccc1)C(F)(F)F]

Under argon, 52.8 g (228.3 mmol) of 2-methyl-4-phenyl-2-(trifluoromethyl)-1,3-oxazolidine (diastereomers) Example 241A were initially charged in dichloromethane (2 l) and cooled to 0° C. 42.85 ml (342.5 mmol) of trimethylsilyl cyanide and 42.1 ml (342.5 mmol) of boron trifluoride/diethyl ether complex were added slowly and the mixture was stirred at RT for 16 h. The reaction solution was then poured into 1.5 l of saturated sodium bicarbonate solution. Another 400 g of sodium bicarbonate were then added, and the solution was adjusted to pH 10 with conc. aqueous sodium hydroxide solution. The aqueous solution was extracted three times with 500 ml of dichloromethane and the combined organic phases were dried over sodium sulphate, filtered off and concentrated. This gave 56.8 g (96% of theory, 2 diastereomers) of the target compound.

LC-MS (Method 2): $R_t$=0.89 min and 0.93 min.
MS (ESIneg): m/z=303 (M−H+HCOOH)$^-$.

Example 243A

2-[(3-Amino-1,1,1-trifluoro-2-methylpropan-2-yl)amino]-2-phenylethanol (diastereomers)

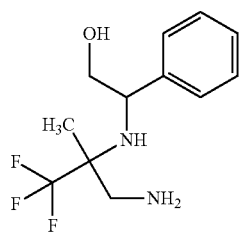 [SMILES: CC(CN)(NC(CO)c1ccccc1)C(F)(F)F]

31 g (120.0 mmol) of 3,3,3-trifluoro-2-[(2-hydroxy-1-phenylethyl)amino]-2-methylpropionitrile Example 242A were initially charged in tert-butyl methyl ether (3.1 l), the mixture was cooled to 0° C., 18.25 g (480.2 mmol) of lithium aluminium hydride were added and the reaction mixture was stirred at RT for 16 h. The mixture was then cooled to 0° C. and initially quenched with 24 ml of water, and 24 ml of 15% strength aqueous potassium hydroxide solution and 48 ml of water were then added. The mixture formed was filtered through silica gel and washed with tert-butyl methyl ether. The organic phase was separated off, dried over sodium sulphate, filtered and concentrated. This gave 29.2 g (83% of theory, purity 89%) of the target compound.

LC-MS (Method 2): $R_t$=0.52 min
MS (ESIpos): m/z=263 (M+H)$^+$.

Example 244A tert-Butyl {3,3,3-trifluoro-2-[(2-hydroxy-1-phenylethyl)amino]-2-methylpropyl}carbamate (diastereomers)

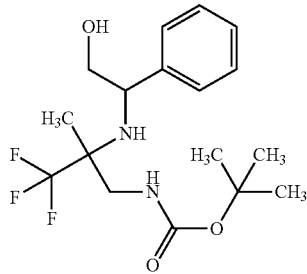 [SMILES: CC(C)(C)OC(=O)NCC(C)(NC(CO)c1ccccc1)C(F)(F)F]

29.1 ml (209.8 mmol) of triethylamine and 23.98 g (109.9 mmol) of di-tert-butyl dicarbonate (dissolved in 286 ml of THF) were added to 26.2 g (99.9 mmol) of 2-[(3-amino-1,1,1-trifluoro-2-methylpropan-2-yl)amino]-2-phenylethanol (diastereomers) Example 243A in THF (500 ml). The reaction mixture was stirred at RT for 16 h. The mixture was then concentrated and taken up in each case 500 ml of saturated aqueous sodium bicarbonate solution and ethyl acetate. The phases were separated and the organic phase was dried over sodium sulphate, filtered off and concentrated. This gave 39.80 g (110% of theory) of the target compound which was used without further purification for the next step.

FIA-MS (Method 10, ESpos): m/z=363 (M+H)$^+$

Example 245A rac-tert-Butyl (2-amino-3,3,3-trifluoro-2-methylpropyl)carbamate

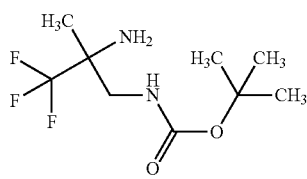 [SMILES: CC(C)(C)OC(=O)NCC(C)(N)C(F)(F)F]

Under argon, 39 g (107.6 mmol) of tert-butyl {3,3,3-trifluoro-2-[(2-hydroxy-1-phenylethyl)amino]-2-methylpropyl}carbamate Example 244A were initially charged in ethanol (700 ml), and 5.44 g (53.8 mmol) of palladium(II) hydroxide (20% on activated carbon, moistened with water about 60%) were added. The reaction mixture was hydrogenated at atmospheric pressure for 16 h. The mixture was then filtered through silica gel and concentrated. The residue was purified by silica gel chromatography (cyclohexane/ethyl acetate gradient: from 9/1 to 6/4). This gave 15.8 g (61% of theory) of the target compound.

FIA-MS (Method 10, ESpos): m/z=243 (M+H)$^+$ $^1$H NMR (400 MHz, CDCl$_3$): δ=1.22 (s, 3H), 1.45 (s, 9H), 3.13-3.23 (m, 1H), 3.37-3.48 (m, 1H), 4.89 (br. s, 1H).

Example 246A rac-3,3,3-Trifluoro-2-methylpropane-1,2-diamine dihydrochloride

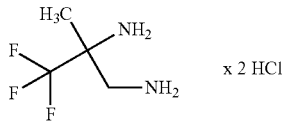

188 ml of 4 M hydrogen chloride in dioxane were added to 15 g (61.9 mmol) of rac-tert-butyl (2-amino-3,3,3-trifluoro-2-methylpropyl)carbamate from Example 245A in dioxane (188 ml). The reaction mixture was stirred at RT for 16 h and then concentrated and kept under argon. This gave 14.4 g (108% of theory) of the target compound which was not purified any further.

FIA-MS (Method 10, ESpos): m/z=143 (M−2HCl+H)$^+$ $^1$H NMR (400 MHz, D$_2$O): δ=1.40 (s, 3H), 3.21-3.31 (m, 2H).

Example 247A ent-Benzyl (2-amino-3-methoxypropyl)carbamate (Enantiomer A)

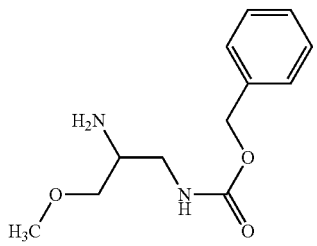 [SMILES: COCC(N)CNC(=O)OCc1ccccc1]

10 g of Example 140A were separated into the enantiomers by preparative separation on a chiral phase after the TFA of the sample had been removed with the silica gel-based sorbent "Bond Elut PSA" (manufacturer: Agilent) [column: Daicel Chiralpak AY-H, 5 μm, 250×20 mm, mobile phase: 50% isohexane, 50% isopropanol+0.2% diethylamine, flow rate: 15 ml/min; 40° C., detection: 220 nm].

Enantiomer A:
Yield: 2.17 g (96% ee)

R$_t$=5.79 min [Daicel Chiralpak AY-H, 5 m, 250×4.6 mm; mobile phase: 50% isohexane, 50% isopropanol+0.2% diethylamine; flow rate 1.0 ml/min; 40° C.; detection: 220 nm].

Example 248A ent-Benzyl (2-amino-3-methoxypropyl)carbamate (Enantiomer B)

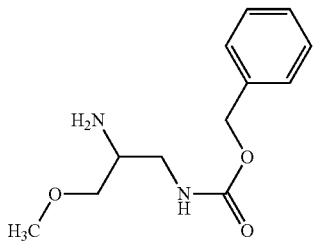 [SMILES: COCC(N)CNC(=O)OCc1ccccc1]

10 g of Example 140A were separated into the enantiomers by preparative separation on a chiral phase after the TFA of the sample had been removed with the silica gel-based sorbent "Bond Elut PSA" (manufacturer: Agilent) [column: Daicel Chiralpak AY-H, 5 μm, 250×20 mm, mobile phase: 50% isohexane, 50% isopropanol+0.2% diethylamine, flow rate: 15 ml/min; 40° C., detection: 220 nm].

Enantiomer B:
Yield: 2.07 g (94% ee)

R$_t$=7.26 min [Daicel Chiralpak AY-H, 5 μm, 250×4.6 mm; mobile phase: 50% isohexane, 50% isopropanol+0.2% diethylamine; flow rate 1.0 ml/min; 40° C.; detection: 220 nm].

Example 249A ent-3-Methoxypropane-1,2-diamine dihydrochloride (Enantiomer A)

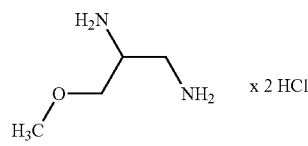

Under argon, 750 mg (3.15 mmol) of ent-benzyl (2-amino-3-methoxypropyl)carbamate (enantiomer A) Example 247A were initially charged in ethanol (22 ml), and 335 mg (0.32 mmol) of 10% palladium on activated carbon and 9.6 ml (94.42 mmol) of cyclohexene were added. The reaction mixture was stirred under reflux for 7 h. 335 mg (0.32 mmol) of 10% palladium on activated carbon were then added and the mixture was stirred under reflux for a further two days. The reaction mixture, cooled to RT, was filtered through a Milipore filter and the filter cake was washed with ethanol. 3.2 ml (6.3 mmol) of 2 N hydrogen chloride in diethyl ether were added to the filtrate and the mixture was concentrated and dried under high vacuum. This gave 440 mg (79% of theory) of the target compound.

$^1$H NMR (400 MHz, DMSO-d$_6$): δ=3.03-3.11 (m, 2H), 3.32 (s, 3H), 3.55-3.64 (m, 3H), 8.31-8.69 (m, 4H).

Example 250A ent-3-Methoxypropane-1,2-diamine dihydrochloride (Enantiomer B)

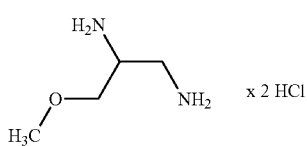

Preparation and purification of the title compound were carried out analogously to Example 249A. Starting with 750 mg (3.15 mmol) of ent-benzyl (2-amino-3-methoxypropyl) carbamate (enantiomer B) from Example 248A, 454 mg (81% of theory) of the target compound were obtained.

$^1$H NMR (400 MHz, DMSO-$d_6$): δ=3.03-3.11 (m, 2H), 3.32 (s, 3H), 3.55-3.64 (m, 3H), 8.31-8.69 (m, 4H).

Example 251A

Ethyl 2,6-dimethyl-8-(3-methylbutoxy)imidazo[1,2-a]pyridine-3-carboxylate

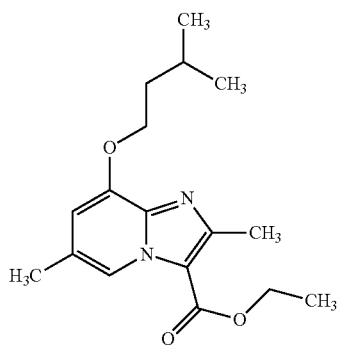 [SMILES: CCOC(=O)c1c(C)nc2c(OCCC(C)C)cc(C)cn12]

1.23 ml (9.4 mmol) of 1-iodo-3-methylbutane and 6.12 g (18.8 mmol) of caesium carbonate were added to 2.0 g (8.5 mmol) of ethyl 8-hydroxy-2,6-dimethylimidazo[1,2-a]pyridine-3-carboxylate Example 239A in 122.3 ml of DMF, and the mixture was stirred at 60° C. for 40 min. 900 ml of water were added to the reaction mixture, which had cooled to RT, and the mixture was stirred at RT for 1 h, and the precipitated solid was filtered off, washed with water and dried under high vacuum. This gave 2.25 g (84% of theory; purity 97%) of the title compound.

LC-MS (Method 7): $R_t$=1.12 min

MS (ESpos): m/z=305 (M+H)$^+$ $^1$H NMR (400 MHz, DMSO-$d_6$): δ=0.96 (d, 6H), 1.35 (t, 3H), 1.70 (q, 2H), 1.77-1.89 (m, 1H), 2.33 (s, 3H), 2.56 (s, 3H), 4.17 (t, 2H), 4.34 (q, 2H), 6.88 (s, 1H), 8.64 (s, 1H).

Example 252A 2,6-Dimethyl-8-(3-methylbutoxy)imidazo[1,2-a]pyridine-3-carboxylic acid

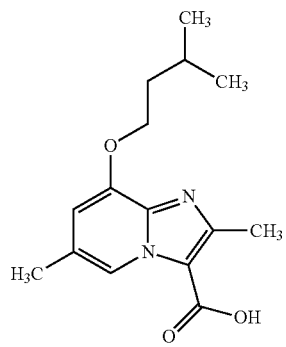

2.25 g (7.4 mmol) of ethyl 2,6-dimethyl-8-(3-methylbutoxy)imidazo[1,2-a]pyridine-3-carboxylate Example 251A were initially charged in 157 ml of THF/methanol 5:1, 37 ml (37 mmol) of 1 N lithium hydroxide solution were added and the reaction mixture stirred at RT over the weekend. The mixture was then cooled to 0° C., acidified to pH 4 with 6 N hydrochloric acid and freed from the organic solvent under reduced pressure. The precipitated solid was filtered off, washed with water and dried under high vacuum. This gave 1.64 g (80% of theory; purity 100%) of the title compound.

LC-MS (Method 2): $R_t$=0.71 min

MS (ESpos): m/z=277 (M+H)$^+$ $^1$H NMR (400 MHz, DMSO-$d_6$): δ=0.96 (d, 6H), 1.70 (q, 2H), 1.78-1.89 (m, 1H), 2.32 (s, 3H), 2.56 (s, 3H), 4.17 (t, 2H), 6.85 (s, 1H), 8.69 (s, 1H), 12.86-13.08 (m, 1H).

Example 253A rac-tert-Butyl 2-{[({8-[(2,6-difluorobenzyl)oxy]-2-methylimidazo[1,2-a]pyridin-3-yl}carbonyl)-amino]methyl}-3,4-dihydroquinoline-1(2H)-carboxylate

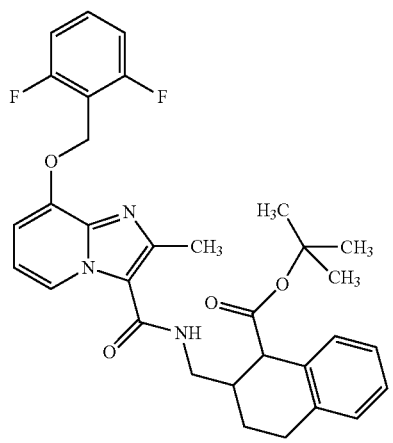 [SMILES: Cc1nc2c(OCc3c(F)cccc3F)cccn2c1C(=O)NCC1CCc2ccccc2C1C(=O)OC(C)(C)C]

145 mg (0.45 mmol) of TBTU and 0.2 ml (1.89 mmol) of 4-methylmorpholine were added to 120 mg (0.38 mmol) of 8-[(2,6-difluorobenzyl)oxy]-2-methylimidazo[1,2-a]pyridine-3-carboxylic acid Example 3A in 2.4 ml of DMF, and the mixture was stirred at RT for 10 min. 124 mg (0.42 mmol) of rac-tert-butyl 2-(aminomethyl)-3,4-dihydroquinoline-1(2H)-carboxylate hydrochloride were added and the reaction mixture was stirred at RT overnight. Water was added, and the reaction mixture was stirred at RT for 30 min. The precipitated solid was filtered off, washed with water and dried under high vacuum. This gave 190 mg (90% of theory; purity 100%) of the title compound.

LC-MS (Method 7): $R_t$=1.13 min

MS (ESpos): m/z=563 (M+H)$^+$ $^1$H NMR (400 MHz, DMSO-d$_6$): δ=1.38 (s, 9H), 1.64-1.75 (m, 1H), 2.11-2.21 (m, 1H), 2.25 (s, 3H), 2.65-2.76 (m, 2H), 3.10-3.20 (m, 1H), 3.57-3.66 (m, 1H), 4.68 (quintet, 1H), 5.29 (s, 2H), 6.91 (t, 1H), 6.96-7.03 (m, 2H), 7.08 (t, 1H), 7.13 (d, 1H), 7.19-7.27 (m, 2H), 7.37 (d, 1H), 7.54-7.63 (m, 1H), 7.83 (t, 1H), 8.58 (d, 1H).

Example 254A ent-tert-Butyl {(1R,2R)-2-[({8-[(2,6-difluorobenzyl)oxy]-2,6-dimethylimidazo[1,2-a]pyridin-3-yl}-carbonyl)amino]cyclohexyl}carbamate

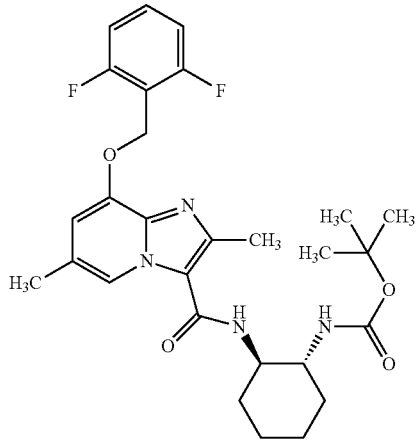 [SMILES: Cc1cc(OCc2c(F)cccc2F)c2nc(C)c(C(=O)N[C@@H]3CCCC[C@H]3NC(=O)OC(C)(C)C)n2c1]

Preparation and purification of the title compound were carried out analogously to Example 253A. Starting with 80 mg (0.24 mmol) of 8-[(2,6-difluorobenzyl)oxy]-2,6-dimethylimidazo[1,2-a]-pyridine-3-carboxylic acid Example 21A and 57 mg (0.27 mmol) of ent-(1R,2R)-trans-N-Boc-1,2-cyclohexanediamine, 107 mg (83% of theory; purity 98%) of the target compound were obtained.

LC-MS (Method 7): $R_t$=1.02 min

MS (ESpos): m/z=529 (M+H)$^+$ $^1$H NMR (400 MHz, DMSO-d$_6$): δ=1.16-1.45 (m, 13H), 1.61-1.74 (m, 2H), 1.76-1.86 (m, 1H), 1.89-1.99 (m, 1H), 2.30 (s, 3H), 2.46 (s, 3H), 3.37-3.46 (m, 1H), 3.67-3.78 (m, 1H), 5.28 (s, 2H), 6.81 (d, 1H), 6.91 (s, 1H), 7.20-7.28 (m, 2H), 7.54-7.64 (m, 2H), 8.46 (s, 1H).

Example 255A rac-Ethyl 8-[1-(2,6-difluorophenyl)ethoxy]-2,6-dimethylimidazo[1,2-a]pyridine-3-carboxylate

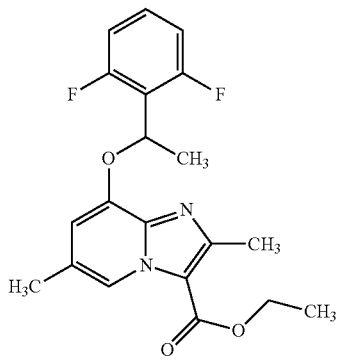 [SMILES: CCOC(=O)c1c(C)nc2c(OC(C)c3c(F)cccc3F)cc(C)cn12]

5.50 g (23.5 mmol) of ethyl 8-hydroxy-2,6-dimethylimidazo[1,2-a]pyridine-3-carboxylate Example 239A, 4.46 g (28.2 mmol) of 1-(2,6-difluorophenyl)ethanol, 5.35 ml (27.0 mmol) of diisopropyl azodicarboxylate and 7.08 g (27.0 mmol) of triphenylphosphine were dissolved in 141 ml of THF and stirred at RT for 2 h. 0.70 ml (3.5 mmol) of diisopropyl azodicarboxylate and 0.62 g (2.3 mmol) of triphenylphosphine were added to the reaction mixture, and the reaction solution was stirred at RT for 1 h. The precipitated solid was filtered off and dried under high vacuum. This gave 4.6 g (52.8% of theory; purity 100%) of the title compound. The fitrate was concentrated and purified twice by silica gel chromatography (cyclohexane:ethyl acetate gradient=from 8:1 to 4:1). All product-containing fractions were re-purified by preparative HPLC (RP18 column, mobile phase: acetonitrile/water gradient with addition of 0.1% TFA). This gave another 2.16 g (25% of theory) of the target compound.

LC-MS (Method 2): $R_t$=1.08 min

MS (ESpos): m/z=375 (M+H)$^+$ $^1$H NMR (400 MHz, DMSO-d$_6$): δ=1.34 (t, 3H), 1.79 (d, 3H), 2.25 (s, 3H), 2.58 (s, 3H), 4.33 (q, 2H), 6.17 (q, 1H), 6.73 (s, 1H), 7.06-7.16 (m, 2H), 7.37-7.48 (m, 1H), 8.67 (s, 1H).

Example 256A ent-Ethyl 8-[1-(2,6-difluorophenyl)ethoxy]-2,6-dimethylimidazo[1,2-a]pyridine-3-carboxylate (Enantiomer B)

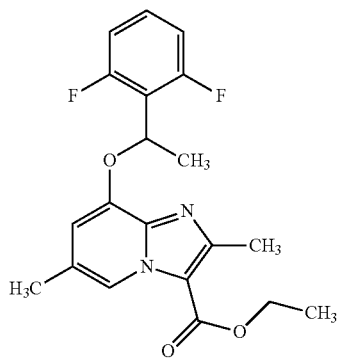 [SMILES: CCOC(=O)c1c(C)nc2c(OC(C)c3c(F)cccc3F)cc(C)cn12]

6.8 g of Example 255A were separated into the enantiomers by preparative separation on a chiral phase [column: Daicel Chiralpak AD-H, 5 µm, 250×30 mm, mobile phase: 70% isohexane, 30% ethanol, flow rate: 50 ml/min; 40° C., detection: 210 nm].
Enantiomer B:
Yield: 2.7 g (98.4% ee)
$R_t$=5.18 min [Daicel Chiralpak AD-H, 5 µm, 250×4.6 mm; mobile phase: 70% isohexane, 30% ethanol; flow rate 1.0 ml/min; 30° C.; detection: 220 nm].

Example 257A ent-8-[1-(2,6-Difluorophenyl)ethoxy]-2,6-dimethylimidazo[1,2-a]pyridine-3-carboxylic acid (Enantiomer B)

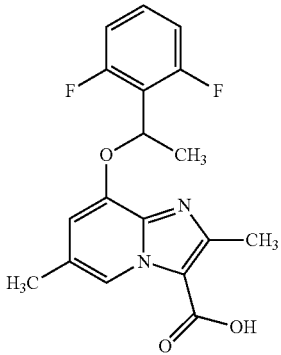

2.58 g (6.9 mmol) of ent-ethyl 8-[1-(2,6-difluorophenyl)ethoxy]-2,6-dimethylimidazo[1,2-a]-pyridine-3-carboxylate Example 256A (enantiomer B) were dissolved in 154 ml of THF/methanol 5:1, 34.5 ml (34.5 mmol) of 1 N aqueous lithium hydroxide solution were added and the mixture was stirred at 40° C. for 5 h. The reaction mixture, cooled to RT, was acidified with 6 N hydrochloric acid solution and concentrated. The solid was filtered off, washed with water and dried under high vacuum. This gave 2.26 g (95% of theory; purity 100%) of the title compound.

LC-MS (Method 2): $R_t$=0.74 min
MS (ESpos): m/z=347 (M+H)$^+$
$^1$H NMR (400 MHz, DMSO-d$_6$): δ=1.79 (d, 3H), 2.24 (s, 3H), 2.57 (s, 3H), 6.16 (q, 1H), 6.67 (s, 1H), 7.06-7.16 (m, 2H), 7.38-7.48 (m, 1H), 8.74 (s, 1H), 12.24-13.90 (br. s, 1H).

Example 258A

Ethyl 2,6-dimethyl-8-[4,4,4-trifluoro-3-(trifluoromethyl)butoxy]imidazo[1,2-a]pyridine-3-carboxylate

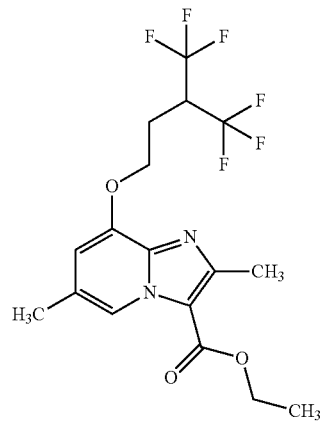 [SMILES: CCOC(=O)c1c(C)nc2c(OCCC(C(F)(F)F)C(F)(F)F)cc(C)cn12]

7.89 g (24.2 mmol) of caesium carbonate and 2.30 g (8.88 mmol) of 4,4,-trifluoro-3-(trifluoromethyl)butyl bromide were added to 1.89 g (8.07 mmol) of ethyl 8-hydroxy-2,6-dimethylimidazo[1,2-a]pyridine-3-carboxylate Example 239A in 60 ml of DMF, and the reaction mixture was stirred at RT for 90 min. 60 ml of water were then added, the precipitated solid was filtered off and the filter residue was washed with 100 ml of water and twice with 20 ml of tert-butyl methyl ether. The precipitate which had precipitated from the filtrate was filtered off and washed with filtrate. Both filter residues were taken up in 50 ml of ethyl acetate. The solution was concentrated under reduced pressure and the residue was dried under reduced pressure overnight. This gave 2.25 g of the target compound (95% pure, 64% of theory).

LC-MS (Method 2): $R_t$=1.16 min
MS (ESpos): m/z=413 (M+H)$^+$
$^1$H NMR (400 MHz, DMSO-d$_6$): δ=1.36 (t, 3H), 2.34 (s, 3H), 2.32-2.38 (m, 2H), 2.58 (s, 3H), 4.18-4.30 (m, 1H), 4.31-4.38 (m, 4H), 6.93 (s, 1H), 8.71 (s, 1H).

Example 259A 2,6-Dimethyl-8-[4,4,4-trifluoro-3-(trifluoromethyl)butoxy]imidazo[1,2-a]pyridine-3-carboxylic acid

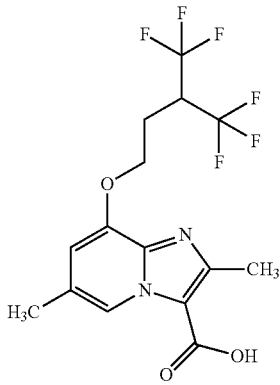 [SMILES: Cc1cc(OCCC(C(F)(F)F)C(F)(F)F)c2nc(C)c(C(=O)O)n2c1]

3.28 g (10.4 mmol) of barium hydroxide octahydrate were added to 1.95 g (4.73 mmol) of ethyl 2,6-dimethyl-8-[4,4,4-trifluoro-3-(trifluoromethyl)butoxy]imidazo[1,2-a]pyridine-3-carboxylate Example 258A in 30 ml of methanol, and the mixture was stirred at RT for 3 days. The suspension was diluted with 30 ml of water and adjusted to pH 6 with 1 M hydrochloric acid. The solid was filtered off, washed with 50 ml of water and dried under reduced pressure at 70° C. for 2 h. This gave 1.64 g of the target compound (90% pure, 81% of theory).

LC-MS (Method 2): $R_t$=0.78 min
MS (ESpos): m/z=385 (M+H)$^+$
$^1$H NMR (400 MHz, DMSO-d$_6$): δ=2.29 (s, 3H), 2.28-2.37 (m, 2H), 2.56 (s, 3H), 4.22-4.35 (m, 3H), 6.74 (s, 1H), 8.99 (s, 1H).

Example 260A rac-2-Amino-4-(benzyloxy)-2-methylbutanonitrile

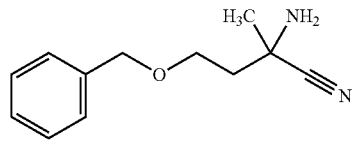

6.37 g (119.1 mmol) of ammonium chloride (dissolved in 15 ml of warm water) and 9 ml (216.6 mmol) of conc. ammonia in water were added to 5.31 g (108.3 mmol) of sodium cyanide in 10 ml of water. 19.3 g (108.3 mmol) of 4-(benzyloxy)butan-2-one, dissolved in 3 ml of ethanol, were then added. The mixture was stirred at RT for 15 min and at 60° C. for 2 h. Another 4 g (81.6 mmol) of sodium cyanide, 4.8 g (89.7 mmol) of ammonium chloride and 6.5 ml (156.4 mmol) of conc. ammonia in water were added and the mixture was stirred at 60° C. for a further 2 h. The reaction solution was then cooled, and 300 ml each of methylenechloride and water were added. After phase separation, the aqueous phase was extracted with 300 ml of methylene chloride. The combined organic phases were dried and concentrated. The crude product was purified on silica gel (cyclohexane/ethyl acetate gradient 6/4-1/1). This gave 19.9 g of the target compound (77% pure, 69% of theory).

LC-MS (Method 11): $R_t$=2.31 min
MS (ESpos): m/z=205 (M+H)$^+$
$^1$H NMR (400 MHz, DMSO-d$_6$): δ=1.37 (s, 3H), 1.81-1.94 (m, 2H), 2.57 (br. s, 2H), 3.58-3.69 (m, 2H), 4.48 (s, 2H), 7.25-7.38 (m, 5H).

Example 261A rac-4-(Benzyloxy)-2-methylbutane-1,2-diamine

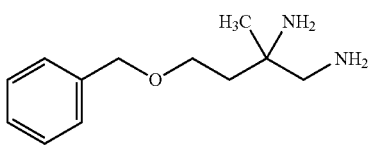

Under argon and at 0° C., 1.59 ml (1.59 mmol) of lithium aluminium hydride (1 N solution in diethyl ether) were added to 0.5 g (2.45 mmol) of 2-amino-4-(benzyloxy)-2-methylbutanonitrile Example 260A in 25 ml of dry THF. The reaction solution was stirred first at 0° C. for 30 min and then for another 1 h whilst slowly warming to room temperature. 245 µl of water, 245 µl of 2 N aqueous sodium hydroxide solution and 490 µl of water were then added carefully. The precipitate was filtered off and washed with THF and methanol, the filtrate was concentrated and the residue was purified by silica gel chromatography (mobile phase: dichloromethane/2 N ammonia in methanol=20/1, isocratic). This gave 0.30 g of the target compound (96% pure, 57% of theory).

LC-MS (Method 11): $R_t$=1.94 min
MS (ESpos): m/z=209 (M+H)$^+$
$^1$H NMR (400 MHz, DMSO-d$_6$): δ=0.90 (s, 3H), 1.56 (t, 2H), 2.27-2.38 (m, 2H), 3.45-3.60 (m, 2H), 4.42 (s, 2H), 7.22-7.36 (m, 5H).

Example 262A rac-2-Amino-3-(benzyloxy)-2-methylpropionitrile

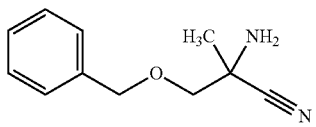

5.07 g (27.79 mmol) of 1-(benzyloxy)acetone were initially charged in 55.6 ml of 2 N aqueous ammonia in methanol, 1.53 g (31.12 mmol) of sodium cyanide and 3.71 g (31.12 mmol) of ammonium chloride were added and the mixture was heated under reflux for 2 h. Another 27.4 ml of 2 N aqueous ammonia in methanol were then added, and the reaction mixture was stirred under reflux for 2 h. The reaction solution was cooled and diluted with 90 ml of dichloromethane. The solid obtained was filtered off and the filtrate was concentrated. The residue was purified using silica gel (mobile phase: cyclohexane/ethyl acetate gradient: from 4/1 to 1/1). This gave 4.94 g of the target compound (90% pure, 84% of theory).

LC-MS (Method 2): R$_t$=0.60 min
MS (ESpos): m/z=191 (M+H)$^+$
$^1$H NMR (400 MHz, DMSO-d$_6$): δ=1.34 (s, 3H), 3.29-3.44 (m, 2H), 4.59 (s, 2H), 7.26-7.39 (m, 5H).

Example 263A rac-3-(Benzyloxy)-2-methylpropane-1,2-diamine

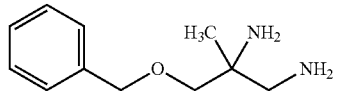

Under argon and at −78° C., 20.9 ml (20.9 mmol) of lithium aluminium hydride (1 N solution in diethyl ether) were added to 6.8 g (32.17 mmol, purity about 90%) of 2-amino-3-(benzyloxy)-2-methylpropionitrile Example 262A in 329 ml of dry THF. The reaction solution was at −78° C. for 1 h, at −20° C. for 2 h and at 0° C. for 2 h. 3.22 ml of water, 3.22 ml of 2 N aqueous sodium hydroxide solution and 6.44 ml of water were then added carefully. The precipitate was filtered off and washed with THF and methanol, and the filtrate was concentrated. This gave 8 g of the crude product. 7 g of this crude product were purified by silica gel chromatography (mobile phase: dichloromethane/2 N ammonia in methanol=from 20/1 to 10/1). This gave 1.52 g of the target compound (about 28% of theory).

LC-MS (Method 11): R$_t$=2.05 min
MS (ESpos): m/z=195 (M+H)$^+$
$^1$H NMR (400 MHz, DMSO-d$_6$): δ=0.88 (s, 3H), 1.39 (br. s, 2H), 2.30-2.47 (m, 2H), 3.12-3.22 (m, 2H), 4.44 (s, 2H), 7.24-7.38 (m, 5H).

Example 264A

Ethyl 2,6-dimethyl-8-[(2,3,6-trifluorobenzyl)oxy]imidazo[1,2-a]pyridine-3-carboxylate

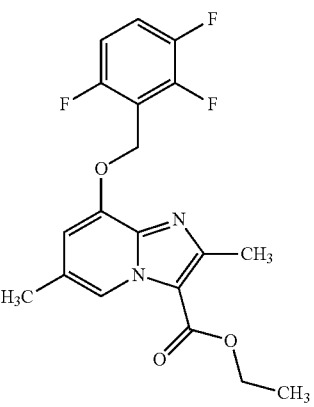 [SMILES: CCOC(=O)c1c(C)nc2c(OCc3c(F)ccc(F)c3F)cc(C)cn12]

3.00 g (12.81 mmol) of ethyl 8-hydroxy-2,6-dimethylimidazo[1,2-a]pyridine-3-carboxylate Example 239A, 3.27 g (14.1 mmol) of 2-(bromomethyl)-1,3,4-trifluorobenzene and 9.18 g (28.17 mmol) of caesium carbonate were initially charged in 183 ml of dry DMF and heated for 30 min in an oil bath warmed to 60° C. About 1.8 l of water were then added, and the mixture was stirred for 30 min. The solid was filtered off, washed with water and dried under reduced pressure. This gave 5.07 g of the title compound (99% of theory; purity about 96%).

LC-MS (Method 2): R$_t$=1.14 min
MS (ESpos): m/z=379 (M+H)$^+$
$^1$H NMR (400 MHz, DMSO-d$_6$): δ=1.35 (t, 3H); 2.36 (s, 3H); 2.55 (s, 3H; superimposed by DMSO signal); 4.36 (q, 2H); 5.35 (s, 2H); 7.09 (s, 1H); 7.22-7.32 (m, 1H); 7.60-7.73 (m, 1H); 8.72 (s, 1H).

Example 265A 2,6-Dimethyl-8-[(2,3,6-trifluorobenzyl)oxy]imidazo[1,2-a]pyridine-3-carboxylic acid

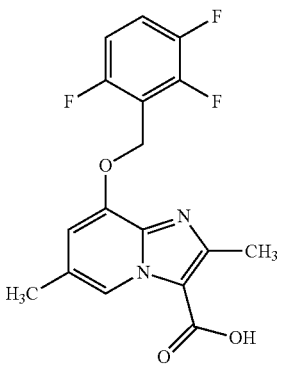

5.07 g (12.87 mmol) of ethyl 2,6-dimethyl-8-[(2,3,6-trifluorobenzyl)oxy]imidazo[1,2-a]pyridine-3-carboxylate Example 264A were dissolved in 275 ml of THF/methanol (5/1), 64.4 ml of 1 N aqueous lithium hydroxide solution were added and the mixture was stirred at 40° C. for 3.5 h. At 0° C., the mixture was acidified to about pH 4 with 6 N aqueous hydrochloric acid and concentrated. The solid formed was filtered off, washed with water and dried under reduced pressure. This gave 4.77 g (98% of theory; purity about 93%) of the title compound.

LC-MS (Method 2): R$_t$=0.72 min
MS (ESpos): m/z=351 (M+H)$^+$
$^1$H NMR (400 MHz, DMSO-d$_6$): δ=2.37 (s, 3H); 2.54 (s, 3H; superimposed by DMSO signal); 5.36 (s, 2H); 7.11 (s, 1H); 7.25-7.33 (m, 1H); 7.61-7.73 (m, 1H); 8.78 (s, 1H); 13.10 (br. s, 1H).

Example 266A

4-Fluoro-2-nitropyridin-3-ol

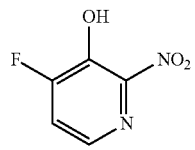 [SMILES: O=[N+]([O-])c1nccc(F)c1O]

With ice cooling, 500 mg (3.43 mmol) of 4-fluoropyridin-3-ol hydrochloride were dissolved carefully in 3.2 ml of concentrated sulphuric acid, and, at 0° C., 0.21 ml of concentrated nitric acid was added carefully. The reaction was warmed to RT and stirred at RT overnight. The mixture was then added to 10 g of ice, and 6 ml of 45% strength aqueous sodium hydroxide solution were added dropwise with ice cooling. The resulting precipitate was filtered off and then dried under reduced pressure overnight. This gave 191 mg (36% of theory) of the title compound.

LC-MS (Method 2): $R_t$=0.36 min
MS (ESneg): m/z=157 (M−H)⁻
¹H NMR (400 MHz, DMSO-$d_6$): δ=7.69 (dd, 1H); 7.95-8.01 (m, 1H); 11.97 (br. s, 1H).

Example 267A

2-Amino-4-fluoropyridin-3-ol

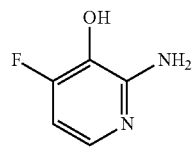

Under argon, 90 mg (0.57 mmol) of 4-fluoro-2-nitropyridin-3-ol Example 266A were dissolved in 30 ml of ethanol, a spatula tip of 10% palladium on activated carbon was added and the mixture was hydrogenated under atmospheric pressure at RT for 1.5 h. The mixture was then filtered off through silica gel and the filter cake was washed with a lot of ethanol. The solution was concentrated and dried. This gave 56 mg (77% of theory) of the title compound.

LC-MS (Method 2): $R_t$=0.16 min
MS (ESpos): m/z=129 (M+H)⁺
¹H NMR (400 MHz, DMSO-$d_6$): δ=5.78 (br. s, 2H); 6.42 (dd, 1H); 7.37-7.43 (m, 1H); 9.47 (br. s, 1H).

Example 268A

3-[(2,6-Difluorobenzyl)oxy]-4-fluoropyridine-2-amine

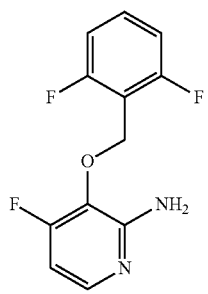 [SMILES: Nc1nccc(F)c1OCc1c(F)cccc1F]

55 mg (0.43 mmol) of 2-amino-4-fluoropyridin-3-ol Example 267A, 98 mg (0.47 mmol) of 2-(bromomethyl)-1,3-difluorobenzene and 308 mg (0.95 mmol) of caesium carbonate were initially charged in 1 ml of dry DMF and heated for 15 min in an oil bath warmed to 50° C. The mixture was then filtered off and purified by preparative HPLC (Method 9). This gave 70 mg of the title compound (64% of theory).

LC-MS (Method 2): $R_t$=0.70 min
MS (ESpos): m/z=255 (M+H)⁺
¹H NMR (400 MHz, DMSO-$d_6$): δ=5.06 (s, 2H); 6.04 (br. s, 2H); 6.42 (dd, 1H); 7.08-7.16 (m, 2H); 7.45-7.54 (m, 1H); 7.62-7.69 (m, 1H).

Example 269A

Ethyl 8-[(2,6-difluorobenzyl)oxy]-7-fluoro-2-methylimidazo[1,2-a]pyridine-3-carboxylate

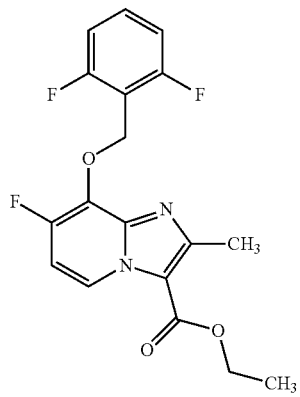 [SMILES: CCOC(=O)c1c(C)nc2c(OCc3c(F)cccc3F)c(F)ccn12]

Under argon, 500 mg (1.97 mmol) of 3-[(2,6-difluorobenzyl)oxy]-4-fluoropyridine-2-amine Example 268A were initially charged in 10 ml of ethanol, 500 mg of powdered molecular sieve 4 Å and 3.24 g (19.67 mmol) of ethyl 2-chloroacetoacetate were added and the mixture was then heated at reflux for 48 h. All volatile components were evaporated at 85° C. under reduced pressure. The crude product was purified by silica gel chromatography (mobile phase: cyclohexane/ethyl acetate=9/1 isocratic). This gave 368 mg (39% of theory; purity about 76%) of the title compound.

LC-MS (Method 2): $R_t$=1.19 min
MS (ESpos): m/z=365 (M+H)⁺
¹H NMR (400 MHz, DMSO-$d_6$): δ=1.37 (t, 3H); 2.62 (s, 3H); 4.38 (q, 2H); 5.60 (s, 2H); 7.09-7.22 (m, 3H); 7.47-7.56 (m, 1H); 8.98 (dd, 1H).

Example 270A

8-[(2,6-Difluorobenzyl)oxy]-7-fluoro-2-methylimidazo[1,2-a]pyridine-3-carboxylic acid

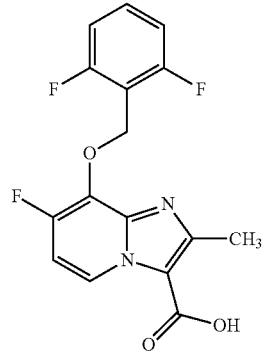 [SMILES: Cc1nc2c(OCc3c(F)cccc3F)c(F)ccn2c1C(=O)O]

1.14 ml (1.14 mmol) of 1 N lithium hydroxide solution were added to 365 mg (0.76 mmol; purity about 76%) of ethyl 8-[(2,6-difluorobenzyl)oxy]-7-fluoro-2-methylimidazo[1,2-a]pyridine-3-carboxylate Example 269A in 16.6 ml of THF/ethanol (5/1), and the mixture was stirred at RT overnight. Another 2.67 ml (2.67 mmol) of 1 N lithium hydroxide solution were added and the mixture was stirred at RT overnight. Under reduced pressure, the reaction mixture was freed from organic solvent, and the aqueous phase was acidified to pH 4 with 6 N hydrochloric acid whilst cooling with ice water. The solid formed was filtered off and dried under high vacuum. This gave 236 mg of the target compound (87% of theory, purity 94%).

LC-MS (Method 2): $R_t$=0.83 min

MS (ESpos): m/z=337 (M+H)$^+$ $^1$H NMR (400 MHz, DMSO-d$_6$): δ=2.62 (s, 3H); 5.60 (s, 2H); 7.09-7.18 (m, 3H); 7.47-7.55 (m, 1H); 9.04 (dd, 1H); 13.22 (br. s, 1H).

Example 271A rac-Benzyl (2-cyanobutan-2-yl)carbamate

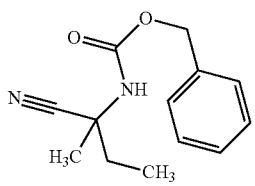 [SMILES: CCC(C)(C#N)NC(=O)OCc1ccccc1]

5.00 g (50.94 mmol) of 2-amino-2-methylbutanonitrile [synthesis described in: Lonza AG, U.S. Pat. No. 5,698,704 (1997); Deng, S. L. et al. *Synthesis* 2001, 2445; Hjorringgaard, C. U. et al. *J. Org. Chem.* 2009, 74, 1329; Ogrel, A. et al. *Eur. J. Org. Chem.* 2000, 857] were initially charged in 50 ml of THF and 6.5 ml of water, 21.83 g (157.92 mmol) of potassium carbonate were added and 7.9 ml (56.04 mmol) of benzyl chlorocarbonate (benzyl chloroformate) were added at 0° C. After addition of 8 ml of THF and 3 ml of water, the reaction mixture was stirred overnight whilst slowly warming to RT. Water was then added, and the mixture was extracted three times with ethyl acetate. The combined organic phases were dried over sodium sulphate and concentrated. The residue was dissolved in diethyl ether and precipitated with petroleum ether. The product was filtered off and the solid was washed with a little petroleum ether and dried under high vacuum. This gave 11.35 g of the target compound (93% of theory, purity 97%).

LC-MS (Method 2): $R_t$=0.97 min

MS (ESpos): m/z=233 (M+H)$^+$ $^1$H NMR (400 MHz, DMSO-d$_6$): δ=0.95 (t, 3H), 1.51 (s, 3H), 1.75-1.95 (m, 2H), 5.07 (s, 2H), 7.30-7.43 (m, 4H), 7.88-8.03 (m, 1H).

Example 272A ent-Benzyl (2-cyanobutan-2-yl)carbamate
(Enantiomer A)

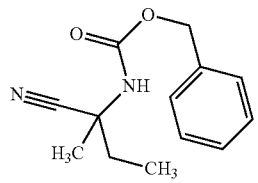

8 g of rac-benzyl (2-cyanobutan-2-yl)carbamate Example 271A were separated into the enantiomers by preparative separation on a chiral phase [column: Daicel Chiralcel OJ-H, 5 μm, 250×20 mm, mobile phase: 50% isohexane, 50% isopropanol, flow rate: 20 ml/min; 40° C., detection: 220 nm].

Enantiomer A: Yield: 3.23 g (>99% ee)

$R_t$=6.69 min [Daicel Chiralcel OJ-H, 5 μm, 250×4.6 mm; mobile phase: 50% isohexane, 50% isopropanol; flow rate 1.0 ml/min; 30° C.; detection: 220 nm].

Example 273A ent-Benzyl (2-cyanobutan-2-yl)carbamate
(Enantiomer B)

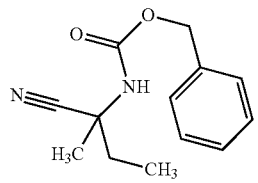

8 g of rac-benzyl (2-cyanobutan-2-yl)carbamate Example compound 271A were separated into the enantiomers by preparative separation on a chiral phase [column: Daicel Chiralcel OJ-H, 5 μm, 250×20 mm, mobile phase: 50% isohexane, 50% isopropanol, flow rate: 20 ml/min; 40° C., detection: 220 nm].

Enantiomer B: Yield: 3.18 g (>99% ee)

$R_t$=8.29 min [Daicel Chiralcel OJ-H, 5 μm, 250×4.6 mm; mobile phase: 50% isohexane, 50% isopropanol; flow rate 1.0 ml/min; 30° C.; detection: 220 nm].

Example 274A ent-Benzyl (1-amino-2-methylbutan-2-yl)carbamate
(Enantiomer A)

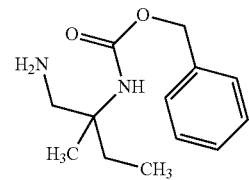 [SMILES: CCC(C)(CN)NC(=O)OCc1ccccc1]

4.00 g (17.22 mmol) of ent-benzyl (2-cyanobutan-2-yl)carbamate Example 272A were dissolved in 50 ml of a 7 N solution of ammonia in methanol, 5.33 g of Raney nickel were added and hydrogenated at about 25 bar at RT for 24 h. The mixture was filtered off through Celite, the filter cake was washed with methanol and the filtrate was concentrated. The crude product was purified by silica gel chromatography (mobile phase: dichloromethane/2N ammonia in methanol=10/0.5). This gave 2.20 g of the target compound (54% of theory).

LC-MS (Method 2): $R_t$=0.56 min
MS (ESpos): m/z=237 (M+H)$^+$

Example 275A ent-Benzyl (1-amino-2-methylbutan-2-yl)carbamate (Enantiomer B)

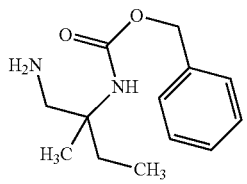 [SMILES: CCC(C)(CN)NC(=O)OCc1ccccc1]

4.00 g (17.22 mmol) of ent-benzyl (2-cyanobutan-2-yl)carbamate Example 273A were dissolved in 50 ml of a 7 N solution of ammonia in methanol, 5.33 g of Raney nickel were added and the mixture was hydrogenated at about 25 bar at RT for 24 h. The reaction mixture was filtered off through Celite, the filter cake was washed thoroughly with methanol and the filtrate was concentrated. The crude product was purified by silica gel chromatography (mobile phase: dichloromethane/2N ammonia in methanol=10/0.5). This gave 3.56 g of the target compound (87% of theory).

LC-MS (Method 13): $R_t$=1.40 min
MS (ESpos): m/z=237 (M+H)$^+$

Example 276A ent-Benzyl {1-[({8-[(2,6-difluorobenzyl)oxy]-2,6-dimethylimidazo[1,2-a]pyridin-3-yl}carbonyl)-amino]-2-methylbutan-2-yl}carbamate (Enantiomer A)

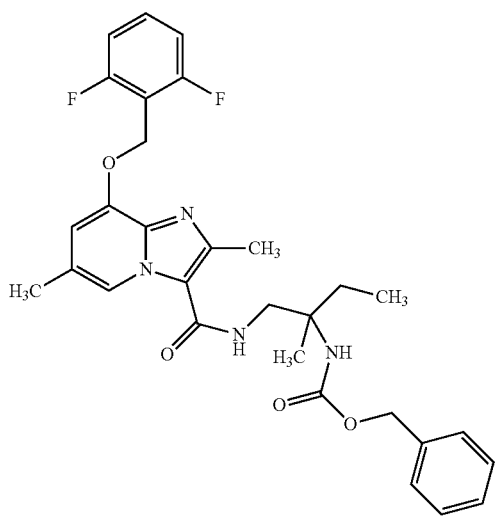 [SMILES: CCC(C)(CNC(=O)c1c(C)nc2c(OCc3c(F)cccc3F)cc(C)cn12)NC(=O)OCc1ccccc1]

2.34 g (6.75 mmol; purity about 96%) of 8-[(2,6-difluorobenzyl)oxy]-2,6-dimethylimidazo[1,2-a]-pyridine-3-carboxylic acid Example 21A, 2.82 g (7.43 mmol) of O-(7-azabenzotriazol-1-yl)-N,N,N'N'-tetramethyluronium hexafluorophosphate (HATU) and 2.62 g (20.25 mmol) of N,N-diisopropylethylamine were initially charged in 43 ml of DMF and stirred at RT for 20 min. 1.80 g (7.43 mmol) of ent-benzyl (1-amino-2-methylbutan-2-yl)carbamate (enantiomer A) Example 274A were then added, and the mixture was stirred at RT overnight. About 200 ml of water were added, and the reaction solution was stirred at RT for 45 min. The solid formed was filtered off, dissolved in ethyl acetate and washed twice with water. The organic phase was dried over sodium sulphate, filtered and concentrated. The residue was dissolved in ethyl acetate and washed with 0.1 N aqueous hydrochloric acid and water. The organic phase was dried over sodium sulphate, filtered and concentrated. This gave 3.55 g of the target compound (96% of theory).

LC-MS (Method 2): $R_t$=1.08 min
MS (ESpos): m/z=551 (M+H)$^+$
$^1$H NMR (400 MHz, DMSO-d$_6$): δ=0.82 (t, 3H), 1.19 (s, 3H), 1.52-1.63 (m, 1H), 1.75-1.87 (m, 1H), 2.31 (s, 3H), 3.46-3.58 (m, 2H), 5.00 (s, 2H), 5.30 (s, 2H), 6.98 (br. s, 1H), 7.05 (s, 1H), 7.19-7.39 (m, 7H), 7.54-7.64 (m, 1H), 7.75 (br. s, 1H), 8.48 (s, 1H), [further signal hidden under DMSO signal].

Example 277A ent-Benzyl {1-[({8-[(2,6-difluorobenzyl)oxy]-2,6-dimethylimidazo[1,2-a]pyridin-3-yl}carbonyl)-amino]-2-methylbutan-2-yl}carbamate (Enantiomer B)

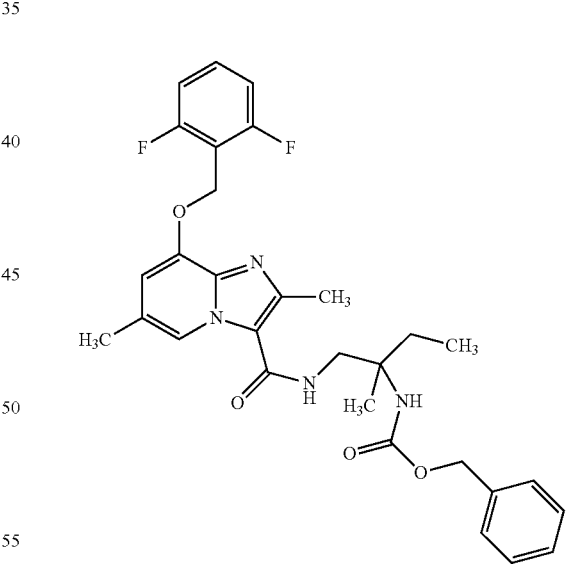

1.40 g (4.03 mmol; purity about 96%) of 8-[(2,6-difluorobenzyl)oxy]-2,6-dimethylimidazo[1,2-a]-pyridine-3-carboxylic acid Example 21A, 1.69 g (4.43 mmol) of O-(7-azabenzotriazol-1-yl)-N,N,N'N'-tetramethyluronium hexafluorophosphate (HATU) and 1.56 g (12.09 mmol) of N,N-diisopropylethylamine were initially charged in 26 ml of DMF and stirred at RT for 20 min. 1.00 g (4.23 mmol) of ent-benzyl (1-amino-2-methylbutan-2-yl)carbamate (enantiomer B) Example 275A was then added, and the mixture was stirred at RT overnight. Another 48 mg (0.20 mmol) of ent-benzyl (1-amino-2-methylbutan-2-yl)carbamate (enantiomer B) were added, and the mixture was stirred at RT for 30 min. About 200 ml of water were added, and the reaction solution was stirred at room temperature for 45 min. The solid formed was filtered off and washed twice with water. This gave 2.06 g of the target compound (89% of theory; purity about 96%). The filter used was rinsed with acetonitrile and the solvent was concentrated. This gave another 0.12 g of the target compound (5% of theory; purity about 96%).

LC-MS (Method 2): $R_t$=1.08 min
MS (ESpos): m/z=551 (M+H)$^+$
$^1$H NMR (400 MHz, DMSO-$d_6$): δ=0.82 (t, 3H), 1.19 (s, 3H), 1.51-1.63 (m, 1H), 1.75-1.87 (m, 1H), 2.31 (s, 3H), 3.46-3.58 (m, 2H), 5.00 (s, 2H), 5.29 (s, 2H), 6.92 (s, 1H), 7.05 (s, 1H), 7.19-7.39 (m, 7H), 7.54-7.64 (m, 1H), 7.69 (t, 1H), 8.48 (s, 1H), [further signal hidden under DMSO signal].

Example 278A ent-Benzyl {1-[({2,6-dimethyl-8-[(2,3,6-trifluorobenzyl)oxy]imidazo[1,2-a]pyridin-3-yl}-carbonyl)amino]-2-methylbutan-2-yl}carbamate trifluoroacetate (Enantiomer A)

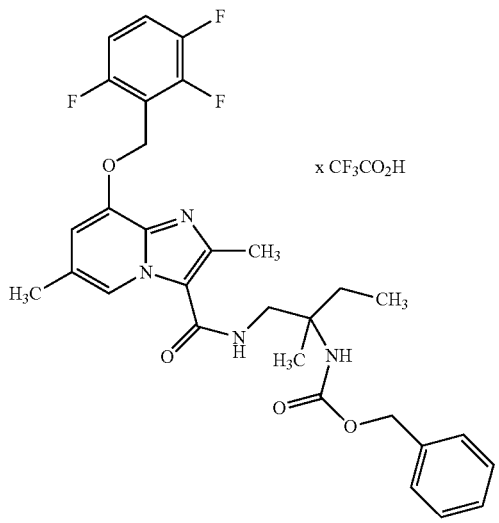 [SMILES: CCC(C)(CNC(=O)c1c(C)nc2c(OCc3c(F)ccc(F)c3F)cc(C)cn12)NC(=O)OCc1ccccc1]

282 mg (0.81 mmol) of 2,6-dimethyl-8-[(2,3,6-trifluorobenzyl)oxy]imidazo[1,2-a]pyridine-3-carboxylic acid Example 265A, 337 mg (0.89 mmol) of O-(7-azabenzotriazol-1-yl)-N,N,N'N'-tetramethyluronium hexafluorophosphate (HATU) and 313 mg (2.42 mmol) of N,N-diisopropylethylamine were initially charged in 5.1 ml of DMF and stirred at RT for 20 min. 219 mg (0.93 mmol) of ent-benzyl (1-amino-2-methylbutan-2-yl)carbamate (enantiomer A) Example 274A were then added, and the mixture was stirred at RT overnight. A little water/acetonitrile was added to the reaction solution, and the product was purified by preparative HPLC (RP18 column, mobile phase: acetonitrile/water gradient with addition of 0.1% TFA). This gave 389 mg of the target compound (71% of theory).

LC-MS (Method 2): $R_t$=1.14 min
MS (ESpos): m/z=569 (M−TFA+H)$^+$
$^1$H NMR (400 MHz, DMSO-$d_6$): δ=0.82 (t, 3H), 1.19 (s, 3H), 1.49-1.62 (m, 1H), 1.76-1.89 (m, 1H), 2.38 (s, 3H), 3.48-3.60 (m, 2H; superimposed by solvent signal), 4.95-5.05 (m, 2H), 5.43 (s, 2H), 7.08 (s, 1H), 7.22-7.43 (m, 7H), 7.64-7.74 (m, 1H), 8.18 (br. s, 1H), 8.53 (s, 1H), [further signal hidden under DMSO signal].

Example 279A ent-Benzyl {1-[({2,6-dimethyl-8-[(2,3,6-trifluorobenzyl)oxy]imidazo[1,2-a]pyridin-3-yl}-carbonyl)amino]-2-methylbutan-2-yl}carbamate trifluoroacetate (Enantiomer B)

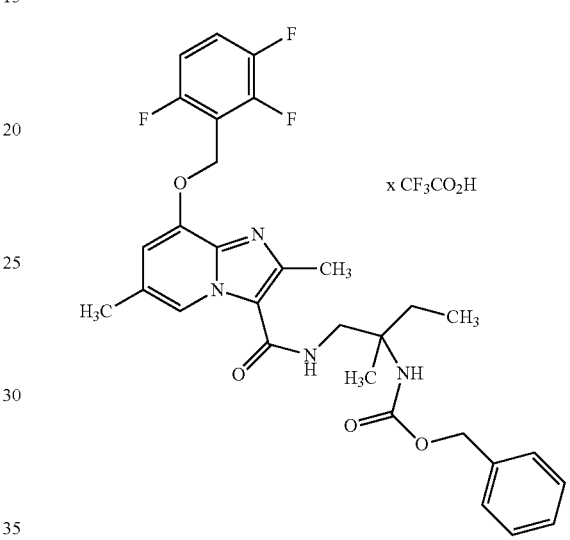

282 mg (0.81 mmol) of 2,6-dimethyl-8-[(2,3,6-trifluorobenzyl)oxy]imidazo[1,2-a]pyridine-3-carboxylic acid Example 265A, 337 mg (0.89 mmol) of O-(7-azabenzotriazol-1-yl)-N,N,N'N'-tetramethyluronium hexafluorophosphate (HATU) and 313 mg (2.42 mmol) of N,N-diisopropylethylamine were initially charged in 5.1 ml of DMF and stirred at RT for 20 min. 200 mg (0.85 mmol) of ent-benzyl (1-amino-2-methylbutan-2-yl)carbamate (enantiomer B) Example 275A were then added, and the mixture was stirred at RT overnight. A little water/acetonitrile was added to the reaction solution, and the product was purified by preparative HPLC (RP18 column, mobile phase: acetonitrile/water gradient with addition of 0.1% TFA). This gave 206 mg of the target compound (36% of theory; purity 97%).

LC-MS (Method 2): $R_t$=1.13 min
MS (ESpos): m/z=569 (M−TFA+H)$^+$
$^1$H NMR (400 MHz, DMSO-$d_6$): δ=0.82 (t, 3H), 1.19 (s, 3H), 1.49-1.62 (m, 1H), 1.76-1.89 (m, 1H), 2.39 (s, 3H), 3.49-3.61 (m, 2H; superimposed by solvent signal), 4.95-5.05 (m, 2H), 5.44 (s, 2H), 7.08 (s, 1H), 7.23-7.46 (m, 7H), 7.64-7.74 (m, 1H), 8.20 (br. s, 1H), 8.53 (s, 1H), [further signal hidden under DMSO signal].

Example 280A

5-Methoxy-2-nitropyridin-3-ole

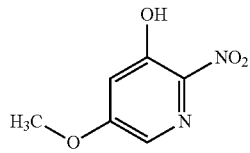

1) Under argon, 0.68 ml (4.8 mmol) of trifluoroacetic anhydride was added slowly, at 0° C., to 1.46 g (4.8 mmol) of tetra-n-butylammonium nitrate in 10 ml of dichloromethane, and the mixture was stirred at 0° C. for 10 min.

2) Under argon, in a separate reaction flask, 500 mg (4 mmol) of 5-methoxypyridin-3-ole were dissolved in 10 ml of dichloromethane, and the solution from step 1) was added dropwise at −30° C. The reaction mixture was stirred in the thawing ice bath (not warmer than 0° C.) for 4 h. Kieselguhr was added to the reaction solution, the mixture was concentrated at a relatively low temperature and the product was purified by silica gel chromatography (mobile phase: cyclohexane/ethyl acetate: 9/1). This gave 637 mg (94% of theory) of the target compound.

LC-MS (Method 2): $R_t$=0.58 min
MS (ESpos): m/z=171 (M+H)$^+$
$^1$H-NMR (400 MHz, DMSO-d$_6$): δ=3.90 (s, 3H), 7.11 (d, 1H), 7.78 (d, 1H), 11.35 (br. 1H).

Example 281A

3-[(2,6-Difluorobenzyl)oxy]-5-methoxy-2-nitropyridine

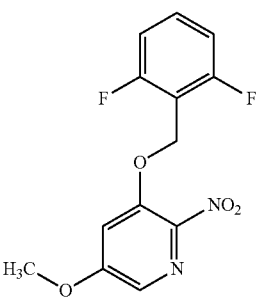 [SMILES: COc1cnc([N+](=O)[O-])c(OCc2c(F)cccc2F)c1]

0.93 g (4.47 mmol) of 2,6-difluorobenzyl bromide was added to 0.76 g (4.47 mmol) of 5-methoxy-2-nitropyridin-3-ole from Example 280A and 2.18 g (6.70 mmol) of caesium carbonate in 12.5 ml of DMF, and the mixture was stirred at RT overnight. The reaction mixture was added to 100 ml of 1 N aqueous hydrochloric acid and stirred at RT for 30 minutes. The solid was filtered off, washed with water and dried under high vacuum. This gave 1.28 g (97% of theory) of the title compound.

LC-MS (Method 2): $R_t$=1.02 min
MS (ESpos): m/z=297 (M+H)$^+$
$^1$H-NMR (400 MHz, DMSO-d$_6$): δ=4.00 (s, 3H), 5.42 (s, 2H), 7.21 (t, 2H), 7.58 (quintet, 1H), 7.70 (d, 1H), 7.88 (d, 1H).

Example 282A

3-[(2,6-Difluorobenzyl)oxy]-5-methoxypyridine-2-amine

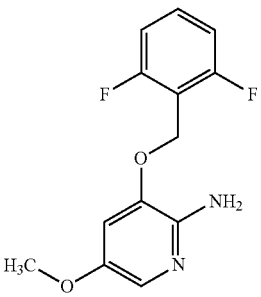

0.73 g (13.1 mmol) of iron powder was added to 1.25 g (4.22 mmol) of 3-[(2,6-difluorobenzyl)oxy]-5-methoxy-2-nitropyridine from Example 281A in 12.7 ml of ethanol, and the mixture was heated to reflux. 3.23 ml (38.8 mmol) of concentrated aqueous hydrochloric acid were slowly added dropwise, and the mixture was stirred at reflux for a further 30 min. The reaction was cooled and stirred into an ice/water mixture and stirred for 30 min. The organic solvent was removed under reduced pressure, the aqueous phase was made alkaline with 1 N aqueous sodium hydroxide solution and stirred with dichloromethane and the mixture was filtered off through Celite. The filter cake was washed with dichloromethane and the aqueous phase was extracted twice with dichloromethane. The combined organic phases were dried over sodium sulphate and filtered, the filtrate was concentrated and the residue was dried under high vacuum. This gave 974 mg of the target compound (85% of theory).

LC-MS (Method 2): $R_t$=0.61 min
MS (ESpos): m/z=267 (M+H)$^+$
$^1$H-NMR (400 MHz, DMSO-d$_6$): δ=3.72 (s, 3H), 5.10 (s, 2H), 5.14 (s, 2H), 7.04 (d, 1H), 7.20 (t, 2H), 7.32 (d, 1H), 7.55 (quintet, 1H).

Example 283A

Ethyl 8-[(2,6-difluorobenzyl)oxy]-6-methoxy-2-methylimidazo[1,2-a]pyridine-3-carboxylate

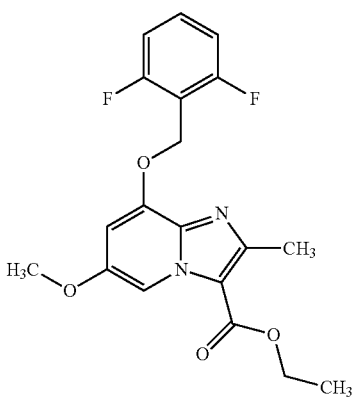 [SMILES: CCOC(=O)c1c(C)nc2c(OCc3c(F)cccc3F)cc(OC)cn12]

0.93 g of powdered molecular sieve 3 Å and 6.0 g (36.43 mmol) of ethyl-2-chloroacetoacetate were added to 0.97 g (3.64 mmol) of 3-[(2,6-difluorobenzyl)oxy]-5-methoxypyridine-2-amine from Example 282A, and the mixture was heated at reflux overnight. The reaction mixture was concentrated on a dry-ice rotary evaporator at a waterbath temperature of 85° C. The crude product was purified by silica gel chromatography (mobile phase: cyclohexane/ethyl acetate: 9/1 isocratic). This gave 583 mg of the target compound (41% of theory).

LC-MS (Method 2): $R_t$=1.09 min

MS (ESpos): m/z=377 (M+H)$^+$ $^1$H-NMR (400 MHz, DMSO-d$_6$): δ=1.36 (t, 3H), 2.54 (s, 3H; obscured by DMSO signal), 3.83 (s, 3H), 4.37 (q, 2H), 5.32 (s, 2H), 7.05 (d, 1H), 7.23 (t, 2H), 7.60 (quintet, 1H), 8.58 (d, 1H).

Example 284A

8-[(2,6-Difluorobenzyl)oxy]-6-methoxy-2-methylimidazo[1,2-a]pyridine-3-carboxylic acid

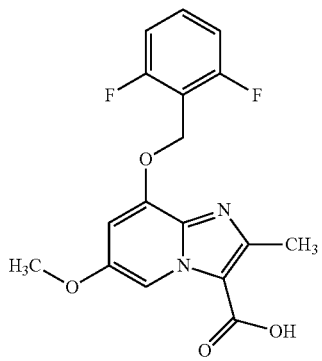

7.7 ml of 1 M aqueous lithium hydroxide solution were added to 580 mg (1.54 mmol) of ethyl 8-[(2,6-difluorobenzyl)oxy]-6-methoxy-2-methylimidazo[1,2-a]pyridine-3-carboxylate from Example 283A in 33 ml of THF/methanol (5/1), and the mixture was stirred at 40° C. overnight. The reaction mixture was cooled, adjusted to pH 4 using 6 N aqueous hydrochloric acid and ice-cooling and then freed from the organic solvents on a rotary evaporator. The solid formed was filtered off, washed with water and then dried under high vacuum. This gave 507 mg of the target compound (94% of theory).

LC-MS (Method 2): $R_t$=0.74 min

MS (ESpos): m/z=349 (M+H)$^+$ $^1$H-NMR (400 MHz, DMSO-d$_6$): δ=2.54 (s, 3H; superimposed by DMSO signal), 3.85 (s, 3H), 5.38 (s, 2H), 7.20-7.32 (m, 3H), 7.61 (quintet, 1H), 8.68 (d, 1H), 13.40 (br. s, 1H).

Example 285A rac-benzyl (2-cyanpentan-2-yl)carbamate

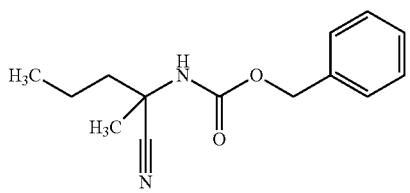 [SMILES: CCCC(C)(C#N)NC(=O)OCc1ccccc1]

76.4 g (552.7 mmol) of potassium carbonate were added to 20 g (178.3 mmol) of rac-2-amino-2-methylpentanonitrile (described in: Deng, S L. et al., Synthesis 2001, 2445-2449; Freifelder, M. et al., J. Am. Chem. Soc. 1960, 696-698) and 2.63 l of THF/water (8/1). At 0° C., 27.6 ml (196.1 mmol) of benzyl chloroformate were slowly added dropwise, and the mixture was stirred at RT overnight. The reaction mixture was concentrated, water was added to the residue and the mixture was extracted twice with ethyl acetate. The combined organic phases were dried over sodium sulphate, filtered and concentrated. The residue was purified by silica gel chromatography (mobile phase: cyclohexane/ethyl acetate 4/1). This gave 43.84 g of the target compound (76% of theory, purity 76%).

LC-MS (Method 2): $R_t$=1.02 min

MS (ESpos): m/z=247 (M+H)$^+$ $^1$H-NMR (400 MHz, DMSO-d$_6$): δ=0.90 (t, 3H), 1.31-1.48 (m, 2H), 1.52 (s, 3H), 1.70-1.88 (m, 2H), 5.07 (s, 2H), 7.30-7.42 (m, 5H), 8.00 (br. s, 1H).

Example 286A ent-Benzyl (2-cyanpentan-2-yl)carbamate (Enantiomer A) from 285A

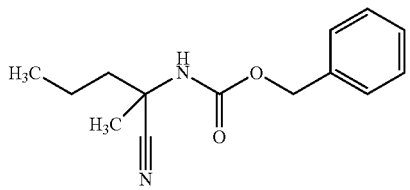 [SMILES: CCCC(C)(C#N)NC(=O)OCc1ccccc1]

43.8 g (135.3 mmol) of rac-benzyl (2-cyanpentan-2-yl) carbamate from Example 285A were separated into the enantiomers by preparative separation on a chiral phase [column: SFC Chiralpak AZ-H, 5 μm, 250×50 mm, mobile phase: 85% CO$_2$, 15% methanol, flow rate: 250 ml/min; temperature: 28° C., backpressure: 100 bar, detection: 220 nm].

Enantiomer A: yield: 13.13 g (>99% ee)

$R_t$=2.76 min [SFC Chiralpak AZ-H, 5 μm, 250×4.6 mm; mobile phase: 90% CO$_2$, 10% methanol; flow rate: 3 ml/min; detection: 220 nm].

Example 287A ent-Benzyl (2-cyanpentan-2-yl)carbamate (Enantiomer B) from 285A

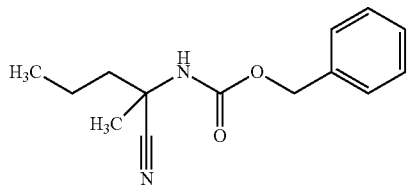 [SMILES: CCCC(C)(C#N)NC(=O)OCc1ccccc1]

43.8 g (135.3 mmol) of rac-benzyl (2-cyanpentan-2-yl)carbamate from Example 285A were separated into the enantiomers by preparative separation on a chiral phase [column: SFC Chiralpak AZ-H, 5 μm, 250×50 mm, mobile phase: 85% CO$_2$, 15% methanol, flow rate: 250 ml/min; temperature: 28° C., backpressure: 100 bar, detection: 220 nm].

Enantiomer B: yield: 13.48 g (about 90.4% ee)

R$_t$=3.93 min [SFC Chiralpak AZ-H, 5 μm, 250×4.6 mm; mobile phase: 90% CO$_2$, 10% methanol; flow rate: 3 ml/min; detection: 220 nm].

Example 288A ent-Benzyl (1-amino-2-methylpentan-2-yl)carbamate (Enantiomer A)

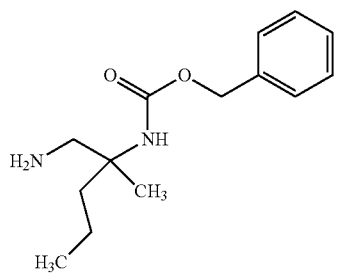 [SMILES: CCCC(C)(CN)NC(=O)OCc1ccccc1]

13.1 g (53.31 mmol) of ent-benzyl (2-cyanpentan-2-yl)carbamate (enantiomer A) from Example 286A VAK5346-1-3 were dissolved in 155 ml of 7 N ammonia solution in methanol, and 16.5 g of Raney nickel (50% strength aqueous suspension) were added under argon. The reaction mixture was hydrogenated in an autoclave at 20-30 bar overnight. The mixture was filtered off through Celite, the filter cake was washed with methanol, dichloromethane/2 N ammonia in methanol (20/1) and the filtrate was concentrated. The residue was purified by silica gel chromatography (mobile phase: dichloromethane/methanol 40/1 to 20/1). This gave 9.85 g of the target compound (63% of theory, purity 86%).

LC-MS (Method 2): R$_t$=0.58 min

MS (ESpos): m/z=251 (M+H)$^+$ $^1$H-NMR (400 MHz, DMSO-d$_6$): δ=0.83 (t, 3H), 1.11 (s, 3H), 1.15-1.24 (m, 2H), 1.37 (br. s, 2H), 1.42-1.51 (m, 1H), 1.53-1.63 (m, 1H), 2.46 (d, 1H), 2.66 (d, 1H), 4.97 (s, 2H), 6.69 (br. s, 1H), 7.26-7.40 (m, 5H).

Example 289A ent-Benzyl (1-amino-2-methylpentan-2-yl)carbamate (Enantiomer B)

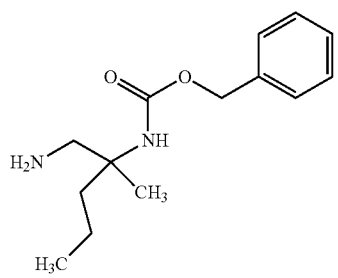 [SMILES: CCCC(C)(CN)NC(=O)OCc1ccccc1]

13.5 g (54.73 mmol) of ent-benzyl (2-cyanpentan-2-yl)carbamate (enantiomer B) from Example 287A VAK5347-1-4 were dissolved in 159 ml of 7 N ammonia solution in methanol, and 16.95 g of Raney nickel (50% strength aqueous suspension) were added under argon. The reaction mixture was hydrogenated in an autoclave at 20-30 bar overnight. The mixture was filtered off through Celite, the filter cake was washed with methanol, dichloromethane/2 N ammonia in methanol (10/1) and the filtrate was concentrated. The residue was purified by silica gel chromatography (mobile phase: dichloromethane/methanol 40/1 to 20/1). This gave 9.46 g of the target compound (61% of theory, purity 88%).

LC-MS (Method 2): R$_t$=0.58 min

MS (ESpos): m/z=251 (M+H)$^+$ $^1$H-NMR (400 MHz, DMSO-d$_6$): δ=0.83 (t, 3H), 1.11 (s, 3H), 1.15-1.24 (m, 2H), 1.37 (br. s, 2H), 1.42-1.51 (m, 1H), 1.53-1.63 (m, 1H), 2.46 (d, 1H), 2.66 (d, 1H), 4.97 (s, 2H), 6.69 (br. s., 1H), 7.26-7.40 (m, 5H).

Example 290A ent-Benzyl {1-[({8-[(2,6-difluorobenzyl)oxy]-6-methoxy-2-methylimidazo[1,2-a]pyridin-3-yl}carbonyl)amino]-2-methylpentan-2-yl}carbamate trifluoroacetate (Enantiomer B)

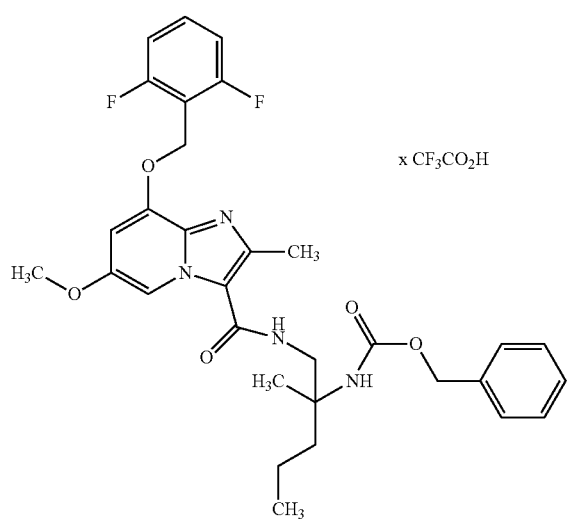 [SMILES: CCCC(C)(CNC(=O)c1c(C)nc2c(OCc3c(F)cccc3F)cc(OC)cn12)NC(=O)OCc1ccccc1]

156 mg (0.41 mmol) of HATU and 0.28 ml (1.58 mmol) of N,N-diisopropylethylamine were added to 110 mg (0.32 mmol) of 8-[(2,6-difluorobenzyl)oxy]-6-methoxy-2-methyl-imidazo[1,2-a]pyridine-3-carboxylic acid from Example 284A. The reaction mixture was stirred at RT for 10 min, 103 mg (0.41 mmol) of ent-benzyl (1-amino-2-methylpentan-2-yl)carbamate (enantiomer B) from Example 289A were then added and the mixture was stirred at RT for 1 hour. TFA was added to the reaction mixture, which was then separated by preparative HPLC (RP18 column, mobile phase: acetonitrile/water gradient with addition of 0.1% TFA). The product fractions were concentrated on a rotary evaporator. This gave 180 mg of the target compound (82% of theory).

LC-MS (Method 2): $R_t$=1.15 min

MS (ESpos): m/z=581 (M−TFA+H)$^+$

Example 291A ent-Benzyl {1-[({8-[(2,6-difluorobenzyl)oxy]-6-methoxy-2-methylimidazo[1,2-a]pyridin-3-yl}carbonyl)amino]-2-methylbutan-2-yl}carbamate trifluoroacetate (Enantiomer A)

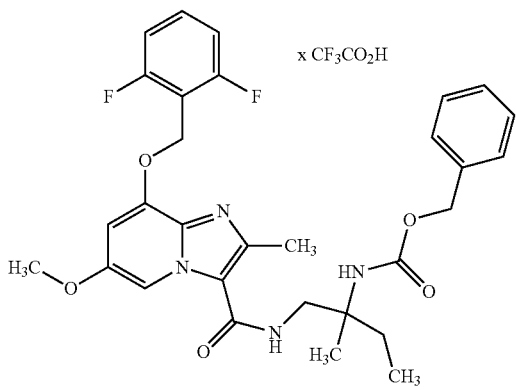 [SMILES: CCC(C)(CNC(=O)c1c(C)nc2c(OCc3c(F)cccc3F)cc(OC)cn12)NC(=O)OCc1ccccc1]

156 mg (0.41 mmol) of HATU and 0.28 ml (1.58 mmol) of N,N-diisopropylethylamine were added to 110 mg (0.32 mmol) of 8-[(2,6-difluorobenzyl)oxy]-6-methoxy-2-methyl-imidazo[1,2-a]pyridine-3-carboxylic acid from Example 284A. The reaction mixture was stirred at RT for 10 min, 97 mg (0.41 mmol) of ent-Benzyl (1-amino-2-methylbutan-2-yl)carbamate (enantiomer A) from Example 274A were then added and the mixture was stirred at RT for 45 min. TFA was added to the reaction mixture, which was then separated by preparative HPLC (RP18 column, mobile phase: acetonitrile/water gradient with addition of 0.1% TFA). The product fractions were concentrated on a rotary evaporator. This gave 157 mg of the target compound (73% of theory).

LC-MS (Method 2): $R_t$=1.09 min

MS (ESpos): m/z=567 (M−TFA+H)$^+$

Example 292A ent-Benzyl {1-[({6-bromo-8-[(2,6-difluorobenzyl)oxy]-2-methylimidazo[1,2-a]pyridin-3-yl}carbonyl)amino]-2-methylpentan-2-yl}carbamate trifluoroacetate (Enantiomer B)

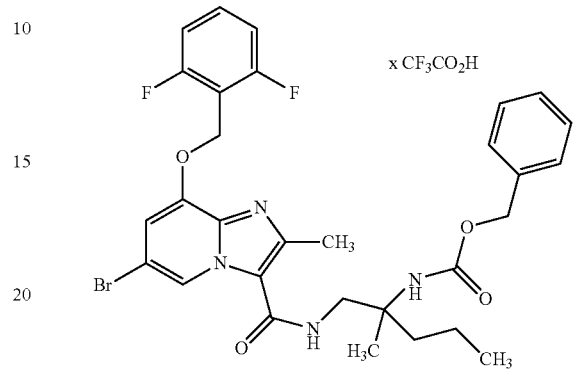

2.57 g (7.99 mmol) of (benzotriazol-1-yloxy)bisdimethylaminomethylium fluoroborate and 4 ml (36.31 mmol) of 4-methylmorpholine were added to 2.88 g (7.26 mmol) of 6-bromo-8-[(2,6-difluorobenzyl)oxy]-2-methylimidazo[1,2-a]pyridine-3-carboxylic acid from Example 19A. 2.0 g (7.99 mmol) of ent-benzyl (1-amino-2-methylpentan-2-yl)carbamate (enantiomer B) from Example 289A were then added, and the reaction mixture was stirred at RT for 1 hour. 200 ml of water were added to the reaction solution, and the solid formed was stirred for about 30 min, filtered off, washed with water and dried under high vacuum. This gave 4.41 g of the target compound (73% of theory, purity 76%).

LC-MS (Method 2): $R_t$=1.38 min

MS (ESpos): m/z=629 (M−TFA+H)$^+$ $^1$H-NMR (400 MHz, DMSO-d$_6$): δ=0.85 (t, 3H), 1.19 (s, 3H), 1.23-1.34 (m, 2H), 1.44-1.54 (m, 1H), 1.71-1.80 (m, 1H), 2.53 (s, 3H), 3.47-3.59 (m, 2H), 5.00 (s, 2H), 5.38 (s, 2H), 7.08 (br. s., 1H), 7.21-7.37 (m, 7H), 7.40 (s, 1H), 7.56-7.66 (m, 1H), 7.91-7.98 (m, 1H), 8.83 (s, 1H).

Example 293A ent-Benzyl {1-[({8-[(2,6-difluorobenzyl)oxy]-2-methyl-6-morpholin-4-yl)imidazo[1,2-a]pyridin-3-yl}carbonyl)amino]-2-methylpentan-2-yl}carbamate (Enantiomer B)

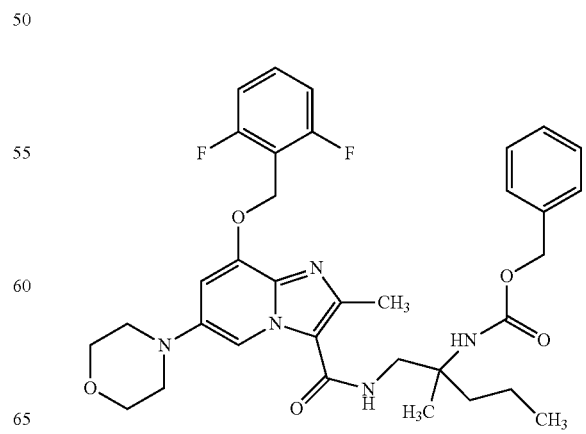

Under argon, 1.7 ml of toluene (abs.) were added to 50 mg (0.07 mmol) of ent-benzyl {1-[({6-bromo-8-[(2,6-difluorobenzyl)oxy]-2-methylimidazo[1,2-a]pyridin-3-yl}carbonyl)amino]-2-methylpentan-2-yl}carbamate trifluoroacetate (enantiomer B) from Example 292A, 0.02 ml (0.20 mmol) of morpholine, 9 mg (0.09 mmol) of sodium tert-butoxide, 2.5 mg (0.003 mmol) of tris(dibenzylideneacetone)dipalladium and 3.8 mg (0.008 mmol) of dicyclohexyl[2',4',6'-tri(propan-2-yl)biphenyl-2-yl]phosphane [X-PHOS], and the mixture was stirred at 100° C. overnight. The reaction solution was concentrated and the residue was taken up in dichloromethane and washed twice with water. The organic phase was concentrated and the residue was purified by preparative HPLC (RP18 column, mobile phase: acetonitrile/water gradient with addition of 0.1% TFA). The product was once more taken up in dichloromethane and washed once with saturated aqueous sodium bicarbonate solution, the aqueous phase was extracted twice with dichloromethane and the combined organic phases were dried over sodium sulphate, filtered and concentrated. The product fraction was then re-purified by thin-layer chromatography (mobile phase: dichloromethane/methanol=20/1). This gave 11 mg of the target compound (26% of theory).

LC-MS (Method 2): $R_t$=1.09 min

MS (ESpos): m/z=636 (M+H)$^+$ $^1$H-NMR (400 MHz, DMSO-d$_6$): δ=0.85 (t, 3H), 1.20 (s, 3H), 1.23-1.34 (m, 2H), 1.45-1.58 (m, 1H), 1.69-1.79 (m, 1H), 2.50 (s, 3H below solvent peak), 3.05 (t, 4H), 3.48-3.54 (m, 2H), 3.76 (t, 4H), 4.99 (s, 2H), 5.32 (s, 2H), 7.02-7.08 (m, 2H), 7.20-7.27 (m, 2H), 7.28-7.37 (m, 5H), 7.54-7.66 (m, 2H), 8.16-8.21 (m, 1H).

Example 294A ent-Benzyl {1-[({6-cyclopropyl-8-[(2,6-difluorobenzyl)oxy]-2-methylimidazo[1,2-a]pyridin-3-yl}carbonyl)amino]-2-methylpentan-2-yl}carbamate trifluoroacetate (Enantiomer B)

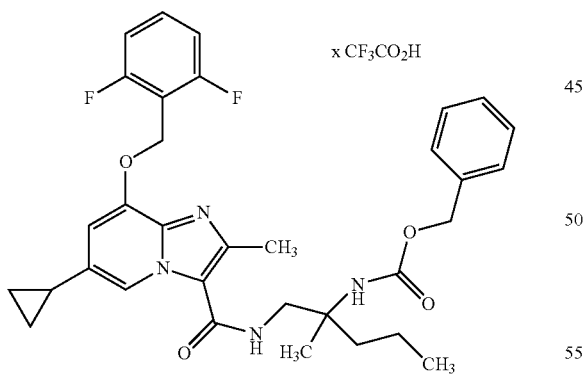

50 mg (0.07 mmol) of ent-benzyl {1-[({6-bromo-8-[(2,6-difluorobenzyl)oxy]-2-methylimidazo[1,2-a]pyridin-3-yl}carbonyl)amino]-2-methylpentan-2-yl}carbamate trifluoroacetate (enantiomer B) from Example 292A, 7.5 mg (0.09 mmol) of cyclopropylboric acid, 57 mg (0.27 mmol) of potassium phosphate, 3 mg (0.01 mmol) of tricyclohexylphosphine and 1.2 mg (0.005 mmol) of palladium(II) acetate were initially charged under argon, and 0.6 ml of toluene/water 20/1 was added. Argon was passed through the reaction mixture for 5 min, and the reaction mixture was stirred at 100° C. overnight. The reaction mixture was concentrated and the residue was purified by preparative HPLC (RP18 column, mobile phase: acetonitrile/water gradient with addition of 0.1% TFA). This gave 27 mg of the target compound (56% of theory).

LC-MS (Method 2): $R_t$=1.20 min

MS (ESpos): m/z=591 (M−TFA+H)$^+$ $^1$H-NMR (400 MHz, DMSO-d$_6$): δ=0.80-0.92 (m, 6H), 1.02 (d, 2H), 1.22 (s, 3H), 1.24-1.36 (m, 3H), 1.44-1.58 (m, 1H), 1.73-1.82 (m, 1H), 2.03-2.15 (m, 1H), 2.55 (br. s., 3H), 3.50-3.62 (m, 2H), 5.01 (s, 2H), 5.44 (br. s., 2H), 7.08 (br. s., 1H), 7.22-7.41 (m, 9H), 7.62 (quin, 1H), 8.54 (s, 1H).

Example 295A rac-2-Amino-3-fluoro-2-methylpropanonitrile

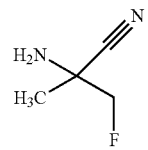

The title compound is known from the literature:
1) McConathy, J. et al., Journal of Medicinal Chemistry 2002, 45, 2240-2249.
2) Bergmann, E. D. et al., Journal of the Chemical Society 1963, 3462-3463.

Further Method:

1.0 g (0.94 ml; 13.15 mmol) of fluoroacetone was initially charged in 11 ml of 2 N ammonia in methanol. At RT, 721 mg (14.72 mmol) of sodium cyanide and 788 mg (14.72 mmol) of ammonium chloride were added in succession, and the mixture was stirred at reflux for 2 hours.

The reaction solution was cooled, filtered and washed with methylene chloride. A solid precipitated from the mother liquor. This solid was filtered off. From the mother liquor, methylene chloride and methanol were removed by distillation under atmospheric pressure. This gave 1.32 g of the target compound (89% of theory, purity about 90%). The product was used without further purification for the next reaction.

GC-MS (Method 14): $R_t$=1.64 min

MS (EIpos): m/z=87 (M−CH$_3$)$^+$

Example 296A rac-Benzyl (2-cyano-1-fluoropropan-2-yl)carbamate

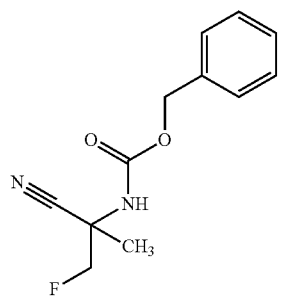 [SMILES: CC(C#N)(CF)NC(=O)OCc1ccccc1]

5.07 g (36.67 mmol) of potassium carbonate were added to 1.34 g (11.83 mmol, about 90% pure) of rac-2-amino-3-fluoro-2-methylpropanonitrile from Example 295A in 29 ml of THF/water (9/1). At 0° C., 1.69 ml (11.83 mmol) of benzyl chloroformate were slowly added dropwise, and the reaction mixture was stirred at RT overnight. The solvent was decanted, the aqueous phase was extracted twice with THF and the THF was then decanted. The combined organic phases were dried with sodium sulphate, filtered off and concentrated. The residue was separated by silica gel chromatography (mobile phase: cyclohexane/ethyl acetate 7/3-9/1) and the product fractions were concentrated on a rotary evaporator. This gave 1.89 g of the target compound (66% of theory; purity 97%).

LC-MS (Method 2): $R_t$=0.89 min

MS (ESpos): m/z=237 (M+H)$^+$ $^1$H-NMR (400 MHz, DMSO-d$_6$): δ=1.58 (d, 3H), 4.47-4.78 (m, 2H), 5.10 (s, 2H), 7.30-7.43 (m, 5H), 8.34 (br. s, 1H).

Example 297A ent-Benzyl (2-cyano-1-fluoropropan-2-yl)carbamate (enantiomer A)

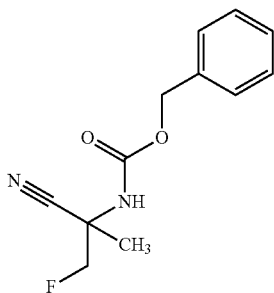 [SMILES: CC(C#N)(CF)NC(=O)OCc1ccccc1]

3.0 g (12.69 mmol) of rac-benzyl (2-cyano-1-fluoropropan-2-yl)carbamate from Example 296A were separated into the enantiomers by preparative separation on a chiral phase [column: Daicel Chiralpak AY-H, 5 μm, 250×20 mm, mobile phase: 80% isohexane, 20% isopropanol, flow rate: 15 ml/min; 40° C., detection: 220 nm].

Enantiomer A: yield: 1.18 g (>99% ee)

$R_t$=5.37 min [Daicel Chiralcel AY-H, 5 m, 250×4.6 mm; mobile phase: 70% isohexane, 30% 2-propanol; flow rate 1.0 ml/min; 40° C.; detection: 220 nm].

Example 298A ent-Benzyl (2-cyano-1-fluoropropan-2-yl)carbamate (Enantiomer B)

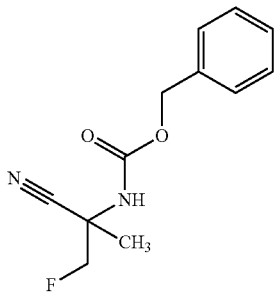 [SMILES: CC(C#N)(CF)NC(=O)OCc1ccccc1]

3.0 g (12.69 mmol) of rac-benzyl (2-cyano-1-fluoropropan-2-yl)carbamate from Example 296A were separated into the enantiomers by preparative separation on a chiral phase [column: Daicel Chiralpak AY-H, 5 μm, 250×20 mm, mobile phase: 80% isohexane, 20% isopropanol, flow rate: 15 ml/min; 40° C., detection: 220 nm].

Enantiomer B: yield: 1.18 g (>99% ee)

$R_t$=6.25 min [Daicel Chiralcel AY-H, 5 μm, 250×4.6 mm; mobile phase: 70% isohexane, 30% 2-propanol; flow rate 1.0 ml/min; 40° C.; detection: 220 nm].

Example 299A rac-Benzyl (1-amino-3-fluoro-2-methylpropan-2-yl)carbamate

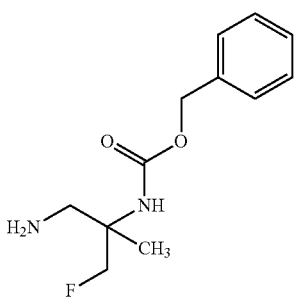 [SMILES: CC(CN)(CF)NC(=O)OCc1ccccc1]

Under argon, 1.55 g of Raney nickel (aqueous suspension) were added to 1.2 g (5.08 mmol) of rac-benzyl (2-cyano-1-fluoropropan-2-yl)carbamate from Example 296A in 14.9 ml of 7 N ammonia in methanol, and the mixture was hydrogenated at a hydrogen pressure of about 25 bar and RT for 24 hours. The reaction mixture was filtered through kieselguhr, the filter cake was washed with methanol and the filtrate was concentrated. This gave 1.2 g of the target compound (98% of theory).

LC-MS (Method 2): $R_t$=0.49 min

MS (ESpos): m/z=241 (M+H)$^+$

Example 300A ent-Benzyl (1-amino-3-fluoro-2-methylpropan-2-yl) carbamate (Enantiomer A)

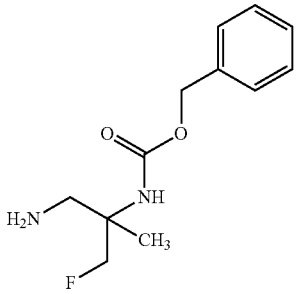 [SMILES: CC(CN)(CF)NC(=O)OCc1ccccc1]

Under argon, 1.55 g of Raney nickel (aqueous suspension) were added to 1.2 g (5.08 mmol) of ent-benzyl (2-cyano-1-fluoropropan-2-yl)carbamate (enantiomer A) from Example 297A in 14.9 ml of 7 N ammonia in methanol, and the mixture was hydrogenated at a hydrogen pressure of about 25 bar and RT for 24 hours. The reaction mixture was filtered through kieselguhr, the filter cake was washed with methanol and the filtrate was concentrated. This gave 700 mg of the target compound (57% of theory; purity about 85%).

LC-MS (Method 2): $R_t$=0.52 min
MS (ESpos): m/z=241 (M+H)$^+$

Example 301A ent-Benzyl (1-amino-3-fluoro-2-methylpropan-2-yl) carbamate (Enantiomer B)

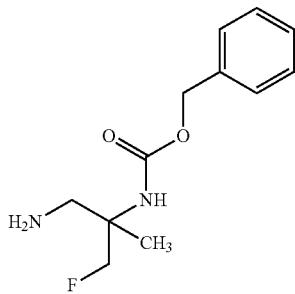 [SMILES: CC(CN)(CF)NC(=O)OCc1ccccc1]

Under argon, 1.55 g of Raney nickel (aqueous suspension) were added to 1.2 g (5.08 mmol) of ent-benzyl (2-cyano-1-fluoropropan-2-yl)carbamate (enantiomer A) from Example 298A in 14.9 ml of 7 N ammonia in methanol, and the mixture was hydrogenated at a hydrogen pressure of about 25 bar and RT for 24 hours. The reaction mixture was filtered through kieselguhr, the filter cake was washed with methanol and the filtrate was concentrated. This gave 1.2 g of the target compound (98% of theory; purity about 85%).

LC-MS (Method 2): $R_t$=0.50 min
MS (ESpos): m/z=241 (M+H)$^+$

Example 302A rac-Benzyl {1-[({8-[(2,6-difluorobenzyl)oxy]-2,6-dimethylimidazo[1,2-a]pyridin-3-yl}carbonyl) amino]-3-fluoro-2-methylpropan-2-yl}carbamate

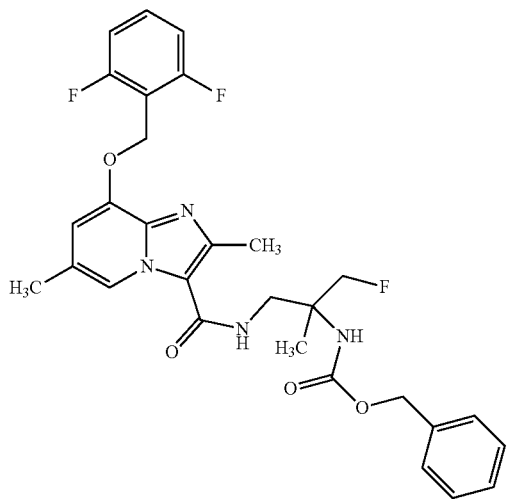 [SMILES: Cc1cc(OCc2c(F)cccc2F)c2nc(C)c(C(=O)NCC(C)(CF)NC(=O)OCc3ccccc3)n2c1]

Under argon, 147 mg (0.44 mmol) of 8-[(2,6-difluorobenzyl)oxy]-2,6-dimethylimidazo[1,2-a]pyridin-3-carboxylic acid from Example 21A, 185 mg (0.49 mmol) of HATU and 0.31 ml (1.77 mmol) of N,N-diisopropylethylamine were stirred in 7 ml of DMF for 20 min, 112 mg (0.39 mmol of rac-benzyl (1-amino-3-fluoro-2-methylpropan-2-yl)carbamate from Example 299A were then added and the mixture was stirred at RT overnight. Water/TFA was added, and the product was purified by preparative HPLC (RP18 column, mobile phase: acetonitrile/water gradient with addition of 0.05% formic acid). The product fractions were concentrated on a rotary evaporator. This gave 56 mg of the target compound (23% of theory).

LC-MS (Method 2): $R_t$=1.02 min
MS (ESpos): m/z=555 (M+H)$^+$
$^1$H-NMR (400 MHz, DMSO-d$_6$): δ=1.25-1.29 (m, 3H), 2.32 (s, 3H), 3.53-3.65 (m, 2H), 4.45-4.56 (m, 1H), 4.57-4.69 (m, 1H), 5.02 (s, 2H), 5.31 (s, 2H), 7.02 (br. s, 1H), 7.20-7.27 (m, 2H), 7.28-7.38 (m, 5H), 7.55-7.65 (m, 1H), 7.89 (br. s, 1H), 8.46 (s, 1H), [further signal below solvent peak].

Example 303A ent-Benzyl {1-[({8-[(2,6-difluorobenzyl)oxy]-2,6-dimethylimidazo[1,2-a]pyridin-3-yl}carbonyl) amino]-3-fluoro-2-methylpropan-2-yl}carbamate trifluoroacetate (Enantiomer A)

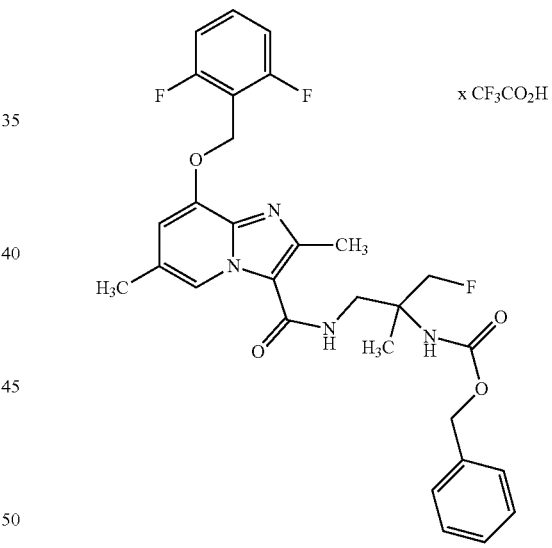

150 mg (0.45 mmol) of 8-[(2,6-difluorobenzyl)oxy]-2,6-dimethylimidazo[1,2-a]pyridine-3-carboxylic acid from Example 21A, 180 mg (0.47 mmol) of HATU and 0.24 ml (1.35 mmol) of N,N-diisopropylethylamine were stirred in 2.9 ml of DMF for 20 min, 134 mg (0.47 mmol, 85% pure) of ent-benzyl (1-amino-3-fluoro-2-methylpropan-2-yl)carbamate (enantiomer A) from Example 300A were then added and the mixture was stirred at RT overnight. Water/TFA was added to the reaction solution, and the product was purified by preparative HPLC (RP 18 column, mobile phase: acetonitrile/water gradient with addition of 0.1% TFA). The product fractions were concentrated on a rotary evaporator. This gave 148 mg of the target compound (47% of theory).

LC-MS (Method 2): $R_t$=1.03 min
MS (ESpos): m/z=555 (M−TFA+H)$^+$

Example 304A ent-Benzyl {1-[({8-[(2,6-difluorobenzyl)oxy]-2,6-dimethylimidazo[1,2-a]pyridin-3-yl}carbonyl)amino]-3-fluoro-2-methylpropan-2-yl}carbamate trifluoroacetate (Enantiomer B)

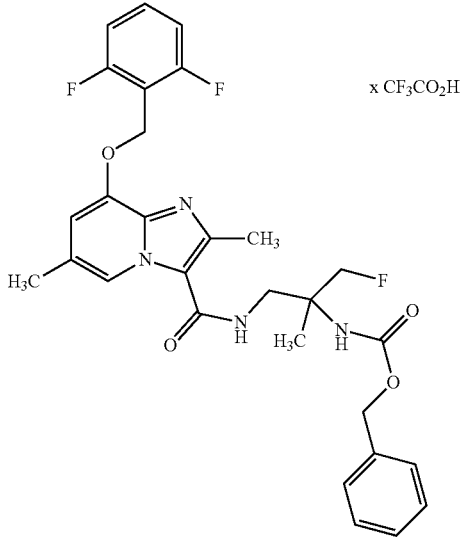 [SMILES: Cc1cc(OCc2c(F)cccc2F)c2nc(C)c(C(=O)NCC(C)(CF)NC(=O)OCc3ccccc3)n2c1]

150 mg (0.45 mmol) of 8-[(2,6-difluorobenzyl)oxy]-2,6-dimethylimidazo[1,2-a]pyridine-3-carboxylic acid from Example 21A, 180 mg (0.47 mmol) of HATU and 0.24 ml (1.35 mmol) of N,N-diisopropylethylamine were stirred in 2.9 ml of DMF for 20 min, 134 mg (0.47 mmol, 85% pure) of ent-benzyl (1-amino-3-fluoro-2-methylpropan-2-yl)carbamate (enantiomer B) from Example 301A were then added and the mixture was stirred at RT overnight. Water/TFA was added to the reaction solution, and the product was purified by preparative HPLC (RP 18 column, mobile phase: acetonitrile/water gradient with addition of 0.1% TFA). The product fractions were concentrated on a rotary evaporator. This gave 201 mg of the target compound (67% of theory).

LC-MS (Method 2): $R_t$=1.04 min

MS (ESpos): m/z=555 (M−TFA+H)$^+$

Example 305A ent-Benzyl {1-[({2,6-dimethyl-8-[(2,3,6-trifluorobenzyl)oxy]imidazo[1,2-a]pyridin-3-yl}carbonyl)amino]-3-fluoro-2-methylpropan-2-yl}carbamate trifluoroacetate (Enantiomer A)

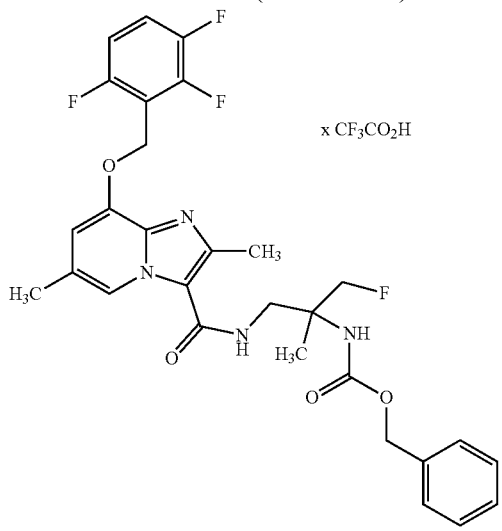

150 mg (0.43 mmol) of 2,6-dimethyl-8-[(2,3,6-trifluorobenzyl)oxy]imidazo[1,2-a]pyridine-3-carboxylic acid from Example 265A, 171 mg (0.45 mmol) of HATU and 0.22 ml (1.29 mmol) of N,N-diisopropylethylamine were stirred in 2.7 ml of DMF for 20 min, 127 mg (0.45 mmol, 85% pure) of ent-benzyl (1-amino-3-fluoro-2-methylpropan-2-yl)carbamate (enantiomer A) from Example 300A were then added and the mixture was stirred at RT overnight. Water/TFA was added to the reaction solution, and the product was purified by preparative HPLC (RP 18 column, mobile phase: acetonitrile/water gradient with addition of 0.1% TFA). The product fractions were concentrated on a rotary evaporator. This gave 170 mg of the target compound (50% of theory, purity 87%).

LC-MS (Method 2): $R_t$=1.05 min

MS (ESpos): m/z=573 (M−TFA+H)$^+$

Example 306A ent-Benzyl {1-[({2,6-dimethyl-8-[(2,3,6-trifluorobenzyl)oxy]imidazo[1,2-a]pyridin-3-yl}carbonyl)amino]-3-fluoro-2-methylpropan-2-yl}carbamate trifluoroacetate (Enantiomer B)

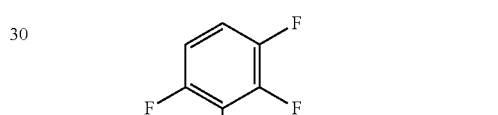
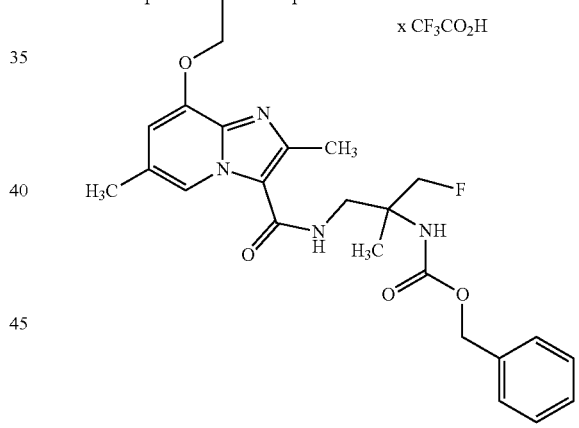

150 mg (0.43 mmol) of 2,6-dimethyl-8-[(2,3,6-trifluorobenzyl)oxy]imidazo[1,2-a]pyridine-3-carboxylic acid from Example 265A, 171 mg (0.45 mmol) of HATU and 0.22 ml (1.29 mmol) of N,N-diisopropylethylamine were stirred in 2.7 ml of DMF for 20 min, 127 mg (0.45 mmol, 85% pure) of ent-benzyl (1-amino-3-fluoro-2-methylpropan-2-yl)carbamate (enantiomer B) from Example 301A were then added and the mixture was stirred at RT overnight. Water/TFA was added to the reaction solution, and the product was purified by preparative HPLC (RP 18 column, mobile phase: acetonitrile/water gradient with addition of 0.1% TFA). The product fractions were concentrated on a rotary evaporator. This gave 202 mg of the target compound (60% of theory, purity 96%).

LC-MS (Method 2): $R_t$=1.06 min

MS (ESpos): m/z=573 (M−TFA+H)$^+$

Example 307A

Ethyl 8-[(2,6-difluorobenzyl)oxy]-2-methyl-6-vinylimidazo[1,2-a]pyridine-3-carboxylate

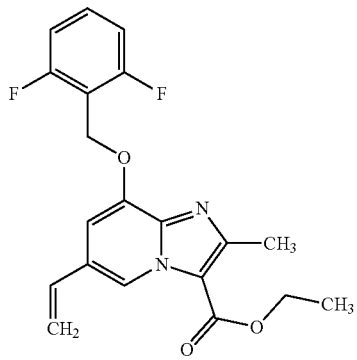 [SMILES: C=Cc1cc(OCc2c(F)cccc2F)c2nc(C)c(C(=O)OCC)n2c1]

Under argon, 1.0 g (2.35 mmol) of ethyl 6-bromo-8-[(2,6-difluorobenzyl)oxy]-2-methylimidazo[1,2-a]pyridine-3-carboxylate from Example 18A, 945 mg (7.06 mmol) of potassium vinyltrifluoroborate, 1.64 ml (11.76 mmol) of triethylamine and 388 mg (0.48 mmol) of dichloro[1,1'-ferrocenylbis(diphenylphosphane)]palladium(II) dichloromethane were initially charged in 50 ml of 2-propanol, and the mixture was stirred at 90° C. for 30 minutes. The reaction mixture was cooled, ethyl acetate was added and the mixture was washed three times with water and once with saturated aqueous sodium chloride solution. The organic phase was dried over sodium sulphate, filtered off, concentrated and dried under high vacuum. This gave 876 mg of the target compound (quantitative yield). The product was used for the subsequent reaction without further purification.

LC-MS (Method 2): $R_t$=1.20 min
MS (ESpos): m/z=373 (M+H)$^+$

Example 308A

Ethyl 8-[(2,6-difluorobenzyl)oxy]-6-formyl-2-methylimidazo[1,2-a]pyridine-3-carboxylate

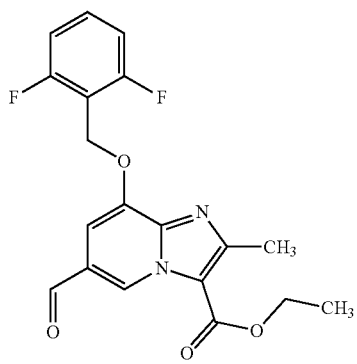

1.45 ml (0.24 mmol, 4% strength solution in water) of osmium tetroxide and 1.52 g (7.13 mol) of sodium periodate were added to 876 mg (2.35 mmol) of ethyl 8-[(2,6-difluorobenzyl)oxy]-2-methyl-6-vinylimidazo[1,2-a]pyridine-3-carboxylate from Example 307A in 20 ml of THF/water (1/1), and the mixture was stirred at RT for 1 h. Ethyl acetate was added to the reaction mixture, and the mixture was washed three times with water and once with saturated aqueous sodium chloride solution. The organic phase was dried over sodium sulphate, filtered off and concentrated. The residue was purified by silica gel chromatography (mobile phase: cyclohexane/ethyl acetate gradient). This gave 478 mg of the target compound (54% of theory).

LC-MS (Method 2): $R_t$=1.12 min
MS (ESpos): m/z=375 (M+H)$^+$ $^1$H-NMR (400 MHz, DMSO-$d_6$): δ=1.39 (t, 3H), 2.60 (s, 3H), 4.41 (q, 2H), 5.40 (s, 2H), 7.20-7.28 (m, 2H), 7.42 (s, 1H), 7.55-7.65 (m, 1H), 9.54 (s, 1H), 10.06 (s, 1H).

Example 309A

Ethyl 8-[(2,6-difluorobenzyl)oxy]-6-(difluoromethyl)-2-methylimidazo[1,2-a]pyridine-3-carboxylate

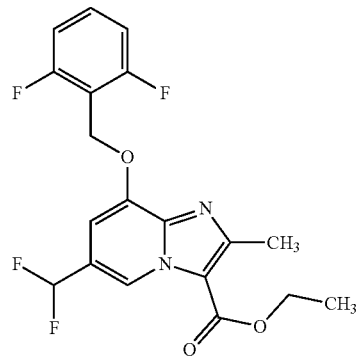 [SMILES: CCOC(=O)c1c(C)nc2c(OCc3c(F)cccc3F)cc(C(F)F)cn12]

Under argon, 0.50 ml (3.77 mmol) of diethylaminosulphur trifluoroide was added dropwise to 235 mg (0.63 mmol) of ethyl 8-[(2,6-difluorobenzyl)oxy]-6-formyl-2-methylimidazo[1,2-a]pyridine-3-carboxylate from Example 308A in 4 ml abs. dichloromethane, and the mixture was stirred at RT overnight. The reaction mixture was cooled in an ice bath, saturated aqueous sodium bicarbonate solution was added carefully and the phases formed were separated. The aqueous phase was extracted twice with dichloromethane. The combined organic phases were dried over sodium sulphate, filtered and concentrated. This gave 249 mg of the target compound (quantitative yield).

LC-MS (Method 2): $R_t$=1.19 min
MS (ESpos): m/z=397 (M+H)$^+$ $^1$H-NMR (400 MHz, DMSO-$d_6$): δ=1.37 (t, 3H), 2.58 (s, 3H), 4.38 (q, 2H), 5.39 (s, 2H), 7.11-7.40 (m, 4H), 7.55-7.66 (m, 1H), 9.17-9.21 (m, 1H).

Example 310A

8-[(2,6-Difluorobenzyl)oxy]-6-(difluoromethyl)-2-methylimidazo[1,2-a]pyridine-3-carboxylic acid

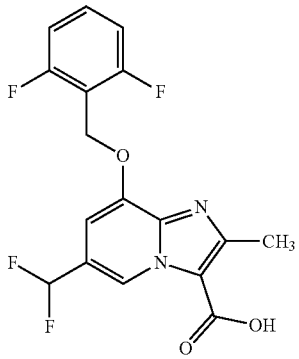 [SMILES: Cc1nc2c(OCc3c(F)cccc3F)cc(C(F)F)cn2c1C(=O)O]

45 mg (1.87 mmol) of lithium hydroxide were added to 247 mg (0.62 mmol) of ethyl-8-[(2,6-difluorobenzyl)oxy]-6-(difluoromethyl)-2-methylimidazo[1,2-a]pyridine-3-carboxylate from Example 309A in 6 ml of THF/methanol (5/1), and the reaction mixture was then stirred at RT overnight. Dichloromethane and water were added to the reaction mixture, the phases were separated and the aqueous phase was acidified with 1 N hydrochloric acid and cooled in an ice bath. The precipitate was filtered off, washed with water and dried under high vacuum overnight. This gave 202 mg of the target compound (88% of theory).

LC-MS (Method 2): $R_t$=0.89 min

MS (ESpos): m/z=369 (M+H)$^+$ $^1$H-NMR (400 MHz, DMSO-d$_6$): δ=2.57 (s, 3H), 5.38 (s, 2H), 7.10-7.41 (m, 4H), 7.55-7.65 (m, 1H), 9.24 (s, 1H), 13.38 (s, 1H).

Example 311A ent-Benzyl {1-[({8-[(2,6-difluorobenzyl)oxy]-6-(difluoromethyl)-2-methylimidazo[1,2-a]pyridin-3-yl}carbonyl)amino]-2-methylbutan-2-yl}carbamate (Enantiomer A)

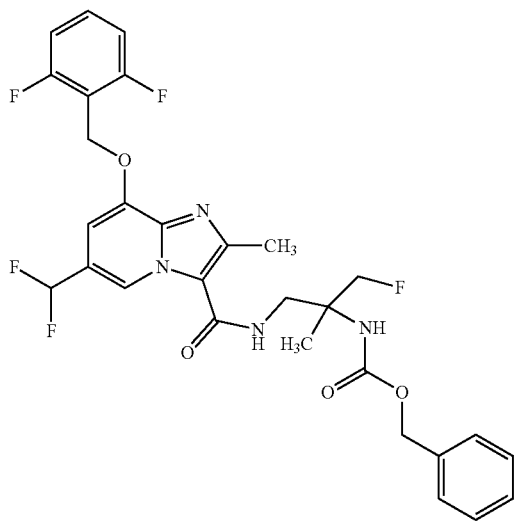 [SMILES: Cc1nc2c(OCc3c(F)cccc3F)cc(C(F)F)cn2c1C(=O)NCC(C)(CF)NC(=O)OCc1ccccc1]

126 mg (0.33 mmol) of HATU and 0.24 ml (1.38 mml) of N,N-diisopropylethylamine were added to 102 mg (0.28 mmol) of 8-[(2,6-difluorobenzyl)oxy]-6-(difluoromethyl)-2-methylimidazo[1,2-a]pyridine-3-carboxylic acid from Example 310A, and the mixture was stirred at room temperature for 10 minutes. 98 mg (0.41 mmol) of ent-benzyl (1-amino-2-methylbutan-2-yl)carbamate (enantiomer A) from Example 274A were then added to the reaction solution, the mixture was stirred at RT overnight and the product was then purified by preparative HPLC (RP18 column, mobile phase: acetonitrile/water gradient with addition of 0.05% formic acid). This gave 124 mg of the target compound (77% of theory).

LC-MS (Method 2): $R_t$=1.23 min

MS (ESpos): m/z=587 (M+H)$^+$ $^1$H-NMR (400 MHz, DMSO-d$_6$): δ=0.82 (t, 3H), 1.19 (s, 3H), 1.49-1.61 (m, 1H), 1.77-1.87 (m, 1H), 3.49-3.60 (m, 2H), 5.00 (s, 2H), 5.37 (s, 2H), 7.01-7.10 (m, 1H), 7.13-7.38 (m, 9H), 7.55-7.65 (m, 1H), 7.89 (t, 1H), 8.98 (s, 1H).

Example 312A ent-Benzyl {1-[({8-[(2,6-difluorobenzyl)oxy]-6-(difluoromethyl)-2-methylimidazo[1,2-a]pyridin-3-yl}carbonyl)amino]-2-methylpentan-2-yl}carbamate (Enantiomer B)

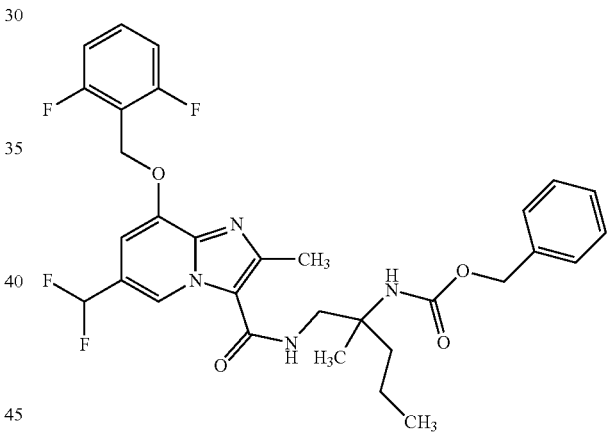

126 mg (0.33 mmol) of HATU and 0.24 ml (1.38 mml) of N,N-diisopropylethylamine were added to 102 mg (0.28 mmol) of 8-[(2,6-difluorobenzyl)oxy]-6-(difluoromethyl)-2-methylimidazo[1,2-a]pyridine-3-carboxylic acid from Example 310A, and the mixture was stirred at room temperature for 10 minutes. 103 mg (0.41 mmol) of ent-benzyl (1-amino-2-methylpentan-2-yl)carbamate (enantiomer B) from Example 289A were then added to the reaction solution, the mixture was stirred at RT overnight and the product was then purified by preparative HPLC (RP18 column, mobile phase: acetonitrile/water gradient with addition of 0.05% formic acid). This gave 123 mg of the target compound (74% of theory).

LC-MS (Method 2): $R_t$=1.31 min

MS (ESpos): m/z=601 (M+H)$^+$ $^1$H-NMR (400 MHz, DMSO-d$_6$): δ=0.85 (t, 3H), 1.20 (s, 3H), 1.23-1.34 (m, 2H), 1.44-1.57 (m, 1H), 1.68-1.82 (m, 1H), 3.49-3.58 (m, 2H), 4.99 (s, 2H), 5.37 (s, 2H), 7.01-7.38 (m, 10H), 7.55-7.65 (m, 1H), 7.90 (t, 1H), 8.98 (s, 1H).

335

Example 313A ent-Benzyl {1-[({8-[(2,6-difluorobenzyl)oxy]-6-(difluoromethyl)-2-methylimidazo[1,2-a]pyridin-3-yl}carbonyl)amino]-3-fluoro-2-methylpropan-2-yl}carbamate trifluoroacetate (Enantiomer A)

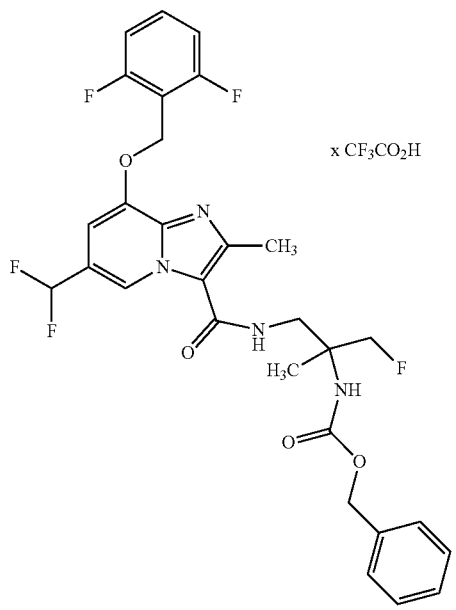 [SMILES: Cc1nc2c(OCc3c(F)cccc3F)cc(C(F)F)cn2c1C(=O)NCC(C)(CF)NC(=O)OCc1ccccc1]

x CF$_3$CO$_2$H 50 mg (0.14 mmol) of 8-[(2,6-difluorobenzyl)oxy]-6-(difluoromethyl)-2-methylimidazo[1,2-a]pyridine-3-carboxylic acid from Example 310A, 54 mg (0.14 mmol) of HATU and 0.07 ml (0.41 mmol) of N,N-diisopropylethylamine in 0.9 ml of DMF were stirred for 20 min, 40 mg (0.14 mmol, 85%) of ent-benzyl (1-amino-3-fluoro-2-methylpropan-2-yl)carbamate (enantiomer A) from Example 300A were then added and the mixture was stirred at RT overnight. Water/THF was added to the reaction solution, and the product was purified by preparative HPLC (RP 18 column, mobile phase: acetonitrile/water gradient with addition of 0.1% TFA). This gave 75 mg of the target compound (78% of theory).

LC-MS (Method 2): R$_t$=1.19 min

MS (ESpos): m/z=591 (M−TFA+H)$^+$

336

Example 314A ent-Benzyl {1-[({8-[(2,6-difluorobenzyl)oxy]-6-(difluoromethyl)-2-methylimidazo[1,2-a]pyridin-3-yl}carbonyl)amino]-3-fluoro-2-methylpropan-2-yl}carbamate trifluoroacetate (Enantiomer B)

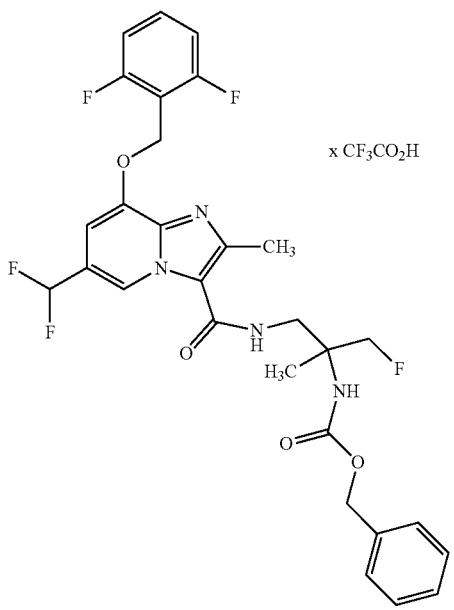 [SMILES: Cc1nc2c(OCc3c(F)cccc3F)cc(C(F)F)cn2c1C(=O)NCC(C)(CF)NC(=O)OCc1ccccc1]

x CF$_3$CO$_2$H 50 mg (0.14 mmol) of 8-[(2,6-difluorobenzyl)oxy]-6-(difluoromethyl)-2-methylimidazo[1,2-a]pyridine-3-carboxylic acid from Example 310A, 54 mg (0.14 mmol) of HATU and 0.07 ml (0.41 mmol) of N,N-diisopropylethylamine in 0.9 ml of DMF were stirred for 20 min, 40 mg (0.14 mmol, 85%) of ent-benzyl (1-amino-3-fluoro-2-methylpropan-2-yl)carbamate (enantiomer B) from Example 301A were then added and the mixture was stirred at RT overnight. Water/TFA was added to the reaction solution, and the product was purified by preparative HPLC (RP18 column, mobile phase: acetonitrile/water gradient with addition of 0.1% TFA). This gave 47 mg of the target compound (44% of theory, purity about 89%).

LC-MS (Method 2): R$_t$=1.20 min

MS (ESpos): m/z=591 (M−TFA+H)$^+$

Example 315A

Methyl N²-(tert-butoxycarbonyl)-N⁶-({8-[(2,6-difluorobenzyl)oxy]-2,6-dimethylimidazo[1,2-a]pyridin-3-yl}carbonyl)-L-lysinate trifluoroacetate

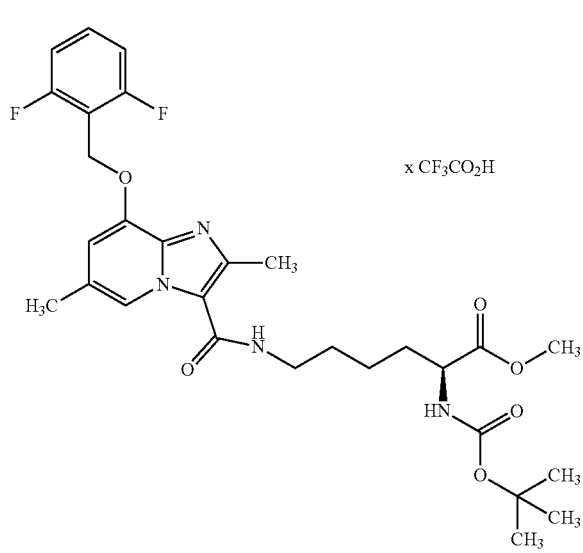 [SMILES: COC(=O)[C@H](CCCCNC(=O)c1c(C)nc2c(OCc3c(F)cccc3F)cc(C)cn12)NC(=O)OC(C)(C)C]

300 mg (0.90 mmol) of 8-[(2,6-difluorobenzyl)oxy]-2,6-dimethylimidazo[1,2-a]pyridine-3-carboxylic acid from Example 21A, 377 mg (1.17 mmol) of (benzotriazol-1-yloxy)bisdimethylaminomethylium fluoroborate and 0.5 ml (4.51 mmol) of 4-methylmorpholine were initially charged in 5.75 ml of DMF, the mixture was stirred at room temperature for 10 min, 318 mg (0.99 mmol) of methyl N²-(tert-butoxycarbonyl)-L-lysinate acetate were then added and the mixture was stirred at RT overnight. Another 188 mg (0.59 mmol) of (benzotriazol-1-yloxy)bisdimethyl-aminomethyliumfluoroborate, 0.4 ml (3.61 mmol) of 4-methylmorpholine and 376 mg (1.17 mmol) of methyl N²-(tert-butoxycarbonyl)-L-lysine acetate were then added to the reaction solution, and the mixture was stirred at room temperature overnight. Water/TFA was added and the product was purified by preparative HPLC (RP18 column, mobile phase: acetonitrile/water gradient with addition of 0.1% TFA). This gave 205 mg of the target compound (33% of theory).

LC-MS (Method 2): $R_t$=0.95 min

MS (ESpos): m/z=575 (M−TFA+H)⁺

¹H-NMR (400 MHz, DMSO-d₆): δ=1.30-1.43 (m, 13H), 1.48-1.72 (m, 2H), 2.41 (s, 3H), 2.54 (s, 3H; obscured by DMSO signal), 3.30 (q, 2H), 3.61 (s, 3H), 3.91-3.98 (m, 1H), 5.40 (s, 2H), 7.01 (s, 1H), 7.13 (s, 1H), 7.22-7.30 (m, 2H), 7.57-7.66 (m, 1H), 8.50-8.55 (m, 1H).

Example 316A rac-2-Amino-3-(4-fluorophenyl)-2-methylpropanonitrile

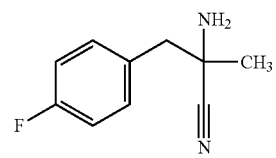

1.0 g (6.57 mmol) of 4-fluorophenylacetone was initially charged in 13.1 ml of 2 N ammonia in methanol, 361 mg (7.36 mmol) of sodium cyanide and 877 mg (7.36 mmol) of ammonium chloride were added and the mixture was stirred under reflux for 2 hours. The reaction solution was cooled and diluted with 20 ml of dichloromethane, and the precipitate solid was filtered off. The filtrate was concentrated and the residue was purified by silica gel chromatography (RP18 column, mobile phase: cyclohexane/ethyl acetate 4/1 to 1/1). This gave 340 mg of the target compound (23% of theory, purity 81%).

LC-MS (Method 15): $R_t$=1.87 min

MS (ESpos): m/z=179 (M+H)⁺

¹H-NMR (400 MHz, DMSO-d₆): δ=1.30 (s, 3H), 2.87 (q, 2H), 7.13-7.20 (m, 2H), 7.28-7.36 (m, 2H).

Example 317A rac-3-(4-Fluorophenyl)-2-methylpropane-1,2-diamine

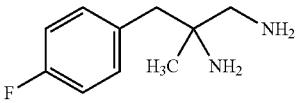

340 mg (1.54 mmol, purity about 81%) of rac-2-amino-3-(4-fluorophenyl)-2-methylpropanonitrile from Example 316A were dissolved in 2 ml of ethanol, and 4.6 ml (4.64 mmol) of 1 N hydrochloric acid in ethanol were added. 5.2 mg (0.02 mmol) of platinum(IV) oxide were added, and the reaction mixture was hydrogenated at 3 bar for 5 hours. Another 5 mg (0.02 mmol) of platinum(IV) oxide were added to the reaction solution, and the mixture was hydrogenated at 3 bar for 5 h. The mixture was then filtered off through Celite, 1.5 ml (3.09 mmol) of 2 N hydrochloric acid in diethyl ether were added to the filtrate, the mixture was concentrated and the product was dried under high vacuum. The product was purified by silica gel chromatography (mobile phase: dichloromethane/2N ammonia in methanol 60/1 to 20/1). This gave 145 mg of the target compound (51% of theory).

LC-MS (Method 13): $R_t$=0.20 min

MS (ESpos): m/z=183 (M+H)⁺

¹H-NMR (400 MHz, DMSO-d₆): δ=0.80 (s, 3H), 1.34 (br. s., 4H), 2.24-2.34 (m, 2H), 2.53 (d, 2H), 7.03-7.12 (m, 2H), 7.18-7.27 (m, 2H).

Example 318A rac-2-Amino-2-methyl-3-(pyridin-2-yl)propanonitrile

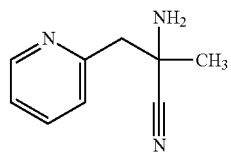

4.88 ml (14.80 mmol) of 1-(pyridin-2-yl)acetone were initially charged in 29.6 ml of 2 N ammonia in methanol, 812 mg (16.57 mmol) of sodium cyanide and 1.97 g (16.57 mmol) of ammonium chloride were added and the mixture was stirred under reflux for 2 hours. The reaction mixture was cooled and diluted with dichloromethane, and the solid obtained was filtered off. The filtrate was concentrated and the residue was purified by silica gel chromatography (mobile phase: cyclohexane/ethyl acetate=1/1). The impure product fractions obtained were re-purified by silica gel chromatography (mobile phase: cyclohexane/ethyl acetate 1/1). This gave a total of 1.1 g of the target compound (45% of theory).

LC-MS (Method 15): $R_t$=1.30 min
MS (ESpos): m/z=162 (M+H)$^+$

Example 319A rac-2-Methyl-3-(pyridin-2-yl)propane-1,2-diamine trihydrochloride

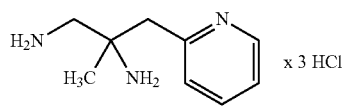

666 mg (4.01 mmol) of 2-amino-2-methyl-3-(pyridin-2-yl)propanonitrile from Example 318A were initially charged in 41 ml of THF, and 2.61 ml (2.61 mmol) of 1 N lithium aluminium hydride solution in THF were slowly added under argon at 0° C. The reaction mixture was stirred at 0° C. for 30 min and at RT overnight. Another 0.7 ml (0.70 mmol) of 1 N lithium aluminium hydride solution in THF was then added, and the mixture was stirred at RT for 2 hours. The reaction mixture was cooled to 0° C., and 0.4 ml of water, 0.4 ml of 2 N aqueous sodium hydroxide solution and 0.8 ml of water were added. The precipitate was filtered off and washed with dichloromethane/methanol (10/1). 2 N hydrogen chloride in diethyl ether was added to the filtrate, and the product was dried under high vacuum. This gave 1.15 g of the target compound (104% of theory).

LC-MS (Method 15): $R_t$=1.26 min
MS (ESpos): m/z=166 (M−3HCl+H)$^+$

Example 320A rac-tert-Butyl 4-[({8-[(2,6-difluorobenzyl)oxy]-2,6-dimethylimidazo[1,2-a]pyridin-3-yl}carbonyl)amino]-3,3-difluoropiperidine-1-carboxylate

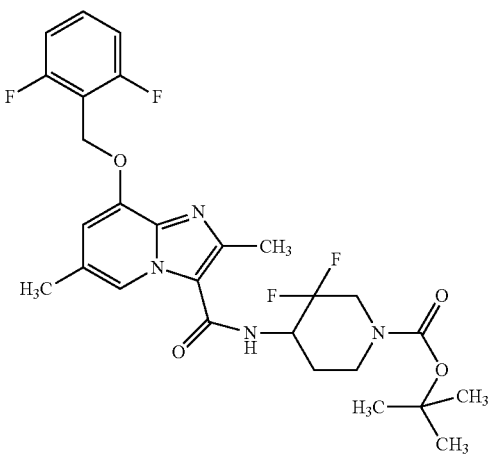 [SMILES: Cc1cc(OCc2c(F)cccc2F)c2nc(C)c(C(=O)NC3CCN(C(=O)OC(C)(C)C)CC3(F)F)n2c1]

75 mg (0.23 mmol) of 8-[(2,6-difluorobenzyl)oxy]-2,6-dimethylimidazo[1,2-a]pyridine-3-carboxylic acid from Example 21A, 94 mg (0.25 mmol) of HATU and 0.2 ml (1.13 mmol) of N,N-diisopropylethylamine in 1.4 ml of DMF were stirred for 20 min, 64 mg (0.27 mmol) of tert-butyl 4-amino-3,3-difluoropiperidine-1-carboxylate were added and the mixture was then stirred at room temperature overnight. Water was added to the reaction solution, and the precipitated solid was stirred at room temperature for 30 min, filtered off, washed with water and dried under high vacuum. This gave 81 mg of the target compound (65% of theory).

LC-MS (Method 2): $R_t$=1.06 min
MS (ESpos): m/z=551 (M+H)$^+$

Example 321A

5-Methyl-2-nitropyridin-3-ole

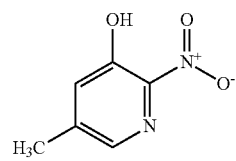

With ice-cooling, 25 g (0.23 mol) of 5-methylpyridin-3-ole were initially charged in 226 ml (4.12 mol) of concentrated sulphuric acid, and the mixture was then warmed to RT. Once the starting material had dissolved completely, the reaction mixture was once more cooled to 0° C. At from 0° C. to 10° C., 14.25 ml (0.34 mol) of fuming nitric acid were then slowly added dropwise, over a period of 3.5 hours, the mixture was warmed to 15° C. and the mixture was then stirred at RT overnight. The reaction solution was poured onto 1000 g of ice and extracted twice with in each case 500 ml of ethyl acetate. The combined organic phases were dried and concentrated. This gave 31.5 g of the target compound (89% of theory).

LC-MS (Method 13): $R_t$=1.21 min

MS (ESpos): m/z=155 (M+H)$^+$

Example 322A

3-[(2,6-Difluorobenzyl)oxy]-5-methyl-2-nitropyridine

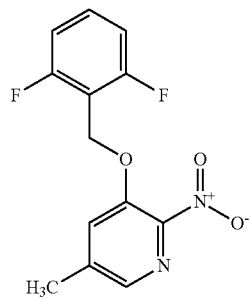 [SMILES: Cc1cnc([N+](=O)[O-])c(OCc2c(F)cccc2F)c1]

31.5 g (0.155 mol) of 5-methyl-2-nitropyridin-3-ole from Example 321A and 75.78 g (0.23 mol) of caesium carbonate were initially charged in 432 ml of DMF, 33.7 g (0.163 mol) of 2,6-difluorobenzyl bromide were added and the mixture was stirred at RT overnight. The reaction solution was stirred into 3600 ml of 0.5 N aqueous hydrochloric acid. The precipitate formed was stirred for another 30 min, filtered off with suction, washed with water and air-dried at RT and atmospheric pressure. This gave 45.8 g of the target compound (105% of theory).

LC-MS (Method 2): $R_t$=0.98 min

MS (ESpos): m/z=281 (M+H)$^+$ $^1$H-NMR (400 MHz, DMSO-d$_6$): δ=2.44 (s, 3H), 5.37 (s, 2H), 7.21 (quint., 2H), 7.52-7.61 (m, 1H), 8.01 (s, 1H), 8.06 (s, 1H).

Example 323A

3-[(2,6-Difluorobenzyl)oxy]-5-methylpyridine-2-amine

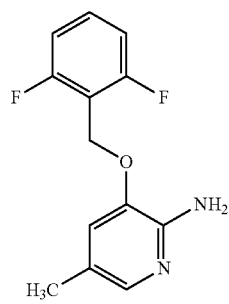

Under argon, 91 g (324.7 mmol) of 3-[(2,6-difluorobenzyl)oxy]-5-methyl-2-nitropyridine from Example 322A were initially charged in 980 ml of ethanol, 56.2 g (1.0 mol) of iron powder were added and the mixture was heated to reflux. 248 ml of concentrated aqueous hydrochloric acid were slowly added dropwise, and the mixture was stirred under reflux for a further 30 min. After cooling, about 2000 ml of water/ice (1/1) were added to the reaction mixture, and the mixture was stirred at RT for 30 min. The solution was concentrated to a point where most of the solvent had been removed. The aqueous phase was made alkaline using concentrated aqueous sodium hydroxide solution, 1200 ml of dichloromethane were added and the mixture was stirred vigorously for 1 h. The mixture was filtered off with suction through kieselguhr and washed repeatedly with a total of about 2800 ml of dichloromethane. The mother liquor was separated and the organic phase was dried and concentrated. This gave 77.8 g of the target compound (96% of theory).

LC-MS (Method 2): $R_t$=0.57 min

MS (ESpos): m/z=251 (M+H)$^+$ $^1$H-NMR (400 MHz, DMSO-d$_6$): δ=2.13 (s, 3H), 5.08 (s, 2H), 5.25 (s, 2H), 7.09 (d, 1H), 7.14-7.22 (m, 2H), 7.37-7.41 (m, 1H), 7.49-7.57 (m, 1H).

Example 324A

Ethyl 8-[(2,6-difluorobenzyl)oxy]-2-ethyl-6-methylimidazo[1,2-a]pyridine-3-carboxylate

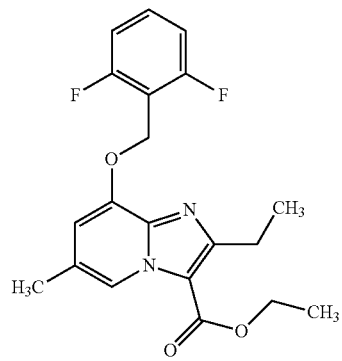 [SMILES: CCOC(=O)c1c(CC)nc2c(OCc3c(F)cccc3F)cc(C)cn12]

Under argon, 3.5 g (13.99 mmol) of 3-[(2,6-difluorobenzyl)oxy]-5-methylpyridine-2-amine from Example 323A and 9.6 ml (69.93 mmol) of methyl 2-chloro-2-propionyl acetate were dissolved in 140 ml of ethanol, and the mixture was stirred under reflux with 500 mg of 3 Å molecular sieve overnight. 500 mg of 3 Å molecular sieve were added, and the mixture was stirred under reflux for a further 16 hours. The reaction mixture was stirred under reflux for 8 days, and every day 3 Å molecular sieve was added. The mixture was cooled and filtered off with suction, and the mother liquor was substantially concentrated. The residue obtained was purified by silica gel chromatography (mobile phase: cyclohexane/ethyl acetate 9/1 to 7/3). This gave 3.8 g of the total compound (68% of theory, as a 1:1 mixture with methyl 8-[(2,6-difluorobenzyl)oxy]-2-ethyl-6-methylimidazo[1,2-a]pyridine-3-carboxylate).

LC-MS (Method 2): $R_t$=1.18 min

MS (ESpos): m/z=361 (M+H)$^+$

Example 325A

8-[(2,6-Difluorobenzyl)oxy]-2-ethyl-6-methylimidazo[1,2-a]pyridine-3-carboxylic acid

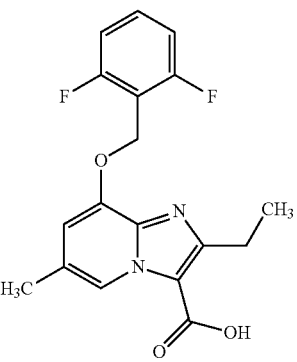 [SMILES: CCc1nc2c(OCc3c(F)cccc3F)cc(C)cn2c1C(=O)O]

2.0 g (5.34 mmol) of ethyl 8-[(2,6-difluorobenzyl)oxy]-2-ethyl-6-methylimidazo[1,2-a]pyridine-3-carboxylate from Example 324A (1:1 mixture of methyl and ethylester) were dissolved in 114 ml of THF/methanol (5/1), 5.34 ml (5.34 mmol) of 1 N aqueous sodium hydroxide solution were added and the mixture was stirred at RT overnight. The reaction mixture was stirred at 40° C. for 4 days, with another 5.34 ml (5.34 mmol) of 1 N aqueous lithium hydroxide solution being added after 3 days. After cooling, the mixture was, with ice-cooling, acidified to pH 4 using 6 N aqueous hydrochloric acid, and the organic solvent was then removed on a rotary evaporator. The precipitated solid was filtered off with suction, washed with water and then dried under high vacuum. This gave 1.94 g of the target compound (99% of theory).

LC-MS (Method 2): $R_t$=0.79 min
MS (ESpos): m/z=347 (M+H)$^+$
$^1$H-NMR (400 MHz, DMSO-d$_6$): δ=1.19 (t, 3H), 2.36 (s, 3H), 2.95 (q, 2H), 5.31 (s, 2H), 7.08 (s, 1H), 7.26 (quin, 2H), 7.55-7.65 (m, 1H), 8.78 (s, 1H), 13.02-13.06 (m, 1H).

Example 326A rac-2-Methylpentane-1,2-diamine dihydrochloride

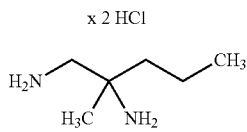

With ice-cooling, 1.0 g (8.91 mmol) of rac-2-amino-2-methylpentanonitrile was initially charged in 26.7 ml (26.74 mmol) of 1 M hydrochloric acid in ethanol and, together with 30 mg (0.13 mmol) of platinum(IV) oxide, hydrogenated at standard pressure overnight. Another 30 mg (0.13 mmol) of platinum(IV) oxide were added, and the reaction mixture was hydrogenated at 3 bar for 6 hours.

The reaction mixture was filtered off through Celite, 9 ml (17.83 mmol) of 2 N hydrochloric acid in diethyl ether were added to the filtrate, the mixture was concentrated and the product was dried under high vacuum. This gave 1.56 g of the target compound (92% of theory).

MS (ESpos): m/z=117 (M+H)$^+$
$^1$H-NMR (400 MHz, DMSO-d$_6$): δ=0.89 (t, 3H), 1.26-1.41 (m, 5H), 1.58-1.68 (m, 2H), 3.03-3.16 (m, 2H), 8.56-8.74 (m, 4H).

Example 327A rac-2-(Trifluoromethyl)piperidine-4-amine hydrochloride

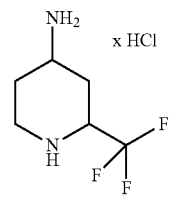 [SMILES: NC1CCNC(C(F)(F)F)C1]

115 mg (0.43 mmol) of rac-tert-butyl [2-(trifluoromethyl)piperidin-4-yl]carbamate were initially charged in 2.2 ml of diethyl ether, 2.14 ml (4.28 mmol) of 2 N hydrochloric acid in diethyl ether were added and the mixture was stirred at RT overnight. The reaction mixture was concentrated and the residue was dried under high vacuum. This gave 89 mg of the target compound (101% of theory).

Example 328A 8-(Benzyloxy)-2,6-dimethylimidazo[1,2-a]pyridine-3-carboxylic acid

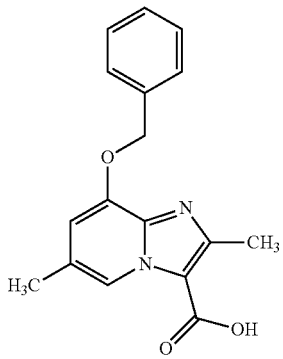

8.0 g (24.66 mmol) of ethyl 8-(benzyloxy)-2,6-dimethylimidazo[1,2-a]pyridine-3-carboxylate from Example 238A were dissolved in 526 ml of THF/methanol (5/1), 123 ml (123.31 mmol) of 1 N aqueous lithium hydroxide solution were added and the mixture was stirred at 40° C. for 6 hours. With ice-cooling, the reaction mixture was acidified to pH 5 using 6 N aqueous hydrochloric acid, then the organic solvent was then removed under reduced pressure. The precipitated solid was filtered off with suction, washed with water and then dried under high vacuum. This gave 7.47 g of the target compound (96% of theory, purity 94%).

LC-MS (Method 2): $R_t$=0.67 min
MS (ESpos): m/z=297 (M+H)$^+$

Example 329A rac-tert-Butyl [1-({[8-(benzyloxy)-2,6-dimethylimidazo[1,2-a]pyridin-3-yl]carbonyl}amino)-2-methylpentan-2-yl]carbamate

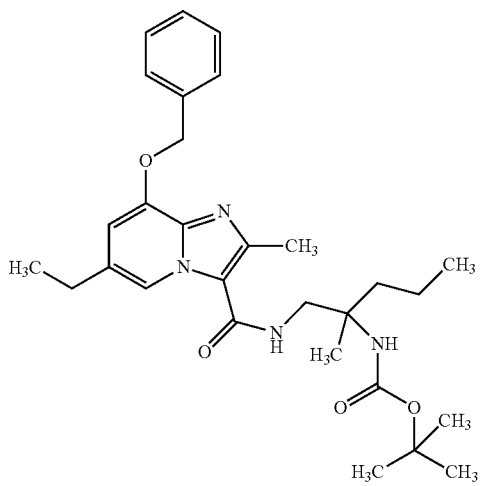 [SMILES: CCCC(C)(CNC(=O)c1c(C)nc2c(OCc3ccccc3)cc(CC)cn12)NC(=O)OC(C)(C)C]

7.0 g (22.20 mmol, purity 94%) of 8-(benzyloxy)-2,6-dimethylimidazo[1,2-a]pyridine-3-carboxylic acid from Example 328A, 10.13 g (26.65 mmol) of HATU and 11.6 ml (66.61 mmol) of N,N-diisopropylethylamine were initially charged in 141 ml of DMF, the mixture was stirred at room temperature for 20 min and 17.4 g (44.41 mmol, purity 74%) of rac-tert-butyl (1-amino-2-methylpentan-2-yl)carbamate from Example 390A were added. The mixture was stirred at RT for 1 hour, about 1.2 l of water were then added and the mixture was stirred at RT for 1 hour. The solid formed was filtered off and dried under high vacuum. This gave 9.98 g of the target compound (88% of theory).

LC-MS (Method 2): $R_t$=1.09 min

MS (ESpos): m/z=495 (M+H)$^+$ $^1$H-NMR (400 MHz, DMSO-d$_6$): δ=0.86 (t, 3H), 1.18 (s, 3H), 1.21-1.33 (m, 2H), 1.38 (s, 9H), 1.46-1.59 (m, 1H), 1.65-1.76 (m, 1H), 2.28 (s, 3H), 2.55 (s, 3H), 3.41-3.54 (m, 2H), 5.27 (s, 2H), 6.50-6.60 (m, 1H), 6.80-6.85 (m, 1H), 7.34-7.40 (m, 1H), 7.40-7.46 (m, 2H), 7.48-7.54 (m, 2H), 7.67 (t, 1H), 8.44 (s, 1H).

Example 330A rac-tert-Butyl (1-{[(8-hydroxy-2,6-dimethylimidazo[1,2-a]pyridin-3-yl)carbonyl]amino}-2-methylpentan-2-yl)carbamate

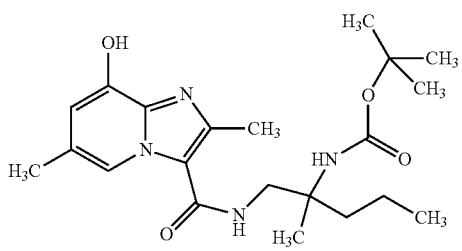 [SMILES: CCCC(C)(CNC(=O)c1c(C)nc2c(O)cc(C)cn12)NC(=O)OC(C)(C)C]

Under argon, 9.06 g (18.31 mmol) of rac-tert-butyl [1-({[8-(benzyloxy)-2,6-dimethylimidazo[1,2-a]pyridin-3-yl]carbonyl}amino)-2-methylpentan-2-yl]carbamate from Example 329A were initially charged in 189 ml of ethanol, 1.95 g (1.83 mmol) of 10% palladium on carbon were added and the mixture was hydrogenated under standard pressure and at RT for 90 min. The reaction mixture was filtered through Celite, the filter cake was washed with ethanol and the filtrate was concentrated. This gave 7.2 g of the target compound (92% of theory).

LC-MS (Method 2): $R_t$=0.86 min

MS (ESpos): m/z=405 (M+H)$^+$ $^1$H-NMR (400 MHz, DMSO-d$_6$): δ=0.86 (t, 3H), 1.18 (s, 3H), 1.21-1.33 (m, 2H), 1.35-1.41 (s, 9H), 1.48-1.59 (m, 1H), 1.65-1.77 (m, 1H), 2.22 (s, 3H), 2.56 (s, 3H), 3.41-3.53 (m, 2H), 6.49 (d, 1H), 6.53-6.59 (m, 1H), 7.63 (t, 1H), 8.34 (s, 1H).

Example 331A

Ethyl 8-[(2,6-difluorobenzyl)oxy]-6-methyl-2-(trifluoromethyl)imidazo[1,2-a]pyridine-3-carboxylate

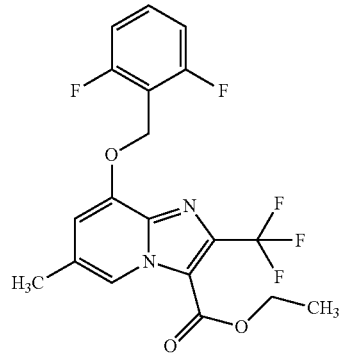 [SMILES: CCOC(=O)c1c(C(F)(F)F)nc2c(OCc3c(F)cccc3F)cc(C)cn12]

Under argon, 1.1 g (4.40 mmol) of 3-[(2,6-difluorobenzyl)oxy]-5-methylpyridine-2-amine from Example 323A and 4.8 g (21.98 mmol) of ethyl 2-chloro-4,4,4-trifluoro-3-oxobutanoate were dissolved in 44 ml of ethanol and stirred under reflux with about 200 mg of 3 Å molecular sieve overnight. About 200 mg of 3 Å molecular sieve were added, and the mixture was stirred under reflux for a further 16 hours. The mixture was then stirred under reflux for 8 days, with 3 Å molecular sieve being added each day. The mixture was cooled, and filtered off with suction, the mother liquor was concentrated virtually completely and the residue obtained was purified by silica gel chromatography (mobile phase: cyclohexane/ethyl acetate 9/1 to 7/3). This gave 600 mg of the target compound (33% of theory).

LC-MS (Method 2): $R_t$=1.33 min

MS (ESpos): m/z=415 (M+H)$^+$

Example 332A

8-[(2,6-Difluorobenzyl)oxy]-6-methyl-2-(trifluoromethyl)imidazo[1,2-a]pyridine-3-carboxylic acid

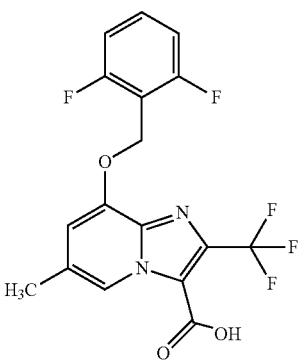 [SMILES: Cc1cc(OCc2c(F)cccc2F)c2nc(C(F)(F)F)c(C(=O)O)n2c1]

491 mg (1.19 mmol) of ethyl 8-[(2,6-difluorobenzyl)oxy]-6-methyl-2-(trifluoro-methyl)imidazo[1,2-a]pyridine-3-carboxylate from Example 331A were dissolved in 26 ml of THF/methanol (5/1), 6 ml of 1 N aqueous lithium hydroxide solution were added and the mixture was stirred at RT for 2 hours. Using 1 N aqueous hydrochloric acid, the reaction solution was 5 adjusted to pH 6, and the organic solvent was distilled off. The precipitate formed was filtered off, washed with water and dried under high vacuum. This gave 336 mg of the target compound (73% of theory).

LC-MS (Method 2): $R_t$=1.04 min

MS (ESpos): m/z=387 (M+H)$^+$ $^1$H-NMR (400 MHz, DMSO-$d_6$): δ=2.42 (s, 3H), 5.35 (s, 2H), 7.20-7.30 (m, 3H), 7.56-7.66 (m, 1H), 8.84 (s, 1H).

Example 333A ent-Benzyl {1-[({8-[(2,6-difluorobenzyl)oxy]-6-methyl-2-(trifluoromethyl)imidazo[1,2-a]pyridin-3-yl}carbonyl)amino]-2-methylpentan-2-yl}carbamate trifluoroacetate

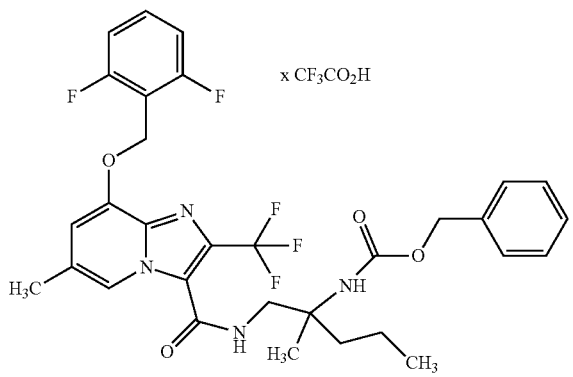 [SMILES: CCCC(C)(CNC(=O)c1c(C(F)(F)F)nc2c(OCc3c(F)cccc3F)cc(C)cn12)NC(=O)OCc1ccccc1]

50 mg (0.13 mmol) of 8-[(2,6-difluorobenzyl)oxy]-6-methyl-2-(trifluoromethyl)imidazo[1,2-a]pyridine-3-carboxylic acid from Example 332A, 45.7 mg (0.14 mmol) of (benzotriazol-1-yloxy)bisdimethylaminomethylium fluoroborate and 0.07 ml (0.65 mmol) of 4-methylmorpholine were initially charged in 0.43 ml of DMF, 35.6 mg (0.14 mmol) of ent-benzyl (1-amino-2-methylpentan-2-yl)carbamate from Example 289A were added and the mixture was stirred at RT for 1 hour. A little water/TFA was added to the reaction solution, and the product was purified by preparative HPLC (RP 18 column, mobile phase: acetonitrile/water gradient with addition of 0.1% TFA). This gave 46 mg of the target compound (48% of theory).

LC-MS (Method 2): $R_t$=1.40 min

MS (ESpos): m/z=619 (M−TFA+H)$^+$ $^1$H-NMR (400 MHz, DMSO-$d_6$): δ=0.85 (t, 3H), 1.20 (s, 3H), 1.23-1.33 (m, 2H), 1.44-1.55 (m, 1H), 1.68-1.78 (m, 1H), 2.32 (s, 3H), 3.50-3.64 (m, 2H), 4.94-5.03 (m, 2H), 5.33 (s, 2H), 6.93-7.00 (m, 1H), 7.06 (s, 1H), 7.20-7.36 (m, 7H), 7.56-7.65 (m, 1H), 7.93 (s, 1H), 8.60-8.67 (m, 1H).

Example 334A tert-Butyl (1-{[({8-[(2,6-difluorobenzyl)oxy]-2,6-dimethylimidazo[1,2-a]pyridin-3-yl}carbonyl)amino]methyl}cyclohexyl)carbamate trifluoroacetate

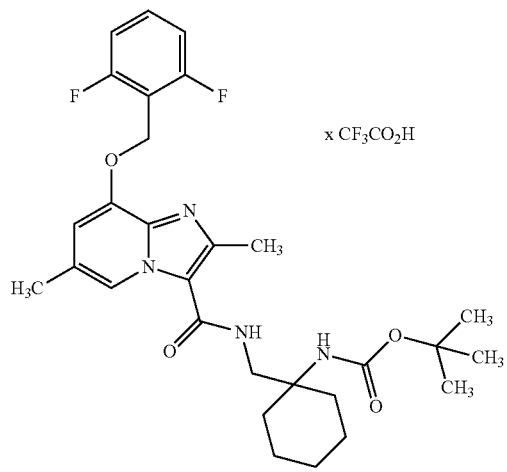 [SMILES: Cc1cc(OCc2c(F)cccc2F)c2nc(C)c(C(=O)NCC3(NC(=O)OC(C)(C)C)CCCCC3)n2c1]

100 mg (0.30 mmol) of 8-[(2,6-difluorobenzyl)oxy]-2,6-dimethylimidazo[1,2-a]pyridine-3-carboxylic acid from Example 21A, 145 mg (0.45 mmol) of (benzotriazol-1-yloxy)bisdimethylaminomethylium fluoroborate and 0.17 ml (1.51 mmol) of 4-methylmorpholine were initially charged in 2 ml of DMF, 82.5 mg (0.36 mmol) of tert-butyl [1-(aminomethyl)cyclohexyl]carbamate were added and the mixture was stirred at RT overnight. A little water/TFA was added to the reaction solution, and the product was purified by preparative HPLC (RP18 column, mobile phase: acetonitrile/water gradient with addition of 0.1% TFA). This gave 163 mg of the target compound (82% of theory).

LC-MS (Method 2): $R_t$=1.15 min

MS (ESpos): m/z=543 (M−TFA+H)$^+$

Example 335A tert-Butyl {3-[({8-[(2,6-difluorobenzyl)oxy]-2,6-dimethylimidazo[1,2-a]pyridin-3-yl}carbonyl)amino]cyclopentyl}carbamate (Stereoisomer Mixture)

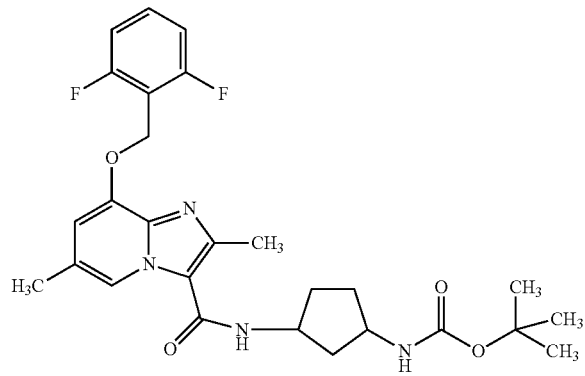 [SMILES: Cc1cc(OCc2c(F)cccc2F)c2nc(C)c(C(=O)NC3CCC(NC(=O)OC(C)(C)C)C3)n2c1]

100 mg (0.30 mmol) of 8-[(2,6-difluorobenzyl)oxy]-2,6-dimethylimidazo[1,2-a]pyridine-3-carboxylic acid from Example 21A, 106 mg (0.33 mmol) of (benzotriazol-1-yloxy)bisdimethylaminomethylium fluoroborate and 0.17 ml (1.51 mmol) of 4-methylmorpholine were initially charged in 1 ml of DMF, 78.4 mg (0.33 mmol) of tert-butyl (3-aminocyclopentyl)carbamate hydrochloride were added and the mixture was stirred at RT overnight. Water was added to the reaction solution, and the solid formed was stirred at RT for 30 min, filtered off, washed with water and dried under high vacuum. This gave 120 mg of the target compound (77% of theory).

LC-MS (Method 2): $R_t$=0.94 min
MS (ESpos): m/z=515 (M+H)$^+$

Example 336A rac-2-Amino-3-(1,3-benzothiazol-2-yl)-2-methylpropanonitrile

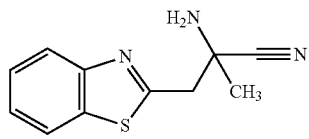

3.0 g (14.12 mmol, purity 90%) of 1-(1,3-benzothiazol-2-yl)acetone were initially charged in 28.2 ml (56.47 mmol) of 2 N ammonia in methanol, 775 mg (15.81 mmol) of sodium cyanide and 1.8 g (15.81 mmol) of ammonium chloride were added and the mixture was stirred under reflux for 3 hours. The reaction solution was cooled and diluted with 90 ml of dichloromethane, the precipitated solid was filtered off and the filtrate was concentrated. The residue was purified by silica gel chromatography (mobile phase: cyclohexane/ethyl acetate 5/1 to 1/1). This gave 1.16 g of the target compound (29% of theory, purity 77%).

LC-MS (Method 2): $R_t$=0.70 min
MS (ESpos): m/z=218 (M+H)$^+$

Example 337A rac-3-(1,3-Benzothiazol-2-yl)-2-methylpropane-1,2-diamine

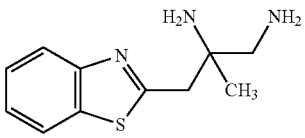

100 mg (0.35 mmol, 77% pure) of rac-2-amino-3-(1,3-benzothiazol-2-yl)-2-methylpropanonitrile from Example 336A were initially charged in 3.6 ml of THF, and 0.23 ml (0.23 mmol) of 1 N lithium aluminium hydride in diethyl ether was added under argon at 0° C. The mixture was stirred at 0° C. for 30 min and then at RT for 1 h. 0.04 ml of water, 0.04 ml of 2 N aqueous sodium hydroxide solution and 0.07 ml of water were added carefully to the reaction mixture. The precipitate was filtered off and washed with THF and a little methanol, the filtrate was concentrated and the residue was purified by silica gel chromatography (mobile phase: dichloromethane/methanol 10/1; dichloromethane/2 N ammonia in methanol 20/1). This gave 17.6 mg of the target compound (21% of theory, purity 94%).

LC-MS (Method 15): $R_t$=1.73 min
MS (ESpos): m/z=222 (M+H)$^+$

Example 338A rac-tert-Butyl 5-[({8-[(2,6-difluorobenzyl)oxy]-2,6-dimethylimidazo[1,2-a]pyridin-3-yl}carbonyl)amino]-3,3-difluoropiperidine-1-carboxylate

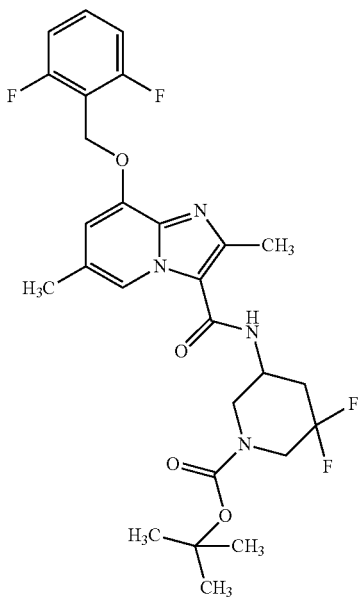 [SMILES: Cc1cc(OCc2c(F)cccc2F)c2nc(C)c(C(=O)NC3CN(C(=O)OC(C)(C)C)CC(F)(F)C3)n2c1]

75 mg (0.23 mmol) of 8-[(2,6-difluorobenzyl)oxy]-2,6-dimethylimidazo[1,2-a]pyridine-3-carboxylic acid from Example 21A, 94 mg (0.25 mmol) of HATU and 0.2 ml (1.13 mmol) of N,N-diisopropylethylamine were initially charged in 1.44 ml of DMF, the mixture was stirred for 20 min, 64 mg (0.27 mmol) of rac-tert-butyl 5-amino-3,3-difluoropiperidine-1-carboxylate were then added and the mixture was stirred at RT overnight. Water was added to the reaction solution, and the precipitated solid was stirred at RT for 30 min, filtered off, washed with water and dried under high vacuum. This gave 95 mg of the target compound (73% of theory).

LC-MS (Method 15): $R_t$=1.07 min

MS (ESpos): m/z=551 (M+H)$^+$ $^1$H-NMR (400 MHz, DMSO-d$_6$): δ=0.89-0.99 (m, 1H), 1.27-1.46 (m, 10H), 2.32 (s, 3H), 2.47 (s, 3H), 2.91-3.07 (m, 1H), 3.37-3.67 (m, 1H), 3.68-4.04 (m, 2H), 4.06-4.15 (m, 1H), 5.29 (s, 2H), 6.95 (s, 1H), 7.20-7.28 (m, 2H), 7.55-7.64 (m, 1H), 7.65-7.82 (m, 1H), 8.42-8.58 (m, 1H).

Example 339A tert-Butyl 3-[({8-[(2,6-difluorobenzyl)oxy]-2,6-dimethylimidazo[1,2-a]pyridin-3-yl}carbon-yl)amino]-4-(trifluoromethyl)pyrrolidine-1-carboxylate trifluoroacetate (Mixture of Stereoisomers)

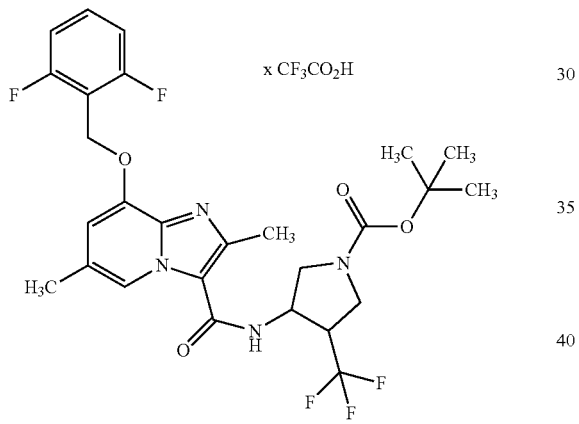

75 mg (0.23 mmol) of 8-[(2,6-difluorobenzyl)oxy]-2,6-dimethylimidazo[1,2-a]pyridine-3-carboxylic acid from Example 21A, 94 mg (0.25 mmol) of HATU and 0.12 ml (0.68 mmol) of N,N-diisopropylethylamine were initially charged in 1.44 ml of DMF, the mixture was stirred for 20 min, 69 mg (0.27 mmol) of rac-tert-butyl 3-amino-4-(trifluoromethyl)pyrrolidine-1-carboxylate (mixture of stereoisomers) were added and the mixture was stirred at RT overnight. Another 47 mg (0.13 mmol) of HATU and 0.05 ml (0.34 mmol) of N,N-diisopropylethylamine were added, and the mixture was stirred at RT for 15 min. 34 mg (0.13 mmol) of tert-butyl 3-amino-4-(trifluoromethyl)pyrrolidine-1-carboxylate (mixture of stereoisomers) were then added, and the mixture was stirred overnight in an oil bath heated to 60° C. Water/TFA was added to the reaction solution, and the product was purified by preparative HPLC (RP18 column, mobile phase: acetonitrile/water gradient with addition of 0.1% TFA). This gave 11 mg of the target compound (6% of theory, purity 80%).

LC-MS (Method 15): $R_t$=1.12 min

MS (ESpos): m/z=569 (M−TFA+H)$^+$

Example 340A ent-Benzyl {2-[({2,6-dimethyl-8-[(2,3,6-trifluorobenzyl)oxy]imidazo[1,2-a]pyridin-3-yl}carbonyl)amino]-2-methylbutyl}carbamate trifluoroacetate 282 mg (0.81 mmol) of 2,6-dimethyl-8-[(2,3,6-trifluorobenzyl)oxy]imidazo[1,2-a]pyridine-3-carboxylic acid from Example 265A, 337 mg (0.89 mmol) of HATU and 0.4 ml (2.42 mmol) of N,N-diisopropylethylamine were initially charged in 5 ml of DMF, the mixture was stirred for 20 min, 200 mg (0.85 mmol) of ent-benzyl (2-amino-2-methylbutyl) carbamate from Example 275A were then added and the mixture was stirred at RT overnight. Water/TFA was added to the reaction solution, and the product was purified by preparative HPLC (RP 18 column, mobile phase: acetonitrile/water gradient with addition of 0.1% TFA). This gave 165 mg of the target compound (30% of theory).

LC-MS (Method 2): $R_t$=1.07 min

MS (ESpos): m/z=569 (M−TFA+H)$^+$ $^1$H-NMR (400 MHz, DMSO-d$_6$): δ=0.87 (t, 3H), 1.26 (s, 3H), 1.49-1.60 (m, 1H), 1.93-2.06 (m, 1H), 2.37 (s, 3H), 2.71 (s, 3H), 3.29-3.37 (m, 1H), 3.51-3.59 (m, 1H), 4.99 (s, 2H), 5.44 (s, 2H), 7.18-7.37 (m, 6H), 7.50 (t, 1H), 7.65-7.75 (m, 2H), 8.41 (s, 1H).

Example 341A rac-tert-Butyl 3-[({8-[(2,6-difluorobenzyl)oxy]-2,6-dimethylimidazo[1,2-a]pyridin-3-yl}carbonyl)amino]azepane-1-carboxylate trifluoroacetate

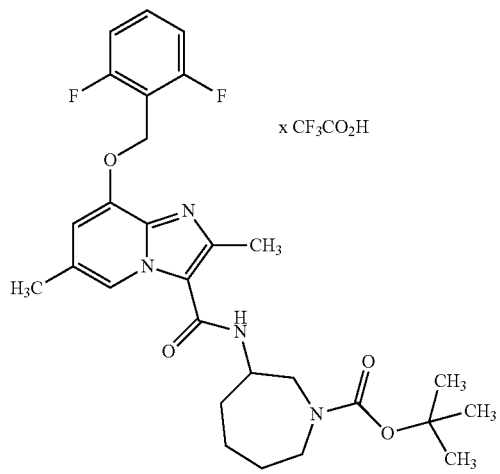 [SMILES: Cc1cc(OCc2c(F)cccc2F)c2nc(C)c(C(=O)NC3CCCCN(C(=O)OC(C)(C)C)C3)n2c1]

125 mg (0.38 mmol) of 8-[(2,6-difluorobenzyl)oxy]-2,6-dimethylimidazo[1,2-a]pyridine-3-carboxylic acid from Example 21A, 157 mg (0.49 mmol) of (benzotriazol-1-yloxy)bisdimethylaminomethylium fluoroborate and 0.12 ml (1.13 mmol) of N-methylmorpholine were initially charged in 2.4 ml of DMF, the mixture was stirred at RT for 10 min, 105 mg (0.49 mmol) of rac-tert-butyl 3-aminoazepane-1-carboxylate were then added and the mixture was stirred at RT overnight. Water/TFA was added to the reaction solution, and the product was purified by preparative HPLC (RP18 column, mobile phase: acetonitrile/water gradient with addition of 0.1% TFA). This gave 194 mg of the target compound (80% of theory).

LC-MS (Method 2): $R_t$=1.11 min

MS (ESpos): m/z=529 (M−TFA+H)$^+$ $^1$H-NMR (400 MHz, DMSO-d$_6$): δ=1.42 (s, 9H), 1.47-1.67 (m, 2H), 1.69-1.96 (m, 3H), 2.41 (br. s., 3H), 2.98-3.15 (m, 1H), 3.26-3.41 (m, 2H), 3.61-3.79 (m, 2H), 4.13-4.25 (m, 1H), 5.39 (s, 2H), 7.22-7.30 (m, 2H), 7.33-7.51 (m, 1H), 7.57-7.67 (m, 1H), 8.06-8.26 (m, 1H), 8.42-8.61 (m, 1H).

Example 351A

Methyl N-(tert-butoxycarbonyl)-3-[({8-[(2,6-difluorobenzyl)oxy]-2,6-dimethylimidazo[1,2-a]pyridin-3-yl}carbonyl)amino]-L-alaninate

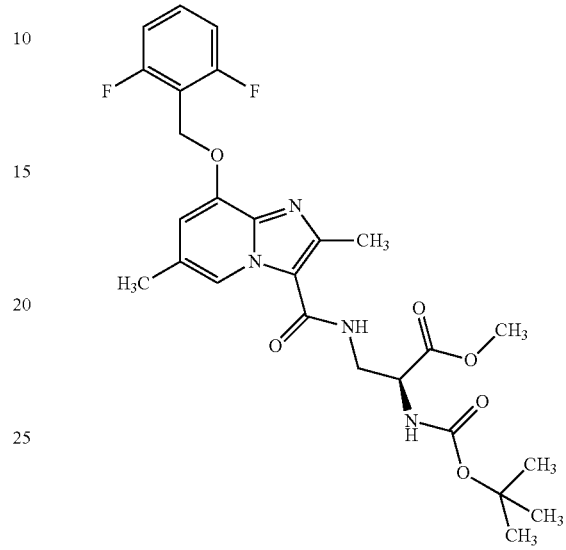

300 mg (0.90 mmol) of 8-[(2,6-difluorobenzyl)oxy]-2,6-dimethylimidazo[1,2-a]pyridine-3-carboxylic acid from Example 21A, 377 mg (1.17 mmol) of (benzotriazol-1-yloxy)bisdimethylaminomethylium fluoroborate and 0.5 ml (4.51 mmol) of N-methylmorpholine were initially charged in 5.7 ml of DMF, the mixture was stirred at RT for 10 min, 253 mg (0.99 mmol) of methyl 3-amino-N-(tert-butoxycarbonyl)-L-alaninate hydrochloride were then added and the mixture was stirred at RT overnight. About 40 ml of water were added to the reaction solution, and the mixture was stirred at RT for about 30 min. The solid was filtered off with suction, washed with water and dried under high vacuum. This gave 377 mg of the target compound (75% of theory).

LC-MS (Method 2): $R_t$=0.96 min

MS (ESpos): m/z=533 (M+H)$^+$ $^1$H-NMR (400 MHz, DMSO-d$_6$): δ=1.37 (s, 9H), 2.31 (s, 3H), 2.47 (s, 3H), 3.55-3.69 (m, 5H), 4.28 (q, 1H), 5.28 (s, 2H), 6.91-6.98 (m, 1H), 7.19-7.28 (m, 2H), 7.33 (d, 1H), 7.54-7.64 (m, 1H), 7.86 (t, 1H), 8.40-8.47 (m, 1H).

Example 352A rac-2-Amino-2-methyl-3-[1-(5-methyl-1,2-oxazol-3-yl)-1H-1,2,4-triazol-3-yl]propanonitrile

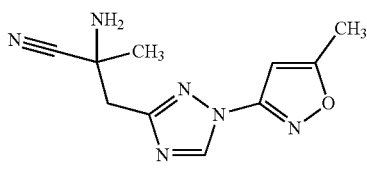 [SMILES: Cc1cc(-n2cnc(CC(C)(N)C#N)n2)no1]

860 mg (4.17 mmol) of 1-[1-(5-methyl-1,2-oxazol-3-yl)-1H-1,2,4-triazol-3-yl]acetone were initially charged in 8.3 ml of 2 N ammonia in methanol, 229 mg (4.67 mmol) of sodium cyanide and 556 mg (4.67 mmol) of ammonium chloride were added and the mixture was stirred under reflux for 4 hours. The reaction solution was cooled and diluted with 90 ml of dichloromethane, the solid obtained was filtered off, the filtrate was concentrated and the residue was purified by silica gel chromatography (mobile phase: cyclohexane/ethyl acetate: 4/1 to 1/1). This gave 761 mg of the target compound (78% of theory, purity 93%).

LC-MS (Method 15): $R_t$=1.48 min

MS (ESpos): m/z=233 (M+H)$^+$ $^1$H-NMR (400 MHz, DMSO-$d_6$): δ=1.51 (s, 3H), 2.82 (s, 2H), 3.08 (q, 2H), 3.33 (s, 3H), 6.81 (d, 1H), 9.25 (s, 1H).

Example 353A rac-2-Methyl-3-[1-(5-methyl-1,2-oxazol-3-yl)-1H-1,2,4-triazol-3-yl]propane-1,2-diamine

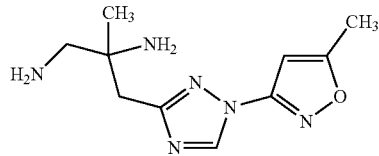 [SMILES: Cc1cc(-n2cnc(CC(C)(N)CN)n2)no1]

250 mg (1.00 mmol, purity 93%) of rac-2-amino-2-methyl-3-[1-(5-methyl-1,2-oxazol-3-yl)-1H-1,2,4-triazol-3-yl]propanonitrile from Example 352A were initially charged in 10.1 ml of THF, and 0.65 ml (0.65 mmol) of 1 M lithium aluminium hydride solution in THF were slowly added under argon and at 0° C. The mixture was stirred at 0° C. for 30 min and then at RT for 2 hours. At 0° C., 0.20 ml (0.20 mmol) of 1 M lithium aluminium hydride solution in THF was added dropwise, and the mixture was then stirred at RT for 2 hours. At 0° C., another 0.40 ml (0.40 mmol) of 1 M lithium aluminium hydride solution in THF was added dropwise, and the mixture was stirred at RT for 2 hours. 0.1 ml of water, 0.1 ml of 2 N aqueous sodium hydroxide solution and 0.2 ml of water were carefully added to the reaction mixture. The precipitate formed was filtered off, and washed with dichloromethane/methanol (10/1), and the filtrate was concentrated and dried under high vacuum. This gave 109 mg of the target compound (46% of theory).

LC-MS (Method 2): $R_t$=0.17 min

MS (ESpos): m/z=237 (M+H)$^+$

Example 354A

Ethyl 2-chloro-3-cyclopropyl-3-oxopropanoate

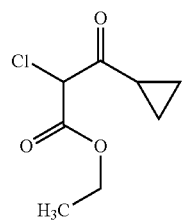

13.5 ml (168.07 mmol) of sulphuryl dichloride were initially charged in 100 ml of dichloromethane. At 15° C., 25 g (160.07 mmol) of ethyl-3-cyclopropyl-3-oxopropanoate were slowly added dropwise, and the mixture was stirred at RT for 2 hours. The reaction mixture was washed with in each case 100 ml of water, 5% strength aqueous sodium bicarbonate solution and saturated aqueous sodium chloride solution. The organic phase was dried over sodium sulphate, filtered off and carefully concentrated on a rotary evaporator (bath temperature 25° C., 200 mbar). This gave 38 g of the target compound (109% of theory, purity about 88%).

LC-MS (Method 2): $R_t$=0.88 min

MS (ESpos): m/z=191 (M+H)$^+$ $^1$H-NMR (400 MHz, DMSO-$d_6$): δ=0.92-1.03 (m, 2H), 1.03-1.14 (m, 2H), 1.22 (t, 3H), 2.22-2.30 (m, 1H), 4.19-4.28 (m, 2H), 5.79 (s, 1H).

Example 355A

Ethyl 2-cyclopropyl-8-[(2,6-difluorobenzyl)oxy]-6-methylimidazo[1,2-a]pyridine-3-carboxylate

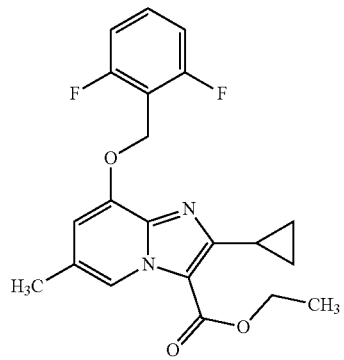 [SMILES: CCOC(=O)c1c(C2CC2)nc2c(OCc3c(F)cccc3F)cc(C)cn12]

Under argon, 4.00 g (15.98 mmol) of 3-[(2,6-difluorobenzyl)oxy]-5-methylpyridine-2-amine from Example 323A and 17.31 g (79.92 mmol, purity 88%) of ethyl 2-chloro-3-cyclopropyl-3-oxopropanoate from Example 354A were dissolved in 160 ml of ethanol, and the mixture was stirred under reflux with about 2 g of 3 Å molecular sieve for 8 days (each day, about 0.5 g of 3 Å molecular sieve was added). The reaction mixture was cooled and filtered off with suction, and the mother liquor was concentrated. The residue was purified by silica gel chromatography (mobile phase: cyclohexane/ethyl acetate gradient: 95/5 to 7/3). This gave 0.6 g of the target compound (10% of theory).

$^1$H-NMR (400 MHz, DMSO-$d_6$): δ=0.93-1.01 (m, 4H), 1.36 (t, 3H), 2.08-2.17 (m, 1H), 2.35 (s, 3H), 4.38 (q, 3H), 5.29 (s, 2H), 7.08 (s, 1H), 7.19-7.28 (m, 2H), 7.54-7.64 (m, 1H), 8.73 (s, 1H).

Example 356A

2-Cyclopropyl-8-[(2,6-difluorobenzyl)oxy]-6-methylimidazo[1,2-a]pyridine-3-carboxylic acid

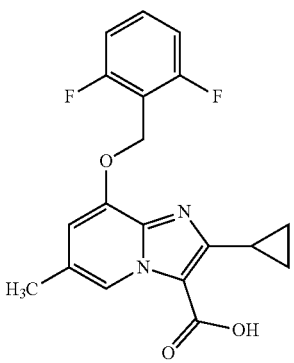 [SMILES: Cc1cc(OCc2c(F)cccc2F)c2nc(C3CC3)c(C(=O)O)n2c1]

100 mg (0.26 mmol) of ethyl 2-cyclopropyl-8-[(2,6-difluorobenzyl)oxy]-6-methylimidazo[1,2-a]pyridine-3-carboxylate from Example 355A were dissolved in 5.6 ml THF/methanol (5/1), 1.3 ml (1.29 mmol) of 1 N aqueous lithium hydroxide solution was added and the mixture was stirred at RT for 2 days. Using 1 N aqueous hydrochloric acid, the reaction solution was adjusted to pH 3, and the organic solvent was distilled off. The precipitate formed was filtered off, washed with water and dried under high vacuum. This gave 64 mg of the target compound (63% of theory, purity 91%).

LC-MS (Method 2): $R_t$=0.92 min
MS (ESpos): m/z=359 (M+H)$^+$

Example 357A ent-Benzyl {1-[({2-cyclopropyl-8-[(2,6-difluorobenzyl)oxy]-6-methylimidazo[1,2-a]pyridin-3-yl}carbonyl)amino]-2-methylpentan-2-yl}carbamate trifluoroacetate

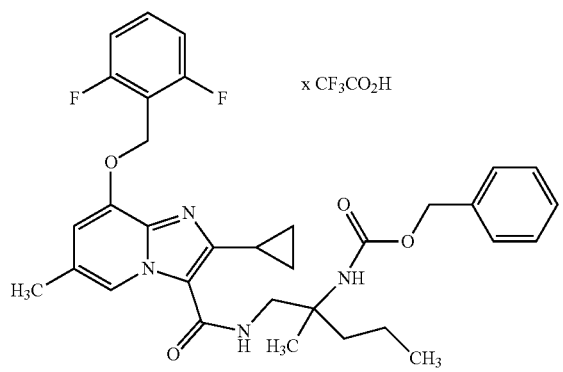 [SMILES: CCCC(C)(CNC(=O)c1c(C2CC2)nc2c(OCc3c(F)cccc3F)cc(C)cn12)NC(=O)OCc1ccccc1 ; "x CF3CO2H"]

50 mg (0.13 mmol, purity 91%) of 2-cyclopropyl-8-[(2,6-difluorobenzyl)oxy]-6-methylimidazo[1,2-a]pyridine-3-carboxylic acid from Example 356A, 45 mg (0.14 mmol) of (benzotriazol-1-yloxy)bisdimethylaminomethylium fluoroborate (TBTU) and 0.07 ml (0.64 mmol) of 4-methylmorpholine were initially charged in 0.5 ml of DMF, 35 mg (0.14 mmol) of ent-benzyl (1-amino-2-methylpentan-2-yl) carbamate from Example 289A were added and the mixture was stirred at RT overnight. A little water/TFA was added to the reaction solution, and the product was purified by preparative HPLC (RP18 column, mobile phase: acetonitrile/water gradient with addition of 0.1% TFA). This gave 75 mg of the target compound (82% of theory).

LC-MS (Method 2): $R_t$=1.32 min
MS (ESpos): m/z=591 (M–TFA+H)$^+$

Example 358A ent-Benzyl {1-[({8-[(2,6-difluorobenzyl)oxy]-2-methyl-6-[(trimethylsilyl)ethinyl]imidazo[1,2-a]pyridin-3-yl}carbonyl)amino]-2-methylpentan-2-yl}carbamate

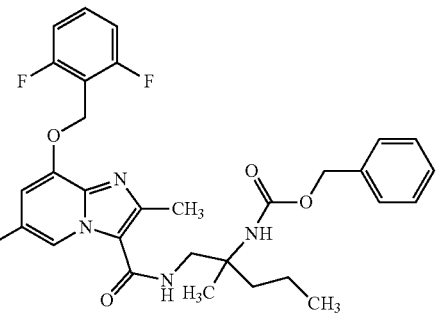

514 mg (0.691 mmol) of ent-benzyl {1-[({6-bromo-8-[(2,6-difluorobenzyl)oxy]-2-methylimidazo[1,2-a]pyridin-3-yl}carbonyl)amino]-2-methylpentan-2-yl}carbamate trifluoroacetate from Example 292A, 97 mg (0.138 mmol) of dichloro[bis(triphenylphosphoranyl)]palladium and 26 mg (0.138 mmol) of copper(I) iodide were initially charged in 7.5 ml of dioxane and 7.5 ml of diisopropylethylamine at RT. 407 mg (4.15 mmol) of ethynyl(trimethyl)silane were then added dropwise, and the mixture was stirred at 50° C. overnight. The reaction mixture was concentrated on a rotary evaporator. The residue was purified by preparative HPLC (RP-C18, mobile phase: acetonitrile/water gradient with addition of 0.05% formic acid). This gave 401 mg (90% of theory) of the title compound.

LC-MS (Method 2): $R_t$=1.53 min
MS (ESpos): m/z=647 (M+H)$^+$
$^1$H-NMR (400 MHz, DMSO-d$_6$): δ=0.26 (s, 9H), 0.85 (t, 3H), 1.20 (s, 3H), 1.23-1.34 (m, 2H), 1.45-1.56 (m, 1H), 1.69-1.82 (m, 1H), 2.52 (s, 3H), 3.45-3.59 (m, 2H), 5.00 (s, 2H), 5.33 (s, 2H), 7.02-7.12 (m, 2H), 7.20-7.37 (m, 7H), 7.53-7.66 (m, 1H), 7.84 (t, 1H), 8.78 (s, 1H).

Example 359A ent-Benzyl {1-[({8-[(2,6-difluorobenzyl)oxy]-6-ethynyl-2-methylimidazo[1,2-a]pyridin-3-yl}carbonyl)amino]-2-methylpentan-2-yl}carbamate

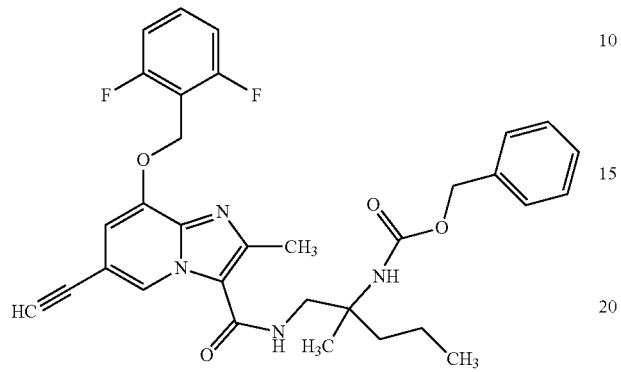

400 mg (0.62 mmol) of ent-benzyl {1-[({8-[(2,6-difluorobenzyl)oxy]-2-methyl-6-[(trimethyl-silyl)ethynyl]imidazo[1,2-a]pyridin-3-yl}carbonyl)amino]-2-methylpentan-2-yl}carbamate from Example 358A were initially charged in 6.2 ml of methanol, 256 mg (1.86 mmol) of potassium carbonate were added at RT and the mixture was stirred at RT for 1.5 h. The reaction mixture was concentrated on a rotary evaporator. Ice-water was added to the residue, and the mixture was extracted three times with ethyl acetate. The combined organic phases were dried over sodium sulphate and concentrated under reduced pressure. This gave 312 mg (89% of theory) of the title compound.

LC-MS (Method 2): $R_t$=1.31 min
MS (ESpos): m/z=575 (M+H)$^+$

Example 360A ent-N-[2-Ethyl-6-(trifluoromethyl)-1,2,3,4-tetrahydro-1,5-naphthyridin-4-yl]acetamide (Enantiomer A)

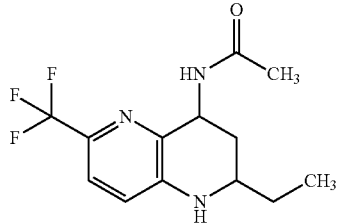 [SMILES: CCC1CC(NC(C)=O)c2nc(C(F)(F)F)ccc2N1]

5.80 g (20.19 mmol) of rac-N-[2-ethyl-6-(trifluoromethyl)-1,2,3,4-tetrahydro-1,5-naphthyridin-4-yl]acetamide (described in: M.-C. Fernandez et al. Bioorg. Med. Chem. Lett. 2012, 22, 3056-3062) were separated into the enantiomers by preparative separation on a chiral phase [column: SFC Chiralpak AY-H, 20 µm, 360×50 mm, mobile phase: 85% carbon dioxide, 15% isopropanol, flow rate: 400 ml/min; temperature: 38° C.; backpressure: 80 bar; detection: 220 nm].

Enantiomer A: yield 2.20 g (>99% ee)

$R_t$=1.30 min [Daicel Chiralpak AY-H, 5 µm, 250×4.6 mm; mobile phase: 70% carbon dioxide, 30% isopropanol; flow rate: 3 ml/min; detection: 210 nm].

Example 361A ent-2-Ethyl-6-(trifluoromethyl)-1,2,3,4-tetrahydro-1,5-naphthyridine-4-amine hydrochloride

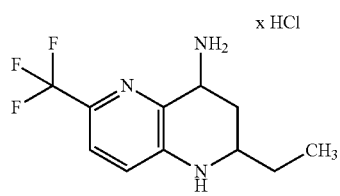 [SMILES: "x HCl" ; CCC1CC(N)c2nc(C(F)(F)F)ccc2N1]

2.8 ml of saturated hydrogen chloride solution in methanol were added to 150 mg (0.52 mmol) of ent-N-[2-ethyl-6-(trifluoromethyl)-1,2,3,4-tetrahydro-1,5-naphthyridin-4-yl]acetamide (enantiomer A) from Example 360A, and the mixture was stirred in a microwave at 80° C. for 1 hour. The reaction mixture was concentrated, dissolved in acetonitrile/water (1:1) and lyophilised. This gave 124 mg of the target compound (80% of theory).

LC-MS (Method 15): $R_t$=2.05 min
MS (ESpos): m/z=246 (M−HCl+H)$^+$
$^1$H-NMR (400 MHz, DMSO-d$_6$): δ=0.96 (t, 3H), 1.47-1.69 (m, 3H), 2.29-2.39 (m, 1H), 3.41-3.52 (m, 1H), 4.50-4.62 (m, 1H), 6.93 (br. s., 1H), 7.09 (d, 1H), 7.52 (d, 1H), 8.45 (br. s., 3H).

Example 362A ent-N-[2-methyl-6-(trifluoromethyl)-1,2,34-tetrahydro-1,5-naphthyridin-4-yl]acetamide (Enantiomer A)

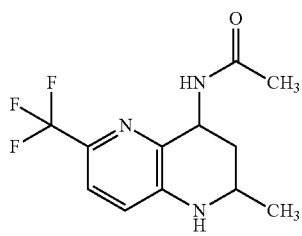 [SMILES: CC(=O)NC1CC(C)Nc2ccc(C(F)(F)F)nc21]

6.00 g (21.96 mmol) of rac-N-[2-methyl-6-(trifluoromethyl)-1,2,3,4-tetrahydro-1,5-naphthyridin-4-yl]acetamide (described in: M.-C. Fernandez et al. Bioorg. Med. Chem. Lett. 2012, 22, 3056-3062) were separated into the enantiomers by preparative separation on a chiral phase [column: SFC Chiralpak AY-H, 20 µm, 360×50 mm, mobile phase: 90% carbon dioxide, 10% methanol, flow rate: 400 ml/min; temperature: 38° C.; backpressure: 80 bar; detection: 220 nm].

Enantiomer A: yield: 2.41 g (>99% ee)
$R_t$=2.66 min [Daicel Chiralpak AY-H, 5 µm, 250×4.6 mm; mobile phase: 90% carbon dioxide, 10% isopropanol; flow rate: 3 ml/min; detection: 210 nm].

Example 363A ent-2-Methyl-6-(trifluoromethyl)-1,2,3,4-tetrahydro-1,5-naphthyridine-4-amine hydrochloride

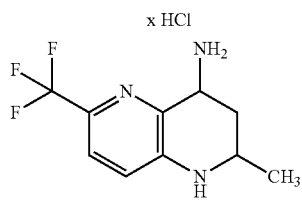 [SMILES: "x HCl" ; CC1CC(N)c2nc(C(F)(F)F)ccc2N1]

2.8 ml of saturated hydrogen chloride solution in methanol were added to 152 mg (0.56 mmol) of ent-N-[2-methyl-6-(trifluoromethyl)-1,2,3,4-tetrahydro-1,5-naphthyridin-4-yl]acetamide (enantiomer A) from Example 362A (described in: M.-C. Fernandez et al. Bioorg. Med. Chem. Lett. 2012, 22, 3056-3062), and the mixture was stirred in a microwave at 80° C. for 1 hour. The reaction mixture was concentrated and lyophilised. This gave 147 mg of the target compound (97% of theory).

LC-MS (Method 2): $R_t$=0.40 min

MS (ESpos): m/z=232 (M−HCl+H)$^+$ $^1$H-NMR (400 MHz, DMSO-$d_6$): δ=1.23 (d, 3H), 1.59 (q, 1H), 2.25-2.35 (m, 1H), 3.58-3.69 (m, 1H), 4.50-4.61 (m, 1H), 6.97-7.05 (m, 2H), 7.52 (d, 1H), 8.40 (br. s., 3H).

Example 364A

Ethyl 8-[(2,6-difluorobenzyl)oxy]-6-methyl-2-propylimidazo[1,2-a]pyridine-3-carboxylate

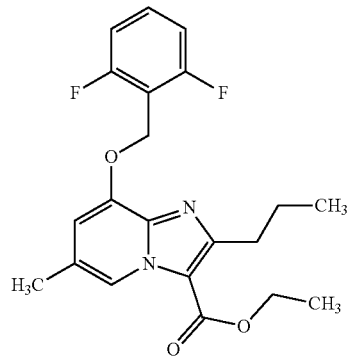 [SMILES: CCCc1nc2c(OCc3c(F)cccc3F)cc(C)cn2c1C(=O)OCC]

Under argon, 3.0 g (11.99 mmol) of 3-[(2,6-difluorobenzyl)oxy]-5-methylpyridine-2-amine from Example 323A were initially charged in 60 ml of ethanol. 18.48 g (95.90 mmol) of ethyl 2-chloro-3-oxohexanoate (described in: M. Altuna-Urquijo et al. Tetrahedron 2009, 65, 975-984) and 600 mg of 3 Å molecular sieve were then added, and the mixture was stirred under reflux for 5 days. The reaction solution was concentrated and partitioned between water and ethyl acetate. The phases were separated and the aqueous phase was extracted with ethyl acetate. The organic phases were combined, dried with sodium sulphate, filtered off and concentrated. The residue was purified by silica gel chromatography (mobile phase: cyclohexane/ethyl acetate=95/5 to 8/2). This gave 2.4 g of the target compound (47% of theory, purity about 92%).

LC-MS (Method 2): $R_t$=1.23 min

MS (ESpos): m/z=389 (M+H)$^+$ $^1$H-NMR (400 MHz, DMSO-$d_6$): δ=0.90 (t, 3H), 1.35 (t, 3H), 1.60-1.70 (m, 2H), 2.37 (s, 3H), 2.87-2.94 (m, 2H), 4.35 (q, 2H), 5.31 (s, 2H), 7.10 (s, 1H), 7.21-7.29 (m, 2H), 7.55-7.65 (m, 1H), 8.74 (s, 1H).

Example 365A

8-[(2,6-Difluorobenzyl)oxy]-6-methyl-2-propylimidazo[1,2-a]pyridine-3-carboxylic acid

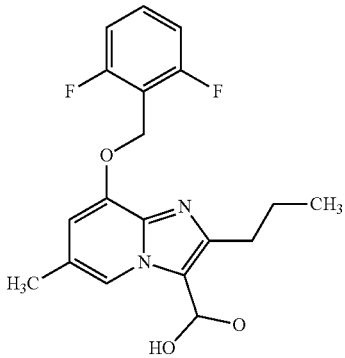 [SMILES: CCCc1nc2c(OCc3c(F)cccc3F)cc(C)cn2c1C(O)O]

2.30 g (5.92 mmol) of ethyl 8-[(2,6-difluorobenzyl)oxy]-6-methyl-2-propylimidazo[1,2-a]pyridine-3-carboxylate from Example 364A were initially charged in 108 ml of THF, 29 ml of water and 21.6 ml of methanol at RT. 1.24 g (29.61 mmol) of lithium hydroxide monohydrate were added, and the mixture was stirred at RT for 16 hours. The reaction mixture was freed from the organic solvents and the aqueous solution obtained was solidified with semiconcentrated hydrochloric acid. The aqueous phase was extracted twice with dichloromethane. The organic phases were combined, dried with sodium sulphate, filtered off and concentrated. This gave 2.50 g of the target compound (115% of theory).

LC-MS (Method 2): $R_t$=0.83 min

MS (ESpos): m/z=361 (M+H)$^+$ $^1$H-NMR (400 MHz, DMSO-$d_6$): δ=0.89 (t, 3H), 1.61-1.72 (m, 2H), 2.41 (s, 3H), 2.95 (t, 2H), 5.35 (s, 2H), 7.19-7.35 (m, 3H), 7.56-7.66 (m, 1H), 8.85 (s, 1H), 12.94-13.92 (br. s, 1H).

Example 366A ent-Benzyl {1-[({8-[(2,6-difluorobenzyl)oxy]-6-methyl-2-propylimidazo[1,2-a]pyridin-3-yl}carbonyl)amino]-2-methylbutan-2-yl}carbamate

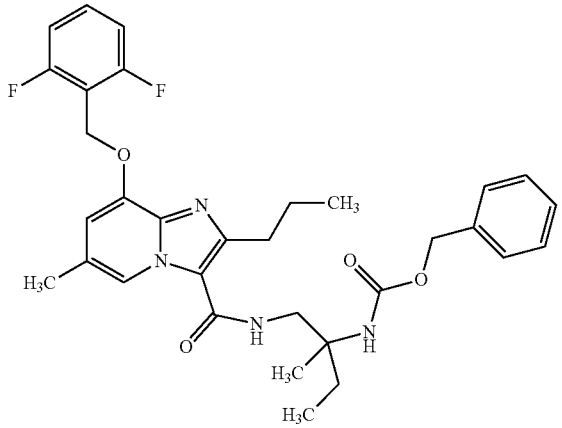 [SMILES: CCCc1nc2c(OCc3c(F)cccc3F)cc(C)cn2c1C(=O)NCC(C)(CC)NC(=O)OCc1ccccc1]

100 mg (0.28 mmol) of 8-[(2,6-difluorobenzyl)oxy]-6-methyl-2-propylimidazo[1,2-a]pyridine-3-carboxylic acid from Example 365A, 127 mg (0.33 mmol) of HATU and 0.24 ml (1.39 mmol) of N,N-diisopropylethylamine were initially charged in 2 ml of DMF, and the mixture was pre-stirred at RT for 10 min. 98.4 mg (0.42 mmol) of ent-benzyl (1-amino-2-methylbutan-2-yl)carbamate from Example 274A were then added to the reaction solution, and the mixture was stirred at RT overnight. The reaction solution was purified by preparative HPLC (RP18 column, solvent: acetonitrile/water gradient with addition of 0.05% formic acid). This gave 109 mg of the target compound (68% of theory).

LC-MS (Method 2): $R_t$=1.15 min
MS (ESpos): m/z=579 (M+H)$^+$
$^1$H-NMR (400 MHz, DMSO-d$_6$): δ=0.79-0.88 (m, 6H), 1.20 (s, 3H), 1.55-1.70 (m, 3H), 1.73-1.86 (m, 1H), 2.29 (s, 3H), 2.83 (t, 2H), 3.45-3.58 (m, 2H), 5.00 (s, 2H), 5.29 (s, 2H), 6.91 (s, 1H), 7.03-7.10 (m, 1H), 7.20-7.28 (m, 2H), 7.28-7.38 (m, 5H), 7.55-7.64 (m, 1H), 7.79 (t, 1H), 8.37 (s, 1H).

Example 367A rac-tert-Butyl {2-[({8-[(2,6-difluorobenzyl)oxy]-2,6-dimethylimidazo[1,2-a]pyridin-3-yl}carbonyl)amino]cyclobutyl}carbamate

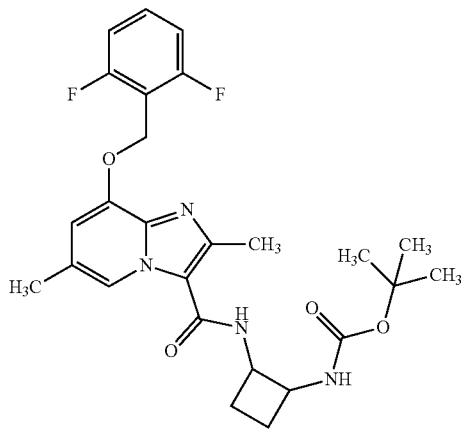 [SMILES: Cc1cc(OCc2c(F)cccc2F)c2nc(C)c(C(=O)NC3CCC3NC(=O)OC(C)(C)C)n2c1]

150 mg (0.45 mmol) of 8-[(2,6-difluorobenzyl)oxy]-2,6-dimethylimidazo[1,2-a]pyridine-3-carboxylic acid from Example 21A, 206 mg (0.54 mmol) of HATU and 0.4 ml (2.26 mmol) of N,N-diisopropylethylamine were initially charged in 4.4 ml of DMF, the mixture was stirred for 10 min, 101 mg (0.54 mmol) of rac-tert-butyl (2-aminocyclobutyl)carbamate were then added at RT and the mixture was stirred at RT overnight. Water was added to the reaction mixture, and the solid formed was stirred at RT for about 30 min and then filtered off and washed thoroughly with water. This gave 185 mg of the target compound (82% of theory).

LC-MS (Method 2): $R_t$=0.94 min
MS (ESpos): m/z=501 (M+H)$^+$
$^1$H-NMR (400 MHz, DMSO-d$_6$): δ=1.37 (s, 9H), 1.48-1.67 (m, 2H), 1.87-2.02 (m, 2H), 2.30 (s, 3H), 2.45 (s, 3H), 3.99-4.12 (m, 1H), 4.23-4.35 (m, 1H), 5.28 (s, 2H), 6.90 (s, 1H), 7.20-7.29 (m, 3H), 7.54-7.64 (m, 1H), 8.17 (d, 1H), 8.35 (s, 1H).

Example 368A ent-tert-Butyl {2-[({8-[(2,6-difluorobenzyl)oxy]-2,6-dimethylimidazo[1,2-a]pyridin-3-yl}carbonyl)amino]cyclobutyl}carbamate (Enantiomer A)

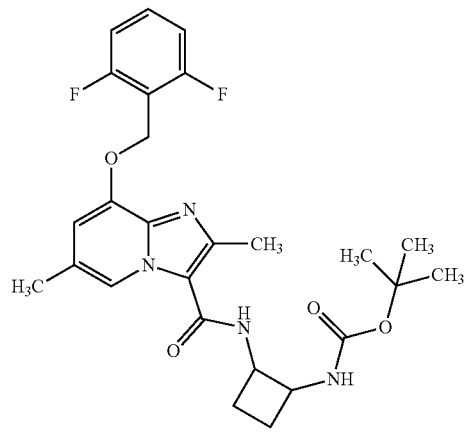 [SMILES: Cc1cc(OCc2c(F)cccc2F)c2nc(C)c(C(=O)NC3CCC3NC(=O)OC(C)(C)C)n2c1]

180 mg (0.37 mmol) of rac-tert-butyl {2-[({8-[(2,6-difluorobenzyl)oxy]-2,6-dimethylimidazo[1,2-a]pyridin-3-yl}carbonyl)amino]cyclobutyl}carbamate from Example 367A were separated into the enantiomers by preparative separation on a chiral phase [column: SFC Chiralpak AZ-H, 5 μm, 250×20 mm, mobile phase: 50% isohexane, 50% ethanol, flow rate: 50 ml/min; temperature: 20° C.; detection: 220 nm].

Enantiomer A: yield: 77 mg (>99% ee)

$R_t$=5.79 min [Daicel Chiralpak AZ-H, 5 μm, 250×4.6 mm; mobile phase: 50% isohexane, 50% ethanol; flow rate: 1 ml/min; detection: 220 nm].

Example 369A ent-tert-Butyl {2-[({8-[(2,6-difluorobenzyl)oxy]-2,6-dimethylimidazo[1,2-a]pyridin-3-yl}carbonyl)amino]cyclobutyl}carbamate (Enantiomer B)

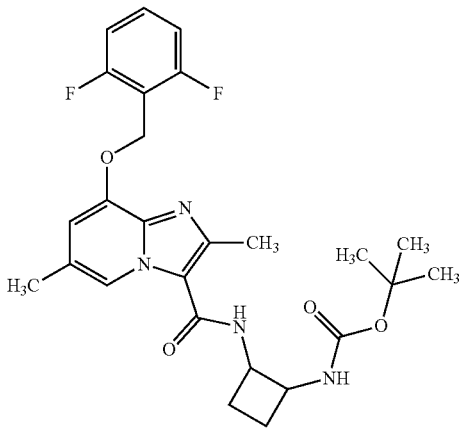 [SMILES: Cc1cc(OCc2c(F)cccc2F)c2nc(C)c(C(=O)NC3CCC3NC(=O)OC(C)(C)C)n2c1]

180 mg (0.37 mmol) of rac-tert-butyl {2-[({8-[(2,6-difluorobenzyl)oxy]-2,6-dimethylimidazo[1,2-a]pyridin-3-yl}carbonyl)amino]cyclobutyl}carbamate from Example 367A were separated into the enantiomers by preparative separation on a chiral phase [column: SFC Chiralpak AZ-H, 5 μm, 250×20 mm, mobile phase: 50% isohexane, 50% ethanol, flow rate: 50 ml/min; temperature: 20° C.; detection: 220 nm].

Enantiomer B: yield: 67 mg (>99% ee)

$R_t$=8.24 min [Daicel Chiralpak AZ-H, 5 μm, 250×4.6 mm; mobile phase: 50% isohexane, 50% ethanol; flow rate: 1 ml/min; detection: 220 nm].

Example 370A ent-Benzyl {1-[({8-[(2,6-difluorobenzyl)oxy]-2-ethyl-6-methylimidazo[1,2-a]pyridin-3-yl}carbonyl)amino]-2-methylpentan-2-yl}carbamate trifluoroacetate

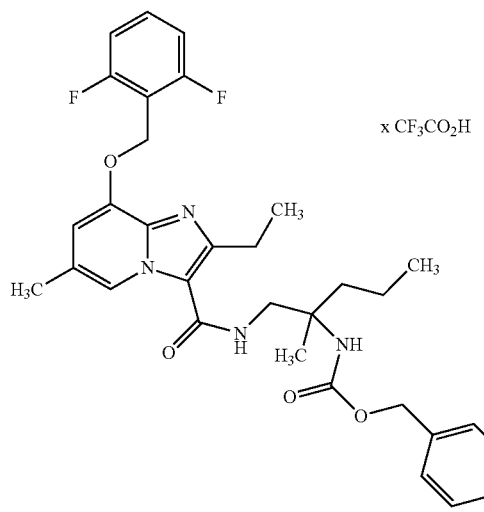

110 mg (0.32 mmol) of 8-[(2,6-difluorobenzyl)oxy]-2-ethyl-6-methylimidazo[1,2-a]pyridine-3-carboxylic acid from Example 325A, 133 mg (0.35 mmol) of HATU and 0.17 ml (0.95 mmol) of N,N-diisopropylethylamine were initially charged in 2 ml of DMF, the mixture was stirred for 20 min, 106 mg (0.36 mmol, purity 86%) of ent-benzyl (1-amino-2-methylpentan-2-yl)carbamate from Example 288A were then added and the mixture was stirred at RT overnight. A little water/TFA was added to the reaction solution, and the product was purified by preparative HPLC (RP18 column, mobile phase: acetonitrile/water gradient with addition of 0.1% TFA). This gave 181 mg of the target compound (82% of theory).

LC-MS (Method 2): $R_t$=1.19 min

MS (ESpos): m/z=579 (M−TFA+H)$^+$ $^1$H-NMR (400 MHz, DMSO-$d_6$): δ=0.86 (t, 3H), 1.17-1.24 (m, 6H), 1.25-1.35 (m, 2H), 1.44-1.57 (m, 1H), 1.69-1.81 (m, 1H), 2.37 (s, 3H), 2.91 (q, 2H), 3.50-3.60 (m, 2H), 4.97-5.02 (m, 2H), 5.38 (s, 2H), 7.09 (s, 1H), 7.22-7.39 (m, 8H), 7.56-7.66 (m, 1H), 8.06-8.31 (m, 1H), 8.42 (s, 1H).

Example 371A rac-tert-Butyl 4-[({8-[(2,6-difluorobenzyl)oxy]-2,6-dimethylimidazo[1,2-a]pyridin-3-yl}carbonyl)amino]hexahydrocyclopenta[b]pyrrole-1(2H)-carboxylate

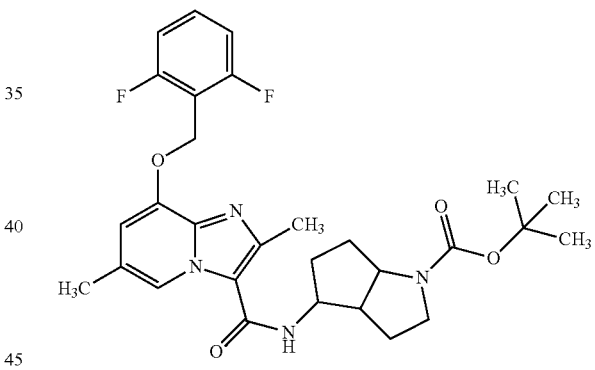

75 mg (0.23 mmol) of 8-[(2,6-difluorobenzyl)oxy]-2,6-dimethylimidazo[1,2-a]pyridine-3-carboxylic acid from Example 21A, 94.4 mg (0.25 mmol) of HATU and 0.12 ml (0.68 mmol) of N,N-diisopropylethylamine were initially charged in 1.4 ml of DMF, the mixture was stirred for 20 min, 61 mg (0.27 mmol) of rac-tert-butyl 4-aminohexahydrocyclopenta[b]pyrrole-1(2H)-carboxylate (commercially available; also described in WO 201056717 A1) were added and the mixture was stirred at RT overnight. Water was added to the reaction solution, and the precipitate solid was stirred at RT for 30 min, filtered off, washed with water and dried under high vacuum. This gave 116 mg of the target compound (95% of theory).

LC-MS (Method 2): $R_t$=1.02 min

MS (ESpos): m/z=541 (M+H)$^+$ $^1$H-NMR (400 MHz, DMSO-$d_6$): δ=0.89-1.08 (m, 3H), 1.40 (s, 9H), 1.58-1.86 (m, 7H), 2.31 (s, 3H), 2.48 (s, 3H), 3.96-4.12 (m, 1H), 4.18-4.30 (m, 1H), 5.29 (s, 2H), 6.91 (s, 1H), 7.19-7.29 (m, 2H), 7.52-7.64 (m, 1H), 7.84-7.94 (m, 1H), 8.33 (s, 1H).

Example 372A rac-tert-Butyl 1-[({8-[(2,6-difluorobenzyl)oxy]-2,6-dimethylimidazo[1,2-a]pyridin-3-yl}carbonyl)amino]-3-azabicyclo[3.2.0]heptane-3-carboxylate

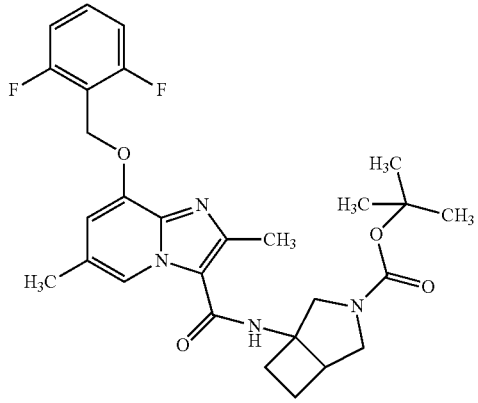 [SMILES: Cc1cc(OCc2c(F)cccc2F)c2nc(C)c(C(=O)NC34CCC3CN(C(=O)OC(C)(C)C)C4)n2c1]

75 mg (0.23 mmol) of 8-[(2,6-difluorobenzyl)oxy]-2,6-dimethylimidazo[1,2-a]pyridine-3-carboxylic acid from Example 21A, 94.4 mg (0.25 mmol) of HATU and 0.20 ml (1.13 mmol) of N,N-diisopropylethylamine were initially charged in 1.4 ml of DMF, the mixture was stirred for 20 min, 57.5 mg (0.27 mmol) of rac-tert-butyl 1-amino-3-azabicyclo[3.2.0]heptane-3-carboxylate (commercially available; CAS-No. 1251009-41-2) were then added and the mixture was stirred at RT overnight. Water was added to the reaction solution, and the precipitated solid was stirred at RT for 30 min, filtered off, washed with water and dried under high vacuum. This gave 97 mg of the target compound (80% of theory).

LC-MS (Method 2): $R_t$=1.05 min
MS (ESpos): m/z=527 (M+H)$^+$

Example 373A rac-tert-Butyl 3-[({8-[(2,6-difluorobenzyl)oxy]-2,6-dimethylimidazo[1,2-a]pyridin-3-yl}carbonyl)amino]-4-fluoropyrrolidine-1-carboxylate trifluoroacetate

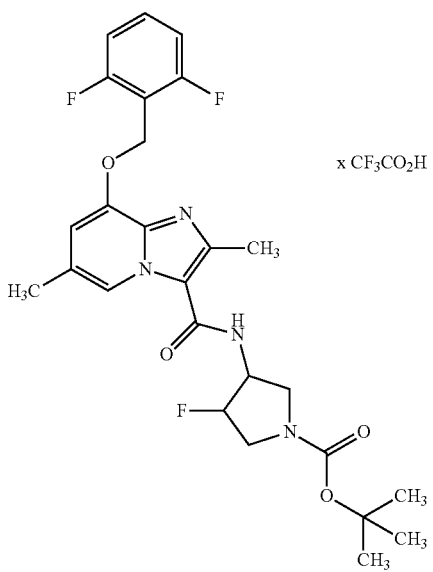 [SMILES: Cc1cc(OCc2c(F)cccc2F)c2nc(C)c(C(=O)NC3CN(C(=O)OC(C)(C)C)CC3F)n2c1]

75 mg (0.23 mmol) of 8-[(2,6-difluorobenzyl)oxy]-2,6-dimethylimidazo[1,2-a]pyridine-3-carboxylic acid from Example 21A, 112 mg (0.29 mmol) of HATU and 0.32 ml (1.81 mmol) of N,N-diisopropylethylamine were initially charged in 0.75 ml of DMF, the mixture was stirred for 10 min, 60 mg (0.29 mmol) of cis-rac-tert-butyl 3-amino-4-fluoropyrrolidine-1-carboxylate were then added at RT and the mixture was stirred at RT for 60 min. TFA was added to the reaction solution, and the product was purified by preparative HPLC (RP18 column, mobile phase: acetonitrile/water gradient with addition of 0.1% TFA). The product fractions were combined, concentrated and lyophilised. This gave 98 mg of the target compound (68% of theory).

LC-MS (Method 2): $R_t$=1.02 min
MS (ESpos): m/z=519 (M−TFA+H)$^+$
$^1$H-NMR (400 MHz, DMSO-d$_6$): δ=2.41 (s, 3H), 2.53 (br. s., 3H), 3.27-3.37 (m, 1H), 3.55-3.62 (m, 4H), 4.59-4.77 (m, 1H), 5.17-5.35 (m, 1H), 5.39 (s, 2H), 7.21-7.30 (m, 2H), 7.32-7.49 (m, 1H), 7.57-7.67 (m, 1H), 8.42-8.65 (m, 2H).

Example 374A

Ethyl 8-[(2-fluoro-6-methoxybenzyl)oxy]-2,6-dimethylimidazo[1,2-a]pyridine-3-carboxylate

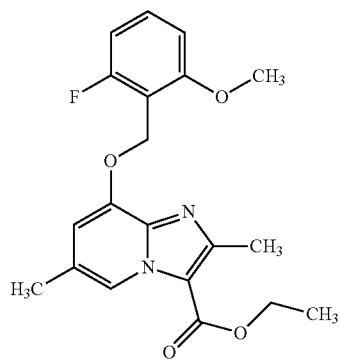 [SMILES: CCOC(=O)c1c(C)nc2c(OCc3c(F)cccc3OC)cc(C)cn12]

710 mg (3.03 mmol) of ethyl 8-hydroxy-2,6-dimethylimidazo[1,2-a]pyridine-3-carboxylate from Example 239A, 730 mg (3.33 mmol) of 2-(bromomethyl)-1-fluoro-3-methoxybenzene and 2.17 g (6.67 mmol) of caesium carbonate in 43 ml of DMF were heated in an oil bath pre-heated to 60° C. for 30 min. The reaction mixture was poured into water and stirred for 60 min, and the precipitated solid was filtered off with suction, washed with water and dried under high vacuum. This gave 859 mg of the target compound (72% of theory, purity about 94%).

LC-MS (Method 2): $R_t$=1.10 min
MS (ESpos): m/z=373 (M+H)$^+$

Example 375A

8-[(2-Fluoro-6-methoxybenzyl)oxy]-2,6-dimethyl-imidazo[1,2-a]pyridine-3-carboxylic acid

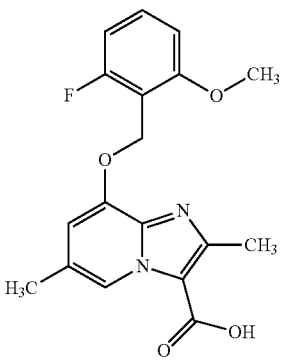

859 mg (2.17 mmol, 94% pure) of ethyl 8-[(2-fluoro-6-methoxybenzyl)oxy]-2,6-dimethylimidazo[1,2-a]pyridine-3-carboxylate from Example 374A were dissolved in 46.8 ml of THF/methanol (5/1), 10.8 ml (10.8 mmol) of 1 N aqueous lithium hydroxide solution were added and the mixture was stirred at RT overnight. The reaction solution was solidified with 1 N aqueous hydrochloric acid, and the organic solvent was distilled off. The precipitate formed was filtered off, washed with water and dried under high vacuum. This gave 785 mg of the target compound (98% of theory, purity about 94%).

LC-MS (Method 2): $R_t$=0.77 min
MS (ESpos): m/z=345 (M+H)$^+$

Example 376A ent-Benzyl {1-[({8-[(2,6-difluorobenzyl)oxy]imidazo[1,2-a]pyridin-3-yl}carbonyl)amino]-2-methylpentan-2-yl}carbamate trifluoroacetate

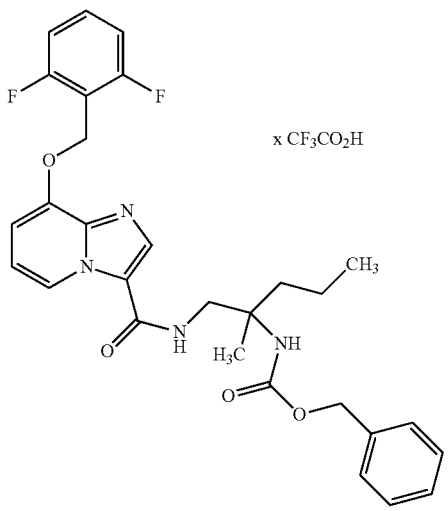 [SMILES: CCCC(C)(CNC(=O)c1cnc2c(OCc3c(F)cccc3F)cccn12)NC(=O)OCc1ccccc1]

54 mg (0.22 mmol) of ent-benzyl (1-amino-2-methylpentan-2-yl)carbamate from Example 289A were added to 60 mg (0.20 mmol) of 8-[(2,6-difluorobenzyl)oxy]imidazo[1,2-a]pyridine-3-carboxylic acid from Example 28A, 70 mg (0.22 mmol) of TBTU and 0.11 ml (0.99 mmol) of 4-methylmorpholine in 0.66 ml of DMF, and the mixture was stirred at RT for 1 h. The reaction solution was diluted with water/TFA and purified by preparative HPLC (RP18 column, mobile phase: acetonitrile/water gradient with addition of 0.1% TFA). The product fractions were concentrated and dried. This gave 117 mg of the target compound (91% of theory).

LC-MS (Method 2): $R_t$=1.20 min
MS (ESpos): m/z=537 (M+H)$^+$

Example 377A

Ethyl 8-[(2,6-difluoro-3-methoxybenzyl)oxy]-2,6-dimethylimidazo[1,2-a]pyridine-3-carboxylate

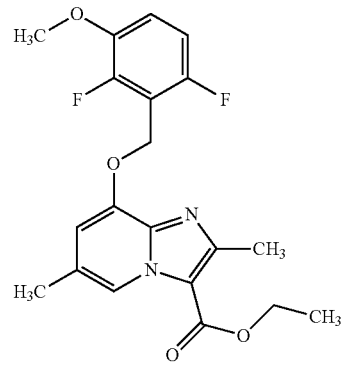 [SMILES: CCOC(=O)c1c(C)nc2c(OCc3c(F)ccc(OC)c3F)cc(C)cn12]

1.35 g (5.75 mmol) of ethyl 8-hydroxy-2,6-dimethylimidazo[1,2-a]pyridine-3-carboxylate from Example 239A and 4.12 g (12.66 mmol) of caesium carbonate were initially charged in 82 ml in DMF. The mixture was heated to 60° C., 1.50 g (6.33 mmol) of 2-(bromomethyl)-1,3-difluoro-4-methoxybenzene were then added and the mixture was stirred at 60° C. for 20 min. The reaction mixture was poured into about 500 ml of water and stirred for 30 min. The solid formed was filtered off with suction, washed with water and dried under high vacuum. This gave 2.11 g of the title compound (86% of theory, purity 92%).

LC-MS (Method 2): $R_t$=1.09 min
MS (ESpos): m/z=391 (M+H)$^+$
$^1$H-NMR (400 MHz, DMSO-$d_6$): δ [ppm]=1.35 (t, 3H), 2.37 (s, 3H), 3.87 (s, 3H), 4.29-4.38 (m, 2H), 5.30 (s, 2H), 7.09 (s, 1H), 7.12-7.22 (m, 1H), 7.27-7.37 (m, 1H), 8.71 (s, 1H), [further signal under solvent peak].

Example 378A

8-[(2,6-Difluoro-3-methoxybenzyl)oxy]-2,6-dimethylimidazo[1,2-a]pyridine-3-carboxylic acid

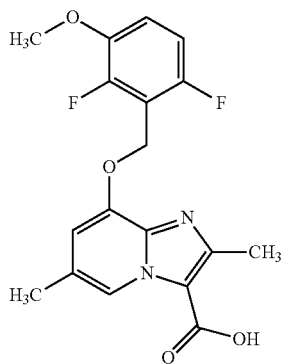

2.00 g (4.69 mmol) of ethyl 8-[(2,6-difluoro-3-methoxybenzyl)oxy]-2,6-dimethylimidazo[1,2-a]pyridine-3-carboxylate from Example 377A were suspended in 50 ml of dioxane, 11.73 ml (23.46 mmol) of 2 N aqueous sodium hydroxide solution were added and the mixture was stirred at 90° C. for 5 h. The reaction solution was acidified with 1 N aqueous hydrochloric acid, and the aqueous phase was extracted three times with ethyl acetate. The organic phase was dried over sodium sulphate, filtered and concentrated using a rotary evaporator. This gave 790 mg of the title compound. The aqueous phase was once more stirred with ethyl acetate for 1.5 h, and the phases were separated. The organic phase was dried over sodium sulphate, filtered and concentrated using a rotary evaporator. This gave 70 mg of the title compound. The aqueous phase was once more stirred with dichloromethane for 2 h, and the phases were separated. The organic phase was dried over sodium sulphate, filtered and concentrated under reduced pressure. This gave 60 mg of the title compound. The aqueous phase was concentrated under reduced pressure and the residue was purified by preparative HPLC (RP18 column, mobile phase: acetonitrile/water gradient with addition of 0.1% TFA). This gave 300 mg of the title compound as trifluoroacetate salt. In total, 920 mg of the title compound (52% of theory) were obtained (some as trifluoroacetate salt).

LC-MS (Method 2): $R_t$=0.69 min
MS (ESpos): m/z=363 (M+H)$^+$
$^1$H-NMR (400 MHz, DMSO-d$_6$): δ [ppm]=2.36 (s, 3H), 3.87 (s, 3H), 5.29 (s, 2H), 7.06 (s, 1H), 7.12-7.23 (m, 1H), 7.28-7.38 (m, 1H), 8.75 (s, 1H), 12.09-13.12 (br. s, 1H), [further signal under solvent peak].

Example 379A

3-Cyclopropyl-2,6-difluorobenzaldehyde

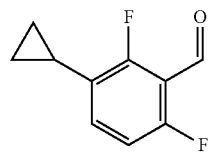 [SMILES: O=Cc1c(F)ccc(C2CC2)c1F]

3.50 g (15.84 mmol) of 3-bromo-2,6-difluorobenzaldehyde were dissolved in 87.5 ml of toluene. A solution of 3.36 g (31.67 mmol) of sodium carbonate in 1.5 ml of water was added, and the mixture was stirred at RT for 10 min. 2.04 g (23.75 mmol) of cyclopropylboronic acid and 366 mg (0.32 mmol) of tetrakis(triphenylphosphine)palladium(0) were then added, and the mixture was stirred under reflux overnight. Another 0.68 g (7.92 mmol) of cyclopropylboronic acid, 0.34 g (3.17 mmol) of sodium carbonate and 183 mg (0.16 mmol) of tetrakis(triphenylphosphine)palladium(0) were added, and the mixture was once more stirred under reflux overnight. The reaction mixture was diluted and extracted with ethyl acetate. The aqueous phase was washed twice with ethyl acetate. The combined organic phases were dried over sodium sulphate, filtered and concentrated under reduced pressure at a bath temperature of 35° C. This gave 3.50 g of the title compound (92% of theory, purity 76%).

LC-MS (Method 13): $R_t$=2.11 min
MS (ESpos): m/z=183 (M+H)$^+$

Example 380A (3-Cyclopropyl-2,6-difluorophenyl)methanol

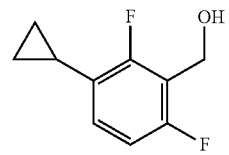 [SMILES: OCc1c(F)ccc(C2CC2)c1F]

Under argon and at 0° C., 221 mg (5.84 mmol) of sodium borohydride were initially charged in 47 ml of tetrahydrofuran. A solution of 3.5 g (14.60 mmol) of 3-cyclopropyl-2,6-difluorobenzaldehyde from Example 379A in 189 ml of tetrahydrofuran was added. 14.8 ml of methanol were then added dropwise at 0° C., and the mixture was stirred at room temperature for 2 h. The reaction solution was added to about 88 ml of ice-water and adjusted to about pH=1 using 2 N aqueous sulphuric acid, and the mixture was extracted three times with dichloromethane. The combined organic phases were dried over sodium sulphate, filtered and concentrated to dryness on a rotary evaporator at a bath temperature of 30° C. The residue was taken up in a little dichloromethane/methanol and purified by silica gel chromatography (mobile phase: cyclohexane/ethyl acetate gradient=10/1 to cyclohexane/ethyl acetate 5/1). The product fractions were combined and concentrated on a rotary evaporator at a bath temperature of 30° C. This gave 2.46 g of the title compound (86% of theory, purity 94%).

LC-MS (Method 13): $R_t$=1.90 min
MS (ESpos): m/z=167 (M−H$_2$O+H)$^+$

Example 381A

Ethyl 8-[(3-cyclopropyl-2,6-difluorobenzyl)oxy]-2,6-dimethylimidazo[1,2-a]pyridine-3-carboxylate trifluoroacetate

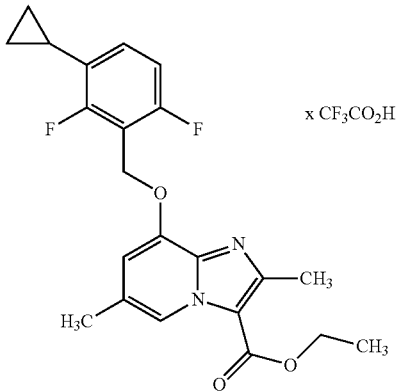 [SMILES: CCOC(=O)c1c(C)nc2c(OCc3c(F)ccc(C4CC4)c3F)cc(C)cn12]

2.67 g (11.41 mmol) of ethyl 8-hydroxy-2,6-dimethylimidazo[1,2-a]pyridine-3-carboxylate from Example 239A were dissolved in 104 ml of THF. 2.46 g (12.55 mmol) of (3-cyclopropyl-2,6-difluorophenyl)methanol from Example 380A and 6.29 g (23.97 mmol) of triphenylphosphine were added. After addition of 4.75 ml (23.97 mmol) of diisopropyl azodicarboxylate (DIAD) the reaction mixture was stirred at RT overnight. The mixture was concentrated and purified by silica gel chromatography (mobile phase: cyclohexane/ethyl acetate gradient=10/1 to 5/1). The product fractions were concentrated and purified again by preparative HPLC (RP18 column, mobile phase: acetonitrile/water gradient with addition of 0.1% TFA). This gave 1.1 g of the title compound (19% of theory).

LC-MS (Method 2): $R_t$=1.23 min
MS (ESpos): m/z=401 (M−TFA+H)$^+$
$^1$H-NMR (400 MHz, DMSO-d$_6$): δ [ppm]=0.70-0.78 (m, 2H), 0.95-1.03 (m, 2H), 1.36 (t, 3H), 2.00-2.13 (m, 1H), 2.40 (s, 3H), 4.33-4.40 (m, 2H), 5.32 (s, 2H), 7.08-7.28 (m, 3H), 8.75 (s, 1H), [further signal under solvent peak].

Example 382A

8-[(3-Cyclopropyl-2,6-difluorobenzyl)oxy]-2,6-dimethylimidazo[1,2-a]pyridine-3-carboxylic acid trifluoroacetate

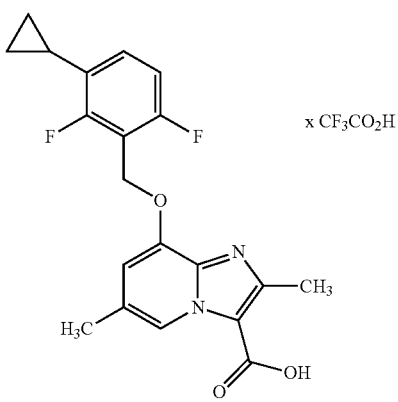 [SMILES: Cc1cc(OCc2c(F)ccc(C3CC3)c2F)c2nc(C)c(C(=O)O)n2c1]

1.1 g (2.14 mmol) of ethyl-8-[(3-cyclopropyl-2,6-difluorobenzyl)oxy]-2,6-dimethylimidazo[1,2-a]pyridine-3-carboxylate trifluoroacetate from Example 381A were suspended in 46 ml of dioxane, 6.4 ml (12.8 mmol) of 2 N aqueous sodium hydroxide solution were added and the mixture was stirred at 90° C. overnight. The mixture was concentrated, and TFA/water/acetonitrile was added to the residue. The solid formed was filtered off and washed with a little water. The product-containing filtrate was concentrated slightly and purified by preparative HPLC (RP18 column: mobile phase: acetonitrile/water gradient with addition of 0.1% TFA). After being combined with the solid that had been filtered off, the appropriate product-containing fractions were concentrated. This gave 950 mg of the title compound (91% of theory).

LC-MS (Method 2): $R_t$=0.87 min
MS (ESpos): m/z=373 (M−TFA+H)$^+$

Example 383A ent-Benzyl {1-[({8-[(3-cyclopropyl-2,6-difluorobenzyl)oxy]-2,6-dimethylimidazo[1,2-a]pyridin-3-yl}carbonyl)amino]-2-methylpentan-2-yl}carbamate trifluoroacetate

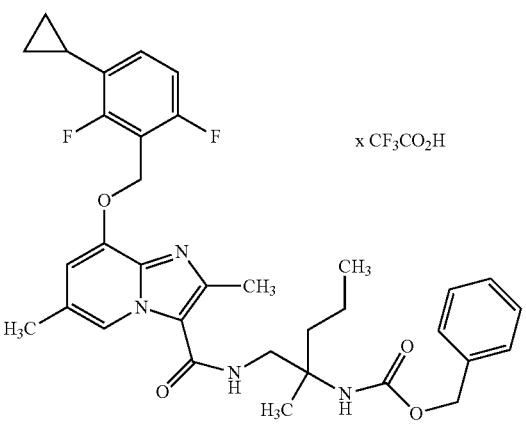 [SMILES: CCCC(C)(CNC(=O)c1c(C)nc2c(OCc3c(F)ccc(C4CC4)c3F)cc(C)cn12)NC(=O)OCc1ccccc1]

150 mg (0.31 mmol) of 8-[(3-cyclopropyl-2,6-difluorobenzyl)oxy]-2,6-dimethylimidazo[1,2-a]pyridine-3-carboxylic acid trifluoroacetate from Example 382A, 129 mg (0.34 mmol) of HATU and 0.22 ml (1.23 mmol) of N,N-diisopropylethylamine were initially charged in 2 ml of DMF, the mixture was stirred for 20 min, 89 mg (0.36 mmol) of ent-benzyl (1-amino-2-methylpentan-2-yl)carbamate (enantiomer B) from Example 289A were then added at RT and the mixture was stirred at RT for 4.5 h. A little water was added to the reaction solution, and the solid formed was filtered off. The solid was dissolved in TFA/water/acetonitrile and then purified by preparative HPLC (RP18 column, mobile phase: acetonitrile/water gradient with addition of 0.1% TFA). This gave 159 mg of the title compound (69% of theory).

LC-MS (Method 2): $R_t$=1.22 min
MS (ESpos): m/z=605 (M−TFA+H)$^+$

The examples shown in Table 15A were prepared analogously to Example 383A by reacting the appropriate carboxylic acid with the appropriate amines [ent-benzyl (1-amino-2-methylpentan-2-yl)carbamate (enantiomer B) from Example 289A; ent-benzyl (1-amino-2-methylbutan-2-yl)carbamate (enantiomer A) from Example 274A; ent-benzyl (1-amino-3-fluoro-2-methylpropan-2-yl)carbamate (enantiomer B) from Example 301A] using the reaction conditions described in the representative procedure 2.

TABLE 15A

| Example | IUPAC Name/Structure (yield) | Analytical data |
|---|---|---|
| 384A | ent-benzyl {1-[({8-[(2,6-difluoro-3-methoxybenzyl)oxy]-2,6-dimethylimidazo[1,2-a]pyridin-3-yl}carbonyl)amino]-2-methylbutan-2-yl}carbamate trifluoroacetate<br><br>(42% of theory) | LC-MS (Method 2): $R_t$ = 1.08 min<br>MS (ESpos): m/z = 581 (M − TFA + H)$^+$ |
| 385A | ent-benzyl {1-[({8-[(2,6-difluoro-3-methoxybenzyl)oxy]-2,6-dimethylimidazo[1,2-a]pyridin-3-yl}carbonyl)amino]-3-fluoro-2-methylpropan-2-yl}carbamate trifluoroacetate<br><br>(42% of theory, purity 94%) | LC-MS (Method 2): $R_t$ = 1.04 min<br>MS (ESpos): m/z = 585 (M − TFA + H)$^+$ |

TABLE 15A-continued

| Example | IUPAC Name/Structure (yield) | Analytical data |
|---|---|---|
| 386A | ent-benzyl {1-[({8-[(2,6-difluoro-3-methoxybenzyl)oxy]-2,6-dimethylimidazo[1,2-a]pyridin-3-yl}carbonyl)amino]-2-methylpentan-2-yl}carbamate trifluoroacetate<br>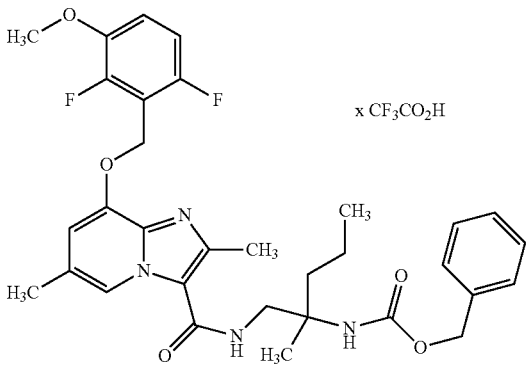<br>(69% of theory) | LC-MS (Method 2): $R_t$ = 1.11 min<br>MS (ESpos): m/z = 595 (M − TFA + H)$^+$ |
| 387A | ent-benzyl {1-[({8-[(3-cyclopropyl-2,6-difluorobenzyl)oxy]-2,6-dimethylimidazo[1,2-a]pyridin-3-yl}carbonyl)amino]-3-fluoro-2-methylpropan-2-yl}carbamate trifluoroacetate<br>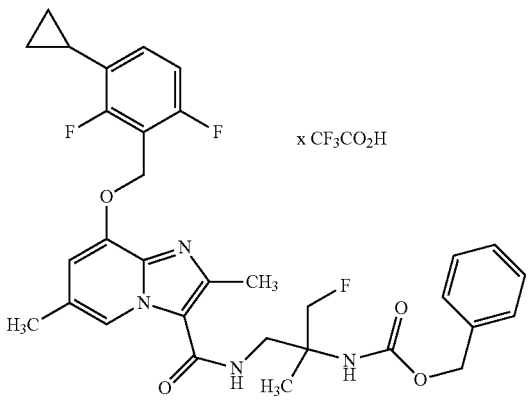<br>(64% of theory) | LC-MS (Method 2): $R_t$ = 1.14 min<br>MS (ESpos): m/z = 595 (M − TFA + H)$^+$ |

TABLE 15A-continued

| Example | IUPAC Name/Structure (yield) | Analytical data |
|---|---|---|
| 388A | ent-benzyl {1-[({8-[(3-cyclopropyl-2,6-difluorobenzyl]oxy]-2,6-dimethylimidazo[1,2-a]pyridin-3-yl}carbonyl)amino]-2-methylbutan-2-yl}carbamate trifluoroacetate 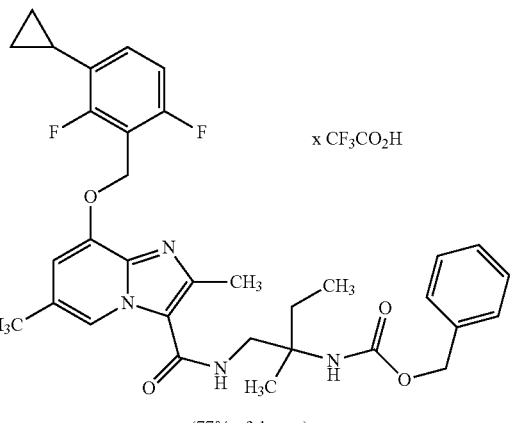 (77% of theory) | LC-MS (Method 2): $R_t$ = 1.17 min<br>MS (ESpos): m/z = 591 (M − TFA + H)$^+$ |

Example 389A rac-tert-butyl (2-cyanopentan-2-yl)carbamate

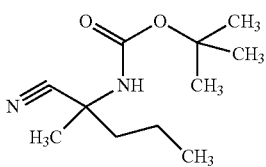

64.2 g (294.2 mmol) of di-tert-butyl dicarbonate were initially charged in a reaction flask, and 30.0 g (267.4 mmol) of rac-2-amino-2-methylpentanonitrile (described in: Deng, S L. et al., Synthesis 2001, 2445-2449; Freifelder, M. et al., J. Am. Chem. Soc. 1960, 696-698) was added very slowly such that the internal temperature did not exceed 30° C. The mixture was stirred at RT overnight. Dichloromethane was then added, and the mixture was washed twice with 1 N aqueous sodium hydroxide solution. The organic phase was dried over sodium sulphate, filtered and concentrated at a bath temperature of 30° C. This gave 76.33 g (quantitative yield; tert-butanol can be detected in the $^1$H-NMR) of the target compound.

LC-MS (Method 15): $R_t$=2.39 min
MS (ESpos): m/z=213 (M+H)$^+$ $^1$H-NMR (400 MHz, DMSO-d$_6$): δ=0.90 (t, 3H), 1.30-1.44 (m, 11H), 1.47 (s, 3H), 1.65-1.86 (m, 2H), 7.48 (br. s, 1H).

Example 390A rac-tert-butyl (1-amino-2-methylpentan-2-yl)carbamate

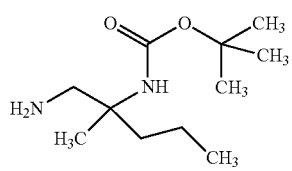

13.50 g (47.13 mmol; some tert-butanol present) of rac-tert-butyl (2-cyanopentan-2-yl)carbamate from Example 389A were dissolved in 137 ml of 7 N ammonia solution in methanol, and 14.6 g of Raney nickel (50% strength aqueous suspension) were added under argon. The reaction mixture was hydrogenated in an autoclave at 20-30 bar overnight. The reaction mixture was filtered off through Celite, the filter cake was rinsed with methanol and the filtrate was concentrated. This gave 18.50 g of the target compound which was used without further purification for the next step.

LC-MS (Method 15): $R_t$=1.96 min
MS (ESpos): m/z=217 (M+H)$^+$

Example 391A rac-3-(3,4-difluorophenoxy)-2-methylpropane-1,2-diamine

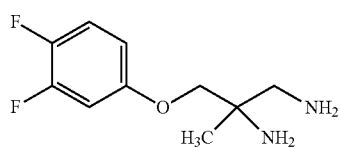

300 mg (1.41 mmol) of rac-2-amino-3-(3,4-difluorophenoxy)-2-methylpropanonitrile were initially charged in 14.4 ml of abs. THF, and 0.92 ml (0.92 mmol) of a 1 N lithium aluminium hydride solution in diethyl ether was added under argon and at 0° C. The reaction solution was stirred at 0° C. for 30 min and then slowly allowed to warm to room temperature and stirred overnight. 140 µl of water, 140 µl of 2 N aqueous sodium hydroxide solution and 280 µl of water were added carefully to the reaction mixture, the precipitate was filtered off and washed with THF and methanol, the filtrate was concentrated and the residue was purified by silica gel chromatography (mobile phase: dichloromethane/ 2N ammonia in methanol=20/1). This gave 87 mg of the target compound (24% of theory; purity about 84%).

LC-MS (Method 15): $R_t$=1.73 min
MS (ESpos): m/z=217 (M+H)$^+$

Example 392A

Ethyl 8-(benzyloxy)-2-methyl-6-vinylimidazo[1,2-a] pyridine-3-carboxylate

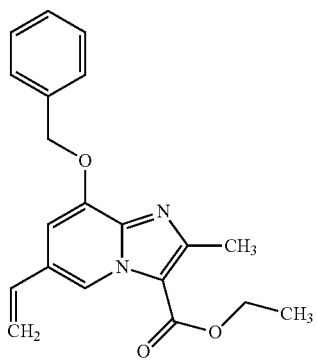 [SMILES: C=Cc1cc(OCc2ccccc2)c2nc(C)c(C(=O)OCC)n2c1]

6.32 g (16.23 mmol) of ethyl 8-(benzyloxy)-6-bromo-2-methylimidazo[1,2-a]pyridine-3-carboxylate from Example 237A, 6.52 g (48.69 mmol) of potassium vinyltrifluoroborate, 8.21 g (81.15 mmol) of triethylamine and 2.68 g (3.28 mmol) of 1,1'-Bis(diphenyl-phosphino)ferrocenepalladium (II) chloride-dichloromethane complex were initially charged in 120 ml of 2-propanol and stirred at 90° C. for 1 hour. Ethyl acetate and water were added to the reaction mixture, the mixture was filtered through Celite and the filter cake was washed with ethyl acetate. The organic phase was washed twice with water and once with saturated aqueous sodium chloride solution. The organic phase was dried over sodium sulphate, filtered, concentrated and dried under high vacuum. The isolated crude product was directly reacted further, without further purification.

LC-MS (Method 2): $R_t$=1.17 min
MS (ESpos): m/z=337 (M+H)$^+$

Example 393A

Ethyl 8-(benzyloxy)-6-formyl-2-methylimidazo[1,2-a]pyridine-3-carboxylate

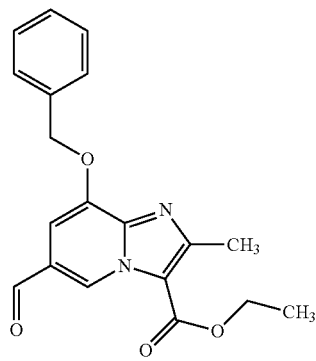 [SMILES: CCOC(=O)c1c(C)nc2c(OCc3ccccc3)cc(C=O)cn12]

The crude product ethyl 8-(benzyloxy)-2-methyl-6-vinylimidazo[1,2-a]pyridine-3-carboxylate from Example 392A was initially charged in 200 ml of tetrahydrofuran/ water (1:1), and 10.42 g (1.64 mmol) of osmium(VIII) oxide and 10.52 g (49.18 mmol) of sodium periodate were added. The reaction mixture was stirred at room temperature for 1 hour. Ethyl acetate was then added, and the mixture was washed three times with water and once with saturated aqueous sodium chloride solution. The organic phase was dried over sodium sulphate, filtered and concentrated. The residue was purified using silica gel (mobile phase: cyclohexane/ethyl acetate gradient; 80% cyclohexane to 10% cyclohexane). This gave 4.05 g of the title compound (74% of theory, over two steps).

LC-MS (Method 2): $R_t$=1.11 min
MS (ESpos): m/z=339 (M+H)$^+$
$^1$H-NMR (400 MHz, DMSO-$d_6$): δ [ppm]=1.39 (t, 3H), 2.63 (s, 3H), 4.37-4.44 (m, 2H), 5.38 (s, 2H), 7.28 (d, 1H), 7.35-7.48 (m, 3H), 7.49-7.55 (m, 2H), 9.51 (s, 1H), 10.03 (s, 1H).

Example 394A

Ethyl 8-(benzyloxy)-6-(hydroxymethyl)-2-methyl-imidazo[1,2-a]pyridine-3-carboxylate

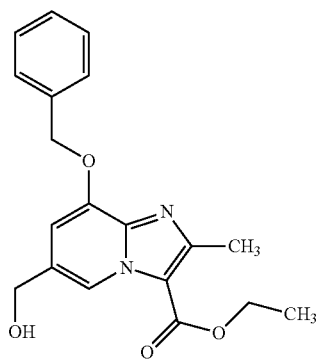 [SMILES: CCOC(=O)c1c(C)nc2c(OCc3ccccc3)cc(CO)cn12]

Under argon, 1.65 g (4.88 mmol) of ethyl 8-(benzyloxy)-6-formyl-2-methylimidazo[1,2-a]pyridine-3-carboxylate from Example 393A were suspended in 66 ml of abs. ethanol. 92 mg (2.44 mmol) of sodium borohydride were added to the reaction mixture, and the mixture was stirred at room temperature for 15 min. The reaction solution was freed from ethanol, and water was added to the residue. The aqueous phase was extracted three times with ethyl acetate. Saturated aqueous sodium chloride solution was added to the combined organic phases, the mixture was filtered off through Celite and the filter cake was washed with ethyl acetate. The two phases were separated from one another. The organic phase was dried over sodium sulphate, filtered, concentrated and dried under high vacuum. This gave 1.49 g of the title compound (90% of theory).

LC-MS (Method 2): $R_t$=0.87 min
MS (ESpos): m/z=341 (M+H)$^+$
$^1$H-NMR (400 MHz, DMSO-d$_6$): δ [ppm]=1.36 (t, 3H), 4.32-4.39 (m, 2H), 4.55 (d, 2H), 5.29 (s, 2H), 5.45 (t, 1H), 7.04 (s, 1H), 7.32-7.48 (m, 3H), 7.48-7.57 (m, 2H), 8.83-5.86 (m, 1H), [further signal hidden under solvent peak].

Example 395A

Ethyl 8-hydroxy-6-(hydroxymethyl)-2-methylimidazo[1,2-a]pyridine-3-carboxylate

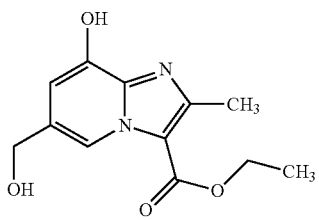 [SMILES: CCOC(=O)c1c(C)nc2c(O)cc(CO)cn12]

1.31 g (3.85 mmol) of ethyl 8-(benzyloxy)-6-(hydroxymethyl)-2-methylimidazo[1,2-a]pyridine-3-carboxylate from Example 394A were initially charged in 99 ml of ethanol. Under argon, 820 mg (0.77 mmol) of 10% palladium on activated carbon were added to the reaction solution, and the mixture was hydrogenated under standard pressure for 3 hours. The reaction mixture was filtered off through a Millipore filter, the filter cake was washed with ethanol and the filtrate was concentrated. This gave 845 mg of the title compound (82% of theory, purity 94%).

LC-MS (Method 2): $R_t$=0.51 min
MS (ESpos): m/z=251 (M+H)$^+$

Example 396A

Ethyl 8-[(2,6-difluorobenzyl)oxy]-6-(hydroxymethyl)-2-methylimidazo[1,2-a]pyridine-3-carboxylate

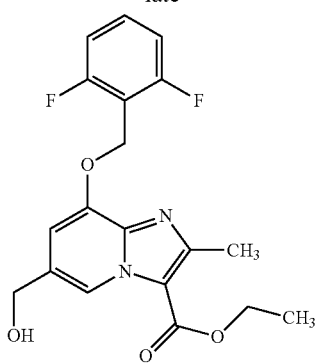

845 mg (3.38 mmol) of ethyl 8-hydroxy-6-(hydroxymethyl)-2-methylimidazo[1,2-a]pyridine-3-carboxylate from Example 395A were dissolved in 48.4 ml of abs. DMF, 2.42 g (7.43 mmol) of caesium carbonate and 699 mg (3.38 mmol) of 2,6-difluorobenzyl bromide were added and the mixture was stirred at room temperature for 1 hour. The reaction mixture was poured into 500 ml of water and stirred at room temperature for 30 min. The solid formed was filtered off and washed with water. This gave 1.14 g of the title compound (87% of theory).

LC-MS (Method 2): $R_t$=0.87 min
MS (ESpos): m/z=377 (M+H)$^+$
$^1$H-NMR (400 MHz, DMSO-d$_6$): δ [ppm]=1.36 (t, 3H), 4.32-4.40 (m, 2H), 4.58 (d, 2H), 5.31 (s, 2H), 5.47 (t, 1H), 7.14 (s, 1H), 7.18-7.31 (m, 2H), 7.45-7.71 (m, 1H), 8.86-8.89 (m, 1H), [further signal hidden under solvent peak].

Example 397A

8-[(2,6-difluorobenzyl)oxy]-6-(hydroxymethyl)-2-methylimidazo[1,2-a]pyridine-3-carboxylic acid trifluoroacetate

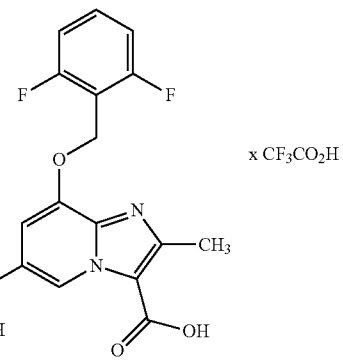

1.08 g (2.78 mmol) of ethyl 8-[(2,6-difluorobenzyl)oxy]-6-(hydroxymethyl)-2-methylimidazo[1,2-a]pyridine-3-carboxylate from Example 396A were suspended in 60.3 ml of dioxane, and 8.35 ml (16.7 mmol) of 2 N aqueous sodium hydroxide solution were added. The reaction solution was stirred at 90° C. overnight. The reaction solution was acidified with 1 N aqueous hydrochloric acid, and the solvent was then evaporated. The residue was stirred with water, and the solid was filtered off. The aqueous phase was concentrated and taken up in acetonitrile/water/TFA. The product-containing solid formed was filtered off. This gave 1.19 g of the title compound. The filtrate was purified by preparative HPLC (RP18 column; mobile phase: acetonitrile/water gradient with addition of 0.1% TFA). This gave another 0.08 g of the title compound. In total, 1.27 g of the title compound (96% of theory) were obtained.

LC-MS (Method 2): $R_t$=0.58 min
MS (ESpos): m/z=349 (M−TFA+H)$^+$

Example 398A ent-benzyl {1-[({8-[(2,6-difluorobenzyl)oxy]-6-(hydroxymethyl)-2-methylimidazo[1,2-a]pyridin-3-yl}carbonyl)amino]-2-methylpentan-2-yl}carbamate

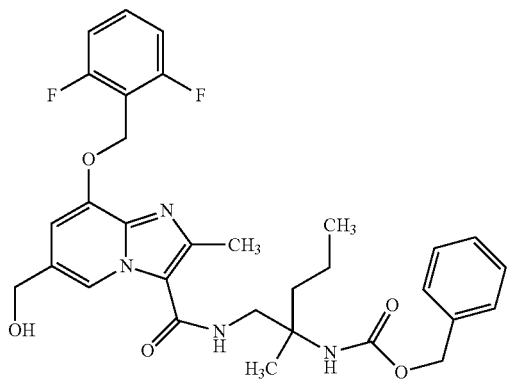 [SMILES: CCCC(C)(CNC(=O)c1c(C)nc2c(OCc3c(F)cccc3F)cc(CO)cn12)NC(=O)OCc1ccccc1]

180 mg (0.38 mmol) of 8-[(2,6-difluorobenzyl)oxy]-6-(hydroxymethyl)-2-methylimidazo[1,2-a]pyridine-3-carboxylic acid trifluoroacetate from Example 397A, 158 mg (0.42 mmol) of HATU and 0.26 ml (1.51 mmol) of N,N-diisopropylethylamine were initially charged in 3.2 ml of DMF, the mixture was stirred for 20 min, 109 mg (0.43 mmol) of ent-benzyl (1-amino-2-methylpentan-2-yl)carbamate (enantiomer B) from Example 289A were then added at room temperature and the mixture was stirred at room temperature for 1 h. The reaction solution was washed with water, and the solid was stirred at room temperature for 30 min, filtered off and washed with water. This gave 199 mg of the title compound (91% of theory).

LC-MS (Method 2): $R_t$=0.99 min
MS (ESpos): m/z=581 (M+H)$^+$

The exemplary compounds shown in Table 16A were prepared analogously to Example 398A by reacting 8-[(2,6-difluorobenzyl)oxy]-6-(hydroxymethyl)-2-methylimidazo[1,2-a]pyridine-3-carboxylic acid trifluoroacetate from Example 397A with the appropriate above-described amines 274A and 301A under the conditions described:

TABLE 16A

| Example | IUPAC Name/Structure (yield) | Analytical data |
|---|---|---|
| 399A | ent-benzyl {1-[({8-[(2,6-difluorobenzyl)oxy]-6-(hydroxymethyl)-2-methylimidazo[1,2-a]pyridin-3-yl}carbonyl)amino]-2-methylbutan-2-yl}carbamate<br><br>(89% of theory) | LC-MS (Method 2): $R_t$ = 0.94 min<br>MS (ESpos): m/z = 567 (M + H)$^+$ |

TABLE 16A-continued

| Example | IUPAC Name/Structure (yield) | Analytical data |
|---|---|---|
| 400A | ent-benzyl {1-[({8-[(2,6-difluorobenzyl)oxy]-6-(hydroxymethyl)-2-methylimidazo[1,2-a]pyridin-3-yl}carbonyl)amino]-3-fluoro-2-methylpropan-2-yl}carbamate | LC-MS (Method 2): $R_t$ = 0.91 min<br>MS (ESpos): m/z = 571 (M + H)$^+$ |

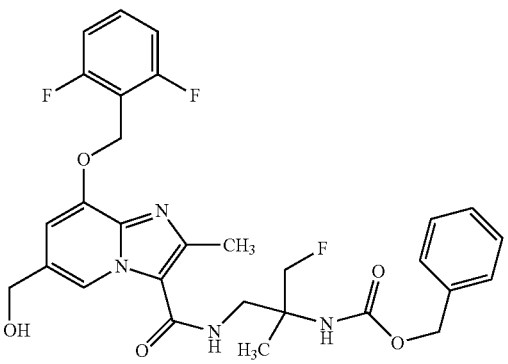

(75% of theory, purity 91%)

Example 401A ent-benzyl {1-[({8-[(2,6-difluorobenzyl)oxy]-6-(fluoromethyl)-2-methylimidazo[1,2-a]pyridin-3-yl}carbonyl)amino]-2-methylpentan-2-yl}carbamate trifluoroacetate

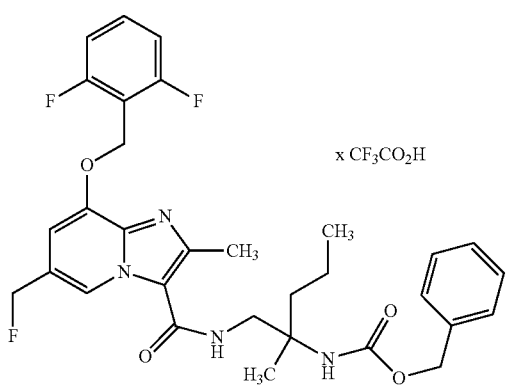 [SMILES: CCCC(C)(CNC(=O)c1c(C)nc2c(OCc3c(F)cccc3F)cc(CF)cn12)NC(=O)OCc1ccccc1]

198 mg (0.34 mmol) of ent-benzyl {1-[({8-[(2,6-difluorobenzyl)oxy]-6-(hydroxymethyl)-2-methylimidazo[1,2-a]pyridin-3-yl}carbonyl)amino]-2-methylpentan-2-yl}carbamate from Example 398A were initially charged in 3.4 ml of dichloromethane, 82.5 mg (0.51 mmol) of diethylaminosulphur trifluoride were added at −78° C., and the mixture was stirred at −78° C. for 90 min and then at room temperature for 30 min. During the reaction at −78° C., another 27.5 mg (0.17 mmol) of diethylaminosulphur trifluoride were added. The reaction solution was then diluted with dichloromethane and washed twice with saturated aqueous sodium bicarbonate solution and once with saturated aqueous sodium chloride solution. The combined aqueous phases were extracted twice with dichloromethane. The combined organic phases were dried over sodium sulphate, filtered and concentrated. The crude product was purified by preparative HPLC (RP18 column, mobile phase: acetonitrile/water gradient with addition of 0.1% TFA). This gave 191 mg of the title compound (70% of theory, purity 87%).

LC-MS (Method 2): $R_t$=1.19 min
MS (ESpos): m/z=583 (M−TFA+H)$^+$

The exemplary compounds shown in Table 17A were prepared analogously to Example 401A by reacting the above-described alcohols with diethylaminosulphur trifluoride under the conditions described:

TABLE 17A

| Example | IUPAC Name/Structure (yield) | Analytical data |
|---|---|---|
| 402A | ent-benzyl {1-[({8-[(2,6-difluorobenzyl)oxy]-6-(fluoromethyl)-2-methylimidazo[1,2-a]pyridin-3-yl}carbonyl)amino]-2-methylbutan-2-yl}carbamate trifluoroacetate<br>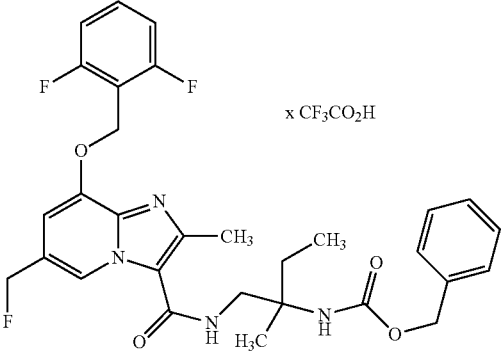<br>(52% of theory, purity 70%) | LC-MS (Method 2): $R_t$ = 1.13 min<br>MS (ESpos): m/z = 569 (M − TFA + H)$^+$ |
| 403A | ent-benzyl {1-[({8-[(2,6-difluorobenzyyl)oxy]-6-(fluoromethyl)-2-methylimidazo[1,2-a]pyridin-3-yl}carbonyl)amino]-3-fluoro-2-methylpropan-2-yl}carbamate trifluoroacetate<br>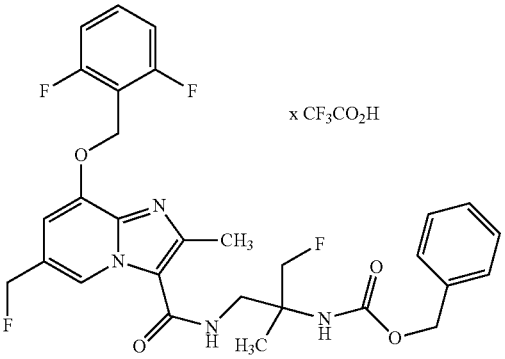<br>(44% of theory, purity 73%) | LC-MS (Method 2): $R_t$ = 1.12 min<br>MS (ESpos): m/z = 573 (M − TFA + H)$^+$ |

Example 404A rac-2-Amino-5,5,5-trifluoro-2-methylpentanonitrile

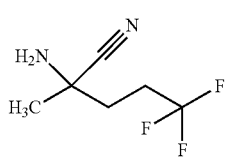

8.0 g (57.1 mmol) of 5,5,5-trifluoropentan-2-one [CAS Registry number: 1341078-97-4; commercially available, or the methyl ketone can be prepared by methods known from the literature and familiar to the person skilled in the art, for example a) in two steps from 4,4,4-trifluorobutanal according to Y. Bai et al. Angewandte Chemie 2012, 51, 4112-4116; K. Hiroi et al. Synlett 2001, 263-265; K. Mikami et al. 1982 Chemistry Letters, 1349-1352; or b) from 4,4,4-trifluorobutanoic acid according to A. A. Wube et al. Bioorganic and Medicinal Chemistry 2011, 19, 567-579; G. M. Rubottom et al. Journal of Organic Chemistry 1983, 48, 1550-1552; T. Chen et al. Journal of Organic Chemistry 1996, 61, 4716-4719. The product can be isolated by distillation or chromatography] were initially charged in 47.8 ml of 2 N ammonia in methanol, 3.69 g (75.4 mmol) of sodium cyanide and 4.03 g (75.4 mmol) of ammonium chloride were added at room temperature and the mixture was stirred under reflux for 4 hours. The reaction mixture was cooled, diethyl ether was added and the solid obtained was filtered off. The solvent was removed from the filtrate by distillation under atmospheric pressure. This gave 8.7 g of the title compound (92% of theory) as a residue which was used for the next step without further purification.

GC-MS (Method 14): $R_t$=1.90 min
MS (ESpos): m/z=151 (M−CH$_3$)$^+$

Example 405A rac-benzyl
(2-cyano-5,5,5-trifluoropentan-2-yl)carbamate

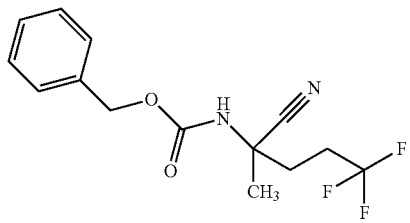 [SMILES: CC(C#N)(CCC(F)(F)F)NC(=O)OCc1ccccc1]

8.7 g (52.36 mmol) of rac-2-amino-5,5,5-trifluoro-2-methylpentanonitrile from Example 404A were initially charged in 128 ml of tetrahydrofuran/water=9/1, and 22.43 g (162.3 mmol) of potassium carbonate were added. At 0° C., 8.93 g (52.36 mmol) of benzyl chloroformate were slowly added dropwise. The mixture was then allowed to warm slowly to room temperature with stirring and stirred at room temperature overnight. The supernatant solvent was decanted and the residue was twice stirred with in each case 100 ml of tetrahydrofuran, with the supernatant solvent being decanted in each case. The combined organic phases were concentrated and the crude product was purified by silica gel chromatography (mobile phase: cyclohexane/ethyl acetate gradient 9/1 to 4/1). This gave 11.14 g of the title compound (68% of theory).

LC-MS (Method 2): $R_t$=1.01 min
MS (ESpos): m/z=301 (M+H)$^+$
$^1$H-NMR (400 MHz, DMSO-$d_6$): δ [ppm]=1.58 (s, 3H), 2.08-2.21 (m, 2H), 2.24-2.52 (m, 2H), 5.09 (s, 2H), 7.29-7.41 (m, 5H), 8.17 (br. s, 1H).

Example 406A ent-benzyl
(2-cyano-5,5,5-trifluoropentan-2-yl)carbamate
(Enantiomer A)

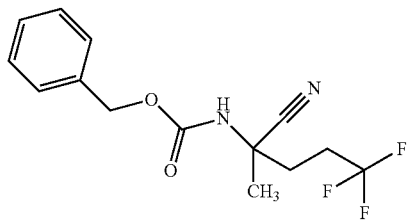 [SMILES: CC(C#N)(CCC(F)(F)F)NC(=O)OCc1ccccc1]

11.14 g of rac-benzyl (2-cyano-5,5,5-trifluoropentan-2-yl)carbamate from Example 405A were separated into the enantiomers by preparative separation on a chiral phase [column: Daicel Chiralpak AZ-H, 5 μm, SFC, 250×50 mm, mobile phase: 94% carbon dioxide, 6% methanol, flow rate: 200 ml/min, temperature: 38° C., pressure: 135 bar; detection: 210 nm].

Enantiomer A: 4.12 g (about 79% ee)
$R_t$=1.60 min [SFC, Daicel Chiralpak AZ-H, 250×4.6 mm, 5 μm, mobile phase: 90% carbon dioxide, 10% methanol, flow rate: 3 ml/min, temperature: 30° C., detection: 220 nm].
LC-MS (Method 2): $R_t$=1.01 min
MS (ESpos): m/z=301 (M+H)$^+$

Example 407A ent-benzyl
(2-cyano-5,5,5-trifluoropentan-2-yl)carbamate
(Enantiomer B)

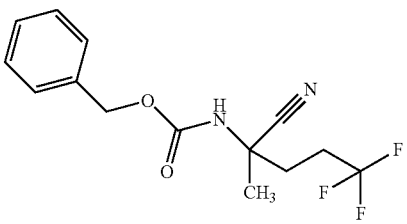 [SMILES: CC(C#N)(CCC(F)(F)F)NC(=O)OCc1ccccc1]

11.14 g of rac-benzyl (2-cyano-5,5,5-trifluoropentan-2-yl)carbamate from Example 405A were separated into the enantiomers by preparative separation on a chiral phase [column: Daicel Chiralpak AZ-H, 5 μm, SFC, 250×50 mm, mobile phase: 94% carbon dioxide, 6% methanol, flow rate: 200 ml/min, temperature: 38° C., pressure: 135 bar; detection: 210 nm].

Enantiomer B: 4.54 g (about 70% ee; purity about 89%)
$R_t$=1.91 min [SFC, Daicel Chiralpak AZ-H, 250×4.6 mm, 5 μm, mobile phase: 90% carbon dioxide, 10% methanol, flow rate: 3 ml/min, temperature: 30° C., detection: 220 nm].
LC-MS (Method 2): $R_t$=1.01 min
MS (ESpos): m/z=301 (M+H)$^+$

Example 408A ent-benzyl (1-amino-5,5,5-trifluoro-2-methylpentan-2-yl)carbamate (Enantiomer A)

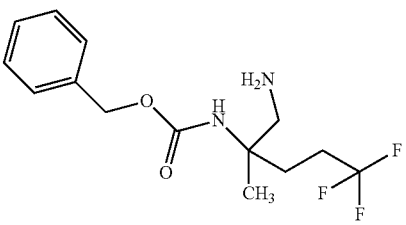 [SMILES: CC(CN)(CCC(F)(F)F)NC(=O)OCc1ccccc1]

4.12 g (13.17 mmol) of ent-benzyl (2-cyano-5,5,5-trifluoropentan-2-yl)carbamate (enantiomer A) from Example 406A were dissolved in 39 ml of 7 N ammonia solution in methanol, and 4 g of Raney nickel (50% strength aqueous suspension) were added under argon. The reaction mixture was hydrogenated in an autoclave at 20-30 bar overnight. Another 1 g of Raney nickel (50% strength aqueous suspension) was added, and the reaction mixture was hydrogenated in an autoclave at 20-30 bar for 5 h. The reaction mixture was filtered off through kieselguhr, the filter cake was rinsed with methanol and the filtrate was concentrated. This gave 3.35 g (56% of theory; purity about 67%) of the target compound which was used for the next step without further purification.

LC-MS (Method 7): $R_t$=1.68 min
MS (ESpos): m/z=305 (M+H)$^+$
$^1$H-NMR (400 MHz, DMSO-$d_6$): δ [ppm]=1.13 (s, 3H), 1.40 (br. s, 2H), 1.70-1.80 (m, 1H), 1.83-1.95 (m, 1H), 2.08-2.2 (m, 2H), 4.98 (s, 2H), 6.85 (br. s, 1H), 7.28-7.41 (m, 5H).

Example 409A ent-benzyl (1-amino-5,5,5-trifluoro-2-methylpentan-2-yl)carbamate (Enantiomer B)

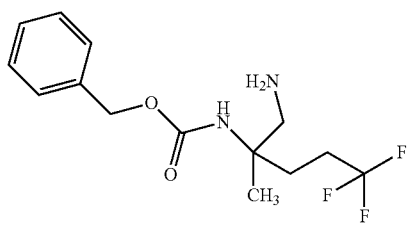 [SMILES: CC(CN)(CCC(F)(F)F)NC(=O)OCc1ccccc1]

4.54 g (13.45 mmol; purity about 89%) of ent-benzyl (2-cyano-5,5,5-trifluoropentan-2-yl)carbamate (enantiomer B) from Example 407A were dissolved in 39 ml of 7 N ammonia solution in methanol, and 5 g of Raney nickel (50% strength aqueous suspension) were added under argon. The reaction mixture was hydrogenated in an autoclave at 20-30 bar for 3 h. The reaction mixture was filtered off through kieselguhr, the filter cake was rinsed with methanol and the filtrate was concentrated. This gave 4.20 g (97% of theory; purity about 95%) of the target compound which was used for the next step without further purification.

LC-MS (Method 15): $R_t$=2.19 min
MS (ESpos): m/z=305 (M+H)$^+$
$^1$H-NMR (400 MHz, DMSO-d$_6$): δ [ppm]=1.13 (s, 3H), 1.40 (br. s, 2H), 1.69-1.80 (m, 1H), 1.83-1.96 (m, 1H), 2.07-2.22 (m, 2H), 4.98 (s, 2H), 6.85 (br. s, 1H), 7.27-7.40 (m, 5H).

Example 410A ent-benzyl {1-[({8-[(2,6-difluorobenzyl)oxy]-2,6-dimethylimidazo[1,2-a]pyridin-3-yl}carbonyl)amino]-5,5,5-trifluoro-2-methylpentan-2-yl}carbamate (Enantiomer A)

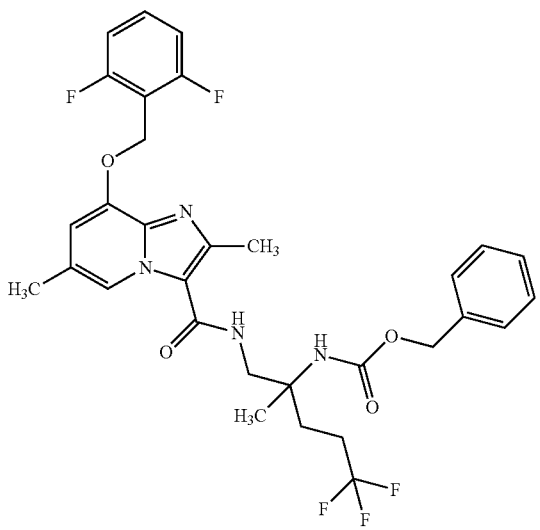 [SMILES: Cc1cc(OCc2c(F)cccc2F)c2nc(C)c(C(=O)NCC(C)(CCC(F)(F)F)NC(=O)OCc3ccccc3)n2c1]

500 mg (1.51 mmol) of 8-[(2,6-difluorobenzyl)oxy]-2,6-dimethylimidazo[1,2-a]pyridine-3-carboxylic acid from Example 21A, 629 mg (1.66 mmol) of HATU and 583 mg (4.51 mmol) of N,N-diisopropylethylamine were initially charged in 9.6 ml of DMF, and the mixture was stirred at RT for 20 min. 957 mg (2.11 mmol; purity about 67%) of ent-benzyl (1-amino-5,5,5-trifluoro-2-methylpentan-2-yl)carbamate (enantiomer A) from Example 408A were then added, and the mixture was stirred at RT overnight. About 70 ml of water were added to the reaction solution, and the mixture was stirred at room temperature for 45 min. The solid obtained was filtered off, washed thoroughly with water and dried under high vacuum. This gave 969 mg (99% of theory) of the target compound which was used for the next step without further purification.

LC-MS (Method 2): $R_t$=1.11 min
MS (ESpos): m/z=619 (M+H)$^+$

Example 411A ent-benzyl {1-[({8-[(2,6-difluorobenzyl)oxy]-2,6-dimethylimidazo[1,2-a]pyridin-3-yl}carbonyl)amino]-5,5,5-trifluoro-2-methylpentan-2-yl}carbamate (Enantiomer B)

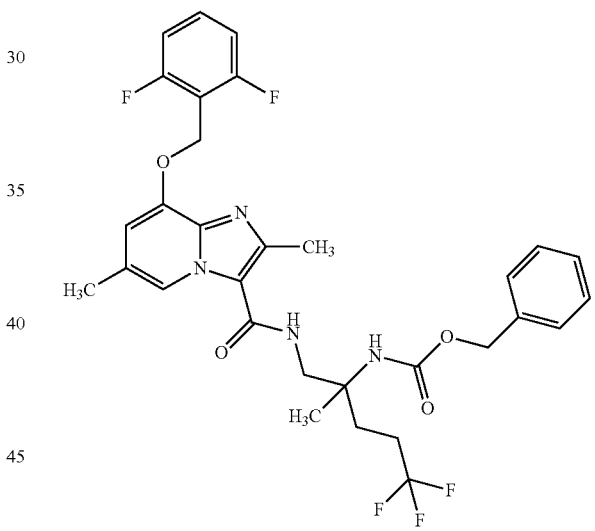

500 mg (1.51 mmol) of 8-[(2,6-difluorobenzyl)oxy]-2,6-dimethylimidazo[1,2-a]pyridine-3-carboxylic acid from Example 21A, 629 mg (1.66 mmol) of HATU and 583 mg (4.51 mmol) of N,N-diisopropylethylamine were initially charged in 9.6 ml of DMF, and the mixture was stirred at RT for 20 min. 675 mg (2.11 mmol; purity about 95%) of ent-benzyl (1-amino-5,5,5-trifluoro-2-methylpentan-2-yl)carbamate (enantiomer B) from Example 409A were then added, and the mixture was stirred at RT overnight. About 70 ml of water were added to the reaction solution, and the mixture was stirred at room temperature for 45 min. The solid obtained was filtered off, washed thoroughly with water and dried under high vacuum. This gave 917 mg (98% of theory) of the title compound which was used for the next step without further purification.

LC-MS (Method 2): $R_t$=1.14 min
MS (ESpos): m/z=619 (M+H)$^+$

395

Example 412A ent-benzyl {1-[({2,6-dimethyl-8-[(2,3,6-trifluorobenzyl)oxy]imidazo[1,2-a]pyridin-3-yl}carbonyl)amino]-5,5,5-trifluoro-2-methylpentan-2-yl}carbamate (Enantiomer A)

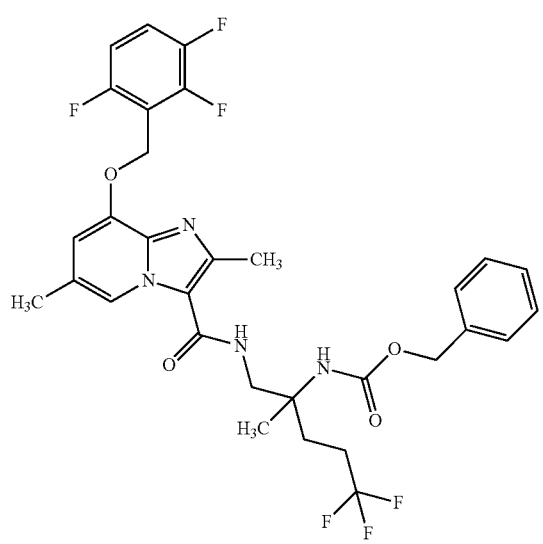 [SMILES: Cc1cc(OCc2c(F)ccc(F)c2F)c2nc(C)c(C(=O)NCC(C)(CCC(F)(F)F)NC(=O)OCc3ccccc3)n2c1]

300 mg (0.86 mmol) of 2,6-dimethyl-8-[(2,3,6-trifluorobenzyl)oxy]imidazo[1,2-a]pyridine-3-carboxylic acid from Example 265A, 358 mg (0.94 mmol) of HATU and 332 mg (2.57 mmol) of N,N-diisopropylethylamine were initially charged in 5.5 ml of DMF, and the mixture was stirred at RT for 20 min. 545 mg (1.20 mmol; purity about 67%) of ent-benzyl (1-amino-5,5,5-trifluoro-2-methylpentan-2-yl)carbamate (enantiomer A) from Example 408A were then added, and the mixture was stirred at RT for 2 h. About 50 ml of water were added to the reaction solution, and the mixture was stirred at room temperature for 45 min. The solid obtained was filtered off, washed thoroughly with water and dried under high vacuum. This gave 553 mg (88% of theory; purity 87%) of the title compound which was used for the next step without further purification.

LC-MS (Method 2): $R_t$=1.13 min
MS (ESpos): m/z=637 (M+H)$^+$

396

Example 413A ent-benzyl {1-[({2,6-dimethyl-8-[(2,3,6-trifluorobenzyl)oxy]imidazo[1,2-a]pyridin-3-yl}carbonyl)amino]-5,5,5-trifluoro-2-methylpentan-2-yl}carbamate (Enantiomer B)

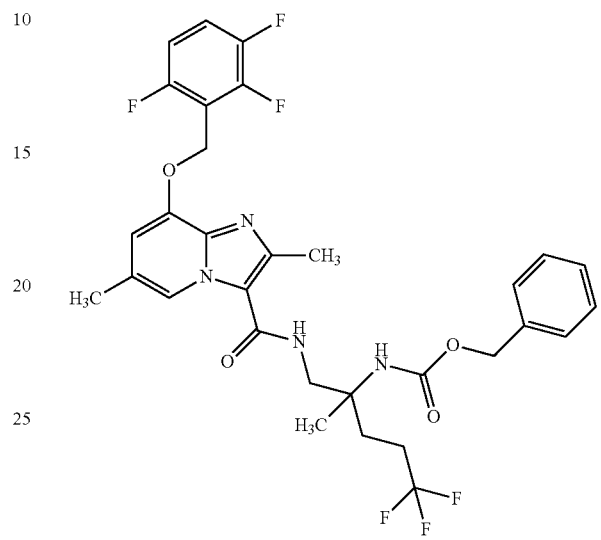

300 mg (0.86 mmol) of 2,6-dimethyl-8-[(2,3,6-trifluorobenzyl)oxy]imidazo[1,2-a]pyridine-3-carboxylic acid from Example 265A, 358 mg (0.94 mmol) of HATU and 332 mg (2.57 mmol) of N,N-diisopropylethylamine were initially charged in 5.5 ml of DMF, and the mixture was stirred at RT for 20 min. 384 mg (1.20 mmol; purity about 95%) of ent-benzyl (1-amino-5,5,5-trifluoro-2-methylpentan-2-yl)carbamate (enantiomer B) from Example 409A were then added, and the mixture was stirred at RT for 2 h. About 50 ml of water were added to the reaction solution, and the mixture was stirred at room temperature for 45 min. The solid obtained was filtered off, washed thoroughly with water and dried under high vacuum. This gave 540 mg (96% of theory) of the title compound which was used for the next step without further purification.

LC-MS (Method 2): $R_t$=1.16 min
MS (ESpos): m/z=637 (M+H)$^+$

Example 414A rac-tert-butyl {2-(3-acetamidophenyl)-2-[({8-[(2,6-difluorobenzyl)oxy]-2,6-dimethylimidazo[1,2-a]pyridin-3-yl}carbonyl)amino]ethyl}carbamate trifluoroacetate

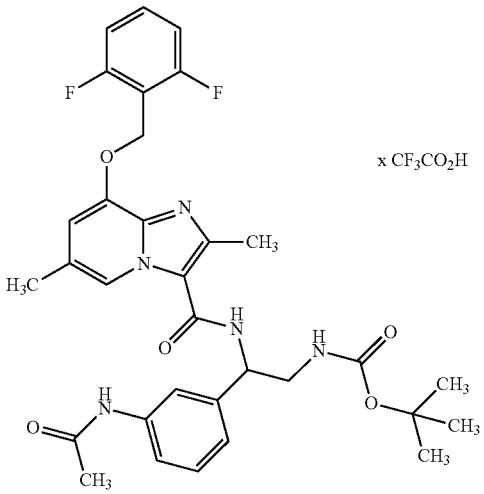 [SMILES: CC(=O)Nc1cccc(C(CNC(=O)OC(C)(C)C)NC(=O)c2c(C)nc3c(OCc4c(F)cccc4F)cc(C)cn23)c1]

x CF₃CO₂H 50 mg (0.15 mmol) of 8-[(2,6-difluorobenzyl)oxy]-2,6-dimethylimidazo[1,2-a]pyridine-3-carboxylic acid from Example 21A, 63 mg (0.17 mmol) of HATU and 58 mg (0.45 mmol) of N,N-diisopropylethylamine were initially charged in 0.5 ml of DMF, and the mixture was stirred at RT for 10 min. 51 mg (0.17 mmol) of tert-butyl [2-(3-acetamidophenyl)-2-aminoethyl]carbamate were then added, and the mixture was stirred at RT for 2 h. Acetonitrile, TFA and water were added to the reaction mixture, and the product was purified by preparative HPLC (RP-C18, mobile phase: acetonitrile/water gradient with addition of 0.1% TFA). This gave 100 mg (92% of theory) of the title compound.

LC-MS (Method 2): $R_t$=0.91 min

MS (ESpos): m/z=608 (M−TFA+H)⁺

The examples shown in Table 18A were prepared analogously to Example 414A by reacting 8-[(2,6-difluorobenzyl)oxy]-2,6-dimethylimidazo[1,2-a]pyridine-3-carboxylic acid from Example 21A with the appropriate amines and HATU under the reaction conditions described in the representative procedure 2.

TABLE 18A

| Example | IUPAC Name/Structure (yield) | Analytical data |
| --- | --- | --- |
| 415A | rac-ethyl 6-{2-[(tert-butoxycarbonyl)amino]-1-[({8-[(2,6-difluorobenzyl)oxy]-2,6-dimethylimidazo[1,2-a]pyridin-3-yl}carbonyl)amino]ethyl}pyridin-2-carboxylate trifluoroacetate<br><br>(35% of theory; purity 94%) | LC-MS (Method 2): $R_t$ = 1.02 min<br>MS (ESpos): m/z = 576 (M − TFA + H)⁺ |

TABLE 18A-continued

| Example | IUPAC Name/Structure (yield) | Analytical data |
|---------|------------------------------|-----------------|
| 416A | rac-tert-butyl {2-(4-cyanophenyl)-2-[({8-[(2,6-difluorobenzyl)oxy]-2,6-dimethylimidazo[1,2-a]pyridin-3-yl}carbonyl)amino]ethyl}carbamate trifluoroacetate 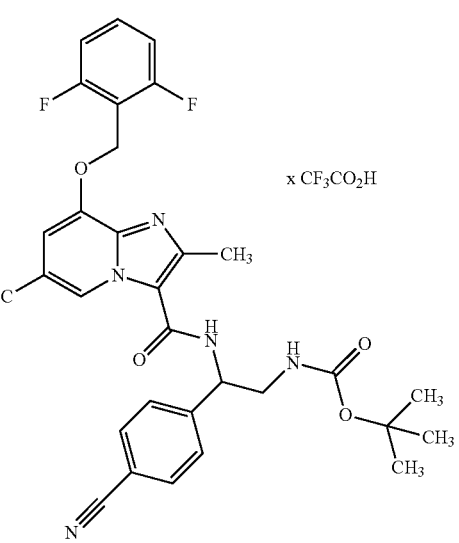 (42% of theory) | LC-MS (Method 2): R$_t$ = 1.04 min<br>MS (ESpos): m/z = 585 (M − TFA + H)$^+$ |

Example 417A rac-tert-butyl 3-{[({8-[(2,6-difluorobenzyl)oxy]-2,6-dimethylimidazo[1,2-a]pyridin-3-yl}carbonyl)amino]methyl}thiomorpholine-4-carboxylate

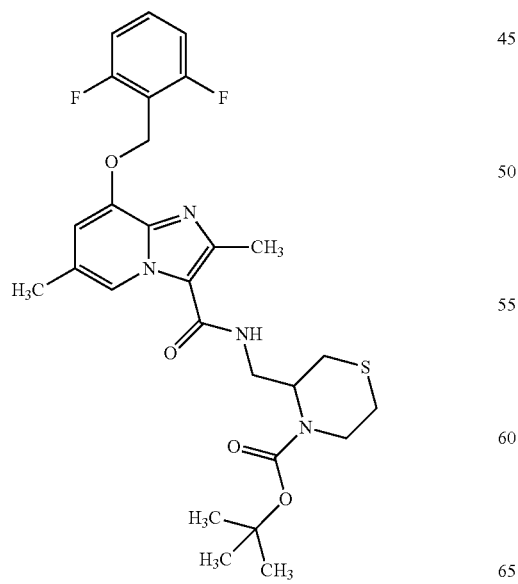

320 mg (0.717 mmol) of rac-8-[(2,6-difluorobenzyl)oxy]-2,6-dimethyl-N-(thiomorpholin-3-ylmethyl)imidazo[1,2-a]pyridine-3-carboxamide from Example 366, 217 mg (2.150 mmol) of triethylamine and 156 mg (0.717 mmol) of di-tert-butyl dicarbonate were initially charged in 3.0 ml of dichloromethane, and the mixture was stirred at RT for 1.5 h. The reaction mixture was diluted with dichloromethane, washed twice with water, dried over sodium sulphate, concentrated on a rotary evaporator and dried under high vacuum. The title compound, 292 mg (75% of theory), was used for the next step without further purification.

LC-MS (Method 16): $R_t$=1.26 min

MS (ESIpos): m/z=547 (M+H)$^+$

Example 418A rac-tert-butyl 3-{[({8-[(2,6-difluorobenzyl)oxy]-2,6-dimethylimidazo[1,2-a]pyridin-3-yl}carbonyl)amino]methyl}thiomorpholine-4-carboxylate 1,1-dioxide trifluoroacetate

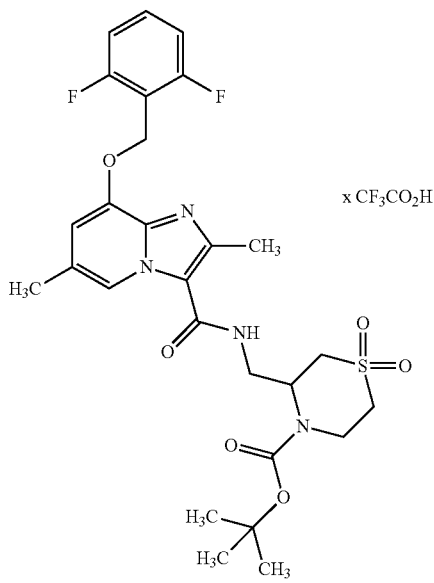 [SMILES: Cc1cc(OCc2c(F)cccc2F)c2nc(C)c(C(=O)NCC3CS(=O)(=O)CCN3C(=O)OC(C)(C)C)n2c1]

At 0° C., 118 mg (0.686 mmol) of 3-chloroperbenzoic acid were added to a solution of 150 mg (0.274 mmol) of rac-tert-butyl 3-{[({8-[(2,6-difluorobenzyl)oxy]-2,6-dimethylimidazo[1,2-a]pyridin-3-yl}carbonyl)amino]methyl}thiomorpholine-4-carboxylate from Example 417A in 3.3 ml of dichloromethane, and the mixture was stirred at 0° C. for 70 min. The reaction mixture was diluted with dichloromethane, washed three times with 1 N aqueous sodium hydroxide solution and once with 10% strength aqueous sodium chloride solution, dried over sodium sulphate and concentrated using a rotary evaporator. The crude product was purified by preparative HPLC (RP18 column, mobile phase: acetonitrile/water gradient with addition of 0.1% TFA). This gave 59 mg of the target compound (31% of theory).

LC-MS (Method 16): $R_t$=1.10 min

MS (ESIpos): m/z=579 (M−TFA+H)$^+$

Example 419A rac-benzyl (2-amino-2-cyanoethyl)carbamate trifluoroacetate

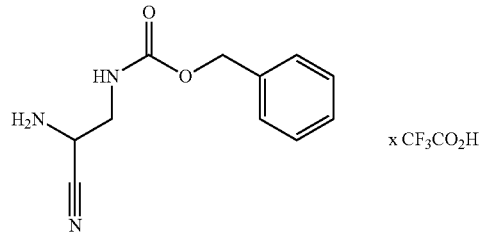 [SMILES: N#CC(N)CNC(=O)OCc1ccccc1]

500 mg (3.16 mmol) of rac-2,3-diaminopropanonitrile dihydrochloride were initially charged in 1.7 ml of abs. dichloromethane. At room temperature, 3.27 g (25.31 mmol) of N,N-diisopropylethylamine and 586.2 mg (3.16 mmol) of benzyl chloroformate were added, and the mixture was stirred at room temperature overnight. TFA and water were added to the reaction solution, and the product was purified by preparative HPLC (RP18 column; mobile phase: acetonitrile/water gradient with addition of 0.1% TFA). This gave 125 mg of the title compound (12% of theory).

LC-MS (Method 13): $R_t$=1.31 min

MS (ESpos): m/z=220 (M−TFA+H)$^+$

Example 420A rac-benzyl {2-cyano-2-[({8-[(2,6-difluorobenzyl)oxy]-2,6-dimethylimidazo[1,2-a]pyridin-3-yl}carbonyl)amino]ethyl}carbamate trifluoroacetate

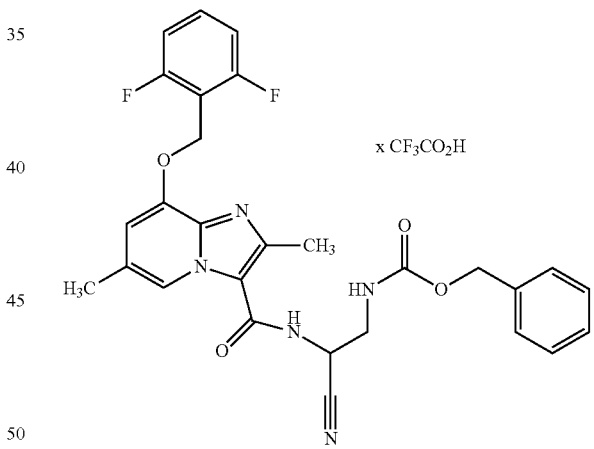

113 mg (0.34 mmol) of 8-[(2,6-difluorobenzyl)oxy]-2,6-dimethylimidazo[1,2-a]pyridine-3-carboxylic acid from Example 21A were initially charged in 0.55 ml of abs. DMF, 136 mg (0.36 mmol) of HATU and 132 mg (1.02 mmol) of N,N-diisopropylethylamine were added, and the mixture was stirred at room temperature for 20 min and then heated to 60° C. 125 mg (0.38 mmol) of rac-benzyl (2-amino-2-cyanoethyl)carbamate trifluoroacetate from Example 419A were dissolved in 0.28 ml of abs. DMF, 44 mg (0.34 mmol) of N,N-diisopropylethylamine were added dropwise to the reaction solution in which had been heated to 60° C., and the mixture was stirred at 60° C. for 1 h. Water/TFA/acetonitrile were added to the reaction solution, and the product was purified by preparative HPLC (RP18 column, mobile phase: acetonitrile/water gradient with addition of 0.1% TFA). This gave 151 mg of the title compound (68% of theory).

LC-MS (Method 2): $R_t$=0.99 min

MS (ESpos): m/z=534 (M−TFA+H)$^+$

WORKING EXAMPLES

Example 1

N-(9-Cyclopropyl-9-azabicyclo[3.3.1]non-3-yl)-8-[(2,6-difluorobenzyl)oxy]-2-methylimidazo[1,2-a]pyridine-3-carboxamide

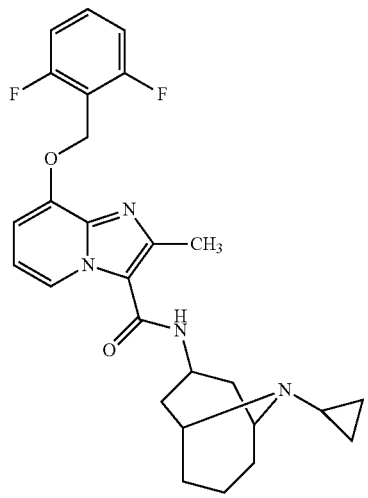 [SMILES: Cc1nc2c(OCc3c(F)cccc3F)cccn2c1C(=O)NC1CC2CCCC(C1)N2C1CC1]

70 mg of 8-[(2,6-difluorobenzyl)oxy]-2-methylimidazo[1,2-a]pyridine-3-carboxylic acid (0.22 mmol), 209 mg of O-(7-azabenzotriazol-1-yl)-N,N,N'N'-tetramethyluronium hexafluorophosphate (HATU, 0.55 mmol) and 85 mg of N,N-diisopropylethylamine (0.66 mmol) were initially charged in 1.5 ml of DMF and stirred for 15 min. 59 mg of 9-cyclopropyl-9-azabicyclo[3.3.1]nonane-3-amine (0.33 mmol) were added, and the mixture was stirred at RT overnight. The mixture was then stirred overnight once more, at 60° C. 12 ml of water were added to the reaction solution, and the precipitate formed was filtered off, washed with water and dried. The residue formed was purified by silica gel chromatography (mobile phase: dichloromethane/methanol 40:1). This gave 60 mg of the title compound (53% of theory, purity 94%).

LC-MS (Method 2): $R_f$=0.63 min
MS (ESpos): m/z=481 (M+H)$^+$
$^1$H NMR (400 MHz, DMSO-$d_6$): δ=0.24 (br s, 2H), 0.45 (d, 2H), 1.04 (d, 2H), 1.48-1.56 (m, 3H), 1.86-1.1.97 (m, 2H), 2.00-2.12 (m, 1H), 2.15-2.28 (m, 2H), 2.30-2.38 (m, 1H), 2.49 (s, 3H), 3.19 (d, 2H), 4.09-4.23 (m, 1H), 5.30 (s, 2H), 6.90 (t, 1H), 6.99 (d, 1H), 7.23 (t, 2H), 7.54-7.68 (m, 2H), 8.50 (d, 1H).

Example 2 rac-N-(1-Amino-4,4,4-trifluorobutan-2-yl)-8-[(2,6-difluorobenzyl)oxy]-2-methylimidazo[1,2-a]-pyridine-3-carboxamide

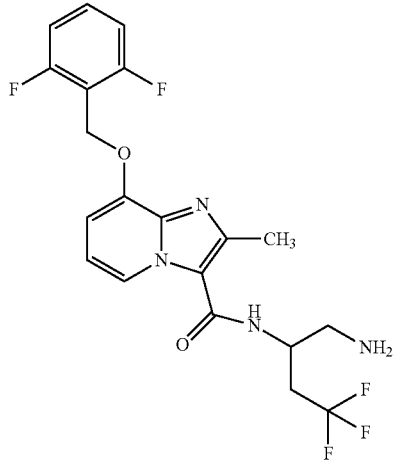 [SMILES: Cc1nc2c(OCc3c(F)cccc3F)cccn2c1C(=O)NC(CN)CC(F)(F)F]

555 mg of rac-N-(1-azido-4,4,4-trifluorobutan-2-yl)-8-[(2,6-difluorobenzyl)oxy]-2-methylimidazo[1,2-a]pyridine-3-carboxamide (Example 41A, 1.19 mmol) were initially charged in 74 ml of ethanol, 126 mg of palladium on activated carbon (10%) were added and the mixture was hydrogenated at hydrogen standard pressure and RT for 60 min. The reaction solution was filtered and concentrated. The crude product was purified by preparative HPLC (RP18 column, mobile phase: acetonitrile/water gradient with addition of 0.1% TFA). The product-containing fractions were taken up in ethyl acetate and washed with saturated aqueous sodium bicarbonate solution. The organic phase was dried over sodium sulphate, filtered and concentrated. This gave 473 mg of the title compound (88% of theory).

LC-MS (Method 2): $R_f$=0.65 min
MS (ESpos): m/z=443 (M+H)$^+$
$^1$H NMR (400 MHz, DMSO-$d_6$): δ=1.92 (br s, 2H), 2.48-2.60 (m, 3+1H), 2.62-2.80 (m, 3H), 4.18-4.30 (m, 1H), 5.30 (s, 2H), 6.93 (t, 1H), 7.00 (d, 1H), 7.22 (t, 2H), 7.59 (quint, 1H), 7.79 (br s, 1H), 8.53 (d, 1H).

Example 3 ent-N-(1-Amino-4,4,4-trifluorobutan-2-yl)-8-[(2,6-difluorobenzyl)oxy]-2-methylimidazo[1,2-a]-pyridine-3-carboxamide (Enantiomer B)

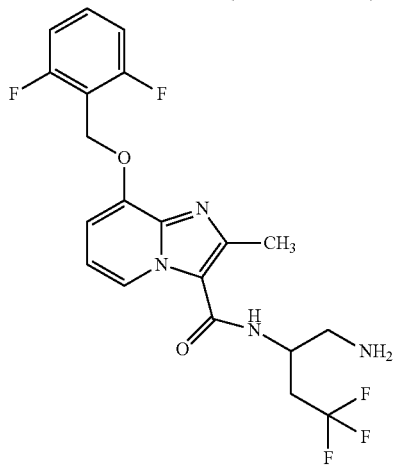 [SMILES: Cc1nc2c(OCc3c(F)cccc3F)cccn2c1C(=O)NC(CN)CC(F)(F)F]

Example 2 was separated into the enantiomers by preparative separation on a chiral phase [column: Daicel Chiralpak AD-H, 5 μm, 250×20 mm; mobile phase: 25% isohexane, 75% ethanol+0.2% diethylamine; flow rate 15 ml/min; 45° C.; detection: 220 nm]

Enantiomer B:
Yield: 154 mg (99% pure, >99% ee)
$R_t$=16.57 min [Chiralpak AD-H, 5 m, 250×4.6 mm; mobile phase: 25% isohexane, 75% ethanol+0.2% diethylamine; flow rate 1.0 ml/min; 40° C.; detection: 220 nm].

The examples shown in Table 1 were prepared analogously to Example 2.

TABLE 1

| Example | IUPAC name/structure (yield) | Analytical data |
|---|---|---|
| 4 | rac-N-(1-amino-6,6,6-trifluorohexan-2-yl)-8-[(2,6-difluorobenzyl)oxy]-2-methylimidazo[1,2-a]pyridine-3-carboxamide<br>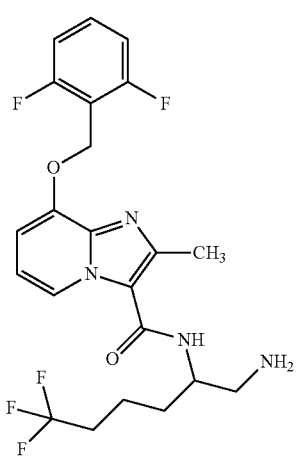<br>(90% of theory) | LC-MS (Method 2): $R_t$ = 1.03 min<br>MS (ESpos): m/z = 497 (M + H)$^+$<br>$^1$H NMR (400 MHz, DMSO-$d_6$): δ = 1.49-1.72 (m, 4H), 2.18-2.41 (m, 2H), 2.50 (s, 3H), 2.69 (d, 2H), 3.87-3.98 (m, 1H), 5.30 (s, 2H), 6.92 (t, 1H), 7.00 (d, 1H), 7.22 (d, 2H), 7.56-7.68 (m, 2H), 8.52 (d, 1H). |
| 5 | rac-N-[1-amino-5,5,5-trifluoro-4-(trifluoromethyl)pentan-2-yl]-8-[(2,6-difluorobenzyl)oxy]-2-methylimidazo[1,2-a]-pyridine-3-carboxamide trifluoroacetate $^{a)}$<br>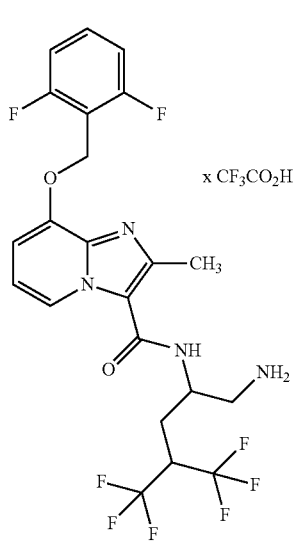<br>(91% of theory) | LC-MS (Method 7): $R_t$ = 0.70 min<br>MS (ESpos): m/z = 525 (M − TFA + H)$^+$<br>$^1$H NMR (400 MHz, DMSO-$d_6$): δ = 2.12-2.28 (m, 2H), 2.60 (s, 3H), 2.99-3.10 (m, 2H), 3.14-3.25 (m, 1H), 3.95-4.10 (m, 1H), 4.37-4.49 (m, 1H), 5.35 (s, 2H), 7.05-7.12 (m, 1H), 7.15-7.28 (m, 3H), 7.60 (q, 1H), 7.69-7.82 (m, 1H), 7.97 (br s, 3H), 8.70 (d, 1H). |

$^{a)}$ There was no aqueous work-up after preparative HPLC.

Example 6 ent-N-(1-Amino-6,6,6-trifluorohexan-2-yl)-8-[(2,6-difluorobenzyl)oxy]-2-methylimidazo[1,2-a]-pyridine-3-carboxamide (enantiomer B)

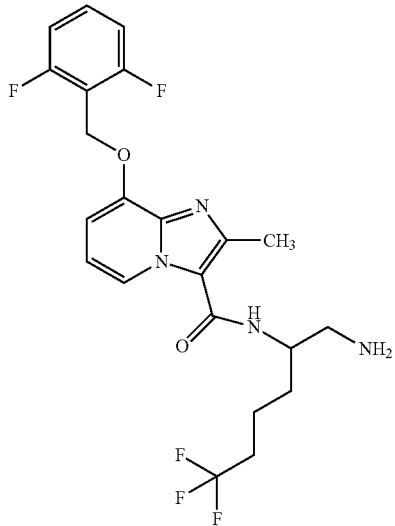 [SMILES: Cc1nc2c(OCc3c(F)cccc3F)cccn2c1C(=O)NC(CN)CCCC(F)(F)F]

The compound of Example 4 (388 mg) was separated into the enantiomers by preparative separation on a chiral phase [column: Daicel Chiralpak AD-H, 5 μm, 250×20 mm; mobile phase: 25% isohexane, 75% ethanol+0.2% diethylamine; flow rate 15 ml/min; 45° C.; detection: 220 nm]

Enantiomer B:

Yield: 136 mg (99% pure, >99% ee)

$R_t$=17.00 min [Chiralpak AD-H, 5 μm, 250×4.6 mm; mobile phase: 25% isohexane, 75% ethanol+0.2% diethylamine; flow rate 1.0 ml/min; 40° C.; detection: 220 nm].

Example 7 ent-N-[1-Amino-5,5,5-trifluoro-4-(trifluoromethyl)pentan-2-yl]-8-[(2,6-difluorobenzyl)oxy]-2-methylimidazo[1,2-a]pyridine-3-carboxamide (Enantiomer A)

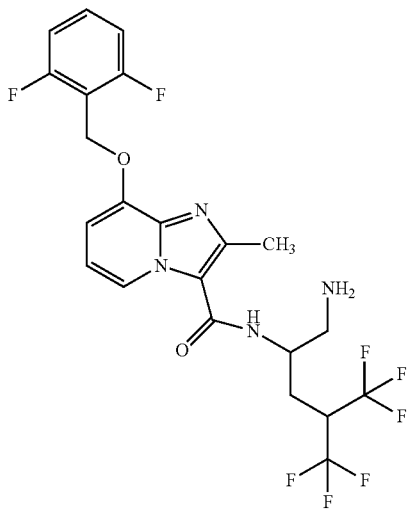 [SMILES: Cc1nc2c(OCc3c(F)cccc3F)cccn2c1C(=O)NC(CN)CC(C(F)(F)F)C(F)(F)F]

The compound of Example 5 (140 mg) was separated into the enantiomers by preparative separation on a chiral phase [column: Daicel Chiralpak OD-H, 5 μm, 250×20 mm; mobile phase: 70% isohexane, 30% ethanol+0.2% diethylamine; flow rate 20 ml/min; 25° C.; detection: 230 nm]

Enantiomer A:

Yield: 31 mg (>99% ee)

$R_t$=4.47 min [Daicel Chiralpak OD-H, 5 m, 250×4.6 mm; mobile phase: 50% isohexane, 50% ethanol+0.2% diethylamine; flow rate 1.0 ml/min; detection: 250 nm].

Example 8

N-[(2R)-1-Aminohexan-2-yl]-8-[(2,6-difluorobenzyl)oxy]-2-methylimidazo[1,2-a]pyridine-3-carboxamide

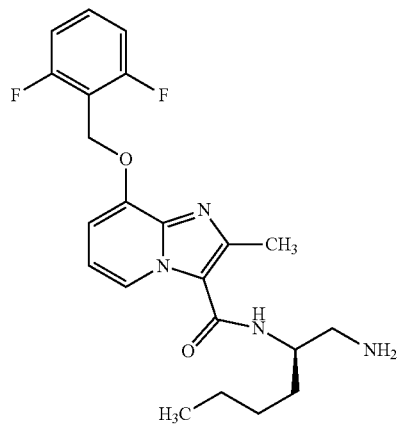 [SMILES: CCCC[C@H](CN)NC(=O)c1c(C)nc2c(OCc3c(F)cccc3F)cccn12]

42 mg of N-[(2R)-1-azidohexan-2-yl]-8-[(2,6-difluorobenzyl)oxy]-2-methylimidazo[1,2-a]-pyridine-3-carboxamide (Example 44A, 0.095 mmol) were initially charged in 0.78 ml of THF/water (10:1.5), 28.3 mg of triphenylphosphine (0.108 mmol) were added and the mixture was stirred at RT overnight. The reaction mixture was concentrated and the residue was purified by preparative thick-layer chromatography (mobile phase ethyl acetate: dichloromethane: diethylamine=2:1:0.1). The combined product fractions were purified by preparative HPLC (RP18 column, mobile phase: acetonitrile/water gradient with addition of 0.1% TFA). The product-containing fractions were taken up in ethyl acetate and washed with saturated aqueous sodium bicarbonate solution. The organic phase was dried over sodium sulphate, filtered and concentrated. This gave 17 mg of the title compound (41% of theory).

LC-MS (Method 1): $R_t$=0.88 min

MS (ESpos): m/z=417 (M+H)$^+$ $^1$H NMR (400 MHz, DMSO-d$_6$): δ=0.88 (t, 3H), 1.21-1.39 (m, 4H), 1.42-1.67 (m, 2H), 2.73 (d, 2H), 3.92-4.08 (m, 1H), 5.30 (s, 2H), 6.93 (t, 1H), 7.00 (d, 1H), 7.22 (t, 2H), 7.56-7.7.62 (m, 2H), 8.56 (d, 1H).

Example 9 rac-N-[2-Amino-1-(4-fluorophenyl)ethyl]-8-[(2,6-difluorobenzyl)oxy]-2-methylimidazo[1,2-a]-pyridine-3-carboxamide

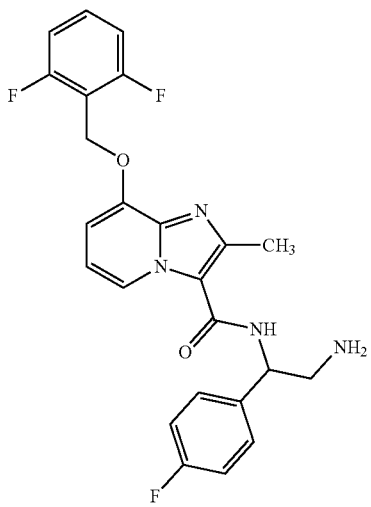 [SMILES: Cc1nc2c(OCc3c(F)cccc3F)cccn2c1C(=O)NC(CN)c1ccc(F)cc1]

7 ml of 2M hydrochloric acid in diethyl ether (14 mmol) were added to 363 mg of tert-butyl {2-[({8-[(2,6-difluorobenzyl)oxy]-2-methylimidazo[1,2-a]pyridin-3-yl}-carbonyl)amino]-2-(4-fluorophenyl)ethyl}carbamate (Example 79A, 0.63 mmol), and the mixture was stirred at RT for 3 h. The resulting precipitate was filtered off, washed with diethyl ether, dissolved in dichloromethane and methanol and washed with saturated aqueous sodium bicarbonate solution. The organic phase was dried over sodium sulphate and filtered and the filtrate was concentrated and dried under high vacuum. This gave 275 mg of the title compound (96% of theory).

LC-MS (Method 2): $R_t$=0.68 min
MS (ESpos): m/z=455 (M+H)$^+$
$^1$H NMR (400 MHz, DMSO-d$_6$): δ=1.62 (br s, 2H), 2.60 (s, 3H), 2.85-2.96 (m, 2H), 4.98 (t, 1H), 5.31 (s, 2H), 6.90 (t, 1H), 6.99 (d, 1H), 7.18 (t, 2H), 7.22 (t, 2H), 7.41 (dd, 2H), 7.59 (quint, 1H), 8.20 (br s, 1H), 8.53 (d, 1H).

Example 10 ent-N-[2-Amino-1-(4-fluorophenyl)ethyl]-8-[(2,6-difluorobenzyl)oxy]-2-methylimidazo[1,2-a]-pyridine-3-carboxamide (Enantiomer B)

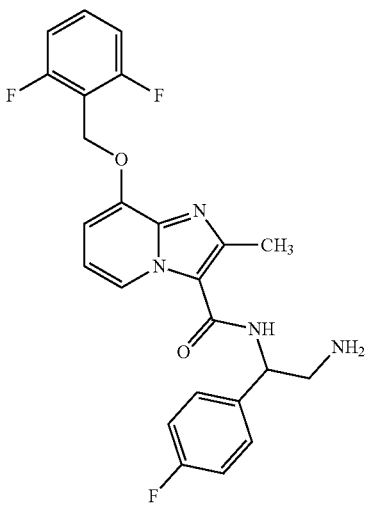 [SMILES: Cc1nc2c(OCc3c(F)cccc3F)cccn2c1C(=O)NC(CN)c1ccc(F)cc1]

The compound of Example 9 (242 mg) was separated into the enantiomers by preparative separation on a chiral phase [column: Daicel Chiralpak AD-H, 5 μm, 250×20 mm, mobile phase: 100% ethanol+0.2% diethylamine, flow rate 15 ml/min; 45° C., detection: 220 nm].

Enantiomer B:
Yield: 110 mg (99% pure, about 99% ee)
$R_t$=10.25 min [Chiralpak AD-H, 5 μm, 250×4.6 mm; mobile phase: 70% isohexane, 30% ethanol+0.2% diethylamine; flow rate 1.0 ml/min; 45° C.; detection: 235 nm].

Example 11 rac-N-[2-Amino-1-(3,4-difluorophenyl)ethyl]-8-[(2,6-difluorobenzyl)oxy]-2-methylimidazo[1,2-a]pyridine-3-carboxamide

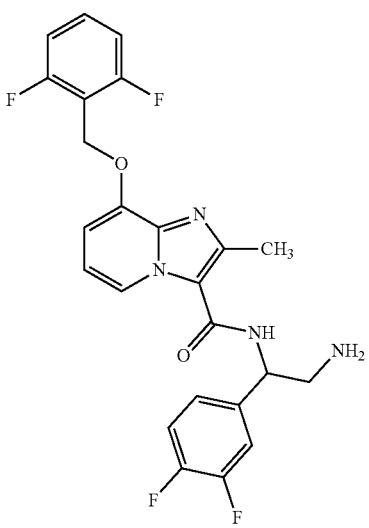 [SMILES: Cc1nc2c(OCc3c(F)cccc3F)cccn2c1C(=O)NC(CN)c1ccc(F)c(F)c1]

3.1 ml of 2 M hydrochloric acid in diethyl ether (6.2 mmol) were added to 355 mg of rac-tert-butyl {2-[({8-[(2,6-difluorobenzyl)oxy]-2-methylimidazo[1,2-a]pyridin-3-yl}carbonyl)amino]-2-(3,4-difluorophenyl)ethyl}carbamate (Example 77A, 0.62 mmol), and the mixture was stirred at RT for 5.5 h. The resulting precipitate was filtered off, washed with diethyl ether, suspended in dichloromethane and washed with saturated aqueous sodium bicarbonate solution. The organic phase was dried over sodium sulphate and filtered and the filtrate was concentrated and dried under high vacuum. This gave 279 mg of the title compound (94% of theory).

LC-MS (Method 2): R$_t$=0.77 min

MS (ESpos): m/z=473 (M+H)$^+$ $^1$H NMR (400 MHz, DMSO-d$_6$): δ=2.18 (br s, 2H), 2.60 (s, 3H), 2.87-2.97 (m, 2H), 4.99 (t, 1H), 5.31 (s, 2H), 6.91 (t, 1H), 7.01 (d, 1H), 7.19-7.28 (m, 3H), 7.36-7.51 (m, 2H), 7.59 (quint, 1H), 8.21 (br s, 1H), 8.54 (d, 1H).

Example 12 (Enantiomer A)

ent-N-[2-Amino-1-(3,4-difluorophenyl)ethyl]-8-[(2,6-difluorobenzyl)oxy]-2-methylimidazo[1,2-a]-pyridine-3-carboxamide (Enantiomer A)

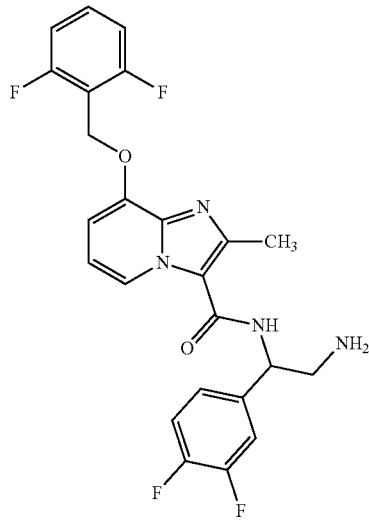 [SMILES: Cc1nc2c(OCc3c(F)cccc3F)cccn2c1C(=O)NC(CN)c1ccc(F)c(F)c1]

The compound of Example 11 (250 mg) was separated into the enantiomers by preparative separation on a chiral phase [column: Daicel Chiralpak AY-H, 5 m, 250×20 mm, mobile phase: 70% isohexane, 30% ethanol+0.2% diethylamine, flow rate 15 ml/min; 45° C., detection: 220 nm]. The product fractions were concentrated, taken up in water/acetonitrile and freeze-dried. The product was then purified by preparative HPLC (RP18 column, mobile phase: acetonitrile/water gradient with addition of 0.1% TFA). The combined fractions were lyophilized and the residue was dissolved in ethyl acetate and washed with a little saturated aqueous sodium bicarbonate solution. The organic phase was dried over sodium sulphate and filtered. The filtrate was concentrated and dried under high vacuum.

Enantiomer A:

Yield: 88 mg (99% pure, about 94% ee)

R$_t$=7.55 min [Chiralpak AY-H, 5 m, 250×4.6 mm; mobile phase: 70% isohexane, 30% ethanol+0.2% diethylamine; flow rate 1.0 ml/min; 45° C.; detection: 235 nm].

LC-MS (Method 2): R$_t$=0.78 min

MS (ESpos): m/z=473 (M+H)$^+$ $^1$H NMR (400 MHz, DMSO-d$_6$): δ=2.59 (s, 3H), 2.88-3.01 (m, 2H), 5.02 (t, 1H), 5.31 (s, 2H), 6.91 (t, 1H), 7.01 (d, 1H), 7.19-7.29 (m, 3H), 7.36-7.52 (m, 2H), 7.59 (quint, 1H), 8.21 (br s, 1H), 8.54 (d, 1H).

Specific rotation [α] (436 nm, 20.4° C.)=+23.8° (c=0.0053 g/ml, acetonitrile)

Example 13 (Enantiomer B)

ent-N-[2-Amino-1-(3,4-difluorophenyl)ethyl]-8-[(2,6-difluorobenzyl)oxy]-2-methylimidazo[1,2-a]-pyridine-3-carboxamide (Enantiomer B)

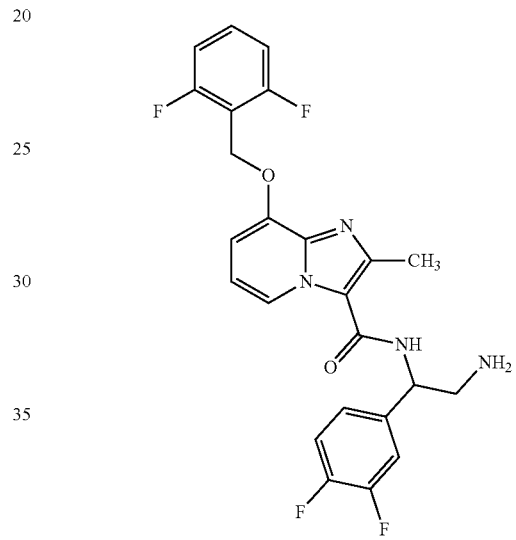

19 ml of 2 M hydrochloric acid in diethyl ether (38 mmol) were added to 2.18 g of ent-tert-butyl {2-[({8-[(2,6-difluorobenzyl)oxy]-2-methylimidazo[1,2-a]pyridin-3-yl}carbonyl)amino]-2-(3,4-difluorophenyl)ethyl}carbamate (Example 118A, 3.80 mmol), and the mixture was stirred at RT overnight. The reaction mixture was diluted with diethyl ether. The precipitate was filtered off, and ethyl acetate and saturated aqueous sodium bicarbonate solution were added. After phase separation, the aqueous phase was extracted twice with ethyl acetate. The combined organic phases were dried over sodium sulphate and filtered and the filtrate was concentrated and lyophilized. This gave 1.85 g of the title compound (quantitative).

LC-MS (Method 2): R$_t$=0.80 min

MS (ESpos): m/z=473 (M+H)$^+$ $^1$H NMR (400 MHz, DMSO-d$_6$): δ=1.55 (br s, 2H), 2.59 (s, 3H), 2.85-2.95 (m, 2H), 4.97 (t, 1H), 5.31 (s, 2H), 6.91 (t, 1H), 7.01 (d, 1H), 7.19-7.28 (m, 3H), 7.36-7.51 (m, 2H), 7.59 (quint, 1H), 8.21 (br s, 1H), 8.54 (d, 1H).

Specific rotation [α] (436 nm, 19.9° C.)=−23.5° (c=0.00505 g/ml, acetonitrile)

Example 14 rac-N-[2-Amino-1-(4-chlorophenyl)ethyl]-8-[(2,6-difluorobenzyl)oxy]-2-methylimidazo[1,2-a]-pyridine-3-carboxamide dihydrochloride

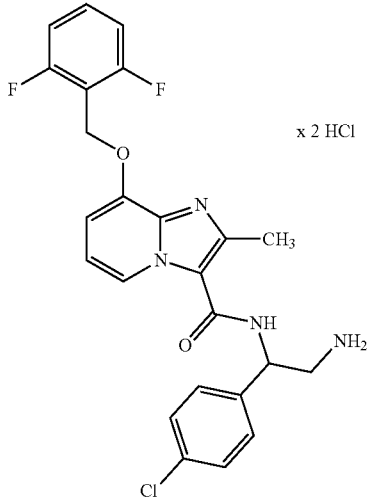 [SMILES: Cc1nc2c(OCc3c(F)cccc3F)cccn2c1C(=O)NC(CN)c1ccc(Cl)cc1]

3.5 ml (7.0 mmol) of a 2 M solution of hydrochloric acid in diethyl ether were added to 396 mg of rac-tert-butyl {2-(4-chlorophenyl)-2-[({8-[(2,6-difluorobenzyl)oxy]-2-methylimidazo[1,2-a]-pyridin-3-yl}carbonyl)amino]ethyl}carbamate (Example 78A, 0.69 mmol), and the mixture was stirred at RT for 5.5 h. The resulting precipitate was filtered off, washed with diethyl ether and dried under high vacuum. This gave 341 mg of the title compound (90% of theory).

LC-MS (Method 2): $R_t$=0.72 min
MS (ESpos): m/z=471 (M−2HCl+H)$^+$
$^1$H NMR (400 MHz, DMSO-$d_6$): δ=2.69 (s, 3H), 3.16-3.28 (m, 1H), 3.38-3.53 (m, 1H), 5.40-5.49 (m, 3H), 7.23 (t, 2H), 7.34 (br s, 1H), 7.41-7.67 (m, 6H), 8.20-8.43 (m, 3H), 8.65 (d, 1H), 9.39 (br s, 1H).

Example 15 ent-N-[2-Amino-1-(4-chlorophenyl)ethyl]-8-[(2,6-difluorobenzyl)oxy]-2-methylimidazo[1,2-a]-pyridine-3-carboxamide (Enantiomer B)

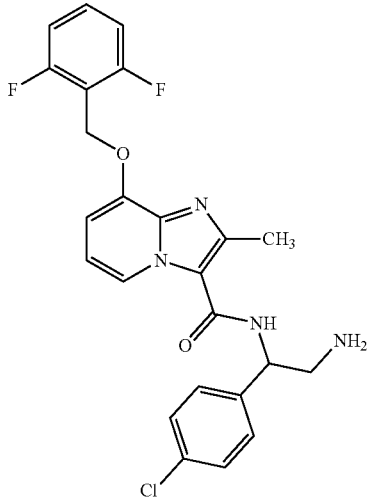 [SMILES: Cc1nc2c(OCc3c(F)cccc3F)cccn2c1C(=O)NC(CN)c1ccc(Cl)cc1]

288 mg compound of Example 14 were suspended in ethyl acetate and washed with saturated aqueous sodium bicarbonate solution. The organic phase was dried over sodium sulphate and filtered. The filtrate was concentrated and dried under high vacuum. The crude product (279 mg) was separated into the enantiomers by preparative separation on a chiral phase [column: Daicel Chiralpak AD-H, 5 μm, 250×20 mm, mobile phase: 30% isohexane, 70% ethanol+ 0.2% diethylamine, flow rate 15 ml/min; 45° C., detection: 220 nm]. The product was re-purified by silica gel (mobile phase: from dichloromethane to dichloromethane:methanol=10:1). This was followed by a further purification by preparative HPLC (RP18 column, mobile phase: methanol/water gradient with addition of 0.1% TFA). The product fractions were dissolved in ethyl acetate and twice washed with a little saturated aqueous sodium bicarbonate solution. The organic phase was dried over sodium sulphate and filtered and the filtrate was concentrated and dried under high vacuum overnight.

Enantiomer B:
Yield: 62 mg (99% pure, 99% ee)
$R_t$=8.77 min [Chiralpak AY-H, 5 m, 250×4.6 mm; mobile phase: 60% isohexane, 40% ethanol+0.2% diethylamine; flow rate 1.0 ml/min; 35° C.; detection: 235 nm].
$^1$H NMR (400 MHz, DMSO-$d_6$): δ=2.04 (br s, 2H), 2.60 (s, 3H), 2.85-2.95 (m, 2H), 4.98 (t, 1H), 5.30 (s, 2H), 6.90 (t, 1H), 7.02 (d, 1H), 7.22 (t, 2H), 7.38-7.44 (m, 4H), 7.59 (quint, 1H), 8.20 (br s, 1H), 8.53 (d, 1H).

Example 16 rac-N-(2-Amino-1-phenylethyl)-8-[(2,6-difluorobenzyl)oxy]-2-methylimidazo[1,2-a]pyridine-3-carboxamide dihydrochloride

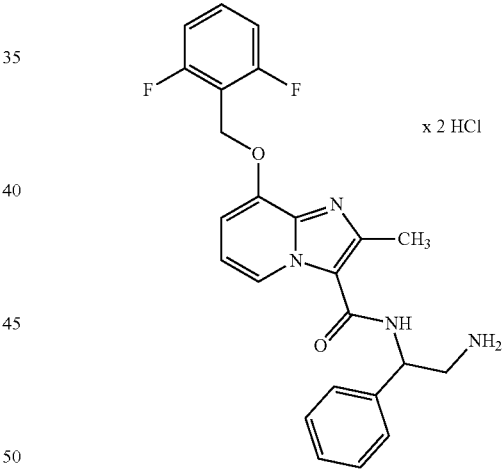

15.75 ml of a 2 M solution of hydrochloric acid in diethyl ether (31.5 mmol) were added to 370 mg of rac-tert-butyl {2-[({8-[(2,6-difluorobenzyl)oxy]-2-methylimidazo[1,2-a]pyridin-3-yl}-carbonyl)amino]-2-phenylethyl}carbamate (Example 80A, 0.69 mmol), and the mixture was stirred at RT for 3.5 h. The resulting precipitate was filtered off, washed with diethyl ether and dried under high vacuum. This gave 306 mg of the title compound (85% of theory, purity 98%).

LC-MS (Method 2): $R_t$=0.70 min
MS (ESpos): m/z=437 (M−2HCl+H)$^+$
$^1$H NMR (400 MHz, DMSO-$d_6$): δ=2.65 (s, 3H), 3.19-3.29 (m, 1H), 3.35-3.54 (m, 1H), 5.38-5.49 (m, 3H), 7.21-7.54 (m, 10H), 7.60 (quint, 1H), 8.12-8.32 (m, 2H), 8.66 (d, 1H), 9.09 (br s, 1H).

The example shown in Table 2 was prepared analogously to Example 16.

TABLE 2

| Example | IUPAC name/structure (yield) | Analytical data |
|---|---|---|
| 17 | rac-N-(1-aminopropan-2-yl)-8-[(2,6-difluorobenzyl)oxy]-2-methylimidazo[1,2-a]pyridine-3-carboxamide dihydrochloride 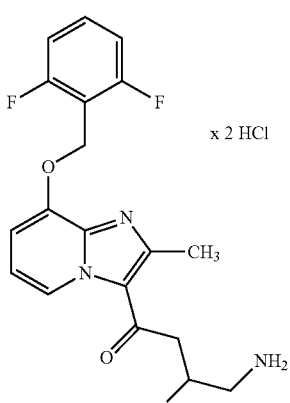 (92% of theory) | LC-MS (Method 1): $R_t$ = 0.69 min<br>MS (ESpos): m/z = 375 (M – HCl + H)$^+$<br>$^1$H NMR (400 MHz, DMSO-d$_6$):<br>δ = 1.28 (d, 3H), 2.64 (s, 3H), 2.96-3.10 (m, 2H), 4.32 (quintet, 1H), 5.44 (s, 2H), 7.22 (t, 2H), 7.33 (br s, 1H), 7.46-7.66 (m, 2H), 8.18 (br s, 3H), 8.58 (br s, 1H), 8.73 (d, 1H). |

Example 18 ent-N-(2-Amino-1-phenylethyl)-8-[(2,6-difluorobenzyl)oxy]-2-methylimidazo[1,2-a]pyridine-3-carboxamide (Enantiomer B)

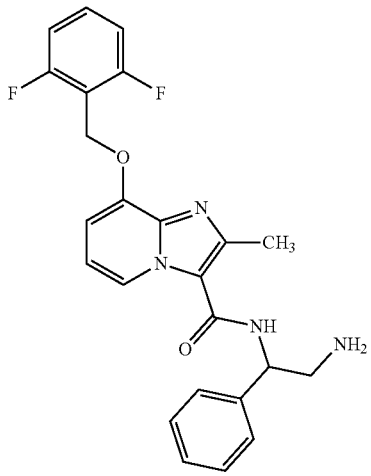 [SMILES: Cc1nc2c(OCc3c(F)cccc3F)cccn2c1C(=O)NC(CN)c1ccccc1]

276 mg of compound of Example 16 were suspended in ethyl acetate/dichloromethane (1:1) and washed with saturated aqueous sodium bicarbonate solution. The organic phase was dried over sodium sulphate, filtered and concentrated. The crude product (247 mg) was separated into the enantiomers by preparative separation on a chiral phase [column: Daicel Chiralpak AD-H, 5 μm, 250×20 mm, mobile phase: 30% isohexane, 70% ethanol+0.2% diethylamine, flow rate 15 ml/min; 45° C., detection: 220 nm]. The product obtained was re-purified on silica gel (mobile phase: from dichloromethane to dichloromethane:methanol=10:1). This was followed by a further purification by preparative HPLC (RP18 column, mobile phase: methanol/water gradient with addition of 0.1% TFA). The product fractions were concentrated, dissolved in ethyl acetate and twice washed with a little saturated aqueous sodium bicarbonate solution. The organic phase was dried over sodium sulphate, filtered and concentrated.

Enantiomer B:

Yield: 78 mg (98% ee)

$R_t$=11.00 min [Chiralpak AY-H, 5 m, 250×4.6 mm; mobile phase: 60% isohexane, 40% ethanol+0.2% diethylamine; flow rate 1.0 ml/min; 35° C.; detection: 235 nm].

$^1$H NMR (400 MHz, DMSO-d$_6$): δ=2.59 (s, 3H), 2.98-3.10 (m, 2H), 4.42 (br s, 2H), 5.09-5.18 (m, 1H), 5.30 (s, 2H), 6.90 (t, 1H), 7.01 (d, 1H), 7.19-7.30 (m, 3H), 7.32-7.44 (m, 4H), 7.59 (quint, 1H), 8.21 (d, 1H), 8.55 (d, 1H).

Example 19 ent-N-(1-Aminopropan-2-yl)-8-[(2,6-difluorobenzyl)oxy]-2-methylimidazo[1,2-a]pyridine-3-carboxamide (Enantiomer A)

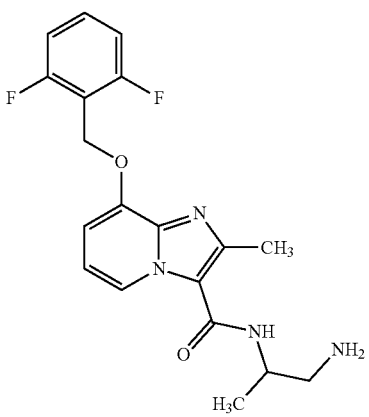 [SMILES: Cc1nc2c(OCc3c(F)cccc3F)cccn2c1C(=O)NC(C)CN]

46 mg compound of Example 17 were separated into the enantiomers by preparative separation on a chiral phase [column: Daicel Chiralpak AY-H, 5 μm, 250×20 mm, mobile phase: 70% isohexane, 30% ethanol+0.2% diethylamine, flow rate: 15 ml/min; 35° C., detection: 220 nm].

Enantiomer A was re-purified by preparative HPLC (RP18 column, mobile phase: acetonitrile/water gradient with addition of 0.1% TFA). The product fractions were concentrated, dissolved in dichloromethane and twice washed with saturated aqueous sodium bicarbonate solution. The organic phase was dried over sodium sulphate, filtered and concentrated.

Enantiomer A:

Yield: 7.3 mg (99% ee)

$R_t$=8.59 min [Chiralpak AY-H, 5 μm, 250×4.6 mm; mobile phase: 70% isohexane, 30% ethanol+0.2% diethylamine; flow rate 1.0 ml/min; 45° C.; detection: 235 nm].

LC-MS (Method 2): $R_t$=0.56 min (purity about 92%)

MS (ESpos): m/z=375 (M+H)$^+$

Example 20 ent-N-(1-Aminopropan-2-yl)-8-[(2,6-difluorobenzyl)oxy]-2-methylimidazo[1,2-a]pyridine-3-carboxamide (Enantiomer B)

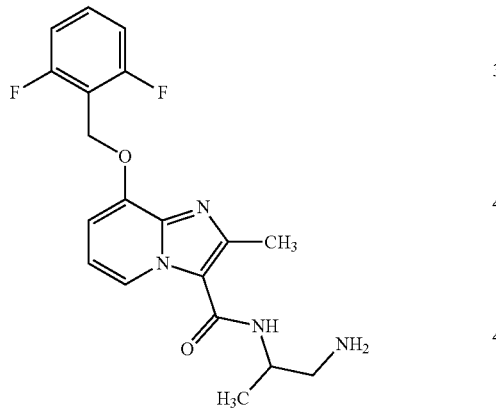

46 mg compound of Example 17 were separated into the enantiomers by preparative separation on a chiral phase [column: Daicel Chiralpak AY-H, 5 μm, 250×20 mm, mobile phase: 70% isohexane, 30% ethanol+0.2% diethylamine, flow rate: 15 ml/min; 35° C., detection: 220 nm].

Enantiomer B:

Yield: 13 mg (98.5% ee)

$R_t$=10.57 min [Chiralpak AY-H, 5 m, 250×4.6 mm; mobile phase: 70% isohexane, 30% ethanol+0.2% diethylamine; flow rate 1.0 ml/min; 45° C.; detection: 235 nm].

LC-MS (Method 2): $R_t$=0.57 min (purity about 92%)

MS (ESpos): m/z=375 (M+H)$^+$

Example 21 ent-N-[2-Amino-1-(2,4-difluorophenyl)ethyl]-8-[(2,6-difluorobenzyl)oxy]-2-methylimidazo[1,2-a]-pyridine-3-carboxamide

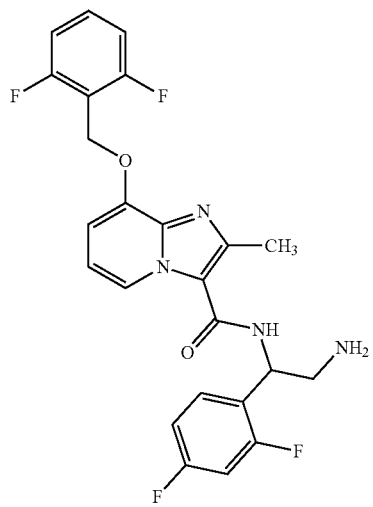 [SMILES: Cc1nc2c(OCc3c(F)cccc3F)cccn2c1C(=O)NC(CN)c1ccc(F)cc1F]

0.63 ml of 2 M hydrochloric acid in diethyl ether (1.26 mmol) was added to 72 mg ent-tert-butyl {2-[({8-[(2,6-difluorobenzyl)oxy]-2-methylimidazo[1,2-a]pyridin-3-yl}carbonyl)amino]-2-(2,4-difluorophenyl)ethyl}carbamate (Example 81A, 0.13 mmol), and the mixture was stirred at RT overnight. The reaction mixture was diluted with diethyl ether and the precipitate was filtered off. Ethyl acetate and saturated aqueous sodium bicarbonate solution were added to the precipitate and the phases were separated. The aqueous phase was extracted twice with ethyl acetate and the combined organic phases were dried over sodium sulphate, filtered, concentrated and lyophilized. This gave 51 mg of the title compound (84% of theory).

LC-MS (Method 2): $R_t$=0.78 min

MS (ESpos): m/z=473 (M+H)$^+$ $^1$H NMR (400 MHz, DMSO-$d_6$): δ=1.69 (br s, 2H), 2.59 (s, 3H), 2.82-2.92 (m, 2H), 5.20 (t, 1H), 5.30 (s, 2H), 6.90 (t, 1H), 7.02 (d, 1H), 7.05-7.11 (m, 1H), 7.18-7.28 (m, 3H), 7.50 (q, 1H), 7.59 (quint, 1H), 8.22 (br s, 1H), 8.53 (d, 1H).

The examples shown in Table 3 were prepared analogously to Example 21.

TABLE 3

| Example | IUPAC name/structure (yield) | Analytical data |
|---|---|---|
| 22 | ent-N-(1-aminopropan-2-yl)-6-chloro-8-[(2,6-difluorobenzyl)oxy]-2-methylimidazo[1,2-a]-pyridine-3-carboxamide [1]<br><br>(88% of theory) | LC-MS (Method 2): $R_t$ = 0.68 min<br>MS (ESpos): m/z = 409 (M + H)$^+$<br>$^1$H NMR (400 MHz, DMSO-d$_6$):<br>δ = 1.24 (d, 3H), 1.63 (br s, 2H), 2.52 (s, 3H), 2.59-2.71 (m, 2H), 3.89-4.00 (m, 1H), 5.33 (s, 2H), 7.19 (s, 1H), 7.23 (t, 2H), 7.60 (quintet, 1H), 7.68 (br s, 1H), 8.70 (s, 1H). |
| 23 | rac-N-(2-aminopropyl)-6-chloro-8-[(2,6-difluorobenzyl)oxy]-2-methylimidazo[1,2-a]-pyridine-3-carboxamide [2]<br><br>(78% of theory, purity about 90%) | LC-MS (Method 2): $R_t$ = 0.71 min<br>MS (ESpos): m/z = 409 (M + H)$^+$<br>$^1$H NMR (400 MHz, DMSO-d$_6$):<br>δ = 1.01 (d, 3H), 1.70 (br s, 2H), 2.52 (s, 3H), 2.99 (sextet, 1H), 3.09-3.27 (m, 2H), 5.33 (s, 2H), 7.19 (s, 1H), 7.24 (t, 2H), 7.61 (quintet, 1H), 7.78 (br s, 1H), 8.76 (s, 1H). |

TABLE 3-continued

| Example | IUPAC name/structure (yield) | Analytical data |
|---|---|---|
| 24 | N-(1-amino-2-methylpropan-2-yl)-6-chloro-8-[(2,6-difluorobenzyl)oxy]-2-methylimidazo[1,2-a]pyridine-3-carboxamide [2)<br>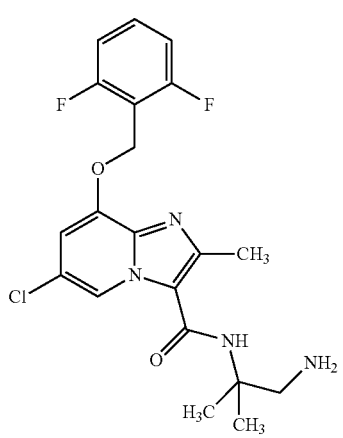<br>(86% of theory) | LC-MS (Method 2): $R_t$ = 0.73 min<br>MS (ESpos): m/z = 423 (M + H)$^+$<br>$^1$H NMR (400 MHz, DMSO-d$_6$):<br>δ = 1.33 (s, 6H), 1.89 (br s, 2H), 2.52 (s, 3H), 2.71 (s, 2H), 5.33 (s, 2H), 7.19 (s, 1H), 7.24 (t, 2H), 7.40 (s, 1H), 7.61 (quintet, 1H), 8.80 (s, 1H). |
| 25 | rac-N-(2-aminopropyl)-8-[(2,6-difluorobenzyl)oxy]-2,6-dimethylimidazo[1,2-a]pyridine-3-carboxamide [3)<br>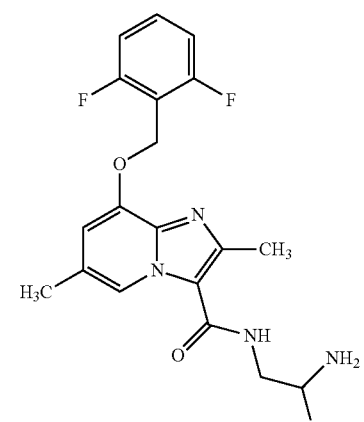<br>(73% of theory, purity about 90%) | LC-MS (Method 2): $R_t$ = 0.55 min<br>MS (ESpos): m/z = 389 (M + H)$^+$<br>$^1$H NMR (400 MHz, DMSO-d$_6$):<br>δ = 1.01 (d, 3H), 1.52 (br s, 2H), 2.31 (s, 3H), 2.52 (s, 3H), 2.99 (sextet, 1H), 3.09-3.28 (m, 2H), 5.29 (s, 2H), 6.91 (s, 1H), 7.24 (t, 2H), 7.59 (quintet, 1H), 7.78 (br s, 1H), 8.45 (s, 1H). |
| 26 | N-(1-amino-2-methylpropan-2-yl)-8-[(2,6-difluorobenzyl)oxy]-2,6-dimethylimidazo[1,2-a]pyridine-3-carboxamide [3) | LC-MS (Method 2): $R_t$ = 0.64 min<br>MS (ESpos): m/z = 403 (M + H)$^+$<br>$^1$H NMR (400 MHz, DMSO-d$_6$):<br>δ = 1.32 (s, 6H), 1.70 (br s, 2H), 2.31 |

TABLE 3-continued

| Example | IUPAC name/structure (yield) | Analytical data |
|---|---|---|
| | 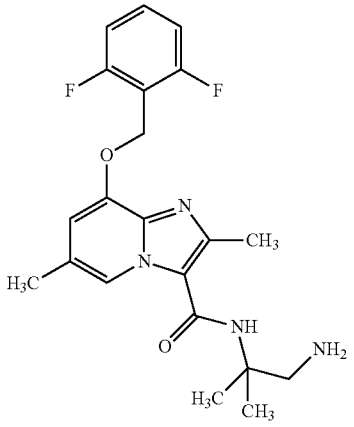(82% of theory) | (s, 3H), 2.52 (s, 3H), 2.69 (s, 2H), 5.28 (s, 2H), 6.90 (s, 1H), 7.24 (t, 2H), 7.30 (s, 1H), 7.60 (quintet, 1H), 8.52 (s, 1H). |
| 27 | N-(9-azabicyclo[3.3.1]non-3-yl)-8-[(2,6-difluorobenzyl)oxy]-2-methylimidazo[1,2-a]pyridine-3-carboxamide [4)]<br>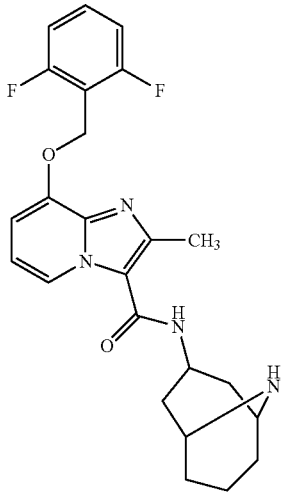(81% of theory) | LC-MS (Method 2): $R_t$ = 0.62 min<br>MS (ESpos): m/z = 441 (M + H)$^+$<br>$^1$H NMR (400 MHz, DMSO-$d_6$):<br>δ = 1.63-1.90 (m, 8H), 1.94-2.03 (m, 2H), 2.48 (s, 3H), 3.28 (br s, 2H), 4.69-4.81 (m, 1H), 5.30 (s, 2H), 6.91 (t, 1H), 6.99 (d, 1H), 7.24 (t, 2H), 7.59 (quintet, 1H), 7.78 (d, 1H), 8.51 (d, 1H). |
| 28 | rac-8-[(2,6-difluorobenzyl)oxy]-N-(2,3-dihydro-1H-indol-3-yl)-2-methylimidazo[1,2-a]pyridine-3-carboxamide | LC-MS (Method 2): $R_t$ = 0.78 min<br>MS (ESpos): m/z = 435 (M + H)$^+$<br>$^1$H NMR (400 MHz, DMSO-$d_6$):<br>δ = 2.50 (s, 3H), 3.31-3.40 (m, 1H), |

TABLE 3-continued

| Example | IUPAC name/structure (yield) | Analytical data |
|---|---|---|
| | 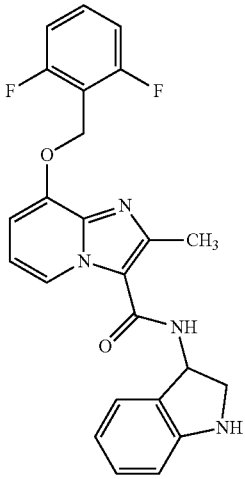(99% of theory) | 3.73-3.80 (m, 1H), 5.30 (s, 2H), 5.58-5.69 (m, 2H), 6.57-6.63 (m, 2H), 6.93 (t, 1H), 6.98-7.05 (m, 2H), 7.18-7.27 (m, 3H), 7.59 (quintet, 1H), 8.40 (d, 1H), 8.60 (d, 1H). |

[1]) prepared from Example 119A, (enantiomer B)
[2]) The starting materials were dissolved in diethyl ether to form a 0.5 M solution.
[3]) The starting materials were dissolved in 1,4-dioxane to form a 0.2-0.5 M solution.
[4]) The reaction time was 2.5 h.

Example 29 ent-N-(2-Aminopropyl)-6-chloro-8-[(2,6-difluorobenzyl)oxy]-2-methylimidazo[1,2-a]pyridine-3-carboxamide (Enantiomer A)

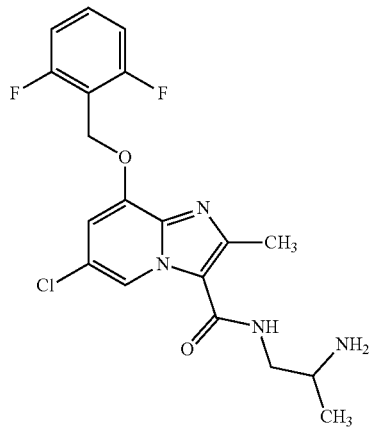 [SMILES: Cc1nc2c(OCc3c(F)cccc3F)cc(Cl)cn2c1C(=O)NCC(C)N]

68 mg of Example 23 were separated into the enantiomers by two preparative separations on a chiral phase:
1) Column: Daicel Chiralpak AD-H, 5 μm, 250×20 mm, mobile phase: 60% isohexane, 40% ethanol+0.2% diethylamine, flow rate: 15 ml/min; 30° C., detection: 220 nm.
2) Column: Daicel Chiralpak AD-H, 5 μm, 250×20 mm, mobile phase: 60% isohexane, 40% isopropanol+0.2% diethylamine, flow rate: 15 ml/min; 30° C., detection: 220 nm.

Enantiomer A:
Yield: 21 mg (99% ee)
$R_t$=10.15 min [Chiralpak AY-H, 5 m, 250×4.6 mm; mobile phase: 80% isohexane, 20% ethanol+0.2% diethylamine; flow rate 1.0 ml/min; 40° C.; detection: 220 nm].

Example 30 ent-N-(2-Aminopropyl)-6-chloro-8-[(2,6-difluorobenzyl)oxy]-2-methylimidazo[1,2-a]pyridine-3-carboxamide (Enantiomer B)

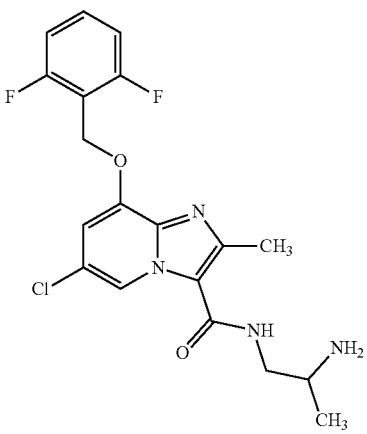 [SMILES: Cc1nc2c(OCc3c(F)cccc3F)cc(Cl)cn2c1C(=O)NCC(C)N]

68 mg of Example 23 were separated into the enantiomers by two preparative separations on a chiral phase:
1) Column: Daicel Chiralpak AD-H, 5 μm, 250×20 mm, mobile phase: 60% isohexane, 40% ethanol+0.2% diethylamine, flow rate: 15 ml/min; 30° C., detection: 220 nm.
2) Column: Daicel Chiralpak AD-H, 5 μm, 250×20 mm, mobile phase: 60% isohexane, 40% isopropanol+0.2% diethylamine, flow rate: 15 ml/min; 30° C., detection: 220 nm.

Enantiomer B:
Yield: 21 mg (95% ee)
$R_t$=9.31 min [Chiralpak AY-H, 5 μm, 250×4.6 mm; mobile phase: 80% isohexane, 20% ethanol+0.2% diethylamine; flow rate 1.0 ml/min; 40° C.; detection: 220 nm].

Example 31 ent-N-(2-Aminopropyl)-8-[(2,6-difluorobenzyl)oxy]-
2,6-dimethylimidazo[1,2-a]pyridine-3-carboxamide
(Enantiomer A)

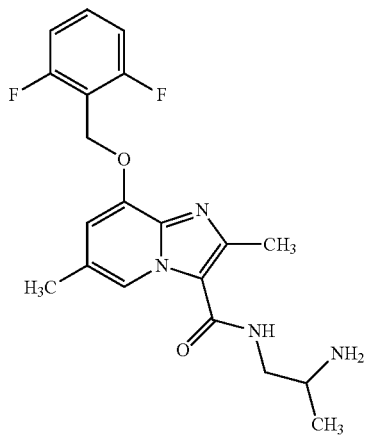

47 mg of Example 25 were separated into the enantiomers by two preparative separations on a chiral phase:
1) Column: Daicel Chiralpak AD-H, 5 μm, 250×20 mm, mobile phase: 50% isohexane, 50% ethanol+0.2% diethylamine, flow rate: 15 ml/min; 40° C., detection: 220 nm.
2) Column: Daicel Chiralpak AD-H, 5 μm, 250×20 mm, mobile phase: 50% isohexane, 50% isopropanol+0.2% diethylamine, flow rate: 15 ml/min; 40° C., detection: 220 nm.

Enantiomer A: Yield: 13 mg (99% ee)

$R_t$=7.00 min [Chiralpak AY-H, 5 μm, 250×4.6 mm; mobile phase: 70% isohexane, 30% ethanol+0.2% diethylamine; flow rate 1.0 ml/min; 40° C.; detection: 220 nm].

Example 32 ent-N-(2-Aminopropyl)-8-[(2,6-difluorobenzyl)oxy]-
2,6-dimethylimidazo[1,2-a]pyridine-3-carboxamide
(Enantiomer B)

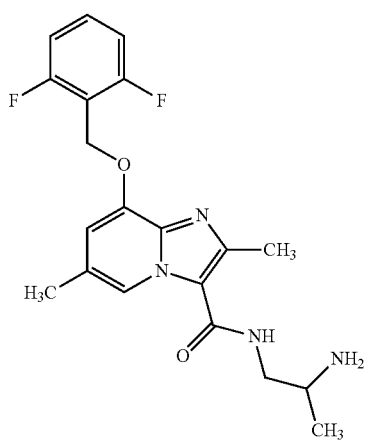 [SMILES: Cc1cc(OCc2c(F)cccc2F)c2nc(C)c(C(=O)NCC(C)N)n2c1]

47 mg of Example 25 were separated into the enantiomers by two preparative separations on a chiral phase:

1) Column: Daicel Chiralpak AD-H, 5 μm, 250×20 mm, mobile phase: 50% isohexane, 50% ethanol+0.2% diethylamine, flow rate: 15 ml/min; 40° C., detection: 220 nm.
2) Column: Daicel Chiralpak AD-H, 5 μm, 250×20 mm, mobile phase: 50% isohexane, 50% isopropanol+0.2% diethylamine, flow rate: 15 ml/min; 40° C., detection: 220 nm.

Enantiomer B:
Yield: 14 mg (97% ee)

$R_t$=6.27 min [Chiralpak AY-H, 5 μm, 250×4.6 mm; mobile phase: 70% isohexane, 30% ethanol+0.2% diethylamine; flow rate 1.0 ml/min; 40° C.; detection: 220 nm].

Example 33

N-[2-(1-Aminocyclohexyl)ethyl]-6-chloro-8-[(2,6-difluorobenzyl)oxy]-2-methylimidazo[1,2-a]-pyridine-3-carboxamide

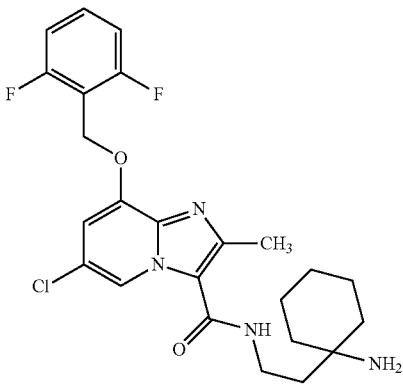 [SMILES: Cc1nc2c(OCc3c(F)cccc3F)cc(Cl)cn2c1C(=O)NCCC1(N)CCCCC1]

99 mg of rac-tert-butyl (1-{2-[({6-chloro-8-[(2,6-difluorobenzyl)oxy]-2-methylimidazo[1,2-a]-pyridin-3-yl}carbonyl)amino]ethyl}cyclohexyl)carbamate trifluoroacetate (Example 93A, 0.14 mmol) were suspended in 0.67 ml of diethyl ether, 0.72 ml of a 2 M solution of hydrochloric acid in diethyl ether (1.43 mmol) were added and the mixture was stirred at RT overnight. The precipitate was filtered off and washed with diethyl ether, and ethyl acetate and saturated aqueous sodium bicarbonate solution were added. After phase separation, the aqueous phase was extracted twice with ethyl acetate and the combined organic phases dried over sodium sulphate. The mixture was then filtered and the filtrate was concentrated and lyophilized. This gave 61 mg of the title compound (89% of theory).

LC-MS (Method 2): $R_t$=0.80 min

MS (ESpos): m/z=477 (M+H)$^+$ $^1$H NMR (400 MHz, DMSO-d$_6$): δ=1.22-1.45 (m, 8H), 1.47-1.80 (m, 6H), 2.52 (s, 3H), 3.40 (t, 2H), 5.32 (s, 2H), 7.19 (s, 1H), 7.24 (t, 2H), 7.60 (quint, 1H), 8.55 (br s, 1H), 8.86 (s, 1H).

The examples shown in Table 4 were prepared analogously to Example 33 by reacting 10-20 equivalents of a 2 N solution of hydrochloric acid in diethyl ether with the corresponding N-Boc compounds under the reaction conditions described. The reaction times were 3 h-5 d.

If appropriate, the purifications were carried out by preparative HPLC (RP18 column, mobile phase: acetonitrile/water gradient with addition of 0.1% trifluoroacetic acid) and/or by silica gel chromatography (mobile phase gradient: dichloromethane/methanol). If appropriate, the product-containing fractions were concentrated and the residue was dissolved in ethyl acetate or dichloromethane/methanol and washed with a little saturated aqueous sodium bicarbonate solution. The organic phase was then dried over sodium sulphate and filtered and the filtrate was concentrated.

If appropriate, the reaction mixture was filtered off from the precipitate and the precipitate was washed with diethyl ether and dried under high vacuum.

If appropriate, the reaction mixture was diluted with diethyl ether, the precipitate was filtered off and ethyl acetate or dichloromethane and saturated aqueous sodium bicarbonate solution were added to the filtrate. The organic phase was washed with saturated aqueous sodium chloride solution, dried over sodium sulphate and filtered, and the filtrate was concentrated and dried under high vacuum.

TABLE 4

| Example | IUPAC name/structure (yield) | Analytical data |
|---|---|---|
| 34 | rac-N-(2-aminopropyl)-8-[(2,6-difluorobenzyl)oxy]-2-methylimidazo[1,2-a]pyridine-3-carboxamide dihydrochloride<br>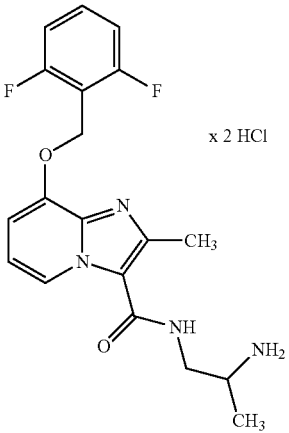<br>(85% of theory) | LC-MS (Method 7): $R_t$ = 0.48 min<br>MS (ESpos): m/z = 375 (M − 2HCl + H)$^+$<br>$^1$H NMR (400 MHz, DMSO-$d_6$):<br>δ = 1.24 (d, 3H), 2.62 (s, 3H), 3.31-3.56 (m, 3H), 5.32 (s, 2H), 7.21-7.32 (m, 3H), 7.45 (br s, 1H), 7.61 (quintet, 1H), 8.08 (br s, 3H), 8.54 (br s, 1H), 8.73 (d, 1H). |
| 35 | ent-N-[(2R)-2-aminobutyl]-6-chloro-8-[(2,6-difluorobenzyl)oxy]-2-methylimidazo[1,2-a]-pyridine-3-carboxamide<br>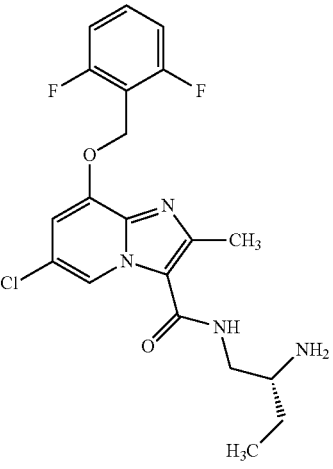<br>(96% of theory) | LC-MS (Method 2): $R_t$ = 0.72 min<br>MS (ESpos): m/z = 423 (M + H)$^+$<br>$^1$H NMR (400 MHz, DMSO-$d_6$):<br>δ = 0.90 (t, 3H), 1.18-1.30 (m, 1H), 1.39-1.75 (m, 3H), 2.49-2.59 (m, 4H), 2.69-2.77 (m, 1H), 3.07-3.16 (m, 1H), 5.33 (s, 2H), 7.19 (s, 1H), 7.24 (t, 2H), 7.60 (quintet, 1H), 7.83 (br s, 1H), 8.77 (s, 1H). |

TABLE 4-continued

| Example | IUPAC name/structure (yield) | Analytical data |
|---|---|---|
| 36 | N-(2-aminoethyl)-6-chloro-8-[(2,6-difluorobenzyl)oxy]-2-methylimidazo[1,2-a]pyridine-3-carboxamide<br>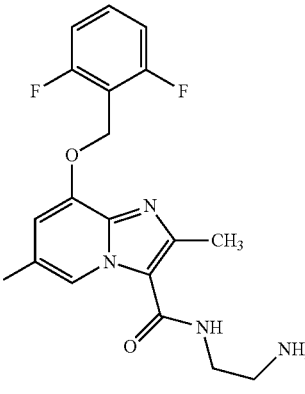<br>(98% of theory) | LC-MS (Method 2): $R_t$ = 0.68 min<br>MS (ESpos): m/z = 395 (M + H)$^+$<br>$^1$H NMR (400 MHz, DMSO-d$_6$):<br>δ = 2.50 (s, 3H), 2.73 (t, 2H), 3.32 (m, covered by the water signal, 2H), 5.33 (s, 2H), 7.19 (s, 1H), 7.24 (t, 2H), 7.60 (quintet, 1H), 7.90 (br s, 1H), 8.77 (s, 1H). |
| 37 | N-(3-aminopropyl)-6-chloro-8-[(2,6-difluorobenzyl)oxy]-2-methylimidazo[1,2-a]pyridine-3-carboxamide<br>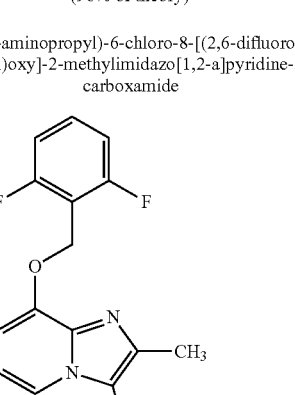<br>(70% of theory) | LC-MS (Method 2): $R_t$ = 0.68 min<br>MS (ESpos): m/z = 409 (M + H)$^+$<br>$^1$H NMR (400 MHz, DMSO-d$_6$):<br>δ = 1.62 (quintet, 2H), 2.52 (s, 3H), 2.63 (t, 2H), 3.32 (m, covered by the water signal, 2H), 5.32 (s, 2H), 7.19 (s, 1H), 7.24 (t, 2H), 7.61 (quintet, 1H), 8.10 (br s, 1H), 8.77 (s, 1H). |
| 38 | N-[(1-aminocyclopropyl)methyl]-8-[(2,6-difluorobenzyl)oxy]-2-methylimidazo[1,2-a]pyridine-3-carboxamide<br>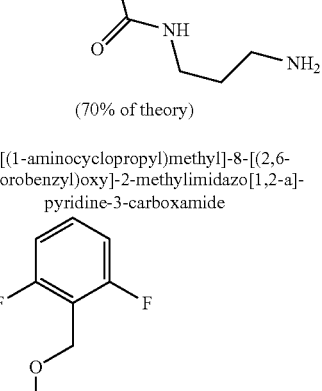<br>(69% of theory) | LC-MS (Method 7): $R_t$ = 0.49 min<br>MS (ESpos): m/z = 387 (M + H)$^+$<br>$^1$H NMR (400 MHz, DMSO-d$_6$):<br>δ = 0.42 (t, 2H), 0.54 (t, 2H), 1.94 (br s, 2H), 2.50 (s, 3H), 3.34 (d, 2H), 5.30 (s, 2H), 6.92 (t, 1H), 7.00 (d, 1H), 7.24 (t, 2H), 7.59 (quintet, 1H), 7.88 (t, 1H), 8.58 (d, 1H). |

TABLE 4-continued

| Example | IUPAC name/structure (yield) | Analytical data |
|---|---|---|
| 39 | N-[(1-aminocyclopropyl)methyl]-6-chloro-8-[(2,6-difluorobenzyl)oxy]-2-methylimidazo[1,2-a]pyridine-3-carboxamide<br>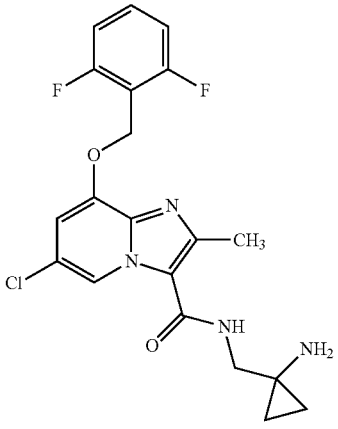<br>(90% of theory) | LC-MS (Method 2): $R_t$ = 0.76 min<br>MS (ESpos): m/z = 401 (M + H)$^+$<br>$^1$H NMR (400 MHz, DMSO-d$_6$):<br>δ = 0.44 (t, 2H), 0.55 (t, 2H), 1.98 (br s, 2H), 2.50 (s, 3H), 3.34 (d, 2H), 5.36 (s, 2H), 7.19 (s, 1H), 7.24 (t, 2H), 7.59 (quintet, 1H), 7.93 (t, 1H), 8.70 (s, 1H). |
| 40 | N-[(1-aminocyclopropyl)methyl]-8-[(2,6-difluorobenzyl)oxy]-2,6-dimethylimidazo[1,2-a]pyridine-3-carboxamide<br>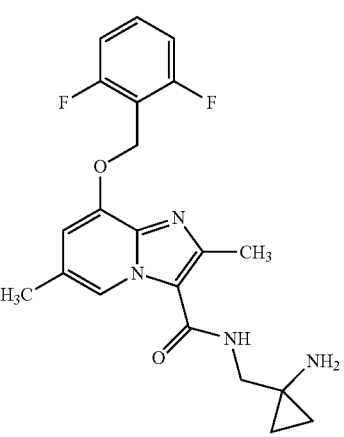<br>(76% of theory) | LC-MS (Method 2): $R_t$ = 0.60 min<br>MS (ESpos): m/z = 401 (M + H)$^+$<br>$^1$H NMR (400 MHz, DMSO-d$_6$):<br>δ = 0.44 (t, 2H), 0.54 (t, 2H), 1.98 (br s, 2H), 2.30 (s, 3H), 2.50 (s, 3H), 3.32 (d, covered by the water signal, 2H), 5.29 (s, 2H), 6.89 (s, 1H), 7.24 (t, 2H), 7.59 (quintet, 1H), 7.83 (t, 1H), 8.41 (s, 1H). |

TABLE 4-continued

| Example | IUPAC name/structure (yield) | Analytical data |
|---|---|---|
| 41 | N-[(1-aminocyclopentyl)methyl]-8-[(2,6-difluorobenzyl)oxy]-2-methylimidazo[1,2-a]-pyridine-3-carboxamide<br>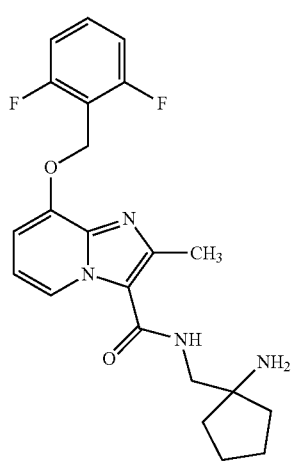<br>(77% of theory) | LC-MS (Method 7): $R_t$ = 0.54 min<br>MS (ESpos): m/z = 415 (M + H)$^+$<br>$^1$H NMR (400 MHz, DMSO-$d_6$):<br>δ =1.32-1.44 (m, 2H), 1.50-1.61 (m, 4H), 1.65-2.10 (m, 4H), 2.50 (s, 3H), 3.32 (d, covered by the water signal, 2H), 5.30 (s, 2H), 6.92 (t, 1H), 7.01 (d, 1H), 7.23 (t, 2H), 7.59 (quintet, 1H), 7.70-7.80 (m, 1H), 8.62 (d, 1H). |
| 42 | N-[(1-aminocyclopentyl)methyl]-6-chloro-8-[(2,6-difluorobenzyl)oxy]-2-methylimidazo[1,2-a]pyridine-3-carboxamide<br>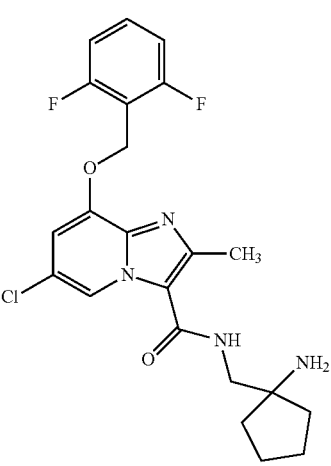<br>(93% of theory) | LC-MS (Method 7): $R_t$ = 0.73 min<br>MS (ESpos): m/z = 449 (M + H)$^+$<br>$^1$H NMR (400 MHz, DMSO-$d_6$):<br>δ = 1.32-1.45 (m, 2H), 1.50-1.80 (m, 8H), 2.50 (s, 3H), 3.32 (d, covered by the water signal, 2H), 5.33 (s, 2H), 7.19 (s, 1H), 7.24 (t, 2H), 7.60 (quintet, 1H), 7.69 (br s, 1H), 8.75 (s, 1H). |

Example 43 rac-N-[2-Amino-1-(4-chlorophenyl)ethyl]-8-(cyclohexylmethoxy)-2-methylimidazo[1,2-a]-pyridine-3-carboxamide

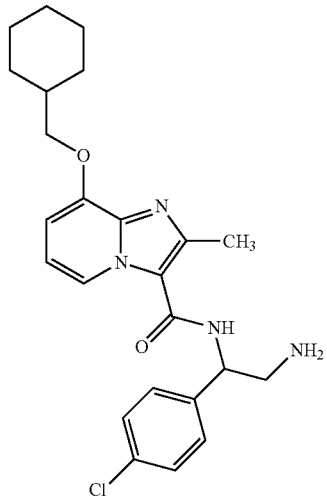 [SMILES: Cc1nc2c(OCC3CCCCC3)cccn2c1C(=O)NC(CN)c1ccc(Cl)cc1]

2 ml of 2 M hydrochloric acid in diethyl ether (4.0 mmol) were added to 107 mg of Example 83A (0.16 mmol), and the mixture was stirred at RT overnight. The precipitate was filtered off, washed with diethyl ether, dissolved in dichloromethane containing a little methanol, washed twice with saturated aqueous sodium bicarbonate solution and finally with water. The organic phase was dried over sodium sulphate, filtered, concentrated and lyophilized. This gave 61 mg of the title compound (85% of theory).

LC-MS (Method 2): $R_t$=0.80 min

MS (ESpos): m/z=441 (M+H)$^+$ $^1$H NMR (400 MHz, DMSO-$d_6$): δ=1.02-1.14 (m, 2H), 1.16-1.38 (m, 3H), 1.48-1.89 (m, 8H), 2.62 (s, 3H), 2.84-2.92 (m, 2H), 3.93 (d, 2H), 4.91-4.99 (m, 1H), 6.78 (d, 1H), 6.82 (t, 1H), 7.38-7.44 (m, 4H), 8.19 (br s, 1H), 8.46 (d, 1H).

Example 44 rac-N-(2-Amino-1-phenylethyl)-8-(cyclohexylmethoxy)-2-methylimidazo[1,2-a]pyridine-3-carboxamide

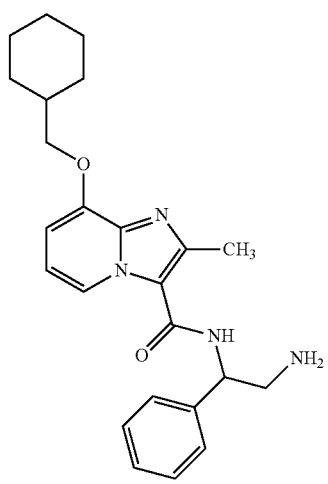 [SMILES: Cc1nc2c(OCC3CCCCC3)cccn2c1C(=O)NC(CN)c1ccccc1]

2 ml of 2 M hydrochloric acid in diethyl ether (4.0 mmol) were added to 70 mg of Example 82A (0.1 mmol), and the mixture was stirred at RT overnight. The precipitate was filtered off, washed with diethyl ether, dissolved in a mixture of dichloromethane and a little methanol, washed twice with saturated aqueous sodium bicarbonate solution and finally with water. The organic phase was dried over sodium sulphate, filtered, concentrated and lyophilized. The product fractions were purified by thick-layer chromatography (mobile phase: toluene/methanol=10/1). This gave 31 mg of the title compound (73% of theory).

LC-MS (Method 7): $R_t$=0.68 min

MS (ESpos): m/z=407 (M+H)$^+$ $^1$H NMR (400 MHz, DMSO-$d_6$): δ=1.03-1.14 (m, 2H), 1.16-1.37 (m, 3H), 1.63-2.20 (m, 8H), 2.63 (s, 3H), 2.85-2.94 (m, 2H), 3.94 (d, 2H), 4.93-5.03 (m, 1H), 6.78 (d, 1H), 6.84 (t, 1H), 7.20-7.27 (m, 1H), 7.30-7.44 (m, 4H), 8.19 (br s, 1H), 8.48 (d, 1H).

Example 45 ent-N-[2-Amino-1-(2,4-difluorophenyl)ethyl]-8-(cyclohexylmethoxy)-2-methylimidazo[1,2-a]-pyridine-3-carboxamide

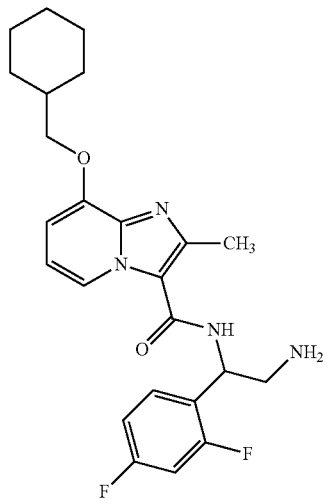 [SMILES: Cc1nc2c(OCC3CCCCC3)cccn2c1C(=O)NC(CN)c1ccc(F)cc1F]

0.27 ml of 2M hydrochloric acid in diethyl ether (0.53 mmol) were added to 35 mg of Example 85A (0.05 mmol), and the mixture was stirred at RT overnight. The precipitate was filtered off, washed with diethyl ether, dissolved in ethyl acetate and washed twice with saturated aqueous sodium bicarbonate solution. The organic phase was dried over sodium sulphate, filtered and the filtrate was concentrated and lyophilized. This gave 23 mg of the title compound (93% of theory).

LC-MS (Method 7): $R_t$=0.73 min

MS (ESpos): m/z=443 (M+H)$^+$ $^1$H NMR (400 MHz, DMSO-$d_6$): δ=1.02-1.13 (m, 2H), 1.14-1.36 (m, 3H), 1.63-1.99 (m, 8H), 2.62 (s, 3H), 2.83-2.94 (m, 2H), 3.95 (d, 2H), 5.18-5.23 (m, 1H), 6.78 (d, 1H), 6.83 (t, 1H), 7.07-7.12 (m, 1H), 7.18-7.26 (m, 1H), 7.50 (q, 1H), 8.12-8.28 (m, 1H), 8.47 (d, 1H).

Example 46 rac-N-[2-Amino-1-(3,4-difluorophenyl)ethyl]-8-(cyclohexylmethoxy)-2-methylimidazo[1,2-a]-pyridine-3-carboxamide

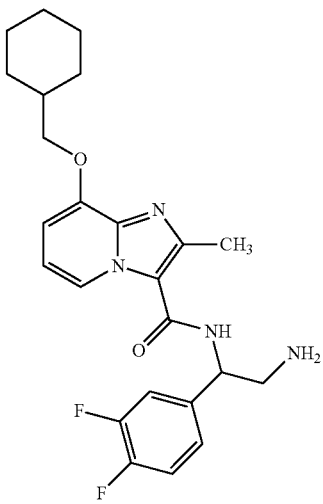 [SMILES: Cc1nc2c(OCC3CCCCC3)cccn2c1C(=O)NC(CN)c1ccc(F)c(F)c1]

1.5 ml of 2 M hydrochloric acid in diethyl ether (3.0 mmol) were added to 198 mg of Example 84A (0.30 mmol), and the mixture was stirred at RT overnight. The precipitate was filtered off, washed thoroughly with diethyl ether, dissolved in ethyl acetate and washed twice with saturated aqueous sodium bicarbonate solution. The organic phase was dried over sodium sulphate and filtered and the filtrate was concentrated and lyophilized. This gave 119 mg of the title compound (89% of theory).

LC-MS (Method 1): $R_t$=1.04 min
MS (ESpos): m/z=443 (M+H)$^+$
$^1$H NMR (400 MHz, DMSO-d$_6$): δ=1.02-1.13 (m, 2H), 1.14-1.34 (m, 3H), 1.50-1.90 (m, 8H), 2.62 (s, 3H), 2.85-2.94 (m, 2H), 3.95 (d, 2H), 4.92-4.99 (m, 1H), 6.79 (d, 1H), 6.83 (t, 1H), 7.20-7.28 (m, 1H), 7.36-7.49 (m, 2H), 8.16 (br s, 1H), 8.48 (d, 1H).

Example 47 ent-8-[(2,6-Difluorobenzyl)oxy]-N-(2,3-dihydro-1H-indol-3-yl)-2-methylimidazo[1,2-a]pyridine-3-carboxamide (Enantiomer B)

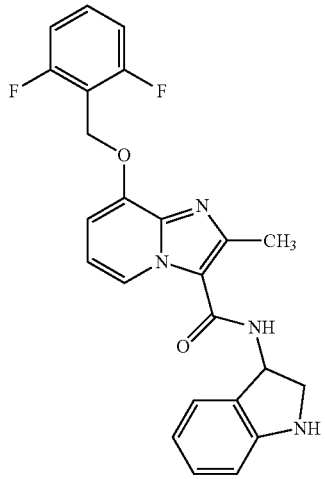 [SMILES: Cc1nc2c(OCc3c(F)cccc3F)cccn2c1C(=O)NC1CNc2ccccc21]

299 mg of Example 28 (69 mmol) were separated into the enantiomers by preparative separation on a chiral phase [column: Daicel Chiralpak IA, 5 µm, 250×20 mm, mobile phase: 40% acetonitrile, 60% methanol, flow rate: 20 ml/min; 25° C., detection: 230 nm]. The product fractions were dissolved in acetonitrile/water and lyophilized.
Enantiomer B:
Yield: 91 mg (99% ee)
$R_t$=4.87 min [Chiralpak IA, 5 m, 250×4.6 mm; mobile phase: 50% acetonitrile, 50% methanol; flow rate 1.0 ml/min; 30° C.; detection: 220 nm].

Example 48 ent-N-(1-Aminopropan-2-yl)-8-[(2,6-difluorobenzyl)oxy]-2,6-dimethylimidazo[1,2-a]pyridine-3-carboxamide

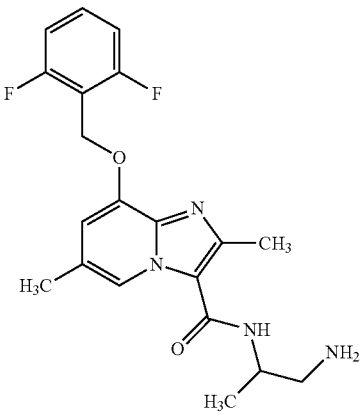 [SMILES: Cc1cc(OCc2c(F)cccc2F)c2nc(C)c(C(=O)NC(C)CN)n2c1]

48 mg of ent-tert-butyl {2-[({8-[(2,6-difluorobenzyl)oxy]-2,6-dimethylimidazo[1,2-a]pyridin-3-yl}carbonyl)

amino]propyl}carbamate (Example 121A—enantiomer A, 0.1 mmol) were dissolved in 2.4 ml of diethyl ether, 0.49 ml of 2 M hydrochloric acid in diethyl ether (0.98 mmol) was added and the mixture was stirred at RT overnight. Another 0.25 ml of 2 M hydrochloric acid in diethyl ether was added, and the reaction solution was stirred at RT overnight. The mixture was then concentrated and the residue was dissolved in dichloromethane and washed with saturated aqueous sodium bicarbonate solution. The organic phase was concentrated. This gave 36 mg of the title compound (92% of theory).

LC-MS (Method 1): $R_t$=0.71 min

MS (ESpos): m/z=389 (M+H)$^+$ $^1$H NMR (400 MHz, DMSO-$d_6$): δ=1.28 (d, 3H), 2.38 (s, 3H), 2.59 (s, 3H), 2.94-3.07 (m, 2H), 4.30 (quintet, 1H), 5.37 (s, 2H), 7.05-7.40 (m, 3H), 7.61 (quintet, 1H), 8.09 (br s, 3H), 8.51 (s, 1H).

Example 49 rac-6-Chloro-8-[(2,6-difluorobenzyl)oxy]-N-(2,3-dihydro-1H-indol-3-yl)-2-methylimidazo[1,2-a]-pyridine-3-carboxamide

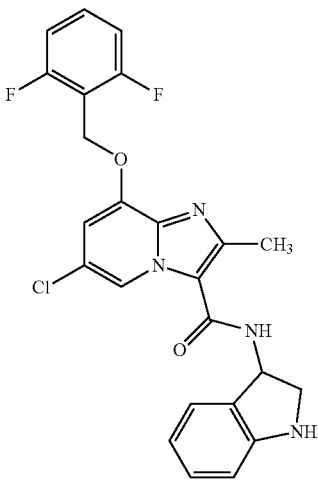 [SMILES: Cc1nc2c(OCc3c(F)cccc3F)cc(Cl)cn2c1C(=O)NC1CNc2ccccc21]

141 mg of rac-tert-butyl 3-[({6-chloro-8-[(2,6-difluorobenzyl)oxy]-2-methylimidazo[1,2-a]pyridin-3-yl}carbonyl)amino]indolin-1-carboxylate (Example 104A, 0.25 mmol) were dissolved in 1.2 ml of diethyl ether, 1.24 ml of a 2 M solution of hydrochloric acid in diethyl ether (2.48 mmol) were added and the mixture was stirred at RT overnight. 1.24 ml of a 2 M solution of hydrochloric acid in diethyl ether (2.48 mmol) were then added, and the mixture was stirred at RT for 3 d. 1.24 ml of a 2 M solution of hydrochloric acid in diethyl ether (2.48 mmol) were then added a little at a time and the mixture was stirred under reflux for 4 h (with additional diethyl ether and hydrochloric acid in diethyl ether being added a little at a time!). The precipitate was filtered off and washed thoroughly with diethyl ether, and ethyl acetate and saturated aqueous sodium bicarbonate solution were then added. After phase separation, the aqueous phase was extracted twice with ethyl acetate.

The combined organic phases were dried over sodium sulphate and filtered, and the filtrate was concentrated and lyophilized. This gave 93 mg of the title compound (80% of theory).

LC-MS (Method 2): $R_t$=1.02 min

MS (ESpos): m/z=469 (M+H)$^+$ $^1$H NMR (400 MHz, DMSO-$d_6$): δ=2.49 (s, 3H), 3.31-3.40 (m, 1H), 3.73-3.81 (m, 1H), 5.33 (s, 2H), 5.61 (q, 1H), 5.68 (s, 1H), 6.56-6.63 (m, 2H), 7.02 (t, 1H), 7.18-7.28 (m, 4H), 7.60 (quintet, 1H), 8.50 (d, 1H), 8.71 (s, 1H).

Example 50 rac-8-[(2,6-Difluorobenzyl)oxy]-2-methyl-N-(1,2,3,4-tetrahydroquinolin-4-yl)imidazo[2-a]-pyridine-3-carboxamide

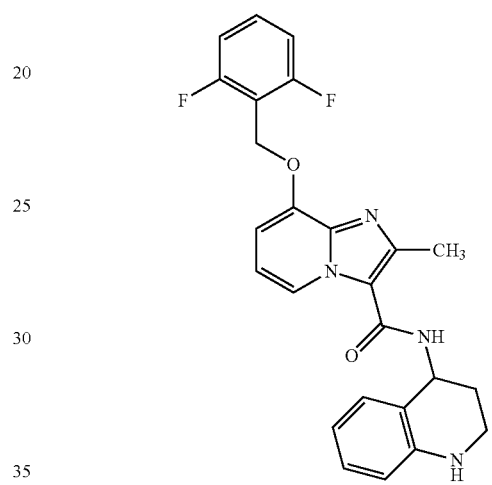

229 mg of rac-tert-butyl 4-[({8-[(2,6-difluorobenzyl)oxy]-2-methylimidazo[1,2-a]pyridin-3-yl}-carbonyl) amino]-3,4-dihydroquinoline-1(2H)-carboxylate (Example 105A, 0.41 mmol) were dissolved in 10 ml of diethyl ether, 2.05 ml of a 2 M solution of hydrochloric acid in diethyl ether (4.09 mmol) were added and the mixture was stirred at RT overnight. Another 1.02 ml of a 2 M solution of hydrochloric acid in diethyl ether were then added, and the mixture was stirred at RT overnight. A little diethyl ether was added to the reaction mixture and the solid obtained was filtered off and washed with diethyl ether. The solid was dissolved in dichloromethane containing a little methanol and washed with saturated aqueous sodium bicarbonate solution. The organic phase was concentrated. The crude product was purified by preparative HPLC (RP18 column, mobile phase: methanol/water gradient with addition of 0.1% TFA). The product fractions were concentrated, taken up in dichloromethane and washed with saturated aqueous sodium bicarbonate solution. The organic phase was dried over sodium sulphate, filtered and concentrated. This gave 140 mg of the title compound (75% of theory).

LC-MS (Method 2): $R_t$=0.83 min

MS (ESpos): m/z=449 (M+H)$^+$ $^1$H NMR (400 MHz, DMSO-$d_6$): δ=1.92-2.05 (m, 2H), 2.50 (s, 3H), 3.20-3.29 (m, 2H), 5.20 (q, 1H), 5.31 (s, 2H), 5.87 (s, 1H), 6.46-6.54 (m, 2H), 6.89-6.94 (m, 2H), 7.00 (d, 1H), 7.10 (d, 1H), 7.23 (t, 2H), 7.59 (quintet, 1H), 8.27 (d, 1H), 8.58 (d, 1H).

Example 51 ent-N-[2-Amino-1-(3,4-difluorophenyl)ethyl]-8-[(2,6-difluorobenzyl)oxy]-2,6-dimethylimidazo-[1,2-a]pyridine-3-carboxamide

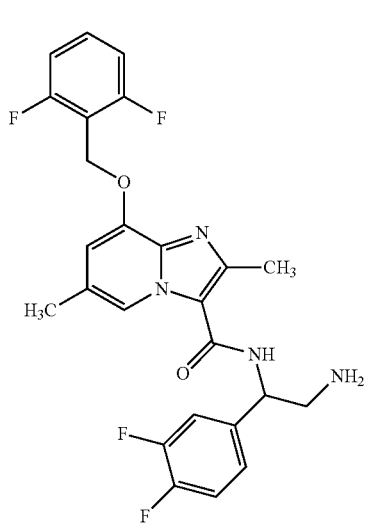 [SMILES: Cc1cc(OCc2c(F)cccc2F)c2nc(C)c(C(=O)NC(CN)c3ccc(F)c(F)c3)n2c1]

120 mg of ent-tert-butyl {2-[({8-[(2,6-difluorobenzyl)oxy]-2,6-dimethylimidazo[1,2-a]pyridin-3-yl}carbonyl)amino]-2-(3,4-difluorophenyl)ethyl}carbamate (Example 107A, 0.20 mmol) were dissolved in 2 ml of diethyl ether, 1 ml of a 2 M solution of hydrochloric acid in diethyl ether were added and the mixture was stirred at RT overnight. Another 1 ml of a 2 M solution of hydrochloric acid in diethyl ether was then added, and the mixture was stirred at RT overnight. The reaction mixture was filtered off and washed with diethyl ether. The solid was dissolved in dichloromethane containing a little methanol and washed with saturated aqueous sodium bicarbonate solution. The organic phase was concentrated. The crude product was purified by preparative HPLC (RP 18 column, mobile phase: acetonitrile/water gradient with addition of 0.1% TFA). The product fractions were concentrated, taken up in dichloromethane and washed with saturated aqueous sodium bicarbonate solution. The organic phase was dried over sodium sulphate, filtered and concentrated. This gave 82 mg of the title compound (84% of theory).

LC-MS (Method 2): $R_t$=0.81 min

MS (ESpos): m/z=487 (M+H)$^+$ $^1$H NMR (400 MHz, DMSO-d$_6$): δ=2.29 (s, 3H), 2.52 (s, 3H), 2.88-3.00 (m, 2H), 4.93-5.05 (m, 1H), 5.29 (s, 2H), 6.90 (s, 1H), 7.19-7.28 (m, 3H), 7.36-7.49 (m, 2H), 7.59 (quintet, 1H), 8.17 (br s, 1H), 8.38 (s, 1H).

Example 52 ent-8-[(2,6-Difluorobenzyl)oxy]-2-methyl-N-(1,2,3,4-tetrahydroquinolin-4-yl)imidazo[1,2-a]-pyridine-3-carboxamide (Enantiomer B)

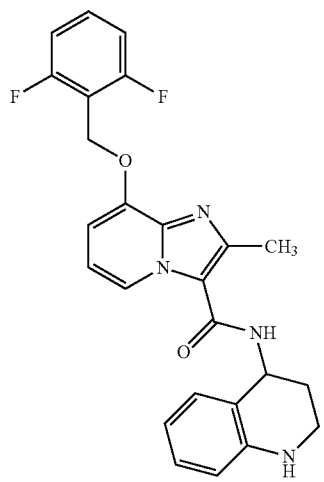 [SMILES: Cc1nc2c(OCc3c(F)cccc3F)cccn2c1C(=O)NC1CCNc2ccccc21]

132 mg of Example 50 were separated into the enantiomers by preparative separation on a chiral phase [column: Daicel Chiralpak AY-H, 5 μm, 250×20 mm, mobile phase: 50% isohexane, 50% ethanol+0.2% diethylamine, flow rate: 15 ml/min; 45° C., detection: 220 nm].

Enantiomer B:

Yield: 64 mg (99% ee)

$R_t$=8.05 min [Daicel Chiralpak AY-H, 5 m, 250×4.6 mm; mobile phase: 50% isohexane, 50% ethanol+0.2% diethylamine; flow rate 1.0 ml/min; 40° C.; detection: 220 nm].

Example 53 ent-N-[2-Amino-1-(3,4-difluorophenyl)ethyl]-8-[(2,6-difluorobenzyl)oxy]-6-fluoro-2-methylimidazo[1,2-a]pyridine-3-carboxamide

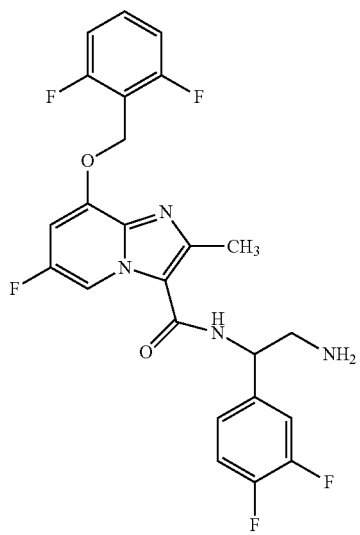 [SMILES: Cc1nc2c(OCc3c(F)cccc3F)cc(F)cn2c1C(=O)NC(CN)c1ccc(F)c(F)c1]

12.5 ml of a 2 M solution of hydrochloric acid in diethyl ether were added to 148 mg of ent-tert-butyl {2-[({8-[(2,6-difluorobenzyl)oxy]-6-fluoro-2-methylimidazo[1,2-a]pyridin-3-yl}carbonyl)-amino]-2-(3,4-difluorophenyl)ethyl}carbamate (Example 106A; 0.251 mmol), and the mixture was stirred at RT overnight. The reaction precipitate was filtered off, washed with diethyl ether, taken up in ethyl acetate and washed with saturated aqueous sodium bicarbonate solution. The combined organic phases were dried over magnesium sulphate and concentrated. The residue was dissolved in methanol and purified by preparative HPLC (Method 9). This gave 63 mg (51% of theory) of the title compound.

LC-MS (Method 2): $R_t$=0.87 min
MS (ESpos): m/z=491.1 (M+H)$^+$
$^1$H NMR (400 MHz, DMSO-d$_6$): δ=1.61 (br. s, 2H), 2.58 (s, 3H), 3.38-3.42 (d, 2H), 4.91 (t, 1H); 5.32 (s, 2H); 7.20-7.26 (m, 4H); 7.34-7.46 (m, 2H); 7.59 (quint, 1H), 8.21 (br. s, 1H), 8.61 (d, 1H).

The examples shown in Table 5 were prepared analogously to Example 53.

TABLE 5

| Example | IUPAC name/structure (yield) | Analytical data |
|---|---|---|
| 54 | ent-N-[2-amino-1-(3,4-difluorophenyl)ethyl]-2-cyclopropyl-8-[(2,6-difluorobenzyl)oxy]-imidazo[1,2-a]pyridine-3-carboxamide<br />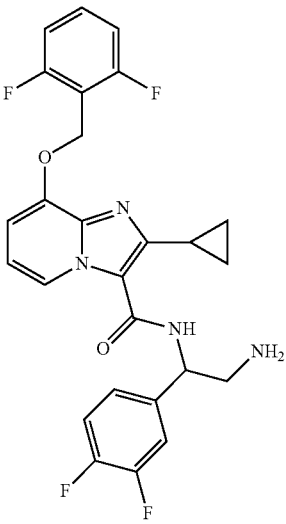<br />(46% of theory) | $^1$H NMR (400 MHz, DMSO-d$_6$): δ = 0.86-1.08 (m, 4H), 2.38-2.46 (m, 1H); 3.12-3.26 (m, 2H); 5.28 (m, 1H); 5.30 (2, 2H); 6.92 (t, 1H); 7.02 (d, 1H); 7.23 (t, 2H); 7.29-7.34 (m, 1H); 7.43-7.62 (m, 3H); 8.53 (br. s, 1H); 8.56 (d, 1H). |

TABLE 5-continued

| Example | IUPAC name/structure (yield) | Analytical data |
|---|---|---|
| 55 | ent-N-[2-amino-1-(3,4-difluorophenyl)ethyl]-8-[(2,6-difluorobenzyl)oxy]imidazo[1,2-a]pyridine-3-carboxamide dihydrochloride<br><br>(95% of theory) | LC-MS (Method 2): $R_t$ = 0.84 min<br>MS (ESpos): m/z = 459.3 (M + H)$^+$<br>$^1$H NMR (400 MHz, DMSO-d$_6$):<br>δ = 3.29-3.35 (m, 2H), 5.38 (m, 1H),<br>5.41 (s, 2H), 7.20-7.38 (m, 4H);<br>7.40-7.48 (m, 2H), 7.55-7.66 (m,<br>2H), 8.30 (br.s, 2H); 8.90 (br. s, 1H),<br>9.12 (d, 1H), 9.70 (br.s, 1H). |
| 56 | ent-N-(1-amino-3-ethoxypropan-2-yl)-8-[(2,6-difluorobenzyl)oxy]-2-methylimidazo[1,2-a]-pyridine-3-carboxamide (enantiomer A)<br><br>(40% of theory) | LC-MS (Method 2): $R_t$ = 0.59 min<br>MS (ESpos): m/z = 419.3 (M + H)$^+$<br>$^1$H NMR (400 MHz, DMSO-d$_6$):<br>δ = 1.10 (t, 3H); 2.55 (s, 3H; obscured by DMSO signal), 2.95-3.12 (m, 2H);<br>3.47-3.58 (m, 4H); 4.41 (m, 1H);<br>5.32 (s, 2H), 6.95-7.10 (m, 2H);<br>7.21 (t, 2H); 7.59 (q, 1H); 7.80 (br. s. 1H); 7.91 (br. s., 2H); 8.60 (d, 1H). |

TABLE 5-continued

| Example | IUPAC name/structure (yield) | Analytical data |
|---|---|---|
| 57 | ent-N-(1-amino-3-ethoxypropan-2-yl)-6-chloro-8-[(2,6-difluorobenzyl)oxy]-2-methylimidazo[1,2-a]pyridine-3-carboxamide (enantiomer B)<br>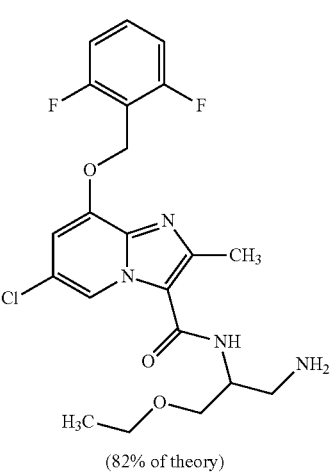 [SMILES: CCOCC(CN)NC(=O)c1c(C)nc2c(OCc3c(F)cccc3F)cc(Cl)cn12]<br>(82% of theory) | LC-MS (Method 2): $R_t$ = 0.73 min<br>MS (ESpos): m/z = 453.3 (M + H)$^+$<br>$^1$H NMR (400 MHz, DMSO-d$_6$):<br>δ = 1.10 (t, 3H); 1.72 (br. s, 2H), 2.55 (s, 3H; superimposed by DMSO signal), 2.71 (d, 2H), 3.48-3.53 (m, 4H); 4.08 (m, 1H), 5.32 (s, 2H), 7.14 (s, 1H); 7.21 (t, 2H), 7.59 (quint, 1H), 7.63 (br.s, 1H); 8.66 (s, 1H). |
| 58 | rac-N-[1-amino-3-(4-fluorophenoxy)propan-2-yl]-8-[(2,6-difluorobenzyl)oxy]-2-methylimidazo[1,2-a]pyridine-3-carboxamide<br>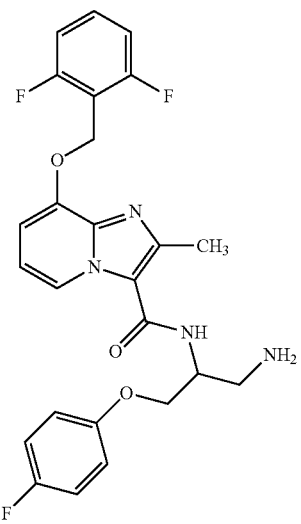<br>(68% of theory) | LC-MS (Method 2): $R_t$ = 0.72 min<br>MS (ESpos): m/z = 485.3 (M + H)$^+$<br>$^1$H NMR (400 MHz, DMSO-d$_6$):<br>δ = 2.55 (s, 3H; obscured by DMSO signal), 2.85-2.90 (d, 2H), 4.05-4.15 (m, 2H), 4.31 (m, 1H), 5.30 (s, 2H), 6.90 (t, 1H), 6.95-7.00 (m, 3H), 7.10 (t, 2H), 7.21 (t, 2H); 7.59 (q, 1H), 7.80 (br. s. 1H), 8.60 (d, 1H). |

TABLE 5-continued

| Example | IUPAC name/structure (yield) | Analytical data |
|---|---|---|
| 59 | rac-N-(1-amino-3-phenoxypropan-2-yl)-8-[(2,6-difluorobenzyl)oxy]-2-methylimidazo[1,2-a]-pyridine-3-carboxamide dihydrochloride<br>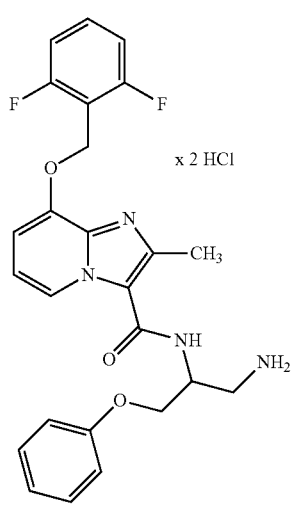<br>(100% of theory) | LC-MS (Method 2): $R_t$ = 0.70 min<br>MS (ESpos): m/z = 467.3 (M + H)$^+$<br>$^1$H NMR (400 MHz, DMSO-$d_6$):<br>δ = 2.60 (s, 3H), 3.10-3.30 (m, 2H), 4.20 (d, 2H), 4.65 (m, 1H), 5.40 (s, 2H), 6.95-7.00 (m, 3H), 7.20 (t, 2H), 7.26 (m, 1H), 7.28 (t, 2H), 7.42 (br. s. 1H), 7.59 (q, 1H), 8.10 (br. s, 3H), 8.58 (br. s, 1H), 8.70 (d, 1H). |
| 60 | 8-[(2,6-difluorobenzyl)oxy]-2-methyl-N-[(3S)-piperidin-3-yl]imidazo[1,2-a]pyridine-3-carboxamide dihydrochloride<br>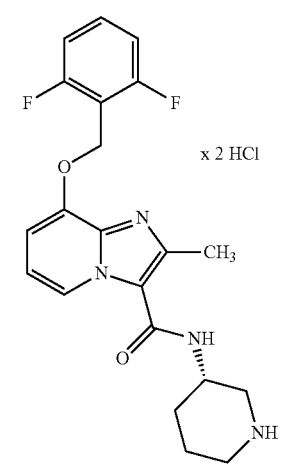<br>(99% of theory) | LC-MS (Method 2): $R_t$ = 0.53 min<br>MS (ESpos): m/z = 401.3 (M + H)$^+$<br>$^1$H NMR (400 MHz, DMSO-$d_6$):<br>δ = 1.63-1.80 (m, 2H); 1.90-2.00 (m, 2H); 2.61 (s, 3H); 2.85-2.98 (m, 2H); 3.20-3.25 (m, 2H); 4.20-4.30 (m, 1H); 5.40 (s, 2H); 7.23 (t, 2H); 7.30 (br. s, 1H); 7.56 (br. s, 1H); 7.60 (quint, 1H), 8.65 (d, 1H); 8.72 (br. s, 1H); 9.02 (br. s, 1H); 9.30 (br. s, 1H). |

Example 61

8-[(2,6-Difluorobenzyl)oxy]-2-methyl-N-[(3S)-pyrrolidin-3-yl]imidazo[1,2-a]pyridine-3-carboxamide

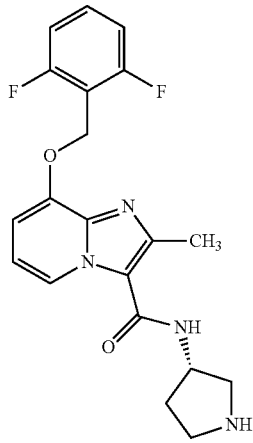 [SMILES: Cc1nc2c(OCc3c(F)cccc3F)cccn2c1C(=O)N[C@H]1CCNC1]

130 mg of benzyl (3S)-3-[({8-[(2,6-difluorobenzyl)oxy]-2-methylimidazo[1,2-a]pyridin-3-yl}-carbonyl)amino]pyrrolidine-1-carboxylate (Example 115A; 0.250 mmol) were initially charged in 60 ml of ethanol, 17.5 mg 20% palladium-(II) hydroxide (0.025 mmol, 0.1 equivalents) were added and the mixture was hydrogenated under hydrogen standard pressure for two hours. The reaction mixture was filtered and concentrated and the residue was purified by preparative HPLC. This gave 42 mg (44% of theory) of the title compound.

LC-MS (Method 2): $R_t$=0.50 min

MS (ESpos): m/z=387.2 (M+H)$^+$ $^1$H NMR (400 MHz, DMSO-$d_6$): δ=1.60-1.70 (m, 1H); 1.95-2.05 (m, 1H); 2.55 (s, 3H; superimposed by DMSO signal); 2.61-2.80 (m, 2H); 2.88-3.03 (m, 2H); 4.28-4.37 (m, 1H); 5.30 (s, 2H); 6.90 (t, 1H); 6.99 (d, 1H); 7.21 (t, 2H); 7.60 (q 1H); 7.81 (d, 1H); 8.51 (d, 1H).

Example 62 ent-N-[2-Amino-2-(3,4-difluorophenyl)ethyl]-8-[(2,6-difluorobenzyl)oxy]-2-methylimidazo[1,2-a]-pyridine-3-carboxamide

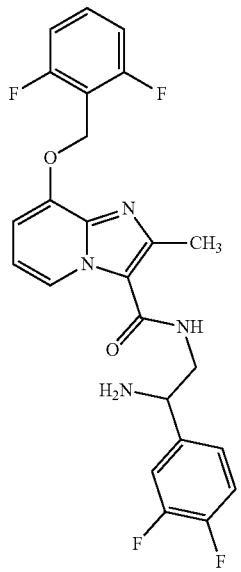 [SMILES: Cc1nc2c(OCc3c(F)cccc3F)cccn2c1C(=O)NCC(N)c1ccc(F)c(F)c1]

160 mg of ent-benzyl {2-[({8-[(2,6-difluorobenzyl)oxy]-2-methylimidazo[1,2-a]pyridin-3-yl}-carbonyl)amino]-1-(3,4-difluorophenyl)ethyl}carbamate (intermediate 117A; 0.264 mmol) were initially charged in 150 ml of ethanol, 100 mg of 10% palladium on activated carbon were added and the mixture was hydrogenated under hydrogen standard pressure for two hours. The reaction mixture was filtered and the filtrate was concentrated. This gave 123 mg (99% of theory) of the title compound.

LC-MS (Method 2): $R_t$=0.67 min

MS (ESpos): m/z=373.3 (M+H)$^+$ $^1$H NMR (400 MHz, DMSO-$d_6$): δ=2.33 (s, 3H); 3.40-3.51 (m, 2H); 4.08 (t, 1H); 5.30 (s, 2H); 6.88 (t, 1H); 7.00 (d, 1H); 7.19-7.24 (m, 3H); 7.32 (q, 1H); 7.48 (dd, 1H); 7.56 (q, 1H); 7.80 (t, 1H); 8.51 (d, 1H).

Example 63 rac-N-(1-Amino-3-isopropoxypropan-2-yl)-8-[(2,6-difluorobenzyl)oxy]-2-methylimidazo[1,2-a]-pyridine-3-carboxamide

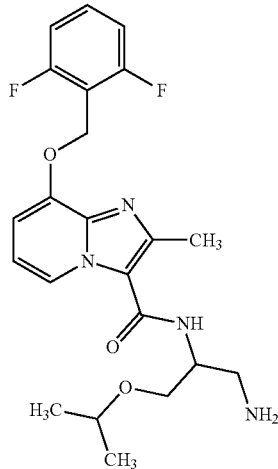 [SMILES: Cc1nc2c(OCc3c(F)cccc3F)cccn2c1C(=O)NC(CN)COC(C)C]

305 mg of rac-benzyl {2-[({8-[(2,6-difluorobenzyl)oxy]-2-methylimidazo[1,2-a]pyridin-3-yl}-carbonyl)amino]-3-isopropoxypropyl}carbamate (intermediate 116A; 0.54 mmol) were initially charged in 46 ml of ethanol, 44 mg of 10% palladium on activated carbon were added and the mixture was hydrogenated under hydrogen standard pressure for 4 hours. The reaction mixture was filtered and concentrated and the residue was purified by preparative HPLC (column: Macherey-Nagel VP 50/21 Nucleodur 100-5 C18 HTEC, 50×21 mm; mobile phase: gradient with 0.1% strength aqueous ammonia solution and methanol). This gave 127 mg of the title compound (54% of theory).

LC-MS (Method 2): $R_t$=0.59 min

MS (ESpos): m/z=433.2 (M+H)$^+$ $^1$H NMR (400 MHz, DMSO-$d_6$): δ=1.10 (d, 6H), 1.74 (br. s, 2H), 2.54 (s, 3H; superimposed by DMSO signal), 2.72 (d, 2H), 3.49 (d, 2H), 3.58 (q, 1H), 3.99 (m, 1H), 5.30 (s, 2H), 6.93 (t, 1H), 7.00 (d, 1H), 7.23 (t, 2H), 7.53 (br. s, 1H), 7.59 (q, 1H), 8.60 (d, 1H).

Example 64 ent-8-[(2,6-Difluorobenzyl)oxy]-2-methyl-N-[(2R)-1-(Morpholin-4-yl)hexan-2-yl]imidazo[1,2-a]-pyridine-3-carboxamide

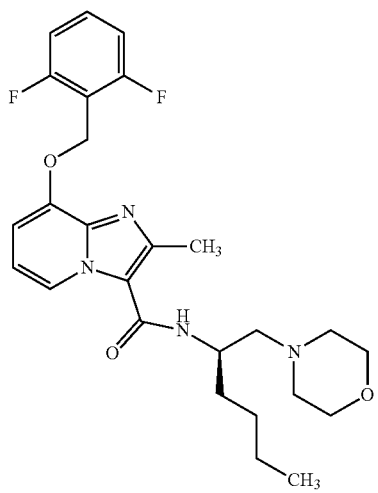 [SMILES: CCCC[C@H](CN1CCOCC1)NC(=O)c1c(C)nc2c(OCc3c(F)cccc3F)cccn12]

59 mg of 8-[(2,6-difluorobenzyl)oxy]-2-methyl-N-[(2R)-1-oxohexan-2-yl]imidazo[1,2-a]pyridine-3-carboxamide (0.12 mmol, 1 equivalent) were suspended in 0.6 ml of dichloromethane, 13.3 μl of morpholine (0.132 mmol, 1.1 equivalents) were added and the mixture was stirred at RT for 3 h. 35.7 mg of sodium triacetoxyborohydride (0.168 mmol, 1.4 equivalents) were added, and the reaction mixture was stirred at RT overnight. 1 N aqueous aqueous sodium hydroxide solution were added, and the reaction mixture was extracted three times with dichloromethane. The combined organic phases were washed with saturated aqueous sodium chloride solution, dried over magnesium sulphate, filtered and concentrated. The residue obtained was dissolved in methanol and purified by preparative HPLC (Method 9). 22.4 mg (36% of theory) of the desired compound were concentrated as a glass-like solid.

LC-MS (Method 2): $R_t$=0.81

MS (ESpos): m/z=487.4 (M+H)$^+$ $^1$H NMR (400 MHz, DMSO-d$_6$): δ=0.88 (t, 3H), 1.20-1.62 (m, 6H), 2.30-2.40 (m, 2H), 2.54 (s+m, 3+4H, obscured by DMSO signal), 3.50-3.60 (m, 4H), 4.13-4.24 (m, 1H), 5.31 (s, 2H), 6.92 (t, 1H), 6.99 (d, 1H), 7.23 (t, 2H), 7.59 (q, 1H), 7.63 (d, 1H), 8.50 (d, 1H).

The examples shown in Table 6 were prepared analogously to Example 64.

TABLE 6

| Example | IUPAC name/structure (yield) | Analytical data |
|---|---|---|
| 65 | ent-8-[(2,6-difluorobenzyl)oxy]-2-methyl-N-[(2R)-1-(piperidin-1-yl)hexan-2-yl]imidazo[1,2-a]-pyridine-3-carboxamide<br><br>(17% of theory) | LC-MS (Method 2): $R_t$ = 0.53 min<br>MS (ESpos): m/z = 401.3 (M + H)$^+$<br>$^1$H NMR (400 MHz, DMSO-d$_6$):<br>δ = 0.88 (t, 3H), 1.20-1.62 (m, 12H), 2.20-2.54 (m, 6H), 2.54 (s, 3H, obscured by DMSO signal), 4.11-4.24 (m, 1H), 5.30 (s, 2H), 6.91 (t, 1H), 6.98 (d, 1H), 7.21 (t, 2H), 7.57 (q, 1H), 7.61 (d, 1H), 8.51 (d, 1H). |

TABLE 6-continued

| Example | IUPAC name/structure (yield) | Analytical data |
|---|---|---|
| 66 | ent-8-[(2,6-difluorobenzyl)oxy]-2-methyl-N-[(2R)-1-(pyrrolidin-1-yl)hexan-2-yl]imidazo[1,2-a]-pyridine-3-carboxamide<br><br>(31% of theory)<br>addition of the reducing agent after 10 min. | LC-MS (Method 5): $R_t$ = 1.52 min<br>MS (ESpos): m/z = 471.3 (M + H)$^+$<br>1H NMR (400 MHz, DMSO-d6):<br>δ = 0.88 (t, 3H), 1.20-1.72 (m, 10H), 2.40-2.60 (m, 9H: partially obscured by DMSO signal), 4.06-4.18 (m, 1H), 5.30 (s, 2H), 6.90 (t, 1H), 6.98 (d, 1H), 7.21 (t, 2H), 7.58 (q, 1H), 7.63 (d, 1H), 8.50 (d, 1H). |
| 67 | ent-8-[(2,6-difluorobenzyl)oxy]-2-methyl-N-[(2R)-1-(4-methylpiperazin-1-yl)hexan-2-yl]imidazo[1,2-a]pyridine-3-carboxamide<br><br>(24% of theory)<br>use of dichloromethane as solvent instead of dimethylformamide | LC-MS (Method 2): Rt = 0.78 min<br>MS (ESpos): m/z = 500.4 (M + H)+<br>1H NMR (400 MHz, DMSO-d6):<br>δ = 0.90 (t, 3H), 1.35-1.62 (m, 6H), 2.10 (s, 3H), 2.20-2.55 (m, 10H: partially obscured by DMSO signal), 2.56 (s, 3H), 4.10-4.21 (m, 1H), 5.30 (s, 2H), 6.90 (t, 1H), 6.98 (d, 1H), 7.21 (t, 2H), 7.58 (q, 1H), 7.63 (d, 1H), 8.50 (d, 1H). |

TABLE 6-continued

| Example | IUPAC name/structure (yield) | Analytical data |
|---|---|---|
| 68 | ent-8-[(2,6-difluorobenzyl)oxy]-N-[(2R)-1-(dimethylamino)hexan-2-yl]-2-methylimidazo[1,2-a]pyridine-3-carboxamide<br><br>(30% of theory)<br>use of 1,2-dichloroethane as solvent instead of dimethylformamide | LC-MS (Method 2): $R_t$ = 0.79 min<br>MS (ESpos): m/z = 445.4 (M + H)$^+$<br>1H NMR (400 MHz, DMSO-d$_6$):<br>δ = 0.88 (t, 3H), 1.25-1.65 (m, 6H), 2.18 (s, 6H), 2.20 (dd, 1H), 2.40 (dd, 1H), 2.56 (s, 3H, obscured by DMSO signal), 4.05-4.18 (m, 1H), 5.30 (s, 2H), 6.90 (t, 1H), 6.98 (d, 1H), 7.21 (t, 2H), 7.58 (q, 2H), 8.50 (d, 1H). |
| 69 | ent-N-[(2R)-1-(diethylamino)hexan-2-yl]-8-[(2,6-difluorobenzyl)oxy]-2-methylimidazo[1,2-a]-pyridine-3-carboxamide<br><br>(19% of theory) | LC-MS (Method 2): $R_t$ = 0.85 min<br>MS (ESpos): m/z = 473.4 (M + H)$^+$<br>1H NMR (400 MHz, DMSO-d$_6$):<br>δ = 0.88 (t, 3H), 0.95 (t, 6H), 1.35-1.70 (m, 6H), 2.40 (dd, 1H), 2.49-2.53 (m, 5H, superimposed by DMSO signal), 2.56 (s, 3H), 4.02-4.12 (m, 1H), 5.30 (s, 2H), 6.90 (t, 1H), 6.98 (d, 1H), 7.21 (t, 2H), 7.55-7.62 (m, 2H), 8.52 (d, 1H). |

TABLE 6-continued

| Example | IUPAC name/structure (yield) | Analytical data |
|---|---|---|
| 70 | ent-8-[(2,6-difluorobenzyl)oxy]-N-{(2R)-1-[(2-methoxyethyl)amino]hexan-2-yl}-2-methylimidazo[1,2-a]pyridine-3-carboxamide 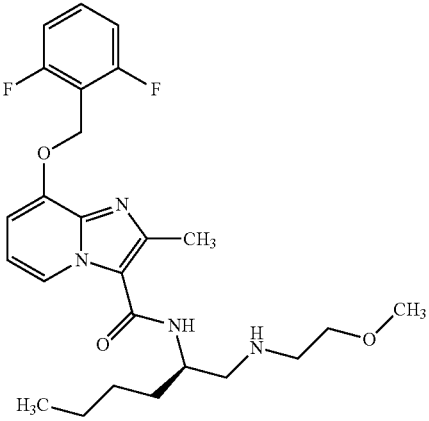 (35% of theory) use of dichloromethane as solvent instead of dimethylformamide | LC-MS (Method 2): $R_t$ = 0.81 min<br>MS (ESpos): m/z = 475.4 (M + H)$^+$<br>1H NMR (400 MHz, DMSO-$d_6$):<br>δ = 0.87 (t, 3H), 1.25-1.68 (m, 6H),<br>2.56 (s, 3H, superimposed by DMSO signal), 2.60-2.78 (m, 4H), 3.33 (t, 2H),<br>4.02-4.12 (m, 1H), 5.30 (s, 2H),<br>6.90 (t, 1H), 6.98 (d, 1H), 7.21 (t, 2H),<br>7.55-7.62 (m, 2H), 8.51 (d, 1H). |

Example 71

8-[(2,6-Difluorobenzyl)oxy]-N-(9-ethyl-9-azabicyclo[3.3.1]non-3-yl)-2-methylimidazo[1,2-a]-pyridine-3-carboxamide

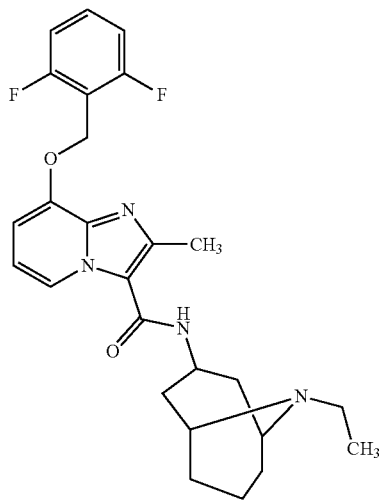 [SMILES: CCN1C2CCCC1CC(NC(=O)c1c(C)nc3c(OCc4c(F)cccc4F)cccn13)C2]

60 mg of N-(9-azabicyclo[3.3.1]non-3-yl)-8-[(2,6-difluorobenzyl)oxy]-2-methylimidazo[1,2-a]-pyridine-3-carboxamide (Example 27, 0.14 mmol) were initially charged in 1.4 ml of abs. THF, 4.2 mg of sodium hydride (purity 95%, 0.16 mmol) were added and the mixture was stirred at RT for 15 min. 0.011 ml of iodoethane (0.14 mmol) were then added dropwise, and the mixture was stirred at RT overnight. The reaction mixture was diluted with ethyl acetate and washed twice with water. The organic phase was washed with saturated aqueous sodium chloride solution, dried over sodium sulphate and filtered. The filtrate was concentrated and dried. The crude product was purified by preparative HPLC (RP 18 column, mobile phase: acetonitrile/water gradient with addition of 0.1% TFA). The product-containing fractions were concentrated and the residue taken up in ethyl acetate and washed with saturated aqueous sodium bicarbonate solution. The organic phase was dried over sodium sulphate and filtered and the filtrate was concentrated and lyophilized. This gave 35 mg of the title compound (55% of theory).

LC-MS (Method 2): $R_t$=0.68 min

MS (ESpos): m/z=469 (M+H)$^+$ $^1$H NMR (400 MHz, DMSO-$d_6$): δ=0.97 (t, 3H), 1.50 (d, 2H), 1.60-1.97 (m, 8H), 2.50 (s, 3H), 2.69 (q, 2H), 2.96 (s, 2H), 4.63-4.79 (m, 1H), 5.30 (s, 2H), 6.91 (t, 1H), 6.99 (d, 1H), 7.23 (t, 2H), 7.59 (quintet, 1H), 7.71 (d, 1H), 8.52 (d, 1H).

Example 72

N-(2-Amino-2-methylpropyl)-8-[(2,6-difluorobenzyl)oxy]-2-methylimidazo[1,2-a]pyridine-3-carboxamide

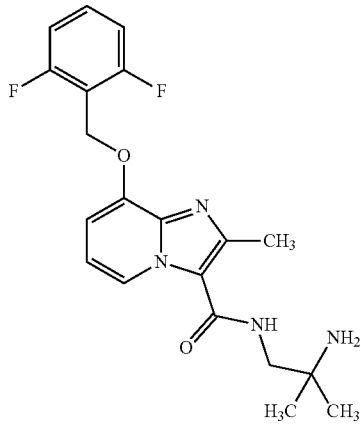 [SMILES: Cc1nc2c(OCc3c(F)cccc3F)cccn2c1C(=O)NCC(C)(C)N]

100 mg of 8-[(2,6-difluorobenzyl)oxy]-2-methylimidazo[1,2-a]pyridine-3-carboxylic acid (0.31 mmol), 151 mg of (benzotriazol-1-yloxy)bisdimethylaminomethylium fluoroborate (TBTU, 0.47 mmol) and 127 mg of 4-methylmorpholine (1.26 mmol) were initially charged in 2 ml of DMF. 55 mg of 2-methylpropane-1,2-diamine (0.63 mmol) were then added, and the mixture was stirred at RT overnight. The reaction solution was purified by preparative HPLC (RP18 column, mobile phase: acetonitrile/water gradient with addition of 0.1% TFA). The crude product was taken up in ethyl acetate and washed twice with saturated aqueous sodium bicarbonate solution. The aqueous phase was extracted twice with ethyl acetate and the combined organic phases were dried over sodium sulphate. The mixture was then filtered and the filtrate was concentrated and lyophilized. This gave 80 mg of the title compound (66% of theory).

LC-MS (Method 2): $R_t$=0.55 min
MS (ESpos): m/z=389 (M+H)$^+$
$^1$H NMR (400 MHz, DMSO-d$_6$): δ=1.08 (s, 6H), 2.00 (br s, 2H), 2.52 (s, 3H), 3.22 (d, 2H), 5.30 (s, 2H), 6.91 (t, 1H), 7.01 (d, 1H), 7.23 (t, 2H), 7.59 (quintet, 1H), 7.74 (br s, 1H), 8.64 (d, 1H).

Example 73

N-(2-Amino-2-methylpropyl)-6-chloro-8-[(2,6-difluorobenzyl)oxy]-2-methylimidazo[1,2-a]-pyridine-3-carboxamide

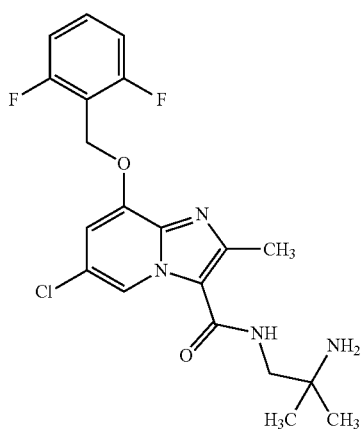 [SMILES: Cc1nc2c(OCc3c(F)cccc3F)cc(Cl)cn2c1C(=O)NCC(C)(C)N]

70 mg of 6-chloro-8-[(2,6-difluorobenzyl)oxy]-2-methylimidazo[1,2-a]pyridine-3-carboxylic acid (0.20 mmol), 96 mg (benzotriazol-1-yloxy)bisdimethylaminomethylium fluoroborate (TBTU, 0.30 mmol) and 80 mg of 4-methylmorpholine (0.79 mmol) were initially charged in 1 ml of DMF. 35 mg of 2-methylpropane-1,2-diamine (0.40 mmol) were then added, and the mixture was stirred at RT overnight. The reaction solution was purified by preparative HPLC (RP18 column, mobile phase: acetonitrile/water gradient with addition of 0.1% TFA). The product was taken up in ethyl acetate and washed twice with saturated aqueous sodium bicarbonate solution. The aqueous phase was extracted twice with ethyl acetate, the combined organic phases were dried over sodium sulphate and filtered. The filtrate was concentrated and lyophilized. This gave 38 mg of the title compound (45% of theory).

LC-MS (Method 1): $R_t$=0.88 min
MS (ESpos): m/z=423 (M+H)$^+$
$^1$H NMR (400 MHz, DMSO-d$_6$): δ=1.05 (s, 6H), 2.04 (br s, 2H), 2.50 (s, 3H), 3.22 (d, 2H), 5.35 (s, 2H), 7.20 (d, 1H), 7.24 (t, 2H), 7.61 (quintet, 1H), 7.80 (br s, 1H), 8.75 (d, 1H).

Example 74

N-(2-Amino-2-methylpropyl)-8-[(2,6-difluorobenzyl)oxy]-2,6-dimethylimidazo[1,2-a]pyridine-3-carboxamide

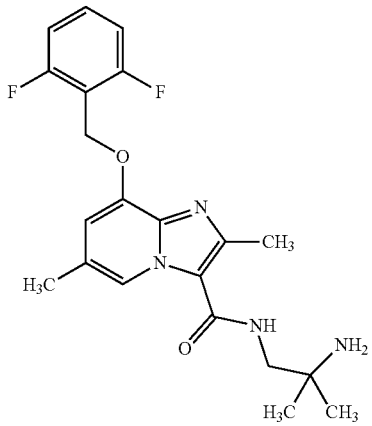 [SMILES: Cc1cc(OCc2c(F)cccc2F)c2nc(C)c(C(=O)NCC(C)(C)N)n2c1]

100 mg of 8-[(2,6-difluorobenzyl)oxy]-2,6-dimethylimidazo[1,2-a]pyridine-3-carboxylic acid (0.30 mmol), 145 mg of (benzotriazol-1-yloxy)bisdimethylaminomethylium fluoroborate (TBTU, 0.45 mmol) and 122 mg of 4-methylmorpholine (1.20 mmol) were initially charged in 1.9 ml of DMF. 53 mg of 2-methylpropane-1,2-diamine (0.60 mmol) were then added, and the mixture was stirred at RT overnight. The reaction solution was purified by preparative HPLC (RP18 column, mobile phase: acetonitrile/water gradient with addition of 0.1% TFA). The product fractions were taken up in dichloromethane and washed with saturated aqueous sodium bicarbonate solution. The aqueous phase was extracted twice with dichloromethane. The combined organic phases were dried over sodium sulphate, filtered, concentrated and lyophilized. This gave 94 mg of the title compound (78% of theory).

LC-MS (Method 2): $R_t$=0.61 min
MS (ESpos): m/z=403 (M+H)$^+$
$^1$H NMR (400 MHz, DMSO-d$_6$): δ=1.05 (s, 6H), 1.53 (br s, 2H), 2.31 (s, 3H), 2.52 (s, 3H), 3.20 (d, 2H), 5.29 (s, 2H), 6.91 (s, 1H), 7.24 (t, 2H), 7.59 (quintet, 1H), 7.64-7.72 (m, 1H), 8.47 (s, 1H).

Example 75 rac-8-[(2,6-Difluorobenzyl)oxy]-2-methyl-N-(1,2,3,4-tetrahydroquinolin-3-yl)imidazo[1,2-a]-pyridine-3-carboxamide

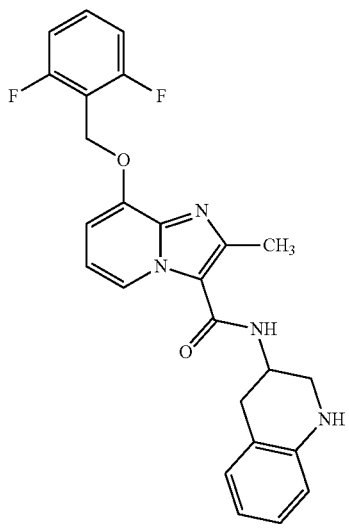 [SMILES: Cc1nc2c(OCc3c(F)cccc3F)cccn2c1C(=O)NC1CNc2ccccc2C1]

70 mg of 8-[(2,6-difluorobenzyl)oxy]-2-methylimidazo[1,2-a]pyridine-3-carboxylic acid (0.22 mmol), 54 mg of (benzotriazol-1-yloxy)bisdimethylaminomethylium fluoroborate (TBTU, 0.26 mmol) and 133 mg of 4-methylmorpholine (1.32 mmol) were initially charged in 1.5 ml of dichloromethane. After 10 min at RT, 53 mg of 1,2,3,4-tetrahydroquinoline-3-amine (0.24 mmol) were added, and the mixture was stirred at RT overnight. About 5 ml of water were added, the reaction solution was stirred for another 30 min and the resulting precipitate was filtered off, washed thoroughly with water and dried under high vacuum. The crude product was purified by preparative thin-layer chromatography (dichloromethane/methanol 20:1). This gave 52 mg of the title compound (52% of theory).

LC-MS (Method 2): $R_t$=0.88 min

MS (ESpos): m/z=449 (M+H)$^+$ $^1$H NMR (400 MHz, DMSO-d$_6$): δ=2.39 (s, 3H), 2.79-2.88 (m, 1H), 2.91-2.99 (m, 1H), 3.09-3.18 (m, 1H), 3.32-3.40 (m, 1H), 4.21-4.30 (m, 1H), 5.30 (s, 2H), 5.70 (s, 1H), 6.47 (t, 1H), 6.51 (d, 1H), 6.90 (d, 2H), 6.93 (t, 1H), 7.01 (d, 1H), 7.23 (t, 2H), 7.59 (quintet, 1H), 7.63 (d, 1H), 8.61 (d, 1H).

The examples shown in Table 7 were prepared analogously to Example 75 by reacting the appropriate carboxylic acid with the appropriate commercially available amines under the reaction conditions described in the Representative Working Procedure 2.

TABLE 7

| Example | IUPAC name/structure (yield) | Analytical data |
|---|---|---|
| 76 | rac-8-[(2,6-difluorobenzyl)oxy]-2,6-dimethyl-N-(1,2,3,4-tetrahydroquinolin-3-yl)imidazo[1,2-a]-pyridine-3-carboxamide<br><br>(80% of theory) | LC-MS (Method 2): $R_t$ = 0.90 min<br>MS (ESpos): m/z = 463 (M + H)$^+$<br>$^1$H NMR (400 MHz, DMSO-d$_6$):<br>δ = 2.32 (s, 3H), 2.38 (s, 3H), 2.79-2.88 (m, 1H), 2.91-2.99 (m, 1H), 3.09-3.18 (m, 1H), 3.32-3.40 (m, 1H), 4.20-4.29 (m, 1H), 5.28 (s, 2H), 5.80 (s, 1H), 6.48 (t, 1H), 6.52 (d, 1H), 6.86-6.92 (m, 3H), 7.23 (t, 2H), 7.55-7.64 (m, 2H), 8.42 (s, 1H). |

TABLE 7-continued

| Example | IUPAC name/structure (yield) | Analytical data |
|---|---|---|
| 77 | rac-8-[(2,6-difluorobenzyl)oxy]-2,6-dimethyl-N-[1-(1-methylpiperidin-4-yl)ethyl]imidazo[1,2-a]pyridine-3-carboxamide<br>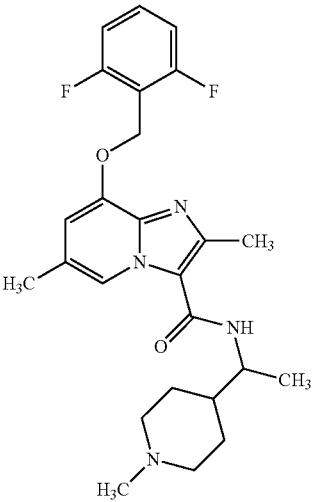<br>(80% of theory) | LC-MS (Method 5): $R_t$ = 1.28 min<br>MS (ESpos): m/z = 457 (M + H)$^+$<br>$^1$H NMR (400 MHz, DMSO-d$_6$):<br>δ = 1.14 (d, 3H), 1.21-1.48 (m, 3H), 1.73 (t, 2H), 2.00 (br s, 2H), 2.27 (br s, 3H), 2.30 (s, 3H), 2.48 (s, 3H), 2.85-2.98 (m, 2H), 3.91 (sextet, 1H), 5.28 (s, 2H), 6.88 (s, 1H), 7.23 (t, 2H), 7.59 (quintet, 1H), 7.68 (d, 1H), 8.31 (s, 1H). |
| 78 | rac-6-chloro-8-[(2,6-difluorobenzyl)oxy]-2-methyl-N-[1-(1-methylpiperidin-4-yl)ethyl]-imidazo[1,2-a]pyridine-3-carboxamide<br>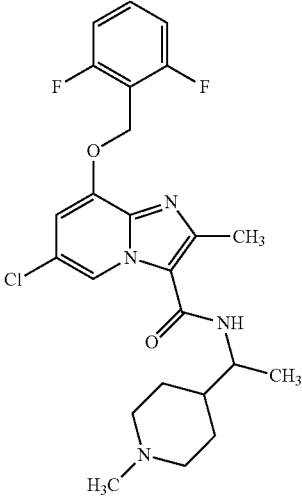<br>(98% of theory) | LC-MS (Method 2): $R_t$ = 0.70 min<br>MS (ESpos): m/z = 477 (M + H)$^+$<br>$^1$H NMR (400 MHz, DMSO-d$_6$):<br>δ = 1.14 (d, 3H), 1.16-1.44 (m, 3H), 1.60-1.86 (m, 4H), 2.14 (s, 3H), 2.50 (s, 3H), 2.79 (d, 2H), 3.91 (sextet, 1H), 5.34 (s, 2H), 7.18 (s, 1H), 7.22 (t, 2H), 7.60 (quintet, 1H), 7.69 (d, 1H), 8.61 (s, 1H). |

TABLE 7-continued

| Example | IUPAC name/structure (yield) | Analytical data |
|---|---|---|
| 79 | 8-[(2,6-difluorobenzyl)oxy]-N-{2-[(4-fluorophenyl)amino]ethyl}-2-methylimidazo[1,2-a]pyridine-3-carboxamide<br><br>(53% of theory) | LC-MS (Method 2): $R_t$ = 0.88 min<br>MS (ESpos): m/z = 455 (M + H)$^+$<br>$^1$H NMR (400 MHz, DMSO-d$_6$):<br>δ = 2.50 (s, 3H), 3.20 (q, 2H), 3.47 (q, 2H), 5.30 (s, 2H), 5.69 (t, 1H), 6.60 (dd, 2H), 6.88-6.97 (m, 3H), 7.02 (d, 1H), 7.23 (t, 2H), 7.59 (quintet, 1H), 7.88 (t, 1H), 8.68 (d, 1H). |
| 80 | rac-8-[(2,6-difluorobenzyl)oxy]-2-methyl-N-(1,2,3,4-tetrahydroisoquinolin-1-ylmethyl)-imidazo[1,2-a]pyridine-3-carboxamide$^{a)}$<br><br>(28% of theory) | LC-MS (Method 2): $R_t$ = 0.70 min<br>MS (ESpos): m/z = 463 (M + H)$^+$<br>$^1$H NMR (400 MHz, DMSO-d$_6$):<br>δ = 2.43 (s, 3H), 2.67-2.75 (m, 2H), 2.84-2.91 (m, 1H), 3.06-3.16 (m, 1H), 3.555-3.70 (m, 2H), 4.12 (dd, 1H), 5.29 (s, 2H), 6.91 (t, 1H), 7.02 (d, 1H), 7.07-7.18 (m, 3H), 7.19-7.28 (m, 3H), 7.59 (quintet, 1H), 7.69 (t, 1H), 8.70 (d, 1H). |

$^{a)}$There was a second chromatographic separation: [column: Sunfire C18, 5 μm, 250 × 20 mm, mobile phase: 60% water, 35% methanol + 5% 1% strength aqeous TFA soln., flow rate: 25 ml/min; 25° C., detection: 210 nm].

Example 81 ent-8-[(2,6-Difluorobenzyl)oxy]-2-methyl-N,N-(1,2,3,4-tetrahydroquinolin-3-yl)imidazo[1,2-a]-pyridine-3-carboxamide (Enantiomer A)

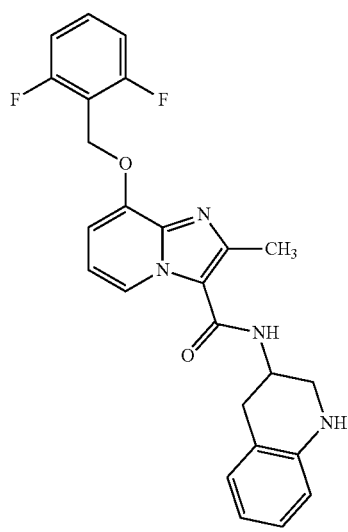 [SMILES: Cc1nc2c(OCc3c(F)cccc3F)cccn2c1C(=O)NC1CNc2ccccc2C1]

38 mg of Example 75 were separated into the enantiomers by preparative separation on a chiral phase [column: Daicel Chiralpak AY-H, 5 μm, 250×20 mm, mobile phase: 50% isohexane, 50% ethanol+0.2% diethylamine, flow rate: 15 ml/min; 40° C., detection: 220 nm].

Enantiomer A:

Yield: 18 mg (99% ee)

$R_t$=5.75 min [Daicel Chiralpak AY-H, 5 μm, 250×4.6 mm; mobile phase: 50% isohexane, 50% ethanol+0.2% diethylamine; flow rate 1.0 ml/min; 40° C.; detection: 220 nm].

Example 82

8-[(2,6-Difluorobenzyl)oxy]-2-methyl-N-(2,2,6,6-tetramethylpiperidin-4-yl)imidazo[1,2-a]-pyridine-3-carboxamide

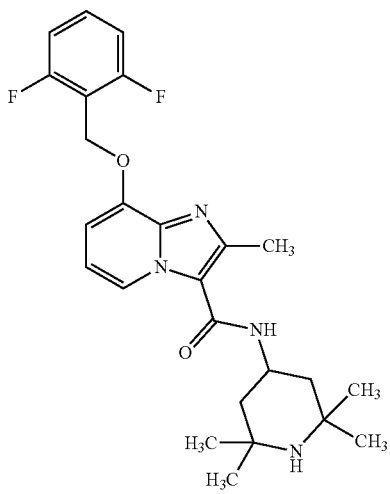 [SMILES: Cc1nc2c(OCc3c(F)cccc3F)cccn2c1C(=O)NC1CC(C)(C)NC(C)(C)C1]

18.8 mg (0.12 mmol) of 2,2,6,6-tetramethylpiperidine-4-amine were initially charged, and 32 mg (0.10 mmol) of 8-[(2,6-difluorobenzyl)oxy]-2-methylimidazo[1,2-a]pyridine-3-carboxylic acid in 0.4 ml of DMF and 42 mg (0.13 mmol) of (benzotriazol-1-yloxy)bisdimethylaminomethylium fluoroborate (TBTU) in 0.2 ml of DMF were added. 20 mg (0.20 mmol) of 4-methylmorpholine were then added, and the reaction was stirred at RT overnight. The mixture was then filtered off and the filtrate was purified by preparative LC-MS (Method 12). The product-containing fractions were concentrated under reduced pressure. This gave 27 mg (59% of theory) of the target product.

LC-MS (Method 8): $R_t$=0.69 min;

MS (ESIpos): m/z=457 (M+H)$^+$

The compounds listed in Table 8 were prepared analogously to Example 82.

TABLE 8
| Example | IUPAC name/structure (yield) | Analytical data |
|---|---|---|
| 83 | 8-[(2,6-difluorobenzyl)oxy]-2-methyl-N-(1,2,2,6,6-pentamethylpiperidin-4-yl)imidazo[1,2-a]pyridine-3-carboxamide 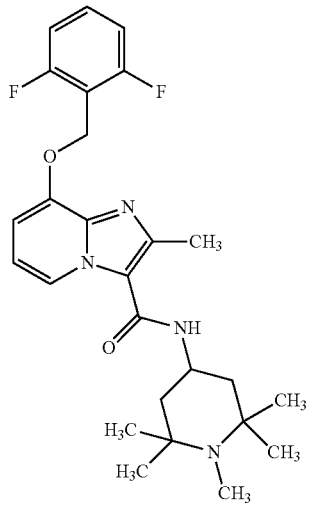 (45% of theory) | LC-MS (Method 8): $R_t$ = 0.69 min<br>MS (ESpos): m/z = 471 (M + H)$^+$ |
| 84 | rac-8-[(2,6-difluorobenzyl)oxy]-2-methyl-N-(1-methylpiperidin-3-yl)imidazo[1,2-a]-pyridine-3-carboxamide 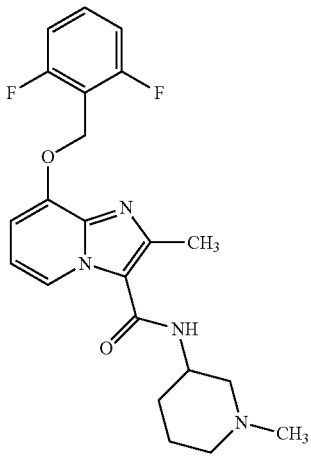 (48% of theory) | LC-MS (Method 8): $R_t$ = 0.64 min<br>MS (ESpos): m/z = 415 (M + H)$^+$ |

TABLE 8-continued

| Example | IUPAC name/structure (yield) | Analytical data |
|---|---|---|
| 85 | rac-N-(1-benzylpyrrolidin-3-yl)-8-[(2,6-difluoro-benzyl)oxy]-2-methylimidazo[1,2-a]-pyridine-3-carboxamide<br />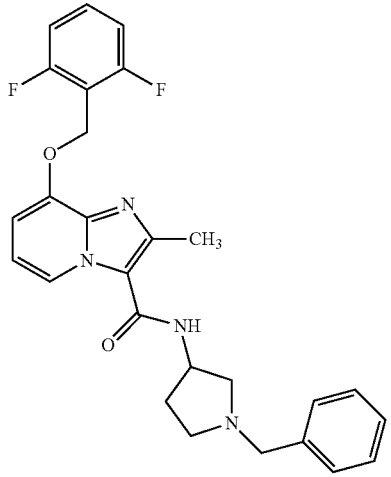<br />(55% of theory) | LC-MS (Method 8): $R_t$ = 0.75 min<br />MS (ESpos): m/z = 477 (M + H)$^+$ |
| 86 | 8-[(2,6-difluorobenzyl)oxy]-N-[2-(dimethyl-amino)ethyl]-2-methylimidazo[1,2-a]pyridine-3-carboxamide<br />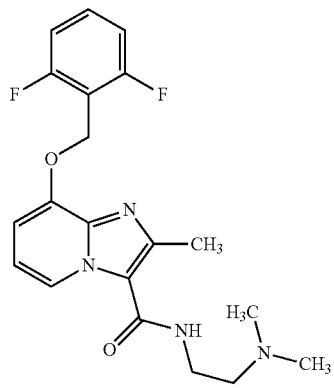<br />(14% of theory) | LC-MS (Method 8): $R_t$ = 0.63 min<br />MS (ESpos): m/z = 389 (M + H)$^+$ |

TABLE 8-continued

| Example | IUPAC name/structure (yield) | Analytical data |
|---|---|---|
| 87 | 8-[(2,6-difluorobenzyl)oxy]-N-[3-(dimethylamino)propyl]-2-methylimidazo[1,2-a]pyridine-3-carboxamide<br>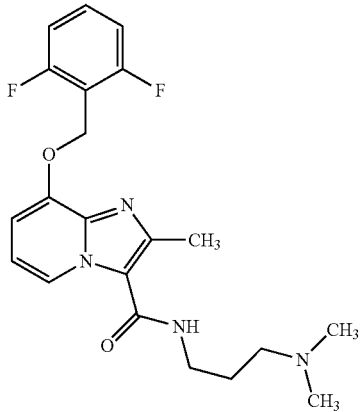<br>(6% of theory) | LC-MS (Method 8): $R_t$ = 0.63 min<br>MS (ESpos): m/z = 403 (M + H)$^+$ |
| 88 | 8-[(2,6-difluorobenzyl)oxy]-N-[2-(diisopropylamino)ethyl]-2-methylimidazo[1,2-a]pyridine-3-carboxamide<br>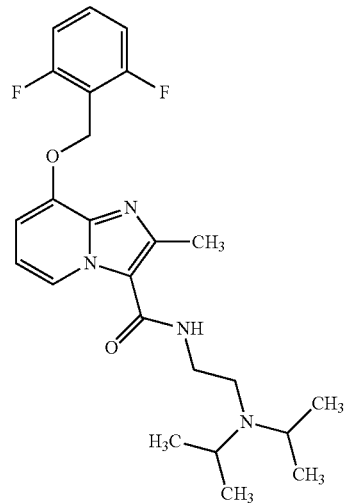<br>(10% of theory) | LC-MS (Method 8): $R_t$ = 0.75 min<br>MS (ESpos): m/z = 445 (M + H)$^+$ |

TABLE 8-continued

| Example | IUPAC name/structure (yield) | Analytical data |
|---|---|---|
| 89 | 8-[(2,6-difluorobenzyl)oxy]-2-methyl-N-[2-(morpholin-4-yl)ethyl]imidazo[1,2-a]pyridine-3-carboxamide<br>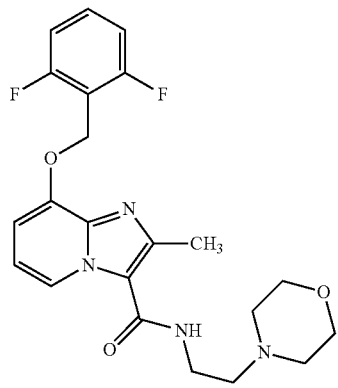<br>(3% of theory) | LC-MS (Method 8): $R_t$ = 0.65 min<br>MS (ESpos): m/z = 431 (M + H)$^+$ |
| 90 | 8-[(2,6-difluorobenzyl)oxy]-2-methyl-N-(9-methyl-9-azabicyclo[3.3.1]non-3-yl)imidazo[1,2-a]pyridine-3-carboxamide<br>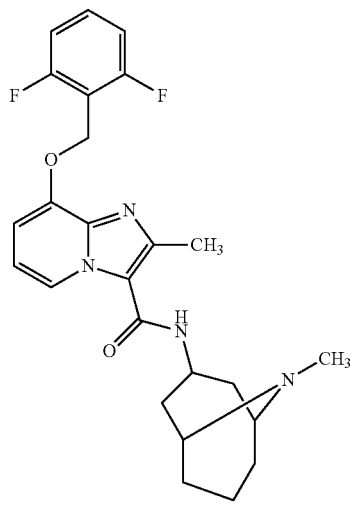<br>(22% of theory) | LC-MS (Method 8): $R_t$ = 0.66 min<br>MS (ESpos): m/z = 455 (M + H)$^+$ |

TABLE 8-continued
| Example | IUPAC name/structure (yield) | Analytical data |
|---|---|---|
| 91 | 8-[(2,6-difluorobenzyl)oxy]-2-methyl-N-(8-methyl-8-azabicyclo[3.2.1]oct-3-yl)imidazo[1,2-a]pyridine-3-carboxamide 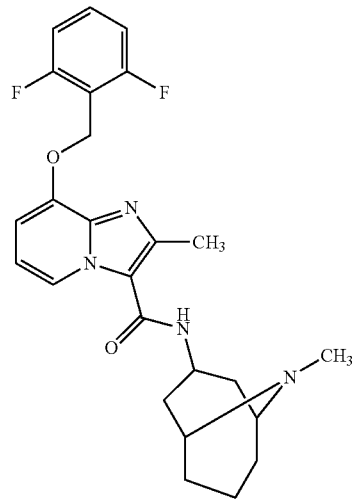 (66% of theory) | LC-MS (Method 8): $R_t$ = 0.65 min<br>MS (ESpos): m/z = 441 (M + H)$^+$ |
| 92 | N-(1-azabicyclo[2.2.2]oct-3-yl)-8-[(2,6-difluorobenzyl)oxy]-2-methylimidazo[1,2-a]pyridine-3-carboxamide 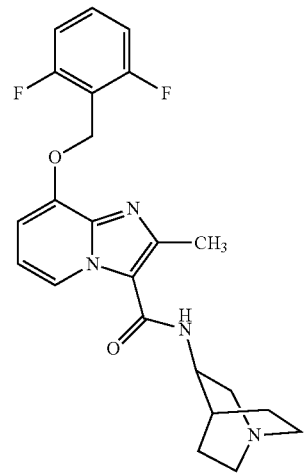 (40% of theory) | LC-MS (Method 8): $R_t$ = 0.65 min<br>MS (ESpos): m/z = 427 (M + H)$^+$ |

Example 93 ent-N-(1-Amino-3-isopropoxypropan-2-yl)-8-[(2,6-difluorobenzyl)oxy]-2-methylimidazo[1,2-a]-pyridine-3-carboxamide (Enantiomer A)

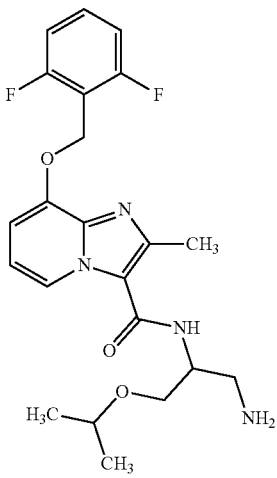 [SMILES: Cc1nc2c(OCc3c(F)cccc3F)cccn2c1C(=O)NC(CN)COC(C)C]

114 mg of Example 63 were dissolved in 2.5 ml of ethanol and separated into the enantiomers on a chiral phase [column: Daicel Chiralpak OD-H, 5 µm, 250×20 mm, mobile phase: 50% isohexane, 50% ethanol, flow rate: 20 ml/min; 25° C., detection: 230 nm].

Yield enantiomer A: 44 mg (100% ee)

Enantiomer A: $R_t$=4.33 min [Daicel Chiralpak OD-H, 5 m, 250×4.6 mm; mobile phase: 50% isohexane, 50% ethanol; flow rate 1.0 ml/min; 40° C.; detection: 220 nm].

$^1$H NMR (400 MHz, DMSO-$d_6$): δ=1.10 (d, 6H), 1.68 (br. s, 2H), 2.54 (s, 3H; superimposed by DMSO signal), 2.72 (d, 2H), 3.49 (d, 2H), 3.58 (q, 1H), 3.99 (m, 1H), 5.30 (s, 2H), 6.91 (t, 1H), 7.01 (d, 1H), 7.23 (t, 2H), 7.53 (br. s, 1H), 7.58 (q, 1H), 8.60 (d, 1H).

Example 94

8-[(2,6-Difluorobenzyl)oxy]-2,6-dimethyl-N-{2-methyl-2-[(2,2,2-trifluoroethyl)amino]propyl}-imidazo[1,2-a]pyridine-3-carboxamide

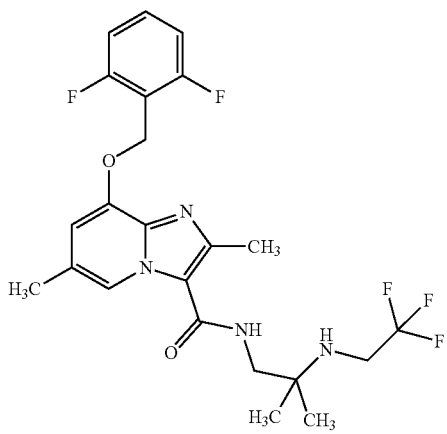 [SMILES: Cc1cc(OCc2c(F)cccc2F)c2nc(C)c(C(=O)NCC(C)(C)NCC(F)(F)F)n2c1]

100 mg (0.25 mmol) of N-(2-amino-2-methylpropyl)-8-[(2,6-difluorobenzyl)oxy]-2,6-dimethylimidazo[1,2-a]pyridine-3-carboxamide (Example 74) were initially charged in 2 ml of DMF, 0.041 ml (0.25 mmol) of 2,2,2-trifluoroethyl trichloromethanesulphonate, 69 mg (0.50 mmol) of potassium carbonate and 4.1 mg (0.025 mmol) of potassium iodide were added and the mixture was then stirred at RT overnight. 0.082 ml (0.50 mmol) of 2,2,2-trifluoroethyl trichloromethanesulphonate was then added, and the mixture was once more stirred at RT overnight. Another 0.123 ml (0.75 mmol) of 2,2,2-trifluoroethyl trichloromethanesulphonate were added, and the mixture was once more stirred at RT overnight. For work-up, 1 ml of water was added, the mixture was filtered through an Extrelut cartridge, eluted with dichloromethane, and the filtrate was concentrated. The crude product was purified by preparative HPLC (RP18 column, mobile phase: acetonitrile/water gradient with addition of 0.5% ammonium hydroxide). The product fractions were combined, evaporated and dried under high vacuum.

Yield: 48 mg (38% of theory)

LC-MS (Method 2): $R_t$=0.96 min

MS (ESpos): m/z=485.4 (M+H)$^+$ $^1$H NMR (400 MHz, DMSO-$d_6$): δ=1.05 (s, 6H), 2.31 (s, 3H), 2.37 (t, 1H), 2.54 (s, 3H; obscured by DMSO signal), 3.18-3.30 (m, 4H), 5.28 (s, 2H), 6.92 (s, 1H), 7.19-7.29 (m, 2H), 7.50 (t, 1H), 7.54-7.64 (m, 1H), 8.50 (s, 1H).

Example 95 ent-N-(3-Amino-2-methylpropyl)-8-[(2,6-difluorobenzyl)oxy]-2-methylimidazo[1,2-a]pyridine-3-carboxamide dihydrochloride (Enantiomer A)

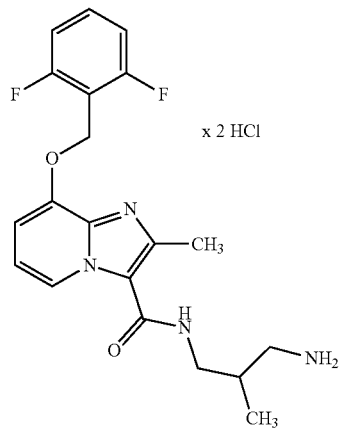 [SMILES: Cc1nc2c(OCc3c(F)cccc3F)cccn2c1C(=O)NCC(C)CN]

68 mg of ent-tert-butyl {3-[({8-[(2,6-difluorobenzyl)oxy]-2-methylimidazo[1,2-a]pyridin-3-yl}carbonyl)amino]-2-methylpropyl}carbamate (Example 213A, 0.14 mmol, 1 equivalent) were dissolved in 2 ml of 4 N hydrochloric acid in 1,4-dioxane (1.4 mmol, 10 equivalents) and stirred at RT overnight. The mixture was then concentrated and dried under reduced pressure. This gave 48 mg (75% of theory; purity 100%) of the title compound.

LC-MS (Method 2): $R_t$=0.56 min

MS (ESpos): m/z=389.2 (M−2HCl+H)$^+$ $^1$H NMR (400 MHz, DMSO-$d_6$): δ=0.99 (d, 3H), 2.05-2.17 (m, 1H), 2.62 (s, 3H), 2.65-2.75 (m, 1H), 2.83-2.93 (m, 1H), 3.32 (t, 2H), 5.43 (s, 2H), 7.21-7.37 (m, 3H), 7.47 (br. s, 1H), 7.56-7.68 (m, 1H), 7.98 (br. s, 3H), 8.56 (br. s, 1H), 8.68 (d, 1H).

Example 96 ent-N-(3-Amino-2-methylpropyl)-8-[(2,6-difluorobenzyl)oxy]-2-methylimidazo[1,2-a]pyridine-3-carboxamide dihydrochloride (Enantiomer B)

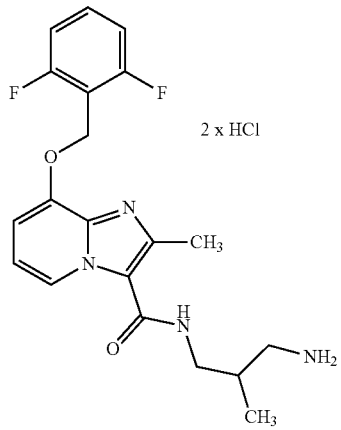 [SMILES: Cc1nc2c(OCc3c(F)cccc3F)cccn2c1C(=O)NCC(C)CN]

79 mg of ent-tert-butyl {3-[({8-[(2,6-difluorobenzyl)oxy]-2-methylimidazo[1,2-a]pyridin-3-yl}carbonyl)amino]-2-methylpropyl}carbamate (Example 214A, 0.16 mmol, 1 equivalent) were dissolved in 2 ml of 4 N hydrochloric acid in 1,4-dioxane (1.6 mmol, 10 equivalents) and stirred at RT overnight. The mixture was then concentrated and dried under reduced pressure. This gave 66 mg (88.5% of theory; purity 100%) of the title compound.

LC-MS (Method 2): $R_t$=0.55 min
MS (ESpos): m/z=389.2 (M−2HCl+H)$^+$
$^1$H NMR (400 MHz, DMSO-$d_6$): δ=0.99 (d, 3H), 2.06-2.19 (m, 1H), 2.63 (s, 3H), 2.66-2.75 (m, 1H), 2.83-2.94 (m, 1H), 3.31 (t, 2H), 5.43 (s, 2H), 7.26 (t, 2H), 7.36 (br. s, 1H), 7.48-7.67 (m, 2H), 8.03 (br. s, 2H), 8.62 (br. s, 1H), 8.71 (d, 1H).

Example 97 ent-N-[2-Amino-1-(3,4-difluorophenyl)ethyl]-8-{[(2,6-difluorophenyl) ($^2$H$_2$)methyl]oxy}-2-methylimidazo[1,2-a]pyridine-3-carboxamide

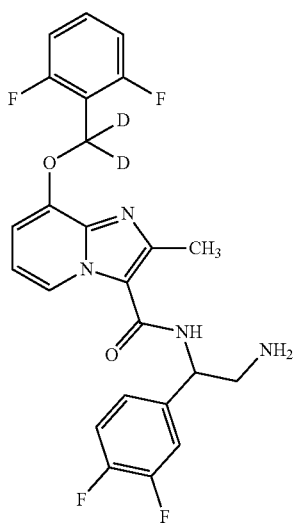 [SMILES: [2H]C([2H])(Oc1cccn2c(C(=O)NC(CN)c3ccc(F)c(F)c3)c(C)nc12)c1c(F)cccc1F]

At RT, 250 mg of ent-tert-butyl [2-(3,4-difluorophenyl)-2-{[(8-{[(2,6-difluorophenyl)-($^2$H$_2$)methyl]oxy}-2-methylimidazo[1,2-a]pyridin-3-yl)carbonyl]amino}ethyl]carbamate (Example 170A, 0.44 mmol, 1 equivalent) were dissolved in 4.4 ml of 4 N hydrochloric acid in 1,4-dioxane (17.4 mmol, 40 equivalents), and the mixture was stirred at RT for 3 h. The mixture was then concentrated, water and saturated aqueous ammonia solution were added to the residue and the mixture was extracted four times with ethyl acetate. The combined organic phases were washed with saturated aqueous sodium chloride solution, dried over magnesium sulphate and concentrated. The crude product obtained in this manner was applied to Extrelut and purified on a silica gel cartridge (Biotage SNAP Cartridge KP-Sil 10 g, mobile phase: dichloromethane/methanol: from 95:5 to 0:100). This gave 198 mg (95% of theory; purity 99%) of the title compound.

LC-MS (Method 7): $R_t$=0.71 min
MS (ESpos): m/z=475.1 (M+H)$^+$
$^1$H NMR (400 MHz, DMSO-$d_6$): δ=1.70 (br. s, 2H), 2.59 (s, 3H), 2.86-2.94 (m, 2H), 4.92-5.01 (m, 1H), 6.91 (t, 1H), 7.01 (d, 1H), 7.20-7.28 (m, 3H), 7.36-7.50 (m, 2H), 7.54-7.63 (m, 1H), 8.18 (br. s, 1H), 8.53 (d, 1H).

Example 98 ent-N-[2-Amino-1-(3,4-difluorophenyl)ethyl]-8-[(2-fluorobenzyl)oxy]-2-methylimidazo[1,2-a]-pyridine-3-carboxamide

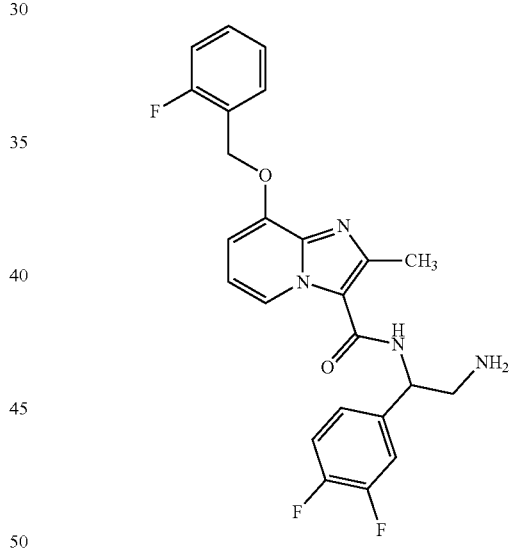

At RT, 0.8 ml of 4 N hydrochloric acid in 1,4-dioxane (3.1 mmol, 10 equivalents) were added to 191 mg of ent-tert-butyl {2-(3,4-difluorophenyl)-2-[({8-[(2-fluorobenzyl)oxy]-2-methylimidazo[1,2-a]pyridin-3-yl}carbonyl)amino]ethyl}carbamate (Example 197A, 0.3 mmol, 1 equivalent). The mixture was stirred at RT overnight and then concentrated. The residue was taken up in ethyl acetate and washed with saturated aqueous sodium bicarbonate solution. The organic phase was dried over magnesium sulphate and concentrated. This gave 101 mg (69% of theory; purity 97%) of the title compound.

LC-MS (Method 7): $R_t$=0.69 min
MS (ESpos): m/z=455.1 (M+H)$^+$
$^1$H NMR (400 MHz, DMSO-$d_6$): δ=1.70 (br. s, 2H); 2.61 (s, 3H), 2.83-2.93 (m, 2H), 4.96 (t, 1H), 5.33 (s, 2H), 6.92 (t, 1H), 6.99 (d, 1H), 7.19-7.34 (m, 3H), 7.35-7.53 (m, 3H), 7.62 (t, 1H), 8.20 (br. s, 1H), 8.51 (d, 1H).

The compounds listed in Table 9 were prepared analogously to Example 98 from the appropriate Boc-protected amines.

TABLE 9

| Example | IUPAC name/structure (yield) | Analytical data |
|---|---|---|
| 99 | ent-N-[2-amino-1-(3,4-difluorophenyl)ethyl]-8-[(2,3-difluorobenzyl)oxy]-2-methylimidazo[1,2-a]pyridine-3-carboxamide<br><br>(66% of theory; purity 100%) | LC-MS (Method 7): $R_t$ = 0.72 min<br>MS (ESpos): m/z = 473.1 (M + H)$^+$<br>$^1$H NMR (400 MHz, DMSO-d$_6$):<br>δ = 1.70 (br. s, 2H), 2.62 (s, 3H), 2.85-2.93 (m, 2H), 4.99 (t, 1H), 5.39 (s, 2H), 6.89 (t, 1H), 6.97 (d, 1H), 7.21-7.34 (m, 2H), 7.36-7.56 (m, 4H), 8.20 (br. s, 1H), 8.52 (d, 1H). |
| 100 | ent-N-[2-amino-1-(3,4-difluorophenyl)ethyl]-2-methyl-8-[(2,3,6-trifluorobenzyl)oxy]imidazo[1,2-a]pyridine-3-carboxamide<br><br>(33% of theory; purity 96%) | LC-MS (Method 7): $R_t$ = 0.72 min<br>MS (ESpos): m/z = 491.1 (M + H)$^+$<br>$^1$H NMR (400 MHz, DMSO-d$_6$):<br>δ = 1.70 (br. s, 2H), 2.60 (s, 3H), 2.85-2.92 (m, 2H), 4.95 (t, 1H), 5.36 (s, 2H), 6.91 (t, 1H), 7.01 (d, 1H), 7.19-7.33 (m, 2H), 7.35-7.51 (m, 2H), 7.60-7.72 (m, 1H), 8.20 (br. s, 1H), 8.54 (d, 1H). |

TABLE 9-continued

| Example | IUPAC name/structure (yield) | Analytical data |
|---|---|---|
| 101 | ent-N-[2-amino-1-(3,4-difluorophenyl)ethyl]-2-methyl-8-[(2,4,6-trifluorobenzyl)oxy]imidazo[1,2-a]pyridine-3-carboxamide<br>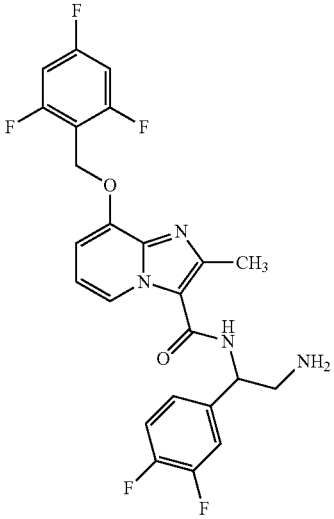<br>(58% of theory; purity 96%) | LC-MS (Method 7): $R_t$ = 0.74 min<br>MS (ESpos): m/z = 491.1 (M + H)$^+$<br>$^1$H NMR (400 MHz, DMSO-d$_6$):<br>δ = 1.70 (br. s, 2H), 2.60 (s, 3H), 2.88 (d, 2H), 4.95 (t, 1H), 5.28 (s, 2H), 6.91 (t, 1H), 7.00 (d, 1H), 7.19-7.28 (m, 1H), 7.30-7.50 (m, 4H), 8.19 (br. s, 1H), 8.54 (d, 1H). |
| 102 | ent-N-[2-amino-1-(3,4-difluorophenyl)ethyl]-8-[(2-chloro-6-fluorobenzyl)oxy]-2-methylimidazo[1,2-a]pyridine-3-carboxamide<br>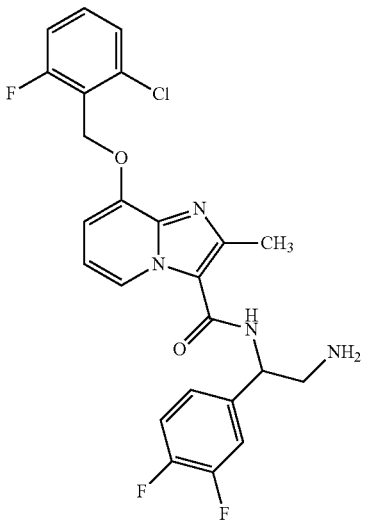<br>(61% of theory; purity 95%) | LC-MS (Method 7): $R_t$ = 0.76 min<br>MS (ESpos): m/z = 489.1 (M + H)$^+$<br>$^1$H NMR (400 MHz, DMSO-d$_6$):<br>δ = 1.70 (br. s, 2H), 2.59 (s, 3H), 2.84-2.93 (m, 2H), 4.96 (t, 1H), 5.34 (s, 2H), 6.93 (t, 1H), 7.03 (d, 1H), 7.21-7.27 (m, 1H), 7.33-7.51 (m, 4H), 7.53-7.62 (m, 1H), 8.18 (br. s, 1H), 8.54 (d, 1H). |

TABLE 9-continued

| Example | IUPAC name/structure (yield) | Analytical data |
|---|---|---|
| 103 | N-(3-amino-2,2-dimethylpropyl)-8-[(2,6-difluorobenzyl)oxy]-2-methylimidazo[1,2-a]-pyridine-3-carboxamide[1)]<br>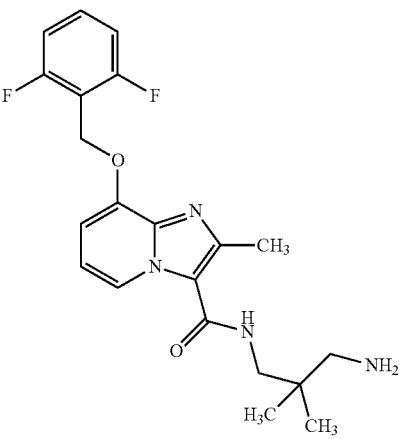<br>(39% of theory; purity 95%) | LC-MS (Method 7): $R_t$ = 0.60 min<br>MS (ESpos): m/z = 403.3 (M + H)$^+$<br>$^1$H NMR (400 MHz, DMSO-d$_6$):<br>δ = 0.87 (s, 6H), 1.08 (br. s, 2H),<br>2.41 (s, 2H), 3.21 (d, 2H), 5.30 (s, 2H),<br>6.93 (t, 1H), 7.01 (d, 1H), 7.23 (t,<br>2H), 7.53-7.65 (m, 1H), 8.21 (t, 1H),<br>8.62 (d, 1H). |

[1)]reaction without addition of solvent, with 20 equivalents of 4 M hydrochloride acid in 1,4-dioxane.

Example 104

N-(3-Amino-3-methylbutyl)-6-chloro-8-[(2,6-difluorobenzyl)oxy]-2-methylimidazo[1,2-a]-pyridine-3-carboxamide

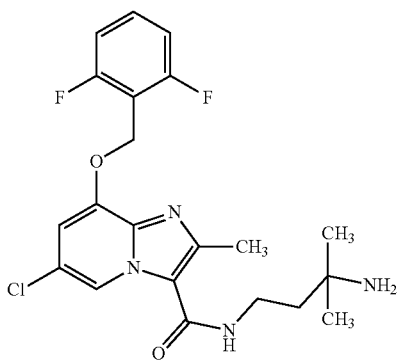 [SMILES: Cc1nc2c(OCc3c(F)cccc3F)cc(Cl)cn2c1C(=O)NCCC(C)(C)N]

118 mg of tert-butyl {4-[({6-chloro-8-[(2,6-difluorobenzyl)oxy]-2-methylimidazo[1,2-a]pyridin-3-yl}carbonyl)amino]-2-methylbutan-2-yl}carbamate trifluoroacetate (Example 179A, 0.22 mmol, 1 equivalent) were initially charged in 4 ml of 2 N hydrochloric acid in diethyl ether (8 mmol, 36 equivalents) and stirred at RT overnight. The resulting precipitate was filtered off, washed thoroughly with diethyl ether and then dissolved in ethyl acetate. The organic phase was washed twice with saturated aqueous sodium bicarbonate solution and with water. The aqueous phase was extracted twice with dichloroethane and the combined organic phases were dried over sodium sulphate, filtered and concentrated. This gave 65.5 mg (68% of theory, purity 99%) of the target compound.

LC-MS (Method 2): $R_t$=0.75 min

MS (ESpos): m/z=437.3 (M+H)$^+$ $^1$H NMR (400 MHz, DMSO-d$_6$): δ=1.09 (s, 6H), 1.59 (t, 2H), 2.10 (br. s, 2H), 3.40 (t, 2H), 5.33 (s, 2H), 7.20 (d, 1H), 7.26 (t, 2H), 7.55-7.65 (m, 1H), 8.42 (br. s, 1H), 8.84 (d, 1H), [further signal hidden under the solvent peaks].

The compounds listed in Table 10 were prepared analogously to Example 104 from the appropriate Boc-protected amines. 10-40 equivalents of 2 N hydrochloric acid were used. For work-up of the reaction, any solid formed was dissolved in ethyl acetate or dichloromethane/methanol and processed further in an analogous manner.

TABLE 10

| Example | IUPAC name/structure (yield) | Analytical data |
|---|---|---|
| 105 | ent-8-[(2,6-difluorobenzyl)oxy]-N-(6-fluoro-1,2,3,4-tetrahydroquinolin-4-yl)-2-methylimidazo[1,2-a]pyridine-3-carboxamide (enantiomer A)[1]<br>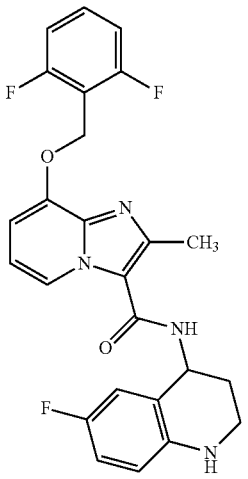<br>(98% of theory; purity 100%) | LC-MS (Method 2): $R_t$ = 0.86 min<br>MS (ESpos): m/z = 467.2 (M + H)$^+$<br>$^1$H NMR (400 MHz, DMSO-d$_6$):<br>δ = 1.94-2.03 (m, 2H), 3.20-3.27 (m, 2H), 5.14-5.23 (m, 1H), 5.31 (s, 2H), 5.82 (s, 1H), 6.48-6.54 (m, 1H), 6.81 (dt, 1H), 6.88-6.94 (m, 1H), 6.96 (d, 1H), 7.02 (d, 1H), 7.23 (t, 2H), 7.54-7.64 (m, 1H), 8.31 (d, 1H), 8.58 (d, 1H), [further signal hidden under DMSO peak]. |
| 106 | ent-8-[(2,6-difluorobenzyl)oxy]-N-(6-fluoro-1,2,3,4-tetrahydroquinolin-4-yl)-2-methylimidazo[1,2-a]pyridine-3-carboxamide (enantiomer B)[1]<br>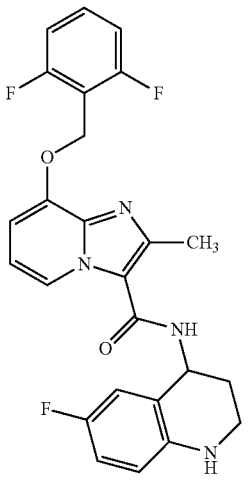<br>(99% of theory; purity 100%) | LC-MS (Method 2): $R_t$ = 0.86 min<br>MS (ESpos): m/z = 467.2 (M + H)$^+$<br>$^1$H NMR (400 MHz, DMSO-d$_6$):<br>δ = 1.93-2.05 (m, 2H), 3.19-3.27 (m, 2H), 5.14-5.23 (m, 1H), 5.31 (s, 2H), 5.83 (s, 1H), 6.48-6.54 (m, 1H), 6.81 (dt, 1H), 6.88-6.94 (m, 1H), 6.96 (d, 1H), 7.02 (d, 1H), 7.24 (t, 2H), 7.54-7.65 (m, 1H), 8.30 (d, 1H), 8.58 (d, 1H), [further signal hidden under DMSO peak]. |

TABLE 10-continued

| Example | IUPAC name/structure (yield) | Analytical data |
|---|---|---|
| 107 | ent-6-chloro-8-[(2,6-difluorobenzyl)oxy]-2-methyl-N-(1,2,3,4-tetrahydroisoquinolin-4-yl)imidazo[1,2-a]pyridine-3-carboxamide (enantiomer A)[1)] 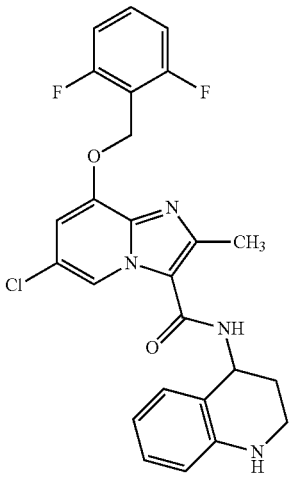 (92% of theory; purity 100%) | LC-MS (Method 2): $R_t$ = 0.81 min<br>MS (ESpos): m/z = 483.2 (M + H)$^+$<br>$^1$H NMR (400 MHz, DMSO-d$_6$):<br>δ = 2.46 (s, 3H), 2.97 (dd, 1H), 3.18 (dd, 1H), 3.80-3.96 (m, 2H), 5.13-5.21 (m, 1H), 5.35 (s, 2H), 7.05-7.11 (m, 1H), 7.17-7.29 (m, 5H), 7.36-7.41 (m, 1H), 7.56-7.65 (m, 1H), 8.26 (d, 1H), 8.74 (d, 1H). |
| 108 | ent-6-chloro-8-[(2,6-difluorobenzyl)oxy]-2-methyl-N-(1,2,3,4-tetrahydroisoquinolin-4-yl)imidazo[1,2-a]pyridine-3-carboxamide (enantiomer B)[1)] 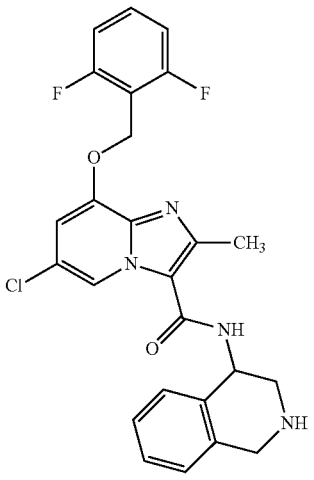 (95% of theory; purity 100%) | LC-MS (Method 2): $R_t$ = 0.81 min<br>MS (ESpos): m/z = 483.2 (M + H)$^+$<br>$^1$H NMR (400 MHz, DMSO-d$_6$):<br>δ = 2.46 (s, 3H), 2.97 (dd, 1H), 3.18 (dd, 1H), 3.80-3.96 (m, 2H), 5.13-5.22 (m, 1H), 5.35 (s, 2H), 7.05-7.11 (m, 1H), 7.16-7.29 (m, 5H), 7.36-7.41 (m, 1H), 7.56-7.65 (m, 1H), 8.26 (d, 1H), 8.74 (d, 1H). |

TABLE 10-continued

| Example | IUPAC name/structure (yield) | Analytical data |
|---|---|---|
| 109 | ent-8-[(2,6-difluorobenzyl)oxy]-2-methyl-N-(1,2,3,4-tetrahydroisoquinolin-4-yl)imidazo[1,2-a]pyridine-3-carboxamide (enantiomer A)[2)] 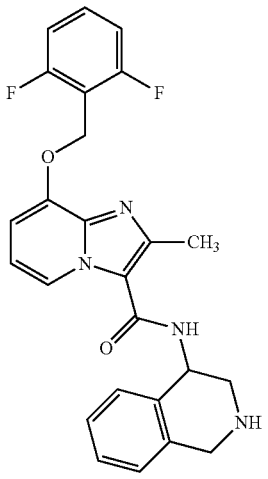 (49% of theory; purity 99%) | LC-MS (Method 7): $R_t$ = 0.65 min<br>MS (ESpos): m/z = 449.2 (M + H)[+]<br>$^1$H NMR (400 MHz, DMSO-$d_6$):<br>δ = 2.47 (s, 3H), 2.97 (dd, 1H), 3.18 (dd, 1H), 3.81-3.96 (m, 2H), 5.14-5.22 (m, 1H), 5.30 (s, 2H), 6.96 (t, 1H), 7.02 (d, 1H), 7.06-7.11 (m, 1H), 7.16-7.28 (m, 4H), 7.35-7.41 (m, 1H), 7.54-7.64 (m, 1H), 8.17 (d, 1H), 8.64 (d, 1H), [further signal hidden under solvent peaks]. |
| 110 | ent-8-[(2,6-difluorobenzyl)oxy]-2-methyl-N-(1,2,3,4-tetrahydroisoquinolin-4-yl)imidazo[1,2-a]pyridine-3-carboxamide (enantiomer B)[2)] 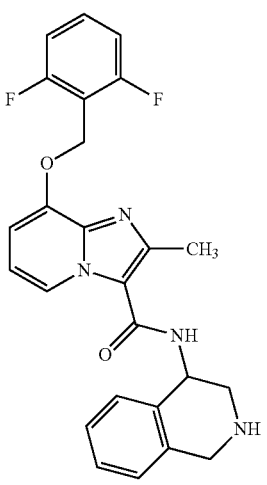 (53% of theory; purity 99%) | LC-MS (Method 7): $R_t$ = 0.69 min<br>MS (ESpos): m/z = 449.2 (M + H)[+]<br>$^1$H NMR (400 MHz, DMSO-$d_6$):<br>δ = 2.47 (s, 3H), 2.97 (dd, 1H), 3.18 (dd, 1H), 3.81-3.96 (m, 2H), 5.15-5.22 (m, 1H), 5.30 (s, 2H), 6.96 (t, 1H), 7.02 (d, 1H), 7.06-7.11 (m, 1H), 7.16-7.29 (m, 4H), 7.35-7.40 (m, 1H), 7.54-7.64 (m, 1H), 8.17 (d, 1H), 8.64 (d, 1H), [further signal hidden under solvent peaks]. |

TABLE 10-continued

| Example | IUPAC name/structure (yield) | Analytical data |
|---|---|---|
| 111 | ent-8-[(2,6-difluorobenzyl)oxy]-2-methyl-N-[6-(trifluoromethyl)-1,2,3,4-tetrahydroquinolin-4-yl]imidazo[1,2-a]pyridine-3-carboxamide (enantiomer A)[1)]<br>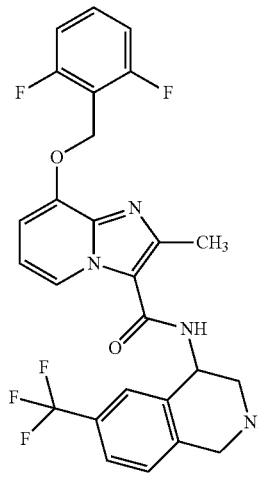<br>(64% of theory; purity 97%) | LC-MS (Method 7): $R_t$ = 1.02 min<br>MS (ESpos): m/z = 517.1 (M + H)$^+$<br>$^1$H NMR (400 MHz, DMSO-d$_6$):<br>δ = 1.91-2.09 (m, 2H), 5.18-5.26 (m, 1H), 5.32 (s, 2H), 6.62 (d, 1H), 6.70 (s, 1H), 6.96 (t, 1H), 7.02 (d, 1H), 7.20-7.29 (m, 3H), 7.37 (s, 1H), 7.53-7.65 (m, 1H), 8.35 (d, 1H), 8.56 (d, 1H), [further signals hidden under solvent peaks]. |
| 112 | ent-8-[(2,6-difluorobenzyl)oxy]-2-methyl-N-[6-(trifluoromethyl)-1,2,3,4-tetrahydroquinolin-4-yl]imidazo[1,2-a]pyridine-3-carboxamide (enantiomer B)[1)]<br>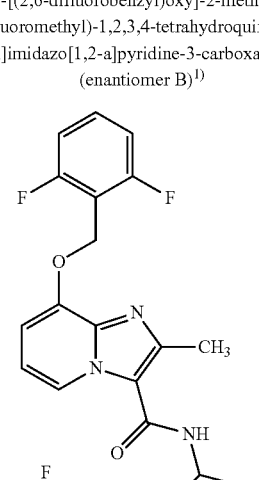<br>(78% of theory; purity 98%) | LC-MS (Method 7): $R_t$ = 1.02 min<br>MS (ESpos): m/z = 517.1 (M + H)$^+$<br>$^1$H NMR (400 MHz, DMSO-d$_6$):<br>δ = 1.91-2.08 (m, 2H), 5.18-5.27 (m, 1H), 5.32 (s, 2H), 6.62 (d, 1H), 6.70 (s, 1H), 6.96 (t, 1H), 7.02 (d, 1H), 7.20-7.29 (m, 3H), 7.37 (s, 1H), 7.53-7.65 (m, 1H), 8.35 (d, 1H), 8.56 (d, 1H), [further signals hidden under solvent peaks]. |

TABLE 10-continued

| Example | IUPAC name/structure (yield) | Analytical data |
|---|---|---|
| 113 | N-(2-aminoethyl)-8-[(2,6-difluorobenzyl)oxy]-2,6-dimethylimidazo[1,2-a]pyridine-3-carboxamide[1]<br>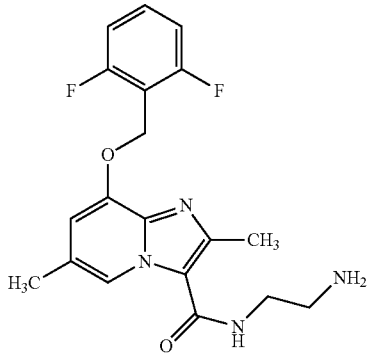<br>(74% of theory; purity 98%) | LC-MS (Method 7): $R_t$ = 0.56 min<br>MS (ESpos): m/z = 375.2 (M + H)$^+$<br>$^1$H NMR (400 MHz, DMSO-d$_6$):<br>δ = 1.62 (br. s, 2H), 2.31 (s, 3H), 2.71 (t, 2H), 5.27 (s, 2H), 6.91 (s, 1H), 7.24 (t, 2H), 7.54-7.65 (m, 1H), 7.72-7.81 (m, 1H), 8.46 (s, 1H), [further signals hidden under solvent peaks]. |
| 114 | N-(3-amino-3-methylbutyl)-8-[(2,6-difluorobenzyl)oxy]-2,6-dimethylimidazo[1,2-a]pyridine-3-carboxamide[1]<br>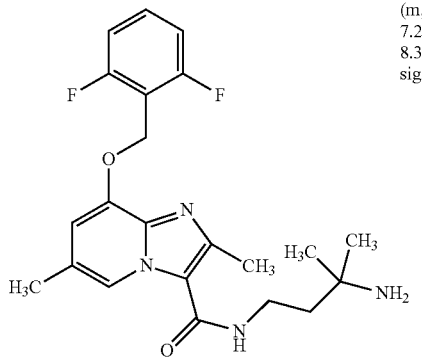<br>(85% of theory; purity 95%) | LC-MS (Method 2): $R_t$ = 0.62 min<br>MS (ESpos): m/z = 417.4 (M + H)$^+$<br>$^1$H NMR (400 MHz, DMSO-d$_6$):<br>δ = 1.08 (s, 6H), 1.58 (t, 2H), 1.78 (br. s, 2H), 2.31 (s, 3H), 3.36-3.43 (m, 2H), 5.28 (s, 2H), 6.91 (s, 1H), 7.24 (t, 2H), 7.54-7.64 (m, 1H), 8.25-8.31 (m, 1H), 8.53 (s, 1H), [further signal hidden under solvent peak]. |

TABLE 10-continued

| Example | IUPAC name/structure (yield) | Analytical data |
|---|---|---|
| 115 | 8-[(2,6-difluorobenzyl)oxy]-2,6-dimethyl-N-[(2S)-pyrrolidin-2-ylmethyl]imidazo[1,2-a]-pyridine-3-carboxamide[1)]<br>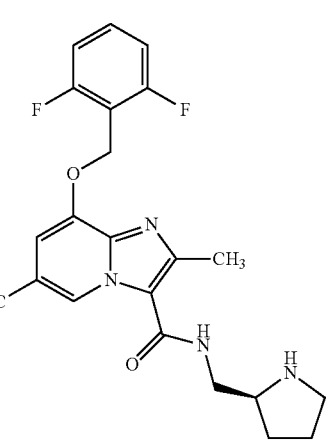<br>(79% of theory; purity 94%) | LC-MS (Method 2): $R_t$ = 0.63 min MS (ESpos): m/z = 415.3 (M + H)$^+$ $^1$H NMR (400 MHz, DMSO-d$_6$): δ = 1.34-1.45 (m, 1H), 1.55-1.71 (m, 2H), 1.72-1.84 (m, 1H), 2.31 (s, 3H), 2.70-2.87 (m, 2H), 3.17-3.28 (m, 3H), 5.28 (s, 2H), 6.92 (s, 1H), 7.23 (t, 2H), 7.54-7.64 (m, 1H), 7.71-7.78 (m, 1H), 8.46 (s, 1H), [further signal hidden under solvent peak]. |
| 116 | 8-[(2,6-difluorobenzyl)oxy]-2,6-dimethyl-N-[(2R)-pyrrolidin-2-ylmethyl]imidazo[1,2-a]-pyridine-3-carboxamide[1)]<br>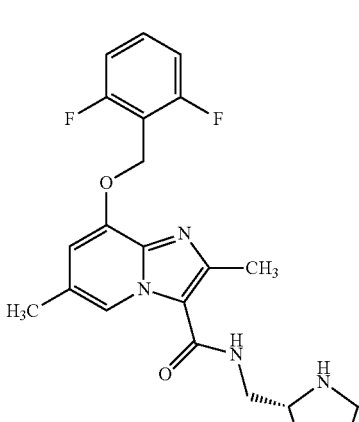<br>(80% of theory; purity 98%) | LC-MS (Method 2): $R_t$ = 0.64 min MS (ESpos): m/z = 415.3 (M + H)$^+$ $^1$H NMR (400 MHz, DMSO-d$_6$): δ = 1.34-1.45 (m, 1H), 1.55-1.71 (m, 2H), 1.72-1.84 (m, 1H), 2.31 (s, 3H), 2.71-2.87 (m, 2H), 3.17-3.28 (m, 3H), 5.28 (s, 2H), 6.92 (s, 1H), 7.23 (t, 2H), 7.54-7.64 (m, 1H), 7.71-7.79 (m, 1H), 8.46 (s, 1H), [further signal hidden under solvent peak]. |

TABLE 10-continued

| Example | IUPAC name/structure (yield) | Analytical data |
|---|---|---|
| 117 | N-(3-amino-3-methylbutyl)-8-[(2,6-difluorobenzyl)oxy]-2-methylimidazo[1,2-a]pyridine-3-carboxamide[3)] 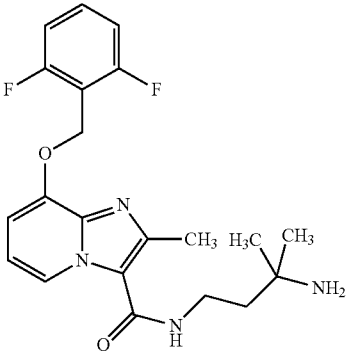 (58% of theory, purity 99%) | LC-MS (Method 2): $R_t$ = 0.59 min<br>MS (ESpos): m/z = 403.3 (M + H)$^+$<br>$^1$H NMR (400 MHz, DMSO-$d_6$):<br>δ = 1.08 (s, 6H), 1.58 (t, 2H), 1.79 (br. s, 2H), 3.37-3.45 (m, 2H), 5.30 (s, 2H), 6.93 (t, 1H), 7.01 (d, 1H), 7.23 (t, 2H), 7.54-7.64 (m, 1H), 8.28-8.36 (m, 1H), 8.70 (d, 1H), [further signal hidden under solvent peak]. |
| 118 | rac-6-chloro-8-[(2,6-difluorobenzyl)oxy]-2-methyl-N-(piperidin-2-ylmethyl)imidazo[1,2-a]pyridine-3-carboxamide 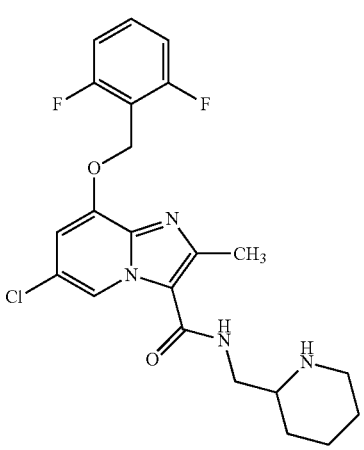 (92% of theory; purity 98%) | LC-MS (Method 7): $R_t$ = 0.73 min<br>MS (ESpos): m/z = 449.1 (M + H)$^+$<br>$^1$H NMR (400 MHz, DMSO-$d_6$):<br>δ = 0.99-1.13 (m, 1H), 1.21-1.37 (m, 2H), 1.45-1.53 (m, 1H), 1.62 (d, 1H), 1.74 (br. s., 1H), 2.16 (br. s, 1H), 2.59-2.70 (m, 1H), 2.94 (d, 1H), 3.17-3.27 (m, 2H), 5.35 (s, 2H), 7.18 (s, 1H), 7.24 (t, 2H), 7.54-7.65 (m, 1H), 7.83 (t, 1H), 8.76 (s, 1H), [further signals hidden under solvent peaks]. |

TABLE 10-continued

| Example | IUPAC name/structure (yield) | Analytical data |
|---|---|---|
| 119 | N-[(1-aminocyclopentyl)methyl]-8-[(2,6-difluorobenzyl)oxy]-2,6-dimethylimidazo[1,2-a]pyridine-3-carboxamide 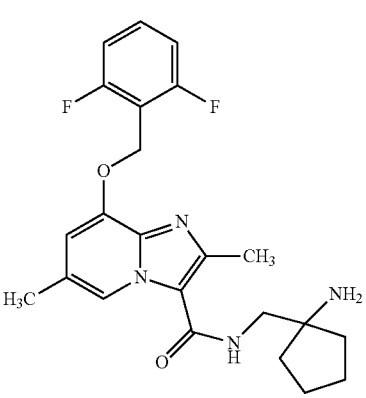 (63% of theory; purity 100%) | LC-MS (Method 2): $R_t$ = 0.58 min<br>MS (ESpos): m/z = 429.3 (M + H)$^+$<br>$^1$H NMR (400 MHz, DMSO-$d_6$):<br>δ = 1.31-1.42 (m, 2H), 1.49-1.62 (m, 6H), 1.66-1.79 (m, 2H), 2.31 (s, 3H), 5.28 (s, 2H), 6.91 (s, 1H), 7.24 (t, 2H), 7.53-7.64 (m, 1H), 7.66-7.74 (m, 1H), 8.46 (s, 1H), [further signals hidden under solvent peaks]. |

$^{1)}$The reaction was carried out using 10 equivalents of 2 M hydrochloric acid in diethyl ether.
$^{2)}$The reaction was carried out using 56 equivalents of 2 M hydrochloric acid in diethyl ether.
$^{3)}$The reaction was carried out using 31 equivalents of 2 M hydrochloric acid in diethyl ether.

Example 120

N-[(3S)-3-Aminobutan-2-yl]-8-[(2,6-difluorobenzyl)oxy]-2-methylimidazo[1,2-a]pyridine-3-carboxamide

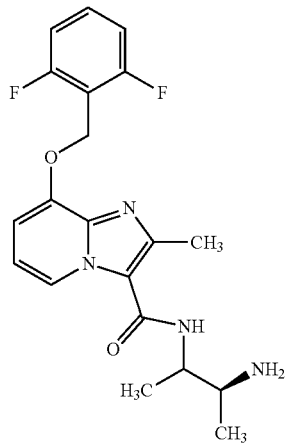 [SMILES: Cc1nc2c(OCc3c(F)cccc3F)cccn2c1C(=O)NC(C)[C@H](C)N]

155 mg of benzyl {(2S)-3-[({6-chloro-8-[(2,6-difluorobenzyl)oxy]-2-methylimidazo[1,2-a]pyridin-3-yl}carbonyl)amino]butan-2-yl}carbamate (Example 191A, 0.28 mmol, 1 equivalent) were dissolved in 50 ml of ethanol, and 40 mg of palladium on activated carbon (5%) were added. The mixture was hydrogenated at RT and standard pressure for 3 h. After the reaction had ended, the mixture was filtered through silica gel, the residue was washed with ethanol and the mother liquor was concentrated under reduced pressure. The crude product obtained was purified by preparative HPLC (Method 9).

LC-MS (Method 2): $R_t$=0.55 min
MS (ESpos): m/z=389.2 (M+H)$^+$
$^1$H NMR (400 MHz, DMSO-$d_6$): δ=1.01 (d, 3H), 1.15 (d, 3H), 1.80 (br. s, 2H), 2.50 (s, 3H; superimposed by DMSO signal), 2.82-2.96 (m, 1H), 3.81-3.95 (m, 1H), 5.30 (s, 2H), 6.92 (t, 1H), 7.01 (d, 1H), 7.23 (t, 2H), 7.47-7.54 (m, 1H), 7.55-7.63 (m, 1H), 8.64 (d, 1H).

Example 121

N-[(3R)-3-Aminobutan-2-yl]-8-[(2,6-difluorobenzyl)oxy]-2-methylimidazo[1,2-a]pyridine-3-carboxamide

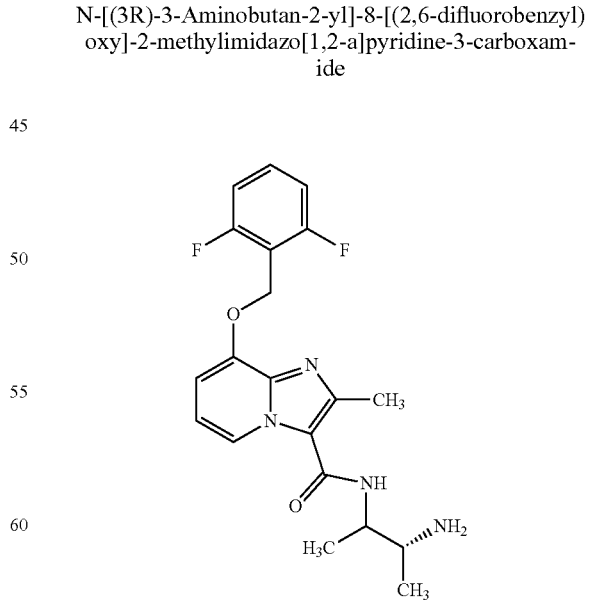

235 mg of benzyl {(2R)-3-[({8-[(2,6-difluorobenzyl)oxy]-2-methylimidazo[1,2-a]pyridin-3-yl}-carbonyl)amino]butan-2-yl}carbamate (Example 184A, 0.45 mmol, 1 equivalent) were dissolved in 260 ml of ethanol, and 63 mg of palladium on activated carbon (10%, 0.45 mmol, 1 equivalent) were added. The mixture was hydrogenated at RT under atmospheric pressure for 1.5 h and then filtered through silica gel and concentrated. The residue was dissolved in methanol and purified by preparative HPLC (Method 9). This gave 96 mg (55% of theory) of the title compound.

Diastereomer ratio 3:1
Main Diastereomer:
LC-MS (Method 2): $R_t$=0.55 min
MS (ESpos): m/z=389.2 (M+H)$^+$
$^1$H NMR (400 MHz, DMSO-d$_6$): δ=1.01 (d, 3H), 1.15 (d, 3H), 1.65 (br. s, 2H), 2.51 (s, 3H; superimposed by DMSO signal), 2.82-2.96 (m, 1H), 3.81-3.95 (m, 1H), 5.30 (s, 2H), 6.92 (t, 1H), 7.01 (d, 1H), 7.23 (t, 2H), 7.47-7.54 (m, 1H), 7.55-7.63 (m, 1H), 8.64 (d, 1H).

Example 122 ent-N-(1-Amino-3-methoxypropan-2-yl)-8-[(2,6-difluorobenzyl)oxy]-2-methylimidazo[1,2-a]-pyridine-3-carboxamide ditrifluoroacetate (Enantiomer A)

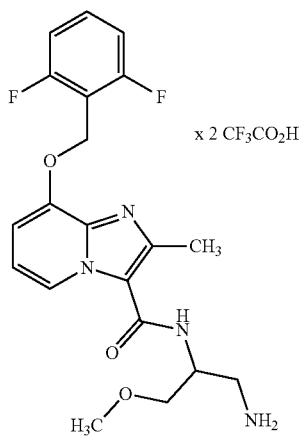 [SMILES: COCC(CN)NC(=O)c1c(C)nc2c(OCc3c(F)cccc3F)cccn12]

58 mg of ent-benzyl {2-[({8-[(2,6-difluorobenzyl)oxy]-2-methylimidazo[1,2-a]pyridin-3-yl}carbonyl)amino]-3-methoxypropyl}carbamate (Example 210A, enantiomer A, 0.1 mmol, 1 equivalent) were dissolved in 10 ml of ethanol, and 10 mg of palladium hydroxide on activated carbon (10%) were added. The mixture was hydrogenated at RT under atmospheric pressure for 3 h and then filtered through silica gel. The residue was washed with ethanol, ethyl acetate and dichloromethane and the organic phase was concentrated. The residue was purified by preparative HPLC (column: Sunfire C18, 5 μm, 250×20 mm, flow rate: 25 ml, wavelength: 210 nm, temperature 40° C., mobile phase: acetonitrile:water+1% TFA=20:80). This gave 27 mg (43% of theory, purity 100%) of the title compound.

LC-MS (Method 2): $R_t$=0.58 min
MS (ESpos): m/z=405.3 (M−2TFA+H)$^+$ $^1$H NMR (400 MHz, DMSO-d$_6$): δ=2.91-3.03 (m, 1H), 3.05-3.16 (m, 1H), 3.32 (s, 3H), 3.45-3.54 (m, 2H), 4.36-4.51 (m, 1H), 5.33 (s, 2H), 7.05-7.12 (m, 1H), 7.15-7.20 (m, 1H), 7.24 (t, 2H), 7.53-7.65 (m, 1H), 7.85 (br. s, 4H), 8.62 (d, 1H), [further signals hidden under solvent peaks].

Example 123 ent-N-(1-Amino-3-methoxypropan-2-yl)-8-[(2,6-difluorobenzyl)oxy]-2-methylimidazo[1,2-a]-pyridine-3-carboxamide ditrifluoroacetate (Enantiomer B)

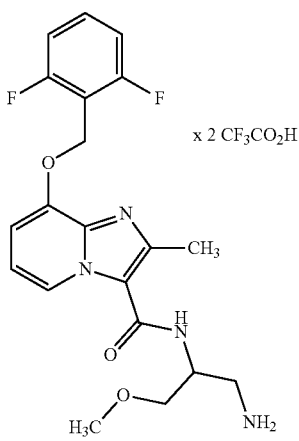 [SMILES: COCC(CN)NC(=O)c1c(C)nc2c(OCc3c(F)cccc3F)cccn12]

53 mg of ent-benzyl {2-[({8-[(2,6-difluorobenzyl)oxy]-2-methylimidazo[1,2-a]pyridin-3-yl}-carbonyl)amino]-3-methoxypropyl}carbamate (Example 211A, enantiomer B, 0.1 mmol, 1 equivalent) were hydrogenated and worked up analogously to Example 122. This gave 22 mg (36% of theory; purity 100%) of the title compound.

LC-MS (Method 2): $R_t$=0.58 min
MS (ESpos): m/z=405.3 (M−2TFA+H)$^+$
$^1$H NMR (400 MHz, DMSO-d$_6$): δ=2.91-3.03 (m, 1H), 3.05-3.16 (m, 1H), 3.32 (s, 3H), 3.45-3.54 (m, 2H), 4.36-4.51 (m, 1H), 5.33 (s, 2H), 7.05-7.12 (m, 1H), 7.15-7.20 (m, 1H), 7.24 (t, 2H), 7.53-7.65 (m, 1H), 7.85 (m, 4H), 8.62 (d, 1H), [further signals hidden under solvent peaks].

Example 124 ent-N-[1-Amino-3-(3,4-difluorophenoxy)propan-2-yl]-8-[(2,6-difluorobenzyl)oxy]-2-methylimidazo[1,2-a]pyridine-3-carboxamide ditrifluoroacetate

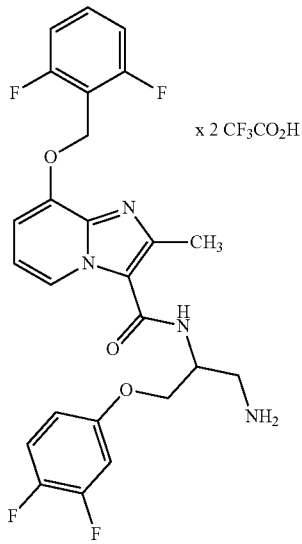 [SMILES: Cc1nc2c(OCc3c(F)cccc3F)cccn2c1C(=O)NC(CN)COc1ccc(F)c(F)c1]

x 2 CF₃CO₂H 110 mg of ent-benzyl {2-[({8-[(2,6-difluorobenzyl)oxy]-2-methylimidazo[1,2-a]pyridin-3-yl}-carbonyl)amino]-3-(3,4-difluorophenoxy)propyl}carbamate (Example 212A, Enantiomer B) were hydrogenated and worked up analogously to Example 122. This gave 69 mg (55% of theory; purity 100%) of the title compound.

LC-MS (Method 2): $R_t$=0.87 min

MS (ESpos): m/z=503.2 (M−2TFA+H)⁺

¹H NMR (400 MHz, DMSO-d₆): δ=3.03-3.15 (m, 1H), 3.16-3.27 (m, 1H), 4.12-4.22 (m, 2H), 4.58-4.70 (m, 1H), 5.33 (s, 2H), 6.80-6.87 (m, 1H), 7.01-7.09 (m, 1H), 7.10-7.19 (m, 2H), 7.24 (t, 2H), 7.34-7.44 (m, 1H), 7.54-7.64 (m, 1H), 7.88-8.05 (m, 4H), 8.62 (d, 1H), [further signal hidden under solvent peaks].

Example 125 rac-N-(3-Azabicyclo[4.1.0]hept-1-yl)-8-[(2,6-difluorobenzyl)oxy]-2-methylimidazo[1,2-a]-pyridine-3-carboxamide

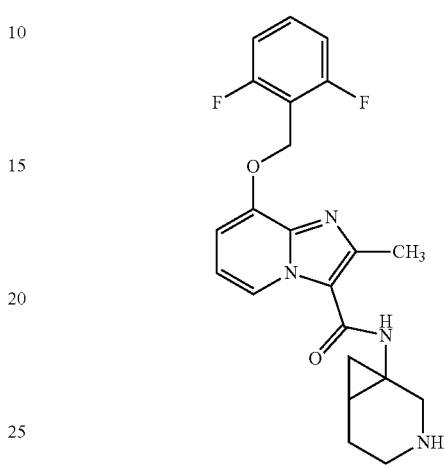

216 mg of rac-benzyl 1-[({8-[(2,6-difluorobenzyl)oxy]-2-methylimidazo[1,2-a]pyridin-3-yl}carbonyl)amino]-3-azabicyclo[4.1.0]heptan-3-carboxylate (Example 176A, 0.4 mmol, 1 equivalent) were reacted [0.2 equivalents of palladium on activated carbon (10%), reaction time: 16 h] and worked up analogously to Example 121 [After the separation by HPLC, the residue was taken up in ethyl acetate and washed twice with saturated aqueous sodium bicarbonate solution. The aqueous phase was extracted with ethyl acetate. The combined organic phases were dried over sodium sulphate, filtered and concentrated]. This gave 123 mg (74% of theory; 98%) of the title compound.

LC-MS (Method 7): $R_t$=0.56 min

MS (ESpos): m/z=413.1 (M+H)⁺

¹H NMR (400 MHz, DMSO-d₆): δ=0.92 (t, 1H), 0.96-1.02 (m, 1H), 1.22-1.31 (m, 1H), 1.57-1.68 (m, 1H), 2.01-2.11 (m, 1H), 2.45 (s, 3H), 2.59-2.76 (m, 2H), 3.19-3.29 (m, 2H), 5.30 (s, 2H), 5.79 (br. s, 1H), 6.94 (t, 1H), 7.02 (d, 1H), 7.23 (t, 2H), 7.53-7.63 (m, 1H), 8.24 (s, 1H), 8.60 (d, 1H).

Example 126 ent-N-(2-Amino-4,4,4-trifluorobutyl)-8-[(2,6-difluorobenzyl)oxy]-2-methylimidazo[1,2-a]pyridine-3-carboxamide (Enantiomer A)

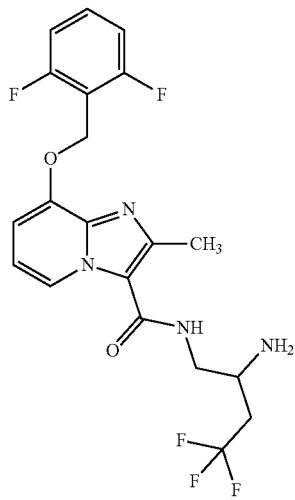 [SMILES: Cc1nc2c(OCc3c(F)cccc3F)cccn2c1C(=O)NCC(N)CC(F)(F)F]

Under argon, 170 mg of ent-benzyl {1-[({8-[(2,6-difluorobenzyl)oxy]-2-methylimidazo[1,2-a]-pyridin-3-yl}carbonyl)amino]-4,4,4-trifluorobutan-2-yl}carbamate (Example 215A, 0.30 mmol, 1 equivalent) were initially charged in 3 ml of ethanol/dichloroethane (2/1), 31 mg of palladium on activated carbon (10%) and 0.60 ml (5.90 mmol, 20 equivalents) of cyclohexene were added and the mixture was stirred under reflux overnight. The reaction solution was filtered through a Millipore® filter, washed thoroughly with ethanol/dichloroethane (2/1), concentrated and dried under high vacuum. The product was purified by silica gel chromatography (mobile phase: dichloromethane/methanol: 40/1 isocratic). This gave 92 mg (67% of theory; 95%) of the title compound.

LC-MS (Method 7): $R_t$=0.62 min

MS (ESpos): m/z=443.2 (M+H)$^+$ $^1$H NMR (400 MHz, DMSO-d$_6$): δ=1.85 (br. s, 2H), 2.15-2.38 (m, 1H), 2.40-2.47 (m, 1H), 3.15-3.28 (m, 2H), 5.30 (s, 2H), 6.94 (t, 1H), 7.01 (d, 1H), 7.24 (t, 2H), 7.54-7.64 (m, 1H), 7.89 (t, 1H), 8.64 (d, 1H), [further signals hidden under solvent peaks].

Example 127 ent-N-(2-Amino-4,4,4-trifluorobutyl)-8-[(2,6-difluorobenzyl)oxy]-2-methylimidazo[1,2-a]pyridine-3-carboxamide (Enantiomer B)

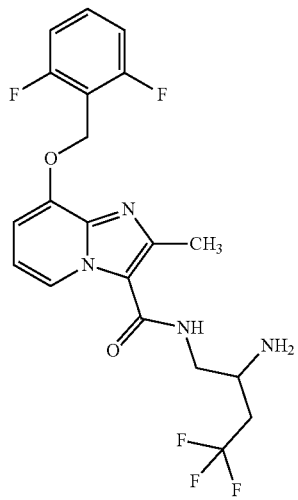

172 mg of ent-benzyl {1-[({8-[(2,6-difluorobenzyl)oxy]-2-methylimidazo[1,2-a]pyridin-3-yl}carbonyl)amino]-4,4,4-trifluorobutan-2-yl}carbamate trifluoroacetate (Example 216A, 0.30 mmol, 1 equivalent) were reacted and worked up analogously to Example 126. This gave 66 mg (50% of theory; 95%) of the title compound.

LC-MS (Method 2): $R_t$=0.60 min

MS (ESpos): m/z=443.3 (M+H)$^+$ $^1$H NMR (400 MHz, DMSO-d$_6$): δ=1.80 (br. s, 2H), 2.15-2.37 (m, 1H), 2.40-2.47 (m, 1H), 3.15-3.28 (m, 2H), 5.30 (s, 2H), 6.94 (t, 1H), 7.01 (d, 1H), 7.24 (t, 2H), 7.55-7.64 (m, 1H), 7.89 (t, 1H), 8.64 (d, 1H), [further signals hidden under solvent peaks].

Example 128 ent-N-(2-Amino-4,4,4-trifluorobutyl)-8-[(2,6-difluorobenzyl)oxy]-2,6-dimethylimidazo[1,2-a]-pyridine-3-carboxamide (Enantiomer A)

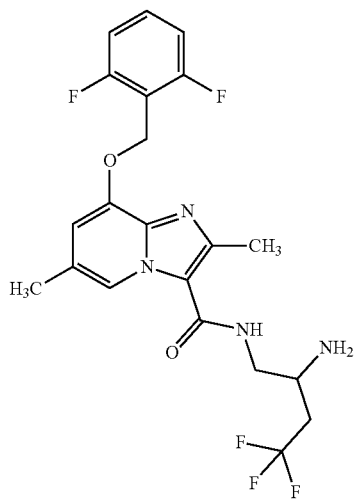 [SMILES: Cc1cc(OCc2c(F)cccc2F)c2nc(C)c(C(=O)NCC(N)CC(F)(F)F)n2c1]

85 mg of ent-benzyl {1-[({8-[(2,6-difluorobenzyl)oxy]-2,6-dimethylimidazo[1,2-a]pyridin-3-yl}-carbonyl)amino]-4,4,4-trifluorobutan-2-yl}carbamate (Example 217A, 0.14 mmol, 1 equivalent) were initially charged in 2.1 ml of a 1:1:0.1 mixture of ethanol/dichloromethane/methanol and, with addition of 0.3 ml of cyclohexene (2.88 mmol, 20 equivalents) and 15 mg of 10% palladium on activated carbon (0.014 mmol, 0.1 equivalent), stirred at reflux for 3 h. Another 0.15 ml of cyclohexene (1.44 mmol, 10 equivalents) and 15 mg of 10% palladium on activated carbon (0.014 mmol, 0.1 equivalent) were then added, and the mixture was stirred at reflux for a further 6 h. The reaction solution was filtered through a Millipore filter, washed thoroughly with methanol and concentrated. The residue was purified by preparative HPLC (RP18 column, mobile phase: acetonitrile/water gradient with addition of 0.1% TFA). The crude product was taken up in dichloromethane and washed twice with saturated aqueous sodium bicarbonate solution. The aqueous phase was extracted twice with dichloromethane and the combined organic phases were dried over sodium sulphate, filtered and concentrated. This gave 52 mg (75% of theory, purity 95%) of the title compound.

LC-MS (Method 2): $R_t$=0.69 min

MS (ESpos): m/z=457.3 (M+H)$^+$ $^1$H NMR (400 MHz, DMSO-d$_6$): δ=1.69 (br. s, 2H), 2.16-2.30 (m, 1H), 2.31 (s, 3H), 2.36-2.46 (m, 1H), 3.13-3.27 (m, 2H), 5.27 (s, 2H), 6.92 (s, 1H), 7.23 (t, 2H), 7.54-7.65 (m, 1H), 7.81-7.88 (m, 1H), 8.47 (s, 1H), [further signals hidden under solvent peaks].

Specific rotation [α] (365 nm, 19.6° C.)=+42.5° (c=0.00445 g/ml, acetonitrile)

Example 129 ent-N-(2-Amino-4,4,4-trifluorobutyl)-8-[(2,6-difluorobenzyl)oxy]-2,6-dimethylimidazo[1,2-a]-pyridine-3-carboxamide (Enantiomer B)

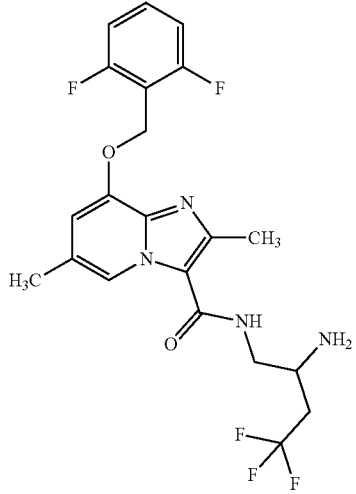 [SMILES: Cc1cc(OCc2c(F)cccc2F)c2nc(C)c(C(=O)NCC(N)CC(F)(F)F)n2c1]

92 mg of ent-benzyl {1-[({8-[(2,6-difluorobenzyl)oxy]-2,6-dimethylimidazo[1,2-a]pyridin-3-yl}carbonyl)amino]-4,4,4-trifluorobutan-2-yl}carbamate (Example 218A, 0.16 mmol, 1 equivalent) were initially charged in 2.1 ml of a 1:1:0.1 mixture of ethanol/dichloromethane/methanol and, with addition of 0.47 ml of cyclohexene (4.67 mmol, 30 equivalents) and 33 mg of 10% palladium on activated carbon (0.03 mmol, 0.1 equivalent), stirred at reflux for 6 h. The reaction solution was filtered through a Millipore® filter, washed thoroughly with methanol and concentrated. The residue was purified by preparative HPLC (RP 18 column, mobile phase: acetonitrile/water gradient with addition of 0.1% TFA). The crude product was taken up in dichloromethane and washed twice with saturated aqueous sodium bicarbonate solution. The aqueous phase was extracted twice with dichloromethane. The combined organic phases were dried over sodium sulphate, filtered and concentrated. This gave 46 mg (64% of theory) of the title compound.

LC-MS (Method 2): $R_t$=0.70 min

MS (ESpos): m/z=457.3 (M+H)$^+$ $^1$H NMR (400 MHz, DMSO-d$_6$): δ=1.71 (br. s, 2H), 2.16-2.30 (m, 1H), 2.31 (s, 3H), 2.36-2.46 (m, 1H), 3.13-3.27 (m, 2H), 5.28 (s, 2H), 6.92 (s, 1H), 7.23 (t, 2H), 7.54-7.65 (m, 1H), 7.81-7.88 (m, 1H), 8.47 (s, 1H), [further signals hidden under solvent peaks].

Specific rotation [α] (365 nm, 19.5° C.)=−39.0° (c=0.005 g/ml, acetonitrile)

The examples shown in Table 11 were prepared analogously to Example 75 by reacting the appropriate carboxylic acid with the appropriate commercially available amines under the reaction conditions described in the Representative Working Procedure 2.

TABLE 11

| Example | IUPAC name/structure (yield) | Analytical data |
|---|---|---|
| 130 | 8-[(2,6-difluorobenzyl)oxy]-N-[2-(isopropylamino)ethyl]-2-methylimidazo[1,2-a]-pyridine-3-carboxamide<br />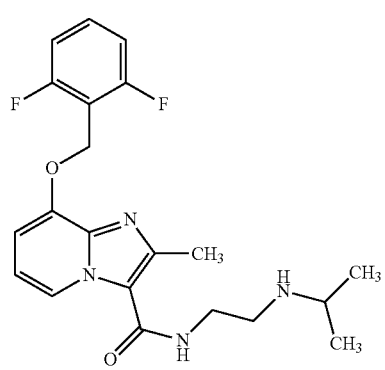<br />(56% of theory; purity 96%) | LC-MS (Method 7): $R_t$ = 0.53 min<br />MS (ESpos): m/z = 403.2 (M + H)$^+$<br />$^1$H NMR (400 MHz, DMSO-d$_6$):<br />δ = 0.98 (d, 6H), 2.66-2.80 (m, 3H), 5.30 (s, 2H), 6.92 (t, 1H), 7.02 (d, 1H), 7.23 (t, 2H), 7.54-7.64 (m, 1H), 7.79 (t, 1H), 8.64 (d, 1H), [further signals hidden under solvent peaks]. |
| 131 | 8-[(2,6-difluorobenzyl)oxy]-N-[2-(1,1-dioxidothiomorpholin-4-yl)ethyl]-2-methylimidazo[1,2-a]pyridine-3-carboxamide<br />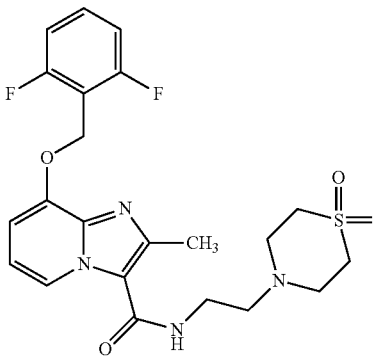<br />(84% of theory; purity 99%) | LC-MS (Method 7): $R_t$ = 0.65 min<br />MS (ESpos): m/z = 479.1 (M + H)$^+$<br />$^1$H NMR (400 MHz, DMSO-d$_6$):<br />δ = 2.53 (s, 3H), 2.69 (t, 2H), 2.94-3.00 (m, 4H), 3.06-3.12 (m, 4H), 3.39-3.46 (m, 2H), 5.30 (s, 2H), 6.93 (t, 1H), 7.02 (d, 1H), 7.23 (d, 2H), 7.54-7.64 (m, 1H), 7.74 (t, 1H), 8.64 (d, 1H). |

TABLE 11-continued

| Example | IUPAC name/structure (yield) | Analytical data |
|---|---|---|
| 132 | rac-8-[(2,6-difluorobenzyl)oxy]-2-methyl-N-[2-(morpholin-4-yl)propyl]imidazo[1,2-a]pyridine-3-carboxamide<br><br>(85% of theory; purity 100%) | LC-MS (Method 7): $R_f$ = 0.53 min<br>MS (ESpos): m/z = 445.2 (M + H)$^+$<br>$^1$H NMR (400 MHz, DMSO-d$_6$):<br>δ = 0.96 (d, 2H), 2.37-2.45 (m, 2H), 2.58 (m, 5H, obscured by DMSO signal), 2.74-2.84 (m, 1H), 3.52-3.63 (m, 4H), 5.30 (s, 2H), 6.94 (t, 1H), 7.02 (d, 1H), 7.23 (t, 2H), 7.54-7.65 (m, 2H), 8.71 (d, 1H), [further signals hidden under solvent peaks]. |
| 133 | 8-[(2,6-difluorobenzyl)oxy]-2-methyl-N-[2-(4-methylpiperazin-1-yl)ethyl]imidazo[1,2-a]-pyridine-3-carboxamide<br><br>(59% of theory; purity 98%) | LC-MS (Method 2): $R_f$ = 0.54 min<br>MS (ESpos): m/z = 444.2 (M + H)$^+$<br>$^1$H NMR (400 MHz, DMSO-d$_6$):<br>δ = 2.15 (s, 3H), 2.24-2.52 (m, 13H; superimposed by DMSO signal), 3.37-3.46 (m, 2H), 5.29 (s, 2H), 6.92 (t, 1H), 7.02 (d, 1H), 7.24 (t, 2H), 7.53-7.64 (m, 1H), 7.69 (t, 1H), 8.66 (d, 1H). |

TABLE 11-continued

| Example | IUPAC name/structure (yield) | Analytical data |
|---|---|---|
| 134 | rac-8-[(2,6-difluorobenzyl)oxy]-2-methyl-N-[2-(morpholin-4-yl)-1-phenylethyl]imidazo[1,2-a]pyridine-3-carboxamide<br>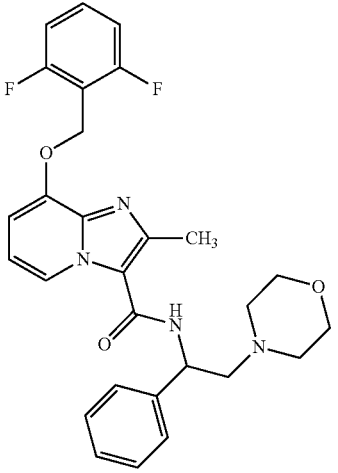<br>(71% of theory; purity 95%) | LC-MS (Method 7): $R_t$ = 0.72 min<br>MS (ESpos): m/z = 507.2 (M + H)$^+$<br>$^1$H NMR (400 MHz, DMSO-d$_6$):<br>δ = 2.34-2.44 (m, 2H), 2.61 (s, 3H), 2.75-2.84 (m, 1H), 3.51-3.63 (m, 4H), 5.13-5.24 (m, 1H), 5.31 (s, 2H), 6.91 (t, 1H), 7.00 (d, 1H), 7.19-7.29 (m, 3H), 7.35 (t, 2H), 7.44 (d, 2H), 7.53-7.66 (m, 2H), 8.27 (d, 1H), 8.52 (d, 1H), [further signals hidden under solvent peaks]. |
| 135 | rac-8-[(2,6-difluorobenzyl)oxy]-N-[2-(isopropylamino)ethyl]-2,6-dimethylimidazo[1,2-a]pyridine-3-carboxamide<br>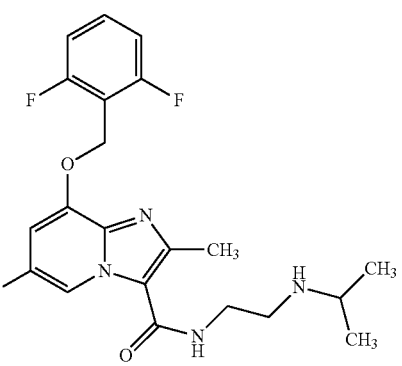<br>(74% of theory; purity: 100%) | LC-MS (Method 7): $R_t$ = 0.59 min<br>MS (ESpos): m/z = 417.2 (M + H)$^+$<br>$^1$H NMR (400 MHz, DMSO-d$_6$):<br>δ = 0.98 (d, 6H), 1.68 (br. s, 1H), 2.30 (s, 3H), 2.66-2.80 (m, 3H), 5.30 (s, 2H), 6.91 (s, 1H), 7.23 (t, 2H), 7.54-7.64 (m, 1H), 7.78 (t, 1H), 8.48 (s, 1H), [further signals hidden under solvent peaks]. |

TABLE 11-continued

| Example | IUPAC name/structure (yield) | Analytical data |
|---|---|---|
| 136 | 8-[(2,6-difluorobenzyl)oxy]-2,6-dimethyl-N-[2-(morpholin-4-yl)ethyl]imidazo[1,2-a]pyridine-3-carboxamide<br>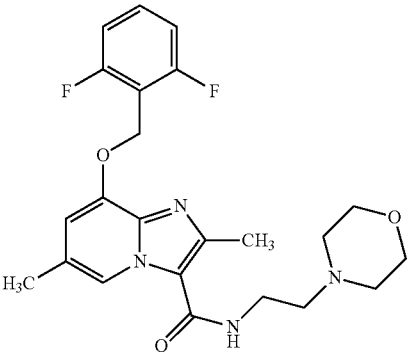<br>(59% of theory; purity 97%) | LC-MS (Method 7): $R_t$ = 0.63 min<br>MS (ESpos): m/z = 445.2 (M + H)$^+$<br>$^1$H NMR (400 MHz, DMSO-d$_6$):<br>δ = 2.30 (s, 3H), 2.39-2.45 (m, 4H), 3.39-3.46 (m, 2H), 3.57 (br. s, 4H), 5.28 (s, 2H), 6.93 (s, 1H), 7.22 (t, 2H), 7.52-7.64 (m, 1H), 7.70 (br. s, 1H), 8.48 (br. s, 1H), [further signals hidden under solvent peaks]. |
| 137 | 8-[(2,6-difluorobenzyl)oxy]-2,6-dimethyl-N-[2-(4-methylpiperazin-1-yl)ethyl]imidazo[1,2-a]-pyridine-3-carboxamide<br>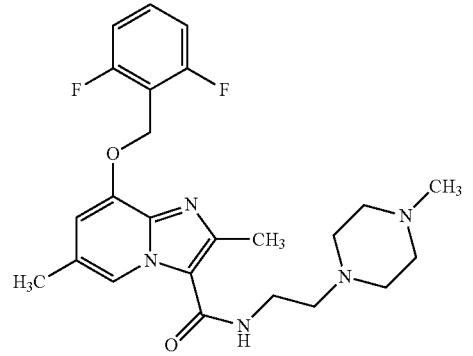<br>(71% of theory; purity 97%) | LC-MS (Method 2): $R_t$ = 0.57 min<br>MS (ESpos): m/z = 458.3 (M + H)$^+$<br>$^1$H NMR (400 MHz, DMSO-d$_6$):<br>δ = 2.31 (s, 3H), 3.38-3.47 (m, 2H), 5.28 (s, 2H), 6.92 (s, 1H), 7.25 (t, 3H), 7.53-7.64 (m, 1H), 7.68 (br. s, 1H), 8.48 (s, 1H), [further signals hidden under solvent peaks]. |
| 138 | rac-8-[(2,6-difluorobenzyl)oxy]-2,6-dimethyl-N-[2-(morpholin-4-yl)propyl]imidazo[1,2-a]-pyridine-3-carboxamide<br>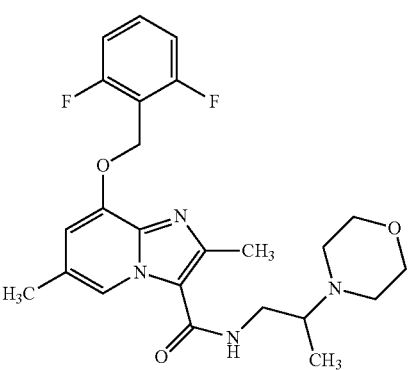<br>(59% of theory; purity 98%) | LC-MS (Method 7): $R_t$ = 0.59 min<br>MS (ESpos): m/z = 459.2 (M + H)$^+$<br>$^1$H NMR (400 MHz, DMSO-d$_6$):<br>δ = 0.97 (d, 3H), 2.31 (s, 3H), 2.38-2.46 (m, 2H), 2.73-2.83 (m, 1H), 3.50-3.64 (m, 4H), 5.29 (s, 2H), 6.93 (s, 1H), 7.23 (t, 2H), 7.54-7.66 (m, 2H), 8.52 (s, 1H), [further signal hidden under solvent peak]. |

TABLE 11-continued

| Example | IUPAC name/structure (yield) | Analytical data |
|---|---|---|
| 139 | 8-[(2,6-difluorobenzyl)oxy]-N-[2-(4-isopropylpiperazin-1-yl)ethyl]-2,6-dimethylimidazo[1,2-a]pyridine-3-carboxamide<br>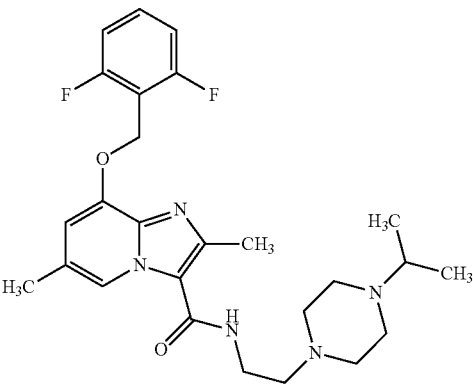<br>(72% of theory; purity 98%) | LC-MS (Method 2): $R_t$ = 0.63 min<br>MS (ESpos): m/z = 486.3 (M + H)$^+$<br>$^1$H NMR (400 MHz, DMSO-$d_6$):<br>$\delta$ = 0.95 (d, 6H), 2.31 (s, 3H), 2.38-2.45 (m, 6H), 3.36-3.45 (m, 2H), 5.28 (s, 2H), 6.91 (s, 1H), 7.24 (t, 2H), 7.52-7.64 (m, 1H), 7.67 (t, 1H), 8.48 (s, 1H), [further signals hidden under solvent peak]. |

Example 140

N-(2-Amino-2-methylpropyl)-8-[(2,6-difluorobenzyl)oxy]-6-fluoro-2-methylimidazo[1,2-a]-pyridine-3-carboxamide

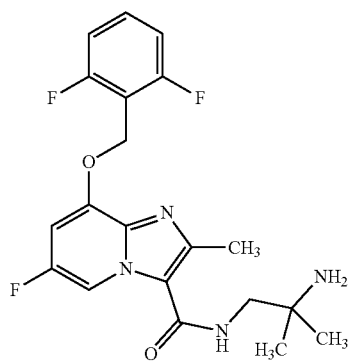 [SMILES: Cc1nc2c(OCc3c(F)cccc3F)cc(F)cn2c1C(=O)NCC(C)(C)N]

45 mg of 8-[(2,6-difluorobenzyl)oxy]-6-fluoro-2-methylimidazo[1,2-a]pyridine-3-carboxylic acid Example 11A, 0.13 mmol, 1 equivalent), 65 mg of (benzotriazol-1-yloxy) bisdimethylaminomethylium fluoroborate (TBTU, 0.2 mmol, 1.5 equivalents) and 54 mg of 4-methylmorpholine (0.54 mmol, 4 equivalents) were initially charged in 0.9 ml of DMF. After 10 min at RT, 24 mg of 1,2-diamino-2-methylpropane (0.27 mmol, 2 equivalents) were added and the mixture was stirred at RT overnight. Another 22 mg equivalents of TBTU (0.07 mmol, 0.5 equivalents) and 12 mg of 1,2-diamino-2-methylpropane (0.13 mmol, 1 equivalent) were added and the reaction was stirred at RT for 2 h. Water was added and the reaction solution was purified by preparative HPLC (RP18 column, mobile phase: acetonitrile/water gradient with addition of 0.1% TFA). The residue was taken up in dichloromethane and washed twice with saturated aqueous sodium bicarbonate solution. The aqueous phase was extracted twice with dichloromethane and the combined organic phases were dried over sodium sulphate. The mixture was filtered and concentrated and the crude product obtained was purified by thick-layer chromatography (mobile phase: dichloromethane/2 N ammonia in methanol: 10:0.5). This gave 31 mg of the title compound (55% of theory; purity 98%).

LC-MS (Method 2): $R_t$=0.64 min
MS (ESpos): m/z=407.2 (M+H)$^+$
$^1$H NMR (400 MHz, DMSO-$d_6$): $\delta$=1.05 (s, 6H), 1.52 (br. s, 2H), 3.15-3.23 (m, 2H), 5.32 (s, 2H), 7.19-7.32 (m, 3H), 7.55-7.66 (m, 1H), 7.75 (br. s, 1H), 8.69-8.76 (m, 1H), [further signal hidden under solvent peaks].

Example 141

N-(3-Amino-2,3-dimethylbutan-2-yl)-8-[(2,6-difluorobenzyl)oxy]-2-methylimidazo[1,2-a]pyridine-3-carboxamide

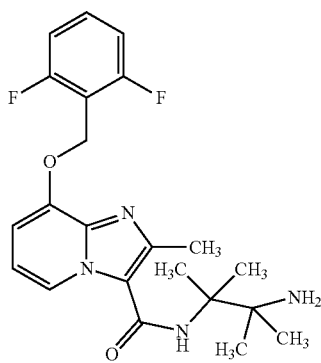 [SMILES: Cc1nc2c(OCc3c(F)cccc3F)cccn2c1C(=O)NC(C)(C)C(C)(C)N]

75 mg of 8-[(2,6-difluorobenzyl)oxy]-2-methylimidazo[1,2-a]pyridine-3-carboxylic acid (Example 3A, 0.24 mmol, 1 equivalent), 116 mg of O-(7-azabenzotriazol-1-yl)-N,N,N'N'-tetramethyluronium hexafluorophosphate (HATU, 0.31 mmol, 1.3 equivalents) and 152 mg of N,N-diisopropylethylamine (0.21 ml, 1.18 mmol, 5 equivalents) were dissolved in 1.6 ml of DMF, after 10 min at RT, 111 mg of 2,3-dimethylbutane-2,3-diamine dihydrochloride (0.6 mmol, 2.5 equivalents) were added and the mixture was stirred at RT overnight. The product was then purified by preparative HPLC (method: RP18 column, mobile phase: acetonitrile/water gradient with addition of 0.1% TFA). The product fraction obtained was dissolved in ethyl acetate and saturated aqueous sodium bicarbonate solution and the aqueous phase was extracted twice with ethyl acetate. The combined organic phases were dried over sodium sulphate, filtered, concentrated and lyophilized. This gave 20 mg (20% of theory; purity 99%) of the title compound.

LC-MS (Method 7): $R_t$=0.57 min
MS (ESpos): m/z=417.2 $(M+H)^+$
$^1$H NMR (400 MHz, DMSO-$d_6$): δ=1.13 (s, 6H), 1.42 (s, 6H), 2.58 (s, 3H), 5.30 (s, 2H), 6.93 (t, 1H), 7.02 (d, 1H), 7.23 (t, 2H), 7.53-7.65 (m, 1H), 7.92 (s, 1H), 8.89 (d, 1H).

The examples shown in Table 12 were prepared analogously to Example 141 by reacting the appropriate carboxylic acids (Example 3A, 16A and 21A) with the appropriate amines, prepared as described above or commercially available (1.05-2.5 equivalents), and N,N-diisopropylethylamine (3-6 equivalents) under the reaction conditions described in the General Working Procedure 3.

Exemplary work-up of the reaction mixture: Water was added to the reaction solution and the precipitate formed was stirred for another 0.5-1.0 h, filtered off, washed with water and dried under high vacuum overnight. Alternatively, the precipitate or the crude reaction mixture was purified further directly by preparative HPLC (RP18 column, mobile phase: acetonitrile/water gradient with addition of 0.1% TFA) and dried under high vacuum overnight. If appropriate, the product fractions were taken up in ethyl acetate or dichloromethane and washed twice with saturated aqueous sodium bicarbonate solution. The aqueous phase was extracted twice with ethyl acetate or dichloromethane and the combined organic phases were dried over sodium sulphate, filtered and concentrated.

TABLE 12

| Example | IUPAC name/structure (yield) | Analytical data |
|---|---|---|
| 142 | rac-8-[(2,6-difluorobenzyl)oxy]-N-[2-(dimethylamino)-3-methylbutyl]-2-methylimidazo[1,2-a]-pyridine-3-carboxamide<br />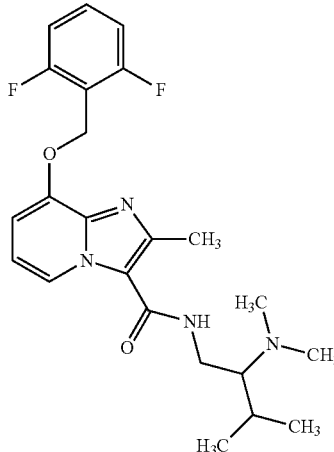<br />(84% of theory; purity 96%) | LC-MS (Method 2): $R_t$ = 0.61 min<br />MS (ESpos): m/z = 431.3 $(M + H)^+$<br />$^1$H NMR (400 MHz, DMSO-$d_6$):<br />δ = 0.95 (dd, 6H), 1.79-1.89 (m, 1H), 2.31-2.41 (m, 7H), 3.25-3.32 (m, 1H), 3.39-3.48 (m, 1H), 5.30 (s, 2H), 6.93 (t, 1H), 7.01 (d, 1H), 7.24 (t, 2H), 7.54-7.67 (m, 2H), 8.71 (d, 1H), [further signal hidden under solvent peaks]. |

TABLE 12-continued

| Example | IUPAC name/structure (yield) | Analytical data |
|---|---|---|
| 143 | 8-[(2,6-difluorobenzyl)oxy]-N-[2-(3,3-difluoropyrrolidin-1-yl)ethyl]-2-methylimidazo[1,2-a]-pyridine-3-carboxamide<br>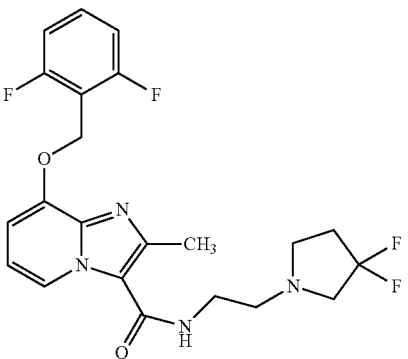<br>(90% of theory; purity 99%) | LC-MS (Method 2): $R_t$ = 0.65 min<br>MS (ESpos): m/z = 451.2 (M + H)$^+$<br>$^1$H NMR (400 MHz, DMSO-d$_6$):<br>δ = 2.16-2.31 (m, 2H), 2.64 (t, 2H), 2.77 (t, 2H), 2.96 (t, 2H), 3.38-3.46 (m, 2H), 5.30 (s, 2H), 6.93 (t, 1H), 7.01 (d, 1H), 7.24 (t, 2H), 7.54-7.64 (m, 1H), 7.82 (t, 1H), 8.63 (d, 1H), [further signal hidden under solvent peaks]. |
| 144 | 8-[(2,6-difluorobenzyl)oxy]-N-{2-[(2-methoxyethyl)amino]ethyl}-2-methylimidazo[1,2-a]-pyridine-3-carboxamide<br>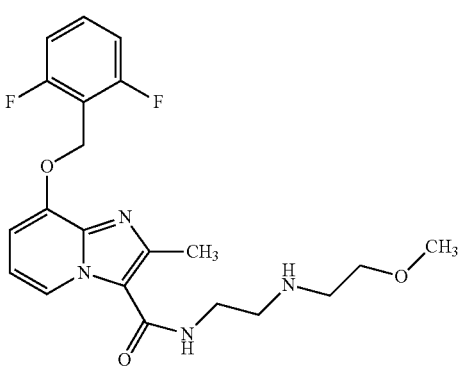<br>(60% of theory; purity 99%) | LC-MS (Method 2): $R_t$ = 0.56 min<br>MS (ESpos): m/z = 419.2 (M + H)$^+$<br>$^1$H NMR (400 MHz, DMSO-d$_6$):<br>δ = 1.82 (br. s, 1H), 2.65-2.75 (m, 4H), 3.23 (s, 3H), 3.38 (m, 4H), 5.28 (s, 2H), 6.93 (t, 1H), 7.01 (d, 1H), 7.24 (t, 2H), 7.54-7.64 (m, 1H), 7.80 (t, 1H), 8.63 (d, 1H), [further signal hidden under solvent peaks]. |
| 145 | 8-[(2,6-difluorobenzyl)oxy]-N-[2-(dimethylamino)-2-methylpropyl]-2-methylimidazo[1,2-a]-pyridine-3-carboxamide<br>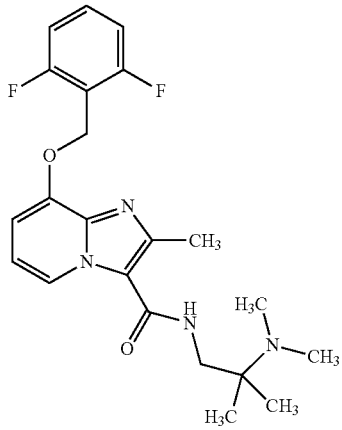<br>(90% of theory; purity 99%) | LC-MS (Method 2): $R_t$ = 0.56 min<br>MS (ESpos): m/z = 417.2 (M + H)$^+$<br>$^1$H NMR (400 MHz, DMSO-d$_6$):<br>δ = 1.01 (s, 6H), 2.20 (s, 6H), 2.56 (s, 3H), 3.29-3.32 (m, 2H; superimposed by solvent signal), 5.31 (s, 2H), 6.94 (t, 1H), 7.02 (d, 1H), 7.24 (t, 2H), 7.37 (t, 1H), 7.54-7.65 (m, 1H), 8.76 (d, 1H). |

TABLE 12-continued

| Example | IUPAC name/structure (yield) | Analytical data |
|---|---|---|
| 146 | N-{2-[cyclopropyl(2,2-difluoroethyl)amino]ethyl}-8-[(2,6-difluorobenzyl)oxy]-2-methylimidazo[1,2-a]-pyridine-3-carboxamide<br>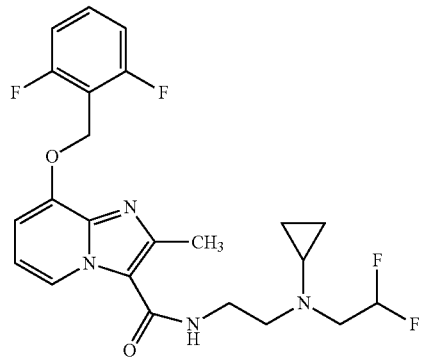<br>(77% of theory; purity: 97%) | LC-MS (Method 2): $R_t$ = 0.97 min<br>MS (ESpos): m/z = 465.3 (M + H)$^+$<br>$^1$H NMR (400 MHz, DMSO-d$_6$):<br>δ = 0.35-0.42 (m, 2H), 0.45-0.51 (m, 2H), 2.05-2.14 (m, 1H), 2.89 (t, 2H), 3.03 (td, 2H), 3.44 (dd, 2H), 5.30 (s, 2H), 6.13 (tt, 1H), 6.92 (t, 1H), 7.01 (d, 1H), 7.24 (t, 2H), 7.54-7.64 (m, 1H), 7.67 (t, 1H), 8.67 (d, 1H), [further signal hidden under solvent peaks]. |
| 147 | rac-N-(2-amino-4,4,4-trifluorobutyl)-6-chloro-8-[(2,6-difluorobenzyl)oxy]-2-methylimidazo[1,2-a]-pyridine-3-carboxamide<br>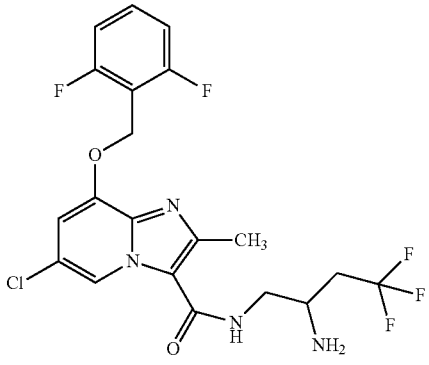<br>(63% of theory; purity 99%) | LC-MS (Method 7): $R_t$ = 0.75 min<br>MS (ESpos): m/z = 477.0 (M + H)$^+$<br>$^1$H NMR (400 MHz, DMSO-d$_6$):<br>δ = 1.72 (br. s, 2H), 2.18-2.32 (m, 1H), 2.34-2.49 (m, 1H), 3.16-3.28 (m, 2H), 3.32-3.41 (m, 1H), 5.32 (s, 2H), 7.18-7.28 (m, 3H), 7.55-7.65 (m, 1H), 7.93 (t, 1H), 8.64 (d, 1H), [further signal hidden under solvent peaks]. |
| 148 | 6-chloro-8-[(2,6-difluorobenzyl)oxy]-2-methyl-N-[2-methyl-2-(pyrrolidin-1-yl)-propyl]imidazo[1,2-a]-pyridine-3-carboxamide<br>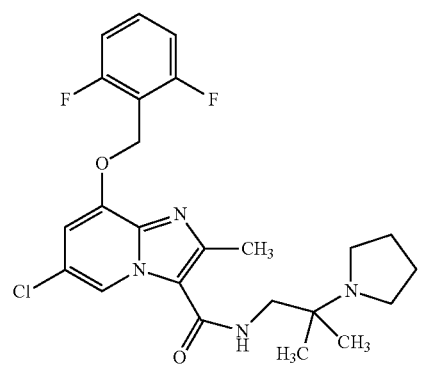<br>(64% of theory; purity: 98%) | LC-MS (Method 7): $R_t$ = 0.76 min<br>MS (ESpos): m/z = 477.1 (M + H)$^+$<br>$^1$H NMR (400 MHz, DMSO-d$_6$):<br>δ = 1.04 (s, 6H), 1.63-1.72 (m, 4H), 2.57-2.63 (m, 4H), 3.28-3.31 (m, 2H), 5.34 (s, 2H), 7.18-7.29 (m, 3H), 7.45-7.53 (m, 1H), 7.56-7.66 (m, 1H), 8.89 (d, 1H), [further signal hidden under DMSO peak]. |

TABLE 12-continued

| Example | IUPAC name/structure (yield) | Analytical data |
|---|---|---|
| 149 | 6-chloro-8-[(2,6-difluorobenzyl)oxy]-N-[2-(isopropylamino)ethyl]-2-methylimidazo[1,2-a]-pyridine-3-carboxamide<br>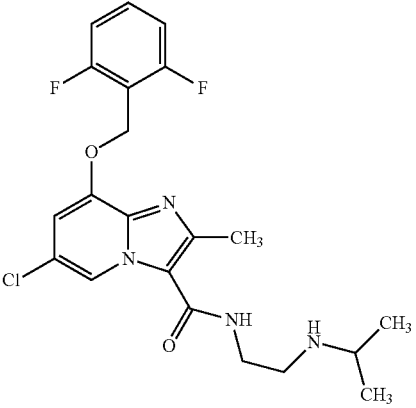<br>(87% of theory; purity 100%) | LC-MS (Method 2): $R_t$ = 0.73 min<br>MS (ESpos): m/z = 437.2 (M + H)$^+$<br>$^1$H NMR (400 MHz, DMSO-d$_6$):<br>δ = 0.98 (d, 6H), 1.63 (br. s, 1H), 2.66-2.79 (m, 3H), 3.32-3.39 (m, 2H, superimposed by solvent signal), 5.34 (s, 2H), 7.19 (d, 1H), 7.22-7.29 (m, 2H), 7.56-7.65 (m, 1H), 7.84-7.90 (m, 1H), 8.77 (d, 1H), [further signal hidden under DMSO peak]. |
| 150 | 6-chloro-N-{2-[cyclopropyl(2,2-difluorobenzyl)-amino]ethyl}-8-[(2,6-difluorobenzyl)oxy]-2-methylimidazo[1,2-a]-pyridine-3-carboxamide<br>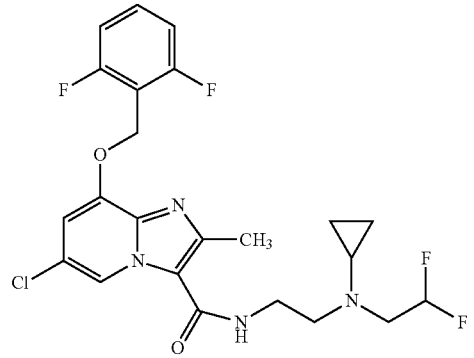<br>(78% of theory; purity: 98%) | LC-MS (Method 2): $R_t$ = 1.22 min<br>MS (ESpos): m/z = 499.3 (M + H)$^+$<br>$^1$H NMR (400 MHz, DMSO-d$_6$):<br>δ = 0.35-0.41 (m, 2H), 0.46-0.52 (m, 2H), 2.06-2.14 (m, 1H), 2.48 (s, 3H), 2.89 (t, 2H), 3.02 (td, 2H), 3.41-3.50 (m, 2H), 5.34 (s, 2H), 6.14 (tt, 1H), 7.20 (d, 1H), 7.26 (t, 2H), 7.56-7.65 (m, 1H), 7.74 (t, 1H), 8.76 (d, 1H). |
| 151 | 6-chloro-8-[(2,6-difluorobenzyl)oxy]-N-[2-(4,4-difluoropiperidin-1-yl)ethyl]-2-methylimidazo[1,2-a]-pyridine-3-carboxamide<br>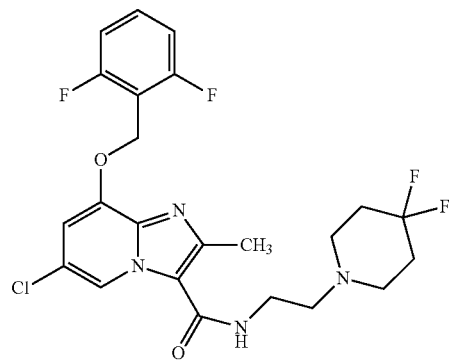<br>(54% of theory; purity: 97%) | LC-MS (Method 2): $R_t$ = 0.79 min<br>MS (ESpos): m/z = 499.2 (M + H)$^+$<br>$^1$H NMR (400 MHz, DMSO-d$_6$):<br>δ = 1.88-2.03 (m, 4H), 3.39-3.47 (m, 2H), 5.34 (s, 2H). 7.19 (d, 1H), 7.25 (t, 2H), 7.55-7.65 (m, 1H), 7.85 (t, 1H), 8.76 (d, 1H), [further signals hidden under solvent peaks]. |

TABLE 12-continued

| Example | IUPAC name/structure (yield) | Analytical data |
| --- | --- | --- |
| 152 | 6-chloro-8-[(2,6-difluorobenzyl)oxy]-N-[2-(4-isopropylpiperazin-1-yl)ethyl]-2-methyl-imidazo[1,2-a]-pyridine-3-carboxamide<br><br>(88% of theory; purity 100%) | LC-MS (Method 2): $R_t$ = 0.77 min<br>MS (ESpos): m/z = 506.4 (M + H)$^+$<br>$^1$H NMR (400 MHz, DMSO-d$_6$):<br>δ = 0.94 (d, 6H), 2.42 (br. s, 6H), 3.37-3.46 (m, 2H), 5.34 (s, 2H), 7.18 (d, 1H), 7.25 (t, 2H), 7.55-7.66 (m, 1H), 7.80 (t, 1H), 8.75 (d, 1H), [further signals hidden under solvent peaks]. |
| 153 | 6-chloro-8-[(2,6-difluorobenzyl)oxy]-N-{2-[(2-methoxyethyl)amino]ethyl}-2-methylimidazo[1,2-a]pyridine-3-carboxamide<br><br>(39% of theory; purity 97%) | LC-MS (Method 2): $R_t$ = 0.72 min<br>MS (ESpos): m/z = 453.2 (M + H)$^+$<br>$^1$H NMR (500 MHz, DMSO-d$_6$):<br>δ = 2.66-2.76 (m, 4H), 3.23 (s, 3H), 3.36-3.41 (m, 4H), 5.34 (s, 2H), 7.19 (s, 1H), 7.25 (t, 2H), 7.56-7.66 (m, 1H), 7.87 (t, 1H), 8.76 (s, 1H), [further signals hidden under solvent peaks]. |
| 154 | 6-chloro-8-[(2,6-difluorobenzyl)oxy]-2-methyl-N-[2-(4-methylpiperazin-1-yl)ethyl]imidazo[1,2-a]pyridine-3-carboxamide<br><br>(81% of theory; purity 100%) | LC-MS (Method 2): $R_t$ = 0.75 min<br>MS (ESpos): m/z = 478.4 (M + H)$^+$<br>$^1$H NMR (400 MHz, DMSO-d$_6$):<br>δ = 2.14 (s, 3H), 2.24-2.52 (m, 10H, superimposed by solvent signal), 3.38-3.45 (m, 2H), 5.34 (s, 2H), 7.19 (d, 1H), 7.26 (t, 2H), 7.55-7.66 (m, 1H), 7.79 (t, 1H), 8.77 (d, 1H), [further signals hidden under solvent peaks]. |

TABLE 12-continued

| Example | IUPAC name/structure (yield) | Analytical data |
|---|---|---|
| 155 | N-[(1-aminocyclobutyl)methyl]-6-chloro-8-[(2,6-difluorobenzyl)oxy]-2-methylimidazo[1,2-a]pyridine-3-carboxamide trifluoroacetate 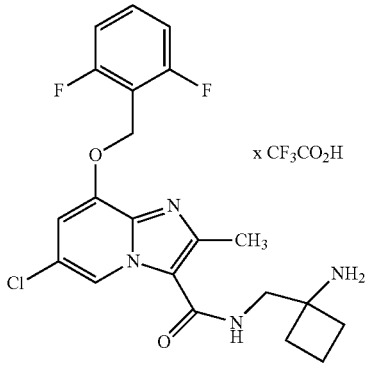 (27% of theory; purity 95%) | LC-MS (Method 2): $R_t$ = 0.77 min<br>MS (ESpos): m/z = 435.3 (M − TFA + H)$^+$<br>$^1$H NMR (500 MHz, DMSO-d$_6$):<br>δ = 1.79-1.97 (m, 2H), 2.12-2.25 (m, 4H), 2.56 (s, 3H), 3.66 (d, 2H), 5.36 (s, 2H), 7.20-7.28 (m, 3H), 7.57-7.65 (m, 1H), 7.98-8.06 (m, 3H), 8.21 (t, 1H), 8.76 (s, 1H). |
| 156 | 6-chloro-8-[(2,6-difluorobenzyl)oxy]-2-methyl-N-{2-[3-(pyrrolidin-1-yl)azetidin-1-yl]ethyl}-imidazo[1,2-a]pyridine-3-carboxamide 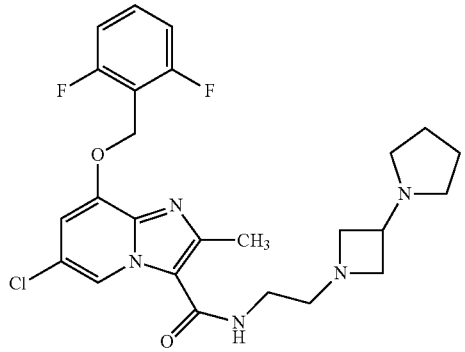 (35% of theory; purity 98%) | LC-MS (Method 7): $R_t$ = 0.62 min<br>MS (ESpos): m/z = 504.2 (M + H)$^+$<br>$^1$H NMR (400 MHz, DMSO-d$_6$):<br>δ = 1.63-1.69 (m, 4H), 2.32-2.36 (m, 4H), 2.87-2.94 (m, 2H), 2.97-3.05 (m, 1H), 3.22-3.28 (m, 2H), 3.40 (t, 2H), 5.34 (s, 2H), 7.19 (d, 1H), 7.25 (t, 2H), 7.56-7.65 (m, 1H), 7.84 (t, 1H), 8.77 (d, 1H), [further signals hidden under the solvent peaks]. |
| 157 | rac-N-(2-amino-2-methylbutyl)-6-chloro-8-[(2,6-difluorobenzyl)oxy]-2-methylimidazo[1,2-a]pyridine-3-carboxamide 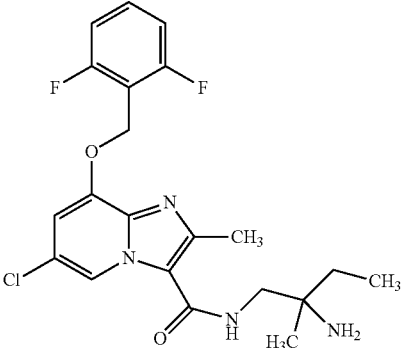 (89% of theory; purity 99%) | LC-MS (Method 7): $R_t$ = 0.69 min<br>MS (ESpos): m/z = 437.1 (M + H)$^+$<br>$^1$H NMR (400 MHz, DMSO-d$_6$):<br>δ = 0.86 (t, 3H), 0.97 (s, 3H), 1.30-1.38 (m, 2H), 1.43 (br. s, 1H), 3.15-3.27 (m, 2H), 5.34 (s, 2H), 7.19 (d, 1H), 7.25 (t, 2H), 7.55-7.65 (m, 1H), 7.66-7.77 (m, 1H), 8.77 (d, 1H), [further signal hidden under the solvent peaks]. |

TABLE 12-continued

| Example | IUPAC name/structure (yield) | Analytical data |
|---|---|---|
| 158 | 6-chloro-8-[(2,6-difluorobenzyl)oxy]-N-{2-[(2R,6S)-2,6-dimethylmorpholin-4-yl]ethyl}-2-methylimidazo[1,2-a]-pyridine-3-carboxamide<br>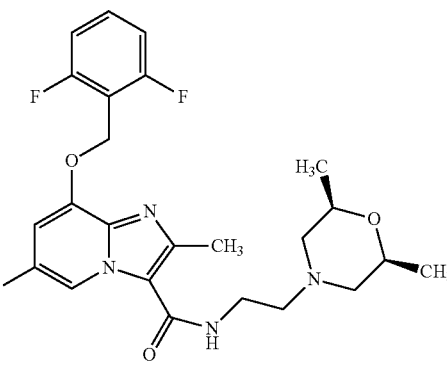<br>(92% of theory; purity 99%) | LC-MS (Method 2): $R_t$ = 0.82 min<br>MS (ESpos): m/z = 493.3 (M + H)$^+$<br>$^1$H NMR (400 MHz, DMSO-d$_6$):<br>δ = 1.05 (d, 6H), 1.67 (t, 2H), 2.81 (d, 2H), 3.38-3.46 (m, 2H), 3.50-3.60 (m, 2H), 5.34 (s, 2H), 7.20 (d, 1H), 7.25 (t, 2H), 7.56-7.66 (m, 1H), 7.81 (t, 1H), 8.76 (d, 1H), [further signals hidden under the solvent peaks]. |
| 159 | rac-N-(2-amino-3-methoxy-2-methylpropyl)-6-chloro-8-[(2,6-difluorobenzyl)oxy]-2-methylimidazo[1,2-a]pyridine-3-carboxamide<br>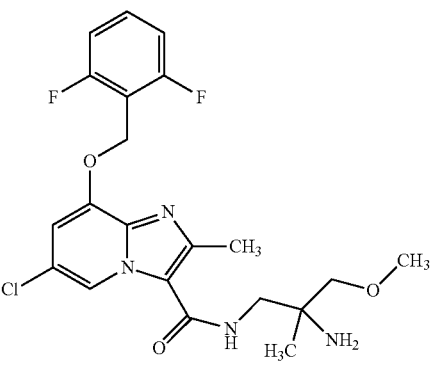<br>(88% of theory; purity 100%) | LC-MS (Method 2): $R_t$ = 0.73 min<br>MS (ESpos): m/z = 453.3 (M + H)$^+$<br>$^1$H NMR (400 MHz, DMSO-d$_6$):<br>δ = 1.00 (s, 3H), 1.72 (br. s, 2H), 3.12-3.20 (m, 2H), 3.22-3.31 (m, 5H, superimposed by solvent signal), 5.34 (s, 2H), 7.20 (d, 1H), 7.25 (t, 2H), 7.56-7.71 (m, 2H), 8.81 (d, 1H), [further signal hidden under the solvent peaks]. |
| 160 | N-(3-aminocyclohexyl)-8-[(2,6-difluorobenzyl)oxy]-2,6-dimethylimidazo[1,2-a]-pyridine-3-carboxamide<br>(mixture of stereoisomers)<br>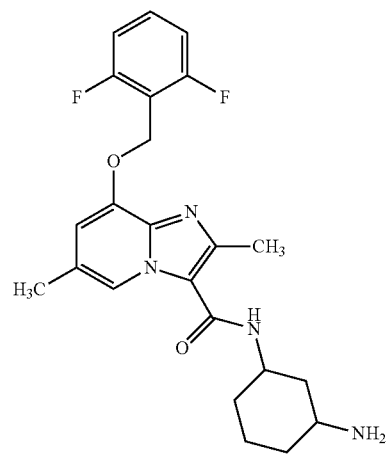<br>(58% of theory; purity 98%) | LC-MS (Method 2): $R_t$ = 0.60 min<br>MS (ESpos): m/z = 429.3 (M + H)$^+$<br>$^1$H NMR (400 MHz, DMSO-d$_6$):<br>δ = 0.89-1.39 (m, 4H), 1.42-1.99 (m, 6H), 2.30 (s, 3H), 2.47 (s, 3H), 2.62-2.72 and 3.06-3.11 (m, together 1H), 3.73-3.89 and 4.21-4.28 (m, together 1H), 5.28 (s, 2H), 6.89 (s, 1H), 7.23 (t, 2H), 7.54-7.63 (m, 1H), 7.79 and 7.92 (2 x d, together 1H), 8.85 and 8.89 (2 x s, together 1H). |

TABLE 12-continued

| Example | IUPAC name/structure (yield) | Analytical data |
|---|---|---|
| 161 | rac-N-(2-amino-2-methylbutyl)-8-[(2,6-difluorobenzyl)oxy]-2,6-dimethylimidazo[1,2-a]pyridine-3-carboxamide<br>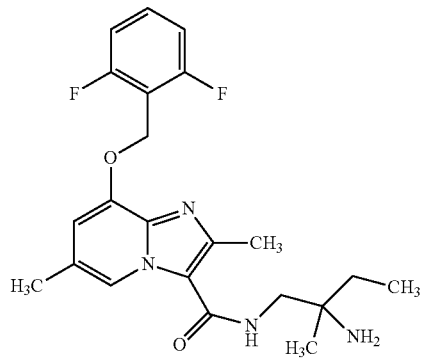<br>(83% of theory; purity 99%) | LC-MS (Method 7): $R_t$ = 0.56 min<br>MS (ESpos): m/z = 417.2 (M + H)$^+$<br>$^1$H NMR (400 MHz, DMSO-d$_6$):<br>δ = 0.86 (t, 3H), 0.97 (s, 3H), 1.30-1.40 (m, 2H), 1.45 (br. s, 2H), 2.31 (s, 3H), 2.53 (s, 3H, superimposed by-solvent peaks), 3.14-3.26 (m, 2H), 5.29 (s, 2H), 6.91 (s, 1H), 7.20-7.28 (m, 2H), 7.54-7.65 (m, 2H), 8.49 (s, 1H). |
| 162 | 8-[(2,6-difluorobenzyl)oxy]-2,6-dimethyl-N-{2-[3-(pyrrolidin-1-yl)azetidin-1-yl]ethyl}imidazo[1,2-a]pyridine-3-carboxamide<br>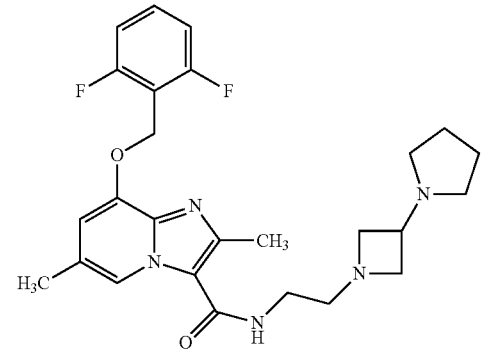<br>(56% of theory; purity 97%) | LC-MS (Method 2): $R_t$ = 0.58 min<br>MS (ESpos): m/z = 484.4 (M + H)$^+$<br>$^1$H NMR (400 MHz, DMSO-d$_6$):<br>δ = 1.64-1.69 (m, 4H), 2.31 (s, 3H), 2.32-2.39 (m, 4H), 2.47 (s, 3H), 2.56-2.62 (m, 2H, superimposed by solvent peaks), 2.88-2.97 (m, 2H), 2.98-3.07 (m, 1H), 3.21-3.28 (m, 2H), 3.38-3.45 (m, 2H), 5.28 (s, 2H), 6.91 (s, 1H), 7.24 (t, 2H), 7.54-7.64 (m, 1H), 7.71 (t, 1H), 8.47 (s, 1H). |
| 163 | 8-[(2,6-difluorobenzyl)oxy]-N-[2-(4,4-difluoro-piperidin-1-yl)ethyl]-2,6-dimethylimidazo[1,2-a]pyridine-3-carboxamide<br>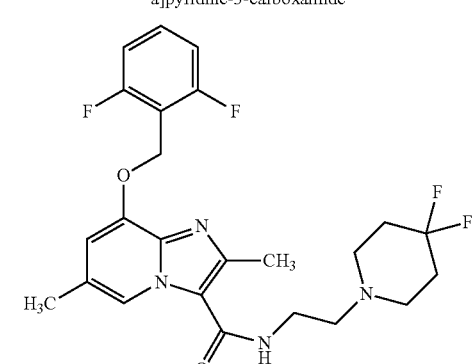<br>(56% of theory; purity 98%) | LC-MS (Method 2): $R_t$ = 0.66 min<br>MS (ESpos): m/z = 479.3 (M + H)$^+$<br>$^1$H NMR (400 MHz, DMSO-d$_6$):<br>δ = 1.88-2.02 (m, 4H), 2.31 (s, 3H), 2.56-2.60 (m, 4H), 3.38-3.46 (m, 2H), 5.27 (s, 2H), 6.92 (s, 1H), 7.24 (t, 2H), 7.55-7.64 (m, 1H), 7.71 (t, 1H), 8.47 (s, 1H), [further signals hidden under solvent peaks]. |

TABLE 12-continued

| Example | IUPAC name/structure (yield) | Analytical data |
|---|---|---|
| 164 | N-{2-[cyclopropyl(2,2-difluoroethyl)amino]ethyl}-8-[(2,6-difluorobenzyl)oxy]-2,6-dimethylimidazo[1,2-a]pyridine-3-carboxamide<br>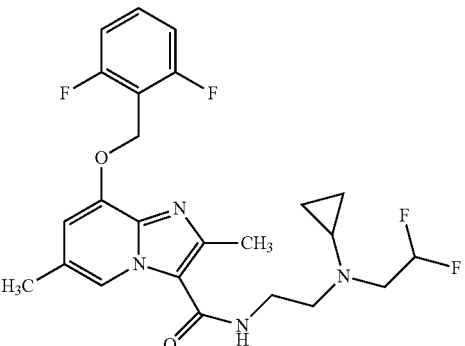<br>(71% of theory; purity 100%) | LC-MS (Method 2): $R_t$ = 0.99 min<br>MS (ESpos): m/z = 479.3 (M + H)$^+$<br>$^1$H NMR (400 MHz, DMSO-$d_6$):<br>δ = 0.35-0.42 (m, 2H), 0.45-0.53 (m, 2H), 2.06-2.13 (m, 1H), 2.30 (s, 3H), 2.46 (s, 3H), 2.89 (t, 2H), 3.03 (td, 2H), 3.39-3.48 (m, 2H), 5.27 (s, 2H), 6.14 (tt, 1H), 6.91 (s, 1H), 7.24 (t, 2H), 7.54-7.66 (m, 2H), 8.48 (s, 1H). |
| 165 | N-[(1-aminocyclobutyl)methyl]-8-[(2,6-difluorobenzyl)oxy]-2,6-dimethylimidazo[1,2-a]pyridine-3-carboxamide $^{1)}$<br>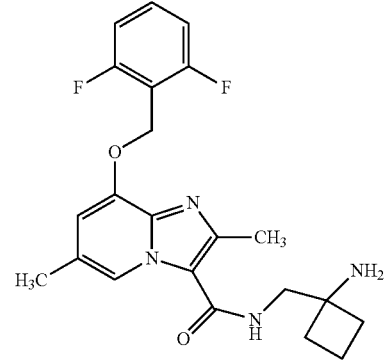<br>(22% of theory; purity 97%) | LC-MS (Method 2): $R_t$ = 0.63 min<br>MS (ESpos): m/z = 415.3 (M + H)$^+$<br>$^1$H NMR (400 MHz, DMSO-$d_6$):<br>δ = 1.56-1.83 (m, 4H), 1.92-2.03 (m, 2H), 2.31 (s, 3H), 3.39 (d, 2H), 5.28 (s, 2H), 6.92 (s, 1H), 7.24 (t, 2H), 7.53-7.65 (m, 2H), 8.49 (s, 1H), [further signal hidden under solvent peaks]. |
| 166 | rac-N-(2-amino-3-methoxy-2-methylpropyl)-8-[(2,6-difluorobenzyl)oxy]-2,6-dimethylimidazo[1,2-a]pyridine-3-carboxamide<br>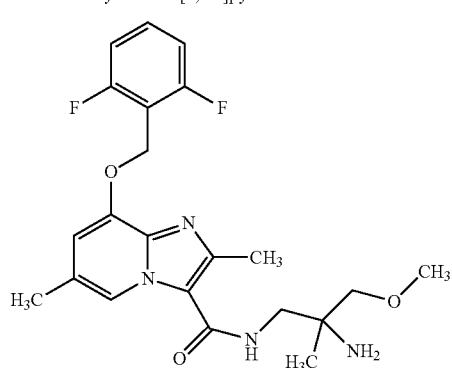<br>(80% of theory; purity 100%) | LC-MS (Method 2): $R_t$ = 0.62 min<br>MS (ESpos): m/z = 433.3 (M + H)$^+$<br>$^1$H NMR (400 MHz, DMSO-$d_6$):<br>δ = 1.00 (s, 3H), 1.52-1.62 (br. s, 2H), 2.31 (s, 3H), 2.53 (s, 3H), 3.123 3.19 (m, 2H), 3.24-3.30 (m, 5H), 5.28 (s, 2H), 6.92 (s, 1H), 7.24 (t, 2H), 7.51-7.64 (m, 2H), 8.52 (s, 1H). |

TABLE 12-continued

| Example | IUPAC name/structure (yield) | Analytical data |
|---|---|---|
| 167 | 8-[(2,6-difluorobenzyl)oxy]-N-{2-[(2R,6S)-2,6-dimethylmorpholin-4-yl]ethyl}-2,6-dimethyl-imidazo[1,2-a]pyridine-3-carboxamide<br><br>(76% of theory; purity 100%) | LC-MS (Method 2): $R_t$ = 0.71 min<br>MS (ESpos): m/z = 473.3 (M + H)$^+$<br>$^1$H NMR (400 MHz, DMSO-$d_6$):<br>δ = 1.05 (d, 6H), 1.67 (t, 2H), 2.31 (s, 3H), 2.80 (d, 2H), 3.38-3.45 (m, 2H), 3.49-3.60 (m, 2H), 5.28 (s, 2H), 6.91 (s, 1H), 7.24 (t, 2H), 7.54-7.64 (m, 1H), 7.68 (t, 1H), 8.48 (s, 1H), [further signals hidden under solvent peaks]. |

[1]) There was an additional chromatographic separation: column: Sunfire C18, 5 μm, 250 x 20 mm, mobile phase: 89% methanol, 11% 1% strength TFA in water, flow rate: 25 ml/min; 25° C., detection: 210 nm].

Example 168

N-[2-(4-Cyclopropylpiperazin-1-yl)ethyl]-8-[(2,6-difluorobenzyl)oxy]-2-methyl-8-[(2,6-difluorobenzyl)oxy]-2-methylimidazo[1,2-a]-pyridine-3-carboxamide

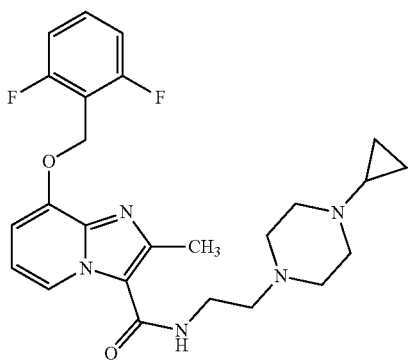 [SMILES: Cc1nc2c(OCc3c(F)cccc3F)cccn2c1C(=O)NCCN1CCN(C2CC2)CC1]

118 mg of 8-[(2,6-difluorobenzyl)oxy]-2-methyl-N-(2-oxoethyl)imidazo[1,2-a]pyridine-3-carboxamide (Example 194A, 0.16 mmol, 1 equivalent) were suspended in 0.8 ml of dry dichloroethane, 23 mg 1-cyclopropylpiperazine (0.18 mmol, 1.1 equivalents) were added and the mixture was stirred at RT for 3 h. 52 mg of sodium triacetoxyborohydride (0.25 mmol, 1.5 equivalents) were then added, and the mixture was stirred at RT overnight. 1 N aqueous sodium hydroxide solution was then added, and the mixture was extracted three times with dichloromethane. The combined organic phases were washed with water and saturated aqueous sodium chloride solution, dried over sodium sulphate, filtered and concentrated. The residue was dissolved in methanol and purified by preparative HPLC (method: RP18 column, mobile phase: acetonitrile/water gradient with addition of 0.1% TFA). The product fraction was taken up in ethyl acetate and washed twice with saturated aqueous sodium bicarbonate solution. The combined organic phases were dried over sodium sulphate, filtered and concentrated. This gave 33.5 mg (43% of theory) of the title compound.

LC-MS (Method 7): $R_t$=0.60 min

MS (ESpos): m/z=470.2 (M+H)$^+$ $^1$H NMR (400 MHz, DMSO-$d_6$): δ=0.22-0.30 (m, 2H), 0.34-0.43 (m, 2H), 1.53-1.62 (m, 1H), 2.30-2.44 (m, 3H), 3.37-3.46 (m, 2H), 5.30 (s, 2H), 6.93 (t, 1H), 7.01 (d, 1H), 7.23 (t, 2H), 7.55-7.64 (m, 1H), 7.70 (t, 1H), 8.67 (d, 1H), [further signals hidden under solvent peaks].

The examples shown in Table 13 were prepared analogously to Example 168 from the aldehydes of Examples 194A, 195A and 196A.

TABLE 13

| Example | IUPAC name/structure (yield) | Analytical data |
|---|---|---|
| 169 | 8-[(2,6-difluorobenzyl)oxy]-N-{2-[(2,2-difluoroethyl)amino]ethyl}-2-methylimidazo[1,2-a]pyridine-3-carboxamide<br>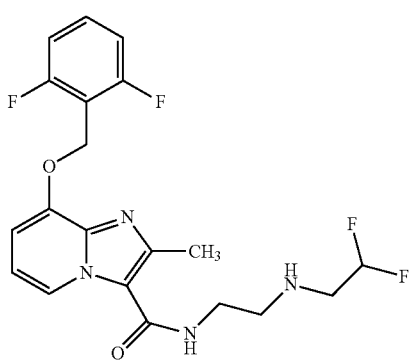<br>(51% of theory; purity 93%) | LC-MS (Method 7): $R_t$ = 0.57 min<br>MS (ESpos): m/z = 425.1 (M + H)$^+$<br>$^1$H NMR (400 MHz, DMSO-d$_6$):<br>δ = 2.78 (t, 2H), 2.93 (dt, 2H), 3.34-3.42 (m, 2H), 5.30 (s, 2H), 6.01 (tt, 1H), 6.93 (t, 1H), 7.01 (d, 1H), 7.23 (t, 2H), 7.55-7.64 (m, 1H), 7.79 (t, 1H), 8.64 (d, 1H), [further signal hidden under solvent peaks]. |
| 170 | 8-[(2,6-difluorobenzyl)oxy]-2-methyl-N-[(2R)-1-(morpholin-4-yl)propan-2-yl]imidazo[1,2-a]pyridine-3-carboxamide[1)]<br>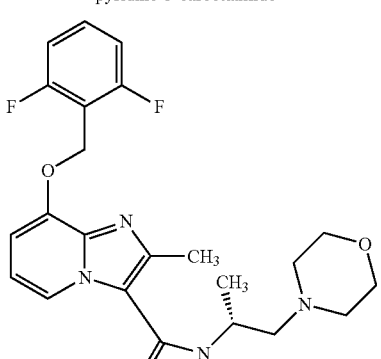<br>(39% of theory; purity 100%) | LC-MS (Method 1): $R_t$ = 0.60 min<br>MS (ESpos): m/z = 445.2 (M + H)$^+$<br>$^1$H NMR (400 MHz, DMSO-d$_6$):<br>δ = 1.17 (d, 3H), 2.17-2.43 (m, 3H), 3.46-3.62 (m, 4H), 4.15-4.28 (m, 1H), 5.29 (s, 2H), 6.91 (t, 1H), 6.99 (d, 1H), 7.18-7.28 (m, 2H), 7.53-7.63 (m, 1H), 7.68 (d, 1H), 8.56 (d, 1H), [further signals hidden under solvent peaks]. |
| 171 | 8-[(2,6-difluorobenzyl)oxy]-2-methyl-N-[(2S)-1-(morpholin-2-yl)propan-2-yl]imidazo[1,2-a]pyridine-3-carboxamide[1)]<br>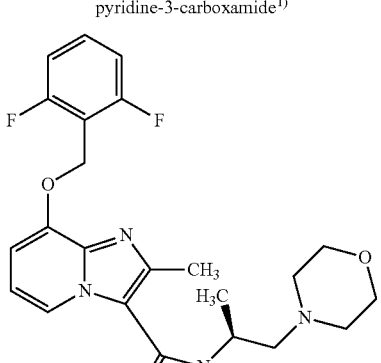<br>(95% of theory; purity 100%) | LC-MS (Method 7): $R_t$ = 0.59 min<br>MS (ESpos): m/z = 445.2 (M + H)$^+$<br>$^1$H NMR (400 MHz, DMSO-d$_6$):<br>δ = 1.17 (d, 3H), 2.15-2.43 (m, 3H), 3.47-3.62 (m, 4H), 4.15-4.28 (m, 1H), 5.30 (s, 2H), 6.92 (t, 1H), 6.99 (d, 1H), 7.18-7.28 (m, 2H), 7.53-7.63 (m, 1H), 7.69 (d, 1H), 8.56 (d, 1H), [further signals hidden under solvent peaks]. |

[1)] The minor enantiomers formed in the reactions (partial racemization under these conditions) were separated off on a chiral phase [column: Daicel Chiralpak AD-H, 5 μm, 250 x 20 mm, mobile phase: 50% isohexane, 50% ethanol, 0.2% diethylamine, flow rate: 20 ml/min; 25° C./40° C., detection: 210/220 nm].

Example 172

8-[(2,6-Difluorobenzyl)oxy]-2,6-dimethyl-N-[(2S)-piperidin-2-ylmethyl]imidazo[1,2-a]pyridine-3-carboxamide

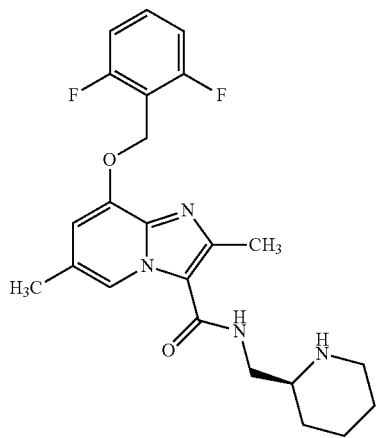 [SMILES: Cc1cc(OCc2c(F)cccc2F)c2nc(C)c(C(=O)NC[C@@H]3CCCCN3)n2c1]

At RT, 53 mg (0.25 mmol, 1.1 equivalents) of tert-butyl (2S)-2-(aminomethyl)piperidin-1-carboxylate were added to 75 mg of 8-[(2,6-difluorobenzyl)oxy]-2,6-dimethylimidazo[1,2-a]-pyridine-3-carboxylic acid (Example 21A, 0.23 mmol, 1 equivalent), 90 mg of O-(7-azabenzotriazol-1-yl)-N,N,N'N'-tetramethyluronium hexafluorophosphate (HATU, 0.24 mmol, 1.05 equivalents) and 88 mg of N,N-diisopropylethylamine (0.12 ml, 0.68 mmol, 3 equivalents) in 1.4 ml of DMF, and the mixture was stirred at RT overnight. After the reaction had ended, the mixture was purified by preparative HPLC (method: RP18 column, mobile phase: acetonitrile/water gradient with addition of 0.1% TFA). The product fractions obtained were dissolved in dichloromethane and washed with saturated aqueous sodium bicarbonate solution. The aqueous phase was extracted twice with dichloromethane and the combined organic phases were dried over sodium sulphate, filtered, concentrated and lyophilized. This gave 66 mg (64% of theory; purity 95%) of the title compound.

LC-MS (Method 2): $R_t$=0.65 min

MS (ESpos): m/z=429.3 (M+H)$^+$ $^1$H NMR (400 MHz, DMSO-d$_6$): δ=0.99-1.14 (m, 1H), 1.21-1.36 (m, 2H), 1.45-1.54 (m, 1H), 1.59-1.66 (m, 1H), 1.70-1.77 (m, 1H), 2.31 (s, 3H), 2.60-2.69 (m, 1H), 2.92-2.98 (m, 1H), 3.16-3.29 (m, 2H), 5.28 (s, 2H), 6.91 (s, 1H), 7.24 (t, 2H), 7.55-7.64 (m, 1H), 7.74 (t, 1H), 8.46 (s, 1H), [further signal hidden under solvent peaks].

Example 173

8-[(2,6-Difluorobenzyl)oxy]-2,6-dimethyl-N-[(2R)-piperidin-2-ylmethyl]imidazo[1,2-a]pyridine-3-carboxamide

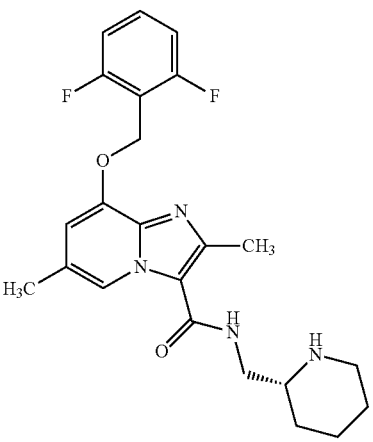 [SMILES: Cc1cc(OCc2c(F)cccc2F)c2nc(C)c(C(=O)NC[C@H]3CCCCN3)n2c1]

56 mg of tert-butyl (2R)-2-{[({8-[(2,6-difluorobenzyl)oxy]-2,6-dimethylimidazo[1,2-a]pyridin-3-yl}carbonyl)amino]methyl}piperidin-1-carboxylate trifluoroacetate Example 183A (0.09 mmol) were initially charged in 2 M hydrochloric acid in diethyl ether, and the mixture was stirred at RT for 5 h. The resulting precipitate was filtered off and washed with diethyl ether, dissolved in dichloromethane and washed with saturated aqueous sodium bicarbonate solution. The aqueous phase was extracted twice with dichloromethane and the combined organic phases were dried over sodium sulphate, filtered, concentrated and lyophilized. This gave 30 mg (78% of theory; purity 95%) of the title compound.

LC-MS (Method 2): $R_t$=0.64 min

MS (ESpos): m/z=429.3 (M+H)$^+$ $^1$H NMR (400 MHz, DMSO-d$_6$): δ=0.99-1.14 (m, 1H), 1.21-1.36 (m, 2H), 1.45-1.54 (m, 1H), 1.59-1.66 (m, 1H), 1.71-1.77 (m, 1H), 2.31 (s, 3H), 2.60-2.69 (m, 1H), 2.92-2.98 (m, 1H), 3.16-3.29 (m, 2H), 5.28 (s, 2H), 6.90 (s, 1H), 7.24 (t, 2H), 7.55-7.64 (m, 1H), 7.74 (t, 1H), 8.46 (s, 1H), [further signal hidden under solvent peaks].

Example 174 ent-N-[(3S)-3-Aminobutan-2-yl]-8-[(2,6-difluorobenzyl)oxy]-2-methylimidazo[1,2-a]pyridine-3-carboxamide (Diastereomer A)

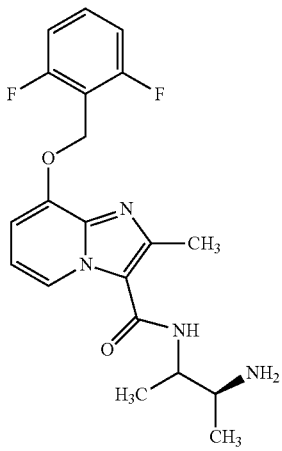 [SMILES: Cc1nc2c(OCc3c(F)cccc3F)cccn2c1C(=O)NC(C)[C@H](C)N]

44.1 mg of N-[(3S)-3-aminobutan-2-yl]-8-[(2,6-difluorobenzyl)oxy]-2-methylimidazo[1,2-a]-pyridine-3-carboxamide (Example 120) were separated into the diastereomers on a chiral phase [column: Daicel Chiralpak AD-H, 5 μm, 250×20 mm, mobile phase: 50% isohexane, 50% ethanol, 0.2% diethylamine, flow rate: 20 ml/min; 25° C., detection: 230 nm].

Yield diastereomer A: 19.7 mg (100% ee)

Diastereomer A: $R_t$=8.90 min [Daicel Chiralpak AD-H, 5 μm, 250×20 mm, mobile phase: mobile phase: 50% isohexane, 50% ethanol, 0.2% diethylamine, flow rate: 1 ml/min; 25° C., detection: 230 nm].

Example 175 ent-N-[(3S)-3-Aminobutan-2-yl]-8-[(2,6-difluorobenzyl)oxy]-2-methylimidazo[1,2-a]pyridine-3-carboxamide (Diastereomer B)

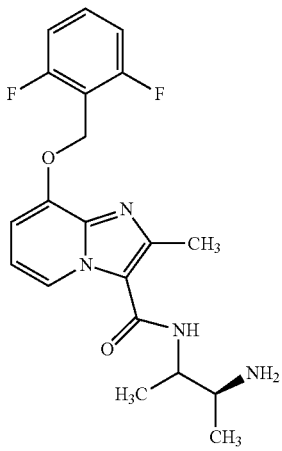 [SMILES: Cc1nc2c(OCc3c(F)cccc3F)cccn2c1C(=O)NC(C)[C@H](C)N]

44.1 mg of rac-N-[(3S)-3-aminobutan-2-yl]-8-[(2,6-difluorobenzyl)oxy]-2-methylimidazo[1,2-a]-pyridine-3-carboxamide (Example 120) were separated into the diastereomers on a chiral phase [column: Daicel Chiralpak AD-H, 5 μm, 250×20 mm, mobile phase: 50% isohexane, 50% ethanol, 0.2% diethylamine, flow rate: 20 ml/min; 25° C., detection: 230 nm].

Yield diastereomer B: 2.3 mg (>90% ee)

Diastereomer A: $R_t$=12.68 min [Daicel Chiralpak AD-H, 5 μm, 250×20 mm, mobile phase: mobile phase: 50% isohexane, 50% ethanol, 0.2% diethylamine, flow rate: 1 ml/min; 25° C., detection: 230 nm].

Example 176 ent-N-[(3R)-3-Aminobutan-2-yl]-8-[(2,6-difluorobenzyl)oxy]-2-methylimidazo[1,2-a]pyridine-3-carboxamide (Diastereomer A)

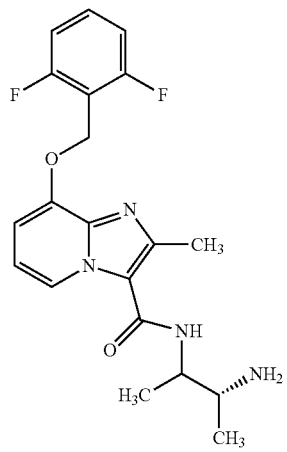 [SMILES: Cc1nc2c(OCc3c(F)cccc3F)cccn2c1C(=O)NC(C)[C@@H](C)N]

90 mg of rac-benzyl {(2R)-3-[({8-[(2,6-difluorobenzyl)oxy]-2-methylimidazo[1,2-a]pyridin-3-yl}carbonyl)amino]butan-2-yl}carbamate (Example 121) were separated into the diastereomers on a chiral phase [column: Daicel Chiralpak OD-H, 5 μm, 250×20 mm, mobile phase: 50% isohexane, 50% isopropanol, 0.2% diethylamine, flow rate: 20 ml/min; 25° C., detection: 230 nm].

Yield diastereomer A: 29.6 mg (100% ee)

Diastereomer A: $R_t$=5.94 min [Daicel Chiralpak OD-H, 5 μm, 250×20 mm, mobile phase: mobile phase: 50% isohexane, 50% ethanol, 0.2% diethylamine, flow rate: 1 ml/min; 25° C., detection: 230 nm].

Example 177 ent-N-[(3R)-3-Aminobutan-2-yl]-8-[(2,6-difluorobenzyl)oxy]-2-methylimidazo[1,2-a]pyridine-3-carboxamide (Diastereomer B)

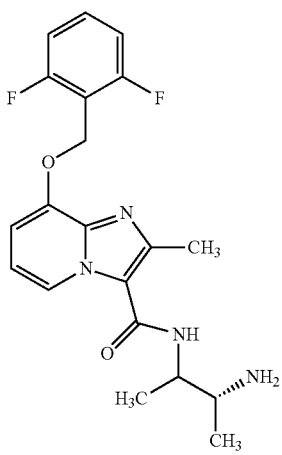 [SMILES: Cc1nc2c(OCc3c(F)cccc3F)cccn2c1C(=O)NC(C)[C@@H](C)N]

90 mg of rac-benzyl {(2R)-3-[({8-[(2,6-difluorobenzyl)oxy]-2-methylimidazo[1,2-a]pyridin-3-yl}carbonyl)amino]butan-2-yl}carbamate (Example 121) were separated into the diastereomers on a chiral phase [column: Daicel Chiralpak OD-H, 5 μm, 250×20 mm, mobile phase: 50% isohexane, 50% isopropanol, 0.2% diethylamine, flow rate: 20 ml/min; 25° C., detection: 230 nm].

Yield diastereomer B: 4.9 mg (88% ee)

Diastereomer B: $R_t$=9.79 min [Daicel Chiralpak OD-H, 5 μm, 250×20 mm, mobile phase: mobile phase: 50% isohexane, 50% ethanol, 0.2% diethylamine, flow rate: 1 ml/min; 25° C., detection: 230 nm]

Example 178 ent-N-[2-Amino-1-(3,4-difluorophenyl)ethyl]-8-(cyclohexylmethoxy)-2-methylimidazo[1,2-a]-pyridine-3-carboxamide (Enantiomer A)

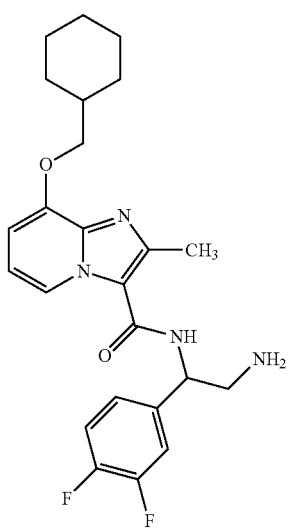 [SMILES: Cc1nc2c(OCC3CCCCC3)cccn2c1C(=O)NC(CN)c1ccc(F)c(F)c1]

113 mg of rac-N-[2-amino-1-(3,4-difluorophenyl)ethyl]-8-(cyclohexylmethoxy)-2-methylimidazo[1,2-a]pyridine-3-carboxamide (Example 46) were separated into the enantiomers on a chiral phase [column: Daicel Chiralpak OD-H, 5 μm, 250×20 mm, mobile phase: 50% isohexane, 50% ethanol, 0.2% diethylamine, flow rate: 20 ml/min; 25° C., detection: 230 nm].

Yield: Enantiomer A: 18.5 mg (89% ee)

Enantiomer A: $R_t$=7.89 min [Daicel Chiralpak OD-H, 5 μm, 250×4.6 mm, mobile phase: mobile phase: 50% isohexane, 50% ethanol, 0.2% diethylamine, flow rate: 1 ml/min; 40° C., detection: 220 nm].

Example 179 ent-N-[2-Amino-1-(3,4-difluorophenyl)ethyl]-8-(cyclohexylmethoxy)-2-methylimidazo[1,2-a]-pyridine-3-carboxamide (Enantiomer B)

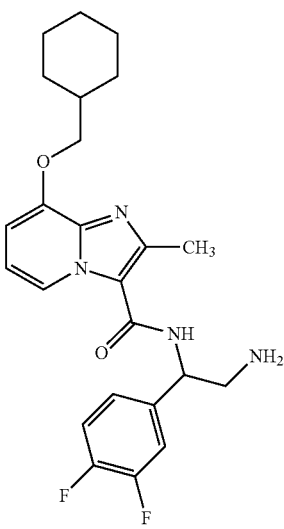 [SMILES: Cc1nc2c(OCC3CCCCC3)cccn2c1C(=O)NC(CN)c1ccc(F)c(F)c1]

113 mg of rac-N-[2-amino-1-(3,4-difluorophenyl)ethyl]-8-(cyclohexylmethoxy)-2-methylimidazo[1,2-a]pyridine-3-carboxamide (Example 46) were separated into the enantiomers on a chiral phase [column: Daicel Chiralpak OD-H, 5 μm, 250×20 mm, mobile phase: 50% isohexane, 50% ethanol, 0.2% diethylamine, flow rate: 20 ml/min; 25° C., detection: 230 nm].

Yield: Enantiomer B: 28 mg (97% ee)

Enantiomer B: $R_t$=12.84 min [Daicel Chiralpak OD-H, 5 μm, 250×4.6 mm, mobile phase: mobile phase: 50% isohexane, 50% ethanol, 0.2% diethylamine, flow rate: 1 ml/min; 40° C., detection: 220 nm].

Example 180 ent-8-[(2,6-Difluorobenzyl)oxy]-2-methyl-N-[2-(morpholin-4-yl)propyl]imidazo[1,2-a]pyridine-3-carboxamide (Enantiomer A)

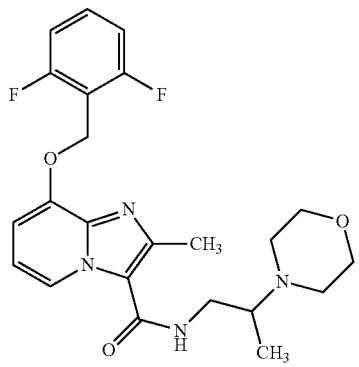 [SMILES: Cc1nc2c(OCc3c(F)cccc3F)cccn2c1C(=O)NCC(C)N1CCOCC1]

120 mg of rac-8-[(2,6-difluorobenzyl)oxy]-2-methyl-N-[2-(morpholin-4-yl)propyl]imidazo[1,2-a]-pyridine-3-carboxamide (Example 132) were separated into the enantiomers on a chiral phase [column: Daicel Chiralpak AD-H, 5 μm, 250×20 mm, mobile phase: 50% isohexane, 50% isopropanol, 0.2% diethylamine, flow rate: 20 ml/min; 40° C., detection: 210 nm].

Yield: Enantiomer A: 45 mg (100% ee)

Enantiomer A: $R_t$=8.99 min [Daicel Chiralpak AD-H, 5 μm, 250×4.6 mm, mobile phase: mobile phase: 50% isohexane, 50% isopropanol, 0.2% diethylamine, flow rate: 1 ml/min; 40° C., detection: 220 nm].

Example 181 ent-8-[(2,6-Difluorobenzyl)oxy]-2-methyl-N-[2-(morpholin-4-yl)propyl]imidazo[1,2-a]pyridine-3-carboxamide (Enantiomer B)

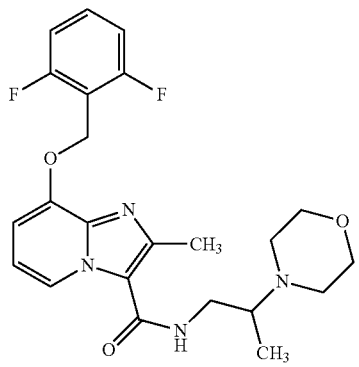

120 mg of rac-8-[(2,6-difluorobenzyl)oxy]-2-methyl-N-[2-(morpholin-4-yl)propyl]imidazo[1,2-a]-pyridine-3-carboxamide (Example 132) were separated into the enantiomers on a chiral phase [column: Daicel Chiralpak AD-H, 5 μm, 250×20 mm, mobile phase: 50% isohexane, 50% isopropanol, 0.2% diethylamine, flow rate: 20 ml/min; 40° C., detection: 210 nm].

Yield: Enantiomer B: 47 mg (97% ee)

Enantiomer B: $R_t$=11.00 min [Daicel Chiralpak AD-H, 5 μm, 250×4.6 mm, mobile phase: mobile phase: 50% isohexane, 50% isopropanol, 0.2% diethylamine, flow rate: 1 ml/min; 40° C., detection: 220 nm].

Example 182 ent-8-[(2,6-Difluorobenzyl)oxy]-2-methyl-N-[2-(morpholin-4-yl)-1-phenylethyl]imidazo[1,2-a]-pyridine-3-carboxamide (Enantiomer A)

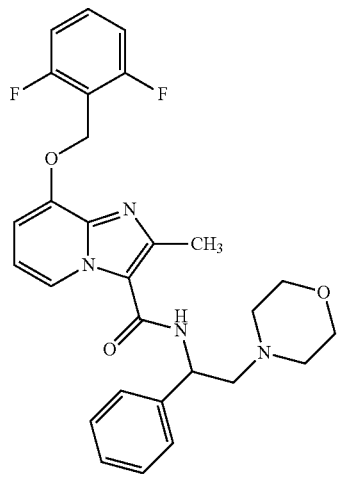 [SMILES: Cc1nc2c(OCc3c(F)cccc3F)cccn2c1C(=O)NC(CN1CCOCC1)c1ccccc1]

128 mg of rac-8-[(2,6-difluorobenzyl)oxy]-2-methyl-N-[2-morpholin-4-yl)-ethyl]-imidazo-[1,2-a]pyridine-3-carboxamide (Example 134) were separated into the enantiomers on a chiral phase [column: Daicel Chiralpak AD-H, 5 μm, 250×20 mm, mobile phase: 50% isohexane, 50% ethanol, 0.2% diethylamine, flow rate: 20 ml/min; 25° C., detection: 230 nm].

Yield: Enantiomer A: 27 mg (100% ee)

Enantiomer A: $R_t$=8.96 min [Daicel Chiralpak AD-H, 5 μm, 250×4.6 mm, mobile phase: 50% isohexane, 50% ethanol, 0.2% diethylamine, flow rate: 1 ml/min; 40° C., detection: 220 nm].

Example 183 ent-8-[(2,6-Difluorobenzyl)oxy]-2-methyl-N-[2-(morpholin-4-yl)-1-phenylethyl]imidazo[1,2-a]-pyridine-3-carboxamide (Enantiomer B)

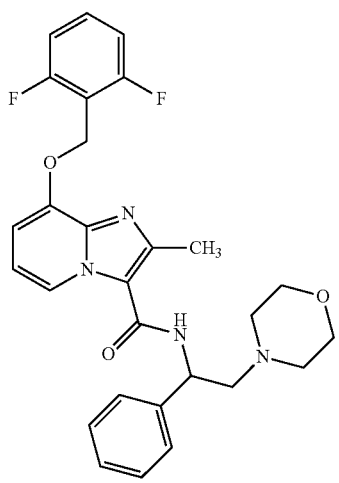 [SMILES: Cc1nc2c(OCc3c(F)cccc3F)cccn2c1C(=O)NC(CN1CCOCC1)c1ccccc1]

128 mg of rac-8-[(2,6-difluorobenzyl)oxy]-2-methyl-N-[2-morpholin-4-yl)-phenylethyl]-imidazo-[1,2-a]pyridine-3-carboxamide (Example 134) were separated into the enantiomers on a chiral phase [column: Daicel Chiralpak AD-H, 5 μm, 250×20 mm, mobile phase: 50% isohexane, 50% ethanol, 0.2% diethylamine, flow rate: 20 ml/min; 25° C., detection: 230 nm].

Yield: Enantiomer B: 23 mg (100% ee)

Enantiomer B: $R_t$=13.66 min [Daicel Chiralpak AD-H, 5 μm, 250×4.6 mm, mobile phase: 50% isohexane, 50% ethanol, 0.2% diethylamine, flow rate: 1 ml/min; 40° C., detection: 220 nm].

Example 184 ent-N-(3-Azabicyclo[4.1.0]hept-1-yl)-8-[(2,6-difluorobenzyl)oxy]-2-methylimidazo[1,2-a]pyridine-3-carboxamide (Enantiomer A)

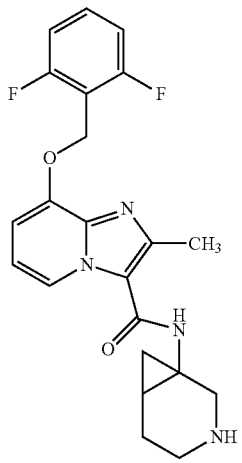

111 mg of Example 125 were separated into the enantiomers on a chiral phase [column: Daicel Chiralpak AD-H, 5 μm, 250×20 mm, mobile phase: 50% isohexane, 50% isopropanol, 0.2% diethylamine, flow rate: 20 ml/min; 40° C., detection: 210 nm].

Yield: Enantiomer A: 32 mg (99% ee)

Enantiomer A: $R_t$=8.04 min [Daicel Chiralpak AD-H, 5 μm, 250×4.6 mm, mobile phase: 50% isohexane, 50% ethanol, 0.2% diethylamine, flow rate: 1 ml/min; 40° C., detection: 220 nm].

Example 185 ent-N-(3-Azabicyclo[4.1.0]hept-1-yl)-8-[(2,6-difluorobenzyl)oxy]-2-methylimidazo[1,2-a]pyridine-3-carboxamide (Enantiomer B)

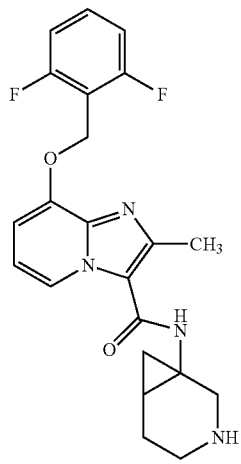 [SMILES: Cc1nc2c(OCc3c(F)cccc3F)cccn2c1C(=O)NC12CNCCC1C2]

111 mg of Example 125 were separated into the enantiomers on a chiral phase [column: Daicel Chiralpak AD-H, 5 μm, 250×20 mm, mobile phase: 50% isohexane, 50% isopropanol, 0.2% diethylamine, flow rate: 20 ml/min; 40° C., detection: 210 nm].

Yield: Enantiomer B: 31 mg (100% ee)

Enantiomer B: $R_t$=11.10 min [Daicel Chiralpak AD-H, 5 μm, 250×4.6 mm, mobile phase: 50% isohexane, 50% ethanol, 0.2% diethylamine, flow rate: 1 ml/min; 40° C., detection: 220 nm].

Example 186 ent-8-[(2,6-Difluorobenzyl)oxy]-2,6-dimethyl-N-[2-(morpholin-4-yl)propyl]imidazo[1,2-a]-pyridine-3-carboxamide (Enantiomer A)

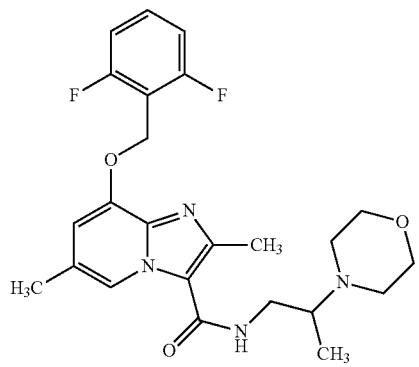 [SMILES: Cc1cc(OCc2c(F)cccc2F)c2nc(C)c(C(=O)NCC(C)N3CCOCC3)n2c1]

63 mg of Example 138 were separated into the enantiomers on a chiral phase [column: Daicel Chiralpak AD-H, 5 μm, 250×20 mm, mobile phase: 50% isohexane, 50% isopropanol, 0.2% diethylamine, flow rate: 20 ml/min; 40° C., detection: 210 nm].

Yield: Enantiomer A: 21 mg (96% ee)

Enantiomer A: $R_f$=8.73 min [Daicel Chiralpak AD-H, 5 μm, 250×4.6 mm, mobile phase: 50% isohexane, 50% isopropanol+0.2% diethylamine, flow rate: 1 ml/min; 40° C., detection: 220 nm].

Example 187 ent-8-[(2,6-Difluorobenzyl)oxy]-2,6-dimethyl-N-[2-(morpholin-4-yl)propyl]imidazo[1,2-a]-pyridine-3-carboxamide (Enantiomer B)

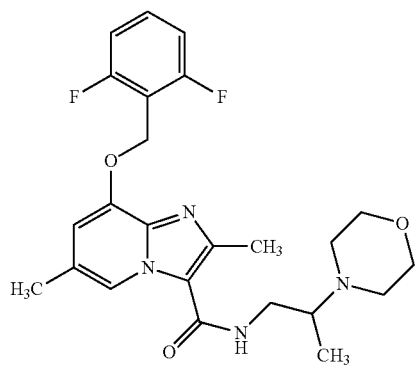 [SMILES: Cc1cc(OCc2c(F)cccc2F)c2nc(C)c(C(=O)NCC(C)N3CCOCC3)n2c1]

63 mg of Example 138 were separated into the enantiomers on a chiral phase [column: Daicel Chiralpak AD-H, 5 μm, 250×20 mm, mobile phase: 50% isohexane, 50% isopropanol, 0.2% diethylamine, flow rate: 20 ml/min; 40° C., detection: 210 nm].

Yield: Enantiomer B: 25 mg (100% ee)

Enantiomer B: $R_f$=9.70 min [Daicel Chiralpak AD-H, 5 μm, 250×4.6 mm, mobile phase: 50% isohexane, 50% isopropanol+0.2% diethylamine, flow rate: 1 ml/min; 40° C., detection: 220 nm].

Example 188 ent-8-[(2,6-Difluorobenzyl)oxy]-N-[2-(dimethylamino)-3-methylbutyl]-2-methylimidazo[1,2-a]-pyridine-3-carboxamide (Enantiomer A)

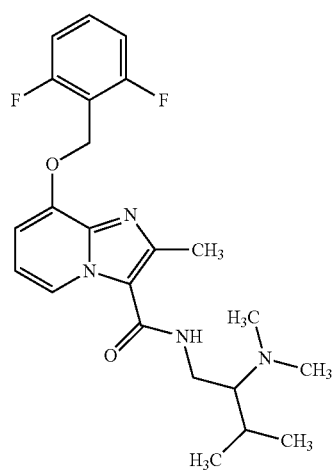 [SMILES: Cc1nc2c(OCc3c(F)cccc3F)cccn2c1C(=O)NCC(C(C)C)N(C)C]

130 mg of Example 142 were separated into the enantiomers on a chiral phase [column: Daicel Chiralpak AD-H, 5 μm, 250×20 mm, mobile phase: 50% isohexane, 50% ethanol+0.2% diethylamine, flow rate: 20 ml/min; 40° C., detection: 210 nm].

Yield: Enantiomer A: 50 mg (99% ee)

Enantiomer A: $R_f$=8.31 min [column: Daicel Chiralpak AD-H, 5 μm, 250×4.6 mm, mobile phase: 50% isohexane, 50% ethanol+0.2% diethylamine, flow rate: 1 ml/min; 40° C., detection: 220 nm].

Example 189 ent-8-[(2,6-Difluorobenzyl)oxy]-N-[2-(dimethylamino)-3-methylbutyl]-2-methylimidazo[1,2-a]-pyridine-3-carboxamide (Enantiomer B)

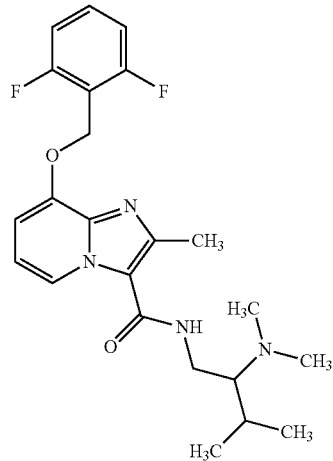 [SMILES: Cc1nc2c(OCc3c(F)cccc3F)cccn2c1C(=O)NCC(C(C)C)N(C)C]

130 mg of Example 142 were separated into the enantiomers on a chiral phase [column: Daicel Chiralpak AD-H, 5 µm, 250×20 mm, mobile phase: 50% isohexane, 50% ethanol+0.2% diethylamine, flow rate: 20 ml/min; 40° C., detection: 210 nm].

Yield: Enantiomer B: 52 mg (96% ee)

Enantiomer B: $R_t$=9.66 min [column: Daicel Chiralpak AD-H, 5 µm, 250×4.6 mm, mobile phase: 50% isohexane, 50% ethanol+0.2% diethylamine, flow rate: 1 ml/min; 40° C., detection: 220 nm].

Example 190 ent-6-Chloro-8-[(2,6-difluorobenzyl)oxy]-2-methyl-N-(piperidin-2-ylmethyl)imidazo[1,2-a]-pyridine-3-carboxamide (Enantiomer A)

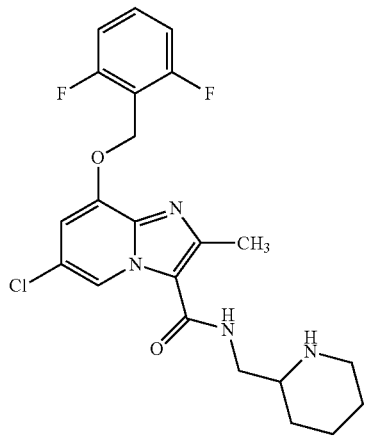 [SMILES: Cc1nc2c(OCc3c(F)cccc3F)cc(Cl)cn2c1C(=O)NCC1CCCCN1]

130 mg of Example 118 were separated into the enantiomers on a chiral phase [column: Daicel Chiralpak OZ-H, 5 µm, 250×20 mm, mobile phase: 50% isohexane, 50% isopropanol+0.2% diethylamine, flow rate: 15 ml/min; 40° C., detection: 220 nm].

Yield: Enantiomer A: 65 mg (99% ee)

Enantiomer A: $R_t$=10.35 min [column: Daicel Chiralpak OZ-H, 5 µm, 250×4.6 mm, mobile phase: 70% isohexane, 30% ethanol+0.2% diethylamine, flow rate: 1.0 ml/min; 40° C., detection: 220 nm].

Example 191 ent-6-Chloro-8-[(2,6-difluorobenzyl)oxy]-2-methyl-N-(piperidin-2-ylmethyl)imidazo[1,2-a]-pyridine-3-carboxamide (Enantiomer B)

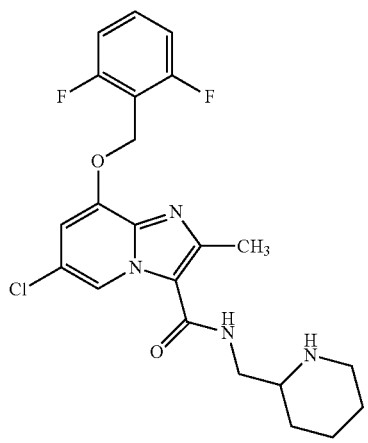 [SMILES: Cc1nc2c(OCc3c(F)cccc3F)cc(Cl)cn2c1C(=O)NCC1CCCCN1]

130 mg of Example 118 were separated into the enantiomers on a chiral phase [column: Daicel Chiralpak OZ-H, 5 µm, 250×20 mm, mobile phase: 50% isohexane, 50% isopropanol+0.2% diethylamine, flow rate: 15 ml/min; 40° C., detection: 220 nm].

Yield: Enantiomer B: 66 mg (98% ee)

Enantiomer B: $R_t$=11.67 min [column: Daicel Chiralpak OZ-H, 5 µm, 250×4.6 mm, mobile phase: 70% isohexane, 30% ethanol+0.2% diethylamine, flow rate: 1.0 ml/min; 40° C., detection: 220 nm].

Example 192 ent-N-(2-Amino-4,4,4-trifluorobutyl)-6-chloro-8-[(2,6-difluorobenzyl)oxy]-2-methylimidazo[1,2-a]pyridine-3-carboxamide (Enantiomer A)

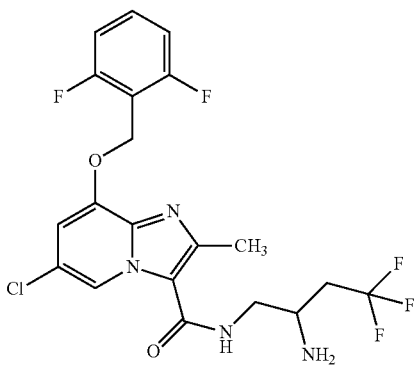 [SMILES: Cc1nc2c(OCc3c(F)cccc3F)cc(Cl)cn2c1C(=O)NCC(N)CC(F)(F)F]

166 mg of Example 147 were separated into the enantiomers on a chiral phase [column: Daicel Chiralpak AD-H, 5 µm, 250×20 mm, mobile phase: 50% isohexane, 50% isopropanol+0.2% diethylamine, flow rate: 12 ml/min; 25° C., detection: 230 nm]. The product fractions were collected on dry ice, combined and concentrated on a rotary evaporator (bath temperature 30° C.) to a residual volume of about 30 ml, and about 60 ml of water were added. The mixture was frozen and lyophilized. The product was re-purified by thick-layer chromatography (mobile phase: dichloromethane/methanol 10:1).

Yield enantiomer A: 23 mg (99% ee)

Enantiomer A: $R_t$=5.63 min [column: Daicel Chiralpak AD-H, 5 µm, 250×4.6 mm, mobile phase: 50% isohexane, 50% isopropanol+0.2% diethylamine, flow rate: 1.0 ml/min; 40° C., detection: 220 nm].

Example 193 ent-N-(2-Amino-4,4,4-trifluorobutyl)-6-chloro-8-[(2,6-difluorobenzyl)oxy]-2-methylimidazo[1,2-a]pyridine-3-carboxamide (Enantiomer B)

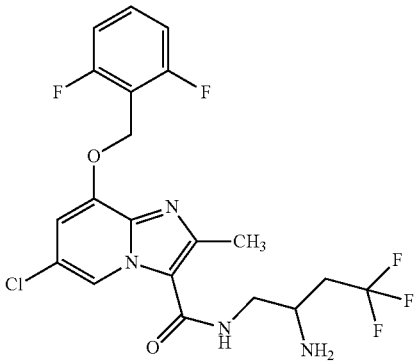 [SMILES: Cc1nc2c(OCc3c(F)cccc3F)cc(Cl)cn2c1C(=O)NCC(N)CC(F)(F)F]

166 mg of Example 147 were separated into the enantiomers on a chiral phase [column: Daicel Chiralpak AD-H, 5 μm, 250×20 mm, mobile phase: 50% isohexane, 50% isopropanol+0.2% diethylamine, flow rate: 12 ml/min; 25° C., detection: 230 nm]. The product fractions were collected on dry ice, combined and concentrated on a rotary evaporator (bath temperature 30° C.) to a residual volume of about 30 ml, and about 60 ml of water were added. The mixture was frozen and lyophilized. The product was re-purified by thick-layer chromatography (mobile phase: dichloromethane/methanol 10:1).

Yield: Enantiomer B: 22 mg (99% ee)

Enantiomer B: $R_t$=6.13 min [column: Daicel Chiralpak AD-H, 5 μm, 250×4.6 mm, mobile phase: 50% isohexane, 50% isopropanol+0.2% diethylamine, flow rate: 1.0 ml/min; 40° C., detection: 220 nm].

Example 194 ent-N-(2-Amino-2-methylbutyl)-6-chloro-8-[(2,6-difluorobenzyl)oxy]-2-methylimidazo[1,2-a]-pyridine-3-carboxamide (Enantiomer A)

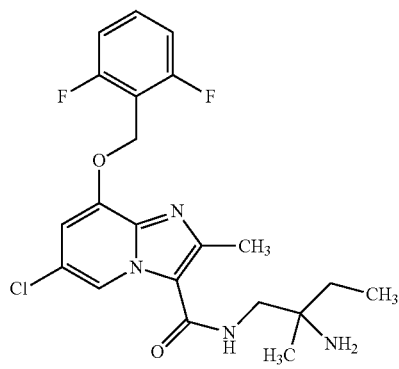 [SMILES: CCC(C)(N)CNC(=O)c1c(C)nc2c(OCc3c(F)cccc3F)cc(Cl)cn12]

190 mg of Example 157 were separated into the enantiomers on a chiral phase [column: Daicel Chiralpak AZ-H, 5 μm, 250×20 mm, mobile phase: 50% isohexane, 50% ethanol+0.2% diethylamine, flow rate: 15 ml/min; 35° C., detection: 220 nm]. The product fractions were collected on dry ice, combined and concentrated on a rotary evaporator (bath temperature 30° C.) to a residual volume of about 30 ml, and about 60 ml of water were added. The mixture was frozen and lyophilized.

Yield: Enantiomer A: 54 mg (98% ee)

Enantiomer A: $R_t$=8.39 min [column: Daicel Chiralpak AZ-H, 5 μm, 250×4.6 mm, mobile phase: 50% isohexane, 50% ethanol+0.2% diethylamine, flow rate: 1.0 ml/min; 35° C., detection: 250 nm].

Specific rotation [α] (436 nm, 19.8° C.)=−3.2° (c=0.0044 g/ml, acetonitrile)

Example 195 ent-N-(2-Amino-2-methylbutyl)-6-chloro-8-[(2,6-difluorobenzyl)oxy]-2-methylimidazo[1,2-a]-pyridine-3-carboxamide (Enantiomer B)

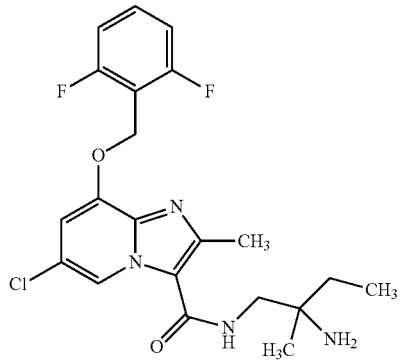 [SMILES: CCC(C)(N)CNC(=O)c1c(C)nc2c(OCc3c(F)cccc3F)cc(Cl)cn12]

190 mg of Example 157 were separated into the enantiomers on a chiral phase [column: Daicel Chiralpak AZ-H, 5 μm, 250×20 mm, mobile phase: 50% isohexane, 50% ethanol+0.2% diethylamine, flow rate: 15 ml/min; 35° C., detection: 220 nm]. The product fractions were collected on dry ice, combined and concentrated on a rotary evaporator (bath temperature 30° C.) to a residual volume of about 30 ml, and about 60 ml of water were added. The mixture was frozen and lyophilized.

Yield: Enantiomer B: 71 mg (90% ee)

Enantiomer B: $R_t$=9.04 min [column: Daicel Chiralpak AZ-H, 5 μm, 250×4.6 mm, mobile phase: 50% isohexane, 50% ethanol+0.2% diethylamine, flow rate: 1.0 ml/min; 35° C., detection: 250 nm].

Example 196 ent-N-(2-Amino-3-methoxy-2-methylpropyl)-6-chloro-8-[(2,6-difluorobenzyl)oxy]-2-methylimidazo[1,2-a]pyridine-3-carboxamide (Enantiomer A)

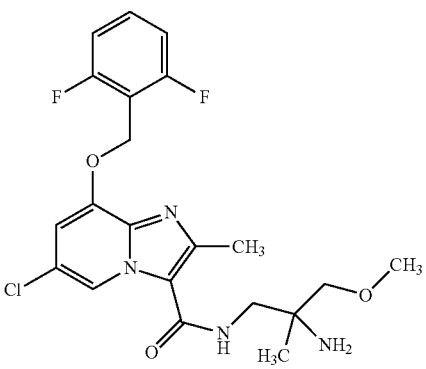

218 mg of Example 159 were separated into the enantiomers on a chiral phase [column: Daicel Chiralpak OZ-H, 5 μm, 250×20 mm, mobile phase: 50% isohexane, 50% ethanol+0.2% diethylamine, flow rate: 15 ml/min; 40° C., detection: 220 nm]. The product fractions were collected on dry ice, combined and concentrated on a rotary evaporator (bath temperature 30° C.) to a residual volume of about 30 ml, and about 60 ml of water were added. The mixture was frozen and lyophilized.

Yield: Enantiomer A: 136 mg (99% ee)

Enantiomer A: $R_t$=7.68 min [column: Daicel Chiralpak OZ-H, 5 μm, 250×4.6 mm, mobile phase: 50% isohexane, 50% ethanol+0.2% diethylamine, flow rate: 1.0 ml/min; 40° C., detection: 270 nm].

Example 197 ent-N-(2-Amino-3-methoxy-2-methylpropyl)-6-chloro-8-[(2,6-difluorobenzyl)oxy]-2-methylimidazo[1,2-a]pyridine-3-carboxamide (Enantiomer B)

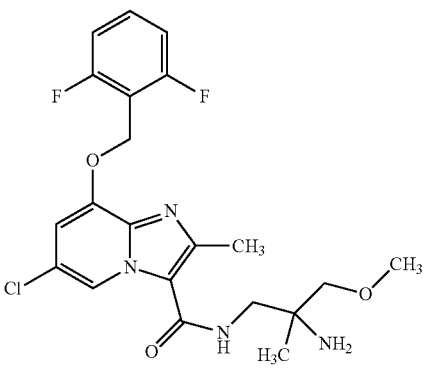

218 mg of Example 159 were separated into the enantiomers on a chiral phase [column: Daicel Chiralpak OZ-H, 5 μm, 250×20 mm, mobile phase: 50% isohexane, 50% ethanol+0.2% diethylamine, flow rate: 15 ml/min; 40° C., detection: 220 nm]. The product fractions were collected on dry ice, combined and concentrated on a rotary evaporator (bath temperature 30° C.) to a residual volume of about 30 ml, and about 60 ml of water were added. The mixture was frozen and lyophilized.

Yield: Enantiomer B: 60 mg (98% ee)

Enantiomer B: $R_t$=10.17 min [column: Daicel Chiralpak OZ-H, 5 μm, 250×4.6 mm, mobile phase: 50% isohexane, 50% ethanol+0.2% diethylamine, flow rate: 1.0 ml/min; 40° C., detection: 270 nm].

Example 198 ent-N-(2-Amino-3-methoxy-2-methylpropyl)-8-[(2,6-difluorobenzyl)oxy]-2,6-dimethylimidazo-[1,2-a]pyridine-3-carboxamide (enantiomer A)

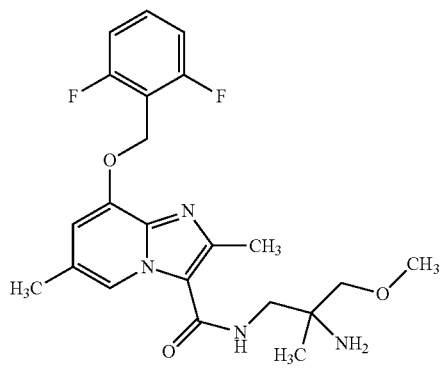

200 mg of Example 166 were separated into the enantiomers on a chiral phase [column: Daicel Chiralpak OZ-H, 5 μm, 250×20 mm, mobile phase: 25% isohexane, 75% ethanol+0.2% diethylamine, flow rate: 12 ml/min; 45° C., detection: 220 nm]. The product fractions were collected on dry ice, combined and concentrated on a rotary evaporator (bath temperature 30° C.) to a residual volume of about 30 ml, and about 60 ml of water were added. The mixture was frozen and lyophilized.

Yield: Enantiomer A: 112 mg (99% ee)

Enantiomer A: $R_t$=7.31 min [column: Daicel Chiralpak OZ-H, 5 μm, 250×4.6 mm, mobile phase: 25% isohexane, 75% ethanol+0.2% diethylamine, flow rate: 1.0 ml/min; 45° C., detection: 235 nm].

Example 199 ent-N-(2-Amino-3-methoxy-2-methylpropyl)-8-[(2,6-difluorobenzyl)oxy]-2,6-dimethylimidazo-[1,2-a]pyridine-3-carboxamide (Enantiomer B)

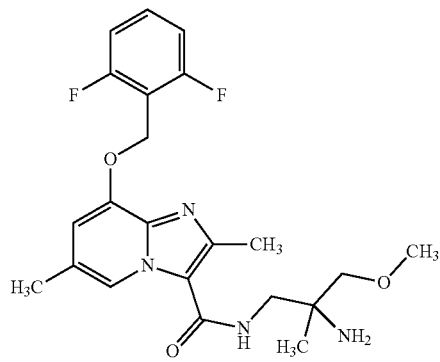

200 mg of Example 166 were separated into the enantiomers on a chiral phase [column: Daicel Chiralpak OZ-H, 5 µm, 250×20 mm, mobile phase: 25% isohexane, 75% ethanol+0.2% diethylamine, flow rate: 12 ml/min; 45° C., detection: 220 nm]. The product fractions were collected on dry ice, combined and concentrated on a rotary evaporator (bath temperature 30° C.) to a residual volume of about 30 ml, and about 60 ml of water were added. The mixture was frozen and lyophilized.

Yield: Enantiomer B: 50 mg (98% ee)

Enantiomer B: $R_f$=10.00 min [column: Daicel Chiralpak OZ-H, 5 µm, 250×4.6 mm, mobile phase: 25% isohexane, 75% ethanol+0.2% diethylamine, flow rate: 1.0 ml/min; 45° C., detection: 235 nm].

Example 200 ent-N-[(2S)-Amino-2-methylbutyl]-8-[(2,6-difluorobenzyl)oxy]-2,6-dimethylimidazo[1,2-a]-pyridine-3-carboxamide (Enantiomer A)

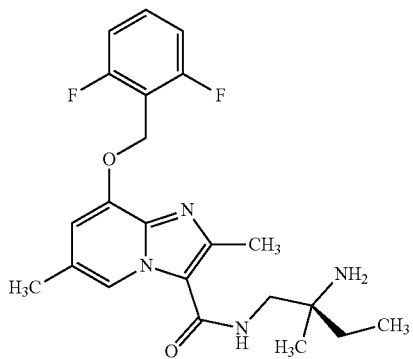 [SMILES: CC[C@](C)(N)CNC(=O)c1c(C)nc2c(OCc3c(F)cccc3F)cc(C)cn12]

With gentle warming, 3.55 g (6.45 mmol) of ent-benzyl {1-[({8-[(2,6-difluorobenzyl)oxy]-2,6-dimethylimidazo[1,2-a]pyridin-3-yl}carbonyl)amino]-2-methylbutan-2-yl}carbamate (enantiomer A) Example 276A were dissolved in 70 ml of ethanol, and 226 mg of palladium(II) hydroxide on activated carbon (20%) were added under argon. The reaction mixture was hydrogenated under atmospheric pressure at RT for 2 h. The reaction mixture was filtered off through Celite, the filter cake was washed thoroughly with ethanol and the filtrate was concentrated. The crude product was purified by silica gel chromatography (mobile phase: dichloromethane/2 N ammonia in methanol=10/0.5). This gave 2.27 g of the target compound (85% of theory; purity 99%).

LC-MS (Method 2): $R_t$=0.62 min

MS (ESIpos): m/z=417 (M+H)$^+$ $^1$H NMR (400 MHz, DMSO-d$_6$): δ=0.87 (t, 3H), 0.97 (s, 3H), 1.31-1.39 (m, 2H), 1.43 (br. s, 2H), 2.31 (s, 3H), 2.53 (s, 3H, superimposed by DMSO signal), 3.14-3.27 (m, 2H), 5.29 (s, 2H), 6.91 (s, 1H), 7.19-7.27 (m, 2H), 7.54-7.64 (m, 2H), 8.49 (s, 1H).

Specific rotation [α] (365 nm, 20.0° C.)=−6.6° (c=0.0044 g/ml, acetonitrile) Single crystal X-ray structure analysis confirmed the S configuration for this enantiomer.

Example 201 ent-N-(2-Amino-2-methylbutyl)-8-[(2,6-difluorobenzyl)oxy]-2,6-dimethylimidazo[1,2-a]pyridine-3-carboxamide (Enantiomer B)

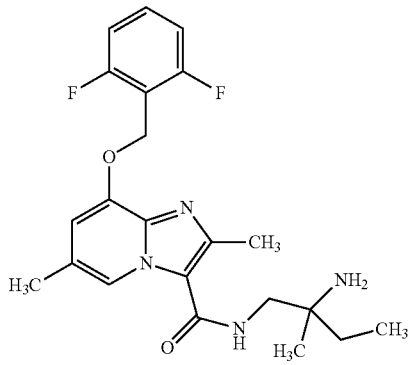 [SMILES: CCC(C)(N)CNC(=O)c1c(C)nc2c(OCc3c(F)cccc3F)cc(C)cn12]

With gentle warming, 2.10 g (3.66 mmol) of ent-benzyl {1-[({8-[(2,6-difluorobenzyl)oxy]-2,6-dimethylimidazo[1,2-a]pyridin-3-yl}carbonyl)amino]-2-methylbutan-2-yl}carbamate (enantiomer B) Example 277A were dissolved in 40 ml of ethanol, and 257 mg of palladium(II) hydroxide on activated carbon (20%) were added under argon. The reaction mixture was hydrogenated under atmospheric pressure at RT for 2 h. The reaction mixture was filtered off through Celite, the filter cake was washed thoroughly with ethanol and the filtrate was concentrated. The crude product was purified by silica gel chromatography (mobile phase: dichloromethane/2 N ammonia in methanol=10/0.5). This gave 1.26 g of the target compound (82% of theory; purity 99%).

LC-MS (Method 2): $R_t$=0.66 min

MS (ESIpos): m/z=417 (M+H)$^+$ $^1$H NMR (400 MHz, DMSO-d$_6$): δ=0.87 (t, 3H), 0.98 (s, 3H), 1.31-1.39 (m, 2H), 1.49 (br. s, 2H), 2.31 (s, 3H), 2.53 (s, 3H, superimposed by DMSO signal), 3.14-3.27 (m, 2H), 5.29 (s, 2H), 6.91 (s, 1H), 7.19-7.27 (m, 2H), 7.54-7.64 (m, 2H), 8.49 (s, 1H).

Specific rotation [α] (365 nm, 20.1° C.)=+4.4° (c=0.0044 g/ml, acetonitrile)

Example 202 rac-N-(2-Amino-2,4-dimethylpentyl)-8-[(2,6-difluorobenzyl)oxy]-2-methylimidazo[1,2-a]pyridine-3-carboxamide

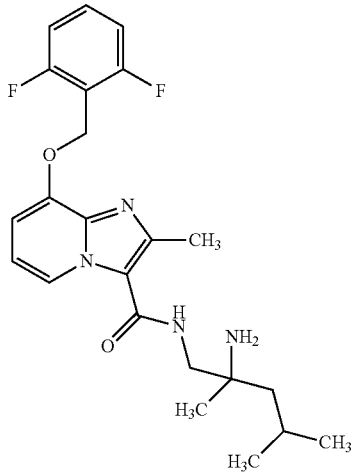 [SMILES: Cc1nc2c(OCc3c(F)cccc3F)cccn2c1C(=O)NCC(C)(N)CC(C)C]

150 mg (0.47 mmol) of 8-[(2,6-difluorobenzyl)oxy]-2-methylimidazo[1,2-a]pyridine-3-carboxylic acid Example 3A were initially charged in DMF (1.7 ml), and 159 mg (0.50 mmol) of TBTU and 0.16 ml (1.41 mmol) of 4-methylmorpholine were added. 68 mg (0.52 mmol) of rac-2,4-dimethylpentane-1,2-diamine were then added, and the reaction mixture was stirred at RT overnight. Another 6.1 mg (0.04 mmol) of rac-2,4-dimethylpentane-1,2-diamine were added, and the reaction mixture was stirred at RT for 20 min. The mixture was diluted with water/TFA and purified by prep. RP-HPLC (acetonitrile/water gradient with addition of 0.1% TFA). The product fraction was concentrated. The residue was taken up in dichloromethane and a few drops of methanol and washed twice with saturated aqueous sodium bicarbonate solution, and the aqueous phase was extracted three times with dichloromethane. The organic phase was dried over sodium sulphate, filtered off and concentrated. This gave 126 mg (61% of theory, purity 97%) of the target compound.

LC-MS (Method 2): $R_t$=0.70 min

MS (ESIpos): m/z=431 (M+H)$^+$ $^1$H NMR (400 MHz, DMSO-d$_6$): δ=0.89 (d, 3H), 0.95 (d, 3H), 1.02 (s, 3H), 1.20-1.33 (m, 2H), 1.42 (br. s, 2H), 1.74-1.85 (m, 1H), 2.56 (s, 3H), 3.14-3.27 (m, 2H), 5.30 (s, 2H), 6.94 (t, 1H), 7.01 (d, 1H), 7.19-7.29 (m, 2H), 7.54-7.63 (m, 1H), 7.64-7.71 (m, 1H), 8.64 (d, 1H).

Example 203 ent-N-(2-Amino-2,4-dimethylpentyl)-8-[(2,6-difluorobenzyl)oxy]-2-methylimidazo[1,2-a]pyridine-3-carboxamide (Enantiomer A)

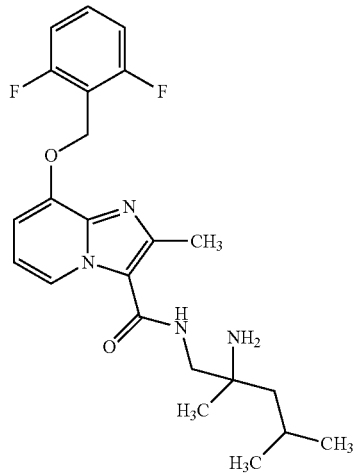

122 mg of Example 202 were separated into the enantiomers by preparative separation on a chiral phase [column: Daicel Chiralpak AD-H, 5 μm, 250×20 mm, mobile phase: 50% isohexane, 50% ethanol+0.2% diethylamine, flow rate: 20 ml/min; 40° C., detection: 210 nm]. The product fractions were collected on dry ice, combined and concentrated on a rotary evaporator (bath temperature 30° C.) to a residual volume of about 30 ml, and about 60 ml of water were added. The solution obtained was frozen and lyophilized.

Enantiomer A: Yield: 28 mg (100% ee)

$R_t$=8.71 min [Daicel Chiralpak AD-H, 5 m, 250×4.6 mm; mobile phase: 50% isohexane, 50% ethanol+0.2% diethylamine; flow rate 1.0 ml/min; 40° C.; detection: 220 nm].

Example 204 ent-N-(2-Amino-2,4-dimethylpentyl)-8-[(2,6-difluorobenzyl)oxy]-2-methylimidazo[1,2-a]pyridine-3-carboxamide (Enantiomer B)

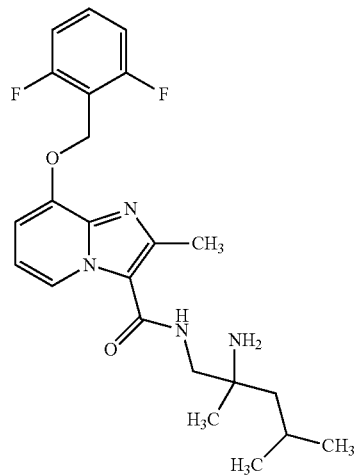 [SMILES: Cc1nc2c(OCc3c(F)cccc3F)cccn2c1C(=O)NCC(C)(N)CC(C)C]

122 mg of Example 202 were separated into the enantiomers by preparative separation on a chiral phase [column: Daicel Chiralpak AD-H, 5 μm, 250×20 mm, mobile phase: 50% isohexane, 50% ethanol+0.2% diethylamine, flow rate: 20 ml/min; 40° C., detection: 210 nm]. The product fractions were collected on dry ice, combined and concentrated on a rotary evaporator (bath temperature 30° C.) to a residual volume of about 30 ml, and about 60 ml of water were added. The solution obtained was frozen and lyophilized.

Enantiomer B: Yield: 68 mg (92% ee)

$R_t$=9.79 min [Daicel Chiralpak AD-H, 5 m, 250×4.6 mm; mobile phase: 50% isohexane, 50% ethanol+0.2% diethylamine; flow rate 1.0 ml/min; 40° C.; detection: 220 nm].

Example 205 rac-N-(2-Amino-3-isopropoxypropyl)-8-[(2,6-difluorobenzyl)oxy]-2-methylimidazo[1,2-a]-pyridine-3-carboxamide

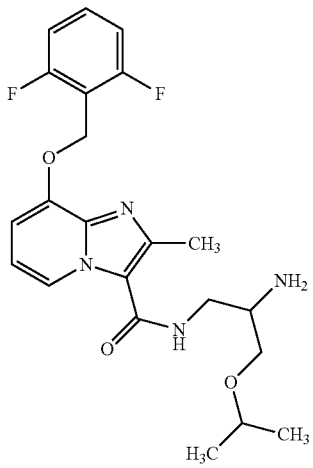 [SMILES: Cc1nc2c(OCc3c(F)cccc3F)cccn2c1C(=O)NCC(N)COC(C)C]

125 mg (0.33 mmol) of HATU and 0.16 ml (0.90 mmol) of N,N-diisopropylethylamine were added to 95 mg (0.30 mmol) of 8-[(2,6-difluorobenzyl)oxy]-2-methylimidazo[1,2-a]pyridine-3-carboxylic acid Example 3A in DMF (1.9 ml), and the mixture was stirred at RT for 20 min. At −20° C., 145 mg (0.54 mmol, 76% pure) of rac-3-isopropoxypropane-1,2-diamine dihydrochloride Example 224A in DMF (0.5 ml), to which 0.31 ml (1.8 mmol) of N,N-diisopropylethylamine had been added beforehand and which had been stirred at RT for 10 min, were then slowly added dropwise to the reaction mixture. The mixture was stirred at RT overnight. The mixture was then diluted with water/TFA and purified by prep. RP-HPLC (acetonitrile/water gradient with addition of 0.1% TFA). The product fraction was concentrated and then re-purified by thick-layer chromatography (dichloromethane/methanol: 10:1). This gave 15 mg (12% of theory) of the target compound.

LC-MS (Method 2): $R_t$=0.68 min.
MS (ESIpos): m/z=433 (M+H)$^+$
$^1$H NMR (400 MHz, DMSO-d$_6$): δ=1.10 (d, 6H), 1.24 (s, 2H), 2.57 (s, 3H; superimposed by DMSO signal), 3.00-3.08 (m, 1H), 3.28-3.48 (m, 4H), 3.51-3.59 (m, 1H), 5.30 (s, 2H), 6.92 (t, 1H), 7.00 (d, 1H), 7.24 (t, 2H), 7.53-7.63 (m, 1H), 7.70 (t, 1H), 8.64 (d, 1H).

Example 206 rac-N-(2-Amino-3-isopropoxypropyl)-8-[(2,6-difluorobenzyl)oxy]-2,6-dimethylimidazo[1,2-a]-pyridine-3-carboxamide

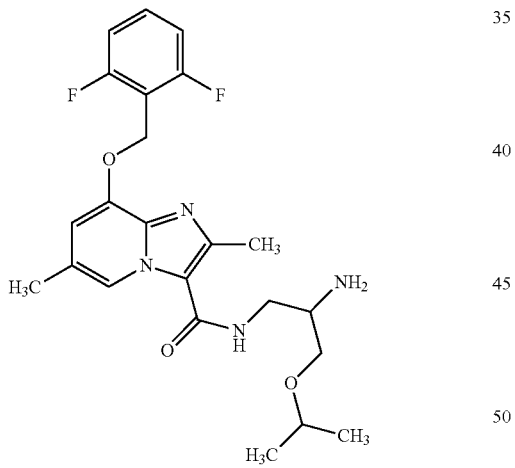

Preparation and purification of the title compound were carried out analogously to Example 205. Starting with 11.2 mg (0.03 mmol) of 8-[(2,6-difluorobenzyl)oxy]-2,6-dimethylimidazo[1,2-a]-pyridine-3-carboxylic acid Example 21A and 15.0 mg (0.05 mmol, 76% pure) of rac-3-isopropoxypropane-1,2-diaminedihydrochloride Example 224A, 1.6 mg (9.5% of theory) of the target compound were obtained.

LC-MS (Method 2): $R_t$=0.65 min
MS (ESIpos): m/z=447 (M+H)$^+$
$^1$H NMR (400 MHz, DMSO-d$_6$): δ=1.14 (d, 6H), 1.25 (s, 2H), 2.32 (s, 3H), 2.54 (s, 3H; superimposed by DMSO signal), 3.35-3.42 (m, 1H), 3.44-3.66 (m, 5H), 5.31 (s, 2H), 6.94 (s, 1H), 7.24 (t, 2H), 7.56-7.66 (m, 1H), 7.80 (t, 1H), 8.53 (s, 1H).

Example 207 rac-N-(2-Amino-3,3,3-trifluoropropyl)-8-[(2,6-difluorobenzyl)oxy]-2-methylimidazo[1,2-a]-pyridine-3-carboxamide

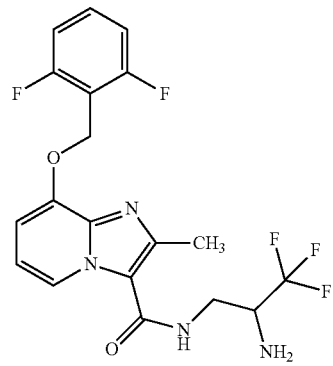 [SMILES: Cc1nc2c(OCc3c(F)cccc3F)cccn2c1C(=O)NCC(N)C(F)(F)F]

Preparation and purification of the title compound were carried out analogously to Example 141. Starting with 400 mg (1.26 mmol) of 8-[(2,6-difluorobenzyl)oxy]-2-methylimidazo[1,2-a]pyridine-3-carboxylic acid Example 3A and 278 mg (1.38 mmol) of rac-1-(trifluoromethyl)ethylene-1,2-diamine dihydrochloride, 340 mg (63% of theory) of the target compound were obtained.

LC-MS (Method 7): $R_t$=0.70 min
MS (ESIpos): m/z=429 (M+H)$^+$.
$^1$H NMR (400 MHz, DMSO-d$_6$): δ=2.55 (s, 3H; superimposed by DMSO signal), 3.49-3.62 (m, 1H), 3.67-3.77 (m, 1H), 3.89-4.10 (m, 1H), 5.31 (s, 2H), 6.99 (t, 1H), 7.07 (d, 1H), 7.19-7.29 (m, 2H), 7.54-7.65 (m, 1H), 7.96 (t, 1H), 8.71 (d, 1H).

Example 208 ent-N-(2-Amino-3,3,3-trifluoropropyl)-8-[(2,6-difluorobenzyl)oxy]-2-methylimidazo[1,2-a]-pyridine-3-carboxamide (Enantiomer A)

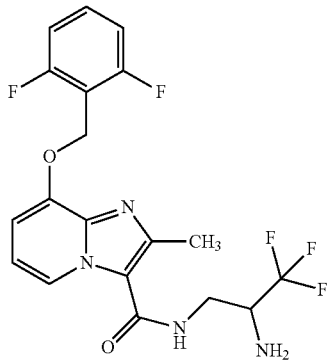 [SMILES: Cc1nc2c(OCc3c(F)cccc3F)cccn2c1C(=O)NCC(N)C(F)(F)F]

464 mg of Example 207 were separated into the enantiomers by preparative separation on a chiral phase [column: Daicel Chiralpak AD-H, 5 μm, 250×20 mm, mobile phase: 50% isohexane, 50% isopropanol+0.2% diethylamine, flow rate: 20 ml/min; 40° C., detection: 210 nm].

Enantiomer A: Yield: 120 mg (100% ee)

R$_t$=8.87 min [Daicel Chiralpak AD-H, 5 m, 250×4.6 mm; mobile phase: 50% isohexane, 50% isopropanol+0.2% diethylamine; flow rate 1.0 ml/min; 40° C.; detection: 220 nm].

Example 209 ent-N-(2-Amino-3,3,3-trifluoropropyl)-8-[(2,6-difluorobenzyl)oxy]-2-methylimidazo[1,2-a]-pyridine-3-carboxamide (Enantiomer B)

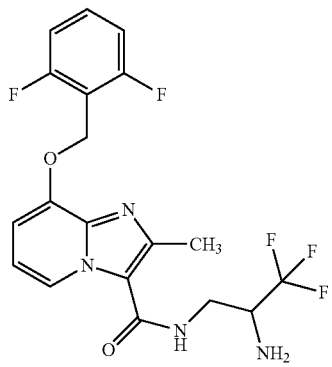 [SMILES: Cc1nc2c(OCc3c(F)cccc3F)cccn2c1C(=O)NCC(N)C(F)(F)F]

464 mg of Example 207 were separated into the enantiomers by preparative separation on a chiral phase [column: Daicel Chiralpak AD-H, 5 μm, 250×20 mm, mobile phase: 50% isohexane, 50% isopropanol+0.2% diethylamine, flow rate: 20 ml/min; 40° C., detection: 210 nm].

Enantiomer B: Yield: 122 mg (92.6% ee)

R$_t$=10.05 min [Daicel Chiralpak AD-H, 5 m, 250×4.6 mm; mobile phase: 50% isohexane, 50% isopropanol+0.2% diethylamine; flow rate 1.0 ml/min; 40° C.; detection: 220 nm].

Example 210 ent-N-(1-amino-3-methoxypropan-2-yl)-8-[(2,6-difluorobenzyl)oxy]-2,6-dimethylimidazo[1,2-a]-pyridine-3-carboxamide trifluoroacetate (Enantiomer B)

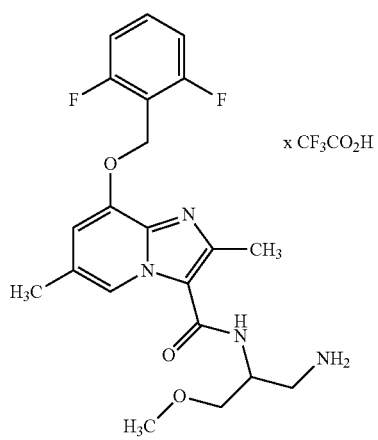 [SMILES: COCC(CN)NC(=O)c1c(C)nc2c(OCc3c(F)cccc3F)cc(C)cn12]

Under argon, 100 mg (0.18 mmol) of ent-benzyl {2-[({8-[(2,6-difluorobenzyl)oxy]-2,6-dimethylimidazo[1,2-a]pyridin-3-yl}carbonyl)amino]-3-methoxypropyl}carbamate, prepared according to the Representative Working Procedure 3 using Examples 21A and 248A) were initially charged in ethanol (1.3 ml), and 19.2 mg (0.02 mmol, 10%) of palladium on activated carbon and 0.37 ml (3.62 mmol) of cyclohexene were added. The reaction mixture was stirred under reflux overnight. The reaction mixture, cooled to RT, was filtered through a Millipore filter, the filter cake was washed with ethanol and the filtrate was concentrated. The residue was purified by prep. RP-HPLC (acetonitrile/water gradient with addition of 0.1% TFA). The product fraction was concentrated, then taken up in dichloromethane and washed twice with saturated aqueous sodium bicarbonate solution. The aqueous phase was extracted twice with dichloromethane. The combined organic phases were dried over sodium sulphate, filtered off and concentrated. This gave 24 mg (22% of theory, purity 90%) of the title compound.

LC-MS (Method 7): R$_t$=0.59 min

MS (ESIpos): m/z=419 (M−TFA+H)$^+$ $^1$H NMR (400 MHz, DMSO-d$_6$): δ=2.36 (s, 3H), 2.53 (s, 3H; superimposed by DMSO signal), 2.93-3.04 (m, 1H), 3.06-3.17 (m, 1H), 3.32 (s, 3H), 3.47-3.54 (m, 2H), 4.37-4.48 (m, 1H), 5.34 (s, 2H), 7.10-7.19 (m, 1H), 7.21-7.39 (m, 2H), 7.61 (quintet, 1H), 7.83-8.00 (m, 2H), 8.46 (s, 1H).

Example 211 ent-N-(2-Amino-3-methylbutyl)-6-chloro-8-[(2,6-difluorobenzyl)oxy]-2-methylimidazo[1,2-a]-pyridine-3-carboxamide (Enantiomer A)

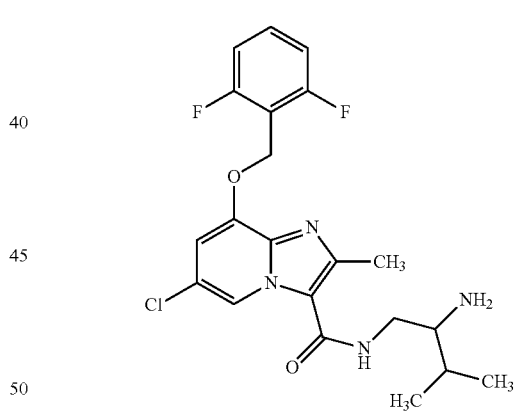

124 mg (0.23 mmol) of ent-tert-butyl {1-[({6-chloro-8-[(2,6-difluorobenzyl)oxy]-2-methylimidazo[1,2-a]pyridin-3-yl}carbonyl)amino]-3-methylbutan-2-yl}carbamate Example 228A were initially charged in 1.16 ml (2.31 mmol) of 2 N hydrogen chloride/diethyl ether, and the mixture was stirred at RT for 3.5 h. The reaction solution was then concentrated. Ethyl acetate and saturated aqueous sodium bicarbonate solution were added to the residue. After phase separation, the aqueous phase was extracted twice with ethyl acetate and the combined organic phases were dried over sodium sulphate, filtered and concentrated. This gave 89 mg (87% of theory, purity 99%) of the title compound.

LC-MS (Method 2): R$_t$=0.73 min

MS (ESIpos): m/z=437 (M+H)$^+$

¹H NMR (400 MHz, DMSO-d₆): δ=0.88 (d, 3H), 0.92 (d, 3H), 1.57-1.68 (m, 1H), 1.86-2.24 (br. s, 2H), 2.53 (s, 3H; superimposed by DMSO signal), 2.63-2.70 (m, 1H), 3.05-3.14 (m, 1H), 3.39-3.46 (m, 1H), 5.34 (s, 2H), 7.19 (d, 1H), 7.26 (t, 2H), 7.61 (quintet, 1H), 7.72-7.88 (br. s, 1H), 8.78 (d, 1H).

Example 212 ent-N-(2-Amino-3-methylbutyl)-6-chloro-8-[(2,6-difluorobenzyl)oxy]-2-methylimidazo[1,2-a]-pyridine-3-carboxamide (Enantiomer B)

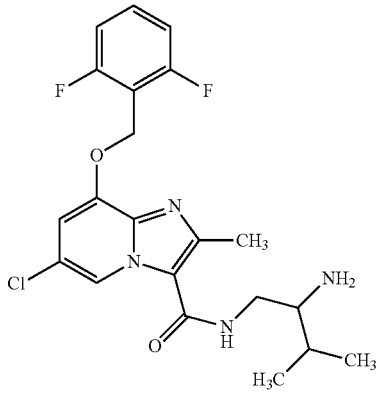 [SMILES: Cc1nc2c(OCc3c(F)cccc3F)cc(Cl)cn2c1C(=O)NCC(N)C(C)C]

Preparation and purification (use of dichloromethane for work-up) of the title compound were carried out analogously to Example 211. Starting with 122 mg (0.23 mmol) of ent-tert-butyl {1-[({6-chloro-8-[(2,6-difluorobenzyl)oxy]-2-methylimidazo[1,2-a]pyridin-3-yl}carbonyl)amino]-3-methylbutan-2-yl}carbamate (enantiomer B) Example 229A, 81 mg (81% of theory, purity 99%) of the title compound were obtained.

LC-MS (Method 2): R_t=0.73 min
MS (ESIpos): m/z=437 (M+H)⁺
¹H NMR (400 MHz, DMSO-d₆): δ=0.88 (d, 3H), 0.91 (d, 1H), 1.45-1.78 (m, 3H), 2.52 (s, 3H; superimposed by DMSO signal), 2.61-2.69 (m, 1H), 3.04-3.13 (m, 1H), 3.38-3.45 (m, 1H), 5.34 (s, 2H), 7.19 (d, 1H), 7.26 (t, 2H), 7.60 (quintet, 1H), 7.71-7.88 (br. s, 1H), 8.78 (d, 1H).

Example 213 rac-N-(2-Amino-3-methoxy-2-methylpropyl)-8-[(2,6-difluorobenzyl)oxy]-2-methylimidazo[1,2-a]-pyridine-3-carboxamide

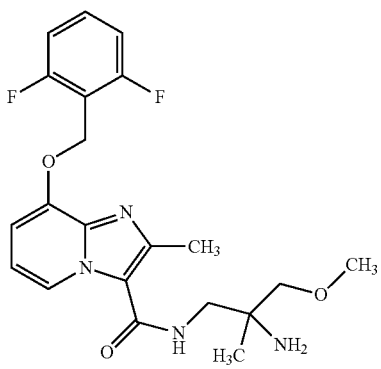 [SMILES: COCC(C)(N)CNC(=O)c1c(C)nc2c(OCc3c(F)cccc3F)cccn12]

180 mg (0.57 mmol) of 8-[(2,6-difluorobenzyl)oxy]-2-methylimidazo[1,2-a]pyridine-3-carboxylic acid Example 3A, 237 mg (0.62 mmol) of HATU and 0.30 ml (1.70 mmol) of N,N-diisopropylethylamine were initially charged in 3.6 ml of DMF, and the mixture was stirred at RT for 20 min. 74 mg (0.62 mmol) of rac-3-methoxy-2-methylpropane-1,2-diamine were then added and the reaction mixture was stirred at RT overnight. The reaction solution was diluted with water/TFA and purified by preparative RP-HPLC (acetonitrile/water gradient with addition of 0.1% TFA). The product fraction was concentrated. The residue was taken up in dichloromethane and washed twice with saturated aqueous sodium bicarbonate solution. The aqueous phase was extracted twice with dichloromethane and the combined organic phases were dried over sodium sulphate, filtered and concentrated. This gave 136 mg (56% of theory, purity 98%) of the title compound.

LC-MS (Method 2): R_t=0.56 min
MS (ESIpos): m/z=419 (M+H)⁺
¹H NMR (400 MHz, DMSO-d₆): δ=1.00 (s, 3H), 1.53 (br. s, 2H), 2.56 (s, 3H; superimposed by DMSO signal), 3.13-3.19 (m, 2H), 3.24-3.32 (m, 5H; superimposed by solvent signal), 5.30 (s, 2H), 6.94 (t, 1H), 7.02 (d, 1H), 7.19-7.29 (m, 2H), 7.59 (quintet, 2H), 8.69 (d, 1H).

Example 214 ent-N-(2-Amino-3-methoxy-2-methylpropyl)-8-[(2,6-difluorobenzyl)oxy]-2-methylimidazo[1,2-a]-pyridine-3-carboxamide (Enantiomer A)

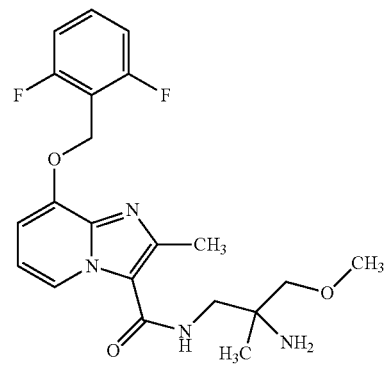 [SMILES: COCC(C)(N)CNC(=O)c1c(C)nc2c(OCc3c(F)cccc3F)cccn12]

130 mg of Example 213 were separated into the enantiomers by preparative separation on a chiral phase [column: Phenomenex Amylose II, 5 µm, 250×20 mm, mobile phase: 50% isohexane, 50% ethanol+0.2% diethylamine, flow rate: 20 ml/min; 25° C., detection: 230 nm].

Enantiomer A: Yield: 32.4 mg (100% ee)

R_t=5.89 min [Daicel Chiralpak AY-H, 5 m, 250×4.6 mm; mobile phase: 50% isohexane, 50% ethanol+0.2% diethylamine; flow rate 1.0 ml/min; 40° C.; detection: 220 nm].

Example 215 ent-N-(2-Amino-3-methoxy-2-methylpropyl)-8-[(2,6-difluorobenzyl)oxy]-2-methylimidazo[1,2-a]-pyridine-3-carboxamide (Enantiomer B)

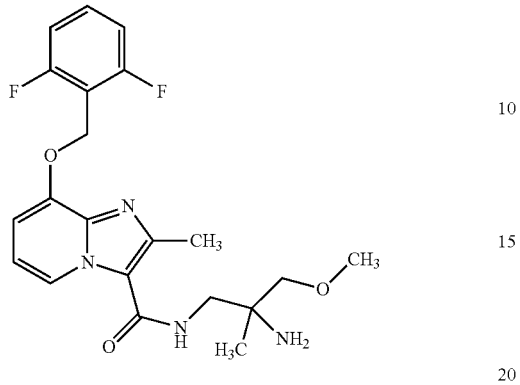

130 mg of Example 213 were separated into the enantiomers by preparative separation on a chiral phase [column: Phenomenex Amylose II, 5 µm, 250×20 mm, mobile phase: 50% isohexane, 50% ethanol+0.2% diethylamine, flow rate: 20 ml/min; 25° C., detection: 230 nm].

Enantiomer B: Yield: 79.5 mg (100% ee)

$R_t$=8.01 min [Daicel Chiralpak AY-H, 5 m, 250×4.6 mm; mobile phase: 50% isohexane, 50% ethanol+0.2% diethylamine; flow rate 1.0 ml/min; 40° C.; detection: 220 nm].

Example 216

N-[(3-Aminooxetan-3-yl)methyl]-8-[(2,6-difluorobenzyl)oxy]-2,6-dimethylimidazo[1,2-a]pyridine-3-carboxamide

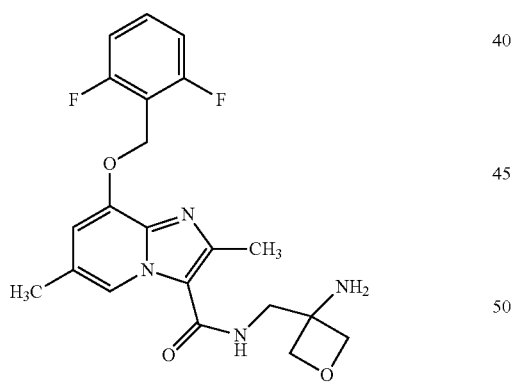

Preparation and purification of the title compound were carried out analogously to Example 205. Starting with 45 mg (0.14 mmol) of 8-[(2,6-difluorobenzyl)oxy]-2,6-dimethylimidazo[1,2-a]-pyridine-3-carboxylic acid Example 21A and 95 mg (0.41 mmol, 75% pure) of 3-(aminomethyl)oxetan-3-amine dihydrochloride Example 226A. After additional purification [column: XBridge C18, 5 µm, 150×19 mm, mobile phase: 32% water, 60% methanol+8% 1% strength ammonia in water, flow rate: 25 ml/min; 25° C., detection: 210 nm], 21 mg (37% of theory, purity 100%) of the target compound were obtained.

LC-MS (Method 2): $R_t$=0.63 min
MS (ESIpos): m/z=417 (M+H)$^+$ $^1$H NMR (400 MHz, DMSO-d$_6$): δ=2.30 (s, 3H), 3.52-3.62 (m, 2H), 4.29 (d, 2H), 4.43 (d, 2H), 5.29 (s, 2H), 6.92 (s, 1H), 7.19-7.28 (m, 2H), 7.54-7.65 (m, 1H), 7.88-7.98 (m, 1H), 8.44 (s, 1H), [additional signal under DMSO peak].

Example 217 rac-N-(2-Amino-3-isopropoxypropyl)-6-chloro-8-[(2,6-difluorobenzyl)oxy]-2-methylimidazo[1,2-a]pyridine-3-carboxamide

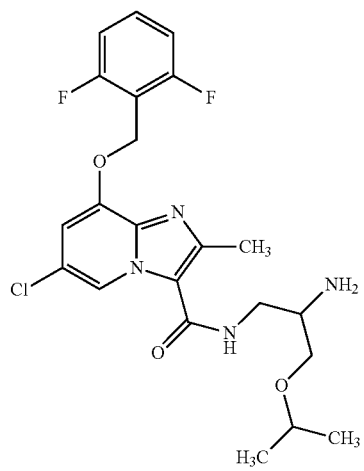 [SMILES: Cc1nc2c(OCc3c(F)cccc3F)cc(Cl)cn2c1C(=O)NCC(N)COC(C)C]

Preparation and purification of the title compound were carried out analogously to Example 205. Starting with 11.9 mg (0.03 mmol) of 6-Chloro-8-[(2,6-difluorobenzyl)oxy]-2-methylimidazo[1,2-a]pyridine-3-carboxylic acid Example 16A and 15.0 mg (0.06 mmol, 76% pure) rac-3-isopropoxy-propane-1,2-diamine dihydrochloride Example 224A, 1.9 mg (11% of theory, purity 90%) of the target compound were obtained.

LC-MS (Method 2): $R_t$=0.76 min
MS (ESIpos): m/z=467 (M+H)$^+$ $^1$H NMR (400 MHz, DMSO-d$_6$): δ=1.14 (d, 6H), 1.23-1.28 (m, 2H), 2.55 (s, 3H; superimposed by DMSO signal), 3.41-3.56 (m, 4H), 3.58-3.65 (m, 1H), 5.34 (s, 2H), 7.19-7.28 (m, 3H), 7.56-7.66 (m, 1H), 8.80 (d, 1H).

Example 218 rac-N-(2-Amino-2,4-dimethylpentyl)-8-[(2,6-difluorobenzyl)oxy]-2,6-dimethylimidazo[1,2-a]-pyridine-3-carboxamide

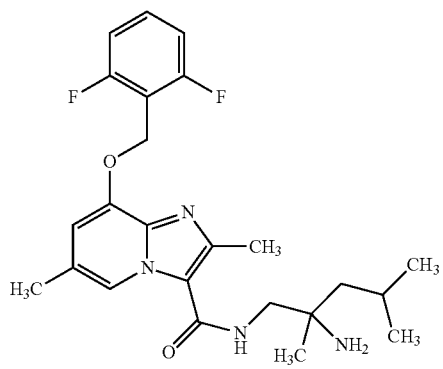 [SMILES: Cc1cc(OCc2c(F)cccc2F)c2nc(C)c(C(=O)NCC(C)(N)CC(C)C)n2c1]

Preparation and purification of the title compound were carried out analogously to Example 202. Starting with 150 mg (0.45 mmol) of 8-[(2,6-difluorobenzyl)oxy]-2,6-dimethylimidazo[1,2-a]-pyridine-3-carboxylic acid Example 21A and 65 mg (0.50 mmol) of rac-2,4-dimethylpentane-1,2-diamine, 155 mg (73% of theory, purity 95%) of the target compound were obtained.

LC-MS (Method 2): $R_t$=0.66 min

MS (ESIpos): m/z=445 (M+H)$^+$ $^1$H NMR (400 MHz, DMSO-d$_6$): δ=0.89-0.96 (m, 6H), 1.02 (s, 3H), 1.21-1.34 (m, 2H), 1.67 (br. s, 2H), 1.74-1.85 (m, 1H), 2.31 (s, 3H), 2.53 (br. s, 3H; superimposed by DMSO signal), 3.14-3.27 (m, 2H), 5.28 (s, 2H), 6.92 (s, 1H), 7.20-7.28 (m, 2H), 7.55-7.68 (m, 2H), 8.48 (s, 1H).

Example 219 ent-N-(2-Amino-2,4-dimethylpentyl)-8-[(2,6-difluorobenzyl)oxy]-2,6-dimethylimidazo[1,2-a]-pyridine-3-carboxamide (Enantiomer A)

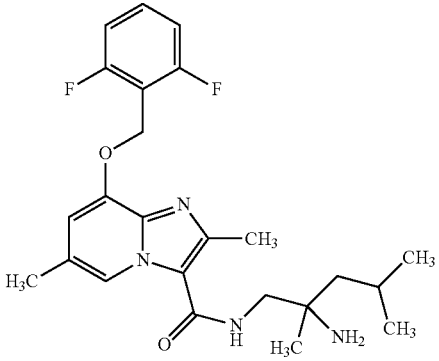 [SMILES: Cc1cc(OCc2c(F)cccc2F)c2nc(C)c(C(=O)NCC(C)(N)CC(C)C)n2c1]

155 mg of Example 218 were separated into the enantiomers by preparative separation on a chiral phase [column: Daicel Chiralpak AD-H, 5 μm, 250×20 mm, mobile phase: 70% isohexane, 30% ethanol+0.2% diethylamine, flow rate: 20 ml/min; 40° C., detection: 210 nm].

Enantiomer A: Yield: 37 mg (100% ee)

$R_t$=11.40 min [Daicel Chiralpak AD-H, 5 m, 250×4.6 mm; mobile phase: 70% isohexane, 30% ethanol+0.2% diethylamine; flow rate 1.0 ml/min; 40° C.; detection: 220 nm].

Example 220 ent-N-(2-Amino-2,4-dimethylpentyl)-8-[(2,6-difluorobenzyl)oxy]-2,6-dimethylimidazo[1,2-a]-pyridine-3-carboxamide (Enantiomer B)

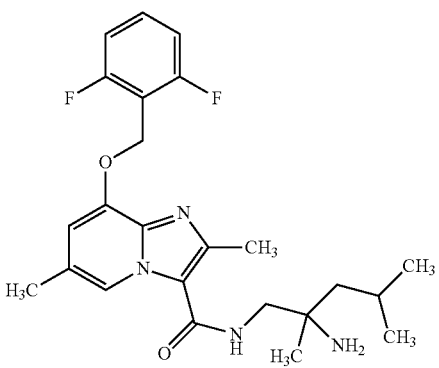

155 mg of Example 218 were separated into the enantiomers by preparative separation on a chiral phase [column: Daicel Chiralpak AD-H, 5 μm, 250×20 mm, mobile phase: 70% isohexane, 30% ethanol+0.2% diethylamine, flow rate: 20 ml/min; 40° C., detection: 210 nm].

Enantiomer B: Yield: 79 mg (93% ee)

$R_t$=12.56 min [Daicel Chiralpak AD-H, 5 m, 250×4.6 mm; mobile phase: 70% isohexane, 30% ethanol+0.2% diethylamine; flow rate 1.0 ml/min; 40° C.; detection: 220 nm].

Specific rotation [α] (365 nm, 19.6° C.)=+17.7° (c=0.005 g/ml, acetonitrile)

Example 221

N-(2-Amino-2-methylpropyl)-8-[(2,6-difluorobenzyl)oxy]-2,6-dimethylimidazo[1,2-a]pyridine-3-carboxamide hydrochloride

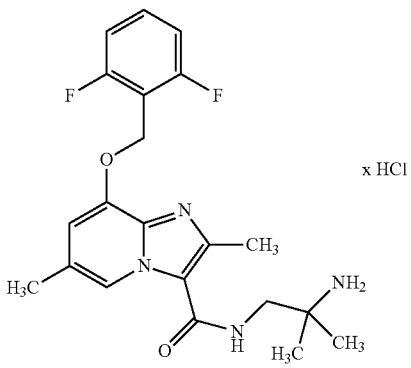 [SMILES: Cc1cc(OCc2c(F)cccc2F)c2nc(C)c(C(=O)NCC(C)(C)N)n2c1]

200 mg (0.50 mmol) of N-(2-amino-2-methylpropyl)-8-[(2,6-difluorobenzyl)oxy]-2,6-dimethylimidazo[1,2-a]pyridine-3-carboxamide Example 74 were initially charged in 4 ml of diethyl ether, 0.26 ml (0.52 mmol) of 2 N hydrochloric acid in diethyl ether was added and the reaction mixture was stirred at RT for 30 min. The mixture was then concentrated and the residue was lyophilized. This gave 217 mg (98.5% of theory, purity 99%) of the target compound.

LC-MS (Method 7): $R_t$=0.57 min

MS (ESIpos): m/z=403 (M−HCl+H)$^+$ $^1$H NMR (400 MHz, DMSO-d$_6$): δ=1.24 (s, 6H), 2.32 (s, 3H), 2.55 (br. s, 3H; superimposed by DMSO signal), 3.42 (d, 2H), 5.29 (s, 2H), 6.95 (s, 1H), 7.15 (br. s, 2H), 7.21-7.28 (m, 2H), 7.55-7.64 (m, 1H), 7.96-8.03 (m, 1H), 8.47 (m, 1H).

Example 222 ent-8-[(2,6-Difluorobenzyl)oxy]-N-{1-(3,4-difluorophenyl)-2-[(2,2,2-trifluoroethyl)amino]ethyl}-2-methylimidazo[1,2-a]pyridine-3-carboxamide (Enantiomer B)

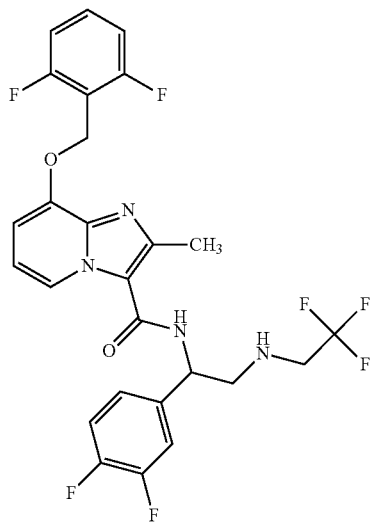 [SMILES: Cc1nc2c(OCc3c(F)cccc3F)cccn2c1C(=O)NC(CNCC(F)(F)F)c1ccc(F)c(F)c1]

100 mg (0.21 mmol) of N-[2-amino-1-(3,4-difluorophenyl)ethyl]-8-[(2,6-difluorobenzyl)oxy]-2-methylimidazo[1,2-a]pyridine-3-carboxamide Example 13 were initially charged in 2 ml of DMF, 35 µl (0.21 mmol) of 2,2,2-trifluoroethyl trichloromethanesulphonate, 59 mg (0.42 mmol) of potassium carbonate and 3.5 mg (0.02 mmol) of potassium iodide were added and the reaction mixture was stirred at RT overnight. 10 ml of water were added, and the reaction solution was extracted twice with 30 ml of ethyl acetate. The combined organic phases were washed twice with 20 ml of water and with saturated aqueous sodium chloride solution, dried over magnesium sulphate, filtered and concentrated. The residue was purified by preparative RP-HPLC (acetonitrile/water with 0.5% strength formic acid gradient). The product fractions were concentrated almost to dryness, 1 ml of tert-butanol was added and the mixture was lyophilized overnight. This gave 18 mg (14% of theory, purity 91%) of the target compound.

LC-MS (Method 2): $R_t$=1.05 min

MS (ESIpos): m/z=555 (M+H)$^+$ $^1$H NMR (400 MHz, DMSO-d$_6$): δ=2.57 (s, 3H), 2.89-3.08 (m, 2H), 5.09-5.18 (m, 1H), 5.30 (s, 2H), 6.91 (t, 1H), 7.02 (d, 1H), 7.18-7.33 (m, 3H), 7.36-7.46 (m, 1H), 7.47-7.56 (m, 1H), 7.57-7.64 (m, 1H), 8.17 (d, 1H), 8.53 (d, 1H), [further signals hidden under solvent peaks].

Example 223 ent-N-(2-Amino-3-methylbutyl)-8-[(2,6-difluorobenzyl)oxy]-2,6-dimethylimidazo[1,2-a]pyridine-3-carboxamide (Enantiomer A)

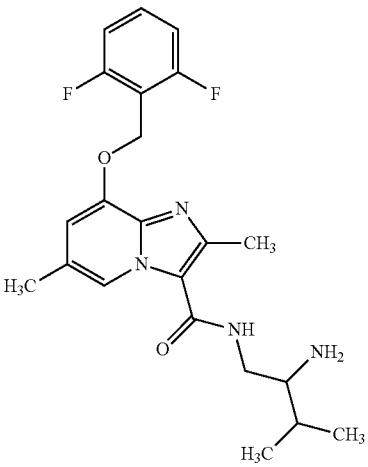 [SMILES: Cc1cc(OCc2c(F)cccc2F)c2nc(C)c(C(=O)NCC(N)C(C)C)n2c1]

88 mg (0.17 mmol) of ent-tert-butyl {1-[({8-[(2,6-difluorobenzyl)oxy]-2,6-dimethylimidazo[1,2-a]pyridin-3-yl}carbonyl)amino]-3-methylbutan-2-yl}carbamate (enantiomer A) Example 231A in 0.85 ml of 2 N hydrochloric acid/diethyl ether were stirred at RT for 4 h. The reaction mixture was concentrated and the residue was dissolved in dichloromethane and saturated aqueous sodium bicarbonate solution. The aqueous phase was extracted twice with dichloromethane and the combined organic phases were dried over sodium sulphate, filtered, concentrated and lyophilized. This gave 64 mg (88% of theory, purity 98%) of the target compound.

LC-MS (Method 7): $R_t$=0.62 min

MS (ESIpos): m/z=417 (M+H)$^+$ $^1$H NMR (400 MHz, DMSO-d$_6$): δ=0.88 (d, 3H), 0.92 (d, 3H), 1.39-1.56 (br. s, 2H), 1.56-1.65 (m, 1H), 2.31 (s, 3H), 2.60-2.66 (m, 1H), 3.02-3.11 (m, 1H), 3.38-3.45 (m, 1H), 5.28 (s, 2H), 6.91 (s, 1H), 7.20-7.28 (m, 2H), 7.55-7.64 (m, 1H), 7.70 (t, 1H), 8.49 (s, 1H), [further signal under DMSO peak].

Example 224 ent-N-(2-Amino-3-methylbutyl)-8-[(2,6-difluorobenzyl)oxy]-2,6-dimethylimidazo[1,2-a]pyridine-3-carboxamide (Enantiomer B)

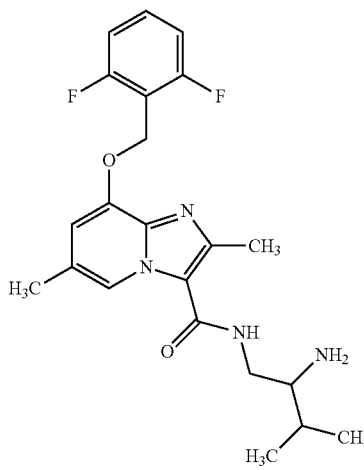

Preparation and purification of the title compound were carried out analogously to Example 223. Starting with 92 mg (0.18 mmol) of ent-tert-butyl {1-[({8-[(2,6-difluorobenzyl)oxy]-2,6-dimethylimidazo[1,2-a]pyridin-3-yl}carbonyl)amino]-3-methylbutan-2-yl}carbamate (enantiomer B) Example 232A, 67 mg (88% of theory, purity 98%) of the target compound were obtained.

LC-MS (Method 7): $R_t$=0.64 min

MS (ESIpos): m/z=417 (M+H)$^+$ $^1$H NMR (400 MHz, DMSO-d$_6$): δ=0.89 (d, 3H), 0.92 (d, 3H), 1.19-1.30 (br. s, 2H), 1.55-1.69 (m, 2H), 2.31 (s, 3H), 2.60-2.68 (m, 1H), 3.02-3.11 (m, 1H), 3.39-3.46 (m, 1H), 5.28 (s, 2H), 6.91 (s, 1H), 7.20-7.28 (m, 2H), 7.55-7.64 (m, 1H), 7.67-7.73 (m, 1H), 8.48 (s, 1H), [further signal under DMSO peak].

Example 225 rac-N-(2-Amino-2,4-dimethylpentyl)-6-chloro-8-[(2,6-difluorobenzyl)oxy]-2-methylimidazo[1,2-a]pyridine-3-carboxamide

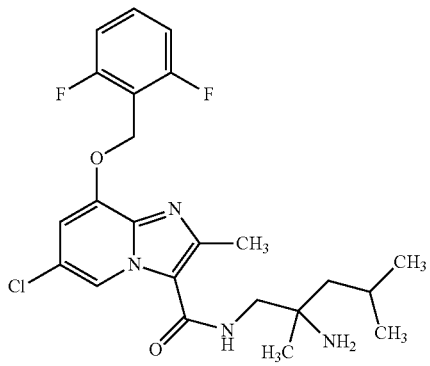

61 mg (0.47 mmol) of rac-2,4-dimethylpentane-1,2-diamine were added to 150 mg (0.43 mmol) of 6-chloro-8-[(2,6-difluorobenzyl)oxy]-2-methylimidazo[1,2-a]pyridine-3-carboxylic acid Example 16A, 143 mg (0.45 mmol) of TBTU and 0.19 ml (1.70 mmol) of 4-methylmorpholine in DMF (1.5 ml), and the reaction mixture was stirred at RT overnight. The mixture was diluted with water/TFA and purified by prep. RP-HPLC (acetonitrile/water gradient with addition of 0.1% TFA). The product fraction was concentrated. Saturated aqueous sodium bicarbonate solution was added to the residue, and the mixture was extracted three times with dichloromethane. The combined organic phases were dried over sodium sulphate, filtered off and concentrated. This gave 162 mg (79% of theory, purity 96%) of the target compound.

LC-MS (Method 7): $R_t$=0.75 min

MS (ESIpos): m/z=465 (M+H)$^+$ $^1$H NMR (400 MHz, DMSO-d$_6$): δ=0.91 (d, 3H), 0.94 (d, 3H), 1.02 (s, 3H), 1.20-1.33 (m, 2H), 1.35-1.55 (br. s, 2H), 1.73-1.85 (m, 1H), 2.55 (s, 3H; superimposed by DMSO signal), 3.21 (q, 2H), 5.35 (s, 2H), 7.20 (d, 1H), 7.22-7.29 (m, 2H), 7.57-7.65 (m, 1H), 7.67-7.80 (br. s, 1H), 8.76 (d, 1H).

Example 226 ent-N-(2-Amino-2,4-dimethylpentyl)-6-chloro-8-[(2,6-difluorobenzyl)oxy]-2-methylimidazo[1,2-a]pyridine-3-carboxamide (Enantiomer A)

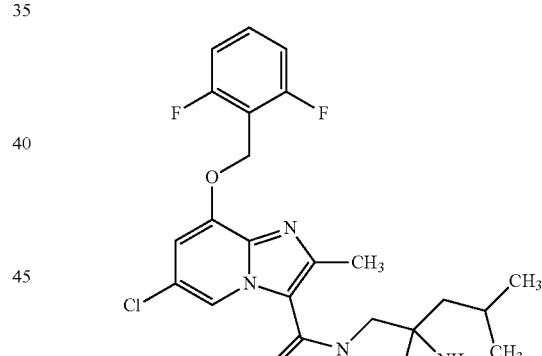

155 mg of Example 225 were separated into the enantiomers by preparative separation on a chiral phase [column: Daicel Chiralpak AZ-H, 5 μm, 250×30 mm, mobile phase: 50% isohexane, 50% ethanol+0.2% diethylamine, flow rate: 40 ml/min; 25° C., detection: 220 nm]. The product fractions were collected on dry ice, combined and concentrated on a rotary evaporator (bath temperature 30° C.) to a residual volume of about 30 ml, and about 60 ml of water were added. The solution obtained was frozen and lyophilized. The product was then re-purified by thick-layer chromatography (mobile phase: dichloromethane/methanol: 20/1).

Enantiomer A: Yield: 18 mg (100% ee)

$R_t$=8.53 min [Daicel Chiralpak AZ-H, 5 m, 250×4.6 mm; mobile phase: 50% isohexane, 50% ethanol+0.2% diethylamine; flow rate 1.0 ml/min; 30° C.; detection: 220 nm].

Example 227 ent-N-(2-Amino-2,4-dimethylpentyl)-6-chloro-8-[(2,6-difluorobenzyl)oxy]-2-methylimidazo[1,2-a]pyridine-3-carboxamide (Enantiomer B)

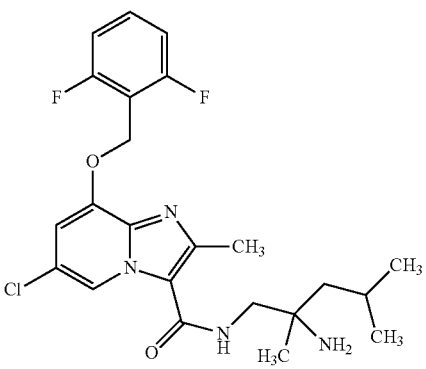 [SMILES: Cc1nc2c(OCc3c(F)cccc3F)cc(Cl)cn2c1C(=O)NCC(C)(N)CC(C)C]

155 mg of Example 225 were separated into the enantiomers by preparative separation on a chiral phase [column: Daicel Chiralpak AZ-H, 5 μm, 250×30 mm, mobile phase: 50% isohexane, 50% ethanol+0.2% diethylamine, flow rate: 40 ml/min; 25° C., detection: 220 nm]. The product fractions were collected on dry ice, combined and concentrated on a rotary evaporator (bath temperature 30° C.) to a residual volume of about 30 ml, and about 60 ml of water were added. The solution obtained was frozen and lyophilized. The product was then re-purified by thick-layer chromatography (mobile phase: dichloromethane/methanol: 20/1).

Enantiomer B: Yield: 31 mg (88% ee)

$R_t$=10.41 min [Daicel Chiralpak AZ-H, 5 m, 250×4.6 mm; mobile phase: 50% isohexane, 50% ethanol+0.2% diethylamine; flow rate 1.0 ml/min; 30° C.; detection: 220 nm].

Example 228 ent-N-(2-Amino-3-methylbutyl)-8-[(2,6-difluorobenzyl)oxy]-2-methylimidazo[1,2-a]pyridine-3-carboxamide (Enantiomer A)

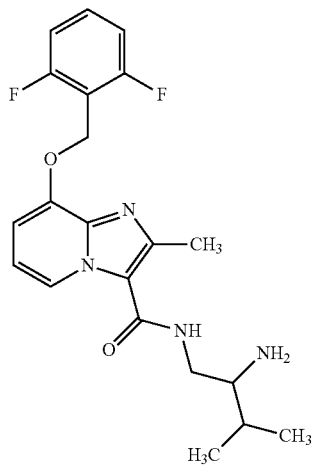 [SMILES: Cc1nc2c(OCc3c(F)cccc3F)cccn2c1C(=O)NCC(N)C(C)C]

Preparation and purification of the title compound were carried out analogously to Example 223. Starting with 88 mg (0.18 mmol) of ent-tert-butyl {1-[({8-[(2,6-difluorobenzyl)oxy]-2-methylimidazo[1,2-a]pyridin-3-yl}carbonyl)amino]-3-methylbutan-2-yl}carbamate (enantiomer A) Example 234A, 64 mg (89% of theory, purity 98%) of the target compound were obtained.

LC-MS (Method 7): $R_t$=0.61 min

MS (ESIpos): m/z=403 (M+H)$^+$ $^1$H NMR (400 MHz, DMSO-d$_6$): δ=0.90 (d, 3H), 0.94 (d, 3H), 1.19-1.30 (br. s, 2H), 1.64-1.75 (m, 1H), 2.72-2.78 (m, 1H), 3.12-3.21 (m, 1H), 3.41-3.49 (m, 1H), 5.30 (s, 2H), 6.94 (t, 1H), 7.01 (d, 1H), 7.20-7.28 (m, 2H), 7.59 (quintet, 1H), 7.74-7.79 (m, 1H), 8.67 (d, 1H), [further signal under DMSO peak].

Example 229 ent-N-(2-Amino-3-methylbutyl)-8-[(2,6-difluorobenzyl)oxy]-2-methylimidazo[1,2-a]pyridine-3-carboxamide (Enantiomer B)

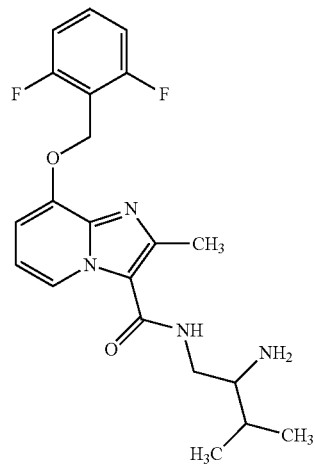 [SMILES: Cc1nc2c(OCc3c(F)cccc3F)cccn2c1C(=O)NCC(N)C(C)C]

Preparation and purification of the title compound were carried out analogously to Example 223. Starting with 72 mg (0.14 mmol) of ent-tert-butyl {1-[({8-[(2,6-difluorobenzyl)oxy]-2-methylimidazo[1,2-a]pyridin-3-yl}carbonyl)amino]-3-methylbutan-2-yl}carbamate (enantiomer B) Example 235A, 52 mg (88% of theory, purity 98%) of the target compound were obtained.

LC-MS (Method 7): $R_t$=0.63 min

MS (ESIpos): m/z=403 (M+H)$^+$ $^1$H NMR (400 MHz, DMSO-d$_6$): δ=0.88-0.97 (m, 6H), 1.19-1.29 (br. s, 2H), 1.64-1.76 (m, 1H), 2.73-2.80 (m, 1H), 3.14-3.23 (m, 1H), 3.41-3.49 (m, 1H), 5.30 (s, 2H), 6.94 (t, 1H), 7.02 (d, 1H), 7.19-7.28 (m, 2H), 7.59 (quintet, 1H), 7.73-7.82 (m, 1H), 8.67 (d, 1H), [further signal under DMSO peak].

Example 230 rac-N-(2-Amino-3,3,4,4-tetrafluorobutyl)-8-[(2,6-difluorobenzyl)oxy]-2-methylimidazo[1,2-a]-pyridine-3-carboxamide

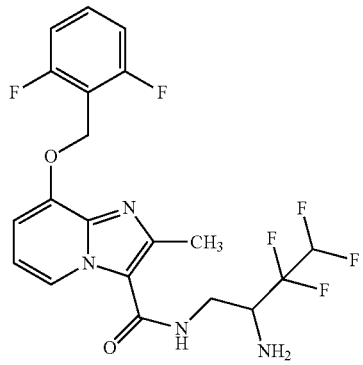 [SMILES: Cc1nc2c(OCc3c(F)cccc3F)cccn2c1C(=O)NCC(N)C(F)(F)C(F)F]

400 mg (1.26 mmol) of 8-[(2,6-difluorobenzyl)oxy]-2-methylimidazo[1,2-a]pyridine-3-carboxylic acid Example 3A, 526 mg (1.38 mmol) of HATU and 1.1 ml (6.28 mmol) of N,N-diisopropylethylamine in DMF (8.0 ml) were stirred at RT for 20 min. 322 mg (1.38 mmol) of rac-1-(1,1,2,2-tetrafluoroethyl)ethylene-1,2-diamine dihydrochloride were then added, and the reaction mixture was stirred at RT overnight. The mixture was then purified directly by preparative RP-HPLC (acetonitrile/water with 0.05% strength formic acid). This gave 283 mg (49% of theory, purity 98%) of the target compound.

LC-MS (Method 2): $R_t$=0.75 min
MS (ESIpos): m/z=461 (M+H)$^+$
$^1$H NMR (400 MHz, DMSO-d$_6$): δ=2.56 (s, 3H; superimposed by DMSO signal), 3.37-3.47 (m, 1H), 3.52-3.67 (m, 1H), 3.67-3.76 (m, 1H), 5.31 (s, 2H), 6.68 (tt, 1H), 6.97 (t, 1H), 7.05 (d, 1H), 7.20-7.28 (m, 2H), 7.54-7.64 (m, 1H), 7.83 (t, 1H), 8.71 (d, 1H).

Example 231 ent-N-(2-Amino-3,3,4,4-tetrafluorobutyl)-8-[(2,6-difluorobenzyl)oxy]-2-methylimidazo[1,2-a]-pyridine-3-carboxamide (Enantiomer A)

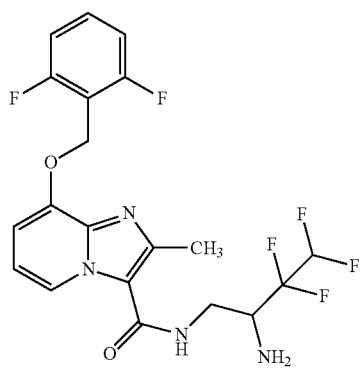 [SMILES: Cc1nc2c(OCc3c(F)cccc3F)cccn2c1C(=O)NCC(N)C(F)(F)C(F)F]

240 mg of Example 230 were separated into the enantiomers by preparative separation on a chiral phase [column: Daicel Chiralcel OZ-H, 5 μm, 250×20 mm, mobile phase: 50% isohexane, 50% ethanol+0.2% diethylamine, flow rate: 20 ml/min; 25° C., detection: 230 nm].

Enantiomer A: Yield: 91.6 mg (100% ee)
$R_t$=9.18 min [Daicel Chiralcel OZ-H, 5 μm, 250×4.6 mm; mobile phase: 50% isohexane, 50% ethanol+0.2% diethylamine; flow rate 1.0 ml/min; 30° C.; detection: 220 nm].

Enantiomer A was re-purified by preparative RP-HPLC (acetonitrile/water with 0.05% strength formic acid). The contaminated product fraction was purified once more [column: Sunfire C18, 5 μm, 250×20 mm, mobile phase: 55% water, 45% acetonitrile, flow rate: 25 ml/min; 25° C., detection: 210 nm]. This gave 48.5 mg (purity 99%) of the target compound.

Example 232 rac-N-(2-Amino-2-methylpentyl)-8-[(2,6-difluorobenzyl)oxy]-2,6-dimethylimidazo[1,2-a]pyridine-3-carboxamide

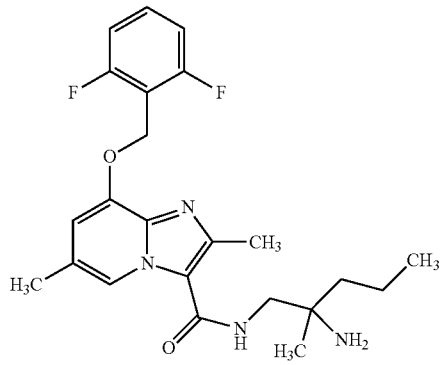

77 mg (0.66 mmol) of rac-2-methylpentane-1,2-diamine were added to 200 mg (0.60 mmol) of 8-[(2,6-difluorobenzyl)oxy]-2,6-dimethylimidazo[1,2-a]pyridine-3-carboxylic acid Example 21A, 203 mg (0.63 mmol) of TBTU and 0.27 ml (2.41 mmol) of 4-methylmorpholine in DMF (2.1 ml), and the reaction mixture was stirred at RT overnight. The mixture was diluted with water/TFA and purified by preparative RP-HPLC (acetonitrile/water gradient with addition of 0.1% TFA). The product fraction was concentrated. Saturated aqueous sodium bicarbonate solution was added to the residue, and the mixture was extracted twice with dichloromethane. The combined organic phases were dried over sodium sulphate, filtered off and concentrated. This gave 199 mg (76% of theory, purity 99%) of the target compound.

LC-MS (Method 2): $R_t$=0.67 min
MS (ESIpos): m/z=431 (M+H)$^+$
$^1$H NMR (400 MHz, DMSO-d$_6$): δ=0.87 (t, 3H), 0.99 (s, 3H), 1.22-1.42 (m, 4H), 1.43-1.67 (br. s, 2H), 2.31 (s, 3H), 2.53 (s, 3H; superimposed by DMSO signal), 3.14-3.26 (m, 2H), 5.28 (s, 2H), 6.91 (s, 1H), 7.20-7.28 (m, 2H), 7.55-7.66 (m, 2H), 8.47 (s, 1H).

Example 233 ent-N-(2-Amino-2-methylpentyl)-8-[(2,6-difluorobenzyl)oxy]-2,6-dimethylimidazo[1,2-a]pyridine-3-carboxamide (Enantiomer A)

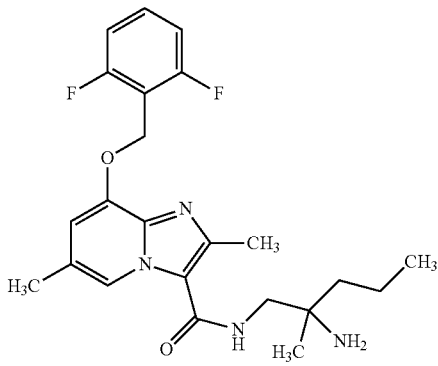

195 mg of Example 232 were separated into the enantiomers by preparative separation on a chiral phase [column: Daicel Chiralpak AY-H, 5 μm, 250×20 mm, mobile phase: 60% isohexane, 40% ethanol+0.2% diethylamine, flow rate: 20 ml/min; 25° C., detection: 220 nm]. The product was then re-purified by preparative RP-HPLC (acetonitrile/water gradient with addition of 0.1% TFA). The product fraction was concentrated. The residue was dissolved in dichloromethane and washed twice with saturated aqueous sodium bicarbonate solution. The combined aqueous phases were extracted twice with dichloromethane. The organic phase was dried over sodium sulphate, filtered and concentrated.

Enantiomer A: Yield: 63 mg (99% ee)

$R_t$=4.32 min [Daicel Chiralpak AY-H, 5 m, 250×4.6 mm; mobile phase: 50% isohexane, 50% ethanol+0.2% diethylamine; flow rate 1.0 ml/min; 40° C.; detection: 220 nm].

Specific rotation [α] (365 nm, 19.9° C.)=+31.8° (c=0.005 g/ml, acetonitrile)

Example 234 ent-N-(2-Amino-2-methylpentyl)-8-[(2,6-difluorobenzyl)oxy]-2,6-dimethylimidazo[1,2-a]pyridine-3-carboxamide (Enantiomer B)

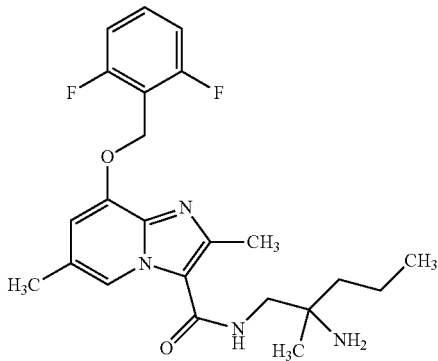 [SMILES: CCCC(C)(N)CNC(=O)c1c(C)nc2c(OCc3c(F)cccc3F)cc(C)cn12]

195 mg of Example 232 were separated into the enantiomers by preparative separation on a chiral phase [column: Daicel Chiralpak AY-H, 5 μm, 250×20 mm, mobile phase: 60% isohexane, 40% ethanol+0.2% diethylamine, flow rate: 20 ml/min; 25° C., detection: 220 nm]. The product was then re-purified by preparative RP-HPLC (acetonitrile/water gradient with addition of 0.1% TFA). The product fraction was concentrated. The residue was dissolved in dichloromethane and washed twice with saturated aqueous sodium bicarbonate solution. The combined aqueous phases were extracted twice with dichloromethane. The organic phase was dried over sodium sulphate, filtered and concentrated.

Enantiomer B: Yield: 64 mg (89% ee)

$R_t$=5.09 min [Daicel Chiralpak AY-H, 5 m, 250×4.6 mm; mobile phase: 50% isohexane, 50% ethanol+0.2% diethylamine; flow rate 1.0 ml/min; 40° C.; detection: 220 nm].

Example 235 rac-8-[(2,6-Difluorobenzyl)oxy]-2,6-dimethyl-N-(1,2,3,4-tetrahydroquinolin-2-ylmethyl)imidazo-[1,2-a]pyridine-3-carboxamide

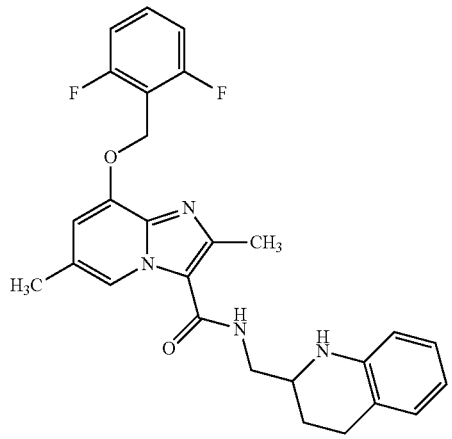 [SMILES: Cc1cc(OCc2c(F)cccc2F)c2nc(C)c(C(=O)NCC3CCc4ccccc4N3)n2c1]

182 mg (0.32 mmol) of rac-tert-butyl 2-{[({8-[(2,6-difluorobenzyl)oxy]-2,6-dimethylimidazo[1,2-a]pyridin-3-yl}carbonyl)amino]methyl}-3,4-dihydroquinoline-1(2H)-carboxylate Example 240A were initially charged in 5 ml of diethyl ether and 1.58 ml (3.16 mmol) of 2 N hydrochloric acid/diethyl ether and the mixture was stirred at RT overnight. 1 ml (2 mmol) of 2 N hydrochloric acid/diethyl ether was then added, and stirring was continued at RT overnight. The reaction mixture was filtered off and the filter cake was washed with diethyl ether. The solid was taken up in dichloromethane and a very small amount of methanol and washed twice with saturated aqueous sodium bicarbonate solution. The aqueous phase was extracted twice with dichloromethane and the combined organic phases were dried over sodium sulphate. The mixture was filtered, concentrated and dried under high vacuum. This gave 140 mg (91% of theory, purity 98%) of the target compound.

LC-MS (Method 2): $R_t$=1.01 min

MS (ESIpos): m/z=477 (M+H)$^+$ $^1$H NMR (400 MHz, DMSO-d$_6$): δ=1.55-1.67 (m, 1H), 1.86-1.96 (m, 1H), 2.31 (s, 3H), 2.69 (t, 2H), 3.36-3.50 (m, 3H), 5.28 (s, 2H), 5.72 (s, 1H), 6.43 (t, 1H), 6.48 (d, 1H), 6.82-6.89 (m, 2H), 6.92 (s, 1H), 7.19-7.28 (m, 2H), 7.54-7.64 (m, 1H), 7.91 (t, 1H), 8.46 (s, 1H), [further signal hidden under DMSO peak].

Example 236 rac-N-(2-Amino-3,3,3-trifluoro-2-methylpropyl)-6-chloro-8-[(2,6-difluorobenzyl)oxy]-2-methylimidazo[1,2-a]pyridine-3-carboxamide

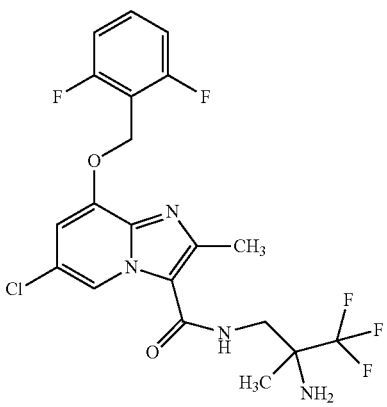 [SMILES: Cc1nc2c(OCc3c(F)cccc3F)cc(Cl)cn2c1C(=O)NCC(C)(N)C(F)(F)F]

Preparation and purification of the title compound were carried out analogously to Example 225. Starting with 200 mg (0.57 mmol) of 6-chloro-8-[(2,6-difluorobenzyl)oxy]-2-methylimidazo[1,2-a]pyridine-3-carboxylic acid Example 16A and 111 mg (0.62 mmol) of rac-3,3,3-trifluoro-2-methylpropane-1,2-diamine hydrochloride Example 246A, 211 mg (74% of theory, purity 95%) of the target compound were obtained.

LC-MS (Method 2): $R_t$=0.98 min
MS (ESIpos): m/z=477 (M+H)$^+$
$^1$H NMR (400 MHz, DMSO-d$_6$): δ=1.23 (s, 3H), 2.55 (s, 3H; superimposed by DMSO signal), 3.47-3.64 (m, 2H), 5.35 (s, 2H), 7.21-7.30 (m, 3H), 7.56-7.67 (m, 1H), 7.92-8.01 (m, 1H), 8.76 (d, 1H).

Example 237 ent-N-(2-Amino-3,33-trifluoro-2-methylpropyl)-6-chloro-8-[(2,6-difluorobenzyl)oxy]-2-methylimidazo[1,2-a]pyridine-3-carboxamide (enantiomer A)

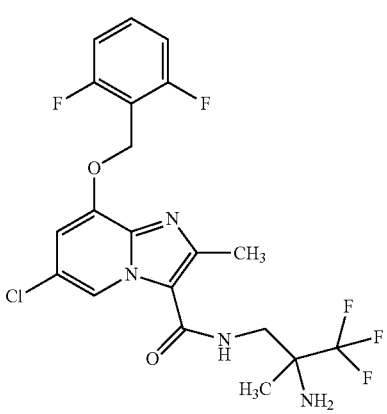 [SMILES: Cc1nc2c(OCc3c(F)cccc3F)cc(Cl)cn2c1C(=O)NCC(C)(N)C(F)(F)F]

204 mg of Example 236 were separated into the enantiomers by preparative separation on a chiral phase [column: Daicel Chiralpak OZ-H, 5 μm, 250×20 mm, mobile phase: 50% isohexane, 50% isopropanol+0.2% diethylamine, flow rate: 17 ml/min; 40° C., detection: 210 nm]. The product fractions were collected on dry ice, combined and concentrated on a rotary evaporator (bath temperature 30° C.) to a residual volume of about 30 ml, and about 60 ml of water were added. The solution obtained was frozen and lyophilized.

Enantiomer A: Yield: 50 mg (99% ee)

$R_t$=9.71 min [Daicel Chiralpak OZ-H, 5 μm, 250×4.6 mm; mobile phase: 50% isohexane, 50% isopropanol+0.2% diethylamine; flow rate 1.0 ml/min; 30° C.; detection: 220 nm].

Example 238 ent-N-(2-Amino-3,3,3-trifluoro-2-methylpropyl)-6-chloro-8-[(2,6-difluorobenzyl)oxy]-2-methylimidazo[1,2-a]pyridine-3-carboxamide (Enantiomer B)

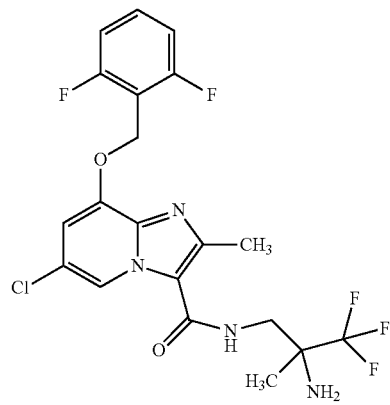 [SMILES: Cc1nc2c(OCc3c(F)cccc3F)cc(Cl)cn2c1C(=O)NCC(C)(N)C(F)(F)F]

204 mg of Example 236 were separated into the enantiomers by preparative separation on a chiral phase [column: Daicel Chiralpak OZ-H, 5 μm, 250×20 mm, mobile phase: 50% isohexane, 50% isopropanol+0.2% diethylamine, flow rate: 17 ml/min; 40° C., detection: 210 nm]. The product fractions were collected on dry ice, combined and concentrated on a rotary evaporator (bath temperature 30° C.) to a residual volume of about 30 ml, and about 60 ml of water were added. The solution obtained was frozen and lyophilized.

Enantiomer B: Yield: 69 mg (91% ee)

$R_t$=11.21 min [Daicel Chiralpak OZ-H, 5 μm, 250×4.6 mm; mobile phase: 50% isohexane, 50% isopropanol+0.2% diethylamine; flow rate 1.0 ml/min; 30° C.; detection: 220 nm].

Example 239 rac-N-(2-Amino-3,3,3-trifluoro-2-methylpropyl)-8-[(2,6-difluorobenzyl)oxy]-2,6-dimethyl-imidazo[1,2-a]pyridine-3-carboxamide

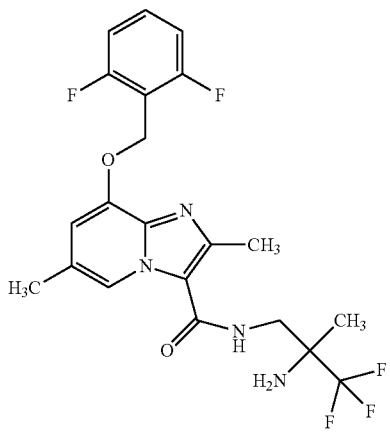 [SMILES: Cc1cc(OCc2c(F)cccc2F)c2nc(C)c(C(=O)NCC(C)(N)C(F)(F)F)n2c1]

118 mg (0.66 mmol) of rac-3,3,3-trifluoro-2-methylpropane-1,2-diamine hydrochloride Example 246A were added to 200 mg (0.60 mmol) of 8-[(2,6-difluorobenzyl)oxy]-2,6-dimethylimidazo[1,2-a]pyridine-3-carboxylic acid Example 21A, 203 mg (0.63 mmol) of TBTU and 0.27 ml (2.41 mmol) of 4-methylmorpholine in DMF (2.1 ml), and the reaction mixture was stirred at RT overnight. 50 mg (0.28 mmol) of rac-3,3,3-trifluoro-2-methylpropane-1,2-diamine hydrochloride Example 246A were added to the reaction mixture, and stirring was continued at RT overnight. The mixture was diluted with water/TFA and purified by preparative RP-HPLC (acetonitrile/water gradient with addition of 0.1% TFA). The product fraction was concentrated. Saturated aqueous sodium bicarbonate solution was added to the residue, and the mixture was extracted three times with dichloromethane. The combined organic phases were dried over sodium sulphate, filtered off and concentrated. This gave 219 mg (79% of theory, purity 99%) of the target compound.

LC-MS (Method 2): $R_t$=0.79 min

MS (ESIpos): m/z=457 (M+H)$^+$ $^1$H NMR (400 MHz, DMSO-$d_6$): δ=1.19 (s, 3H), 2.31 (s, 3H), 2.53 (s, 3H; superimposed by DMSO peak), 3.41-3.49 (m, 1H), 3.53-3.61 (m, 1H), 5.29 (s, 2H), 6.94 (s, 1H), 7.20-7.28 (m, 2H), 7.59 (quintet, 1H), 7.78 (t, 1H), 8.48 (s, 1H).

Example 240 ent-N-(2-Amino-3,3,3-trifluoro-2-methylpropyl)-8-[(2,6-difluorobenzyl)oxy]-2,6-dimethylimidazo-[1,2-a]pyridine-3-carboxamide (Enantiomer A)

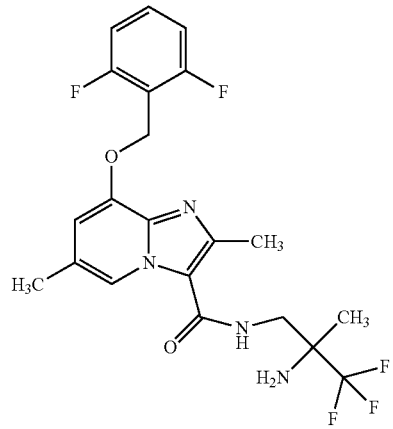 [SMILES: Cc1cc(OCc2c(F)cccc2F)c2nc(C)c(C(=O)NCC(C)(N)C(F)(F)F)n2c1]

210 mg of Example 239 were separated into the enantiomers by preparative separation on a chiral phase [column: Daicel Chiralcel OZ-H, 5 μm, 250×20 mm, mobile phase: 25% isohexane, 75% isopropanol; flow rate: 20 ml/min; 23° C., detection: 210 nm]. The product fractions were collected on dry ice, combined and concentrated on a rotary evaporator (bath temperature 30° C.) to a residual volume of about 30 ml, and about 60 ml of water were added. The solution obtained was frozen and lyophilized.

Enantiomer A: Yield: 63 mg (100% ee)

$R_t$=6.53 min [Daicel Chiralcel OZ-H, 5 μm, 250×4.6 mm; mobile phase: 50% isohexane, 50% ethanol+0.2% diethylamine; flow rate 1.0 ml/min; 30° C.; detection: 220 nm].

Example 241 ent-N-(2-Amino-3,3,3-trifluoro-2-methylpropyl)-8-[(2,6-difluorobenzyl)oxy]-2,6-dimethylimidazo-[1,2-a]pyridine-3-carboxamide (Enantiomer B)

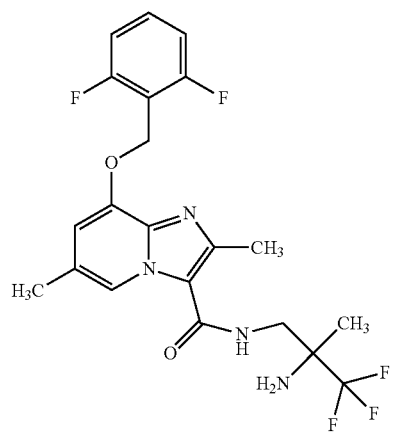 [SMILES: Cc1cc(OCc2c(F)cccc2F)c2nc(C)c(C(=O)NCC(C)(N)C(F)(F)F)n2c1]

210 mg of Example 239 were separated into the enantiomers by preparative separation on a chiral phase

[column: Daicel Chiralcel OZ-H, 5 μm, 250×20 mm, mobile phase: 25% isohexane, 75% isopropanol; flow rate: 20 ml/min; 23° C., detection: 210 nm]. The product fractions were collected on dry ice, combined and concentrated on a rotary evaporator (bath temperature 30° C.) to a residual volume of about 30 ml, and about 60 ml of water were added. The solution obtained was frozen and lyophilized.

Enantiomer B: Yield: 50 mg (92% ee)

$R_t$=7.07 min [Daicel Chiralcel OZ-H, 5 μm, 250×4.6 mm; mobile phase: 50% isohexane, 50% ethanol+0.2% diethylamine; flow rate 1.0 ml/min; 30° C.; detection: 220 nm].

Example 242 ent-N-(2-Amino-3-methoxypropyl)-8-[(2,6-difluorobenzyl)oxy]-2,6-dimethylimidazo[1,2-a]-pyridine-3-carboxamide (Enantiomer A)

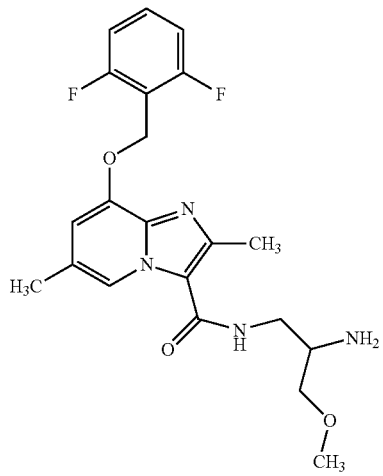 [SMILES: COCC(N)CNC(=O)c1c(C)nc2c(OCc3c(F)cccc3F)cc(C)cn12]

100 mg (0.29 mmol, 96% pure) 8-[(2,6-difluorobenzyl)oxy]-2,6-dimethylimidazo[1,2-a]pyridine-3-carboxylic acid Example 21A were initially charged in DMF (1.84 ml), 121 mg (0.32 mmol) of HATU and 0.15 ml (0.87 mmol) of N,N-diisopropylethylamine were added and the mixture was stirred at RT for 20 min. 72 mg (0.40 mmol) of ent-3-methoxypropane-1,2-diamine dihydrochloride (enantiomer A) Example 249A were dissolved in 0.48 ml of DMF, 0.30 ml (1.73 mmol) of N,N-diisopropylethylamine were added and the mixture was stirred at RT for 10 min. This solution was then added at −20° C. to the reaction solution prepared beforehand, and the reaction mixture was stirred at RT overnight. The mixture was then diluted with water/TFA and purified by preparative RP-HPLC (acetonitrile/water gradient with addition of 0.1% TFA). The product fraction was concentrated. Dichloromethane/ethyl acetate and saturated aqueous sodium bicarbonate solution were added to the residue. After phase separation, the aqueous phase was extracted twice with dichloromethane. The combined organic phases were washed with saturated aqueous sodium bicarbonate solution, dried over sodium sulphate, filtered off and concentrated. This gave 77 mg (63% of theory, purity 99%) of the target compound.

LC-MS (Method 2): $R_t$=0.67 min
MS (ESIpos): m/z=419 (M+H)$^+$
$^1$H NMR (400 MHz, DMSO-d$_6$): δ=2.31 (s, 3H), 3.09-3.16 (m, 1H), 3.19-3.27 (m, 2H), 3.28 (s, 3H), 3.38-3.44 (m, 2H; superimposed by water signal), 5.28 (s, 2H), 6.92 (s, 1H), 7.18-7.29 (m, 2H), 7.54-7.65 (m, 1H), 7.74 (t, 1H), 8.50 (s, 1H), [further signal under DMSO peak].

Example 243 ent-N-(2-Amino-3-methoxypropyl)-8-[(2,6-difluorobenzyl)oxy]-2,6-dimethylimidazo[1,2-a]-pyridine-3-carboxamide (Enantiomer B)

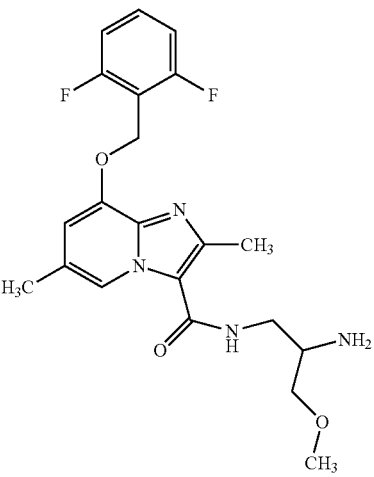 [SMILES: COCC(N)CNC(=O)c1c(C)nc2c(OCc3c(F)cccc3F)cc(C)cn12]

Preparation and purification of the title compound were carried out analogously to Example 242.

Starting with 100 mg (0.29 mmol, 96% pure) 8-[(2,6-difluorobenzyl)oxy]-2,6-dimethyl-imidazo[1,2-a]pyridine-3-carboxylic acid Example 21A and 72 mg (0.40 mmol) of ent-3-methoxypropane-1,2-diamine dihydrochloride (enantiomer B) Example 250A, 63 mg (51% of theory, purity 99%) of the target compound were obtained.

LC-MS (Method 2): $R_t$=0.67 min
MS (ESIpos): m/z=419 (M+H)$^+$
$^1$H NMR (400 MHz, DMSO-d$_6$): δ=1.95-2.25 (br. s, 2H), 2.31 (s, 3H), 3.02-3.10 (m, 1H), 3.15-3.25 (m, 2H), 3.27-3.41 (m, 5H; superimposed by water signal), 5.28 (s, 2H), 6.92 (s, 1H), 7.19-7.28 (m, 2H), 7.55-7.64 (m, 1H), 7.72 (t, 1H), 8.49 (s, 1H).

Example 244 rac-N-(2-Amino-2-methylpentyl)-6-chloro-8-[(2,6-difluorobenzyl)oxy]-2-methylimidazo[1,2-a]-pyridine-3-carboxamide

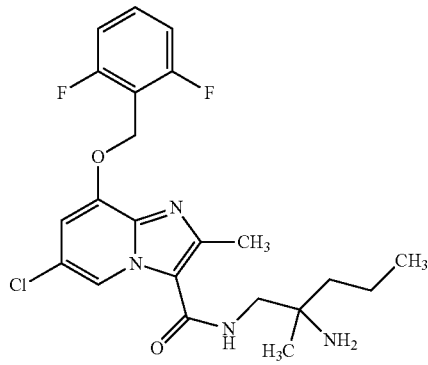 [SMILES: CCCC(C)(N)CNC(=O)c1c(C)nc2c(OCc3c(F)cccc3F)cc(Cl)cn12]

191 mg (0.62 mmol) of TBTU and 0.25 ml (2.27 mmol) of 4-methylmorpholine and 72 mg (0.62 mmol) of rac-2-methylpentane-1,2-diamine were added to 200 mg (0.57 mmol) of 6-chloro-8-[(2,6-difluorobenzyl)oxy]-2-methylimidazo[1,2-a]pyridine-3-carboxylic acid Example 16A in DMF (2.0 ml), and the reaction mixture was stirred at RT overnight. 36 mg (0.31 mmol) of rac-2-methylpentane-1,2-diamine and 0.06 ml (0.57 mmol) of 4-methylmorpholine were then added, and stirring was continued at RT overnight. The mixture was diluted with water/TFA and purified by preparative RP-HPLC (acetonitrile/water gradient with addition of 0.1% TFA). The product fraction was concentrated. Saturated aqueous sodium bicarbonate solution was added to the residue, and the mixture was extracted three times with dichloromethane. The combined organic phases were dried over sodium sulphate, filtered off and concentrated. The residue was purified by silica gel chromatography (dichloromethane/methanol: 10:1, then dichloromethane/2N ammonia in methanol 20:1). This gave 189 mg (73% of theory, purity 99%) of the target compound.

LC-MS (Method 2): $R_t$=0.78 min

MS (ESIpos): m/z=451 (M+H)$^+$ $^1$H NMR (400 MHz, DMSO-d$_6$): δ=0.83-0.89 (m, 3H), 0.99 (s, 3H), 1.22-1.42 (m, 4H), 1.52-1.88 (br. s, 2H), 2.55 (s, 3H; superimposed by DMSO peak), 3.15-3.26 (m, 2H), 5.35 (s, 2H), 7.20 (d, 1H), 7.22-7.29 (m, 2H), 7.56-7.65 (m, 1H), 7.67-7.82 (br. s, 1H), 8.76 (d, 1H).

Example 245 ent-N-(2-Amino-2-methylpentyl)-6-chloro-8-[(2,6-difluorobenzyl)oxy]-2-methylimidazo[1,2-a]-pyridine-3-carboxamide (Enantiomer A)

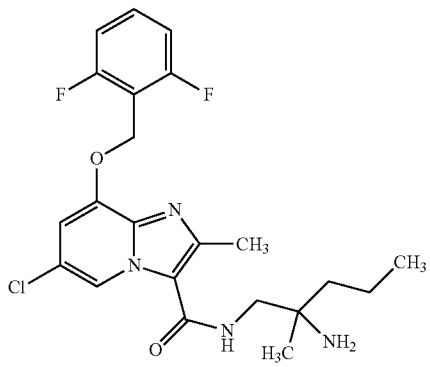

182 mg of Example 244 were separated into the enantiomers by preparative separation on a chiral phase [column: Daicel Chiralpak AZ-H, 5 μm, 250×30 mm, mobile phase: 50% isohexane, 50% ethanol+0.2% diethylamine, flow rate: 40 ml/min; 25° C., detection: 220 nm]. The product fractions were collected on dry ice, combined and concentrated on a rotary evaporator (bath temperature 30° C.). The product was then purified again by preparative RP-HPLC (acetonitrile/water gradient with addition of 0.1% TFA). The product fraction was concentrated. The residue was dissolved in dichloromethane and washed with saturated aqueous sodium bicarbonate solution. The combined aqueous phases were extracted three times with dichloromethane. The combined organic phases were dried over sodium sulphate, filtered and concentrated.

Enantiomer A: Yield: 30 mg (88% ee)

$R_t$=7.90 min [Daicel Chiralpak AZ-H, 5 μm, 250×4.6 mm; mobile phase: 50% isohexane, 50% ethanol+0.2% diethylamine; flow rate 1.0 ml/min; 35° C.; detection: 220 nm].

Specific rotation [α] (589 nm, 19.7° C.)=−2.6° (c=0.005 g/ml, acetonitrile)

Example 246 ent-N-(2-Amino-2-methylpentyl)-6-chloro-8-[(2,6-difluorobenzyl)oxy]-2-methylimidazo[1,2-a]-pyridine-3-carboxamide (Enantiomer B)

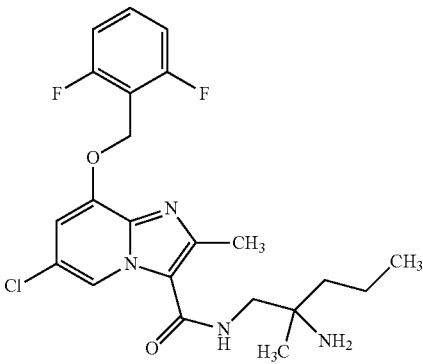 [SMILES: CCCC(C)(N)CNC(=O)c1c(C)nc2c(OCc3c(F)cccc3F)cc(Cl)cn12]

182 mg of Example 244 were separated into the enantiomers by preparative separation on a chiral phase [column: Daicel Chiralpak AZ-H, 5 μm, 250×30 mm, mobile phase: 50% isohexane, 50% ethanol+0.2% diethylamine, flow rate: 40 ml/min; 25° C., detection: 220 nm]. The product fractions were collected on dry ice, combined and concentrated on a rotary evaporator (bath temperature 30° C.). The product was then purified again by preparative RP-HPLC (acetonitrile/water gradient with addition of 0.1% TFA). The product fraction was concentrated. The residue was dissolved in dichloromethane and washed with saturated aqueous sodium bicarbonate solution. The combined aqueous phases were extracted three times with dichloromethane. The combined organic phases were dried over sodium sulphate, filtered and concentrated.

Enantiomer B: Yield: 24 mg (77% ee)

$R_t$=9.07 min [Daicel Chiralpak AZ-H, 5 μm, 250×4.6 mm; mobile phase: 50% isohexane, 50% ethanol+0.2% diethylamine; flow rate 1.0 ml/min; 35° C.; detection: 220 nm].

Specific rotation [α] (589 nm, 19.9° C.)=+2.5° (c=0.0048 g/ml, acetonitrile)

Example 247 ent-N-(2-Amino-3-methoxypropyl)-8-[(2,6-difluorobenzyl)oxy]-2-methylimidazo[1,2-a]pyridine-3-carboxamide (Enantiomer A)

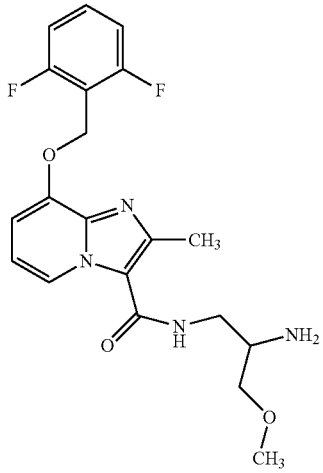 [SMILES: COCC(N)CNC(=O)c1c(C)nc2c(OCc3c(F)cccc3F)cccn12]

Preparation and purification of the title compound were carried out analogously to Example 242. Starting with 100 mg (0.31 mmol) of 8-[(2,6-difluorobenzyl)oxy]-2-methyl-imidazo[1,2-a]pyridine-3-carboxylic acid Example 3A and 78 mg (0.44 mmol) of ent-3-methoxypropane-1,2-diamine dihydrochloride (enantiomer A) Example 249 A, 76 mg (59% of theory, purity 98%) of the target compound were obtained.

LC-MS (Method 2): $R_t$=0.62 min

MS (ESIpos): m/z=405 (M+H)$^+$ $^1$H NMR (400 MHz, DMSO-d$_6$): δ=1.57-1.87 (br. s, 2H), 2.53 (s, 3H; superimposed by DMSO peak), 3.00-3.08 (m, 1H), 3.14-3.25 (m, 2H), 3.26-3.42 (m, 5H; superimposed by water signal), 5.30 (s, 2H), 6.93 (t, 1H), 7.01 (d, 1H), 7.19-7.28 (m, 2H), 7.54-7.64 (m, 1H), 7.75 (t, 1H), 8.65 (d, 1H).

Example 248 ent-N-(2-Amino-3-methoxypropyl)-8-[(2,6-difluorobenzyl)oxy]-2-methylimidazo[1,2-a]pyridine-3-carboxamide (Enantiomer B)

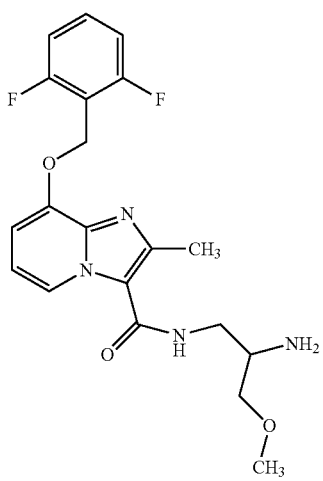 [SMILES: COCC(N)CNC(=O)c1c(C)nc2c(OCc3c(F)cccc3F)cccn12]

Preparation and purification of the title compound were carried out analogously to Example 242. Starting with 100 mg (0.31 mmol) of 8-[(2,6-difluorobenzyl)oxy]-2-methyl-imidazo[1,2-a]pyridine-3-carboxylic acid Example 3A and 78 mg (0.44 mmol) of ent-3-methoxypropane-1,2-diamine dihydrochloride (enantiomer B) Example 250A, 72 mg (56% of theory, purity 99%) of the target compound were obtained.

LC-MS (Method 2): $R_t$=0.62 min

MS (ESIpos): m/z=405 (M+H)$^+$ $^1$H NMR (400 MHz, DMSO-d$_6$): δ=1.56-1.85 (br. s, 2H), 2.53 (s, 3H; superimposed by DMSO peak), 3.00-3.07 (m, 1H), 3.14-3.26 (m, 2H), 3.26-3.42 (m, 5H; superimposed by water signal), 5.30 (s, 2H), 6.93 (t, 1H), 7.01 (d, 1H), 7.19-7.28 (m, 2H), 7.54-7.64 (m, 1H), 7.75 (t, 1H), 8.66 (d, 1H).

Example 249 rac-N-(2-Amino-2,4-dimethylpentyl)-2,6-dimethyl-8-(3-methylbutoxy)imidazo[1,2-a]pyridine-3-carboxamide

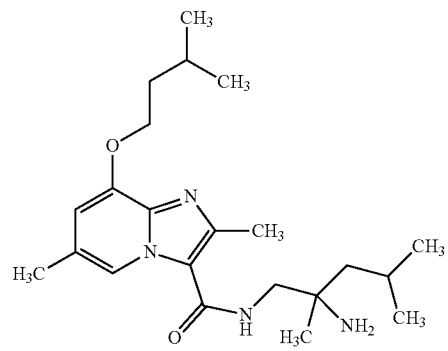 [SMILES: Cc1cc(OCCC(C)C)c2nc(C)c(C(=O)NCC(C)(N)CC(C)C)n2c1]

175 mg (0.63 mmol) of 2,6-dimethyl-8-(3-methylbutoxy)imidazo[1,2-a]pyridine-3-carboxylic acid Example 252A were initially charged in DMF (2.2 ml), 214 mg (0.67 mmol) of TBTU, 0.28 ml (2.53 mmol) of 4-methylmorpholine and 91 mg (0.70 mmol) of rac-2,4-dimethylpentane-1,2-diamine were added and the reaction mixture stirred at RT overnight. The mixture was diluted with water/TFA and purified by preparative RP-HPLC (acetonitrile/water gradient with addition of 0.1% TFA). After concentration, saturated aqueous sodium bicarbonate solution was added to the residue and the mixture was extracted three times with dichloromethane. The combined organic phases were dried over sodium sulphate, filtered off and concentrated. This gave 225 mg (90% of theory, purity 98%) of the target compound.

LC-MS (Method 7): $R_t$=0.62 min

MS (ESIpos): m/z=389 (M+H)$^+$ $^1$H NMR (400 MHz, DMSO-d$_6$): δ=0.90-0.98 (m, 12H), 1.07 (s, 3H), 1.25-1.38 (m, 2H), 1.65-1.73 (m, 2H), 1.75-1.88 (m, 2H), 2.27 (s, 3H), 2.57 (s, 3H), 3.18-3.29 (m, 2H), 4.15 (t, 2H), 6.71 (s, 1H), 7.66 (t, 1H), 8.42 (s, 1H).

Example 250 rac-8-[(2,6-Difluorobenzyl)oxy]-2-methyl-N-(1,2,3,4-tetrahydroquinolin-2-ylmethyl)imidazo[1,2-a]pyridine-3-carboxamide

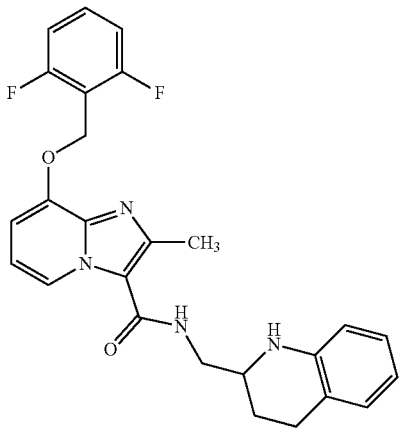 [SMILES: Cc1nc2c(OCc3c(F)cccc3F)cccn2c1C(=O)NCC1CCc2ccccc2N1]

Preparation and purification of the title compound were carried out analogously to Example 235. Starting with 190 mg (0.34 mmol) of rac-tert-butyl 2-{[({8-[(2,6-difluorobenzyl)oxy]-2-methylimidazo[1,2-a]pyridin-3-yl}carbonyl)amino]methyl}-3,4-dihydroquinoline-1(2H)-carboxylate Example 253A, 149 mg (93% of theory, purity 98%) of the target compound were obtained.

LC-MS (Method 2): $R_t$=0.99 min
MS (ESIpos): m/z=463 (M+H)$^+$
$^1$H NMR (400 MHz, DMSO-d$_6$): δ=1.56-1.67 (m, 1H), 1.86-1.95 (m, 1H), 2.66-2.73 (m, 2H), 3.37-3.50 (m, 3H), 5.31 (s, 2H), 5.70-5.77 (m, 1H), 6.43 (t, 1H), 6.48 (d, 1H), 6.82-6.89 (m, 2H), 6.95 (t, 1H), 7.03 (d, 1H), 7.20-7.28 (m, 2H), 7.54-7.64 (m, 1H), 7.96 (t, 1H), 8.64 (d, 1H), [further signals under solvent peaks].

Example 251 ent-N-[(1R,2R)-2-Aminocyclohexyl]-8-[(2,6-difluorobenzyl)oxy]-2,6-dimethylimidazo[1,2-a]-pyridine-3-carboxamide

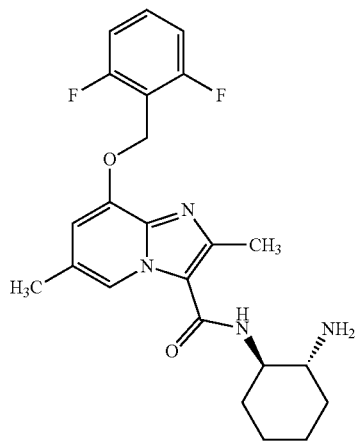 [SMILES: Cc1cc(OCc2c(F)cccc2F)c2nc(C)c(C(=O)N[C@@H]3CCCC[C@H]3N)n2c1]

Preparation and purification of the title compound were carried out analogously to Example 235. Starting with 107 mg (0.2 mmol, 98% pure) of ent-tert-butyl {(1R,2R)-2-[({8-[(2,6-difluorobenzyl)oxy]-2,6-dimethylimidazo[1,2-a]pyridin-3-yl}carbonyl)amino]cyclohexyl}-carbamate Example 254A, 83 mg (97% of theory, purity 99%) of the target compound were obtained.

LC-MS (Method 7): $R_t$=0.59 min
MS (ESIpos): m/z=429 (M+H)$^+$
$^1$H NMR (400 MHz, DMSO-d$_6$): δ=1.08-1.35 (m, 4H), 1.61-1.72 (m, 2H), 1.81-1.89 (m, 1H), 1.90-1.97 (m, 1H), 2.30 (s, 3H), 3.45-3.56 (m, 1H), 5.28 (s, 2H), 6.89 (s, 1H), 7.20-7.28 (m, 2H), 7.54-7.64 (m, 1H), 7.67 (d, 1H), 8.37 (s, 1H), [further signals under solvent peaks].

Example 252

N-(2-Amino-2-ethylbutyl)-8-[(2,6-difluorobenzyl)oxy]-2,6-dimethylimidazo[1,2-a]pyridine-3-carboxamide

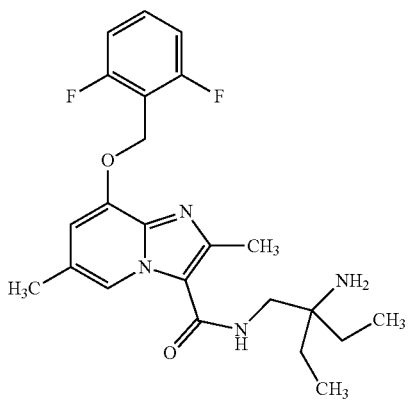 [SMILES: CCC(N)(CC)CNC(=O)c1c(C)nc2c(OCc3c(F)cccc3F)cc(C)cn12]

70 mg (0.60 mmol) of 2-ethylbutane-1,2-diamine were added to 100 mg (0.30 mmol) of 8-[(2,6-difluorobenzyl)oxy]-2,6-dimethylimidazo[1,2-a]pyridine-3-carboxylic acid Example 21A, 145 mg (0.45 mmol) of TBTU and 0.13 ml (1.20 mmol) of 4-methylmorpholine in DMF (1.9 ml), and the reaction mixture was stirred at RT overnight. The mixture was then diluted with water/TFA and purified by preparative RP-HPLC (acetonitrile/water gradient with addition of 0.1% TFA). After concentration, the residue was taken up in dichloromethane and washed twice with saturated aqueous sodium bicarbonate solution. The aqueous phase was extracted twice with dichloromethane. The combined organic phases were dried over sodium sulphate, filtered off, concentrated and lyophilized. This gave 110 mg (85% of theory, purity 100%) of the target compound.

LC-MS (Method 2): $R_t$=0.60 min
MS (ESIpos): m/z=431 (M+H)$^+$
$^1$H NMR (400 MHz, DMSO-d$_6$): δ=0.82 (t, 6H), 1.22-1.49 (m, 6H), 2.31 (s, 3H), 2.52 (s, 3H; superimposed by DMSO peak), 3.17-3.23 (m, 2H), 5.28 (s, 2H), 6.91 (s, 1H), 7.19-7.28 (m, 2H), 7.51 (t, 1H), 7.55-7.64 (m, 1H), 8.50 (s, 1H).

Example 253

N-(2-Amino-2-ethylbutyl)-8-[(2,6-difluorobenzyl)oxy]-2-methylimidazo[1,2-a]pyridine-3-carboxamide

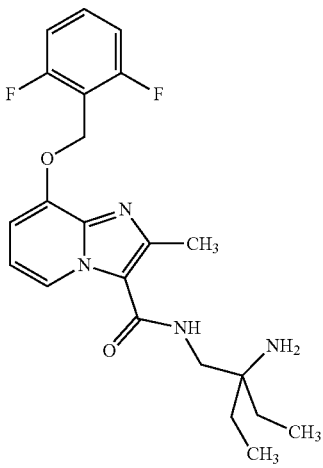 [SMILES: CCC(N)(CC)CNC(=O)c1c(C)nc2c(OCc3c(F)cccc3F)cccn12]

Preparation and purification of the title compound were carried out analogously to Example 252. Starting with 75 mg (0.24 mmol) of 8-[(2,6-difluorobenzyl)oxy]-2-methylimidazo[1,2-a]pyridine-3-carboxylic acid Example 3A and 41 mg (0.35 mmol) of 2-ethylbutane-1,2-diamine, 73 mg (74% of theory, purity 99%) of the target compound were obtained.

LC-MS (Method 2): $R_t$=0.64 min

MS (ESIpos): m/z=417 (M+H)$^+$ $^1$H NMR (400 MHz, DMSO-d$_6$): δ=0.83 (t, 6H), 1.26-1.43 (m, 4H), 1.89 (br. s, 2H), 2.56 (s, 3H; superimposed by DMSO signal), 3.20-3.26 (m, 2H), 5.31 (s, 2H), 6.94 (t, 1H), 7.01 (d, 1H), 7.23 (t, 2H), 7.50-7.64 (m, 2H), 8.68 (d, 1H).

Example 254 rac-N-(2-Amino-2-methylbutyl)-8-[(2,6-difluorobenzyl)oxy]-2-methylimidazo[1,2-a]pyridine-3-carboxamide

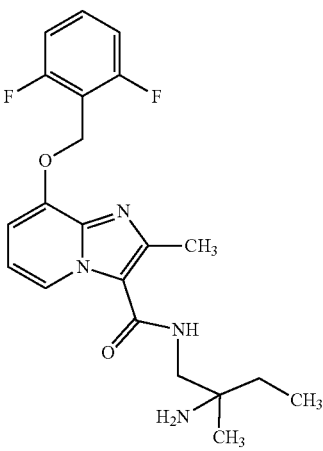 [SMILES: CCC(C)(N)CNC(=O)c1c(C)nc2c(OCc3c(F)cccc3F)cccn12]

Preparation and purification of the title compound were carried out analogously to Example 252. Starting with 120 mg (0.38 mmol) of 8-[(2,6-difluorobenzyl)oxy]-2-methylimidazo[1,2-a]pyridine-3-carboxylic acid Example 3A and 58 mg (0.57 mmol) of rac-2-methylbutane-1,2-diamine, 98 mg (63% of theory, purity 98%) of the target compound were obtained.

LC-MS (Method 2): $R_t$=0.58 min

MS (ESIpos): m/z=403 (M+H)$^+$ $^1$H NMR (400 MHz, DMSO-d$_6$): δ=0.86 (t, 3H), 0.97 (s, 3H), 1.28-1.39 (m, 2H), 1.40-1.49 (br s., 2H), 2.56 (s, 3H; superimposed by DMSO signal), 3.14-3.27 (m, 2H), 5.30 (s, 2H), 6.94 (t, 1H), 7.01 (d, 1H), 7.19-7.27 (m, 2H), 7.54-7.69 (m, 2H), 8.65 (d, 1H).

Example 255

N-[2-(tert-Butylamino)ethyl]-8-[(2,6-difluorobenzyl)oxy]-2,6-dimethylimidazo[1,2-a]pyridine-3-carboxamide

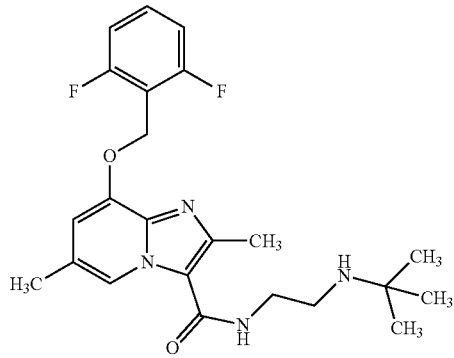 [SMILES: Cc1cc(OCc2c(F)cccc2F)c2nc(C)c(C(=O)NCCNC(C)(C)C)n2c1]

70 mg (0.21 mmol) of 8-[(2,6-difluorobenzyl)oxy]-2,6-dimethylimidazo[1,2-a]pyridine-3-carboxylic acid Example 21A, 71 mg (0.22 mmol) of TBTU and 128 mg (1.26 mmol) of 4-methylmorpholine were initially charged in DMF (0.74 ml), 44 mg (0.23 mmol) of N-tert-butylethane-1,2-diamine dihydrochloride were added and the reaction mixture was stirred at RT overnight. Another 22 mg (0.12 mmol) of N-tert-butylethane-1,2-diamine dihydrochloride and 21 mg (0.21 mmol) of 4-methylmorpholine were added, and the mixture was stirred at RT for 1.5 h. The mixture was diluted with a few drops of water/TFA and purified by preparative RP-HPLC (acetonitrile/water with addition of 0.1% TFA), and the product fractions were concentrated. Saturated aqueous sodium bicarbonate solution was added to the residue, and the mixture was extracted three times with dichloromethane. The combined organic phases were dried over sodium sulphate, filtered off and concentrated. This gave 78 mg (86% of theory, purity 96%) of the target compound.

LC-MS (Method 2): $R_t$=0.66 min

MS (ESIpos): m/z=431 (M+H)$^+$ $^1$H NMR (400 MHz, DMSO-d$_6$): δ=1.18 (br. s, 9H), 2.32 (s, 3H), 2.52 (s, 3H, obscured by DMSO signal), 2.70-3.12 (br. s, 2H), 3.38-3.62 (m, 2H), 5.29 (s, 2H), 6.92 (s, 1H), 7.20-7.27 (m, 2H), 7.59 (quintet, 1H), 7.74 (br. s, 1H), 8.34 (br. s, 1H), 8.53 (s, 1H).

Example 256 ent-N-(2-Amino-2-methylpropyl)-8-[1-(2,6-difluorophenyl)ethoxy]-2,6-dimethylimidazo[1,2-a]-pyridine-3-carboxamide (Enantiomer B)

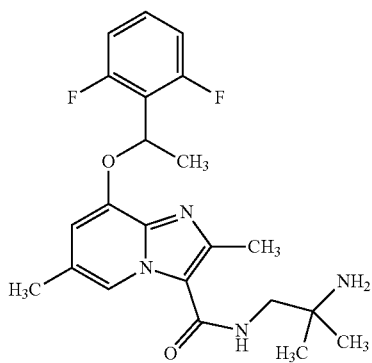 [SMILES: Cc1cc(OC(C)c2c(F)cccc2F)c2nc(C)c(C(=O)NCC(C)(C)N)n2c1]

84 mg (0.24 mmol) of ent-8-[1-(2,6-difluorophenyl)ethoxy]-2,6-dimethylimidazo[1,2-a]pyridine-3-carboxylic acid Example 257A were initially charged in DMF (1.54 ml), 117 mg (0.36 mmol) of TBTU, 98 mg (0.97 mmol) of 4-methylmorpholine and 43 mg (0.49 mmol) of 2-methylpropane-1,2-diamine were added and the reaction mixture was stirred at RT overnight. The mixture was then purified by preparative RP-HPLC (acetonitrile/water gradient with addition of 0.10% TFA) and the product fraction was concentrated. The residue was taken up in dichloromethane and washed twice with saturated aqueous sodium bicarbonate solution. The combined organic phases were dried over sodium sulphate, filtered off, and concentrated. The residue was dried under high vacuum and then lyophilized. This gave 85 mg (84% of theory, purity 99%) of the target compound.

LC-MS (Method 13): $R_t$=1.48 min
MS (ESIpos): m/z=417 (M+H)$^+$
$^1$H NMR (400 MHz, DMSO-d$_6$): δ=1.05 (s, 6H), 1.61-1.74 (m, 2H), 1.78 (d, 3H), 2.18 (s, 3H), 2.57 (s, 3H), 3.19 (d, 2H), 6.20 (q, 1H), 6.56 (s, 1H), 7.06-7.14 (m, 2H), 7.37-7.46 (m, 1H), 7.69 (t, 1H), 8.40 (s, 1H).

Example 257

N-(2-Amino-2-methylpentyl)-8-[1-(2,6-difluorophenyl)ethoxy]-2,6-dimethylimidazo[1,2-a]-pyridine-3-carboxamide

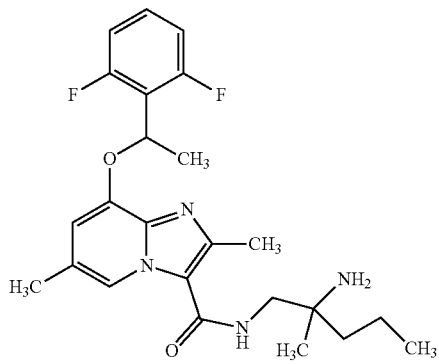 [SMILES: CCCC(C)(N)CNC(=O)c1c(C)nc2c(OC(C)c3c(F)cccc3F)cc(C)cn12]

16 mg (0.14 mmol) of rac-2-methylpentane-1,2-diamine were added to 40 mg (0.12 mmol) of ent-8-[1-(2,6-difluorophenyl)ethoxy]-2,6-dimethylimidazo[1,2-a]pyridine-3-carboxylic acid Example 257A, 45 mg (0.14 mmol) of TBTU and 47 mg (0.46 mmol) of 4-methylmorpholine in DMF (0.77 ml), and the reaction mixture was stirred at RT overnight. A few drops of water/TFA were added, and the mixture was purified by preparative RP-HPLC (acetonitrile/water gradient with addition of 0.1% TFA). The product fraction was concentrated. The residue was taken up in dichloromethane and washed with saturated aqueous sodium bicarbonate solution. The aqueous phase was extracted three times with dichloromethane and the combined organic phases were dried over sodium sulphate, filtered off, concentrated, dried under high vacuum and then lyophilized. This gave 27.4 mg (52% of theory, purity 97%) of the target compound.

LC-MS (Method 2): $R_t$=0.71 min
MS (ESIpos): m/z=445 (M+H)$^+$
$^1$H NMR (400 MHz, DMSO-d$_6$): δ=0.87 (t, 3H), 0.98 (s, 3H), 1.22-1.39 (m, 4H), 1.48 (br. s, 2H), 1.78 (d, 3H), 2.19 (s, 3H), 2.57 (s, 3H), 3.13-3.26 (m, 2H), 6.20 (q, 1H), 6.56 (s, 1H), 7.06-7.14 (m, 2H), 7.37-7.44 (m, 1H), 7.58-7.64 (m, 1H), 8.41 (s, 1H).

Example 258 rac-N-(2-Amino-2,4-dimethylpentyl)-2,6-dimethyl-8-[4,4,4-trifluoro-3-(trifluoromethyl)butoxy]-imidazo[1,2-a]pyridine-3-carboxamide

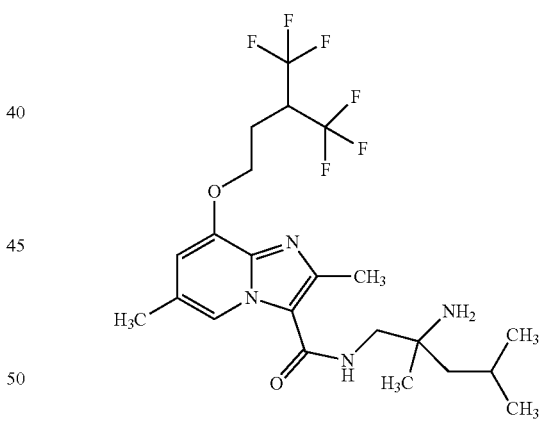

31 mg (0.08 mmol) of 2,6-dimethyl-8-[4,4,4-trifluoro-3-(trifluoromethyl)butoxy]imidazo[1,2-a]-pyridine-3-carboxylic acid Example 259A, dissolved in 0.3 ml of DMF, 40 mg (0.104 mmol) of HATU, dissolved in 0.3 ml of DMF, and then 16 mg (0.16 mmol) of 4-methylmorpholine were added to 10 mg (0.08 mmol) of rac-2,4-dimethylpentane-1,2-diamine. The mixture was shaken at RT overnight. The target compound was concentrated by preparative HPLC (Method 12). This gave 10 mg (25% of theory).

LC-MS (Method 8): $R_t$=0.78 min
MS (ESpos): m/z=497 (M+H)$^+$

Example 259 rac-N-(2-Amino-2-cyclopropylpropyl)-8-[(2,6-difluorobenzyl)oxy]-2,6-dimethylimidazo[1,2-a]-pyridine-3-carboxamide

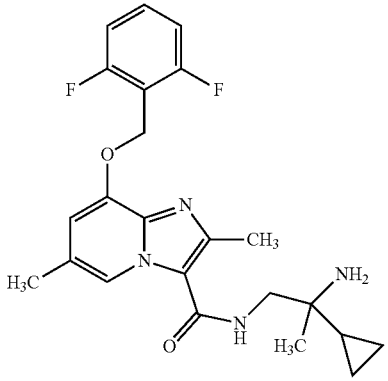 [SMILES: Cc1cc(OCc2c(F)cccc2F)c2nc(C)c(C(=O)NCC(C)(N)C3CC3)n2c1]

160 mg (0.48 mmol) of 8-[(2,6-difluorobenzyl)oxy]-2,6-dimethylimidazo[1,2-a]pyridine-3-carboxylic acid Example 21A, 162 mg (0.51 mmol) of TBTU and 292 mg (2.89 mmol) of 4-methylmorpholine were initially charged in DMF (1.7 ml), and 99 mg (0.53 mmol) of rac-2-cyclopropylpropane-1,2-diamine dihydrochloride were added at 0° C. The reaction mixture was allowed to warm to room temperature and then stirred at RT overnight. Another 50 mg (0.27 mmol) of 2-cyclopropylpropane-1,2-diamine dihydrochloride and 49 mg (0.48 mmol) of 4-methylmorpholine were added, and the mixture was stirred at RT for 1.5 h. The mixture was diluted with a few drops of water/TFA and purified by prep. RP-HPLC (acetonitrile/water gradient with addition of 0.1% TFA). The product fractions were concentrated. Saturated aqueous sodium bicarbonate solution was added to the residue and the mixture was extracted three times with dichloromethane. The combined organic phases were dried over sodium sulphate, filtered off and concentrated. This gave 156 mg (76% of theory) of the target compound.

LC-MS (Method 2): $R_t$=0.63 min
MS (ESIpos): m/z=429 (M+H)$^+$
$^1$H NMR (400 MHz, DMSO-d$_6$): δ=0.18-0.38 (m, 4H), 0.79-0.88 (m, 1H), 0.97 (s, 3H), 1.13-1.36 (m, 2H), 2.31 (s, 3H), 2.54 (s, 3H, obscured by DMSO signal), 3.20-3.3.26 (m, 1H), 3.30-3.38 (m, 1H), 5.29 (s, 2H), 6.91 (s, 1H), 7.19-7.27 (m, 2H), 7.54-7.63 (m, 2H), 8.50 (s, 1H).

Example 260 ent-N-(2-Amino-2-cyclopropylpropyl)-8-[(2,6-difluorobenzyl)oxy]-2,6-dimethylimidazo[1,2-a]-pyridine-3-carboxamide (Enantiomer A)

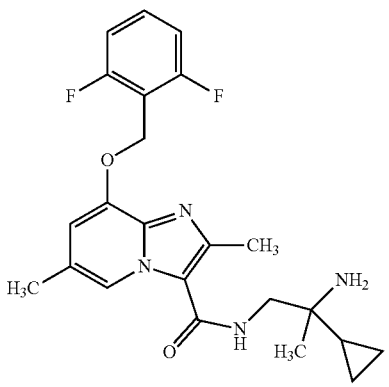 [SMILES: Cc1cc(OCc2c(F)cccc2F)c2nc(C)c(C(=O)NCC(C)(N)C3CC3)n2c1]

140 mg of Example 259 were separated into the enantiomers by preparative separation on a chiral phase [column: Daicel Chiralpak AD-H, 5 μm, 250×20 mm, mobile phase: 50% isohexane, 50% isopropanol+0.2% diethylamine, flow rate: 17 ml/min; 40° C., detection: 210 nm].

Enantiomer A: Yield: 48 mg (100% ee)
$R_t$=8.53 min [Daicel Chiralpak AD-H, 5 μm, 250×4.6 mm; mobile phase: 50% isohexane, 50% ethanol+0.2% diethylamine; flow rate 1.0 ml/min; 40° C.; detection: 220 nm].

Specific rotation [α] (365 nm, 20.5° C.)=−8.4° (c=0.005 g/ml, acetonitrile)

Example 261 ent-N-(2-Amino-2-cyclopropylpropyl)-8-[(2,6-difluorobenzyl)oxy]-2,6-dimethylimidazo[1,2-a]-pyridine-3-carboxamide (Enantiomer B)

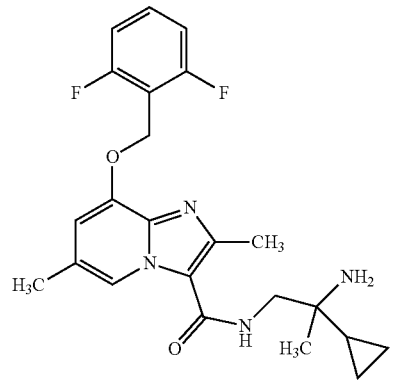 [SMILES: Cc1cc(OCc2c(F)cccc2F)c2nc(C)c(C(=O)NCC(C)(N)C3CC3)n2c1]

140 mg of Example 259 were separated into the enantiomers by preparative separation on a chiral phase [column: Daicel Chiralpak AD-H, 5 μm, 250×20 mm, mobile phase: 50% isohexane, 50% isopropanol+0.2% diethylamine; flow rate: 17 ml/min; 40° C., detection: 210 nm].

Enantiomer B: Yield: 38 mg (90% ee)
$R_t$=9.12 min [Daicel Chiralpak AD-H, 5 μm, 250×4.6 mm; mobile phase: 50% isohexane, 50% ethanol+0.2% diethylamine; flow rate 1.0 ml/min; 40° C.; detection: 220 nm].

Example 262 rac-N-[2-Amino-4-(benzyloxy)-2-methylbutyl]-8-[(2,6-difluorobenzyl)oxy]-2,6-dimethylimidazo-[1,2-a]pyridine-3-carboxamide

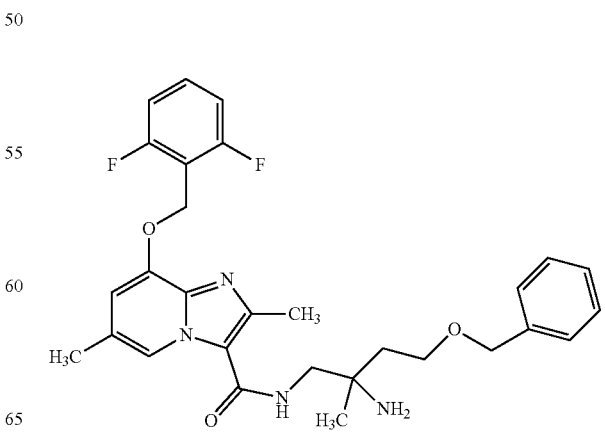

503 mg (1.32 mmol) of HATU and 1.05 ml (6.0 mmol) of N,N-diisopropylethylamine in DMF (7.7 ml) were added to 400 mg (1.2 mmol) of 8-[(2,6-difluorobenzyl)oxy]-2,6-dimethylimidazo[1,2-a]-pyridine-3-carboxylic acid Example 21A, and the mixture was stirred at RT for 20 min. 300 mg (1.38 mmol) of rac-4-(benzyloxy)-2-methylbutane-1,2-diamine Example 261A were dissolved in 2 ml of DMF and, at 0° C., added to the reaction solution. The mixture was stirred at 0° C. for 1 h and then diluted with water/TFA and purified by preparative RP-HPLC (acetonitrile/water gradient with addition of 0.1% strength TFA). This gave 600 mg (88% of theory, purity 93%) of the target compound.

LC-MS (Method 2): $R_t$=0.78 min
MS (ESIpos): m/z=523 (M+H)$^+$
$^1$H NMR (400 MHz, DMSO-d$_6$): δ=1.30 (s, 3H), 1.87-2.01 (m, 2H), 2.36 (s, 3H), 2.56 (s, 3H), 3.47-3.70 (m, 4H), 4.50 (s, 2H), 5.34 (s, 2H), 7.12-7.38 (m, 8H), 7.55-7.64 (m, 1H), 7.73 (br. s, 2H), 8.08 (br. s, 1H), 8.55 (s, 1H).

The examples shown in Table 14 were prepared analogously to Example 262 by reacting the appropriate carboxylic acids (Example 3A and 21A) with the appropriate amines, prepared as described above or commercially available, (1.05-2.5 equivalents) and N,N-diisopropylethylamine (3-6 equivalents) under the reaction conditions described in the General Working Procedure 3.

Exemplary work-up of the reaction mixture: Water was added to the reaction solution and the mixture was extracted three times with ethyl acetate or dichloromethane. The combined organic phases were dried over sodium sulphate, filtered, concentrated and purified by preparative HPLC (RP18 column, mobile phase: acetonitrile/water gradient with addition of 0.1% TFA). Alternatively, the precipitate or the reaction mixture was directly purified further by preparative HPLC (RP 18 column, mobile phase: acetonitrile/water gradient with addition of 0.1% TFA) and dried under high vacuum overnight. If appropriate, the product fractions were taken up in ethyl acetate or dichloromethane and washed twice with saturated aqueous sodium bicarbonate solution. The aqueous phase was extracted twice with ethyl acetate or dichloromethane and the combined organic phases were dried over sodium sulphate, filtered and concentrated.

TABLE 14

| Example | IUPAC name/structure (yield) | Analytical data |
|---|---|---|
| 263 | rac-N-[2-amino-3-(benzyloxy)-2-methylpropyl]-8-[(2,6-difluorobenzyl)oxy]-2-methylimidazo[1,2-a]pyridine-3-carboxamide<br><br>(81% of theory) | LC-MS (Method 2): $R_t$ = 0.74 min<br>MS (ESpos): m/z = 495.3 (M + H)$^+$<br>$^1$H NMR (400 MHz, DMSO-d$_6$): δ = 1.03 (s, 3H), 1.66 (br. s, 2H), 2.49 (s, 3H), 3.28-3.38 (m, 2H; superimposed by water signal), 4.51 (s, 2H), 5.30 (s, 2H), 6.92 (t, 1H), 7.01 (d, 1H), 7.19-7.37 (m, 7H), 7.50-7.67 (m, 2H), 8.69 (d, 1H). |

TABLE 14-continued

| Example | IUPAC name/structure (yield) | Analytical data |
|---|---|---|
| 264 | rac-N-[2-amino-4-(benzyloxy)-2-methylbutyl]-8-[(2,6-difluorobenzyl)oxy]-2-methylimidazo[1,2-a]pyridine-3-carboxamide<br>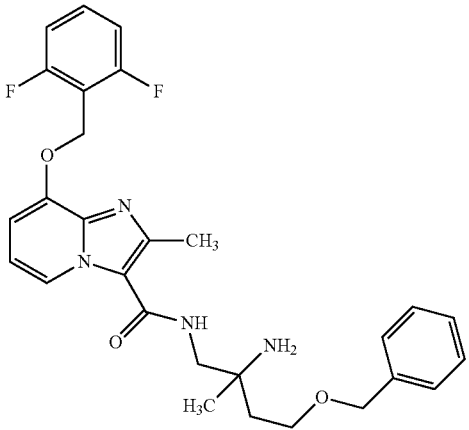<br>(81% of theory) | LC-MS (Method 2): $R_t$ = 0.77 min<br>MS (ESpos): m/z = 509.1 (M + H)$^+$<br>$^1$H NMR (400 MHz, DMSO-d$_6$): δ = 1.11 (s, 3H), 1.74 (t, 2H), 2.51 (s, 3H; superimposed by DMSO peak), 3.28-3.38 (m, 2H; superimposed by water signal), 3.59-3.67 (m, 2H), 4.47 (s, 2H), 5.31 (s, 2H), 6.93 (t, 1H), 7.02 (d, 1H), 7.19-7.38 (m, 7H), 7.54-7.71 (m, 2H), 8.68 (d, 1H). |
| 265 | rac-N-[2-amino-3-(benzyloxy)-2-methylpropyl]-8-[(2,6-difluorobenzyl)oxy]-2,6-dimethylimidazo[1,2-a]pyridine-3-carboxamide<br>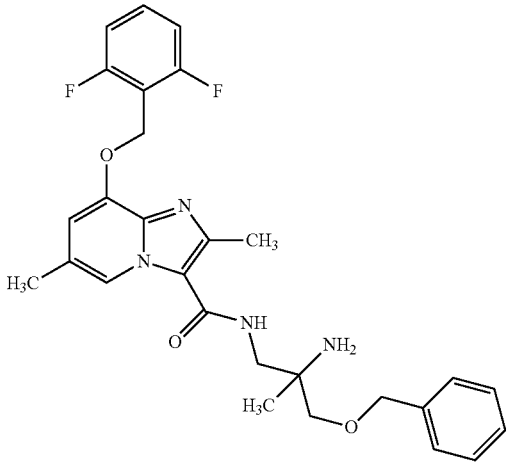<br>(74% of theory) | LC-MS (Method 2): $R_t$ = 0.80 min<br>MS (ESpos): m/z = 509.1 (M + H)$^+$<br>$^1$H NMR (400 MHz, DMSO-d$_6$): δ = 1.05 (s, 3H), 2.30 (s, 3H), 2.49 (s, 3H), 3.30-3.38 (m, 2H; superimposed by water signal), 4.52 (s, 2H), 5.30 (s, 2H), 6.91 (s, 1H), 7.19-7.38 (m, 8H), 7.52-7.65 (m, 2H), 8.51 (s, 1H). |

Example 266 ent-N-[2-Amino-4-(benzyloxy)-2-methylbutyl]-8-[(2,6-difluorobenzyl)oxy]-2-methylimidazo[1,2-a]pyridine-3-carboxamide (Enantiomer A)

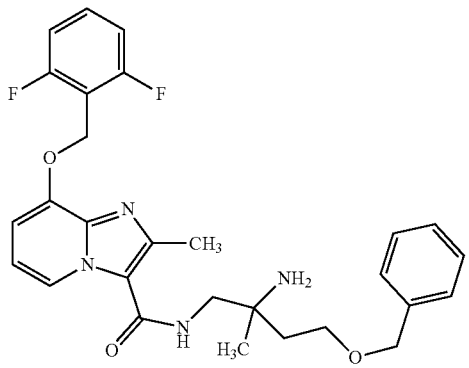 [SMILES: Cc1nc2c(OCc3c(F)cccc3F)cccn2c1C(=O)NCC(C)(N)CCOCc1ccccc1]

637 mg of Example 264 were separated into the enantiomers by preparative separation on a chiral phase [column: Daicel Chiralcel OD-H, 5 μm, 250×20 mm, mobile phase: 100% ethanol+0.2% diethylamine, flow rate: 15 ml/min; 40° C., detection: 220 nm].

Enantiomer A: Yield: 267 mg (99% ee)

$R_t$=5.45 min [Daicel Chiralcel OD-H, 5 μm, 250×4.6 mm; mobile phase: 100% ethanol+0.2% diethylamine; flow rate 1.0 ml/min; 40° C.; detection: 220 nm].

Example 267 ent-N-[2-Amino-4-(benzyloxy)-2-methylbutyl]-8-[(2,6-difluorobenzyl)oxy]-2-methylimidazo[1,2-a]pyridine-3-carboxamide (Enantiomer B)

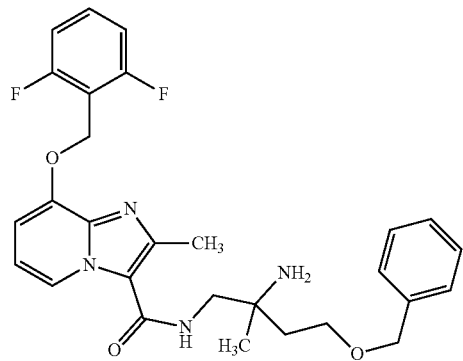 [SMILES: Cc1nc2c(OCc3c(F)cccc3F)cccn2c1C(=O)NCC(C)(N)CCOCc1ccccc1]

637 mg of Example 264 were separated into the enantiomers by preparative separation on a chiral phase [column: Daicel Chiralcel OD-H, 5 μm, 250×20 mm, mobile phase: 100% ethanol+0.2% diethylamine, flow rate: 15 ml/min; 40° C., detection: 220 nm].

Enantiomer B: Yield: 292 mg (99% ee)

$R_t$=7.10 min [Daicel Chiralcel OD-H, 5 μm, 250×4.6 mm; mobile phase: 100% ethanol+0.2% diethylamine; flow rate 1.0 ml/min; 40° C.; detection: 220 nm].

Example 268 ent-N-(2-Amino-3-hydroxy-2-methylpropyl)-8-[(2,6-difluorobenzyl)oxy]-2,6-dimethylimidazo-[1,2-a]pyridine-3-carboxamide (Enantiomer A)

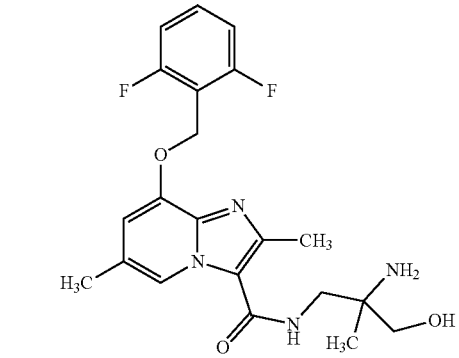 [SMILES: Cc1cc(OCc2c(F)cccc2F)c2nc(C)c(C(=O)NCC(C)(N)CO)n2c1]

460 mg of Example 265 were separated into the enantiomers by preparative separation on a chiral phase [column: Daicel Chiralcel OZ-H, 5 μm, 250×20 mm, mobile phase: 100% ethanol+0.2% diethylamine, flow rate: 15 ml/min; 40° C., detection: 220 nm]. The product fractions were collected on dry ice, combined and concentrated on a rotary evaporator (bath temperature 30° C.) to a residual volume of about 15 ml, and about 60 ml of water were added. The solution obtained was frozen and lyophilized.

Yield of the intermediate ent-N-[(2R)-2-amino-3-(benzyloxy)-2-methylpropyl]-8-[(2,6-difluorobenzyl)oxy]-2,6-dimethylimidazo[1,2-a]pyridine-3-carboxamide (enantiomer A):

183 mg (99% ee).

$R_t$=6.61 min [Daicel Chiralcel OZ-H, 5 μm, 250×4.6 mm; mobile phase: 100% ethanol+0.2% diethylamine; flow rate 1.0 ml/min; 40° C.; detection: 235 nm].

Under argon, 183 mg (0.36 mmol) of ent-N-[(2R)-2-amino-3-(benzyloxy)-2-methylpropyl]-8-[(2,6-difluorobenzyl)oxy]-2,6-dimethylimidazo[1,2-a]pyridine-3-carboxamide (enantiomer A) were initially charged in 3.7 ml of ethanol, and 38.3 mg of palladium on activated carbon (10%) and 1.09 ml (10.8 mmol) of cyclohexene were added. The reaction mixture was stirred under reflux for 6 h. The reaction mixture was directly applied to Celite and purified by silica gel chromatography (mobile phase: dichloromethane/methanol 10/1, dichloromethane/2N ammonia in methanol 10/1). This gave 80 mg of the target compound (52% of theory; purity 98%).

LC-MS (Method 2): $R_t$=0.61 min

MS (ESIpos): m/z=419 (M+H)$^+$ $^1$H NMR (400 MHz, DMSO-$d_6$): δ=0.97 (s, 3H), 1.92 (br. s, 2H), 2.31 (s, 3H), 2.54 (s, 3H, obscured by DMSO signal), 3.15-3.32 (m, 4H), 4.73-4.82 (m, 1H), 5.28 (s, 2H), 6.92 (s, 1H), 7.22 (t, 2H), 7.53-7.66 (m, 2H), 8.51 (s, 1H).

Example 269 ent-N-(2-Amino-3-hydroxy-2-methylpropyl)-8-[(2,6-difluorobenzyl)oxy]-2,6-dimethylimidazo-[1,2-a]pyridine-3-carboxamide (Enantiomer B)

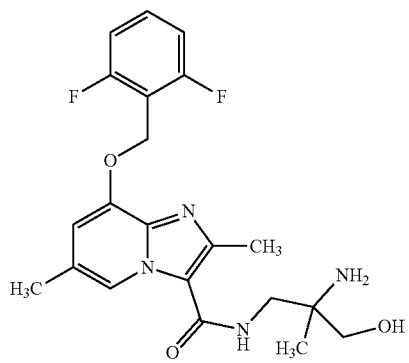 [SMILES: Cc1cc(OCc2c(F)cccc2F)c2nc(C)c(C(=O)NCC(C)(N)CO)n2c1]

460 mg of Example 265 were separated into the enantiomers by preparative separation on a chiral phase [column: Daicel Chiralcel OZ-H, 5 µm, 250×20 mm, mobile phase: 100% ethanol+0.2% diethylamine, flow rate: 15 ml/min; 40° C., detection: 220 nm]. The product fractions were collected on dry ice, combined and concentrated on a rotary evaporator (bath temperature 30° C.) to a residual volume of about 15 ml, and about 60 ml of water were added. The solution obtained was frozen and lyophilized.

Yield of the intermediate ent-N-[(2R)-2-amino-3-(benzyloxy)-2-methylpropyl]-8-[(2,6-difluorobenzyl)oxy]-2,6-dimethylimidazo[1,2-a]pyridine-3-carboxamide (enantiomer B):

189 mg (99% ee).

$R_t$=8.47 min [Daicel Chiralcel OZ-H, 5 µm, 250×4.6 mm; mobile phase: 100% ethanol+0.2% diethylamine; flow rate 1.0 ml/min; 40° C.; detection: 235 nm].

Under argon, 189 mg (0.37 mmol) of ent-N-[(2R)-2-amino-3-(benzyloxy)-2-methylpropyl]-8-[(2,6-difluorobenzyl)oxy]-2,6-dimethylimidazo[1,2-a]pyridine-3-carboxamide (enantiomer B) were initially charged in 3.8 ml of ethanol, and 39.5 mg of palladium on activated carbon (10%) and 1.13 ml (11.2 mmol) of cyclohexene were added. The reaction mixture was stirred under reflux for 12 h. The reaction mixture was applied directly to Celite and purified by silica gel chromatography (mobile phase: dichloromethane/methanol 10/1, dichloromethane/2N ammonia in methanol 10/1). This gave 85 mg of the target compound (54% of theory; purity 98%).

LC-MS (Method 2): $R_t$=0.52 min

MS (ESIpos): m/z=419 (M+H)$^+$ $^1$H NMR (400 MHz, DMSO-d$_6$): δ=0.97 (s, 3H), 1.83 (br. s, 2H), 2.30 (s, 3H), 2.54 (s, 3H, obscured by DMSO signal), 3.15-3.32 (m, 4H), 4.73-4.82 (m, 1H), 5.28 (s, 2H), 6.91 (s, 1H), 7.22 (t, 2H), 7.53-7.66 (m, 2H), 8.51 (s, 1H).

Example 270 rac-N-(2-Amino-4-hydroxy-2-methylbutyl)-8-[(2,6-difluorobenzyl)oxy]-2,6-dimethylimidazo[1,2-a]pyridine-3-carboxamide

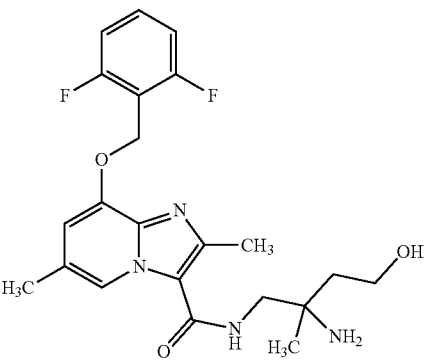 [SMILES: Cc1cc(OCc2c(F)cccc2F)c2nc(C)c(C(=O)NCC(C)(N)CCO)n2c1]

Under argon, 295 mg (0.52 mmol) of rac-N-[2-amino-4-(benzyloxy)-2-methylbutyl]-8-[(2,6-difluorobenzyl)oxy]-2,6-dimethylimidazo[1,2-a]pyridine-3-carboxamide Example 262 were initially charged in 5.4 ml of ethanol, 56 mg of Pd/carbon (10%) were added and the mixture was hydrogenated under atmospheric pressure at room temperature for 6.5 h. The reaction mixture was left under hydrogen overnight. The reaction mixture was applied to silica gel, concentrated and purified by silica gel chromatography (mobile phase: dichloromethane/2N ammonia in methanol 10/1 isocratic). This gave 95 mg of the target compound (42% of theory).

LC-MS (Method 2): $R_t$=0.70 min

MS (ESIpos): m/z=433 (M+H)$^+$ $^1$H NMR (400 MHz, DMSO-d$_6$): δ=1.07 (s, 3H), 1.49-1.68 (m, 2H), 2.31 (s, 3H), 2.54 (s, 3H, obscured by DMSO signal), 3.26 (br. s, 2H), 3.51-3.68 (m, 2H), 5.28 (s, 2H), 6.91 (s, 1H), 7.22 (t, 2H), 7.53-7.70 (m, 2H), 8.50 (s, 1H).

Example 271 ent-N-(2-Amino-4-hydroxy-2-methylbutyl)-8-[(2,6-difluorobenzyl)oxy]-2,6-dimethylimidazo[1,2-a]pyridine-3-carboxamide (Enantiomer A)

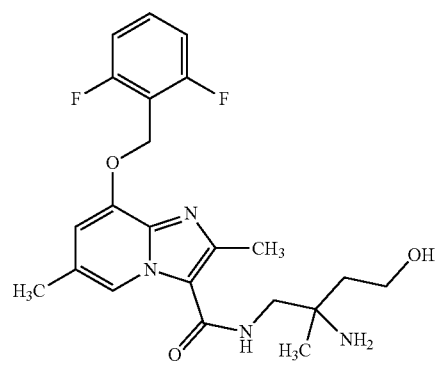 [SMILES: Cc1cc(OCc2c(F)cccc2F)c2nc(C)c(C(=O)NCC(C)(N)CCO)n2c1]

187 mg of Example 270 were separated into the enantiomers by preparative separation on a chiral phase

[column: Daicel Chiralcel OZ-H, 5 µm, 250×20 mm; mobile phase: 50% isohexane, 50% ethanol+0.2% diethylamine; flow rate: 15 ml/min; 40° C.; detection: 220 nm]. The product fractions were collected on dry ice, combined and concentrated on a rotary evaporator (bath temperature 30° C.) to a residual volume of about 15 ml, and about 60 ml of water were added. The solution obtained was frozen and lyophilized.

Enantiomer A: Yield: 63 mg (99% ee)

$R_t$=5.57 min [Daicel Chiralcel OZ-H, 5 m, 250×4.6 mm; mobile phase: 100% ethanol+0.2% diethylamine; flow rate 1.0 ml/min; 40° C.; detection: 235 nm].

Specific rotation [α] (365 nm, 20.2° C.)=−8.3° (c=0.005 g/ml, acetonitrile)

Example 272 ent-N-(2-Amino-4-hydroxy-2-methylbutyl)-8-[(2,6-difluorobenzyl)oxy]-2-methylimidazo[1,2-a]-pyridine-3-carboxamide (Enantiomer A)

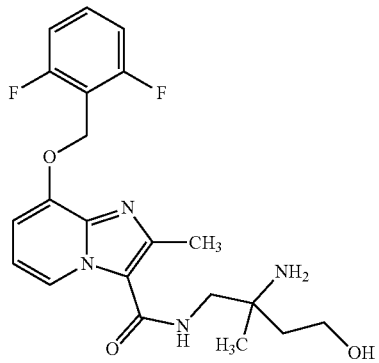 [SMILES: Cc1nc2c(OCc3c(F)cccc3F)cccn2c1C(=O)NCC(C)(N)CCO]

Under argon, 257 mg (0.51 mmol) of ent-N-[2-amino-4-(benzyloxy)-2-methylbutyl]-8-[(2,6-difluorobenzyl)oxy]-2-methylimidazo[1,2-a]pyridine-3-carboxamide (enantiomer A) Example 266 were initially charged in 5.2 ml of ethanol, and 54 mg of palladium on activated carbon (10%) and 1.54 ml (15.2 mmol) of cyclohexene were added. The reaction mixture was stirred under reflux for 6.5 h and then applied to Celite and purified by silica gel chromatography (mobile phase: dichloromethane/2N ammonia in methanol 20/1). This gave 122 mg of the target compound (56% of theory; purity 98%).

LC-MS (Method 2): $R_t$=0.60 min

MS (ESIpos): m/z=419 (M+H)⁺

¹H NMR (400 MHz, DMSO-$d_6$): δ=1.03 (s, 3H), 1.46-1.62 (m, 2H), 1.71 (br. s, 2H), 2.55 (s, 3H, obscured by DMSO signal), 3.19-3.28 (m, 2H), 3.52-3.68 (m, 2H), 4.75 (br. s, 1H), 5.30 (s, 2H), 6.92 (t, 1H), 7.00 (d, 1H), 7.22 (t, 2H), 7.59 (quintet, 1H), 7.63-7.73 (m, 1H), 8.67 (d, 1H).

Example 273 rac-N-(2-Amino-3-hydroxy-2-methylpropyl)-8-[(2,6-difluorobenzyl)oxy]-2-methylimidazo[1,2-a]-pyridine-3-carboxamide

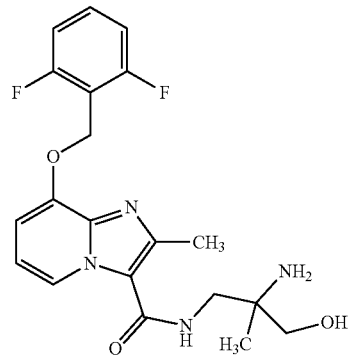 [SMILES: Cc1nc2c(OCc3c(F)cccc3F)cccn2c1C(=O)NCC(C)(N)CO]

Under argon, 800 mg (1.57 mmol) of rac-N-[2-amino-3-(benzyloxy)-2-methylpropyl]-8-[(2,6-difluorobenzyl)oxy]-2-methylimidazo[1,2-a]pyridine-3-carboxamide Example 263 were initially charged in 16.2 ml of ethanol, and 167 mg of palladium on activated carbon (10%) and 4.77 ml (47.1 mmol) of cyclohexene were added. The reaction mixture was stirred under reflux for 18 h and then applied to Celite and purified by silica gel chromatography (mobile phase: dichloromethane/methanol 10/1, dichloromethane/2N ammonia in methanol 10/1). This gave 366 mg of the target compound (56% of theory; purity 97%).

LC-MS (Method 2): $R_t$=0.54 min

MS (ESIpos): m/z=405 (M+H)⁺

¹H NMR (400 MHz, DMSO-$d_6$): δ=0.96 (s, 3H), 1.79 (br. s, 2H), 2.56 (s, 3H, superimposed by DMSO signal), 3.19-3.33 (m, 4H; superimposed by water signal), 4.74-4.80 (m, 1H), 5.30 (s, 2H), 6.92 (t, 1H), 7.01 (d, 1H), 7.22 (t, 2H), 7.55-7.69 (m, 2H), 8.69 (d, 1H).

Example 274 ent-N-(2-Amino-2-methylbutyl)-2,6-dimethyl-8-[(2,3,6-trifluorobenzyl)oxy]imidazo[1,2-a]-pyridine-3-carboxamide (Enantiomer A)

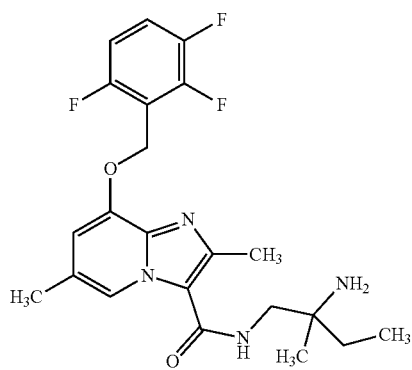 [SMILES: CCC(C)(N)CNC(=O)c1c(C)nc2c(OCc3c(F)ccc(F)c3F)cc(C)cn12]

Under argon, 383 mg (0.56 mmol) of ent-benzyl {1-[({2,6-dimethyl-8-[(2,3,6-trifluorobenzyl)oxy]imidazo[1,2-a]

pyridin-3-yl}carbonyl)amino]-2-methylbutan-2-yl}carbamate trifluoroacetate (enantiomer A) Example 278A were initially charged in 5.75 ml of ethanol, and 39 mg of palladium(II) hydroxide on activated carbon (20%) were added. The reaction mixture was hydrogenated at standard pressure at RT for 2 h, applied to Celite and purified by silica gel chromatography (mobile phase: dichloromethane/2 N ammonia in methanol=40/1). This gave 208 mg of the target compound (85% of theory).

LC-MS (Method 2): $R_t$=0.62 min

MS (ESIpos): m/z=435 (M+H)$^+$ $^1$H NMR (400 MHz, DMSO-d$_6$): δ=0.86 (t, 3H), 0.97 (s, 3H), 1.31-1.39 (m, 2H), 1.42 (br. s, 2H), 2.31 (s, 3H), 2.53 (s, 3H, superimposed by DMSO signal), 3.14-3.26 (m, 2H), 5.34 (s, 2H), 6.92 (s, 1H), 7.25-7.34 (m, 1H), 7.58-7.72 (m, 2H), 8.49 (s, 1H).

Single crystal X-ray structure analysis confirmed the S configuration for this enantiomer.

Example 275 ent-N-(2-Amino-2-methylbutyl)-2,6-dimethyl-8-[(2,3,6-trifluorobenzyl)oxy]imidazo[1,2-a]-pyridine-3-carboxamide (Enantiomer B)

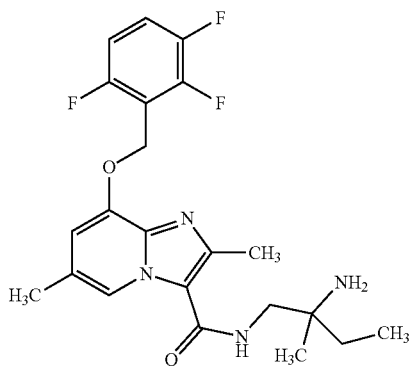 [SMILES: CCC(C)(N)CNC(=O)c1c(C)nc2c(OCc3c(F)ccc(F)c3F)cc(C)cn12]

Under argon, 200 mg (0.29 mmol) of ent-benzyl {1-[({2,6-dimethyl-8-[(2,3,6-trifluorobenzyl)oxy]imidazo[1,2-a]pyridin-3-yl}carbonyl)amino]-2-methylbutan-2-yl}carbamate trifluoroacetate (enantiomer B) Example 279A were initially charged in 3.0 ml of ethanol, and 10.3 mg of palladium(II) hydroxide on activated carbon (20%) were added. The reaction mixture was hydrogenated under atmospheric pressure at RT for 6 h. Another 10.3 mg of palladium(II) hydroxide on activated carbon (20%) were added, and the mixture was hydrogenated under atmospheric pressure at RT for 1 h. The reaction mixture was applied to Celite and purified by silica gel chromatography (mobile phase: dichloromethane/2 N ammonia in methanol=40/1). This gave 92 mg of the target compound (72% of theory).

LC-MS (Method 2): $R_t$=0.66 min

MS (ESIpos): m/z=435 (M+H)$^+$ $^1$H NMR (400 MHz, DMSO-d$_6$): δ=0.87 (t, 3H), 0.98 (s, 3H), 1.32-1.41 (m, 2H), 1.81 (br. s, 2H), 2.31 (s, 3H), 2.54 (s, 3H, superimposed by DMSO signal), 3.15-3.28 (m, 2H), 5.34 (s, 2H), 6.92 (s, 1H), 7.25-7.34 (m, 1H), 7.59-7.73 (m, 2H), 8.49 (s, 1H).

Example 276

N-(2-Amino-2-methylpropyl)-2,6-dimethyl-8-[(2,3,6-trifluorobenzyl)oxy]imidazo[1,2-a]pyridine-3-carboxamide

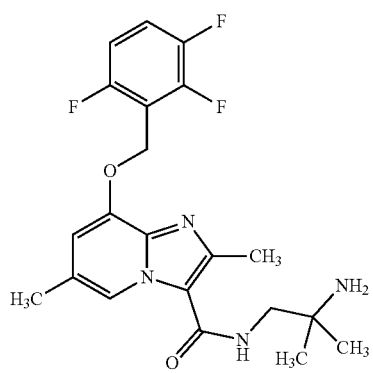 [SMILES: Cc1cc(OCc2c(F)ccc(F)c2F)c2nc(C)c(C(=O)NCC(C)(C)N)n2c1]

70 mg (0.20 mmol) of 2,6-dimethyl-8-[(2,3,6-trifluorobenzyl)oxy]imidazo[1,2-a]pyridine-3-carboxylic acid Example 265A, 84 mg (0.22 mmol) of O-(7-azabenzotriazol-1-yl)-N,N,N'N'-tetramethyluronium hexafluorophosphate (HATU) and 77 mg (0.60 mmol) of N,N-diisopropylethylamine were dissolved in 1.3 ml of DMF, and after 20 min at 0° C., 19.4 mg (0.22 mmol) of 2-methylpropane-1,2-diamine were added. The mixture was stirred at 0° C. for 45 min and then purified by preparative HPLC (method: RP18 column, mobile phase: acetonitrile/water gradient with addition of 0.1% TFA). The product fraction obtained was taken up in dichloromethane and washed twice with saturated aqueous sodium bicarbonate solution. The aqueous phase was extracted twice with dichloromethane. The combined organic phases were dried over sodium sulphate, filtered, concentrated and lyophilized. This gave 54 mg (64% of theory) of the title compound.

LC-MS (Method 2): $R_t$=0.65 min

MS (ESpos): m/z=421 (M+H)$^+$ $^1$H NMR (500 MHz, DMSO-d$_6$): δ=1.05 (s, 6H), 1.93 (br. s, 2H), 2.30 (s, 3H), 2.54 (s, 3H; superimposed by DMSO peak), 3.21 (d, 2H), 5.32 (s, 2H), 6.92 (s, 1H), 7.27-7.32 (m, 1H), 7.62-7.74 (m, 2H), 8.48 (s, 1H).

Example 277 rac-N-(2-Amino-2-methylpentyl)-8-[(2,6-difluorobenzyl)oxy]-7-fluoro-2-methylimidazo[1,2-a]-pyridine-3-carboxamide

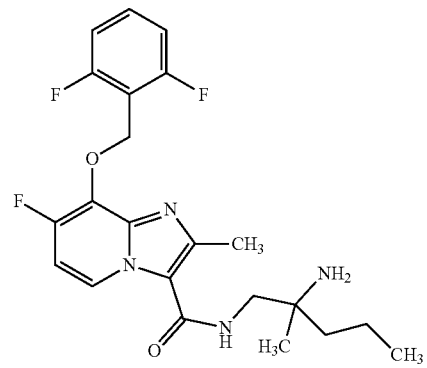 [SMILES: CCCC(C)(N)CNC(=O)c1c(C)nc2c(OCc3c(F)cccc3F)c(F)ccn12]

50 mg (0.15 mmol) of 8-[(2,6-difluorobenzyl)oxy]-7-fluoro-2-methylimidazo[1,2-a]pyridine-3-carboxylic acid Example 270A, 62 mg (0.16 mmol) of O-(7-azabenzotriazol-1-yl)-N,N,N'N'-tetramethyluronium hexafluorophosphate (HATU) and 58 mg (0.45 mmol) of N,N-diisopropylethylamine were dissolved in 1.0 ml of DMF, and after 20 min at 0° C., 21.4 mg (0.18 mmol) of 2-methylpentane-1,2-diamine were added. The mixture was stirred at 0° C. for 1.5 h, acetonitrile/TFA were added and the mixture was purified by preparative HPLC (method: RP18 column, mobile phase: acetonitrile/water gradient with addition of 0.1% TFA). The product fraction obtained was taken up in dichloromethane and washed with saturated aqueous sodium bicarbonate solution. The aqueous phase was extracted twice with dichloromethane. The combined organic phases were dried over sodium sulphate, filtered, concentrated and lyophilized. This gave 31 mg (45% of theory; purity 94%) of the title compound.

LC-MS (Method 2): $R_t$=0.77 min

MS (ESpos): m/z=435 (M+H)$^+$

1H NMR (400 MHz, DMSO-d6): δ=0.83-0.92 (m, 3H), 1.02 (s, 3H), 1.26-1.43 (m, 4H), 1.87 (br. s, 2H), 2.63 (s, 3H), 3.15-3.30 (m, 2H), 5.60 (s, 2H), 6.97-7.06 (m, 1H), 7.08-7.18 (m, 2H), 7.51 (quintet, 1H), 7.64-7.78 (m, 1H), 8.77 (dd, 1H).

Example 278 ent-N-(2-amino-2-methylpentyl)-8-[(2,6-difluorobenzyl)oxy]-6-methoxy-2-methylimidazo[1,2-a]pyridine-3-carboxamide (Enantiomer B)

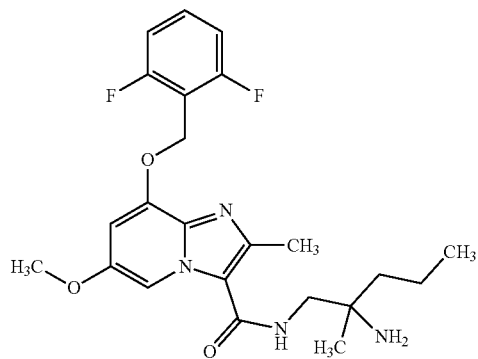 [SMILES: CCCC(C)(N)CNC(=O)c1c(C)nc2c(OCc3c(F)cccc3F)cc(OC)cn12]

Under argon, 9 mg of 20% palladium(II) hydroxide on carbon were added to 180 mg (0.26 mmol) of ent-benzyl-{1-[({8-[(2,6-difluorobenzyl)oxy]-6-methoxy-2-methylimidazo[1,2-a]pyridin-3-yl}carbonyl)amino]-2-methylpentan-2-yl}carbamate trifluoroacetate from Example 290A in 2.8 ml of ethanol, and the mixture was hydrogenated at RT and under standard pressure for 2 h. The reaction mixture was filtered off, the filter cake was washed with ethanol and the filtrate was concentrated. The residue was purified by silica gel chromatography (mobile phase: dichloromethane/2N ammonia in methanol=40/1). The isolated product fraction was separated by preparative HPLC (RP 18 column, mobile phase: acetonitrile/water gradient with addition of 0.1% TFA). The product fractions were concentrated on a rotary evaporator. The residue was taken up in dichloromethane and washed twice with saturated aqueous sodium bicarbonate solution, and the combined aqueous phases were extracted twice with dichloromethane. The organic phase was dried over sodium sulphate, filtered off and concentrated, and the residue was lyophilised. This gave 73 mg of the target compound (63% of theory).

LC-MS (Method 2): $R_t$=0.68 min

MS (ESpos): m/z=447 (M+H)$^+$ $^1$H-NMR (400 MHz, DMSO-d$_6$): δ=0.87 (t, 3H), 0.99 (s, 3H), 1.23-1.41 (m, 4H), 2.53 (s, 3H), 3.14-3.26 (m, 2H), 3.79 (s, 3H), 5.30 (s, 2H), 6.87 (d, 1H), 7.24 (quin., 2H), 7.54-7.65 (m, 2H), 8.37 (d, 1H).

Example 279 ent-N-(2-amino-2-methylbutyl)-8-[(2,6-difluorobenzyl)oxy]-6-methoxy-2-methylimidazo[1,2-a]pyridine-3-carboxamide (Enantiomer A)

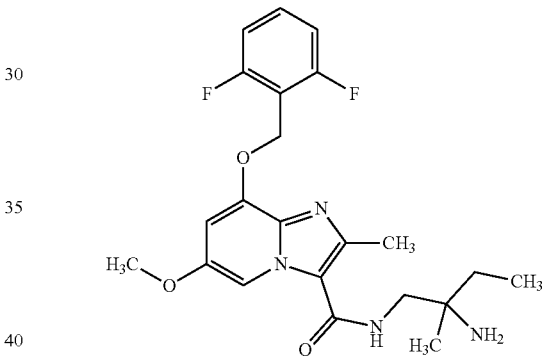

Under argon, 8 mg of 20% palladium(II) hydroxide on carbon were added to 157 mg (0.23 mmol) of ent-benzyl-{1-[({8-[(2,6-difluorobenzyl)oxy]-6-methoxy-2-methylimidazo[1,2-a]pyridin-3-yl}carbonyl)amino]-2-methylbutan-2-yl}carbamate trifluoroacetate (enantiomer A) from Example 291A in 2.5 ml of ethanol, and the mixture was hydrogenated at RT and under standard pressure for 2 h. The reaction mixture was filtered off through a Millipore filter, the filter cake was washed with ethanol and the filtrate was concentrated. The residue was purified by silica gel chromatography (mobile phase: dichloromethane/2N ammonia in methanol=40/1). This gave 90 mg of the target compound (90% of theory).

LC-MS (Method 2): $R_t$=0.63 min

MS (ESpos): m/z=433 (M+H)$^+$ $^1$H-NMR (400 MHz, DMSO-d$_6$): δ=0.87 (t, 3H), 0.97 (s, 3H), 1.31-1.39 (m, 2H), 1.40-1.49 (m, 2H), 2.53 (s, 3H), 3.14-3.27 (m, 2H), 3.79 (s, 3H), 5.30 (s, 2H), 6.87 (d, 1H), 7.24 (quin, 2H), 7.54-7.64 (m, 2H), 8.39 (d, 1H).

Example 280 ent-N-(2-amino-2-methylpentyl)-8-[(2,6-difluorobenzyl)oxy]-2-methyl-6-(morpholin-4-yl)imidazo[1,2-a]pyridine-3-carboxamide (Enantiomer B)

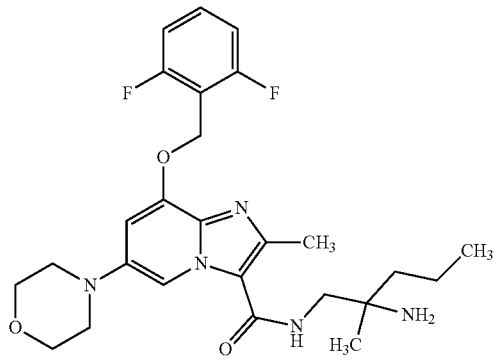 [SMILES: CCCC(C)(N)CNC(=O)c1c(C)nc2c(OCc3c(F)cccc3F)cc(N3CCOCC3)cn12]

Under argon, 1.2 mg of 20% palladium(II) hydroxide on carbon were added to 22 mg (0.04 mmol) of ent-benzyl-{1-[({8-[(2,6-difluorobenzyl)oxy]-2-methyl-6-(morpholin-4-yl)imidazo[1,2-a]pyridin-3-yl}carbonyl)amino]-2-methylpentan-2-yl}carbamate (enantiomer B) from Example 293A in 0.38 ml of ethanol, and the mixture was hydrogenated at RT and under standard pressure for 2 h. The reaction mixture was filtered through a Millipore filter, the filter cake was washed with ethanol and the filtrate was concentrated. The residue was purified by preparative thin-layer chromatography (mobile phase: dichloromethane/2N ammonia in methanol=20/1). This gave 9 mg of the target compound (48% of theory; purity 92%).

LC-MS (Method 2): $R_t$=0.68 min
MS (ESpos): m/z=502 (M+H)$^+$
$^1$H-NMR (400 MHz, DMSO-d$_6$): δ=0.87 (t, 3H), 0.98 (s, 3H), 1.26-1.36 (m, 2H), 1.38-1.45 (m, 2H), 2.55-2.57 (s, 3H, hidden under solvent peak), 3.05 (t, 4H), 3.16-3.22 (m, 2H), 3.77 (t, 4H), 5.31 (s, 2H), 6.99-7.05 (m, 1H), 7.20-7.28 (m, 2H), 7.54-7.64 (m, 2H), 8.20 (s, 1H).

Example 281 ent-N-(2-amino-2-methylpentyl)-6-cyclopropyl-8-[(2,6-difluorobenzyl)oxy]-2-methylimidazo[1,2-a]pyridine-3-carboxamide (Enantiomer B)

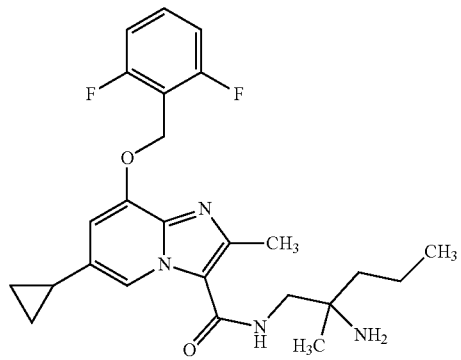 [SMILES: CCCC(C)(N)CNC(=O)c1c(C)nc2c(OCc3c(F)cccc3F)cc(C3CC3)cn12]

Under argon, 7.8 mg of 10% palladium on carbon were added to 5.52 mg (0.07 mmol) of ent-benzyl-{1-[({6-cyclopropyl-8-[(2,6-difluorobenzyl)oxy]-2-methylimidazo[1,2-a]pyridin-3-yl}carbonyl)amino]-2-methylpentan-2-yl}carbamate trifluoroacetate (enantiomer B) from Example 294A in 0.76 ml of ethanol, and the mixture was hydrogenated at RT and under standard pressure for 1 h. The reaction mixture was filtered through a Millipore filter, the filter cake was washed with ethanol and the filtrate was concentrated. The residue was taken up in dichloromethane and washed twice with saturated aqueous sodium bicarbonate solution. The combined aqueous phases were extracted twice with dichloromethane. The combined organic phases were dried over sodium sulphate and filtered, and the filtrate was concentrated and dried under high vacuum. The product was purified by silica gel chromatography (mobile phase: dichloromethane/2N ammonia in methanol=40/1). This gave 27 mg of the target compound (76% of theory).

LC-MS (Method 2): $R_t$=0.79 min
MS (ESpos): m/z=457 (M+H)$^+$
$^1$H-NMR (400 MHz, DMSO-d$_6$): δ=0.72-0.77 (m, 2H), 0.87 (t, 3H), 0.90-0.97 (m, 2H), 0.99 (s, 3H), 1.22-1.42 (m, 4H), 1.43-1.51 (m, 2H), 1.94-2.03 (m, 1H), 2.52 (s, 3H), 3.13-3.26 (m, 2H), 5.31 (s, 2H), 6.68 (s, 1H), 7.23 (quin, 2H), 7.54-7.66 (m, 2H), 8.50 (s, 1H).

Example 282 rac-N-(2-amino-3-fluoro-2-methylpropyl)-8-[(2,6-difluorobenzyl)oxy]-2,6-dimethylimidazo[1,2-a]pyridine-3-carboxamide formate

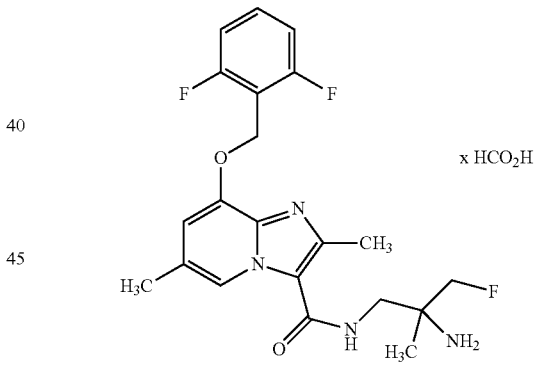

Under argon, 1.4 mg (0.01 mmol, 20%) of palladium(II) hydroxide were added to 54 mg (0.09 mmol) of rac-benzyl-{1-[({8-[(2,6-difluorobenzyl)oxy]-2,6-dimethylimidazo[1,2-a]pyridin-3-yl}carbonyl)amino]-3-fluoro-2-methylpropan-2-yl}carbamate from Example 302A in 5 ml of ethanol, and the reaction mixture was hydrogenated at standard pressure overnight. The mixture was then filtered through Celite, the filter cake was washed with ethanol and the filtrate was concentrated and purified by preparative HPLC (RP18 column, mobile phase: acetonitrile/water gradient with addition of 0.1% TFA). The product fractions were concentrated on a rotary evaporator. This gave 18.4 mg of the target compound (40% of theory).

LC-MS (Method 2): $R_t$=0.66 min
MS (ESpos): m/z=421 (M-HCO$_2$H+H)$^+$
$^1$H-NMR (400 MHz, DMSO-d$_6$): δ=1.08 (d, 3H), 2.31 (s, 3H), 2.53 (s, 3H), 3.28-3.43 (m, 2H), 4.17 (s, 1H), 4.29 (s, 1H), 5.29 (s, 2H), 6.93 (s, 1H), 7.24 (quin., 2H), 7.54-7.65 (m, 1H), 7.74 (t, 1H), 8.19 (s, 1H), 8.47 (s, 1H).

Example 283 ent-N-(2-amino-3-fluoro-2-methylpropyl)-8-[(2,6-difluorobenzyl)oxy]-2,6-dimethylimidazo[1,2-a]pyridine-3-carboxamide (Enantiomer A)

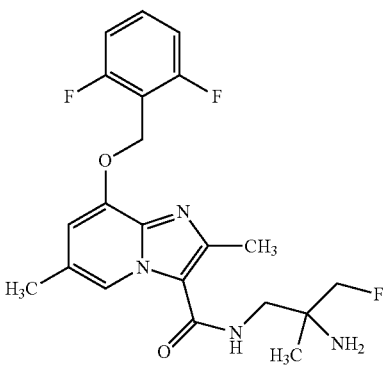 [SMILES: Cc1cc(OCc2c(F)cccc2F)c2nc(C)c(C(=O)NCC(C)(N)CF)n2c1]

Under argon, 14.8 mg (0.02 mmol) of palladium(II) hydroxide (20%) on activated carbon were added to 148 mg (0.21 mmol, purity 95%) of ent-benzyl-{1-[({8-[(2,6-difluorobenzyl)oxy]-2,6-dimethylimidazo[1,2-a]pyridin-3-yl}carbonyl)amino]-3-fluoro-2-methylpropan-2-yl}carbamate trifluoroacetate (enantiomer A) from Example 303A in 9 ml of ethanol, and the reaction mixture was hydrogenated at standard pressure for 5.5 h. The mixture was then filtered through a Millipore filter, the filter cake was washed with ethanol and the filtrate was then concentrated. The residue was purified by preparative HPLC (RP18 column, mobile phase: acetonitrile/water gradient with addition of 0.1% TFA). The collected product fractions were taken up in dichloromethane and a little methanol and washed twice with saturated aqueous sodium bicarbonate solution. The combined organic phases were extracted twice with dichloromethane. The combined organic phases were dried over sodium sulphate, filtered off and concentrated. This gave 61 mg of the target compound (68% of theory).

LC-MS (Method 2): $R_t$=0.61 min
MS (ESpos): m/z=421 (M+H)$^+$
$^1$H-NMR (400 MHz, DMSO-d$_6$): δ=1.01-1.06 (m, 3H), 1.67 (br. s, 2H), 2.31 (s, 3H), 2.53 (s, 3H; superimposed by solvent peak), 3.24-3.39 (m, 2H; superimposed by water peak), 4.07-4.15 (m, 1H), 4.19-4.27 (m, 1H), 5.29 (s, 2H), 6.92 (s, 1H), 7.20-7.28 (m, 2H), 7.54-7.64 (m, 1H), 7.68 (t, 1H), 8.47 (s, 1H).

Example 284 ent-N-(2-amino-3-fluoro-2-methylpropyl)-8-[(2,6-difluorobenzyl)oxy]-2,6-dimethylimidazo[1,2-a]pyridine-3-carboxamide (Enantiomer B)

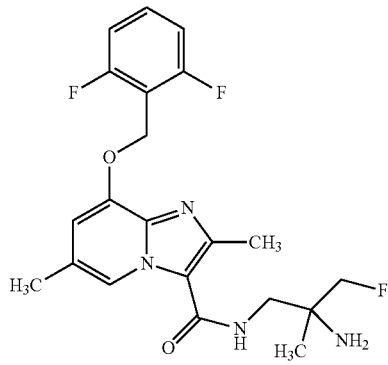 [SMILES: Cc1cc(OCc2c(F)cccc2F)c2nc(C)c(C(=O)NCC(C)(N)CF)n2c1]

Under argon, 20 mg (0.03 mmol) of palladium(II) hydroxide (20%) on activated carbon were added to 201 mg (0.29 mmol, 95% pure) of ent-benzyl-{1-[({8-[(2,6-difluorobenzyl)oxy]-2,6-dimethylimidazo[1,2-a]pyridin-3-yl}carbonyl)amino]-3-fluoro-2-methylpropan-2-yl}carbamate trifluoroacetate (enantiomer B) from Example 304A in 9 ml of ethanol, and the reaction mixture was hydrogenated at standard pressure for 4 h. The reaction mixture was filtered through a Millipore filter, the filter cake was washed with ethanol and the filtrate was then concentrated. The residue was taken up in acetonitrile/water, TFA was added and the mixture was purified twice by preparative HPLC (RP 18 column, mobile phase: acetonitrile/water gradient with addition of 0.1% TFA). The collected product fractions were concentrated. The residue was taken up in dichloromethane and a little methanol and washed twice with saturated aqueous sodium bicarbonate solution. The combined aqueous phases were extracted twice with dichloromethane. The combined organic phases were dried over sodium sulphate, filtered off, concentrated and lyophilised. This gave 69 mg of the target compound (59% of theory).

LC-MS (Method 2): $R_t$=0.58 min
MS (ESpos): m/z=421 (M+H)$^+$
$^1$H-NMR (400 MHz, DMSO-d$_6$): δ=1.01-1.07 (m, 3H), 1.64 (br. s, 2H), 2.31 (s, 3H), 2.53 (s, 3H; superimposed by solvent peak), 3.24-3.39 (m, 2H; superimposed by water peak), 4.08-4.15 (m, 1H), 4.20-4.27 (m, 1H), 5.29 (s, 2H), 6.92 (s, 1H), 7.20-7.28 (m, 2H), 7.55-7.64 (m, 1H), 7.66 (t, 1H), 8.47 (s, 1H).

Example 285 ent-N-(2-amino-3-fluoro-2-methylpropyl)-2,6-dimethyl-8-[(2,3,6-trifluorobenzyl)oxy]imidazo[1,2-a]pyridine-3-carboxamide (Enantiomer A)

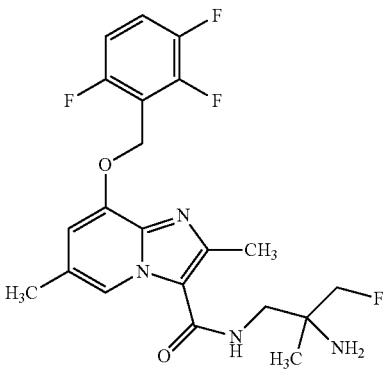 [SMILES: Cc1cc(OCc2c(F)ccc(F)c2F)c2nc(C)c(C(=O)NCC(C)(N)CF)n2c1]

Under argon, 15 mg (0.02 mmol) of palladium(II) hydroxide (20%) on activated carbon were added to 170 mg (0.21 mmol, 87% pure) of ent-benzyl-{1-[({2,6-dimethyl-8-[(2,3,6-trifluoro-benzyl)oxy]imidazo[1,2-a]pyridin-3-yl}carbonyl)amino]-3-fluoro-2-methylpropan-2-yl}carbamate trifluoroacetate (enantiomer A) from Example 305A in 9 ml of ethanol, and the reaction mixture was hydrogenated at standard pressure for 5.5 hours. The mixture was then filtered through a Millipore filter, the filter cake was washed with ethanol and the filtrate was then concentrated. The residue was purified by preparative HPLC (RP18 column, mobile phase: acetonitrile/water gradient with addition of 0.1% TFA). The collected fractions were taken up in dichloromethane and a little methanol and washed twice with saturated aqueous sodium bicarbonate solution. The combined aqueous phases were extracted twice with dichloromethane. The combined organic phases were dried over sodium sulphate, filtered and concentrated. This gave 68 mg of the target compound (71% of theory).

LC-MS (Method 2): $R_t$=0.62 min
MS (ESpos): m/z=439 (M+H)$^+$
$^1$H-NMR (400 MHz, DMSO-d$_6$): δ=1.00-1.07 (m, 3H), 1.67 (br. s, 2H), 2.31 (s, 3H), 2.53 (s, 3H; superimposed by solvent peak), 3.24-3.39 (m, 2H; superimposed by water peak), 4.08-4.15 (m, 1H), 4.20-4.27 (m, 1H), 5.34 (s, 2H), 6.92 (s, 1H), 7.25-7.34 (m, 1H), 7.62-7.73 (m, 2H), 8.48 (s, 1H).

Example 286 ent-N-(2-amino-3-fluoro-2-methylpropyl)-2,6-dimethyl-8-[(2,3,6-trifluorobenzyl)oxy]imidazo[1,2-a]pyridine-3-carboxamide (Enantiomer B)

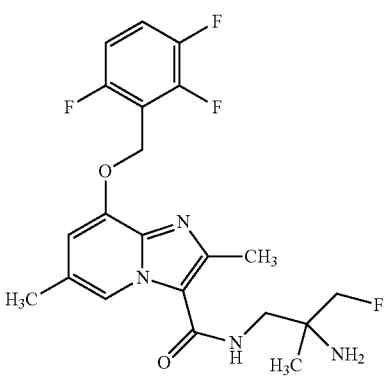 [SMILES: Cc1cc(OCc2c(F)ccc(F)c2F)c2nc(C)c(C(=O)NCC(C)(N)CF)n2c1]

Under argon, 20 mg (0.03 mmol) of palladium(II) hydroxide (20%) on activated carbon were added to 202 mg (0.28 mmol) of ent-benzyl-{1-[({2,6-dimethyl-8-[(2,3,6-trifluorobenzyl)oxy]imidazo[1,2-a]pyridin-3-yl}carbonyl)amino]-3-fluoro-2-methylpropan-2-yl}carbamate trifluoroacetate (enantiomer B) from Example 306A in 9.1 ml of ethanol, and the reaction mixture was hydrogenated at standard pressure for 2 h. The mixture as then filtered through a Millipore filter, and the filtrate was concentrated and dried under high vacuum. The residue was taken up in acetonitrile/water, TFA was added and the product was purified by preparative HPLC (RP18 column, mobile phase: acetonitrile/water gradient with addition of 0.1% TFA). The collected product fractions were taken up in dichloromethane and a little methanol and washed twice with saturated aqueous sodium bicarbonate solution. The combined aqueous phases were extracted twice with dichloromethane. The combined organic phases were dried over sodium sulphate, filtered off, concentrated and lyophilised. This gave 82 mg of the target compound (66% of theory).

LC-MS (Method 2): $R_t$=0.64 min
MS (ESpos): m/z=439 (M+H)$^+$
$^1$H-NMR (400 MHz, DMSO-d$_6$): δ=1.01-1.06 (m, 3H), 1.65 (br. s, 2H), 2.31 (s, 3H), 2.53 (s, 3H; superimposed by solvent peak), 3.24-3.39 (m, 2H, superimposed by water peak), 4.08-4.14 (m, 1H), 4.19-4.27 (m, 1H), 5.34 (s, 2H), 6.92 (s, 1H), 7.25-7.34 (m, 1H), 7.62-7.73 (m, 2H), 8.48 (s, 1H).

Example 287 ent-N-(2-amino-2-methylbutyl)-8-[(2,6-difluorobenzyl)oxy]-6-(difluoromethyl)-2-methylimidazo[1,2-a]pyridine-3-carboxamide formate (Enantiomer A)

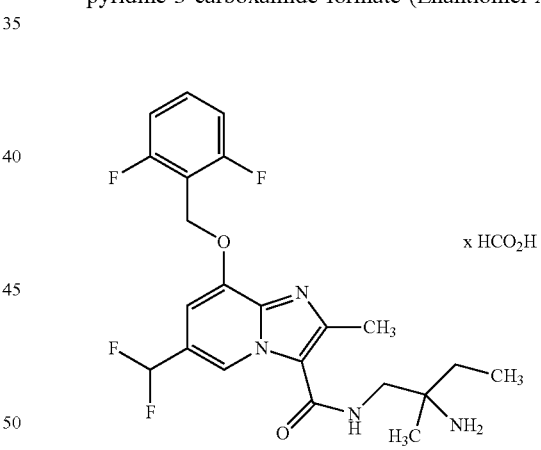

Under argon, 17 mg of 10% palladium on carbon were added to 122 mg (0.21 mmol) of ent-benzyl-{1-[({8-[(2,6-difluorobenzyl)oxy]-6-(difluoromethyl)-2-methylimidazo[1,2-a]pyridin-3-yl}carbonyl)amino]-2-methylbutan-2-yl}carbamate (enantiomer A) from Example 311A in 2 ml of DMF, and the mixture was hydrogenated at RT and under standard pressure for 2 h. The reaction mixture was filtered through Celite, the filter cake was washed with DMF and the filtrate was concentrated. The residue was dissolved in dichloromethane and purified by silica gel chromatography (mobile phase: dichloromethane/7 N ammonia in methanol=1/0 to 30/1). The product fractions were concentrated. The residue was re-purified by preparative HPLC (RP18 column, mobile phase: acetonitrile/water gradient with addition of 0.05% formic acid). The product fractions were concentrated and the residue was dried under high vacuum. This gave 47 mg of the target compound (44% of theory).

LC-MS (Method 2): $R_t$=0.75 min

MS (ESpos): m/z=453 (M−HCO$_2$H+H)$^+$ $^1$H-NMR (400 MHz, DMSO-d$_6$): δ=0.91 (t, 3H), 1.12 (s, 3H), 1.43-1.60 (m, 2H), 2.58 (s, 3H), 3.30-3.46 (m, 2H; superimposed by water peak), 5.37 (s, 2H), 7.03-7.34 (m, 4H), 7.55-7.65 (m, 1H), 8.11 (br. s, 1H), 8.29 (s, 1H), 8.97 (s, 1H).

Example 288 ent-N-(2-amino-2-methylbutyl)-8-[(2,6-difluorobenzyl)oxy]-6-(difluoromethyl)-2-methylimidazo[1,2-a]pyridine-3-carboxamide (Enantiomer A)

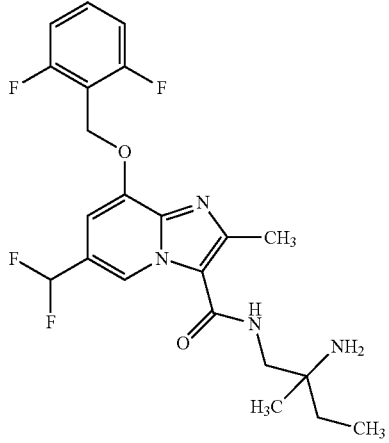 [SMILES: CCC(C)(N)CNC(=O)c1c(C)nc2c(OCc3c(F)cccc3F)cc(C(F)F)cn12]

16.6 mg (0.03 mmol) of ent-N-(2-amino-2-methylbutyl)-8-[(2,6-difluorobenzyl)oxy]-6-(difluoromethyl)-2-methylimidazo[1,2-a]pyridine-3-carboxamide formate from Example 287 were taken up in dichloromethane and a little methanol, and the mixture was washed twice with saturated aqueous sodium bicarbonate solution. The combined aqueous phases were extracted twice with dichloromethane. The combined organic phases were washed with saturated aqueous sodium chloride solution, then dried over sodium sulphate, filtered off and concentrated. This gave 13 mg of the target compound (85% of theory).

LC-MS (Method 2): $R_t$=0.79 min

MS (ESpos): m/z=453 (M+H)$^+$ $^1$H-NMR (400 MHz, DMSO-d$_6$): δ=0.87 (t, 3H), 0.98 (s, 3H), 1.29-1.43 (m, 2H), 1.58 (br. s, 2H), 2.57 (s, 3H), 3.22 (q, 2H), 5.37 (s, 2H), 7.02-7.33 (m, 4H), 7.55-7.65 (m, 1H), 7.79 (br. s, 1H), 8.99 (s, 1H).

Example 289 ent-N-(2-amino-2-methylpentyl)-8-[(2,6-difluorobenzyl)oxy]-6-(difluoromethyl)-2-methylimidazo[1,2-a]pyridine-3-carboxamide formate (Enantiomer B)

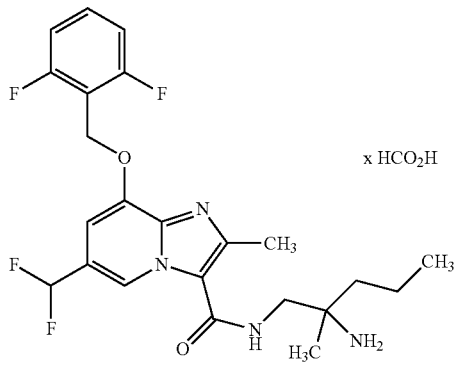 [SMILES: CCCC(C)(N)CNC(=O)c1c(C)nc2c(OCc3c(F)cccc3F)cc(C(F)F)cn12]

Under argon, 16 mg of 10% palladium on carbon were added to 121 mg (0.20 mmol) of ent-benzyl-{1-[({8-[(2,6-difluorobenzyl)oxy]-6-(difluoromethyl)-2-methylimidazo[1,2-a]pyridin-3-yl}carbonyl)amino]-2-methylpentan-2-yl}carbamate (enantiomer B) from Example 312A in 2 ml of DMF, and the mixture was hydrogenated at RT and under standard pressure for 2 hours. The mixture was then filtered through Celite, the filter cake was washed with DMF and the filtrate was concentrated. The residue was dissolved in dichloromethane and purified by silica gel chromatography (mobile phase: dichloromethane/7 N ammonia in methanol=1/0 to 30/1). The product fractions were concentrated. The residue was re-purified by preparative HPLC (RP18 column, mobile phase: acetonitrile/water gradient with addition of 0.05% formic acid). The product fractions were concentrated and the residue was dried under high vacuum. This gave 49 mg of the target compound (46% of theory).

LC-MS (Method 2): $R_t$=0.77 min

MS (ESpos): m/z=467 (M−HCO$_2$H+H)$^+$ $^1$H-NMR (400 MHz, DMSO-d$_6$): δ=0.89 (t, 3H), 1.13 (s, 3H), 1.29-1.55 (m, 4H), 2.58 (s, 3H), 3.30-3.45 (m, 2H; superimposed by water peak), 5.37 (s, 2H), 7.02-7.35 (m, 4H), 7.55-7.66 (m, 1H), 8.17 (br. s., 1H), 8.33 (s, 1H), 8.96 (s, 1H).

Example 290 ent-N-(2-amino-2-methylpentyl)-8-[(2,6-difluorobenzyl)oxy]-6-(difluoromethyl)-2-methylimidazo[1,2-a]pyridine-3-carboxamide (Enantiomer B)

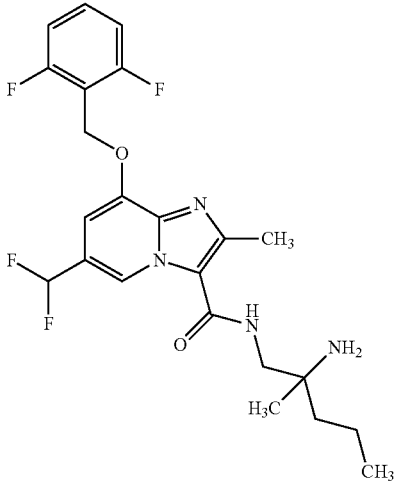 [SMILES: CCCC(C)(N)CNC(=O)c1c(C)nc2c(OCc3c(F)cccc3F)cc(C(F)F)cn12]

17 mg (0.03 mmol) of ent-N-(2-amino-2-methylpentyl)-8-[(2,6-difluorobenzyl)oxy]-6-(difluoromethyl)-2-methylimidazo[1,2-a]pyridine-3-carboxamide formate from Example 289 were taken up in dichloromethane and a little methanol, and the mixture was washed twice with saturated aqueous sodium bicarbonate solution. The combined aqueous phases were extracted twice with dichloromethane. The combined organic phases were washed with saturated aqueous sodium chloride solution, dried over sodium sulphate, filtered off and concentrated. This gave 15 mg of the target compound (96% of theory).

LC-MS (Method 2): $R_t$=0.83 min
MS (ESpos): m/z=467 (M+H)$^+$
$^1$H-NMR (400 MHz, DMSO-d$_6$): δ=0.87 (t, 3H), 0.99 (s, 3H), 1.25-1.41 (m, 4H), 1.51 (br. s, 2H), 2.57 (s, 3H), 3.22 (q, 2H), 5.37 (s, 2H), 7.02-7.33 (m, 4H), 7.55-7.65 (m, 1H), 7.80 (br. s, 1H), 8.98 (s, 1H).

Example 291 ent-N-(2-amino-3-fluoro-2-methylpropyl)-8-[(2,6-difluorobenzyl)oxy]-6-(difluoromethyl)-2-methylimidazo[1,2-a]pyridine-3-carboxamide (Enantiomer A)

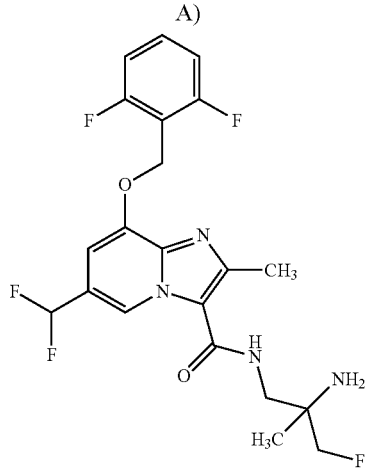

Under argon, 7.4 mg (0.01 mmol) of palladium(II) hydroxide (20%) on activated carbon were added to 74.6 mg (0.11 mmol) of ent-benzyl-{1-[({8-[(2,6-difluorobenzyl)oxy]-6-(difluoromethyl)-2-methylimidazo[1,2-a]pyridin-3-yl}carbonyl)amino]-3-fluoro-2-methylpropan-2-yl}carbamate trifluoroacetate (enantiomer A) from Example 313A in 4.5 ml of ethanol, and the mixture was hydrogenated at standard pressure for 4 hours. The reaction mixture was filtered through a Millipore filter, the filter cake was washed with ethanol and the filtrate was then concentrated. The residue was purified by preparative HPLC (RP18 column, mobile phase: acetonitrile/water gradient with addition of 0.1% TFA). The product fractions were taken up in dichloromethane and a little methanol and washed twice with saturated aqueous sodium bicarbonate solution. The combined aqueous phases were extracted twice with dichloromethane. The combined organic phases were dried over sodium sulphate, filtered off and concentrated. This gave 16 mg of the target compound (31% of theory).

LC-MS (Method 2): $R_t$=0.74 min
MS (ESpos): m/z=457 (M+H)$^+$
$^1$H-NMR (500 MHz, DMSO-d$_6$): δ=1.02-1.06 (m, 3H), 1.68 (br. s, 2H), 2.57 (s, 3H), 3.30-3.40 (m, 2H, partially obscured by water peak), 4.10-4.16 (m, 1H), 4.20-4.26 (m, 1H), 5.37 (s, 2H), 7.05-7.31 (m, 4H), 7.56-7.63 (m, 1H), 7.84 (t, 1H), 8.98 (s, 1H).

Example 292 ent-N-(2-amino-3-fluoro-2-methylpropyl)-8-[(2,6-difluorobenzyl)oxy]-6-(difluoromethyl)-2-methylimidazo[1,2-a]pyridine-3-carboxamide (Enantiomer B)

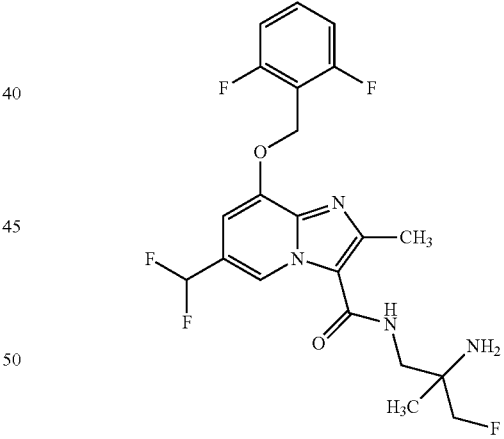

Under argon, 4.2 mg (0.01 mmol) of palladium(II) hydroxide (20%) on activated carbon were added to 47 mg (0.06 mmol, 89% pure) of ent-benzyl-{1-[({8-[(2,6-difluorobenzyl)oxy]-6-(difluoromethyl)-2-methylimidazo[1,2-a]pyridin-3-yl}carbonyl)amino]-3-fluoro-2-methylpropan-2-yl}carbamate trifluoroacetate (enantiomer B) from Example 314A in 2 ml of ethanol, and the mixture was hydrogenated at standard pressure for 5 hours. The mixture was then filtered through a Millipore filter, the filter cake was washed with ethanol and the filtrate was then concentrated. The residue was purified by preparative HPLC (RP18 column, mobile phase: acetonitrile/water gradient with addition of 0.1% TFA). The product fractions were taken up in dichloromethane and a little methanol and washed twice with saturated aqueous sodium bicarbonate solution. The combined aqueous phases were extracted twice with dichloromethane. The combined organic phases were dried over sodium sulphate, filtered and concentrated. The residue was taken up in dichloromethane and a little methanol and separated by thick-layer chromatography (mobile phase: dichloromethane/2 N ammonia in methanol=15:1). The product fractions were concentrated and lyophilised. This gave 16 mg of the target compound (56% of theory).

LC-MS (Method 2): $R_t$=0.75 min
MS (ESpos): m/z=457 (M+H)$^+$
$^1$H-NMR (500 MHz, DMSO-d$_6$): δ=1.02-1.06 (m, 3H), 1.71 (br. s, 2H), 2.57 (s, 3H), 3.30-3.40 (m, 2H, partially obscured by water peak), 4.10-4.16 (m, 1H), 4.20-4.26 (m, 1H), 5.37 (s, 2H), 7.05-7.31 (m, 4H), 7.56-7.63 (m, 1H), 7.84 (t, 1H), 8.98 (s, 1H).

Example 293 rac-N-(2-amino-2-methylpentyl)-2,6-dimethyl-8-[(2,3,6-trifluorobenzyl)oxy]imidazo[1,2-a]pyridine-3-carboxamide

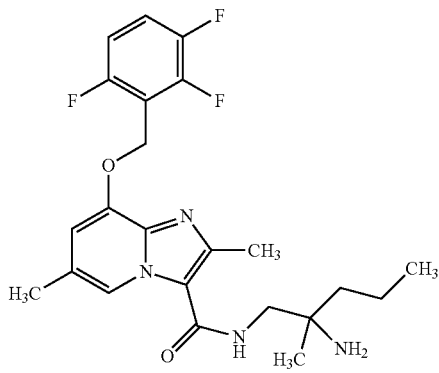 [SMILES: CCCC(C)(N)CNC(=O)c1c(C)nc2c(OCc3c(F)ccc(F)c3F)cc(C)cn12]

250 mg (0.71 mmol) of 2,6-dimethyl-8-[(2,3,6-trifluorobenzyl)oxy]imidazo[1,2-a]pyridine-3-carboxylic acid from Example 265A, 298 mg (0.79 mmol) of HATU and 0.37 ml (2.14 mmol) of N,N-diisopropylethylamine were stirred in 4.8 ml of DMF for 20 min. At 0° C., 103 mg (0.86 mmol, purity 97%) of rac-2-methylpentane-1,2-diamine were then added, and the mixture was stirred at 0° C. for 30 min. Acetonitrile/TFA was added to the reaction solution, and the product was purified by preparative HPLC (RP18 column, mobile phase: acetonitrile/water gradient with addition of 0.1% TFA). The product-containing fractions were concentrated and the residue was taken up in dichloromethane and washed once with saturated aqueous sodium bicarbonate solution. The aqueous phase was washed twice with dichloromethane, the combined organic phases were dried over sodium sulphate and filtered, the filtrate was concentrated and the residue was lyophilised. This gave 222 mg of the target compound (69% of theory).

LC-MS (Method 2): $R_t$=0.69 min
MS (ESpos): m/z=449 (M+H)$^+$
$^1$H-NMR (400 MHz, DMSO-d$_6$): 0.87 (t, 3H), 0.99 (s, 3H), 1.22-1.43 (m, 4H), 1.60 (br. s, 2H), 2.30 (s, 3H), 2.55 (s, 3H), 3.14-3.28 (m, 2H), 5.32 (s, 2H), 6.91 (s, 1H), 7.25-7.33 (m, 1H), 7.59-7.73 (m, 2H), 8.48 (s, 1H).

Example 294

Methyl N$^6$-({8-[(2,6-difluorobenzyl)oxy]-2,6-dimethylimidazo[1,2-a]pyridin-3-yl}carbonyl)-L-lysinate

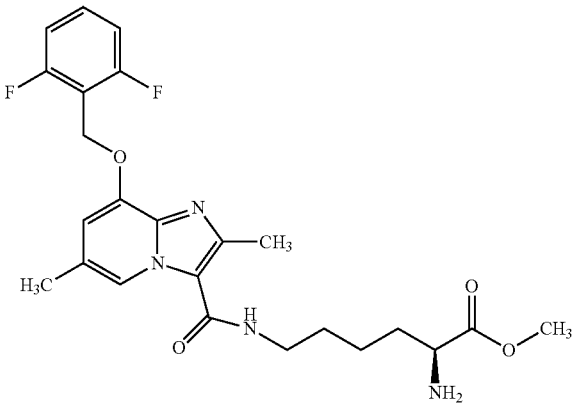 [SMILES: COC(=O)[C@@H](N)CCCCNC(=O)c1c(C)nc2c(OCc3c(F)cccc3F)cc(C)cn12]

75 mg (0.11 mmol) of methyl N$^2$-(tert-butoxycarbonyl)-N$^6$-({8-[(2,6-difluorobenzyl)oxy]-2,6-dimethyl-imidazo[1,2-a]pyridin-3-yl}carbonyl)-L-lysinate trifluoroacetate from Example 315A were initially charged in 0.54 ml of diethyl ether, 0.54 ml (1.08 mmol) of 2N hydrochloric acid in diethyl ether was added and the mixture was stirred at room temperature overnight. The reaction solution was concentrated and the residue was dissolved in dichloromethane and washed twice with saturated aqueous sodium bicarbonate solution. The combined aqueous phases were extracted twice with dichloromethane. The combined organic phases were dried over sodium sulphate, filtered and concentrated. The crude product was purified by thick-layer chromatography (mobile phase: dichloromethane/2N ammonia in methanol=20/1). This gave 22 mg of the target compound (42% of theory).

LC-MS (Method 2): $R_t$=0.64 min
MS (ESpos): m/z=475 (M+H)$^+$
$^1$H-NMR (400 MHz, DMSO-d$_6$): δ=1.31-1.42 (m, 2H), 1.43-1.65 (m, 4H), 1.66-1.81 (m, 2H), 2.30 (s, 3H), 2.47 (s, 3H), 3.25-3.29 (m, 2H), 3.60 (s, 3H), 5.28 (s, 2H), 6.87-6.91 (m, 1H), 7.19-7.27 (m, 2H), 7.54-7.64 (m, 1H), 7.82 (t, 1H), 8.42 (s, 1H).

Example 295 ent-N-(2-amino-2-methylpentyl)-2,6-dimethyl-8-[(2,3,6-trifluorobenzyl)oxy]imidazo[1,2-a]pyridine-3-carboxamide

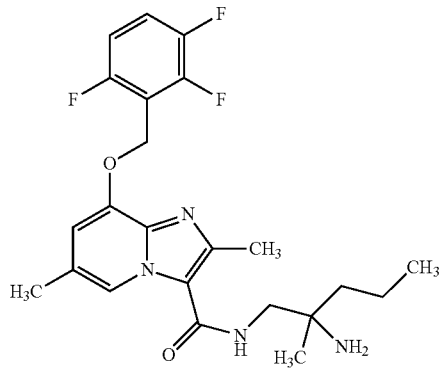 [SMILES: CCCC(C)(N)CNC(=O)c1c(C)nc2c(OCc3c(F)ccc(F)c3F)cc(C)cn12]

215 mg of rac-N-(2-amino-2-methylpentyl)-2,6-dimethyl-8-[(2,3,6-trifluorobenzyl)oxy]imidazo[1,2-a]pyridine-3-carboxamide from Example 293 were separated into the enantiomers by preparative separation on a chiral phase [column: Daicel Chiralcel OZ-H, 5 µm, 250×20 mm, mobile phase: 50% isohexane, 50% ethanol+0.2% diethylamine, flow rate: 17 ml/min; temperature: 40° C., detection: 210 nm].

Enantiomer A: yield: 83 mg (>99% ee)

$R_t$=11.59 min [Daicel Chiralcel OZ-H, 5 µm, 250×4.6 mm; mobile phase: 50% isohexane, 50% ethanol+0.2% diethylamine; flow rate 1 ml/min; temperature: 40° C.; detection: 235 nm].

Example 296 rac-N-[2-amino-3-(4-fluorophenyl)-2-methylpropyl]-8-[(2,6-difluorobenzyl)oxy]-2,6-dimethylimidazo[1,2-a]pyridine-3-carboxamide

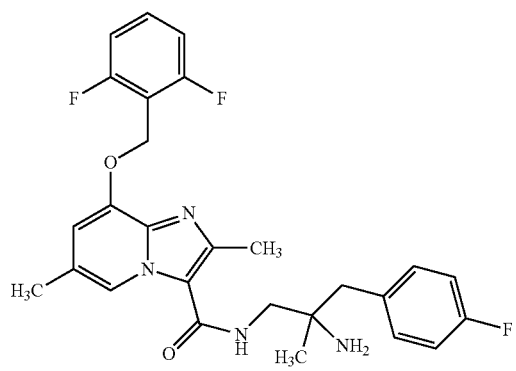 [SMILES: Cc1cc(OCc2c(F)cccc2F)c2nc(C)c(C(=O)NCC(C)(N)Cc3ccc(F)cc3)n2c1]

106 mg (0.32 mmol) of 8-[(2,6-difluorobenzyl)oxy]-2,6-dimethylimidazo[1,2-a]pyridine-3-carboxylic acid from Example 21A, 134 mg (0.35 mmol) of HATU and 0.28 ml (1.60 mmol) of N,N-diisopropylethylamine were initially charged in 2 ml DMF and stirred for 20 min. At 0° C., 70 mg (0.38 mmol) of rac-3-(4-fluorophenyl)-2-methylpropane-1,2-diamine from Example 317A were then added, and the mixture was stirred at 0° C. for 45 min. Acetonitrile/TFA was added to the reaction solution, and the product was purified by preparative HPLC (RP 18 column, mobile phase: acetonitrile/water gradient with addition of 0.1% TFA). The product fractions were combined and the residue was taken up in dichloromethane and washed twice with saturated aqueous sodium bicarbonate solution. The aqueous phase was extracted twice with dichloromethane, the combined organic phases were dried over sodium sulphate and filtered and the filtrate was concentrated and lyophilised. This gave 121 mg of the target compound (75% of theory).

LC-MS (Method 2): $R_t$=0.71 min

MS (ESpos): m/z=497 (M+H)$^+$ $^1$H-NMR (400 MHz, DMSO-d$_6$): δ=0.94 (s, 3H), 2.31 (s, 3H), 2.55 (br. s., 3H), 2.63-2.69 (m, 2H), 3.17-3.25 (m, 1H), 3.27-3.30 (m, 1H), 5.29 (s, 2H), 6.90-6.94 (m, 1H), 7.07-7.15 (m, 2H), 7.19-7.32 (m, 4H), 7.54-7.63 (m, 1H), 7.67 (t, 1H), 8.46-8.51 (m, 1H).

Example 297 rac-N-[2-amino-2-methyl-3-(pyridin-2-yl)propyl]-8-[(2,6-difluorobenzyl)oxy]-2,6-dimethylimidazo[1,2-a]pyridine-3-carboxamide

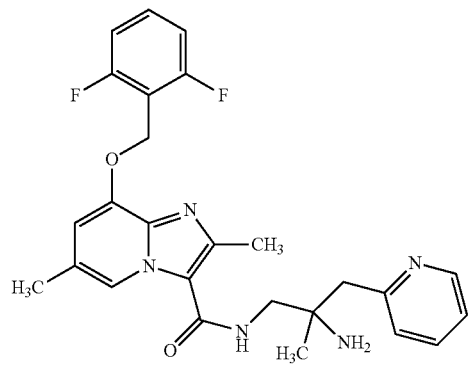 [SMILES: Cc1cc(OCc2c(F)cccc2F)c2nc(C)c(C(=O)NCC(C)(N)Cc3ccccn3)n2c1]

174 mg (0.52 mmol) of 8-[(2,6-difluorobenzyl)oxy]-2,6-dimethylimidazo[1,2-a]pyridine-3-carboxylic acid from Example 21A, 219 mg (0.58 mmol) of HATU and 0.46 ml (2.62 mmol) of N,N-diisopropylethylamine were initially charged in 3.3 ml of DMF and stirred for 20 min. At 0° C., 1.15 g (0.63 mmol, assumed purity about 15%) of rac-2-methyl-3-(pyridin-2-yl)propane-1,2-diamine trihydrochloride from Example 319A were then added, and the mixture was stirred at RT overnight. Acetonitrile/TFA was added to the reaction solution, and the product was purified by preparative HPLC (RP 18 column, mobile phase: acetonitrile/water gradient with addition of 0.1% TFA). The product fractions were concentrated and the residue was taken up in dichloromethane and washed with saturated aqueous sodium bicarbonate solution. The aqueous phase was extracted twice with dichloromethane, the combined organic phases were dried over sodium sulphate and filtered off and the filtrate was concentrated and lyophilised. This gave 106 mg of the target compound (42% of theory).

LC-MS (Method 2): $R_t$=0.70 min

MS (ESpos): m/z=480 (M+H)$^+$ $^1$H-NMR (400 MHz, DMSO-d$_6$): δ=1.01 (s, 3H), 1.67-2.12 (br. s, 2H), 2.31 (s, 3H), 2.60 (s, 3H), 2.84 (s, 2H), 3.23 (d, 2H), 5.29 (s, 2H), 6.93 (s, 1H), 7.19-7.28 (m, 3H), 7.32 (d, 1H), 7.54-7.64 (m, 1H), 7.69-7.79 (m, 2H), 8.51 (d, 1H), 8.57 (s, 1H).

Example 298 ent-N-[2-amino-2-methyl-3-(pyridin-2-yl)propyl]-8-[(2,6-difluorobenzyl)oxy]-2,6-dimethyl-imidazo[1,2-a]pyridine-3-carboxamide (Enantiomer A)

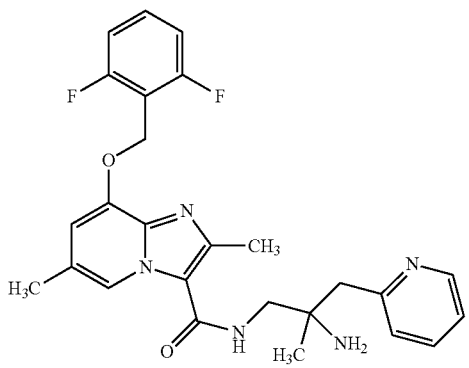 [SMILES: Cc1cc(OCc2c(F)cccc2F)c2nc(C)c(C(=O)NCC(C)(N)Cc3ccccn3)n2c1]

106 mg of rac-N-[2-amino-2-methyl-3-(pyridin-2-yl)propyl]-8-[(2,6-difluorobenzyl)oxy]-2,6-dimethylimidazo[1,2-a]pyridine-3-carboxamide from Example 297 were separated into the enantiomers by preparative separation on a chiral phase [column: Daicel Chiralpak ID, 5 µm, 250×20 mm, mobile phase: 70% methyl tert-butyl ether, 30% acetonitrile+0.2% diethylamine, flow rate: 15 ml/min; temperature: 40° C., detection: 220 nm].

Enantiomer A: yield: 27 mg (98% ee)

$R_t$=11.80 min [Daicel Chiralcel ID, 5 m, 250×4.6 mm; mobile phase: 70% methyl tert-butyl ether, 30% acetonitrile+0.2% diethylamine; flow rate 1 ml/min; temperature: 40° C.; detection: 235 nm].

Example 299 rac-8-[(2,6-difluorobenzyl)oxy]-N-(3,3-difluoropiperidin-4-yl)-2,6-dimethylimidazo[1,2-a]pyridine-3-carboxamide

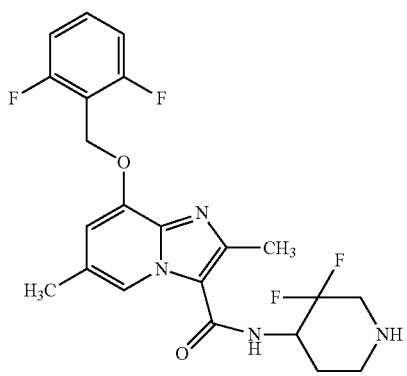 [SMILES: Cc1cc(OCc2c(F)cccc2F)c2nc(C)c(C(=O)NC3CCNCC3(F)F)n2c1]

81 mg (0.15 mmol) of rac-tert-butyl 4-[({8-[(2,6-difluorobenzyl)oxy]-2,6-dimethylimidazo[1,2-a]pyridin-3-yl}carbonyl)amino]-3,3-difluoropiperidine-1-carboxylate from Example 320A were initially charged in 0.8 ml of diethyl ether, 0.74 ml (1.47 mmol) of 2 N hydrochloric acid in diethyl ether was added and the mixture was stirred at room temperature overnight. The mixture was then concentrated, dichloromethane and a drop of methanol were added to the residue and the mixture was washed twice with saturated aqueous sodium bicarbonate solution. The combined aqueous phases were extracted twice with dichloromethane. The combined organic phases were dried over sodium sulphate, filtered and concentrated. This gave 18 mg of the target compound (26% of theory).

LC-MS (Method 2): $R_t$=0.60 min

MS (ESpos): m/z=451 (M+H)$^+$ $^1$H-NMR (400 MHz, DMSO-$d_6$): δ=1.18-1.31 (m, 1H), 1.80-2.02 (m, 2H), 2.31 (s, 3H), 2.48 (s, 3H), 2.87-2.98 (m, 1H), 3.09-3.18 (m, 1H), 3.21-3.28 (m, 1H), 3.45-3.56 (m, 1H), 4.58-4.76 (m, 1H), 5.29 (s, 2H), 6.92-6.95 (m, 1H), 7.20-7.28 (m, 2H), 7.55-7.64 (m, 1H), 8.20 (d, 1H), 8.25-8.31 (m, 1H).

Example 300 ent-N-(2-amino-2-methylbutyl)-2,6-dimethyl-8-[(2,3,6-trifluorobenzyl)oxy]imidazo[1,2-a]pyridine-3-carboxamide (Enantiomer A) hydrochloride

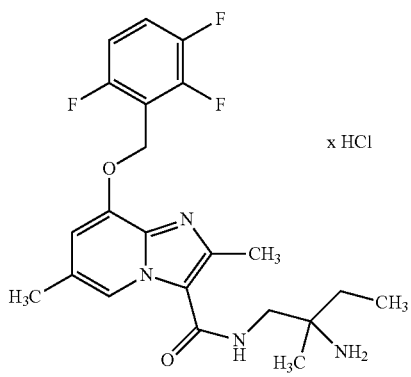 [SMILES: CCC(C)(N)CNC(=O)c1c(C)nc2c(OCc3c(F)ccc(F)c3F)cc(C)cn12]

76 mg (0.18 mmol) of ent-N-(2-amino-2-methylbutyl)-2,6-dimethyl-8-[(2,3,6-trifluorobenzyl)oxy]imidazo[1,2-a]pyridine-3-carboxamide from Example 274 were initially charged in 1.4 ml of diethyl ether, 0.11 ml (0.21 mmol) of 2 N hydrochloric acid in diethyl ether was added and the mixture was stirred at RT for 30 min. The solvent was then distilled off and the residue was dried under high vacuum. This gave 86 mg of the target compound (99% of theory).

LC-MS (Method 2): $R_t$=0.62 min

MS (ESpos): m/z=435 (M–HCl+H)$^+$ $^1$H-NMR (400 MHz, DMSO-$d_6$): δ=0.86 (t, 3H), 0.97 (s, 3H), 1.30-1.40 (m, 2H), 1.41-1.52 (m, 2H), 2.31 (s, 3H), 2.53 (s, 3H), 3.14-3.27 (m, 2H), 5.34 (s, 2H), 6.90-6.94 (m, 1H), 7.25-7.34 (m, 1H), 7.57-7.72 (m, 2H), 8.49 (s, 1H).

Example 301 rac-N-(2-amino-2-methylpentyl)-8-[(2,6-difluorobenzyl)oxy]-2-ethyl-6-methylimidazo[1,2-a]pyridine-3-carboxamide

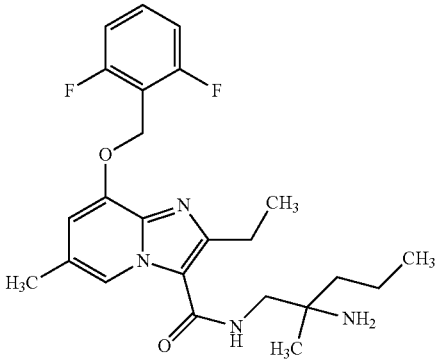 [SMILES: CCCC(C)(N)CNC(=O)c1c(CC)nc2c(OCc3c(F)cccc3F)cc(C)cn12]

75 mg (0.22 mmol) of 8-[(2,6-difluorobenzyl)oxy]-2-ethyl-6-methylimidazo[1,2-a]pyridine-3-carboxylic acid from Example 325A, 73 mg (0.23 mmol) of (benzotriazol-1-yloxy)bisdimethylaminomethylium fluoroborate and 0.14 ml (1.30 mmol) of 4-methylmorpholine were initially charged in 0.8 ml of DMF, 45 mg (0.24 mmol) of rac-2-methylpentane-1,2-diamine dihydrochloride from Example 326A were added and the mixture was stirred at RT overnight. A few drops of water and TFA were added to the reaction solution, and the product was purified by preparative HPLC (RP18 column, mobile phase: acetonitrile/water gradient with addition of 0.1% TFA). The product fractions were concentrated and the residue was dissolved in dichloromethane and washed with saturated aqueous sodium bicarbonate solution. The aqueous phase was extracted three times with dichloromethane, the combined organic phases were dried over sodium sulphate and filtered, the filtrate was concentrated and the residue was lyophilised. This gave 68 mg of the target compound (69% of theory).

LC-MS (Method 2): $R_t$=0.67 min
MS (ESpos): m/z=445 (M+H)$^+$
$^1$H-NMR (400 MHz, DMSO-d$_6$): δ=0.83-0.91 (m, 3H), 1.04 (s, 3H), 1.22 (t, 3H), 1.28-1.41 (m, 4H), 2.31 (s, 3H), 2.91 (q, 2H), 3.18-3.30 (m, 2H), 5.29 (s, 2H), 6.92 (s, 1H), 7.25 (quin, 2H), 7.55-7.65 (m, 1H), 7.69-7.79 (m, 1H), 8.41 (s, 1H).

Example 302 rac-8-[(2,6-difluorobenzyl)oxy]-2,6-dimethyl-N-[2-(trifluoromethyl)piperidin-4-yl]imidazo[1,2-a]pyridine-3-carboxamide

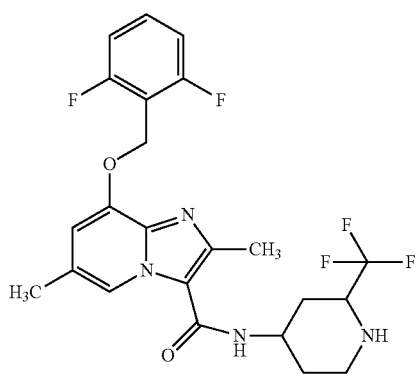 [SMILES: Cc1cc(OCc2c(F)cccc2F)c2nc(C)c(C(=O)NC3CCNC(C(F)(F)F)C3)n2c1]

75 mg (0.23 mmol) of 8-[(2,6-difluorobenzyl)oxy]-2,6-dimethylimidazo[1,2-a]pyridine-3-carboxylic acid from Example 21A, 94 mg (0.25 mmol) of HATU and 0.24 ml (1.35 mmol) of N,N-diisopropylethylamine were initially charged in 1.4 ml of DMF and stirred for 20 min. 55 mg (0.27 mmol) of rac-2-(trifluoromethyl)piperidine-4-amine hydrochloride from Example 327A were then added, and the mixture was stirred at RT overnight. The reaction solution was diluted with water/TFA and purified by preparative HPLC (RP18 column, mobile phase: acetonitrile/water gradient with addition of 0.1% TFA). The product fractions were concentrated under reduced pressure and then taken up in dichloromethane and washed twice with saturated aqueous sodium bicarbonate solution. The combined aqueous phases were extracted twice with dichloromethane. The combined organic phases were dried over sodium sulphate and filtered, the filtrate was concentrated and the residue was lyophilised. This gave 65 mg of the target compound (60% of theory).

LC-MS (Method 2): $R_t$=0.69 min
MS (ESpos): m/z=483 (M+H)$^+$
$^1$H-NMR (400 MHz, DMSO-d$_6$): δ=1.60-1.95 (m, 4H), 2.31 (s, 3H), 2.81-2.98 (m, 2H), 3.55-3.74 (m, 1H), 4.24-4.33 (m, 1H), 5.29 (s, 2H), 6.92 (s, 1H), 7.24 (quin, 2H), 7.55-7.64 (m, 1H), 7.89 (d, 1H), 8.36 (s, 1H).

Example 303 rac-N-(2-amino-2-methylpentyl)-8-[(2,3-difluorobenzyl)oxy]-2,6-dimethylimidazo[1,2-a]pyridine-3-carboxamide

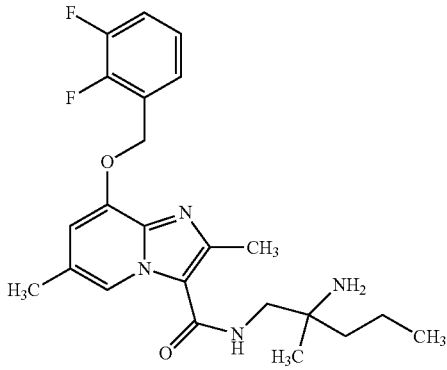 [SMILES: CCCC(C)(N)CNC(=O)c1c(C)nc2c(OCc3cccc(F)c3F)cc(C)cn12]

80 mg (0.19 mmol, purity 95%) of rac-tert-butyl (1-{[(8-hydroxy-2,6-dimethylimidazo[1,2-a]pyridin-3-yl)carbonyl]amino}-2-methylpentan-2-yl)carbamate from Example 330A, 43 mg (0.21 mmol) of 2,3-difluorobenzyl bromide, 135 mg (0.41 mmol) of caesium carbonate and 3.1 mg (0.02 mmol) of potassium iodide were initially charged in 3.6 ml of DMF and heated for 30 min in a warm oil bath pre-heated to 60° C. The reaction solution was concentrated and dried under high vacuum overnight. The residue was taken up in diethyl ether, 0.94 ml (1.88 mmol) of 2 N hydrochloric acid in diethyl ether was added and the mixture was stirred at RT overnight. The reaction mixture was concentrated and purified by preparative HPLC (RP 18 column, mobile phase: acetonitrile/water gradient with addition of 0.1% TFA). The product fractions were concentrated and the residue was taken up in dichloromethane and washed twice with saturated aqueous sodium bicarbonate solution. The aqueous phase was extracted twice with dichloromethane. The combined organic phases were dried over sodium sulphate and filtered, the filtrate was concentrated and the residue was lyophilised. This gave 51 mg of the target compound (61% of theory).

LC-MS (Method 2): $R_t$=0.67 min
MS (ESpos): m/z=431 (M+H)$^+$

Example 304 ent-N-(2-amino-2-methylpentyl)-2,6-dimethyl-8-[(2,3,6-trifluorobenzyl)oxy]imidazo[1,2-a]pyridine-3-carboxamide

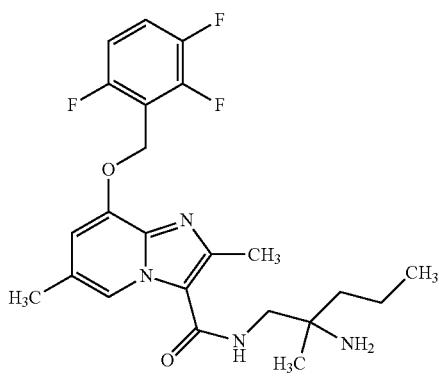 [SMILES: CCCC(C)(N)CNC(=O)c1c(C)nc2c(OCc3c(F)ccc(F)c3F)cc(C)cn12]

215 mg of rac-N-(2-amino-2-methylpentyl)-2,6-dimethyl-8-[(2,3,6-trifluorobenzyl)oxy]imidazo[1,2-a]pyridine-3-carboxamide from Example 293 were separated into the enantiomers by preparative separation on a chiral phase [column: Daicel Chiralcel OZ-H, 5 μm, 250×20 mm, mobile phase: 50% isohexane, 50% ethanol+0.2% diethylamine, flow rate: 17 ml/min; temperature: 40° C., detection: 210 nm].

Enantiomer B: yield: 86 mg (97.5% ee)
$R_t$=14.00 min [Daicel Chiralcel OZ-H, 5 μm, 250×4.6 mm; mobile phase: 50% isohexane, 50% ethanol+0.2% diethylamine; flow rate 1 ml/min; temperature: 40° C.; detection: 235 nm].

Example 305 ent-N-(2-amino-2-methylpentyl)-8-[(2,6-difluorobenzyl)oxy]-6-methyl-2-(trifluoromethyl)imidazo[1,2-a]pyridine-3-carboxamide

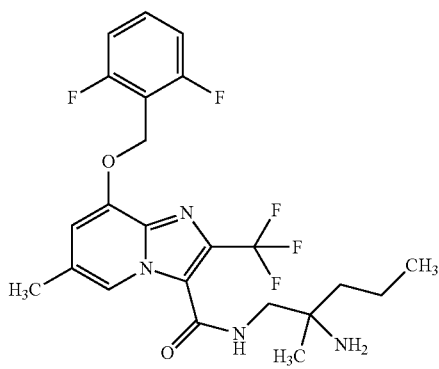 [SMILES: CCCC(C)(N)CNC(=O)c1c(C(F)(F)F)nc2c(OCc3c(F)cccc3F)cc(C)cn12]

46 mg (0.06 mmol) of ent-benzyl-{1-[({8-[(2,6-difluorobenzyl)oxy]-6-methyl-2-(trifluoromethyl)imidazo[1,2-a]pyridin-3-yl}carbonyl)amino]-2-methylpentan-2-yl}carbamate trifluoroacetate from Example 333A were dissolved in 0.7 ml of ethanol, and 4.4 mg (0.01 mmol) of 20% palladium(II) hydroxide on carbon were added under argon. The reaction mixture was then hydrogenated at RT and under standard pressure for 2 hours. The reaction mixture was absorbed on diatomaceous earth and purified by silica gel chromatography (mobile phase: dichloromethane/2 N ammonia in methanol=50/1). This gave 30 mg of the target compound (99% of theory).

LC-MS (Method 2): $R_t$=0.91 min
MS (ESpos): m/z=485 (M+H)$^+$
$^1$H-NMR (400 MHz, DMSO-$d_6$): δ=0.87 (t, 3H), 0.99 (s, 3H), 1.21-1.42 (m, 4H), 1.49-1.89 (m, 2H), 2.34 (s, 3H), 3.23 (s, 2H), 5.33 (s, 2H), 7.08 (s, 1H), 7.20-7.30 (m, 2H), 7.56-7.66 (m, 1H), 8.02 (s, 1H), 8.31-8.80 (m, 1H).

Example 306 ent-N-(2-amino-2-methylpentyl)-6-bromo-8-[(2,6-difluorobenzyl)oxy]-2-methylimidazo[1,2-a]pyridine-3-carboxamide

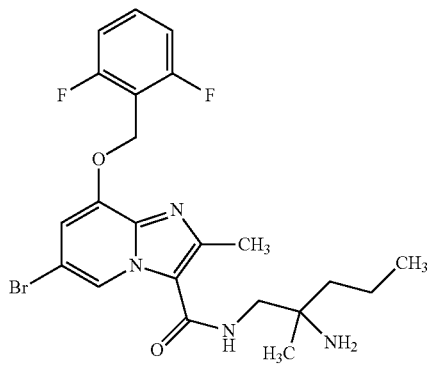

Under argon, 70 mg (0.09 mmol) of ent-benzyl-{1-[({6-bromo-8-[(2,6-difluorobenzyl)oxy]-2-methylimidazo[1,2-a]pyridin-3-yl}carbonyl)amino]-2-methylpentan-2-yl}carbamate trifluoroacetate from Example 292A were initially charged in 1.9 ml of dichloromethane, and 0.14 ml (0.14 mmol) of 1 N boron tribromide in dichloromethane was added at 0° C. and under argon. The mixture was stirred at RT for 2.5 hours. Water was added to the reaction mixture, the mixture was concentrated and the residue was purified by preparative HPLC (RP18 column, mobile phase: acetonitrile/water gradient with addition of 0.1% TFA). The product was dissolved in dichloromethane and washed with saturated aqueous sodium bicarbonate solution. The aqueous phase was extracted twice with dichloromethane. The combined organic phases were dried over sodium sulphate and filtered. The filtrate was concentrated and the residue was purified by preparative thin-layer chromatography (mobile phase: dichloromethane/2 N ammonia in methanol=20/1). The collected product fractions were concentrated on a rotary evaporator. This gave 5 mg of the target compound (11% of theory).

LC-MS (Method 2): $R_t$=0.84 min
MS (ESpos): m/z=495 (M+H)$^+$
$^1$H-NMR (400 MHz, DMSO-$d_6$): δ=0.87 (t, 3H), 1.01 (s, 3H), 1.26-1.42 (m, 4H), 1.44-1.58 (m, 2H), 2.55 (s, 3H), 3.17-3.26 (m, 2H), 5.35 (s, 2H), 7.19-7.29 (m, 3H), 7.55-7.65 (m, 1H), 7.66-7.85 (m, 1H), 8.83 (d, 1H).

Example 307

N-[(1-aminocyclohexyl)methyl]-8-[(2,6-difluorobenzyl)oxy]-2,6-dimethylimidazo[1,2-a]pyridine-3-carboxamide

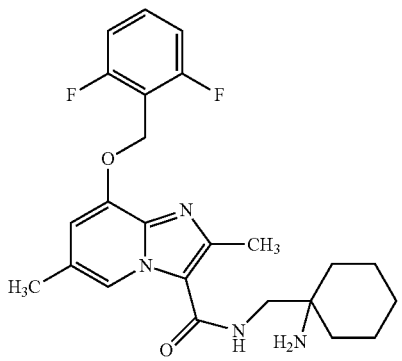 [SMILES: Cc1cc(OCc2c(F)cccc2F)c2nc(C)c(C(=O)NCC3(N)CCCCC3)n2c1]

163 mg (0.25 mmol) of tert-butyl (1-{[({8-[(2,6-difluorobenzyl)oxy]-2,6-dimethylimidazo[1,2-a]pyridin-3-yl}carbonyl)amino]methyl}cyclohexyl)carbamate trifluoroacetate from Example 334A were initially charged in 1.24 ml of diethyl ether, 1.24 ml (2.48 mmol) of 2 N hydrochloric acid in diethyl ether were added and the mixture was stirred at RT for 3 hours. Another 0.5 ml (1 mmol) of 2 N hydrochloric acid in diethyl ether was added, and the mixture was stirred at RT for 4 hours. The reaction mixture was concentrated and the residue was taken up in dichloromethane and washed twice with saturated aqueous sodium bicarbonate solution. The combined aqueous phases were washed twice with dichloromethane, the combined organic phases were dried over sodium sulphate and filtered and the residue was dried under high vacuum. This gave 89 mg of the target compound (81% of theory).

LC-MS (Method 2): $R_t$=0.65 min
MS (ESpos): m/z=443 (M+H)$^+$
$^1$H-NMR (400 MHz, DMSO-d$_6$): δ=1.19-1.48 (m, 8H), 1.49-1.61 (m, 2H), 1.62-1.77 (m, 2H), 2.31 (s, 3H), 2.53 (br. s., 3H), 3.24 (d, 2H), 5.28 (s, 2H), 6.92 (s, 1H), 7.18-7.29 (m, 2H), 7.54-7.66 (m, 2H), 8.49 (s, 1H).

Example 308

N-(3-aminocyclopentyl)-8-[(2,6-difluorobenzyl)oxy]-2,6-dimethylimidazo[1,2-a]pyridine-3-carboxamide (Stereoisomer Mixture)

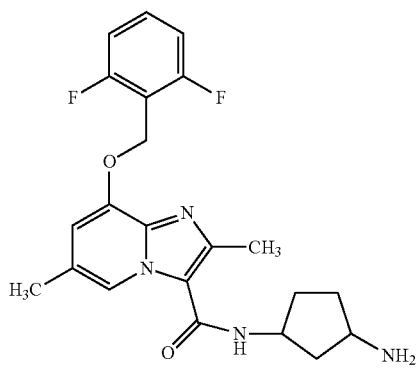 [SMILES: Cc1cc(OCc2c(F)cccc2F)c2nc(C)c(C(=O)NC3CCC(N)C3)n2c1]

119 mg (0.23 mmol) of tert-butyl {3-[({8-[(2,6-difluorobenzyl)oxy]-2,6-dimethylimidazo[1,2-a]pyridin-3-yl}carbonyl)amino]cyclopentyl}carbamate from Example 335A were initially charged in 1.2 ml of diethyl ether, 1.2 ml (2.31 mmol) of 2 N hydrochloric acid in diethyl ether were added and the mixture was stirred at RT overnight. The reaction mixture was concentrated, dichloromethane and a drop of methanol were added to the residue and the mixture was washed twice with saturated aqueous sodium bicarbonate solution. The combined aqueous phases were extracted twice with dichloromethane, and the combined organic phases were concentrated. This gave 93 mg of the target compound (92% of theory).

LC-MS (Method 2): $R_t$=0.60 min
MS (ESpos): m/z=415 (M+H)$^+$
$^1$H-NMR (400 MHz, DMSO-d$_6$): δ=1.37-1.50 (m, 2H), 1.67-1.83 (m, 2H), 1.87-2.02 (m, 2H), 2.31 (s, 3H), 2.49 (s, 3H), 3.36-3.42 (m, 1H), 4.30-4.40 (m, 1H), 5.28 (s, 2H), 6.91 (s, 1H), 7.20-7.28 (m, 2H), 7.54-7.64 (m, 1H), 8.12 (d, 1H), 8.53 (s, 1H).

Example 309 ent-N-(3-aminocyclopentyl)-8-[(2,6-difluorobenzyl)oxy]-2,6-dimethylimidazo[1,2-a]pyridine-3-carboxamide

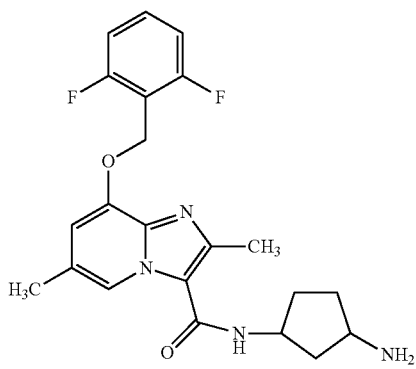 [SMILES: Cc1cc(OCc2c(F)cccc2F)c2nc(C)c(C(=O)NC3CCC(N)C3)n2c1]

85 mg of N-(3-aminocyclopentyl)-8-[(2,6-difluorobenzyl)oxy]-2,6-dimethylimidazo[1,2-a]pyridine-3-carboxamide from Example 308 were separated into the stereoisomers by preparative separation on a chiral phase [column: Daicel Chiralcel AY-H, 5 μm, 250×20 mm, mobile phase: 50% isohexane, 50% ethanol+0.2% diethylamine, flow rate: 15 ml/min; temperature: 25° C., detection: 220 nm]. The product fraction was re-purified by preparative HPLC (RP18 column, mobile phase: acetonitrile/water gradient with addition of 0.1% TFA). The product fraction was taken up in dichloromethane and washed twice with saturated aqueous sodium bicarbonate solution. The combined aqueous phases were extracted twice with dichloromethane. The combined organic phases were dried over sodium sulphate, filtered and concentrated.

Stereoisomer A: yield: 15.7 mg (>99% ee)

$R_t$=4.82 min [Daicel Chiralcel AY-H, 5 μm, 250×4.6 mm; mobile phase: 50% isohexane, 50% ethanol+0.2% diethylamine; flow rate 1 ml/min; temperature: 40° C.; detection: 220 nm].

Example 310 rac-N-[2-amino-3-(1,3-benzothiazol-2-yl)-2-methyl-propyl]-8-[(2,6-difluorobenzyl)oxy]-2,6-dimethyl-imidazo[1,2-a]pyridine-3-carboxamide

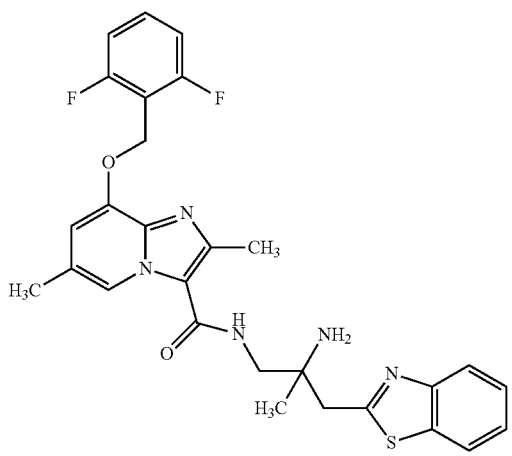 [SMILES: Cc1cc(OCc2c(F)cccc2F)c2nc(C)c(C(=O)NCC(C)(N)Cc3nc4ccccc4s3)n2c1]

14 mg (0.04 mmol) of 8-[(2,6-difluorobenzyl)oxy]-2,6-dimethylimidazo[1,2-a]pyridine-3-carboxylic acid from Example 21A, 18 mg (0.05 mmol) of HATU and 0.04 ml (0.21 mmol) of N,N-diisopropylethylamine were initially charged in 0.3 ml of DMF, the mixture was stirred for 20 min, 17 mg (0.07 mmol, purity 94%) of rac-3-(1,3-benzothiazol-2-yl)-2-methylpropane-1,2-diamine from Example 337A were then added at 0° C. and the mixture was stirred at 0° C. for 60 min. Water/TFA was added to the reaction solution, and the product was purified by preparative HPLC (RP 18 column, mobile phase: acetonitrile/water gradient with addition of 0.1% TFA). The product fractions were concentrated under reduced pressure, the residue was then dissolved in dichloromethane and washed twice with saturated aqueous sodium bicarbonate solution and the combined aqueous phases were extracted twice with dichloromethane. The combined organic phases were dried over sodium sulphate, filtered off and concentrated. This gave 16 mg of the target compound (68% of theory).

LC-MS (Method 2): $R_t$=0.82 min
MS (ESpos): m/z=536 (M+H)$^+$
$^1$H-NMR (400 MHz, DMSO-d$_6$): δ=1.11 (s, 3H), 1.18-1.29 (m, 2H), 2.31 (s, 3H), 2.58 (s, 3H), 3.16-3.27 (m, 2H), 3.38-3.45 (m, 2H), 5.29 (s, 2H), 6.90-6.95 (m, 1H), 7.20-7.29 (m, 2H), 7.37-7.43 (m, 1H), 7.44-7.50 (m, 1H), 7.54-7.64 (m, 1H), 7.78 (t, 1H), 7.95 (d, 1H), 8.05 (d, 1H), 8.49 (s, 1H).

Example 311 rac-N-(2-amino-2-methylpentyl)-2,6-dimethyl-8-[(2,3,5,6-tetrafluorobenzyl)oxy]imidazo[1,2-a]pyridine-3-carboxamide

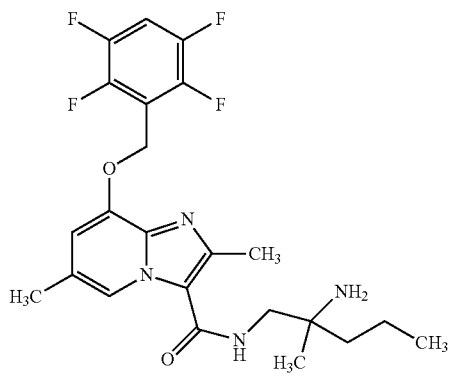 [SMILES: CCCC(C)(N)CNC(=O)c1c(C)nc2c(OCc3c(F)c(F)cc(F)c3F)cc(C)cn12]

80 mg (0.19 mmol) of rac-tert-butyl (1-{[(8-hydroxy-2,6-dimethylimidazo[1,2-a]pyridin-3-yl)carbonyl]amino}-2-methylpentan-2-yl)carbamate from Example 330A, 50 mg (0.21 mmol) of 2,3,5,6-tetrafluorobenzyl bromide, 135 mg (0.41 mmol) of caesium carbonate and 3 mg (0.02 mmol) of potassium iodide were initially charged in 4 ml of DMF, and the mixture was heated for 60 min in a warm oil bath preheated to 60° C. The reaction solution was concentrated and dried under high vacuum overnight. The residue was taken up in 1 ml of diethyl ether, 0.94 ml (1.88 mmol) of 2 N hydrochloric acid in diethyl ether was added and the mixture was stirred at RT overnight. The reaction mixture was concentrated and purified by preparative HPLC (RP18 column, mobile phase: acetonitrile/water gradient with addition of 0.1% TFA). The product fractions were concentrated and the residue was taken up in dichloromethane and washed twice with saturated aqueous sodium bicarbonate solution. The aqueous phase was extracted twice with dichloromethane. The combined organic phases were dried over sodium sulphate, filtered and concentrated. This gave 60 mg of the target compound (68% of theory).

LC-MS (Method 2): $R_t$=0.73 min
MS (ESpos): m/z=467 (M+H)$^+$

Example 312 rac-8-[(2,6-difluorobenzyl)oxy]-N-(5,5-difluoropiperidin-3-yl)-2,6-dimethylimidazo[1,2-a]pyridine-3-carboxamide

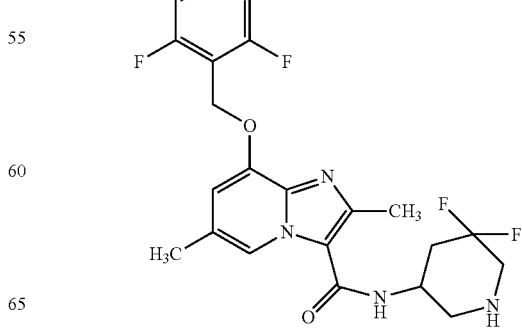

89 mg (0.16 mmol) of rac-tert-butyl 5-[({8-[(2,6-difluorobenzyl)oxy]-2,6-dimethylimidazo[1,2-a]pyridin-3-yl}carbonyl)amino]-3,3-difluoropiperidine-1-carboxylate from Example 338A were initially charged in 0.8 ml of diethyl ether, 0.78 ml (1.55 mmol) of 2 N hydrochloric acid in diethyl ether was added and the mixture was stirred at RT overnight. The reaction mixture was concentrated, dichloromethane and one drop of methanol were added to the residue and the mixture was washed twice with saturated aqueous sodium bicarbonate solution. The combined aqueous phases were extracted twice with dichloromethane. The combined organic phases were dried over sodium sulphate, filtered off and concentrated. This gave 67 mg of the target compound (91% of theory).

LC-MS (Method 2): $R_t$=0.64 min

MS (ESpos): m/z=451 (M+H)$^+$ $^1$H-NMR (400 MHz, DMSO-d$_6$): δ=1.22-1.28 (m, 1H), 1.99-2.18 (m, 1H), 2.31 (s, 3H), 2.38-2.45 (m, 1H), 2.48 (s, 3H), 2.57-2.64 (m, 1H), 2.82-2.98 (m, 1H), 3.01-3.18 (m, 2H), 4.12-4.23 (m, 1H), 5.28 (s, 2H), 6.91-6.95 (m, 1H), 7.20-7.28 (m, 2H), 7.54-7.65 (m, 1H), 7.77 (d, 1H), 8.42 (s, 1H).

Example 313

8-[(2,6-Difluorobenzyl)oxy]-2,6-dimethyl-N-[4-(trifluoromethyl)pyrrolidin-3-yl]imidazo[1,2-a]pyridine-3-carboxamide (Mixture of Stereoisomers)

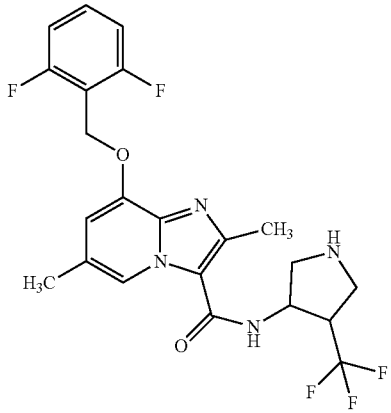 [SMILES: Cc1cc(OCc2c(F)cccc2F)c2nc(C)c(C(=O)NC3CNCC3C(F)(F)F)n2c1]

18 mg (0.03 mmol) of rac-tert-butyl 3-[({8-[(2,6-difluorobenzyl)oxy]-2,6-dimethylimidazo[1,2-a]pyridin-3-yl}carbonyl)amino]-4-(trifluoromethyl)pyrrolidine-1-carboxylate trifluoroacetate (mixture of stereoisomers) from Example 339A were initially charged in 0.1 ml of diethyl ether, 0.13 ml (0.26 mmol) of 2 N hydrochloric acid in diethyl ether was added and the mixture was stirred at RT overnight. The reaction mixture was concentrated and the residue was partitioned between dichloromethane and saturated aqueous sodium bicarbonate solution. The aqueous phase was extracted twice with dichloromethane, the combined organic phases were dried over sodium sulphate and filtered off and the filtrate was concentrated. The residue was purified by preparative thin-layer chromatography (mobile phase: dichloromethane/methanol=20/1). This gave 5.8 mg of the target compound (45% of theory).

LC-MS (Method 2): $R_t$=0.74 min

MS (ESpos): m/z=469 (M+H)$^+$ $^1$H-NMR (400 MHz, DMSO-d$_6$): d [ppm]=2.31 (s, 3H), 2.48 (s, 3H), 2.75-2.82 (m, 1H), 2.90-2.98 (m, 1H), 3.04-3.22 (m, 2H), 3.24-3.28 (m, 2H), 4.51-4.59 (m, 1H), 5.29 (s, 2H), 6.93 (s, 1H), 7.19-7.27 (m, 2H), 7.54-7.63 (m, 1H), 8.06 (d, 1H), 8.39 (s, 1H).

Example 314

8-[(2,6-Difluorobenzyl)oxy]-2,6-dimethyl-N-[(7S,8aS)-2-methyloctahydropyrrolo[1,2-a]pyrazin-7-yl]imidazo[1,2-a]pyridine-3-carboxamide

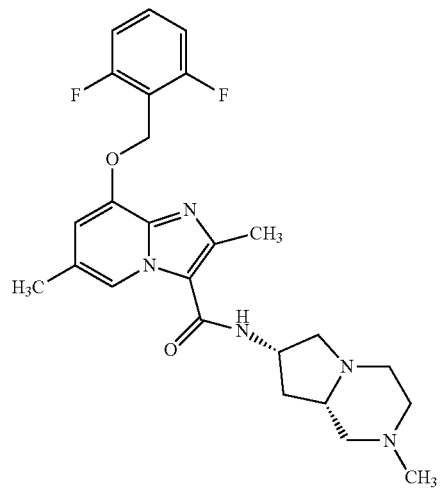

75 mg (0.23 mmol) of 8-[(2,6-difluorobenzyl)oxy]-2,6-dimethylimidazo[1,2-a]pyridine-3-carboxylic acid from Example 21A, 111 mg (0.29 mmol) of HATU and 0.20 ml (1.13 mmol) of N,N-diisopropylethylamine were initially charged in 2 ml of DMF, the mixture was stirred for 10 min, 88 mg (0.29 mmol) of (7S,8aS)-2-methyloctahydropyrrolo[1,2-a]pyrazine-7-amine trihydrochloride dihydrate (commercially available, CAS Registry No.: 1268326-45-9) were then added at RT and the mixture was stirred at RT overnight. TFA was added to the reaction solution, and the product was purified by preparative HPLC (RP18 column, mobile phase: acetonitrile/water gradient with addition of 0.1% TFA). The product fractions were combined, the solvent was concentrated and the residue was lyophilised. The residue was taken up in dichloromethane and washed once with saturated aqueous sodium bicarbonate solution, and the aqueous phase was extracted twice with dichloromethane. The combined organic phases were dried over sodium sulphate and filtered, and the filtrate was concentrated and lyophilised. This gave 81 mg of the target compound (75% of theory).

LC-MS (Method 2): $R_t$=0.62 min

MS (ESpos): m/z=470 (M+H)$^+$ $^1$H-NMR (400 MHz, DMSO-d$_6$): δ=1.36-1.49 (m, 1H), 1.84-2.05 (m, 1H), 2.06-2.28 (m, 5H), 2.30 (s, 3H), 2.45 (s, 3H), 2.72-2.84 (m, 1H), 2.86-3.00 (m, 3H), 4.40 (quin, 1H), 5.28 (s, 2H), 6.90 (s, 1H), 7.24 (quin, 2H), 7.54-7.64 (m, 1H), 8.06 (d, 1H), 8.35 (s, 1H).

Example 315 ent-N-(1-amino-2-methylbutan-2-yl)-2,6-dimethyl-
8-[(2,36-trifluorobenzyl)oxy]imidazo[1,2-a]pyridine-
3-carboxamide

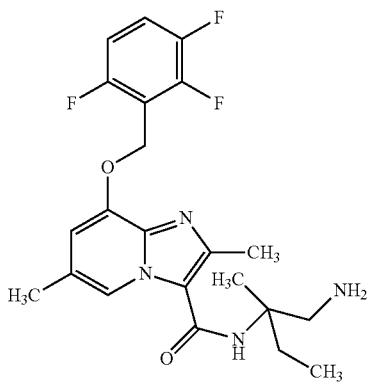 [SMILES: CCC(C)(CN)NC(=O)c1c(C)nc2c(OCc3c(F)ccc(F)c3F)cc(C)cn12]

165 mg (0.24 mmol) of benzyl {2-[({2,6-dimethyl-8-[(2,3,6-trifluorobenzyl)oxy]imidazo[1,2-a]pyridin-3-yl}carbonyl)amino]-2-methylbutyl}carbamate from Example 340A were initially charged in 2.5 ml of ethanol, and 17 mg (0.02 mmol) of 20% palladium(II) hydroxide on carbon were added under argon. The mixture was then hydrogenated at RT and under standard pressure for 2.5 hours. The reaction mixture was absorbed on Celite and purified by silica gel chromatography (mobile phase: dichloromethane/2 N ammonia in methanol=40/1). This gave 90 mg of the target compound (84% of theory).

LC-MS (Method 2): $R_t$=0.68 min
MS (ESpos): m/z=435 (M+H)$^+$
$^1$H-NMR (500 MHz, DMSO-d$_6$): δ=0.83 (t, 3H), 1.28 (s, 3H), 1.57-1.72 (m, 1H), 1.73-1.86 (m, 2H), 2.31 (s, 3H), 2.61 (d, 1H), 2.84 (d, 1H), 5.34 (s, 2H), 6.90 (d, 1H), 7.18 (s, 1H), 7.25-7.32 (m, 1H), 7.62-7.71 (m, 1H), 8.49 (s, 1H).

Example 316 rac-N-(azepan-3-yl)-8-[(2,6-difluorobenzyl)oxy]-2,6-dimethylimidazo[1,2-a]pyridine-3-carboxamide

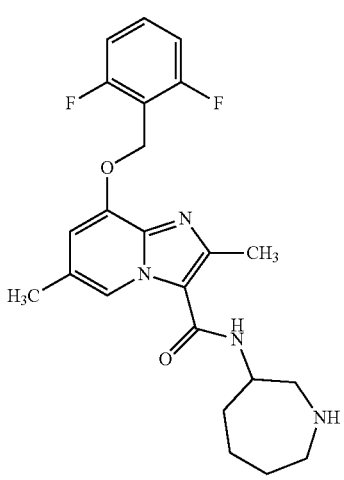 [SMILES: Cc1cc(OCc2c(F)cccc2F)c2nc(C)c(C(=O)NC3CCCCNC3)n2c1]

1.5 ml (3.00 mmol) of 2 N hydrogen chloride in diethyl ether were added to 193 mg (0.30 mmol) of rac-tert-butyl 3-[({8-[(2,6-difluorobenzyl)oxy]-2,6-dimethylimidazo[1,2-a]pyridin-3-yl}carbon-yl)amino]azepane-1-carboxylate trifluoroacetate from Example 341A, and the mixture was stirred at RT overnight. The reaction mixture was concentrated and purified by preparative HPLC (RP18 column, mobile phase: acetonitrile/water gradient with addition of 0.1% TFA). The product-containing fractions were concentrated and the residue was dissolved in dichloromethane and washed once with saturated aqueous sodium bicarbonate solution. The aqueous phase was extracted twice with dichloromethane, the combined organic phases were dried over sodium sulphate and filtered and the filtrate was concentrated and lyophilised. This gave 114 mg of the target compound (89% of theory).

LC-MS (Method 2): $R_t$=0.63 min
MS (ESpos): m/z=429 (M+H)$^+$
$^1$H-NMR (400 MHz, DMSO-d$_6$): δ=1.43-1.74 (m, 5H), 1.78-1.88 (m, 1H), 2.31 (s, 3H), 2.48 (s, 3H), 2.66-2.73 (m, 1H), 2.77 (t, 2H), 2.92-2.99 (m, 1H), 3.98-4.08 (m, 1H), 5.28 (s, 2H), 6.90 (s, 1H), 7.20-7.28 (m, 2H), 7.55-7.68 (m, 2H), 8.45 (s, 1H).

Example 317 rac-N-(2-amino-2-methylpentyl)-8-[(2-fluoro-3-methylbenzyl)oxy]-2,6-dimethylimidazo[1,2-a]pyridine-3-carboxamide

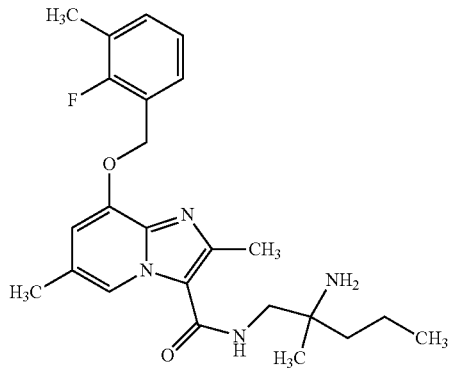 [SMILES: CCCC(C)(N)CNC(=O)c1c(C)nc2c(OCc3cccc(C)c3F)cc(C)cn12]

90 mg (0.21 mmol) of rac-tert-butyl (1-{[(8-hydroxy-2,6-dimethylimidazo[1,2-a]pyridin-3-yl)carbonyl]amino}-2-methylpentan-2-yl)carbamate from Example 330A, 47 mg (0.23 mmol) of 2-fluoro-3-methylbenzyl bromide, 152 mg (0.46 mmol) of caesium carbonate and 3.5 mg (0.02 mmol) of potassium iodide were initially charged in 4 ml of DMF, and the mixture was heated for 30 min in a warm oil bath pre-heated to 60° C. The reaction solution was concentrated and dried under high vacuum overnight. The residue was taken up in 1 ml of diethyl ether, 1.06 ml (2.11 mmol) of 2 N hydrochloric acid in diethyl ether were added and the mixture was stirred at RT overnight. The reaction mixture was concentrated and purified by preparative HPLC (RP18 column, mobile phase: methanol/water gradient with addition of 0.1% TFA). The product fractions were concentrated and the residue was taken up in dichloromethane and washed twice with saturated aqueous sodium bicarbonate solution. The aqueous phase was extracted twice with dichloromethane. The combined organic phases were dried over sodium sulphate, filtered and concentrated. This gave 48 mg of the target compound (53% of theory).

LC-MS (Method 2): $R_t$=0.72 min
MS (ESpos): m/z=427 (M+H)$^+$

Example 318 ent-N-(2-amino-2-methylpentyl)-8-[(2,6-difluorobenzyl)oxy]-2-methylimidazo[1,2-a]pyridine-3-carboxamide

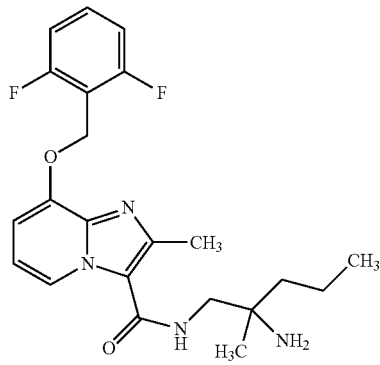

Under argon, 50 mg (0.07 mmol) of ent-benzyl {1-[({6-bromo-8-[(2,6-difluorobenzyl)oxy]-2-methylimidazo[1,2-a]pyridin-3-yl}carbonyl)amino]-2-methylpentan-2-yl}carbamate from Example 292A were initially charged in 0.7 ml of ethanol, 7 mg (0.01 mmol, 10%) of palladium on carbon were added and the mixture was hydrogenated at RT and under standard pressure for 1 hour. The reaction mixture was transferred to Celite and purified by silica gel chromatography (mobile phase dichloromethane/2 N ammonia in methanol=60/1). This gave 27 mg of the target compound (94% of theory).

LC-MS (Method 2): $R_t$=0.61 min
MS (ESpos): m/z=417 (M+H)$^+$
$^1$H-NMR (400 MHz, DMSO-d$_6$): δ=0.86 (t, 3H), 0.99 (s, 3H), 1.21-1.42 (m, 4H), 1.43-1.72 (m, 2H), 2.56 (s, 3H), 3.14-3.27 (m, 2H), 5.31 (s, 2H), 6.94 (t, 1H), 7.00 (d, 1H), 7.20-7.28 (m, 2H), 7.55-7.63 (m, 1H), 7.64-7.69 (m, 1H), 8.64 (d, 1H).

Example 319

Methyl 3-[({8-[(2,6-difluorobenzyl)oxy]-2,6-dimethylimidazo[1,2-a]pyridin-3-yl}carbonyl)amino]-L-alaninate

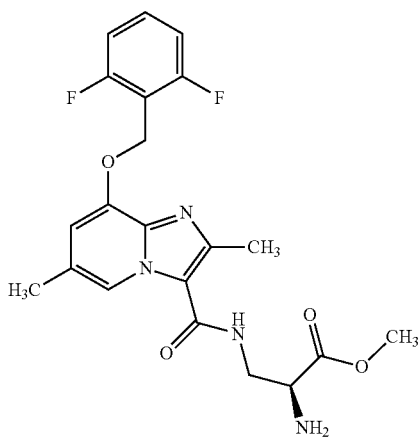

75 mg (0.14 mmol) of methyl N-(tert-butoxycarbonyl)-3-[({8-[(2,6-difluorobenzyl)oxy]-2,6-dimethylimidazo[1,2-a]pyridin-3-yl}carbonyl)amino]-L-alaninate from Example 351A were initially charged in 0.7 ml of diethyl ether, 0.67 ml (1.35 mmol) of 2 N hydrochloric acid in diethyl ether was added and the mixture was stirred at RT overnight. The reaction solution was concentrated and the residue was dissolved in dichloromethane and washed twice with saturated aqueous sodium bicarbonate solution. The combined aqueous phases were extracted twice with dichloromethane. The combined organic phases were dried over sodium sulphate, filtered and concentrated. This gave 55 mg of the target compound (92% of theory).

LC-MS (Method 2): $R_t$=0.63 min
MS (ESpos): m/z=433 (M+H)$^+$
$^1$H-NMR (400 MHz, DMSO-d$_6$): δ=1.84-2.03 (m, 2H), 2.31 (s, 3H), 2.48 (s, 3H), 3.46-3.51 (m, 2H), 3.56-3.61 (m, 1H), 3.63 (s, 3H), 5.28 (s, 2H), 6.89-6.94 (m, 1H), 7.19-7.27 (m, 2H), 7.53-7.63 (m, 1H), 7.81 (t, 1H), 8.41-8.46 (m, 1H).

Example 320 rac-N-(2-amino-1,2-dimethylcyclopropyl)-8-[(2,6-difluorobenzyl)oxy]-2,6-dimethylimidazo[1,2-a]pyridine-3-carboxamide (racemate)

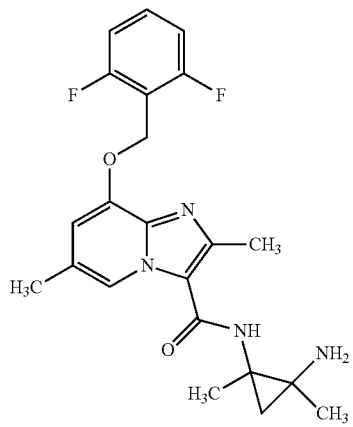

0.94 ml of DMF and 1.26 ml (7.22 mmol) of N,N-diisopropylethylamine were added to 631 mg (2.41 mmol) of rac-1,2-dimethylcyclopropane-1,2-diamine dihydrobromide (described in: W. v. d. Saal et al. Liebigs Annalen der Chemie 1994, 569-580), and the mixture was heated to 60° C. A solution of 200 mg (0.60 mmol) of 8-[(2,6-difluorobenzyl)oxy]-2,6-dimethylimidazo[1,2-a]pyridine-3-carboxylic acid from Example 21A, 0.21 ml (1.20 mmol) of N,N-diisopropylethylamine and 275 mg (0.72 mmol) of HATU in 2.8 ml of DMF, which had been stirred at RT for 10 min beforehand, was added dropwise to the reaction mixture, and the mixture was stirred at 60° C. for 30 min. Water and TFA were added to the mixture, and the product was purified by preparative HPLC (RP18 column, mobile phase: acetonitrile/water gradient with addition of 0.1% TFA). The product-containing fractions were concentrated and the residue was taken up in dichloromethane and washed twice with saturated aqueous sodium bicarbonate solution. The aqueous phase was extracted twice with dichloromethane, the combined organic phases were dried over sodium sulphate, the

Example 321 rac-N-{2-amino-2-methyl-3-[1-(5-methyl-1,2-ox-azol-3-yl)-1H-1,2,4-triazol-3-yl]propyl}-8-[(2,6-difluorobenzyl)oxy]-2,6-dimethylimidazo[1,2-a]pyridine-3-carboxamide

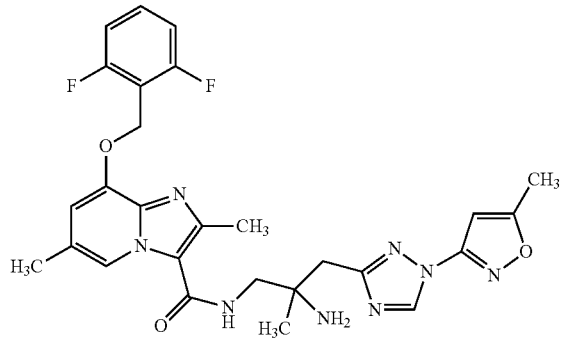

114 mg (0.34 mmol) of 8-[(2,6-difluorobenzyl)oxy]-2,6-dimethylimidazo[1,2-a]pyridine-3-carboxylic acid from Example 21A, 143 mg (0.38 mmol) of HATU and 0.18 ml (1.03 mmol) of N,N-diisopropylethylamine were initially charged in 2.2 ml of DMF, the mixture was stirred for 20 min, 105 mg (0.44 mmol) of rac-2-methyl-3-[1-(5-methyl-1,2-oxazol-3-yl)-1H-1,2,4-triazol-3-yl]propane-1,2-diamine from Example 353A were then added at 0° C. and the mixture was stirred at 0° C. for 60 min. The reaction mixture was purified by preparative HPLC (RP18 column, mobile phase: acetonitrile/water gradient with addition of 0.1% TFA). The concentrated product fractions were partitioned between dichloromethane and saturated aqueous sodium bicarbonate solution. The aqueous phase was extracted two more times with dichloromethane, the combined organic phases were dried over sodium sulphate and filtered and the filtrate was concentrated and lyophilised. This gave 73 mg of the target compound (38% of theory).

LC-MS (Method 2): $R_t$=0.74 min

MS (ESpos): m/z=551 (M+H)$^+$ $^1$H-NMR (400 MHz, DMSO-d$_6$): δ=1.11 (s, 3H), 1.32-1.46 (m, 1H), 2.30 (s, 3H), 2.49 (br. s., 3H), 2.57 (s, 3H), 2.89 (s, 2H), 3.36-3.43 (m, 1H), 5.29 (s, 2H), 6.73-6.78 (m, 1H), 6.92 (s, 1H), 7.19-7.29 (m, 2H), 7.53-7.67 (m, 2H), 8.52 (s, 1H), 9.21 (s, 1H).

Example 322 ent-N-(2-amino-2-methylpentyl)-2-cyclopropyl-8-[(2,6-difluorobenzyl)oxy]-6-methylimidazo[1,2-a]pyridine-3-carboxamide

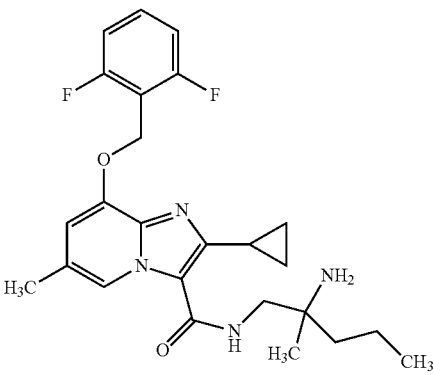 [SMILES: CCCC(C)(N)CNC(=O)c1c(C2CC2)nc2c(OCc3c(F)cccc3F)cc(C)cn12]

Under argon, 74 mg (0.10 mmol) of ent-benzyl {1-[({2-cyclopropyl-8-[(2,6-difluorobenzyl)oxy]-6-methylimidazo[1,2-a]pyridin-3-yl}carbonyl)amino]-2-methylpentan-2-yl}carbamate trifluoroacetate from Example 357A were initially charged in 1 ml of ethanol, 11 mg (0.01 mmol) of 10% palladium on carbon were added and the mixture was hydrogenated at RT and under standard pressure for 1 hour. The reaction mixture was filtered through a Millipore filter, the filter cake was washed with ethanol and the filtrate was concentrated. The product was dissolved in dichloromethane and washed twice with saturated aqueous sodium bicarbonate solution. The combined aqueous phases were extracted twice with dichloromethane. The combined organic phases were dried over sodium sulphate, filtered and concentrated. This gave 41 mg of the target compound (82% of theory).

LC-MS (Method 2): $R_t$=0.78 min

MS (ESpos): m/z=457 (M+H)$^+$ $^1$H-NMR (400 MHz, DMSO-d$_6$): δ=0.86 (t, 3H), 0.92-0.98 (m, 4H), 1.00 (s, 3H), 1.21-1.42 (m, 4H), 1.54-2.00 (br. s, 2H), 2.25-2.34 (m, 4H), 3.15-3.29 (m, 2H), 5.28 (s, 2H), 6.92 (s, 1H), 7.19-7.28 (m, 2H), 7.54-7.64 (m, 1H), 7.75 (t, 1H), 8.54 (s, 1H).

Example 323 ent-N-(2-amino-2-methylpentyl)-8-[(2,6-difluorobenzyl)oxy]-6-ethyl-2-methylimidazo[1,2-a]pyridine-3-carboxamide

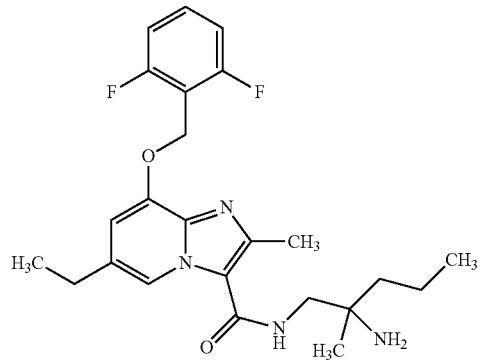 [SMILES: CCCC(C)(N)CNC(=O)c1c(C)nc2c(OCc3c(F)cccc3F)cc(CC)cn12]

25 mg (0.04 mmol, purity 76%) of ent-benzyl {1-[({8-[(2,6-difluorobenzyl)oxy]-6-ethynyl-2-methylimidazo[1,2-a]pyridin-3-yl}carbonyl)amino]-2-methylpentan-2-yl}carbamate from Example 359A were dissolved in 0.5 ml of ethanol, and 2.3 mg (0.002 mmol) of 10% palladium on carbon were added under argon. The reaction mixture was then hydrogenated at RT and under standard pressure for 2 hours. The reaction mixture was filtered through a Millipore filter, the filter cake was washed with ethanol and the filtrate was concentrated and dried under high vacuum. The residue was purified by preparative thin-layer chromatography (mobile phase: dichloromethane/2 N ammonia in methanol=40/1). This gave 2.8 mg of the target compound (13% of theory, purity 92%).

LC-MS (Method 2): $R_t$=0.72 min

MS (ESpos): m/z=445 (M+H)$^+$ $^1$H-NMR (500 MHz, DMSO-$d_6$): δ=1.04 (s, 3H), 1.23 (t, 6H), 1.30-1.40 (m, 6H), 1.42-1.57 (m, 2H), 2.54 (s, 3H), 2.60-2.66 (m, 2H), 5.32 (s, 2H), 6.94-6.96 (m, 1H), 7.20-7.26 (m, 2H), 7.55-7.62 (m, 1H), 7.63-7.72 (m, 1H), 8.48-8.51 (m, 1H).

Example 324

N-[(1R,3S)-3-amino-2,2,3-trimethylcyclopentyl]-8-[(2,6-difluorobenzyl)oxy]-2,6-dimethylimidazo[1,2-a]pyridine-3-carboxamide

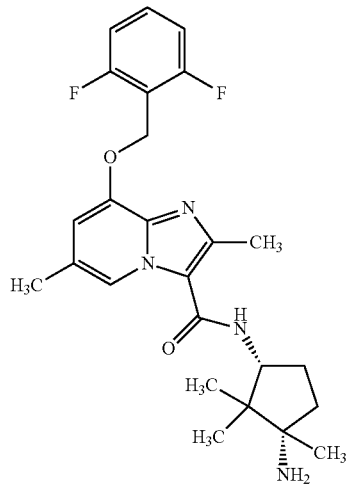

75 mg (0.23 mmol) of 8-[(2,6-difluorobenzyl)oxy]-2,6-dimethylimidazo[1,2-a]pyridine-3-carboxylic acid from Example 21A, 112 mg (0.29 mmol) of HATU and 0.20 ml (1.13 mmol) of N,N-diisopropylethylamine were initially charged in 2.2 ml of DMF, the mixture was stirred for 10 min, 63 mg (0.29 mmol) of (1S,3R)-1,2,2-trimethylcyclopentane-1,3-diamine dihydrochloride were then added at RT and the mixture was stirred at RT for one hour. TFA was added to the reaction solution, and the product was purified by preparative HPLC (RP18 column, mobile phase: acetonitrile/water gradient with addition of 0.1% TFA). The product fractions were concentrated and dried under high vacuum. The residue was taken up in dichloromethane and washed once with saturated aqueous sodium bicarbonate solution, and the aqueous phase was extracted twice with dichloromethane. The combined organic phases were dried over sodium sulphate and filtered, and the filtrate was concentrated. This gave 90 mg of the target compound (85% of theory).

LC-MS (Method 2): $R_t$=0.62 min

MS (ESpos): m/z=457 (M+H)$^+$ $^1$H-NMR (400 MHz, DMSO-$d_6$): δ=0.86-0.92 (m, 6H), 1.10 (s, 3H), 1.56-1.66 (m, 1H), 1.70 (t, 2H), 2.07-2.17 (m, 1H), 2.31 (s, 3H), 2.53 (s, 3H), 4.18-4.27 (m, 1H), 5.28 (s, 2H), 6.92 (s, 1H), 7.20-7.28 (m, 2H), 7.54-7.64 (m, 1H), 8.38 (d, 1H), 8.65 (s, 1H).

Example 325 ent-8-[(2,6-Difluorobenzyl)oxy]-N-[2-ethyl-6-(trifluoromethyl)-1,2,3,4-tetrahydro-1,5-naphthyridin-4-yl]-2,6-dimethylimidazo[1,2-a]pyridine-3-carboxamide

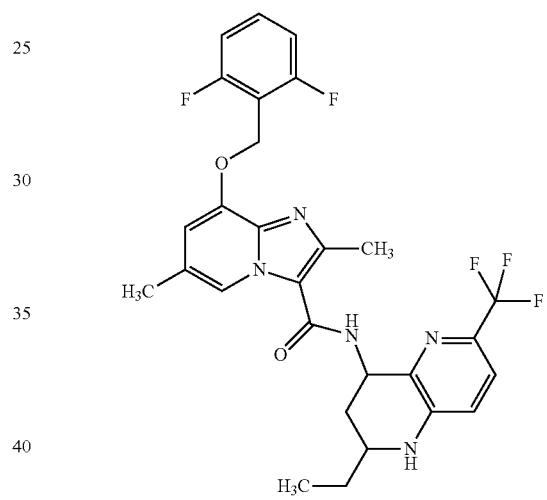

50 mg (0.15 mmol) of 8-[(2,6-difluorobenzyl)oxy]-2,6-dimethylimidazo[1,2-a]pyridine-3-carboxylic acid from Example 21A, 69 mg (0.18 mmol) of HATU and 0.13 ml (0.75 mmol) of N,N-diisopropylethylamine were initially charged in 1.5 ml of DMF, the mixture was stirred for 10 min, 51 mg (0.18 mmol) of ent-2-ethyl-6-(trifluoromethyl)-1,2,3,4-tetrahydro-1,5-naphthyridine-4-amine hydrochloride from Example 361A were then added at RT and the mixture was stirred at RT for 2.5 hours. Water was added to the reaction mixture, and the solid formed was filtered off and dried under high vacuum. This gave 66 mg of the target compound (76% of theory).

LC-MS (Method 2): $R_t$=1.12 min

MS (ESpos): m/z=560 (M+H)$^+$ $^1$H-NMR (400 MHz, DMSO-$d_6$): δ=0.99 (t, 3H), 1.48-1.72 (m, 3H), 2.32 (s, 3H), 2.36-2.44 (m, 1H), 2.57 (s, 3H), 3.49-3.59 (m, 1H), 5.20-5.27 (m, 1H), 5.29 (s, 2H), 6.70 (s, 1H), 6.93 (s, 1H), 7.02 (d, 1H), 7.20-7.29 (m, 2H), 7.43 (d, 1H), 7.54-7.65 (m, 1H), 8.09 (d, 1H), 8.50 (s, 1H).

Example 326 ent-8-[(2,6-Difluorobenzyl)oxy]-2,6-dimethyl-N-[2-methyl-6-(trifluoromethyl)-1,2,3,4-tetrahydro-1,5-naphthyridin-4-yl]imidazo[1,2-a]pyridine-3-carboxamide

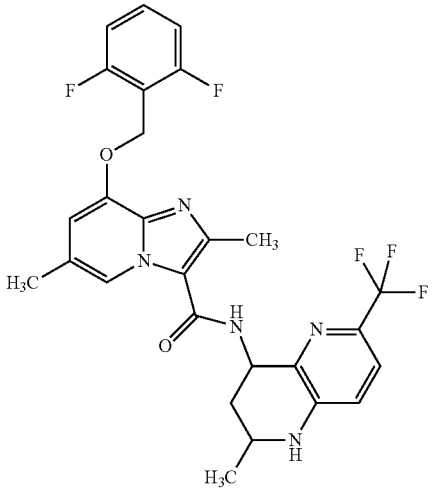 [SMILES: Cc1cc(OCc2c(F)cccc2F)c2nc(C)c(C(=O)NC3CC(C)Nc4ccc(C(F)(F)F)nc43)n2c1]

49 mg (0.15 mmol) of 8-[(2,6-difluorobenzyl)oxy]-2,6-dimethylimidazo[1,2-a]pyridine-3-carboxylic acid from Example 21A, 67 mg (0.18 mmol) of HATU and 0.13 ml (0.74 mmol) of N,N-diisopropylethylamine were initially charged in 1.5 ml of DMF, 47 mg (0.18 mmol) of ent-2-methyl-6-(trifluoromethyl)-1,2,3,4-tetrahydro-1,5-naphthyridine-4-amine hydrochloride from Example 363A were added at RT and the mixture was stirred at RT for 3 hours. Water was added to the reaction mixture, and the solid formed was filtered off and dried under high vacuum. This gave 63 mg of the target compound (74% of theory).

LC-MS (Method 2): $R_t$=1.06 min
MS (ESpos): m/z=546 (M+H)$^+$
$^1$H-NMR (400 MHz, DMSO-d$_6$): δ=0.91-0.97 (m, 1H), 1.23 (d, 3H), 1.62-1.73 (m, 1H), 2.32 (s, 3H), 2.56 (br. s., 3H), 3.66-3.78 (m, 1H), 5.20-5.27 (m, 1H), 5.29 (s, 2H), 6.76-6.82 (m, 1H), 6.90-6.99 (m, 2H), 7.19-7.29 (m, 2H), 7.43 (d, 1H), 7.55-7.64 (m, 1H), 8.07-8.13 (m, 1H), 8.48 (s, 1H).

Example 327 ent-N-(2-amino-2-methylbutyl)-8-[(2,6-difluorobenzyl)oxy]-6-methyl-2-propylimidazo[1,2-a]pyridine-3-carboxamide

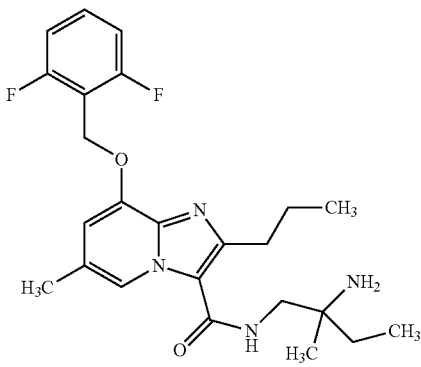 [SMILES: CCCc1nc2c(OCc3c(F)cccc3F)cc(C)cn2c1C(=O)NCC(C)(N)CC]

Under argon, 107 mg (0.18 mmol) of ent-benzyl {1-[({8-[(2,6-difluorobenzyl)oxy]-6-methyl-2-propylimidazo[1,2-a]pyridin-3-yl}carbonyl)amino]-2-methylbutan-2-yl}carbamate from Example 366A were initially charged in 3 ml of DMF, 15 mg of 10% palladium on activated carbon were added and the mixture was hydrogenated at RT and under standard pressure for 2 hours. The reaction mixture was filtered through Celite, the filter cake was washed thoroughly with DMF and the filtrate was concentrated. The residue was taken up in ethanol and once more filtered through Celite and concentrated. The residue was dissolved in dichloromethane and purified by silica gel chromatography (mobile phase: dichloromethane/7 N ammonia in methanol: 1/0 to 5/1). This gave 77 mg of the target compound (93% of theory).

LC-MS (Method 2): $R_t$=0.71 min
MS (ESpos): m/z=445 (M+H)$^+$
$^1$H-NMR (400 MHz, DMSO-d$_6$): δ=0.82-0.93 (m, 6H), 1.00 (s, 3H), 1.31-1.45 (m, 2H), 1.60-1.72 (m, 2H), 2.30 (s, 3H), 2.86 (t, 2H), 3.15-3.28 (m, 2H), 5.29 (s, 2H), 6.91 (s, 1H), 7.24 (t, 2H), 7.55-7.64 (m, 1H), 7.70 (t, 1H), 8.41 (s, 1H).

Example 328 ent-N-(2-aminocyclobutyl)-8-[(2,6-difluorobenzyl)oxy]-2,6-dimethylimidazo[1,2-a]pyridine-3-carboxamide (Enantiomer A)

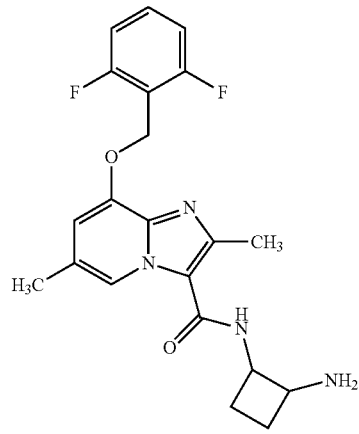 [SMILES: Cc1cc(OCc2c(F)cccc2F)c2nc(C)c(C(=O)NC3CCC3N)n2c1]

77 mg (0.15 mmol) of ent-tert-butyl {2-[({8-[(2,6-difluorobenzyl)oxy]-2,6-dimethylimidazo[1,2-a]pyridin-3-yl}carbonyl)amino]cyclobutyl}carbamate (enantiomer A) from Example 368A were initially charged in 0.8 ml of diethyl ether, 0.77 ml (1.54 mmol) of 2 N hydrochloric acid and diethyl ether was added and the mixture was stirred at RT overnight. The reaction solution was concentrated and the residue was taken up in dichloromethane and washed twice with saturated aqueous sodium bicarbonate solution. The combined aqueous phases were extracted twice with dichloromethane. The combined organic phases were dried over sodium sulphate, filtered and concentrated. This gave 56 mg of the target compound (89% of theory).

LC-MS (Method 2): $R_t$=0.60 min
MS (ESpos): m/z=401 (M+H)$^+$
$^1$H-NMR (400 MHz, DMSO-d$_6$): δ=1.32-1.45 (m, 1H), 1.47-1.59 (m, 1H), 1.92-2.03 (m, 2H), 2.31 (s, 3H), 2.49 (br. s., 3H), 3.25-3.30 (m, 1H), 4.00-4.11 (m, 1H), 5.28 (s, 2H), 6.91 (s, 1H), 7.20-7.28 (m, 2H), 7.55-7.64 (m, 1H), 8.00 (d, 1H), 8.41 (s, 1H).

Example 329 ent-N-(2-aminocyclobutyl)-8-[(2,6-difluorobenzyl) oxy]-2,6-dimethylimidazo[1,2-a]pyridine-3-carboxamide (Enantiomer B)

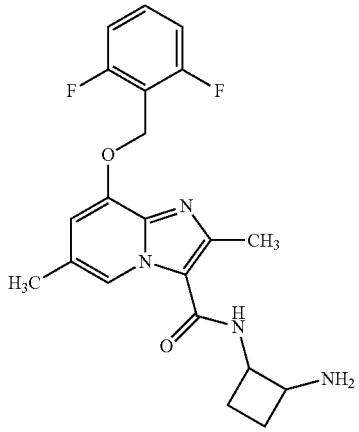 [SMILES: Cc1cc(OCc2c(F)cccc2F)c2nc(C)c(C(=O)NC3CCC3N)n2c1]

67 mg (0.13 mmol) of ent-tert-butyl {2-[({8-[(2,6-difluorobenzyl)oxy]-2,6-dimethylimidazo[1,2-a]pyridin-3-yl}carbonyl)amino]cyclobutyl}carbamate (enantiomer B) from Example 369A were initially charged in 0.7 ml of diethyl ether, 0.67 ml (1.34 mmol) of 2 N hydrochloric acid in diethyl ether was added and the mixture was stirred at RT overnight. The reaction solution was concentrated and the residue was taken up in dichloromethane and washed twice with saturated aqueous sodium bicarbonate solution. The combined aqueous phases were extracted twice with dichloromethane. The combined organic phases were dried over sodium sulphate, filtered and concentrated. This gave 51 mg of the target compound (94% of theory).

LC-MS (Method 2): $R_t$=0.60 min
MS (ESpos): m/z=401 (M+H)$^+$
$^1$H-NMR (400 MHz, DMSO-$d_6$): δ=1.32-1.45 (m, 1H), 1.47-1.59 (m, 1H), 1.92-2.03 (m, 2H), 2.31 (s, 3H), 2.49 (br. s., 3H), 3.25-3.30 (m, 1H), 4.00-4.11 (m, 1H), 5.28 (s, 2H), 6.91 (s, 1H), 7.20-7.28 (m, 2H), 7.55-7.64 (m, 1H), 8.00 (d, 1H), 8.41 (s, 1H).

Example 330 rac-N-(2-aminocyclopropyl)-8-[(2,6-difluorobenzyl) oxy]-2,6-dimethylimidazo[1,2-a]pyridine-3-carboxamide

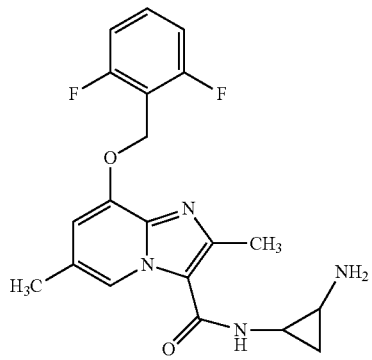 [SMILES: Cc1cc(OCc2c(F)cccc2F)c2nc(C)c(C(=O)NC3CC3N)n2c1]

150 mg (0.45 mmol) of 8-[(2,6-difluorobenzyl)oxy]-2,6-dimethylimidazo[1,2-a]pyridine-3-carboxylic acid from Example 21A, 206 mg (0.54 mmol) of HATU and 0.47 ml (2.71 mmol) of N,N-diisopropylethylamine were initially charged in 1.34 ml of DMF, and the mixture was stirred at RT for 10 min. The reaction mixture was slowly added dropwise to 0.54 ml (1.13 mmol) of rac-cyclopropane-1,2-diamine hydrochloride in 0.45 ml of DMF, and the mixture was stirred at RT overnight. TFA was added to the reaction solution, and the product was purified by preparative HPLC (RP 18 column, mobile phase: acetonitrile/water gradient with addition of 0.1% TFA). The product-containing fractions were concentrated and the residue was purified by thick-layer chromatography (mobile phase: dichloromethane/2 N ammonia in methanol=10/1). This gave 18 mg of the target compound (10% of theory).

LC-MS (Method 2): $R_t$=0.58 min
MS (ESpos): m/z=387 (M+H)$^+$
$^1$H-NMR (400 MHz, DMSO-$d_6$): δ=0.66-0.72 (m, 1H), 0.73-0.79 (m, 1H), 1.85-1.95 (m, 2H), 2.31 (s, 3H), 2.33-2.36 (m, 1H), 2.40 (s, 3H), 2.60-2.66 (m, 1H), 5.27 (s, 2H), 6.90 (s, 1H), 7.19-7.28 (m, 2H), 7.54-7.64 (m, 1H), 7.82 (d, 1H), 8.40 (s, 1H).

Example 331 rac-N-(2-amino-2-methylcyclobutyl)-8-[(2,6-difluorobenzyl)oxy]-2,6-dimethylimidazo[1,2-a]pyridine-3-carboxamide

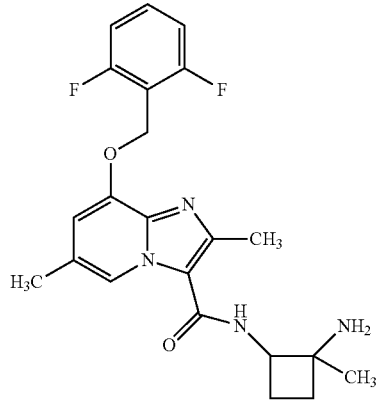

150 mg (0.45 mmol) of 8-[(2,6-Difluorobenzyl)oxy]-2,6-dimethylimidazo[1,2-a]pyridine-3-carboxylic acid from Example 21A, 206 mg (0.54 mmol) of HATU and 0.47 ml (2.71 mmol) of N,N-diisopropylethylamine were initially charged in 1.34 ml of DMF, and the mixture was stirred at RT for 10 min. The reaction mixture was slowly added dropwise to 0.54 ml (1.81 mmol) of rac-1-methylcyclobutane-1,2-diamine dihydrochloride (described in: K.-H. Scholz; J. Hinz; H.-G. Heine; W. Hartmann, Liebigs Annalen der Chemie, 1981, 248-255; Duschinsky; Dolan Journal of the American Chemical Society, 1945, 67, 2079, 2082) in 0.9 ml of DMF, and the mixture was stirred at RT overnight. Water/TFA was added to the reaction solution, and the product was purified by preparative HPLC (RP18 column, mobile phase: acetonitrile/water gradient with addition of 0.1% TFA). The concentrated fractions were taken up in dichloromethane and a little methanol and washed twice with saturated aqueous sodium bicarbonate solution. The combined aqueous phases were extracted twice with dichloromethane. The combined organic phases were dried over sodium sulphate, filtered and concentrated. This gave 100 mg of the target compound (52% of theory).

LC-MS (Method 2): $R_t$=0.58 min

MS (ESpos): m/z=415 (M+H)$^+$ $^1$H-NMR (400 MHz, DMSO-d$_6$): δ=1.12 (s, 3H), 1.57-1.73 (m, 3H), 1.88-1.97 (m, 1H), 1.98-2.07 (m, 2H), 2.31 (s, 3H), 2.51 (br. s., 3H), 4.20 (q, 1H), 5.28 (s, 2H), 6.90 (s, 1H), 7.19-7.28 (m, 2H), 7.54-7.64 (m, 1H), 7.76 (d, 1H), 8.38 (s, 1H).

Example 332 ent-N-[2-amino-2-methylcyclobutyl]-8-[(2,6-difluorobenzyl)oxy]-2,6-dimethylimidazo[1,2-a]pyridine-3-carboxamide (Enantiomer A)

95 mg of rac-N-[2-amino-2-methylcyclobutyl]-8-[(2,6-difluorobenzyl)oxy]-2,6-dimethylimidazo-[1,2-a]pyridine-3-carboxamide (Example 331) were separated into the enantiomers on a chiral phase [column: Daicel Chiralcel OZ-H, 5 µm, 250×20 mm, mobile phase: 50% isohexane, 50% ethanol+0.2% diethylamine, flow rate 20 ml/min; temperature: 20° C., detection: 250 nm].

Enantiomer A: 29 mg (>99% ee)

$R_t$=9.47 min [Daicel Chiralcel OZ-H, 5 m, 250×4.6 mm; mobile phase: 50% isohexane, 50% ethanol+0.2% diethylamine; flow rate 1.0 ml/min; temperature: 30° C.; detection: 220 nm].

LC-MS (Method 2): $R_t$=0.55 min

MS (ESpos): m/z=415 (M+H)$^+$ $^1$H NMR (400 MHz, DMSO-d$_6$) δ=1.12 (s, 3H), 1.55-1.75 (m, 3H), 1.85-2.01 (m, 1H), 2.31 (s, 3H), 4.21 (q, 1H), 5.28 (s, 2H), 6.90 (s, 1H), 7.24 (t, 2H), 7.54-7.64 (m, 1H), 7.77 (d, 1H), 8.38 (s, 1H).

Example 333 ent-N-[2-amino-2-methylcyclobutyl]-8-[(2,6-difluorobenzyl)oxy]-2,6-dimethylimidazo[1,2-a]pyridine-3-carboxamide (Enantiomer B)

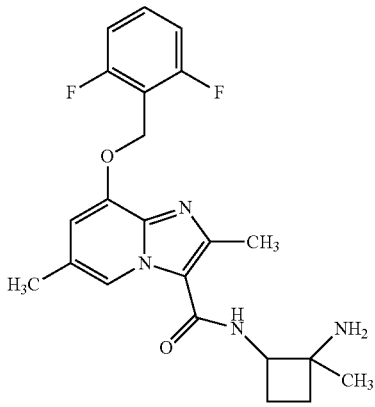

95 mg of rac-N-[2-amino-2-methylcyclobutyl]-8-[(2,6-difluorobenzyl)oxy]-2,6-dimethylimidazo-[1,2-a]pyridine-3-carboxamide (Example 331) were separated into the enantiomers on a chiral phase [column: Daicel Chiralcel OZ-H, 5 µm, 250×20 mm, mobile phase: 50% isohexane, 50% ethanol+0.2% diethylamine, flow rate 20 ml/min; temperature: 20° C., detection: 250 nm].

Enantiomer B: 32 mg (purity 90%, >83% ee)

$R_t$=15.21 min [Daicel Chiralcel OZ-H, 5 m, 250×4.6 mm; mobile phase: 50% isohexane, 50% ethanol+0.2% diethylamine; flow rate 1.0 ml/min; temperature: 30° C.; detection: 220 nm].

LC-MS (Method 2): $R_t$=0.55 min

MS (ESpos): m/z=415 (M+H)$^+$ $^1$H NMR (400 MHz, DMSO-d$_6$) δ=1.12 (s, 3H), 1.55-1.75 (m, 3H), 1.85-2.00 (m, 1H), 2.31 (s, 3H), 4.21 (q, 1H), 5.28 (s, 2H), 6.90 (s, 1H), 7.24 (t, 2H), 7.54-7.64 (m, 1H), 7.77 (d, 1H), 8.38 (s, 1H).

Example 334

N-(3-aminocyclobutyl)-8-[(2,6-difluorobenzyl)oxy]-2,6-dimethylimidazo[1,2-a]pyridine-3-carboxamide (Cis/Trans Mixture)

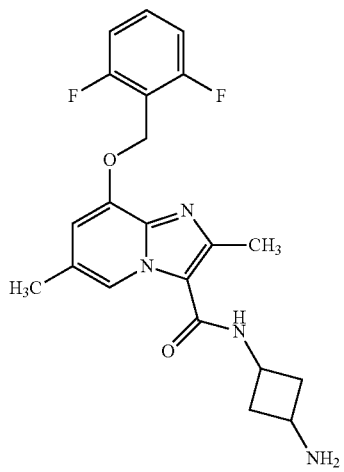 [SMILES: Cc1cc(OCc2c(F)cccc2F)c2nc(C)c(C(=O)NC3CC(N)C3)n2c1]

0.75 ml of DMF, 0.94 ml (5.42 mmol) of N,N-diisopropylethylamine and 0.75 ml of DMSO were added to 287 mg (1.81 mmol) of cyclobutane-1,3-diamine dihydrochloride (cis/trans mixture) and the mixture was stirred at RT for one hour. The suspension was heated to 60° C. 0.75 ml of DMSO was added, and a solution of 150 mg (0.45 mmol) of 8-[(2,6-difluorobenzyl)oxy]-2,6-dimethylimidazo[1,2-a]pyridine-3-carboxylic acid from Example 21A, 0.16 ml (0.90 mmol) of N,N-diisopropylethylamine and 206 mg (0.54 mmol) of HATU in 1.3 ml of DMF, which had been stirred at RT for 10 min beforehand, was then added. The mixture was stirred at 60° C. for 30 min, water and TFA were then added and the product was purified by preparative HPLC (RP18 column, mobile phase: acetonitrile/water gradient with addition of 0.1% TFA). The product-containing fractions were concentrated and the residue was taken up in dichloromethane and washed twice with saturated aqueous sodium bicarbonate solution. The aqueous phase was extracted twice with dichloromethane, the combined organic phases were dried over sodium sulphate, the filtrate was concentrated and the residue was concentrated. This gave 110 mg of the target compound (60% of theory).

LC-MS (Method 2): $R_t$=0.60 min

MS (ESpos): m/z=401 (M+H)$^+$ $^1$H NMR (400 MHz, DMSO-d$_6$) δ=1.66-1.82 (m, 3H), 1.94-2.06 and 2.19-2.27 (m, 1H), 2.30 (s, 3H), 2.47 (s, 3H), 2.97-3.08 and 3.91-4.03 (m, 1H), 5.28 (s, 2H), 6.90 (s, 1H), 7.24 (t, 2H), 7.52-7.64 (m, 1H), 7.92 and 8.08 (d and d, 1H), 8.35-8.40 (m, 1H).

Example 335 rac-N-[2-amino-1,2-dimethylcyclobutyl]-8-[(2,6-difluorobenzyl)oxy]-2,6-dimethylimidazo[1,2-a]pyridine-3-carboxamide

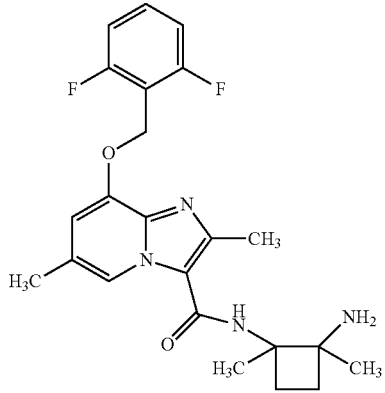

1 ml of DMF, 1.26 ml (7.22 mmol) of N,N-diisopropylethylamine and 2 ml of DMSO were added to 451 mg (2.41 mmol) of rac-1,2-dimethylcyclobutane-1,2-diamine dihydrochloride (described in: K.-H. Scholz; J. Hinz; H.-G. Heine; W. Hartmann, Liebigs Annalen der Chemie, 1981, 248-255; J. L. Gagnon; W. W. Zajac, Synthetic Communications 1996, 26, 837-846), and the mixture was stirred at 60° C. A solution of 200 mg (0.60 mmol) of 8-[(2,6-difluorobenzyl)oxy]-2,6-dimethylimidazo[1,2-a]pyridine-3-carboxylic acid from Example 21A, 0.21 ml (1.20 mmol) of N,N-diisopropylethylamine and 275 mg (0.72 mmol) of HATU in 1.8 ml of DMF, which had been stirred at RT for 10 min beforehand, was added dropwise. The solution was stirred at 60° C. for 30 min, water and TFA were then added and the product was purified by preparative HPLC (RP 18 column, mobile phase: acetonitrile/water gradient with addition of 0.1% TFA). The product-containing fractions were concentrated and the residue was taken up in dichloromethane and washed twice with saturated aqueous sodium bicarbonate solution. The aqueous phase was extracted twice with dichloromethane, the organic phases were dried over sodium sulphate and filtered, the filtrate was concentrated and the residue was concentrated. This gave 198 mg of the target compound (77% of theory).

LC-MS (Method 2): $R_t$=0.64 min

MS (ESpos): m/z=429 (M+H)$^+$ $^1$H NMR (400 MHz, DMSO-d$_6$) δ=1.23 (s, 3H), 1.45 (s, 3H), 1.60-1.76 (m, 3H), 1.93-2.04 (m, 1H), 2.31 (s, 3H), 2.47 (s, 3H), 5.29 (s, 2H), 6.88 (s, 1H), 7.22 (t, 2H), 7.54-7.63 (m, 1H), 7.80 (s, 1H), 8.36 (s, 1H).

Example 336 ent-N-[(2-amino-1,2-dimethylcyclobutyl]-8-[(2,6-difluorobenzyl)oxy]-2,6-dimethylimidazo[1,2-a]pyridine-3-carboxamide (Enantiomer A)

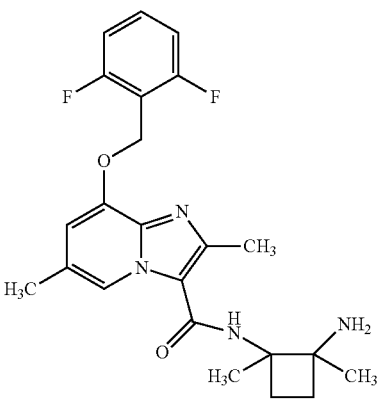

190 mg of rac-N-[2-amino-1,2-dimethylcyclobutyl]-8-[(2,6-difluorobenzyl)oxy]-2,6-dimethylimidazo[1,2-a]pyridine-3-carboxamide (Example 335) were separated into the enantiomers on a chiral phase [column: Daicel Chiralcel OZ-H, 5 μm, 250×20 mm, mobile phase: 45% isopropanol, 50% isohexane, 5%+isopropanol+2% diethylamine, flow rate 20 ml/min; temperature: 25° C., detection: 210 nm].

Enantiomer A: 20 mg (>99% ee)

$R_t$=6.26 min [Daicel Chiralcel OZ-H, 5 μm, 250×4.6 mm; mobile phase: 50% isohexane, 50% isopropanol+0.2% diethylamine; flow rate 1.0 ml/min; 30° C.; detection: 220 nm].

LC-MS (Method 2): $R_t$=0.59 min

MS (ESpos): m/z=429 (M+H)$^+$ $^1$H NMR (500 MHz, DMSO-d$_6$) δ=1.25 (s, 3H), 1.48 (s, 3H), 1.63-1.82 (m, 3H), 1.93-2.04 (m, 1H), 2.31 (s, 3H), 2.49 (s, 3H), 5.29 (s, 2H), 6.89 (s, 1H), 7.23 (t, 2H), 7.54-7.63 (m, 1H), 7.81 (s, 1H), 8.37 (s, 1H).

Example 337 ent-N-[(2-amino-1,2-dimethylcyclobutyl]-8-[(2,6-difluorobenzyl)oxy]-2,6-dimethylimidazo[1,2-a]pyridine-3-carboxamide (Enantiomer B)

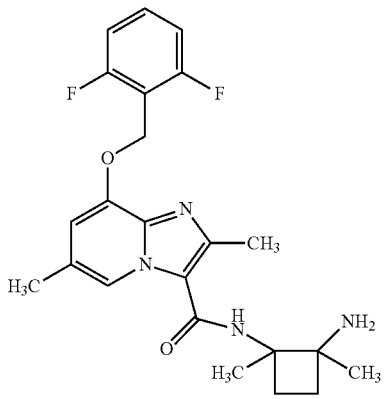

190 mg of rac-N-[(1S,2S)-2-amino-1,2-dimethylcyclobutyl]-8-[(2,6-difluorobenzyl)oxy]-2,6-dimethylimidazo[1,2-a]pyridine-3-carboxamide (Example 335) were separated into the enantiomers on a chiral phase [column: Daicel Chiralcel OZ-H, 5 μm, 250×20 mm, mobile phase: 45% isopropanol, 50% isohexane, 5%+isopropanol+2% diethylamine, flow rate 20 ml/min; temperature: 25° C., detection: 210 nm].

Enantiomer B: 16 mg (>99% ee)
$R_t$=13.44 min [Daicel Chiralcel OZ-H, 5 μm, 250×4.6 mm; mobile phase: 50% isohexane, 50% isopropanol+0.2% diethylamine; flow rate 1.0 ml/min; temperature: 30° C.; detection: 220 nm].
LC-MS (Method 2): $R_t$=0.59 min
MS (ESpos): m/z=429 (M+H)$^+$
$^1$H NMR (500 MHz, DMSO-d$_6$) δ=1.26 (s, 3H), 1.48 (s, 3H), 1.61-1.78 (m, 3H), 1.93-2.04 (m, 1H), 2.31 (s, 3H), 2.49 (s, 3H), 5.29 (s, 2H), 6.89 (s, 1H), 7.23 (t, 2H), 7.54-7.63 (m, 1H), 7.81 (s, 1H), 8.36 (s, 1H).

Example 338 ent-N-(2-amino-2-methylpentyl)-8-[(2,6-difluorobenzyl)oxy]-2-ethyl-6-methylimidazo[1,2-a]pyridine-3-carboxamide

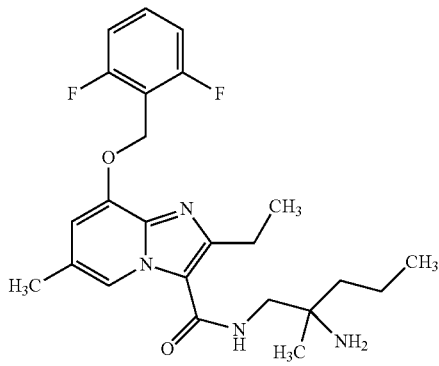 [SMILES: CCCC(C)(N)CNC(=O)c1c(CC)nc2c(OCc3c(F)cccc3F)cc(C)cn12]

180 mg (0.26 mmol) of ent-benzyl {1-[({8-[(2,6-difluorobenzyl)oxy]-2-ethyl-6-methylimidazo[1,2-a]pyridin-3-yl}carbonyl)amino]-2-methylpentan-2-yl}carbamate trifluoroacetate from Example 370A were dissolved in 2.8 ml of ethanol, and 18.2 mg (0.03 mmol) of 20% palladium(II) hydroxide on carbon were added under argon. The reaction mixture was then hydrogenated at RT and under standard pressure for two hours. The reaction mixture was transferred to diatomaceous earth and purified by silica gel chromatography (mobile phase: dichloromethane/2N ammonia in methanol=50/1). This gave 94 mg of the target compound (81% of theory).
LC-MS (Method 2): $R_t$=0.69 min
MS (ESpos): m/z=445 (M+H)$^+$
$^1$H-NMR (400 MHz, DMSO-d$_6$): δ=0.87 (t, 3H), 0.99 (s, 3H), 1.22 (t, 3H), 1.26-1.40 (m, 4H), 1.41-1.54 (m, 2H), 2.30 (s, 3H), 2.91 (q, 2H), 3.14-3.25 (m, 2H), 5.29 (s, 2H), 6.91 (s, 1H), 7.20-7.28 (m, 2H), 7.55-7.71 (m, 2H), 8.41 (s, 1H).

Example 339 rac-8-[(2,6-Difluorobenzyl)oxy]-N-(6-methoxy-1,2,3,4-tetrahydroquinolin-4-yl)-2,6-dimethylimidazo[1,2-a]pyridine-3-carboxamide

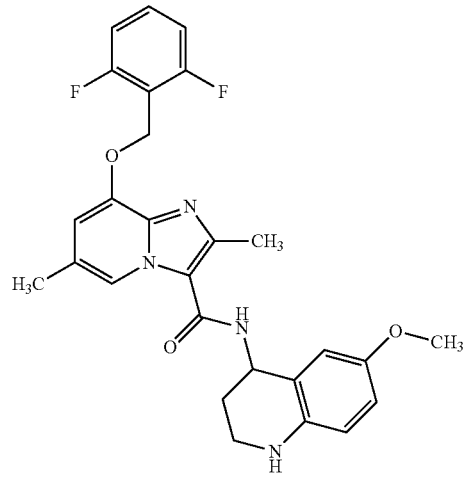

100 mg (0.30 mmol) of 8-[(2,6-difluorobenzyl)oxy]-2,6-dimethylimidazo[1,2-a]pyridine-3-carboxylic acid from Example 21A, 126 mg (0.33 mmol) of HATU and 117 mg (0.90 mmol) of N,N-diisopropylethylamine were initially charged in 1 ml of DMF, and the mixture was stirred at RT for 10 min. 62 mg (0.35 mmol) of rac-6-methoxy-1,2,3,4-tetrahydroquinoline-4-amine were then added, and the mixture was stirred at RT for 1 h. Acetonitrile, TFA and water were added to the reaction mixture, and the product was purified by preparative HPLC (RP-C18, mobile phase: acetonitrile/water gradient with addition of 0.1% TFA). The product-containing fractions were concentrated and the residue was taken up in dichloromethane and washed twice with saturated aqueous sodium bicarbonate solution. The aqueous phase was extracted twice with dichloromethane. The combined organic phases were dried over sodium sulphate and filtered, and the filtrate was concentrated. This gave 129 mg (87% of theory) of the title compound.
LC-MS (Method 2): $R_t$=0.82 min
MS (ESpos): m/z=493 (M+H)$^+$ ¹H-NMR (400 MHz, DMSO-d₆): δ=1.89-2.10 (m, 2H), 2.32 (s, 3H), 2.48 (s, 3H), 3.15-3.28 (m, 2H), 3.61 (s, 3H), 5.12-5.20 (m, 1H), 5.29 (s, 2H), 5.42-5.47 (m, 1H), 6.48 (d, 1H), 6.59-6.65 (m, 1H), 6.76 (d, 1H), 6.90 (s, 1H), 7.19-7.26 (m, 2H), 7.55-7.64 (m, 1H), 8.23 (d, 1H), 8.39 (s, 1H).

Example 340 rac-N-(2-amino-2-methylpentyl)-8-(benzyloxy)-2,6-dimethylimidazo[1,2-a]pyridine-3-carboxamide

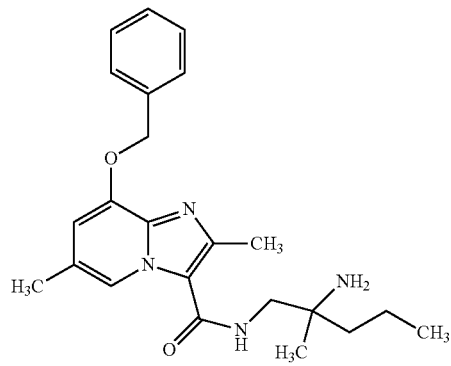

75 mg (0.15 mmol) of rac-tert-butyl [1-({[8-(benzyloxy)-2,6-dimethylimidazo[1,2-a]pyridin-3-yl]carbonyl}amino)-2-methylpentan-2-yl]carbamate from Example 329A were initially charged in 0.74 ml of diethyl ether, 0.74 ml (1.47 mmol) of 2 N hydrochloric acid in diethyl ether was added and the mixture was stirred at RT overnight. 0.74 ml (1.47 mmol) of 2 N hydrochloric acid in diethyl ether was added to the reaction mixture, and the mixture was stirred at RT overnight. The mixture was then concentrated, the residue was dissolved in dichloromethane and the solution was washed twice with saturated aqueous sodium bicarbonate solution. The combined organic phases were extracted twice with dichloromethane. The combined organic phases were dried over sodium sulphate, filtered and concentrated. This gave 57 mg of the target compound (96% of theory).

LC-MS (Method 2): R_f=0.67 min

MS (ESpos): m/z=395 (M+H)⁺

¹H-NMR (400 MHz, DMSO-d₆): δ=0.87 (t, 3H), 1.00 (s, 3H), 1.24-1.43 (m, 4H), 1.52-1.92 (m, 2H), 2.27 (s, 3H), 2.56 (s, 3H), 3.14-3.27 (m, 2H), 5.27 (s, 2H), 6.81 (s, 1H), 7.34-7.40 (m, 1H), 7.43 (t, 2H), 7.48-7.54 (m, 2H), 7.63 (t, 1H), 8.45 (s, 1H).

Example 341 rac-N-(3-amino-2,2-dimethylcyclopropyl)-8-[(2,6-difluorobenzyl)oxy]-2,6-dimethylimidazo[1,2-a]pyridine-3-carboxamide (racemate)

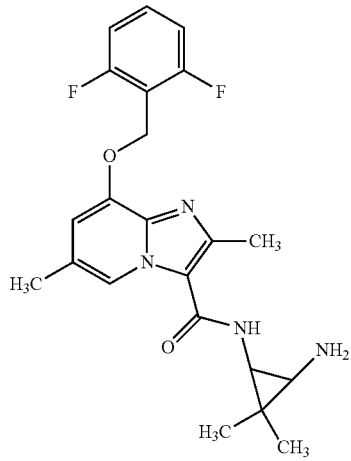 [SMILES: Cc1cc(OCc2c(F)cccc2F)c2nc(C)c(C(=O)NC3C(N)C3(C)C)n2c1]

0.5 ml of DMF and 0.39 ml (2.26 mmol) of N,N-diisopropylethylamine were added to 195 mg (1.13 mmol) of rac-3,3-dimethylcyclopropane-1,2-diamine dihydrochloride (described in: G.-Q. Feng et al. Tetrahedron: Asymmetry 2006, 17, 2775-2780). A solution of 150 mg (0.45 mmol) of 8-[(2,6-difluorobenzyl)oxy]-2,6-dimethylimidazo[1,2-a]pyridine-3-carboxylic acid from Example 21A, 0.47 ml (2.71 mmol) of N,N-diisopropylethylamine and 206 mg (0.54 mmol) of HATU in 1.34 ml of DMF, which had been stirred at RT for 10 min beforehand, was added dropwise to the reaction mixture. The mixture was stirred at RT for 30 min, water and TFA were then added and the product was purified by preparative HPLC (RP18 column, mobile phase: acetonitrile/water gradient with addition of 0.1% TFA). The product-containing fractions were concentrated and the residue was taken up in dichloromethane and washed twice with saturated aqueous sodium bicarbonate solution. The aqueous phase was extracted twice with dichloromethane, the combined organic phases were dried over sodium sulphate and filtered, the filtrate was concentrated and the residue was concentrated. This gave 78 mg of the target compound (40% of theory).

LC-MS (Method 2): R_f=0.61 min

MS (ESpos): m/z=415 (M+H)⁺

¹H NMR (500 MHz, DMSO-d₆) δ=0.99 (s, 3H), 1.14 (s, 3H), 2.15-2.18 (m, 1H), 2.28-2.32 (m, 4H), 2.44 (s, 3H), 5.28 (s, 2H), 6.89 (s, 1H), 7.23 (t, 2H), 7.54-7.63 (m, 1H), 7.79 (s, 1H), 8.39-8.43 (m, 1H).

Example 342 rac-8-[(2,6-Difluorobenzyl)oxy]-2,6-dimethyl-N-(octahydrocyclopenta[b]pyrrol-4-yl)imidazo[1,2-a]pyridine-3-carboxamide

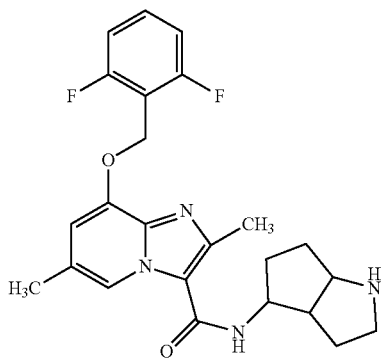 [SMILES: Cc1cc(OCc2c(F)cccc2F)c2nc(C)c(C(=O)NC3CCC4NCCC43)n2c1]

115 mg (0.21 mmol) of rac-tert-butyl-4-[({8-[(2,6-difluorobenzyl)oxy]-2,6-dimethylimidazo[1,2-a]pyridin-3-yl}carbonyl)amino]hexahydrocyclopenta[b]pyrrole-1(2H)-carboxylate from Example 371A were initially charged in 1 ml of diethyl ether, 1 ml (2.13 mmol) of 2 N hydrochloric acid and diethyl ether was added and the mixture was stirred at RT for 4 hours. The reaction mixture was concentrated, dichloromethane was added to the residue and the mixture was washed twice with saturated aqueous sodium bicarbonate solution. The combined aqueous phases were extracted twice with dichloromethane. The combined organic phases were dried over sodium sulphate, filtered and concentrated. The residue was lyophilised. This gave 72 mg of the target compound (75% of theory).

LC-MS (Method 2): $R_t$=0.57 min
MS (ESpos): m/z=441 (M+H)$^+$
$^1$H-NMR (400 MHz, DMSO-$d_6$): δ=1.47-1.66 (m, 4H), 1.67-1.79 (m, 2H), 2.31 (s, 3H), 2.48 (s, 3H), 2.57-2.65 (m, 1H), 2.68-2.79 (m, 1H), 2.84-2.92 (m, 1H), 3.58 (t, 1H), 4.12-4.24 (m, 1H), 5.28 (s, 2H), 6.90 (s, 1H), 7.18-7.29 (m, 2H), 7.53-7.66 (m, 1H), 7.84 (d, 1H), 8.37 (s, 1H).

Example 343 rac-N-(2-amino-2-methylpentyl)-8-[(2-chlorobenzyl)oxy]-2,6-dimethylimidazo[1,2-a]pyridine-3-carboxamide

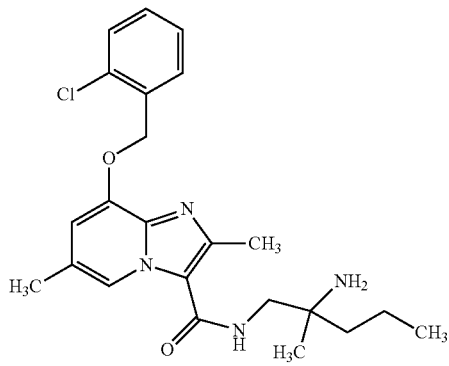 [SMILES: CCCC(C)(N)CNC(=O)c1c(C)nc2c(OCc3ccccc3Cl)cc(C)cn12]

80 mg (0.19 mmol) of rac-tert-butyl (1-{[(8-hydroxy-2,6-dimethylimidazo[1,2-a]pyridin-3-yl)carbonyl]amino}-2-methylpentan-2-yl)carbamate from Example 330A, 33 mg (0.21 mmol) of 2-chlorobenzyl chloride, 135 mg (0.41 mmol) of caesium carbonate and 3.1 mg (0.02 mmol) of potassium iodide were initially charged in 3.6 ml of DMF, and the mixture was heated for 30 min in a warm oil bath pre-heated to 60° C. The reaction solution was concentrated and dried under high vacuum overnight. The residue was taken up in 1 ml of diethyl ether, 0.94 ml (1.88 mmol) of 2 N hydrochloric acid and diethyl ether was added and the mixture was stirred at RT overnight. The reaction mixture was concentrated and purified by preparative HPLC (RP 18 column, mobile phase: methanol/water gradient with addition of 0.1% formic acid). The product fractions were combined and concentrated. The residue was taken up in dichloromethane and washed twice with saturated aqueous sodium bicarbonate solution. The aqueous phase was extracted twice with dichloromethane. The combined organic phases were dried over sodium sulphate, filtered, concentrated and lyophilised. This gave 49 mg of the target compound (61% of theory).

LC-MS (Method 2): $R_t$=0.72 min
MS (ESpos): m/z=429 (M+H)$^+$

Example 344 rac-N-[(4-benzylmorpholin-2-yl)methyl]-8-[(2,6-difluorobenzyl)oxy]-2,6-dimethylimidazo[1,2-a]pyridine-3-carboxamide

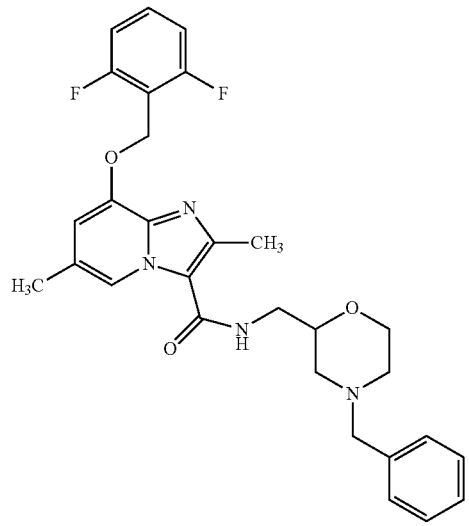 [SMILES: Cc1cc(OCc2c(F)cccc2F)c2nc(C)c(C(=O)NCC3CN(Cc4ccccc4)CCO3)n2c1]

20 mg (0.06 mmol) of 8-[(2,6-difluorobenzyl)oxy]-2,6-dimethylimidazo[1,2-a]pyridine-3-carboxylic acid from Example 21A, 25 mg (0.07 mmol) of HATU and 0.05 ml (0.30 mmol) of N,N-diisopropylethylamine were initially charged in 0.4 ml of DMF, and the mixture was stirred for 20 min. 24.8 mg (0.12 mmol) of rac-1-(4-benzylmorpholin-2-yl)methaneamine were then added at 0° C., and the mixture was stirred at 0° C. for 60 min. Water/TFA was added to the reaction solution, and the product was purified by preparative HPLC (RP18 column, mobile phase: acetonitrile/water gradient with addition of 0.1% TFA). The product fractions were concentrated and the residue was taken up in dichloromethane and washed twice with saturated aqueous sodium bicarbonate solution. The combined aqueous phases were extracted twice with dichloromethane. The combined organic phases were dried over sodium sulphate, filtered and concentrated. This gave 31 mg of the target compound (94% of theory).

LC-MS (Method 2): R_f=1.94 min
MS (ESpos): m/z=521 (M+H)⁺
¹H-NMR (400 MHz, DMSO-d₆): δ=1.78-1.88 (m, 1H), 2.05-2.15 (m, 1H), 2.30 (s, 3H), 2.37 (s, 3H), 2.60-2.67 (m, 1H), 2.74-2.80 (m, 1H), 3.25-3.31 (m, 2H), 3.42-3.46 (m, 1H), 3.47-3.57 (m, 2H), 3.58-3.66 (m, 1H), 3.78-3.85 (m, 1H), 5.28 (s, 2H), 6.91 (s, 1H), 7.20-7.27 (m, 3H), 7.28-7.34 (m, 4H), 7.54-7.64 (m, 1H), 7.87 (t, 1H), 8.37 (s, 1H).

Example 345 rac-8-[(2,6-Difluorobenzyl)oxy]-2,6-dimethyl-N-(morpholin-2-ylmethyl)imidazo[1,2-a]pyridine-3-carboxamide

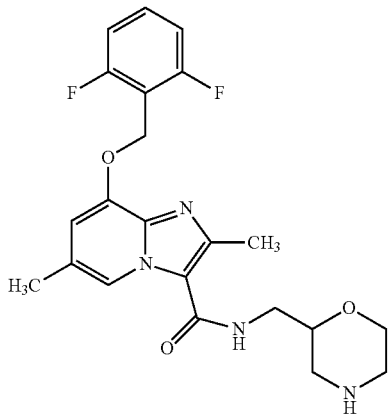 [SMILES: Cc1cc(OCc2c(F)cccc2F)c2nc(C)c(C(=O)NCC3CNCCO3)n2c1]

Under argon, 78 mg (0.15 mmol) of rac-N-[(4-benzylmorpholin-2-yl)methyl]-8-[(2,6-difluorobenzyl)oxy]-2,6-dimethylimidazo[1,2-a]pyridine-3-carboxamide from Example 344 were initially charged in 1.6 ml of ethanol, 16 mg (0.02 mmol) of 10% palladium on carbon were added and the mixture was hydrogenated at RT and under standard pressure for one hour. The reaction mixture was filtered through a Millipore filter, the filter cake was washed with ethanol and the filtrate was concentrated under reduced pressure. The residue was dissolved in dichloromethane and washed twice with saturated aqueous sodium bicarbonate solution. The combined aqueous phases were extracted twice with dichloromethane. The combined organic phases were dried over sodium sulphate, filtered and concentrated. This gave 43 mg of the target compound (63% of theory).

LC-MS (Method 2): R_f=0.61 min
MS (ESpos): m/z=431 (M+H)⁺
¹H-NMR (400 MHz, DMSO-d₆): δ=2.31 (s, 3H), 2.41-2.46 (m, 1H), 2.48 (s, 3H), 2.62-2.78 (m, 3H), 2.84-2.94 (m, 1H), 3.28-3.32 (m, 2H), 3.43-3.51 (m, 1H), 3.53-3.61 (m, 1H), 3.74-3.81 (m, 1H), 5.28 (s, 2H), 6.92 (s, 1H), 7.20-7.28 (m, 2H), 7.54-7.64 (m, 1H), 7.88 (t, 1H), 8.42 (s, 1H).

Example 346 rac-N-(3-azabicyclo[3.2.0]hept-1-yl)-8-[(2,6-difluorobenzyl)oxy]-2,6-dimethylimidazo[1,2-a]pyridine-3-carboxamide

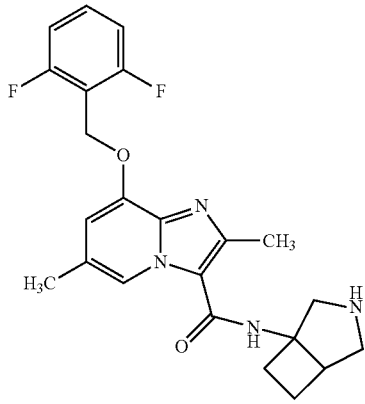 [SMILES: Cc1cc(OCc2c(F)cccc2F)c2nc(C)c(C(=O)NC34CCC3CNC4)n2c1]

95 mg (0.18 mmol) of rac-tert-butyl 1-[({8-[(2,6-difluorobenzyl)oxy]-2,6-dimethylimidazo[1,2-a]pyridin-3-yl}carbonyl)amino]-3-azabicyclo[3.2.0]heptane-3-carboxylate from Example 372A were initially charged in 0.9 ml of diethyl ether, 0.88 ml (1.77 mmol) of 2 N hydrochloric acid in diethyl ether was added and the mixture was stirred at RT overnight. The reaction mixture was concentrated, dichloromethane and a drop of methanol were added to the residue and the mixture was washed twice with saturated aqueous sodium bicarbonate solution. The combined aqueous phases were extracted twice with dichloromethane. The combined organic phases were dried over sodium sulphate, filtered and concentrated. This gave 70 mg of the target compound (90% of theory).

LC-MS (Method 2): R_f=0.58 min
MS (ESpos): m/z=427 (M+H)⁺
¹H-NMR (400 MHz, DMSO-d₆): δ=1.38-1.48 (m, 1H), 2.03-2.15 (m, 2H), 2.21-2.29 (m, 1H), 2.31 (s, 3H), 2.48 (s, 3H), 2.65-2.74 (m, 2H), 2.83-2.95 (m, 2H), 3.11-3.18 (m, 1H), 5.28 (s, 2H), 6.90 (s, 1H), 7.20-7.28 (m, 2H), 7.54-7.64 (m, 1H), 8.08 (s, 1H), 8.42 (s, 1H).

Example 347 rac-8-[(2,6-Difluorobenzyl)oxy]-N-(4-fluoropyrrolidin-3-yl)-2,6-dimethylimidazo[1,2-a]pyridine-3-carboxamide

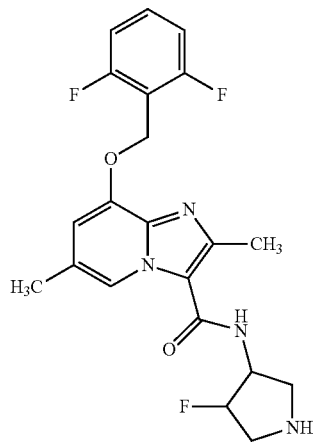 [SMILES: Cc1cc(OCc2c(F)cccc2F)c2nc(C)c(C(=O)NC3CNCC3F)n2c1]

98 mg (0.15 mmol) of rac-tert-butyl 3-[({8-[(2,6-difluorobenzyl)oxy]-2,6-dimethylimidazo[1,2-a]pyridin-3-yl}carbonyl)amino]-4-fluoropyrrolidin-1-carboxylate trifluoroacetate from Example 373A were initially charged in 0.8 ml of diethyl ether, 0.77 ml (1.54 mmol) of 2 N hydrochloric acid in diethyl ether were added and the mixture was stirred at RT overnight. Another 0.77 ml (1.54 mmol) of 2 N hydrochloric acid in diethyl ether was added to the reaction mixture, and the mixture was stirred at RT overnight. The reaction solution was concentrated and the residue was dissolved in dichloromethane and washed twice with saturated aqueous sodium bicarbonate solution. The combined aqueous phases were extracted twice with dichloromethane. The combined organic phases were dried over sodium sulphate, filtered, concentrated and lyophilised. This gave 64 mg of the target compound (99% of theory).

LC-MS (Method 2): $R_t$=0.63 min
MS (ESpos): m/z=419 (M+H)$^+$
$^1$H-NMR (400 MHz, DMSO-d$_6$): δ=1.13-1.35 (m, 1H), 2.31 (s, 3H), 2.48 (s, 3H), 2.76 (t, 1H), 2.90-3.04 (m, 1H), 3.11 (dd, 1H), 3.23 (dd, 1H), 4.26-4.42 (m, 1H), 5.02-5.21 (m, 1H), 5.29 (s, 2H), 6.92 (s, 1H), 7.19-7.28 (m, 2H), 7.54-7.64 (m, 1H), 7.80 (d, 1H), 8.40 (s, 1H).

Example 348 rac-N-(2-amino-2-methylpentyl)-8-[(3-fluorobenzyl)oxy]-2,6-dimethylimidazo[1,2-a]pyridine-3-carboxamide

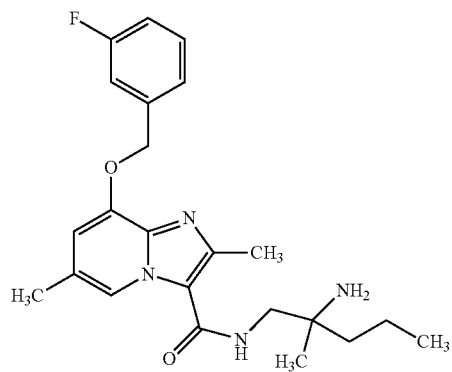 [SMILES: CCCC(C)(N)CNC(=O)c1c(C)nc2c(OCc3cccc(F)c3)cc(C)cn12]

80 mg (0.19 mmol) of rac-tert-butyl (1-{[(8-hydroxy-2,6-dimethylimidazo[1,2-a]pyridin-3-yl)carbonyl]amino}-2-methylpentan-2-yl)carbamate from Example 330A, 39 mg (0.21 mmol) of 3-fluorobenzyl bromide, 135 mg (0.41 mmol) of caesium carbonate and 3.1 mg (0.02 mmol) of potassium iodide were initially charged in 3.6 ml of DMF, and the mixture was heated for 30 min in a warm oil bath pre-heated to 60° C. The reaction solution was concentrated and dried under high vacuum overnight. The residue was taken up in 0.9 ml of diethyl ether, 0.94 ml (1.88 mmol) of 2 N hydrochloric acid in diethyl ether was added and the mixture was stirred at RT overnight. The reaction mixture was concentrated and purified by preparative HPLC (RP 18 column, mobile phase: acetonitrile/water gradient with addition of 0.1% TFA). The product-containing fractions were concentrated and the residue was taken up in dichloromethane and washed twice with saturated aqueous sodium bicarbonate solution. The aqueous phase was extracted twice with dichloromethane. The combined organic phases were dried over sodium sulphate and filtered, the filtrate was concentrated and the residue was lyophilised. This gave 51 mg of the target compound (64% of theory).

LC-MS (Method 2): $R_t$=0.68 min
MS (ESpos): m/z=413 (M+H)$^+$

Example 349

8-[(2,6-Difluorobenzyl)oxy]-N-{2-[(2-hydroxyethyl)amino]-2-methylpropyl}-2,6-dimethylimidazo[1,2-a]pyridine-3-carboxamide

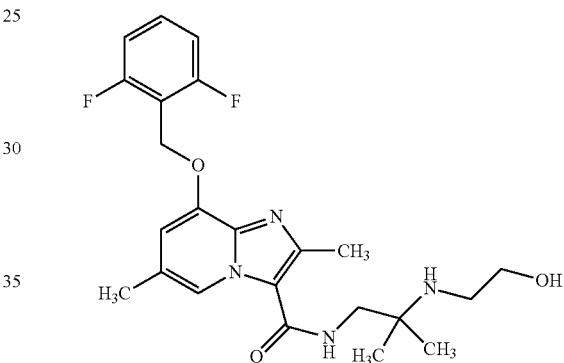

100 mg (0.25 mmol) of N-(2-amino-2-methylpropyl)-8-[(2,6-difluorobenzyl)oxy]-2,6-dimethylimidazo[1,2-a]pyridine-3-carboxamide from Example 74 were initially charged in 1 ml of DMF, and 0.023 ml (0.30 mmol) of iodoethanol and 69 mg (0.50 mmol) of potassium carbonate were added. The reaction mixture was stirred at RT overnight. 0.23 ml (3.0 mmol) of iodoethanol and 69 mg (0.50 mmol) of potassium carbonate were added, and the mixture was stirred under reflux overnight. The reaction mixture was diluted with water and acetonitrile and purified by preparative HPLC (RP 18 column, mobile phase: acetonitrile/water gradient with addition of 0.1% TFA). The product fractions were concentrated and dried under high vacuum. This gave 5 mg of the target compound (4% of theory, purity 90%).

LC-MS (Method 2): $R_t$=0.60 min
MS (ESpos): m/z=447 (M+H)$^+$
$^1$H-NMR (400 MHz, DMSO-d$_6$): δ=1.05 (s, 6H), 1.54 (t, 1H), 2.31 (s, 3H), 3.24 (d, 2H), 3.28-3.31 (m, 1H), 3.42 (q, 2H), 4.48 (t, 1H), 5.28 (s, 2H), 6.92 (s, 1H), 7.20-7.28 (m, 2H), 7.50 (t, 1H), 7.54-7.64 (m, 1H), 8.52-8.56 (m, 1H).

Example 350 rac-N-[2-amino-3-(3,4-difluorophenoxy)-2-methyl-propyl]-8-[(2,6-difluorobenzyl)oxy]-2,6-dimethyl-imidazo[1,2-a]pyridine-3-carboxamide

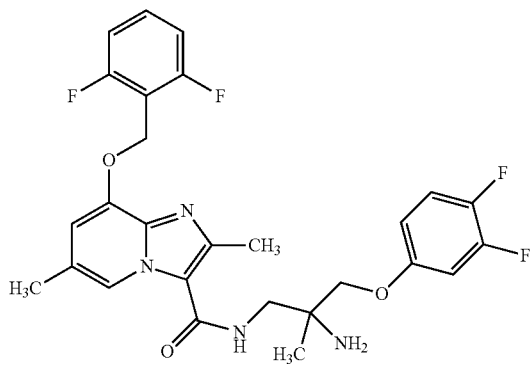 [SMILES: Cc1cc(OCc2c(F)cccc2F)c2nc(C)c(C(=O)NCC(C)(N)COc3ccc(F)c(F)c3)n2c1]

51 mg (0.15 mmol) of 8-[(2,6-difluorobenzyl)oxy]-2,6-dimethylimidazo[1,2-a]pyridine-3-carboxylic acid from Example 21A, 64.5 mg (0.17 mmol) of HATU and 0.13 ml (0.77 mmol) of N,N-diisopropylethylamine were initially charged in 1 ml DMF, and the mixture was stirred for 20 min. At 0° C., 40 mg (0.19 mmol) of rac-3-(3,4-difluorophenoxy)-2-methylpropane-1,2-diamine from Example 391A were then added, and the mixture was stirred at 0° C. for 45 min. Acetonitrile and TFA were added to the reaction solution, and the product was purified by preparative HPLC (RP18 column, mobile phase: acetonitrile/water gradient with addition of 0.1% TFA). The product fractions were concentrated and the residue was taken up in dichloromethane and washed twice with saturated aqueous sodium bicarbonate solution. The aqueous phase was extracted twice with dichloromethane. The combined organic phases were dried over sodium sulphate and filtered, and the filtrate was concentrated and lyophilised. This gave 62 mg of the target compound (72% of theory).

LC-MS (Method 2): $R_t$=0.80 min
MS (ESpos): m/z=531 (M+H)$^+$
$^1$H-NMR (400 MHz, DMSO-$d_6$): δ=1.29 (s, 3H), 2.30 (s, 3H), 2.53 (br. s., 3H), 3.49-3.66 (m, 2H), 3.89-3.96 (m, 1H), 3.98-4.05 (m, 1H), 5.29 (s, 2H), 6.78-6.85 (m, 1H), 6.94 (s, 1H), 7.04-7.13 (m, 1H), 7.20-7.29 (m, 2H), 7.39 (q, 1H), 7.54-7.65 (m, 1H), 7.89 (t, 1H), 8.43 (s, 1H).

Example 351 rac-N-(2-amino-2-methylpentyl)-8-[(2-fluoro-6-methoxybenzyl)oxy]-2,6-dimethylimidazo[1,2-a]pyridine-3-carboxamide

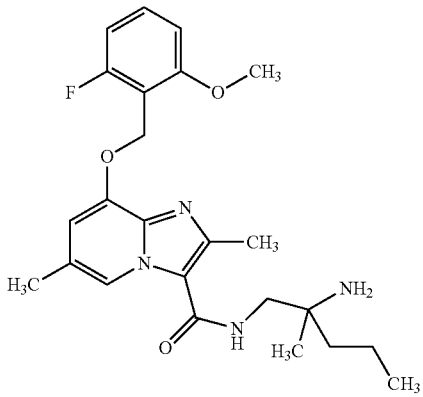 [SMILES: CCCC(C)(N)CNC(=O)c1c(C)nc2c(OCc3c(F)cccc3OC)cc(C)cn12]

50 mg (0.14 mmol, purity 94%) of 8-[(2-fluoro-6-methoxybenzyl)oxy]-2,6-dimethylimidazo[1,2-a]pyridine-3-carboxylic acid from Example 375A, 57 mg (0.15 mmol) of HATU and 0.12 ml (0.68 mmol) of N,N-diisopropylethylamine were initially charged in 0.9 ml of DMF, and the mixture was stirred at RT for 20 min. At 0° C., 28 mg (0.15 mmol) of rac-2-methylpentane-1,2-diamine dihydrochloride from Example 326A were then added, and the mixture was stirred at 0° C. for 30 min. The reaction solution was diluted with water/TFA and purified by preparative HPLC (RP18 column, mobile phase: acetonitrile/water gradient with addition of 0.1% TFA). The product fractions were taken up in dichloromethane and a little methanol and washed twice with saturated aqueous sodium bicarbonate solution. The combined aqueous phases were extracted twice with dichloromethane. The combined organic phases were dried over sodium sulphate, filtered and concentrated. This gave 45 mg of the target compound (71% of theory).

LC-MS (Method 2): $R_t$=0.69 min
MS (ESpos): m/z=443 (M+H)$^+$
$^1$H-NMR (400 MHz, DMSO-$d_6$): δ=0.87 (t, 3H), 1.00 (s, 3H), 1.22-1.44 (m, 4H), 1.72-2.11 (m, 2H), 2.31 (s, 3H), 2.52 (s, 3H), 3.15-3.27 (m, 2H), 3.85 (s, 3H), 5.18 (s, 2H), 6.87-6.95 (m, 2H), 6.99 (d, 1H), 7.44-7.53 (m, 1H), 7.62 (t, 1H), 8.44 (s, 1H).

Example 352

N-(2-amino-2-methylpropyl)-8-[(2-fluoro-6-methoxybenzyl)oxy]-2,6-dimethylimidazo[1,2-a]pyridine-3-carboxamide

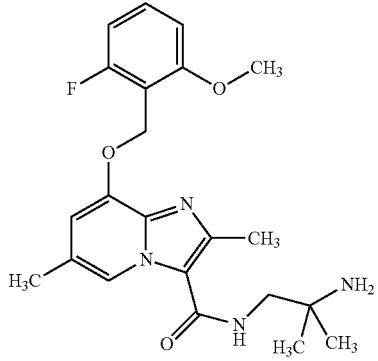 [SMILES: COc1cccc(F)c1COc1cc(C)cn2c(C(=O)NCC(C)(C)N)c(C)nc12]

50 mg (0.14 mmol, purity 94%) of 8-[(2-fluoro-6-methoxybenzyl)oxy]-2,6-dimethylimidazo[1,2-a]pyridine-3-carboxylic acid from Example 375A, 57 mg (0.15 mmol) of HATU and 0.07 ml (0.41 mmol) of N,N-diisopropylethylamine were initially charged in 0.9 ml of DMF, and the mixture was stirred at RT for 20 min. At 0° C., 0.02 ml (0.15 mmol) of 1,2-diamino-2-methylpropane was then added, and the mixture was stirred at 0° C. for 30 min. The reaction solution was diluted with water/TFA and purified by preparative HPLC (RP18 column, mobile phase: acetonitrile/water gradient with addition of 0.1% TFA). The product fractions were taken up in dichloromethane and a little methanol and washed twice with saturated aqueous sodium bicarbonate solution. The combined aqueous phases were extracted twice with dichloromethane. The combined organic phases were dried over sodium sulphate, filtered and concentrated. This gave 48 mg of the target compound (83% of theory).

LC-MS (Method 2): $R_t$=0.62 min
MS (ESpos): m/z=415 (M+H)$^+$
$^1$H-NMR (400 MHz, DMSO-d$_6$): δ=1.05 (s, 6H), 1.47-1.78 (m, 2H), 2.31 (s, 3H), 2.52 (s, 3H), 3.20 (d, 2H), 3.85 (s, 3H), 5.18 (s, 2H), 6.86-6.95 (m, 2H), 6.99 (d, 1H), 7.49 (q, 1H), 7.65 (t, 1H), 8.44 (s, 1H).

Example 353

N-(2-amino-2-methylpentyl)-8-[(2-bromobenzyl)oxy]-2,6-dimethylimidazo[1,2-a]pyridine-3-carboxamide

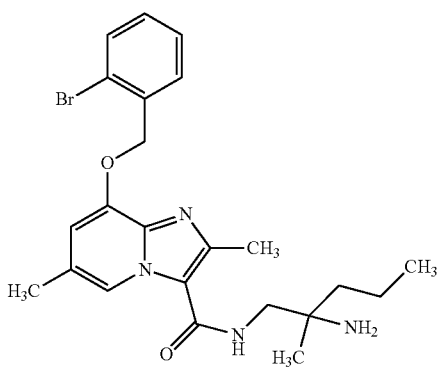 [SMILES: CCCC(C)(N)CNC(=O)c1c(C)nc2c(OCc3ccccc3Br)cc(C)cn12]

80 mg (0.19 mmol) of rac-tert-Butyl (1-{[(8-hydroxy-2,6-dimethylimidazo[1,2-a]pyridin-3-yl)carbonyl]amino}-2-methylpentan-2-yl)carbamate 330A, 53 mg (0.21 mmol) of 2-bromobenzyl bromide, 135 mg (0.41 mmol) of caesium carbonate and 3.1 mg (0.02 mmol) of potassium iodide were initially charged in 3.6 ml of DMF, and the mixture was heated for 30 min in a warm oil bath preheated to 60° C. The reaction solution was concentrated and dried under high vacuum overnight. The residue was taken up in diethyl ether, 0.94 ml (1.88 mmol) of 2 N hydrochloric acid in diethyl ether was added and the mixture was stirred at RT overnight. The reaction mixture was concentrated and purified by preparative HPLC (RP18 column, mobile phase: acetonitrile/water gradient with addition of 0.1% TFA). The product-containing fractions were concentrated and the residue was taken up in dichloromethane and washed twice with saturated aqueous sodium bicarbonate solution. The aqueous phase was extracted twice with dichloromethane. The combined organic phases were dried over sodium sulphate and filtered, the filtrate was concentrated and the residue was lyophilised. This gave 60 mg of the target compound (67% of theory).

LC-MS (Method 2): $R_t$=0.74 min
MS (ESpos): m/z=473 (M+H)$^+$

Example 354 ent-N-(2-amino-2-methylpentyl)-8-[(2,6-difluorobenzyl)oxy]imidazo[1,2-a]pyridine-2-carboxamide

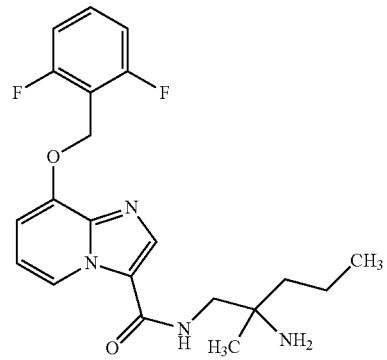 [SMILES: CCCC(C)(N)CNC(=O)c1cnc2c(OCc3c(F)cccc3F)cccn12]

Under argon, 117 mg (0.18 mmol) of ent-benzyl {1-[({8-[(2,6-difluorobenzyl)oxy]imidazo[1,2-a]pyridin-3-yl}carbonyl)amino]-2-methylpentan-2-yl}carbamate trifluoroacetate from Example 376A were initially charged in 1.9 ml of ethanol, 19.2 mg (0.02 mmol) of 10% palladium on carbon were added and the mixture was hydrogenated at RT and under standard pressure for 1 hour. The reaction mixture was absorbed on Celite and purified by silica gel chromatography (mobile phase: dichloromethane/2 N ammonia in methanol=40/1 to 30/1). This gave 30 mg of the target compound (41% of theory).

LC-MS (Method 2): $R_t$=0.67 min
MS (ESpos): m/z=403 (M+H)$^+$
$^1$H NMR (400 MHz, DMSO-d$_6$) δ=0.86 (t, 4H), 0.95 (s, 3H), 1.18-1.43 (m, 4H), 1.44-1.56 (m, 1H), 3.12-3.23 (m, 2H), 5.34 (s, 2H), 6.99-7.11 (m, 2H), 7.24 (t, 2H), 7.53-7.65 (m, 1H), 8.17-8.26 (m, 1H), 8.31 (s, 1H), 9.08 (d, 1H).

Example 355 ent-N-(2-amino-2-methylpentyl)-8-[(2,6-difluorobenzyl)oxy]-6-ethynyl-2-methylimidazo[1,2-a]pyridine-3-carboxamide formate

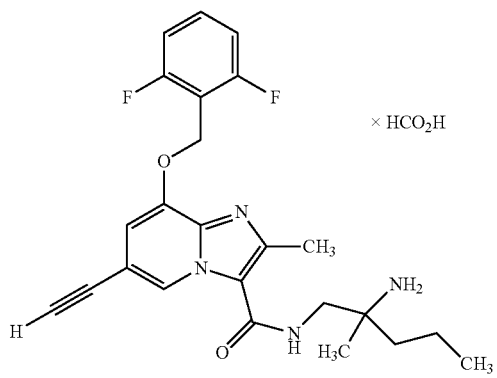 [SMILES: C#Cc1cc(OCc2c(F)cccc2F)c2nc(C)c(C(=O)NCC(C)(N)CCC)n2c1]

At 0° C., 161 mg (0.28 mmol) of ent-benzyl {1-[({8-[(2,6-difluorobenzyl)oxy]-6-ethynyl-2-methylimidazo[1,2-a]pyridin-3-yl}carbonyl)amino]-2-methylpentan-2-yl}carbamate from Example 359A and 0.2 ml of anisole were initially charged in 2.5 ml of dichloromethane, and 2.5 ml of a 70% strength solution of hydrogen fluoride in pyridine were added. The mixture was then stirred at RT for 6 h and stored at −20° C. overnight. The reaction mixture was diluted with 20 ml of dichloromethane and, at 0° C., added dropwise to 100 ml of a saturated aqueous sodium bicarbonate solution, and the mixture was stirred at 0° C. for 30 min. The two phases were separated and the organic phase was washed twice with saturated aqueous sodium bicarbonate solution and once with water, then dried over sodium sulphate, filtered and concentrated. The residue was purified by preparative HPLC (RP-C18, mobile phase: acetonitrile/water gradient with addition of 0.05% formic acid). This gave 107 mg (78% of theory) of the title compound.

LC-MS (Method 2): $R_t$=0.76 min

MS (ESpos): m/z=441 (M−HCO$_2$H+H)$^+$ $^1$H-NMR (400 MHz, DMSO-d$_6$): δ [ppm]=0.86-0.93 (d, 3H), 1.14 (s, 3H), 1.30-1.55 (m, 4H), 2.56 (s, 3H), 3.30-3.45 (m, 2H), 4.34 (s, 1H), 5.33 (s, 2H), 7.08 (d, 1H), 7.20-7.29 (m, 2H), 7.55-7.65 (m, 1H), 8.14 (br. s, 1H), 8.32 (s, 1H), 8.79 (s, 1H).

Example 356 ent-N-(2-amino-2-methylpentyl)-8-[(2,6-difluorobenzyl)oxy]-6-ethynyl-2-methylimidazo[1,2-a]pyridine-3-carboxamide

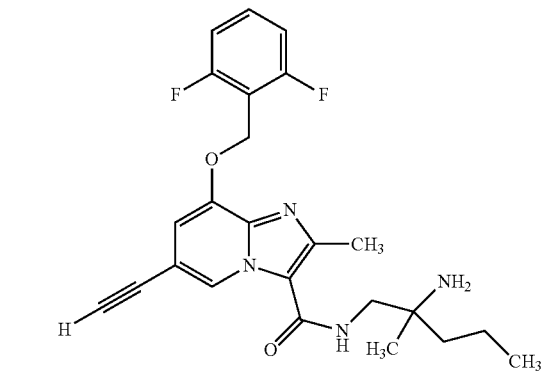 [SMILES: C#Cc1cc(OCc2c(F)cccc2F)c2nc(C)c(C(=O)NCC(C)(N)CCC)n2c1]

88 mg (0.18 mmol) of ent-N-(2-amino-2-methylpentyl)-8-[(2,6-difluorobenzyl)oxy]-6-ethynyl-2-methylimidazo[1,2-a]pyridine-3-carboxamide formate from Example 355 were dissolved in dichloromethane and washed twice with saturated aqueous sodium bicarbonate solution. The combined aqueous phases were extracted twice with dichloromethane. The combined organic phases were dried over sodium sulphate, filtered and concentrated. This gave 79 mg of the title compound (99% of theory).

LC-MS (Method 2): $R_t$=0.78 min

MS (ESpos): m/z=441 (M+H)$^+$ $^1$H-NMR (400 MHz, DMSO-d$_6$): δ [ppm]=0.82-0.90 (m, 3H), 1.00 (s, 3H), 1.25-1.41 (m, 4H), 1.68-2.15 (br. s, 2H), 3.17-3.32 (m, 2H), 4.32 (s, 1H), 5.33 (s, 2H), 7.07 (s, 1H), 7.20-7.28 (m, 2H), 7.55-7.66 (m, 1H), 7.76 (br. s, 1H), 8.80 (s, 1H), [further signal under solvent peak].

Example 357 ent-N-(2-amino-2-methylbutyl)-8-[(2,6-difluorobenzyl)oxy]-2,6-dimethylimidazo[1,2-a]pyridine-3-carboxamide hydrochloride (Enantiomer A)

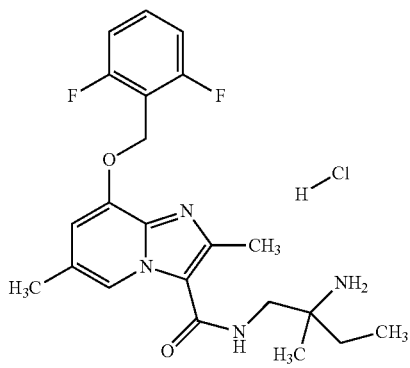 [SMILES: CCC(C)(N)CNC(=O)c1c(C)nc2c(OCc3c(F)cccc3F)cc(C)cn12 ; Cl]

302 mg (0.71 mmol) of ent-N-(2-amino-2-methylbutyl)-8-[(2,6-difluorobenzyl)oxy]-2,6-dimethylimidazo[1,2-a]pyridine-3-carboxamide (enantiomer A) from Example 200 were initially charged in 5.7 ml of diethyl ether, 0.43 ml (0.85 mmol) of 2 N hydrochloric acid in diethyl ether was added and the mixture was stirred at room temperature for 30 min. The solvent was then evaporated. This gave 326 mg of the target compound (99% of theory).

LC-MS (Method 2): $R_t$=0.64 min

MS (ESIpos): m/z=417 (M−HCl+H)$^+$ $^1$H-NMR (400 MHz, DMSO-d$_6$): δ=0.95 (t, 3H), 1.24 (s, 3H), 1.55-1.73 (m, 2H), 2.34 (s, 3H), 2.57 (s, 3H), 3.41-3.56 (m, 2H), 5.32 (s, 2H), 7.06 (br. s, 1H), 7.19-7.30 (m, 2H), 7.54-7.66 (m, 1H), 7.87 (br. s, 3H), 8.11 (br. s, 1H), 8.50 (s, 1H).

Example 358

N-(2-amino-3,3-dimethylcyclobutyl)-8-[(2,6-difluorobenzyl)oxy]-2,6-dimethylimidazo[1,2-a]pyridine-3-carboxamide formate (Isomer Mixture)

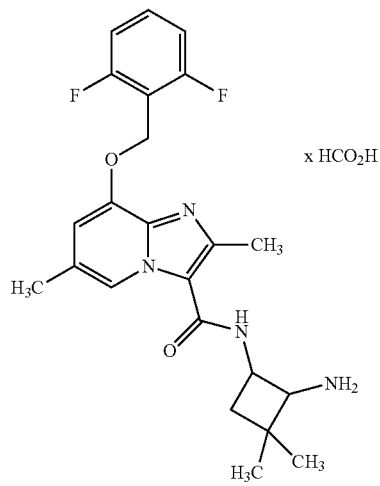 [SMILES: Cc1cc(OCc2c(F)cccc2F)c2nc(C)c(C(=O)NC3CC(C)(C)C3N)n2c1]

200 mg (0.60 mmol) of 8-[(2,6-difluorobenzyl)oxy]-2,6-dimethylimidazo[1,2-a]pyridine-3-carboxylic acid (Example 21A), 218 mg (0.57 mmol) of HATU and 308 mg (2.39 mmol) of N,N-diisopropylethylamine were initially charged in 3.5 ml of DMF, and the mixture was stirred at RT for 10 min. The reaction mixture was then added dropwise to a mixture of 296 mg (1.50 mmol) of 3,3-dimethylcyclobutane-1,2-diamine dihydrochloride (isomer mixture; described in: K. Scholz et al. Liebigs Annalen der Chemie, 1981, (2), 248-55; D. Hossain et al. Synthetic Communications 2012 42, 1200-1210; M. Klapper et al. Angewandte Chemie 2003, 115, 4835-4690) and 467 mg (3.61 mmol) of N,N-diisopropylethylamine dissolved in 0.7 ml of DMF, and the mixture was stirred at RT for 30 min. The reaction mixture was purified by preparative HPLC (RP-C18, mobile phase: acetonitrile/water gradient with addition of 0.05% formic acid). This gave 131 mg (44% of theory) of the title compound.

LC-MS (Method 2): $R_t$=0.62 min

MS (ESpos): m/z=429 (M+H)$^+$

Example 359 ent-N-(2-amino-2-methylpentyl)-8-[(3-cyclopropyl-2,6-difluorobenzyl)oxy]-2,6-dimethylimidazo[1,2-a]pyridine-3-carboxamide

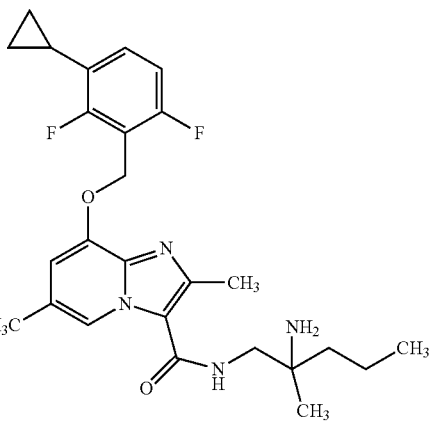

A mixture of 159 mg (0.21 mmol) of ent-benzyl {1-[({8-[(3-cyclopropyl-2,6-difluorobenzyl)oxy]-2,6-dimethylimidazo[1,2-a]pyridin-3-yl}carbonyl)amino]-2-methylpentan-2-yl}carbamate trifluoroacetate from Example 383A and 45 mg (0.04 mmol) of 10% palladium hydroxide on carbon in 5.4 ml of ethanol was hydrogenated at RT and standard pressure for 1 h. The mixture was then filtered through a Millipore filter. The filtrate was concentrated and the residue was purified by thick-layer chromatography (dichloromethane/methanol=10/1). The product fraction was taken up in dichloromethane and washed twice with saturated aqueous sodium bicarbonate solution. The combined aqueous phases were extracted twice with dichloromethane. The combined organic phases were dried over sodium sulphate, filtered and concentrated. This gave 75 mg of the title compound (73% of theory).

LC-MS (Method 2): $R_t$=0.81 min

MS (ESpos): m/z=471 (M+H)$^+$ $^1$H-NMR (400 MHz, DMSO-d$_6$): δ [ppm]=0.71-078 (m, 2H), 0.83-0.91 (m, 3H), 0.94-1.04 (m, 5H), 1.26-1.41 (m, 4H), 2.00-2.09 (m, 1H), 2.31 (s, 3H), 3.16-3.28 (m, 2H), 5.27 (s, 2H), 6.92 (s, 1H), 7.07-7.22 (m, 2H), 7.61-7.69 (m, 1H), 8.47 (s, 1H), [further signal under solvent peak].

The examples shown in Table 15 were prepared analogously to Example 359 by hydrogenating the appropriate Cbz-protected amines with palladium/carbon (10%; 0.1-0.3 equivalents) in ethanol at RT and under standard pressure under the reaction conditions described. Here, the reaction times were between 1 h and 3 h.

TABLE 15

| Example | IUPAC Name/Structure (yield) | Analytical data |
|---|---|---|
| 360 | ent-N-(2-amino-2-methylbutyl)-8-[(2,6-difluoro-3-methoxybenzyl)oxy]-2,6-dimethylimidazo[1,2-a]pyridine-3-carboxamide<br>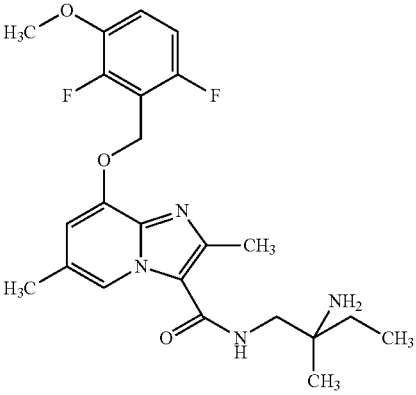<br>(36% of theory) | LC-MS (Method 2): $R_t$ = 0.64 min<br>MS (ESpos): m/z = 447 (M + H)$^+$<br>$^1$H NMR (400 MHz, DMSO-d$_6$) δ [ppm] = 0.87 (t, 3H), 0.98 (s, 3H), 1.30-1.40 (m, 2H), 1.41-1.69 (br. s, 2H), 2.30 (s, 3H), 3.14-3.26 (m, 2H), 3.87 (s, 3H), 5.28 (s, 2H), 6.91 (s, 1H), 7.14-7.21 (m, 1H), 7.28-7.37 (m, 1H), 7.57-7.64 (m, 1H), 8.48 (s, 1H) [further signal under solvent peak]. |
| 361 | ent-N-(2-amino-3-fluoro-2-methylpropyl)-8-[(2,6-difluoro-3-methoxybenzyl)oxy]-2,6-dimethylimidazo[1,2-a]pyridine-3-carboxamide<br>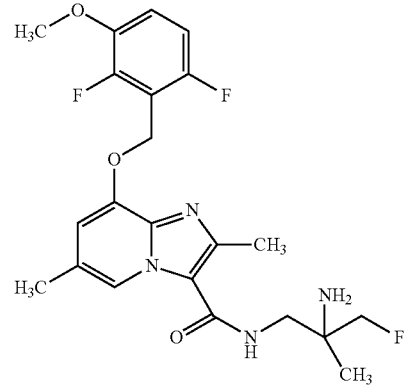<br>(77% of theory) | LC-MS (Method 2): $R_t$ = 0.62 min<br>MS (ESpos): m/z = 451 (M + H)$^+$<br>$^1$H-NMR (400 MHz, DMSO-d$_6$): δ [ppm] = 1.03 (d, 3H), 1.57-1.71 (br. s, 2H), 2.31 (s, 3H), 3.23-3.38 (m, 2H), 3.87 (s, 3H), 4.09-4.15 (m, 1H), 4.20-4.26 (s, 1H), 5.28 (s, 2H), 6.91 (s, 1H), 7.13-7.21 (m, 1H), 7.28-7.37 (m, 1H), 7.64-7.71 (m, 1H), 8.47 (s, 1H), [further signal under solvent peak]. |

TABLE 15-continued

| Example | IUPAC Name/Structure (yield) | Analytical data |
|---|---|---|
| 362 | N-(2-amino-3-fluoro-2-methylpropyl)-8-[(3-cyclopropyl-2,6-difluorobenzyl)oxy]-2,6-dimethylimidazo[1,2-a]pyridine-3-carboxamide<br/>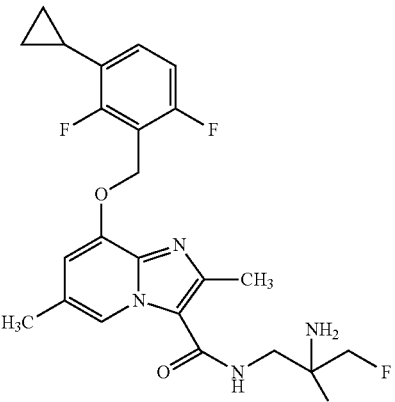<br/>(72% of theory) | LC-MS (Method 2): $R_t$ = 0.75 min<br/>MS (ESpos): m/z = 461 (M + H)$^+$<br/>$^1$H-NMR (400 MHz, DMSO-d$_6$): δ [ppm] = 0.72-0.78 (m, 2H), 0.94-1.01 (m, 2H), 1.05 (d, 3H), 1.99-2.43 (br. s, 2H), 2.00-2.09 (m, 1H), 2.32 (s, 3H), 3.25-3.40 (m, 2H), 4.10-4.16 (m, 1H), 4.22-4.28 (m, 1H), 5.27 (s, 2H), 6.93 (s, 1H), 7.07-7.22 (m, 2H), 7.65-7.72 (m, 1H), 8.47 (s, 1H), [further signal under solvent peak]. |
| 363 | ent-N-(2-amino-2-methylbutyl)-8-[(3-cyclopropyl-2,6-difluorobenzyl)oxy]-2,6-dimethylimidazo[1,2-a]pyridine-3-carboxamide<br/>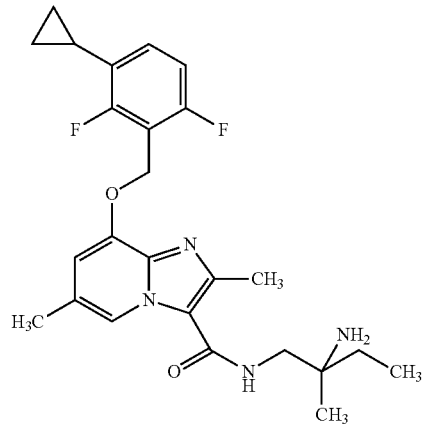<br/>(62% of theory) | LC-MS (Method 2): $R_t$ = 0.76 min<br/>MS (ESpos): m/z = 457 (M + H)$^+$<br/>$^1$H-NMR (400 MHz, DMSO-d$_6$): δ [ppm] = 0.72-0.78 (m, 2H), 0.87 (t, 3H), 0.94-1.03 (m, 5H), 1.32-1.44 (m, 2H), 2.00-2.10 (m, 1H), 2.31 (s, 3H), 3.16-3.29 (m, 2H), 5.27 (s, 2H), 6.93 (s, 1H), 7.07-7.22 (m, 2H), 7.61-7.68 (m, 1H), 8.49 (s, 1H), [further signal under solvent peak]. |

Example 364 ent-N-(2-amino-2-methylpentyl)-8-[(2,6-difluoro-3-methoxybenzyl)oxy]-2,6-dimethylimidazo[1,2-a]pyridine-3-carboxamide

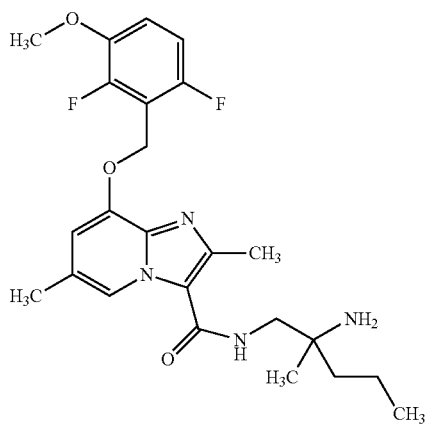 [SMILES: CCCC(C)(N)CNC(=O)c1c(C)nc2c(OCc3c(F)ccc(OC)c3F)cc(C)cn12]

A mixture of 205 mg (0.28 mmol) of ent-benzyl {1-[({8-[(2,6-difluoro-3-methoxybenzyl)oxy]-2,6-dimethylimidazo[1,2-a]pyridin-3-yl}carbonyl)amino]-2-methylpentan-2-yl}carbamate trifluoroacetate from Example 386A and 59 mg (0.06 mmol) of 10% palladium hydroxide on carbon in 7.1 ml of ethanol was hydrogenated at RT and standard pressure for 2 h. The mixture was then filtered through a Millipore filter. The filtrate was concentrated on a rotary evaporator and the residue was purified by thick-layer chromatography (dichloromethane/methanol=7.5/1). The product fraction was taken up in dichloromethane and washed twice with saturated aqueous sodium bicarbonate solution. The combined aqueous phases were extracted twice with dichloromethane. The combined organic phases were dried over sodium sulphate, filtered and concentrated. This gave 80 mg of the title compound (63% of theory).

LC-MS (Method 2): $R_t$=0.69 min
MS (ESpos): m/z=461 (M+H)$^+$ $^1$H-NMR (400 MHz, DMSO-d$_6$): δ [ppm]=0.87 (t, 3H), 0.99 (s, 3H), 1.24-1.40 (m, 4H), 1.50-1.90 (br. s, 2H), 2.30 (s, 3H), 3.14-3.26 (m, 2H), 3.87 (s, 3H), 5.28 (s, 2H), 6.91 (s, 1H), 7.13-7.21 (m, 1H), 7.28-7.37 (m, 1H), 7.58-7.67 (m, 1H), 8.47 (s, 1H) [further signal under solvent peak].

Example 365

N-(3-aminoadamantan-1-yl)-8-[(2,6-difluorobenzyl)oxy]-2,6-dimethylimidazo[1,2-a]pyridine-3-carboxamide formate

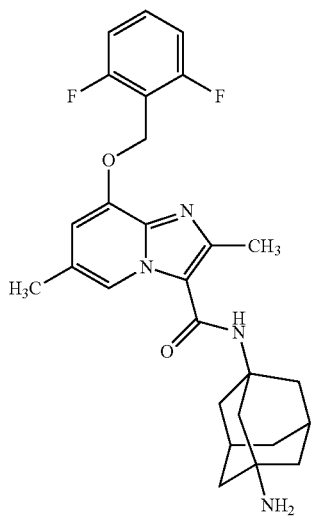

150 mg (0.45 mmol) of 8-[(2,6-difluorobenzyl)oxy]-2,6-dimethylimidazo[1,2-a]pyridine-3-carboxylic acid (Example 21A), 206 mg (0.54 mmol) of HATU and 117 mg (0.90 mmol) of N,N-diisopropylethylamine were initially charged in 1.3 ml of DMF, and the mixture was stirred at RT for 10 min. At 60° C., the mixture was then added dropwise to a mixture of 324 mg (1.35 mmol) of adamantane-1,3-diamine dihydrochloride (G. Senchyk et al. Inorganica Chimica Acta, 2009, 362(12), 4439-4448) and 700 mg (5.42 mmol) of N,N-diisopropylethylamine in 0.6 ml of DMF and 3.2 ml of DMSO, and the mixture was stirred at 60° C. for 1 h. The reaction mixture was cooled and filtered off. The filtrate was purified by preparative HPLC (RP-C18, mobile phase: acetonitrile/water gradient with addition of 0.05% formic acid). This gave 60 mg (25% of theory) of the title compound.

LC-MS (Method 2): $R_t$=0.66 min
MS (ESpos): m/z=481 (M+H)$^+$

Example 366 rac-8-[(2,6-Difluorobenzyl)oxy]-2,6-dimethyl-N-(thiomorpholin-3-ylmethyl)imidazo[1,2-a]pyridine-3-carboxamide

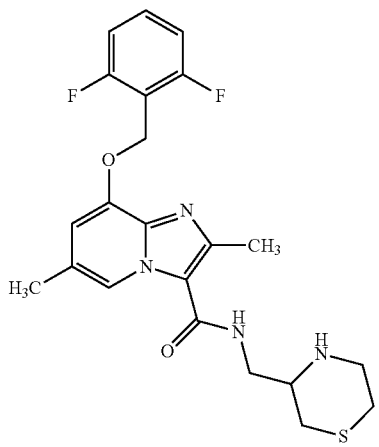 [SMILES: Cc1cc(OCc2c(F)cccc2F)c2nc(C)c(C(=O)NCC3CSCCN3)n2c1]

13 mg (0.1 mmol) of 1-(thiomorpholin-3-yl)methanamine (see A. Eremeev et al., Zhurnal Organicheskoi Khimii, 21(10), 2239-41; 1985) were initially charged in a 96 well deep well multititer plate. A solution of 33 mg (0.1 mmol) of 8-[(2,6-difluorobenzyl)oxy]-2,6-dimethylimidazo[1,2-a]pyridine-3-carboxylic acid from Example 21A in 0.3 ml of DMF and a solution of 45 mg (0.12 mmol) of HATU in 0.3 ml of DMF were added in succession. After addition of 20 mg (0.2 mmol) of 4-methylmorpholine, the mixture was shaken at RT overnight. The mixture was then filtered, and the target compound was isolated from the filtrate by preparative LC-MS (Method 12). The product-containing fractions were concentrated under reduced pressure in a centrifugal dryer. The residue of the product fractions was in each case dissolved in 0.6 ml of DMSO. These solutions were combined and then freed from the solvent in a centrifugal dryer. This gave 17.8 mg (39% of theory).

LC-MS (Method 8): $R_t$=0.65 min

MS (ESpos): m/z=447 (M+H)$^+$

The exemplary compounds shown in Table 16 were prepared analogously to Example 366 by reacting 8-[(2,6-difluorobenzyl)oxy]-2,6-dimethylimidazo[1,2-a]pyridine-3-carboxylic acid from Example 21A with the appropriate commercially available or above-described amines under the conditions described:

TABLE 16

| Example | IUPAC-Name/Structure (yield) | Analytical data |
|---|---|---|
| 367 | rac-N-{2-amino-2-[3-(2-hydroxyethoxy)phenyl]ethyl}-8-[(2,6-difluorobenzyl)oxy]-2,6-dimethylimidazo[1,2-a]pyridine-3-carboxamide<br><br>(17% of theory; purity 82%) | LC-MS (Method 8): $R_t$ = 0.65 min<br>MS (ESpos): m/z = 511 (M + H)$^+$ |

TABLE 16-continued

| Example | IUPAC-Name/Structure (yield) | Analytical data |
|---|---|---|
| 368 | rac-N-[2-amino-3-(4-methoxyphenyl)-2-methylpropyl]-8-[(2,6-difluorobenzyl)oxy]-2,6-dimethylimidazo[1,2-a]pyridine-3-carboxamide<br>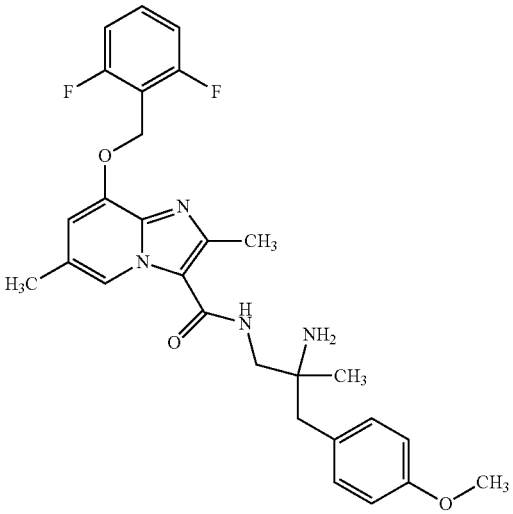<br>(36% of theory; purity 94%) | LC-MS (Method 8): $R_t$ = 0.73 min<br>MS (ESpos): m/z = 509 (M + H)$^+$ |
| 369 | rac-N-[2-amino-2-(5-methyl-2-furyl)ethyl]-8-[(2,6-difluorobenzyl)oxy]-2,6-dimethylimidazo[1,2-a]pyridine-3-carboxamide<br>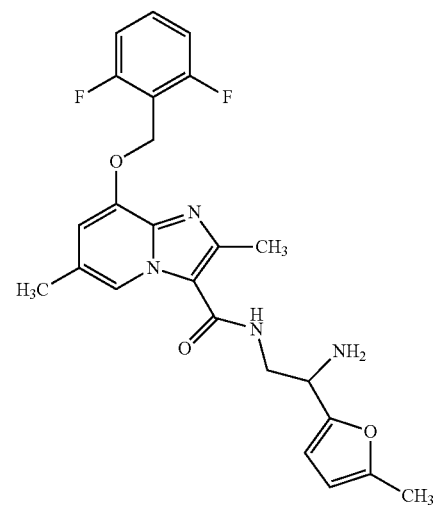<br>(19% of theory; purity 89%) | LC-MS (Method 8): $R_t$ = 0.67 min<br>MS (ESpos): m/z = 455 (M + H)$^+$ |

TABLE 16-continued

| Example | IUPAC-Name/Structure (yield) | Analytical data |
|---|---|---|
| 370 | rac-N-[2-amino-2-(1-methyl-1H-pyrazol-4-yl)ethyl]-8-[(2,6-difluorobenzyl)oxy]-2,6-dimethylimidazo[1,2-a]pyridine-3-carboxamide<br />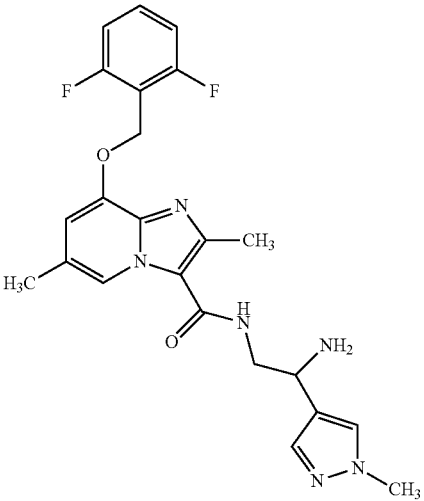<br />(6% of theory; purity 90%) | LC-MS (Method 8): $R_t$ = 0.62 min<br />MS (ESpos): m/z = 455 (M + H)$^+$ |
| 371 | rac-N-[2-amino-2-(2,3-dihydro-1,4-benzodioxin-6-yl)ethyl]-8-[(2,6-difluorobenzyl)oxy]-2,6-dimethylimidazo[1,2-a]pyridine-3-carboxamide<br />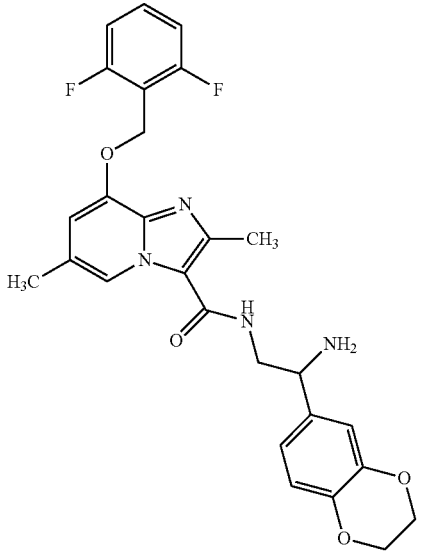<br />(1% of theory; purity 82%) | LC-MS (Method 8): $R_t$ = 0.69 min<br />MS (ESpos): m/z = 509 (M + H)$^+$ |

TABLE 16-continued

| Example | IUPAC-Name/Structure (yield) | Analytical data |
|---|---|---|
| 372 | rac-N-[2-amino-2-(quinolin-6-yl)ethyl]-8-[(2,6-difluorobenzyl)oxy]-2,6-dimethylimidazo[1,2-a]pyridine-3-carboxamide<br>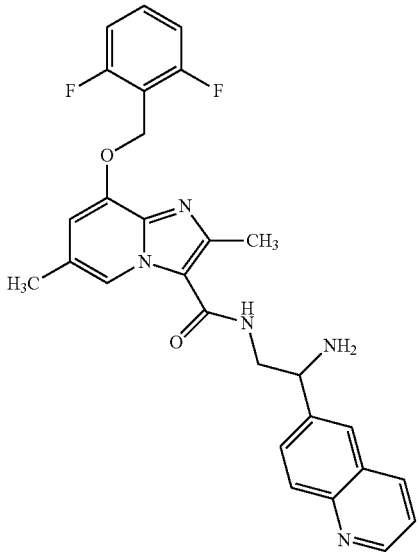<br>(6% of theory; purity 78%) | LC-MS (Method 8): $R_t$ = 0.66 min<br>MS (ESpos): m/z = 502 (M + H)$^+$ |
| 373 | rac-N-[2-amino-2-(1-benzothiophen-3-yl)ethyl]-8-[(2,6-difluorobenzyl)oxy]-2,6-dimethylimidazo[1,2-a]pyridine-3-carboxamide<br>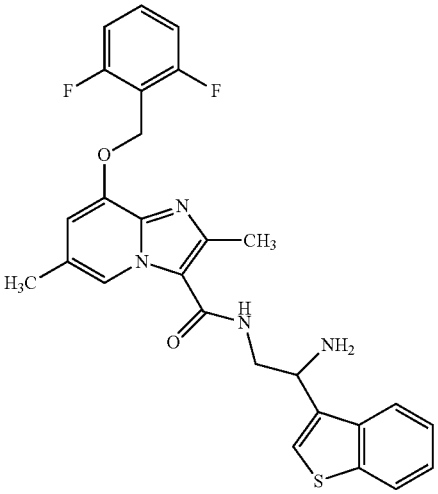<br>(8% of theory; purity 75%) | LC-MS (Method 8): $R_t$ = 0.74 min<br>MS (ESpos): m/z = 507 (M + H)$^+$ |

TABLE 16-continued

| Example | IUPAC-Name/Structure (yield) | Analytical data |
|---|---|---|
| 374 | rac-N-[2-amino-2-(3,4,5-trifluorophenyl)ethyl]-8-[(2,6-difluorobenzyl)oxy]-2,6-dimethylimidazo[1,2-a]pyridine-3-carboxamide<br>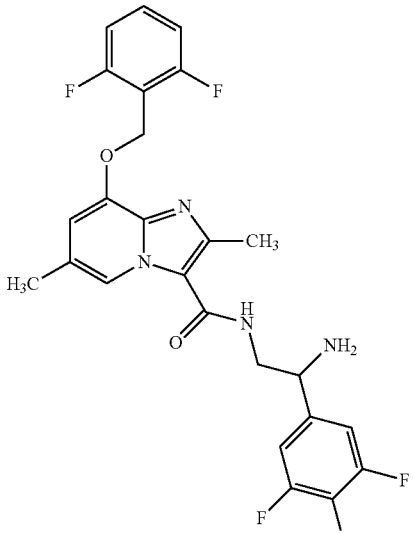<br>(4% of theory; purity 91%) | LC-MS (Method 8): $R_t$ = 0.73 min<br>MS (ESpos): m/z = 505 (M + H)$^+$ |
| 375 | rac-N-{2-amino-2-[3-(difluoromethoxy)phenyl]ethyl}-8-[(2,6-difluorobenzyl)oxy]-2,6-dimethylimidazo[1,2-a]pyridine-3-carboxamide<br>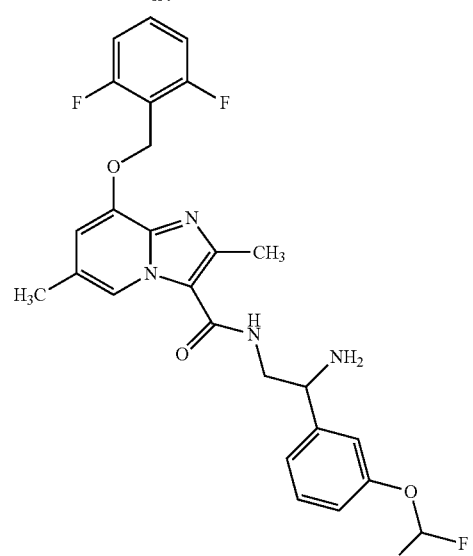<br>(5% of theory; purity 80%) | LC-MS (Method 8): $R_t$ = 0.73 min<br>MS (ESpos): m/z = 517 (M + H)$^+$ |

TABLE 16-continued

| Example | IUPAC-Name/Structure (yield) | Analytical data |
|---|---|---|
| 376 | rac-N-{2-amino-2-[3-(trifluoromethyl)phenyl]ethyl}-8-[(2,6-difluorobenzyl)oxy]-2,6-dimethylimidazo[1,2-a]pyridine-3-carboxamide<br>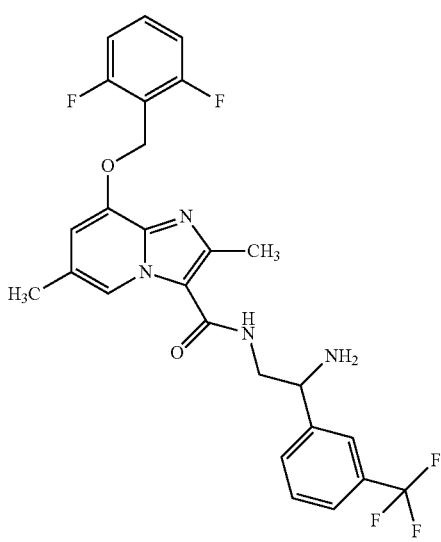<br>(32% of theory) | LC-MS (Method 8): $R_t$ = 0.74 min<br>MS (ESpos): m/z = 519 (M + H)+ |

Example 377 rac-N-{2-amino-2-[3-(trifluoromethoxy)phenyl]ethyl}-8-[(2,6-difluorobenzyl)oxy]-2,6-dimethylimidazo[1,2-a]pyridine-3-carboxamide

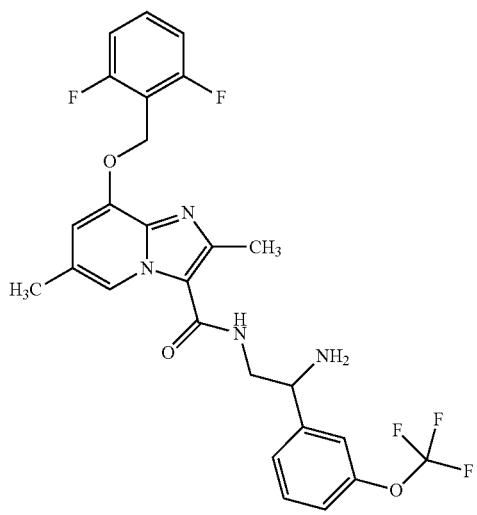 [SMILES: Cc1cc(OCc2c(F)cccc2F)c2nc(C)c(C(=O)NCC(N)c3cccc(OC(F)(F)F)c3)n2c1]

In a round-bottomed flask, 100 mg (0.31 mmol) of tert-butyl {2-amino-2-[3-(trifluoromethoxy)phenyl]ethyl}carbamate were dissolved in 2 ml of dichloromethane, 2 ml (8 mmol) of hydrogen chloride in dioxane (4 M) were added and the mixture was stirred at RT for 4 hours. The mixture was then evaporated to dryness, and 30 mg of the solid obtained were transferred onto a 96-well deep well multititer plate. A solution of 33 mg (0.1 mmol) of 8-[(2,6-difluorobenzyl)oxy]-2,6-dimethylimidazo[1,2-a]pyridine-3-carboxylic acid from Example 21A in 0.3 ml of DMF and 49 mg (0.13 mmol) of HATU in 0.3 ml of DMF were added successively, 20 mg (0.2 mmol) of 4-methylmorpholine were then added and the mixture was shaken at RT overnight. The reaction mixture was then filtered, and the target compound was isolated from the filtrate by preparative LC-MS (Method 12). The product-containing fractions were concentrated under reduced pressure using a centrifugal dryer. The residue of the product fractions was in each case dissolved in 0.6 ml of DMSO. These solutions were combined and then freed from the solvent in a centrifugal dryer. This gave 10.3 mg (19% of theory).

LC-MS (Method 8): $R_t$=0.75 min
MS (ESpos): m/z=535 (M+H)+

The exemplary compounds shown in Table 17 were prepared analogously to Example 377 by reacting 8-[(2,6-difluorobenzyl)oxy]-2,6-dimethylimidazo[1,2-a]pyridine-3-carboxylic acid from Example 21A with the appropriate commercially available or above-described amines under the conditions described:

TABLE 17

| Example | IUPAC-Name/Structure (yield) | Analytical data |
|---|---|---|
| 378 | rac-N-[2-amino-2-(3-methoxyphenyl)ethyl]-8-[(2,6-difluorobenzyl)oxy]-2,6-dimethylimidazo[1,2-a]pyridine-3-carboxamide<br />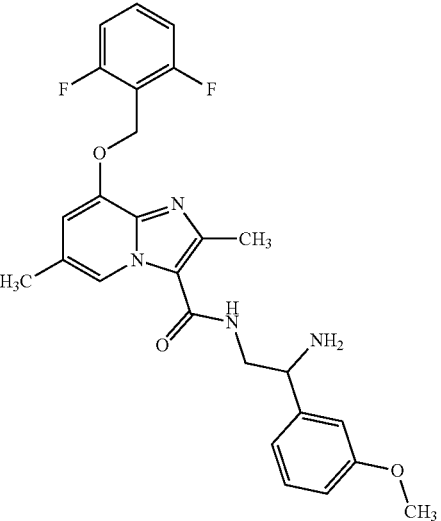<br />(9% of theory; purity 88%) | LC-MS (Method 8): $R_t$ = 0.69 min<br />MS (ESpos): m/z = 481 (M + H)$^+$ |

Example 379 rac-N-[2-amino-1-(2-naphthyl)ethyl]-8-[(2,6-difluorobenzyl)oxy]-2,6-dimethylimidazo[1,2-a]pyridine-3-carboxamide

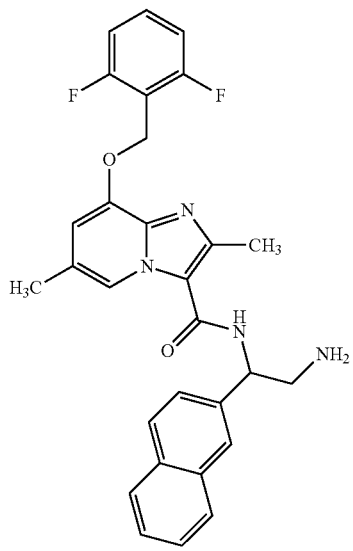 [SMILES: Cc1cc(OCc2c(F)cccc2F)c2nc(C)c(C(=O)NC(CN)c3ccc4ccccc4c3)n2c1]

29 mg (0.1 mmol) of tert-butyl [2-amino-2-(2-naphthyl)ethyl]carbamate were initially charged in a 96-well deep well multititer plate. A solution of 33 mg (0.1 mmol) of 8-[(2,6-difluorobenzyl)oxy]-2,6-dimethylimidazo[1,2-a]pyridine-3-carboxylic acid from Example 21A in 0.3 ml of DMF and a solution of 45 mg (0.12 mmol) of HATU in 0.3 ml of DMF were added successively. After addition of 20 mg (0.2 mmol) of 4-methylmorpholine, the mixture was shaken at RT overnight. The solvent was then evaporated completely, 0.6 ml of TFA was added to the residue and the mixture was shaken at RT overnight. The mixture was then evaporated, the residue was once more dissolved in DMF and filtered and the target compound was isolated from the filtrate by preparative LC-MS (Method 12). The product-containing fractions were concentrated under reduced pressure using a centrifugal dryer. The residue of the product fractions was in each case dissolved in 0.6 ml of DMSO. These solutions were combined and then freed from the solvent in a centrifugal dryer. This gave 25.8 mg (49% of theory; purity 94%).

LC-MS (Method 8): $R_t$=0.76 min
MS (ESpos): m/z=501 (M+H)$^+$

The exemplary compounds shown in Table 18 were prepared analogously to Example 379 by reacting 8-[(2,6-difluorobenzyl)oxy]-2,6-dimethylimidazo[1,2-a]pyridine-3-carboxylic acid from Example 21A with the appropriate commercially available or above-described amines under the conditions described:

TABLE 18

| Example | IUPAC Name/Structure (yield) | Analytical data |
|---|---|---|
| 380 | rac-N-{2-amino-1-[3-(trifluoromethoxy)phenyl]ethyl}-8-[(2,6-difluorobenzyl)oxy]-2,6-dimethylimidazo[1,2-a]pyridine-3-carboxamide 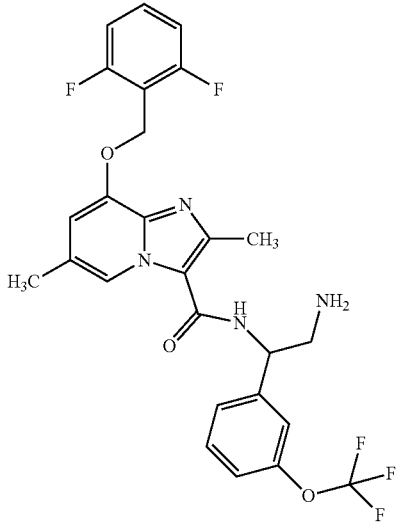 [SMILES: Cc1cc(OCc2c(F)cccc2F)c2nc(C)c(C(=O)NC(CN)c3cccc(OC(F)(F)F)c3)n2c1] (55% of theory; purity 87%) | LC-MS (Method 8): $R_t$ = 0.78 min<br>MS (ESpos): m/z = 535 (M + H)$^+$ |
| 381 | rac-N-[2-amino-1-(1,3-benzodioxol-5-yl)ethyl]-8-[(2,6-difluorobenzyl)oxy]-2,6-dimethylimidazo[1,2-a]pyridine-3-carboxamide 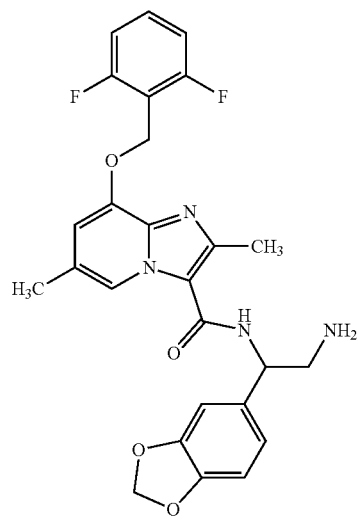 [SMILES: Cc1cc(OCc2c(F)cccc2F)c2nc(C)c(C(=O)NC(CN)c3ccc4c(c3)OCO4)n2c1] | LC-MS (Method 8): $R_t$ = 0.70 min<br>MS (ESpos): m/z = 495 (M + H)$^+$ |

TABLE 18-continued

| Example | IUPAC Name/Structure (yield) | Analytical data |
|---|---|---|
| | (69% of theory; purity 94%) | |
| 382 | rac-N-[2-amino-1-(3-methoxyphenyl)ethyl]-8-[(2,6-difluorobenzyl)oxy]-2,6-dimethylimidazo[1,2-a]pyridine-3-carboxamide | LC-MS (Method 8): $R_t$ = 0.71 min<br>MS (ESpos): m/z = 481 (M + H)$^+$ |

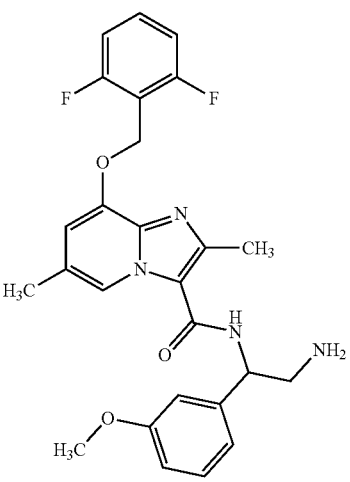 [SMILES: COc1cccc(C(CN)NC(=O)c2c(C)nc3c(OCc4c(F)cccc4F)cc(C)cn23)c1]

| | (62% of theory; purity 89%) | |
|---|---|---|
| 383 | rac-N-[2-amino-1-(3-bromophenyl)ethyl]-8-[(2,6-difluorobenzyl)oxy]-2,6-dimethylimidazo[1,2-a]pyridine-3-carboxamide | LC-MS (Method 8): $R_t$ = 0.75 min<br>MS (ESpos): m/z = 529 (M + H)$^+$ |

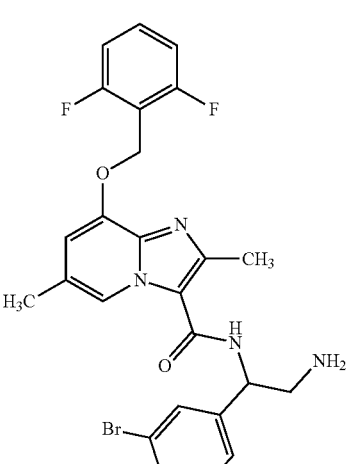

TABLE 18-continued

| Example | IUPAC Name/Structure (yield) | Analytical data |
|---|---|---|
| 384 | (51% of theory; purity 92%)<br>rac-N-[2-amino-1-(4-nitrophenyl)ethyl]-8-[(2,6-difluorobenzyl)oxy]-2,6-dimethylimidazo[1,2-a]pyridine-3-carboxamide | LC-MS (Method 8): $R_t$ = 0.73 min<br>MS (ESpos): m/z = 496 (M + H)+ |

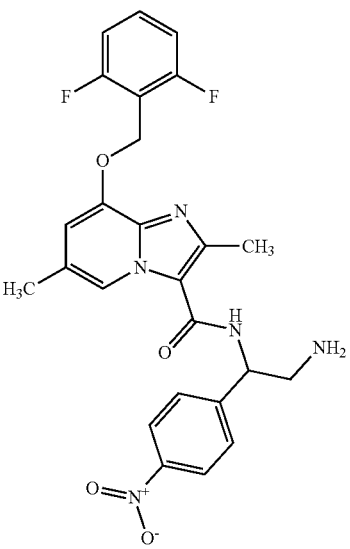 [SMILES: Cc1cc(OCc2c(F)cccc2F)c2nc(C)c(C(=O)NC(CN)c3ccc([N+](=O)[O-])cc3)n2c1]

(53% of theory; purity 91%)

Example 385 rac-N-[2-amino-1-(3-ethenylphenyl)ethyl]-8-[(2,6-difluorobenzyl)oxy]-2,6-dimethylimidazo[1,2-a]pyridine-3-carboxamide

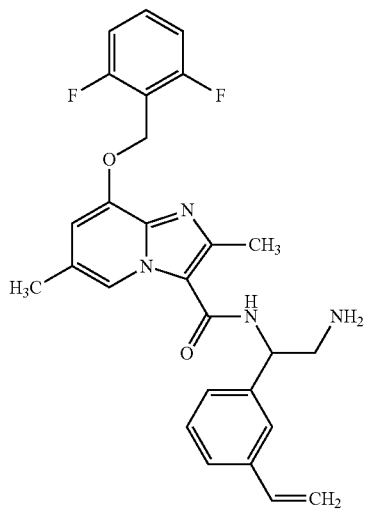 [SMILES: C=Cc1cccc(C(CN)NC(=O)c2c(C)nc3c(OCc4c(F)cccc4F)cc(C)cn23)c1]

16 mg (0.1 mmol) of 1-(3-vinylphenyl)ethane-1,2-diamine were initially charged in a 96-well deep well multititer plate, 0.2 ml of dichloromethane and a solution of 22 mg (0.1 mmol) of di-tert-butyl carbonate in 0.2 ml of dichloromethane were added successively and the mixture was shaken at RT for 2 hours. In a flask, 33 mg (0.1 mmol) of 8-[(2,6-difluorobenzyl)oxy]-2,6-dimethylimidazo[1,2-a]pyridine-3-carboxylic acid from Example 21A and 49 mg (0.13 mmol) of HATU were dissolved in 0.4 ml of DMF, 20 mg (0.2 mmol) of 4-methylmorpholine were added and the mixture was stirred at RT for 30 min. This mixture was then pipetted onto the multititer plate, and the plate was shaken at RT for 48 hours. The solvent was evaporated completely, and 0.6 ml of TFA was added to the residue and the mixture was shaken at RT overnight. The mixture was then concentrated, the residue was dissolved in DMF and filtered and the target compound was isolated from the filtrate by preparative LC-MS (Method 12). The product-containing fractions were concentrated under reduced pressure using a centrifugal dryer. The residue of the product fractions was in each case dissolved in 0.6 ml of DMSO. These solutions were combined and then freed from the solvent in a centrifugal dryer. This gave 2.9 mg (6% of theory).

LC-MS (Method 8): $R_t$=0.72 min
MS (ESpos): m/z=477 (M+H)+

The exemplary compounds shown in Table 19 were prepared analogously to Example 385 by reacting 8-[(2,6-difluorobenzyl)oxy]-2,6-dimethylimidazo[1,2-a]pyridine-3-carboxylic acid from Example 21A with the appropriate commercially available or above-described amines under the conditions described:

TABLE 19

| Example | IUPAC Name/Structure (yield) | Analytical data |
|---|---|---|
| 386 | rac-N-[1-amino-3-(4-methoxyphenyl)-2-methylpropan-2-yl]-8-[(2,6-difluorobenzyl)oxy]-2,6-dimethylimidazo[1,2-a]pyridine-3-carboxamide<br><br>(16% of theory) | LC-MS (Method 8): $R_t$ = 0.75 min<br>MS (ESpos): m/z = 509 (M + H)$^+$ |
| 387 | rac-N-[2-amino-1-(1-methyl-1H-pyrazol-4-yl)ethyl]-8-[(2,6-difluorobenzyl)oxy]-2,6-dimethylimidazo[1,2-a]pyridine-3-carboxamide | LC-MS (Method 8): $R_t$ = 0.62 min<br>MS (ESpos): m/z = 455 (M + H)$^+$ |

TABLE 19-continued

| Example | IUPAC Name/Structure (yield) | Analytical data |
|---|---|---|
| 388 | (8% of theory; purity 84%) rac-N-[2-amino-1-(2,3-dihydro-1,4-benzodioxin-6-yl)ethyl]-8-[(2,6-difluorobenzyl)oxy]-2,6-dimethylimidazo[1,2-a]pyridine-3-carboxamide | LC-MS (Method 8): $R_t$ = 0.69 min MS (ESpos): m/z = 509 (M + H)$^+$ |

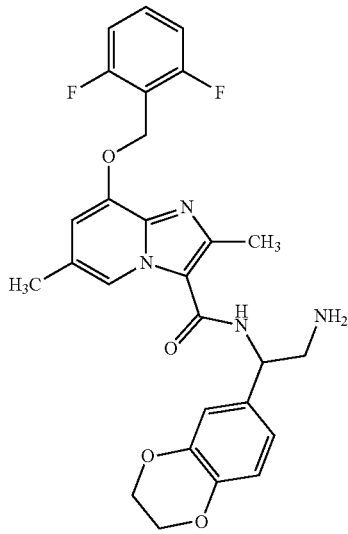 [SMILES: Cc1cc(OCc2c(F)cccc2F)c2nc(C)c(C(=O)NC(CN)c3ccc4c(c3)OCCO4)n2c1]

| | | |
|---|---|---|
| 389 | (12% of theory) rac-N-[2-amino-1-(1-benzothiophen-3-yl)ethyl]-8-[(2,6-difluorobenzyl)oxy]-2,6-dimethylimidazo[1,2-a]pyridine-3-carboxamide | LC-MS (Method 8): $R_t$ = 0.75 min MS (ESpos): m/z = 507 (M + H)$^+$ |

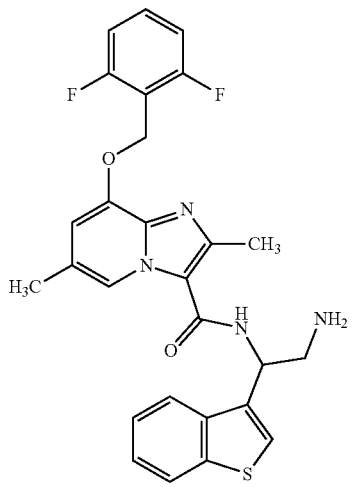 [SMILES: Cc1cc(OCc2c(F)cccc2F)c2nc(C)c(C(=O)NC(CN)c3csc4ccccc34)n2c1]

TABLE 19-continued

| Example | IUPAC Name/Structure (yield) | Analytical data |
|---|---|---|
| | (22% of theory) | |
| 390 | rac-N-[2-amino-1-(3,4,5-trifluorophenyl)ethyl]-8-[(2,6-difluorobenzyl)oxy]-2,6-dimethylimidazo[1,2-a]pyridine-3-carboxamide | LC-MS (Method 8): $R_t$ = 0.73 min<br>MS (ESpos): m/z = 505 (M + H)⁺ |

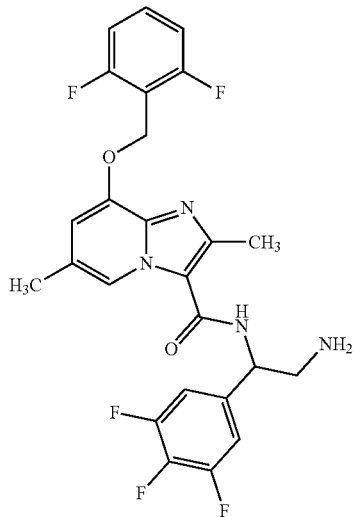 [SMILES: Cc1cc(OCc2c(F)cccc2F)c2nc(C)c(C(=O)NC(CN)c3cc(F)c(F)c(F)c3)n2c1]

| | (13% of theory) | |
|---|---|---|
| 391 | rac-N-[1-amino-4-(methylsulfanyl)butan-2-yl]-8-[(2,6-difluorobenzyl)oxy]-2,6-dimethylimidazo[1,2-a]pyridine-3-carboxamide | LC-MS (Method 8): $R_t$ = 0.66 min<br>MS (ESpos): m/z = 449 (M + H)⁺ |

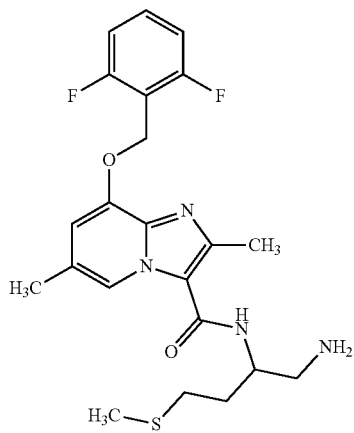 [SMILES: CSCCC(CN)NC(=O)c1c(C)nc2c(OCc3c(F)cccc3F)cc(C)cn12]

TABLE 19-continued

| Example | IUPAC Name/Structure (yield) | Analytical data |
|---|---|---|
| | (12% of theory; purity 84%) | |
| 392 | rac-N-{2-amino-1-[3-(difluoromethoxy)phenyl]ethyl}-8-[(2,6-difluorobenzyl)oxy]-2,6-dimethylimidazo[1,2-a]pyridine-3-carboxamide | LC-MS (Method 8): $R_t$ = 0.72 min<br>MS (ESpos): m/z = 517 (M + H)⁺ |

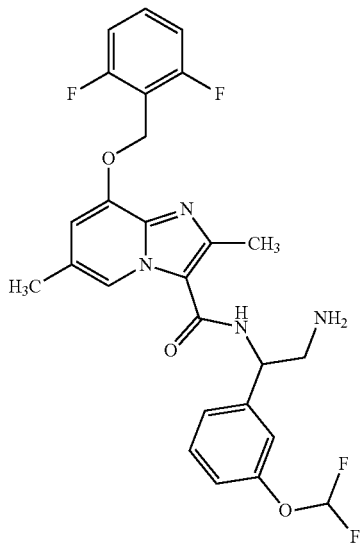 [SMILES: Cc1cc(OCc2c(F)cccc2F)c2nc(C)c(C(=O)NC(CN)c3cccc(OC(F)F)c3)n2c1]

| | (16% of theory) | |
|---|---|---|
| 393 | rac-N-{2-amino-1-[3-(2-hydroxyethoxy)phenyl]ethyl}-8-[(2,6-difluorobenzyl)oxy]-2,6-dimethylimidazo[1,2-a]pyridine-3-carboxamide | LC-MS (Method 8): $R_t$ = 0.65 min<br>MS (ESpos): m/z = 511 (M + H)⁺ |

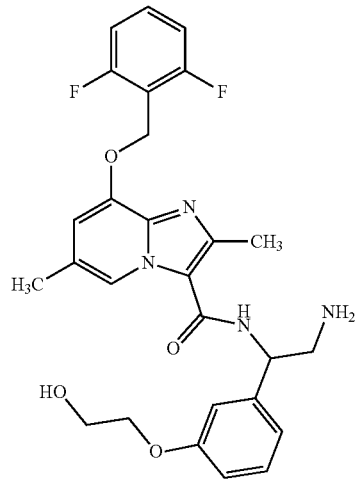 [SMILES: Cc1cc(OCc2c(F)cccc2F)c2nc(C)c(C(=O)NC(CN)c3cccc(OCCO)c3)n2c1]

TABLE 19-continued

| Example | IUPAC Name/Structure (yield) | Analytical data |
|---|---|---|
| | (8% of theory; purity 85%) | |
| 394 | rac-N-{2-amino-1-[3-(trifluoromethyl)phenyl]ethyl}-8-[(2,6-difluorobenzyl)oxy]-2,6-dimethylimidazo[1,2-a]pyridine-3-carboxamide | LC-MS (Method 8): $R_t$ = 0.77 min<br>MS (ESpos): m/z = 519 (M + H)$^+$ |

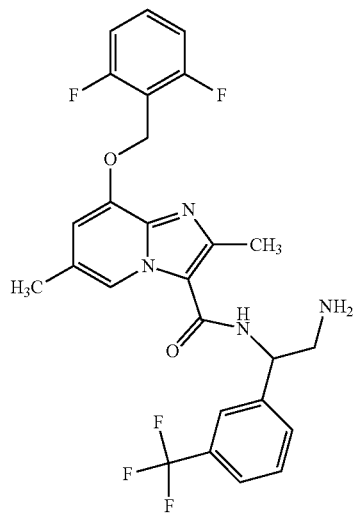 [SMILES: Cc1cc(OCc2c(F)cccc2F)c2nc(C)c(C(=O)NC(CN)c3cccc(C(F)(F)F)c3)n2c1]

(15% of theory)

| 395 | rac-N-[2-amino-1-(quinolin-6-yl)ethyl]-8-[(2,6-difluorobenzyl)oxy]-2,6-dimethylimidazo[1,2-a]pyridine-3-carboxamide | LC-MS (Method 8): $R_t$ = 0.68 min<br>MS (ESpos): m/z = 502 (M + H)$^+$ |

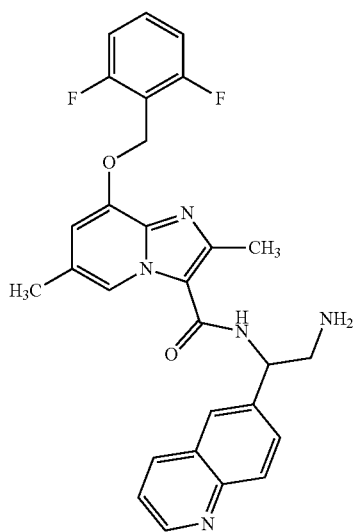 [SMILES: Cc1cc(OCc2c(F)cccc2F)c2nc(C)c(C(=O)NC(CN)c3ccc4ncccc4c3)n2c1]

(2% of theory)

Example 396 rac-N-[1-(3-acetamidophenyl)-2-aminoethyl]-8-[(2,6-difluorobenzyl)oxy]-2,6-dimethylimidazo[1,2-a]pyridine-3-carboxamide

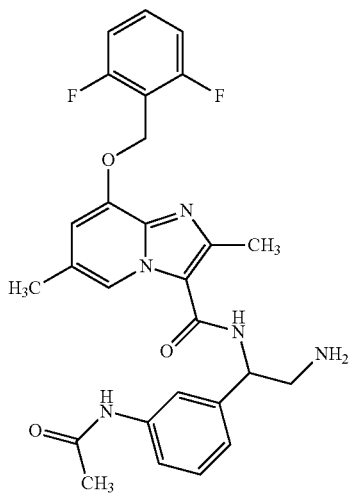 [SMILES: CC(=O)Nc1cccc(C(CN)NC(=O)c2c(C)nc3c(OCc4c(F)cccc4F)cc(C)cn23)c1]

100 mg (0.14 mmol) rac-tert-butyl-{2-(3-acetamidophenyl)-2-[({8-[(2,6-difluorobenzyl)oxy]-2,6-dimethylimidazo[1,2-a]pyridin-3-yl}carbonyl)amino]ethyl}carbamate trifluoroacetate from Example 414A were initially charged in 0.6 ml of diethyl ether, 2.1 ml (4.2 mmol) of 2 N hydrogen chloride in diethyl ether were added and the mixture was stirred at RT overnight. The reaction mixture was concentrated, dichloromethane was added to the residue and the mixture was washed twice with saturated aqueous sodium bicarbonate solution. The combined aqueous phases were extracted twice with dichloromethane. The combined organic phases were dried with sodium sulphate, filtered and concentrated. This gave 52 mg of the target compound (72% of theory).

LC-MS (Method 2): $R_t$=0.62 min

MS (ESpos): m/z=508 (M+H)$^+$ $^1$H-NMR (500 MHz, DMSO-d$_6$): δ [ppm]=1.62 (br. s, 2H), 2.02 (s, 3H), 2.29 (s, 3H), 2.60 (s, 3H), 2.89 (d, 2H), 4.86-4.94 (m, 1H), 5.29 (s, 2H), 6.90 (s, 1H), 7.07 (d, 1H), 7.19-7.28 (m, 3H), 7.43 (d, 1H), 7.54-7.63 (m 2H), 8.11 (br. s, 1H), 8.38 (s. 1H), 9.89 (s, 1H).

The examples shown in Table 20 were prepared analogously to Example 396 by reacting the above-described Boc-protected diamines under the reaction conditions described with hydrogen chloride solution.

TABLE 20

| Example | IUPAC Name/Structure (yield) | Analytical data |
|---------|------------------------------|-----------------|
| 397 | rac-ethyl 6-{2-amino-1-[({8-[(2,6-difluorobenzyl)oxy]-2,6-dimethylimidazo[1,2-a]pyridin-3-yl}carbonyl)amino]ethyl}pyridine-2-carboxylate | LC-MS (Method 2): $R_t$ = 0.74 min<br>MS (ESpos): m/z = 524 (M + H)$^+$<br>$^1$H-NMR (500 MHz, DMSO-d$_6$): δ [ppm] = 1.34 (t, 3H), 2.29 (s, 3H), 2.68 (s, 3H), 2.97-3.11 (m, 2H), 4.37 (q, 2H), 5.14-5.19 (m, 1H), 5.31 (s, 2H), 6.93 (s, 1H), 7.19-7.28 (m, 2H), 7.56-7.63 (m, 1H), 7.72 (d, 1H), 7.92-8.02 (m, 2H), 8.10-8.24 (m, 1H), 8.53 (s, 1H). |

| Example | IUPAC Name/Structure (yield) | Analytical data |
|---|---|---|
| 398 | (76% of theory)<br>rac-N-[2-amino-1-(4-cyanophenyl)ethyl]-8-[(2,6-difluorobenzyl)oxy]-2,6-dimethylimidazo[1,2-a]pyridine-3-carboxamide<br>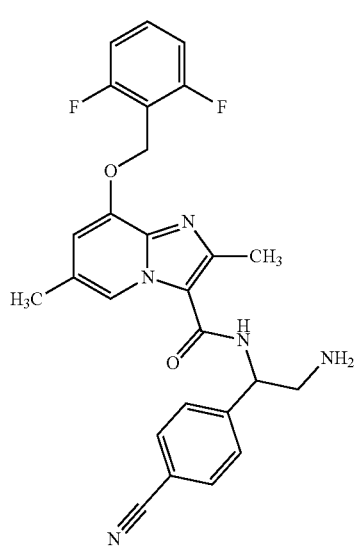 [SMILES: Cc1cc(OCc2c(F)cccc2F)c2nc(C)c(C(=O)NC(CN)c3ccc(C#N)cc3)n2c1]<br>(76% of theory) | LC-MS (Method 2): $R_t$ = 0.72 min<br>MS (ESpos): m/z = 476 (M + H)$^+$<br>$^1$H-NMR (500 MHz, DMSO-$d_6$): δ [ppm] = 1.85 (br. s, 2H), 2.28 (s, 3H), 2.60 (s, 3H), 2.93 (d, 2H), 4.98-5.06 (m, 1H), 5.29 (s, 2H), 6.91 (s, 1H), 7.19-7.26 (m, 2H), 7.55-7.63 (m, 3H), 7.82 (d, 2H), 8.20 (br. s, 1H), 8.37 (s, 1H). |

Example 399 rac-Methyl 3-{1-amino-2-[({8-[(2,6-difluorobenzyl)oxy]-2,6-dimethylimidazo[1,2-a]pyridin-3-yl}carbonyl)amino]ethyl}benzoate

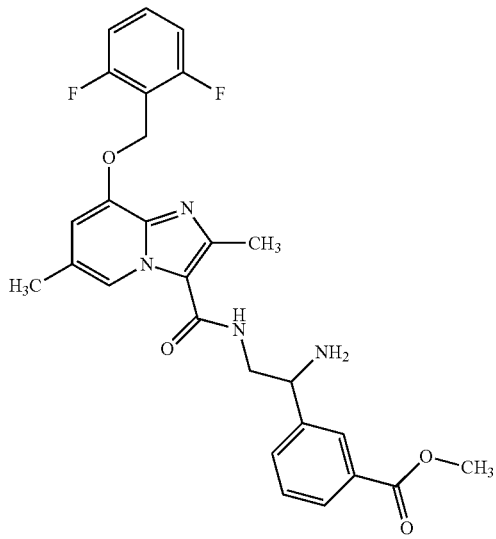

100 mg (0.30 mmol) of 8-[(2,6-difluorobenzyl)oxy]-2,6-dimethylimidazo[1,2-a]pyridine-3-carboxylic acid from Example 21A, 126 mg (0.33 mmol) of HATU and 117 mg (0.90 mmol) of N,N-diisopropylethylamine were initially charged in 1 ml of DMF, and the mixture was stirred at RT for 10 min. 67 mg (0.35 mmol) of rac-methyl 3-(1,2-diaminoethyl)benzoate were then added, and the mixture was stirred at RT for 2 h. Acetonitrile, TFA and water were added to the reaction mixture, and the product was purified by preparative HPLC (RP-C18, mobile phase: acetonitrile/water gradient with addition of 0.1% TFA). The product-containing fractions were concentrated and the residue was taken up in dichloromethane and washed twice with saturated aqueous sodium bicarbonate solution. The combined aqueous phases were extracted twice with dichloromethane. The combined organic phases were dried over sodium sulphate and filtered, and the filtrate was concentrated. This gave 21 mg (13% of theory) of the title compound.

LC-MS (Method 2): $R_t$=0.70 min

MS (ESpos): m/z=509 (M+H)$^+$ $^1$H-NMR (500 MHz, DMSO-$d_6$): δ=2.11 (br. s, 2H), 2.28 (s, 3H), 2.35 (s, 3H), 3.38-3.46 (m, 1H), 3.48-3.56 (m, 1H), 3.72 (s, 3H), 4.18 (t, 1H), 5.29 (s, 2H), 6.88 (s, 1H), 7.19-7.26 (m, 2H), 7.48 (t, 1H), 7.55-7.64 (m, 1H), 7.70 (d, 1H), 7.78 (t, 1H), 7.83 (d, 1H), 8.03 (s, 1H), 8.28 (s, 1H).

Example 400 rac-N-(2-amino-2-cyanoethyl)-8-[(2,6-difluorobenzyl)oxy]-2,6-dimethylimidazo[1,2-a]pyridine-3-carboxamide

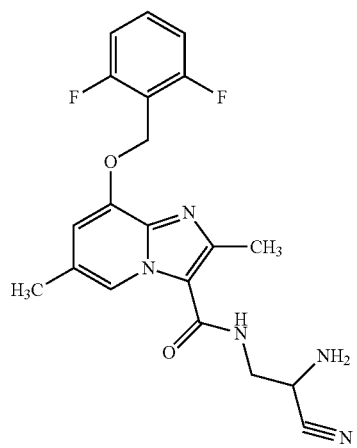 [SMILES: Cc1cc(OCc2c(F)cccc2F)c2nc(C)c(C(=O)NCC(N)C#N)n2c1]

200 mg (0.60 mmol) of 8-[(2,6-difluorobenzyl)oxy]-2,6-dimethylimidazo[1,2-a]pyridine-3-carboxylic acid from Example 21A were initially charged in 1.8 ml of DMF, 252 mg (0.66 mmol) of HATU and 311 mg (2.41 mmol) of N,N-diisopropylethylamine were added and the mixture was stirred at room temperature for 10 min. The reaction mixture was cooled to 0° C. A solution of 109 mg (0.69 mmol) of rac-2,3-diaminopropanonitrile dihydrochloride (commercially available; see also A. H. Cook et al. Journal of the Chemical Society 1949, 3001) and 194 mg (1.51 mmol) of N,N-diisopropylethylamine in 0.67 ml of DMF was slowly added dropwise, and the mixture was stirred at 0° C. for 1 h. The reaction solution was diluted with TFA/water and acetonitrile and the product was purified by preparative HPLC (RP18 column, mobile phase: acetonitrile/water gradient with addition of 0.1% TFA). The concentrated residue was taken up in dichloromethane and a little methanol and washed twice with saturated aqueous sodium bicarbonate solution. The combined aqueous phases were extracted twice with dichloromethane. The combined organic phases were dried over sodium sulphate, filtered and concentrated. This gave 197 mg of the title compound (79% of theory).

LC-MS (Method 2): $R_t$=0.65 min

MS (ESpos): m/z=400 (M+H)$^+$ $^1$H-NMR (400 MHz, DMSO-d$_6$): δ [ppm]=2.30 (s, 3H), 2.50 (s, 3H), 3.40-3.60 (m, 2H), 3.95-4.08 (m, 1H), 5.29 (s, 2H), 6.92 (s, 1H), 7.18-7.28 (m, 2H), 7.54-7.63 (m, 1H), 8.10 (t, 1H), 8.45 (s, 11-).

Example 401 ent-N-(2-amino-2-cyanoethyl)-8-[(2,6-difluorobenzyl)oxy]-2,6-dimethylimidazo[1,2-a]pyridine-3-carboxamide (Enantiomer A)

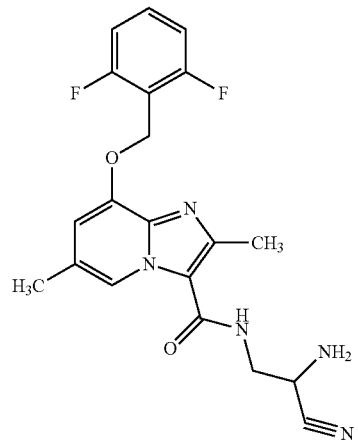 [SMILES: Cc1cc(OCc2c(F)cccc2F)c2nc(C)c(C(=O)NCC(N)C#N)n2c1]

170 mg of rac-N-(2-amino-2-cyanoethyl)-8-[(2,6-difluorobenzyl)oxy]-2,6-dimethylimidazo[1,2-a]pyridine-3-carboxamide from Example 400 were separated into the enantiomers by preparative separation on a chiral phase [column: Daicel Chiralpak AD-H, 5 μm, SFC, 250×20 mm, mobile phase: 70% carbon dioxide, 30% ethanol, flow rate: 80 ml/min, temperature: 40° C., detection: 210 nm].

Enantiomer A: 70 mg (>99% ee)

$R_t$=7.67 min [SFC, Daicel Chiralpak AD-H, 250×4.6 mm, 5 μm, mobile phase: 70% carbon dioxide, 30% ethanol, flow rate: 3 ml/min, temperature: 30° C., detection: 220 nm].

Example 402 ent-N-(2-amino-2-cyanoethyl)-8-[(2,6-difluorobenzyl)oxy]-2,6-dimethylimidazo[1,2-a]pyridine-3-carboxamide (Enantiomer B)

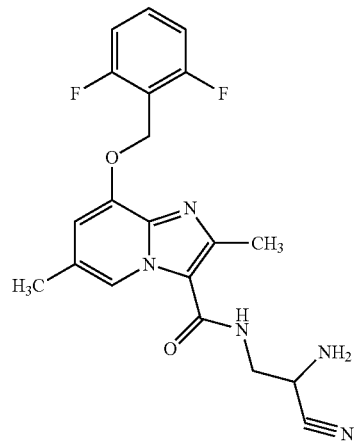 [SMILES: Cc1cc(OCc2c(F)cccc2F)c2nc(C)c(C(=O)NCC(N)C#N)n2c1]

170 mg of rac-N-(2-amino-2-cyanoethyl)-8-[(2,6-difluorobenzyl)oxy]-2,6-dimethylimidazo[1,2-a]pyridine-3-carboxamide from Example 400 were separated into the enantiomers by preparative separation on a chiral phase [column: Daicel Chiralpak AD-H, 5 μm, SFC, 250×20 mm, mobile phase: 70% carbon dioxide, 30% ethanol, flow rate: 80 ml/min, temperature: 40° C., detection: 210 nm].

Enantiomer B: 60 mg (>99% ee)

$R_t$=12.45 min [SFC, Daicel Chiralpak AD-H, 250×4.6 mm, 5 μm, mobile phase: 70% carbon dioxide, 30% ethanol, flow rate: 3 ml/min, temperature: 30° C., detection: 220 nm].

Example 403 ent-N-(2-amino-2-methylpentyl)-8-[(2,6-difluorobenzyl)oxy]-6-(fluoromethyl)-2-methylimidazo[1,2-a]pyridine-3-carboxamide

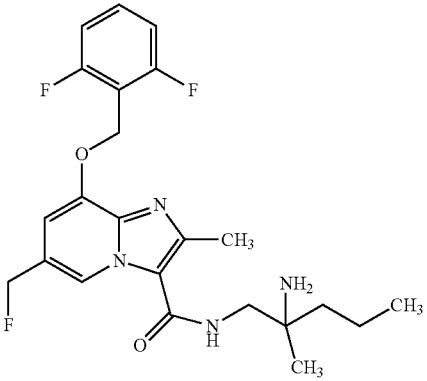 [SMILES: CCCC(C)(N)CNC(=O)c1c(C)nc2c(OCc3c(F)cccc3F)cc(CF)cn12]

A mixture of 171 mg (0.21 mmol, purity 87%) of ent-benzyl {1-[({8-[(2,6-difluorobenzyl)oxy]-6-(fluoromethyl)-2-methylimidazo[1,2-a]pyridin-3-yl}carbonyl)amino]-2-methylpentan-2-yl}carbamate trifluoroacetate from Example 401A and 11.4 mg of 10% palladium carbon (0.01 mmol) in 17 ml of ethanol was hydrogenated at room temperature and standard pressure for 2 h. During the reaction, another 20 mg of 10% palladium on carbon (0.02 mmol) were added to the reaction mixture. The mixture was then filtered off through a filter, the filter cake was washed with ethanol and the filtrate was concentrated. The residue was taken up in dichloromethane and washed twice with saturated aqueous sodium bicarbonate solution. The combined aqueous phases were extracted twice with dichloromethane. The combined organic phases were dried over sodium sulphate, filtered and concentrated. The crude product was pre-purified by thick-layer chromatography (mobile phase: dichloromethane/methanol 10/1). The pre-purified product obtained was re-purified on a chiral phase [column: Daicel Chiralpak AY-H 5 μm, 250×20 mm; mobile phase: 70% isohexane, 30% isopropanol+0.2% diethylamine; flow rate: 20 ml/min; temperature 23° C.; detection 220 nm]. This gave 13 mg of the title compound (13% of theory).

LC-MS (Method 2): $R_t$=0.72 min

MS (ESpos): m/z=449 (M+H)$^+$ $^1$H-NMR (500 MHz, DMSO-d$_6$): δ [ppm]=0.82-0.92 (m, 3H), 1.01 (s, 3H), 1.25-1.47 (m, 4H), 1.95-2.30 (br.s, 2H), 2.56 (s, 3H), 3.14-3.27 (m, 2H), 5.33 (s, 2H), 5.47 (d$_{H-F}$, 2H), 7.11 (s, 1H), 7.21-7.28 (m, 2H), 7.55-7.64 (m, 1H), 7.69-7.78 (m, 1H), 8.77-8.81 (m, 1H).

The exemplary compounds shown in Table 21 were prepared analogously to Example 403 by hydrogenating the above-described Cbz protected amines from Example 402A and Example 403A under the conditions described:

TABLE 21

| Example | IUPAC Name/Structure (yield) | Analytical data |
|---|---|---|
| 404 | ent-N-(2-amino-2-methylbutyl)-8-[(2,6-difluorobenzyl)oxy]-6-(fluoromethyl)-2-methylimidazo[1,2-a]pyridine-3-carboxamide | LC-MS (Method 2): $R_t$ = 0.67 min<br>MS (ESpos): m/z = 435 (M + H)$^+$<br>$^1$H NMR (500 MHz, DMSO-d$_6$) δ [ppm] = 0.87 (t, 3H), 0.99 (s, 3H), 1.32-1.45 (m, 2H), 2.56 (s, 3H), 3.16-3.28 (m, 2H), 5.33 (s, 2H), 5.47 (d$_{H-F}$, 2H), 7.11 (s, 1H), 7.21-7.28 (m, 2H), 7.55-7.64 (m, 1H), 7.67-7.76 (m, 1H), 8.77-8.81 (m, 1H). |

TABLE 21-continued

| Example | IUPAC Name/Structure (yield) | Analytical data |
|---|---|---|
| 405 | ent-N-(2-amino-3-fluoro-2-methylpropyl)-8-[(2,6-difluorobenzyl)oxy]-6-(fluoromethyl)-2-methylimidazo[1,2-a]pyridine-3-carboxamide<br><br>(13% of theory)<br><br>(36% of theory) | LC-MS (Method 2): $R_t$ = 0.65 min<br>MS (ESpos): m/z = 439 (M + H)$^+$<br>$^1$H-NMR (500 MHz, DMSO-d$_6$): δ [ppm] = 1.01-1.07 (m, 3H), 1.70 (br. s, 2H), 2.56 (s, 3H), 3.30-3.40 (m, 2H), 4.10-4.16 (m, 1H), 4.20-4.26 (m, 1H), 5.33 (s, 2H), 5.47 (d$_{H-F}$, 2H), 7.11 (s, 1H), 7.21-7.28 (m, 2H), 7.55-7.64 (m, 1H), 7.74-7.81 (m, 1H), 8.76-8.80 (m, 1H). |

Example 406 rac-N-[(4E/Z)-2-aminohex-4-en-1-yl]-8-[(2,6-difluorobenzyl)oxy]-2,6-dimethylimidazo[1,2-a]pyridine-3-carboxamide

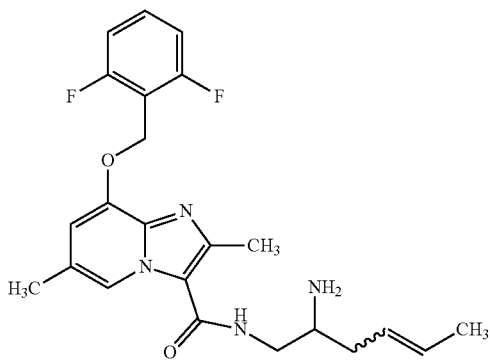 [SMILES: CC=CCC(N)CNC(=O)c1c(C)nc2c(OCc3c(F)cccc3F)cc(C)cn12]

200 mg (0.60 mmol) of 8-[(2,6-difluorobenzyl)oxy]-2,6-dimethylimidazo[1,2-a]pyridine-3-carboxylic acid from Example 21A were initially charged in 1.8 ml of DMF, 252 mg (0.66 mmol) of HATU and 467 mg (3.61 mmol) of N,N-diisopropylethylamine were added and the mixture was stirred at room temperature for 10 min. The reaction mixture was cooled to 0° C. A solution of 130 mg (0.69 mmol) of rac-(4E/Z)-hex-4-ene-1,2-diamine dihydrochloride and 194 mg (1.51 mmol) of N,N-diisopropylethylamine in 0.67 ml of DMF was added dropwise, and the mixture was stirred at 0° C. for 1 h. The reaction solution was diluted with TFA/water and acetonitrile and purified by preparative HPLC (RP18 column, mobile phase: acetonitrile/water gradient with addition of 0.1% TFA). The concentrated residue was taken up in dichloromethane and washed twice with saturated aqueous sodium bicarbonate solution. The combined aqueous phases were extracted twice with dichloromethane. The combined organic phases were dried over sodium sulphate, filtered and concentrated. This gave 114 mg of the title compound (42% of theory, purity 94%).

LC-MS (Method 2): $R_t$=0.65 min
MS (ESpos): m/z=429 (M+H)$^+$
$^1$H-NMR (500 MHz, DMSO-d$_6$): δ [ppm]=1.56-1.67 (m, 3H), 1.94-2.08 (m, 1H), 2.09-2.23 (m, 1H), 2.31 (s, 3H), 2.50 (s, 3H), 2.83-2.94 (m, 1H), 3.07-3.18 (m, 1H), 3.29-3.41 (m, 1H), 5.29 (s, 2H), 5.42-5.58 (m, 2H), 6.91 (s, 1H), 7.19-7.27 (m, 2H), 7.54-7.63 (m, 1H), 7.68-7.78 (m, 1H), 8.47 (m, 1H).

Example 407 rac-Ethyl 6-{1-amino-2-[({8-[(2,6-difluorobenzyl)oxy]-2,6-dimethylimidazo[1,2-a]pyridin-3-yl}carbonyl)amino]ethyl}pyridine-2-carboxylate

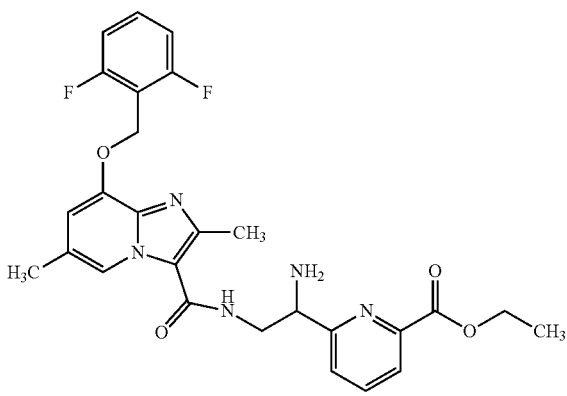 [SMILES: CCOC(=O)c1cccc(C(N)CNC(=O)c2c(C)nc3c(OCc4c(F)cccc4F)cc(C)cn23)n1]

35 mg (0.11 mmol) of 8-[(2,6-difluorobenzyl)oxy]-2,6-dimethylimidazo[1,2-a]pyridine-3-carboxylic acid from Example 21A were initially charged in 0.32 ml of DMF, 45 mg (0.12 mmol) of HATU and 55 mg (0.43 mmol) of

729

N,N-diisopropylethylamine were added and the mixture was stirred at room temperature for 10 min. The reaction mixture was cooled to 0° C. A solution of 106 mg (0.13 mmol) of rac-ethyl 6-(1,2-diaminoethyl)pyridine-2-carboxylate dihydrochloride (prepared from ethyl 6-{1-amino-2-[(tert-butoxycarbonyl)amino]ethyl}pyridine-2-carboxylate by treatment with 2 N hydrochloric acid in diethyl ether and concentration of the reaction mixture) and 50 mg (0.38 mmol) of N,N-diisopropylethylamine in 0.12 ml of DMF was slowly added dropwise, and the mixture was stirred at 0° C. for 1 h. The reaction solution was diluted with TFA/water and acetonitrile and purified by preparative HPLC (RP18 column, mobile phase: acetonitrile/water gradient with addition of 0.1% TFA). The product fractions were concentrated and the residue was taken up in dichloromethane and a little methanol and washed twice with saturated aqueous sodium bicarbonate solution. The combined aqueous phases were extracted twice with dichloromethane. The combined organic phases were dried over sodium sulphate, filtered and concentrated. The crude product was re-purified by thick-layer chromatography (mobile phase: dichloromethane/methanol=10/1). This gave 8.5 mg of the title compound (9% of theory, purity 65%).

LC-MS (Method 2): $R_t$=0.72 min
MS (ESpos): m/z=524 (M+H)$^+$

Example 408 ent-N-(2-amino-5,5,5-trifluoro-2-methylpentyl)-8-[(2,6-difluorobenzyl)oxy]-2,6-dimethylimidazo[1,2-a]pyridine-3-carboxamide (Enantiomer A)

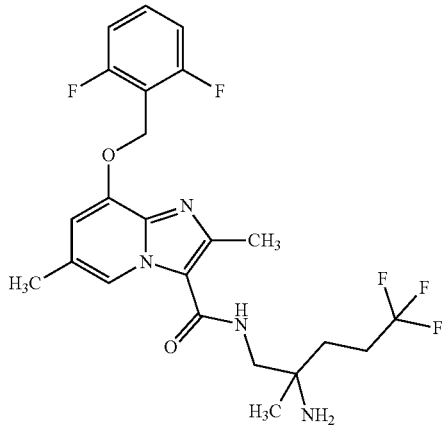 [SMILES: Cc1cc(OCc2c(F)cccc2F)c2nc(C)c(C(=O)NCC(C)(N)CCC(F)(F)F)n2c1]

A mixture of 1.02 g (1.56 mmol) of ent-benzyl {1-[({8-[(2,6-difluorobenzyl)oxy]-2,6-dimethylimidazo[1,2-a]pyridin-3-yl}carbonyl)amino]-5,5,5-trifluoro-2-methylpentan-2-yl}carbamate (enantiomer A) from Example 410A and 332 mg of 10% palladium on activated carbon in 40 ml of ethanol was hydrogenated at room temperature and standard pressure for 2 h. The mixture was then filtered off through Celite, the filter cake was washed with ethanol and the filtrate was concentrated. The crude product was purified by preparative HPLC (RP-C18, mobile phase: acetonitrile/water gradient with addition of 0.1% TFA). The product fractions were taken up in dichloromethane and washed twice with saturated aqueous sodium bicarbonate solution. The combined aqueous phases were extracted twice with dichloromethane. The combined organic phases were dried over sodium sulphate, filtered and concentrated. This gave 601 mg of the title compound (79% of theory).

LC-MS (Method 2): $R_t$=0.73 min
MS (ESpos): m/z=485 (M+H)$^+$
$^1$H-NMR (500 MHz, DMSO-d$_6$): δ [ppm]=1.02 (s, 3H), 1.48-1.56 (m, 2H), 1.60 (br. s, 2H), 2.27-2.46 (m, 5H), 2.50 (s, 3H; superimposed by solvent peak), 3.18-3.29 (m, 2H), 5.29 (s, 2H), 6.91 (s, 1H), 7.19-7.27 (m, 2H), 7.54-7.63 (m, 1H), 7.73-7.80 (m, 1H), 8.41 (s, 1H).

Enantiomer A: about 97% ee
$R_t$=5.77 min [Daicel Chiralpak AZ-H, 5 µm, 250×4.6 mm; mobile phase: 50% isohexane, 50% ethanol+0.2% diethylamine; flow rate 1.0 ml/min; temperature: 35° C.; detection: 220 nm].

Example 409 ent-N-(2-amino-5,5,5-trifluoro-2-methylpentyl)-8-[(2,6-difluorobenzyl)oxy]-2,6-dimethylimidazo[1,2-a]pyridine-3-carboxamide (Enantiomer B)

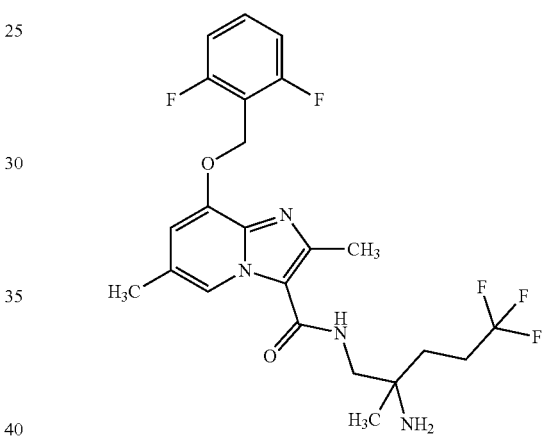

A mixture of 965 mg (1.56 mmol) of ent-benzyl {1-[({8-[(2,6-difluorobenzyl)oxy]-2,6-dimethylimidazo[1,2-a]pyridin-3-yl}carbonyl)amino]-5,5,5-trifluoro-2-methylpentan-2-yl}carbamate (enantiomer B) from Example 411A and 332 mg of 10% palladium on activated carbon in 40 ml of ethanol was hydrogenated at room temperature and standard pressure for 2 h. The mixture was then filtered off through Celite, the filter cake was washed with ethanol and the filtrate was concentrated. The crude product was purified by preparative HPLC (RP-C18, mobile phase: acetonitrile/water gradient with addition of 0.1% TFA). The product fractions were taken up in dichloromethane and washed twice with saturated aqueous sodium bicarbonate solution. The combined aqueous phases were extracted twice with dichloromethane. The combined organic phases were dried over sodium sulphate, filtered and concentrated. This gave 586 mg of the title compound (77% of theory).

LC-MS (Method 2): $R_t$=0.72 min
MS (ESpos): m/z=485 (M+H)$^+$
$^1$H-NMR (500 MHz, DMSO-d$_6$): δ [ppm]=1.02 (s, 3H), 1.48-1.56 (m, 2H), 1.59 (br. s, 2H), 2.27-2.46 (m, 5H), 2.50 (s, 3H; superimposed by solvent peak), 3.18-3.29 (m, 2H), 5.29 (s, 2H), 6.91 (s, 1H), 7.19-7.27 (m, 2H), 7.54-7.63 (m, 1H), 7.73-7.80 (m, 1H), 8.41 (s, 1H).

Enantiomer B: about 78% ee $R_t$=5.02 min [Daicel Chiralpak AZ-H, 5 μm, 250×4.6 mm; mobile phase: 50% isohexane, 50% ethanol+0.2% diethylamine; flow rate 1.0 ml/min; temperature: 35° C.; detection: 220 nm].

The title compound was purified further as follows:

280 mg of enantiomer B (about 78% ee) from the enantiomer separation described above were separated into the enantiomers by preparative separation on a chiral phase [column: Daicel Chiralpak IF, 5 μm, 250×20 mm, mobile phase: 50% isohexane, 50% ethanol+0.2% diethylamine, flow rate: 50 ml/min, temperature: 23° C.; detection: 220 nm]. The product fractions were collected on dry ice and concentrated, acetonitrile/water was added and the product was lyophilised.

Enantiomer B: 158 mg (>99% ee; purity about 97%)

$R_t$=5.05 min [Daicel Chiralpak AZ-H, 5 μm, 250×4.6 mm; mobile phase: 50% isohexane, 50% ethanol+0.2% diethylamine; flow rate 1.0 ml/min; temperature: 35° C.; detection: 220 nm].

Example 410 ent-N-(2-amino-5,5,5-trifluoro-2-methylpentyl)-2,6-dimethyl-8-[(2,3,6-trifluorobenzyl)oxy]imidazo[1,2-a]pyridine-3-carboxamide (Enantiomer A)

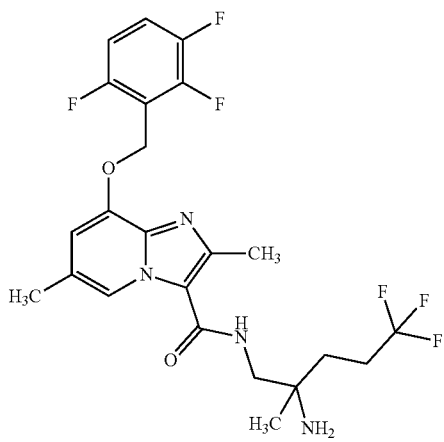 [SMILES: Cc1cc(OCc2c(F)ccc(F)c2F)c2nc(C)c(C(=O)NCC(C)(N)CCC(F)(F)F)n2c1]

A mixture of 550 mg (0.75 mmol, purity 87%) of ent-benzyl {1-[({2,6-dimethyl-8-[(2,3,6-trifluorobenzyl)oxy]imidazo[1,2-a]pyridin-3-yl}carbonyl)amino]-5,5,5-trifluoro-2-methylpentan-2-yl}carbamate (enantiomer A) from Example 412A and 160 mg of 10% palladium on activated carbon in 19.4 ml of ethanol was hydrogenated at room temperature and standard pressure for 2 h. The mixture was then filtered off through kieselguhr, the filter cake was washed with ethanol and the filtrate was concentrated. The crude product was purified by preparative HPLC (RP-C18, mobile phase: acetonitrile/water gradient with addition of 0.1% TFA). The product fractions were taken up in dichloromethane and washed twice with saturated aqueous sodium bicarbonate solution. The combined aqueous phases were extracted twice with dichloromethane. The combined organic phases were dried over sodium sulphate, filtered and concentrated. This gave 262 mg of the title compound (69% of theory).

LC-MS (Method 2): $R_t$=0.74 min
MS (ESpos): m/z=503 (M+H)$^+$ $^1$H-NMR (500 MHz, DMSO-$d_6$): δ [ppm]=1.03 (s, 3H), 1.49-1.57 (m, 2H), 1.75 (br. s, 2H), 2.27-2.46 (m, 5H), 2.50 (s, 3H; superimposed by solvent peak), 3.18-3.29 (m, 2H), 5.34 (s, 2H), 6.91 (s, 1H). 7.25-7.32 (m, 1H), 7.61-7.70 (m, 1H), 7.75-7.82 (m, 1H), 8.42 (s, 1H).

Enantiomer A: about 98% ee $R_t$=5.70 min [Daicel Chiralpak AZ-H, 5 μm, 250×4.6 mm; mobile phase: 50% isohexane, 50% ethanol+0.2% diethylamine; flow rate 1.0 ml/min; temperature: 35° C.; detection: 220 nm].

Example 411 ent-N-(2-amino-5,5,5-trifluoro-2-methylpentyl)-2,6-dimethyl-8-[(2,3,6-trifluorobenzyl)oxy]imidazo[1,2-a]pyridine-3-carboxamide (Enantiomer B)

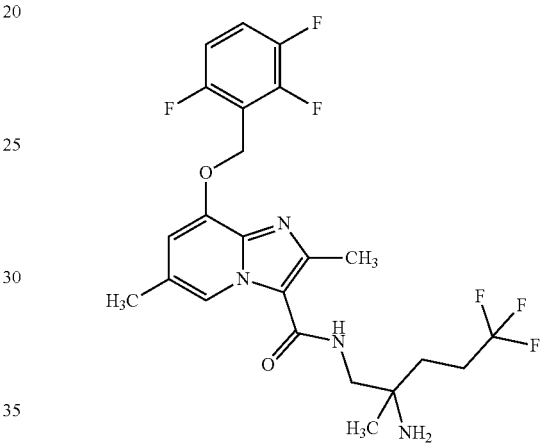

A mixture of 535 mg (0.75 mmol) of ent-benzyl {1-[({2,6-dimethyl-8-[(2,3,6-trifluorobenzyl)oxy]imidazo[1,2-a]pyridin-3-yl}carbonyl)amino]-5,5,5-trifluoro-2-methylpentan-2-yl}carbamate (enantiomer B) from Example 413A and 173 mg of 10% palladium on activated carbon in 21 ml of ethanol was hydrogenated at room temperature and standard pressure for 2 h. The mixture was then filtered off through kieselguhr, the filter cake was washed with ethanol and the filtrate was concentrated. The crude product was purified by preparative HPLC (RP-C18, mobile phase: acetonitrile/water gradient with addition of 0.1% TFA). The product fractions were taken up in dichloromethane and washed twice with saturated aqueous sodium bicarbonate solution. The combined aqueous phases were extracted twice with dichloromethane. The combined organic phases were dried over sodium sulphate, filtered and concentrated. This gave 262 mg of the title compound (68% of theory).

LC-MS (Method 2): $R_t$=0.71 min
MS (ESpos): m/z=503 (M+H)$^+$ $^1$H-NMR (500 MHz, DMSO-$d_6$): δ [ppm]=1.03 (s, 3H), 1.48-1.56 (m, 2H), 1.60 (br. s, 2H), 2.27-2.46 (m, 5H), 2.50 (s, 3H; superimposed by solvent peak), 3.18-3.29 (m, 2H), 5.34 (s, 2H), 6.91 (s, 1H), 7.25-7.32 (m, 1H), 7.61-7.70 (m, 1H), 7.74-7.81 (m, 1H), 8.42 (s, 1H).

Enantiomer B: about 78% ee $R_t$=4.90 min [Daicel Chiralpak AZ-H, 5 μm, 250×4.6 mm; mobile phase: 50% isohexane, 50% ethanol+0.2% diethylamine; flow rate 1.0 ml/min; temperature: 35° C.; detection: 220 nm].

The title compound was purified further as follows:

140 mg of enantiomer B (about 78% ee) from the enantiomer separation described above were separated into the enantiomers by preparative separation on a chiral phase [column: Daicel Chiralpak IF, 5 µm, 250×20 mm, mobile phase: 50% isohexane, 50% ethanol+0.2% diethylamine, flow rate: 20 ml/min, temperature: 23° C.; detection: 220 nm]. The product fractions were collected on dry ice and concentrated, the acetonitrile/water was added and the product was lyophilised.

Enantiomer B: 97 mg (>99% ee; purity about 98%)

$R_t$=4.93 min [Daicel Chiralpak AZ-H, 5 µm, 250×4.6 mm; mobile phase: 50% isohexane, 50% ethanol+0.2% diethylamine; flow rate 1.0 ml/min; temperature: 35° C.; detection: 220 nm].

Example 412 rac-N-[2-amino-4-(methylsulfanyl)butyl]-8-[(2,6-difluorobenzyl)oxy]-2,6-dimethylimidazo[1,2-a]pyridine-3-carboxamide

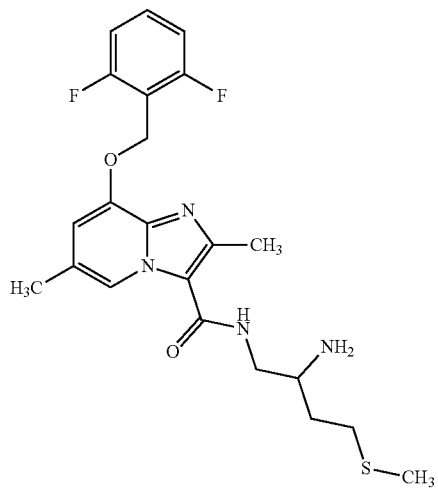

150 mg (0.45 mmol) of 8-[(2,6-difluorobenzyl)oxy]-2,6-dimethylimidazo[1,2-a]pyridine-3-carboxylic acid from Example 21A, 189 mg (0.50 mmol) of HATU and 175 mg (1.35 mmol) of N,N-diisopropylethylamine were initially charged in 2 ml of DMF, and the mixture was stirred at RT for 10 min. The reaction mixture was then, at 0° C., added dropwise to a mixture of 112 mg (0.54 mmol) of rac-4-(methylsulphanyl)butane-1,2-diamine dihydrochloride and 175 mg (1.35 mmol) of N,N-diisopropylethylamine dissolved in 0.26 ml of DMF. The mixture was stirred at 0° C. for 1 h and then at RT for 30 min. Water/TFA/acetonitrile was added to the reaction solution, and the product was purified by preparative HPLC (RP-C18, mobile phase: acetonitrile/water gradient with addition of 0.1% TFA). The product fractions were taken up in dichloromethane and washed twice with saturated aqueous sodium bicarbonate solution. The combined aqueous phases were extracted twice with dichloromethane. The combined organic phases were dried over sodium sulphate, filtered and concentrated. This gave 106 mg (51% of theory) of the title compound.

LC-MS (Method 2): $R_t$=0.60 min

MS (ESpos): m/z=449 (M+H)$^+$ $^1$H-NMR (500 MHz, DMSO-d$_6$): δ=1.42-1.52 (m, 1H), 1.62-1.93 (m, 3H), 2.07 (s, 3H), 2.30 (s, 3H), 2.49-2.68 (m, 5H; partly superimposed by solvent peak), 2.86-2.94 (m, 1H), 3.17-3.23 (m, 1H), 3.25-3.39 (m, 1H; superimposed by solvent peak); 5.29 (s, 2H), 6.91 (s, 1H), 7.19-7.26 (m, 2H), 7.55-7.64 (m, 1H), 7.73-7.79 (m, 1H), 8.47 (s, 1H).

Example 413 rac-N-[2-amino-4-(methylsulfonyl)butyl]-8-[(2,6-difluorobenzyl)oxy]-2,6-dimethylimidazo[1,2-a]pyridine-3-carboxamide

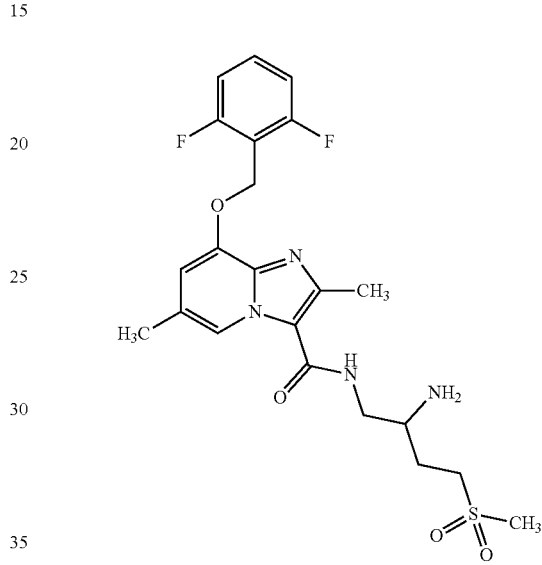

88 mg (0.20 mmol) of rac-N-[2-amino-4-(methylsulfanyl)butyl]-8-[(2,6-difluorobenzyl)oxy]-2,6-dimethylimidazo[1,2-a]pyridine-3-carboxamide from Example 412 were initially charged in 2 ml of dichloromethane, the mixture was cooled to 0° C. and 3-chloroperbenzoic acid was added a little at a time at this temperature. The mixture was stirred at 0° C. for 30 min. The mixture was then diluted with dichloromethane, and the filtrate was washed in each case once with 1 N aqueous sodium hydroxide solution and water. The mixture was then dried over sodium sulphate, filtered and concentrated under reduced pressure. The crude product was purified by preparative HPLC (RP 18 column, mobile phase: acetonitrile/water gradient with addition of 0.1% TFA). The product fractions were concentrated and the residue was taken up in dichloromethane and washed twice with saturated aqueous sodium bicarbonate solution. The combined aqueous phases were extracted twice with dichloromethane. The combined organic phases were dried over sodium sulphate, filtered and concentrated on a rotary evaporator. This gave 53 mg (55% of theory; purity 98%) of the title compound.

LC-MS (Method 2): $R_t$=0.56 min

MS (ESpos): m/z=481 (M+H)$^+$ $^1$H-NMR (500 MHz, DMSO-d$_6$): δ=1.57-1.64 (m, 1H), 1.72 (br. s, 2H), 1.84-1.93 (m, 1H), 2.30 (s, 3H), 2.50 (s, 3H; under solvent peak), 2.87-3.00 (m, 4H), 3.14-3.32 (m, 4H; superimposed by solvent peak), 5.29 (s, 2H), 6.91 (s, 1H), 7.19-7.26 (m, 2H), 7.55-7.64 (m, 1H), 7.81 (t, 1H), 8.47 (s, 1H).

Example 414 rac-8-[(2,6-difluorobenzyl)oxy]-N-[(1,1-dioxidothiomorpholin-3-yl)methyl]-2,6-dimethylimidazo[1,2-a]pyridine-3-carboxamide

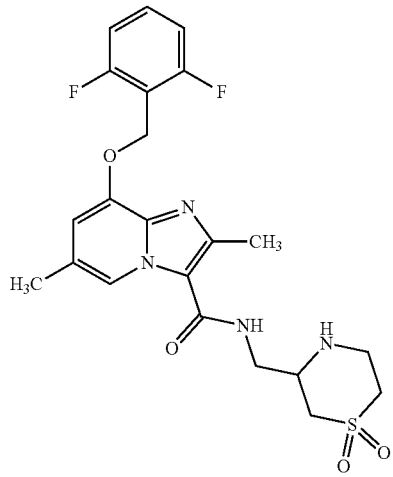 [SMILES: Cc1cc(OCc2c(F)cccc2F)c2nc(C)c(C(=O)NCC3CS(=O)(=O)CCN3)n2c1]

59 mg (0.09 mmol) of rac-tert-butyl 3-{[({8-[(2,6-difluorobenzyl)oxy]-2,6-dimethylimidazo[1,2-a]pyridin-3-yl}carbonyl)amino]methyl}thiomorpholine-4-carboxylate 1,1-dioxide trifluoroacetate from Example 418A were dissolved in 0.5 ml of diethyl ether, and 1.28 ml (2.56 mmol) of 2 N hydrochloric acid in diethyl ether were added. The reaction mixture was stirred at room temperature overnight. The mixture was then concentrated, and the crude product was purified by preparative HPLC (RP 18 column, mobile phase: acetonitrile/water gradient with addition of 0.1% TFA). The product fractions were concentrated and the residue was taken up in dichloromethane and a little methanol and washed twice with saturated aqueous sodium bicarbonate solution. The combined aqueous phases were extracted twice with dichloromethane. The combined organic phases were dried over sodium sulphate, filtered and concentrated. This gave 30 mg of the target compound (74% of theory).

LC-MS (Method 2): $R_t$=0.62 min
MS (ESIpos): m/z=479 (M+H)$^+$
$^1$H-NMR (500 MHz, DMSO-$d_6$): δ [ppm]=2.31 (s, 3H), 2.47-2.54 (m, 4H; superimposed by solvent peak), 2.76-2.83 (m, 1H), 2.85-3.05 (m, 3H), 3.08-3.23 (m, 2H), 3.30-3.47 (m, 3H; superimposed by solvent peak), 5.29 (s, 2H), 6.92 (s, 1H), 7.18-7.25 (m, 2H), 7.54-7.63 (m, 1H), 7.80 (t, 1H), 8.48 (s, 1H).

Example 415 rac-N-[2-amino-2-(2-methyl-1,3-thiazol-4-yl)ethyl]-8-[(2,6-difluorobenzyl)oxy]-2,6-dimethylimidazo[1,2-a]pyridine-3-carboxamide triformate

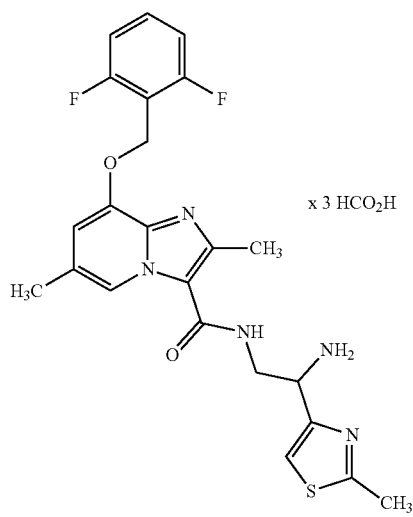

100 mg (0.30 mmol) of 8-[(2,6-difluorobenzyl)oxy]-2,6-dimethylimidazo[1,2-a]pyridine-3-carboxylic acid from Example 21A, 137 mg (0.36 mmol) of HATU and 121 mg (1.20 mmol) of 4-methylmorpholine were initially charged in 1.5 ml of DMF, and the mixture was stirred at RT for 60 min. 69 mg (0.30 mmol) of rac-1-(2-methyl-1,3-thiazol-4-yl)ethane-1,2-diamine dihydrochloride were then added, and the mixture was stirred at RT overnight. The reaction mixture was purified by preparative HPLC (RP-C18, mobile phase: acetonitrile/water gradient with addition of 0.05% formic acid). This gave 18 mg (10% of theory) of the title compound.

LC-MS (Method 2): $R_t$=0.61 min
MS (ESIpos): m/z=472 (M−3HCO$_2$H+H)$^+$
$^1$H-NMR (400 MHz, DMSO-$d_6$): δ [ppm]=2.35 (s, 3H), 2.40 (s, 3H), 2.70 (s, 3H), 3.71-3.88 (m, 2H), 4.60-4.68 (m, 1H), 5.32 (s, 2H), 7.13 (br.s, 1H), 7.21-7.28 (m, 2H), 7.56-7.65 (m, 1H), 7.65 (s, 1H), 8.06 (br.s, 1H), 8.44-8.55 (2 br. s, 4H).

Example 416 rac-N-(2-amino-1-cyanoethyl)-8-[(2,6-difluorobenzyl)oxy]-2,6-dimethylimidazo[1,2-a]pyridine-3-carboxamide

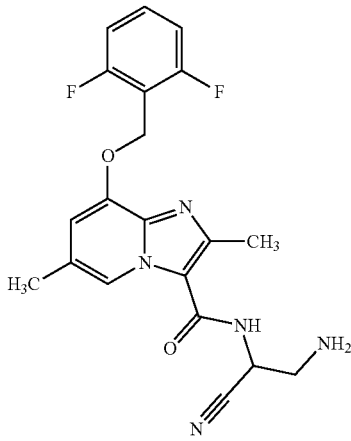 [SMILES: Cc1cc(OCc2c(F)cccc2F)c2nc(C)c(C(=O)NC(C#N)CN)n2c1]

A mixture of 151 mg (0.23 mmol) of rac-benzyl {2-cyano-2-[({8-[(2,6-difluorobenzyl)oxy]-2,6-dimethylimidazo[1,2-a]pyridin-3-yl}carbonyl)amino]ethyl}carbamate trifluoroacetate from Example 420A and 50 mg of 10% palladium on activated carbon (0.05 mmol) in 6 ml of ethanol was hydrogenated at room temperature and atmospheric pressure for 2 h. The reaction mixture was filtered off through a filter, the filter cake was washed with ethanol and the filtrate was concentrated. The residue was taken up in dichloromethane and washed twice with saturated aqueous sodium bicarbonate solution. The combined aqueous phases were extracted twice with dichloromethane. The combined organic phases were dried over sodium sulphate, filtered and concentrated. The crude product was purified by thick-layer chromatography (mobile phase: dichloromethane/methanol=10/1). This gave 4 mg of the title compound (4% of theory).

LC-MS (Method 2): $R_t$=0.62 min

MS (ESpos): m/z=400 (M+H)$^+$ $^1$H-NMR (500 MHz, DMSO-d$_6$): δ [ppm]=2.33 (s, 3H), 2.93-3.10 (m, 2H), 4.82-4.82 (t, 1H), 5.30 (s, 2H), 6.98 (s, 1H), 7.20-7.26 (m, 2H), 7.51-7.66 (m, 1H), 8.47 (s, 1H), [further signal under solvent peak].

B. ASSESSMENT OF THE PHARMACOLOGICAL ACTIVITY

The following abbreviations are used:
ATP adenosine triphosphate
Brij35 polyoxyethylene (23) lauryl ether
BSA bovine serum albumin
DTT dithiothreitol
TEA triethanolamine The pharmacological effect of the compounds according to the invention can be shown in the following assays:

B-1. Measurement of sGC Enzyme Activity by Detection of PPi

Soluble guanylate cyclase (sGC) converts on stimulation GTP into cGMP and pyrophosphate (PPi). PPi is detected with the aid of the method described in WO 2008/061626. The signal produced in the test increases as the reaction progresses and serves as a measure of the sGC enzyme activity. With the aid of a PPi reference curve, the enzyme can be characterized in a known manner, for example with respect to conversion rate, stimulability or Michaelis constant.

Practice of the Test

To carry out the test, 29 µl of enzyme solution (0-10 nM soluble guanylate cyclase (prepared according to Hönicka et al., Journal of Molecular Medicine 77(1999)14-23) in 50 mM TEA, 2 mM magnesium chloride, 0.1% BSA (fractionV), 0.005% Brij 35, pH 7.5) were initially introduced into the microplate, and 1 µl of the stimulator solution (0-10 µM 3-morpholinosydnonimine, SIN-1, Merck in DMSO) were added. The mixture was incubated at RT for 10 min. 20 µl of detection mix (1.2 nM Firefly Luciferase (*Photinus pyralis* Luziferase, Promega), 29 µM dehydroluciferin (prepared according to Bitler & McElroy, Arch. Biochem. Biophys. 72 (1957) 358), 122 µM luciferin (Promega), 153 µM ATP (Sigma) and 0.4 mM DTT (Sigma) in 50 mM TEA, 2 mM magnesium chloride, 0.1% BSA (fraction V), 0.005% Brij 35, pH 7.5) were added. The enzyme reaction was started by addition of 20 µl of substrate solution (1.25 mM guanosine 5'-triphosphate (Sigma) in 50 mM TEA, 2 mM magnesium chloride, 0.1% BSA (fraction V), 0.005% Brij 35, pH 7.5) and measured continuously in a luminometer.

B-2. Action on Recombinant Guanylate Cyclase Reporter Cell Line

The cellular action of the compounds according to the invention is determined on a recombinant guanylate cyclase reporter cell line, as described in F. Wunder et al., *Anal. Biochem.* 339, 104-112 (2005).

Representative MEC values (MEC=minimal effective concentration) for the compounds according to the invention are shown in the following table (in some cases as mean values obtained from individual determinations):

TABLE A

| Example | MEC [µM] |
|---|---|
| 1 | 0.10 |
| 2 | 0.65 |
| 3 | 0.30 |
| 4 | 0.30 |
| 5 | 1.00 |
| 6 | 0.23 |
| 7 | 1.00 |
| 8 | 0.10 |
| 9 | 0.30 |
| 10 | 0.30 |
| 11 | 0.30 |
| 12 | 1.00 |
| 13 | 0.23 |
| 14 | 1.00 |
| 15 | 0.53 |
| 16 | 0.30 |
| 17 | 1.00 |
| 18 | 0.55 |
| 19 | 1.66 |
| 20 | 1.00 |
| 21 | 0.30 |
| 22 | 0.30 |
| 23 | 0.30 |
| 24 | 0.65 |
| 25 | 1.00 |
| 26 | 0.30 |
| 27 | 1.00 |
| 28 | 0.30 |
| 29 | 0.20 |
| 30 | 0.30 |
| 31 | 0.30 |
| 32 | 0.30 |
| 33 | 0.30 |

TABLE A-continued

| Example | MEC [μM] |
|---|---|
| 34 | 1.00 |
| 35 | 1.00 |
| 36 | 1.00 |
| 37 | 1.00 |
| 38 | 0.40 |
| 39 | 0.10 |
| 40 | 0.10 |
| 41 | 0.30 |
| 42 | 1.00 |
| 43 | 1.00 |
| 44 | 0.30 |
| 45 | 1.00 |
| 46 | 1.00 |
| 47 | 0.30 |
| 48 | 1.00 |
| 49 | 0.30 |
| 50 | 0.03 |
| 51 | 0.20 |
| 52 | 0.03 |
| 53 | 0.30 |
| 54 | 1.00 |
| 55 | 2.00 |
| 56 | 1.00 |
| 57 | 0.30 |
| 58 | 1.00 |
| 59 | 3.00 |
| 60 | 0.30 |
| 61 | 3.00 |
| 62 | 1.00 |
| 63 | 0.30 |
| 64 | 0.30 |
| 65 | 1.00 |
| 66 | 1.00 |
| 67 | 0.30 |
| 68 | 0.30 |
| 69 | 1.00 |
| 70 | 1.00 |
| 71 | 0.30 |
| 72 | 0.30 |
| 73 | 0.30 |
| 74 | 0.20 |
| 75 | 1.00 |
| 76 | 0.30 |
| 77 | 1.00 |
| 78 | 1.00 |
| 79 | 1.00 |
| 80 | 1.00 |
| 81 | 1.00 |
| 82 | 0.20 |
| 83 | 0.10 |
| 84 | 1.00 |
| 85 | 1.00 |
| 86 | 2.00 |
| 87 | 1.00 |
| 88 | 1.00 |
| 89 | 0.65 |
| 90 | 0.10 |
| 91 | 1.00 |
| 92 | 0.30 |
| 93 | 0.30 |
| 94 | 0.30 |
| 95 | 1.00 |
| 96 | 1.00 |
| 97 | 0.10 |
| 98 | 1.00 |
| 99 | 1.00 |
| 100 | 0.30 |
| 101 | 1.00 |
| 102 | 1.00 |
| 103 | 3.00 |
| 104 | 0.30 |
| 105 | 0.30 |
| 106 | 0.03 |
| 107 | 0.30 |
| 108 | 1.00 |
| 109 | 1.00 |
| 110 | 0.30 |
| 111 | 1.00 |
| 112 | 0.10 |
| 113 | 0.65 |
| 114 | 0.30 |
| 115 | 1.00 |
| 116 | 3.00 |
| 117 | 1.00 |
| 118 | 1.00 |
| 119 | 0.10 |
| 120 | 0.30 |
| 121 | 0.30 |
| 122 | 1.00 |
| 123 | 3.00 |
| 124 | 1.00 |
| 125 | 1.00 |
| 126 | 0.30 |
| 127 | 1.00 |
| 128 | 0.10 |
| 129 | 0.10 |
| 130 | 1.00 |
| 131 | 3.00 |
| 132 | 1.00 |
| 133 | 3.00 |
| 134 | 3.00 |
| 135 | 1.00 |
| 136 | 0.10 |
| 137 | 1.00 |
| 138 | 0.30 |
| 139 | 1.00 |
| 140 | 1.00 |
| 141 | 3.00 |
| 142 | 1.00 |
| 143 | 0.30 |
| 144 | 3.00 |
| 145 | 3.00 |
| 146 | 1.00 |
| 147 | 0.30 |
| 148 | 1.00 |
| 149 | 1.00 |
| 150 | 0.10 |
| 151 | 0.10 |
| 152 | 1.00 |
| 153 | 1.00 |
| 154 | 1.00 |
| 155 | 0.30 |
| 156 | 3.00 |
| 157 | 0.30 |
| 158 | 0.30 |
| 159 | 0.30 |
| 160 | 1.00 |
| 161 | 0.10 |
| 162 | 3.00 |
| 163 | 0.30 |
| 164 | 0.10 |
| 165 | 0.10 |
| 166 | 0.30 |
| 167 | 1.00 |
| 168 | 1.00 |
| 169 | 1.65 |
| 170 | 3.00 |
| 171 | 1.00 |
| 172 | 0.30 |
| 173 | 0.30 |
| 174 | 0.30 |
| 175 | 1.00 |
| 176 | 1.00 |
| 177 | 1.00 |
| 178 | 0.30 |
| 179 | 1.00 |
| 180 | 1.00 |
| 181 | 1.00 |
| 182 | 3.00 |
| 183 | 1.00 |
| 184 | 1.00 |
| 185 | 1.00 |
| 186 | 0.30 |
| 187 | 0.30 |
| 188 | 1.00 |
| 189 | 3.00 |

TABLE A-continued

| Example | MEC [μM] |
|---|---|
| 190 | 1.00 |
| 191 | 1.00 |
| 192 | 0.30 |
| 193 | 1.00 |
| 194 | 0.10 |
| 195 | 0.30 |
| 196 | 1.00 |
| 197 | 1.00 |
| 198 | 0.30 |
| 199 | 0.30 |
| 200 | 0.04 |
| 201 | 0.10 |
| 202 | 0.10 |
| 203 | 0.10 |
| 204 | 1.00 |
| 205 | 0.30 |
| 206 | 0.30 |
| 207 | 1.00 |
| 208 | 0.30 |
| 209 | 0.30 |
| 210 | 0.30 |
| 211 | 0.30 |
| 212 | 1.00 |
| 213 | 1.00 |
| 214 | 0.30 |
| 215 | 1.00 |
| 216 | 1.00 |
| 217 | 1.00 |
| 218 | 0.10 |
| 219 | 0.30 |
| 220 | 0.10 |
| 221 | 0.30 |
| 222 | 0.30 |
| 223 | 0.30 |
| 224 | 0.30 |
| 225 | 0.30 |
| 226 | 0.10 |
| 227 | 0.30 |
| 228 | 1.00 |
| 229 | 1.00 |
| 230 | 1.00 |
| 231 | 0.30 |
| 232 | 0.10 |
| 233 | 0.10 |
| 234 | 0.03 |
| 235 | 0.30 |
| 236 | 0.30 |
| 237 | 0.30 |
| 238 | 1.00 |
| 239 | 0.30 |
| 240 | 0.30 |
| 241 | 0.30 |
| 242 | 0.30 |
| 243 | 1.00 |
| 244 | 0.30 |
| 245 | 0.10 |
| 246 | 0.30 |
| 247 | 3.00 |
| 248 | 1.00 |
| 249 | 1.00 |
| 250 | 1.00 |
| 251 | 3.00 |
| 252 | 0.10 |
| 253 | 0.10 |
| 254 | 0.30 |
| 255 | 0.30 |
| 256 | 3.00 |
| 257 | 1.00 |
| 258 | 1.00 |
| 259 | 0.03 |
| 260 | 0.10 |
| 261 | 0.10 |
| 262 | 0.10 |
| 263 | 1.00 |
| 264 | 0.03 |
| 265 | 0.30 |
| 266 | 0.03 |
| 267 | 0.10 |
| 268 | 0.55 |
| 269 | 0.65 |
| 270 | 1.00 |
| 271 | 0.30 |
| 272 | 5.5 |
| 273 | 1.00 |
| 274 | 0.10 |
| 275 | 0.10 |
| 276 | 0.10 |
| 277 | 1.00 |
| 278 | 0.3 |
| 279 | 0.3 |
| 280 | 0.65 |
| 281 | 0.3 |
| 282 | 0.3 |
| 283 | 0.3 |
| 284 | 0.1 |
| 285 | 0.3 |
| 286 | 0.1 |
| 287 | 0.3 |
| 288 | 0.3 |
| 289 | 0.3 |
| 290 | 0.3 |
| 291 | 1.0 |
| 292 | 0.03 |
| 293 | 0.03 |
| 294 | 0.065 |
| 295 | 0.10 |
| 296 | 0.10 |
| 297 | 0.10 |
| 298 | 0.10 |
| 299 | 0.10 |
| 300 | 0.10 |
| 301 | 0.10 |
| 302 | 0.10 |
| 303 | 0.20 |
| 304 | 0.10 |
| 305 | 0.10 |
| 306 | 0.10 |
| 307 | 0.65 |
| 308 | 0.20 |
| 309 | 0.30 |
| 310 | 0.30 |
| 311 | 0.30 |
| 312 | 0.30 |
| 313 | 0.30 |
| 314 | 0.30 |
| 315 | 0.30 |
| 316 | 0.30 |
| 317 | 0.30 |
| 318 | 0.30 |
| 319 | 0.30 |
| 320 | 0.30 |
| 321 | 0.30 |
| 322 | 0.30 |
| 323 | 0.30 |
| 324 | 1.00 |
| 325 | 0.30 |
| 326 | 0.30 |
| 327 | 1.00 |
| 328 | 3.00 |
| 329 | 0.30 |
| 330 | 0.30 |
| 331 | 0.30 |
| 332 | 1.00 |
| 333 | 1.00 |
| 334 | 1.00 |
| 335 | 0.30 |
| 336 | 0.30 |
| 337 | 0.55 |
| 338 | 0.10 |
| 340 | 1.00 |
| 341 | 0.30 |
| 342 | 1.00 |
| 343 | 1.00 |
| 344 | 1.00 |
| 345 | 1.00 |
| 346 | 1.00 |

TABLE A-continued

| Example | MEC [µM] |
|---|---|
| 347 | 1.00 |
| 348 | 1.00 |
| 349 | 1.00 |
| 350 | 1.00 |
| 351 | 3.00 |
| 352 | 3.00 |
| 353 | 3.00 |
| 354 | 3.00 |
| 355 | 0.30 |
| 356 | 0.10 |
| 357 | 0.03 |
| 358 | 0.30 |
| 359 | 3.00 |
| 360 | 1.00 |
| 361 | 1.00 |
| 362 | 1.00 |
| 363 | 3.00 |
| 364 | 0.30 |
| 365 | 1.00 |
| 366 | 0.10 |
| 367 | 3.00 |
| 368 | 0.10 |
| 369 | 0.30 |
| 370 | 3.00 |
| 371 | 3.00 |
| 372 | 3.00 |
| 373 | 3.00 |
| 374 | 1.00 |
| 375 | 3.00 |
| 376 | 3.00 |
| 377 | 3.00 |
| 378 | 1.00 |
| 379 | 1.00 |
| 380 | 1.00 |
| 381 | 0.30 |
| 382 | 0.30 |
| 383 | 0.30 |
| 384 | 0.30 |
| 385 | 1.00 |
| 386 | 0.65 |
| 387 | 10.0 |
| 388 | 0.30 |
| 389 | 1.00 |
| 390 | 0.30 |
| 391 | 0.10 |
| 392 | 1.00 |
| 393 | 1.00 |
| 394 | 0.30 |
| 395 | 1.00 |
| 396 | 3.00 |
| 397 | 1.00 |
| 398 | 0.30 |
| 399 | 1.00 |
| 400 | 0.65 |
| 401 | 1.00 |
| 402 | 0.30 |
| 403 | 0.10 |
| 404 | 0.30 |
| 405 | 0.30 |
| 406 | 0.10 |
| 408 | 0.10 |
| 409 | 0.03 |
| 410 | 0.10 |
| 411 | 0.03 |
| 412 | 0.10 |
| 413 | 5.5 |
| 414 | 0.30 |
| 415 | 5.5 |
| 416 | 1.00 |

B-3. Vessel-Relaxing Action In Vitro

Rabbits are stunned with a blow on the back of the neck and exsanguinated. The aorta is removed, freed from adhering tissue, separated into rings with a width of 1.5 mm, and placed individually, with preloading, in 5-ml organ baths with carbogen-gassed Krebs-Henseleit solution at 37° C. with the following composition (mM in each case): sodium chloride: 119; potassium chloride: 4.8; calcium chloride dihydrate: 1; magnesium sulphate heptahydrate: 1.4; potassium dihydrogen phosphate: 1.2; sodium hydrogen carbonate: 25; glucose: 10. The contraction force is recorded with Statham UC2 cells, amplified and digitized via an A/D converter (DAS-1802 HC, Keithley Instruments Munich) and recorded in parallel on a continuous-line recorder. To produce contraction, phenylephrine is added to the bath cumulatively in increasing concentration. After several control cycles, the test substance is added in increasing dosage in each subsequent pass and the level of contraction is compared with the level of contraction reached in the immediately preceding pass. This is used for calculating the concentration that is required to reduce the level of the control value by 50% ($IC_{50}$ value). The standard application volume is 5 µl, and the proportion of DMSO in the bath solution corresponds to 0.1%.

B-4. Measurement of Blood Pressure on Anaesthetized Rats

Male Wistar rats having a body weight of 300-350 g are anaesthetized with thiopental (100 mg/kg i.p.). After tracheotomy, a catheter for measuring the blood pressure is introduced into the femoral artery. The substances to be tested are administered as solutions either orally by gavage or intravenously via the femoral vein (Stasch et al. Br. J. Pharmacol. 2002; 135: 344-355).

B-5. Radiotelemetric Blood Pressure Measurement on Awake, Spontaneously Hypertensive Rats The blood pressure measurement on awake rats described below uses a commercially available telemetry system from the company DATA SCIENCES INTERNATIONAL DSI, USA.

The system consists of 3 main components:
implantable transmitter (Physiotel® Telemetry Transmitter)
receiver (Physiotel® Receiver), which are connected via a multiplexer (DSI Data Exchange Matrix) to a
data acquisition computer.

The telemetry system provides continuous acquisition of blood pressure, heart rate and body movement on awake animals in their usual living space.

Animal Material

The investigations are carried out on adult female, spontaneously hypertensive rats (SHR Okamoto) with a body weight of >200 g. SHR/NCrl from Okamoto Kyoto School of Medicine, 1963 were crossed from male Wistar Kyoto rats with greatly increased blood pressure and females with slightly raised blood pressure and were delivered in F13 to the U.S. National Institutes of Health.

After transmitter implantation, the experimental animals are kept individually in Makrolon cages, type 3. They have free access to standard feed and water.

The day-night rhythm in the testing laboratory is alternated by the room lighting at 06:00 hours in the morning and at 19:00 hours in the evening.

Transmitter Implantation

The TA11 PA-C40 telemetry transmitters used are implanted surgically in the experimental animals under aseptic conditions at least 14 days before the first test. The animals provided with this instrumentation can be used again after the wound has healed and the implant has become incorporated.

For implantation, the fasting animals are anaesthetized with pentobarbital (Nembutal, Sanofi: 50 mg/kg i.p.) and are shaved and disinfected on a wide area of the abdomen. After opening the abdominal cavity along the linea alba, the liquid-filled measuring catheter of the system is inserted above the bifurcation in the cranial direction into the aorta descendens and secured with tissue adhesive (VetBonD™, 3M). The transmitter housing is fixed intraperitoneally on the abdominal wall musculature and the wound is closed layer by layer.

Postoperatively, an antibiotic is administered to prevent infection (Tardomyocel COMP Bayer 1 ml/kg s.c.)

Substances and Solutions

Unless described otherwise, the test substances are in each case administered orally by stomach tube to a group of animals (n=6). Corresponding to an application volume of 5 ml/kg body weight, the test substances are dissolved in suitable solvent mixtures or suspended in 0.5% Tylose.

A group of animals treated with solvents is used as control.

Test Procedure

The present telemetry measuring device is configured for 24 animals. Each test is recorded under a test number (Vtest year month day).

The instrumented rats living in the unit are each assigned their own receiving antenna (1010 Receiver, DSI).

The implanted transmitters can be activated from outside by an in-built magnetic switch. They are switched to transmission at the start of the tests. The signals emitted can be recorded online by a data acquisition system (Dataquest™ A.R.T. for WINDOWS, DSI) and processed appropriately. The data are saved in each case to a folder opened for this, which bears the test number.

In the standard procedure, the following are measured, in each case for 10 seconds:
systolic blood pressure (SBP)
diastolic blood pressure (DBP)
mean arterial pressure (MAP)
heart rate (HR)
activity (ACT).

Recording of the measured values is repeated at 5-minute intervals under computer control. The source data recorded as absolute value are corrected in the diagram with the currently measured barometric pressure (Ambient Pressure Reference Monitor; APR-1) and saved in individual data.

Further technical details can be found in the extensive documentation of the manufacturer (DSI).

Unless described otherwise, the test substances are administered on the test day at 09.00 hours. Following application, the parameters described above are measured for 24 hours.

Evaluation

After the end of the test, the individual data recorded are sorted with the analysis software (DATAQUEST™ A.R.T.™ ANALYSIS). The 2 hours before application are taken as the blank value here, so that the selected data set comprises the period from 07:00 hours on the test day to 09:00 hours on the next day.

The data are smoothed for a pre-settable time by mean value determination (15-minute average) and transferred as text file to a storage medium. The pre-sorted and compressed measured values are transferred to Excel templates and presented as tables. The data recorded are saved per test day in a specific folder, which bears the test number. Results and test protocols are filed in folders, sorted in paper form by numbers.

LITERATURE

Klaus Witte, Kai Hu, Johanna Swiatek, Claudia Müssig, Georg Ertl and Björn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured with Radio-Telemetry. Physiology & Behavior 55(4): 783-787, 1994.

B-6. Determination of Pharmacokinetic Parameters Following Intravenous and Oral Administration The pharmacokinetic parameters of the compounds according to the invention are determined in male CD-1 mice, male Wistar rats and female beagles. Intravenous administration in the case of mice and rats is carried out by means of a species-specific plasma/DMSO formulation, and in the case of dogs by means of a water/PEG400/ethanol formulation. In all species, oral administration of the dissolved substance is performed via gavage, based on a water/PEG400/ethanol formulation. The taking of blood from rats is simplified by inserting a silicone catheter into the right Vena jugularis externa prior to substance administration. The operation is carried out at least one day prior to the experiment with isofluran analgesia and administration of an analgesic (atropin/Rimadyl (3/1) 0.1 ml s.c.). The blood is taken (generally more than 10 time points) within a time window including terminal time points of at least 24 to a maximum of 72 hours after substance administration. When the blood is taken, it is passed into heparinised tubes. Then the blood plasma is obtained by centrifugation and is optionally stored at −20° C. until further processing.

An internal standard (which may also be a chemically unrelated substance) is added to the samples of the compounds according to the invention, calibration samples and qualifiers, and there follows protein precipitation by means of excess acetone. Addition of a buffer solution matched to the LC conditions, and subsequent vortexing, is followed by centrifugation at 1000 g. The supernatant is analysed by LC-MS/MS using C18 reversed-phase columns and variable mobile phase mixtures. The substances are quantified via the peak heights or areas from extracted ion chromatograms of specific selected ion monitoring experiments.

The plasma concentration/time plots determined are used to calculate the pharmacokinetic parameters such as AUC, $C_{max}$, $t_{1/2}$ (terminal half life), F (bioavailability), MRT (mean residence time) and CL (clearance), using a validated pharmacokinetic calculation program.

Since the substance quantification is carried out in plasma, it is necessary to determine the blood/plasma distribution of the substance in order to be able to adjust the pharmacokinetic parameters correspondingly. For this purpose, a defined amount of substance is incubated in heparinized whole blood of the species in question in a rocking roller mixture for 20 min. After centrifugation at 1000 g, the plasma concentration is measured (by means of LC-MS/MS; see above) and determined by calculating the ratio of the $C_{blood}/C_{plasma}$ value.

Table B shows data of representative compounds of the present invention following intravenous administration in rats:

TABLE B

| Example | $AUC_{norm}$ [kg · h/L] | $CL_{blood}$ [L/h/kg] | $t_{1/2}$ [h] | MRT [h] |
|---|---|---|---|---|
| 4 | 0.58 | 1.67 | 5.2 | 6.7 |
| 8 | 1.09 | 0.92 | 4.5 | 6.6 |
| 10 | 2.26 | 0.74 | 4.8 | 6.9 |
| 13 | 1.71 | 0.83 | 3.5 | 4.4 |
| 73 | 1.55 | 0.51 | 8.6 | 11.8 |
| 74 | 0.81 | 1.23 | 3.7 | 5.0 |

TABLE B-continued

| Example | AUC$_{norm}$ [kg·h/L] | CL$_{blood}$ [L/h/kg] | t$_{1/2}$ [h] | MRT [h] |
|---|---|---|---|---|
| 119 | 1.06 | 0.86 | 4.9 | 7.4 |
| 155 | 0.97 | 1.27 | 7.7 | 11.2 |
| 173 | 0.54 | 1.68 | 3.3 | 3.9 |
| 194 | 2.06 | 0.48 | 16.8 | 24.4 |
| 200 | 0.69 | 0.92 | 5.9 | 8.5 |
| 211 | 0.78 | 1.07 | 4.8 | 6.6 |
| 223 | 0.87 | 1.09 | 4.8 | 6.1 |
| 261 | 0.47 | 2.29 | 3.7 | 4.7 |
| 274 | 1.29 | 0.69 | 5.8 | 8.4 |
| 275 | 0.64 | 1.25 | 4.1 | 7.2 |
| 276 | 0.70 | 1.27 | 2.9 | 4.5 |
| 279 | 0.42 | 2.76 | 2.3 | 2.9 |
| 281 | 0.28 | 2.34 | 5.5 | 6.9 |
| 282 | 0.73 | 1.41 | 4.5 | 5.7 |
| 283 | 0.67 | 0.87 | 3.1 | 3.9 |
| 284 | 1.20 | 0.97 | 4.6 | 5.3 |
| 285 | 0.54 | 1.02 | 3.6 | 4.4 |
| 286 | 0.82 | 1.39 | 3.8 | 4.5 |
| 287 | 0.66 | 1.76 | 5.4 | 8.4 |
| 289 | 0.38 | 2.51 | 4.4 | 6.8 |
| 291 | 0.87 | 0.84 | 4.8 | 5.7 |
| 292 | 0.56 | 2.17 | 3.2 | 4.1 |
| 295 | 0.56 | 1.23 | 6.6 | 8.8 |
| 303 | 0.26 | 2.74 | 5.7 | 8.2 |
| 304 | 0.34 | 2.27 | 6.2 | 9.4 |
| 307 | 0.35 | 1.78 | 6.9 | 9.8 |
| 356 | 0.61 | 0.98 | 10.3 | 13.9 |
| 408 | 0.19 | 3.07 | 3.8 | 4.7 |
| 409 | 0.28 | 2.15 | 5.8 | 7.4 |
| 410 | 0.21 | 2.77 | 4.3 | 5.4 |
| 411 | 0.41 | 1.52 | 8.2 | 11.2 |

B-7. Metabolic Study

To determine the metabolic profile of the compounds according to the invention, they are incubated with recombinant human cytochrome P450 (CYP) enzymes, liver microsomes or primary fresh hepatocytes from various animal species (e.g. rats, dogs), and also of human origin, in order to obtain and to compare information about substantially the complete hepatic phase I and phase II metabolism, and about the enzymes involved in the metabolism.

The compounds according to the invention were incubated with a concentration of about 0.1-10 µM. To this end, stock solutions of the compounds according to the invention having a concentration of 0.01-1 mM in acetonitrile were prepared, and then pipetted with 1:100 dilution into the incubation mixture. The liver microsomes and recombinant enzymes were incubated at 37° C. in 50 mM potassium phosphate buffer pH 7.4 with and without NADPH-generating system consisting of 1 mM NADP$^+$, 10 mM glucose 6-phosphate and 1 unit of glucose 6-phosphate dehydrogenase. Primary hepatocytes were incubated in suspension in Williams E medium, likewise at 37° C. After an incubation time of 0-4 h, the incubation mixtures were stopped with acetonitrile (final concentration about 30%), and the protein was centrifuged off at about 15 000×g. The samples thus stopped were either analysed directly or stored at −20° C. until analysis.

The analysis is carried out by means of high-performance liquid chromatography with ultraviolet and mass spectrometry detection (HPLC-UV-MS/MS). To this end, the supernatants of the incubation samples are chromatographed with suitable C18 reversed-phase columns and variable mobile phase mixtures of acetonitrile and 10 mM aqueous ammonium formate solution or 0.05% formic acid. The UV chromatograms in conjunction with mass spectrometry data serve for identification, structural elucidation and quantitative estimation of the metabolites, and for quantitative metabolic assessment of the compound according to the invention in the incubation mixtures.

B-8. Caco-2 Permeability Test

The permeability of a test substance was determined with the aid of the Caco-2 cell line, an established in vitro model for permeability predictions at the gastrointestinal barrier (Artursson, P. and Karlsson, J. (1991). Correlation between oral drug absorption in humans and apparent drug permeability coefficients in human intestinal epithelial (Caco-2) cells. Biochem. Biophys. 175 (3), 880-885). The CaCo-2 cells (ACC No. 169, DSMZ, Deutsche Sammlung von Mikroorganismen und Zellkulturen, Braunschweig, Germany) were sown in 24-well plates with inset and cultivated for 14 to 16 days. For the permeability studies, the test substance was dissolved in DMSO and diluted with transport buffer (Hanks Buffered Salt Solution, Gibco/Invitrogen, with 19.9 mM glucose and 9.8 mM HEPES) to the final test concentration. To determine the permeability from apical to basolateral ($P_{app}$A-B) of the test substance, the solution comprising the test substance was placed on the apical side of the Caco-2 cell monolayer, and the transport buffer on the basolateral side. To determine the permeability from basolateral to apical ($P_{app}$B-A) of the test substance, the solution comprising the test substance was placed on the basolateral side of the Caco-2 cell monolayer, and the transport buffer on the apical side. At the start of the experiment, samples were taken from the respective donor compartment to ensure mass balance. After a two-hour incubation at 37° C., samples were taken from the two compartments. The samples were analysed by LC-MS/MS, and the apparent permeability coefficients ($P_{app}$) were calculated. For each cell monolayer, the permeability of Lucifer Yellow was determined to ensure cell layer integrity. In each test run, the permeability of atenolol (marker for low permeability) and sulfasalazine (marker for active excretion) was also determined as quality control.

B-9. hERG Potassium Current Assay

The hERG (human ether-a-go-go related gene) potassium current contributes substantially to the repolarization of the human cardiac action potential (Scheel et al., 2011). An inhibition of this current by pharmaceuticals may, in rare cases, result in potentially fatal cardiac arrhythmias and is therefore studied at an early stage during drug development.

The functional hERG assay used herein is based on a recombinant HEK293 cell line stably expressing the KCNH2(HERG) gene (Zhou et al., 1998). These cells are examined using the whole-cell voltage clamp technique (Hamill et al., 1981) in an automated system (Patchliner™; Nanion, Munich, Germany) which controls membrane voltage and measures the hERG potassium current at room temperature. The PatchControlHT™ Software (Nanion) controls Patchliner System, data collection and data analysis. Voltage is controlled by 2 EPC-10 quadro amplifiers controlled by the PatchMasterPro™ Software (both: HEKA Elektronik, Lambrecht, Germany). NPC-16 chips of medium resistance (~2 MΩ; Nanion) serve as planar substrate for the voltage clamp experiments.

NPC-16 chips are filled with intra- and extracellular solution (cf. Himmel, 2007) and with cell suspension. After formation of a GigaOhm seal and after the whole-cell mode has been established (including a plurality of automated quality control steps), the cell membrane is patched to a maintenance potential of −80 mV. The subsequent voltage clamp protocol changes the control voltage to +20 mV (duration 1000 ms), −120 mV (duration 500 ms) and back to the maintenance potential of −80 mV; this is repeated every 12 s. After an initial stabilization phase (about 5-6 minutes), test substance solution is pipetted in in increasing concentrations (for example 0.1, 1 and 10 µmol/l) (exposition about 5-6 minutes per concentration), followed by several washing steps).

The amplitude of the inward tail stream generated by changing the potential from +20 mV to −120 mV serves to quantify the hERG potassium current and is shown as a function of time (IgorPro™ Software). The current amplitude at the end of various intervals (for example stabilization phase prior to test substance, first/second/third concentration of test substance) serves to establish a concentration/activity curve which is used to calculate the half-maximal inhibitory concentration $IC_{50}$ of the test substance.

Hamill O P, Marty A, Neher E, Sakmann B, Sigworth F J. Improved patch-clamp techniques for high-resolution current recording from cells and cell-free membrane patches. Pfluegers Arch 1981; 391:85-100.

Himmel H M. Suitability of commonly used excipients for electrophysiological in-vitro safety pharmacology assessment of effects on hERG potassium current and on rabbit Purkinje fiber action potential. J Pharmacol Toxicol Methods 2007; 56:145-158.

Scheel O, Himmel H, Rascher-Eggstein G, Knott T. Introduction of a modular automated voltage-clamp platform and its correlation with manual human ether-a-go-go related gene voltage-clamp data. Assay Drug Dev Technol 2011; 9:600-607.

Zhou Z F, Gong Q, Ye B, Fan Z, Makielski J C, Robertson G A, January C T. Properties of hERG channels stably expressed in HEK293 cells studied at physiological temperature. Biophys J 1998; 74:230-241.

C. EXEMPLARY EMBODIMENTS OF PHARMACEUTICAL COMPOSITIONS

The compounds according to the invention can be converted into pharmaceutical preparations in the following ways:

Tablet:
Composition:
100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:
The mixture of compound according to the invention, lactose and starch is granulated with a 5% strength solution (m/m) of the PVP in water. The granules are dried and then mixed with the magnesium stearate for 5 minutes. This mixture is compressed in a conventional tablet press (see above for format of the tablet). A guideline compressive force for the compression is 15 kN.

Suspension which can be Administered Orally:
Composition:
1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:
The Rhodigel is suspended in ethanol, and the compound according to the invention is added to the suspension. The water is added while stirring. The mixture is stirred for about 6 h until the swelling of the Rhodigel is complete.

Solution which can be Administered Orally:
Composition:
500 mg of the compound according to the invention, 2.5 g of polysorbate and 97 g of polyethylene glycol 400. 20 g of oral solution correspond to a single dose of 100 mg of the compound according to the invention.

Production:
The compound according to the invention is suspended in the mixture of polyethylene glycol and polysorbate with stirring. The stirring process is continued until the compound according to the invention has completely dissolved.

i.v. solution:
The compound according to the invention is dissolved in a concentration below the saturation solubility in a physiologically tolerated solvent (e.g. isotonic saline, 5% glucose solution and/or 30% PEG 400 solution). The solution obtained is sterilized by filtration and used to fill sterile and pyrogen-free injection containers.

We claim:
1. A compound that is N-(2-amino-5,5,5-trifluoro-2-methylpentyl)-8-[(2,6-difluorobenzyl)oxy]-2,6-dimethylimidazo[1,2-a]pyridine-3-carboxamide

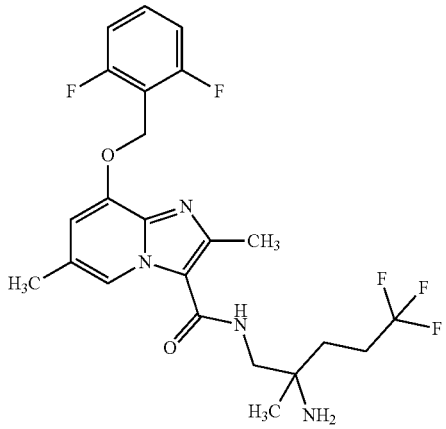 [SMILES: Cc1cc(OCc2c(F)cccc2F)c2nc(C)c(C(=O)NCC(C)(N)CCC(F)(F)F)n2c1]

or an N-oxide, physiologically acceptable salt, solvate, physiologically acceptable salt of an N-oxide or solvate of an N-oxide or physiologically acceptable salt.

2. The compound of claim 1 that is N-(2-amino-5,5,5-trifluoro-2-methylpentyl)-8-[(2,6-difluorobenzyl)oxy]-2,6-dimethylimidazo [1,2-a] pyridine-3-carboxamide

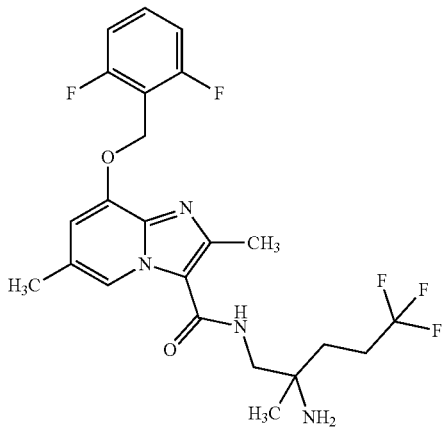 [SMILES: Cc1cc(OCc2c(F)cccc2F)c2nc(C)c(C(=O)NCC(C)(N)CCC(F)(F)F)n2c1]

or a physiologically acceptable salt thereof.

3. A pharmaceutical composition comprising the compound of claim 1 and an inert, non-toxic, pharmaceutically suitable auxiliary.

4. The compound of claim 1 that is ent-N-(2-amino-5,5,5-trifluoro-2-methylpentyl)-8-[(2,6-difluorobenzyl)oxy]-2,6-dimethylimidazo[1,2-a]pyridine-3-carboxamide (enantiomer B)

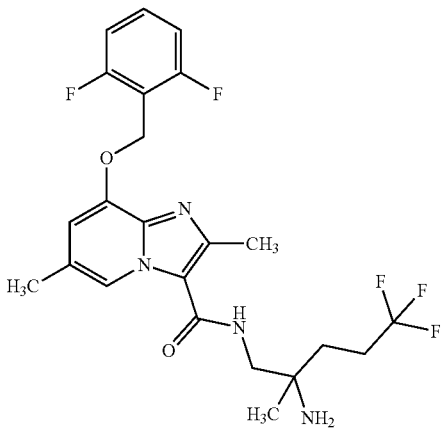 [SMILES: Cc1cc(OCc2c(F)cccc2F)c2nc(C)c(C(=O)NCC(C)(N)CCC(F)(F)F)n2c1]

or an N-oxide, physiologically acceptable salt, solvate, physiologically acceptable salt of an N-oxide or solvate of an N-oxide or physiologically acceptable salt.

5. The compound of claim 4 that is ent-N-(2-amino-5,5,5-trifluoro-2-methylpentyl)-8-[(2,6-difluorobenzyl)oxy]-2,6-dimethylimidazo [1,2-a] pyridine-3-carboxamide (enantiomer B)

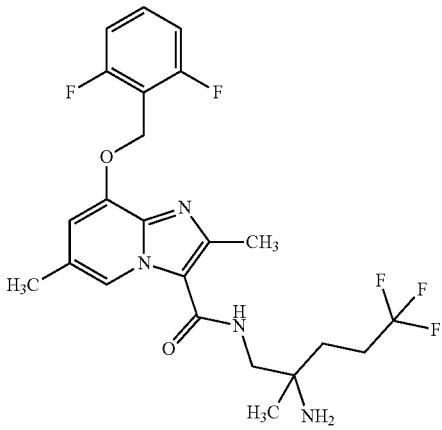 [SMILES: Cc1cc(OCc2c(F)cccc2F)c2nc(C)c(C(=O)NCC(C)(N)CCC(F)(F)F)n2c1]

or a physiologically acceptable salt thereof.

6. A pharmaceutical composition comprising the compound of claim 4 and an inert, non-toxic, pharmaceutically suitable auxiliary.

7. The compound of claim 1 that is ent-N-(2-amino-5,5,5-trifluoro-2-methylpentyl)-8-[(2,6-difluorobenzyl)oxy]-2,6-dimethylimidazo[1,2-a]pyridine-3-carboxamide (enantiomer A)

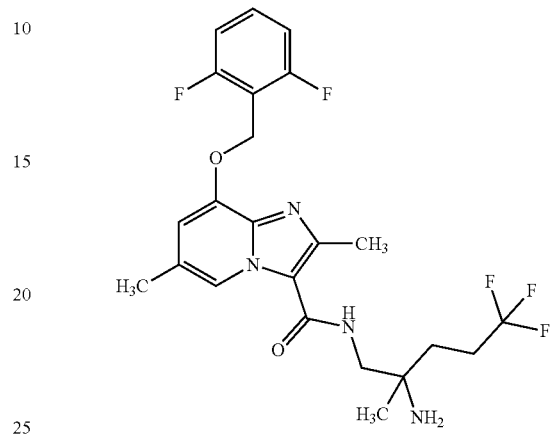

or an N-oxide, physiologically acceptable salt, solvate, physiologically acceptable salt of an N-oxide or solvate of an N-oxide or physiologically acceptable salt.

8. A racemic mixture of N-(2-amino-5,5,5-trifluoro-2-methylpentyl)-8-[(2,6-difluorobenzyl)oxy]-2,6-dimethyl-imidazo[1,2-a]pyridine-3-carboxamide

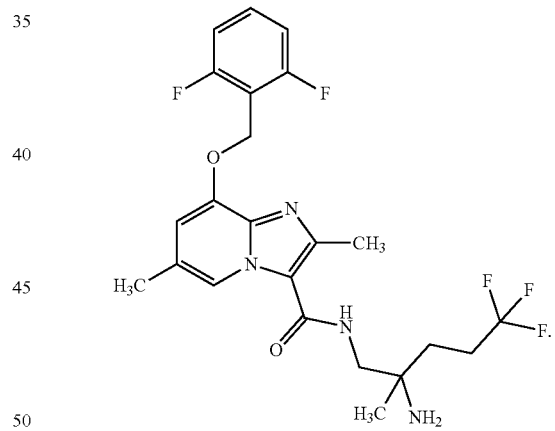

9. A pharmaceutical composition comprising the racemic mixture of claim 8 and an inert, non-toxic, pharmaceutically suitable auxiliary.

* * * * *